US012747253B2

(12) United States Patent
Wang et al.

(10) Patent No.: US 12,747,253 B2
(45) Date of Patent: Sep. 29, 2026

(54) KRas G12D INHIBITORS

(71) Applicants: Mirati Therapeutics, Inc., Princeton, NJ (US); Array BioPharma Inc., Boulder, CO (US)

(72) Inventors: Xiaolun Wang, San Diego, CA (US); Aaron Craig Burns, San Diego, CA (US); James Gail Christensen, San Diego, CA (US); John Michael Ketcham, San Diego, CA (US); John David Lawson, Carlsbad, CA (US); Matthew Arnold Marx, San Diego, CA (US); Christopher Ronald Smith, San Diego, CA (US); Shelley Allen, Boulder, CO (US); James Francis Blake, Longmont, CO (US); Mark Joseph Chicarelli, Boulder, CO (US); Joshua Ryan Dahlke, Longmont, CO (US); Donghua Dai, Superior, CO (US); Jay Bradford Fell, Longmont, CO (US); John Peter Fischer, Longmont, CO (US); Macedonio J. Mejia, Denver, CO (US); Brad Newhouse, Boulder, CO (US); Phong Nguyen, Boulder, CO (US); Jacob Matthew O'Leary, Denver, CO (US); Spencer Pajk, Boulder, CO (US); Martha E. Rodriguez, Boulder, CO (US); Pavel Savechenkov, Boulder, CO (US); Tony P. Tang, Boulder, CO (US); Guy P.A. Vigers, Boulder, CO (US); Qian Zhao, Boulder, CO (US); Dean Russell Kahn, Boulder, CO (US); John Gaudino, Boulder, CO (US); Michael Christopher Hilton, Boulder, CO (US)

(73) Assignees: MIRATI THERAPEUTICS, INC., Princeton, NJ (US); ARRAY BIOPHARMA INC., Boulder, CO (US)

( * ) Notice: Subject to any disclaimer, the term of this patent is extended or adjusted under 35 U.S.C. 154(b) by 689 days.

(21) Appl. No.: 18/015,691

(22) PCT Filed: Feb. 25, 2021

(86) PCT No.: PCT/US2021/019678

§ 371 (c)(1),
(2) Date: Jan. 11, 2023

(87) PCT Pub. No.: WO2022/015375

PCT Pub. Date: Jan. 20, 2022

(65) Prior Publication Data

US 2023/0279025 A1 Sep. 7, 2023

Related U.S. Application Data

(63) Continuation-in-part of application No. PCT/US2020/048194, filed on Aug. 27, 2020.

(60) Provisional application No. 63/058,188, filed on Jul. 29, 2020, provisional application No. 63/052,840, filed on Jul. 16, 2020.

(51) Int. Cl.
*C07D 519/00* (2006.01)

(52) U.S. Cl.
CPC ........ *C07D 519/00* (2013.01); *C07B 2200/05* (2013.01)

(58) Field of Classification Search
None
See application file for complete search history.

(56) References Cited

U.S. PATENT DOCUMENTS

| | | | | |
|---|---|---|---|---|
| 6,924,284 | B2 | 8/2005 | Beaton et al. | |
| 8,163,763 | B2 | 4/2012 | Bergeron et al. | |
| 8,426,401 | B2 | 4/2013 | Bian et al. | |
| 9,562,019 | B2 | 2/2017 | Djaballah et al. | |
| 9,840,516 | B2 | 12/2017 | Li et al. | |
| 10,125,134 | B2 | 11/2018 | Blake et al. | |
| 11,453,683 | B1 | 9/2022 | Wang et al. | |
| 11,964,989 | B2 * | 4/2024 | Wang | C07D 519/00 |
| 2002/0169300 | A1 | 11/2002 | Waterman et al. | |
| 2003/0191143 | A1 | 10/2003 | Pitts et al. | |
| 2006/0229307 | A1 | 10/2006 | Blurton et al. | |
| 2007/0021445 | A1 | 1/2007 | Berthel et al. | |
| 2009/0312342 | A1 | 12/2009 | Wilson et al. | |

(Continued)

FOREIGN PATENT DOCUMENTS

| | | | |
|---|---|---|---|
| CA | 3082579 | A1 | 5/2019 |
| EP | 4223761 | A1 | 8/2023 |

(Continued)

OTHER PUBLICATIONS (2017) "AACR Project GENIE: Powering Precision Medicine through an International Consortium", AACR Project GENIE Consortium, 7(8):818-831.

(Continued)

*Primary Examiner* — Brian J Davis
(74) *Attorney, Agent, or Firm* — Mintz, Levin, Cohn, Ferris, Glovsky and Popeo, P.C.

(57) ABSTRACT

The present invention relates to compounds that inhibit KRas G12D. In particular, the present invention relates to compounds that inhibit the activity of KRas G12D, pharmaceutical compositions comprising the compounds and methods of use therefor.

41 Claims, No Drawings

(56) References Cited

U.S. PATENT DOCUMENTS

| | | | |
|---|---|---|---|
| 2010/0081654 | A1 | 4/2010 | Stockwell et al. |
| 2011/0269244 | A1 | 11/2011 | Petter et al. |
| 2013/0029978 | A1 | 1/2013 | Kamino et al. |
| 2014/0288045 | A1 | 9/2014 | Ren et al. |
| 2015/0175558 | A1 | 6/2015 | Stockwell et al. |
| 2015/0176010 | A1 | 6/2015 | Wersinger |
| 2015/0239900 | A1 | 8/2015 | Li et al. |
| 2016/0031898 | A1 | 2/2016 | Ren et al. |
| 2016/0108019 | A1 | 4/2016 | Li et al. |
| 2016/0152576 | A9 | 6/2016 | Mitchell et al. |
| 2016/0166571 | A1 | 6/2016 | Janes et al. |
| 2016/0229836 | A1 | 8/2016 | Stockwell et al. |
| 2016/0264627 | A1 | 9/2016 | Henning et al. |
| 2016/0297774 | A1 | 10/2016 | Li et al. |
| 2017/0022184 | A1 | 1/2017 | Li et al. |
| 2017/0115303 | A1 | 4/2017 | Cravatt et al. |
| 2017/0190672 | A1 | 7/2017 | Mani et al. |
| 2017/0197945 | A1 | 7/2017 | Li et al. |
| 2017/0275289 | A1 | 9/2017 | Albrecht et al. |
| 2018/0015087 | A1 | 1/2018 | Liu et al. |
| 2018/0072723 | A1 | 3/2018 | Blake et al. |
| 2018/0118757 | A1 | 5/2018 | Li et al. |
| 2018/0118761 | A1 | 5/2018 | Sebti et al. |
| 2018/0127396 | A1 | 5/2018 | Li et al. |
| 2018/0141927 | A1 | 5/2018 | Li et al. |
| 2018/0155348 | A1 | 6/2018 | Li et al. |
| 2018/0162812 | A1 | 6/2018 | Ren et al. |
| 2018/0177767 | A1 | 6/2018 | Lanman et al. |
| 2018/0194748 | A1 | 7/2018 | Li et al. |
| 2018/0201610 | A1 | 7/2018 | Tao et al. |
| 2018/0273515 | A1 | 9/2018 | Li et al. |
| 2018/0273523 | A1 | 9/2018 | Li et al. |
| 2018/0273577 | A1 | 9/2018 | Revenko et al. |
| 2018/0282307 | A1 | 10/2018 | Li et al. |
| 2018/0282308 | A1 | 10/2018 | Li et al. |
| 2018/0289683 | A1 | 10/2018 | Mccormick et al. |
| 2019/0144444 | A1 | 5/2019 | Blake et al. |
| 2019/0270743 | A1 | 9/2019 | Marx et al. |
| 2019/0374542 | A1 | 12/2019 | Allen et al. |
| 2020/0069657 | A1 | 3/2020 | Lanman et al. |
| 2020/0262837 | A1 | 8/2020 | Marx et al. |
| 2020/0331911 | A1 | 10/2020 | Marx et al. |
| 2020/0399297 | A1 | 12/2020 | Campbell et al. |
| 2021/0024501 | A1 | 1/2021 | Li et al. |
| 2021/0139517 | A1 | 5/2021 | Gill et al. |

FOREIGN PATENT DOCUMENTS

| | | | |
|---|---|---|---|
| TW | 201922739 | A | 6/2019 |
| WO | 02/053558 | A1 | 7/2002 |
| WO | 02/087513 | A2 | 11/2002 |
| WO | 2007/146122 | A2 | 12/2007 |
| WO | 2008/009078 | A2 | 1/2008 |
| WO | 2009/047255 | A1 | 4/2009 |
| WO | 2010/014939 | A1 | 2/2010 |
| WO | 2010/120996 | A1 | 10/2010 |
| WO | 2013/155223 | A1 | 10/2013 |
| WO | 2014/143659 | A1 | 9/2014 |
| WO | 2014/152588 | A1 | 9/2014 |
| WO | 2016/049568 | A1 | 3/2015 |
| WO | 2015/054572 | A1 | 4/2015 |
| WO | 2016/025650 | A1 | 2/2016 |
| WO | 2016/044772 | A1 | 3/2016 |
| WO | 2016/049565 | A1 | 3/2016 |
| WO | 2016130460 | A2 | 8/2016 |
| WO | 2016/164675 | A1 | 10/2016 |
| WO | 2016/168540 | A1 | 10/2016 |
| WO | 2017/058728 | A1 | 4/2017 |
| WO | 2017/058768 | A1 | 4/2017 |
| WO | 2017/058792 | A1 | 4/2017 |
| WO | 2017/058805 | A1 | 4/2017 |
| WO | 2017/058807 | A1 | 4/2017 |
| WO | 2017/058902 | A1 | 4/2017 |
| WO | 2017/058915 | A1 | 4/2017 |
| WO | 2017/070256 | A2 | 4/2017 |
| WO | 2017/079864 | A1 | 5/2017 |
| WO | 2017/080980 | A1 | 5/2017 |
| WO | 2017/087528 | A1 | 5/2017 |
| WO | 2017/100546 | A1 | 6/2017 |
| WO | 2017201161 | A1 | 11/2017 |
| WO | 2018/064510 | A1 | 4/2018 |
| WO | 2018/068017 | A1 | 4/2018 |
| WO | 2018/102452 | A2 | 6/2018 |
| WO | 2018/102453 | A1 | 6/2018 |
| WO | 2018/112420 | A1 | 6/2018 |
| WO | 2018/115380 | A1 | 6/2018 |
| WO | 2018/119183 | A2 | 6/2018 |
| WO | 2018/140512 | A1 | 8/2018 |
| WO | 2018/140513 | A1 | 8/2018 |
| WO | 2018/140514 | A1 | 8/2018 |
| WO | 2018/140598 | A1 | 8/2018 |
| WO | 2018/140599 | A1 | 8/2018 |
| WO | 2018/140600 | A1 | 8/2018 |
| WO | 2018/143315 | A1 | 8/2018 |
| WO | 2018/195439 | A2 | 10/2018 |
| WO | 2018217651 | A1 | 11/2018 |
| WO | 2018218070 | A2 | 11/2018 |
| WO | 2019/051291 | A1 | 3/2019 |
| WO | 2019099524 | A1 | 5/2019 |
| WO | 202063594 | | 4/2020 |
| WO | 202098488 | | 5/2020 |
| WO | 2020097537 | A2 | 5/2020 |
| WO | 2020118066 | A1 | 6/2020 |
| WO | 2020123395 | A1 | 6/2020 |
| WO | 2020146613 | A1 | 7/2020 |
| WO | 202027202 | | 8/2020 |
| WO | 2020163598 | | 8/2020 |
| WO | 2020165670 | | 8/2020 |
| WO | 2020169838 | | 8/2020 |
| WO | 2020171499 | | 8/2020 |
| WO | 2020172332 | | 8/2020 |
| WO | 2020176693 | | 9/2020 |
| WO | 2020176963 | | 9/2020 |
| WO | 2020177629 | | 9/2020 |
| WO | 2020178282 | | 9/2020 |
| WO | 2020180770 | A1 | 9/2020 |
| WO | 2020181142 | | 9/2020 |
| WO | 2020198125 | | 10/2020 |
| WO | 2020204359 | | 10/2020 |
| WO | 2020205473 | | 10/2020 |
| WO | 2020205486 | | 10/2020 |
| WO | 2020212895 | | 10/2020 |
| WO | 2020214537 | | 10/2020 |
| WO | 2020221239 | | 11/2020 |
| WO | 2020230028 | | 11/2020 |
| WO | 2020230091 | | 11/2020 |
| WO | 2020231806 | | 11/2020 |
| WO | 2020231808 | | 11/2020 |
| WO | 2020232130 | | 11/2020 |
| WO | 2020233592 | | 11/2020 |
| WO | 2020234103 | | 11/2020 |
| WO | 2020236940 | | 11/2020 |
| WO | 2020236947 | | 11/2020 |
| WO | 2020236948 | | 11/2020 |
| WO | 2020247914 | | 12/2020 |
| WO | 2020252336 | | 12/2020 |
| WO | 2020252353 | | 12/2020 |
| WO | 2021000885 | | 1/2021 |
| WO | 2021023154 | | 2/2021 |
| WO | 2021023247 | | 2/2021 |
| WO | 2021027911 | | 2/2021 |
| WO | 2021027943 | | 2/2021 |
| WO | 2021031952 | | 2/2021 |
| WO | 2021034992 | | 2/2021 |
| WO | 2021037018 | | 3/2021 |
| WO | 2021041671 | | 3/2021 |
| WO | 2021043322 | | 3/2021 |
| WO | 2021045279 | | 3/2021 |
| WO | 2021050732 | | 3/2021 |
| WO | 2021051034 | | 3/2021 |
| WO | 2021052499 | | 3/2021 |
| WO | 2021055728 | | 3/2021 |
| WO | 2021057832 | | 4/2021 |
| WO | 2021058018 | | 4/2021 |

(56) References Cited

FOREIGN PATENT DOCUMENTS

| | | | |
|---|---|---|---|
| WO | 2021061515 | | 4/2021 |
| WO | 2021061749 | | 4/2021 |
| WO | 2021063346 | | 4/2021 |
| WO | 2021068898 | | 4/2021 |
| WO | 2021075147 | | 4/2021 |
| WO | 2021076655 | | 4/2021 |
| WO | 2021078285 | | 4/2021 |
| WO | 2021078312 | | 4/2021 |
| WO | 2021080359 | | 4/2021 |
| WO | 2021081212 | | 4/2021 |
| WO | 2021083167 | | 5/2021 |
| WO | 2021084765 | | 5/2021 |
| WO | 2021085653 | | 5/2021 |
| WO | 2021086833 | | 5/2021 |
| WO | 2021088458 | | 5/2021 |
| WO | 2021088938 | | 5/2021 |
| WO | 2021091956 | | 5/2021 |
| WO | 2021091967 | | 5/2021 |
| WO | 2021091982 | | 5/2021 |
| WO | 2021093758 | A1 | 5/2021 |
| WO | 2021104431 | A1 | 6/2021 |
| WO | 2021106230 | A1 | 6/2021 |
| WO | 2021106231 | A1 | 6/2021 |
| WO | 2021107160 | A1 | 6/2021 |
| WO | 2021108683 | A1 | 6/2021 |
| WO | 2021109737 | A1 | 6/2021 |
| WO | 2021113595 | A1 | 6/2021 |
| WO | 2021120045 | A1 | 6/2021 |
| WO | 2021121330 | A1 | 6/2021 |
| WO | 2021121367 | A1 | 6/2021 |
| WO | 2021121371 | A1 | 6/2021 |
| WO | 2021121397 | A1 | 6/2021 |
| WO | 2021126120 | A1 | 6/2021 |
| WO | 2021126799 | A1 | 6/2021 |
| WO | 2021127404 | A1 | 6/2021 |
| WO | 2021129820 | A1 | 7/2021 |
| WO | 2021129824 | A1 | 7/2021 |
| WO | 2021139678 | A1 | 7/2021 |
| WO | 2021139748 | A1 | 7/2021 |
| WO | 2021141628 | A1 | 7/2021 |
| WO | 2021142252 | A1 | 7/2021 |
| WO | 2021143693 | A1 | 7/2021 |
| WO | 2021145520 | A1 | 7/2021 |
| WO | 2021145521 | A1 | 7/2021 |
| WO | 2021147965 | A1 | 7/2021 |
| WO | 2021147967 | A1 | 7/2021 |
| WO | 2021150613 | A1 | 7/2021 |
| WO | 2021152149 | A1 | 8/2021 |
| WO | 2021168193 | A1 | 8/2021 |
| WO | 2021169963 | A1 | 9/2021 |
| WO | 2021169990 | A1 | 9/2021 |
| WO | 2021173923 | A1 | 9/2021 |
| WO | 2021175199 | A1 | 9/2021 |
| WO | 2021177721 | A1 | 9/2021 |
| WO | 2021178740 | A2 | 9/2021 |
| WO | 2021178741 | A1 | 9/2021 |
| WO | 2021180181 | A1 | 9/2021 |
| WO | 2021185233 | A1 | 9/2021 |
| WO | 2021190467 | A2 | 9/2021 |
| WO | 2021197499 | A1 | 10/2021 |
| WO | 2021203768 | A1 | 10/2021 |
| WO | 2021207172 | A1 | 10/2021 |
| WO | 2021211864 | A1 | 10/2021 |
| WO | 2021215544 | A1 | 10/2021 |
| WO | 2021216770 | A1 | 10/2021 |
| WO | 2021217019 | A1 | 10/2021 |
| WO | 2021090855 | A1 | 11/2021 |
| WO | 2021218110 | A1 | 11/2021 |
| WO | 2021219072 | A1 | 11/2021 |
| WO | 2021219090 | A2 | 11/2021 |
| WO | 2021219091 | A1 | 11/2021 |
| WO | 2021228161 | A1 | 11/2021 |
| WO | 2021231526 | A1 | 11/2021 |
| WO | 2021236475 | A1 | 11/2021 |
| WO | 2021239058 | A1 | 12/2021 |
| WO | 2021243280 | A1 | 12/2021 |
| WO | 2021244603 | A1 | 12/2021 |
| WO | 2021245051 | A1 | 12/2021 |
| WO | 2021245055 | A1 | 12/2021 |
| WO | 2021245499 | A1 | 12/2021 |
| WO | 2021248079 | A1 | 12/2021 |
| WO | 2021248082 | A1 | 12/2021 |
| WO | 2021248083 | A1 | 12/2021 |
| WO | 2021248090 | A1 | 12/2021 |
| WO | 2021248095 | A1 | 12/2021 |
| WO | 2021249563 | A1 | 12/2021 |
| WO | 2021252339 | A1 | 12/2021 |
| WO | 2021257828 | A1 | 12/2021 |
| WO | 2021259331 | A1 | 12/2021 |
| WO | 2022002102 | A1 | 1/2022 |
| WO | 2022015375 | A1 | 1/2022 |
| WO | 2022017339 | A1 | 1/2022 |
| WO | 2022028346 | A1 | 2/2022 |
| WO | 2022028492 | A1 | 2/2022 |
| WO | 2022031678 | A1 | 2/2022 |
| WO | 2022036176 | A1 | 2/2022 |
| WO | 2022042630 | A1 | 3/2022 |
| WO | 2022157629 | A1 | 7/2022 |

OTHER PUBLICATIONS

Extended European Search Report for EP Application No. 21843038.7, mailed on Sep. 6, 2024, 9 pages.

Intenational Search Report and Written Opinion for corresponding PCT Application No. PCT/US2020/048194, mailed Dec. 8, 2020, 6 pages.

(Retrieved on Sep. 23, 2024) "P01116-Rask_Human", UniProtKB/Swiss-Prot, 14 pages.

Alamgeer et al. (2013) "Novel Therapeutic Targets in Non-small Cell Lung Cancer", Curr Opin Pharmacol., 13 (3):394-401.

Fell et al. (2020) "Identification of the Clinical Development Candidate MRTX849, a Covalent KRASG12C Inhibitor for the Treatment of Cancer", Journal of Medicinal Chemistry, 63(13): 6679-6693.

Mccormick, Frank (2015) "KRAS as a Therapeutic Target", Clin Cancer Res., 21(8):1797-1801.

Santos et al. (1984) "Malignant Activation of a K-Ras Oncogene in Lung Carcinoma but Not in Normal Tissue of the Same Patient", Science, 223(4637):661-664.

International Search Report and Written Opinion for PCT Application No. PCT/US2017/33099 mailed Aug. 24, 2017.

Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col. Para 2.

Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.

Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.

Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.

Burgess, M. et al., "KRAS Allelic Imbalance Enhances Fitness and Modulates MAP Kinase Dependence in Cancer", Cell 168, 817-829, Feb. 23, 2017, Elsevier Inc.

Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.

Costa-Cabral, S. et al., "CDK1 Is a Synthetic Lethal Target for KRAS Mutant Tumours", PLOS ONE | DOI:10.1371/journal.pone.0149099 Feb. 16, 2016.

Cully, "Closing the door on KRAS-mutant lung cancer", Nature Reviews Drug Discovery | Published online Nov. 3, 2016; doi:10.1038/nrd.2016.216, MacMillan Publishers.

(56) References Cited

OTHER PUBLICATIONS

Dharmaiah, S. et al., "Structural basis of recognition of farnesylated and methylated KRAS4b by PDEδ", E6766-E6775, PNAS, Published online Oct. 17, 2016.
Fiala, O. et al., "The dominant role of G12C over other KRAS mutation types in the negative prediction of efficacy of epidermal growth factor receptor tyrosine kinase inhibitors in nonesmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of July 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer The End of the Beginning for Targeted Therapies", JAMA May 9, 2017 Volume 317, No. 18.
Kerr, E. et al., "Mutant Kras copy No. defines metabolic reprogramming and therapeutic susceptibilities", Nature 531, 110-113, (Mar. 3, 2016) doi:10.1038/nature 16967.
Kim, J. et al., "CPS1 maintains pyrimidine pools and DNA synthesis in KRAS/LKB1-mutant lung cancer cells", Nature 546, 168-172, (Jun. 1, 2017) doi: 10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S. et al.l., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Nadal, E. et al., "Abstract C141: KRAS G12C mutation is prognostic of poor outcome in resected lung adenocarcinomas and predictive of poor response to MEK inhibition in vitro", Mol Cancer Ther Nov. 2013 12; C141, doi: 10.1158/1535-7163.TARG-13-C141.
Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J. et al., "K-Ras(G12C) inhibitors allosterically control GTP affinity and effector interactions", Nature, vol. 503: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.
Rudoni, S. et al., "Role of guanine nucleotides in the regulation of the Ras/cAMP pathway in *Saccharomyces cerevisiae*", Biochimica et Biophysica Acta 1538 (2001) 181ˆ189.
Samatar, A. et al., "Targeting RAS-ERK signalling in cancer: promises and challenges", Nature Reviews Drug Discovery, vol. 13, pp. 928-942, Dec. 2014.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation** ", Angew. Chem. Int. Ed. 2012, 51, 1-5, 2012 Wiley-VCH Verlag Gmbh & Co. KGaA, Weinheim.
Sun, Q., et al., "A method for the second-site screening of K-Ras in the presence of a covalently attached first-site igand", J Biomol NMR (2014) 60:11-14 DOI 10.1007/s10858-014-9849-8.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Sung, Y. et al., "Mutagenesis of the H-ras p21 at Glycine-60 Residue Disrupts GTP-Induced Conformational Change", Biochemistry 1995, 34, 3470-3477, American Chemical Society.
Tape, C. et al., "Oncogenic KRAS Regulates Tumor Cell Signaling via Stromal Reciprocation", Cell 165, 1-11May 5, 2016.
Thierry, A. et al., "Clinical validation of the detection of KRAS and BRAF mutations from circulating tumor DNA", Nature Medicine, vol. 20, No. 4, pp. 430-436 , Apr. 2014.
Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.
Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.
Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.
Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.
Winter, J. et al., "Small Molecule Binding Sites on the Ras:SOS Complex Can Be Exploited for Inhibition of Ras Activation", J.

(56) References Cited

OTHER PUBLICATIONS

Med. Chem. 2015, 58, 2265-2274; DOI: 10.1021/jm501660t; 2015 American Chemical Society, ACS Publications.
Wood, K. et al., "Reply" Comments & Response, Letters JAMA Oncology Published online Jul. 21, 2016, American Medical Association.
Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.
Xiong, Y. et al., "Covalent Guanosine Mimetic Inhibitors of G12C KRAS" Acs Med. Chem. Lett. 2017, 8, 61-66, DOI: 10.1021/acsmedchemlett 6b00373; 2016 American Chemical Society, ACS Publications.
Janes et al., "Targeting KRAS Mutant Cancers with a Covalent G12C-Specific Inhibitor", Cell 172, 578-589, Jan. 25, 2018.
Singh et al., A Gene Expression Signature Associated with "K-Ras Addiction" Reveals Regulators of EMT and Tumor Cell Survival, Cancer Cell 15, p. 489-500, Jun. 2, 2009.
Stephen et al., "Dragging Ras Back in the Ring", Cancer Cell 25, p. 272, Mar. 17, 2014.
Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.
Simanshu et al., "RAS Proteins and Their Regulators in Human Disease", Cell 170, p. 17, Jun. 29, 2017.
Pacold et al., "Crystal Structure and Functional Analysis of Ras Binding to Its Effector Phosphoinositide 3-Kinase gamma", Cell, vol. 103, p. 931-943, Dec. 8, 2000.
Lech-Gustav et al., "The Renaissance of Ras", ACS Chem. Biol., 2014, 9, 2447-2458.
Karachaliou et al., "KRAS Mutations in Lung Cancer", Clinical Lung Cancer, vol. 14, No. 3, p. 2015-14, 2013.
Schwartz et al., "Covalent EGFR inhibitor analysis reveals importance of reversible interactions to potency and mechanisms of drug resistance", PNAS, vol. 111, No. 1, p. 173-178, Jan. 7, 2014.
Sun et al., "A method for the second-site screening of K-Ras in the presence of a covalently attached first-site ligand", J. Biomol. NMR (2014) vol. 60 p. 11-14.
Kyriakis, J., "Thinking Outside the Box about Ras", J. Biol. Chem. 2009, 284:10993-10994, published online Dec. 17, 2008.
Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.
Walker et al., "Structural insights into phosphoinositide 3-kinase catalysis and signalling", Nature vol. 402, p. Nov. 18, 1999; www.nature.com.
Barbie et al., "Systematic RNA interference reveals that oncogenic KRAS-driven cancers require TBK1", Nature, vol. 462, p. 108, Nov. 5, 2009; doi:10.1038/nature08460.
Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.
Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.
Grant et al., "Novel Allosteric Sites on Ras for Lead Generation", PLOS ONE, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.
Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36 (2): 65-77. doi: 10.1016/j.tibs.2010.09.006.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 mailed Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K Inhibition, Downloaded from clincancerres.aacrjournals.org on Oct. 22, 2018. © 2018 American Association for Cancer Research.
O'Bryan, J., "Pharmacological Targeting of RAS: Recent Success with Direct Inhibitors", Pharmacological Research (2018), https://doi.org/10.1016/j.phrs.2018.10.021.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18-1640, Downloaded from clincancerres.aacrjournals.org on Oct. 29, 2018. © 2018 American Association for Cancer Research.

(56) References Cited

OTHER PUBLICATIONS

Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer A Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/s41598-018-32683-w.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
Abe et al. (Feb. 2011) "Discovery of a Highly Potent and Selective MEK Inhibitor: GSK1120212 (JTP-74057 DMSO Solvate)", ACS Medicinal Chemistry Letters, 2(4):320-324.
Bakalova et al. (2004) "Electronic Absorption and Emission Spectra and Computational Studies Of Some 2-aryl, 2-styryl, and 2-(40-aryl)butadienyl Quinazolin-4-ones", Journal of Molecular Structure, 710:229-234.
Canon et al. (Nov. 2019) "The Clinical KRAS(G12C) Inhibitor AMG 510 Drives Anti-Tumour Immunity", Nature, 575(7781):217-223 (26 pages).
Lanman et al. (2019) "Discovery of a Covalent Inhibitor of KRASG12C (AMG 510) for the Treatment of Solid Tumors" Journal of Medicinal Chemistry, 63(1):52-65.
Orlov et al. (2020) "Rapid Improvement of the Performance Status and Reduction of the Tumor Size in KRAS-Mutated Colorectal Cancer Patient Receiving Binimetinib, Hydroxychloroquine, and Bevacizumab", Case Reports in Oncology, 13(2):985-989.
Pubchem (Modify Date: May 31, 2019) "SID-132593111", 2 pages.
Broutin et al. (Aug. 23, 2016) "Insights Into Significance of Combined Inhibition of MEK and m-TOR Signalling Output in KRAS Mutant Non-small-cell Lung Cancer", British Journal of Cancer, 115(5):549-552.
Costa-Cabral et al. (Feb. 16, 2016) "CDK1 Is a Synthetic Lethal Target for KRAS Mutant Tumours", PLoS One, 11(2):e0149099 (22 pages).
Cully, Megan (Nov. 3, 2016) "Closing the Door on KRAS-mutant Lung Cancer", Nature Reviews Drug Discovery, 15(11):747.
Ihle et al. (Feb. 8, 2012) "Effect of KRAS Oncogene Substitutions on Protein Behavior: Implications for Signaling and Clinical Outcome", Journal of the National Cancer Institute, 104(3):228-239.
Ischenko et al. (2013) "Direct Reprogramming by Oncogenic Ras and Myc", PNAS, early edition 1, 110 (10):3937-3942.
Kaufman et al. (May 9, 2017) "Treatment of KRAS-Mutant Non-Small Cell Lung Cancer: The End of the Beginning for Targeted Therapies", JAMA, 317(18):1835-1837.
Kitai et al. (Jul. 3, 2017) "Key Roles of EMT for Adaptive Resistance to MEK Inhibitor in KRAS Mutant Lung Cancer", Small GTPases, Accepted Manuscript, 8(3):172-176 (15 pages).
Loncle et al. (Jul. 14, 2016) "The Pancreatitis-Associated Protein VMP1, a Key Regulator of Inducible Autophagy, Promotes Kras(G12D)-Mediated Pancreatic Cancer Initiation", Cell Death and Disease, 7(7):e2295 (7 pages).
Muller et al. (Jun. 16, 2017) "Nucleotide Based Covalent Inhibitors of KRas Can Only Be Efficient in Vivo if They Bind Reversibly With GTP-like Affinity", Scientific Reports, 7(1):3687 (11 pages).
Nabet et al. (2018) "It Takes Two To Target: A Study in KRAS Dimerization", Biochemistry, 57(16):2289-2290.
Nadal et al. (2013) "Abstract C141: Kras G12C Mutation is Prognostic of Poor Outcome in Resected Lung Adenocarcinomas and Predictive of Poor Response to Mek Inhibition in Vitro", Molecular Cancer Therapeutics, 12 (11_Supplement):C141.
Nussinov et al. (Aug. 2016) "Independent and Core Pathways in Oncogenic KRAS Signaling", Expert Review of Proteomics, 13(8):711-716.
Pantsar et al. (Sep. 10, 2018) "Assessment of Mutation Probabilities of KRAS G12 Missense Mutants and Their Long-timescale Dynamics by Atomistic Molecular Simulations and Markov State Modeling", PLOS Computational Biology, 14(9):e1006458 (23 pages).
Patricelli et al. (Mar. 2016) "Selective Inhibition of Oncogenic KRAS Output with Small Molecules Targeting the Inactive State", Cancer Discovery, 6(3):316-329.
Perera et al. (Jul. 2016) "Oncogenic KRAS Triggers MAPK-dependent Errors in Mitosis and MYC-dependent Sensitivity to Anti-mitotic Agents", Scientific Reports, 6:29741 (15 pages).
Renaud et al. (2016) "KRAS in Non-Small-Cell Lung Cancer: Oncogenic Addiction and Epidermal Growth Factor Receptor Tyrosine Kinase Inhibitors", JAMA Oncology, 2(10):1373.
Riquelme et al. (2015) "Modulation of EZH2 Expression by MEK-ERK or PI3K-AKT Signaling in Lung Cancer Is Dictated by Different KRAS Oncogene Mutations", Cancer Research, 76(3):675-685.
Ross et al. (2017) "Targeting KRAS-dependent Tumors With AZD4785, a High-affinity Therapeutic Antisense Oligonucleotide Inhibitor of KRAS", Science Translational Medicine, 9(394):eaal5253.
Ruess et al. (2018) "Mutant KRAS-Driven Cancers Depend on PTPN11/SHP2 Phosphatase", Nature Medicine, 24 (7):954-960 (13 pages).
Sautier et al. (Dec. 23, 2016) "Latest Advances Towards Ras Inhibition: A Medicinal Chemistry Perspective", Angewandte Chemie International Edition, 55(52)15982-15988.
Serafimova et al. (2012) "Reversible Targeting of Noncatalytic Cysteines With Chemically Tuned Electrophiles", Nature Chemical Biology, 8(5):471-476.

* cited by examiner

KRas G12D INHIBITORS

CROSS REFERENCE

This application claims benefit of priority of PCT Application No. PCT/US2020/048194 filed Aug. 20, 2020, U.S. Provisional Application No. 63/052,840 filed Jul. 16, 2020 and U.S. Provisional Application No. 63/058,188 filed Jul. 29, 2020, and the entire content of each of these applications is hereby incorporated by reference in their entirety.

FIELD OF THE INVENTION

The present invention relates to compounds that inhibit KRas G12D. In particular, the present invention relates to compounds that inhibit the activity of KRas G12D, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma. KRAS G12D mutation is present in 25.0% of all pancreatic ductal adenocarcinoma patients, 13.3% of all colorectal carcinoma patients, 10.1% of all rectal carcinoma patients, 4.1% of all non-small cell lung carcinoma patients and 1.7% of all small cell lung carcinoma patients (e.g., see The AACR Project GENIE Consortium, (2017) Cancer Discovery; 7(8):818-831. Dataset Version 4).

The well-known role of KRas in malignancy and the discovery of these frequent mutations in KRas in various tumor types made KRas a highly attractive target of the pharmaceutical industry for cancer therapy. Notwithstanding thirty years of large-scale discovery efforts to develop inhibitors of KRas for treating cancer, no KRas inhibitor has yet demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well recent advances in the covalent targeting of an allosteric pocket of KRas G12C (e.g., see Ostrem et al., (2013) Nature 503:548-551 and Fell et al., (2018) ACS Med. Chem. Lett. 9:1230-1234). Clearly there remains a continued interest and effort to develop inhibitors of KRas, particularly inhibitors of activating KRas mutants, especially KRas G12D.

Thus, there is a need to develop new KRas G12D inhibitors that demonstrate sufficient efficacy for treating KRas G12D-mediated cancer.

SUMMARY OF THE INVENTION

In one aspect of the invention, compounds are provided that inhibit KRas G12D activity.

In certain embodiments, the compounds are represented by Formula (I):

Formula (I)

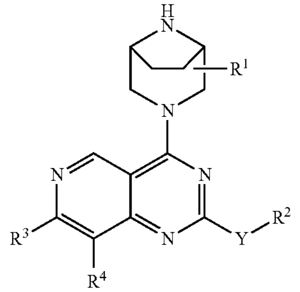

or a pharmaceutically acceptable salt thereof:

wherein:

$R^1$ is hydrogen, hydroxy, halogen, C1-C3 alkyl, C1-C3 cyanoalkyl, C1-C3 hydroxyalkyl, HC(═O)—, —$CO_2R^5$, —$CO_2N(R^5)_2$ or a 5-6 membered heteroaryl;

Y is a bond, O or $NR^5$;

$R^2$ is hydrogen, —$N(R^5)_2$, heterocyclyl, C1-C6 alkyl, -L-heterocyclyl, -L-aryl, -L-heteroaryl, -L-cycloalkyl, -L-$N(R^5)_2$, -L-NHC(═NH)$NH_2$, -L-C(O)$N(R^5)_2$, -L-C1-C6 haloalkyl, -L-$OR^5$, -L-$(CH_2OR^5)(CH_2)_n$ $OR^5$, -L-$NR^5$C(O)-aryl, -L-COOH, or -LC(═O)OC1-C6 alkyl, wherein the heterocyclyl and the aryl portion of -L-$NR^5$C(O)-aryl and the heterocyclyl portion of -L-heterocyclyl and the cycloalkyl portion of the -L-cycloalkyl may be optionally substituted with one or more $R^6$, and wherein the aryl or heteroaryl of the -L-aryl and the -L-heteroaryl may be optionally substituted with one or more $R^7$;

each L is independently a C1-C4 alkylene optionally substituted with hydroxy, C1-C4 hydroxyalkyl or heteroaryl;

$R^3$ is aryl or heteroaryl, wherein the aryl or the heteroaryl is optionally substituted with one or more $R^8$;

$R^4$ is hydrogen, halogen or C1-C3 alkyl;

each $R^5$ is independently hydrogen or C1-C3 alkyl;

each $R^6$ is independently halogen, hydroxy, C1-C3 hydroxyalkyl, C1-C3 alkyl, C1-C3 haloalkyl, C1-C3 alkoxy, cyano, -Q-phenyl, -Q-phenyl$SO_2F$, —NHC(O)phenyl, —NHC(O)phenyl$SO_2F$, C1-C3 alkyl substituted pyrazolyl, araC1-C3 alkyl-, tert-butyldimethylsilyloxy$CH_2$—, —$N(R^5)_2$, (C1-C3 alkoxy)C1-C3 alkyl-, (C1-C3 alkyl)C(═O), oxo, (C1-C3 haloalkyl)C(═O)—, —$SO_2F$, (C1-C3 alkoxy)C1-C3 alkoxy, —$CH_2OC(O)N(R^5)_2$, —$CH_2NHC(O)OC1$-C6 alkyl, —$CH_2NHC(O)N(R^5)_2$, —$CH_2NHC(O)C1$-C6 alkyl, —$CH_2$(pyrazolyl), —$CH_2NHSO_2C1$-C6 alkyl, —$CH_2OC(O)$heterocyclyl, —OC(O)$N(R^5)_2$, —OC(O)NH(C1-C3 alkyl)O(C1-C3 alkyl), —OC(O)NH(C1-C3 alkyl)O(C1-C3 alkyl)phenyl(C1-C3 alkyl)N($CH_3$)$_2$, —OC(O)NH(C1-C3 alkyl)O(C1-C3 alkyl)phenyl or —OC(O)heterocyclyl, —$CH_2$heterocyclyl, wherein the phenyl of —NHC(O)phenyl or —OC(O)NH(C1-C3 alkyl)O(C1-C3 alkyl)phenyl is optionally substituted with —C(O)H or OH and wherein the heterocyclyl of —$CH_2$heterocyclyl is optionally substituted with oxo;

Q is a bond or O;

each $R^7$ is independently halogen, hydroxy, HC(═O)—, C1-C4 alkyl, C1-C4 alkoxy, C1-C4 haloalkyl, C1-C4 hydroxyalkyl, or —N($R^5$)$_2$; and each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —$CH_2$C(═O)N($R^5$)$_2$, —C3-C4 alkynyl(N$R^5$)$_2$, —N($R^5$)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl.

In certain other embodiments, the compounds are represented by Formula (II):

Formula (II)

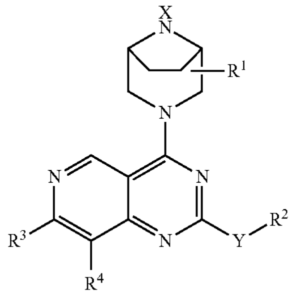

or a pharmaceutically acceptable salt thereof, wherein:

$R^1$ is hydrogen, hydroxy, halogen, C1-C3 alkyl, C1-C3 cyanoalkyl, C1-C3 hydroxyalkyl, HC(═O)—, —$CO_2R^5$, —$CO_2$N($R^5$)$_2$ or a 5-6 membered heteroaryl;

X is hydrogen, —C(O)—O—CH($R^9$)—O—C(O)—Z, —C(O)—O-aryl or —C(O)—C1-C6 alkyl;

Y is a bond, O or N$R^5$;

Z is —(CH2)n-CH3 or C1-C3 alkyl;

n is 0-20;

$R^2$ is hydrogen, —N($R^5$)$_2$, heterocyclyl, C1-C6 alkyl, -L-heterocyclyl, -L-aryl, -L-heteroaryl, -L-cycloalkyl, -L-N($R^5$)$_2$, -L-NHC(═NH)$NH_2$, -L-C(O)N($R^5$)$_2$, -L-C1-C6 haloalkyl, -L-O$R^5$, -L-($CH_2$O$R^5$)($CH_2$)$_n$O$R^5$, -L-N$R^5$C(O)-aryl, -L-COOH, or -LC (═O)OC1-C6 alkyl, wherein the heterocyclyl and the aryl portion of -L-N$R^5$C(O)-aryl and the heterocyclyl portion of -L-heterocyclyl and the cycloalkyl portion of the -L-cycloalkyl may be optionally substituted with one or more $R^6$, and wherein the aryl or heteroaryl of the -L-aryl and the -L-heteroaryl may be optionally substituted with one or more $R^7$;

each L is independently a C1-C4 alkylene optionally substituted with hydroxy, C1-C4 hydroxyalkyl, heteroaryl or 1-2 deuterium;

$R^3$ is aryl or heteroaryl, wherein the aryl or the heteroaryl is optionally substituted with one or more $R^8$;

$R^4$ is hydrogen, halogen or C1-C3 alkyl;

each $R^5$ is independently hydrogen or C1-C3 alkyl;

each $R^6$ is independently halogen, hydroxy, C1-C3 hydroxyalkyl, C1-C3 alkyl, C1-C3 haloalkyl, C1-C3 alkoxy, cyano, -Q-phenyl, -Q-phenyl$SO_2$F, —NHC(O)phenyl, —NHC(O)phenyl$SO_2$F, C1-C3 alkyl substituted pyrazolyl, araC1-C3 alkyl-, tert-butyldimethylsilyloxy$CH_2$—, —N($R^5$)$_2$, (C1-C3 alkoxy)C1-C3 alkyl-, (C1-C3 alkyl)C(═O), oxo, (C1-C3 haloalkyl)C(═O)—, —$SO_2$F, (C1-C3 alkoxy)C1-C3 alkoxy, —$CH_2$OC(O)N($R^5$)$_2$, —$CH_2$NHC(O)OC1-C6 alkyl, —$CH_2$NHC(O)N($R^5$)$_2$, —$CH_2$NHC(O)C1-C6 alkyl, —$CH_2$ (pyrazolyl), —$CH_2$NH$SO_2$C1-C6 alkyl, —$CH_2$OC(O)heterocyclyl, —OC(O)N(R$) 2, —OC(O)NH(C1-C3 alkyl)O(C1-C3 alkyl), —OC(O)NH(C1-C3 alkyl)O(C1-C3 alkyl)phenyl(C1-C3 alkyl)N($CH_3$) 2, —OC(O)NH(C1-C3 alkyl)O(C1-C3 alkyl)phenyl, —OC(O)heterocyclyl, —$CH_2$heterocyclyl or deuterium, wherein the phenyl of —NHC(O)phenyl or —OC(O)NH(C1-C3 alkyl)O(C1-C3 alkyl)phenyl is optionally substituted with —C(O)H or OH and wherein the heterocyclyl of —$CH_2$heterocyclyl is optionally substituted with oxo;

Q is a bond or O;

each $R^7$ is independently, halogen, hydroxy, HC(═O)—, C1-C4 alkyl, C1-C4 alkoxy, C1-C4 haloalkyl, C1-C4 hydroxyalkyl, or —N($R^5$)$_2$;

each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxy C1-C3 alkyl, —$CH_2$C(═O)N($R^5$)$_2$, —C3-C4 alkynyl(N$R^5$)$_2$, —N($R^5$)$_2$, deuteroC2-C4 alkynyl, (C1-C3 alkoxy)haloC1-C3 alkyl-, —O—C(O)—Z, or C3-C6 cycloalkyl wherein said C3-C6 cycloalkyl is optionally substituted with halogen or C1-C3 alkyl; and $R^9$ is hydrogen or C1-C3 alkyl.

In another aspect of the invention, pharmaceutical compositions are provided comprising a therapeutically effective amount of a compound of the present invention or a pharmaceutically acceptable salt thereof and a pharmaceutically acceptable excipient.

In another aspect there is provided a method for inhibiting KRas G12D activity in a cell, comprising contacting the cell in which inhibition of KRas G12D activity is desired with an effective amount of a compound described herein.

In yet another aspect of the invention, methods for inhibiting KRas G12D activity in a in a cell, comprising contacting the cell with a compound of Formula (I) or (II), or a pharmaceutically acceptable salt thereof, or a pharmaceutical composition thereof as defined herein. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I) or (II), or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas G12D-associated disease or disorder in a patient in need of such treatment, the method comprising administering to the patient a therapeutically effective amount of a compound of Formula (I) or (II), or a pharmaceutically acceptable salt thereof, or a pharmaceutical composition thereof as defined herein.

Also provided herein is a compound of Formula (I) or (II), or a pharmaceutically acceptable salt thereof, or a pharmaceutical composition thereof as defined herein for use in therapy.

Also provided herein is a compound of Formula (I) or (II), or a pharmaceutically acceptable salt thereof or a pharmaceutical composition thereof as defined herein for use in the treatment of cancer.

Also provided herein is a compound of Formula (I) or (II), or a pharmaceutically acceptable salt thereof for use in the inhibition of KRas G12D.

Also provided herein is a compound of Formula (I) or (II), or a pharmaceutically acceptable salt thereof or a pharmaceutical composition thereof as defined herein, for use in the treatment of a KRas G12D-associated disease or disorder.

Also provided herein is the use of a compound of Formula (I) or (II), or a pharmaceutically acceptable salt thereof, as defined herein in the manufacture of a medicament for the treatment of cancer.

Also provided herein is a use of a compound of Formula (I) or (II), or a pharmaceutically acceptable salt thereof, as defined herein in the manufacture of a medicament for the inhibition of activity of KRas G12D.

Also provided herein is the use of a compound of Formula (I) or (II), or a pharmaceutically acceptable salt thereof, as defined herein, in the manufacture of a medicament for the treatment of a KRas G12D-associated disease or disorder.

Also provided herein is a method for treating cancer in a patient in need thereof, the method comprising (a) determining that the cancer is associated with a KRas G12D mutation (i.e., a KRas G12D-associated cancer); and (b) administering to the patient a therapeutically effective amount of a compound of Formula (I) or (II), or a pharmaceutically acceptable salt thereof, or a pharmaceutical composition thereof.

Also provided herein is a process for preparing a compound of Formula (I) or (II), or a pharmaceutically acceptable salt thereof.

Also provided herein is a compound of Formula (I) or (II), or a pharmaceutically acceptable salt thereof obtained by a process of preparing the compound as defined herein.

DETAILED DESCRIPTION OF THE INVENTION

The present invention relates to inhibitors of KRas G12D. In particular, the present invention relates to compounds that inhibit the activity of KRas G12D, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12D" refers to a mutant form of a mammalian KRas protein that contains an amino acid substitution of an aspartic acid for a glycine at amino acid position 12. The assignment of amino acid codon and residue positions for human KRas is based on the amino acid sequence identified by UniProtKB/Swiss-Prot P01116: Variantp.Gly12Asp.

As used herein, a "KRas G12D inhibitor" refers to compounds of the present invention that are represented by Formula (I) or (II), as described herein. These compounds are capable of negatively modulating or inhibiting all or a portion of the enzymatic activity of KRas G12D.

A "KRas G12D-associated disease or disorder" as used herein refers to diseases or disorders associated with or mediated by or having a KRas G12D mutation. A non-limiting example of a KRas G12D-associated disease or disorder is a KRas G12D-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12D mutation (e.g., as determined using a regulatory agency-approved, e.g., FDA-approved, assay or kit). In some embodiments, the subject has a tumor that is positive for a KRas G12D mutation (e.g., as determined using a regulatory agency-approved assay or kit). The subject can be a subject with a tumor(s) that is positive for a KRas G12D mutation (e.g., identified as positive using a regulatory agency-approved, e.g., FDA-approved, assay or kit). The subject can be a subject whose tumors have a KRas G12D mutation (e.g., where the tumor is identified as such using a regulatory agency-approved, e.g., FDA-approved, kit or assay). In some embodiments, the subject is suspected of having a KRas G12D gene-associated cancer. In some embodiments, the subject has a clinical record indicating that the subject has a tumor that has a KRas G12D mutation (and optionally the clinical record indicates that the subject should be treated with any of the compositions provided herein).

In some embodiments of any of the methods or uses described herein, an assay is used to determine whether the patient has KRas G12D mutation using a sample (e.g., a biological sample or a biopsy sample (e.g., a paraffin-embedded biopsy sample) from a patient (e.g., a patient suspected of having a KRas G12D-associated cancer, a patient having one or more symptoms of a KRas G12D-associated cancer, and/or a patient that has an increased risk of developing a KRas G12D-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "acyl" refers to —C(O)$CH_3$.

The terms "C1-C6 alkyl", "C1-C4 alkyl" and "C1-C3 alkyl" as employed herein refers to straight and branched chain aliphatic groups having from 1-6 carbon atoms, or 1-4 carbon atoms, or 1-3 carbon atoms, respectively. Examples of alkyl groups include, without limitation, methyl, ethyl, propyl, isopropyl, butyl, isobutyl, sec-butyl, tert-butyl, pentyl, and hexyl.

The terms "C1-C3 haloalkyl" and "C1-C4 haloalkyl" refer to a C1-C3 alkyl chain or C1-C4 alkyl chain, respectively, as defined herein in which one or more hydrogen has been replaced by a halogen. Examples include trifluoromethyl, difluoromethyl and fluoromethyl.

An "C1-C4 alkylene," group is a C1-C4 alkyl group, as defined hereinabove, that is positioned between and serves to connect two other chemical groups. Exemplary alkylene groups include, without limitation, methylene, ethylene, propylene, and butylene.

The terms "C1-C3 alkoxy" and "C1-C4 alkoxy" refer to —OC1-C3 alkyl and —OC1-C4 alkyl, respectively, wherein the alkyl portion is as defined herein above.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted with one or more $R^6$ groups as defined herein. Examples of cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkyl" also includes bridged cycloalkyls, such as bicyclo[1.1.1]pentanyl.

As used herein, the terms "C1-C3 hydroxyalkyl" and "C1-C4 hydroxyalkyl" refer to —C1-C3 alkylene-OH and —C1-C4 alkylene-OH, respectively.

As used herein, the term "C2-C4 hydroxyalkynyl" refers to —C2-C4 alkynylene-OH.

An "aryl" group is a C6-C14 aromatic moiety comprising one to three aromatic rings, which is optionally substituted with one or more $R^6$ or with one or more $R^7$ as defined herein. As one embodiment, the aryl group is a C6-C10 aryl group. Examples of aryl groups include, without limitation, phenyl, naphthyl, anthracenyl, fluorenyl, and dihydrobenzofuranyl. "Aryl" also refers to bicyclic or tricyclic ring systems in which one or two rings, respectively, of said aryl ring system may be saturated or partially saturated, and wherein if said ring system includes two saturated rings, said saturated rings may be fused or spirocyclic. An example of an aryl ring system comprising two saturated rings wherein the rings are spirocyclic includes the following ring system:

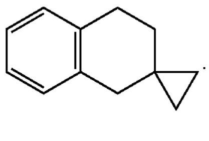 [SMILES: c1ccc2c(c1)CCC1(CC1)C2]

An "araC1-C6 alkyl" or "arylalkyl" group comprises an aryl group covalently linked to an alkyl group, either of which may independently be optionally substituted or unsubstituted. An example of an aralkyl group is (C6-C10) aryl(C1-C6)alkyl-, including, without limitation, benzyl, phenethyl, and naphthylmethyl. An example of a substituted araC1-C6 alkyl is wherein the alkyl group is substituted with hydroxyalkyl.

A "heterocyclyl" or "heterocyclic" group is a ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or SO2, the remainder of the ring atoms being carbon. The heterocyclyl may be a monocyclic, a bicyclic, a spirocyclic or a bridged ring system. The heterocyclic group is optionally substituted with one or more $R^6$ on ring carbon or ring nitrogen at one or more positions, wherein $R^6$ is as defined for Formula I. The heterocyclic group is also independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1 dioxide, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H,3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4 (1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 $\pi$ electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a]imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. "Heteroaryl" also refers to bicyclic ring systems having, in addition to carbon atoms, from one to three heteroatoms per ring selected from the group consisting of N, O, and S in which one ring system may be saturated or partially saturated.

As used herein, "an effective amount" of a compound is an amount that is sufficient to negatively modulate or inhibit the activity of KRas G12D. Such amount may be administered as a single dosage or may be administered according to a regimen, whereby it is effective.

As used herein, a “therapeutically effective amount” of a compound is an amount that is sufficient to ameliorate, or in some manner reduce a symptom or stop or reverse progression of a condition, or negatively modulate or inhibit the activity of KRas G12D. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In one aspect of the invention, compounds are provided represented by Formula (I):

Formula (I)

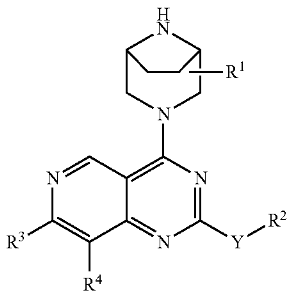

or a pharmaceutically acceptable salt thereof:

wherein:

$R^1$ is hydrogen, hydroxy, halogen, C1-C3 alkyl, C1-C3 cyanoalkyl, C1-C3 hydroxyalkyl, HC(=O)—, —$CO_2R^5$, —$CO_2N(R^5)_2$ or a 5-6 membered heteroaryl;

Y is a bond, O or $NR^5$;

$R^2$ is hydrogen, —$N(R^5)_2$, heterocyclyl, C1-C6 alkyl, -L-heterocyclyl, -L-aryl, -L-heteroaryl, -L-cycloalkyl, -L-$N(R^5)_2$, -L-NHC(=NH)$NH_2$, -L-C(O)$N(R^5)_2$, -L-C1-C6 haloalkyl, -L-$OR^5$, -L-($CH_2OR^5$)$(CH_2)_n$ $OR^5$, -L-$NR^5$C(O)-aryl, -L-COOH, or -LC(=O)OC1-C6 alkyl, wherein the heterocyclyl and the aryl portion of -L-$NR^5$C(O)-aryl and the heterocyclyl portion of -L-heterocyclyl and the cycloalkyl portion of the -L-cycloalkyl may be optionally substituted with one or more $R^6$, and wherein the aryl or heteroaryl of the -L-aryl and the -L-heteroaryl may be optionally substituted with one or more $R^7$;

each L is independently a C1-C4 alkylene optionally substituted with hydroxy, C1-C4 hydroxyalkyl or heteroaryl;

$R^3$ is aryl or heteroaryl, wherein the aryl or the heteroaryl is optionally substituted with one or more $R^8$;

$R^4$ is hydrogen, halogen or C1-C3 alkyl;

each $R^5$ is independently hydrogen or C1-C3 alkyl;

each $R^6$ is independently halogen, hydroxy, C1-C3 hydroxyalkyl, C1-C3 alkyl, C1-C3 haloalkyl, C1-C3 alkoxy, cyano, -Q-phenyl, -Q-phenyl$SO_2$F, —NHC(O)phenyl, —NHC(O)phenyl$SO_2$F, C1-C3 alkyl substituted pyrazolyl, araC1-C3 alkyl-, tert-butyldimethylsilyloxy$CH_2$—, —$N(R^5)_2$, (C1-C3 alkoxy)C1-C3 alkyl-, (@1-C3 alkyl)C(=O), oxo, (C1-C3 haloalkyl)C(=O)—, —$SO_2$F, (C1-C3 alkoxy)C1-C3 alkoxy, —$CH_2$OC(O)$N(R^5)_2$, —$CH_2$NHC(O)OC1-C6 alkyl, —$CH_2$NHC(O)$N(R^5)_2$, —$CH_2$NHC(O)C1-C6 alkyl, —$CH_2$ (pyrazolyl), —$CH_2NHSO_2$C1-C6 alkyl, —$CH_2$OC(O)heterocyclyl, —OC(O)$N(R^5)_2$, —OC(O)NH(C1-C3 alkyl)O(C1-C3 alkyl), —OC(O)NH(C1-C3 alkyl)O(C1-C3 alkyl)phenyl(C1-C3 alkyl)$N(CH_3)$ 2, —OC(O)NH(C1-C3 alkyl)O(C1-C3 alkyl)phenyl or —OC(O)heterocyclyl, —$CH_2$heterocyclyl, wherein the phenyl of —NHC(O)phenyl or —OC(O)NH(C1-C3 alkyl)O(C1-C3 alkyl)phenyl is optionally substituted with —C(O)H or OH and wherein the heterocyclyl of-$CH_2$heterocyclyl is optionally substituted with oxo;

Q is a bond or O;

each $R^7$ is independently halogen, hydroxy, HC(=O)—, C1-C4 alkyl, C1-C4 alkoxy, C1-C4 haloalkyl, C1-C4 hydroxyalkyl, or —$N(R^5)_2$; and each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —$CH_2$C(=O)$N(R^5)_2$, —C3-C4 alkynyl($NR^5$)$_2$, —$N(R^5)_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl.

In another aspect of the invention, compounds are represented by Formula (II):

Formula (II)

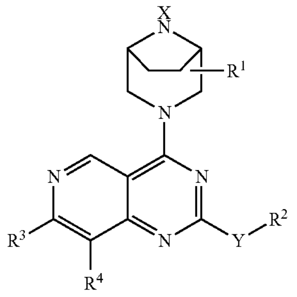

or a pharmaceutically acceptable salt thereof, wherein:

$R^1$ is hydrogen, hydroxy, halogen, C1-C3 alkyl, C1-C3 cyanoalkyl, C1-C3 hydroxyalkyl, HC(=O)—, —$CO_2R^5$, —$CO_2N(R^5)_2$ or a 5-6 membered heteroaryl;

X is hydrogen, —C(O)—O—CH($R^9$)—O—C(O)—Z, —C(O)—O-aryl or —C(O)—C1-C6 alkyl;

Y is a bond, O or $NR^5$;

Z is —($CH_2$) n-$CH_3$ or C1-C3 alkyl;

n is 0-20;

$R^2$ is hydrogen, —$N(R^5)_2$, heterocyclyl, C1-C6 alkyl, -L-heterocyclyl, -L-aryl, -L-heteroaryl, -L-cycloalkyl, -L-$N(R^5)_2$, -L-NHC(=NH)$NH_2$, -L-C(O)$N(R^5)_2$, -L-C1-C6 haloalkyl, -L-$OR^5$, -L-($CH_2OR^5$)$(CH_2)_n$ $OR^5$, -L-$NR^5$C(O)-aryl, -L-COOH, or -LC(=O)OC1-C6 alkyl, wherein the heterocyclyl and the aryl portion of -L-$NR^5$C(O)-aryl and the heterocyclyl portion of -L-heterocyclyl and the cycloalkyl portion of the -L-cycloalkyl may be optionally substituted with one or more $R^6$, and wherein the aryl or heteroaryl of the -L-aryl and the -L-heteroaryl may be optionally substituted with one or more $R^7$;

each L is independently a C1-C4 alkylene optionally substituted with hydroxy, C1-C4 hydroxyalkyl, heteroaryl or 1-2 deuterium;

$R^3$ is aryl or heteroaryl, wherein the aryl or the heteroaryl is optionally substituted with one or more $R^8$;

$R^4$ is hydrogen, halogen or C1-C3 alkyl;

each $R^5$ is independently hydrogen or C1-C3 alkyl;

each $R^6$ is independently halogen, hydroxy, C1-C3 hydroxyalkyl, C1-C3 alkyl, C1-C3 haloalkyl, C1-C3 alkoxy, cyano, -Q-phenyl, -Q-phenyl$SO_2F$, —NHC(O)phenyl, —NHC(O)phenyl$SO_2F$, C1-C3 alkyl substituted pyrazolyl, araC1-C3 alkyl-, tert-butyldimethylsilyloxy$CH_2$—, —$N(R^5)_2$, (C1-C3 alkoxy)C1-C3 alkyl-, (C1-C3 alkyl)C(═O), oxo, (C1-C3 haloalkyl)C(═O)—, —$SO_2F$, (C1-C3 alkoxy)C1-C3 alkoxy, —$CH_2OC(O)N(R^5)_2$, —$CH_2NHC(O)OC1$-C6 alkyl, —$CH_2NHC(O)N(R^5)_2$, —$CH_2NHC(O)C1$-C6 alkyl, —$CH_2$ (pyrazolyl), —$CH_2NHSO_2C1$-C6 alkyl, —$CH_2OC(O)$heterocyclyl, —OC(O)N(R$) 2, —OC(O)NH(C1-C3 alkyl)O(C1-C3 alkyl), —OC(O)NH(C1-C3 alkyl)O(C1-C3 alkyl)phenyl(C1-C3 alkyl)N($CH_3$) 2, —OC(O)NH(C1-C3 alkyl)O(C1-C3 alkyl)phenyl, —OC(O)heterocyclyl, —$CH_2$heterocyclyl or deuterium, wherein the phenyl of —NHC(O)phenyl or —OC(O)NH(C1-C3 alkyl)O(C1-C3 alkyl)phenyl is optionally substituted with —C(O)H or OH and wherein the heterocyclyl of —$CH_2$heterocyclyl is optionally substituted with oxo;

Q is a bond or O;

each $R^7$ is independently, halogen, hydroxy, HC(═O)—, C1-C4 alkyl, C1-C4 alkoxy, C1-C4 haloalkyl, C1-C4 hydroxyalkyl, or —$N(R^5)_2$;

each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxy C1-C3 alkyl, —$CH_2C(═O)N(R^5)_2$, —C3-C4 alkynyl$(NR^5)_2$, —$N(R^5)_2$, deuteroC2-C4 alkynyl, (C1-C3 alkoxy)haloC1-C3 alkyl-, —O—C(O)—Z, or C3-C6 cycloalkyl wherein said C3-C6 cycloalkyl is optionally substituted with halogen or C1-C3 alkyl; and $R^9$ is hydrogen or C1-C3 alkyl, are provided.

In one embodiment of the compounds of Formula (I) or (II), $R^1$ is halogen, hydroxy, C1-C3 alkyl, C1-C3 cyanoalkyl, C1-C3 hydroxyalkyl, HC(═O)—, —$CO_2R^5$, or —$CO_2N(R^5)_2$.

In certain embodiments, $R^1$ is hydrogen.

In certain embodiments, $R^1$ is hydroxy.

In other embodiments, $R^1$ is —$CO_2R^5$. In certain embodiments, $R^5$ is hydrogen. In other embodiments, $R^5$ is C1-C3 alkyl.

In another embodiment, $R^1$ is —C(O) $2N(R^5)_2$. In certain embodiments, each $R^5$ is hydrogen, each $R^5$ is an independently selected C1-C3 alkyl, or one $R^5$ is hydrogen and the second $R^5$ is C1-C3 alkyl.

In one embodiment, X is —C(O)—O—CH($R^9$)—O—C(O)—Z, $R^9$ is hydrogen or $CH_2$, and Z is —$CH_3$, —$(CH_2)_8$—$CH_3$, —$(CH_2)_{14}$—$CH_3$ or —$CH(CH_3)_2$.

In one embodiment, at least one $R^6$ is fluoro, X is —C(O)—O—CH($R^9$)—O—C(O)—Z, $R^9$ is hydrogen or $CH_3$, and Z is —$(CH_2)_8$—$CH_3$.

In one embodiment, at least one $R^6$ is fluoro, X is —C(O)—O—CH($R^9$)—O—C(O)—Z, $R^9$ is hydrogen or $CH_3$, and Z is —$(CH_2)_{14}$—$CH_3$.

In one embodiment, X is —C—C(O)—$C(CH_3)_3$.

In one embodiment, X is hydrogen.

In one embodiment, X is —C(O)-phenyl.

In one embodiment, Y is a bond.

In one embodiment of the compounds of Formula (I) or (II), Y is a bond and $R^2$ is hydrogen, —$N(R^5)_2$, or heterocyclyl optionally substituted with one or more $R^6$.

In certain embodiments, $R^2$ is —$N(R^5)_2$. In one embodiment, each $R^5$ is hydrogen. In one embodiment, each $R^5$ is an independently selected C1-C3 alkyl. In one embodiment, one $R^5$ is hydrogen and the second $R^5$ is C1-C3 alkyl. In certain embodiments, Y is a bond and $R^2$ is —$N(R^5)_2$.

In other embodiments, $R^2$ is heterocyclyl. In one embodiment $R^2$ is heterocyclyl and the heterocyclyl is azetidinyl, pyrrolidinyl, tetrahydro-2H-thiopyran 1,1-dioxide or 1,6$\lambda^2$-diazaspiro[3.3]heptanyl. In certain embodiments, Y is a bond and $R^2$ is heterocyclyl.

In another embodiment, $R^2$ is L-heterocycle, where L is C1-C2 alkylene and heterocycle is:

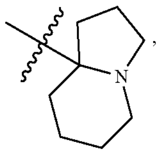,
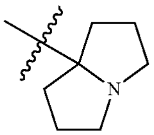
or
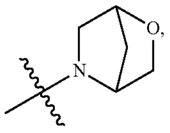, optionally substituted with $R^7$. In some of these embodiments, the heterocycle is:

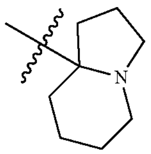.

In some of these embodiments, the heterocycle is:

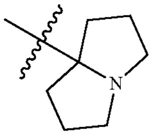.

In some of these embodiments, the heterocycle is:

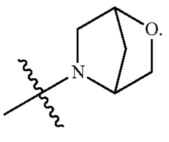.

In some embodiments, $R^2$ is L-heterocycle and one or two $R^6$ are deuterium.

In some of the above embodiments, the heterocycle is aryl is substituted with one or more $R^6$ selected from: oxo and halogen.

In some of the above embodiments where L is L is C1-C2 alkylene, the alkylene is substituted with one or more deuterium, forming for instance: $-CD_2-$, CDH-, $-CD_2-CH_2-$, $-CDH-CH_2-$, or other moieties.

In certain embodiments, the heterocyclyl is azetidinyl substituted with one $R^6$. In certain embodiments, the heterocyclyl is azetidinyl substituted with one $R^6$, wherein $R^6$ is hydroxy, hydroxyalkyl, or $-N(R^5)_2$. In certain embodiments, the heterocyclyl is azetidinyl substituted with two $R^6$ groups independently selected from $-N(R^5)_2$ and C1-C3 alkyl. In certain embodiments, Y is a bond and the heterocyclyl is azetidinyl substituted with one $R^6$, wherein $R^6$ is hydroxy, hydroxyalkyl, or $-N(R^5)_2$. In certain embodiments, Y is a bond and the heterocyclyl is azetidinyl substituted with two $R^6$ groups independently selected from $-N(R^5)_2$ and C1-C3 alkyl.

In one embodiment, Y is O.

In one embodiment, Y is O and $R^2$ is C1-C6 alkyl, -L-heterocyclyl optionally substituted with one or more $R^6$, -L-heteroaryl, wherein the heteroaryl portion is optionally substituted with one or more $R^7$, -L-aryl, wherein the aryl portion is optionally substituted with one or more $R^7$, -L-cycloalkyl, wherein the cycloalkyl portion is optionally substituted with one or more $R^6$, $-L-N(R^5)_2$, $-L-NC(=NH)-NH_2$, $-L-C(O)N(R^5)_2$, -L-C1-C6 haloalkyl, $-L-COR^5$, $-L-(CH_2OR^5)(CH_2)_nOR^5$, $-L-NR^5C(O)$-aryl.

In one embodiment of the compounds of Formula (I) or (II), Y is O and $R^2$ is C1-C6 alkyl. In certain embodiments, the C1-C6 alkyl is methyl, ethyl, isopropyl or isobutyl.

In one embodiment of the compounds of Formula (I) or (II), Y is O and $R^2$ is -L-heterocyclyl optionally substituted with one or more $R^6$.

In one embodiment, Y is O and $R^2$ is heterocyclyl wherein the heterocyclyl is tetrahydropyranyl optionally substituted with two halogens. In certain embodiment, the two halogens are both fluoro.

In another embodiment, Y is O and $R^2$ is -L-heterocyclyl wherein L is methylene and the heterocyclyl is hexahydro-1H-pyrrolizinyl, hexahydro-3H-pyrrolizin-3-one, hexahydro-1H-pyrrolo[2,1-c][1,4]oxazinyl, octahydroindolizinyl, hexahydropyrrolizine 4 (1H)-oxide, azetidinyl, pyrrolidinyl, pyrrolidin-2-one, oxetanyl, piperidinyl, 1-azabicyclo[2.2.1]heptanyl, morpholinyl, oxa-5-azabicyclo[2.2.1]heptan-5-yl, thiopyranyl, 6-oxa-2$\lambda^2$-azaspiro[3.4]octanyl, 7-oxa-2$\lambda^2$-azaspiro[3.5]nonanyl, 2',3'-dihydrospiro[cyclopropane-1,1'-indenyl], (2S)-1-azabicyclo[2.2.1]heptan-2-yl or tetrahydrofuranyl.

In certain embodiments, Y is O and $R^2$ is -L-heterocyclyl wherein L is methylene and the heterocyclyl is hexahydro-1H-pyrrolizinyl.

In certain embodiments, Y is O and $R^2$ is -L-heterocyclyl wherein L is methylene and the heterocyclyl is hexahydro-1H-pyrrolizinyl is optionally substituted with one $R^6$, wherein $R^6$ is halogen, hydroxy, hydroxyalkyl, C1-C3 haloalkyl, C1-C3 alkyl, C1-C3 alkoxy, phenyl, tert-butyldimethylsilyloxy$CH_2-$ or pyrazolyl, wherein the pyrazolyl is optionally substituted with C1-C3 alkyl. In one embodiment, the C1-C3 haloalkyl is chloromethyl. In another embodiment, the pyrazolyl is substituted with C1-C3 alkyl. In other embodiments, the hexahydro-1H-pyrrolizinyl is substituted with two $R^6$ groups, wherein each $R^6$ is an independently selected C1-C3 alkyl. In certain embodiments, the heterocyclyl is hexahydro-1H-pyrrolizinyl which is unsubstituted.

In certain embodiments, Y is O and $R^2$ is -L-heterocyclyl wherein L is methylene and the heterocyclyl is azetidinyl substituted with one $R^6$, wherein $R^6$ is C1-C3 alkyl.

In certain embodiments, Y is O and $R^2$ is -L-heterocyclyl wherein L is methylene and the heterocyclyl is pyrrolidinyl substituted with one $R^6$, wherein $R^6$ is C1-C3 hydroxyalkyl, C1-C3 haloalkyl, C1-C3 alkyl, C1-C3 alkoxy, C1-C3 aralkyl, or -Q-phenyl, wherein Q is O, and $-NHC(O)$phenyl. In one embodiment, the phenyl group of the -Q-phenyl is substituted with $SO_2F$. In another embodiment, the phenyl group of the $-NHC(O)$phenyl is substituted with $SO_2F$. In one embodiment, the C1-C3 aralkyl is benzyl.

In other embodiments, Y is O and $R^2$ is -L-heterocyclyl wherein L is methylene and the pyrrolidinyl is substituted with two $R^6$ groups, wherein one $R^6$ is C1-C3 alkyl and the other $R^6$ is C1-C3 alkoxy or halogen.

In certain embodiments, Y is O and $R^2$ is -L-heterocyclyl wherein L is methylene and the heterocyclyl is pyrrolidin-2-one substituted with one $R^6$, wherein $R^6$ is C1-C3 alkyl.

In certain embodiments, Y is O and $R^2$ is -L-heterocyclyl wherein L is methylene and the heterocyclyl is piperidinyl substituted with one $R^6$, wherein $R^6$ is acetyl, (C1-C3 alkoxy)C1-C3 alkoxy, or $-C(O)CH_2Cl$.

In certain embodiments, Y is O and $R^2$ is -L-heterocyclyl wherein L is methylene and the heterocyclyl is (2S)-1-azabicyclo[2.2.1]heptan-2-yl.

In one embodiment of the compounds of Formula (I) or (II), Y is O, $R^2$ is -L-heterocyclyl wherein L is ethylene or propylene and the heterocyclyl is morpholinyl or oxa-5-azabicyclo[2.2.1]heptan-5-yl.

In one embodiment of the compounds of Formula (I) or (II), Y is O and $R^2$ is -L-heteroaryl, wherein the heteroaryl portion is optionally substituted with one or more $R^7$. In certain embodiments, L is ethylene and the heteroaryl is benzimidazolyl, optionally substituted with one or more $R^7$. In one embodiment, $R^7$ is C1-C4 alkyl.

In certain embodiments, Y is O and $R^2$ is -L-heteroaryl.

In certain embodiments, Y is O and $R^2$ is -L-heteroaryl, wherein L is methylene or ethylene. In certain embodiments, Y is O and $R^2$ is -L-heteroaryl, wherein L is methylene or ethylene and the heteroaryl is pyridyl, pyrazolyl, imidazolyl, triazolyl, 4,5,6,7-tetrahydro-1H-indazolyl, benzimidazolyl, imidazo[1,2-a]pyridinyl, or pyrimidinyl.

In certain embodiments, Y is O and $R^2$ is -L-heteroaryl, wherein the heteroaryl is pyridyl substituted with one $R^7$. In certain embodiments, Y is O and $R^2$ is -L-heteroaryl, wherein the heteroaryl is pyridyl substituted with one $R^7$ wherein $R^7$ is halogen, C1-C4 haloalkyl, C1-C4 hydroxyalkyl, C1-C4 alkyl, $-N(R^5)_2$, or C1-C4 alkoxy.

In certain embodiments, Y is O and $R^2$ is -L-heteroaryl, wherein L is methylene or ethylene and the heteroaryl is pyrazolyl substituted with one $R^7$. In certain embodiments, Y is O and $R^2$ is -L-heteroaryl, wherein L is methylene or ethylene and the heteroaryl is pyrazolyl substituted with one $R^7$ wherein $R^7$ is halogen, C1-C4 haloalkyl, C1-C4 hydroxyalkyl, C1-C4 alkyl, alkoxy or $-N(R^5)_2$.

In certain embodiments, Y is O and $R^2$ is -L-heteroaryl, wherein L is methylene or ethylene and the heteroaryl is imidazolyl substituted with one $R^7$. In certain embodiments, Y is O and $R^2$ is -L-heteroaryl, wherein L is methylene or ethylene and the heteroaryl is imidazolyl substituted with one $R^7$ wherein $R^7$ is C1-C4 alkyl, C1-C4 haloalkyl, or C1-C4 hydroxyalkyl.

In certain embodiments, Y is O and $R^2$ is -L-heteroaryl, wherein L is methylene or ethylene and the heteroaryl is triazolyl substituted with one $R^7$. In certain embodiments, Y is O and $R^2$ is -L-heteroaryl, wherein L is methylene or ethylene and the heteroaryl is triazolyl substituted with one $R^7$, wherein $R^7$ is C1-C4 alkyl.

In one embodiment of the compounds of Formula (I) or (II), Y is O and $R^2$ is -L-aryl, wherein the aryl portion is optionally substituted with one or more $R^7$. In certain embodiments, L is ethylene and the aryl is phenyl. In one embodiment, the phenyl is substituted with one $R^7$. In one embodiment, the phenyl is substituted with one $R^7$, wherein $R^7$ is halogen. In one embodiment, the phenyl is substituted with two $R^7$ groups. In one embodiment, the phenyl is substituted with two $R^7$ groups. In one embodiment, the phenyl is substituted with two $R^7$ groups wherein one $R^7$ is hydroxy and one $R^7$ is HC(═O)—.

In one embodiment of the compounds of Formula (I) or (II), Y is O and $R^2$ is -L-cycloalkyl, wherein the cycloalkyl portion is optionally substituted with one or more $R^6$. In one embodiment, L is methylene. In one embodiment, the cycloalkyl is cyclopropyl, cyclobutyl, cyclopentyl or cyclohexyl. In certain embodiments, the cyclopropyl and cyclopentyl are each substituted with one $R^6$. In certain embodiments, the cyclopropyl and cyclopentyl are each substituted with one $R^6$, wherein $R^6$ is haloalkyl. In certain embodiments, the cyclobutyl and cyclohexyl are each substituted with two $R^6$ groups. In certain embodiments, the cyclobutyl and cyclohexyl are each substituted with two $R^6$ groups, wherein each $R^6$ group is halogen.

In one embodiment of the compounds of Formula (I) or (II), Y is O, and $R^2$ is -L-N($R^5$)$_2$. In certain embodiments, L is ethylene. In certain embodiments, $R^5$ is C1-C3 alkyl.

In one embodiment of the compounds of Formula (I) or (II), Y is O, and $R^2$ is -L-NC(═NH)—$NH_2$. In certain embodiments, L is ethylene or propylene.

In one embodiment of the compounds of Formula (I) or (II), Y is O, and $R^2$ is -L-C(O)N($R^5$)$_2$. In certain embodiments, L is ethylene and each $R^5$ is C1-C3 alkyl.

In one embodiment of the compounds of Formula (I) or (II), Y is O, and $R^2$ is -L-C1-C6 haloalkyl. In certain embodiments, L is methylene. In certain embodiments, the haloalkyl is 1,1,3,3-tetrafluoropropanyl or trifluoromethyl. In other embodiments, L is ethylene or propylene and the haloalkyl is trifluoromethyl.

In one embodiment of the compounds of Formula (I) or (II), Y is O, and $R^2$ is -L-COR$^5$. In certain embodiments, L is propylene and $R^5$ is hydrogen or C1-C3 alkyl. In certain embodiments, L is propylene that is substituted with hydroxy, hydroxyalkyl or heteroaryl and $R^5$ is hydrogen or C1-C3 alkyl. In one embodiment, the heteroaryl is pyridyl.

In one embodiment of the compounds of Formula (I) or (II), Y is O, and $R^2$ is -L-($CH_2OR^5$)($CH_2$)$_n$OR$^5$. In certain embodiments, L is methylene, each $R^5$ is independently hydrogen or C1-C3 alkyl, and n is one or two.

In one embodiment of the compounds of Formula (I) or (II), Y is O, and $R^2$ is -L-NR$^5$C(O)-aryl. In certain embodiments, L is methylene, $R^5$ is hydrogen. In one embodiment the aryl is phenyl. In one embodiment, the phenyl is substituted with one $R^6$, wherein $R^6$ is —$SO_2F$.

In one embodiment of the compounds of Formula (I) or (II), $R^3$ is aryl optionally substituted with one or more $R^8$. In certain embodiments, the aryl is selected from the group consisting of phenyl, naphthyl, 1,2,3,4-tetrahydronaphthalenyl and 2,3-dihydro-1H-indenyl, wherein each is optionally substituted with one or more $R^8$.

In one embodiment, the aryl is phenyl substituted with one or more $R^8$ groups. In one embodiment, the aryl is phenyl substituted with one or more $R^8$ groups independently selected from halogen, C1-C3 haloalkyl and —O—C1-C3 haloalkyl. In certain embodiments the phenyl is substituted with two $R^8$ groups. In certain embodiments the phenyl is substituted with two $R^8$ groups, wherein the two $R^8$ groups are two independently selected C1-C3 haloalkyl groups, or —O—C1-C3 haloalkyl and halogen.

In one embodiment, the aryl is 2,3-dihydro-1H-indenyl optionally substituted with one or more $R^8$. In one embodiment, the aryl is 2,3-dihydro-1H-indenyl optionally substituted with one $R^8$. In one embodiment, $R^8$ is C1-C alkyl.

In one embodiment, the aryl is naphthyl substituted with one or more $R^8$ groups.

In one embodiment, the aryl is naphthyl substituted with one or more $R^8$ groups independently selected from halogen, cyano, hydroxy, C1-C3 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl and —O—C1-C3 haloalkyl.

In one embodiment, the aryl is naphthyl substituted with one or more $R^8$ groups independently selected from halogen, hydroxy, cyano, C1-C2 alkyl, C3-C6 cycloalkyl optionally substituted with C1-C3 alkyl, or —O—C(O)—Z. In some of these embodiments, Z is Z is —$CH_3$, —($CH_2$)$_8$—$CH_3$, or —($CH_2$)$_{14}$—$CH_3$.

In one embodiment, the naphthyl is substituted with —O—C(O)—($CH_2$)$_8$—$CH_3$.

In another embodiment, the naphthyl is substituted with —O—C(O)—($CH_2$)$_{14}$—$CH_3$.

In one embodiment, the aryl is naphthyl substituted with hydroxy. In one embodiment, the aryl is naphthyl substituted with halogen. In certain embodiments, the halogen is chlorine, fluorine or bromine. In other embodiments, the halogen is chlorine.

In one embodiment, the aryl is naphthyl substituted with C1-C3 alkyl, wherein the C1-C3 alkyl is methyl or ethyl.

In one embodiment, the aryl is naphthyl substituted with C2-C4 alkenyl. In certain embodiments, the C2-C4 alkenyl is prop-2-enyl.

In one embodiment, the aryl is naphthyl substituted with C2-C4 alkynyl. In certain embodiments, the C2-C4 alkynyl is ethyne or prop-2-ynyl.

In one embodiment, the aryl is naphthyl substituted with one or two $R^8$, wherein each $R^8$ is halogen, cyano, hydroxy, C1-C3 alkyl, —S—C1-C3 alkyl, C2-C4 alkenyl, C2-C4 alkynyl, C2-C4 hydroxyalkynyl, C1-C3 cyanoalkyl, or triazolyl. In one embodiment, the aryl is naphthyl substituted with two $R^8$ groups independently selected from halogen, hydroxy, C1-C3 alkyl and C2-C4 alkynyl.

In one embodiment of the compounds of Formula (I) or (II), $R^3$ is heteroaryl optionally substituted with one or more $R^8$. In one embodiment, the heteroaryl is isoquinolinyl, indazolyl, or benzo[d][1,3]dioxolyl optionally substituted with one or more $R^8$. In one embodiment, the heteroaryl is indazolyl optionally substituted with one or more $R^8$. In one embodiment, the heteroaryl is indazolyl optionally substituted with C1-C3 alkyl. In other embodiments, the heteroaryl is isoquinolinyl optionally substituted with one or more $R^8$. In other embodiments, the heteroaryl is isoquinolinyl optionally substituted with halogen or C2-C4 alkynyl. In certain embodiments, the heteroaryl is benzo[d][1,3]dioxolyl optionally substituted with two $R^8$ groups. In certain embodiments, the heteroaryl is benzo[d][1,3]dioxolyl optionally substituted with two $R^8$ groups, wherein each $R^8$ group is an independently selected halogen. In one embodiment, the two halogens are gem-difluoro substitutions.

In one embodiment of the compounds of Formula (I) or (II), $R^4$ is hydrogen.

In one embodiment of the compounds of Formula (I) or (II), $R^4$ is halogen. In one embodiment, $R^4$ is fluorine. In one embodiment, $R^4$ is chlorine.

In one embodiment of the compounds of Formula (I) or (II), $R^4$ is C1-C3 alkyl. In one embodiment, $R^4$ is methyl.
Nonlimiting examples of compounds of Formula (I) or (II) are selected from the group consisting of:
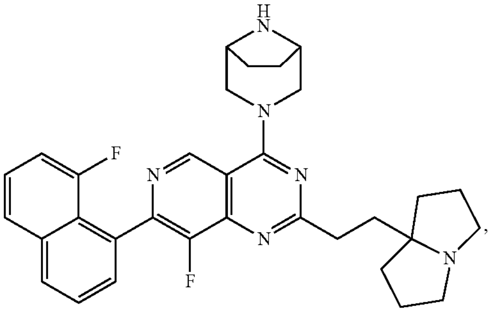
,
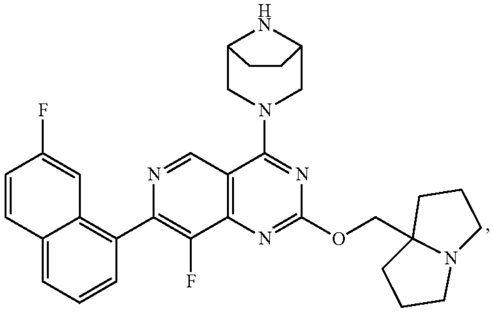
,
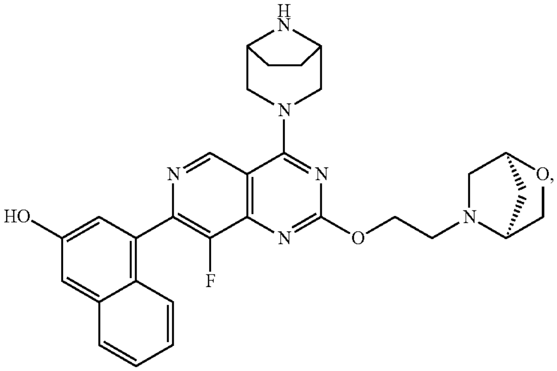
,
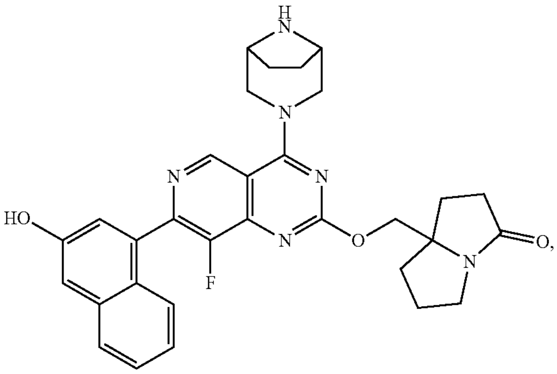
,
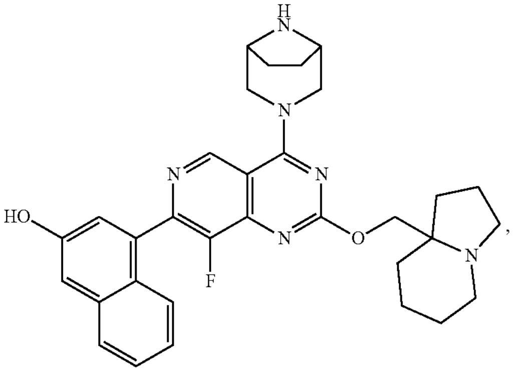
,
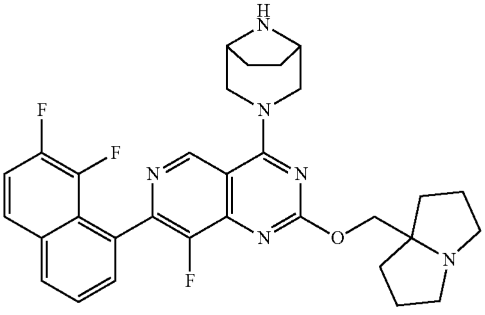
,
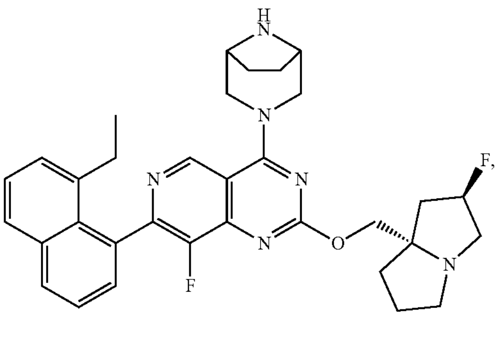
,
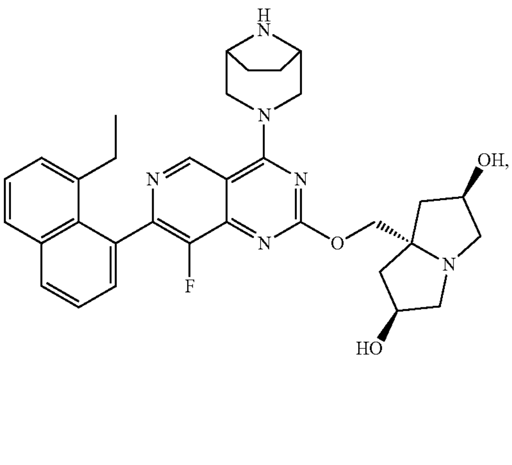
, -continued
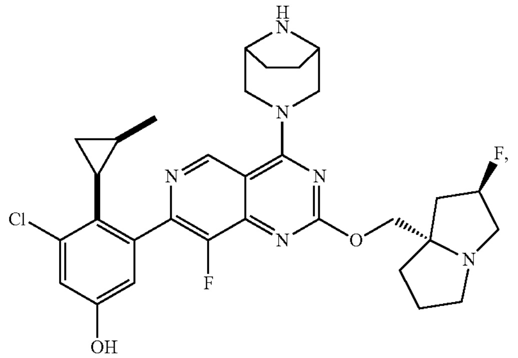
,
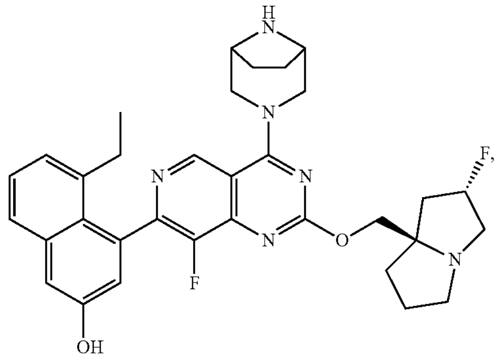
,
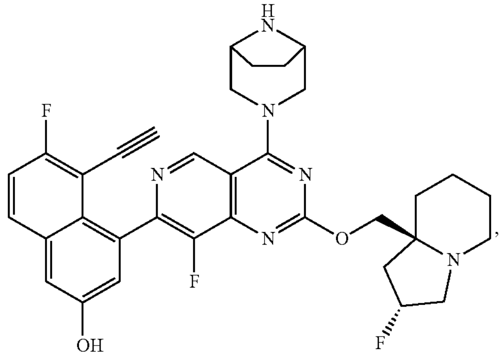
,
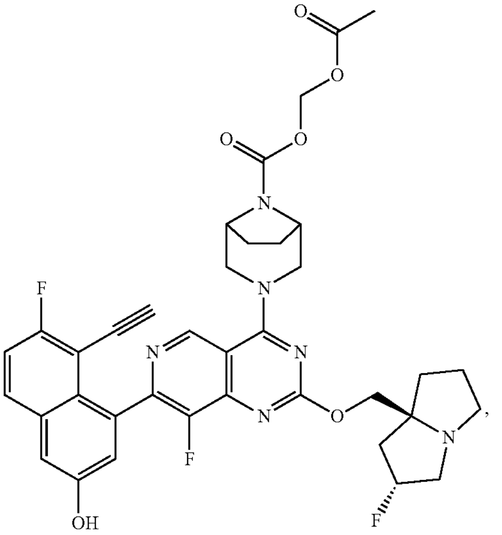
,
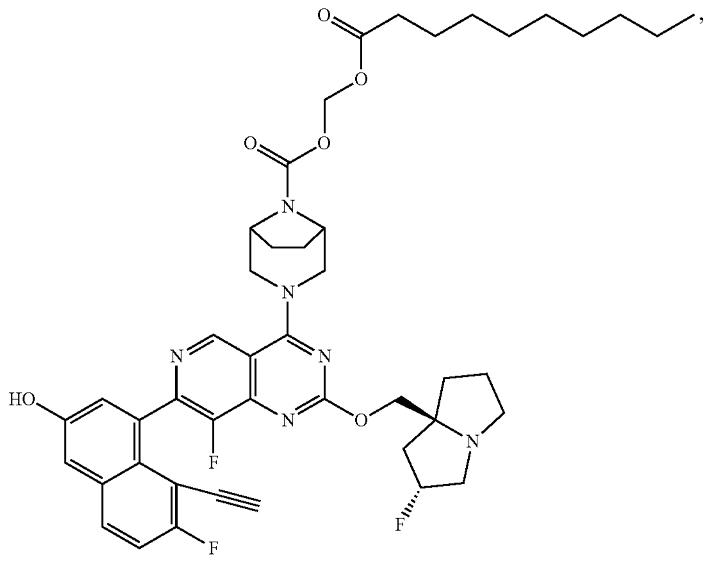
, -continued
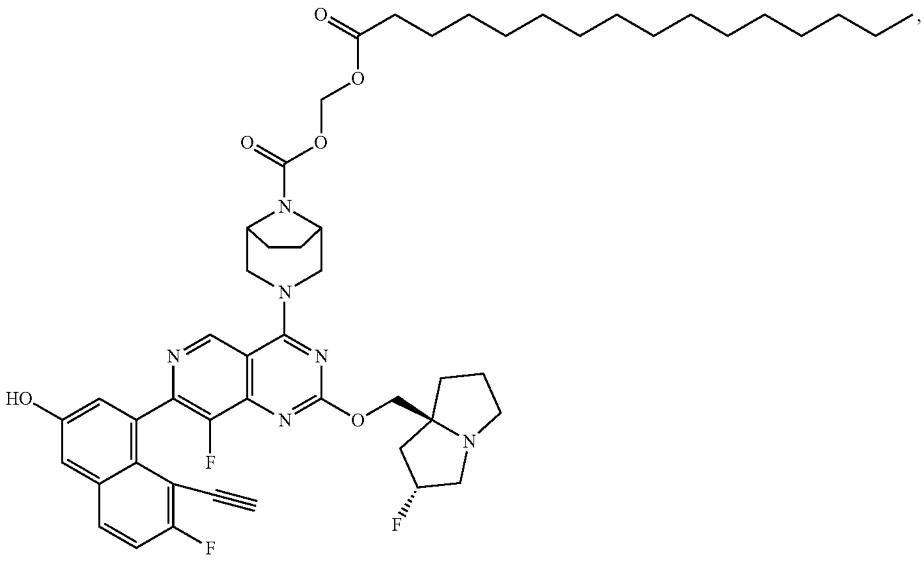
,
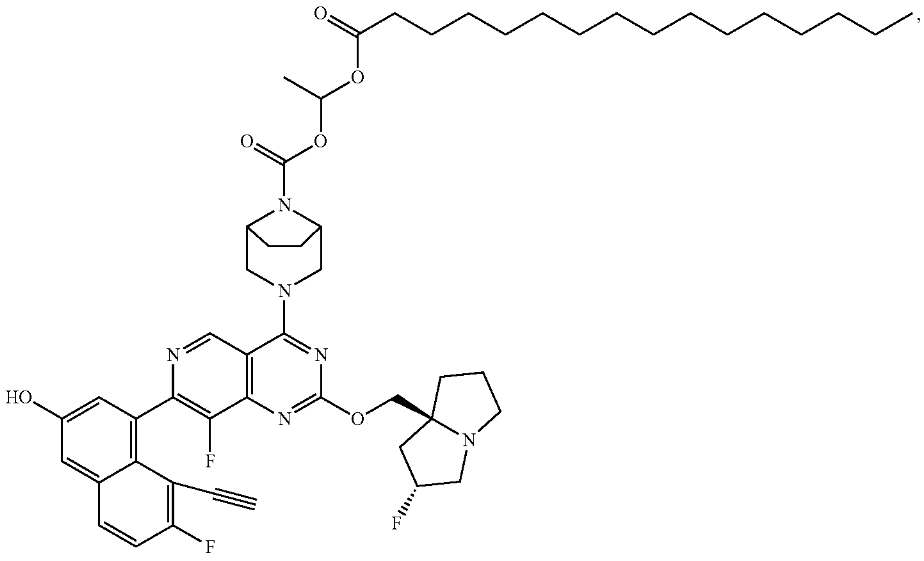
,
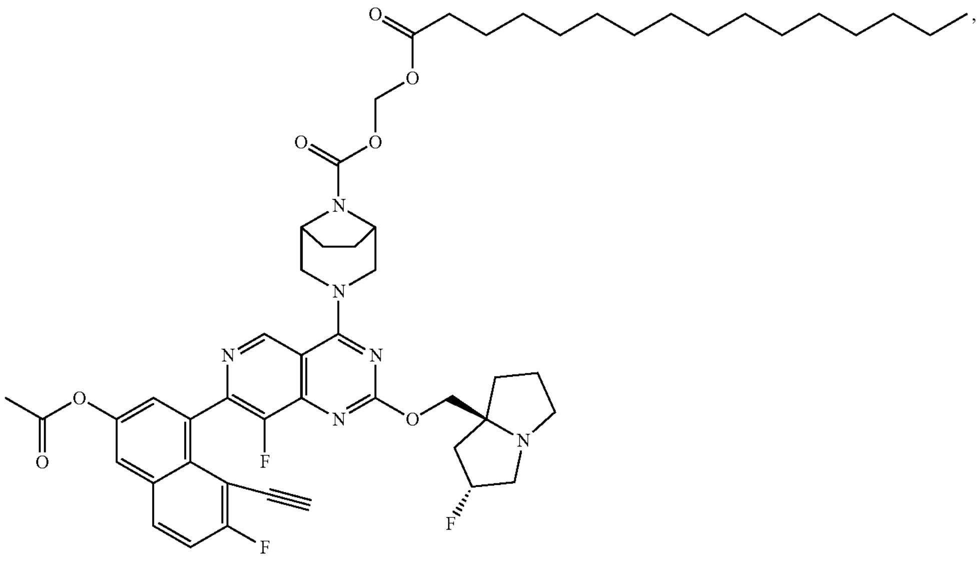
, -continued
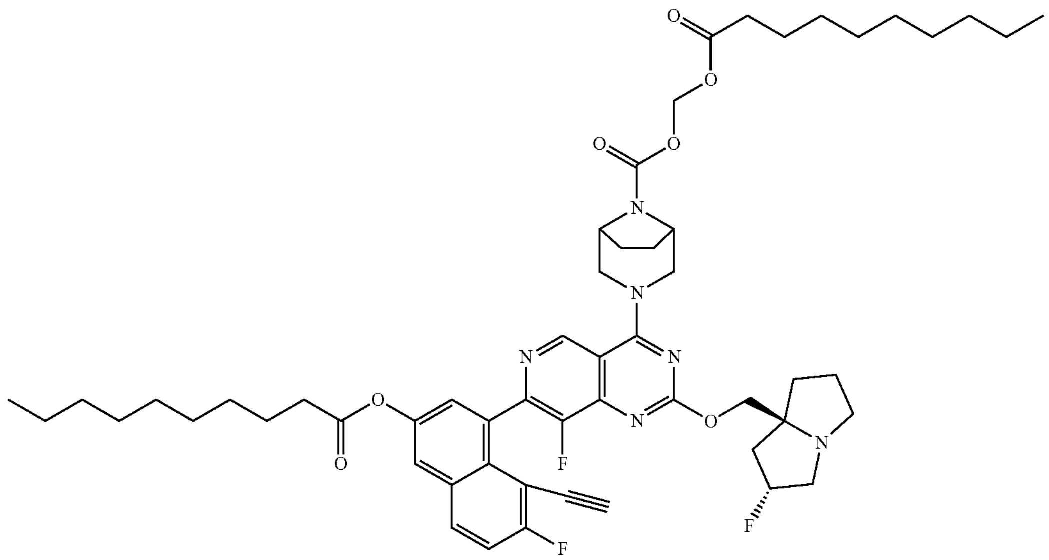
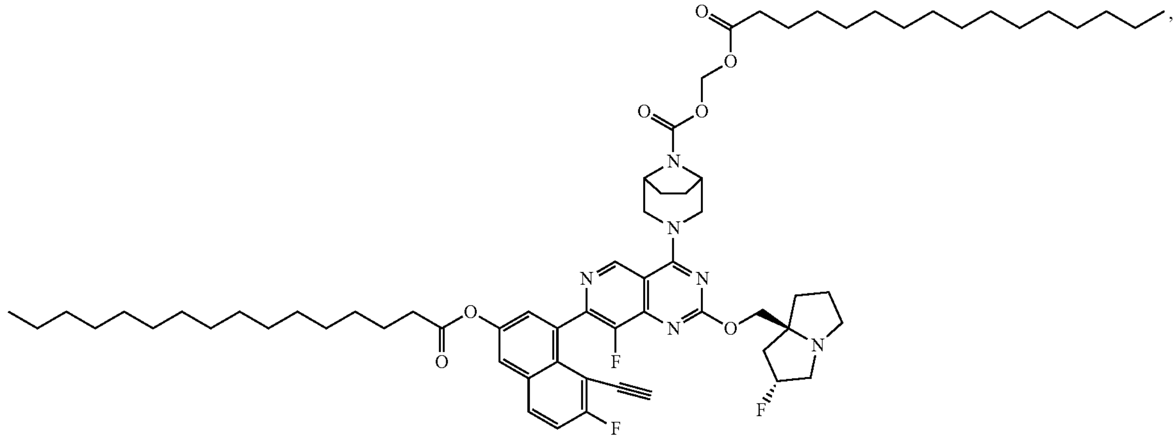
,
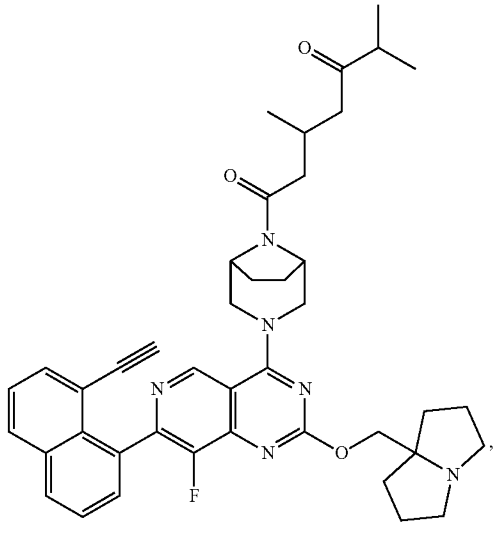
,
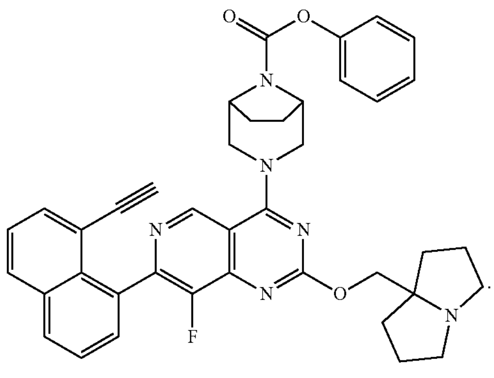
.

-continued

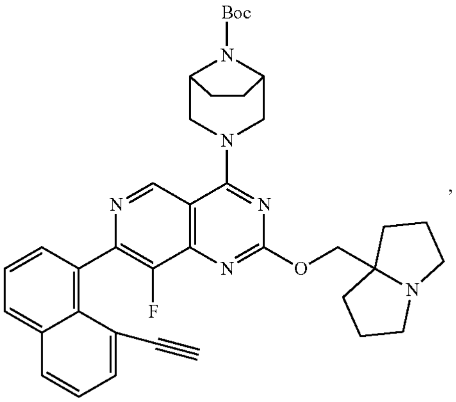

,

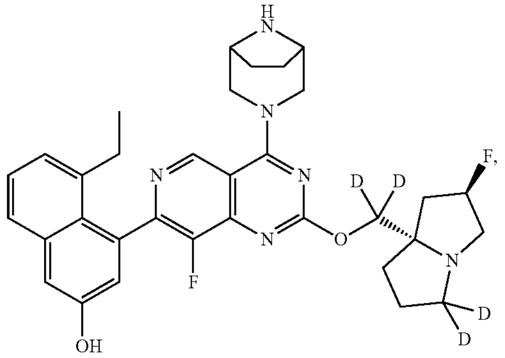

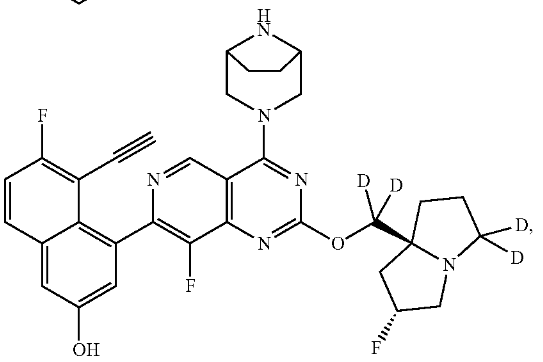

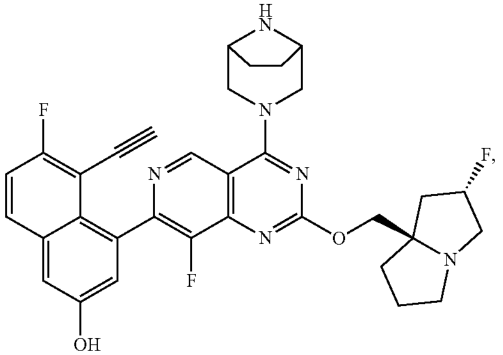

and pharmaceutically acceptable salts thereof. In one embodiment, the compounds of Formula (I) or (II) include bis-hydrochloride, tris-hydrochloride, trifluoroacetic acid, bis-trifluoroacetic acid, and tris-trifluoracetic acid salts of the above compounds. The compounds of Formula (I) or (II) or pharmaceutically acceptable salt thereof may be formulated into pharmaceutical compositions.

Pharmaceutical Compositions

In another aspect, the invention provides pharmaceutical compositions comprising a KRas G12D inhibitor according to the invention and a pharmaceutically acceptable carrier, excipient, or diluent. Compounds of the invention may be formulated by any method well known in the art and may be prepared for administration by any route, including, without limitation, parenteral, intraperitoneal, intradermal, intracardiac, intraventricular, intracranial, intracerebrospinal, intrasynovial, intrathecal administration, intramuscular injection, intravitreous injection, intravenous injection, intra-arterial injection, oral, buccal, sublingual, transdermal, topical, intranasal, intratracheal, intrarectal, subcutaneous, and topical administration. In certain embodiments, compounds of the invention are administered intravenously in a hospital setting. In one embodiment, administration may be by the oral route. In some embodiments, the provided pharmaceutical compositions may be administered to a subject in need of treatment by injection systemically, such as by intravenous injection; or by injection or application to the relevant site, such as by direct injection via syringe, or direct application to the site when the site is exposed in surgery; or by topical administration.

Parenteral administration can be by bolus injection or continuous infusion. Pharmaceutical compositions for injection may be presented in unit dosage form, e.g., in ampoules or in multi-dose containers, with an added preservative.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or a medical device, including but not limited to a dispenser device which may contain one or more unit dosage forms containing the active ingredient. In one embodiment the dispenser device can comprise a syringe having a single dose of the liquid formulation ready for injection. The syringe can be accompanied by instructions for administration.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. In some embodiments, patients are administered between about 0.01 to 100 mg/kg per day, or between about 0.1 to 50 mg/kg per day.

A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting KRas G12D activity in a cell, comprising contacting the cell in which inhibition of KRas G12D activity is desired with an effective amount of a compound of Formula (I) or (II), pharmaceutically acceptable salts thereof, or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRas G12D with a compound provided herein includes the administration of a compound provided herein to an individual or patient, such as a human, having KRas G12D, as well as, for example, introducing a compound provided herein into a sample containing a cellular or purified preparation containing the KRas G12D.

In one embodiment, a cell in which inhibition of KRas G12D activity is desired is contacted with an effective amount of a compound of Formula (I) or (II) or pharmaceutically acceptable salt thereof to negatively modulate the activity of KRas G12D.

By negatively modulating the activity of KRas G12D, the methods described herein are designed to inhibit undesired cellular proliferation resulting from enhanced KRas G12D activity within the cell. The cells may be contacted in a single dose or multiple doses in accordance with a particular treatment regimen to effect the desired negative modulation of KRas G12D. The ability of compounds to bind KRas G12D may be monitored in vitro using well known methods, including those described in Examples A and B below. In addition, the inhibitory activity of exemplary compounds in cells may be monitored, for example, by measuring the inhibition of KRas G12D activity of the amount of phosphorylated ERK, for example using the method described in Example C below.

In another aspect, methods of treating cancer in a patient in need thereof, comprising administering to said patient a therapeutically effective amount of a compound of Formula (I) or (II) or a pharmaceutically acceptable salt thereof, or a pharmaceutical composition comprising the compound or pharmaceutically acceptable salt thereof are provided.

The compositions and methods provided herein may be used for the treatment of a KRas G12D-associated cancer in a patient in need thereof, comprising administering to said patient a therapeutically effective amount of a compound of Formula (I) or (II), a pharmaceutically acceptable salt thereof, or a pharmaceutical composition comprising the compound or pharmaceutically acceptable salt thereof are provided. In one embodiment, the KRas G12D-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer, small cell lung cancer, colorectal cancer, rectal cancer or pancreatic cancer. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula (I) or (II) or a pharmaceutically acceptable salt thereof, or a pharmaceutical composition thereof as defined herein for use in therapy.

Also provided herein is a compound of Formula (I) or (II) or a pharmaceutically acceptable salt thereof, or a pharmaceutical composition thereof as defined herein for use in the treatment of cancer.

Also provided herein is a compound of Formula (I) or (II) or a pharmaceutically acceptable salt thereof, or a pharmaceutical composition thereof for use in the inhibition of KRas G12D.

Also provided herein is a compound of Formula (I) or (II) or a pharmaceutically acceptable salt thereof, or a pharmaceutical composition thereof as defined herein, for use in the treatment of a KRas G12D-associated disease or disorder.

Also provided herein is the use of a compound of Formula (I) or (II) or a pharmaceutically acceptable salt thereof, as defined herein in the manufacture of a medicament for the treatment of cancer.

Also provided herein is a use of a compound of Formula (I) or (II) or a pharmaceutically acceptable salt thereof, as defined herein in the manufacture of a medicament for the inhibition of activity of KRas G12D.

Also provided herein is the use of a compound of Formula (I) or (II) or a pharmaceutically acceptable salt thereof, as defined herein, in the manufacture of a medicament for the treatment of a KRas G12D-associated disease or disorder.

Also provided herein is a method for treating cancer in a patient in need thereof, the method comprising (a) determining that cancer is associated with a KRas G12D mutation (e.g., a KRas G12D-associated cancer) (e.g., as determined using a regulatory agency-approved, e.g., FDA-approved, assay or kit); and (b) administering to the patient a therapeutically effective amount of a compound of Formula (I) or (II), or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

REACTION SCHEMES AND EXAMPLES

The compounds of the present invention may be prepared from commercially available reagents using the synthetic methods and reaction schemes described herein, or using other reagents and conventional methods well known to those skilled in the art.

For instance, compounds of the present invention may be prepared according to the General Reaction Schemes I-V.

General Reaction Schemes

SCHEME I

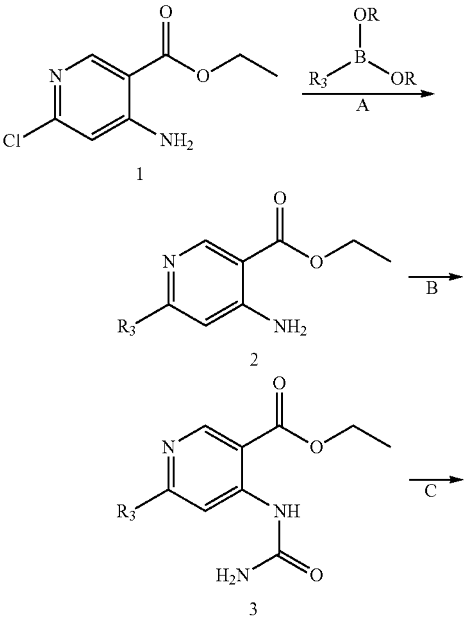

1

2

3

-continued

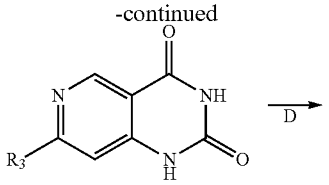

4

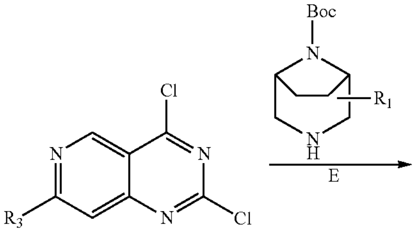

5

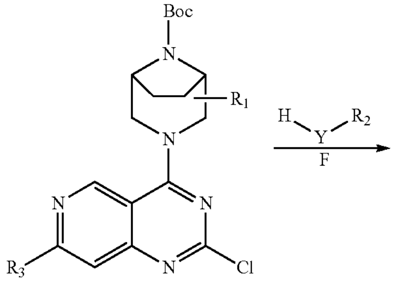

6

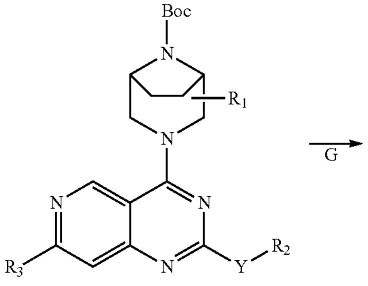

7

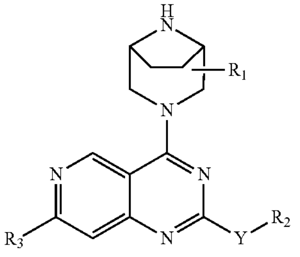

I

Compounds of Formula (I) wherein all of the substituents are as defined for Formula I, with the exception that —Y—$R^2$ is other than hydrogen, can be prepared according to Scheme I. In step A, ethyl 4-amino-6-chloronicotinate (1) is coupled to an aryl boronic acid (ester) to provide compound (2). This Suzuki coupling proceeds in a solvent such as dioxane and in the presence of a base such as potassium carbonate and a catalyst such as Xphos/$Pd_2(dba)_3$. In step B, compound (2) is subjected to phosgene and then reacts with ammonia in a solvent such as dichloromethane and in the presence of a base such as N-ethyl-N-isopropylpropan-2-amine to form urea (3). In step C, the cyclization of compound (3) in the presence of a base such as cesium carbonate in a solvent such as toluene and at elevated temperature gives compound (4). In step D, dichloroazaquinazoline (5) is prepared from compound (4) with phosphoryl trichloride and N-ethyl-N-isopropylpropan-2-amine. In step E, compound (5) undergoes a $S_NAr$ reaction with optionally substituted mono-Boc protected diazabicyclo[3.2.1]octane in a solvent such as dimethylformamide and in the presence of a base such as N-ethyl-N-isopropylpropan-2-amine to give compound (6). In step F, the substituent —Y—$R^2$ is introduced by substitution of the chlorine with a nucleophile having the formula H—Y—$R^2$ in a polar solvent such as dioxane in the presence of a base such as cesium carbonate to provide compound (7). In step G, the Boc group of compound (7) is removed using conditions known in the art, for example with cold 4 N HCl in a solvent such as dioxane, to provide compound (I). In some cases, the species $R^2$ and/or $R^3$ will also contain protecting group(s), which can be removed before or after step G in the synthetic sequence.

Compounds (1), (2), (3), (4), (5) (6) and (7) as shown and described above for Scheme I are useful as intermediates for preparing compounds of Formula (I) and are provided as further aspects of the invention.

SCHEME II

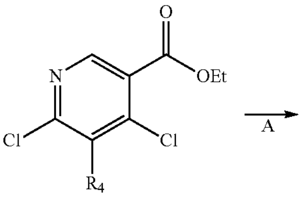

8

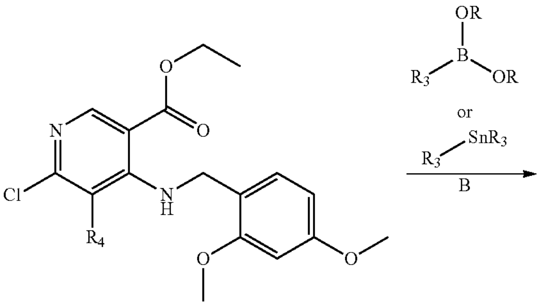

9

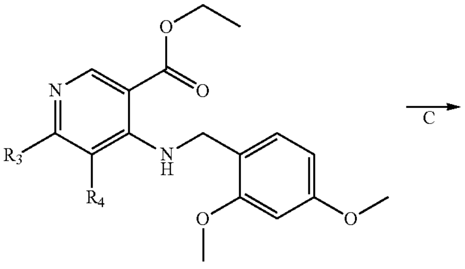

10

-continued

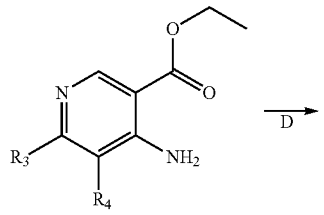

11

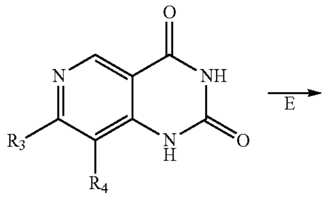

12

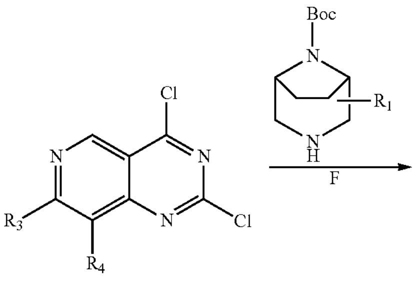

13

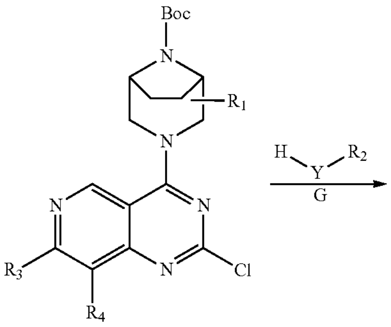

14

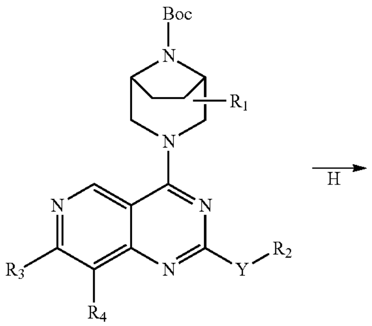

15

-continued

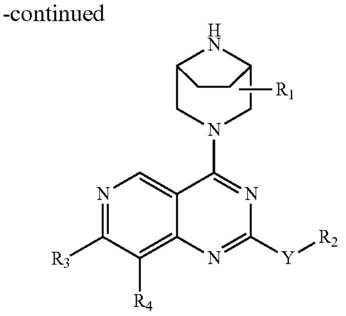

I

Compounds of Formula (I) wherein all of the substituents are as defined for Formula I, with the exception that —Y—$R^2$ is other than hydrogen, can be prepared according to Scheme II. In step A, the 4-chlorine of nicotinate derivative (8) is substituted with 2,4-dimethoxybenzylamine in a polar solvent such as dioxane and in the presence of a base such as N-ethyl-N-isopropylpropan-2-amine to give compound (9). In step B, compound (9) is coupled with an aryl boronic acid ester or aryl stannane under the Suzuki or Stille reaction conditions to give compound (10). In step C, the 2,4-dimethoxybenzyl group of compound (10) is removed with trifluoroacetic acid and in a solvent such as dichloromethane to give compound (11). In step D, compound (11) is treated with trichloroacetyl isocyanate in THF and then ammonia in methanol, and the cyclization is facilitated with heat to give pyridopyrimidinedione (12). In step E, dichloroazaquinazoline (13) is prepared from compound (12) with phosphoryl trichloride and N-ethyl-N-isopropylpropan-2-amine. In step F, compound (13) undergoes a $S_NAr$ reaction with optionally substituted mono-Boc protected diazabicyclo[3.2.1]octane in a solvent such as N,N-dimethylacetamide and in the presence of a base such as N-ethyl-N-isopropylpropan-2-amine to give compound (14). In step G, the substituent —Y—$R^2$ is introduced by substitution of the chlorine with a nucleophile having the formula H—Y—$R^2$ in a polar solvent such as dioxane in the presence of a base such as cesium carbonate to provide compound (15). In step H, the Boc group of compound (15) is removed using conditions known in the art, for example with trifluoroacetic acid in a solvent such as dichloromethane, to provide compound (I). In some cases, the species $R^2$ and/or $R^3$ will also contain protecting group(s), which can be removed before or after step H in the synthetic sequence.

Compounds (8), (9), (10), (11), (12), (13), (14) and (15) as shown and described above for Scheme II are useful as intermediates for preparing compounds of Formula (I) and are provided as further aspects of the invention.

SCHEME III

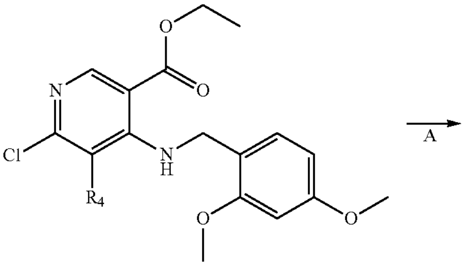

9

-continued

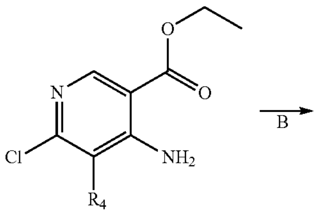

16

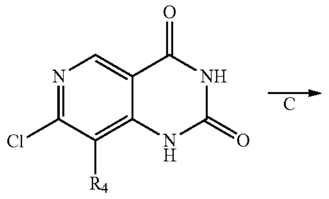

17

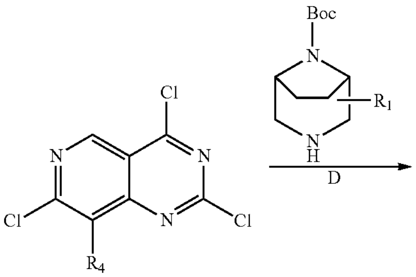

18

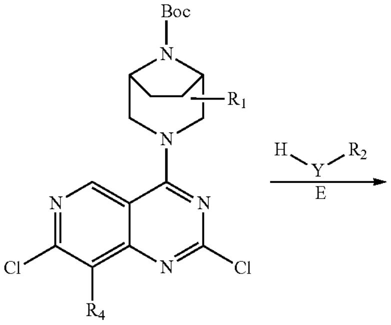

19

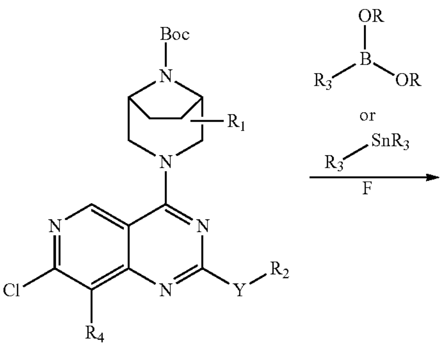

20

-continued

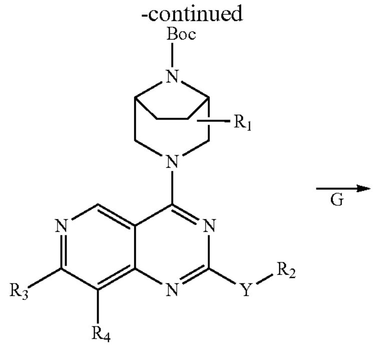

15

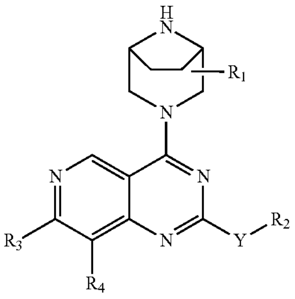

I

Compounds of Formula (I) wherein all of the substituents are as defined for Formula I, with the exception that —Y—$R^2$ is other than hydrogen, can be prepared according to Scheme III. In step A, the 2,4-dimethoxybenzyl group of compound (9) is removed with trifluoroacetic acid in a solvent such as dichloromethane to give compound (16). In step B, compound (16) is treated with trichloroacetyl isocyanate in THF and then ammonia in methanol, and the cyclization is facilitated with heat to give pyridopyrimidinedione (17). In step C, trichloroazaquinazoline (18) is prepared from compound (17) with phosphoryl trichloride and N-ethyl-N-isopropylpropan-2-amine. In step D, compound (18) undergoes a $S_NAr$ reaction with optionally substituted mono-Boc protected diazabicyclo[3.2.1]octane to give compound (19) in a solvent such as N,N-dimethylacetamide and in the presence of a base such as N-ethyl-N-isopropylpropan-2-amine. In step E, the substituent —Y—$R^2$ is introduced by substitution of 2-chlorine of compound (19) with a nucleophile having the formula H—Y—$R^2$ in a polar solvent such as dioxane and in the presence of a base such as cesium carbonate to provide compound (20). In step F, compound (20) is coupled with an aryl boronic acid ester or aryl stannane under the Suzuki or Stille reaction conditions to give compound (15). In step G, the Boc group of compound (15) is removed using conditions known in the art, for example with trifluoroacetic acid in a solvent such as dichloromethane, to provide compound (I). In some cases, the species $R^2$ and/or $R^3$ will also contain protecting group(s), which can be removed before or after step G in the synthetic sequence.

Compounds (16), (17), (18), (19), and (20) as shown and described above for Scheme III are useful as intermediates for preparing compounds of Formula (I) and are provided as further aspects of the invention.

SCHEME IV

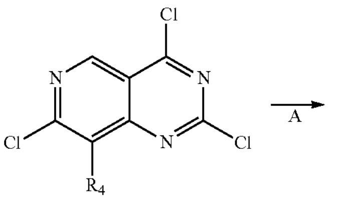

18

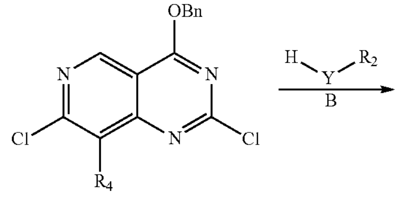

21

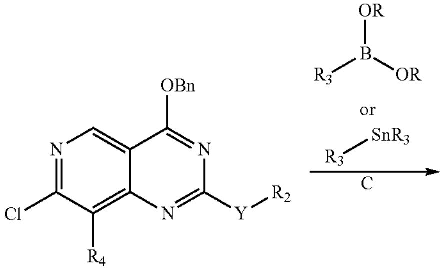

22

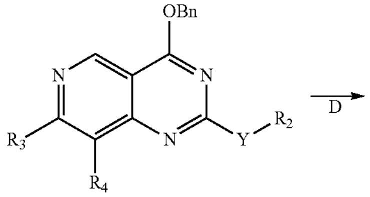

23

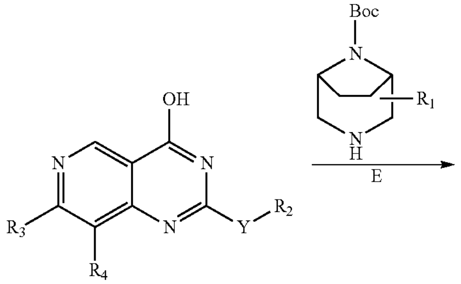

24

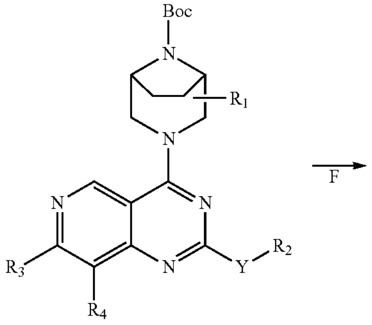

15

-continued

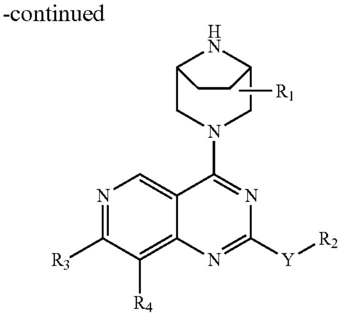

I

Compounds of Formula (I) wherein all of the substituents are as defined for Formula I, with the exception that —Y—$R^2$ is other than hydrogen, can be prepared according to Scheme IV. In step A, 4-chlorine of trichloroazaquinazoline (18) is substituted with a benzyl alcohol in a polar solvent such as dioxane and in the presence of a base such as N-ethyl-N-isopropylpropan-2-amine to provide compound (21). In step B, the substituent —Y—$R^2$ is introduced by substitution of 2-chlorine of compound (21) with a nucleophile having the formula H—Y—$R^2$ in a polar solvent such as dioxane and in the presence of a base such as cesium carbonate to provide compound (20). In step C, compound (22) is coupled with an aryl boronic acid ester or aryl stannane under the Suzuki or Stille reaction conditions to give compound (23). In step D, the benzyl group of compound (23) is removed under the palladium-catalyzed hydrogenation condition in a solvent such as ethyl acetate to give compound (24). In step E, compound (24) is coupled with optionally substituted mono-Boc protected diazabicyclo [3.2.1]octane to provide compound (15). This reaction proceeds with an activating reagent such as 2-(3H-[1,2,3] triazolo[4,5-b]pyridin-3-yl)-1,1,3,3-tetramethylisouronium hexafluorophosphate (V) in a polar solvent such as N,N-dimethylacetamide. In step F, the Boc group of compound (15) is removed using conditions known in the art, for example with trifluoroacetic acid in a solvent such as dichloromethane, to provide compound (I). In some cases, the species $R^2$ and/or $R^3$ will also contain protecting group(s), which can be removed before or after step G in the synthetic sequence.

Compounds (21), (22), (23), and (24) as shown and described above for Scheme IV are useful as intermediates for preparing compounds of Formula (I) and are provided as further aspects of the invention.

SCHEME V

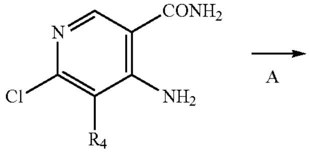

25

-continued

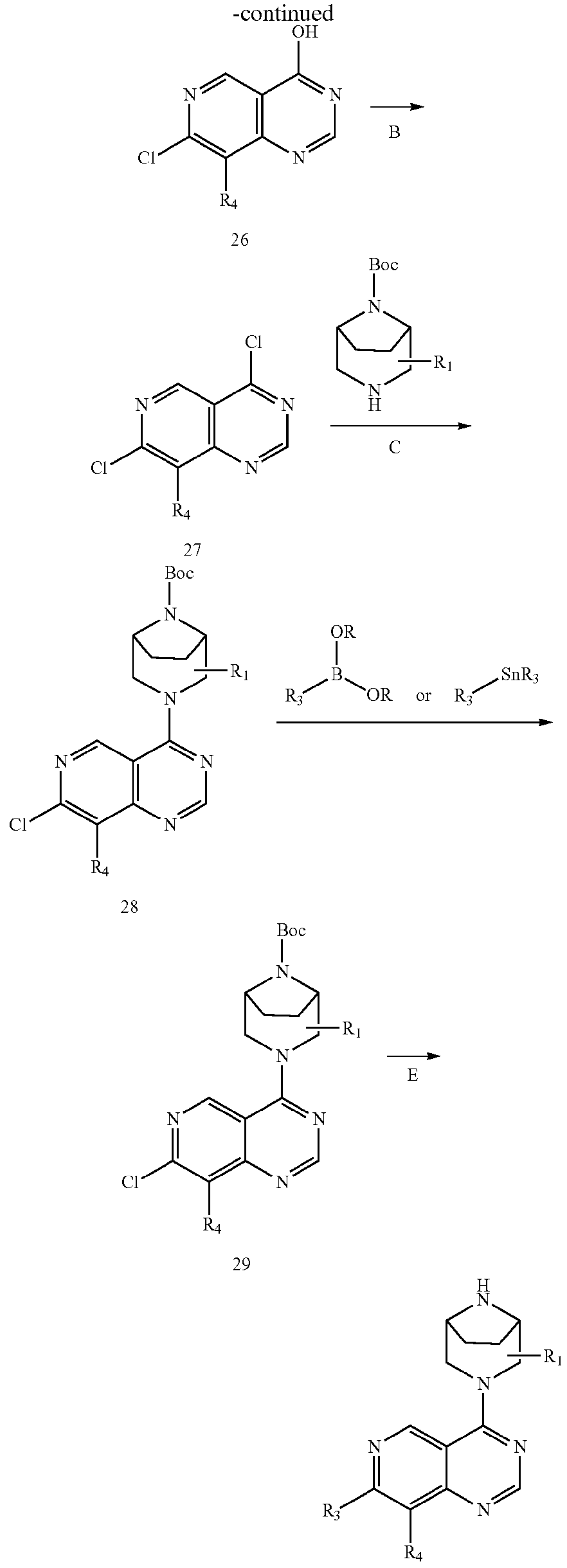

26

27

28

29

30

(I, where R2—Y = H)

Compounds of Formula (I) wherein Y is a bond, $R^2$ is hydrogen, and $R^1$, $R^3$ and $R^4$ are as defined for Formula I can be prepared according to Scheme V. In step A, nicotinamide derivative (25) reacts with trimethoxymethane in acetic acid to give azaquinazoline compound (26). In step B, the chlorination of compound 26 with phosphoryl trichloride and N-ethyl-N-isopropylpropan-2-amine provides dichloro-azaquinazoline (27). In step C, compound (27) undergoes a $S_NAr$ reaction with optionally substituted mono-Boc protected diazabicyclo[3.2.1]octane in a solvent such as N,N-dimethylacetamide and in the presence of a base such as N-ethyl-N-isopropylpropan-2-amine to give compound (28). In step D, compound (28) is coupled with an aryl boronic acid ester or aryl stannane under the Suzuki or Stille reaction conditions to give compound (29). In step E, the Boc group of compound (29) is removed using conditions known in the art, for example with cold 4N HCl and in a solvent such as dioxane, to provide compound (30). In some cases, the species $R^3$ will also contain a protecting group, which can be removed before or after step G in the synthetic sequence.

Compounds (25), (26), (27), (28), and (29) as shown and described above for Scheme V are useful as intermediates for preparing compounds of Formula (I) and are provided as further aspects of the invention.

SCHEME VI

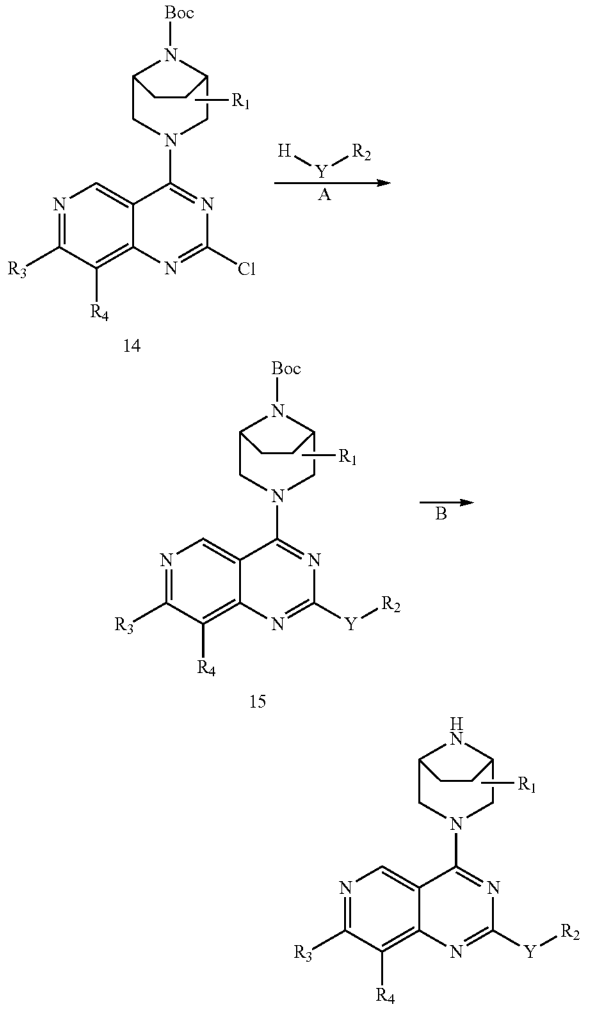

14

15

I

Compounds of Formula (I) wherein all substituents are as defined for Formula I, with the exception that —Y—$R^2$ is other than hydrogen, can be prepared according to Scheme VI. In step A, compound (14) undergoes a Sonogashira coupling reaction in a polar solvent such as acetonitrile to provide compound (15). In step B, the Boc group of compound (15) is removed using conditions known in the art, for example with trifluoroacetic acid in a solvent such as dichloromethane, to provide compound (I). In some cases, the species $R^2$ and/or $R^3$ will also contain protecting/masking group(s), which can be removed before or after step B in the synthetic sequence.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The compounds of the present invention may be in anhydrous, solvated or hydrated forms, and all such forms are included within the scope of the invention.

The following Intermediates are intended to illustrate further certain embodiments of the invention and are not intended to limit the scope of the invention.

Intermediate 1

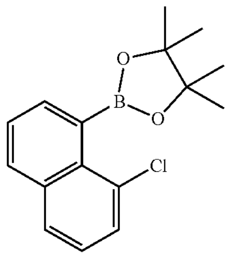

2-(8-chloronaphthalen-1-yl)-4,4,5,5-tetramethyl-1,3,2-dioxaborolane

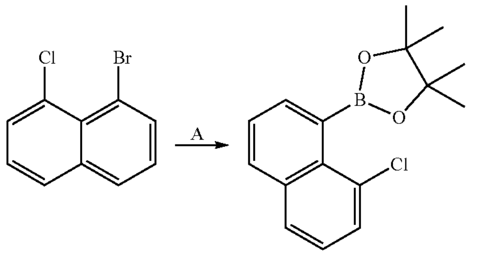

Step A. To a solution of 1-bromo-8-chloronaphthalene (20.0 g, 82.81 mmol) in dioxane (414 ml, 82.8 mmol) was added KOAc (24.38 g, 248.4 mmol) and 4,4,4',4',5,5,5',5'-octamethyl-2,2'-bi (1,3,2-dioxaborolane) (63.09 g, 248.4 mmol) and the reaction was degassed with Ar for 15 minutes followed by the addition of $PdCl_2(dppf)$ (6.059 g, 8.281 mmol). The reaction was heated to 95° C. for 18 hrs. The dark mixture was filtered, and the filtrate was partitioned between water (400 mL) and EtOAc (400 mL). The aqueous layer was extracted with EtOAc (2×200 mL) and the combined organic phases were washed with brine (200 mL), dried over $Na_2SO_4$, filtered and concentrated to afford a black solid. The solid was filtered through a silica gel plug in a 2 L fritted funnel eluting with hexanes to 10% EtOAc/hexanes to afford partially purified product as a bright yellow solid. This was further purified by dividing in half and purifying on a 330 g Redisep cartridge (Isolera) eluting with 0-8% EtOAc/hexanes. Clean fractions from both lots were combined and concentrated to afford the product as a pale yellow solid. (14.8 g, 62%). $^1$H NMR (400 MHz, $(CDCl_3)$ δ 7.86 (dd, J=8.0, 1.2 Hz, 1H), 7.75 (dd, J=7.7, 1.2 Hz, 1H), 7.66 (dd, J=7.0, 1.2 Hz, 1H), 7.57 (dd, J=7.5, 1.1 Hz, 1H), 7.50 (dd, J=7.1, 6.9 Hz, 1H), 7.36 (dd, J=8.2, 7.4 Hz, 1H), 1.44 (s, 12H).

Intermediate 2

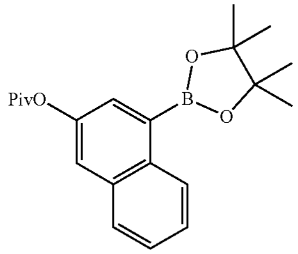

4-(4,4,5,5-tetramethyl-1,3,2-dioxaborolan-2-yl)naphthalen-2-yl pivalate

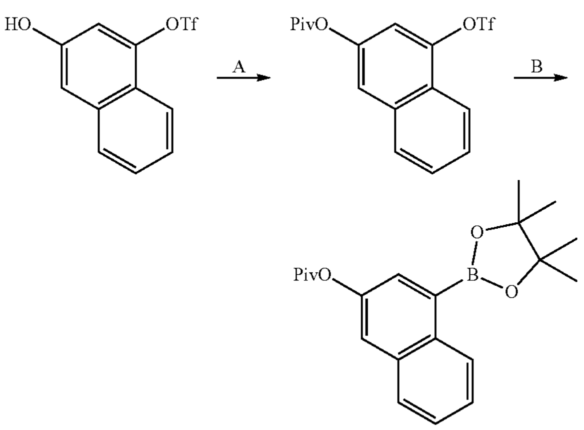

Step A: 4-(((trifluoromethyl)sulfonyl)oxy)naphthalen-2-yl pivalate. A solution of 3-hydroxynaphthalen-1-yl trifluoromethanesulfonate (1.00 g, 3.42 mmol) in DCM (17 mL) was cooled to 0° C. Triethylamine (0.52 mL, 3.8 mmol) was added followed by pivaloyl chloride (0.46 mL, 3.8 mmol) and reaction mixture stirred at 0° C. for 1 hour. The reaction was warmed to r.t. and poured into hexane (100 mL). The organics washed with sat. $NaHCO_3$, water and brine (10 mL each), dried over $Na_2SO_4$ and evaporated in vacuo. The residue was chromatographed on silica gel eluting with 2 to 10% EtOAc/hexanes to yield 4-(((trifluoromethyl)sulfonyl)oxy)naphthalen-2-yl pivalate (1.229 g, 95%). $^1H$ NMR (400 MHz, $CDCl_3$): 8.07-8.02 (m, 1H), 7.87-7.82 (m, 1H), 7.64-7.56 (m, 3H), 7.26 (d, J=2.1 Hz, 1H), 1.39 (s, 9H).

Step B: 4-(4,4,5,5-tetramethyl-1,3,2-dioxaborolan-2-yl)naphthalen-2-yl pivalate. A mixture of 4-(((trifluoromethyl)sulfonyl)oxy)naphthalen-2-yl pivalate (1.220 g, 3.24 mmol), potassium acetate (0.95 g, 9.7 mmol, 3 eq.), 1,1'-bis(diphenylphosphino) ferrocene (90 mg, 0.16 mmol), dichloro[1,1'-bis(diphenylphosphino) ferrocene]palladium dichloromethane adduct (132 mg, 0.16 mmol, 0.05 eq.), 4,4,4',4',5,5,5',5'-octamethyl-2,2'-bi (1,3,2-dioxaborolane) (1.207 g, 4.76 mmol) and dioxane (15 mL) under $N_2$ atmosphere was stirred for 5 hours at 100° C. The reaction was cooled to r.t and partitioned between a mixture of EtOAc and hexanes (20 mL/100 mL) and water (50 mL). The layers were separated. The organic layer was washed with water and brine (20 mL each), dried over $Na_2SO_4$ and concentrated in vacuo. The residue was chromatographed on silica gel eluting with 20 to 50% dichloromethane/hexanes to yield 4-(4,4,5,5-tetramethyl-1,3,2-dioxaborolan-2-yl)naphthalen-2-yl pivalate (0.778 g, 68%). $^1H$ NMR (400 MHz, $CDCl_3$): 8.75 (dm, J~8.3 Hz, 1H), 7.79-7.71 (m, 2H), 7.60 (d, J=2.4 Hz, 1H), 7.51-7.43 (m, 2H), 1.40 (s, 12H), 1.39 (s, 9H).

Intermediate 3

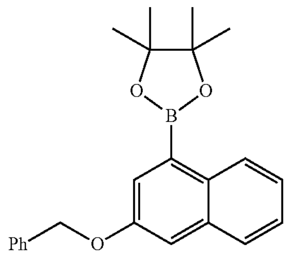

2-(3-(benzyloxy)naphthalen-1-yl)-4,4,5,5-tetramethyl-1,3,2-dioxaborolane

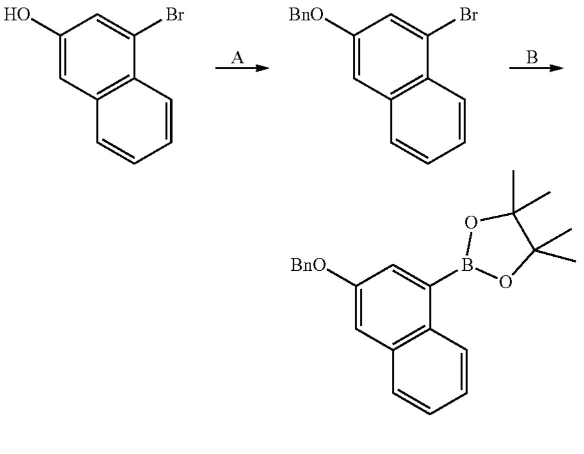

Step A. 3-(benzyloxy)-1-bromonaphthalene. A solution of 4-bromonaphthalen-2-ol (5.0 g, 22.41 mmol) in DMF (50 mL) was treated with sodium hydride (986 mg, 60%, 24.66 mmol) and heated to 50° C. for 1 hr under $N_2$. After cooling to room temperature, benzyl bromide (3.47 mL, 29.1 mmol) was added, followed by tetrabutylammonium iodide (828 mg, 2.24 mmol). The mixture was stirred for 16 h and then partitioned between water (200 mL) and EtOAc (200 mL). The aqueous layer was extracted with EtOAc (2×100 mL) and the combined organic phases were washed with water (4×100 mL) and brine (50 mL) then dried over $Na_2SO_4$, filtered and concentrated. The residue was purified by flash column chromatography eluting with 0-15% EtOAc/hexanes, then for a second time eluting with 0-5% EtOAc/hexanes to afford 3-(benzyloxy)-1-bromonaphthalene (6.16 g, 19.7 mmol, 88%).

Step B. 2-(3-(benzyloxy)naphthalen-1-yl)-4,4,5,5-tetramethyl-1,3,2-dioxaborolane. 3-(Benzyloxy)-1-bromonaphthalene (1.23 g, 3.93 mmol), 4,4,4',4',5,5,5',5'-octamethyl-2,2'-bi (1,3,2-dioxaborolane) (2.99 g, 11.8 mmol) and potassium acetate (1.16 g, 11.8 mmol) were combined in dioxanes (20 mL) and purged with Ar for 5 min. $PdCl_2$(dppf) (0.287 g, 0.393 mmol) was added and the reaction heated to 95° C. for 6 h and then stirred at room temperature for 16 h. The mixture was partitioned between water (100 mL) and EtOAc (50 mL) and the aqueous layer was extracted with EtOAc (2×30 mL). The combined organic phases were washed with brine (30 mL), dried over $Na_2SO_4$, filtered and concentrated in vacuo. The residue was purified by flash column chromatography, eluting with 0-15% EtOAc/hexanes to afford 2-(3-(benzyloxy)naphthalen-1-yl)-4,4,5,5-tetramethyl-1,3,2-dioxaborolane (1.25 g, 3.47 mmol, 88%) $^1H$ NMR (400 MHz, ($CDCl_3$) δ 8.66 (d, J=8.3 Hz, 1H), 7.85 (d, J=2.3 Hz, 1H), 7.49 (d, J=8.2 Hz, 2H), 7.35 (m, 7H), 5.19 (s, 2H), 1.41 (s, 12H).

Intermediate 4

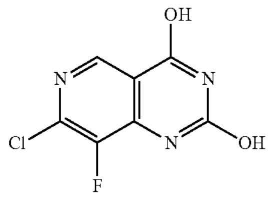

7-chloro-8-fluoro-pyrido[4,3-d]pyrimidine-2,4-diol

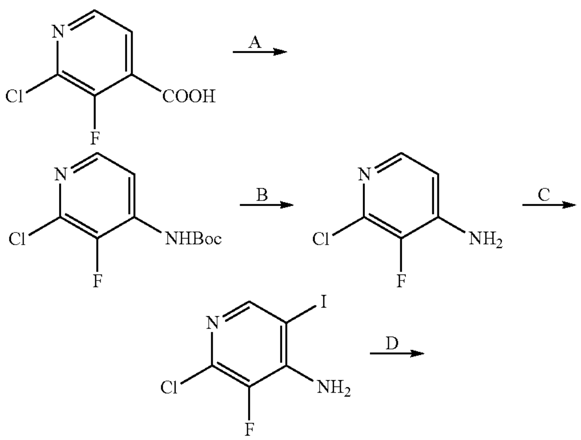

-continued

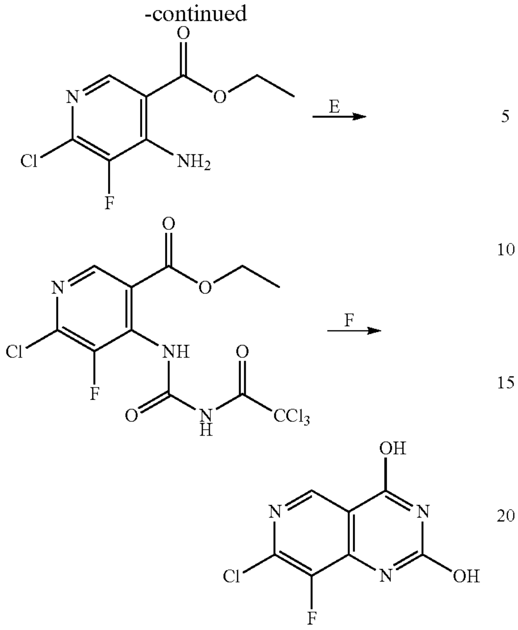

Step A. tert-butyl N-(2-chloro-3-fluoro-4-pyridyl)carbamate. A mixture of 2-chloro-3-fluoro-pyridine-4-carboxylic acid (180 g, 1.03 mol, 1.0 eq), 4 A molecular sieve (300 g) and $Et_3N$ (311 g, 3.08 mol, 428 mL, 3.0 eq) in toluene (1.3 L) and t-BuOH (1.01 kg, 13.6 mol, 1.3 L, 13.3 eq) was stirred at 110° C. for 0.5 hour under nitrogen. The mixture was cooled to 25° C. and diphenylphosphoryl azide (423 g, 1.54 mol, 333 mL, 1.5 eq) was added. The mixture was stirred at 110° C. for 5 hours. Upon completion, the mixture was diluted with water (2000 mL) and extracted with ethyl acetate (2×2000 mL). The combined organic layers were washed with brine (1×2000 mL), dried over sodium sulfate, filtered and concentrated under vacuum. The residue was purified by column chromatography ($SiO_2$, Petroleum ether/Ethyl acetate=100/1 to 5/1). tert-butyl N-(2-chloro-3-fluoro-4-pyridyl)carbamate (197 g, 799 mmol, 78% yield, 100% purity) was obtained as a white solid. LCMS [ESI, M+1]: 247; LCMS [ESI, M−55]: 191. $^1H$ NMR (400 MHz, methanol-$d_4$) δ=8.11 (t, J=5.6 Hz, 1H), 7.99 (d, J=5.6 Hz, 1H), 1.52 (s, 9H).

Step B. 2-chloro-3-fluoro-pyridin-4-amine. To a solution of tert-butyl N-(2-chloro-3-fluoro-4-pyridyl)carbamate (199 g, 807 mmol, 1.0 eq) in MeCN (250 mL) was added HCl/dioxane (4 M, 796 mL, 3.95 eq). The mixture was stirred at 25° C. for 2 hours. Upon completion, the mixture was filtered, and the filter cake was diluted with saturated $NaHCO_3$ solution (2000 mL) and extracted with ethyl acetate (2×2000 mL). The combined organic layers were dried over sodium sulfate, filtered and concentrated under vacuum. 2-chloro-3-fluoro-pyridin-4-amine (107 g, 731 mmol, 91% yield, 99.9% purity) was obtained as a yellow solid and used in the next step without further purification. LCMS [ESI, M+1]: 147. $^1H$ NMR (400 MHz, methanol-$d_4$) δ=7.61 (d, J=5.6 Hz, 1H), 6.67 (t, J=6.0 Hz, 1H).

Step C. 2-chloro-3-fluoro-5-iodo-pyridin-4-amine. To a solution of 2-chloro-3-fluoro-pyridin-4-amine (107 g, 730 mmol, 1.0 eq) and NIS (197 g, 876 mmol, 1.2 eq) in MeCN (550 mL) was added p-toluene sulfonic acid monohydrate (6.94 g, 36.5 mmol, 0.05 eq). The mixture was stirred at 70° C. for 16 hours. Upon completion, the mixture was diluted with water (300 mL) and ethyl acetate (2000 mL). The organic layer was washed with saturated $Na_2CO_3$ solution (2×1500 mL), saturated $Na_2SO_3$ (1×2000 mL) solution and brine (1×1500 mL), dried over $Na_2SO_4$, filtered and concentrated under vacuum. 2-chloro-3-fluoro-5-iodo-pyridin-4-amine (190 g, 676 mmol, 93% yield, 97.2% purity) was obtained as a yellow solid and used for next steps without further purification. LCMS [ESI, M+1]: 273. $^1H$ NMR (400 MHz, methanol-$d_4$) δ=8.06 (s, 1H).

Step D. 4-amino-6-chloro-5-fluoro-pyridine-3-carboxylate. To a solution of 2-chloro-3-fluoro-5-iodo-pyridin-4-amine (78.4 g, 288 mmol, 1.0 eq) in EtOH (1500 mL) was added $Pd(PPh_3)_2Cl_2$ (20.2 g, 28.8 mmol, 0.1 eq) and $Et_3N$ (105 g, 1.04 mol, 144 mL, 3.61 eq) under nitrogen. The suspension was degassed under vacuum and purged with nitrogen several times. The mixture was stirred under $CO_2$ (15.0 psi) at 80° C. for 15 hours. Upon completion, the mixture was filtered, and the filtrate was concentrated under vacuum to remove 70% of MeOH and the residue was filtered. The combined filter cakes were concentrated under vacuum, ethyl 4-amino-6-chloro-5-fluoro-pyridine-3-carboxylate (142 g, crude) was obtained as a yellow solid. LCMS [ESI, M+1]: 219. $^1H$ NMR (400 MHz, dmso-$d_6$) δ=8.36 (s, 1H), 7.49-7.42 (m, 2H), 4.31 (q, J=7.2 Hz, 2H), 1.31 (t, J=7.2 Hz, 3H).

Step E. ethyl-6-chloro-5-fluoro-4-[(2,2,2-trichloroacetyl)carbamoylamino] pyridine-3-carboxylate. To a solution of ethyl 4-amino-6-chloro-5-fluoro-pyridine-3-carboxylate (20.3 g, 73.2 mmol, 1.0 eq) in THF (60 mL) was added 2,2,2-trichloroacetyl isocyanate (20.7 g, 110 mmol, 13.0 mL, 1.5 eq) at 25° C. The mixture was stirred at 25° C. for 10 min. Upon completion, the mixture was concentrated under vacuum. The crude product was triturated with MTBE (200 mL) at 25° C. for 5 min. Ethyl 6-chloro-5-fluoro-4-[(2,2,2-trichloroacetyl)carbamoylamino]pyridine-3-carboxylate (29.3 g, 67.74 mmol, 92% yield, 94.1% purity) was obtained as a gray solid. LCMS [ESI, M+1]: 408.

Step F. 7-chloro-8-fluoro-pyrido[4,3-d]pyrimidine-2,4-diol. To a solution of ethyl 6-chloro-5-fluoro-4-[(2,2,2-trichloroacetyl)carbamoylamino]pyridine-3-carboxylate (29.3 g, 63.1 mmol, 1.0 eq) in MeOH (290 mL) was added $NH_3$·MeOH (29 mL, 20% purity) at 25° C. The mixture was stirred at 25° C. for 1 h. Upon completion, the mixture was concentrated under vacuum. The crude product was triturated with MTBE (200 mL) at 25° C. for 10 min. 7-Chloro-8-fluoro-pyrido[4,3-d]pyrimidine-2,4-diol (18 g, crude) was obtained as a brown solid. LCMS [ESI, M+1]: 216. $^1H$ NMR (400 MHz, dmso-$d_6$) δ=8.35 (br s, 1H).

Intermediate 5

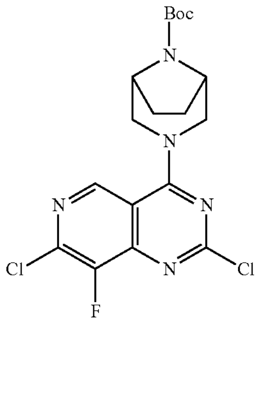

tert-butyl3-(2,7-dichloro-8-fluoro-pyrido[4,3-d]pyrimidin-4-yl)-3,8-diazabicyclo[3.2.1]octane-8-carboxylate

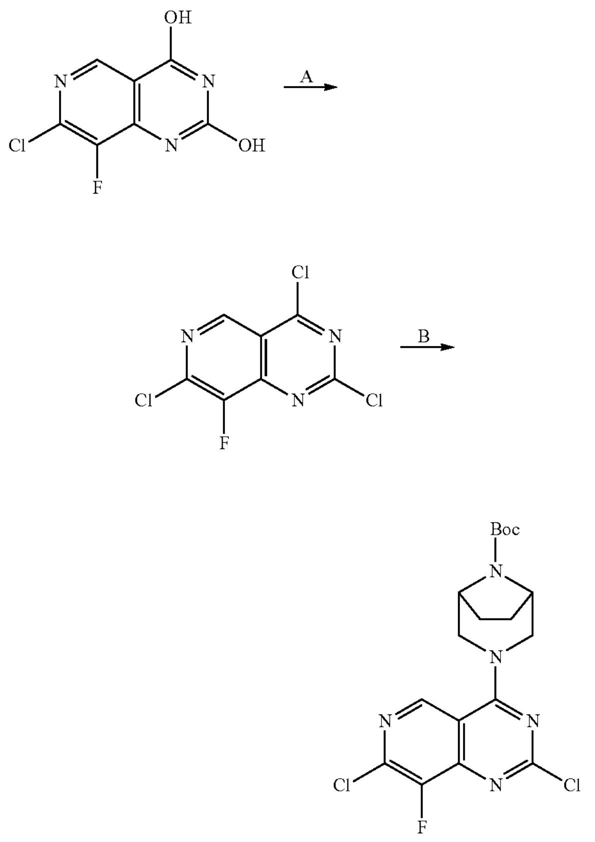

Step A. 2,4,7-trichloro-8-fluoro-pyrido[4,3-d]pyrimidine. A mixture of 7-chloro-8-fluoro-pyrido[4,3-d]pyrimidine-2,4-diol (5 g, 23.2 mmol, 1.0 eq) and N-ethyl-N-isopropyl-propan-2-amine (15 g, 116 mmol, 20.2 mL, 5.0 eq) in $POCl_3$ (82.5 g, 538 mmol, 50 mL, 23.2 eq) was stirred at 100° C. for 1 hour. After completion, the mixture was concentrated under vacuum to give 2,4,7-trichloro-8-fluoro-pyrido[4,3-d]pyrimidine (6.5 g, crude) and used in next step without further purification. Yellow oil.

Step B. tert-butyl-3-(2,7-dichloro-8-fluoro-pyrido[4,3-d]pyrimidin-4-yl)-3,8-diazabicyclo[3.2.1]octane-8-carboxylate. To a solution of 2,4,7-trichloro-8-fluoro-pyrido[4,3-d]pyrimidine (6.5 g, crude) and N-ethyl-N-isopropylpropan-2-amine (20 g, 155 mmol, 26.9 mL,) in dichloromethane (20 mL) was added tert-butyl 3,8-diazabicyclo[3.2.1]octane-8-carboxylate (4.92 g, 23.2 mmol) at −40° C. After stirring at −40° C. for 0.5 h, the mixture was diluted with water (20 mL), extracted with dichloromethane (2×20 mL). The combined organic layers were washed with brine (30 mL), dried over $Na_2SO_4$, filtered and concentrated under vacuum, affording tert-butyl-3-(2,7-dichloro-8-fluoro-pyrido[4,3-d]pyrimidin-4-yl)-3,8-diazabicyclo[3.2.1]octane-8-carboxylate (4 g, two steps 42% yield). Yellow solid. LCMS [ESI, M+1]: 428.

Intermediate 6

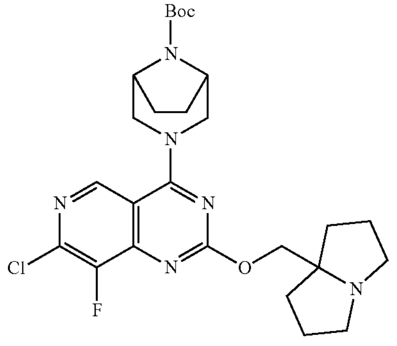

tert-butyl(1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate

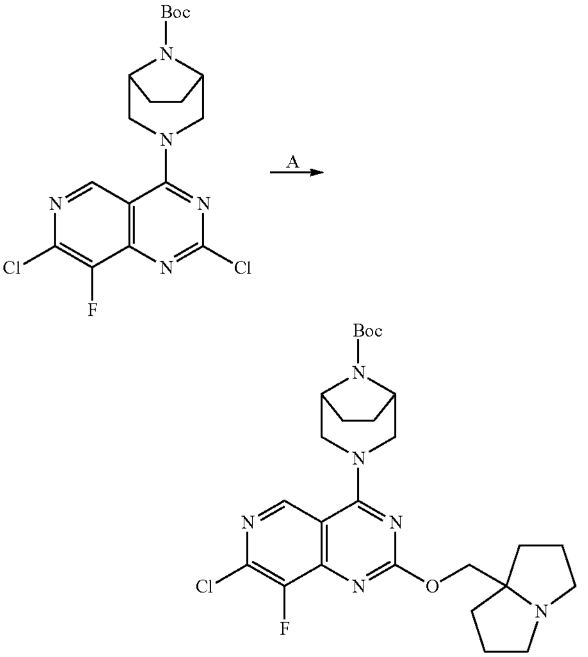

Step A. tert-butyl(1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl-3-(2,7-dichloro-8-fluoro-pyrido[4,3-d]pyrimidin-4-yl)-3,8-diazabicyclo[3.2.1]octane-8-carboxylate (2 g, 4.67 mmol, 1.0 eq), (tetrahydro-1H-pyrrolizin-7a(5H)-yl)methanol (1.32 g, 9.34 mmol, 2.0 eq) and DIEA (1.81 g, 14.0 mmol, 2.44 mL, 3.0 eq) in dioxane (30 mL) was stirred at 80° C. for 6 hours. After completion, the mixture was diluted with water (30 mL), extracted with ethyl acetate (2×40 mL). The combined organic layers were washed with brine (30 mL), dried over $Na_2SO_4$, filtered and concentrated under vacuum. The residue was purified by reversed phase flash chromatography [water (formic acid, 0.1%)/acetonitrile] to give the title compound (1.83 g, 73% yield). Yellow solid. LCMS (ESI, M+1): 533.

Intermediate 7

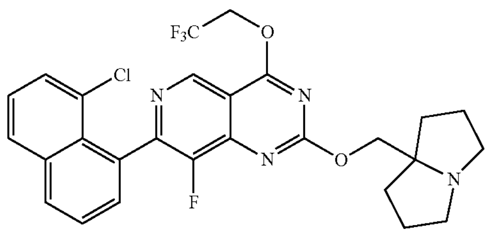

7-(8-chloronaphthalen-1-yl)-8-fluoro-2-((tetrahydro-1H-pyrrolizin-7a(5H)-yl)methoxy)-4-(2,2,2-trifluoroethoxy)pyrido[4,3-d]pyrimidine

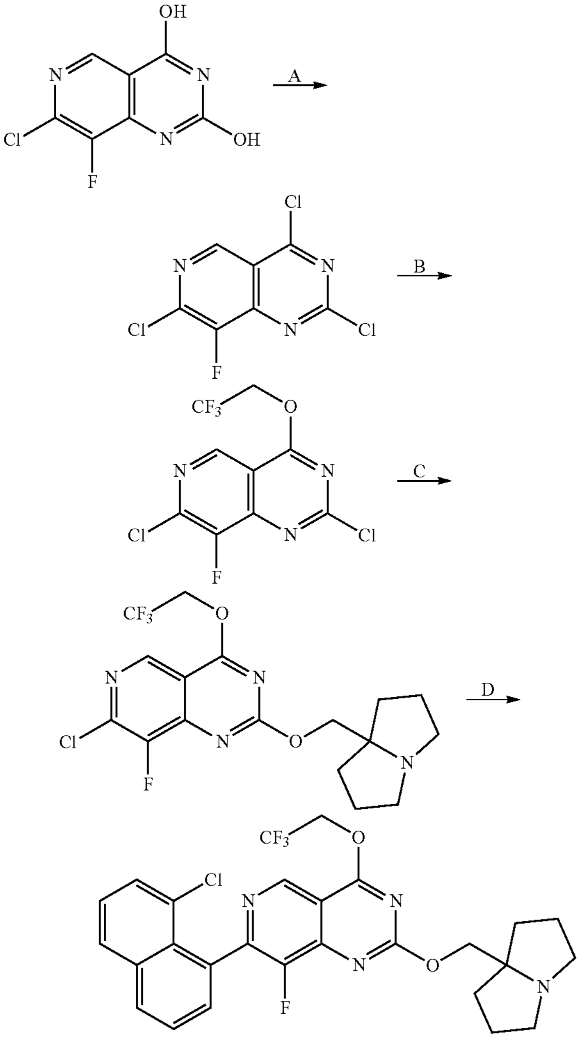

Step A. 2,4,7-trichloro-8-fluoro-pyrido[4,3-d]pyrimidine. To a mixture of -chloro-8-fluoro-pyrido[4,3-d]pyrimidine-2,4-diol (20 g, 92.8 mmol, 1.00 eq) in toluene (100 mL) was added $POCl_3$ (42.7 g, 278 mmol, 25.9 mL, 3.00 eq) and N-ethyl-N-isopropylpropan-2-amine (36.0 g, 278 mmol, 48.5 mL, 3.00 eq) at 0° C. The mixture was stirred at 110° C. for 3 hours. After completion, the mixture was concentrate under reduced pressure at 40° C. to dryness affording 2,4,7-trichloro-8-fluoro-pyrido[4,3-d]pyrimidine (23.4 g, crude) as a black oil.

Step B. 2,7-dichloro-8-fluoro-4-(2,2,2-trifluoroethoxy)pyrido[4,3-d]pyrimidine. To a solution of 2,2,2-trifluoroethanol (11.1 g, 111 mmol, 8.01 mL, 1.20 eq) in toluene (200 mL) was added t-BuONa (26.7 g, 278 mmol, 3.00 eq) at 0° C. The mixture was first stirred at 10° C. for 0.5 hour. Then the above mixture was added to 2,4,7-trichloro-8-fluoro-pyrido[4,3-d]pyrimidine (23.4 g, 92.7 mmol, 1.00 eq) in toluene (200 mL) at −10° C. After addition, the mixture was stirred at −10° C.~25° C. for 16 hours. After monitored, a mixture of t-BuONa (1.78 g, 18.5 mmol, 0.2 eq) and 2,2,2-trifluoroethanol (1.85 g, 18.5 mmol, 1.33 mL, 0.20 eq) in toluene (20.0 mL) was added thereto at 0° C. The mixture was continued to stir at 25° C. for 30 hours. After completion, the mixture was poured onto $SiO_2$ column, purified by column chromatography ($SiO_2$, petroleum ether/ethyl acetate=30/1 to 10/1), and then further purified by reversed-phase flash (0.1% formic acid condition) affording 2,7-dichloro-8-fluoro-4-(2,2,2-trifluoroethoxy)pyrido[4,3-d]pyrimidine (16.3 g, 55.6% yield); Yellow solid; LCMS [ESI, M+1]: 316.

Step C. 7-chloro-8-fluoro-2-((tetrahydro-1H-pyrrolizin-7a(5H)-yl)methoxy)-4-(2,2,2-trifluoroethoxy)pyrido[4,3-d]pyrimidine. To a mixture of (tetrahydro-1H-pyrrolizin-7a(5H)-yl)methanol (17.9 g, 126 mmol, 2.00 eq), 4 Å MS (15.0 g) and N-ethyl-N-isopropylpropan-2-amine (16.4 g, 126 mmol, 22.0 mL, 2.00 eq) in 2-methyltetrahydrofuran (200 mL) was added 2,7-dichloro-8-fluoro-4-(2,2,2-trifluoroethoxy)pyrido[4,3-d]pyrimidine (20.0 g, 63.3 mmol, 1.00 eq) in 2-methyltetrahydrofuran (200 mL) at 0~5° C. The mixture was stirred at 0-25° C. for 2 hours. After completion, the mixture was filtered and washed with ethyl acetate (100 mL). The filtrate was quenched by saturated $NH_4Cl$ aqueous solution (300 mL), and the organic layer was separated and dried over anhydrous $Na_2SO_4$. The mixture was filtered, and the filtrate was concentrated under reduced pressure at 40° C. to dryness. The crude product was triturated with $CH_3CN$ (20 mL) at 25° C. for 15 minutes and filtered, the filter cake was dried in vacuum at 40° C. affording the title compound (18.2 g, 64.6% yield). Light yellow solid. $^1H$ NMR (400 MHz, $CDCl_3$) δ 8.99 (s, 1H), 5.03 (q, J=8.4 Hz, 2H), 4.32 (s, 2H), 3.23-3.05 (m, 2H), 2.67 (td, J=6.8, 10.4 Hz, 2H), 2.11-1.96 (m, 2H), 1.96-1.85 (m, 4H), 1.74-1.69 (m, 2H); LCMS [ESI, M+1]: 421.

Step D. 7-(8-chloronaphthalen-1-yl)-8-fluoro-2-((tetrahydro-1H-pyrrolizin-7a(5H)-yl)methoxy)-4-(2,2,2-trifluoroethoxy)pyrido[4,3-d]pyrimidine. To a mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (5.00 g, 11.9 mmol, 1.00 eq), (8-chloronaphthalen-1-yl)trimethylstannane (7.73 g, 23.8 mmol, 2.00 eq) in toluene (150 mL) was added 4 Å MS (5.00 g) at 25° C. The mixture was stirred at 25° C. for 1 hour. Then CuI (792 mg, 4.16 mmol, 0.35 eq), $Pd(dppf)Cl_2$ (1.30 g, 1.78 mmol, 0.15 eq) and BINAP (1.85 g, 2.97 mmol, 0.25 eq) were added thereto at 25° C. The mixture was degassed under vacuum and purged with $N_2$ several times over 30 minutes. Then the mixture was heated to 90° C. and stirred for 2 hours. The mixture was cooled to 25° C., and then (8-chloronaphthalen-1-yl)trimethylstannane (1.93 g, 5.94 mmol, 0.50 eq) was added thereto at 25° C. The mixture was heated to 90° C. and stirred for 1 hour. After completion, the mixture was filtered, and the filtrate was concentrated under reduced pressure at 40° C. to dryness. The crude product was purified by reversed-phase flash (0.1% formic acid condition) affording the title compound (2.3 g, 33.9% yield); Yellow solid. $^1H$ NMR (400 MHz, $CDCl_3$) δ 9.25 (s, 1H), 8.02 (dd, J=1.2, 8.0 Hz, 1H), 7.89 (dd, J=0.8, 8.0 Hz, 1H), 7.65-7.60 (m, 1H), 7.59-7.53 (m, 2H), 7.46-7.41 (m, 1H), 5.08 (q, J=8.0 Hz, 2H), 4.46 (s, 2H), 3.32 (br d, J=3.8 Hz, 2H), 2.83-2.70 (m, 2H), 2.20-2.09 (m, 2H), 2.03-1.90 (m, 4H), 1.82-1.72 (m, 2H); LCMS [ESI, M+1]: 547.

Intermediate 8

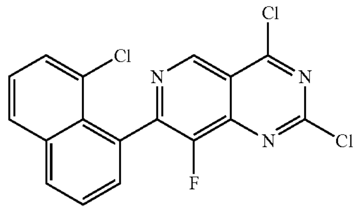

2,4-dichloro-7-(8-chloro-1-naphthyl)-8-fluoro-pyrido[4,3-d]pyrimidine

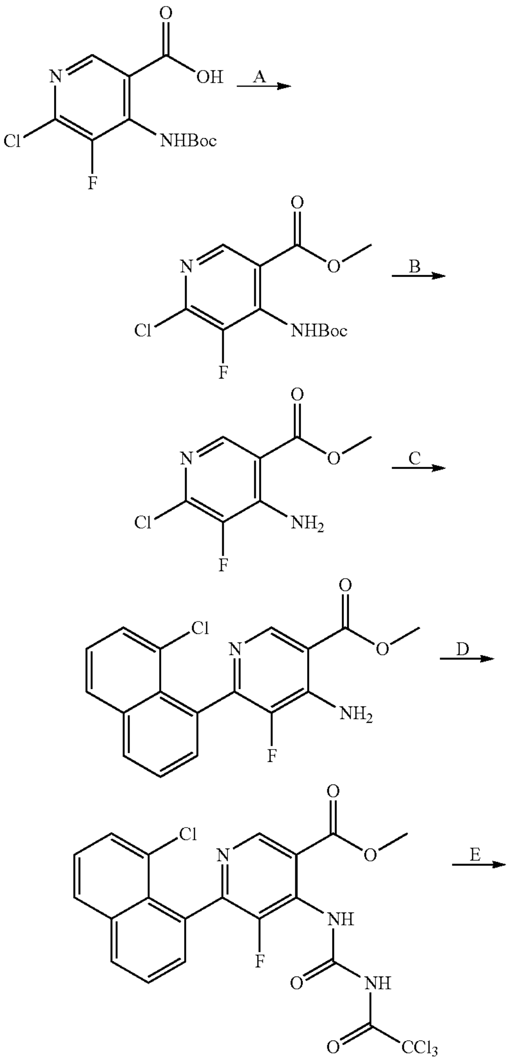

-continued

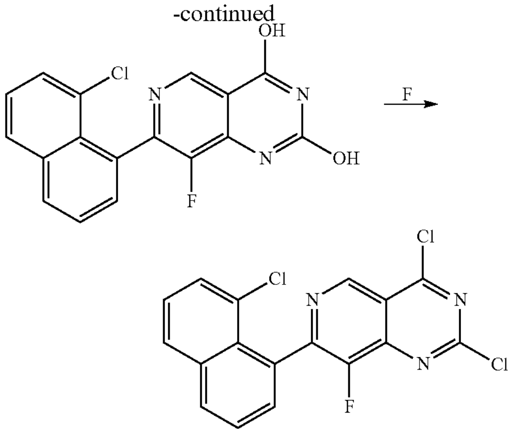

Step A. methyl 4-(tert-butoxycarbonylamino)-6-chloro-5-fluoro-pyridine-3-carboxylate. To a solution of 4-((tert-butoxycarbonyl)amino)-6-chloro-5-fluoronicotinic acid (14.3 g, 49.2 mmol, 1 eq) in MeOH (70 mL) and toluene (210 mL) was added $TMSCHN_2$ (2 M in hexane, 44.3 mL, 1.8 eq) slowly. After stirring at 15° C. for 2 hours, the mixture was quenched with 2N HCl (100 mL) and layers were separated. The organic phase was washed with saturated aqueous $NaHCO_3$ (150 mL), followed by brine (150 mL). The organic layer was dried over $Na_2SO_4$, filtered and concentrated under vacuum. The residue was purified by silica gel chromatography (petroleum ether/ethyl acetate 10/1 to 1/1) to give methyl 4-(tert-butoxycarbonylamino)-6-chloro-5-fluoro-pyridine-3-carboxylate (15 g, 91%). Colorless oil; Rf=0.50 (3:1 petroleum ether/ethyl acetate); $^1H$ NMR (400 MHz, $CDCl_3$): δ 8.85 (br s, 1H), 8.68 (s, 1H), 3.98 (s, 3H), 1.57-1.49 (m, 9H); LCMS [ESI, M+1]: 305.

Step B. methyl 4-amino-6-chloro-5-fluoro-pyridine-3-carboxylate. To a solution of methyl 4-(tert-butoxycarbonylamino)-6-chloro-5-fluoro-pyridine-3-carboxylate (15 g, 49.2 mmol, 1.0 eq) in MeCN (150 mL) was added HCl·dioxane (4 M, 290 mL, 23.6 eq) at 0° C. The mixture was stirred at 15° C. for 0.5 hour, and the solvent was removed under reduced pressure. The residue was diluted with saturated $Na_2CO_3$ solution (100 mL) and extracted with ethyl acetate (3×200 mL). The organic layers were dried over $Na_2SO_4$ and concentrated under vacuum to give methyl 4-amino-6-chloro-5-fluoro-pyridine-3-carboxylate (9.07 g, 89%) which was used directly in the next step without further purification. Orange solid; LCMS [ESI, M+1]: 205.

Step C. methyl 4-amino-6-(8-chloro-1-naphthyl)-5-fluoro-pyridine-3-carboxylate. A mixture of methyl 4-amino-6-chloro-5-fluoro-pyridine-3-carboxylate (6 g, 29.3 mmol, 1.0 eq), (8-chloronaphthalen-1-yl)trimethylstannane (21.0 g, 64.5 mmol, 2.2 eq), CuI (1.68 g, 8.80 mmol, 0.3 eq), Pd(dppf)$Cl_2$ (2.15 g, 2.93 mmol, 0.1 eq), and BINAP (3.65 g, 5.87 mmol, 0.2 eq) in toluene (120 mL) was degassed and then heated to 100° C. for 11 hours under $N_2$. The mixture was filtered and the filtrate was concentrated under vacuum. The residue was diluted with water (50 mL) and extracted with ethyl acetate (2×60 mL). The organic layers were dried over $Na_2SO_4$ and concentrated under vacuum. The residue was purified by chromatography ($Al_2O_3$, petroleum ether/ethyl acetate 30/1 to 1/1). The product was triturated with a mixed solution (DMAc/methanol 1/2, 30 mL) at 15° C. for 10 minutes to give methyl 4-amino-6-(8-chloro-1-naphthyl)-5-fluoro-pyridine-3-carboxylate (5.33 g, 54%). Yellow solid; Rf=0.20 (3:1 petroleum ether/ethyl acetate); LCMS [ESI, M+1]: 331.

Step D. methyl 6-(8-chloro-1-naphthyl)-5-fluoro-4-[(2,2,2-trichloroacetyl)carbamoylamino]pyridine-3-carboxylate. To a solution of methyl 4-amino-6-(8-chloro-1-naphthyl)-5-fluoro-pyridine-3-carboxylate (5.5 g, 16.6 mmol, 1.0 eq) in THF (82 mL) was added 2,2,2-trichloroacetyl isocyanate (3.45 g, 18.3 mmol, 2.17 mL, 1.1 eq) dropwise. The mixture was stirred at 15° C. for 10 minutes, and the mixture was concentrated under vacuum. The residue was triturated with MTBE (20 mL) at 15° C. for 15 minutes to give methyl 6-(8-chloro-1-naphthyl)-5-fluoro-4-[(2,2,2-trichloroacetyl)carbamoylamino]pyridine-3-carboxylate (8 g, crude). Yellow solid; LCMS [ESI, M+1]: 520.

Step E. 7-(8-chloro-1-naphthyl)-8-fluoro-pyrido[4,3-d]pyrimidine-2,4-diol. A suspension of methyl 6-(8-chloro-1-naphthyl)-5-fluoro-4-[(2,2,2-trichloroacetyl)carbamoylamino]pyridine-3-carboxylate (8 g, 15.4 mmol, 1.0 eq) in $NH_3$·MeOH (20 mL, 20% purity) was stirred at 15° C. for 0.5 hour, the mixture was concentrated under vacuum. The residue was triturated with MTBE (30 mL) at 15° C. for 15 minutes to give 7-(8-chloro-1-naphthyl)-8-fluoro-pyrido[4,3-d]pyrimidine-2,4-diol (5.3 g, two steps 93%). Yellow solid; $^1$H NMR (400 MHz, DMSO): δ 9.59-8.27 (m, 1H), 8.24-8.13 (m, 1H), 8.11-8.03 (m, 1H), 7.74-7.61 (m, 2H), 7.60-7.52 (m, 2H), 3.59-3.31 (m, 2H); LCMS [ESI, M+1]: 342.

Step F. 2,4-dichloro-7-(8-chloro-1-naphthyl)-8-fluoro-pyrido[4,3-d]pyrimidine. A solution of $POCl_3$ (1.62 g, 10.6 mmol, 985 μL, 36.2 eq) and N-ethyl-N-isopropylpropan-2-amine (189 mg, 1.46 mmol, 255 μL, 5.0 eq) was stirred at 0° C., followed by the addition of 7-(8-chloro-1-naphthyl)-8-fluoro-pyrido[4,3-d]pyrimidine-2,4-diol (0.1 g, 293 μmol, 1.0 eq). The suspension was stirred at 110° C. for 1 hour, the mixture was concentrated under vacuum to give 2,4-dichloro-7-(8-chloro-1-naphthyl)-8-fluoro-pyrido[4,3-d]pyrimidine (0.11 g, crude) which was used directly in the next step without further purification. Black oil.

Intermediate 9

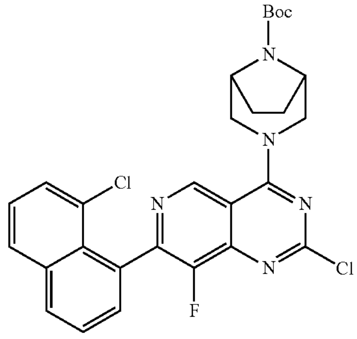

tert-butyl 3-[2-chloro-7-(8-chloro-1-naphthyl)-8-fluoro-pyrido[4,3-d]pyrimidin-4-yl]-3,8-diazabicyclo[3.2.1]octane-8-carboxylate

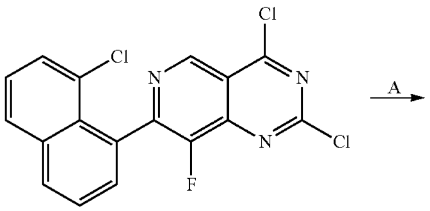

-continued

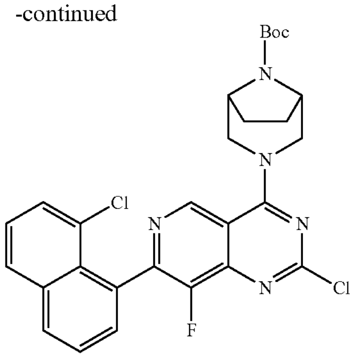

Step A. tert-butyl 3-[2-chloro-7-(8-chloro-1-naphthyl)-8-fluoro-pyrido[4,3-d]pyrimidin-4-yl]-3,8-diazabicyclo[3.2.1]octane-8-carboxylate. To a solution of 2,4-dichloro-7-(8-chloronaphthalen-1-yl)-8-fluoropyrido[4,3-d]pyrimidine (2.11 g, 5.57 mmol, 1.0 eq) in DCM (40 mL) was added N-ethyl-N-isopropylpropan-2-amine (3.60 g, 27.9 mmol, 4.85 mL, 5.0 eq) at −40° C. until the pH of the resulting mixture was adjusted to 8 followed by the addition of tert-butyl 3,8-diazabicyclo[3.2.1]octane-8-carboxylate (1.06 g, 5.02 mmol, 0.9 eq). Then mixture was stirred at −40° C. for 0.5 hour, the mixture was added to water (50 mL) and layers were separated. The aqueous phase was extracted with ethyl acetate (50 mL). Combined organic layers were dried over $Na_2SO_4$, filtered and concentrated under vacuum. The residue was purified by chromatography ($Al_2O_3$, petroleum ether/ethyl acetate 10/1 to 1/1) to give tert-butyl 3-[2-chloro-7-(8-chloro-1-naphthyl)-8-fluoro-pyrido[4,3-d]pyrimidin-4-yl]-3,8-diazabicyclo[3.2.1]octane-8-carboxylate (2 g, 63%). Yellow solid; $R_f$=0.30 (petroleum ether/ethyl acetate 3/1); LCMS [ESI, M+1]: 554.

Intermediate 10

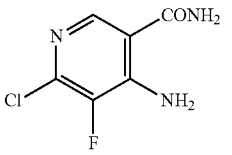

4-amino-6-chloro-5-fluoro-pyridine-3-carboxamide

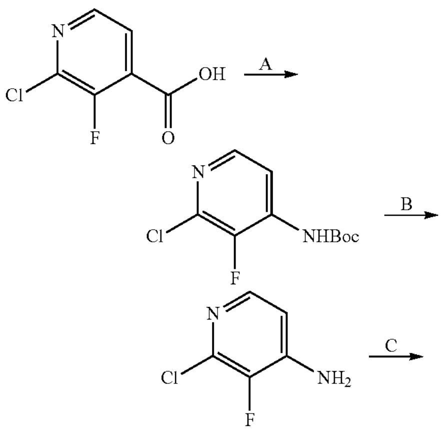

-continued

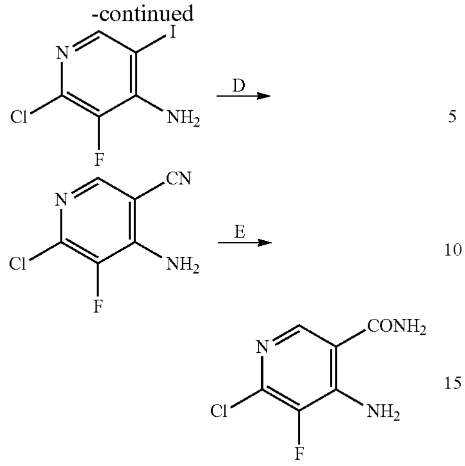

Step A. tert-butyl N-(2-chloro-3-fluoro-4-pyridyl)carbamate. A mixture of 2-chloro-3-fluoro-pyridine-4-carboxylic acid (180 g, 1.03 mol, 1.0 eq), 4 A molecular sieve (300 g) and $Et_3N$ (311 g, 3.08 mol, 428 mL, 3.0 eq) in toluene (1.3 L) and t-BuOH (1.01 kg, 13.6 mol, 1.3 L, 13.3 eq) was stirred at 110° C. for 0.5 hour under nitrogen. The mixture was cooled to 25° C. and diphenylphosphoryl azide (423 g, 1.54 mol, 333 mL, 1.5 eq) was added. The mixture was stirred at 110° C. for 5 hours. Upon completion, the mixture was diluted with water (2000 mL) and extracted with ethyl acetate (2×2000 mL). The combined organic layers were washed with brine (1×2000 mL), dried over sodium sulfate, filtered and concentrated under vacuum. The residue was purified by column chromatography ($SiO_2$, Petroleum ether/Ethyl acetate=100/1 to 5/1). tert-butyl N-(2-chloro-3-fluoro-4-pyridyl)carbamate (197 g, 799 mmol, 78% yield, 100% purity) was obtained as a white solid. LCMS [ESI, M+1]: 247; LCMS [ESI, M−55]: 191. $^1H$ NMR (400 MHz, methanol-$d_4$) δ=8.11 (t, J=5.6 Hz, 1H), 7.99 (d, J=5.6 Hz, 1H), 1.52 (s, 9H).

Step B. 2-chloro-3-fluoropyridin-4-amine. To a solution of tert-butyl N-(2-chloro-3-fluoro-4-pyridyl)carbamate (199 g, 807 mmol, 1.0 eq) in MeCN (250 mL) was added HCl/dioxane (4 M, 796 mL, 3.95 eq). The mixture was stirred at 25° C. for 2 hours. Upon completion, the mixture was filtered, and the filter cake was diluted with saturated $NaHCO_3$ solution (2000 mL) and extracted with ethyl acetate (2×2000 mL). The combined organic layers were dried over sodium sulfate, filtered and concentrated under vacuum. 2-chloro-3-fluoropyridin-4-amine (107 g, 91% yield) was obtained as a yellow solid. LCMS [ESI, M+1]: 147. $^1H$ NMR (400 MHz, methanol-$d_4$) δ=7.61 (d, J=5.6 Hz, 1H), 6.67 (t, J=6.0 Hz, 1H).

Step C. 2-chloro-3-fluoro-5-iodopyridin-4-amine. To a solution of 2-chloro-3-fluoropyridin-4-amine (107 g, 730 mmol, 1.0 eq) and NIS (197 g, 876 mmol, 1.2 eq) in MeCN (550 mL) was added p-toluene sulfonic acid monohydrate (6.94 g, 36.5 mmol, 0.05 eq). The mixture was stirred at 70° C. for 16 hours. Upon completion, the mixture was diluted with water (300 mL) and ethyl acetate (2000 mL), The organic layer was washed with saturated $Na_2CO_3$ solution (2×1500 mL), saturated $Na_2SO_3$ (2000 mL) solution and brine (1500 mL), dried over $Na_2SO_4$, filtered and concentrated under vacuum. 2-chloro-3-fluoro-5-iodopyridin-4-amine (190 g, 93% yield) was obtained as a yellow solid. LCMS [ESI, M+1]: 273. $^1H$ NMR (400 MHz, methanol-$d_4$) δ=8.06 (s, 1H).

Step D. 4-amino-6-chloro-5-fluoro-pyridine-3-carbonitrile. To a mixture of 2-chloro-3-fluoro-5-iodopyridin-4-amine (440 g, 1.61 mol, 1.0 eq) and 4 A MS (150 g) in DMF (3.5 L) was added $Pd(PPh_3)_4$ (93.31 g, 80.75 mmol, 0.05 eq) and $Zn(CN)_2$ (246.54 g, 2.10 mol, 133.27 mL, 1.3 eq) in one portion at 25° C. under $N_2$. Then the mixture was heated to 100° C. and stirred for 2 hours. The mixture was cooled to 20° C., then poured into brine (2000 mL) and stirred for 5 min. The aqueous phase was extracted with ethyl acetate (2000 mL×6). The combined organic phase was washed with brine (2000 mL*3), dried with anhydrous $Na_2SO_4$, filtered and concentrated in vacuum. The crude product (1100 g) was triturated with ethyl acetate (100 mL) at 25° C. for 30 min, filtered and concentrated in vacuum. 4-amino-6-chloro-5-fluoro-pyridine-3-carbonitrile (230 g, 83% yield) was obtained as a yellow solid. $^1H$ NMR (400 MHz, DMSO-$d_6$) δ=8.20 (s, 1H), 7.65 (br s, 2H).

Step E. 4-amino-6-chloro-5-fluoro-pyridine-3-carboxamide. To the $H_2SO_4$ (146 g, 1.46 mol, 79.3 mL, 98% purity, 5.0 eq) was added 4-amino-6-chloro-5-fluoro-pyridine-3-carbonitrile (50 g, 291 mmol, 1.0 eq) at 10° C. The reaction mixture was heated to 60° C. for 1 h. Upon completion, the reaction mixture was poured into ice water (1 L) with stirring. A yellow solid was precipitated. The mixture was filtered. The filter cake was triturated with saturated $NaHCO_3$ (50 mL) and filtered. The combined filtrate was basified by solid $Na_2CO_3$ to pH=7. A yellow solid was precipitated. The mixture was filtered. The filter cake was washed with water (2× 10 mL). The combined filter cakes were dried in vacuum to provide 4-amino-6-chloro-5-fluoro-pyridine-3-carboxamide (44 g, 80% yield). Yellow solid. LCMS [ESI, M+1]: 190; 1H $^1H$ NMR (400 MHz, $CD_3SOCD_3$) δ 8.31 (s, 1H), 8.10 (br s, 1H), 7.77-7.47 (m, 3H).

Intermediate 11

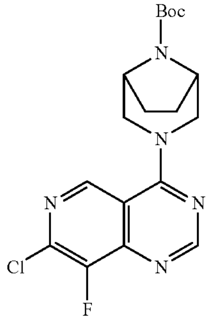

(1R,5S)-tert-butyl-3-(7-chloro-8-fluoropyrido[4,3-d]pyrimidin-4-yl)-3,8-diazabicyclo [3.2.1]octane-8-carboxylate

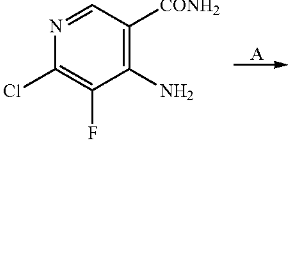

-continued

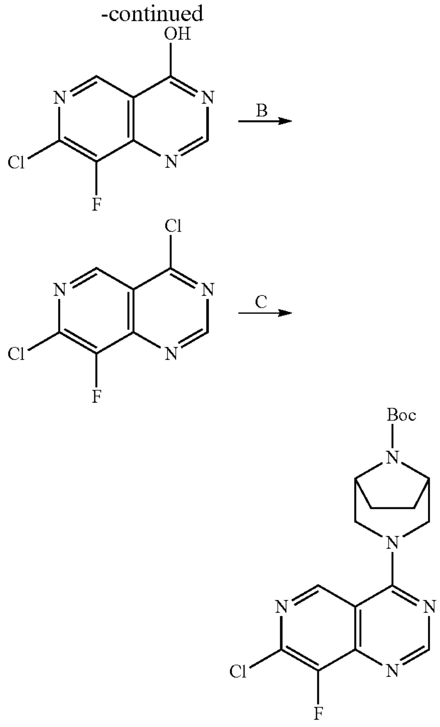

Step A. 7-chloro-8-fluoropyrido[4,3-d]pyrimidin-4-ol. To a solution of 4-amino-6-chloro-5-fluoronicotinamide (4 g, 21.1 mmol, 1.0 eq) in acetic acid (40 mL) was added trimethoxymethane (49.3 g, 464 mmol, 50.9 mL, 22 eq) dropwise. The mixture was stirred at 135° C. for 2 hours. The mixture was diluted with water (150 mL) and extracted with ethyl acetate (2× 100 mL). The combined organic layers were washed with brine (60 mL), dried over $Na_2SO_4$, filtered and concentrated in vacuum. The residue was triturated with acetonitrile (10 mL) to give 7-chloro-8-fluoropyrido[4,3-d]pyrimidin-4-ol (2.2 g, 52% yield). Yellow solid. $^1$H NMR (400 MHz, DMSO-$d_6$) δ=12.99 (br s, 1H), 8.94 (s, 1H), 8.40 (s, 1H). LCMS [ESI, M+1]: 200.

Step B. 4,7-dichloro-8-fluoropyrido[4,3-d]pyrimidine. To a solution of 7-chloro-8-fluoropyrido[4,3-d]pyrimidin-4-ol (2.2 g, 11.0 mmol, 1.0 eq) in N-ethyl-N-isopropylpropan-2-amine (2.85 g, 22.0 mmol, 3.84 mL, 2 eq) was added $POCl_3$ (82.5 g, 538 mmol, 50 mL, 48.8 eq). The mixture was stirred at 110° C. for 3 h. The mixture was concentrated in vacuum to give 4,7-dichloro-8-fluoropyrido[4,3-d]pyrimidine (8.3 g, crude). Yellow oil.

Step C. (1R,5S)-tert-butyl 3-(7-chloro-8-fluoropyrido[4,3-d]pyrimidin-4-yl)-3,8-diazabicyclo[3.2.1]octane-8-carboxylate. To a solution of 4,7-dichloro-8-fluoropyrido[4,3-d]pyrimidine (7.8 g, crude) and (1R,5S)-tert-butyl 3,8-diazabicyclo[3.2.1]octane-8-carboxylate (9.11 g, 42.9 mmol) in dichloromethane (80 mL) was added N-ethyl-N-isopropylpropan-2-amine (23.1 g, 179 mmol, 31.2 mL). The mixture was stirred at 15° C. for 1 h. After completion, the mixture was diluted with water (150 mL) and extracted with ethyl acetate (2×80 mL). The combined organic layers were washed with brine (60 mL), dried over $Na_2SO_4$, filtered and concentrated in vacuum. The residue was triturated with ethyl acetate (8 mL) and filtered. The filter cake was dried in vacuum to give (1R,5S)-tert-butyl-3-(7-chloro-8-fluoropyrido[4,3-d]pyrimidin-4-yl)-3,8-diazabicyclo[3.2.1]octane-8-carboxylate (2 g, two steps 46%). Yellow solid. $^1$H NMR (400 MHz, $CDCl_3$) δ=8.86 (s, 1H), 8.75 (s, 1H), 4.56 (br d, J=11.2 Hz, 2H), 4.38 (br s, 2H), 3.71 (s, 2H), 1.98-1.92 (m, 2H), 1.67 (br d, J=7.6 Hz, 2H), 1.53 (s, 9H). LCMS [ESI, M+1]: 394.

Intermediate 12

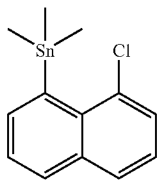

(8-chloro-1-naphthyl)-trimethyl-stannane

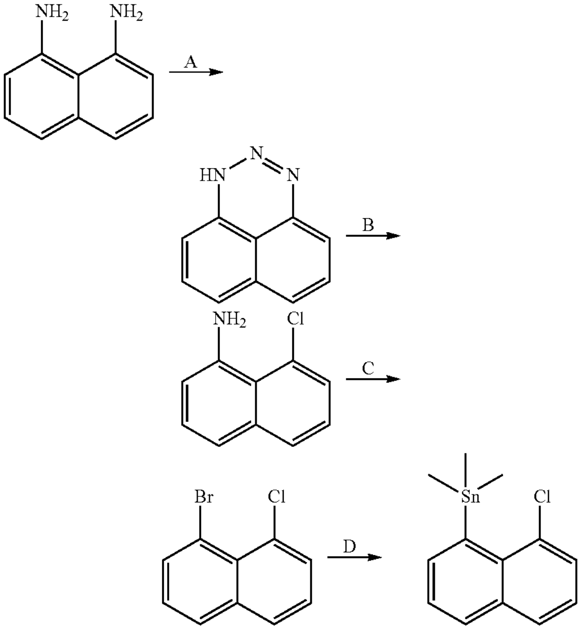

Step A. 1H-naphtho[1,8-de][1,2,3]triazine. To a solution of naphthalene-1,8-diamine (100 g, 632 mmol, 1 eq) in AcOH (200 mL) and EtOH (1000 mL) was added isoamyl nitrite (72.6 g, 619 mmol, 83.4 mL, 0.98 eq) dropwise over a period of 2 hours with temperature controlled between 18 and 21° C. under a cold-water bath. After the addition, the resulting red suspension was stirred at 25° C. for 16 hours. The solid was collected by filtration, washed with ethanol (2×500 mL) and dried under vacuum to give 1H-naphtho[1,8-de][1,2,3]triazine (84 g, 496 mmol, 79% yield). Red crystalline solid; LCMS [ESI, M+1]: 170.

Step B. 8-chloronaphthalen-1-amine. To a solution of 1H-naphtho[1,8-de][1,2,3]triazine (84 g, 496 mmol, 1 eq) in HCl (1.5 L) was added Cu (2.10 g, 33.1 mmol, 234 μL, 0.07 eq). The mixture was stirred at 25° C. for 12 hours. The resulting mixture was diluted with water (500 mL) and heated at 85° C. for 30 mins. The resulting almost clear aqueous solution was filtered, cooled, basified with aqueous ammonia (until blue to litmus paper) and the solution was extracted with ether acetate (2×1000 mL). The combined extracts were dried over $Na_2SO_4$, filtered and concentrated under vacuum. The residue was purified by column chromatography ($SiO_2$, Petroleum ether/Ethyl acetate=200/1 to 5/1) to give 8-chloronaphthalen-1-amine (57 g, 259 mmol, 52% yield, 81% purity). Red solid; LCMS [ESI, M+1]: 178.

Step C. 1-bromo-8-chloronaphthalene. To a solution of 8-chloronaphthalen-1-amine (57 g, 320 mmol, 1 eq) and TsOH·$H_2O$ (219 g, 1.16 mol, 3.6 eq) in MeCN (1000 mL) was added a solution of $NaNO_2$ (39.8 g, 577 mmol, 1.8 eq) and CuBr (138 g, 963 mmol, 29.3 mL, 3 eq) in $H_2O$ (120 mL) at −5° C., then the reaction mixture was stirred at 25° C. for 12 hours. The reaction mixture was added saturated $Na_2SO_3$ solution (100 mL), stirred for 15 mins, and then extracted with ethyl acetate (3×1000 mL). The combined organic layers were washed with brine (500 mL), dried over $Na_2SO_4$, filtered and concentrated under reduced pressure to give a residue. The residue was purified by column chromatography ($SiO_2$, Petroleum ether) to give 1-bromo-8-chloronaphthalene (56 g, 229 mmol, 72% yield, 99% purity). White solid; $^1H$ NMR (400 MHz, $CDCl_3$) δ 7.93 (dd, J=1.2, 7.6 Hz, 1H), 7.82 (dd, J=1.2, 8.4, 1H), 7.79 (dd, J=1.2, 8.4, 1H), 7.67 (dd, J=1.2, 7.6 Hz, 1H), 7.37 (t, J=8.0 Hz, 1H), 7.28 (t, J=8.0 Hz, 1H).

Step D. (8-chloronaphthalen-1-yl)trimethylstannane. To a mixture of 1-bromo-8-chloronaphthalene (37 g, 153 mmol, 1.0 eq) and trimethyl(trimethylstannyl) stannane (151 g, 460 mmol, 95.3 mL, 3 eq) in toluene (750 mL) was added $Pd(PPh_3)_4$ (17.7 g, 15.3 mmol, 0.1 eq) in one portion at 100° C. under $N_2$. The mixture was stirred at 100° C. for 12 hours. The reaction mixture was diluted with $H_2O$ (500 mL) and extracted with ethyl acetate (2×1 L). The combined organic layers were washed with saturated brine (3×500 mL), dried over $Na_2SO_4$, filtered and concentrated under vacuum. The residue was purification by column chromatography ($SiO_2$, petroleum ether:ethyl acetate=1:0), and then further purified by reversed phase flash chromatography [water (0.1% FA/acetonitrile)] to give (8-chloronaphthalen-1-yl)trimethylstannane (47 g, 144 mmol, 94% yield). Yellow oil. $^1H$ NMR (400 MHz, $CDCl_3$) δ 7.88-7.82 (m, 2H), 7.82-7.76 (m, 1H), 7.64-7.59 (m, 1H), 7.52-7.44 (m, 1H), 7.41-7.34 (m, 1H), 0.52-0.34 (m, 9H).

Intermediate 13

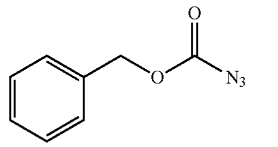

Benzyl Carbonazidate

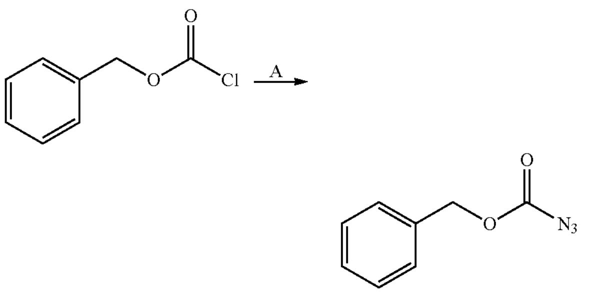

Step A. Benzyl carbonazidate. Benzyl carbonochloridate (100 mg, 586 μmol, 83.3 μL, 1.0 equivalent) was added to a well-stirred suspension of $NaN_3$ (45.7 mg, 703 μmol, 1.2 equivalent) in acetone (10 mL) at 10° C. The mixture was stirred at 10° C. for 1 hour. The mixture was then poured into a Celite pad. The filtrate was collected and concentrated by rotary evaporation to give benzyl N-diazocarbamate (100 mg, crude) as colorless oil and used to next step without purification.

Intermediate 14

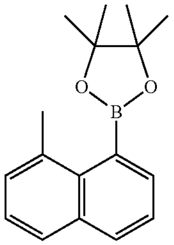

4,4,5,5-tetramethyl-2-(8-methylnaphthalen-1-yl)-1,3,2-dioxaborolane

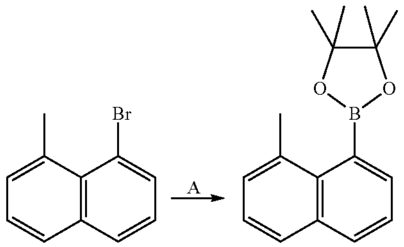

Step A. 4,4,5,5-tetramethyl-2-(8-methylnaphthalen-1-yl)-1,3,2-dioxaborolane. To a solution of 1-bromo-8-methylnaphthalene (0.700 g, 3.17 mmol) in dioxane (15.8 ml) was added potassium acetate (0.932 g, 9.50 mmol) and 4,4,4',4',5,5,5',5'-octamethyl-2,2'-bi (1,3,2-dioxaborolane) (2.41 g, 9.50 mmol) and the reaction sparged with $N_2$ for 15 minutes, followed by the addition of $PdCl_2(dppf)$ (0.232 g, 0.317 mmol). The reaction was heated to 95° C. for 18 hrs. The reaction was concentrated in vacuo and taken up in DCM. The slurry was filtered through GF/F filter paper and the organics was concentrated in vacuo. The material was chromatographed twice using 10→100% Ethyl acetate/hexane as eluent to give 4,4,5,5-tetramethyl-2-(8-methylnaphthalen-1-yl)-1,3,2-dioxaborolane (576 mg, 2.15 mmol, 68% yield). HPLC (5-95% ACN/$H_2O$+0.1% TFA) 3.701 min.

Intermediate 15

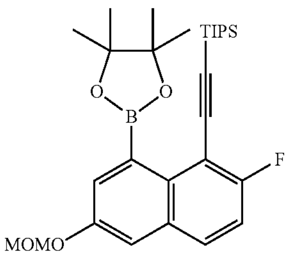

((2-fluoro-6-(methoxymethoxy)-8-(4,4,5,5-tetramethyl-1,3,2-dioxaborolan-2-yl)naphthalen-1-yl)ethynyl)triisopropylsilane

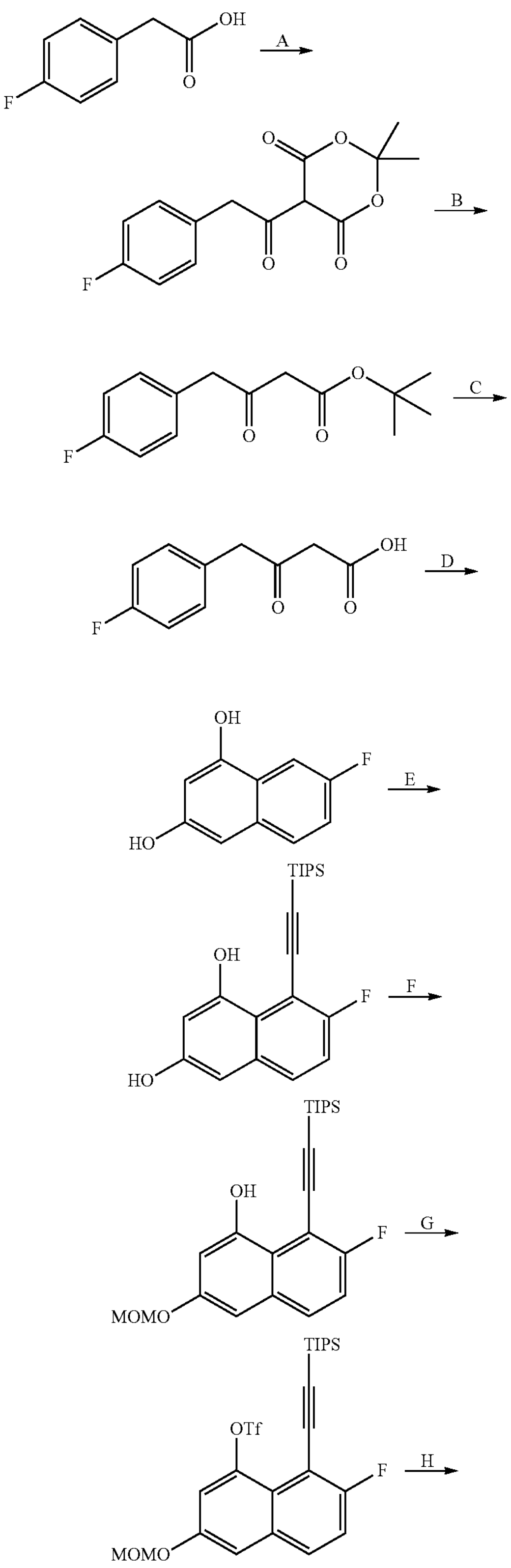

-continued

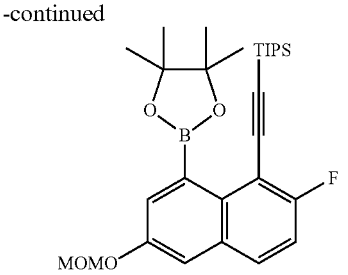

Step A. 5-(2-(4-fluorophenyl) acetyl)-2,2-dimethyl-1,3-dioxane-4,6-dione. To a solution of 2-(4-fluorophenyl) acetic acid (500 g, 3.24 mol, 1 eq), Meldrum's acid (514 g, 3.57 mol, 1.1 eq), DMAP (33.7 g, 275 mmol, 0.085 eq) in $CH_3CN$ (1500 mL) was added DIPEA (901 g, 6.97 mol, 1.21 L, 2.15 eq) while maintaining the temperature below 45° C., and then pivaloyl chloride (430 g, 3.57 mol, 439 mL, 1.1 eq) was slowly added over 3 hours while maintaining the temperature below 45° C. The resulted solution was stirred at 45° C. for 3 hours. The mixture solution was cooled to 0° C., then 1N HCl (5 L) was slowly added, and the resulted solution was stirred at 0° C. for 2 hours. Lot of solid was generated, and the mixture was filtered to give the crude yellow solid. The crude was washed with $CH_3CN/H_2O$ (3 L/12 L) to give 5-(2-(4-fluorophenyl) acetyl)-2,2-dimethyl-1,3-dioxane-4,6-dione (800 g, 88% yield). White Solid; $^1H$ NMR (400 MHz, DMSO-d6) δ=15.35 (s, 1H), 7.40-7.38 (m, 2H), 7.05-7.01 (m, 2H), 4.40 (s, 2H), 1.72 (s, 6H).

Step B. tert-butyl 4-(4-fluorophenyl)-3-oxobutanoate. A solution of 5-(2-(4-fluorophenyl) acetyl)-2,2-dimethyl-1,3-dioxane-4,6-dione (1 kg) in t-BuOH (3 L) was stirred at 90° C. for 2 hours, then the mixture solution was concentrated to give the crude solid, and the crude solid was washed with petroleum ether (350 mL) to give tert-butyl 4-(4-fluorophenyl)-3-oxobutanoate (850 g, 94% yield). Light-yellow Solid; $^1H$ NMR (400 MHz, DMSO-d6) δ=7.27-7.18 (m, 2H), 7.18-7.08 (m, 2H), 3.86 (s, 2H), 3.55 (s, 2H), 1.40 (s, 9H).

Step C. 4-(4-fluorophenyl)-3-oxobutanoic acid. A solution of tert-butyl 4-(4-fluorophenyl)-3-oxobutanoate (800 g, 3.17 mol, 1 eq) and TFA (2.46 kg, 21.6 mol, 1.6 L, 6.81 eq) in DCM (1.6 L) was stirred at 20° C. for 1 hour. The mixture was concentrated to dryness. The residue was washed with petroleum ether (500 mL) to give 4-(4-fluorophenyl)-3-oxobutanoic acid (516 g, 83% yield). White Solid; $^1H$ NMR (400 MHz, $CDCl_3$-d) δ=10.01 (s, 1H), 7.20-7.17 (m, 2H), 7.07-7.03 (m, 2H), 3.84 (s, 2H), 3.54-3.52 (m, 2H).

Step D. 7-fluoronaphthalene-1,3-diol. A solution of 4-(4-fluorophenyl)-3-oxobutanoic acid (450 g, 2.29 mol, 1 eq) in $CF_3SO_3H$ (8.5 kg, 56 mol, 5 L, 25 eq) was stirred at 25° C. for 24 hours, the reaction was cooled to 0° C., and slowly added to ice-water (15 L). Precipitates were formed, and the mixture was filtered to give the crude product. Then the crude was slurred with petroleum ether (1 L), and filtered to give the 7-fluoronaphthalene-1,3-diol (325 g, 79% yield). Light-yellow Solid.

Step E. 7-fluoro-8-((triisopropylsilyl)ethynyl)naphthalene-1,3-diol. To the mixture of 7-fluoronaphthalene-1,3-diol (120 g, 673 mmol, 1 eq), 2-bromoethynyl(triisopropyl)silane (184 g, 707 mmol, 1.05 eq), AcOK (132 g, 1.34 mol, 2 eq) in dioxane (800 mL) was added dichlororuthenium; 1-isopropyl-4-methyl-benzene dimer (41.3 g, 67.4 mmol, 0.1 eq) under $N_2$. The mixture was stirred at 110° C. for 2 hours. The mixture was filtered and concentrated to give a residue. Then the residue was purified by column chromatography ($SiO_2$, Petroleum ether/Ethyl acetate=1/0 to 5/1) to give 7-fluoro-8-((triisopropylsilyl)ethynyl)naphthalene-1,3-diol (213 g, 88% yield) was obtained. Black Oil; LCMS [ESI, M+1]: 359.2

Step F. 7-fluoro-3-(methoxymethoxy)-8-((triisopropylsilyl)ethynyl)naphthalen-1-ol. To the mixture of 7-fluoro-8-((triisopropylsilyl)ethynyl)naphthalene-1,3-diol (170 g, 474 mmol, 1 eq), DIEA (184 g, 1.42 mol, 3 eq) and DCM (1700 mL) was added MOMCl (49.8 g, 618 mmol, 1.3 eq) at 0° C. The mixture was warmed to 15° C. and stirred for 0.5 hour. The reaction mixture was diluted with ice-water (1000 mL) and extracted with ethyl acetate (500 mL×2). The combined organic phase was washed with brine (1000 mL), dried over anhydrous sodium sulfate, filtered and concentrated to give a residue. The residue was purified by column chromatography ($SiO_2$, Petroleum ether/Ethyl acetate=1/0 to 50/1) to give 7-fluoro-3-(methoxymethoxy)-8-((triisopropylsilyl)ethynyl)naphthalen-1-ol (96 g, 50% yield). Yellow Solid; $^1H$ NMR (400 MHz, $CDCl_3$-d) δ=9.13 (s, 1H), 7.68-7.64 (m, 1H), 7.21-7.16 (m, 1H), 6.97-6.96 (m, 1H), 6.81-6.80 (m, 1H), 5.26 (s, 2H), 3.51 (s, 3H), 1.24-1.17 (m, 21H). LCMS [ESI, M+1]: 403.2.

Step G: 7-fluoro-3-(methoxymethoxy)-8-((triisopropylsilyl)ethynyl)naphthalen-1-yl trifluoromethanesulfonate. To the solution of 7-fluoro-3-(methoxymethoxy)-8-((triisopropylsilyl)ethynyl)naphthalen-1-ol (80 g, 198 mmol, 1 eq), DIEA (77.0 g, 596 mmol, 104 mL, 3 eq) in DCM (1200 mL) was added $Tf_2O$ (84.1 g, 298 mmol, 49.2 mL, 1.5 eq) at −40° C., and the mixture was stirred at −40° C. for 0.5 hour. The reaction mixture was diluted with ice-water (500 mL), and then extracted with DCM (300 mL). The combined organic phase was dried over $Na_2SO_4$ and concentrated to dryness. The residue was purified by column chromatography ($SiO_2$, Petroleum ether/Ethyl acetate=1/0 to 60/1) to afford 7-fluoro-3-(methoxymethoxy)-8-((triisopropylsilyl)ethynyl)naphthalen-1-yl trifluoromethanesulfonate (100 g, 94% yield). Yellow oil;

Step H. ((2-fluoro-6-(methoxymethoxy)-8-(4,4,5,5-tetramethyl-1,3,2-dioxaborolan-2-yl)naphthalen-1-yl)ethynyl)triisopropylsilane. To the mixture of 7-fluoro-3-(methoxymethoxy)-8-((triisopropylsilyl)ethynyl)naphthalen-1-yl trifluoromethanesulfonate (105 g, 196 mmol, 1 eq), 4,4,5,5-tetramethyl-2-(4,4,5,5-tetramethyl-1,3,2-dioxaborolan-2-yl)-1,3,2-dioxaborolane (100 g, 393 mmol, 2 eq), AcOK (57.8 g, 589 mmol, 3 eq) in toluene (1100 mL) was added $Pd(dppf)Cl_2$ (14.4 g, 20 mmol, 0.1 eq). The mixture was degassed and stirred at 130° C. for 3 hours. The reaction mixture was filtered and concentrated to give a residue. To the residue was added EtOAc (1000 mL) and water (800 mL). The organic phase was washed with brine (500 mL), dried over anhydrous sodium sulfate, filtered and concentrated to give a residue. The residue was purified by column chromatography ($SiO_2$, Petroleum ether/Ethyl acetate=100/1 to 3/1) and triturated with MeCN (40 mL) to give ((2-fluoro-6-(methoxymethoxy)-8-(4,4,5,5-tetramethyl-1,3,2-dioxaborolan-2-yl)naphthalen-1-yl)ethynyl)triisopropylsilane (41 g, 43% yield). Yellow Solid; $^1H$ NMR (400 MHz, $CDCl_3$-d) δ=7.69-7.65 (m, 1H), 7.51 (d, J=2.4 Hz, 1H), 7.38 (d, J=2.4 Hz, 1H), 7.25 (t, J=8.8 Hz, 1H), 5.28 (s, 2H), 3.50 (s, 3H), 1.44 (s, 12H), 1.18-1.16 (m, 21H); LCMS [ESI, M+1]: 513.4.

Intermediate 16

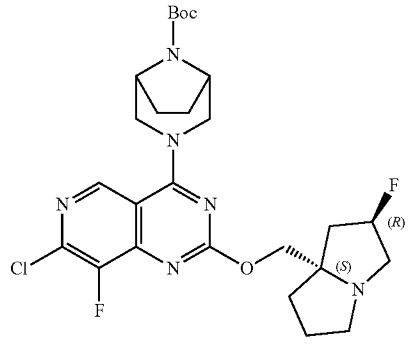

tert-butyl(1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate

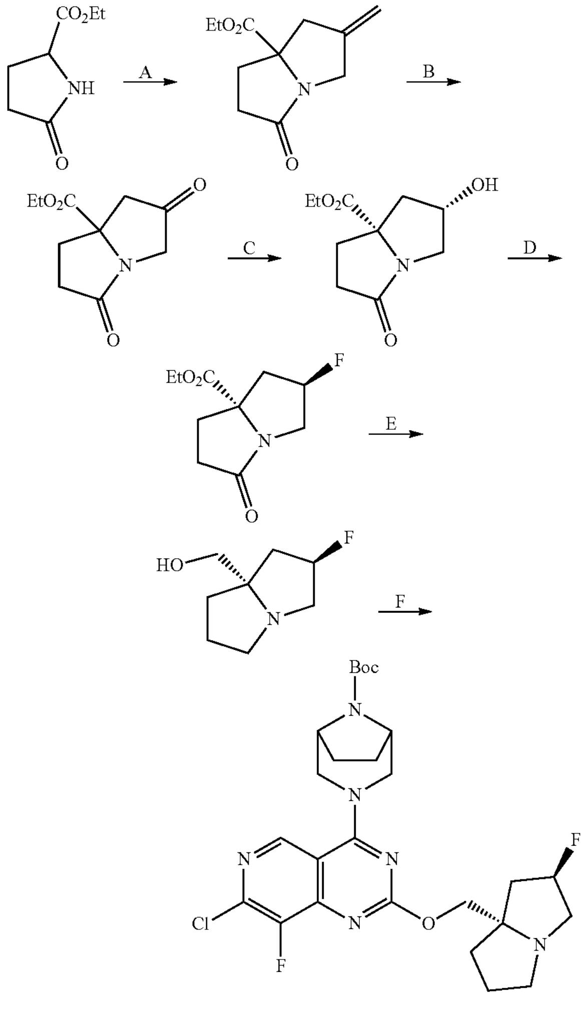

Step A. Ethyl 2-methylene-5-oxotetrahydro-1H-pyrrolizine-7a(5H)-carboxylate. To a mixture of ethyl 5-oxopyrrolidine-2-carboxylate (1.50 kg, 9.54 mol, 1.00 eq) and 3-chloro-2-(chloromethyl) prop-1-ene (1.91 kg, 15.3 mol, 1.77 L, 1.60 eq) in THF (7.50 L) was added LiHMDS (1 M, 19.1 L, 2.00 eq) drop-wise at −40° C. under $N_2$. The mixture was stirred at 25° C. for 20 hrs. The reaction mixture was poured into HCl (1 M, 2.50 L) and pH was adjusted to 7 with HCl (2 M) at 0° C. The mixture was extracted with EtOAc (4.50 L×3). The combined organic layers were washed with brine (4.50 L), dried over $Na_2SO_4$, filtered and concentrated under reduced pressure to give a residue. The residue was purified by column chromatography ($SiO_2$, Petroleum ether/Ethyl acetate=10/1 to 1/1, Rf=0.40) to afford the title compound (898 g, 3.88 mol, 40.6% yield, 82% purity) as a yellow oil. LCMS: Rt=0.716 min, m/z=210.1 (M+H). $^1H$ NMR: 400 MHz $CDCl_3$ δ:5.02-5.07 (m, 2H), 4.28 (m, 1H), 4.16-4.22 (m, 2H), 3.71 (dd, J=15.6, 1.6 Hz, 1H), 3.04 (m, 1H), 2.73-2.80 (m, 1H), 2.57-2.64 (m, 1H), 2.41-2.49 (m, 2H), 2.03-2.17 (m, 2H), 1.24-1.30 (m, 3H).

Step B. ethyl 2,5-dioxotetrahydro-1H-pyrrolizine-7a(5H)-carboxylate. To a mixture of ethyl 2-methylene-5-oxotetrahydro-1H-pyrrolizine-7a(5H)-carboxylate (165 g, 646 mmol, 1.00 eq) in DCM (1650 mL) and MeOH (165 mL) was added $O_3$ (15 psi) at −70° C. under $N_2$. The solution became pale blue, and then the mixture was purged by $N_2$ for 30 min. $Me_2S$ (80.4 g, 1.29 mol, 95.0 mL, 2.00 eq) was added to the mixture at −70° C. The mixture was stirred at 25° C. for 16 hours. The reaction mixture was concentrated under reduced pressure to give a residue. The residue was purified by column chromatography ($SiO_2$, Petroleum ether/Ethyl acetate=10/1 to 1/1, Rt=0.50) to afford the title compound (821 g, 3.62 mol, 93.3% yield, 93.1% purity) as a yellow oil. LCMS: Rt=0.543 min, m/z=212.1 (M+H). $^1H$ NMR: 400 MHz $CDCl_3$ δ:4.23 (m, 2H), 4.12 (m, 1H), 3.56 (m, 1H), 2.96-3.01 (m, 2H), 2.77-2.86 (m, 1H), 2.43-2.50 (m, 2H), 2.14-2.22 (m, 1H), 1.28 (m, 1H).

Step C. ethyl 2-hydroxy-5-oxotetrahydro-1H-pyrrolizine-7a(5H)-carboxylate. To a solution of ethyl 2,5-dioxotetrahydro-1H-pyrrolizine-7a(5H)-carboxylate (257 g, 1.22 mol, 1.00 eq) in EtOH (1300 mL) was slowly added $NaBH_4$ (13.8 g, 365 mmol, 0.30 eq) at 0° C. under $N_2$. The mixture was stirred at 0° C. for 10 min. The reaction was quenched with saturated $NH_4Cl$ (65.0 mL) at 5° C. and stirred at 5° C. for 0.5 hr, then the mixture was concentrated under reduced pressure to give a residue. The residue was purified by column chromatography ($SiO_2$, Petroleum ether/Ethyl acetate=10/1 to 1/1) to afford the title compound (56.8% yield) as a yellow oil. $^1H$ NMR: 400 MHz $CDCl_3$ δ:4.65 (s, 1H), 4.14 (q, J=7.2 Hz, 2H), 3.95 (dd, J=12.8, 6.0 Hz, 1H), 3.10 (d, J=12.8 Hz, 1H), 2.75-2.84 (m, 2H), 2.49-2.49 (m, 2H), 2.39-2.45 (m, 1H), 2.02-2.10 (m, 1H), 1.84 (dd, J=13.6, 6.0 Hz, 1H), 1.30 (t, J=7.2 Hz, 1H).

Step D. ethyl(2S,7aR)-2-fluoro-5-oxotetrahydro-1H-pyrrolizine-7a(5H)-carboxylate. To a solution of ethyl 2-hydroxy-5-oxotetrahydro-1H-pyrrolizine-7a(5H)-carboxylate (150 g, 642 mmol, 1.00 eq) in DCM (750 mL) was added a solution of DAST (131 g, 813 mmol, 107 mL, 1.50 eq) drop-wise at −70° C. under $N_2$. The reaction mixture was warmed to 25° C. stirred at 25° C. for 16 hours. The reaction mixture was quenched with MeOH (40.0 mL) at 10° C., then diluted with water (750 mL) and extracted with DCM (750 mL×3). The combined organic layers were washed with brine (750 mL), dried over $Na_2SO_4$, filtered and concentrated under reduced pressure to give a residue. The residue was purified by column chromatography ($SiO_2$, Petroleum ether/Ethyl acetate=1/0 to 0/1, Rf=0.30) to afford ethyl 2-fluoro-5-oxotetrahydro-1H-pyrrolizine-7a(5H)-carboxylate (50.6% yield, 74.7% purity) as a yellow oil. This compound (61 g, 283.43 mmol, 1.00 eq) was further purified by HPLC (column: Welch ultimate XB—$NH_2$ 250*50*10 um; mobile phase: [Heptane-EtOH (0.1% $NH_3H_2O$)]; B %: 10%-10%, 10 min) to give a yellow oil (49.0 g, 226.08 mmol, 99.3% purity). $^1H$ NMR: 400 MHz $CDCl_3$ δ:5.30 (m, 1H), 4.10-4.23 (m, 3H), 3.11-3.14 (m, 1H), 2.67-2.76 (m, 3H), 2.41-2.45 (m, 1H), 2.03-2.12 (m, 2H), 1.23-1.29 (m, 3H). SFC separation (column: DAICEL CHIRALPAK IC (250 mm*50 mm, 10 um); mobile phase: [0.1% $NH_3{\cdot}H_2O$ IPA]; B %: 40%-40%, 4.7 min; 200 minmin, desired product: Peak 2, Rt=1.959 min) of the racemic material (280 g, 1.22 mol, 1 eq) gave the title compound (114 g, 96.0% purity).

Step E. ((2R,7aS)-2-fluorotetrahydro-1H-pyrrolizin-7a(5H)-yl)methanol. To a suspension of LiAlH4 (33.1 g, 871 mmol, 1.50 eq) in THF (625 mL) was added a solution of ethyl(2S,7aR)-2-fluoro-5-oxotetrahydro-1H-pyrrolizine-7a(5H)-carboxylate (125 g, 581 mmol, 1.00 eq) in THF (375 mL) drop-wise at 0° C. under $N_2$. The reaction mixture was warmed to 70° C. and stirred at 70° C. for 3 hours. The mixture was cooled to 0° C. Then to the mixture was added water (33.0 mL), NaOH (15%, 99.0 mL) and water (99 mL) dropwise in sequence 0° C. After addition, the mixture was stirred at 0° C. stirred for 5 min. The mixture was filtered, and the filtered cake was washed with EtOAc (1000 mL×2). The filtrate was dried with $MgSO_4$, filtered, and concentrated under reduced pressure to give a residue. The residue was purified by column chromatography ($SiO_2$, DCM: MeOH=100/1 to 10/1) to afford the title compound (180 g, 1.10 mol, 94.7% yield, 97.3% purity) as a yellow oil. $^1H$ NMR: 400 MHz $CDCl_3$ δ:5.12-5.27 (m, 1H), 3.25 (s, 2H), 3.14-3.18 (m, 2H), 3.12-3.13 (m, 1H), 3.02-3.09 (m, 1H), 2.01-2.11 (m, 2H), 1.75-1.86 (m, 4H).

Step F. tert-butyl(1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. To the mixture of tert-butyl(1R,5S)-3-(2,7-dichloro-8-fluoropyrido[4,3-d]pyrimidin-4-yl)-3,8-diazabicyclo[3.2.1]octane-8-carboxylate (538 mg, 1.26 mmol, 1.0 eq), ((2R,7aS)-2-fluorotetrahydro-1H-pyrrolizin-7a(5H)-yl)methanol (200 mg, 1.26 mmol, 1.0 eq), DIEA (487 mg, 3.77 mmol, 3.0 eq) in dioxane (6 mL) was added 4 A MS (150 mg). The mixture was stirred at 90° C. for 24 hours. After completion, the reaction mixture was diluted with ethyl acetate (20 mL) and water (15 mL), and then extracted with ethyl acetate (20 mL×2). The combined organic phases were washed with saturated brine 20 mL, dried over $Na_2SO_4$ and concentrated. The residue was purified by reversed phase flash chromatography [water (FA 0.1%)/acetonitrile] to give the title compound (260 mg, 37% yield). Yellow solid. LCMS [ESI, M+1]: 551.2.

Intermediate 17

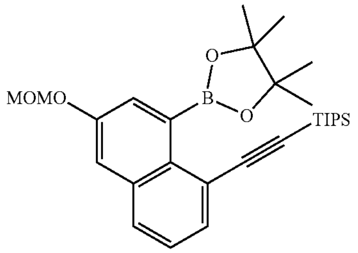

triisopropyl-[2-[6-(methoxymethoxy)-8-(4,4,5,5-tetramethyl-1,3,2-dioxaborolan-2-yl)-1-naphthyl]ethynyl]silane

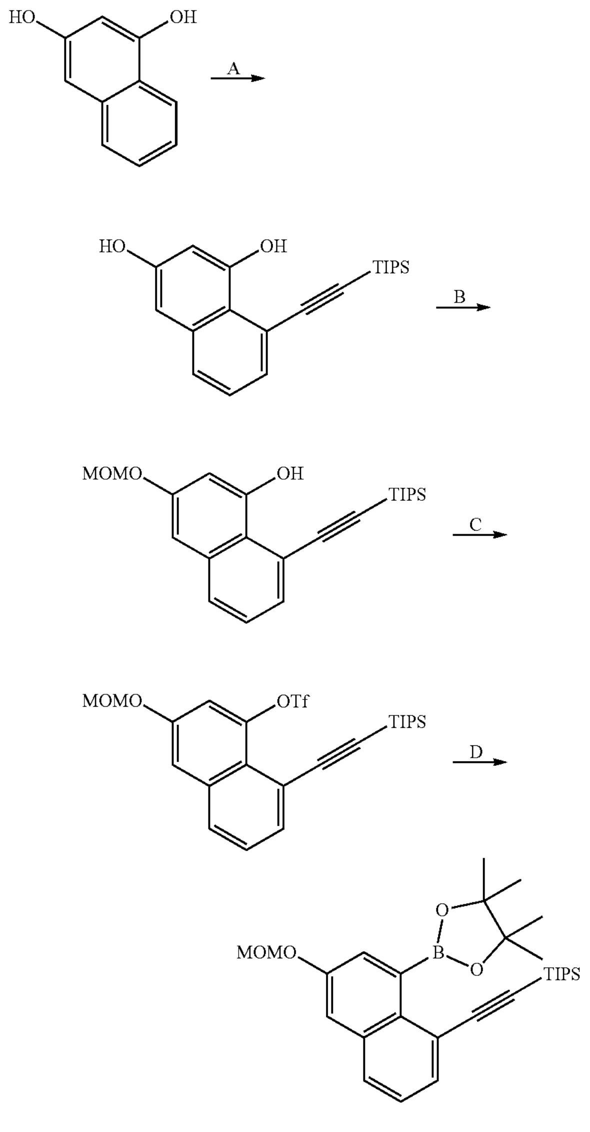

Step A. 8-(2-triisopropylsilylethynyl)naphthalene-1,3 diol. A mixture of naphthalene-1,3-diol (50 g, 312 mmol, 1 eq), 2-bromoethynyl(triisopropyl)silane (97.9 g, 375 mmol, 1.2 eq), dichlororuthenium; 1-isopropyl-4-methyl-benzene (19.1 g, 31.2 mmol, 0.1 eq), AcOK (61.3 g, 624 mmol, 2 eq) in dioxane (600 mL) was stirred at 110° C. for 12 hours. After completion, the mixture was filtered, diluted with water (1 L), and extracted with ethyl acetate (2×1 L). The combined organic layer was washed with brine (1 L), dried over $Na_2SO_4$, filtered and concentrated under vacuum. The residue was purified by column chromatography ($SiO_2$, petroleum ether/ethyl acetate=3/1, Rf=0.68) to give the title compound (100 g, 89% yield). Yellow oil. Rf=0.68 (petroleum ether/ethyl acetate=3/1). LCMS [ESI, M+1]: 341.3.

Step B. 3-(methoxymethoxy)-8-(2-triisopropylsilylethynyl)naphthalen-1-ol. To a mixture of 8-(2-triisopropylsilylethynyl)naphthalene-1,3-diol (180 g, 529 mmol, 1 eq) and DIEA (205 g, 1.59 mol, 276 mL, 3 eq) in dichloromethane (1500 mL) was added MOMCl (63.8 g, 793 mmol, 60.2 mL, 1.5 eq) at 0° C. After stirred at 0° C. for 0.5 hour, the mixture was diluted with water (1 L) and separated. The water phase was extracted with dichloromethane (500 mL). The combined organic layer was washed with brine (1 L), dried over $Na_2SO_4$, filtered and concentrated under vacuum. The residue was purified by column chromatography ($SiO_2$, petroleum ether/ethyl acetate=3/1, Rf=0.6) to give the title compound (126 g, 60% yield). Black solid. LCMS [ESI, M+1]: 285.3. $^1$H NMR (400 MHz, chloroform-d) δ=9.25 (s, 1H), 7.69 (dd, J=0.8, 8.0 Hz, 1H), 7.50 (dd, J=1.2, 7.2 Hz, 1H), 7.31 (dd, J=7.2, 8.4 Hz, 1H), 6.98 (d, J=2.4 Hz, 1H), 6.78 (d, J=2.4 Hz, 1H), 5.27 (s, 2H), 3.51 (s, 3H), 1.20-1.16 (m, 21H).

Step C. [3-(methoxymethoxy)-8-(2-triisopropylsilylethynyl)-1-naphthyl]trifluoromethanesulfonate. To a mixture of 3-(methoxymethoxy)-8-(2-triisopropylsilylethynyl)naphthalen-1-ol (200 g, 520.04 mmol, 1 eq) and DIEA (202 g, 1.56 mol, 272 mL, 3 eq) in dichloromethane (2000 mL) was added $Tf_2O$ (220 g, 780 mmol, 129 mL, 1.5 eq) at −40° C. After stirred at −40° C. for 0.5 hour, the mixture was quenched with water (2 L) and separated. The water phase was extracted with dichloromethane (500 mL). The combined organic layer was washed with brine (1 L), dried over $Na_2SO_4$, filtered and concentrated under vacuum. The residue was purified by column chromatography ($SiO_2$, petroleum ether/ethyl acetate=5/1, Rf=0.24), to give the title compound (250 g, 92% yield). Yellow oil.

Step D. triisopropyl-[2-[6-(methoxymethoxy)-8-(4,4,5,5-tetramethyl-1,3,2-dioxaborolan-2-yl)-1-naphthyl]ethynyl]silane. A mixture of [3-(methoxymethoxy)-8-(2-triisopropylsilylethynyl)-1-naphthyl]trifluoromethanesulfonate (230 g, 445 mmol, 1 eq), 4,4,5,5-tetramethyl-2-(4,4,5,5-tetramethyl-1,3,2-dioxaborolan-2-yl)-1,3,2-dioxaborolane (226 g, 890 mmol, 2 eq), $Pd(dppf)Cl_2$ (32.6 g, 44.5 mmol, 0.1 eq) and KOAc (152.92 g, 1.56 mol, 3.5 eq) in toluene (2 L) was stirred at 110° C. for 3 hours under $N_2$. After completion, the mixture was filtered and concentrated under vacuum. The residue was diluted with water (1 L) and extracted with ethyl acetate (1 L×2). The combined organic layer was washed with brine (1 L), dried over $Na_2SO_4$, filtered and concentrated under vacuum. The residue was purified by column chromatography ($SiO_2$, petroleum ether/ethyl acetate=20/1, Rf=0.39). The compound was triturated with acetonitrile (500 mL) to give 98 g pure product. The filtrate was purified by reversed phase flash chromatography [water (FA, 0.1%)/acetonitrile] to further give 27 g product. Total of the title compound is 125 g (57% yield). Yellow solid. $^1$H NMR (400 MHz, chloroform-d) δ=7.72-7.67 (m, 2H), 7.48 (d, J=2.4 Hz, 1H), 7.40-7.32 (m, 2H), 5.29 (s, 2H), 3.51 (s, 3H), 1.44 (s, 12H), 1.19-1.15 (m, 21H).

Intermediate 18

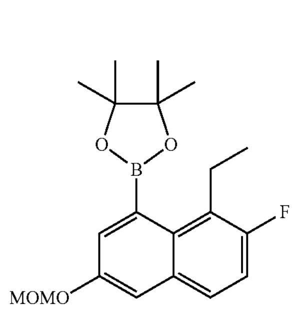

2-(8-ethyl-7-fluoro-3-(methoxymethoxy)naphthalen-1-yl)-4,4,5,5-tetramethyl-1,3,2-dioxaborolane

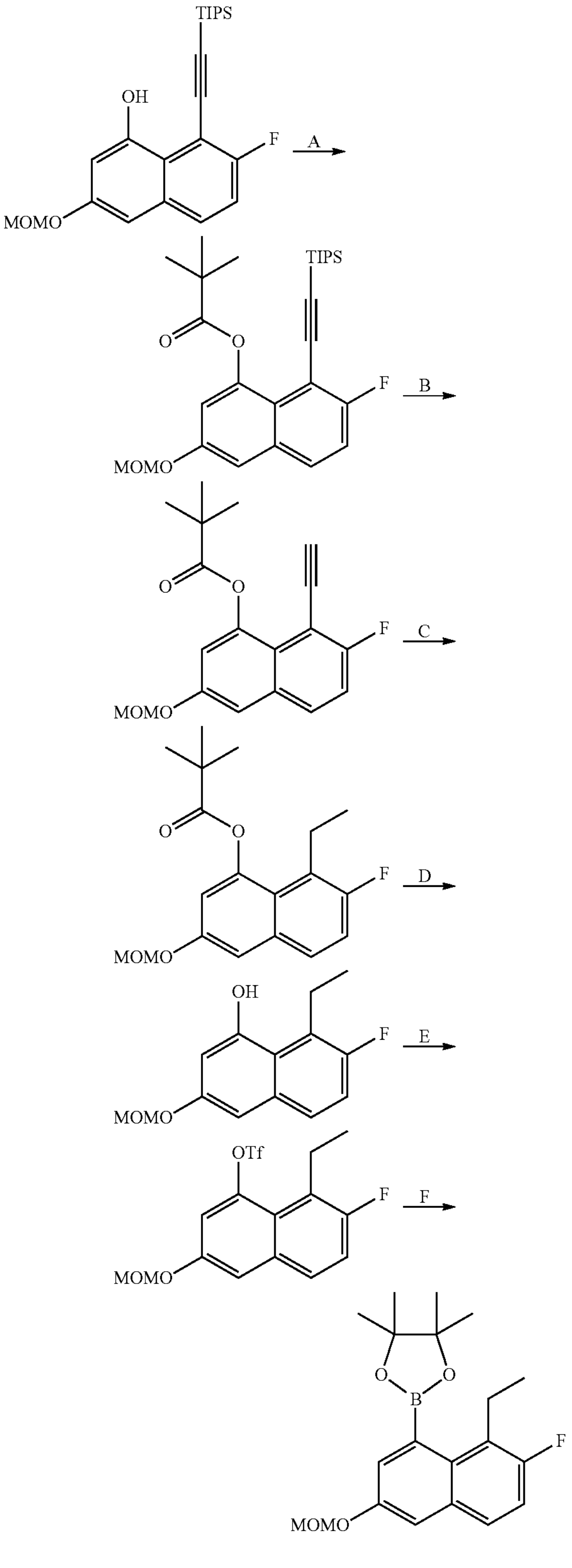

Step A. 7-fluoro-3-(methoxymethoxy)-8-((triisopropylsilyl)ethynyl)naphthalen-1-yl pivalate. To the solution of 7-fluoro-3-(methoxymethoxy)-8-((triisopropylsilyl)ethynyl)naphthalen-1-ol (2.00 g, 4.97 mmol, 1.0 eq), DMAP (122 mg, 999 μmol, 0.2 eq), TEA (1.51 g, 14.9 mmol, 3.0 eq) in DCM (20 mL) was added 2,2-dimethylpropanoyl chloride (1.80 g, 14.9 mmol, 3.0 eq) dropwise at 0° C., and then the mixture was stirred at 20° C. for 1 hour. After completion, the reaction mixture was diluted with DCM (15 mL) and water (15 mL), and then the aqueous layer was extracted with DCM (10 mL), The combined organic phase was dried over $Na_2SO_4$ and concentrated. The residue was purified by column chromatography ($SiO_2$, Petroleum ether/Ethyl acetate=1/0 to 15/1) to give the title compound (3.00 g, crude). Yellow oil. LCMS [ESI, M+1]: 487.2.

Step B. 8-ethynyl-7-fluoro-3-(methoxymethoxy)naphthalen-1-yl pivalate. To the solution of 7-fluoro-3-(methoxymethoxy)-8-((triisopropylsilyl)ethynyl)naphthalen-1-yl pivalate (3.00 g, 6.16 mmol, 1.0 eq) in DMF (50 mL) was added CsF (9.36 g, 61.6 mmol, 10 eq), and the mixture was stirred at 20° C. for 0.25 hour. After completion, to the reaction mixture was added water (250 mL), and then the mixture was extracted with ethyl acetate (2×120 mL). The combined organic phase was washed with brine 100 mL, dried over $Na_2SO_4$ and concentrated to give the title compound (2.20 g, crude). Yellow oil. LCMS [ESI, M+1]: 331.1.

Step C. 8-ethyl-7-fluoro-3-(methoxymethoxy)naphthalen-1-yl pivalate. To the solution of 8-ethynyl-7-fluoro-3-(methoxymethoxy)naphthalen-1-yl pivalate (2.00 g, 6.05 mmol, 1.0 eq) in MeOH (20 mL) was added Pd/C (200 mg, 10% purity) under $N_2$. The suspension was degassed under vacuum and purged with $H_2$ several times. The mixture was stirred under $H_2$ (15 psi) at 20° C. for 20 minutes. After completion, the mixture was filtered and concentrated to give the title compound (1.06 g, crude). LCMS [ESI, M+1]: 335.1.

Step D. 8-ethyl-7-fluoro-3-(methoxymethoxy)naphthalen-1-ol. To the solution of 8-ethyl-7-fluoro-3-(methoxymethoxy)naphthalen-1-yl pivalate (1.00 g, 2.99 mmol, 1.0 eq) in MeOH (15 mL) was added KOH (504 mg, 8.98 mmol, 3.0 eq), and the mixture was stirred at 20° C. for 0.5 hour. After completion, the reaction solution was adjusted to pH=4 with 0.5 M HCl at 0° C. and extracted with ethyl acetate (80 mL×2), the combined organic phase was washed with brine 50 mL, dried over anhydrous sodium sulfate, filtered and concentrated. The residue was purified by column chromatography ($SiO_2$, Petroleum ether/Ethyl acetate=50/1 to 10/1) to give the title compound (570 mg, four steps 51% yield). Yellow solid. $^1H$ NMR (400 MHz, $CDCl_3$) δ=7.55-7.43 (m, 1H), 7.18 (t, J=9.2 Hz, 1H), 6.98 (d, J=2.4 Hz, 1H), 6.57 (d, J=2.0 Hz, 1H), 5.32 (s, 1H), 5.25 (s, 2H), 3.52 (s, 3H), 3.40-3.25 (m, 2H), 1.30 (t, J=7.6 Hz, 3H).

Step E. 8-ethyl-7-fluoro-3-(methoxymethoxy)naphthalen-1-yl trifluoromethane sulfonate. To the solution of 8-ethyl-7-fluoro-3-(methoxymethoxy)naphthalen-1-ol (520 mg, 2.08 mmol, 1.0 eq), DIEA (806 mg, 6.24 mmol, 3.0 eq) in DCM (10 mL), trifluoromethylsulfonyl trifluoromethanesulfonate (879 mg, 3.12 mmol, 1.5 eq) was added dropwise at −40° C., and then the mixture was stirred at −40° C. for 0.5 hr. After completion, the reaction mixture was quenched with ice-water (15 mL), and then extracted with DCM (2×15 mL). The combined organic phase was dried over $Na_2SO_4$ and concentrated. The residue was purified by column chromatography ($SiO_2$, Petroleum ether/Ethyl acetate=100/1 to 30/1) to give the title compound (620 mg, 78% yield). Yellow oil. $^1H$ NMR (400 MHz, $CDCl_3$) δ=7.67-7.59 (m, 1H), 7.43 (d, J=2.4 Hz, 1H), 7.37 (d, J=2.4

Hz, 1H), 7.33-7.27 (m, 1H), 5.29 (s, 2H), 3.53 (s, 3H), 3.33-3.14 (m, 2H), 1.25 (t, J=7.6 Hz, 3H).

Step F. 2-(8-ethyl-7-fluoro-3-(methoxymethoxy)naphthalen-1-yl)-4,4,5,5-tetramethyl-1,3,2-dioxaborolane. To the mixture of 8-ethyl-7-fluoro-3-(methoxymethoxy)naphthalen-1-yl trifluoromethane sulfonate (500 mg, 1.31 mmol, 1.0 eq), 4,4,5,5-tetramethyl-2-(4,4,5,5-tetramethyl-1,3,2-dioxaborolan-2-yl)-1,3,2-dioxaborolane (665 mg, 2.62 mmol, 2.0 eq), AcOK (385 mg, 3.92 mmol, 3.0 eq) in dioxane (6 mL) was added Pd(dppf)$Cl_2$ (96.0 mg, 131 μmol, 0.1 eq) under $N_2$. The mixture was degassed and stirred at 100° C. for 1 hour. After completion, the mixture was diluted with ethyl acetate (20 mL) and water (10 mL), and extracted with ethyl acetate (10 mL). The combined organic phases were washed with saturated brine (10 mL), dried over anhydrous sodium sulfate, filtered and concentrated. The residue was purified by column chromatography ($SiO_2$, Petroleum ether/Ethyl acetate=100/1 to 25/1) to give the title compound (143 mg, 30% yield). Yellow oil. $^1H$ NMR (400 MHz, $CDCl_3$) δ=7.62-7.53 (m, 1H), 7.44-7.34 (m, 2H), 7.21 (t, J=9.2 Hz, 1H), 5.28 (s, 2H), 3.51 (s, 3H), 3.20-3.06 (m, 2H), 1.45 (s, 12H), 1.30-1.25 (m, 3H).

Intermediate 19

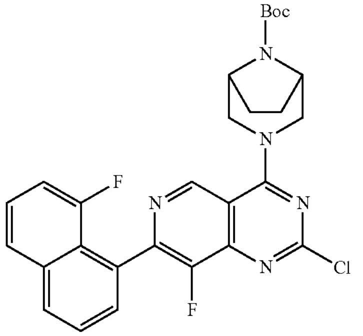

tert-butyl(1R,5S)-3-(2-chloro-8-fluoro-7-(8-fluoronaphthalen-1-yl)pyrido[4,3-d]pyrimidin-4-yl)-3,8-diazabicyclo[3.2.1]octane-8-carboxylate

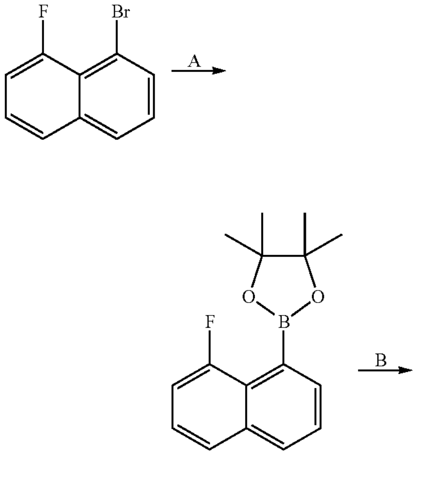

-continued

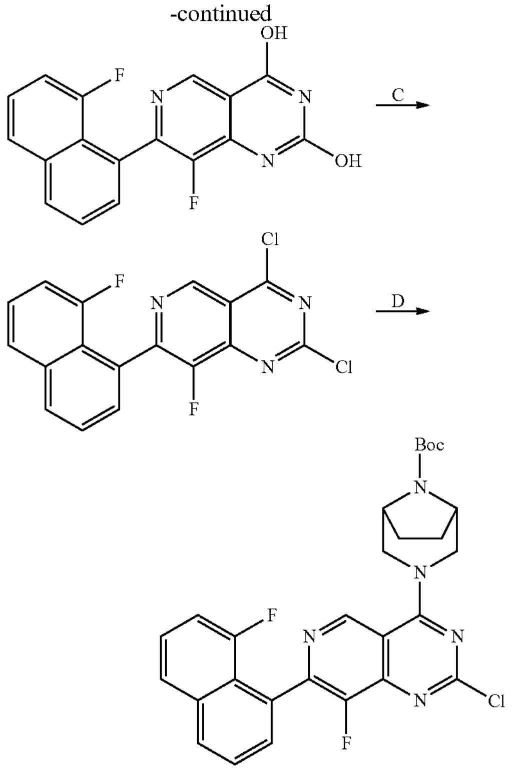

Step A. 2-(8-fluoronaphthalen-1-yl)-4,4,5,5-tetramethyl-1,3,2-dioxaborolane. A solution of 1-bromo-8-fluoronaphthalene (55.0 g, 244 mmol, 1.00 eq) in THF (850 mL) was degassed and purged with $N_2$ for 3 times, and then n-BuLi (2.5 M, 117 mL, 1.20 eq) was added drop-wise at −70° C. The mixture was stirred at −70° C. for 1 hr under $N_2$ atmosphere. Then added a solution of 2-isopropoxy-4,4,5,5-tetramethyl-1,3,2-dioxaborolane (63.6 g, 342 mmol, 69.8 mL, 1.40 eq) in THF (150 mL) at −70° C. The resulting mixture was stirred at −70° C. for 1 hr. LCMS showed 1-bromo-8-fluoronaphthalene was consumed completely and one main peak with desired mass (RT=1.073 min) was detected. The reaction mixture was quenched by $NH_4Cl$ solution (500 mL) at 10° C., then diluted with $H_2O$ (300 mL) and extracted with PE (500 mL×3). The combined organic layers were washed with brine (500 mL×2), dried over $Na_2SO_4$, filtered and concentrated under reduced pressure to give a residue. The residue was purified by flash silica gel chromatography (ISCO®; 100 g SepaFlash® Silica Flash Column, Eluent of 0~4% Ethyl acetate/Petroleum ether, TLC:Petroleum ether/Ethyl acetate=10/1, Rf=0.67) to give compound the title compound (30.0 g, 110 mmol, 45.1% yield, 100% purity) as a light yellow solid. LCMS: M+1, 273.

Step B. 8-fluoro-7-(8-fluoronaphthalen-1-yl)pyrido[4,3-d]pyrimidine-2,4-diol. To a solution of 2-(8-fluoronaphthalen-1-yl)-4,4,5,5-tetramethyl-1,3,2-dioxaborolane (947 mg, 3.48 mmol, 1.50 eq) and 7-chloro-8-fluoropyrido[4,3-d]pyrimidine-2,4-diol (0.50 g, 2.32 mmol, 1.0 eq) in EtOH (15 mL) were added $K_3PO_4$ (1.50 M, 4.64 mL, 3.0 eq) and Ad2nBuP Pd G3 (cataCXium® A Pd G3) (253 mg, 348 μmol, 0.15 eq) under $N_2$. The mixture was stirred at 80° C. for 2 hours. The reaction mixture was diluted with water (100 mL) and extracted with ethyl acetate (3×200 mL). The combined organic layers were dried over $Na_2SO_4$, filtered and concentrated under reduced pressure to give a residue.

The residue was purified by reversed phase flash chromatography (C18, 0.1% FA in water, 0-40% ACN) to give the title compound (800 mg, 50% yield); White solid. $^1H$ NMR (400 MHz, chloroform-d) δ 11.24-9.47 (m, 2H), 9.04 (s, 1H), 8.01-7.85 (m, 1H), 7.66 (d, J=8.4 Hz, 1H), 7.57-7.32 (m, 3H), 7.09-6.96 (m, 1H). LCMS [ESI, M+1]: 326.1.

Step C. 2,4-dichloro-8-fluoro-7-(8-fluoronaphthalen-1-yl)pyrido[4,3-d]pyrimidine. To a solution of 8-fluoro-7-(8-fluoronaphthalen-1-yl)pyrido[4,3-d]pyrimidine-2,4-diol (800 mg, 2.46 mmol, 1.0 eq) in $POCl_3$ (10 mL) was added DIEA (954 mg, 7.38 mmol, 1.29 mL, 3.0 eq) under $N_2$. The mixture was stirred at 110° C. for 1 hour. The mixture was concentrated under vacuum to give the title compound (900 mg, crude). Black oil.

Step D. (1R,5S)-tert-butyl 3-(2-chloro-8-fluoro-7-(8-fluoronaphthalen-1-yl)pyrido[4,3-d]pyrimidin-4-yl)-3,8-diazabicyclo[3.2.1]octane-8-carboxylate. To a solution of 2,4-dichloro-8-fluoro-7-(8-fluoronaphthalen-1-yl)pyrido[4,3-d]pyrimidine (390 mg, 872 μmol, 81% purity, 1.0 eq) in DMAc (10 mL) were added DIEA (338 mg, 2.62 mmol, 456 μL, 3.0 eq) and tert-butyl 3,8-diazabicyclo[3.2.1]octane-8-carboxylate (194 mg, 916 μmol, 1.05 eq). The mixture was stirred at 20° C. for 1 hour. The reaction mixture was diluted with water (30 mL) and extracted with ethyl acetate (3×10 mL). The combined organic layers were dried over $Na_2SO_4$, filtered and concentrated under reduced pressure to give a residue. The residue was purified by reversed phase flash chromatography (C18, 0.1% FA in water, 0-90% ACN) affording the title compound (420 mg, two steps yield: 32%). Yellow solid. $^1H$ NMR (400 MHz, chloroform-d) δ 9.13 (s, 1H), 8.05-7.98 (m, 1H), 7.75 (d, J=8.0 Hz, 1H), 7.68-7.55 (m, 2H), 7.51-7.42 (m, 1H), 7.18-7.08 (m, 1H), 4.80-4.51 (m, 2H), 4.50-4.27 (m, 2H), 3.95-3.56 (m, 2H), 2.04-1.93 (m, 2H), 1.85-1.72 (m, 2H), 1.53 (s, 9H). LCMS [ESI, M+1]: 538.2.

Intermediate 20

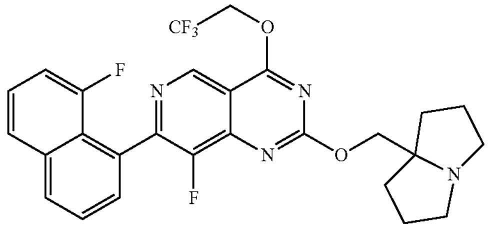

8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine

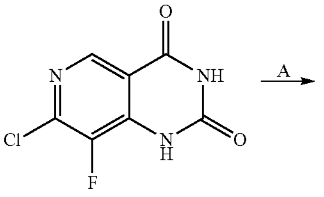

-continued

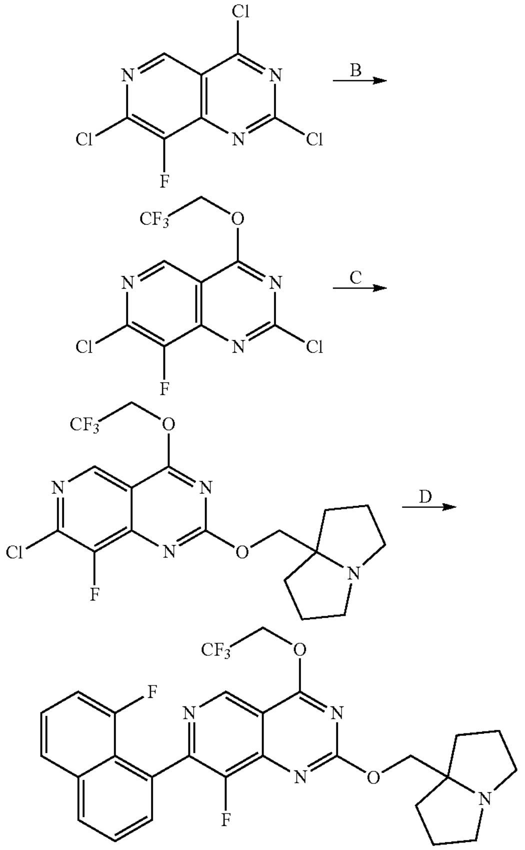

Step A. 2,4,7-trichloro-8-fluoropyrido[4,3-d]pyrimidine. To a solution of 7-chloro-8-fluoropyrido[4,3-d]pyrimidine-2,4 (1H,3H)-dione (100 g, 463 mmol, 1.00 eq) in toluene (500 mL) were added $POCl_3$ (213 g, 1.39 mol, 129 mL, 3.00 eq) and DIEA (179 g, 1.39 mol, 242 mL, 3.00 eq) at 0° C. The mixture was stirred at 110° C. for 5 h. The reaction was distilled in vacuum (80° C., water pump) to give 2,4,7-trichloro-8-fluoropyrido[4,3-d]pyrimidine (100 g, 396.10 mmol, 85.39% yield) as brown oil.

Step B. 2,7-dichloro-8-fluoro-4-(2,2,2-trifluoroethoxy) pyrido[4,3-d]pyrimidine. To a solution of 2,4,7-trichloro-8-fluoropyrido[4,3-d]pyrimidine (100 g, 396 mmol, 1.00 eq) and 2,2,2-trifluoroethanol (59.4 g, 594 mmol, 42.7 mL, 1.50 eq) in toluene (2 L) was added t-BuONa (152 g, 1.58 mol, 4.00 eq) at 25° C. The mixture was stirred at 25° C. for 2 hr. The reaction mixture was filtered through a pad of Celite, washed with brine (3 L×2) and concentrated under reduced pressure to give a residue, which was purified by reversed-phase HPLC (0.1% FA condition) to give 2,7-dichloro-8-fluoro-4-(2,2,2-trifluoroethoxy)pyrido[4,3-d]pyrimidine (45.0 g, 140 mmol, 35.5% yield, 99.0% purity) as a brown solid. LCMS: M+1, 316.

Step C. 7-chloro-8-fluoro-2-((tetrahydro-1H-pyrrolizin-7a(5H)-yl)methoxy)-4-(2,2,2-trifluoroethoxy)pyrido[4,3-d] pyrimidine. A mixture of (tetrahydro-1H-pyrrolizin-7a(5H)-yl)methanol (35.7 g, 253 mmol, 2.00 eq), DIEA (32.7 g, 253 mmol, 44.0 mL, 2.00 eq) and 4 A MS (40.0 g) in 2-methyltetrahydrofuran (400 mL) was stirred at 25° C. for 1 hr. Then a solution of 2,7-dichloro-8-fluoro-4-(2,2,2-trifluoroethoxy)pyrido[4,3-d]pyrimidine (40.0 g, 126 mmol, 1.00 eq) in 2-methyltetrahydrofuran (400 mL) was added and the resulting mixture was stirred at 25° C. for 2 hrs. The reaction mixture was filtered. The filtrate was washed with sat. aq. $NH_4Cl$ solution (1 L×2), dried over $Na_2SO_4$, filtered and concentrated under reduced pressure to give a residue. The residue was triturated with acetonitrile (300 mL) at 25° C. for 30 min to give 7-chloro-8-fluoro-2-((tetrahydro-1H-pyrrolizin-7a(5H)-yl)methoxy)-4-(2,2,2-trifluoroethoxy)pyrido[4,3-d]pyrimidine (26.0 g, 61.1 mmol, 48.3% yield, 99.0% purity) as a light yellow solid. LCMS: M+1, 421.

Step D. 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine. A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (17.0 g, 40.4 mmol, 1.00 eq), 2-(8-fluoronaphthalen-1-yl)-4,4,5,5-tetramethyl-1,3,2-dioxaborolane (16.4 g, 60.6 mmol, 1.50 eq), BrettPhos Pd G3 (4.25 g, 4.69 mmol, 1.16e-1 eq), $K_3PO_4$ (1.5 M, 80.8 mL, 3.00 eq) in toluene (170 mL) was degassed and purged with $N_2$ for 3 times, and then the mixture was stirred at 65° C. for 4 hrs under $N_2$ atmosphere. The reaction mixture was filtered. The filtrate was extracted with toluene (170 mL×3). The combined organic layers were dried over $Na_2SO_4$, filtered and concentrated under reduced pressure to give a residue. The residue was purified by reversed-phase HPLC (0.1% FA condition) to give 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (10.85 g, 16.6 mmol, 41.2% yield, 95.8% purity) as a yellow solid. NMR: δ 9.28 (s, 1H), 8.23 (d, J=8.1 Hz, 1H), 7.97 (d, J=8.1 Hz, 1H), 7.81-7.76 (m, 1H), 7.68 (dd, J=0.9, 7.2 Hz, 1H), 7.61 (dt, J=5.1, 7.9 Hz, 1H), 7.34 (dd, J=7.1, 13.3 Hz, 1H), 5.47-5.37 (m, 2H), 4.77-4.67 (m, 2H), 3.56-3.49 (m, 2H), 3.22 (td, J=6.0, 11.7 Hz, 2H), 2.27-2.00 (m, 8H); LCMS: M+1, 531.

Intermediate 21

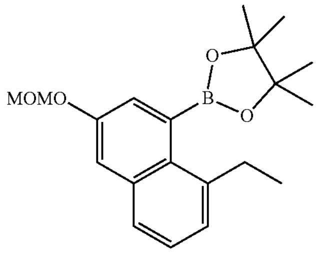

2-[8-ethyl-3-(methoxymethoxy)-1-naphthyl]-4,4,5,5-tetramethyl-1,3,2-dioxaborolane

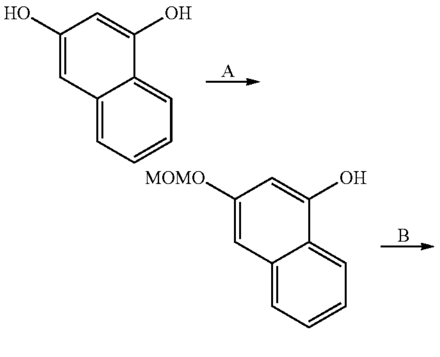

-continued

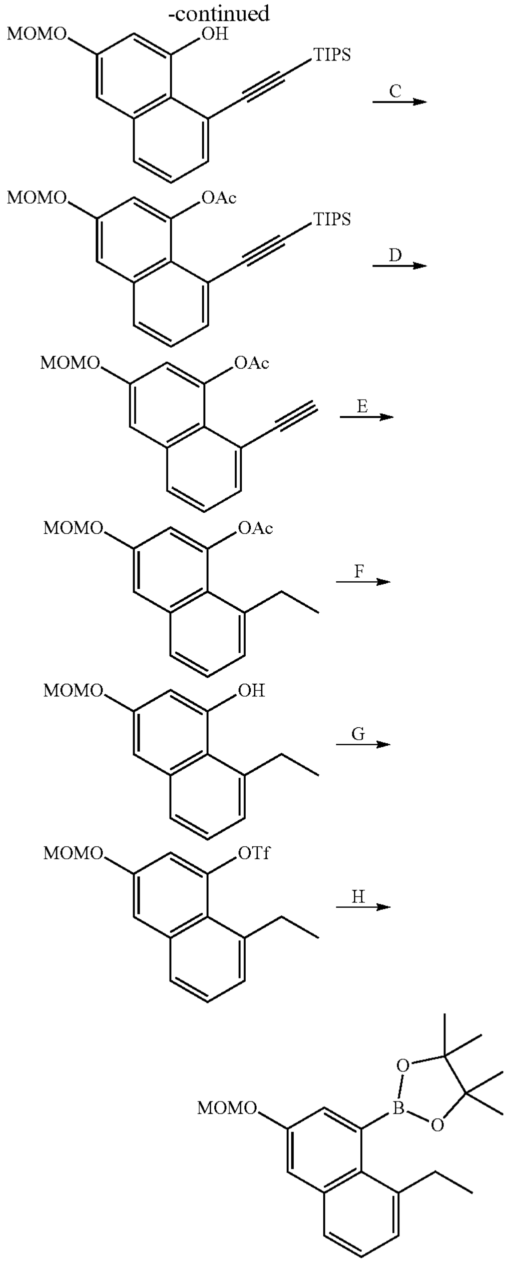

Step A. 3-(methoxymethoxy)naphthalen-1-ol. To a solution of naphthalene-1,3-diol (50 g, 312 mmol, 1.0 eq) and DIEA (120 g, 935 mmol, 163 mL, 3.0 eq) in dichloromethane (400 mL) was added chloro(methoxy)methane (27.5 g, 342 mmol, 1.1 eq) dropwise at 0~5° C. over 30 minutes. The mixture was stirred at 25° C. for 16 hours. The reaction mixture was quenched with saturated $NaHCO_3$ aqueous solution (100 mL) below 5° C. and diluted with $H_2O$ (300 mL). The organic layer was separated and $H_2O$ (100 mL) was added. The pH of the mixture was adjusted to 3~4 with 2N HCl below 10° C. The organic layer was separated, dried over $Na_2SO_4$, filtered and concentrated under reduced pressure to give a residue. The residue was purified by silica gel column chromatography (petroleum ether/ethyl acetate=10/1, 8/1) to give the title compound (31.3 g, 49% yield). Red brown liquid. $^1H$ NMR (400 MHz, chloroform-d) δ=8.17-8.08 (m, 1H), 7.71-7.61 (m, 1H), 7.45-7.30 (m, 2H), 7.02-6.63 (m, 2H), 5.38-5.28 (m, 2H), 3.56-3.53 (m, 3H).

Step B. 3-(methoxymethoxy)-8-(2-triisopropylsilylethynyl)naphthalen-1-ol. A mixture of 3-(methoxymethoxy) naphthalen-1-ol (20 g, 97.9 mmol, 1.0 eq), (bromoethynyl) triisopropylsilane (32 g, crude), $K_2CO_3$ (13.6 g, 98.4 mmol, 1.0 eq), sodium acetate (2 g, 24.4 mmol, 0.25 eq) and dichlororuthenium; 1-isopropyl-4-methyl-benzene dimer (9.00 g, 14.7 mmol, 0.15 eq) in DCE (200 mL) was degassed and purged with $N_2$ for 3 times. The mixture was stirred at 40° C. for 13 hours under $N_2$ atmosphere. The reaction mixture was filtered through a pad of Celite. The filtrate was concentrated under reduced pressure to give a residue. The residue was purified by silica gel column chromatography ($SiO_2$, petroleum ether/ethyl acetate=1/0 to 50/1) to give the title compound (10.6 g, 28% yield). Yellow liquid. $^1$H NMR (400 MHz, chloroform-d) δ=9.26 (s, 1H), 7.69 (dd, J=0.8, 8.4 Hz, 1H), 7.50 (dd, J=1.2, 7.2 Hz, 1H), 7.33-7.29 (m, 1H), 6.97 (d, J=2.4 Hz, 1H), 6.77 (d, J=2.4 Hz, 1H), 5.27 (s, 2H), 3.52 (s, 3H), 1.29-1.14 (m, 21H).

Step C. 3-(methoxymethoxy)-8-(2-triisopropylsilylethynyl)-1-naphthyl acetate. To a mixture of 3-(methoxymethoxy)-8-(2-triisopropylsilylethynyl)naphthalen-1-ol (10 g, 26.0 mmol, 1.0 eq) and DIEA (8.40 g, 65.0 mmol, 11.3 mL, 2.5 eq) in dichloromethane (100 mL) was added acetyl chloride (3.06 g, 39.0 mmol, 2.78 mL, 1.5 eq) at 0° C. The mixture was stirred at 0° C. for 0.5 hour. After completion, the mixture was diluted with water (100 mL) and separated. The water phase was extracted with dichloromethane (50 mL). The combined organic layer was washed with brine (70 mL), dried over $Na_2SO_4$, filtered and concentrated under vacuum. The residue was purified by column chromatography ($SiO_2$, petroleum ether/ethyl acetate=3/1.) to give the title compound (9 g, 80% yield). Yellow oil. Rf=0.28 (petroleum ether/ethyl acetate=3/1). $^1$H NMR (400 MHz, chloroform-d) δ=7.72 (dd, J=0.8, 8.4 Hz, 1H), 7.67 (dd, J=1.2, 7.2 Hz, 1H), 7.36 (dd, J=7.2, 8.4 Hz, 1H), 7.32 (d, J=2.4 Hz, 1H), 6.96 (d, J=2.4 Hz, 1H), 5.28 (s, 2H), 3.52 (s, 3H), 2.44 (s, 3H), 1.19 (s, 21H).

Step D. 8-ethynyl-3-(methoxymethoxy)naphthalen-1-yl acetate. A mixture of 3-(methoxymethoxy)-8-(2-triisopropylsilylethynyl)-1-naphthyl acetate (9.3 g, 21.8 mmol, 1 eq) and CsF (23.2 g, 153 mmol, 5.63 mL, 7 eq) in DMF (90 mL) was stirred at 25° C. for 1 hour. After completion, the mixture was diluted with ethyl acetate (150 mL), washed with brine (3×100 mL), dried over $Na_2SO_4$, filtered and concentrated under vacuum. The residue was purified by column chromatography ($SiO_2$, petroleum ether/ethyl acetate=3/1) to give the title compound (2.5 g, 42% yield). Yellow oil. Rf=0.21 (petroleum ether/ethyl acetate=3/1). [ESI, M+1]: 271.2

Step E. [8-ethyl-3-(methoxymethoxy)-1-naphthyl]acetate. A mixture of [8-ethynyl-3-(methoxymethoxy)-1-naphthyl]acetate (2.5 g, 9.25 mmol, 1 eq) and Pd/C (60 mg, 10% purity) in methanol (10 mL) was stirred at 25° C. for 10 minutes under $H_2$ at 15 psi. After completion, the mixture was filtered and concentrated under vacuum to give the title compound (2.1 g, 83% yield) and used in the next step without further purification. Yellow oil. [ESI, M−41]: 233.3.

Step F. 8-ethyl-3-(methoxymethoxy)naphthalen-1-ol. A mixture of [8-ethyl-3-(methoxymethoxy)-1-naphthyl]acetate (2 g, 7.29 mmol, 1 eq) and LiOH (873 mg, 36.5 mmol, 5 eq) in THF (20 mL) and $H_2O$ (6 mL) was stirred at 25° C. for 1 hour. After completion, the mixture was diluted with water (50 mL), and extracted with ethyl acetate (2×50 mL). The combined organic layer was washed with brine. The residue was purified by column chromatography ($SiO_2$, petroleum ether/ethyl acetate=5/1,) to give the title compound (1.42 g, 66% yield). Yellow oil. Rf=0.26 (petroleum ether/ethyl acetate=5/1). $^1$H NMR (400 MHz, chloroform-d) δ=7.53 (d, J=8.0 Hz, 1H), 7.3 (t, J=3.6 Hz, 1H), 7.11 (d, J=7.2 Hz, 1H), 7.00 (d, J=2.4 Hz, 1H), 6.55 (d, J=2.4 Hz, 1H), 5.27 (s, 2H), 3.53 (s, 3H), 3.30 (q, J=7.4 Hz, 2H), 1.33 (t, J=7.2 Hz, 3H).

Step G. [8-ethyl-3-(methoxymethoxy)-1-naphthyl]trifluoromethanesulfonate. To a mixture of 8-ethyl-3-(methoxymethoxy)naphthalen-1-ol (1.4 g, 6.03 mmol, 1 eq) and DIEA (3.12 g, 24.1 mmol, 4.20 mL, 4 eq) in dichloromethane (20 mL) was added $Tf_2O$ (2.55 g, 9.04 mmol, 1.49 mL, 1.5 eq) at −40° C. The mixture was stirred at −40° C. for 0.5 hour. After completion, the mixture was diluted with water (20 mL) and separated. The water phase was extracted with dichloromethane (10 mL), and the combined organic layer was washed with brine (20 mL), dried over $Na_2SO_4$, filtered and concentrated under vacuum. The residue was purified by column chromatography ($SiO_2$, petroleum ether/ethyl acetate=5/1, Rf=0.67) to give the title compound (1.87 g, 83% yield). Yellow oil. Rf=0.67 (petroleum ether/ethyl acetate=5/1).

Step H. 2-[8-ethyl-3-(methoxymethoxy)-1-naphthyl]-4,4,5,5-tetramethyl-1,3,2-dioxaborolane. A mixture of [8-ethyl-3-(methoxymethoxy)-1-naphthyl]trifluoromethanesulfonate (1.8 g, 4.94 mmol, 1 eq), 4,4,5,5-tetramethyl-2-(4,4,5,5-tetramethyl-1,3,2-dioxaborolan-2-yl)-1,3,2-dioxaborolane (3.14 g, 12.4 mmol, 2.5 eq), KOAc (1.21 g, 12.4 mmol, 2.5 eq) and Pd(dppf)$Cl_2$ (362 mg, 494 μmol, 0.1 eq) in dioxane (20 mL) was stirred at 110° C. for 2 hours. After completion, the mixture was diluted with water (20 mL) and extracted with ethyl acetate (2×20 mL). The combined organic layer was washed with brine (20 mL), dried over $Na_2SO_4$, filtered and concentrated under vacuum. The residue was purified by column chromatography ($SiO_2$, petroleum ether/ethyl acetate=30/1) to give the title compound (810 mg, 46% yield). Yellow oil. Rf=0.7 (petroleum ether/ethyl acetate=10/1). $^1$H NMR (400 MHz, chloroform-d) δ=7.60 (dd, J=0.8, 8.0 Hz, 1H), 7.42 (d, J=2.8 Hz, 1H), 7.40-7.33 (m, 2H), 7.27-7.24 (m, 1H), 5.30 (s, 2H), 3.52 (s, 3H), 3.19 (q, J=7.2 Hz, 2H), 1.45 (s, 12H), 1.36 (t, J=7.2 Hz, 3H).

Intermediate 22

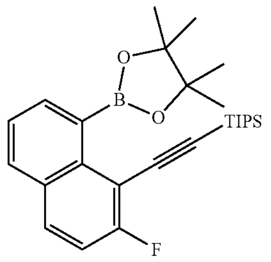

((2-fluoro-8-(4,4,5,5-tetramethyl-1,3,2-dioxaborolan-2-yl)naphthalen-1-yl)ethynyl)triisopropylsilane

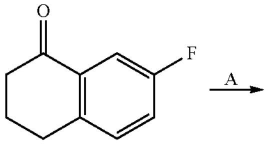

-continued

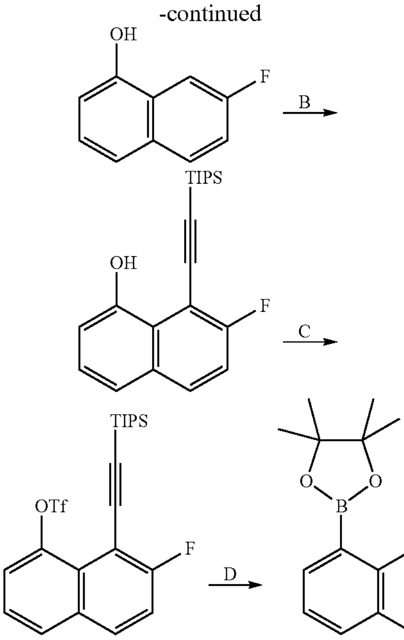

Step A. 7-fluoronaphthalen-1-ol. To a solution of 7-fluoro-3,4-dihydronaphthalen-1(2H)-one (75.0 g, 457 mmol, 1.00 eq) in acetic acid (1.50 L) and hydrogen bromide in AcOH (33%, 7.50 mL) was added bromine (80.3 g, 503 mmol, 25.9 mL, 1.1 eq) in acetic acid (50 mL) at 0° C., and the mixture was stirred at 25° C. for 3 hours. The mixture was diluted with DCM (1.5 L), washed with water (3×500 mL). The organic layer was dried over anhydrous sodium sulfate, filtered and concentrated to afford a brown oil, which was dissolved in DMF (750 mL). Lithium bromide (67.4 g, 777 mmol, 19.5 mL, 1.70 eq), lithium carbonate (57.4 g, 777 mmol, 1.70 eq) were added. The reaction mixture was stirred at 160° C. for 3.5 hours. The reaction was diluted with ethyl acetate (1.00 L), washed with brine (2×500 mL), dried with anhydrous sodium sulfate, filtered and concentrated in vacuum to give a residue. The residue was purified by silica gel chromatography (petroleum ether/ethyl acetate=1/0 to 5/1) affording the title compound (61.0 g, 82% yield). Brown solid; $^1$H NMR (400 MHz, $CDCl_3$) δ=7.84-7.77 (m, 2H), 7.44 (d, J=8.0 Hz, 1H), 7.31-7.24 (m, 2H), 6.84 (d, J=7.6 Hz, 1H), 5.39 (s, 1H).

Step B. 7-fluoro-8-(2-triisopropylsilylethynyl)naphthalen-1-ol. To a solution of (bromoethynyl)triisopropylsilane (72.0 g, 275 mmol, 1.20 eq) and 7-fluoronaphthalen-1-ol (37.2 g, 230 mmol, 1.0 eq) in DCE (500 mL) were added dichlororuthenium; 1-isopropyl-4-methyl-benzene (21.1 g, 34.4 mmol, 0.15 eq), $K_2CO_3$ (31.7 g, 230 mmol, 1.0 eq) and NaOAc (3.77 g, 45.9 mmol, 0.20 eq). The mixture was stirred at 40° C. for 12 hours. The reaction mixture was filtered and concentrated under reduced pressure to give a residue. The residue was purified by column chromatography ($SiO_2$, petroleum ether/ethyl acetate=1/0 to 50/1) affording the title compound (73.0 g, 93% yield). Yellow oil; $^1$H NMR (400 MHz, $CDCl_3$) δ 9.10 (s, 1H), 7.79 (dd, J=5.6, 8.8 Hz, 1H), 7.41-7.33 (m, 2H), 7.23 (t, J=8.8 Hz, 1H), 7.08-7.00 (m, 1H), 1.24-1.14 (m, 21H); LCMS [ESI, M+1, 2M+1]: 343.1, 685.3.

Step C. [7-fluoro-8-(2-triisopropylsilylethynyl)-1-naphthyl]trifluoromethanesulfonate. To a solution of 7-fluoro-8-(2-triisopropylsilylethynyl)naphthalen-1-ol (73.0 g, 213 mmol, 1.00 eq) in DCM (600 mL) were added DIEA (55.1 g, 426 mmol, 74.2 mL, 2.00 eq) and $Tf_2O$ (90.2 g, 320 mmol, 52.7 mL, 1.50 eq) at −40° C. The mixture was stirred at −40° C. for 0.5 hour. The combined reaction mixture was filtered and concentrated under reduced pressure to give a residue. The mixture was purified by column chromatography ($SiO_2$, petroleum ether/ethyl acetate=1/0 to 50/1) affording the title compound (78.0 g, 77% yield). Yellow solid; $^1$H NMR (400 MHz, $CDCl_3$) δ 7.88-7.79 (m, 2H), 7.59-7.52 (m, 1H), 7.46 (t, J=8.0 Hz, 1H), 7.37 (t, J=8.8 Hz, 1H), 1.32-1.16 (m, 21H).

Step D. ((2-fluoro-8-(4,4,5,5-tetramethyl-1,3,2-dioxaborolan-2-yl)naphthalen-1-yl)ethynyl)triisopropylsilane. To a solution of [7-fluoro-8-(2-triisopropylsilylethynyl)-1-naphthyl]trifluoromethanesulfonate (20.0 g, 42.1 mmol, 1.00 eq) and bis(pinacolato)diboron (16.0 g, 63.2 mmol, 1.50 eq) in dioxane (6.00 mL) were added KOAc (8.27 g, 84.3 mmol, 2.0 eq) and Pd(dppf)$Cl_2$ (3.08 g, 4.21 mmol, 0.10 eq). The mixture was stirred at 110° C. for 12 hours. The mixture was filtered and concentrated under reduced pressure to give a residue. The residue was purified by column chromatography ($SiO_2$, petroleum ether/ethyl acetate=1/0 to 10/1) affording the title compound (9.0 g, 47% yield). Yellow solid; $^1$H NMR (400 MHz, $CDCl_3$) δ 7.85-7.75 (m, 3H), 7.43 (dd, J=7.2, 8.0 Hz, 1H), 7.30-7.24 (m, 1H), 1.45 (s, 12H), 1.21-1.14 (m, 21H); LCMS [ESI, M+1]: 453.2.

Intermediate 23

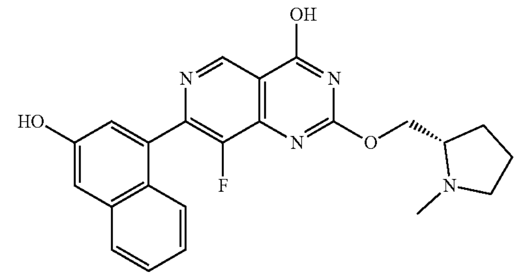

(S)-8-fluoro-7-(3-hydroxynaphthalen-1-yl)-2-((1-methylpyrrolidin-2-yl)methoxy)pyrido[4,3-d]pyrimidin-4-ol

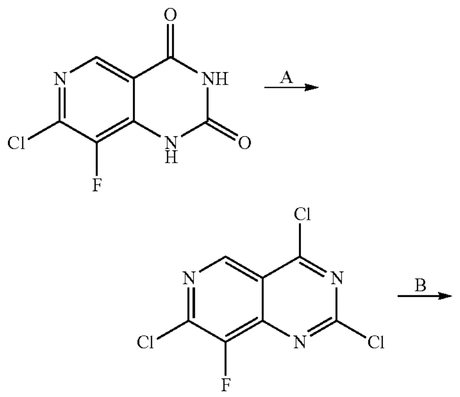

-continued

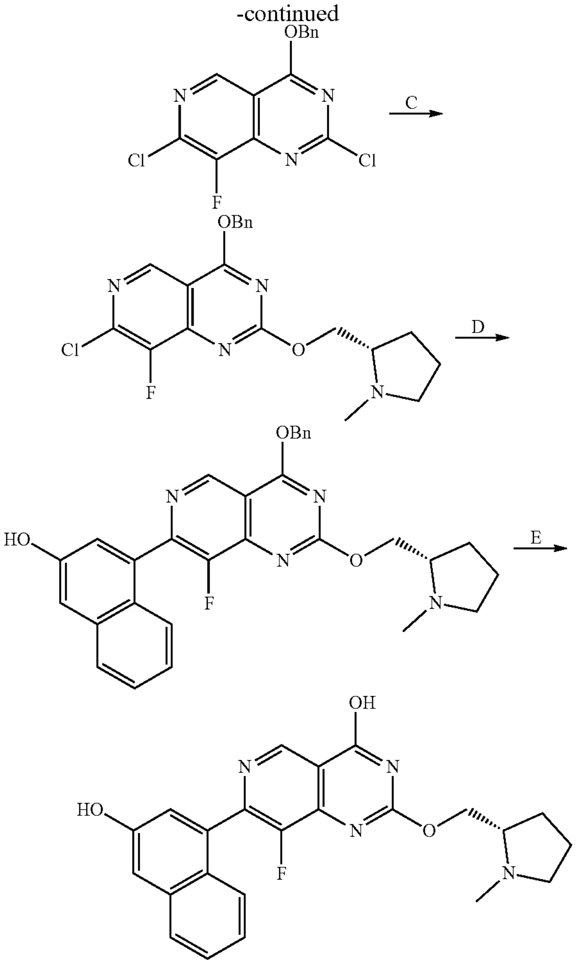

Step A. 2,4,7-trichloro-8-fluoropyrido[4,3-d]pyrimidine. To a flask containing 7-chloro-8-fluoropyrido[4,3-d]pyrimidine-2,4 (1H,3H)-dione (0.93 g, 4.3 mmol) was added $POCl_3$ (8 mL, 86 mmol). The mixture was cooled with an ice bath and DIPEA (2 mL, 13 mmol) was added. The ice bath was removed and the mixture was stirred at 100° C. for 20 hours. The solution was cooled and concentrated to give a brown oil. The oil was dissolved in DCM and the solution was quenched with a mixture of $K_3PO_4$ (37%, 10 mL) and ice (20 g). The mixture was stirred for 10 minutes. The two layers were separated, and the organic layer was further washed with brine, dried over $Na_2SO_4$, and concentrated to give crude 2,4,7-trichloro-8-fluoropyrido[4,3-d]pyrimidine which was used immediately without purification assuming 100% yield Step B. 4-(benzyloxy)-2,7-dichloro-8-fluoropyrido[4,3-d] pyrimidine. To a flask containing crude 2,4,7-trichloro-8-fluoropyrido[4,3-d]pyrimidine (1.5 g, 4.3 mmol) were added molecular sieves (3 Å, 0.4 g), 1,4-dioxane (22 mL), benzyl alcohol (0.50 mL, 4.7 mmol) and DIPEA (2.0 mL, 13 mmol). The mixture was stirred at 60° C. under $N_2$ for 7 hours. The mixture was concentrated to dryness and diluted with EtOAc. The mixture was filtered through a pad of Celite, and the filtrate was concentrated in vacuo. The residue was purified by flash chromatography eluting with 0-25% ethyl acetate/hexanes to afford 4-(benzyloxy)-2,7-dichloro-8-fluoropyrido[4,3-d]pyrimidine (0.68 g, 49%). LCMS (MM-ES+APCI, Pos): m/z 324.1 (M+H).

Step C. (S)-4-(benzyloxy)-7-chloro-8-fluoro-2-((1-methylpyrrolidin-2-yl)methoxy)pyrido[4,3-d]pyrimidine. To a solution of 4-(benzyloxy)-2,7-dichloro-8-fluoropyrido[4,3-d]pyrimidine (1.3 g, 4.0 mmol) in 1,4-dioxane (40 mL) was added(S)-(1-methylpyrrolidin-2-yl)methanol (0.67 mL, 5.6 mmol) followed by $Cs_2CO_3$ (3.27 g, 10 mmol). The mixture was heated at 80° C. under $N_2$ for 3 hours followed by stirring at room temperature for 15 hours. The mixture was diluted with ethyl acetate and filtered through a pad of Celite. The filtrate was concentrated, and the residue was purified by preparative C18 HPLC (Gilson, 0-95% $CH_3CN$/$H_2O$ with 0.1% TFA as modifier). The desired fractions were combined, basified with $Na_2CO_3$ (2 M), and extracted with EtOAc. The combined organic extract was washed with brine, dried over $Na_2SO_4$ and concentrated to afford (S)-4-(benzyloxy)-7-chloro-8-fluoro-2-((1-methylpyrrolidin-2-yl) methoxy)pyrido[4,3-d]pyrimidine (0.91 g, 56%). LCMS (MM-ES+APCI, Pos): m/z 403.1 (M+H).

Step D. (S)-4-(4-(benzyloxy)-8-fluoro-2-((1-methylpyrrolidin-2-yl)methoxy)pyrido[4,3-d]pyrimidin-7-yl)naphthalen-2-ol. A flask containing a solution of 4-(4,4,5,5-tetramethyl-1,3,2-dioxaborolan-2-yl)naphthalen-2-ol (0.58 g, 2.1 mmol), (S)-4-(benzyloxy)-7-chloro-8-fluoro-2-((1-methylpyrrolidin-2-yl)methoxy)pyrido[4,3-d]pyrimidine (0.66 g, 1.6 mmol), $Na_2CO_3$ (2 mL, 4 mmol), $Pd(PPh_3)_4$ (0.19 g, 0.16 mmol) in dioxane (16 mL) was sparged with $N_2$. The mixture was heated under $N_2$ at 80° C. for 7 hours and cooled to room temperature. The resulting mixture was quenched with water and extracted with EtOAc. The combined EtOAc extract was dried over $Na_2SO_4$, concentrated, and purified by preparative C18 HPLC (Gilson, 5-95% $CH_3CN/H_2O$ with 0.1% TFA). The desired fractions were combined, basified with $NaHCO_3$(Sat.) and extracted with DCM. The combined DOM extract was dried over $Na_2SO_4$, filtered and concentrated to afford (S)-4-(4-(benzyloxy)-8-fluoro-2-((1-methylpyrrolidin-2-yl)methoxy)pyrido[4,3-d] pyrimidin-7-yl)naphthalen-2-ol (0.39 g, 46% yield). LCMS (MM-ES+APCI, Pos): m/z 511.2 (M+H).

Step E. (S)-8-fluoro-7-(3-hydroxynaphthalen-1-yl)-2-((1-methylpyrrolidin-2-yl)methoxy)pyrido[4,3-d]pyrimidin-4-ol. To a flask with a stir bar was added Pd/C (160 mg, 0.15 mmol). A solution of (S)-4-(4-(benzyloxy)-8-fluoro-2-((1-methylpyrrolidin-2-yl)methoxy)pyrido[4,3-d]pyrimidin-7-yl)naphthalen-2-ol (0.39 g, 0.75 mmol) in EtOAc (15 mL) was added. The flask was closed with a septum and stirred under a balloon of $H_2$ at room temperature for 15 hours. The mixture was filtered through Celite and the Celite was further washed with DCM/MeOH (2:1, 200 mL). The combined organics were concentrated and dried to afford (S)-8-fluoro-7-(3-hydroxynaphthalen-1-yl)-2-((1-methylpyrrolidin-2-yl)methoxy)pyrido[4,3-d]pyrimidin-4-ol (0.29 g, 92% yield). LCMS (MM-ES+APCI, Pos): m/z 421.2 (M+H).

Intermediate 24

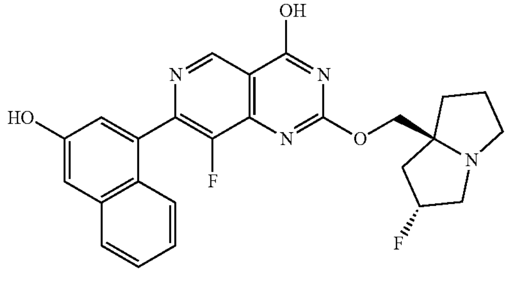

8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol (racemic, trans)

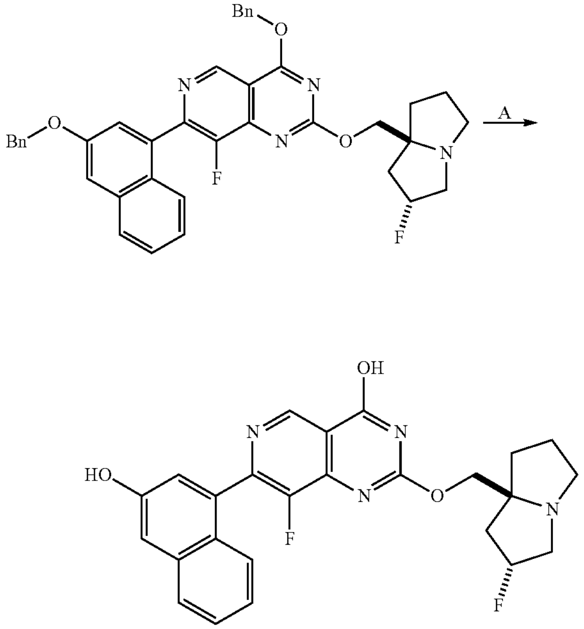

4-(benzyloxy)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidine. Synthesized according to intermediate 23 substituting racemic ((2R,7aS)-2-fluorotetrahydro-1H-pyrrolizin-7a(5H)-yl)methanol for (S)-(1-methylpyrrolidin-2-yl)methanol in step C and 2-(3-(benzyloxy)naphthalen-1-yl)-4,4,5,5-tetramethyl-1,3,2-dioxaborolane for 4-(4,4,5,5-tetramethyl-1,3,2-dioxaborolan-2-yl)naphthalen-2-ol in step D. LCMS (MM-ES+APCI, Pos): m/z 645.3 (M+H).

Step A. 8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol. To 4-(benzyloxy)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidine (1.0 g, 1.6 mmol) in DCM (200 mL) at −70° C. were added 1,2,3,4,5-pentamethylbenzene (1.2 g, 7.8 mmol) and dropwise trichloroborane (8.0 mL, 7.7 mmol). The reaction was stirred at −70° C. for 30 minutes and warmed to 0° C. The reaction was stirred at 0° C. for two hours and quenched with sat. $NaHCO_3$ (150 mL). The aqueous layer was extracted with IPA/DCM (20%, 3×). The combined organic phases were then dried over $Na_2SO_4$, filtered, and concentrated. The material was triturated with ether and the solids filtered to give 8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol (0.59 g, 82% yield). LCMS (MM-ES+APCI, Pos): m/z 465.1 (M+H).

Intermediate 25

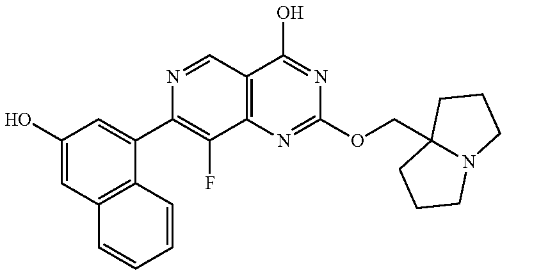

8-fluoro-7-(3-hydroxynaphthalen-1-yl)-2-((tetrahydro-1H-pyrrolizin-7a(5H)-yl)methoxy)pyrido[4,3-d]pyrimidin-4-ol

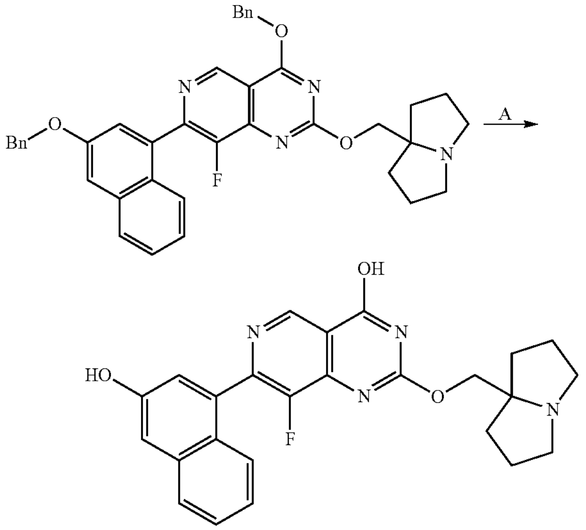

4-(benzyloxy)-7-(3-(benzyloxy)naphthalen-1-yl)-8-fluoro-2-((tetrahydro-1H-pyrrolizin-7a(5H)-yl)methoxy)pyrido[4,3-d]pyrimidine. Synthesized according to intermediate 23 substituting tetrahydro-1H-pyrrolizin-7a(5H)-yl)methanol for(S)-(1-methylpyrrolidin-2-yl)methanol in step C and 2-(3-(benzyloxy)naphthalen-1-yl)-4,4,5,5-tetramethyl-1,3,2-dioxaborolane for 4-(4,4,5,5-tetramethyl-1,3,2-dioxaborolan-2-yl)naphthalen-2-ol in step D. LCMS (MM-ES+APCI, Pos): m/z 627.3 (M+H).

Step A. 8-fluoro-7-(3-hydroxynaphthalen-1-yl)-2-((tetrahydro-1H-pyrrolizin-7a(5H)-yl)methoxy)pyrido[4,3-d]pyrimidin-4-ol. To 4-(benzyloxy)-7-(3-(benzyloxy)naphthalen-1-yl)-8-fluoro-2-((tetrahydro-1H-pyrrolizin-7a(5H)-yl)methoxy)pyrido[4,3-d]pyrimidine (5.3 g, 8.38 mmol) in THF/MeOH (10 mL/6 mL) was added $Pd(OH)_2/C$ (4.7 g, 3.4 mmol). The mixture was flushed with $N_2$ and $H_2$, and then stirred at 45 psi $H_2$ for 16 hours. The reaction was filtered through Celite and the Celite was washed with 20% MeOH/DCM. The filtrate was concentrated to afford 8-fluoro-7-(3-hydroxynaphthalen-1-yl)-2-((tetrahydro-1H-pyrrolizin-7a(5H)-yl)methoxy)pyrido[4,3-d]pyrimidin-4-ol (2.1 g, 56% yield). LCMS (MM-ES+APCI, Pos): m/z 447.3 (M+H).

Intermediate 26

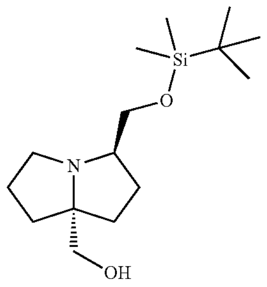

((3R,7aR)-3-(((tert-butyldimethylsilyl)oxy)methyl)tetrahydro-1H-pyrrolizin-7a(5H)-yl)methanol

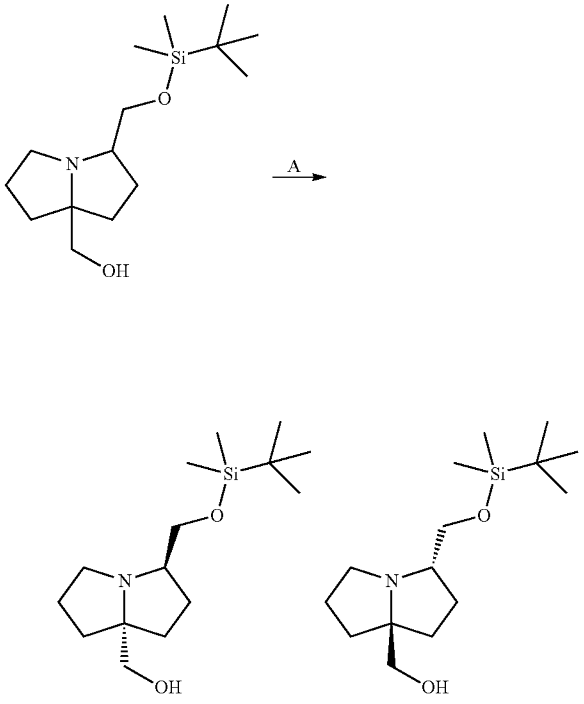

A mixture of (3-(((tert-butyldimethylsilyl)oxy)methyl)tetrahydro-1H-pyrrolizin-7a(5H)-yl)methanol was separated by Lotus Separations using chiral SFC using an AD-H (3×25 cm) column injecting with 1 mL of a 20 mg/mL solution of compound in methanol eluting with 20% methanol/$CO_2$ at 100 bar of pressure with 70 mL/min. flow rate and monitoring 220 nM.

The following Examples are intended to illustrate further certain embodiments of the invention and are not intended to limit the scope of the invention.

EXAMPLE 1

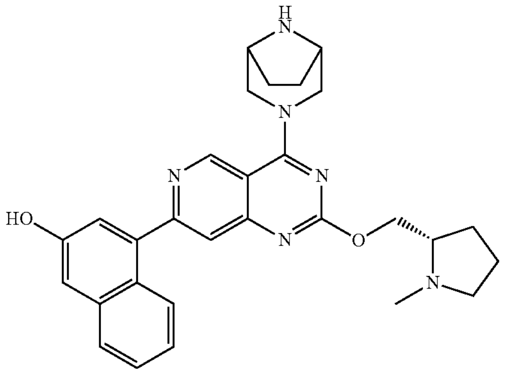

4-(4-((1R,5S)-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol tris-hydrochloride salt

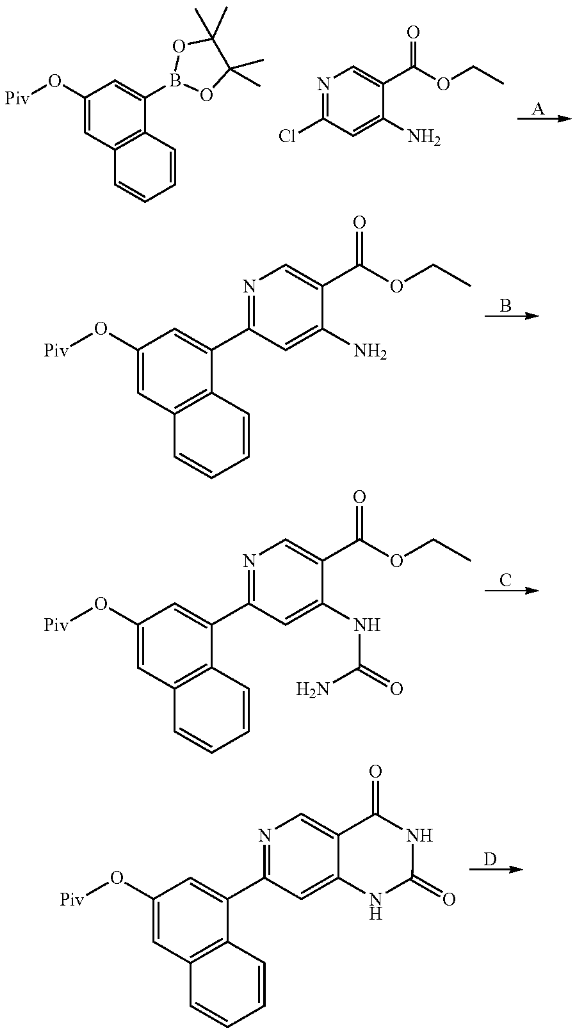

-continued
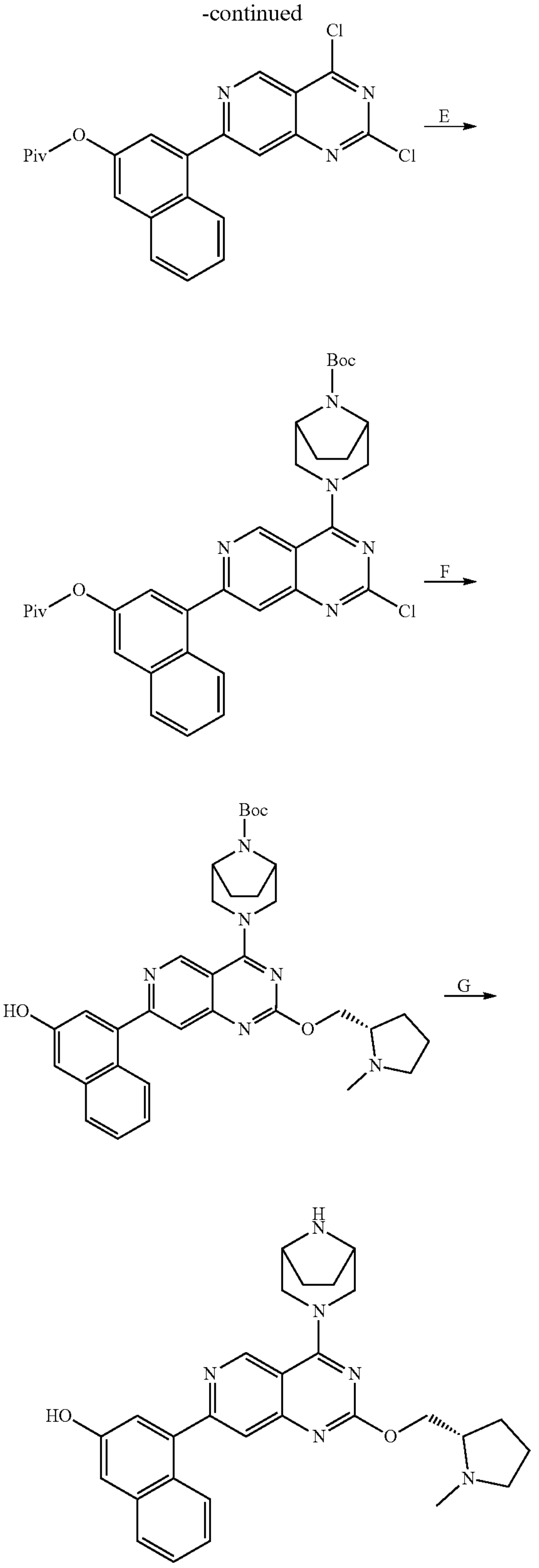
4-(4-((1R,5S)-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol tris-hydrochloride salt (11.0 mg, 0.018 mmol, 100%). LCMS (MM-ES+APCI, Pos): m/z 497.3 (M+H).
Example 2
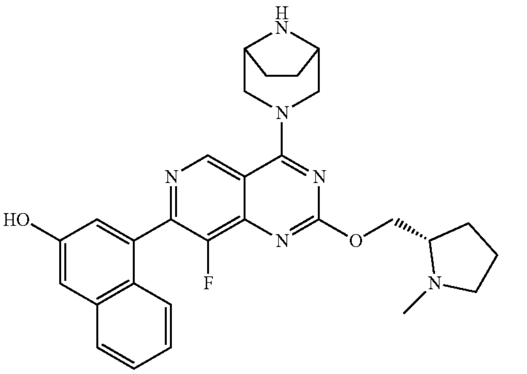 [SMILES: CN1CCC[C@H]1COc1nc(N2CC3CCC(C2)N3)c2cnc(-c3cc(O)cc4ccccc34)c(F)c2n1]
4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-2-ol bis(2,2,2-trifluoroacetate)
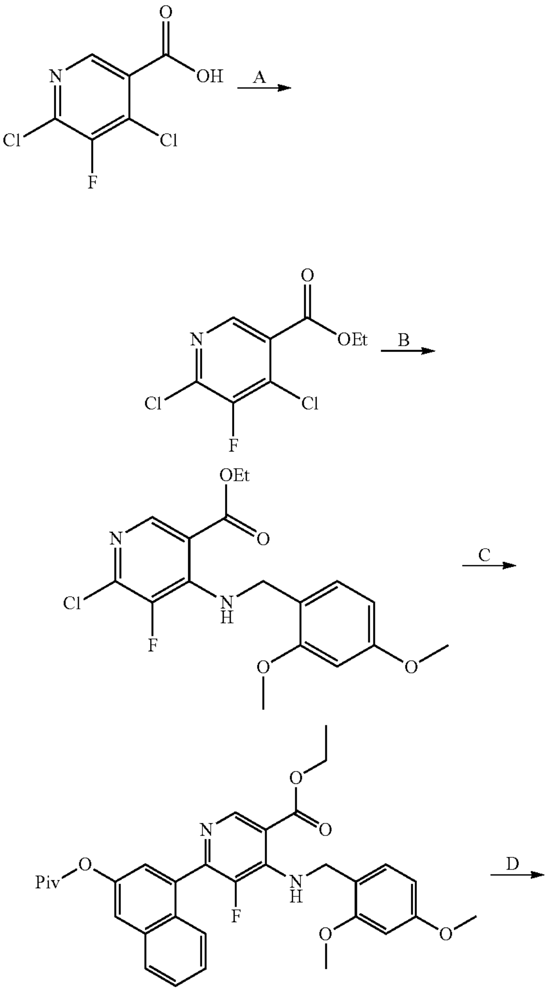

-continued
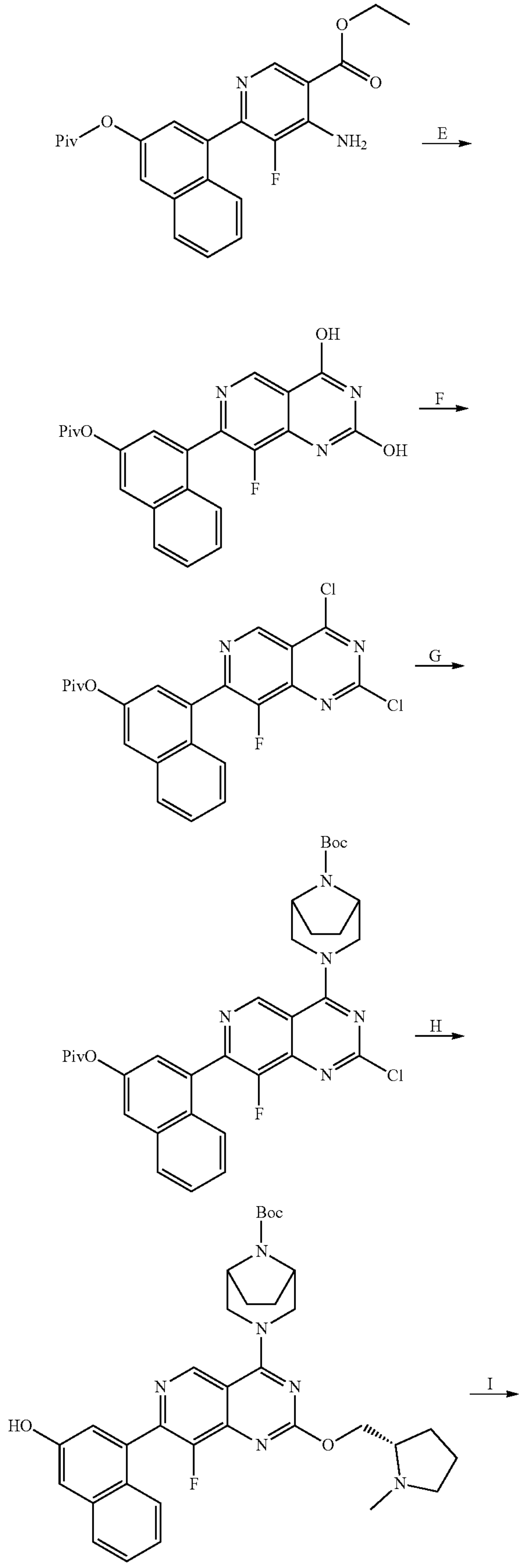
-continued
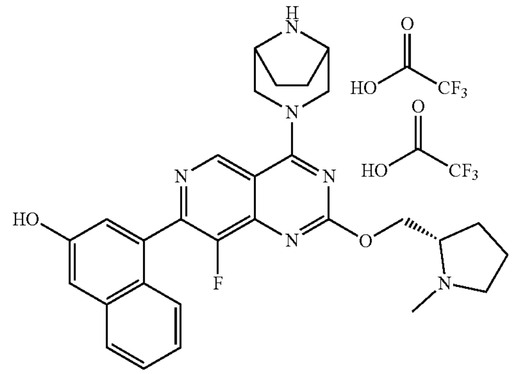
4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-2-ol bis(2,2,2-trifluoroacetate) (9.00 mg, 0.012 mmol, 74% yield). LCMS (MM-ES+APCI, Pos): m/z 515.2 (100%)(M+H).
Example 3
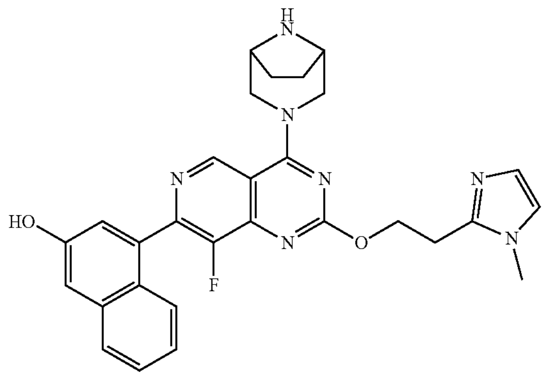 [SMILES: Cn1ccnc1CCOc1nc(N2CC3CCC(C2)N3)c2cnc(-c3cc(O)cc4ccccc34)c(F)c2n1]
4-(4-((1R,5S)-3,8-diazabicyclo[3.2.1]octan-3-yl)-8-fluoro-2-(2-(1-methyl-1H-imidazol-2-yl)ethoxy)pyrido[4,3-d]pyrimidin-7-yl)naphthalen-2-ol
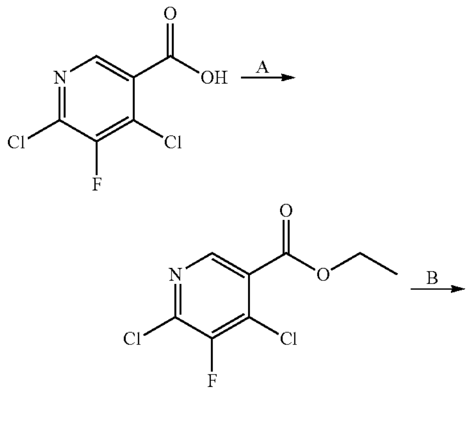

-continued

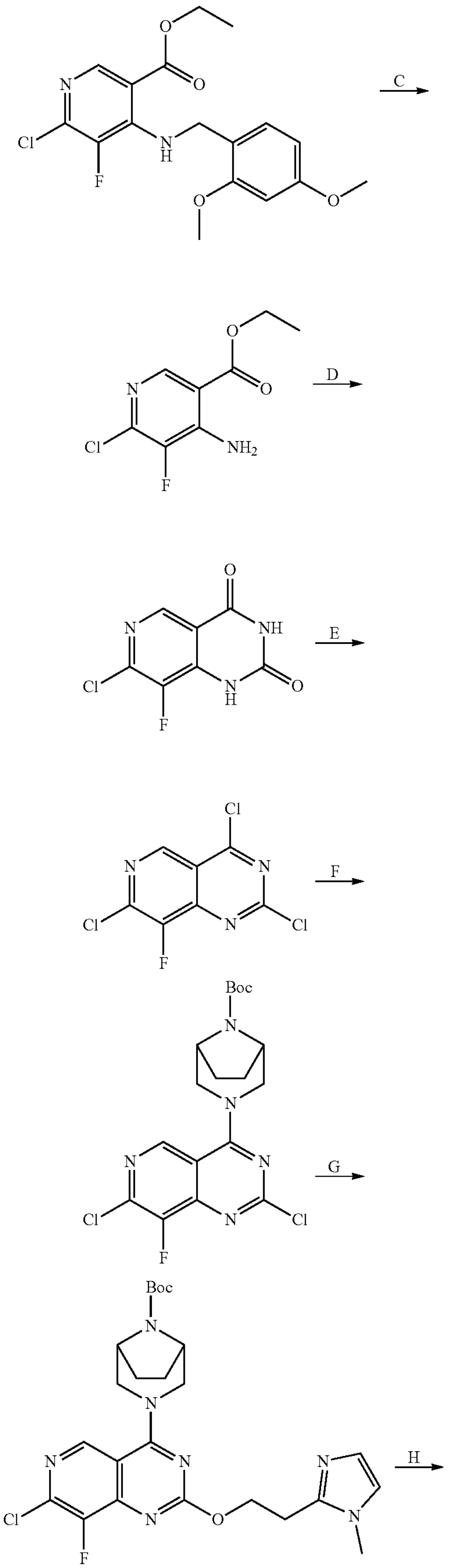

-continued

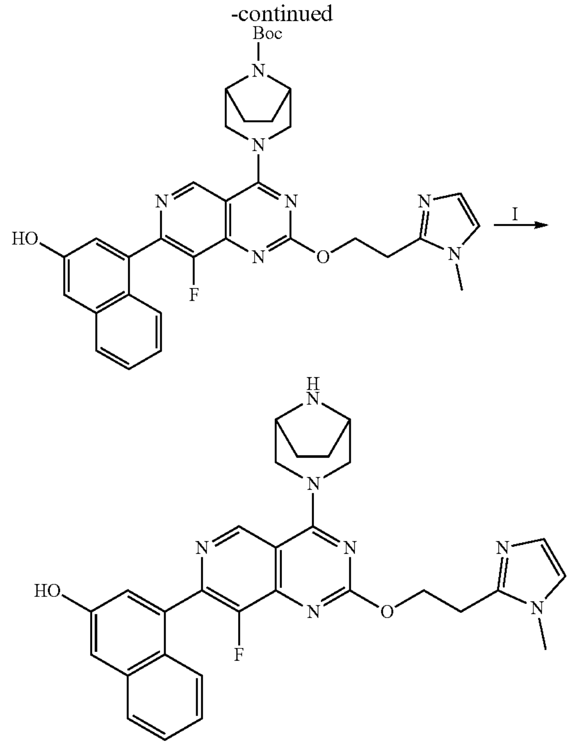

4-(4-((1R,5S)-3,8-diazabicyclo[3.2.1]octan-3-yl)-8-fluoro-2-(2-(1-methyl-1H-imidazol-2-yl)ethoxy)pyrido[4,3-d]pyrimidin-7-yl)naphthalen-2-ol (9 mg, 43% yield) as a beige film. LCMS (MM-ES+APCI, Pos): m/z 526.2 (M+H).

Example 4

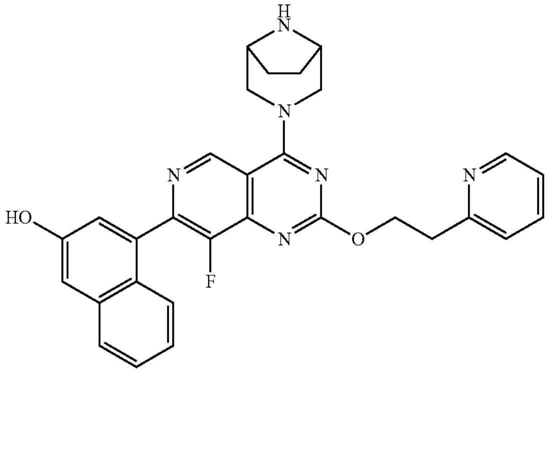 [SMILES: Oc1cc(-c2ncc3c(N4CC5CCC(C4)N5)nc(OCCc4ccccn4)nc3c2F)c2ccccc2c1]

4-(4-((1R,5S)-3,8-diazabicyclo[3.2.1]octan-3-yl)-8-fluoro-2-(2-(pyridin-2-yl)ethoxy)pyrido[4,3-d]pyrimidin-7-yl)naphthalen-2-ol Synthesized according to Example 3, Steps G-I substituting 2-(pyridin-2-yl)ethan-1-ol in place of 2-(1-methyl-1H-imidazol-2-yl)ethan-1-ol (28.1 mg, 64%). LCMS (MM-ES+APCI, Pos): m/z 523.2 (M+H).

Example 5

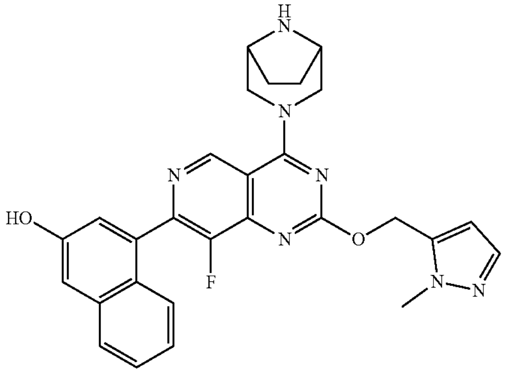 [SMILES: Cn1nccc1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-((1-methyl-1H-pyrazol-5-yl)methoxy)pyrido[4,3-d]pyrimidin-7-yl)naphthalen-2-ol Synthesized according to Example 3, Steps G-I substituting (1-methyl-1H-pyrazol-5-yl)methanol in place of 2-(1-methyl-1H-imidazol-2-yl)ethan-1-ol (23.7 mg, 63%). LCMS (MM-ES+APCI, Pos): m/z 512.2 (M+H).

Example 6

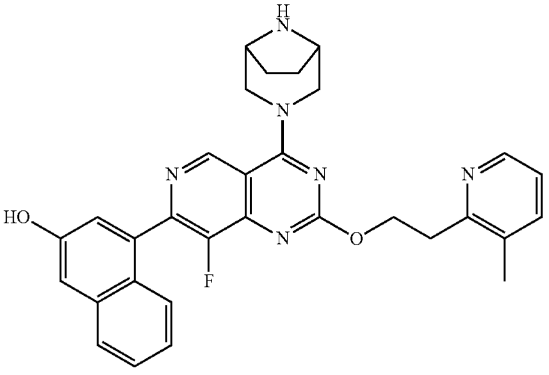 [SMILES: Cc1cccnc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(3-methylpyridin-2-yl)ethoxy)pyrido[4,3-d]pyrimidin-7-yl)naphthalen-2-ol Synthesized according to Example 3, Steps G-I substituting 2-(3-methylpyridin-2-yl)ethan-1-ol in place of 2-(1-methyl-1H-imidazol-2-yl)ethan-1-ol (14.9 mg, 30%). LCMS (MM-ES+APCI, Pos): m/z 537.2 (M+H).

Example 7

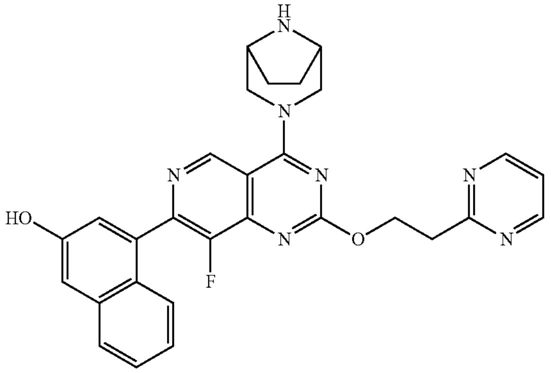

4-(4-((1R,5S)-3,8-diazabicyclo[3.2.1]octan-3-yl)-8-fluoro-2-(2-(pyrimidin-2-yl)ethoxy)pyrido[4,3-d]pyrimidin-7-yl)naphthalen-2-ol Synthesized according to Example 3, Steps G-I substituting 2-(pyrimidin-2-yl)ethan-1-ol in place of 2-(1-methyl-1H-imidazol-2-yl)ethan-1-ol (7.1 mg, x mmol, 17%). LCMS (MM-ES+APCI, Pos): m/z 524.2 (M+H).

Example 8

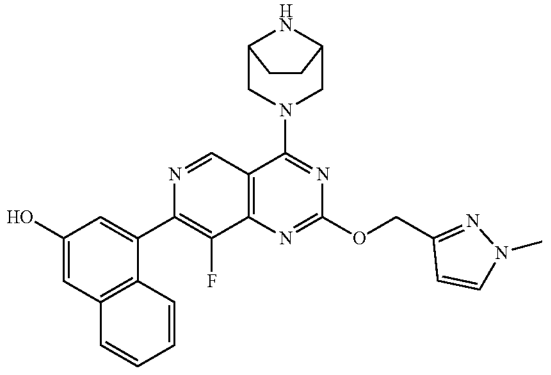 [SMILES: Cn1ccc(COc2nc(N3CC4CCC(C3)N4)c3cnc(-c4cc(O)cc5ccccc45)c(F)c3n2)n1]

4-(4-((1R,5S)-3,8-diazabicyclo[3.2.1]octan-3-yl)-8-fluoro-2-((1-methyl-1H-pyrazol-3-yl)methoxy)pyrido[4,3-d]pyrimidin-7-yl)naphthalen-2-ol Synthesized according to Example 3, Steps G-I substituting (1-methyl-1H-pyrazol-3-yl)methanol in place of 2-(1-methyl-1H-imidazol-2-yl)ethan-1-ol (9.2 mg, 11%). LCMS (MM-ES+APCI, Pos): m/z 512.2 (M+H).

Example 9

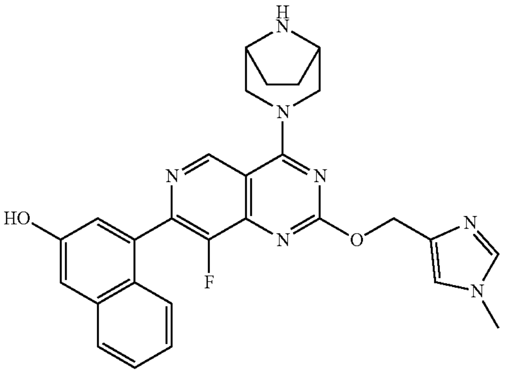 [SMILES: Cn1cnc(COc2nc(N3CC4CCC(C3)N4)c3cnc(-c4cc(O)cc5ccccc45)c(F)c3n2)c1]

4-(4-((1R,5S)-3,8-diazabicyclo[3.2.1]octan-3-yl)-8-fluoro-2-((1-methyl-1H-imidazol-4-yl)methoxy)pyrido[4,3-d]pyrimidin-7-yl)naphthalen-2-ol Synthesized according to Example 3, Steps G-I substituting (1-methyl-1H-imidazol-4-yl)methanol in place of 2-(1-methyl-1H-imidazol-2-yl)ethan-1-ol (8.6 mg, 36%). LCMS (MM-ES+APCI, Pos): m/z 512.2 (M+H).

Example 10

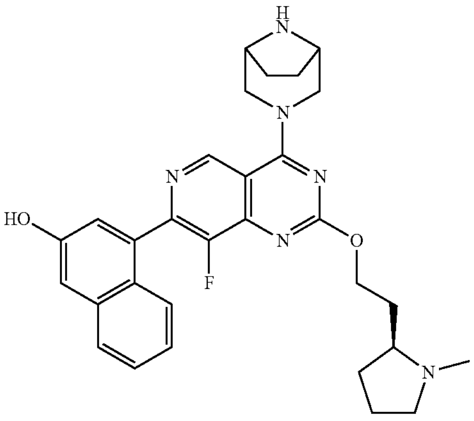 [SMILES: CN1CCC[C@H]1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-((S)-1-methylpyrrolidin-2-yl)ethoxy)pyrido[4,3-d]pyrimidin-7-yl)naphthalen-2-ol Synthesized similarly to Example 3, Steps G-I substituting (S)-2-(1-methylpyrrolidin-2-yl)ethanol in place of 2-(1-methyl-1H-imidazol-2-yl)ethan-1-ol (1.03 mg, 0.00195 mmol, 3.5%). LCMS (MM-ES+APCI, Pos): m/z 529.3 (M+H).

Example 11

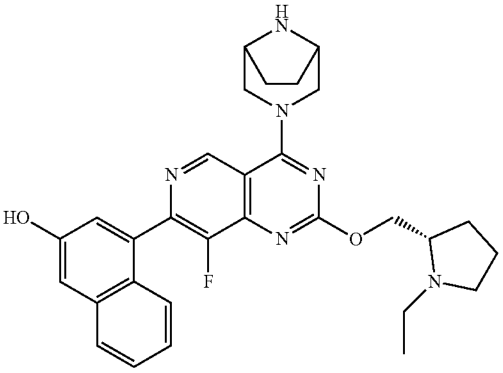 [SMILES: CCN1CCC[C@H]1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-2-(((S)-1-ethylpyrrolidin-2-yl)methoxy)-8-fluoro-pyrido[4,3-d]pyrimidin-7-yl)naphthalen-2-ol Synthesized similarly to Example 3, Steps G-I substituting [(2S)-1-Ethyl-2-pyrrolidinyl]methanol in place of 2-(1-methyl-1H-imidazol-2-yl)ethan-1-ol (1.38 mg, 0.00262 mmol, 2.4%). LCMS (MM-ES+APCI, Pos): m/z 529.3 (M+H).

Example 12

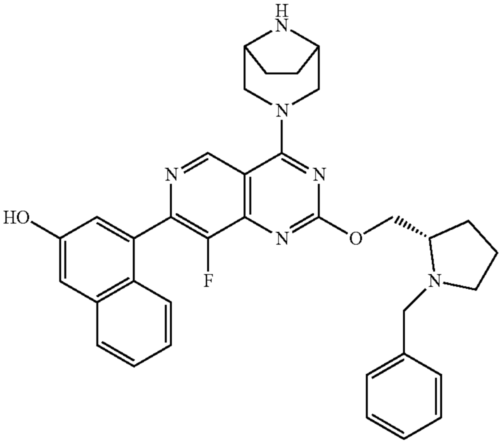 [SMILES: Oc1cc(-c2ncc3c(N4CC5CCC(C4)N5)nc(OC[C@@H]4CCCN4Cc4ccccc4)nc3c2F)c2ccccc2c1]

4-(2-(((S)-1-benzylpyrrolidin-2-yl)methoxy)-4-((1R,5S)-3,8-diazabicyclo[3.2.1]octan-3-yl)-8-fluoro-pyrido[4,3-d]pyrimidin-7-yl)naphthalen-2-ol Synthesized similarly to Example 3, Steps G-I substituting (S)-(−)-1-benzyl-2-pyrrolidinemethanol in place of 2-(1-methyl-1H-imidazol-2-yl)ethan-1-ol (2.67 mg, 0.00452 mmol, 10.4%). LCMS (MM-ES+APCI, Pos): m/z 591.2 (M+H).

Example 13

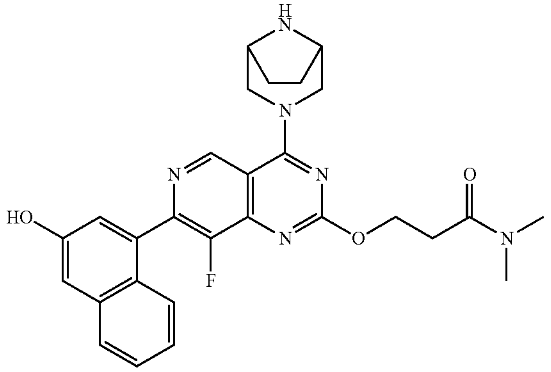 [SMILES: CN(C)C(=O)CCOc1nc(N2CC3CCC(C2)N3)c2cnc(-c3cc(O)cc4ccccc34)c(F)c2n1]

3-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)-N,N-dimethylpropanamide Synthesized similarly to Example 3, Steps G-I substituting 3-hydroxy-N,N-dimethylpropanamide in place of 2-(1-methyl-1H-imidazol-2-yl)ethan-1-ol (0.885 mg, 0.00171 mmol, 3.52%). LCMS (MM-ES+APCI, Pos): m/z 517.2 (M+H).

Example 14

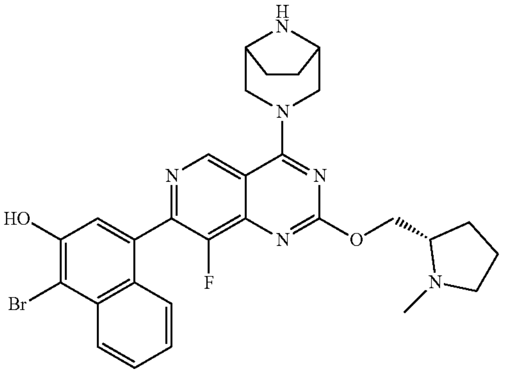 [SMILES: CN1CCC[C@H]1COc1nc(N2CC3CCC(C2)N3)c2cnc(-c3cc(O)c(Br)c4ccccc34)c(F)c2n1]

4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)-1-bromonaphthalen-2-ol

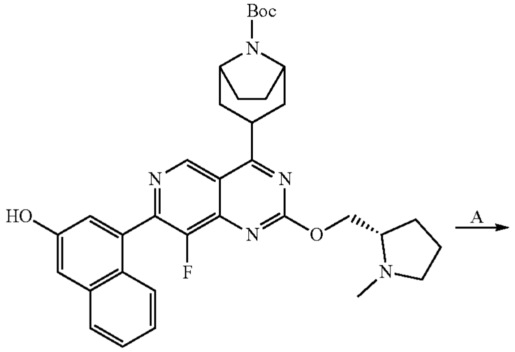

-continued

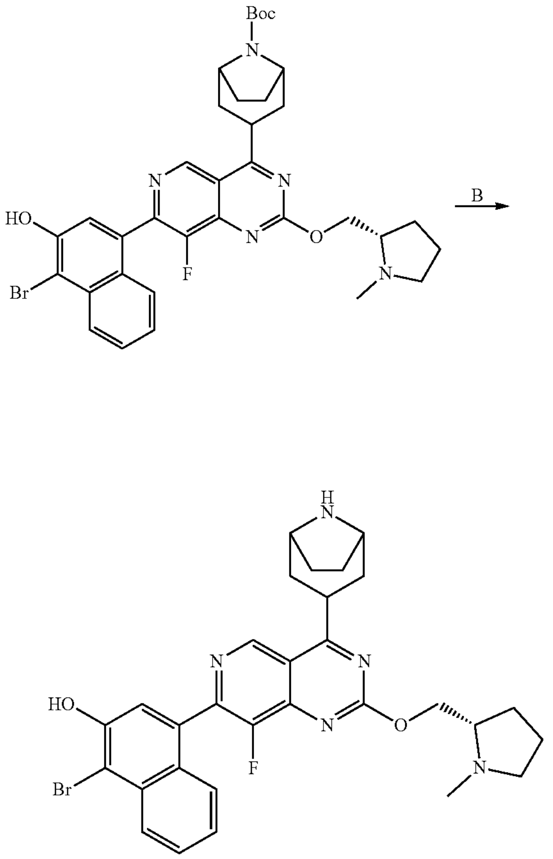

Yellow solid (5.16 mg, 8.70 mmol, 17%). LCMS (MM-ES+APCI, Pos): m/z 593.2 (M+H).

Example 15

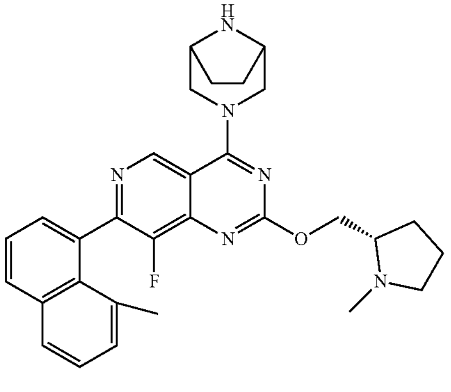 [SMILES: Cc1cccc2cccc(-c3ncc4c(N5CC6CCC(C5)N6)nc(OC[C@@H]5CCCN5C)nc4c3F)c12]

4-((1R,5S)-3,8-diazabicyclo[3.2.1]octan-3-yl)-8-fluoro-7-(8-methylnaphthalen-1-yl)-2-(((S)-1-methylpyrrolidin-2-yl)methoxy)pyrido[4,3-d]pyrimidine

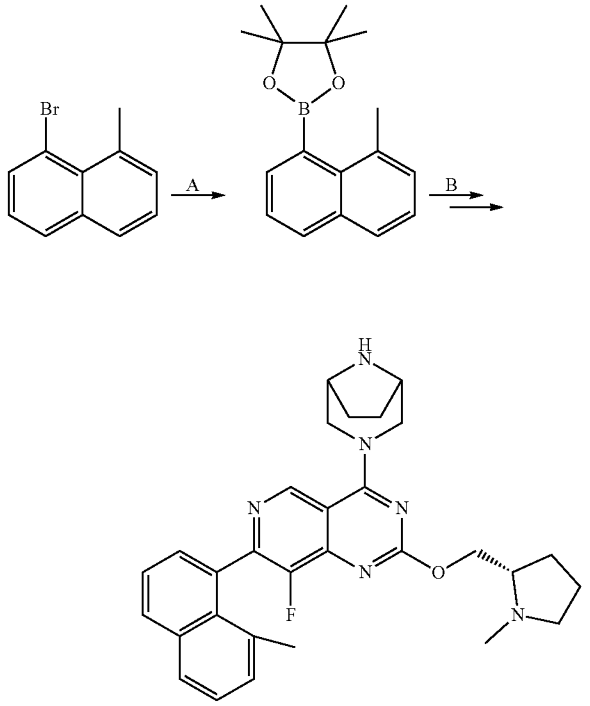

Synthesized according to Example 2, Steps C—I substituting 4,4,5,5-tetramethyl-2-(8-methylnaphthalen-1-yl)-1,3,2-dioxaborolane in place of 4-(4,4,5,5-tetramethyl-1,3,2-dioxaborolan-2-yl)naphthalen-2-yl pivalate (17.0 mg, 78%). LCMS (MM-ES+APCI, Pos): m/z 513.3 [M+H].

Example 16

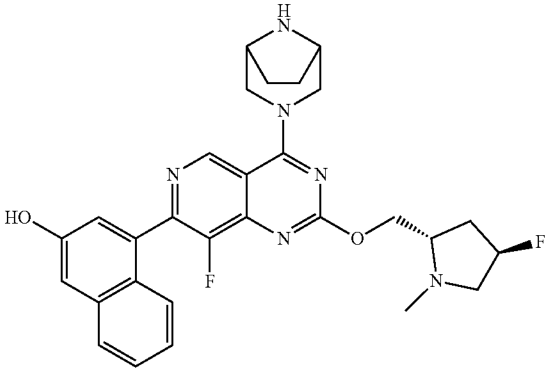 [SMILES: CN1C[C@H](F)C[C@H]1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(((2S,4R)-4-fluoro-1-methylpyrrolidin-2-yl)methoxy)pyrido[4,3-d]pyrimidin-7-yl)naphthalen-2-ol

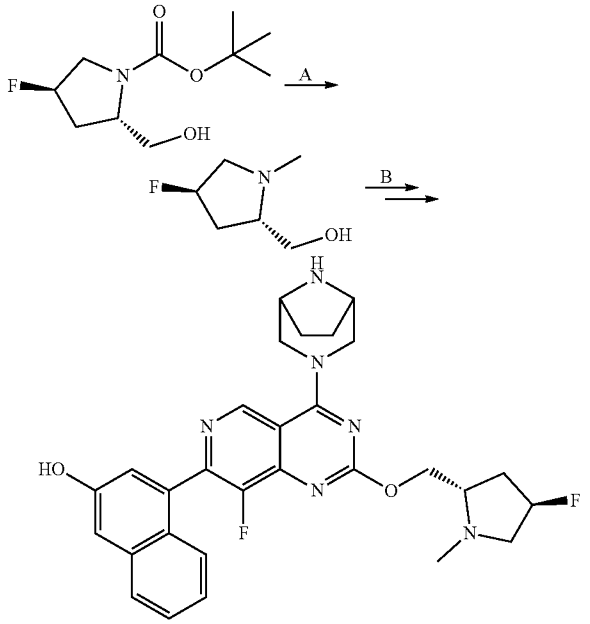

The title compound was synthesized according to Example 3, Steps G-I substituting ((2S,4R)-4-fluoro-1-methylpyrrolidin-2-yl)methanol in place of 2-(1-methyl-1H-imidazol-2-yl)ethan-1-ol (8.00 mg, 65%). LCMS (MM-ES+APCI, Pos): m/z 533.2 [M+H].

Example 17

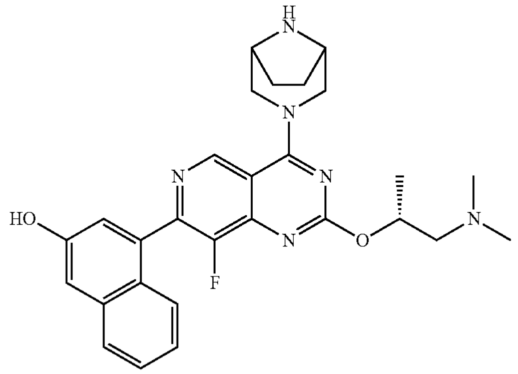 [SMILES: C[C@H](CN(C)C)Oc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-2-(((R)-1-(dimethylamino) propan-2-yl)oxy)-8-fluoropyrido[4,3-d]pyrimidin-7-yl)naphthalen-2-ol Synthesized according to Example 2, Steps D-I substituting (R)-1-(dimethylamino) propan-2-ol in place of (S)-(1-methylpyrrolidin-2-yl)methanol (4.00 mg, 33%). LCMS (MM-ES+APCI, Pos): m/z 503.2 [M+H].

Example 18

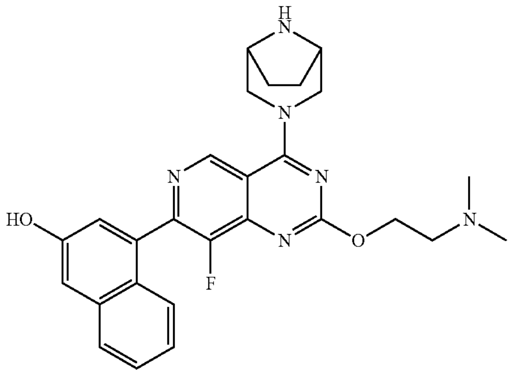 [SMILES: CN(C)CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-2-(2-(dimethylamino)ethoxy)-8-fluoropyrido[4,3-d]pyrimidin-7-yl)naphthalen-2-ol Synthesized according to Example 2, Steps D-I substituting N,N-dimethylethanolamine in place of (S)-(1-methylpyrrolidin-2-yl)methanol (7.00 mg, 58%). LCMS (MM-ES+APCI, Pos): m/z 489.2 [M+H].

Example 19

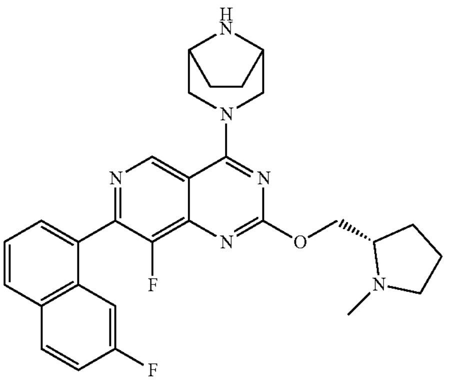 [SMILES: CN1CCC[C@H]1COc1nc(N2CC3CCC(C2)N3)c2cnc(-c3cccc4ccc(F)cc34)c(F)c2n1]

4-((1R,5S)-3,8-diazabicyclo[3.2.1]octan-3-yl)-8-fluoro-7-(7-fluoronaphthalen-1-yl)-2-(((S)-1-methylpyrrolidin-2-yl)methoxy)pyrido[4,3-d]pyrimidine

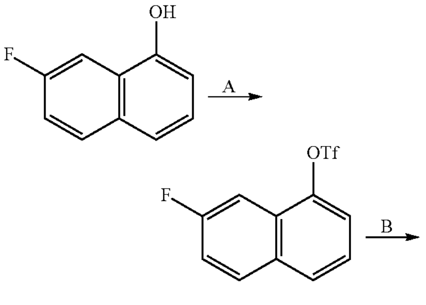

-continued

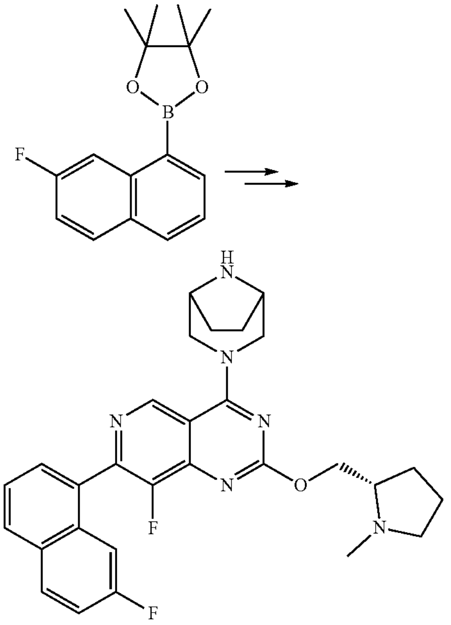

The title compound was synthesized according to Example 3, Steps G-I substituting (S)-(1-methylpyrrolidin-2-yl)methanol in place of 2-(1-methyl-1H-imidazol-2-yl)ethan-1-ol and 2-(7-fluoronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol (6 mg, 50%). LCMS (MM-ES+APCI, Pos): m/z 517.3 (M+H).

Example 20

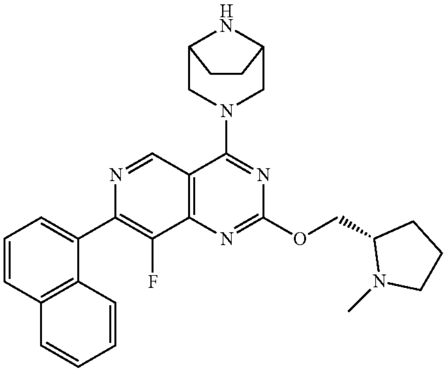 [SMILES: CN1CCC[C@H]1COc1nc(N2CC3CCC(C2)N3)c2cnc(-c3cccc4ccccc34)c(F)c2n1]

4-((1R,5S)-3,8-diazabicyclo[3.2.1]octan-3-yl)-8-fluoro-2-(((S)-1-methylpyrrolidin-2-yl)methoxy)-7-(naphthalen-1-yl)pyrido[4,3-d]pyrimidine Synthesized according Example 3, Steps G-I substituting (S)-(1-methylpyrrolidin-2-yl)methanol in place of 2-(1-methyl-1H-imidazol-2-yl)ethan-1-ol and naphthalen-1-ylboronic acid in place of 4-(4,4,5,5-tetramethyl-1,3,2-dioxaborolan-2-yl)naphthalen-2-ol (2.00 mg, 8%). LCMS (MM-ES+APCI, Pos): m/z 499.2 (M+H).

Example 21

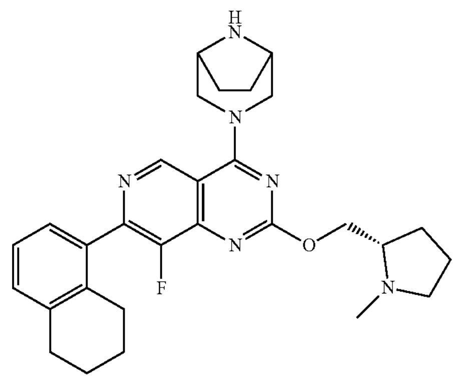 [SMILES: CN1CCC[C@H]1COc1nc(N2CC3CCC(C2)N3)c2cnc(-c3cccc4c3CCCC4)c(F)c2n1]

4-((1R,5S)-3,8-diazabicyclo[3.2.1]octan-3-yl)-8-fluoro-2-(((S)-1-methylpyrrolidin-2-yl)methoxy)-7-(5,6,7,8-tetrahydronaphthalen-1-yl)pyrido[4,3-d]pyrimidine

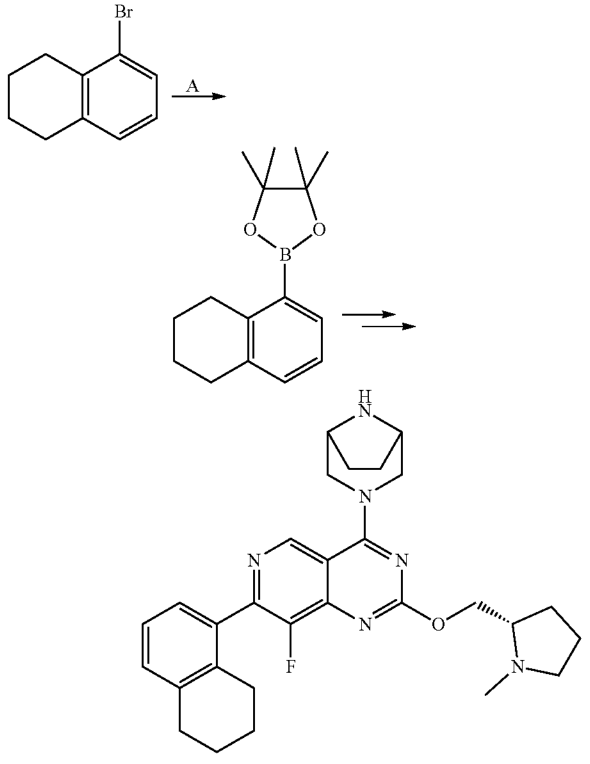

The title compound was synthesized according to Example 3, Steps G-I substituting (S)-(1-methylpyrrolidin-2-yl)methanol in place of 2-(1-methyl-1H-imidazol-2-yl)ethan-1-ol and 4,4,5,5-tetramethyl-2-(5,6,7,8-tetrahydronaphthalen-1-yl)-1,3,2-dioxaborolane in place of 4-(4,4,5,5-tetramethyl-1,3,2-dioxaborolan-2-yl)naphthalen-2-ol (23.0 mg, 100%). LCMS (MM-ES+APCI, Pos): m/z 503.3 (M+H).

Example 22

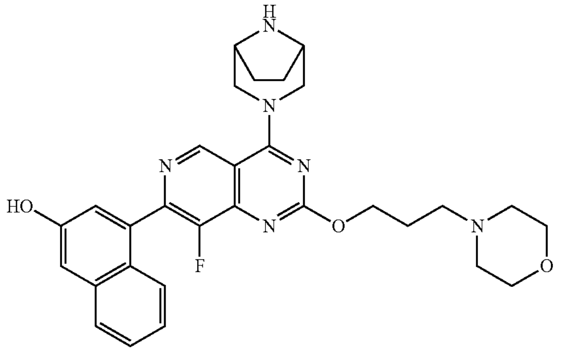 [SMILES: Oc1cc(-c2ncc3c(N4CC5CCC(C4)N5)nc(OCCCN4CCOCC4)nc3c2F)c2ccccc2c1]

4-(4-((1R,5S)-3,8-diazabicyclo[3.2.1]octan-3-yl)-8-fluoro-2-(3-morpholinopropoxy)pyrido[4,3-d]pyrimidin-7-yl)naphthalen-2-ol Synthesized according Example 3, Steps G-I substituting N-3-morpholinopropan-1-ol in place of 2-(1-methyl-1H-imidazol-2-yl)ethan-1-ol (6.00 mg, 100%). LCMS (MM-ES+APCI, Pos): m/z 545.3 (M+H).

Example 23

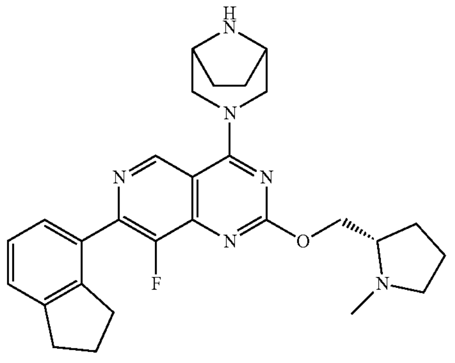 [SMILES: CN1CCC[C@H]1COc1nc(N2CC3CCC(C2)N3)c2cnc(-c3cccc4c3CCC4)c(F)c2n1]

4-((1R,5S)-3,8-diazabicyclo[3.2.1]octan-3-yl)-7-(2,3-dihydro-1H-inden-4-yl)-8-fluoro-2-(((S)-1-methylpyrrolidin-2-yl)methoxy)pyrido[4,3-d]pyrimidine

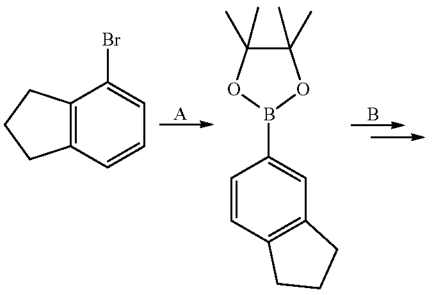

-continued

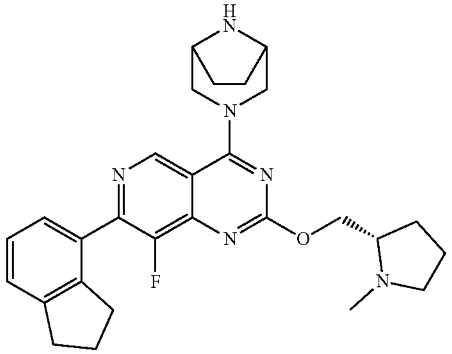

The title compound was synthesized according Example 3, Steps G-I substituting (S)-(1-methylpyrrolidin-2-yl) methanol in place of 2-(1-methyl-1H-imidazol-2-yl)ethan-1-ol and substituting 2-(2,3-dihydro-1H-inden-4-yl)-4,4,5,5-tetramethyl-1,3,2-dioxaborolane in place of 4-(4,4,5,5-tetramethyl-1,3,2-dioxaborolan-2-yl)naphthalen-2-ol (2.00 mg, 21%). LCMS (MM-ES+APCI, Pos): m/z 489.2 (M+H).

Example 24

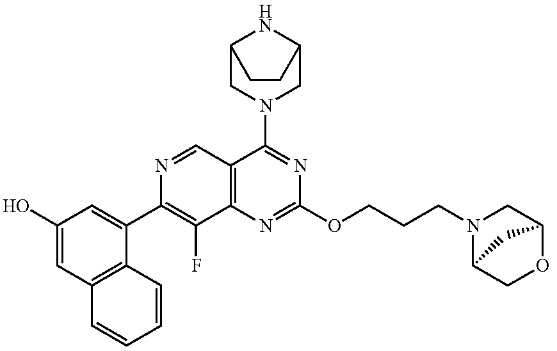 [SMILES: Oc1cc(-c2ncc3c(N4CC5CCC(C4)N5)nc(OCCCN4C[C@@H]5C[C@H]4CO5)nc3c2F)c2ccccc2c1]

4-(2-(3-((1S,4S)-2-oxa-5-azabicyclo[2.2.1]heptan-5-yl) propoxy)-4-((1R,5S)-3,8-diazabicyclo[3.2.1] octan-3-yl)-8-fluoropyrido[4,3-d]pyrimidin-7-yl) naphthalen-2-ol Synthesized according Example 3, Steps G-I substituting 3-((1S,4S)-2-oxa-5-azabicyclo[2.2.1]heptan-5-yl) propan-1-ol in place of 2-(1-methyl-1H-imidazol-2-yl)ethan-1-ol (4.00 mg, 100%). LCMS (MM-ES+APCI, Pos): m/z 557.3 (M+H).

Example 25

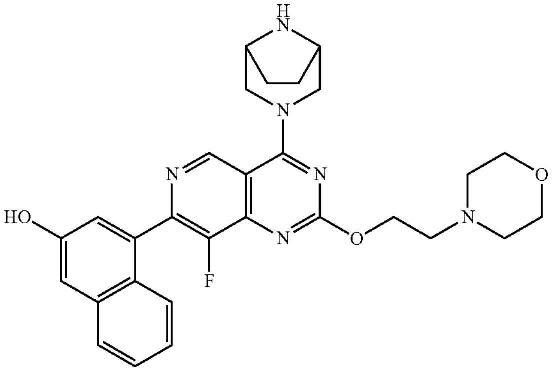 [SMILES: Oc1cc(-c2ncc3c(N4CC5CCC(C4)N5)nc(OCCN4CCOCC4)nc3c2F)c2ccccc2c1]

4-(4-((1R,5S)-3,8-diazabicyclo[3.2.1]octan-3-yl)-8-fluoro-2-(2-morpholinoethoxy)pyrido[4,3-d]pyrimidin-7-yl)naphthalen-2-ol Synthesized according to Example 3, Steps G-I substituting N-hydroxyethylmorpholine in place of 2-(1-methyl-1H-imidazol-2-yl)ethan-1-ol (15.0 mg, 100%). LCMS (MM-ES+APCI, Pos): m/z 531.2 (M+H).

Example 26

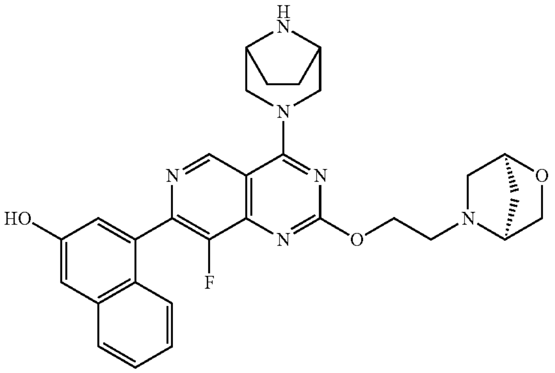 [SMILES: Oc1cc(-c2ncc3c(N4CC5CCC(C4)N5)nc(OCCN4C[C@@H]5C[C@H]4CO5)nc3c2F)c2ccccc2c1]

4-(2-(2-((1S,4S)-2-oxa-5-azabicyclo[2.2.1]heptan-5-yl)ethoxy)-4-((1R,5S)-3,8-diazabicyclo[3.2.1]octan-3-yl)-8-fluoropyrido[4,3-d]pyrimidin-7-yl)naphthalen-2-ol The title compound was synthesized according to Example 3, Steps G-I substituting 2-((1S,4S)-2-oxa-5-azabicyclo[2.2.1]heptan-5-yl)ethan-1-ol in place of 2-(1-methyl-1H-imidazol-2-yl)ethan-1-ol (4 mg, 0.005 mmol, 56%). LCMS (MM-ES+APCI, Pos): m/z 543.2 (M+H).

Example 27

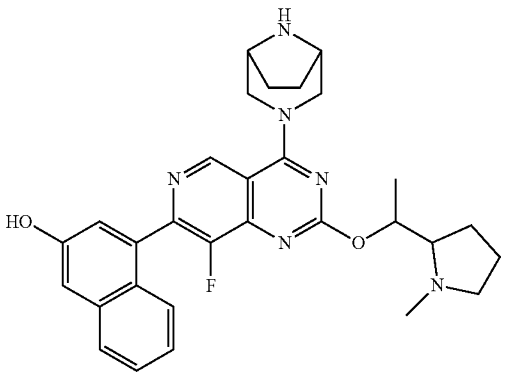 [SMILES: CC(Oc1nc(N2CC3CCC(C2)N3)c2cnc(-c3cc(O)cc4ccccc34)c(F)c2n1)C1CCCN1C]

4-(4-((1R,5S)-3,8-diazabicyclo[3.2.1]octan-3-yl)-8-fluoro-2-(1-(1-methylpyrrolidin-2-yl)ethoxy)pyrido[4,3-d]pyrimidin-7-yl)naphthalen-2-ol

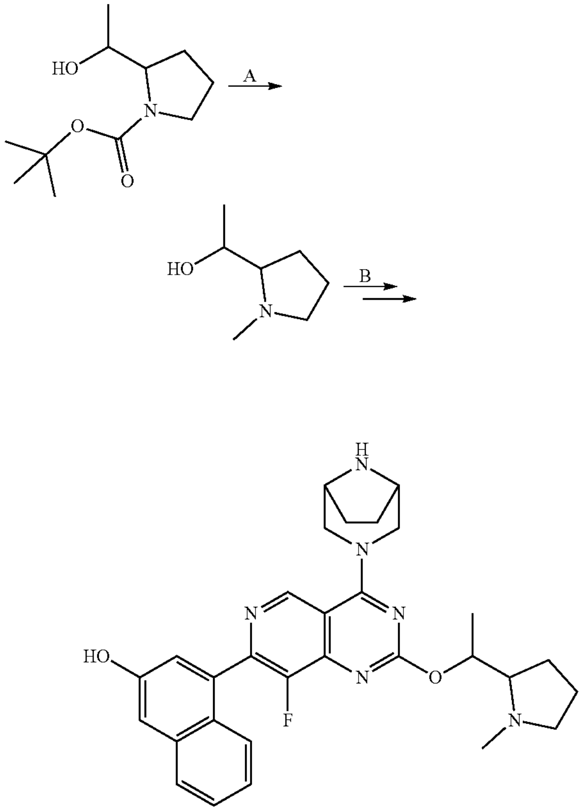

The title compound was synthesized according to Example 3, Steps G-I substituting 1-(1-methylpyrrolidin-2-yl)ethan-1-ol in place of 2-(1-methyl-1H-imidazol-2-yl)ethan-1-ol (4.00 mg, 83%). LCMS (MM-ES+APCI, Pos): m/z 529.3 (M+H).

Example 28

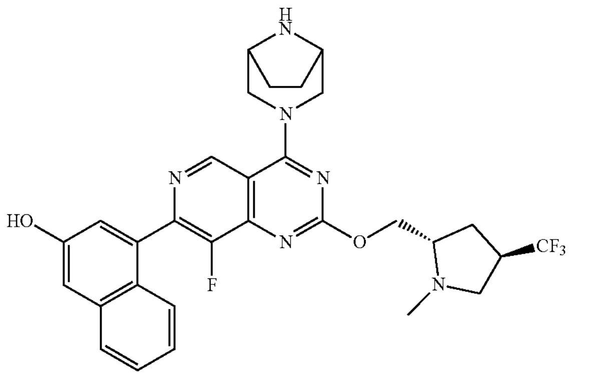 [SMILES: CN1C[C@H](C(F)(F)F)C[C@H]1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(((2S,4R)-1-methyl-4-(trifluoromethyl)pyrrolidin-2-yl)methoxy)pyrido[4,3-d]pyrimidin-7-yl)naphthalen-2-ol

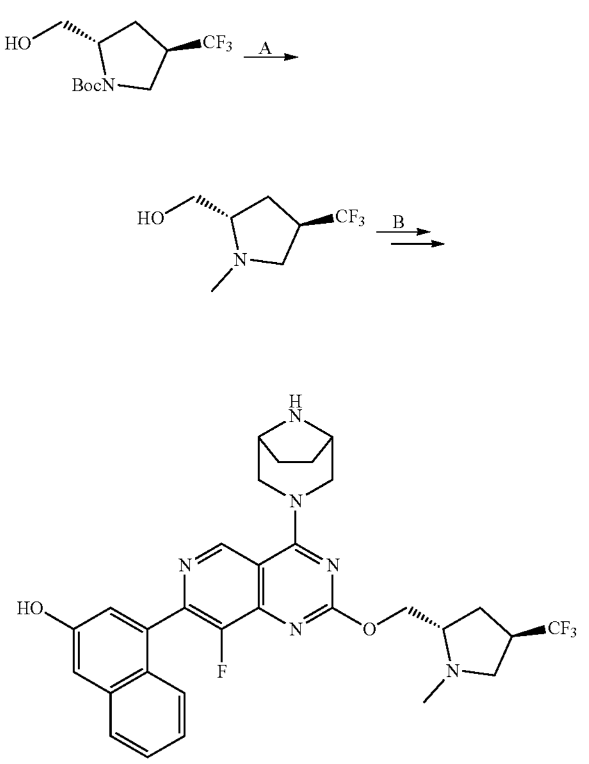

The title compound was synthesized according to Example 3, Steps G-I substituting ((2S,4R)-1-methyl-4-(trifluoromethyl)pyrrolidin-2-yl)methanol in place of 2-(1-methyl-1H-imidazol-2-yl)ethan-1-ol (3.00 mg, 42%). LCMS (MM-ES+APCI, Pos): m/z 583.2 (M+H).

Example 29
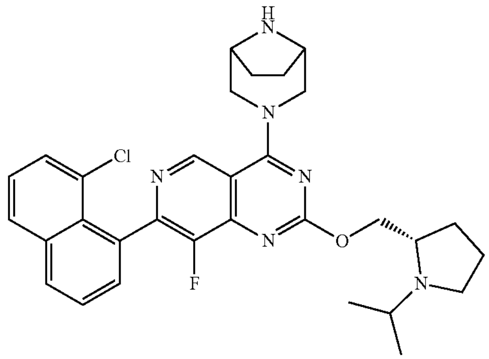 [SMILES: CC(C)N1CCC[C@H]1COc1nc(N2CC3CCC(C2)N3)c2cnc(-c3cccc4cccc(Cl)c34)c(F)c2n1]
4-((1R,5S)-3,8-diazabicyclo[3.2.1]octan-3-yl)-7-(8-chloronaphthalen-1-yl)-8-fluoro-2-(((S)-1-isopropylpyrrolidin-2-yl)methoxy)pyrido[4,3-d]pyrimidine
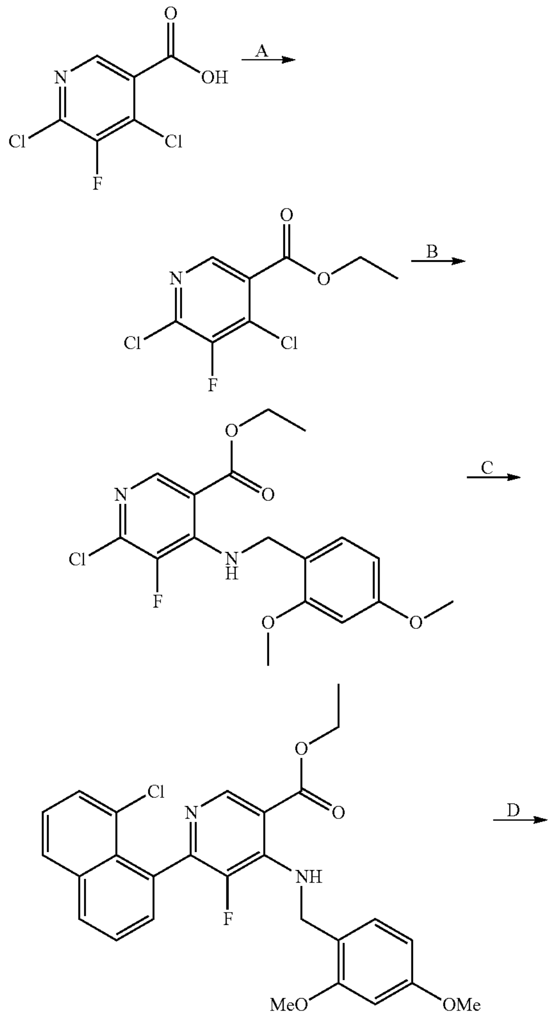
-continued
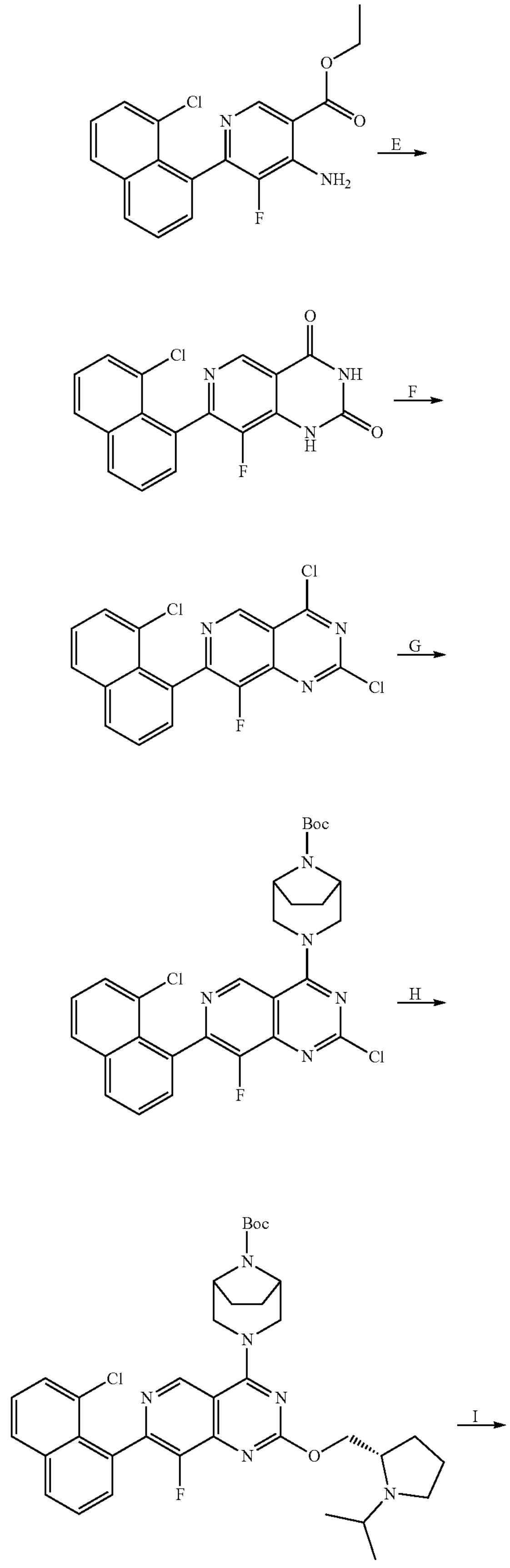

-continued
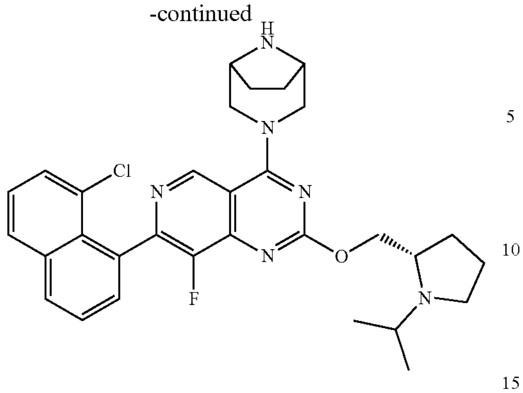
4-((1R,5S)-3,8-diazabicyclo[3.2.1]octan-3-yl)-7-(8-chloronaphthalen-1-yl)-8-fluoro-2-(((S)-1-isopropylpyrrolidin-2-yl)methoxy)pyrido[4,3-d]pyrimidine (11 mg, 0.02 mmol, 68% yield). LCMS (MM-ES+APCI, Pos): m/z 561.2 (M+).
Example 30
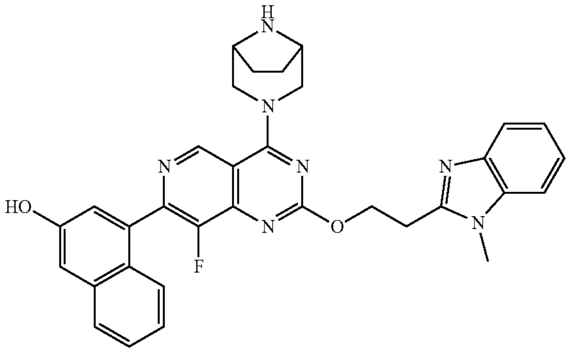 [SMILES: Cn1c(CCOc2nc(N3CC4CCC(C3)N4)c3cnc(-c4cc(O)cc5ccccc45)c(F)c3n2)nc2ccccc21]
4-(4-((1R,5S)-3,8-diazabicyclo[3.2.1]octan-3-yl)-8-fluoro-2-(2-(1-methyl-1H-benzo[d]imidazol-2-yl)ethoxy)pyrido[4,3-d]pyrimidin-7-yl)naphthalen-2-ol
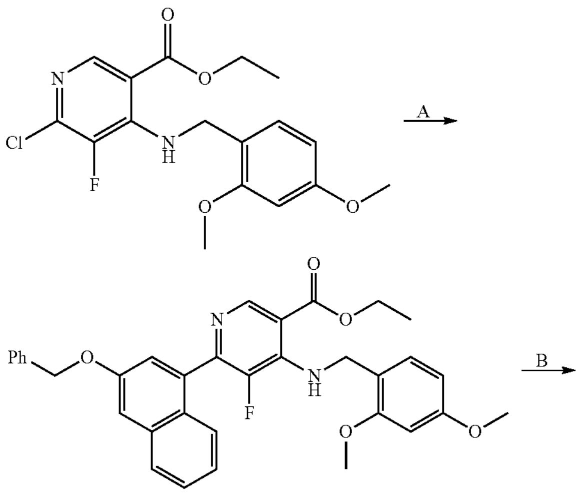
-continued
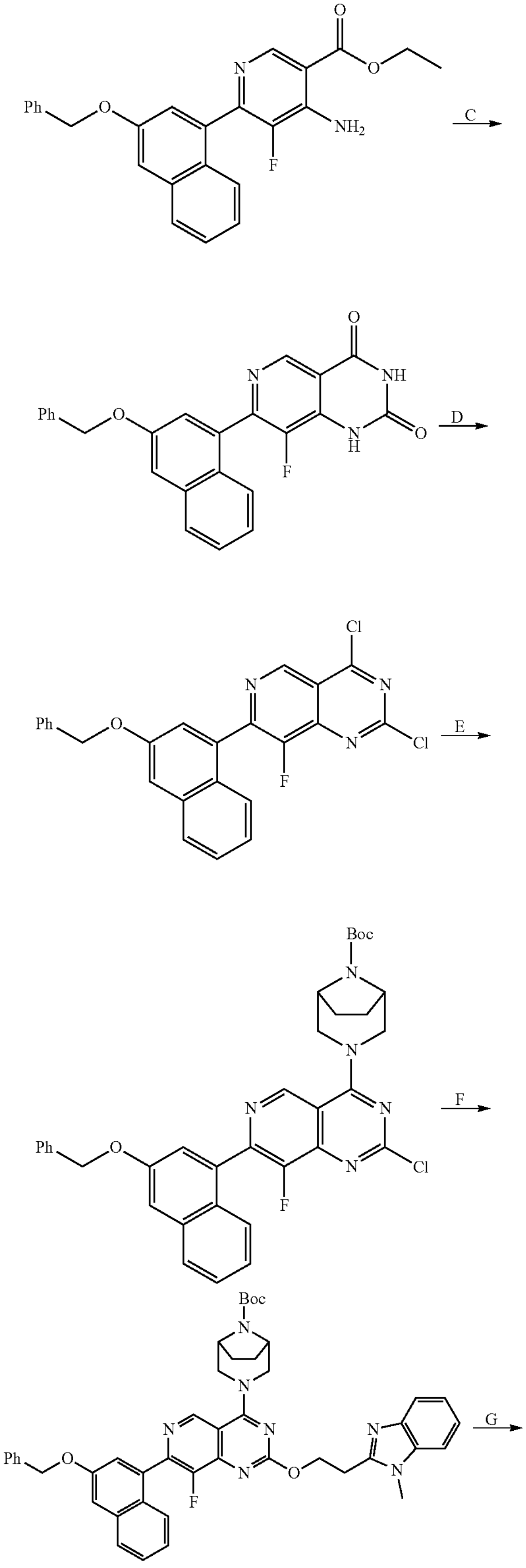

-continued
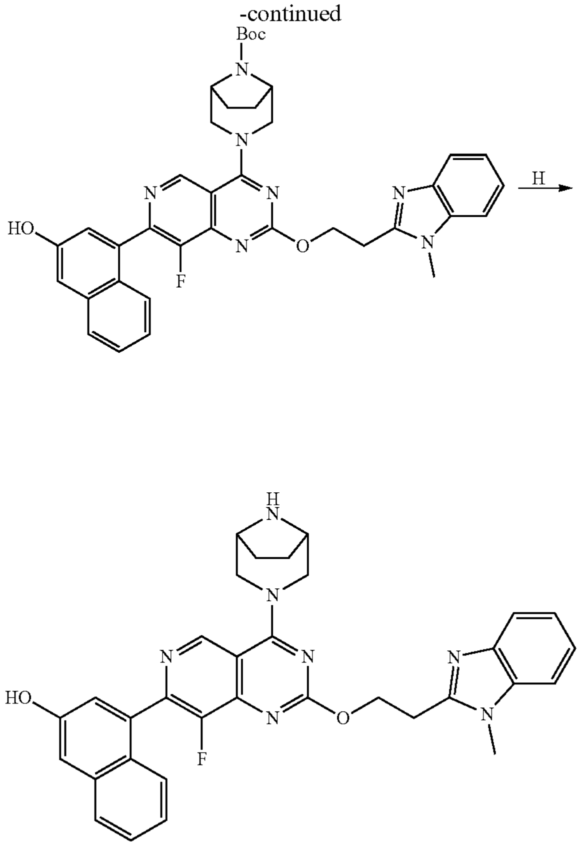
4-(4-((1R,5S)-3,8-diazabicyclo[3.2.1]octan-3-yl)-8-fluoro-2-(2-(1-methyl-1H-benzo[d]imidazol-2-yl)ethoxy)pyrido[4,3-d]pyrimidin-7-yl)naphthalen-2-ol (6.3 mg, 0.011 mmol, 34%) as a white solid. LCMS (MM-ES+APCI, Pos): m/z 576.2 (M+H).
Example 31
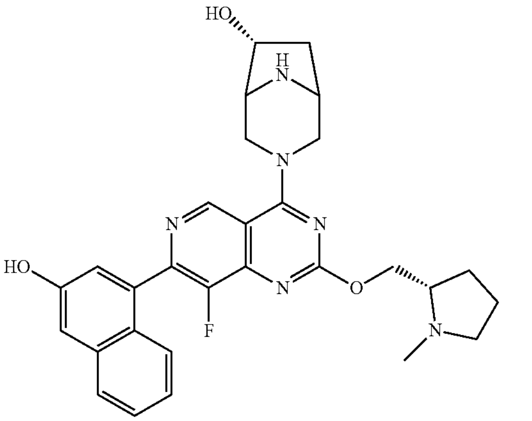 [SMILES: CN1CCC[C@H]1COc1nc(N2CC3C[C@@H](O)C(C2)N3)c2cnc(-c3cc(O)cc4ccccc34)c(F)c2n1]
3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octan-6-ol
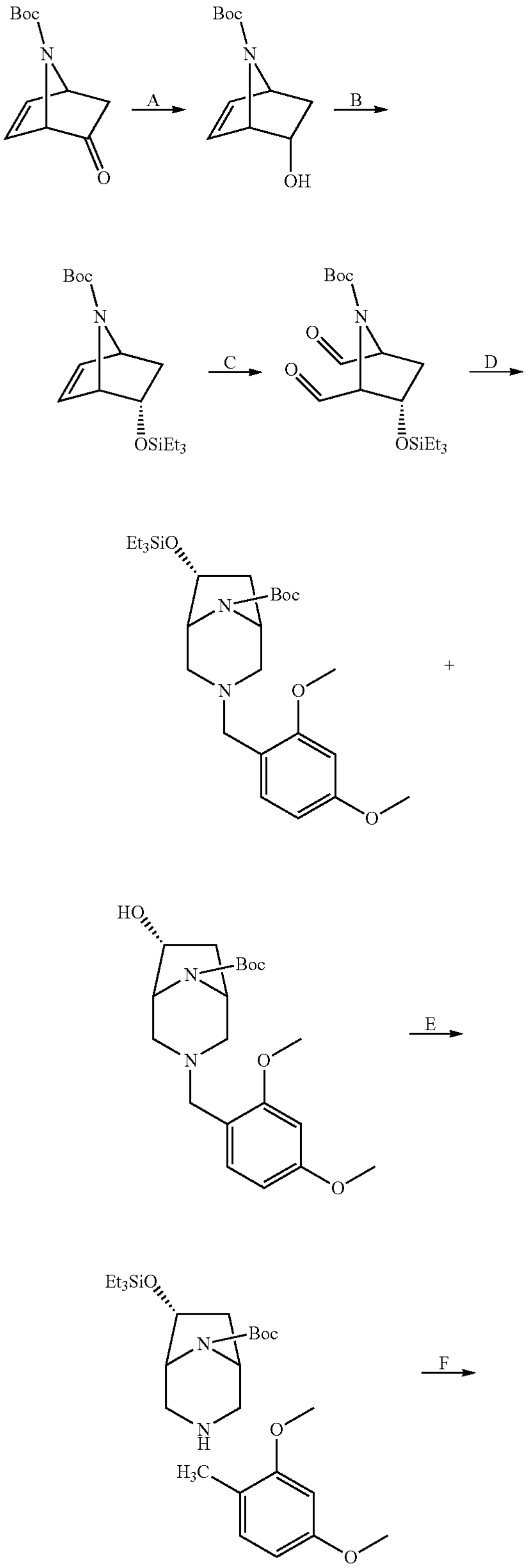

-continued

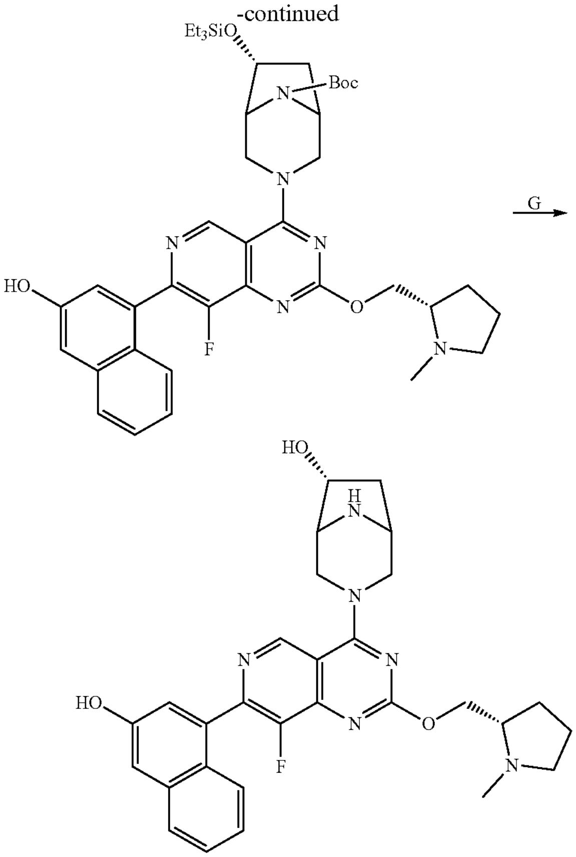

3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octan-6-ol was synthesized according to Example 2, Step I using tert-butyl 3-(8-fluoro-7-(3-hydroxynaphthalen-1-yl)-2-(((S)-1-methylpyrrolidin-2-yl)methoxy)pyrido[4,3-d]pyrimidin-4-yl)-6-((triethylsilyl)oxy)-3,8-diazabicyclo[3.2.1]octane-8-carboxylate in place of tert-butyl(1R,5S)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. Colorless solid, yield 30%. LCMS (MM-ES+APCI, Pos): m/z 531.2 (M+H).

Example 32

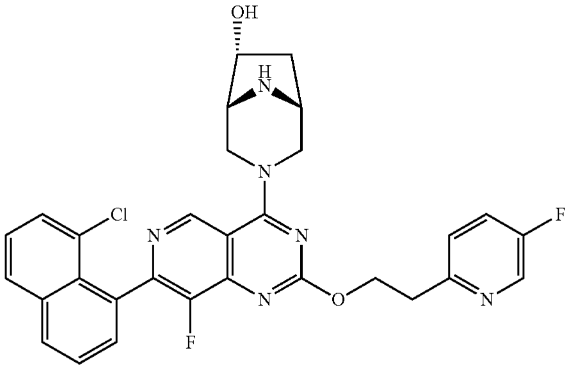 [SMILES: O[C@@H]1C[C@@H]2CN(c3nc(OCCc4ccc(F)cn4)nc4c(F)c(-c5cccc6cccc(Cl)c56)ncc34)C[C@H]1N2]

(1R,5R,6R)-3-(7-(8-chloronaphthalen-1-yl)-8-fluoro-2-(2-(5-fluoropyridin-2-yl)ethoxy)pyrido[4,3-d]pyrimidin-4-yl)-3,8-diazabicyclo[3.2.1]octan-6-ol

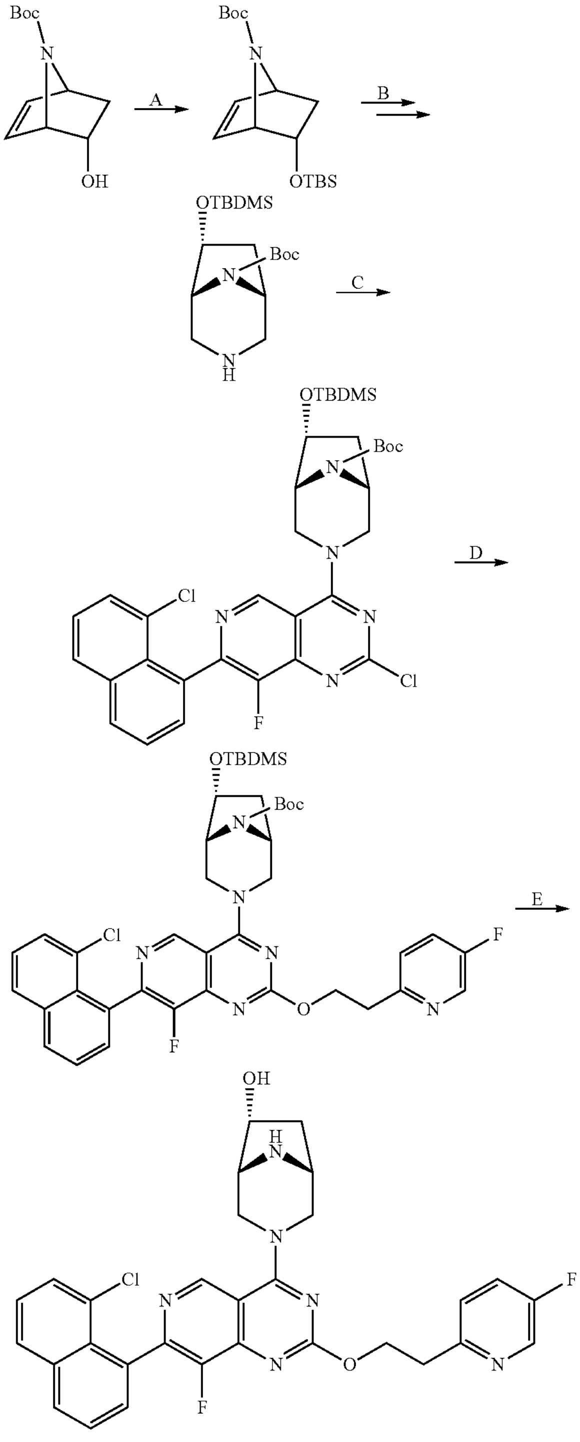

(1R,5R,6R)-3-(7-(8-chloronaphthalen-1-yl)-8-fluoro-2-(2-(5-fluoropyridin-2-yl)ethoxy)pyrido[4,3-d]pyrimidin-4-yl)-3,8-diazabicyclo[3.2.1]octan-6-ol (5 mg, 0.0087 mmol, 31% yield). LCMS (MM-ES+APCI, Pos): m/z 575.2 (M+H).

Example 33

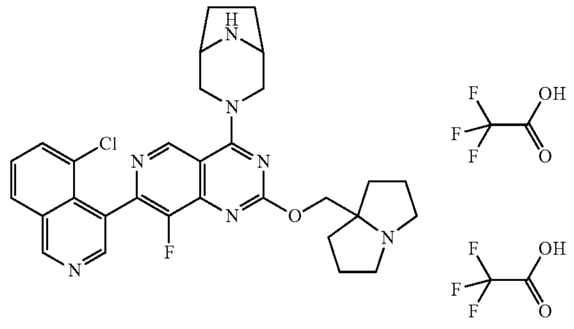 [SMILES: Fc1c(-c2cncc3cccc(Cl)c23)ncc2c(N3CC4CCC(C3)N4)nc(OCC34CCCN3CCC4)nc12 ; O=C(O)C(F)(F)F ; O=C(O)C(F)(F)F]

4-((1R,5S)-3,8-diazabicyclo[3.2.1]octan-3-yl)-7-(5-chloroisoquinolin-4-yl)-8-fluoro-2-((tetrahydro-1H-pyrrolizin-7a(5H)-yl)methoxy)pyrido[4,3-d]pyrimidine bis(2,2,2-trifluoroacetate)

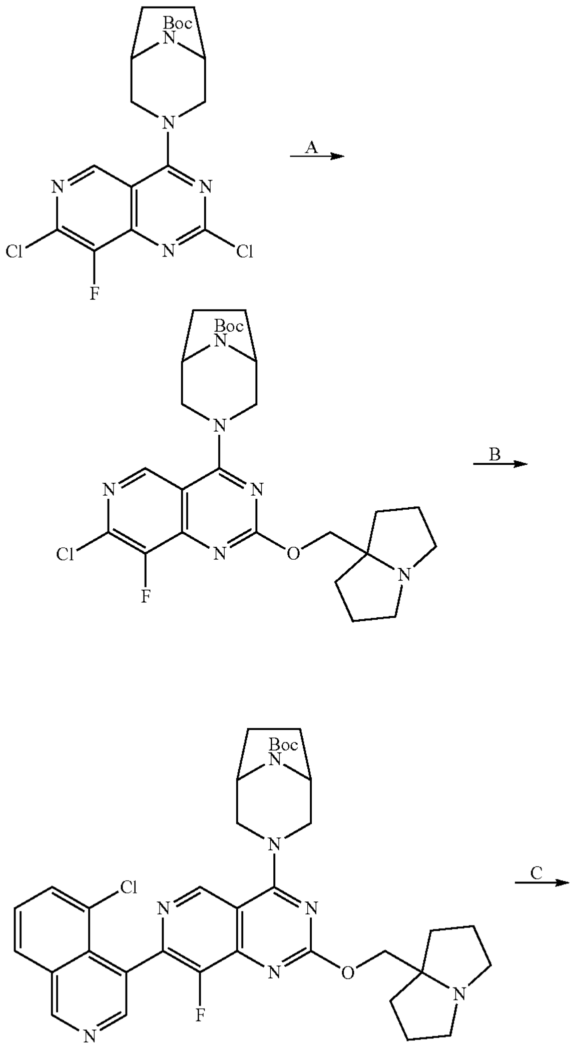

-continued

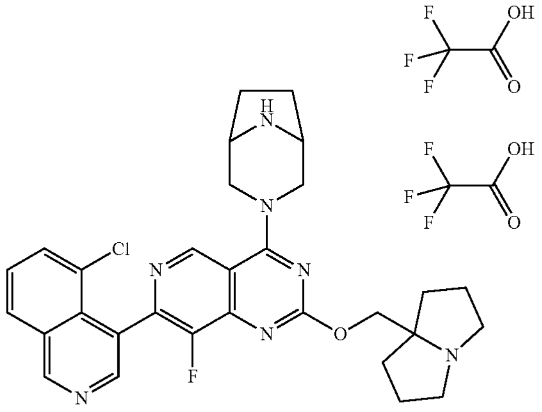

4-((1R,5S)-3,8-diazabicyclo[3.2.1]octan-3-yl)-7-(5-chloroisoquinolin-4-yl)-8-fluoro-2-((tetrahydro-1H-pyrrolizin-7a(5H)-yl)methoxy)pyrido[4,3-d]pyrimidine bis(2,2,2-trifluoroacetate) (6.4 mg, 0.008 mmol, 52%). LCMS (MM-ES+APCI, Pos): m/z 560.2 (M+H).

Example 34

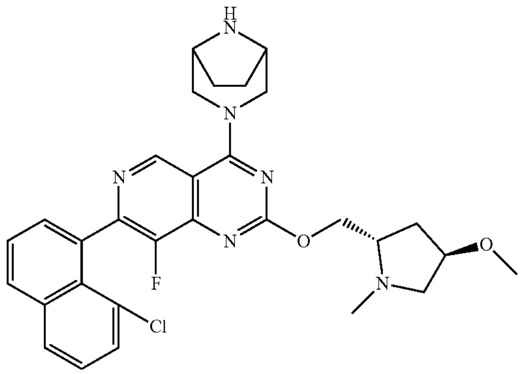 [SMILES: CO[C@@H]1C[C@@H](COc2nc(N3CC4CCC(C3)N4)c3cnc(-c4cccc5cccc(Cl)c45)c(F)c3n2)N(C)C1]

4-((1R,5S)-3,8-diazabicyclo[3.2.1]octan-3-yl)-7-(8-chloronaphthalen-1-yl)-8-fluoro-2-(((2S,4R)-4-methoxy-1-methylpyrrolidin-2-yl)methoxy)pyrido[4,3-d]pyrimidine

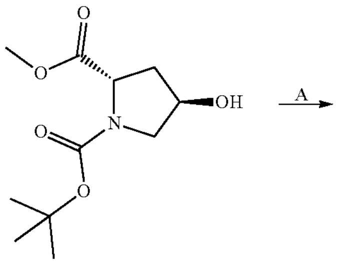

-continued

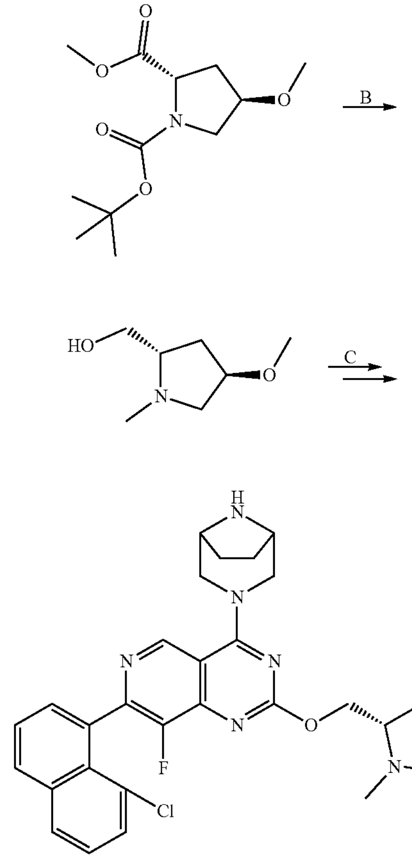

4-((1R,5S)-3,8-Diazabicyclo[3.2.1]octan-3-yl)-7-(8-chloronaphthalen-1-yl)-8-fluoro-2-(((2S,4R)-4-methoxy-1-methylpyrrolidin-2-yl)methoxy)pyrido[4,3-d]pyrimidine synthesized according to Example 29, Step H substituting ((2S,4R)-4-methoxy-1-methylpyrrolidin-2-yl)methanol in place of (S)-(1-isopropylpyrrolidin-2-yl)methanol followed by deprotection using Example 2, Step I (13.10 mg, 0.023 mmol, 26% yield). LCMS (MM-ES+APCI, Pos): m/z 563.2 [M+H].

Example 35

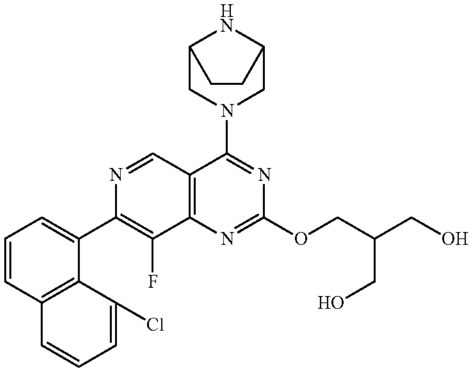 [SMILES: OCC(CO)COc1nc(N2CC3CCC(C2)N3)c2cnc(-c3cccc4cccc(Cl)c34)c(F)c2n1]

2-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl) propane-1,3-diol

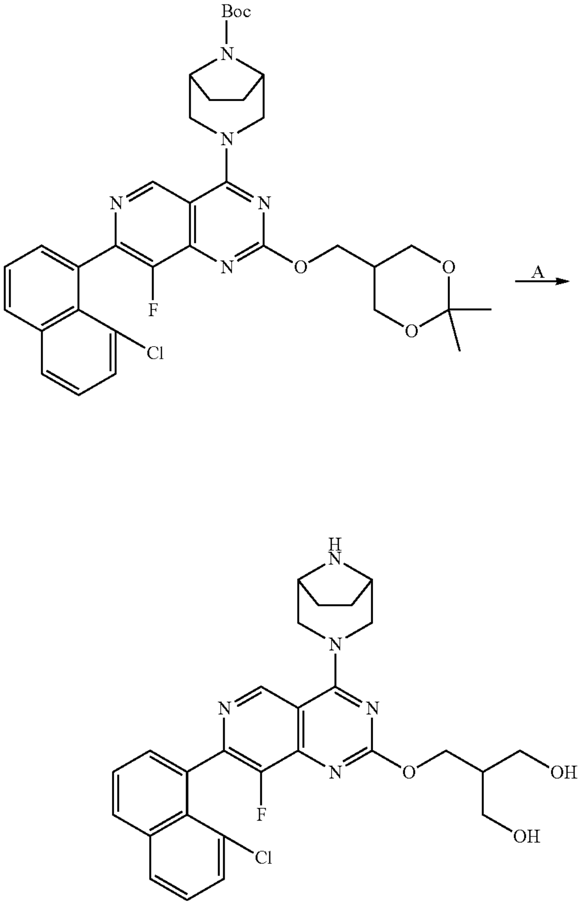

2-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl) propane-1,3-diol: To a crude mixture of tert-butyl(1R,5S)-3-(7-(8-chloronaphthalen-1-yl)-2-((2,2-dimethyl-1,3-dioxan-5-yl)methoxy)-8-fluoropyrido[4,3-d]pyrimidin-4-yl)-3,8-diazabicyclo[3.2.1]octane-8-carboxylate (60 mg, 0.09034 mmol) were added DCM (0.5 ml), TFA (0.25 ml), and water (0.25 ml), and the mixture was stirred at rt for 3 hours. The solvent was removed and the residue was purified by preparative HPLC (5 to 95% $CH_3CN$:$H_2O$ with 0.1% TFA, 15 minutes) to give impure product which was further purified by preparative HPLC (5 to 95% $CH_3CN$:$H_2O$ with 0.1% TFA, 20 minutes) to give desired product (TFA salt). The fraction containing product was added to sat. $NaHCO_3$, and extracted 2x with ethyl acetate. Pooled organic layers were dried over magnesium sulfate, filtered, and concentrated to give desired product (free base) as a white solid (4.31 mg, 0.00823 mmol, 9.1% yield). LCMS (MM-ES+APCI, Pos): m/z 524.2 [M+H].

Example 36
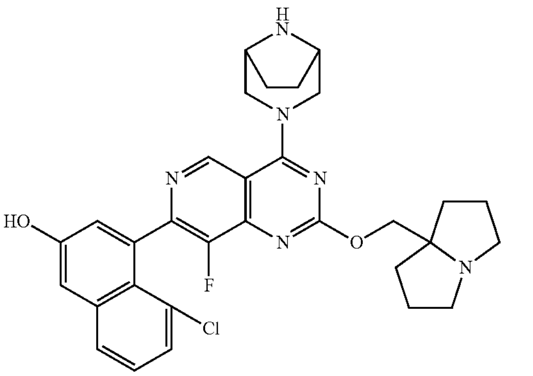 [SMILES: Oc1cc(-c2ncc3c(N4CC5CCC(C4)N5)nc(OCC45CCCN4CCC5)nc3c2F)c2c(Cl)cccc2c1]
4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-chloronaphthalen-2-ol
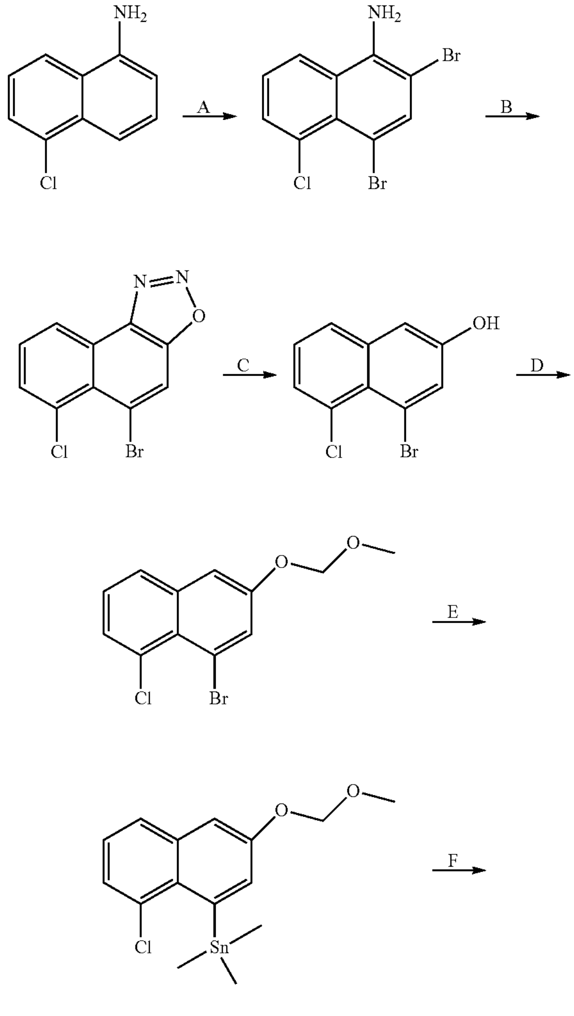
-continued
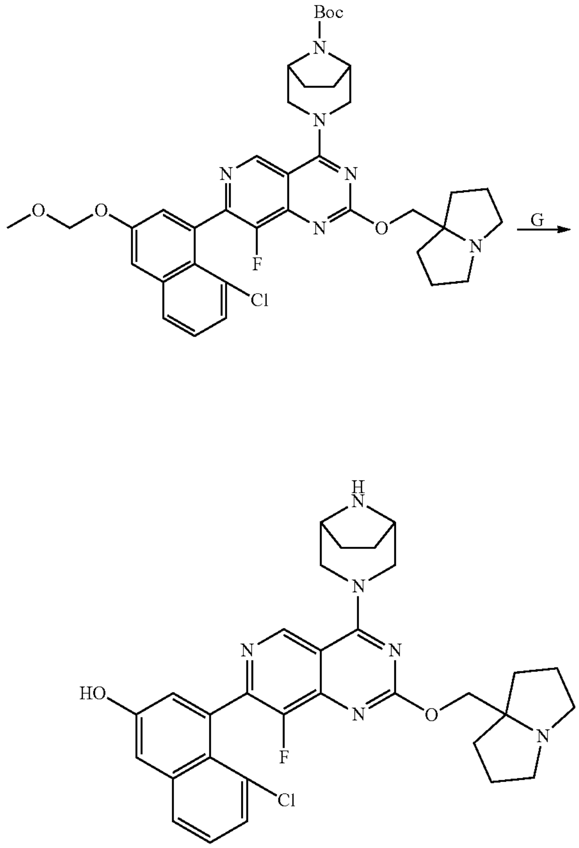
4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-chloronaphthalen-2-ol (7.86 mg, 0.00978 mmol, 8.8% yield.) LCMS (MM-ES+APCI, Pos): m/z 575.1 [M+H].
Example 37
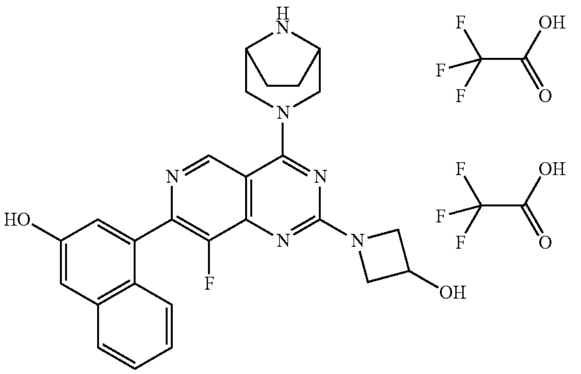

1-(4-((1R,5S)-3,8-diazabicyclo[3.2.1]octan-3-yl)-8-fluoro-7-(3-hydroxynaphthalen-1-yl)pyrido[4,3-d]pyrimidin-2-yl)azetidin-3-ol bis(2,2,2-trifluoroacetate)

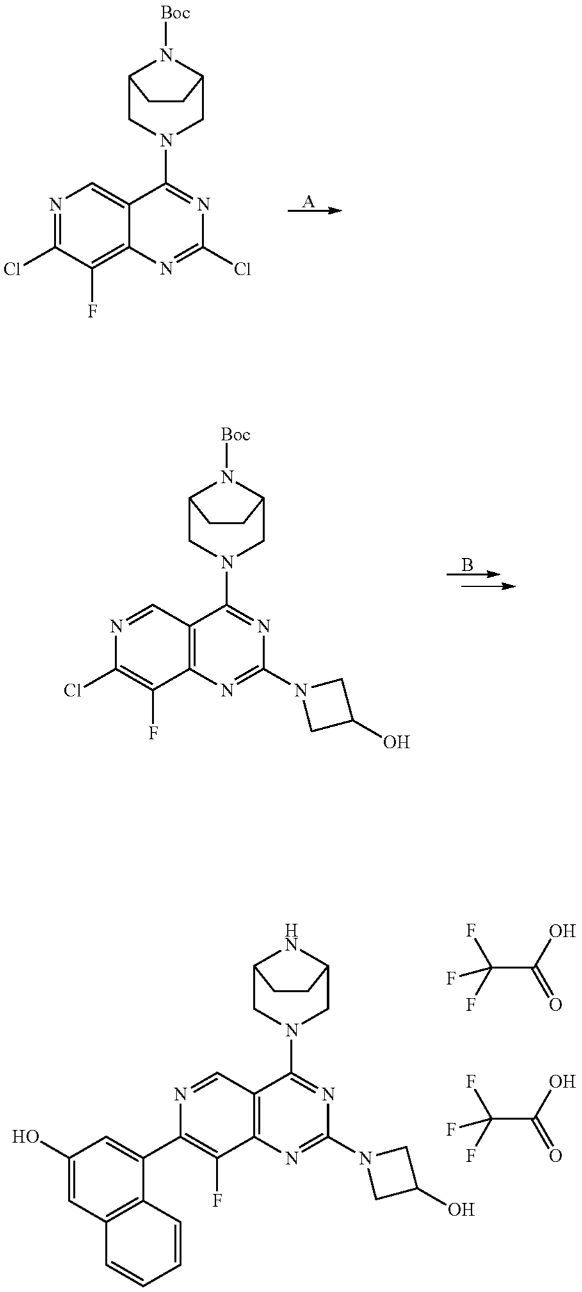

The title compound was synthesized according to Example 3, Step H substituting tert-butyl(1R,5S)-3-(7-chloro-8-fluoro-2-(3-hydroxyazetidin-1-yl)pyrido[4,3-d]pyrimidin-4-yl)-3,8-diazabicyclo[3.2.1]octane-8-carboxylate in place of tert-butyl(1R,5S)-3-(7-chloro-8-fluoro-2-(2-(1-methyl-1H-imidazol-2-yl)ethoxy)pyrido[4,3-d]pyrimidin-4-yl)-3,8-diazabicyclo[3.2.1]octane-8-carboxylate followed by Example 2, step I (1.16 mg, 0.0024 mmol, 70%). LCMS (MM-ES+APCI, Pos): m/z 473.2 (M+H).

Example 38

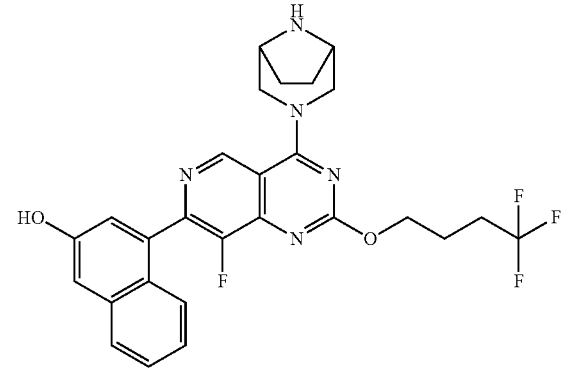 [SMILES: Oc1cc(-c2ncc3c(N4CC5CCC(C4)N5)nc(OCCCC(F)(F)F)nc3c2F)c2ccccc2c1]

4-(4-((1R,5S)-3,8-diazabicyclo[3.2.1]octan-3-yl)-8-fluoro-2-(4,4,4-trifluorobutoxy)pyrido[4,3-d]pyrimidin-7-yl)naphthalen-2-ol Synthesized according to Example 3, Step G and H substituting 4,4,4-trifluorobutan-1-ol in place of 2-(1-methyl-1H-imidazol-2-yl)ethan-1-ol followed by deprotection using Example 2, Step I (45.0 mg, 0.085 mmol, 80%). LCMS (MM-ES+APCI, Pos): m/z 528.2 [M+H].

Example 39

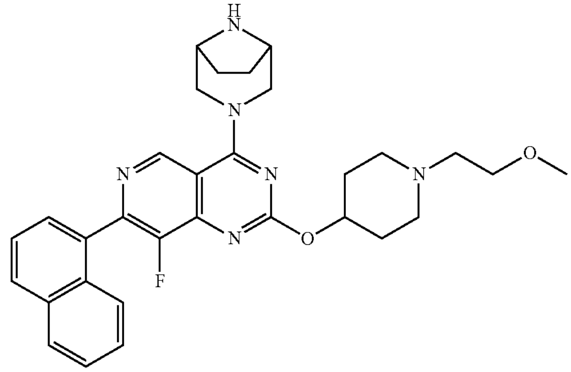 [SMILES: COCCN1CCC(Oc2nc(N3CC4CCC(C3)N4)c3cnc(-c4cccc5ccccc45)c(F)c3n2)CC1]

4-((1R,5S)-3,8-diazabicyclo[3.2.1]octan-3-yl)-8-fluoro-2-((1-(2-methoxyethyl) piperidin-4-yl)oxy)-7-(naphthalen-1-yl)pyrido[4,3-d]pyrimidine Synthesized according to Example 3, Step G substituting 1-(2-methoxyethyl) piperidin-4-ol in place of 2-(1-methyl-1H-imidazol-2-yl)ethan-1-ol and Example 3, Step H substituting naphthalen-1-ylboronic acid in place of 4-(4,4,5,5-tetramethyl-1,3,2-dioxaborolan-2-yl)naphthalen-2-ol followed by deprotection according to the method of Example 2, Step I (7.26 mg, 0.012 mmol, 91% yield). LCMS (MM-ES+APCI, Pos): m/z 543.2 [M+H].

Example 40

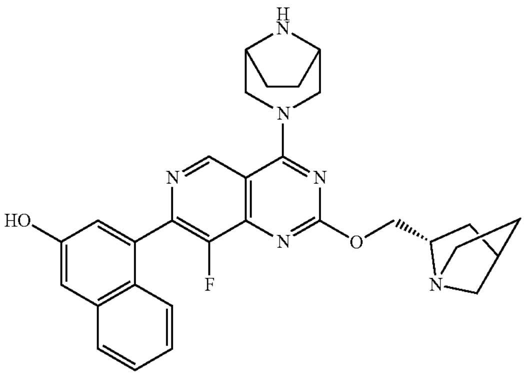 [SMILES: Oc1cc(-c2ncc3c(N4CC5CCC(C4)N5)nc(OC[C@@H]4CC5CCN4C5)nc3c2F)c2ccccc2c1]

4-(2-(((2S)-1-azabicyclo[2.2.1]heptan-2-yl)methoxy)-4-((1R,5S)-3,8-diazabicyclo[3.2.1]octan-3-yl)-8-fluoropyrido[4,3-d]pyrimidin-7-yl)naphthalen-2-ol

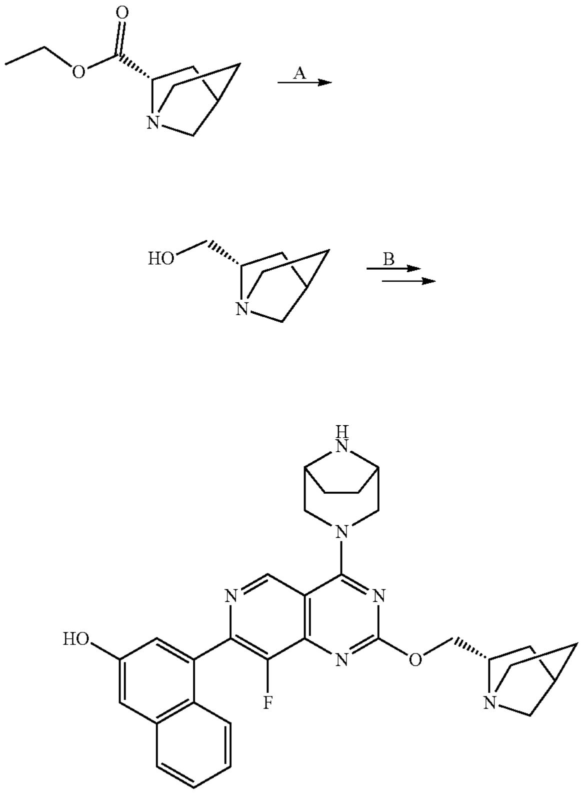

The title compound was synthesized according to Example 3, Step G and H substituting (1R,2S,4R)-1-azabicyclo[2.2.1]heptan-2-yl)methanol in place of 2-(1-methyl-1H-imidazol-2-yl)ethan-1-ol followed by deprotection using Example 2, Step I (15.59 mg, 0.030 mmol, 22% yield). LCMS (MM-ES+APCI, Pos): m/z 527.3 [M+H].

Example 41

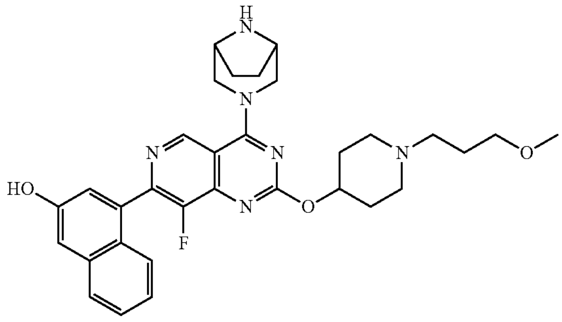 [SMILES: COCCCN1CCC(Oc2nc(N3CC4CCC(C3)N4)c3cnc(-c4cc(O)cc5ccccc45)c(F)c3n2)CC1]

4-(4-((1R,5S)-3,8-diazabicyclo[3.2.1]octan-3-yl)-8-fluoro-2-((1-(3-methoxypropyl) piperidin-4-yl)oxy)pyrido[4,3-d]pyrimidin-7-yl)naphthalen-2-ol Synthesized according to Example 3, Step G and H substituting 1-(3-methoxypropyl)-4-piperidinol in place of 2-(1-methyl-1H-imidazol-2-yl)ethan-1-ol followed by deprotection using Example 2, Step I (11.6 mg, 0.020 mmol, 34% yield), LCMS (MM-ES+APCI, Pos): m/z 573.3 [M+H].

Example 42

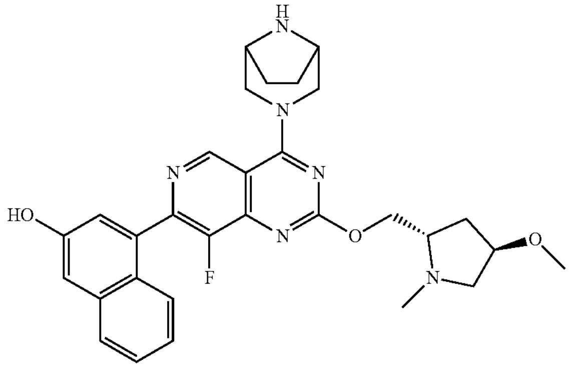 [SMILES: CO[C@@H]1C[C@@H](COc2nc(N3CC4CCC(C3)N4)c3cnc(-c4cc(O)cc5ccccc45)c(F)c3n2)N(C)C1]

4-(4-((1R,5S)-3,8-diazabicyclo[3.2.1]octan-3-yl)-8-fluoro-2-(((2S,4R)-4-methoxy-1-methylpyrrolidin-2-yl)methoxy)pyrido[4,3-d]pyrimidin-7-yl)naphthalen-2-ol Synthesized according to Example 3, Step G and H substituting ((2S,4R)-4-methoxy-1-methylpyrrolidin-2-yl)methanol in place of 2-(1-methyl-1H-imidazol-2-yl)ethan-1-ol followed by deprotection using Example 2, Step I (8.32 mg, 0.015 mmol, 35% yield). LCMS (MM-ES+APCI, Pos): m/z 545.3 [M+H].

Example 43

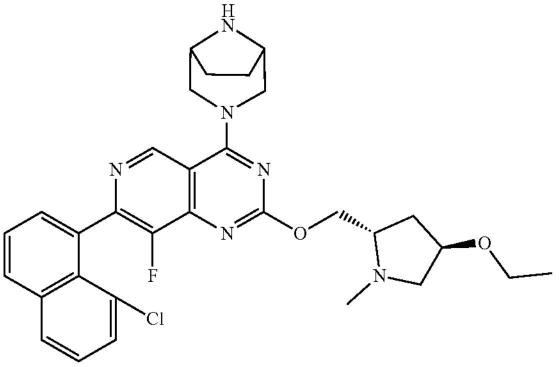 [SMILES: CCO[C@@H]1C[C@@H](COc2nc(N3CC4CCC(C3)N4)c3cnc(-c4cccc5cccc(Cl)c45)c(F)c3n2)N(C)C1]

4-((1R,5S)-3,8-diazabicyclo[3.2.1]octan-3-yl)-7-(8-chloronaphthalen-1-yl)-2-(((2S,4R)-4-ethoxy-1-methylpyrrolidin-2-yl)methoxy)-8-fluoropyrido[4,3-d]pyrimidine Synthesized according to Example 34 substituting ethyl iodide for methyl iodide in Step A (6.95 mg, 0.00897 mmol, 87% yield). LCMS (MM-ES+APCI, Pos): m/z 577.2 [M+H].

Example 44

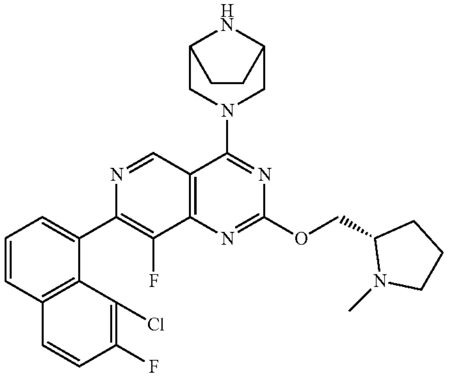 [SMILES: CN1CCC[C@H]1COc1nc(N2CC3CCC(C2)N3)c2cnc(-c3cccc4ccc(F)c(Cl)c34)c(F)c2n1]

4-((1R,5S)-3,8-diazabicyclo[3.2.1]octan-3-yl)-7-(8-chloro-7-fluoronaphthalen-1-yl)-8-fluoro-2-(((S)-1-methylpyrrolidin-2-yl)methoxy)pyrido[4,3-d]pyrimidine

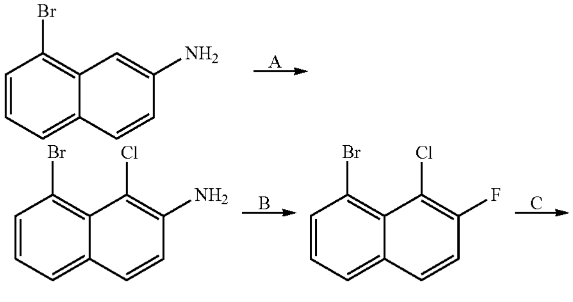

-continued

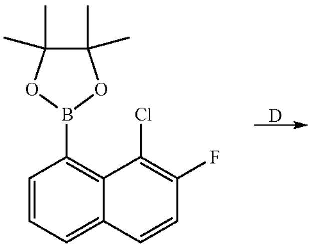

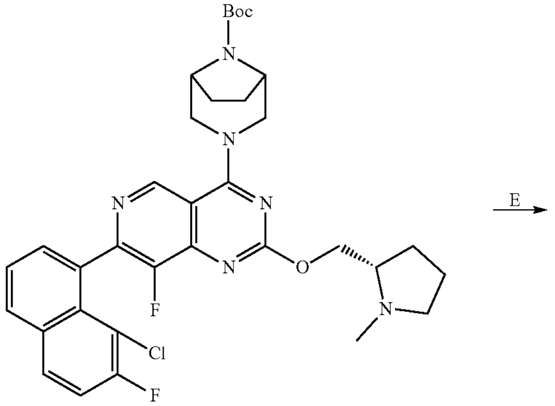

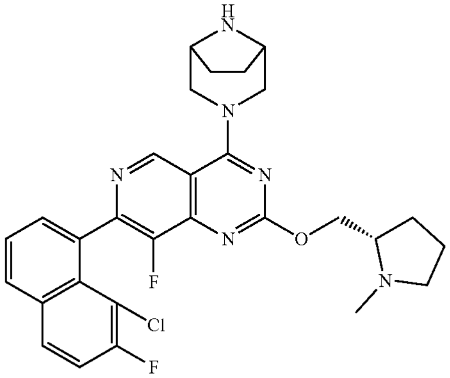

The title compound was synthesized according to the method of Example 2, step I (6.93 mg, 0.093 mmol, 86% yield). LCMS (MM-ES+APCI, Pos): m/z 551.2 [M+H].

Example 45

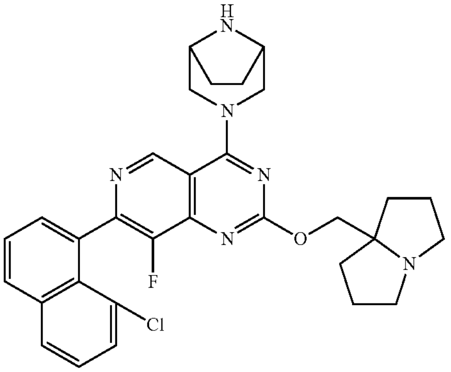 [SMILES: Fc1c(-c2cccc3cccc(Cl)c23)ncc2c(N3CC4CCC(C3)N4)nc(OCC34CCCN3CCC4)nc12]

4-((1R,5S)-3,8-diazabicyclo[3.2.1]octan-3-yl)-7-(8-chloronaphthalen-1-yl)-8-fluoro-2-((tetrahydro-1H-pyrrolizin-7a(5H)-yl)methoxy)pyrido[4,3-d]pyrimidine Synthesized according to Example 29, Step H substituting tetrahydro-1H-pyrrolizine-7a(5H)-methanol in place of (S)-(1-isopropylpyrrolidin-2-yl)methanol followed by deprotection using Example 2, Step I (5.93 mg, 0.00786 mmol, 18% yield). LCMS (MM-ES+APCI, Pos): m/z 559.2 [M+H].

Example 46

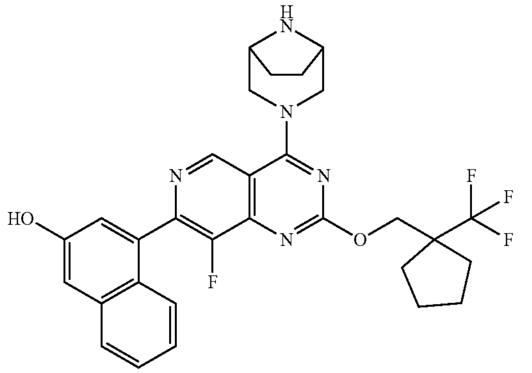 [SMILES: Oc1cc(-c2ncc3c(N4CC5CCC(C4)N5)nc(OCC4(C(F)(F)F)CCCC4)nc3c2F)c2ccccc2c1]

4-(4-((1R,5S)-3,8-diazabicyclo[3.2.1]octan-3-yl)-8-fluoro-2-((1-(trifluoromethyl)cyclopentyl)methoxy)pyrido[4,3-d]pyrimidin-7-yl)naphthalen-2-ol Synthesized according to Example 3, Step G and H substituting [1-(trifluoromethyl)cyclopentyl]methanol in place of 2-(1-methyl-1H-imidazol-2-yl)ethan-1-ol followed by deprotection according to the method of Example 2, Step I (10.29 mg, 0.013 mmol, 9% yield). LCMS (MM-ES+APCI, Pos): m/z 568.2 [M+H].

Example 47

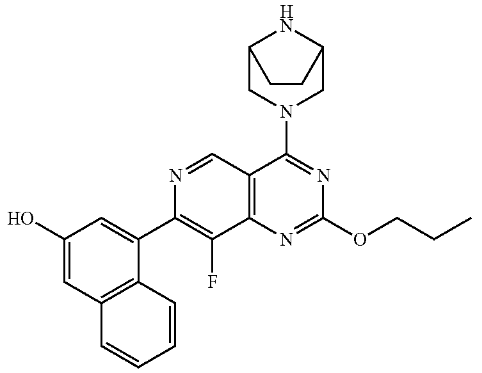 [SMILES: CCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-propoxypyrido[4,3-d]pyrimidin-7-yl)naphthalen-2-ol Synthesized according to Example 3, Step G and H substituting 1-Propanol in place of 2-(1-methyl-1H-imidazol-2-yl)ethan-1-ol followed by deprotection according to the method of Example 2, Step I (37.91 mg, 0.0578 mmol, 32% yield). LCMS (MM-ES+APCI, Pos): m/z 460.2 [M+H].

Example 48

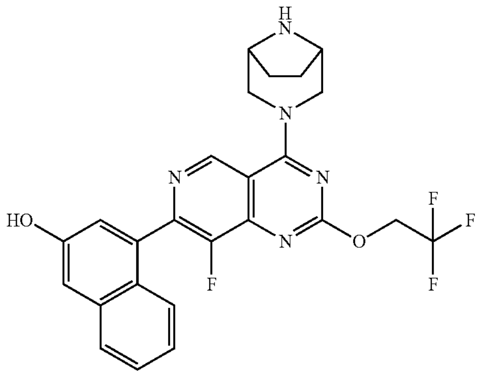 [SMILES: Oc1cc(-c2ncc3c(N4CC5CCC(C4)N5)nc(OCC(F)(F)F)nc3c2F)c2ccccc2c1]

4-(4-((1R,5S)-3,8-diazabicyclo[3.2.1]octan-3-yl)-8-fluoro-2-(2,2,2-trifluoroethoxy)pyrido[4,3-d]pyrimidin-7-yl)naphthalen-2-ol Synthesized according to Example 3, Step G and H substituting 2,2,2-Trifluoroethanol in place of 2-(1-methyl-1H-imidazol-2-yl)ethan-1-ol followed by deprotection according to the method of Example 2, Step I (42.15 mg, 0.0606 mmol, 33% yield). LCMS (MM-ES+APCI, Pos): m/z 500.2 [M+H].

Example 49

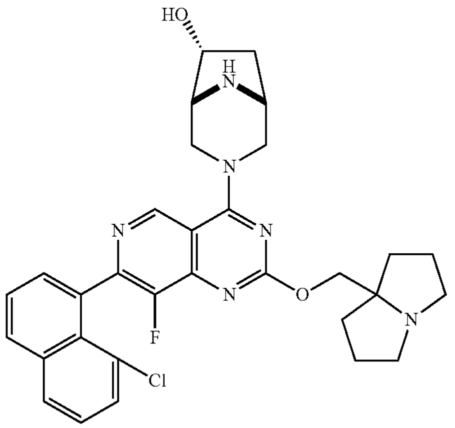

(1R,5R,6R)-3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octan-6-ol

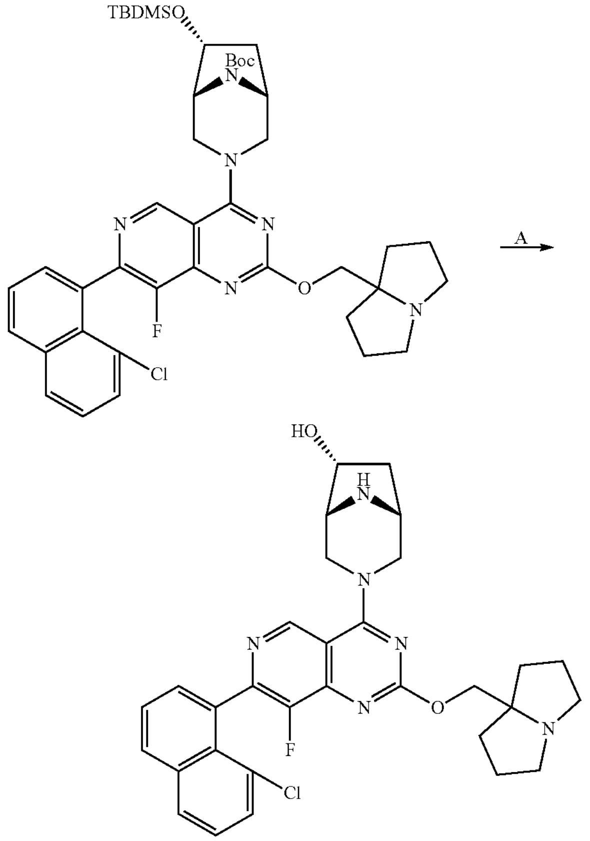

3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octan-6-ol (10.29, 0.0128 mmol, 38% yield). LCMS (MM-ES+APCI, Pos): m/z 575.2 [M+H].

Example 50

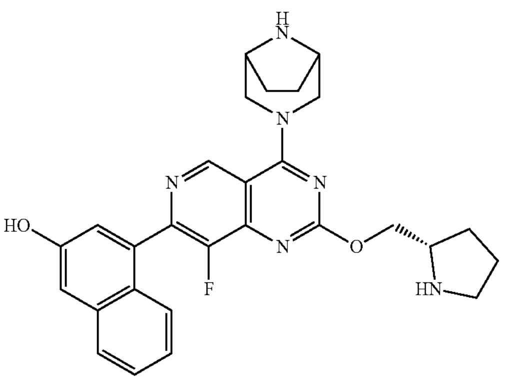 [SMILES: Oc1cc(-c2ncc3c(N4CC5CCC(C4)N5)nc(OC[C@@H]4CCCN4)nc3c2F)c2ccccc2c1]

4-(4-((1R,5S)-3,8-diazabicyclo[3.2.1]octan-3-yl)-8-fluoro-2-(((S)-pyrrolidin-2-yl)methoxy)pyrido[4,3-d]pyrimidin-7-yl)naphthalen-2-ol Synthesized according to Example 3, Step G and H substituting tert-butyl(S)-2-(hydroxymethyl)pyrrolidine-1-carboxylate in place of 2-(1-methyl-1H-imidazol-2-yl)ethan-1-ol followed by deprotection according to the method of Example 2, Step I (53.03 mg, 0.0761 mmol, 97% yield). LCMS (MM-ES+APCI, Pos): m/z 501.2 [M+H].

Example 51

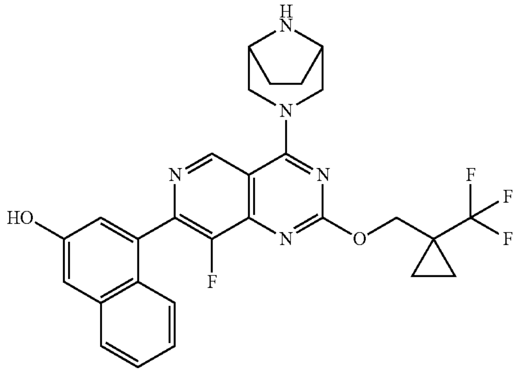 [SMILES: Oc1cc(-c2ncc3c(N4CC5CCC(C4)N5)nc(OCC4(C(F)(F)F)CC4)nc3c2F)c2ccccc2c1]

4-(4-((1R,5S)-3,8-diazabicyclo[3.2.1]octan-3-yl)-8-fluoro-2-((1-(trifluoromethyl)cyclopropyl)methoxy)pyrido[4,3-d]pyrimidin-7-yl)naphthalen-2-ol Synthesized according to Example 3, Step G and H substituting [1-(Trifluoromethyl)cyclopropyl]methanol in place of 2-(1-methyl-1H-imidazol-2-yl)ethan-1-ol followed by deprotection according to the method of Example 2, Step I (18.0 mg, 0.0245 mmol, 15.7% yield). LCMS (MM-ES+APCI, Pos): m/z 540.2 [M+H].

Example 52

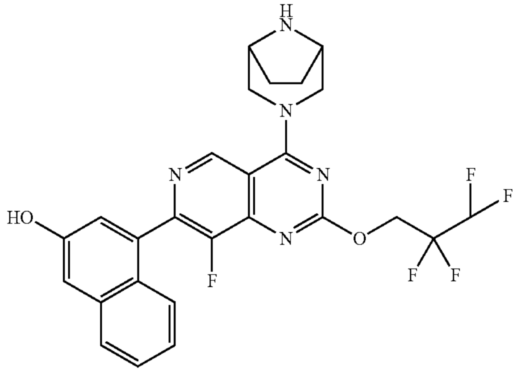 [SMILES: Oc1cc(-c2ncc3c(N4CC5CCC(C4)N5)nc(OCC(F)(F)C(F)F)nc3c2F)c2ccccc2c1]

4-(4-((1R,5S)-3,8-diazabicyclo[3.2.1]octan-3-yl)-8-fluoro-2-(2,2,3,3-tetrafluoropropoxy)pyrido[4,3-d]pyrimidin-7-yl)naphthalen-2-ol Synthesized according to Example 3, Step G and H substituting 2,2,3,3-Tetrafluoropropan-1-ol in place of 2-(1-methyl-1H-imidazol-2-yl)ethan-1-ol and deprotection according to the method of Example 2, Step I (31.7 mg, 0.0435 mmol, 33.5% yield). LCMS (MM-ES+APCI, Pos): m/z 532.2 [M+H].

Example 53

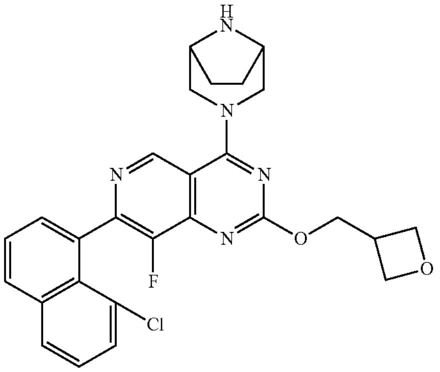 [SMILES: Fc1c(-c2cccc3cccc(Cl)c23)ncc2c(N3CC4CCC(C3)N4)nc(OCC3COC3)nc12]

4-((1R,5S)-3,8-diazabicyclo[3.2.1]octan-3-yl)-7-(8-chloronaphthalen-1-yl)-8-fluoro-2-(oxetan-3-yl-methoxy)pyrido[4,3-d]pyrimidine Synthesized according to Example 29, Step H substituting oxetan-3-ylmethanol in place of (S)-(1-isopropylpyrrolidin-2-yl)methanol followed by deprotection using Example 2, Step I (10.4 mg, 0.0206 mmol, 34% yield). LCMS (MM-ES+APCI, Pos): m/z 506.2 [M+H].

Example 54

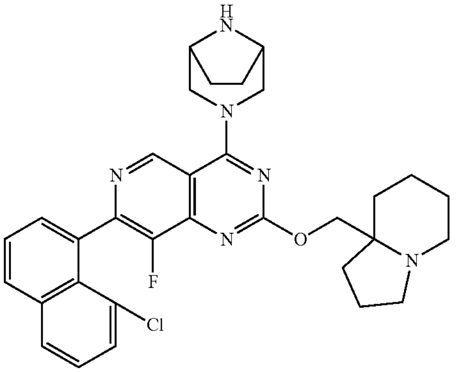 [SMILES: Fc1c(-c2cccc3cccc(Cl)c23)ncc2c(N3CC4CCC(C3)N4)nc(OCC34CCCCN3CCC4)nc12]

4-((1R,5S)-3,8-diazabicyclo[3.2.1]octan-3-yl)-7-(8-chloronaphthalen-1-yl)-8-fluoro-2-((hexahydroin-dolizin-8a(1H)-yl)methoxy)pyrido[4,3-d]pyrimidine Synthesized according to Example 29, Step H substituting (hexahydroindolizin-8a(1H)-yl)methanol in place of (S)-(1-isopropylpyrrolidin-2-yl)methanol followed by deprotection using Example 2, Step I (6.20 mg, 0.00806 mmol, 42% yield). LCMS (MM-ES+APCI, Pos): m/z 573.3 [M+H].

Example 55

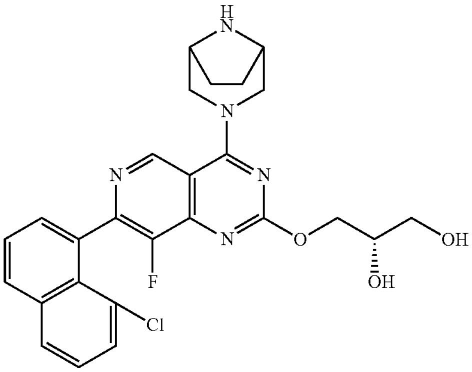 [SMILES: OC[C@H](O)COc1nc(N2CC3CCC(C2)N3)c2cnc(-c3cccc4cccc(Cl)c34)c(F)c2n1]

(S)-3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) propane-1,2-diol Synthesized according to Example 29, Step H substituting (R)-(−)-2,2-Dimethyl-1,3-dioxolane-4-methanol in place of (S)-(1-isopropylpyrrolidin-2-yl)methanol followed by deprotection using Example 35, Step A (15.1, 0.025 mmol, 23% yield). LCMS (MM-ES+APCI, Pos): m/z 510.2 [M+H].

Example 56

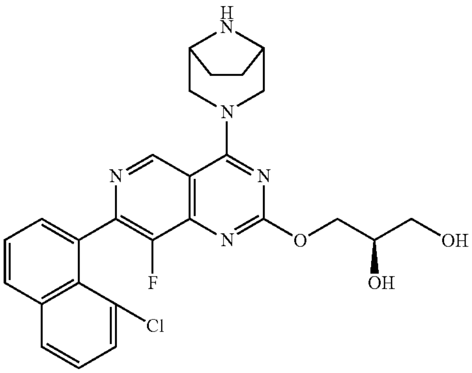 [SMILES: OC[C@@H](O)COc1nc(N2CC3CCC(C2)N3)c2cnc(-c3cccc4cccc(Cl)c34)c(F)c2n1]

(R)-3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) propane-1,2-diol Synthesized according to Example 29, Step H substituting (s)-(+)-2,2-dimethyl-1,3-dioxolane-4-methanol in place of (S)-(1-isopropylpyrrolidin-2-yl)methanol followed by deprotection using Example 35, Step A (16.6 mg, 0.0324 mmol, 30% yield). LCMS (MM-ES+APCI, Pos): m/z 510.2 [M+H].

Example 57

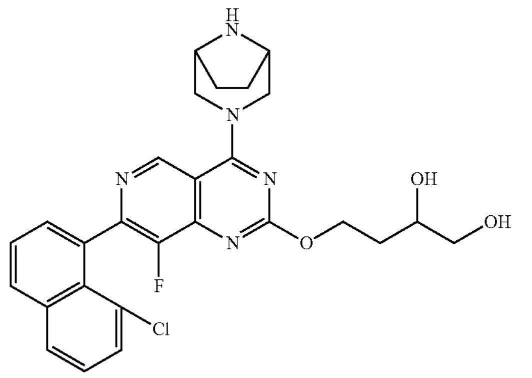 [SMILES: OCC(O)CCOc1nc(N2CC3CCC(C2)N3)c2cnc(-c3cccc4cccc(Cl)c34)c(F)c2n1]

4-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) butane-1,2-diol Synthesized according to Example 29, Step H substituting 2-(2,2-Dimethyl-1,3-dioxolan-4-yl)ethanolin place of (S)-(1-isopropylpyrrolidin-2-yl)methanol followed by deprotection using Example 35, Step A (12.1 mg, 0.0194 mmol, 31% yield). LCMS (MM-ES+APCI, Pos): m/z 524.2 [M+H].

Example 58

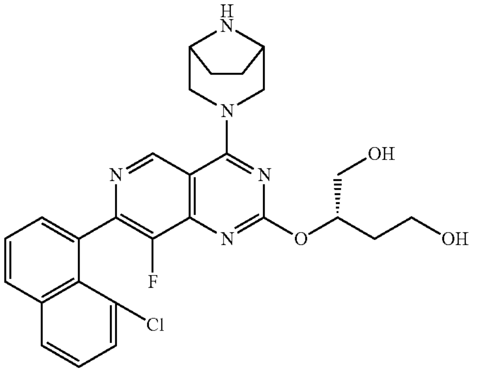 [SMILES: OCC[C@@H](CO)Oc1nc(N2CC3CCC(C2)N3)c2cnc(-c3cccc4cccc(Cl)c34)c(F)c2n1]

(S)-2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) butane-1,4-diol

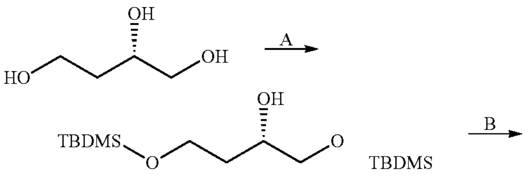

-continued

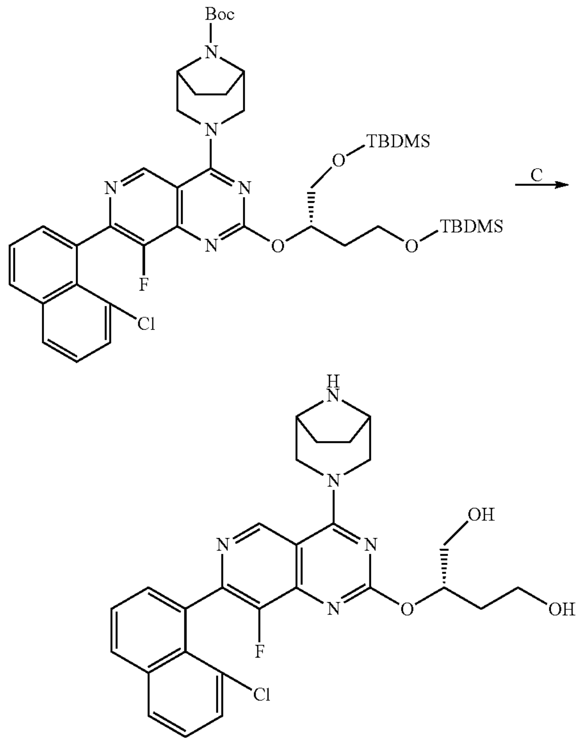

(S)-2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) butane-1,4-diol (3.52 mg, 0.00566 mmol, 44% yield). LCMS (MM-ES+APCI, Pos): m/z 524.2 [M+H].

Example 59

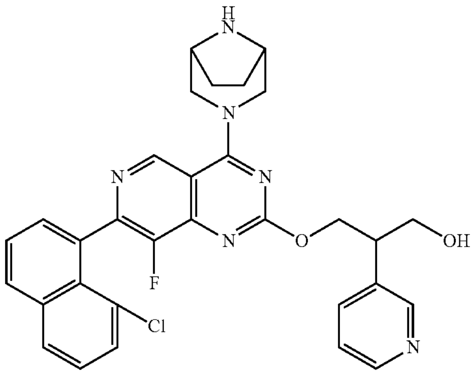 [SMILES: OCC(COc1nc(N2CC3CCC(C2)N3)c2cnc(-c3cccc4cccc(Cl)c34)c(F)c2n1)c1cccnc1]

3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)-2-(pyridin-3-yl) propan-1-ol Synthesized according to Example 29, Step H substituting 2-(pyridin-3-yl) propane-1,3-diol in place of (S)-(1-isopropylpyrrolidin-2-yl)methanol followed by deprotection using Example 2, Step I (25.23 mg, 0.0377 mmol, 87% yield). LCMS (MM-ES+APCI, Pos): m/z 571.3 [M+H].

Example 60

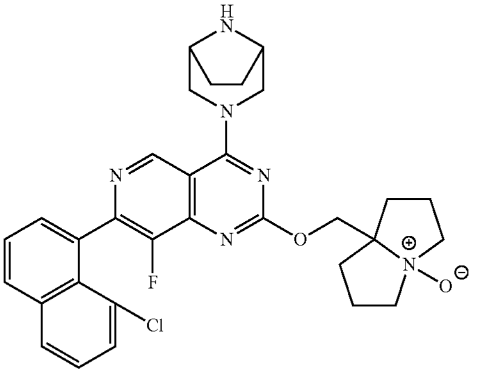 [SMILES: [O-][N+]12CCCC1(COc1nc(N3CC4CCC(C3)N4)c3cnc(-c4cccc5cccc(Cl)c45)c(F)c3n1)CCC2]

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydropyrrolizine 4 (1H)-oxide

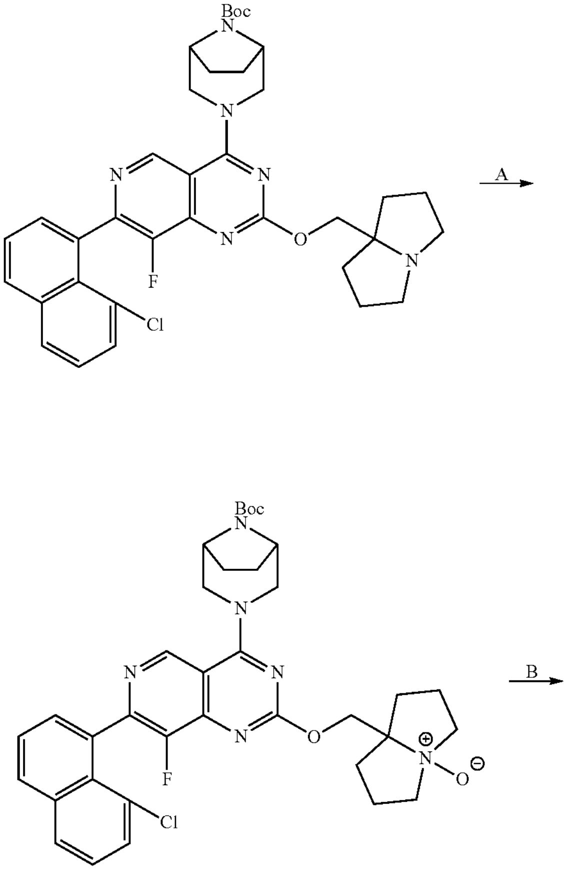

-continued

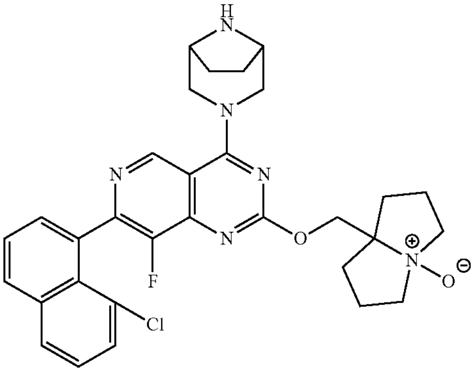

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydropyrrolizine 4 (1H)-oxide. 7a-(((4-((1R,5S)-8-(tert-butoxycarbonyl)-3,8-diazabicyclo[3.2.1]octan-3-yl)-7-(8-chloronaphthalen-1-yl)-8-fluoropyrido[4,3-d]pyrimidin-2-yl)oxy)methyl)hexahydropyrrolizine 4 (1H)-oxide was deprotected according to the method of Example 2, Step I (5.55 mg, 0.00825 mmol, 37% yield). LCMS (MM-ES+APCI, Pos): m/z 575.3 [M+H].

Example 61

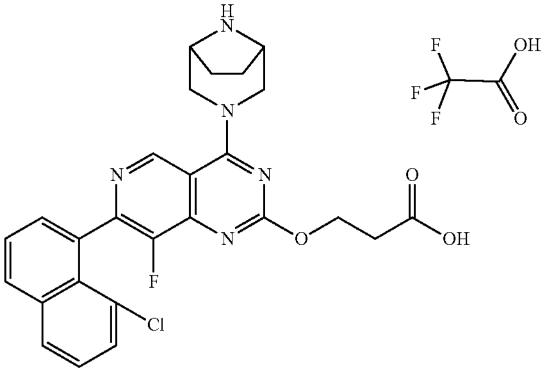 [SMILES: O=C(O)CCOc1nc(N2CC3CCC(C2)N3)c2cnc(-c3cccc4cccc(Cl)c34)c(F)c2n1 ; O=C(O)C(F)(F)F]

3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)propanoic acid Compound with 2,2,2-trifluoroacetaldehyde Synthesized according to Example 29, Step H substituting ethyl 3-hydroxypropanoate in place of (S)-(1-isopropylpyrrolidin-2-yl)methanol followed by deprotection using Example 2, Step I (1.66 mg, 0.00275 mmol, 16% yield). LCMS (MM-ES+APCI, Pos): m/z 530.3 [M+Na].

Example 62
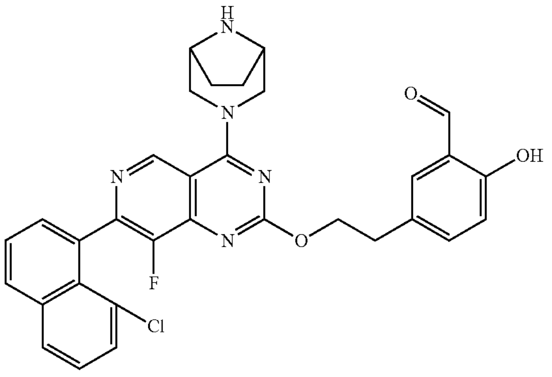 [SMILES: O=Cc1cc(CCOc2nc(N3CC4CCC(C3)N4)c3cnc(-c4cccc5cccc(Cl)c45)c(F)c3n2)ccc1O]
5-(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)-2-hydroxybenzaldehyde
5-(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)-2-hydroxybenzaldehyde (8.83 mg, 0.015 mmol, 45% yield). LCMS (MM-ES+APCI, Pos): m/z 584.2 [M+H].
Example 63
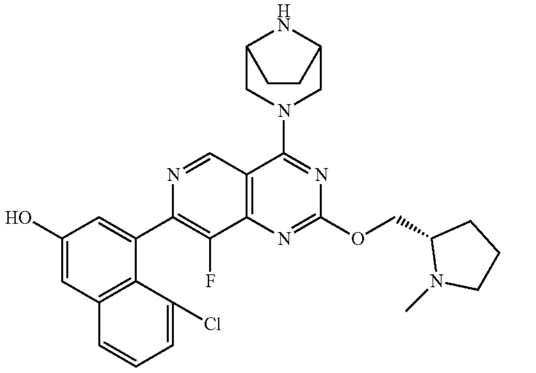 [SMILES: CN1CCC[C@H]1COc1nc(N2CC3CCC(C2)N3)c2cnc(-c3cc(O)cc4cccc(Cl)c34)c(F)c2n1]
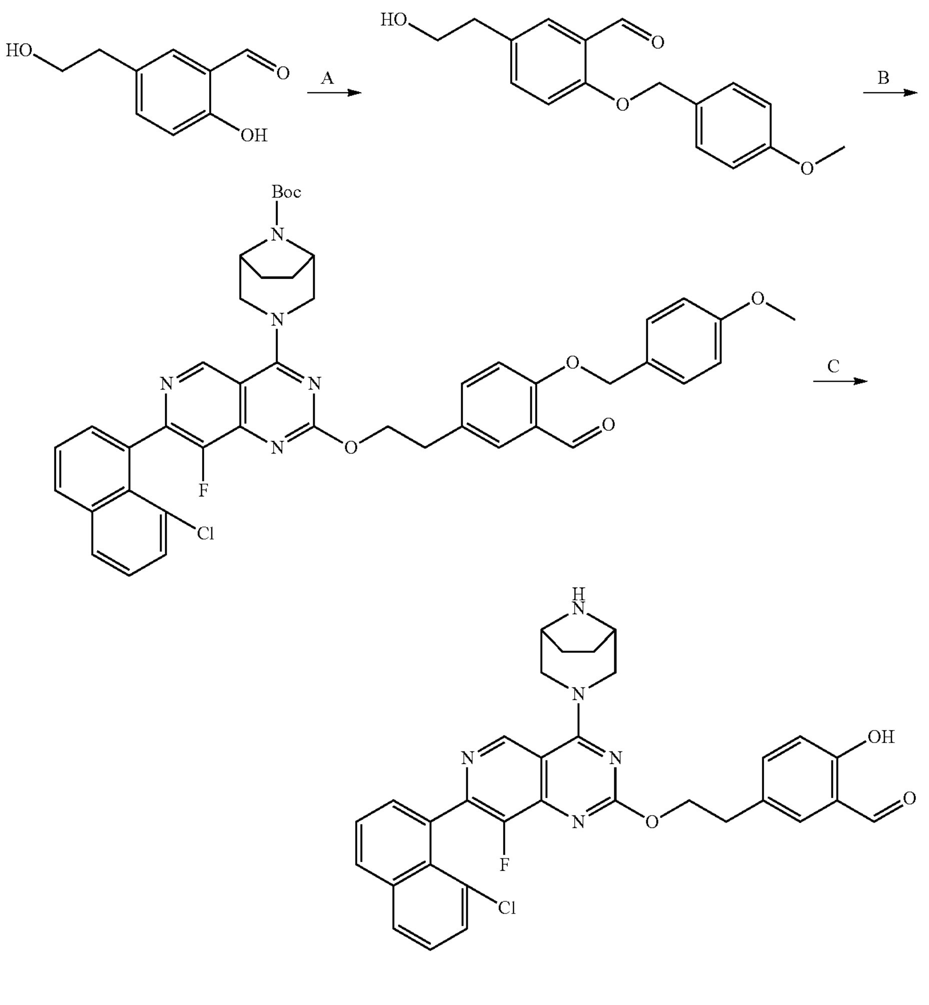

4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)-5-chloronaphthalen-2-ol Synthesized according to Example 36, Step A to G substituting tert-butyl(1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methylpyrrolidin-2-yl)methanol in place of 2-(1-methyl-1H-imidazol-2-yl)ethan-1-ol) in place of tert-butyl(1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate in step F (6.08 mg, 0.00816 mmol, 7.2% yield). LCMS (MM-ES+APCI, Pos): m/z 549.3 [M+H].

Example 64

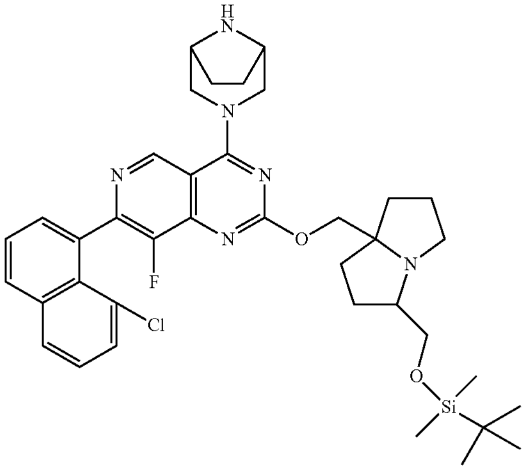 [SMILES: CC(C)(C)[Si](C)(C)OCC1CCC2(COc3nc(N4CC5CCC(C4)N5)c4cnc(-c5cccc6cccc(Cl)c56)c(F)c4n3)CCCN12]

4-((1R,5S)-3,8-diazabicyclo[3.2.1]octan-3-yl)-2-((3-(((tert-butyldimethylsilyl)oxy)methyl)tetrahydro-1H-pyrrolizin-7a(5H)-yl)methoxy)-7-(8-chloronaphthalen-1-yl)-8-fluoropyrido[4,3-d]pyrimidine Synthesized according to Example 2, Step H using tert-butyl(1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate and (3-(((tert-butyldimethylsilyl)oxy)methyl)tetrahydro-1H-pyrrolizin-7a(5H)-yl)methanol as starting materials and deprotection according to the method of Example 2, Step I (5.72 mg, 0.00614 mmol, 21% yield). LCMS (MM-ES+APCI, Pos): m/z 703.3 [M+H].

Examples 65 & 66

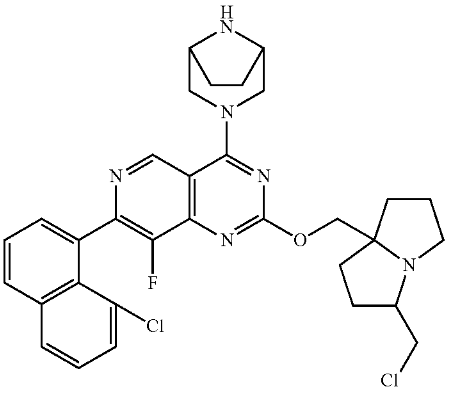

first eluting peak

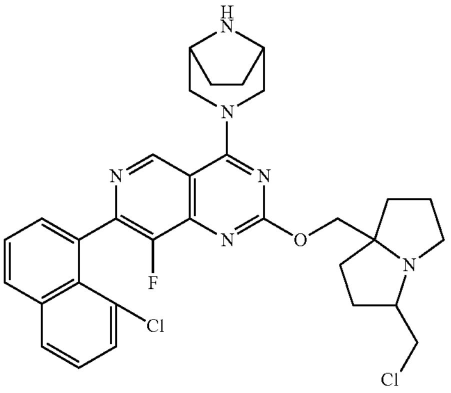

second eluting peak 4-((1R,5S)-3,8-diazabicyclo[3.2.1]octan-3-yl)-2-((3-(chloromethyl)tetrahydro-1H-pyrrolizin-7a(5H)-yl)methoxy)-7-(8-chloronaphthalen-1-yl)-8-fluoropyrido[4,3-d]pyrimidine isomer 1 and 4-((1R,5S)-3,8-diazabicyclo[3.2.1]octan-3-yl)-2-((3-(chloromethyl)tetrahydro-1H-pyrrolizin-7a(5H)-yl)methoxy)-7-(8-chloronaphthalen-1-yl)-8-fluoropyrido[4,3-d]pyrimidine isomer 2

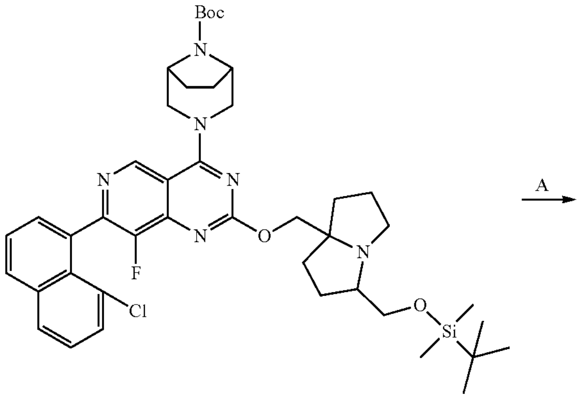

-continued

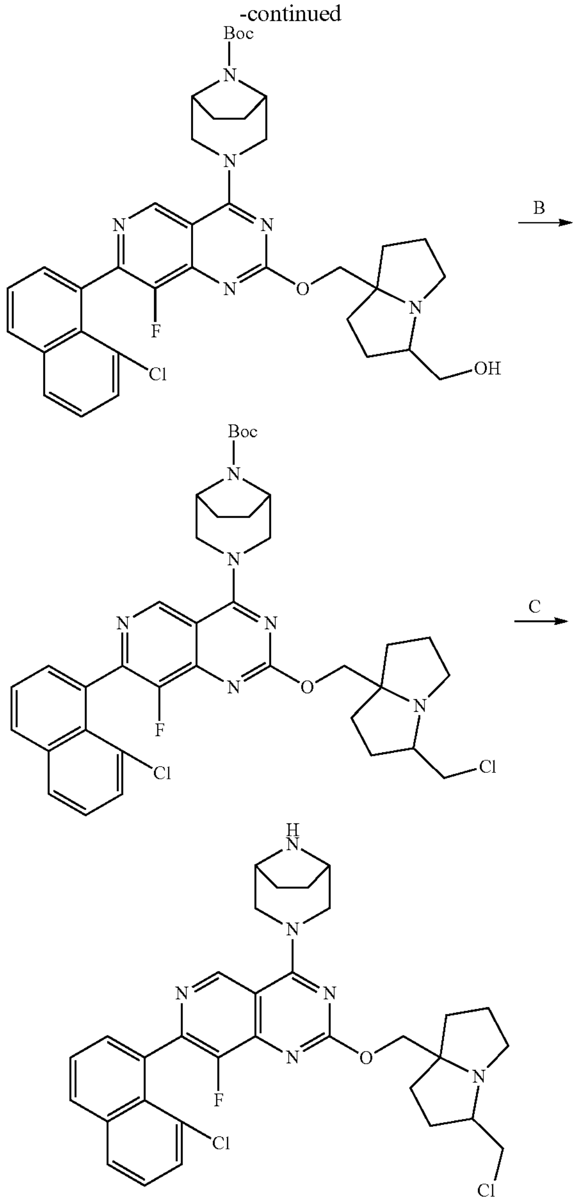

first eluting peak

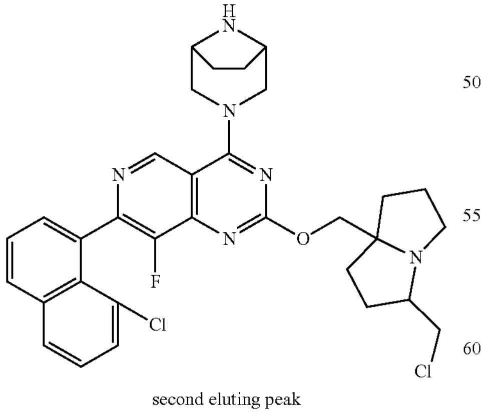

second eluting peak 4-((1R,5S)-3,8-diazabicyclo[3.2.1]octan-3-yl)-2-(((3R,7aS)-3-(chloromethyl)tetrahydro-1H-pyrrolizin-7a(5H)-yl)methoxy)-7-(8-chloronaphthalen-1-yl)-8-fluoropyrido[4,3-d]pyrimidine and 4-((1R,5S)-3,8-diazabicyclo[3.2.1]octan-3-yl)-2-(((3S,7aS)-3-(chloromethyl)tetrahydro-1H-pyrrolizin-7a(5H)-yl)methoxy)-7-(8-chloronaphthalen-1-yl)-8-fluoropyrido[4,3-d]pyrimidine: Synthesized according to Example 2, Step I to yield two isomeric products. (9.45 mg, 0.0113 mmol). LCMS (MM-ES+APCI, Pos): m/z 607.2 [M+H]. (3.57 mg, 0.00428 mmol). LCMS (MM-ES+APCI, Pos): m/z 607.2 [M+H].

Example 67

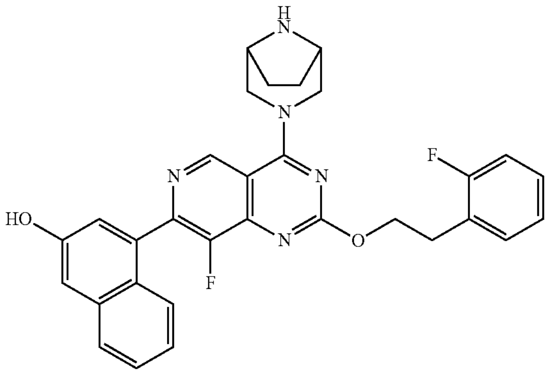 [SMILES: Oc1cc(-c2ncc3c(N4CC5CCC(C4)N5)nc(OCCc4ccccc4F)nc3c2F)c2ccccc2c1]

4-(4-((1R,5S)-3,8-diazabicyclo[3.2.1]octan-3-yl)-8-fluoro-2-(2-fluorophenethoxy)pyrido[4,3-d]pyrimidin-7-yl)naphthalen-2-ol Synthesized similarly to Example 3 Steps G-H substituting 2-fluorophenethyl alcohol in place of 2-(1-methyl-1H-imidazol-2-yl)ethan-1-ol and deprotected according to the method of Example 2, Step I (67.5 mg, 0.125 mmol, 53%). LCMS (MM-ES+APCI, Pos): m/z 540.2 (M+H).

Example 68

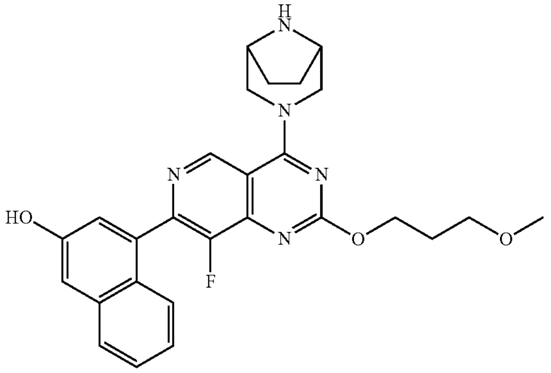 [SMILES: COCCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(3-methoxypropoxy)pyrido[4,3-d]pyrimidin-7-yl)naphthalen-2-ol Synthesized similarly to Example 3 Steps G-H substituting 3-methoxypropan-1-ol in place of 2-(1-methyl-1H-imidazol-2-yl)ethan-1-ol and deprotected according to the method of Example 2, Step I (86.5 mg, 0.177 mmol, 95%). LCMS (MM-ES+APCI, Pos): m/z 490.2 (M+H).

Example 69

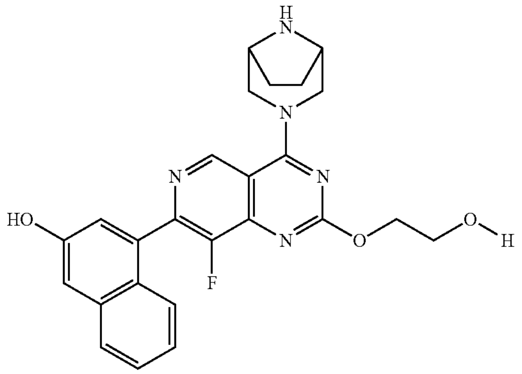 [SMILES: OCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-hydroxyethoxy)pyrido[4,3-d]pyrimidin-7-yl)naphthalen-2-ol Synthesized similarly to Example 3 Steps G-H substituting ethylene glycol (40 equivalents) in place of 2-(1-methyl-1H-imidazol-2-yl)ethan-1-ol and deprotected according to the method of Example 2, Step I (86.0 mg, 0.186 mmol, 95%). LCMS (MM-ES+APCI, Pos): m/z 462.2 (M+H).

Example 70

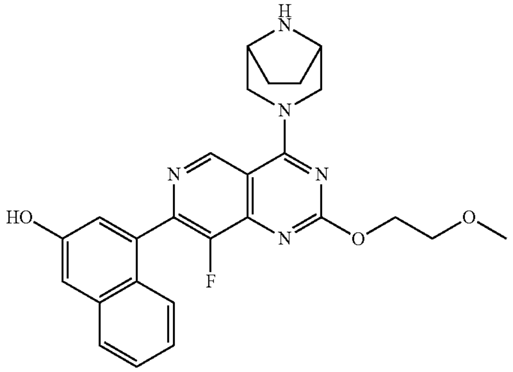 [SMILES: COCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-methoxyethoxy)pyrido[4,3-d]pyrimidin-7-yl)naphthalen-2-ol Synthesized similarly to Example 3 Steps G-H substituting 2-methoxyethanol in place of 2-(1-methyl-1H-imidazol-2-yl)ethan-1-ol and deprotected according to the method of Example 2, Step I (28.0 mg, 0.0588 mmol, 68%). LCMS (MM-ES+APCI, Pos): m/z 476.2 (M+H).

Example 71

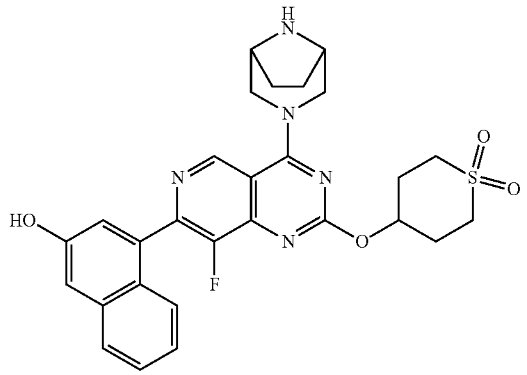 [SMILES: O=S1(=O)CCC(Oc2nc(N3CC4CCC(C3)N4)c3cnc(-c4cc(O)cc5ccccc45)c(F)c3n2)CC1]

4-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)tetrahydro-2H-thiopyran 1,1-dioxide Synthesized similarly to Example 3 Steps G-H substituting 1,1-dioxo-hexahydro-2H-thiopyran-4-ol in place of 2-(1-methyl-1H-imidazol-2-yl)ethan-1-ol and deprotected according to the method of Example 2, Step I (10.6 mg, 0.0192 mmol, 42%). LCMS (MM-ES+APCI, Pos): m/z 550.2 (M+H).

Example 72

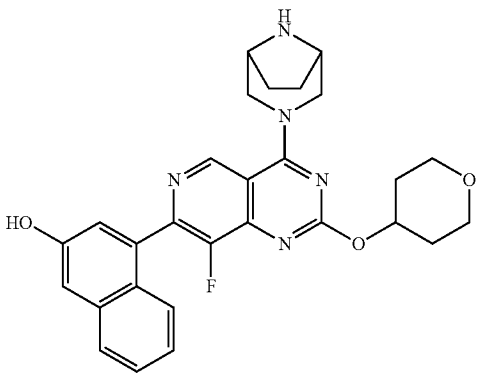 [SMILES: Oc1cc(-c2ncc3c(N4CC5CCC(C4)N5)nc(OC4CCOCC4)nc3c2F)c2ccccc2c1]

4-(4-((1R,5S)-3,8-diazabicyclo[3.2.1]octan-3-yl)-8-fluoro-2-((tetrahydro-2H-pyran-4-yl)oxy)pyrido[4,3-d]pyrimidin-7-yl)naphthalen-2-ol Synthesized similarly to Example 3 Steps G-H substituting tetrahydro-2H-pyran-4-ol in place of 2-(1-methyl-1H-imidazol-2-yl)ethan-1-ol and deprotected according to the method of Example 2, Step I (75.9 mg, 0.151 mmol, 91%). LCMS (MM-ES+APCI, Pos): m/z 502.3 (M+H).

Example 73

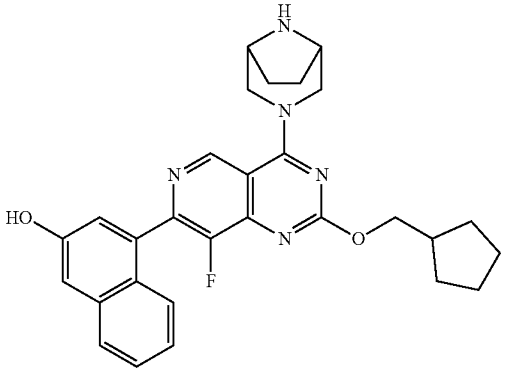 [SMILES: Oc1cc(-c2ncc3c(N4CC5CCC(C4)N5)nc(OCC4CCCC4)nc3c2F)c2ccccc2c1]

4-(4-((1R,5S)-3,8-diazabicyclo[3.2.1]octan-3-yl)-2-(cyclopentylmethoxy)-8-fluoropyrido[4,3-d]pyrimidin-7-yl)naphthalen-2-ol Synthesized similarly to Example 3 Steps G-H substituting cyclopentanemethanol in place of 2-(1-methyl-1H-imidazol-2-yl)ethan-1-ol and deprotected according to the method of Example 2, Step I (28.0 mg, 0.056 mmol, 26%). LCMS (MM-ES+APCI, Pos): m/z 500.3 (M+H).

Example 74

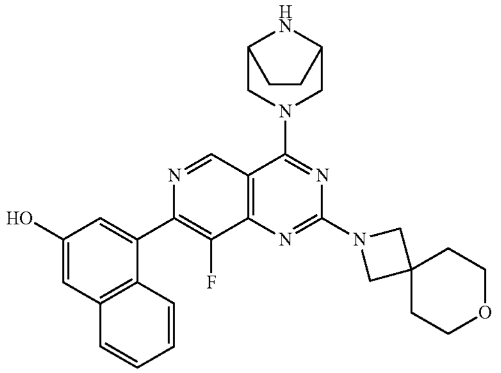 [SMILES: Oc1cc(-c2ncc3c(N4CC5CCC(C4)N5)nc(N4CC5(CCOCC5)C4)nc3c2F)c2ccccc2c1]

4-(4-((1R,5S)-3,8-diazabicyclo[3.2.1]octan-3-yl)-8-fluoro-2-(7-oxa-2-azaspiro[3.5]nonan-2-yl)pyrido[4,3-d]pyrimidin-7-yl)naphthalen-2-ol Synthesized similarly to Example 3 Steps G-H substituting 7-oxa-2-azaspiro[3.5]nonane HCl in place of 2-(1-methyl-1H-imidazol-2-yl)ethan-1-ol and deprotected according to the method of Example 2, Step I (94.1 mg, 0.179 mmol, 64%). LCMS (MM-ES+APCI, Pos): m/z 527.2 (M+H).

Example 75

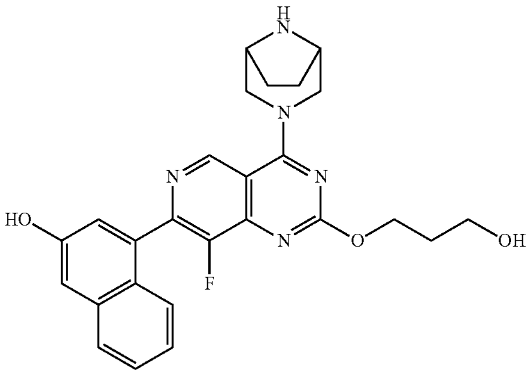 [SMILES: OCCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(3-hydroxypropoxy)pyrido[4,3-d]pyrimidin-7-yl)naphthalen-2-ol Synthesized similarly to Example 3 Steps G-H substituting 1,3-propanediol (40 equivalence) in place of 2-(1-methyl-1H-imidazol-2-yl)ethan-1-ol and deprotected according to the method of Example 2, Step I (11.4 mg, 0.0239 mmol, 20%). LCMS (MM-ES+APCI, Pos): m/z 476.2 (M+H).

Example 76

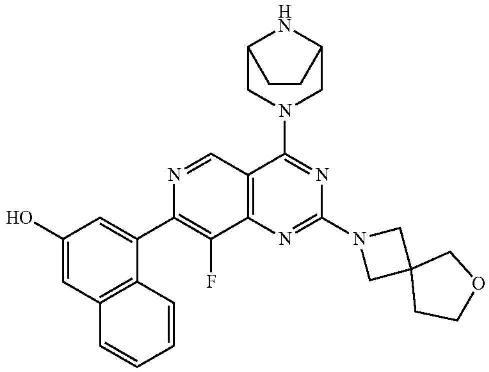 [SMILES: Oc1cc(-c2ncc3c(N4CC5CCC(C4)N5)nc(N4CC5(CCOC5)C4)nc3c2F)c2ccccc2c1]

4-(4-((1R,5S)-3,8-diazabicyclo[3.2.1]octan-3-yl)-8-fluoro-2-(6-oxa-2-azaspiro[3.4]octan-2-yl)pyrido[4,3-d]pyrimidin-7-yl)naphthalen-2-ol Synthesized similarly to Example 3 Steps G-H substituting 6-oxa-2-azaspiro[3.4]octane in place of 2-(1-methyl-1H-imidazol-2-yl)ethan-1-ol and deprotected according to the method of Example 2, Step I (52.0 mg, 0.101 mmol, 79%). LCMS (MM-ES+APCI, Pos): m/z 513.3 (M+H).

Example 77

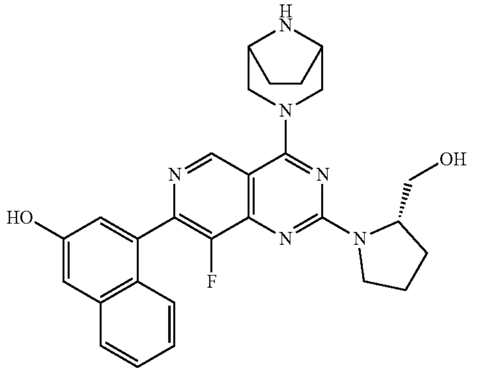 [SMILES: OC[C@@H]1CCCN1c1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-((S)-2-(hydroxymethyl)pyrrolidin-1-yl)pyrido[4,3-d]pyrimidin-7-yl)naphthalen-2-ol Synthesized similarly to Example 3 Steps G-H substituting (S)-pyrrolidin-2-ylmethanol in place of 2-(1-methyl-1H-imidazol-2-yl)ethan-1-ol and deprotected according to the method of Example 2, Step I (50.0 mg, 0.100 mmol, 17%). LCMS (MM-ES+APCI, Pos): m/z 501.2 (M+H).

Example 78

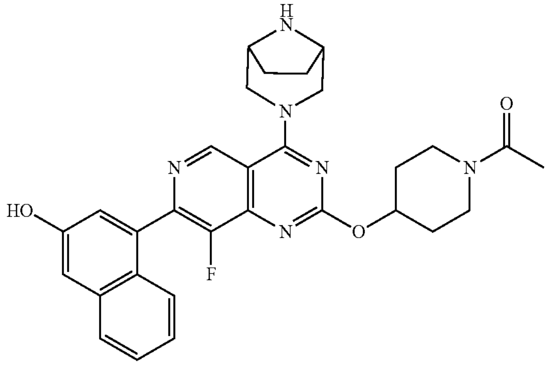 [SMILES: CC(=O)N1CCC(Oc2nc(N3CC4CCC(C3)N4)c3cnc(-c4cc(O)cc5ccccc45)c(F)c3n2)CC1]

1-(4-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy) piperidin-1-yl)ethan-1-one Synthesized similarly to Example 3 Steps G-H substituting 1-(4-hydroxypiperidin-1-yl)ethan-1-one in place of 2-(1-methyl-1H-imidazol-2-yl)ethan-1-ol and deprotected according to the method of Example 2, Step I (6.50 mg, 0.0120 mmol, 38%). LCMS (MM-ES+APCI, Pos): m/z 543.3 (M+H).

Example 79

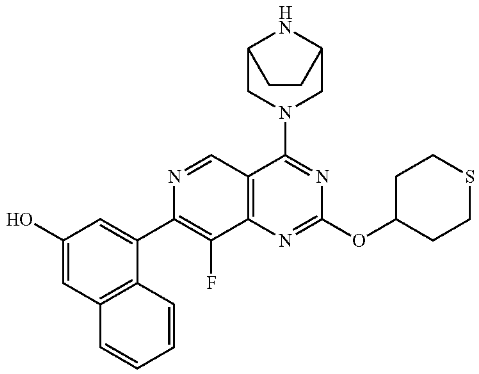 [SMILES: Oc1cc(-c2ncc3c(N4CC5CCC(C4)N5)nc(OC4CCSCC4)nc3c2F)c2ccccc2c1]

4-(4-((1R,5S)-3,8-diazabicyclo[3.2.1]octan-3-yl)-8-fluoro-2-((tetrahydro-2H-thiopyran-4-yl)oxy)pyrido[4,3-d]pyrimidin-7-yl)naphthalen-2-ol Synthesized similarly to Example 3 Steps G-H substituting tetrahydro-2H-thiopyran-4-ol in place of 2-(1-methyl-1H-imidazol-2-yl)ethan-1-ol and deprotected according to the method of Example 2, Step I (53.9 mg, 0.104 mmol, 82%). LCMS (MM-ES+APCI, Pos): m/z 518.2 (M+H).

Example 80

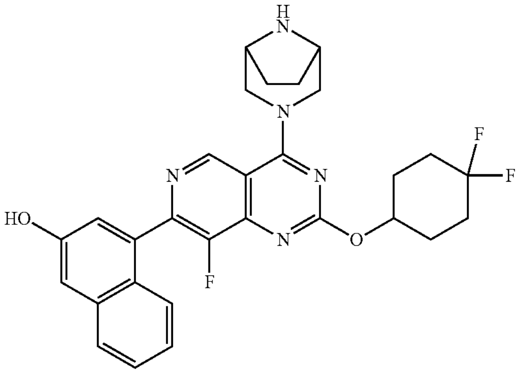 [SMILES: Oc1cc(-c2ncc3c(N4CC5CCC(C4)N5)nc(OC4CCC(F)(F)CC4)nc3c2F)c2ccccc2c1]

4-(4-((1R,5S)-3,8-diazabicyclo[3.2.1]octan-3-yl)-2-((4,4-difluorocyclohexyl)oxy)-8-fluoropyrido[4,3-d]pyrimidin-7-yl)naphthalen-2-ol Synthesized similarly to Example 3 Steps G-H substituting 4,4-difluorocyclohexanol in place of 2-(1-methyl-1H-imidazol-2-yl)ethan-1-ol and deprotected according to the method of Example 2, Step I (14.3 mg, 0.0268 mmol, 24%). LCMS (MM-ES+APCI, Pos): m/z 536.2 (M+H).

Example 81

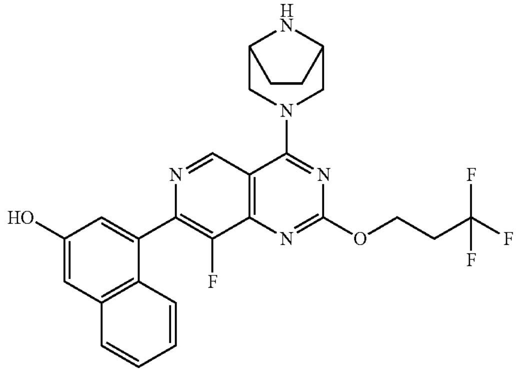 [SMILES: Oc1cc(-c2ncc3c(N4CC5CCC(C4)N5)nc(OCCC(F)(F)F)nc3c2F)c2ccccc2c1]

4-(4-((1R,5S)-3,8-diazabicyclo[3.2.1]octan-3-yl)-8-fluoro-2-(3,3,3-trifluoropropoxy)pyrido[4,3-d]pyrimidin-7-yl)naphthalen-2-ol Synthesized similarly to Example 3 Steps G-H substituting 3,3,3-trifluoropropan-1-ol in place of 2-(1-methyl-1H-imidazol-2-yl)ethan-1-ol and deprotected according to the method of Example 2, Step I (77.2 mg, 0.150 mmol, 62%). LCMS (MM-ES+APCI, Pos): m/z 514.2 (M+H).

Example 82

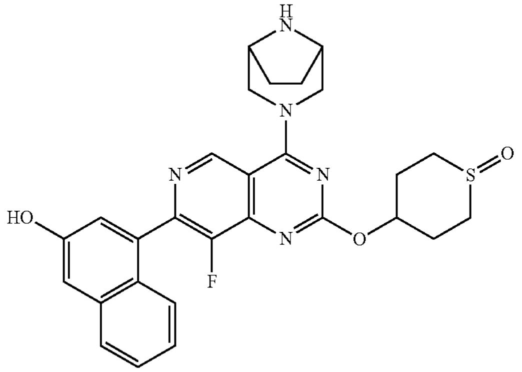 [SMILES: O=S1CCC(Oc2nc(N3CC4CCC(C3)N4)c3cnc(-c4cc(O)cc5ccccc45)c(F)c3n2)CC1]

4-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)tetrahydro-2H-thiopyran 1-oxide

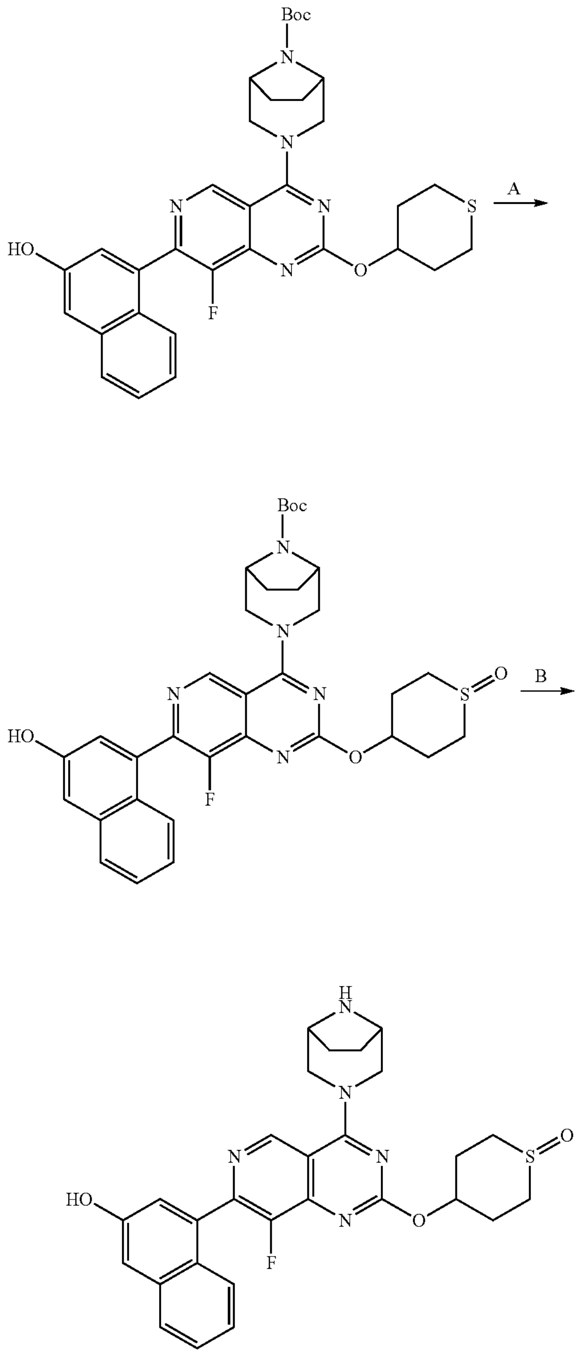

4-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)tetrahydro-2H-thiopyran 1-oxide: tert-butyl (1R,5S)-3-(8-fluoro-7-(3-hydroxynaphthalen-1-yl)-2-((1-oxidotetrahydro-2H-thiopyran-4-yl)oxy)pyrido[4,3-d]pyrimidin-4-yl)-3,8-diazabicyclo[3.2.1]octane-8-carboxylate was deprotected according to the method of Example 2, Step I (37.9 mg, 0.0498 mmol, 85%). LCMS (MM-ES+APCI, Pos): m/z 534.1 (M+H).

Example 83

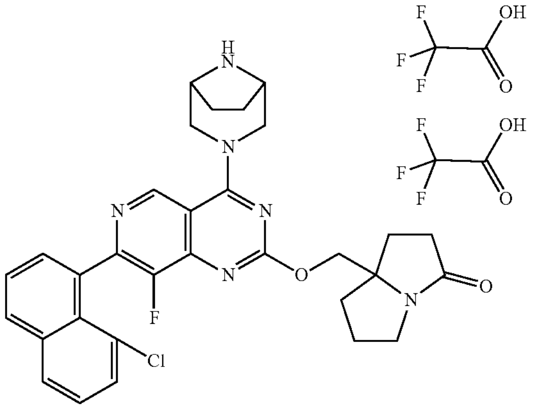

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-3H-pyrrolizin-3-one bis(2,2,2-trifluoroacetate)

Synthesized according to Example 29 substituting 7a-(hydroxymethyl)hexahydro-3H-pyrrolizin-3-one in place of (S)-(1-methylpyrrolidin-2-yl)methanol in Step G (39.6 mg, 0.25 mmol, 68%). The final product was prepared as the TFA salt. LCMS (MM-ES+APCI, Pos): m/z 573.2 [M+H].

Example 84

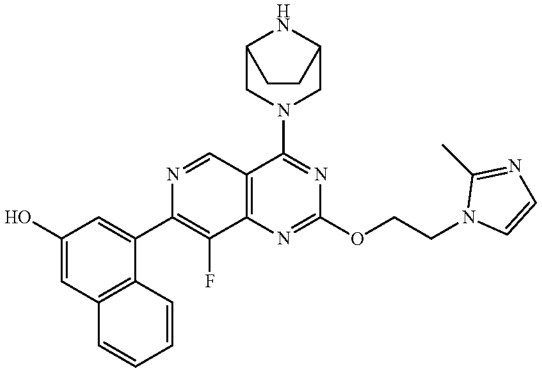 [SMILES: Cc1nccn1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(2-methyl-1H-imidazol-1-yl)ethoxy)pyrido[4,3-d]pyrimidin-7-yl)naphthalen-2-ol Synthesized according to Example 3, Steps G-I substituting 2-(2-methyl-1H-imidazol-1-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(2-methyl-1H-imidazol-1-yl)ethoxy)pyrido[4,3-d]pyrimidin-7-yl)naphthalen-2-ol (13.1 mg, 0.24 mmol, 40%). LCMS (MM-ES+APCI, Pos): m/z 526.2 (M+H).

Example 85

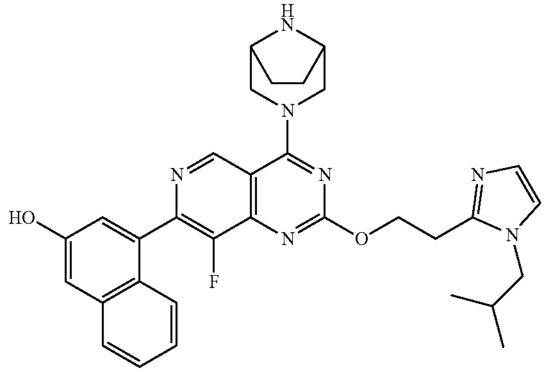 [SMILES: CC(C)Cn1ccnc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(1-isobutyl-1H-imidazol-2-yl)ethoxy)pyrido[4,3-d]pyrimidin-7-yl)naphthalen-2-ol Synthesized according to Example 3, Steps G-I substituting 2-(1-isobutyl-1H-imidazol-2-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(1-isobutyl-1H-imidazol-2-yl)ethoxy)pyrido[4,3-d]pyrimidin-7-yl)naphthalen-2-ol (42.4 mg, 0.71 mmol, 55%). LCMS (MM-ES+APCI, Pos): m/z 568.2 (M+H).

Example 86

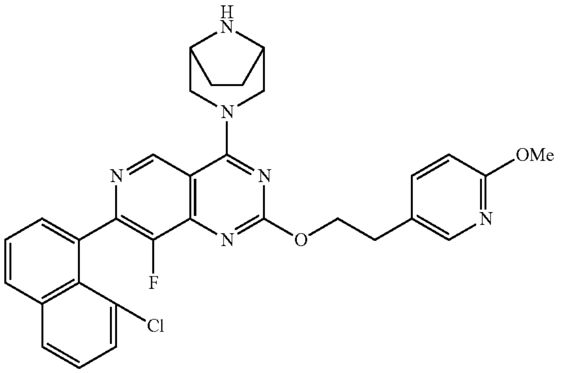 [SMILES: COc1ccc(CCOc2nc(N3CC4CCC(C3)N4)c3cnc(-c4cccc5cccc(Cl)c45)c(F)c3n2)cn1]

4-((1R,5S)-3,8-diazabicyclo[3.2.1]octan-3-yl)-7-(8-chloronaphthalen-1-yl)-8-fluoro-2-(2-(6-methoxy-pyridin-3-yl)ethoxy)pyrido[4,3-d]pyrimidine Synthesized according to Example 29, Steps H—I substituting 2-(6-methoxypyridin-3-yl)ethan-1-ol in place of (S)-(1-isopropylpyrrolidin-2-yl)methanol to afford 4-((1R,5S)-3,8-diazabicyclo[3.2.1]octan-3-yl)-7-(8-chloronaphthalen-1-yl)-8-fluoro-2-(2-(6-methoxypyridin-3-yl)ethoxy)pyrido[4,3-d]pyrimidine (36.6 mg, 0.027 mmol, 42%). LCMS (MM-ES+APCI, Pos): m/z 571.2 (M+H).

Example 87

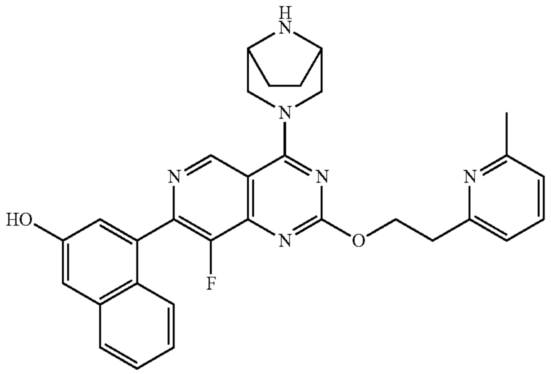 [SMILES: Cc1cccc(CCOc2nc(N3CC4CCC(C3)N4)c3cnc(-c4cc(O)cc5ccccc45)c(F)c3n2)n1]

4-(4-((1R,5S)-3,8-diazabicyclo[3.2.1]octan-3-yl)-8-fluoro-2-(2-(6-methylpyridin-2-yl)ethoxy)pyrido[4,3-d]pyrimidin-7-yl)naphthalen-2-ol Synthesized according to Example 3, Steps G-I substituting 2-(6-methylpyridin-2-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(6-methylpyridin-2-yl)ethoxy)pyrido[4,3-d]pyrimidin-7-yl)naphthalen-2-ol (33.8 mg, 0.061 mmol, 56%). LCMS (MM-ES+APCI, Pos): m/z 537.2 (M+H).

Example 88

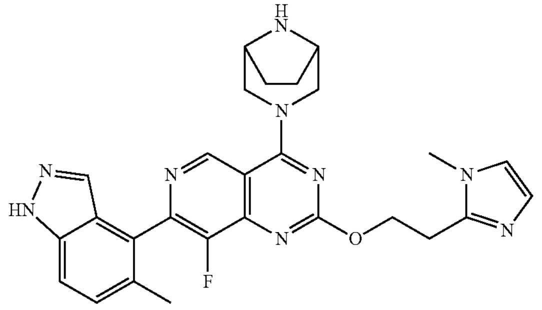 [SMILES: Cc1ccc2[nH]ncc2c1-c1ncc2c(N3CC4CCC(C3)N4)nc(OCCc3nccn3C)nc2c1F]

4-((1R,5S)-3,8-diazabicyclo[3.2.1]octan-3-yl)-8-fluoro-2-(2-(1-methyl-1H-imidazol-2-yl)ethoxy)-7-(5-methyl-1H-indazol-4-yl)pyrido[4,3-d]pyrimidine Synthesized according to Example 3, Steps H—I substituting (5-methyl-1H-indazol-4-yl) boronic acid in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-8-fluoro-2-(2-(1-methyl-1H-imidazol-2-yl)ethoxy)-7-(5-methyl-1H-indazol-4-yl)pyrido[4,3-d]pyrimidine (7.1 mg, 0.013 mmol, 48%). LCMS (MM-ES+APCI, Pos): m/z 514.2 (M+H).

Example 89

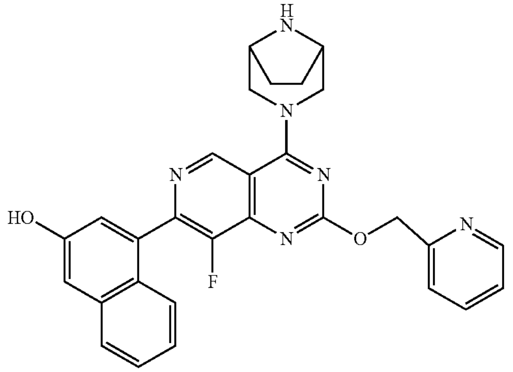 [SMILES: Oc1cc(-c2ncc3c(N4CC5CCC(C4)N5)nc(OCc4ccccn4)nc3c2F)c2ccccc2c1]

4-(4-((1R,5S)-3,8-diazabicyclo[3.2.1]octan-3-yl)-8-fluoro-2-(pyridin-2-ylmethoxy)pyrido[4,3-d]pyrimidin-7-yl)naphthalen-2-ol Synthesized according to Example 3, Steps G-I substituting pyridin-2-ylmethanol in place of 2-(1-methyl-1H-imidazol-2-yl)ethan-1-ol to afford 4-(4-((1R,5S)-3,8-diazabicyclo[3.2.1]octan-3-yl)-8-fluoro-2-(pyridin-2-ylmethoxy)pyrido[4,3-d]pyrimidin-7-yl)naphthalen-2-ol (2.8 mg, 0.053 mmol, 56%). LCMS (MM-ES+APCI, Pos): m/z 509.2 (M+H).

Example 90

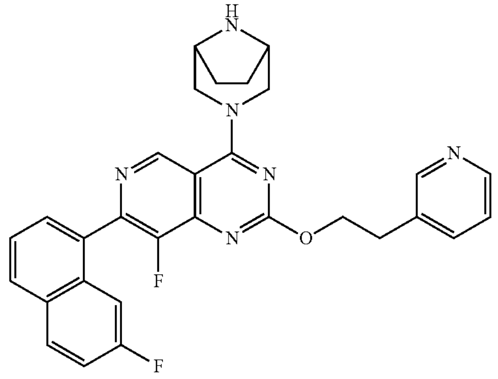 [SMILES: Fc1ccc2cccc(-c3ncc4c(N5CC6CCC(C5)N6)nc(OCCc5cccnc5)nc4c3F)c2c1]

4-((1R,5S)-3,8-diazabicyclo[3.2.1]octan-3-yl)-8-fluoro-7-(7-fluoronaphthalen-1-yl)-2-(2-(pyridin-3-yl)ethoxy)pyrido[4,3-d]pyrimidine Synthesized according to Example 3, Steps G-I substituting 2-(pyridin-3-yl)ethan-1-ol in place of 2-(1-methyl-1H-imidazol-2-yl)ethan-1-ol in Step G and 2-(7-fluoronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-7-(7-fluoronaphthalen-1-yl)-2-(2-(pyridin-3-yl)ethoxy)pyrido[4,3-d]pyrimidine (16.9 mg, 0.032 mmol, 54%). LCMS (MM-ES+APCI, Pos): m/z 525.2 (M+H).

Example 91

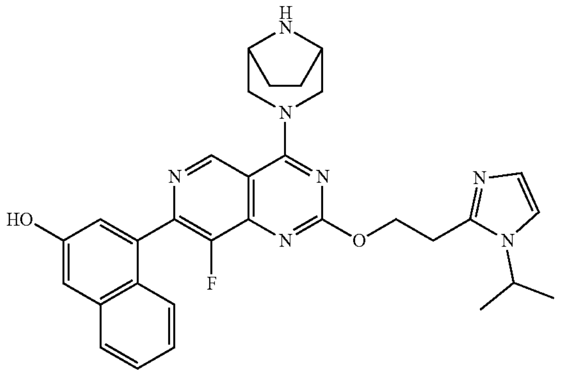 [SMILES: CC(C)n1ccnc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(1-isopropyl-1H-imidazol-2-yl)ethoxy) pyrido[4,3-d]pyrimidin-7-yl)naphthalen-2-ol Synthesized according to Example 3, Steps G-I substituting 2-(1-isopropyl-1H-imidazol-2-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(1-isopropyl-1H-imidazol-2-yl)ethoxy)pyrido[4,3-d]pyrimidin-7-yl)naphthalen-2-ol (30.9 mg, 0.053 mmol, 64%). LCMS (MM-ES+APCI, Pos): m/z 554.3 (M+H).

Example 92

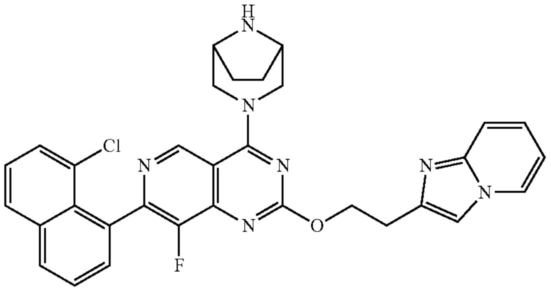 [SMILES: Fc1c(-c2cccc3cccc(Cl)c23)ncc2c(N3CC4CCC(C3)N4)nc(OCCc3cn4ccccc4n3)nc12]

4-((1R,5S)-3,8-diazabicyclo[3.2.1]octan-3-yl)-7-(8-chloronaphthalen-1-yl)-8-fluoro-2-(2-(imidazo[1,2-a]pyridin-2-yl)ethoxy)pyrido[4,3-d]pyrimidine Synthesized according to Example 30, Steps A-F,H substituting 2-(8-chloronaphthalen-1-yl)-4,4,5,5-tetramethyl-1,3,2-dioxaborolane in place of 2-(3-(benzyloxy)naphthalen-1-yl)-4,4,5,5-tetramethyl-1,3,2-dioxaborolane in Step A and 2-(imidazo[1,2-a]pyridin-2-yl)ethan-1-ol in place of 2-(1-methyl-1H-benzo[d]imidazol-2-yl)ethan-1-ol dihydrate in Step F to afford 4-((1R,5S)-3,8-diazabicyclo[3.2.1]octan-3-yl)-7-(8-chloronaphthalen-1-yl)-8-fluoro-2-(2-(imidazo[1,2-a]pyridin-2-yl)ethoxy)pyrido[4,3-d]pyrimidine (5.2 mg, 0.009 mmol, 55%). LCMS (MM-ES+APCI, Pos): m/z 580.2 (M+H).

Example 93

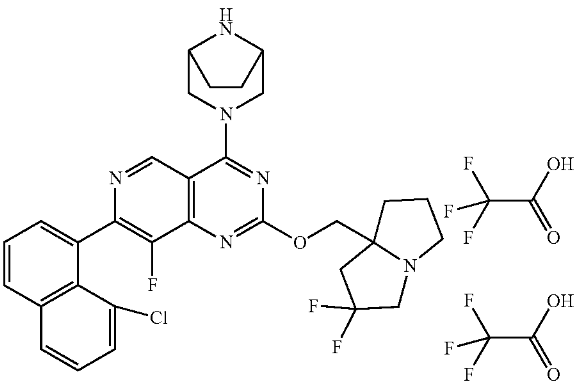

4-((1R,5S)-3,8-diazabicyclo[3.2.1]octan-3-yl)-7-(8-chloronaphthalen-1-yl)-2-((2,2-difluorotetrahydro-1H-pyrrolizin-7a(5H)-yl)methoxy)-8-fluoropyrido[4,3-d]pyrimidine bis(2,2,2-trifluoroacetate)

Synthesized according to Example 29, Steps H—I substituting (2,2-difluorotetrahydro-1H-pyrrolizin-7a(5H)-yl) methanol in place of (S)-(1-isopropylpyrrolidin-2-yl)methanol to afford 4-((1R,5S)-3,8-diazabicyclo[3.2.1]octan-3-yl)-7-(8-chloronaphthalen-1-yl)-2-((2,2-difluorotetrahydro-1H-pyrrolizin-7a(5H)-yl)methoxy)-8-fluoropyrido[4,3-d] pyrimidine bis(2,2,2-trifluoroacetate) (9.4 mg, 0.011 mmol, 25%). LCMS (MM-ES+APCI, Pos): m/z 595.2 (M+H).

Example 94

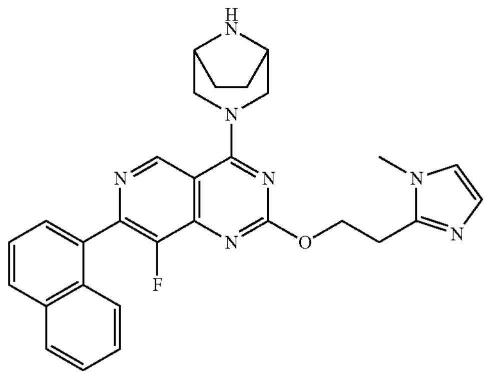 [SMILES: Cn1ccnc1CCOc1nc(N2CC3CCC(C2)N3)c2cnc(-c3cccc4ccccc34)c(F)c2n1]

4-((1R,5S)-3,8-diazabicyclo[3.2.1]octan-3-yl)-8-fluoro-2-(2-(1-methyl-1H-imidazol-2-yl)ethoxy)-7-(naphthalen-1-yl)pyrido[4,3-d]pyrimidine Synthesized according to Example 3, Steps H—I substituting 4,4,5,5-tetramethyl-2-(naphthalen-1-yl)-1,3,2-dioxaborolane in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-8-fluoro-2-(2-(1-methyl-1H-imidazol-2-yl)ethoxy)-7-(naphthalen-1-yl)pyrido[4,3-d] pyrimidine (8.1 mg, 0.015 mmol, 49%). LCMS (MM-ES+APCI, Pos): m/z 510.2 (M+H).

Example 95

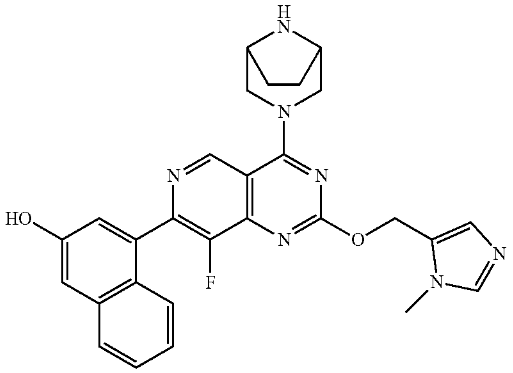 [SMILES: Cn1cncc1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-((1-methyl-1H-imidazol-5-yl)methoxy)pyrido[4,3-d]pyrimidin-7-yl)naphthalen-2-ol Synthesized according to Example 3, Steps G-I substituting (1-methyl-1H-imidazol-5-yl)methanol in place of 2-(1-methyl-1H-imidazol-2-yl)ethan-1-ol to afford 4-(4-((1R,5S)-3,8-diazabicyclo[3.2.1]octan-3-yl)-8-fluoro-2-((1-methyl-1H-imidazol-5-yl)methoxy)pyrido[4,3-d]pyrimidin-7-yl)naphthalen-2-ol (10.6 mg, 0.019 mmol, 45%). LCMS (MM-ES+APCI, Pos): m/z 512.3 (M+H).

Example 96

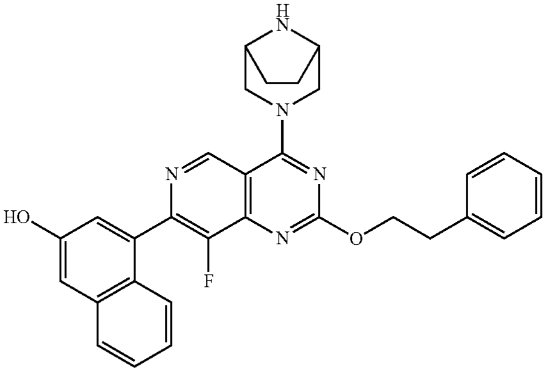 [SMILES: Oc1cc(-c2ncc3c(N4CC5CCC(C4)N5)nc(OCCc4ccccc4)nc3c2F)c2ccccc2c1]

4-(4-((1R,5S)-3,8-diazabicyclo[3.2.1]octan-3-yl)-8-fluoro-2-phenethoxypyrido[4,3-d]pyrimidin-7-yl)naphthalen-2-ol Synthesized according to Example 3, Steps G-I substituting 2-phenylethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-phenethoxypyrido[4,3-d]pyrimidin-7-yl)naphthalen-2-ol (29.8 mg, 0.055 mmol, 75%). LCMS (MM-ES+APCI, Pos): m/z 522.2 (M+H).

Example 97

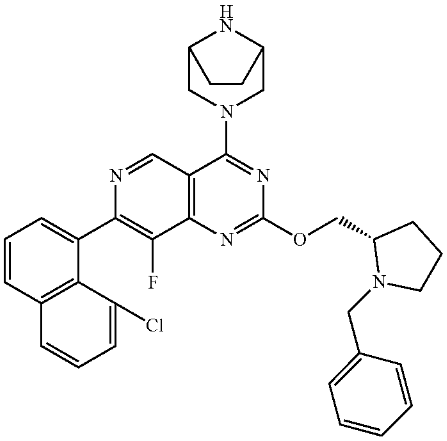 [SMILES: Fc1c(-c2cccc3cccc(Cl)c23)ncc2c(N3CC4CCC(C3)N4)nc(OC[C@@H]3CCCN3Cc3ccccc3)nc12]

2-(((S)-1-benzylpyrrolidin-2-yl)methoxy)-4-((1R,5S)-3,8-diazabicyclo[3.2.1]octan-3-yl)-7-(8-chloronaphthalen-1-yl)-8-fluoropyrido[4,3-d]pyrimidine Synthesized according to Example 30, Steps A-F,H substituting 2-(8-chloronaphthalen-1-yl)-4,4,5,5-tetramethyl-1,3,2-dioxaborolane in place of 2-(3-(benzyloxy)naphthalen-1-yl)-4,4,5,5-tetramethyl-1,3,2-dioxaborolane in Step A and (S)-(1-benzylpyrrolidin-2-yl)methanol in place of 2-(1-methyl-1H-benzo[d]imidazol-2-yl)ethan-1-ol dihydrate in Step F to afford 2-(((S)-1-benzylpyrrolidin-2-yl)methoxy)-4-((1R,5S)-3,8-diazabicyclo[3.2.1]octan-3-yl)-7-(8-chloronaphthalen-1-yl)-8-fluoropyrido[4,3-d]pyrimidine (1.4 mg, 0.002 mmol, 4%). LCMS (MM-ES+APCI, Pos): m/z 609.3 (M+H).

Example 98

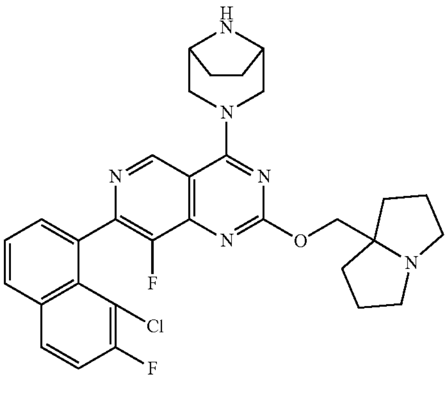 [SMILES: Fc1ccc2cccc(-c3ncc4c(N5CC6CCC(C5)N6)nc(OCC56CCCN5CCC6)nc4c3F)c2c1Cl]

4-((1R,5S)-3,8-diazabicyclo[3.2.1]octan-3-yl)-7-(8-chloro-7-fluoronaphthalen-1-yl)-8-fluoro-2-((tetrahydro-1H-pyrrolizin-7a(5H)-yl)methoxy)pyrido[4,3-d]pyrimidine bis(2,2,2-trifluoroacetate)

Synthesized according to Example 29, Steps C—I substituting 2-(8-chloro-7-fluoronaphthalen-1-yl)-4,4,5,5-tetramethyl-1,3,2-dioxaborolane (Synthesized according to Example 44, step A-C) in place of 2-(8-chloronaphthalen-1-yl)-4,4,5,5-tetramethyl-1,3,2-dioxaborolane in Step C and (tetrahydro-1H-pyrrolizin-7a(5H)-yl)methanol in place of (S)-(1-isopropylpyrrolidin-2-yl)methanol in Step H to afford 4-((1R,5S)-3,8-diazabicyclo[3.2.1]octan-3-yl)-7-(8-chloro-7-fluoronaphthalen-1-yl)-8-fluoro-2-((tetrahydro-1H-pyrrolizin-7a(5H)-yl)methoxy)pyrido[4,3-d]pyrimidine bis(2,2,2-trifluoroacetate) (10.4 mg, 0.013 mmol, 22%). LCMS (MM-ES+APCI, Pos): m/z 577.2 (M+H).

Example 99

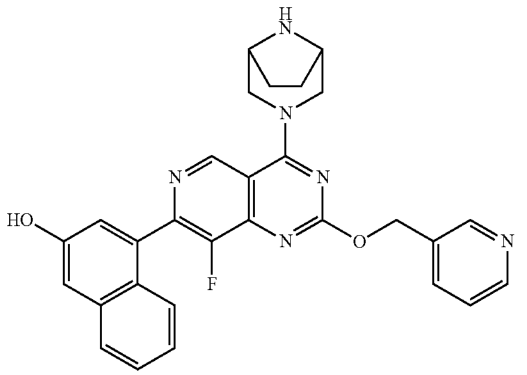 [SMILES: Oc1cc(-c2ncc3c(N4CC5CCC(C4)N5)nc(OCc4cccnc4)nc3c2F)c2ccccc2c1]

4-(4-((1R,5S)-3,8-diazabicyclo[3.2.1]octan-3-yl)-8-fluoro-2-(pyridin-3-ylmethoxy)pyrido[4,3-d]pyrimidin-7-yl)naphthalen-2-ol Synthesized according to Example 3, Steps G-I substituting pyridin-3-ylmethanol in place of 2-(1-methyl-1H-imidazol-2-yl)ethan-1-ol to afford 4-(4-((1R,5S)-3,8-diazabicyclo[3.2.1]octan-3-yl)-8-fluoro-2-(pyridin-3-ylmethoxy) pyrido[4,3-d]pyrimidin-7-yl)naphthalen-2-ol (22.1 mg, 0.042 mmol, 47%). LCMS (MM-ES+APCI, Pos): m/z 509.2 (M+H).

Example 100

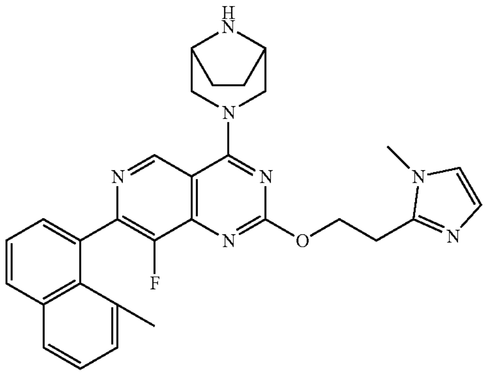 [SMILES: Cc1cccc2cccc(-c3ncc4c(N5CC6CCC(C5)N6)nc(OCCc5nccn5C)nc4c3F)c12]

4-((1R,5S)-3,8-diazabicyclo[3.2.1]octan-3-yl)-8-fluoro-2-(2-(1-methyl-1H-imidazol-2-yl)ethoxy)-7-(8-methylnaphthalen-1-yl)pyrido[4,3-d]pyrimidine Synthesized according to Example 3, Steps H—I substituting 4,4,5,5-tetramethyl-2-(8-methylnaphthalen-1-yl)-1,3,2-dioxaborolane in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-8-fluoro-2-(2-(1-methyl-1H-imidazol-2-yl)ethoxy)-7-(8-methylnaphthalen-1-yl)pyrido [4,3-d]pyrimidine (4.1 mg, 0.007 mmol, 30%). LCMS (MM-ES+APCI, Pos): m/z 524.2 (M+H).

Example 101

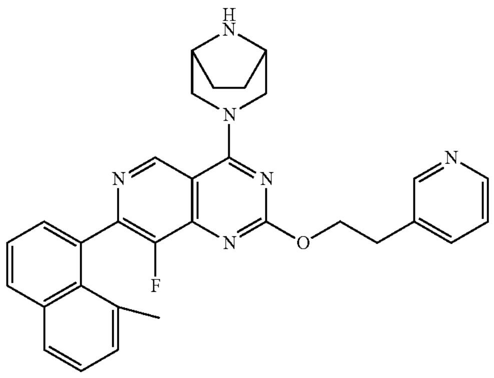 [SMILES: Cc1cccc2cccc(-c3ncc4c(N5CC6CCC(C5)N6)nc(OCCc5cccnc5)nc4c3F)c12]

(1S,4S)-5-(3-((4-((1R,5S)-3,8-diazabicyclo[3.2.1] octan-3-yl)-7-(8-chloronaphthalen-1-yl)-8-fluoro-pyrido[4,3-d]pyrimidin-2-yl)oxy) propyl)-2-oxa-5-azabicyclo[2.2.1]heptane Synthesized according to Example 3, Steps G-I substituting 2-(pyridin-3-yl)ethan-1-ol in place of 2-(1-methyl-1H-imidazol-2-yl)ethan-1-ol in Step G and 4,4,5,5-tetramethyl-2-(8-methylnaphthalen-1-yl)-1,3,2-dioxaborolane in place of 4-(4,4,5,5-tetramethyl-1,3,2-dioxaborolan-2-yl)naphthalen-2-ol in Step H to afford 4-((1R,5S)-3,8-diazabicyclo [3.2.1]octan-3-yl)-8-fluoro-7-(8-methylnaphthalen-1-yl)-2-(2-(pyridin-3-yl)ethoxy)pyrido[4,3-d]pyrimidine (13.0 mg, 0.024 mmol, 36%). LCMS (MM-ES+APCI, Pos): m/z 521.2 (M+H).

Example 102

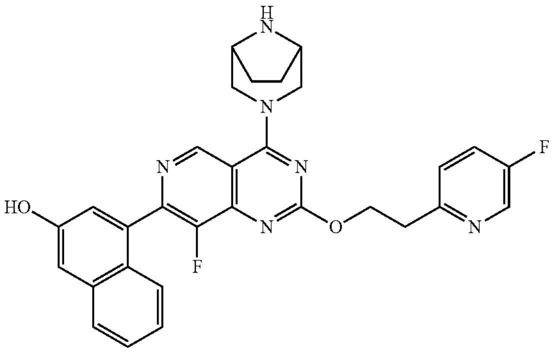 [SMILES: Oc1cc(-c2ncc3c(N4CC5CCC(C4)N5)nc(OCCc4ccc(F)cn4)nc3c2F)c2ccccc2c1]

4-(4-((1R,5S)-3,8-diazabicyclo[3.2.1]octan-3-yl)-8-fluoro-2-(2-(5-fluoropyridin-2-yl)ethoxy)pyrido[4,3-d]pyrimidin-7-yl)naphthalen-2-ol Synthesized according to Example 3, Steps G-I substituting 2-(5-fluoropyridin-2-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(5-fluoropyridin-2-yl)ethoxy)pyrido[4,3-d]pyrimidin-7-yl)naphthalen-2-ol (79.2 mg, 0.145 mmol, 76%). LCMS (MM-ES+APCI, Pos): m/z 541.2 (M+H).

Example 103

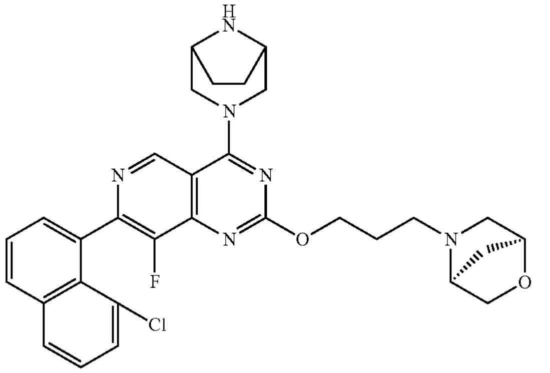 [SMILES: Fc1c(-c2cccc3cccc(Cl)c23)ncc2c(N3CC4CCC(C3)N4)nc(OCCCN3C[C@@H]4C[C@H]3CO4)nc12]

(1S,4S)-5-(3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) propyl)-2-oxa-5-azabicyclo[2.2.1]heptane Synthesized according to Example 3, Steps G-I substituting 3-((1S,4S)-2-oxa-5-azabicyclo[2.2.1]heptan-5-yl) propan-1-ol in place of 2-(1-methyl-1H-imidazol-2-yl)ethan-1-ol in Step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford (1S,4S)-5-(3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) propyl)-2-oxa-5-azabicyclo[2.2.1]heptane (5.1 mg, 0.009 mmol, 29%). LCMS (MM-ES+APCI, Pos): m/z 575.2 (M+H).

Example 104

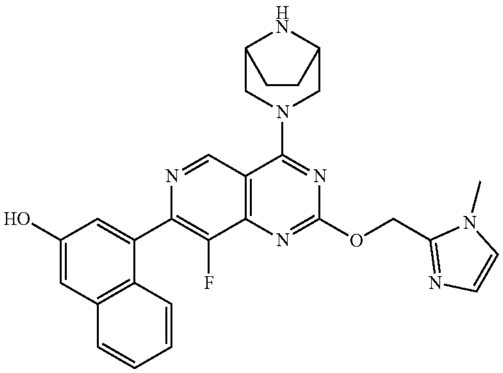 [SMILES: Cn1ccnc1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-((1-methyl-1H-imidazol-2-yl)methoxy)pyrido[4,3-d]pyrimidin-7-yl)naphthalen-2-ol Synthesized according to Example 3, Steps G-I substituting (1-methyl-1H-imidazol-2-yl)methanol in place of 2-(1-methyl-1H-imidazol-2-yl)ethan-1-ol to afford 4-(4-((1R,5S)-3,8-diazabicyclo[3.2.1]octan-3-yl)-8-fluoro-2-((1-methyl-1H-imidazol-2-yl)methoxy)pyrido[4,3-d]pyrimidin-7-yl)naphthalen-2-ol (12.8 mg, 0.025 mmol, 42%). LCMS (MM-ES+APCI, Pos): m/z 512.2 (M+H).

Example 105

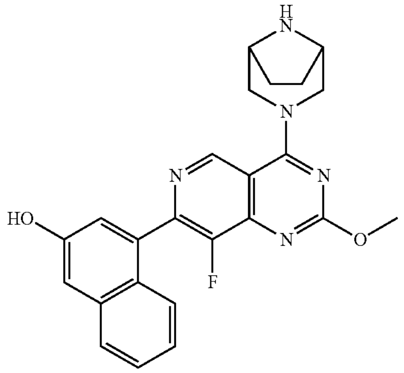 [SMILES: COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-methoxypyrido[4,3-d]pyrimidin-7-yl)naphthalen-2-ol

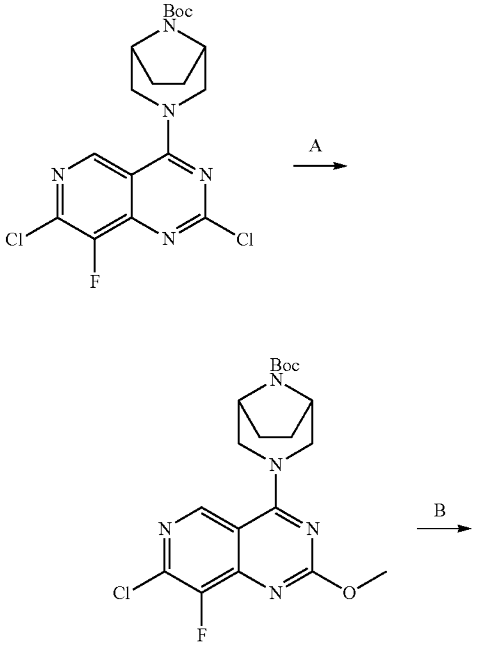

-continued

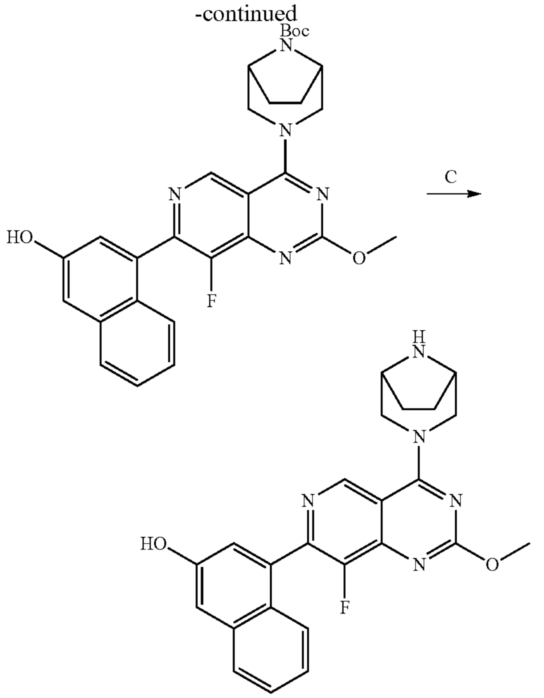

4-(4-((1R,5S)-3,8-diazabicyclo[3.2.1]octan-3-yl)-8-fluoro-2-methoxypyrido[4,3-d]pyrimidin-7-yl)naphthalen-2-ol: To a solution of tert-butyl(1R,5S)-3-(8-fluoro-7-(3-hydroxynaphthalen-1-yl)-2-methoxypyrido[4,3-d]pyrimidin-4-yl)-3,8-diazabicyclo[3.2.1]octane-8-carboxylate (106 mg, 0.2002 mmol) in $CH_2Cl_2$ (4 ml, 0.2002 mmol) was added TFA (0.308 mL, 4.003 mmol) at 0° C. The mixture was stirred at room temperature for 4 hours. The solution was poured into a mixture of saturated bicarbonate (20 mL) and EtOAc (15 mL). The aqueous layer was washed with EtOAc (2×15 mL). The combined organic layers were washed with saturated bicarbonate (15 mL), brine (15 mL), dried over $Na_2SO_4$, and concentrated in vacuo. The residue was purified by flash column chromatography eluting with 0-100% (20% MeOH/$CH_2Cl_2$)/$CH_2Cl_2$ gradient to afford 4-(4-((1R,5S)-3,8-diazabicyclo[3.2.1]octan-3-yl)-8-fluoro-2-methoxypyrido[4,3-d]pyrimidin-7-yl)naphthalen-2-ol (71.9 mg, 0.167 mmol, 83%). LCMS (MM-ES+APCI, Pos): m/z 432.1 (M+H).

Example 106

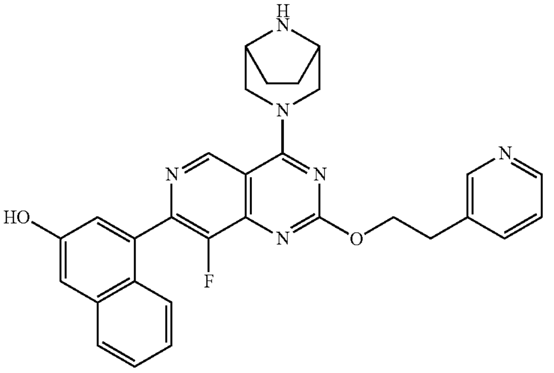 [SMILES: Oc1cc(-c2ncc3c(N4CC5CCC(C4)N5)nc(OCCc4cccnc4)nc3c2F)c2ccccc2c1]

4-(4-((1R,5S)-3,8-diazabicyclo[3.2.1]octan-3-yl)-8-fluoro-2-(2-(pyridin-3-yl)ethoxy)pyrido[4,3-d]pyrimidin-7-yl)naphthalen-2-ol Synthesized according to Example 3, Steps G-I substituting 2-(pyridin-3-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(pyridin-3-yl)ethoxy)pyrido[4,3-d]pyrimidin-7-yl)naphthalen-2-ol (16.5 mg, 0.031 mmol, 38%). LCMS (MM-ES+APCI, Pos): m/z 523.2 (M+H).

Example 107

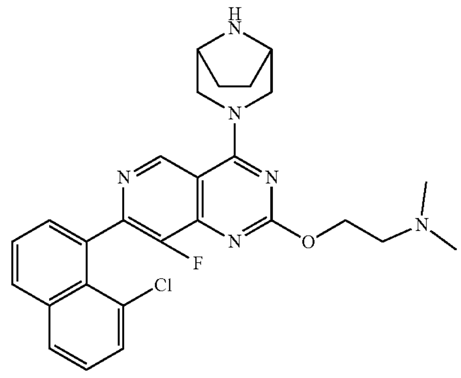 [SMILES: CN(C)CCOc1nc(N2CC3CCC(C2)N3)c2cnc(-c3cccc4cccc(Cl)c34)c(F)c2n1]

2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)-N,N-dimethylethan-1-amine Synthesized according to Example 3, Steps G-I substituting 2-(dimethylamino)ethan-1-ol in place of 2-(1-methyl-1H-imidazol-2-yl)ethan-1-ol in Step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford 2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)-N,N-dimethylethan-1-amine (5.1 mg, 0.010 mmol, 9%). LCMS (MM-ES+APCI, Pos): m/z 507.2 (M+H).

Example 108

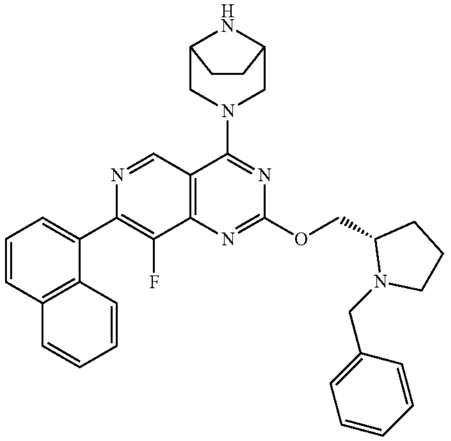 [SMILES: Fc1c(-c2cccc3ccccc23)ncc2c(N3CC4CCC(C3)N4)nc(OC[C@@H]3CCCN3Cc3ccccc3)nc12]

2-(((S)-1-benzylpyrrolidin-2-yl)methoxy)-4-((1R,5S)-3,8-diazabicyclo[3.2.1]octan-3-yl)-8-fluoro-7-(naphthalen-1-yl)pyrido[4,3-d]pyrimidine Synthesized according to Example 3, Steps G-I substituting (S)-(1-benzylpyrrolidin-2-yl)methanol in place of 2-(1-methyl-1H-imidazol-2-yl)ethan-1-ol in Step G and 4,4,5,5-tetramethyl-2-(naphthalen-1-yl)-1,3,2-dioxaborolane in place of 4-(4,4,5,5-tetramethyl-1,3,2-dioxaborolan-2-yl)naphthalen-2-ol in Step H to afford 2-(((S)-1-benzylpyrrolidin-2-yl)methoxy)-4-((1R,5S)-3,8-diazabicyclo[3.2.1]octan-3-yl)-8-fluoro-7-(naphthalen-1-yl)pyrido[4,3-d]pyrimidine (23 mg, 0.039 mmol, 56%). LCMS (MM-ES+APCI, Pos): m/z 575.3 (M+H).

Example 109

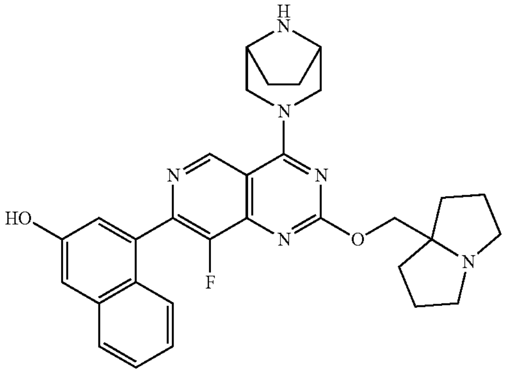 [SMILES: Oc1cc(-c2ncc3c(N4CC5CCC(C4)N5)nc(OCC45CCCN4CCC5)nc3c2F)c2ccccc2c1]

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-2-ol bis(2,2,2-trifluoroacetate)

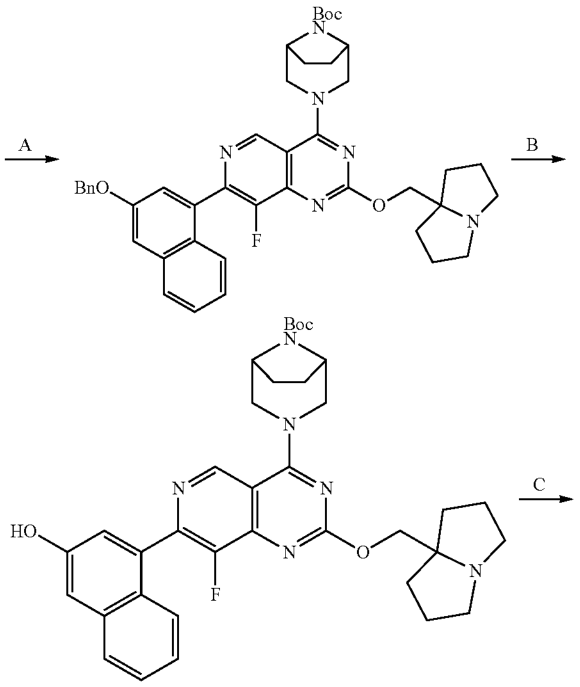

-continued

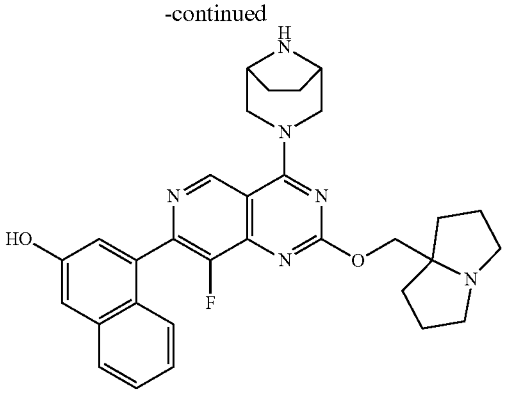

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-2-ol bis(2,2,2-trifluoroacetate) (7.5 mg, 0.010 mmol, 30%). LCMS (MM-ES+APCI, Pos): m/z 541.3 (M+H).

Example 110

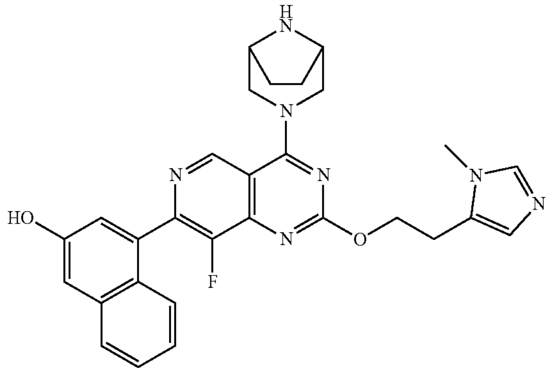 [SMILES: Cn1cncc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(1-methyl-1H-imidazol-5-yl)ethoxy)pyrido[4,3-d]pyrimidin-7-yl)naphthalen-2-ol Synthesized according to Example 3, Steps G-I substituting 2-(1-methyl-1H-imidazol-5-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(1-methyl-1H-imidazol-5-yl)ethoxy)pyrido[4,3-d]pyrimidin-7-yl)naphthalen-2-ol (14.6 mg, 0.027 mmol, 57%). LCMS (MM-ES+APCI, Pos): m/z 526.2 (M+H).

Example 111

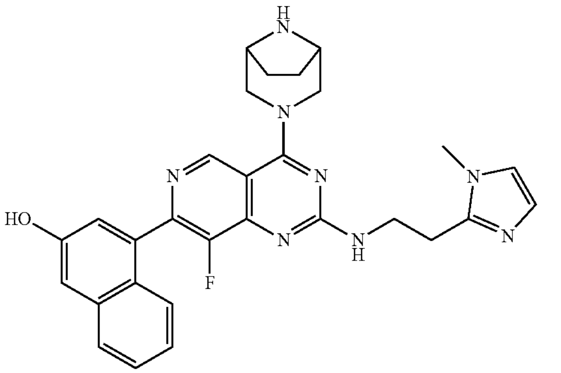 [SMILES: Cn1ccnc1CCNc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-((2-(1-methyl-1H-imidazol-2-yl)ethyl)amino)pyrido[4,3-d]pyrimidin-7-yl)naphthalen-2-ol Synthesized according to Example 3, Steps G-I substituting 2-(1-methyl-1H-imidazol-2-yl)ethan-1-amine dihydrochloride in place of 2-(1-methyl-1H-imidazol-2-yl)ethan-1-ol to afford 4-(4-((1R,5S)-3,8-diazabicyclo[3.2.1]octan-3-yl)-8-fluoro-2-((2-(1-methyl-1H-imidazol-2-yl)ethyl)amino)pyrido[4,3-d]pyrimidin-7-yl)naphthalen-2-ol (16.9 mg, 0.032 mmol, 39%). LCMS (MM-ES+APCI, Pos): m/z 525.2 (M+H).

Example 112

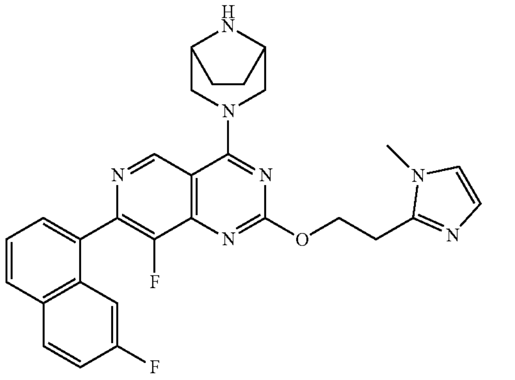 [SMILES: Cn1ccnc1CCOc1nc(N2CC3CCC(C2)N3)c2cnc(-c3cccc4ccc(F)cc34)c(F)c2n1]

4-((1R,5S)-3,8-diazabicyclo[3.2.1]octan-3-yl)-8-fluoro-7-(7-fluoronaphthalen-1-yl)-2-(2-(1-methyl-1H-imidazol-2-yl)ethoxy)pyrido[4,3-d]pyrimidine Synthesized according to Example 3, Steps G-I substituting 2-(7-fluoronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-8-fluoro-7-(7-fluoronaphthalen-1-yl)-2-(2-(1-methyl-1H-imidazol-2-yl)ethoxy)pyrido[4,3-d]pyrimidine (12.5 mg, 0.024 mmol, 65%). LCMS (MM-ES+APCI, Pos): m/z 528.2 (M+H).

Example 113

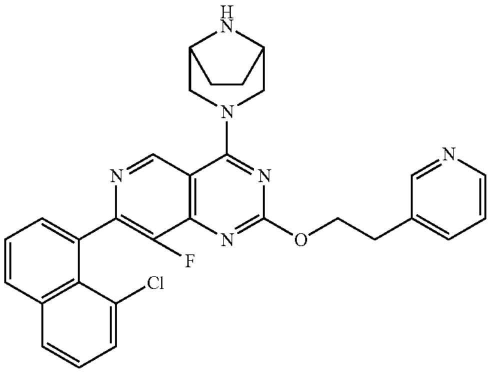 [SMILES: Fc1c(-c2cccc3cccc(Cl)c23)ncc2c(N3CC4CCC(C3)N4)nc(OCCc3cccnc3)nc12]

4-((1R,5S)-3,8-diazabicyclo[3.2.1]octan-3-yl)-7-(8-chloronaphthalen-1-yl)-8-fluoro-2-(2-(pyridin-3-yl)ethoxy)pyrido[4,3-d]pyrimidine Synthesized according to Example 3, Steps G-I substituting 2-(pyridin-3-yl)ethan-1-ol in place of 2-(1-methyl-1H-imidazol-2-yl)ethan-1-ol in Step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-7-(8-chloronaphthalen-1-yl)-8-fluoro-2-(2-(pyridin-3-yl)ethoxy)pyrido[4,3-d]pyrimidine (9.0 mg, 0.016 mmol, 28%). LCMS (MM-ES+APCI, Pos): m/z 541.2 (M+H).

Example 114

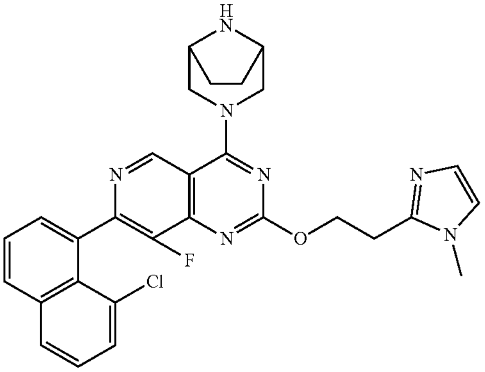 [SMILES: Cn1ccnc1CCOc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(2-(1-methyl-1H-imidazol-2-yl)ethoxy)pyrido[4,3-d]pyrimidine Synthesized according to Example 3, Steps G-I substituting 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-7-(8-chloronaphthalen-1-yl)-8-fluoro-2-(2-(1-methyl-1H-imidazol-2-yl)ethoxy)

pyrido[4,3-d]pyrimidine (3.7 mg, 0.007 mmol, 20%). LCMS (MM-ES+APCI, Pos): m/z 544.2 (M+H).

Example 115

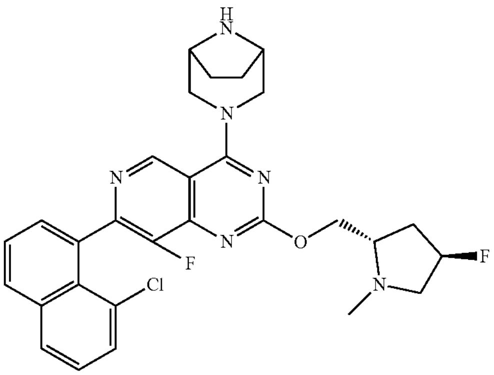 [SMILES: CN1C[C@H](F)C[C@H]1COc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(((2S,4R)-4-fluoro-1-methylpyrrolidin-2-yl)methoxy)pyrido[4,3-d]pyrimidine Synthesized according to Example 3, Steps G-I substituting ((2S,4R)-4-fluoro-1-methylpyrrolidin-2-yl)methanol in place of 2-(1-methyl-1H-imidazol-2-yl)ethan-1-ol in Step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-7-(8-chloronaphthalen-1-yl)-8-fluoro-2-(((2S,4R)-4-fluoro-1-methylpyrrolidin-2-yl)methoxy)pyrido[4,3-d]pyrimidine (6.5 mg, 0.012 mmol, 19%). LCMS (MM-ES+APCI, Pos): m/z 551.2 (M+H).

Example 116

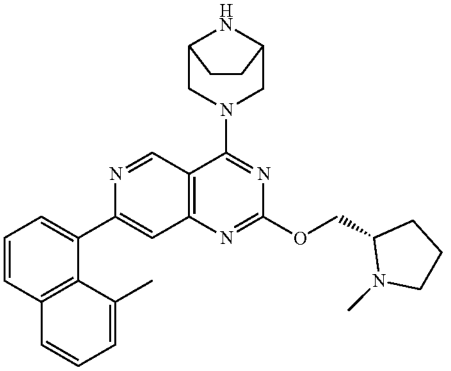 [SMILES: Cc1cccc2cccc(-c3cc4nc(OC[C@@H]5CCCN5C)nc(N5CC6CCC(C5)N6)c4cn3)c12]

4-((1R,5S)-3,8-diazabicyclo[3.2.1]octan-3-yl)-7-(8-methylnaphthalen-1-yl)-2-(((S)-1-methylpyrrolidin-2-yl)methoxy)pyrido[4,3-d]pyrimidine

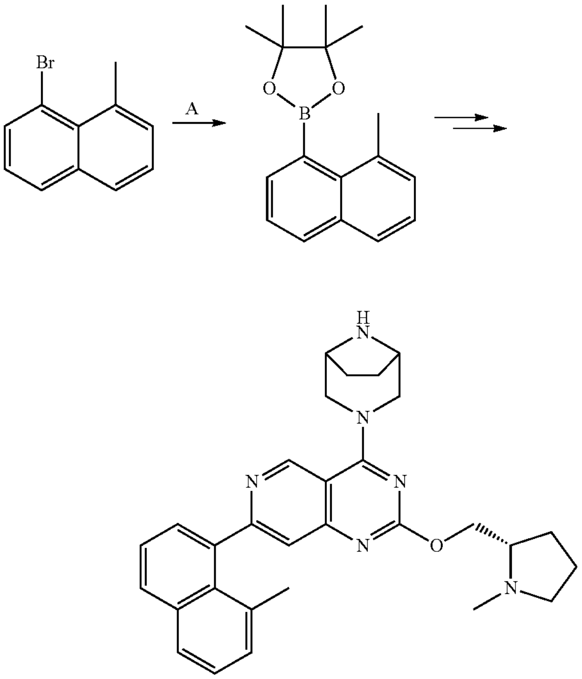

4-((1R,5S)-3,8-diazabicyclo[3.2.1]octan-3-yl)-7-(8-methylnaphthalen-1-yl)-2-(((S)-1-methylpyrrolidin-2-yl)methoxy)pyrido[4,3-d]pyrimidine. Synthesized according to Example 3, Steps G-I substituting (S)-(1-methylpyrrolidin-2-yl)methanol in place of 2-(1-methyl-1H-imidazol-2-yl)ethan-1-ol and 4,4,5,5-tetramethyl-2-(8-methylnaphthalen-1-yl)-1,3,2-dioxaborolane in place of 4-(4,4,5,5-tetramethyl-1,3,2-dioxaborolan-2-yl)naphthalen-2-ol (8.0 mg, 0.015 mmol, 25%). LCMS (MM-ES+APCI, Pos): m/z 495.2 (M+H).

Example 117

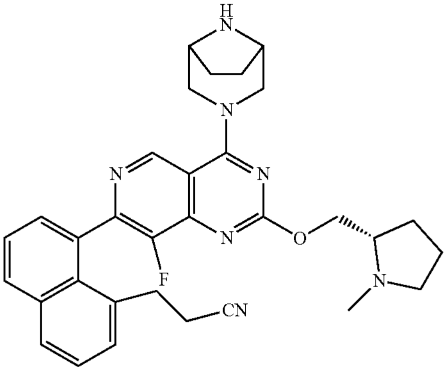 [SMILES: CN1CCC[C@H]1COc1nc(N2CC3CCC(C2)N3)c2cnc(-c3cccc4cccc(CCC#N)c34)c(F)c2n1]

3-(8-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-1-yl)propanenitrile bis(2,2,2-trifluoroacetate)

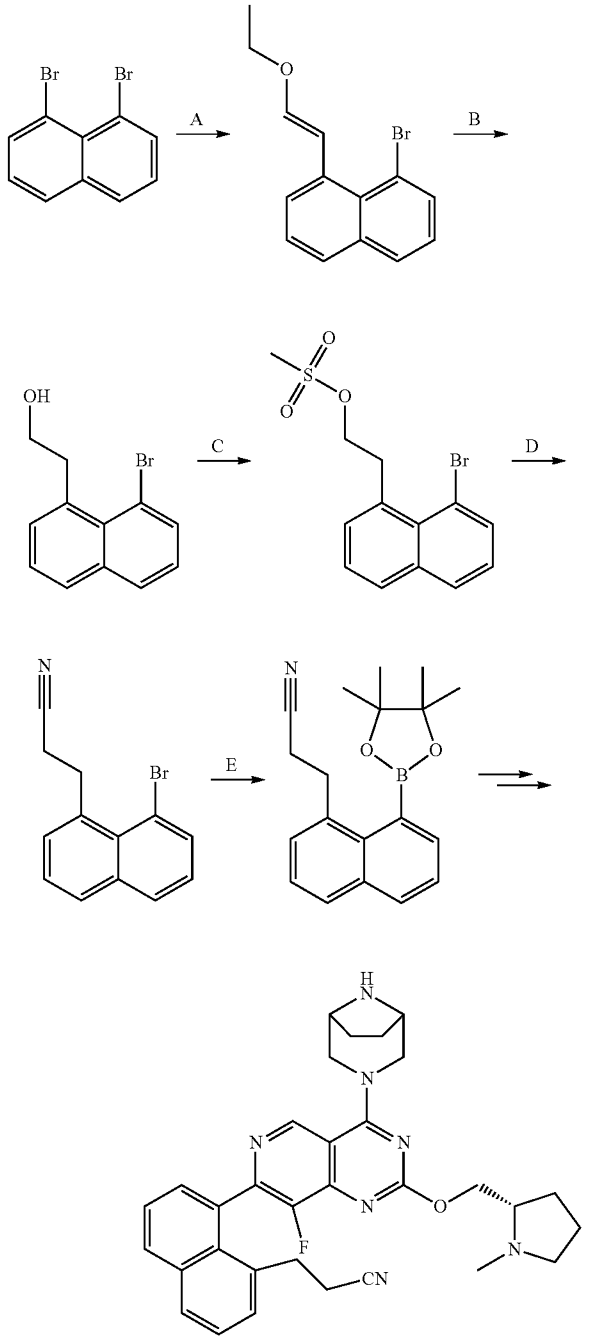

3-(8-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-1-yl)propanenitrile bis(2,2,2-trifluoroacetate). Synthesized according to Example 3, Steps G-I substituting (S)-(1-methylpyrrolidin-2-yl)methanol in place of 2-(1-methyl-1H-imidazol-2-yl)ethan-1-ol and 3-(8-(4,4,5,5-tetramethyl-1,3,2-dioxaborolan-2-yl)naphthalen-1-yl)propanenitrile (32.5 mg, 0.074 mmol) in place of 4-(4,4,5,5-tetramethyl-1,3,2-dioxaborolan-2-yl)naphthalen-2-ol (5.0 mg, 0.006 mmol, 60%). LCMS (MM-ES+APCI, Pos): m/z 552.3 (M+H).

Example 118

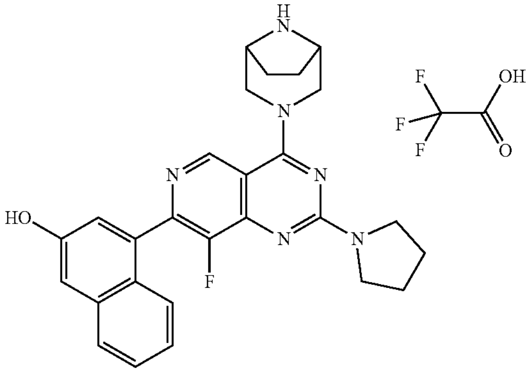 [SMILES: Oc1cc(-c2ncc3c(N4CC5CCC(C4)N5)nc(N4CCCC4)nc3c2F)c2ccccc2c1 ; O=C(O)C(F)(F)F]

4-(4-((1R,5S)-3,8-diazabicyclo[3.2.1]octan-3-yl)-8-fluoro-2-(pyrrolidin-1-yl)pyrido[4,3-d]pyrimidin-7-yl)naphthalen-2-ol 2,2,2-trifluoroacetate Synthesized according to Example 3, Steps G-I substituting pyrrolidine in place of 2-(1-methyl-1H-imidazol-2-yl)ethan-1-ol (49 mg, 0.084 mmol, 68%). LCMS (MM-ES+APCI, Pos): m/z 471.2 (M+H).

Example 119

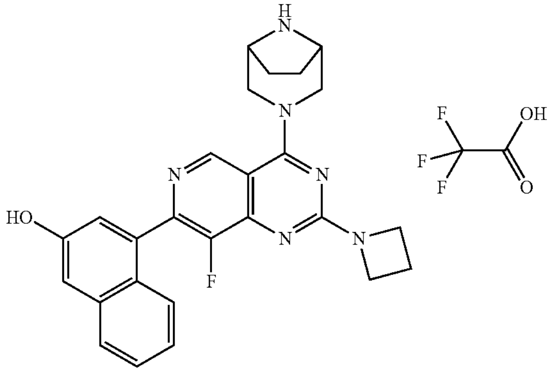

4-(2-(azetidin-1-yl)-4-((1R,5S)-3,8-diazabicyclo[3.2.1]octan-3-yl)-8-fluoropyrido[4,3-d]pyrimidin-7-yl)naphthalen-2-ol 2,2,2-trifluoroacetate Synthesized according to Example 3, Steps G-I substituting azetidine in place of 2-(1-methyl-1H-imidazol-2-yl)ethan-1-ol (34 mg, 0.06 mmol, 88%). LCMS (MM-ES+APCI, Pos): m/z 457.2 (M+H).

Example 120

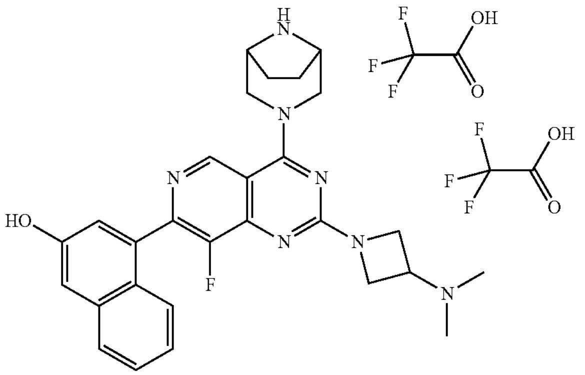

4-(4-((1R,5S)-3,8-diazabicyclo[3.2.1]octan-3-yl)-2-(3-(dimethylamino)azetidin-1-yl)-8-fluoropyrido[4,3-d]pyrimidin-7-yl)naphthalen-2-ol bis(2,2,2-trifluoroacetate)

Synthesized according to Example 3, Steps G-I substituting N,N-dimethylazetidin-3-amine hydrochloride in place of 2-(1-methyl-1H-imidazol-2-yl)ethan-1-ol (30 mg, 0.041 mmol, 88%). LCMS (MM-ES+APCI, Pos): m/z 500.3 (M+H).

Example 121

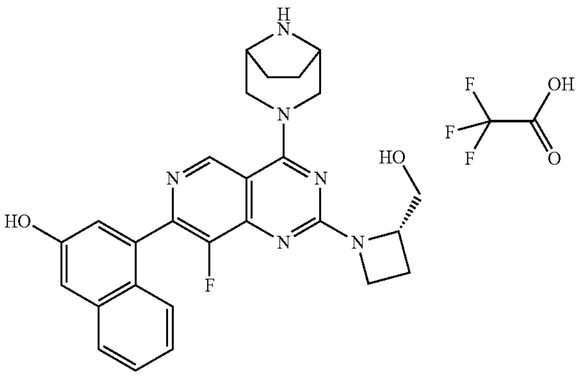

4-(4-((1R,5S)-3,8-diazabicyclo[3.2.1]octan-3-yl)-8-fluoro-2-((S)-2-(hydroxymethyl)azetidin-1-yl)pyrido[4,3-d]pyrimidin-7-yl)naphthalen-2-ol 2,2,2-trifluoroacetate Synthesized according to Example 3, Steps G-I substituting (S)-2-azetidinemethanol in place of 2-(1-methyl-1H-imidazol-2-yl)ethan-1-ol (20.9 mg, 0.035 mmol, 100%). LCMS (MM-ES+APCI, Pos): m/z 487.2 (M+H).

Example 122

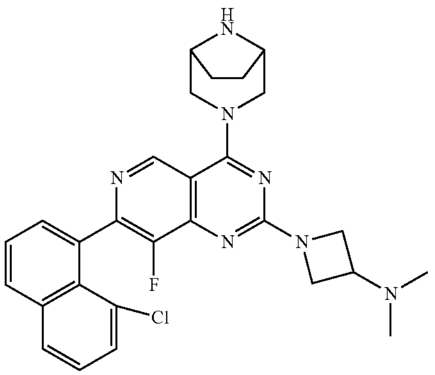 [SMILES: CN(C)C1CN(c2nc(N3CC4CCC(C3)N4)c3cnc(-c4cccc5cccc(Cl)c45)c(F)c3n2)C1]

1-(4-((1R,5S)-3,8-diazabicyclo[3.2.1]octan-3-yl)-7-(8-chloronaphthalen-1-yl)-8-fluoropyrido[4,3-d]pyrimidin-2-yl)-N,N-dimethylazetidin-3-amine Synthesized according to Example 3, Steps G-I substituting N, N-dimethylazetidin-3-amine hydrochloride in place of 2-(1-methyl-1H-imidazol-2-yl)ethan-1-ol and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol (5 mg, 0.01 mmol, 37%). LCMS (MM-ES+APCI, Pos): m/z 518.2 (M+H).

Example 123

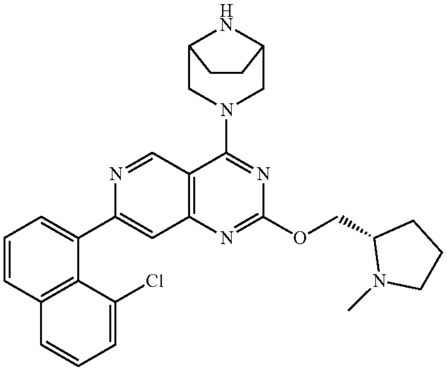

4-((1R,5S)-3,8-diazabicyclo[3.2.1]octan-3-yl)-7-(8-chloronaphthalen-1-yl)-2-(((S)-1-methylpyrrolidin-2-yl)methoxy)pyrido[4,3-d]pyrimidine Synthesized according to Example 3 steps D-I, substituting ethyl 4-amino-6-chloronicotinate for ethyl 4-amino-6-chloro-5-fluoronicotinate in step D while substituting (S)-(1-methylpyrrolidin-2-yl)methanol in place of 2-(1-methyl-1H-imidazol-2-yl)ethan-1-ol in step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in step H (6 mg, 0.012 mmol, 21%). LCMS (MM-ES+APCI, Pos): m/z 515.2 (M+H).

Example 124

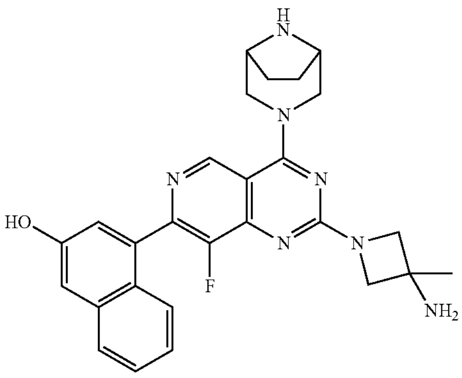 [SMILES: CC1(N)CN(c2nc(N3CC4CCC(C3)N4)c3cnc(-c4cc(O)cc5ccccc45)c(F)c3n2)C1]

4-(2-(3-amino-3-methylazetidin-1-yl)-4-((1R,5S)-3,8-diazabicyclo[3.2.1]octan-3-yl)-8-fluoropyrido[4,3-d]pyrimidin-7-yl)naphthalen-2-ol Synthesized according to Example 3, Steps G-I substituting 3-(Boc-amino)-3-methylazetidine hydrochloride in place of 2-(1-methyl-1H-imidazol-2-yl)ethan-1-ol (24 mg, 0.05 mmol, 42%). LCMS (MM-ES+APCI, Pos): m/z 486.2 (M+H).

Example 125

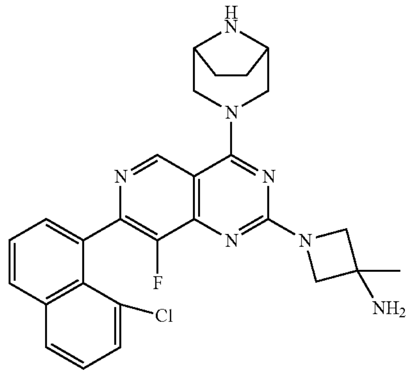 [SMILES: CC1(N)CN(c2nc(N3CC4CCC(C3)N4)c3cnc(-c4cccc5cccc(Cl)c45)c(F)c3n2)C1]

1-(4-((1R,5S)-3,8-diazabicyclo[3.2.1]octan-3-yl)-7-(8-chloronaphthalen-1-yl)-8-fluoropyrido[4,3-d]pyrimidin-2-yl)-3-methylazetidin-3-amine Synthesized according to Example 3, Steps G-I substituting 3-(Boc-amino)-3-methylazetidine hydrochloride in place of 2-(1-methyl-1H-imidazol-2-yl)ethan-1-ol and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol (54 mg, 0.11 mmol, 51%). LCMS (MM-ES+APCI, Pos): m/z 504.2 (M+H).

Example 126

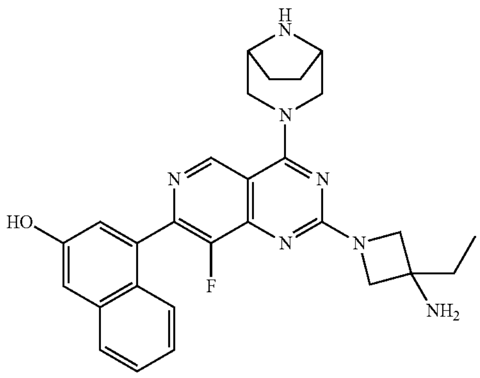 [SMILES: CCC1(N)CN(c2nc(N3CC4CCC(C3)N4)c3cnc(-c4cc(O)cc5ccccc45)c(F)c3n2)C1]

4-(2-(3-amino-3-ethylazetidin-1-yl)-4-((1R,5S)-3,8-diazabicyclo[3.2.1]octan-3-yl)-8-fluoropyrido[4,3-d]pyrimidin-7-yl)naphthalen-2-ol Synthesized according to Example 3, Steps G-I substituting 3-(Boc-amino)-3-ethylazetidine hydrochloride in place of 2-(1-methyl-1H-imidazol-2-yl)ethan-1-ol (34 mg, 0.068 mmol, 41%). LCMS (MM-ES+APCI, Pos): m/z 500.2 (M+H).

Example 127

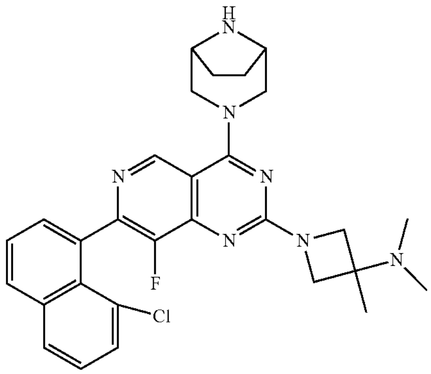 [SMILES: CN(C)C1(C)CN(c2nc(N3CC4CCC(C3)N4)c3cnc(-c4cccc5cccc(Cl)c45)c(F)c3n2)C1]

1-(4-((1R,5S)-3,8-diazabicyclo[3.2.1]octan-3-yl)-7-(8-chloronaphthalen-1-yl)-8-fluoropyrido[4,3-d]pyrimidin-2-yl)-N,N,3-trimethylazetidin-3-amine Synthesized according to Example 29, Steps H—I substituting N,N,3-trimethylazetidin-3-amine hydrochloride in place of (S)-(1-isopropylpyrrolidin-2-yl)methanol (21 mg, 0.039 mmol, 100%). LCMS (MM-ES+APCI, Pos): m/z 532.2 (M+H).

Example 128

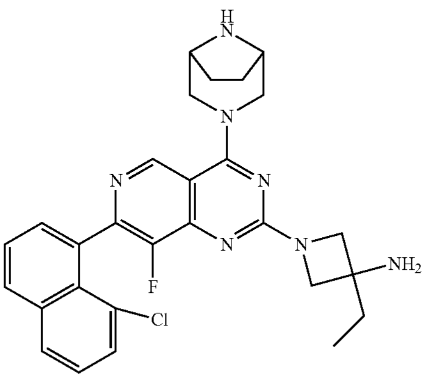 [SMILES: CCC1(N)CN(c2nc(N3CC4CCC(C3)N4)c3cnc(-c4cccc5cccc(Cl)c45)c(F)c3n2)C1]

1-(4-((1R,5S)-3,8-diazabicyclo[3.2.1]octan-3-yl)-7-(8-chloronaphthalen-1-yl)-8-fluoropyrido[4,3-d]pyrimidin-2-yl)-3-ethylazetidin-3-amine Synthesized according to Example 29, Steps H—I substituting 3-(Boc-amino)-3-ethylazetidine hydrochloride in place of (S)-(1-isopropylpyrrolidin-2-yl)methanol (7 mg, 0.013 mmol, 88%). LCMS (MM-ES+APCI, Pos): m/z 518.2 (M+H).

Example 129

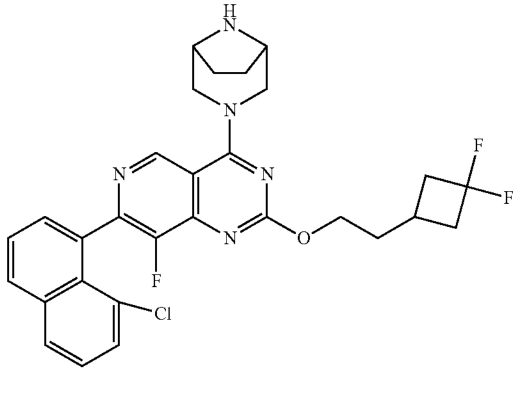 [SMILES: Fc1c(-c2cccc3cccc(Cl)c23)ncc2c(N3CC4CCC(C3)N4)nc(OCCC3CC(F)(F)C3)nc12]

4-((1R,5S)-3,8-diazabicyclo[3.2.1]octan-3-yl)-7-(8-chloronaphthalen-1-yl)-2-(2-(3,3-difluorocyclobutyl)ethoxy)-8-fluoropyrido[4,3-d]pyrimidine Synthesized according to Example 29, Steps H—I substituting (3,3-Difluorocyclobutyl)ethanol in place of (S)-(1-isopropylpyrrolidin-2-yl)methanol (15 mg, 0.027 mmol, 59%). LCMS (MM-ES+APCI, Pos): m/z 554.2 (M+H).

Example 130

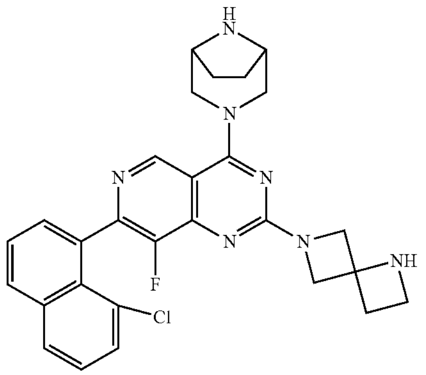 [SMILES: Fc1c(-c2cccc3cccc(Cl)c23)ncc2c(N3CC4CCC(C3)N4)nc(N3CC4(CCN4)C3)nc12]

4-((1R,5S)-3,8-diazabicyclo[3.2.1]octan-3-yl)-7-(8-chloronaphthalen-1-yl)-8-fluoro-2-(1,6-diazaspiro[3.3]heptan-6-yl)pyrido[4,3-d]pyrimidine Synthesized according to Example 29, Steps H—I substituting 3,6-Diazaspiro[3.3]heptane-3-carboxylic acid tert-butyl ester in place of (S)-(1-isopropylpyrrolidin-2-yl)methanol (7 mg, 0.014 mmol, 18%). LCMS (MM-ES+APCI, Pos): m/z 516.2 (M+H).

Example 131

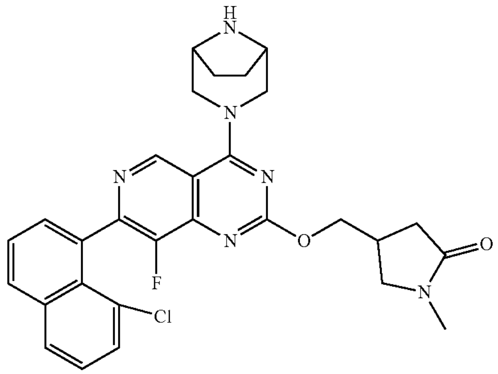 [SMILES: CN1CC(COc2nc(N3CC4CCC(C3)N4)c3cnc(-c4cccc5cccc(Cl)c45)c(F)c3n2)CC1=O]

4-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-2-one Synthesized according to Example 29, Steps H—I substituting 4-(Hydroxymethyl)-1-methylpyrrolidin-2-one in place of (S)-(1-isopropylpyrrolidin-2-yl)methanol (25 mg, 0.046 mmol, 67%). LCMS (MM-ES+APCI, Pos): m/z 547.2 (M+H).

Example 132

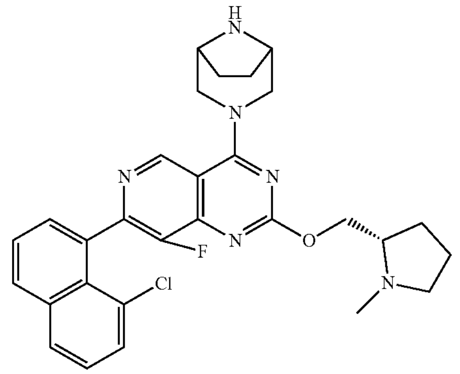 [SMILES: CN1CCC[C@H]1COc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(((S)-1-methylpyrrolidin-2-yl)methoxy)pyrido[4,3-d]pyrimidine Synthesized according to Example 3, Steps G-I substituting (S)-(1-methylpyrrolidin-2-yl)methanol in place of 2-(1-methyl-1H-imidazol-2-yl)ethan-1-ol and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol (7 mg, 0.013 mmol, 72%). LCMS (MM-ES+APCI, Pos): m/z 533.2 (M+H).

Example 133

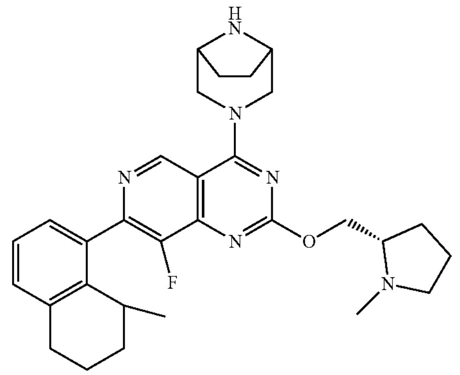 [SMILES: CC1CCCc2cccc(-c3ncc4c(N5CC6CCC(C5)N6)nc(OC[C@@H]5CCCN5C)nc4c3F)c21]

4-((1R,5S)-3,8-diazabicyclo[3.2.1]octan-3-yl)-8-fluoro-7-(8-methyl-5,6,7,8-tetrahydronaphthalen-1-yl)-2-(((S)-1-methylpyrrolidin-2-yl)methoxy)pyrido[4,3-d]pyrimidine

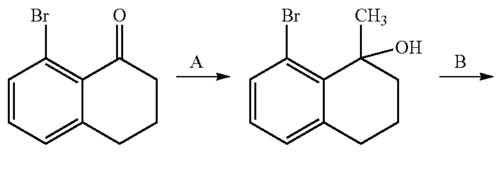

-continued

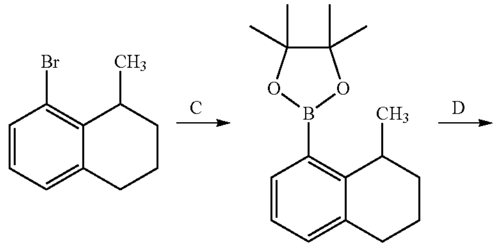

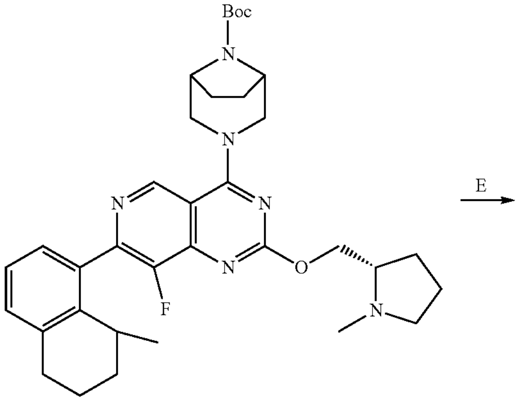

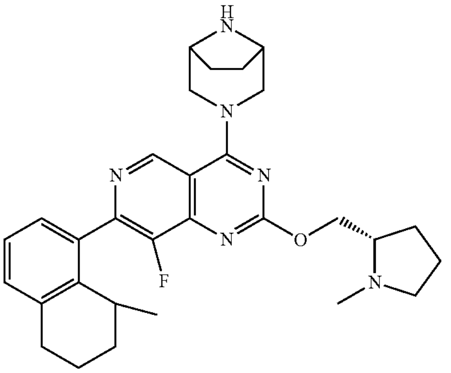

4-((1R,5S)-3,8-diazabicyclo[3.2.1]octan-3-yl)-8-fluoro-7-(8-methyl-5,6,7,8-tetrahydronaphthalen-1-yl)-2-(((S)-1-methylpyrrolidin-2-yl)methoxy)pyrido[4,3-d]pyrimidine. Synthesized similarly to Example 3 Step I, using tert-butyl (1R,5S)-3-(8-fluoro-7-(8-methyl-5,6,7,8-tetrahydronaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate in place of tert-butyl(1R,5S)-3-(8-fluoro-7-(3-hydroxynaphthalen-1-yl)-2-(2-(1-methyl-1H-imidazol-2-yl)ethoxy)pyrido[4,3-d]pyrimidin-4-yl)-3,8-diazabicyclo[3.2.1]octane-8-carboxylate. Submitted as the freebase LCMS (MM-ES+APCI, Pos): m/z 517.3 (M+H).

Example 134

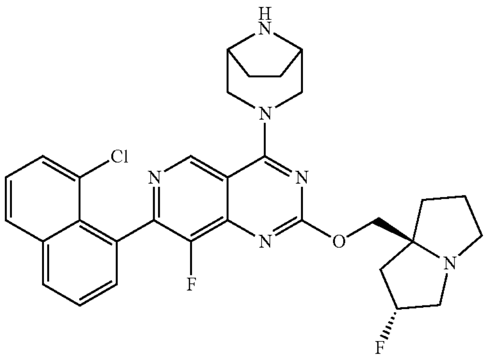 [SMILES: Fc1c(-c2cccc3cccc(Cl)c23)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-7-(8-chloronaphthalen-1-yl)-8-fluoro-2-((2-fluorotetrahydro-1H-pyrrolizin-7a(5H)-yl)methoxy)pyrido[4,3-d]pyrimidine

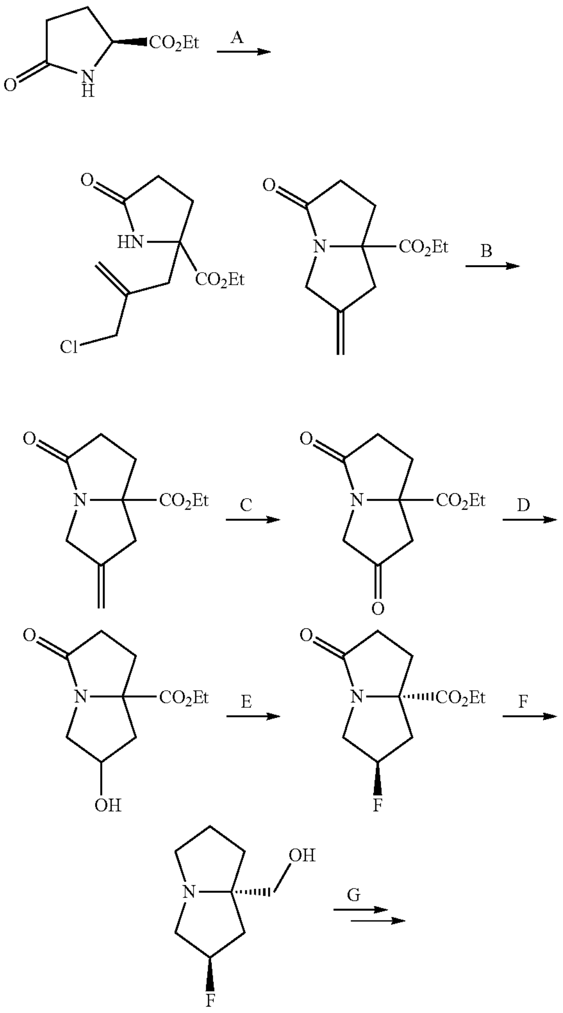

-continued

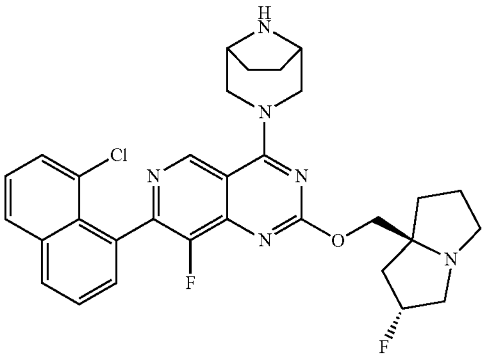

4-((1R,5S)-3,8-diazabicyclo[3.2.1]octan-3-yl)-7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidine was synthesized according to Example 29, Steps H—I substituting ((2R,7aS)-2-fluorotetrahydro-1H-pyrrolizin-7a(5H)-yl)methanol in place of (S)-(1-isopropylpyrrolidin-2-yl)methanol (34 mg, 0.058 mmol, 62%). Submitted as a TFA salt. LCMS (MM-ES+APCI, Pos): m/z 577.2 (M+H).

Example 135

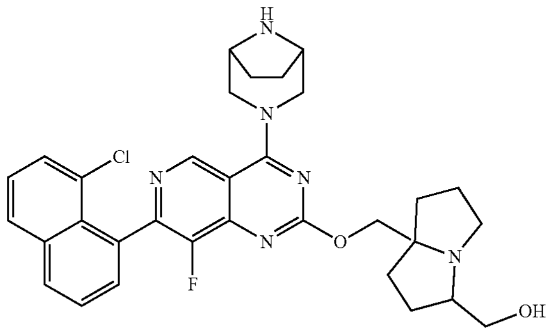

(7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methanol

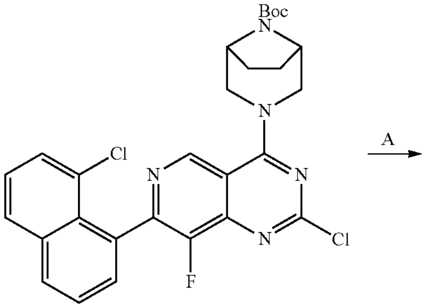

-continued

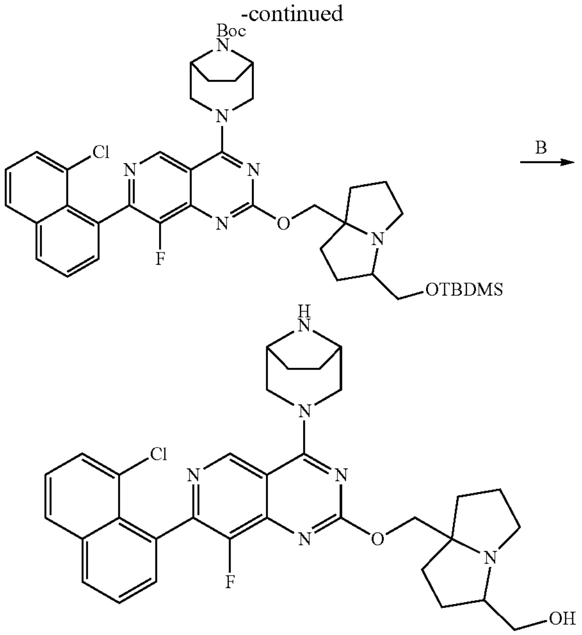

(7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methanol: Tert-butyl(1R,5S)-3-(2-((3-(((tert-butyldimethylsilyl)oxy)methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (0.015 g, 0.0187 mmol) was constituted in dichloromethane (0.5 ml, 0.0187 mmol) and stirred at room temperature. 2,2,2-trifluoroacetic acid (0.5 ml, 0.0187 mmol) was added dropwise to the vessel and the mixture was stirred at room temperature for 2.25 hours. The mixture was concentrated in vacuo and purified by reverse phase preparative HPLC (5-95% ACN/water/0.1% TFA over 20 min). Fractions containing the product were frozen and lyophilized overnight to provide the desired product as a white solid. LCMS (MM-ES+APCI, Pos): m/z 589.3 (M+H).

Example 136

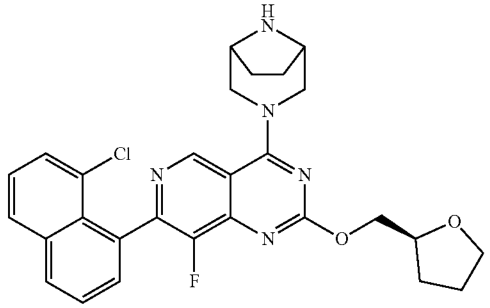 [SMILES: Fc1c(-c2cccc3cccc(Cl)c23)ncc2c(N3CC4CCC(C3)N4)nc(OC[C@@H]3CCCO3)nc12]

4-((1R,5S)-3,8-diazabicyclo[3.2.1]octan-3-yl)-7-(8-chloronaphthalen-1-yl)-8-fluoro-2-(((S)-tetrahydrofuran-2-yl)methoxy)pyrido[4,3-d]pyrimidine Synthesized according to Example 29, Steps H—I substituting (S)-(tetrahydrofuran-2-yl)methanol in place of (S)-

(1-isopropylpyrrolidin-2-yl)methanol (21 mg, 0.033 mmol, 49%). Submitted as a TFA salt. LCMS (MM-ES+APCI, Pos): m/z 520.2 (M+H).

Example 137

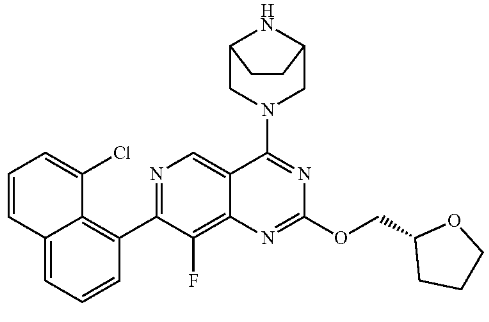 [SMILES: Fc1c(-c2cccc3cccc(Cl)c23)ncc2c(N3CC4CCC(C3)N4)nc(OC[C@H]3CCCO3)nc12]

4-((1R,5S)-3,8-diazabicyclo[3.2.1]octan-3-yl)-7-(8-chloronaphthalen-1-yl)-8-fluoro-2-(((R)-tetrahydrofuran-2-yl)methoxy)pyrido[4,3-d]pyrimidine Synthesized according to Example 29, Steps H—I substituting (R)-(tetrahydrofuran-2-yl)methanol in place of (S)-(1-isopropylpyrrolidin-2-yl)methanol (21 mg, 0.033 mmol, 49%). Submitted as a TFA salt. LCMS (MM-ES+APCI, Pos): m/z 520.2 (M+H).

Example 138

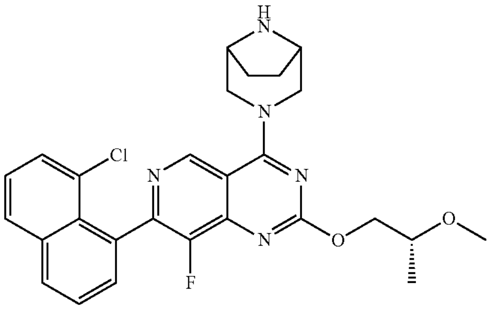 [SMILES: CO[C@H](C)COc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-((R)-2-methoxypropoxy)pyrido[4,3-d]pyrimidine Synthesized according to Example 29, Steps H—I substituting (R)-2-methoxypropan-1-ol in place of (S)-(1-isopropylpyrrolidin-2-yl)methanol (1 mg, 0.0014 mmol, 4%). LCMS (MM-ES+APCI, Pos): m/z 508.2 (M+H).

Example 139

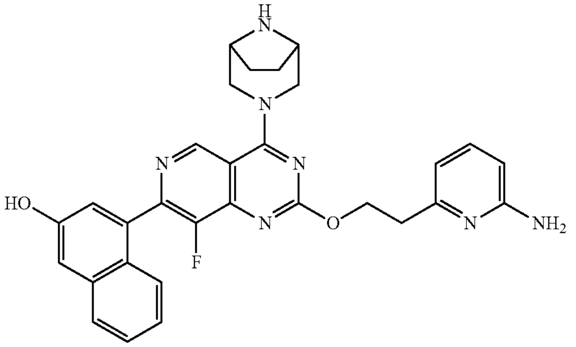 [SMILES: Nc1cccc(CCOc2nc(N3CC4CCC(C3)N4)c3cnc(-c4cc(O)cc5ccccc45)c(F)c3n2)n1]

4-(2-(2-(6-aminopyridin-2-yl)ethoxy)-4-((1R,5S)-3,8-diazabicyclo[3.2.1]octan-3-yl)-8-fluoropyrido[4,3-d]pyrimidin-7-yl)naphthalen-2-ol Synthesized according to Example 30 substituting 2-(6-aminopyridin-2-yl)ethan-1-ol in place of 2-(1-methyl-1H-benzo[d]imidazol-2-yl)ethan-1-ol dihydrate in Step F (9.7 mg, 0.018 mmol, 46%). LCMS (MM-ES+APCI, Pos): m/z 538.2 (M+H).

Example 140

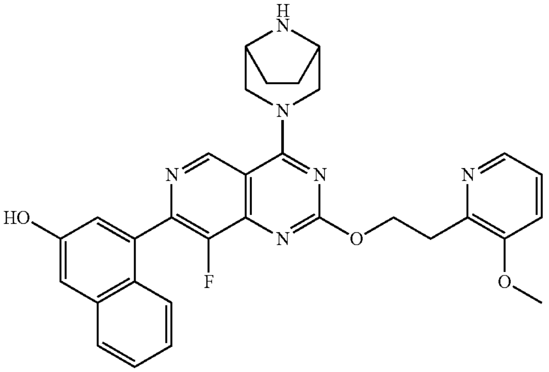 [SMILES: COc1cccnc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(3-methoxypyridin-2-yl)ethoxy)pyrido[4,3-d]pyrimidin-7-yl)naphthalen-2-ol Synthesized according to Example 30 substituting 2-(3-methoxypyridin-2-yl)ethan-1-ol in place of 2-(1-methyl-1H-benzo[d]imidazol-2-yl)ethan-1-ol dihydrate in Step F (12.7 mg, 0.023 mmol, 68%). LCMS (MM-ES+APCI, Pos): m/z 553.2 (M+H).

Example 141

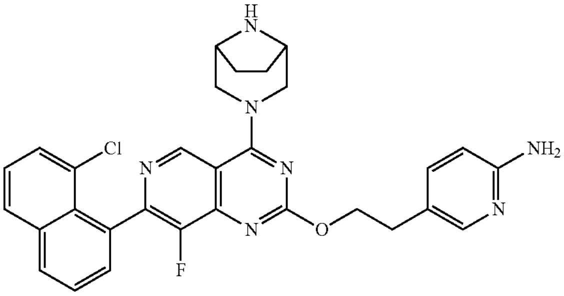 [SMILES: Nc1ccc(CCOc2nc(N3CC4CCC(C3)N4)c3cnc(-c4cccc5cccc(Cl)c45)c(F)c3n2)cn1]

5-(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)pyridin-2-amine Synthesized according to Example 29 substituting 2-(6-aminopyridin-3-yl)ethan-1-ol in place of (S)-(1-isopropylpyrrolidin-2-yl)methanol in Step H (21 mg, 0.038 mmol, 69%). LCMS (MM-ES+APCI, Pos): m/z 556.2 (M+H).

Example 142

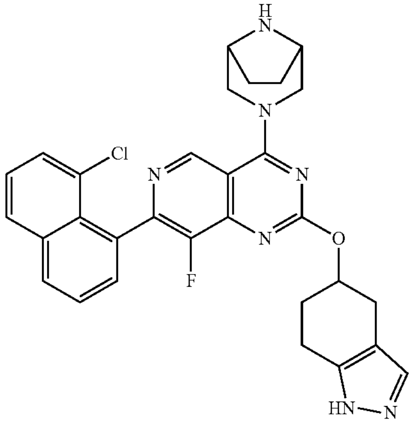 [SMILES: Fc1c(-c2cccc3cccc(Cl)c23)ncc2c(N3CC4CCC(C3)N4)nc(OC3CCc4[nH]ncc4C3)nc12]

4-((1R,5S)-3,8-diazabicyclo[3.2.1]octan-3-yl)-7-(8-chloronaphthalen-1-yl)-8-fluoro-2-((4,5,6,7-tetrahydro-1H-indazol-5-yl)oxy)pyrido[4,3-d]pyrimidine Synthesized according to Example 29 substituting 4,5,6,7-tetrahydro-1H-indazol-5-ol in place of (S)-(1-isopropylpyrrolidin-2-yl)methanol in Step H (8.6 mg, 0.015 mmol, 41%). LCMS (MM-ES+APCI, Pos): m/z 556.2 (M+H).

Example 143

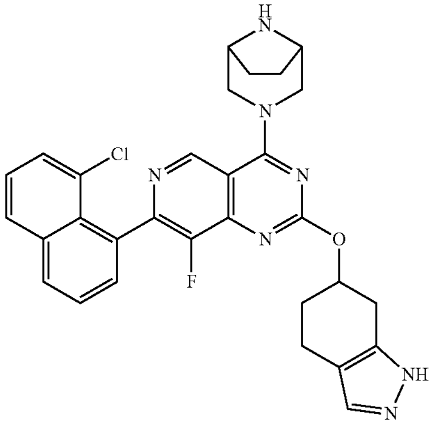 [SMILES: Fc1c(-c2cccc3cccc(Cl)c23)ncc2c(N3CC4CCC(C3)N4)nc(OC3CCc4cn[nH]c4C3)nc12]

4-((1R,5S)-3,8-diazabicyclo[3.2.1]octan-3-yl)-7-(8-chloronaphthalen-1-yl)-8-fluoro-2-((4,5,6,7-tetrahydro-1H-indazol-6-yl)oxy)pyrido[4,3-d]pyrimidine Synthesized according to Example 29 substituting 4,5,6,7-tetrahydro-1H-indazol-6-ol in place of (S)-(1-isopropylpyrrolidin-2-yl)methanol in Step H (16 mg, 0.029 mmol, 56%). LCMS (MM-ES+APCI, Pos): m/z 556.2 (M+H).

Example 144

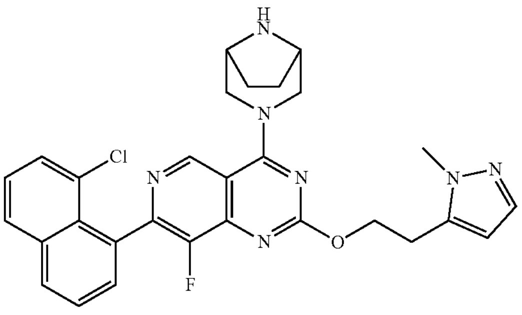 [SMILES: Cn1nccc1CCOc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(2-(1-methyl-1H-pyrazol-5-yl)ethoxy)pyrido[4,3-d]pyrimidine Synthesized according to Example 29 substituting 2-(1-methyl-1H-pyrazol-5-yl)ethan-1-ol in place of (S)-(1-isopropylpyrrolidin-2-yl)methanol in Step H (11 mg, 0.020 mmol, 52%). LCMS (MM-ES+APCI, Pos): m/z 544.2 (M+H).

Example 145

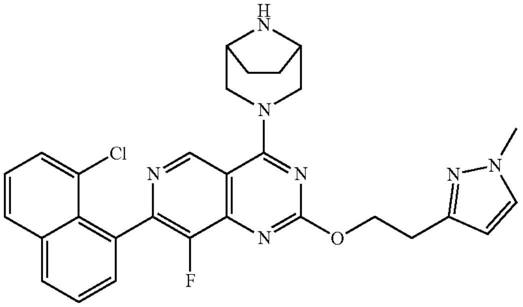 [SMILES: Cn1ccc(CCOc2nc(N3CC4CCC(C3)N4)c3cnc(-c4cccc5cccc(Cl)c45)c(F)c3n2)n1]

4-((1R,5S)-3,8-diazabicyclo[3.2.1]octan-3-yl)-7-(8-chloronaphthalen-1-yl)-8-fluoro-2-(2-(1-methyl-1H-pyrazol-3-yl)ethoxy)pyrido[4,3-d]pyrimidine Synthesized according to Example 29 substituting 2-(1-methyl-1H-pyrazol-3-yl)ethan-1-ol in place of (S)-(1-isopropylpyrrolidin-2-yl)methanol in Step H (10 mg, 0.018 mmol, 39%). LCMS (MM-ES+APCI, Pos): m/z 544.2 (M+H).

Example 146

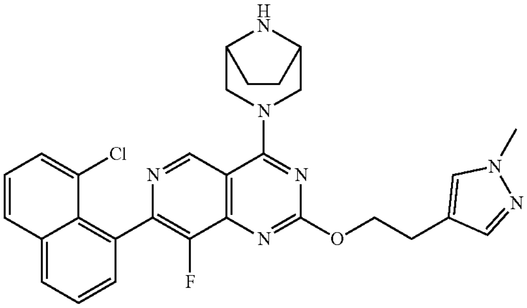 [SMILES: Cn1cc(CCOc2nc(N3CC4CCC(C3)N4)c3cnc(-c4cccc5cccc(Cl)c45)c(F)c3n2)cn1]

4-((1R,5S)-3,8-diazabicyclo[3.2.1]octan-3-yl)-7-(8-chloronaphthalen-1-yl)-8-fluoro-2-(2-(1-methyl-1H-pyrazol-4-yl)ethoxy)pyrido[4,3-d]pyrimidine Synthesized according to Example 29 substituting 2-(1-methyl-1H-pyrazol-4-yl)ethan-1-ol in place of (S)-(1-isopropylpyrrolidin-2-yl)methanol in Step H (19 mg, 0.035 mmol, 70%). LCMS (MM-ES+APCI, Pos): m/z 544.2 (M+H).

Example 147

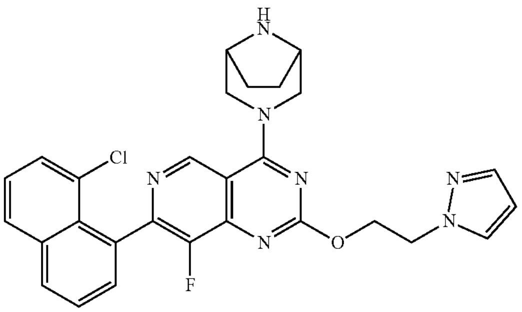 [SMILES: Fc1c(-c2cccc3cccc(Cl)c23)ncc2c(N3CC4CCC(C3)N4)nc(OCCn3cccn3)nc12]

2-(2-(1H-pyrazol-1-yl)ethoxy)-4-((1R,5S)-3,8-diazabicyclo[3.2.1]octan-3-yl)-7-(8-chloronaphthalen-1-yl)-8-fluoropyrido[4,3-d]pyrimidine Synthesized according to Example 29 substituting 2-(1H-pyrazol-1-yl)ethan-1-ol in place of (S)-(1-isopropylpyrrolidin-2-yl)methanol in Step H (12 mg, 0.023 mmol, 22%). LCMS (MM-ES+APCI, Pos): m/z 530.2 (M+H).

Example 148

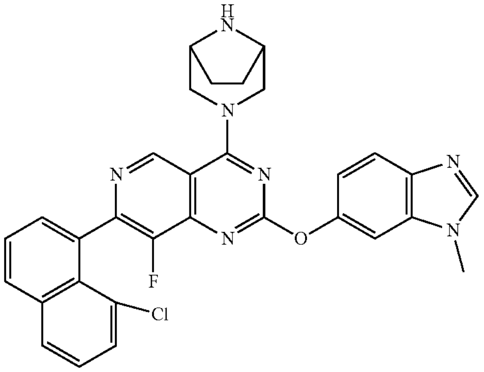 [SMILES: Cn1cnc2ccc(Oc3nc(N4CC5CCC(C4)N5)c4cnc(-c5cccc6cccc(Cl)c56)c(F)c4n3)cc21]

4-((1R,5S)-3,8-diazabicyclo[3.2.1]octan-3-yl)-7-(8-chloronaphthalen-1-yl)-8-fluoro-2-((1-methyl-1H-benzo[d]imidazol-6-yl)oxy)pyrido[4,3-d]pyrimidine Synthesized according to Example 29 substituting 1-methyl-1H-benzo[d]imidazol-6-ol in place of (S)-(1-isopropylpyrrolidin-2-yl)methanol in Step H (20 mg, 0.035 mmol, 57%). LCMS (MM-ES+APCI, Pos): m/z 566.2 (M+H).

Example 149

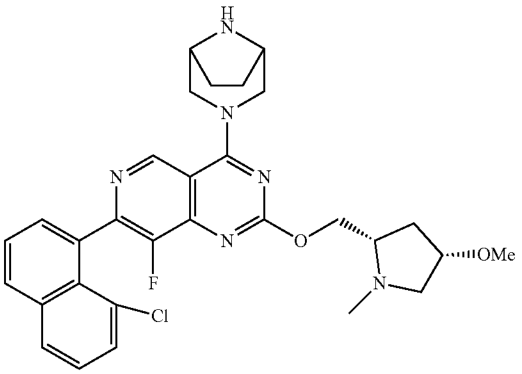 [SMILES: CO[C@H]1C[C@@H](COc2nc(N3CC4CCC(C3)N4)c3cnc(-c4cccc5cccc(Cl)c45)c(F)c3n2)N(C)C1]

4-((1R,5S)-3,8-diazabicyclo[3.2.1]octan-3-yl)-7-(8-chloronaphthalen-1-yl)-8-fluoro-2-(((2S,4S)-4-methoxy-1-methylpyrrolidin-2-yl)methoxy)pyrido[4,3-d]pyrimidine Synthesized according to Example 29 substituting ((2S,4S)-4-methoxy-1-methylpyrrolidin-2-yl)methanol in place of (S)-(1-isopropylpyrrolidin-2-yl)methanol in Step H (16 mg, 0.028 mmol, 67%). LCMS (MM-ES+APCI, Pos): m/z 563.3 (M+H).

Example 150

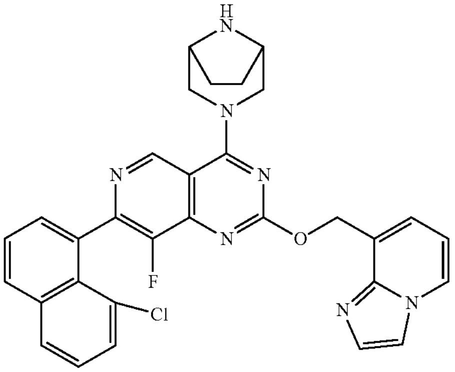 [SMILES: Fc1c(-c2cccc3cccc(Cl)c23)ncc2c(N3CC4CCC(C3)N4)nc(OCc3cccn4ccnc34)nc12]

4-((1R,5S)-3,8-diazabicyclo[3.2.1]octan-3-yl)-7-(8-chloronaphthalen-1-yl)-8-fluoro-2-(imidazo[1,2-a]pyridin-8-ylmethoxy)pyrido[4,3-d]pyrimidine Synthesized according to Example 29 substituting imidazo[1,2-a]pyridin-8-ylmethanol in place of (S)-(1-isopropylpyrrolidin-2-yl)methanol in Step H (17 mg, 0.030 mmol, 43%). LCMS (MM-ES+APCI, Pos): m/z 566.2 (M+H).

Example 151

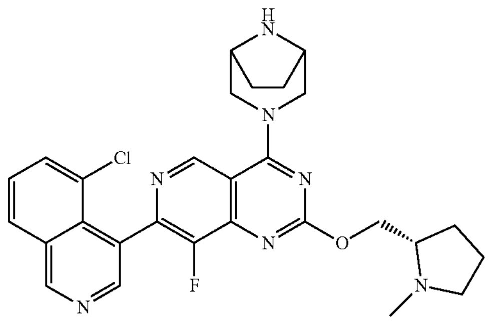 [SMILES: CN1CCC[C@H]1COc1nc(N2CC3CCC(C2)N3)c2cnc(-c3cncc4cccc(Cl)c34)c(F)c2n1]

4-((1R,5S)-3,8-diazabicyclo[3.2.1]octan-3-yl)-7-(5-chloroisoquinolin-4-yl)-8-fluoro-2-(((S)-1-methylpyrrolidin-2-yl)methoxy)pyrido[4,3-d]pyrimidine Synthesized according to Example 33 substituting (S)-(1-methylpyrrolidin-2-yl)methanol in place of (tetrahydro-1H-pyrrolizin-7a(5H)-yl)methanol in Step G (14 mg, 0.026 mmol, 44%). LCMS (MM-ES+APCI, Pos): m/z 534.2 (M+H).

Example 152

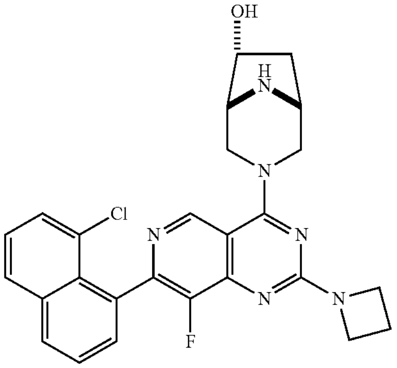

(1R,5R,6R)-3-(2-(azetidin-1-yl)-7-(8-chloronaphthalen-1-yl)-8-fluoropyrido[4,3-d]pyrimidin-4-yl)-3,8-diazabicyclo[3.2.1]octan-6-ol Synthesized according to Example 32 substituting azetidine in place of 2-(5-fluoropyridin-2-yl)ethan-1-ol in Step B (26 mg, 0.053 mmol, 52% yield). LCMS (MM-ES+APCI, Pos): m/z 491.2 (M+H).

Example 153

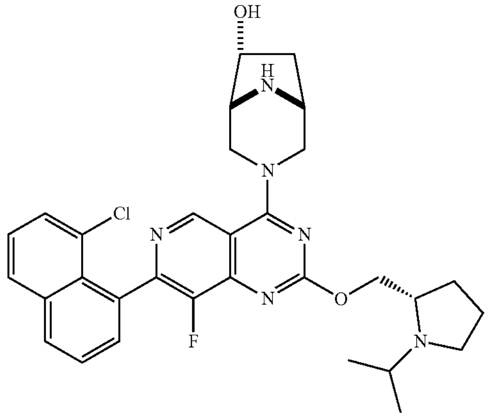

(1R,5R,6R)-3-(7-(8-chloronaphthalen-1-yl)-8-fluoro-2-(((S)-1-isopropylpyrrolidin-2-yl)methoxy)pyrido[4,3-d]pyrimidin-4-yl)-3,8-diazabicyclo[3.2.1]octan-6-ol Synthesized according to Example 32 substituting (S)-(1-isopropylpyrrolidin-2-yl)methanol in place of 2-(5-fluoropyridin-2-yl)ethan-1-ol in Step B (5 mg, 0.0087 mmol, 62% yield). LCMS (MM-ES+APCI, Pos): m/z 577.3 (M+H).

Example 154

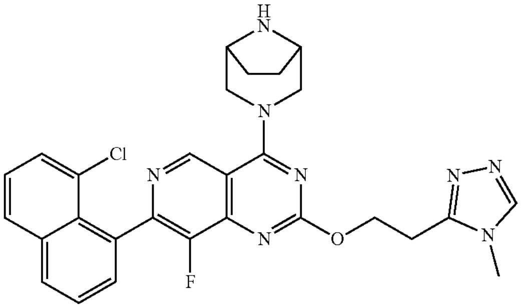 [SMILES: Cn1cnnc1CCOc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(2-(4-methyl-4H-1,2,4-triazol-3-yl)ethoxy)pyrido[4,3-d]pyrimidine Synthesized according to Example 29 substituting 2-(4-methyl-4H-1,2,4-triazol-3-yl)ethan-1-ol in place of (S)-(1-isopropylpyrrolidin-2-yl)methanol in Step H (19 mg, 0.035 mmol, 53% yield). LCMS (MM-ES+APCI, Pos): m/z 545.2 (M+H).

Example 155

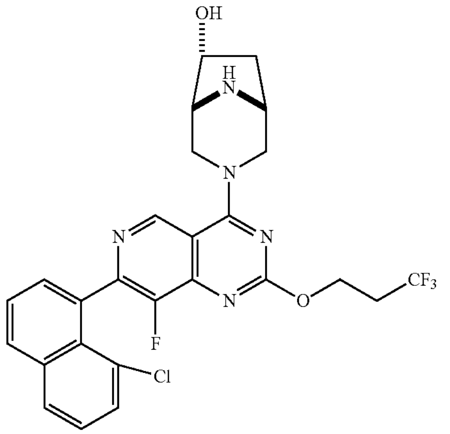

(1R,5R,6R)-3-(7-(8-chloronaphthalen-1-yl)-8-fluoro-2-(3,3,3-trifluoropropoxy)pyrido[4,3-d]pyrimidin-4-yl)-3,8-diazabicyclo[3.2.1]octan-6-ol Synthesized according to Example 32 substituting 3,3,3-trifluoropropan-1-ol in place of 2-(5-fluoropyridin-2-yl)ethan-1-ol in Step B (12 mg, 0.022 mmol, 24% yield). LCMS (MM-ES+APCI, Pos): m/z 548.2 (M+H).

Example 156

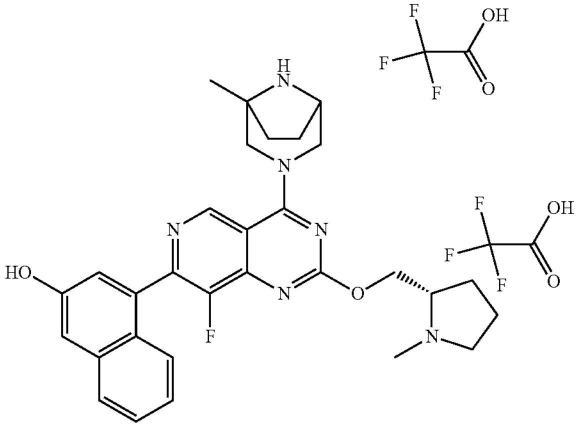

4-(8-fluoro-4-(1-methyl-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol bis(2,2,2-trifluoroacetate)

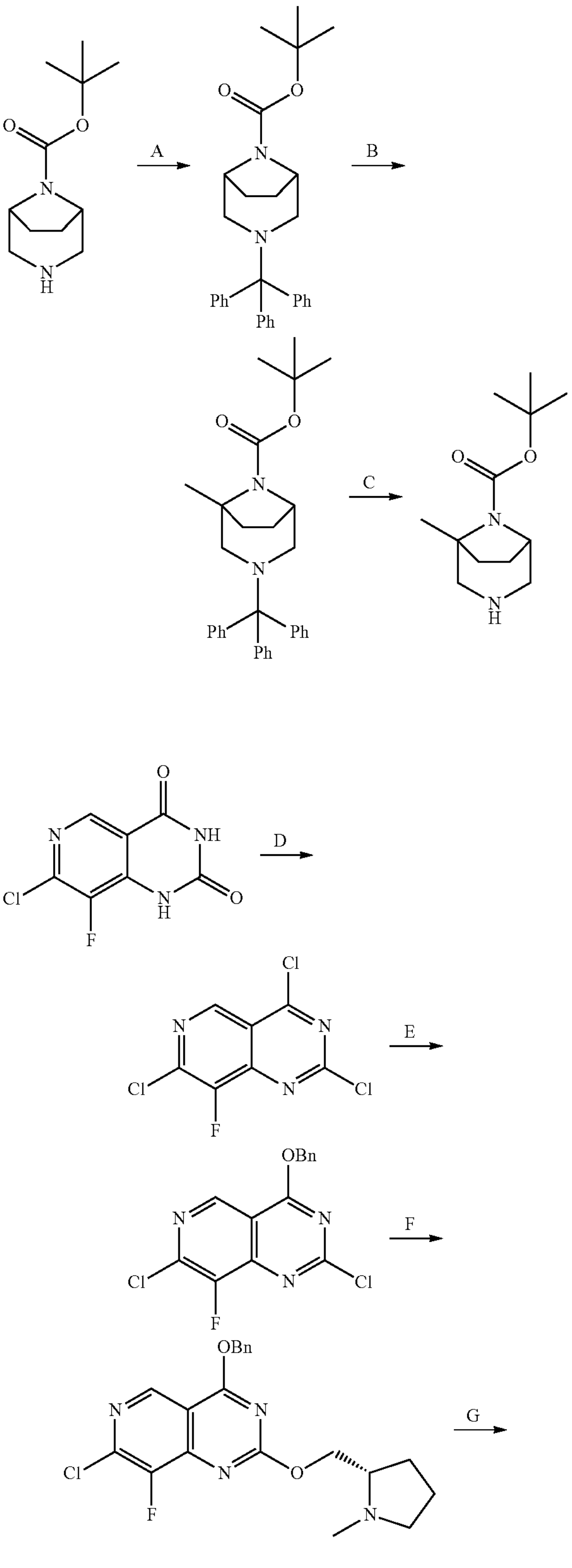

-continued

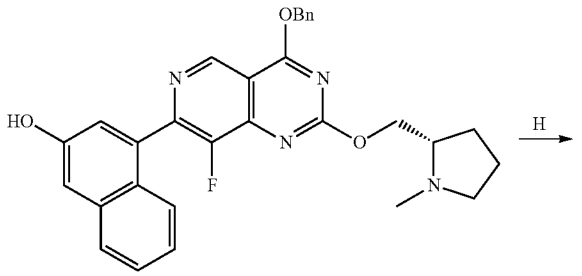

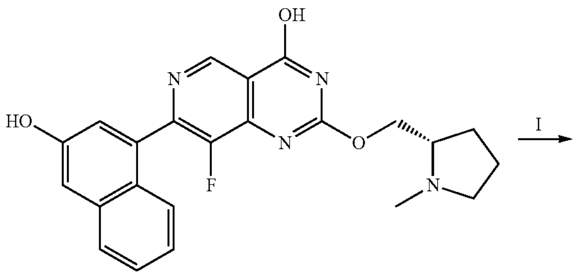

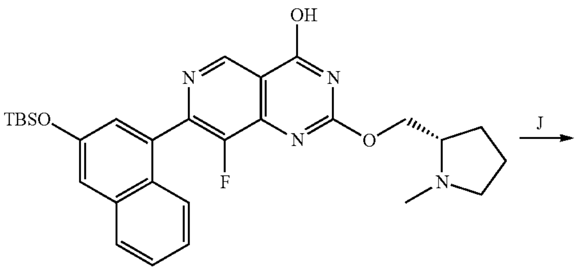

-continued

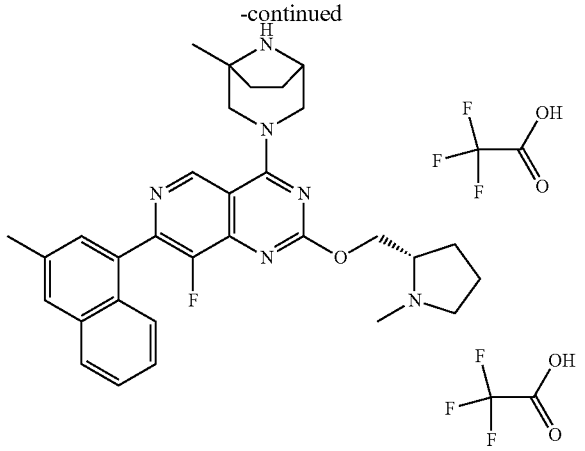

4-(8-fluoro-4-(1-methyl-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol bis(2,2,2-trifluoroacetate. To a solution of the crude tert-butyl 3-(7-(3-((tert-butyldimethylsilyl)oxy)naphthalen-1-yl)-8-fluoro-2-(((S)-1-methylpyrrolidin-2-yl)methoxy)pyrido[4,3-d]pyrimidin-4-yl)-1-methyl-3,8-diazabicyclo[3.2.1]octane-8-carboxylate (17 mg, 0.023 mmol) in DCM (1.0 ml) was added TFA (0.3 ml). The solution was stirred at rt for 3 h. To the mixture was then added TBAF (0.1 ml, 1 M, 0.1 mmol). The resulting mixture was stirred at rt for 10 min and concentrated to dryness. The residue was purified by preparative C18 HPLC (Gilson, 5-95% $CH_3CN/H_2O$ with 0.1% TFA). The desired fractions were combined and concentrated to give the title compound (6 mg, 0.008 mmol, 35% over 2 steps) as a yellow solid. LCMS (MM-ES+APCI, Pos): m/z 529.3 (M+H).

Example 157

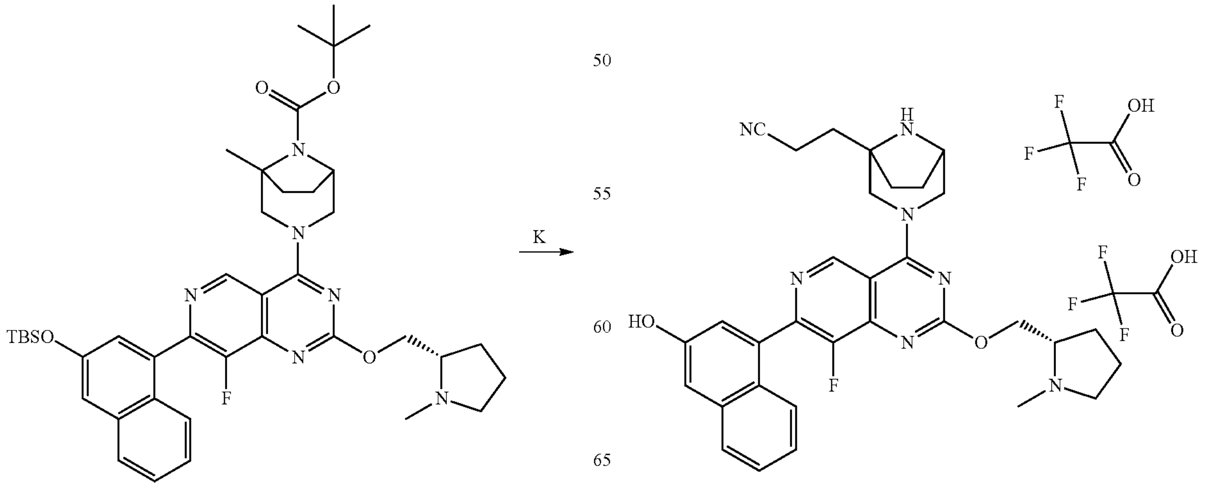

3-(3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octan-1-yl)propanenitrile bis(2,2,2-trifluoroacetate)
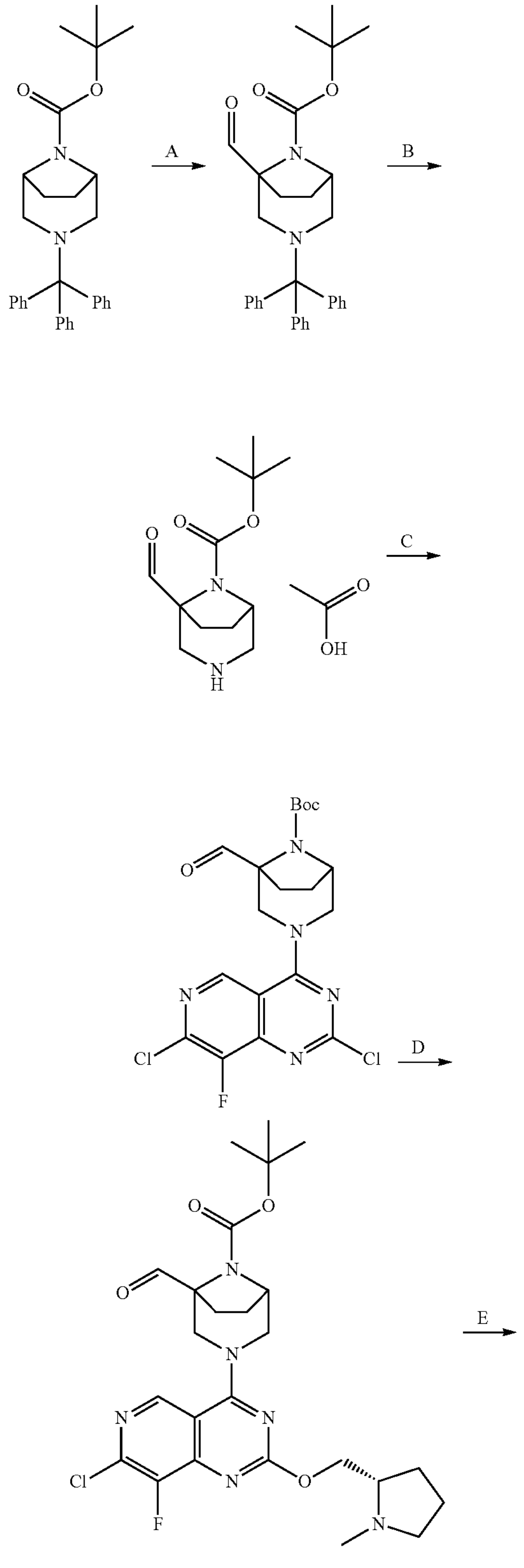
-continued
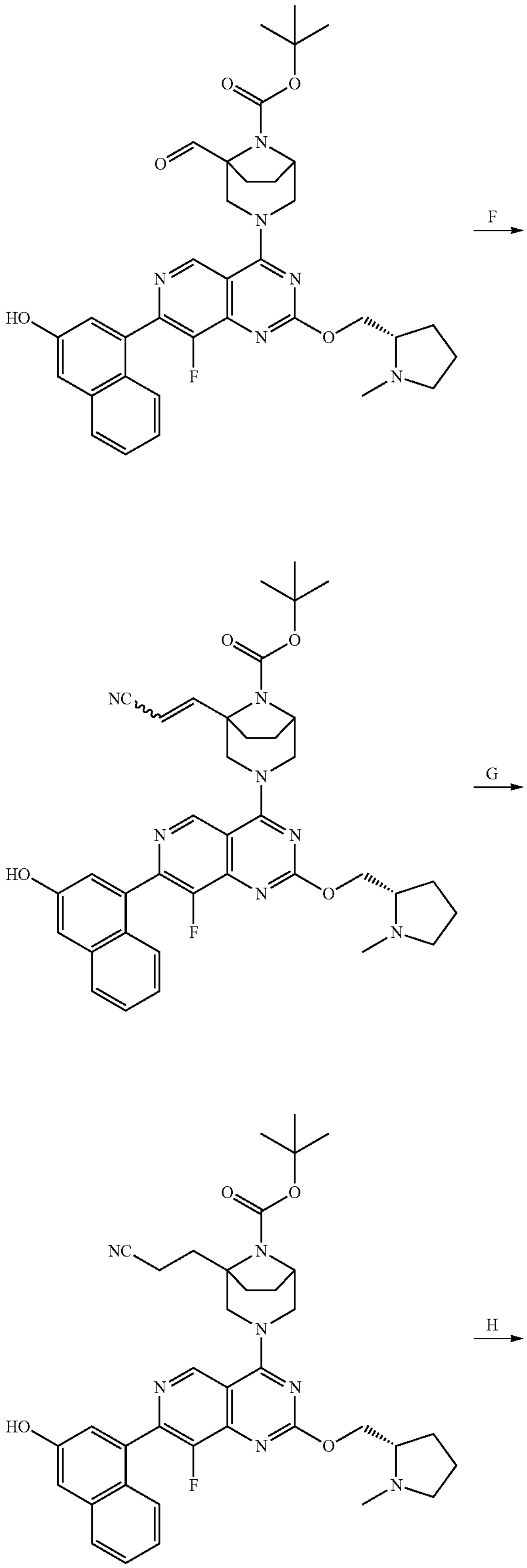

-continued

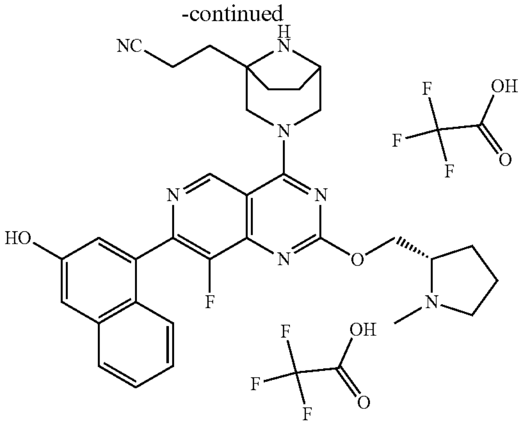

3-(3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octan-1-yl)propanenitrile bis(2,2,2-trifluoroacetate). To a solution of tert-butyl 1-(2-cyanoethyl)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (24 mg, 0.036 mmol) in DCM (1.0 ml) was added TFA (0.3 ml). The mixture was stirred at rt for 2 h and concentrated. The residue was purified by preparative C18 HPLC (Gilson, 0-95% $CH_3CN/H_2O$ with 0.1% TFA). The desired fractions were combined and concentrated to give the title compound (13 mg, 0.016 mmol, 45%) as a yellow solid. LCMS (MM-ES+APCI, Pos): m/z 568.2 (M+H).

Example 158

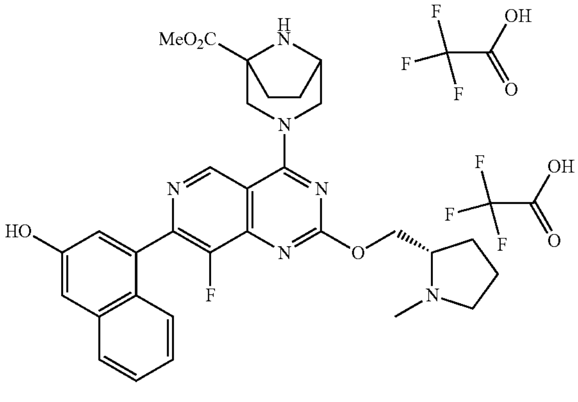

methyl 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carboxylate bis(2,2,2-trifluoroacetate)

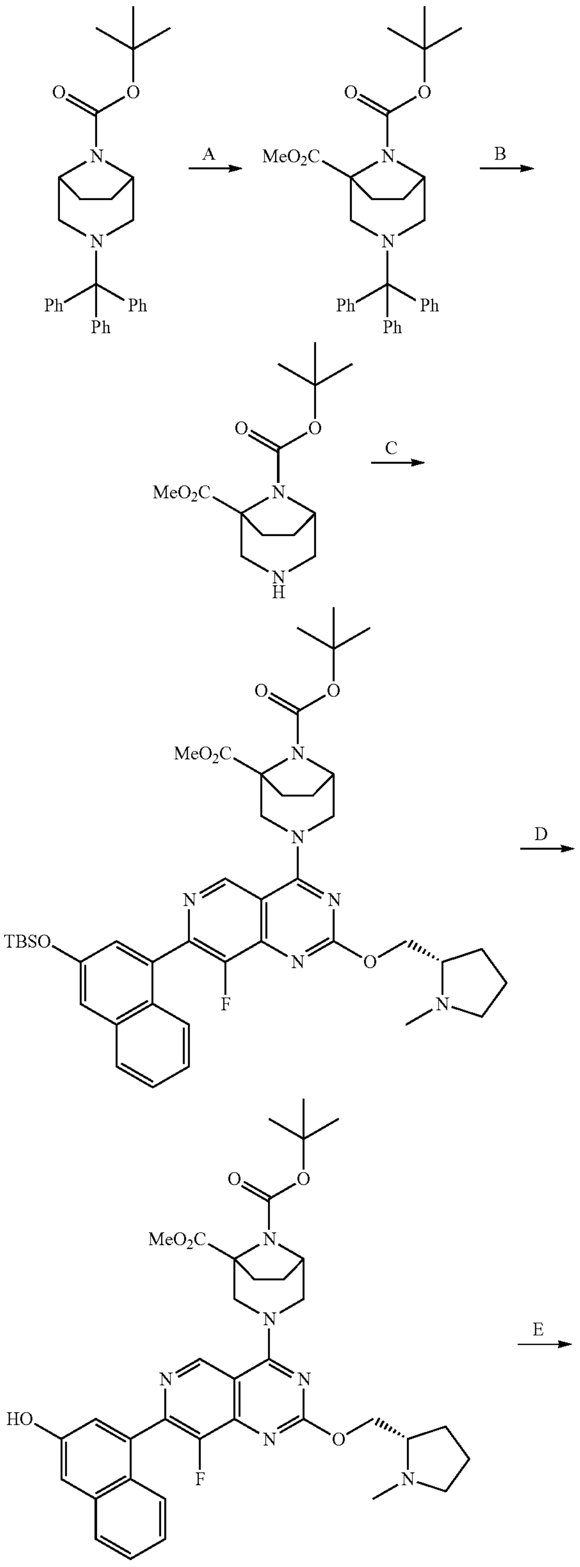

-continued

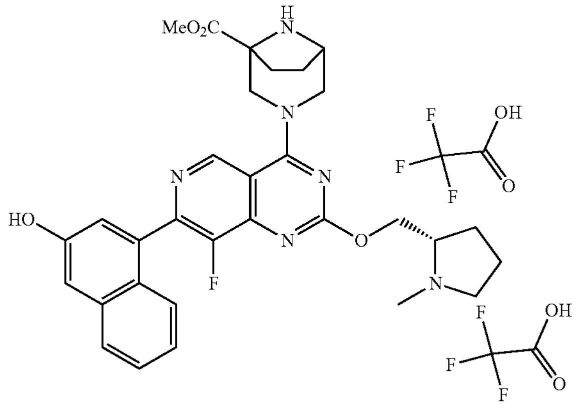

methyl 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carboxylate bis(2,2,2-trifluoroacetate). To a solution of 8-(tert-butyl) 1-methyl 3-(8- fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1,8-dicarboxylate (8.0 mg, 0.012 mmol) in DCM (1.0 ml) was added TFA (0.3 ml). The mixture was stirred at rt for 4 h and concentrated. The residue was purified by preparative C18 HPLC (Gilson, 0-95% $CH_3CN/H_2O$ with 0.1% TFA). The desired fractions were combined and concentrated to give the desired product (8.0 mg, 0.010 mmol, 84%) as a yellow solid. LCMS (MM-ES+APCI, Pos): m/z 573.2 (M+H).

Example 159

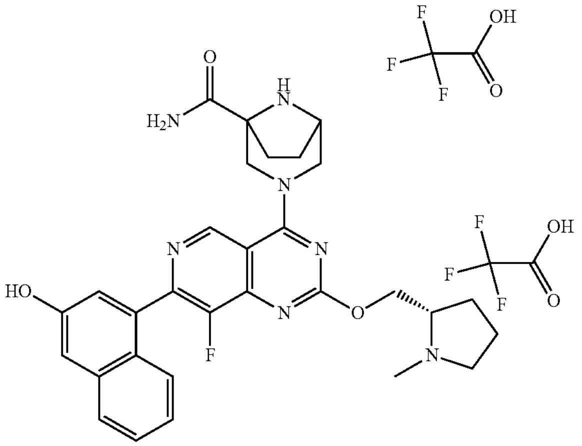

3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carboxamide bis(2,2,2-trifluoroacetate)

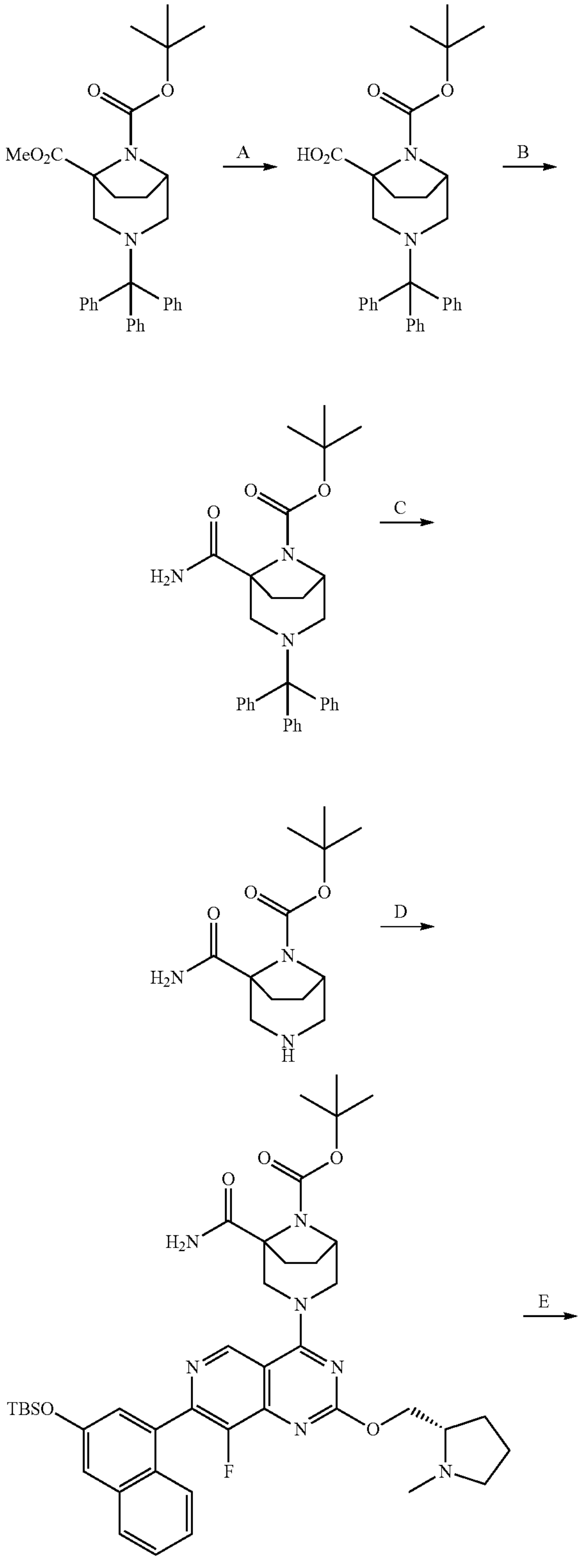

-continued

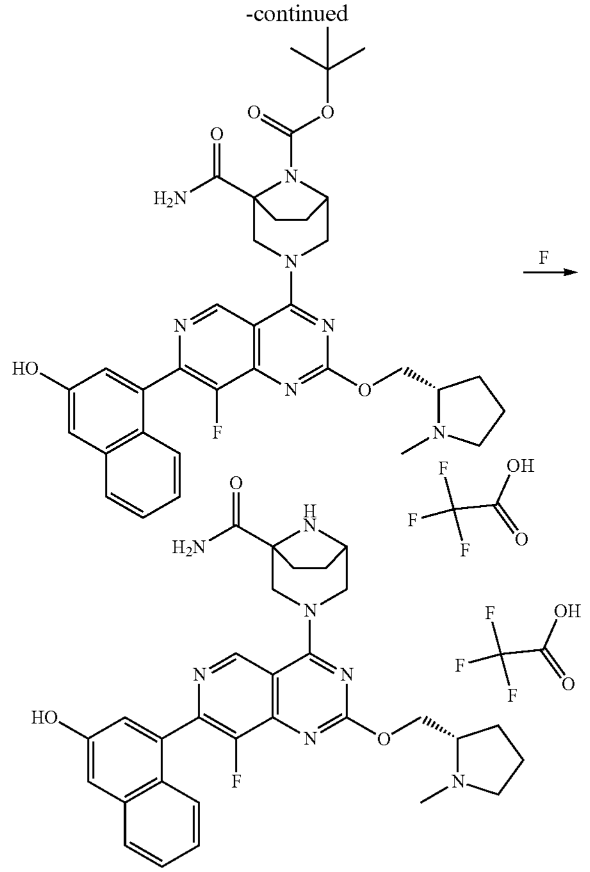

3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carboxamide bis(2,2,2-trifluoroacetate). To a solution of tert-butyl 1-carbamoyl-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (25 mg, 0.038 mmol) in dichloromethane (1.0 ml) was added 2,2,2-trifluoroacetic acid (0.3.0 ml). The mixture was concentrated, and the residue was purified by preparative C18 HPLC (Gilson, 0-95% $CH_3CN/H_2O$ with 0.1% TFA). The desired fractions were combined and lyophilized to give the title compound (5 mg, 0.0064 mmol, 17%) as a hygroscopic yellow solid. LCMS (MM-ES+APCI, Pos): m/z 558.2 (M+H).

Example 160

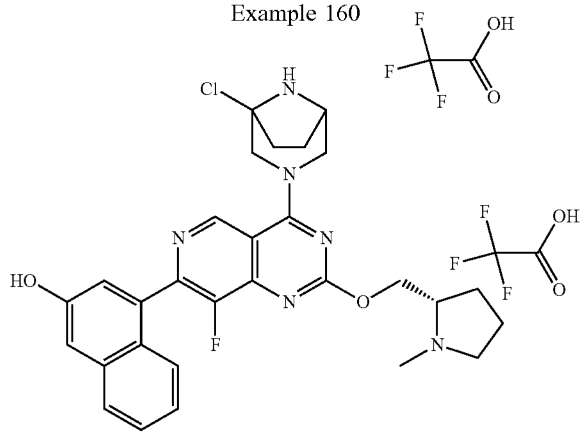

4-(4-(1-chloro-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-2-ol bis(2,2,2-trifluoroacetate)

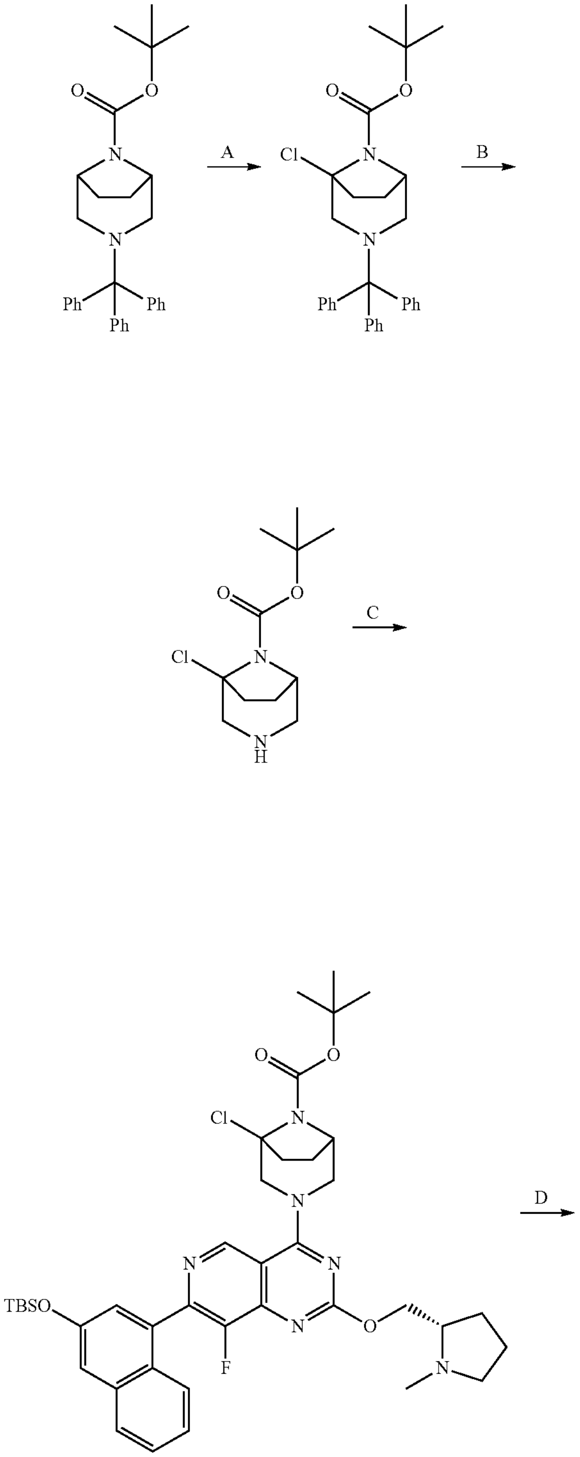

-continued

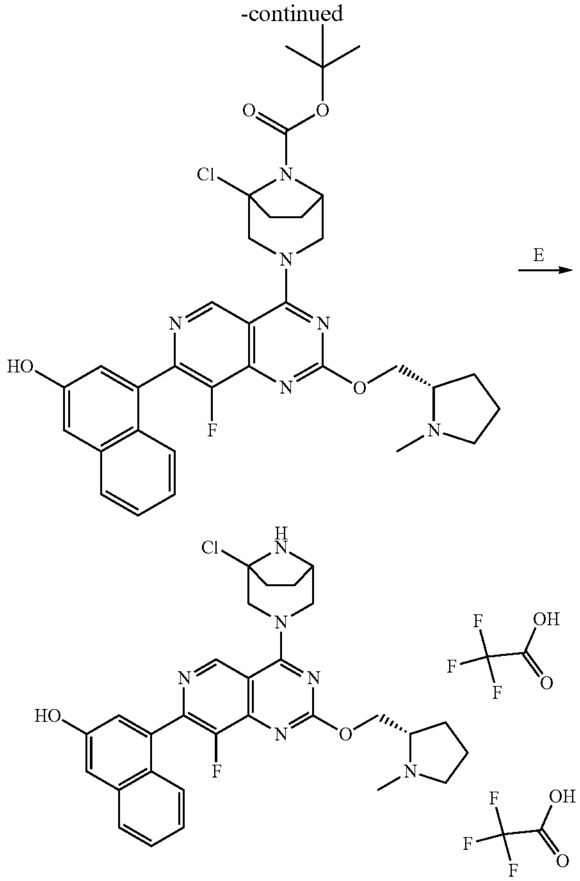

4-(4-(1-chloro-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-2-ol bis(2,2,2-trifluoroacetate). To a solution of tert-butyl 1-chloro-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (26 mg, 0.04 mmol) in DCM (2.0 ml, 0.040 mmol) was added TFA (0.40 ml, 0.040 mmol). The solution was stirred at rt for 1 h and concentrated to dryness. The residue was purified by preparative C18 HPLC (Gilson, 0-95% $CH_3CN/H_2O$ with 0.1% TFA). The desired fractions were combined and concentrated to the title compound (16 mg, 0.020 mmol, 50%) as a yellow solid. LCMS (MM-ES+APCI, Pos): m/z 549.2 (M+H).

Example 161

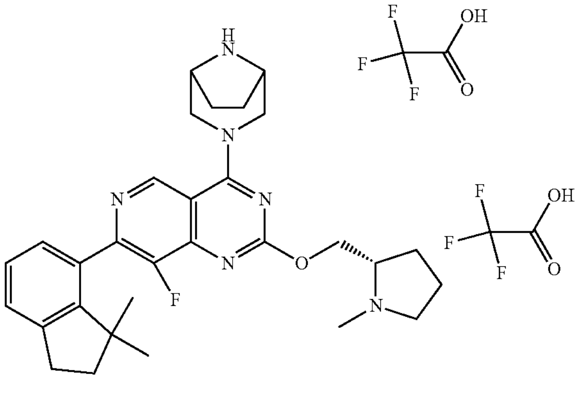

4-((1R,5S)-3,8-diazabicyclo[3.2.1]octan-3-yl)-7-(3,3-dimethyl-2,3-dihydro-1H-inden-4-yl)-8-fluoro-2-(((S)-1-methylpyrrolidin-2-yl)methoxy)pyrido[4,3-d]pyrimidine bis(2,2,2-trifluoroacetate)

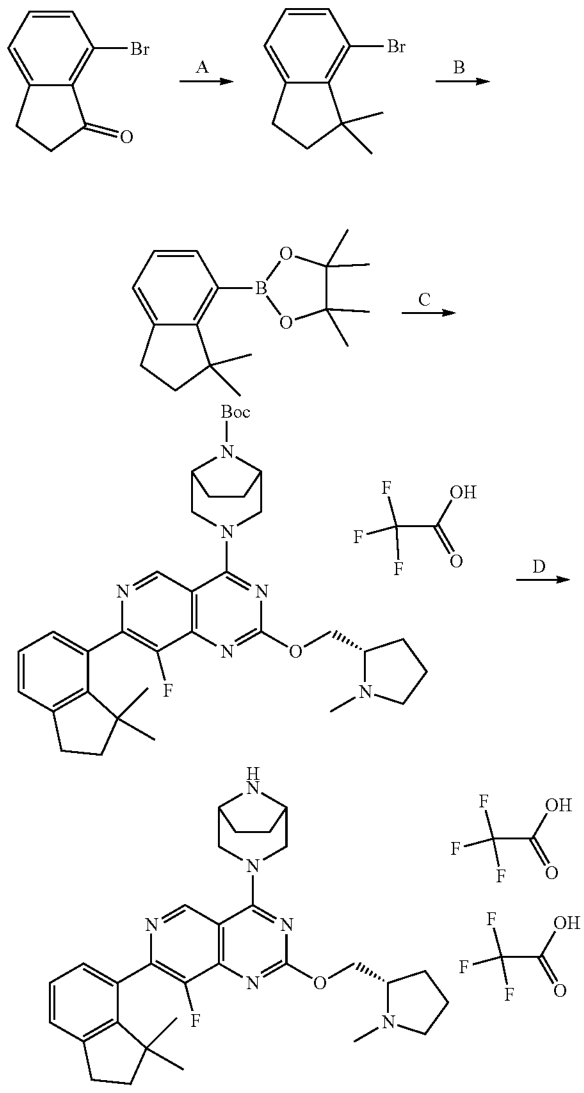

4-((1R,5S)-3,8-diazabicyclo[3.2.1]octan-3-yl)-7-(3,3-dimethyl-2,3-dihydro-1H-inden-4-yl)-8-fluoro-2-(((S)-1-methylpyrrolidin-2-yl)methoxy)pyrido[4,3-d]pyrimidine bis(2,2,2-trifluoroacetate). To a solution of tert-butyl(1R,5S)-3-(7-(3,3- dimethyl-2,3-dihydro-1H-inden-4-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (11 mg, 0.018 mmol) in DCM (1.0 ml) was added TFA (0.30 ml). The solution was stirred at rt for 1 h and was concentrated to dryness. The residue was purified by preparative C18 HPLC (Gilson, 0-95% $CH_3CN/H_2O$ with 0.1% TFA). The desired fractions were combined and concentrated to give the title compound (8 mg, 0.015 mmol, 87%) as a yellow material. LCMS (MM-ES+APCI, Pos): m/z 517.3 (M+H).

Example 162

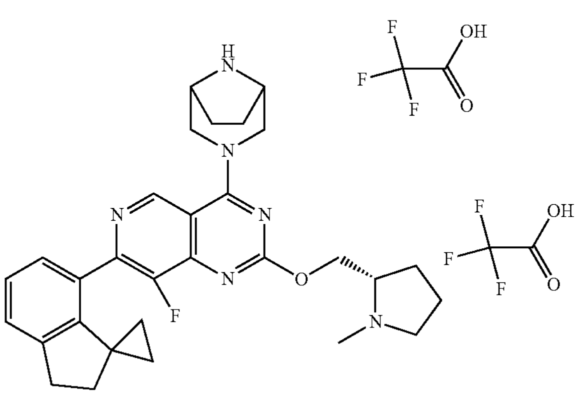

4-((1R,5S)-3,8-diazabicyclo[3.2.1]octan-3-yl)-7-(2',3'-dihydrospiro[cyclopropane-1,1'-inden]-7'-yl)-8-fluoro-2-(((S)-1-methylpyrrolidin-2-yl)methoxy)pyrido[4,3-d]pyrimidine bis(2,2,2-trifluoroacetate)

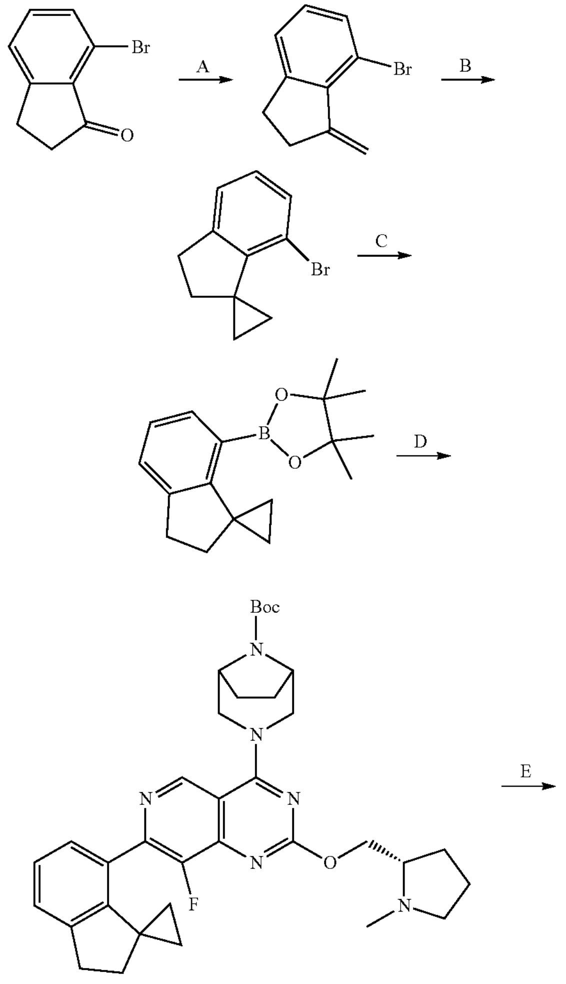

-continued

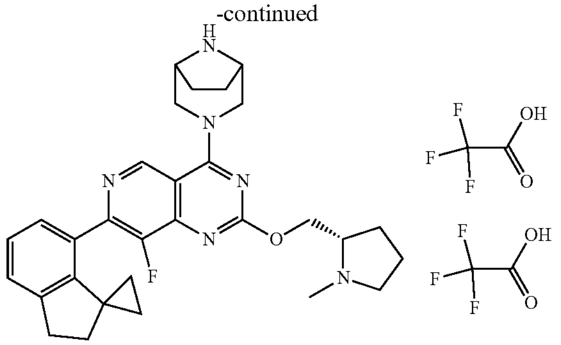

4-((1R,5S)-3,8-diazabicyclo[3.2.1]octan-3-yl)-7-(2',3'-dihydrospiro[cyclopropane-1,1'-inden]-7'-yl)-8-fluoro-2-(((S)-1-methylpyrrolidin-2-yl)methoxy)pyrido[4,3-d]pyrimidine bis(2,2,2-trifluoroacetate). To a solution of tert-butyl(1R,5S)-3-(7-(2',3'-dihydrospiro[cyclopropane-1,1'-inden]-7'-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (12 mg, 0.020 mmol) in DCM (1.2 ml) was added TFA (0.3 ml). The mixture was stirred at rt for 1.5 h and concentrated to dryness. The residue was purified by preparative C18 HPLC (Gilson, 0-95% $CH_3CN$/$H_2O$ with 0.1% TFA). The desired fractions were combined and concentrated to give the title compound (10 mg, 0.013 mmol, 69%) as an off-white solid. LCMS (MM-ES+APCI, Pos): m/z 515.3 (M+H).

Example 163

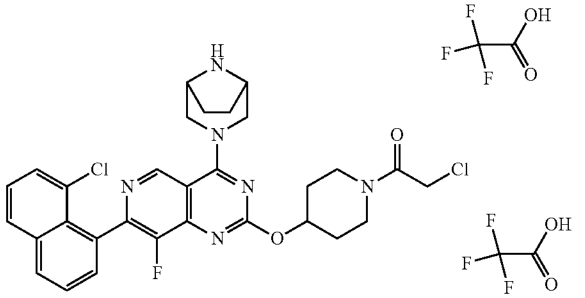 [SMILES: O=C(CCl)N1CCC(Oc2nc(N3CC4CCC(C3)N4)c3cnc(-c4cccc5cccc(Cl)c45)c(F)c3n2)CC1 ; O=C(O)C(F)(F)F ; O=C(O)C(F)(F)F]

1-(4-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) piperidin-1-yl)-2-chloroethan-1-one bis(2,2,2-trifluoroacetate)

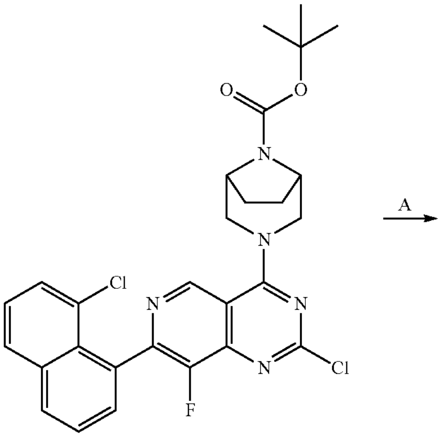

-continued

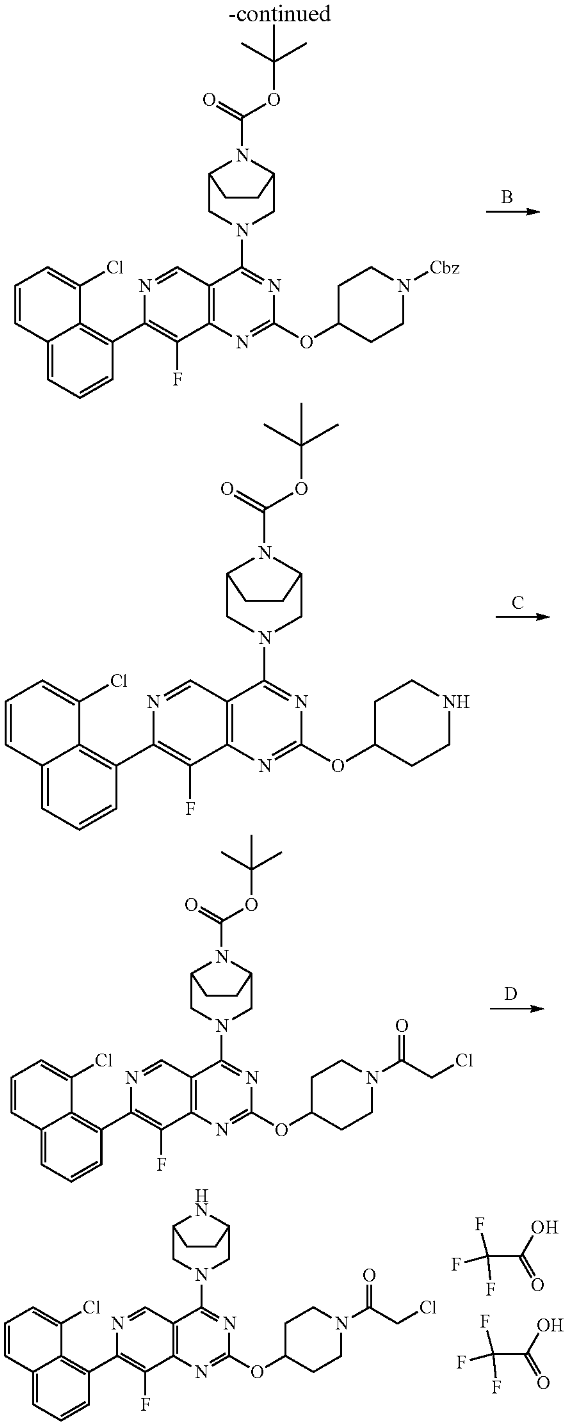

1-(4-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) piperidin-1-yl)-2-chloroethan-1-one bis(2,2,2-trifluoroacetate). To a solution of tert-butyl(1R,5S)-3-(2-((1-(2-chloroacetyl) piperidin-4-yl)oxy)-7-(8-chloronaphthalen-1-yl)-8-fluoropyrido[4,3-d]pyrimidin-4-yl)-3,8-diazabicyclo[3.2.1]octane-8-carboxylate (13 mg, 0.019 mmol) in DCM (1.0 ml) was added TFA (1.0 ml). The mixture was stirred at rt for 1 h and concentrated to dryness. The residue was dissolved in DCM (1 ml), followed by addition of hexanes (1 ml). The resulting suspension was concentrated and dried to give the title compound (15 mg, 0.018 mmol, 97%) as a light-yellow solid. Note: the crude product contained about 2:1 ratio of the desired product and the Des-C1 product. LCMS (MM-ES+APCI, Pos): m/z 595.2 (100%), 597.2 (50%)(M+H, M+3).

Example 164

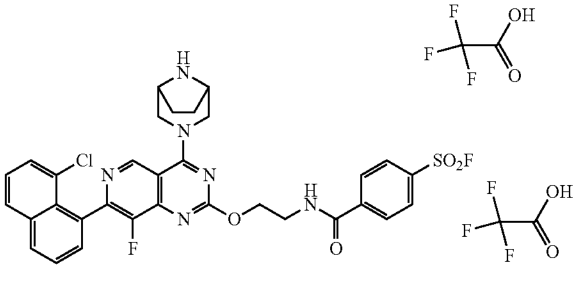 [SMILES: O=C(NCCOc1nc(N2CC3CCC(C2)N3)c2cnc(-c3cccc4cccc(Cl)c34)c(F)c2n1)c1ccc(S(=O)(=O)F)cc1 ; O=C(O)C(F)(F)F ; O=C(O)C(F)(F)F]

4-((2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)carbamoyl)benzenesulfonyl fluoride bis(2,2,2-trifluoroacetate)

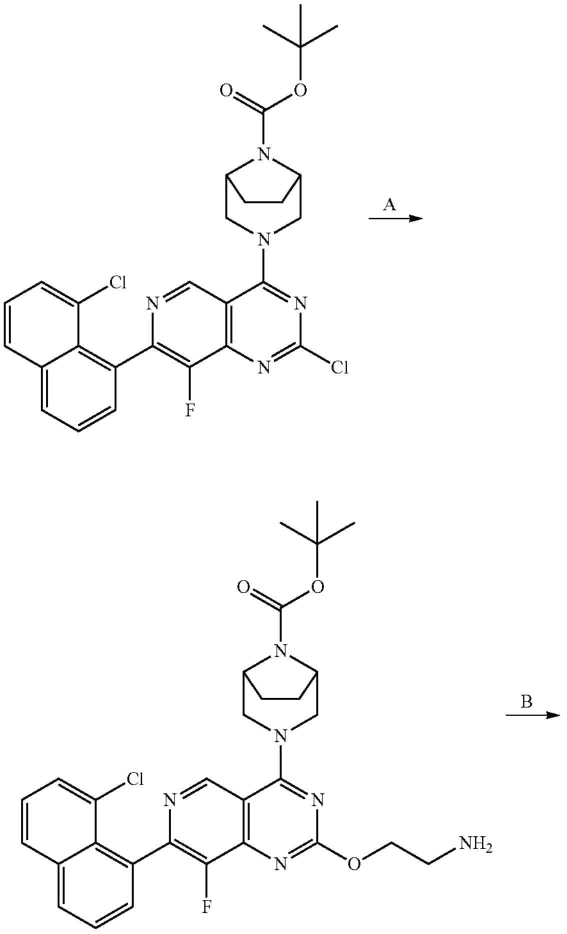

-continued

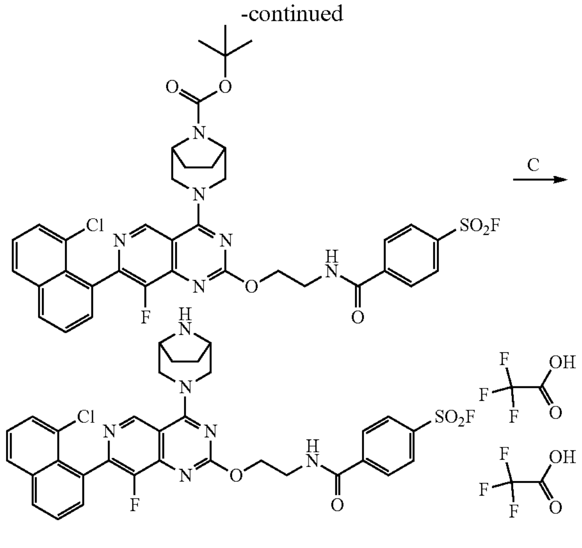

S4-((2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)carbamoyl)benzenesulfonyl fluoride bis(2,2,2-trifluoroacetate). To a solution of tert-butyl(1R,5S)-3-(7-(8- chloronaphthalen-1-yl)-8-fluoro-2-(2-(4-(fluorosulfonyl)benzamido)ethoxy)pyrido[4,3-d]pyrimidin-4-yl)-3,8-diazabicyclo[3.2.1]octane-8-carboxylate (13 mg, 0.017 mmol) in DCM (1.0 ml) was added TFA (1.0 ml). The solution was stirred at rt for 1 h and concentrated to dryness. The residue was dissolved in DCM and transferred into a vial containing hexanes. The suspension was concentrated to dryness to give the crude title compound (16 mg, 0.018 mmol, 105%) as a white solid. LCMS (MM-ES+APCI, Pos): m/z 665.2 (100%), 667.1 (50%)(M+H, M+3).

Example 165

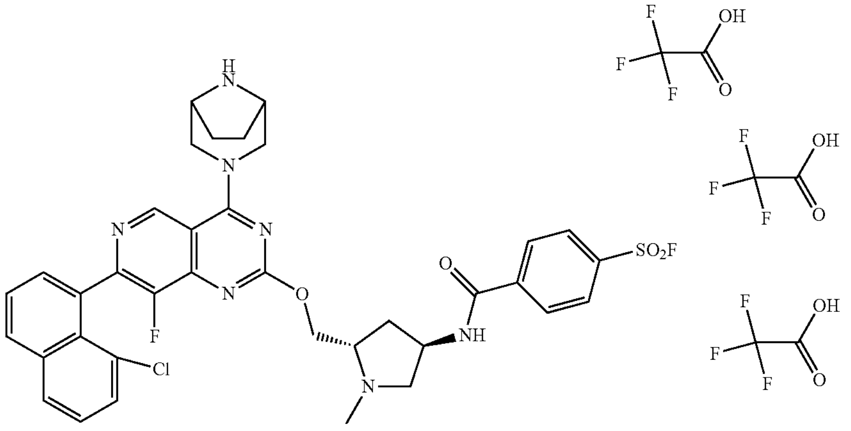

4-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)carbamoyl)benzenesulfonyl fluoride tris(2,2,2-trifluoroacetate)

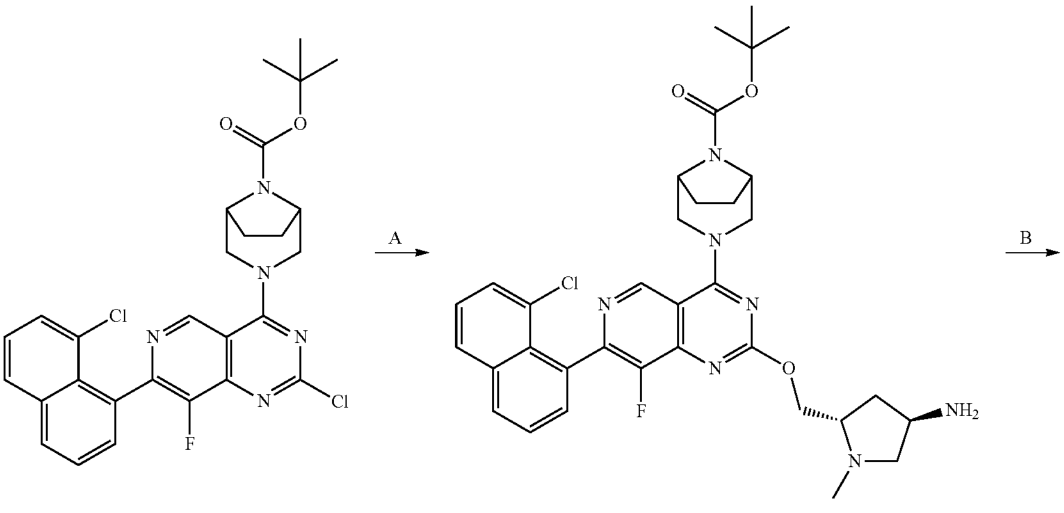

-continued

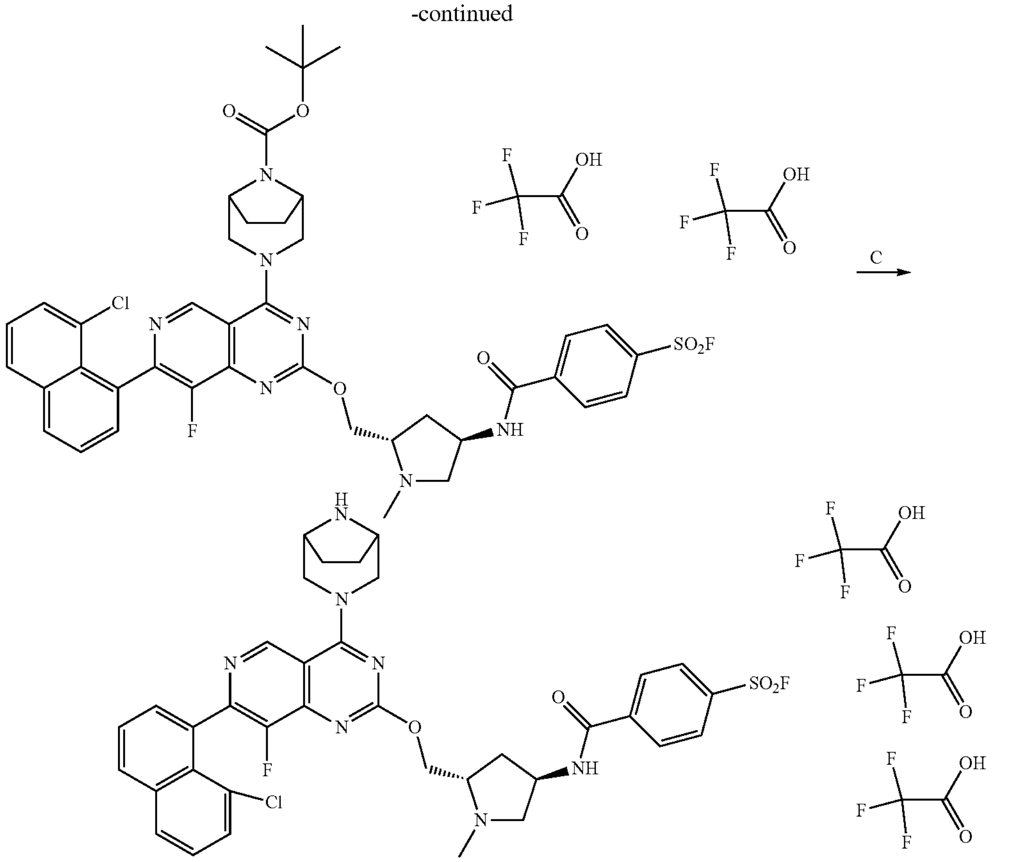

4-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)carbamoyl)benzenesulfonyl fluoride tris(2,2,2-trifluoroacetate). To a solution of tert-butyl(1R,5S)-3-(7-(8-chloronaphthalen-1-yl)-8-fluoro-2-(((2S,4R)-4-(4-(fluorosulfonyl)benzamido)-1-methylpyrrolidin-2-yl)methoxy)pyrido[4,3-d]pyrimidin-4-yl)-3,8-diazabicyclo[3.2.1]octane-8-carboxylate (25 mg, 0.02354 mmol) in dichloromethane (0.95 ml, 0.024 mmol) was added 2,2,2-trifluoroacetic acid (0.47 ml). The solution was stirred at rt for 0.5 h and concentrated to dryness to give the title compound (26 mg, 0.024 mmol, 103% yield) as a white solid. LCMS (MM-ES+APCI, Pos): m/z 734.2 (100%), 736.2 (50%)(M+H, M+3).

Example 166

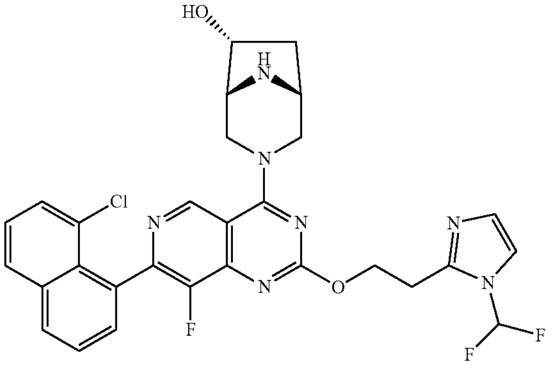 [SMILES: O[C@@H]1C[C@@H]2CN(c3nc(OCCc4nccn4C(F)F)nc4c(F)c(-c5cccc6cccc(Cl)c56)ncc34)C[C@H]1N2]

(1R,5R,6R)-3-(7-(8-chloronaphthalen-1-yl)-2-(2-(1-(difluoromethyl)-1H-imidazol-2-yl)ethoxy)-8-fluoropyrido[4,3-d]pyrimidin-4-yl)-3,8-diazabicyclo[3.2.1]octan-6-ol

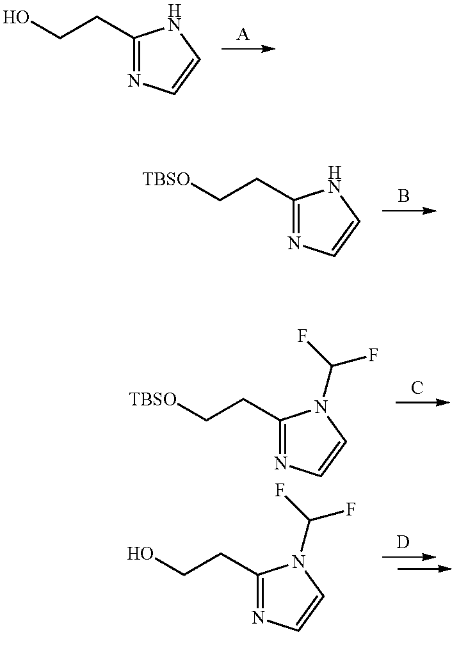

-continued

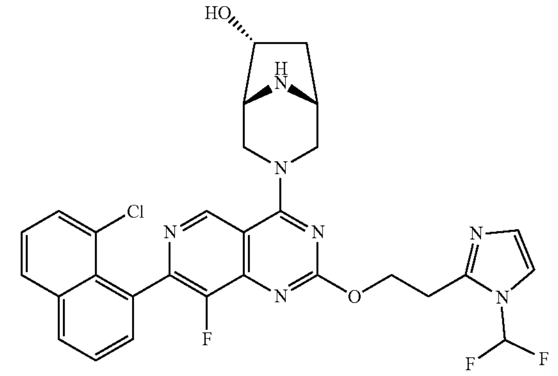

(1R,5R,6R)-3-(7-(8-chloronaphthalen-1-yl)-2-(2-(1-(difluoromethyl)-1H-imidazol-2-yl)ethoxy)-8-fluoropyrido[4,3-d]pyrimidin-4-yl)-3,8-diazabicyclo[3.2.1]octan-6-ol. Synthesized according to Example 32 substituting 2-(1-(difluoromethyl)-1H-imidazol-2-yl)ethan-1-ol in place of 2-(5-fluoropyridin-2-yl)ethan-1-ol in Step B (15 mg, 0.024 mmol, 65% yield). LCMS (MM-ES+APCI, Pos): m/z 596.2 (M+H).

Example 167

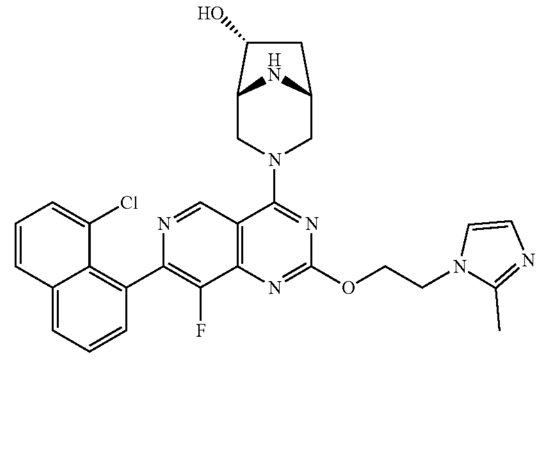 [SMILES: Cc1nccn1CCOc1nc(N2C[C@H]3C[C@@H](O)[C@@H](C2)N3)c2cnc(-c3cccc4cccc(Cl)c34)c(F)c2n1]

(1R,5R,6R)-3-(7-(8-chloronaphthalen-1-yl)-8-fluoro-2-(2-(2-methyl-1H-imidazol-1-yl)ethoxy)pyrido[4,3-d]pyrimidin-4-yl)-3,8-diazabicyclo[3.2.1]octan-6-ol Synthesized according to Example 32 substituting 2-(1-methyl-1H-imidazol-2-yl)ethan-1-ol in place of 2-(5-fluoropyridin-2-yl)ethan-1-ol in Step B (10 mg, 0.017 mmol, 53% yield). LCMS (MM-ES+APCI, Pos): m/z 560.1 (M+).

Example 168

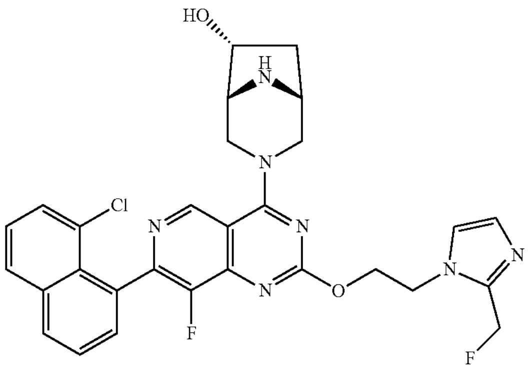 [SMILES: O[C@@H]1C[C@@H]2CN(c3nc(OCCn4ccnc4CF)nc4c(F)c(-c5cccc6cccc(Cl)c56)ncc34)C[C@H]1N2]

(1R,5R,6R)-3-(7-(8-chloronaphthalen-1-yl)-8-fluoro-2-(2-(2-(fluoromethyl)-1H-imidazol-1-yl)ethoxy)pyrido[4,3-d]pyrimidin-4-yl)-3,8-diazabicyclo[3.2.1]octan-6-ol

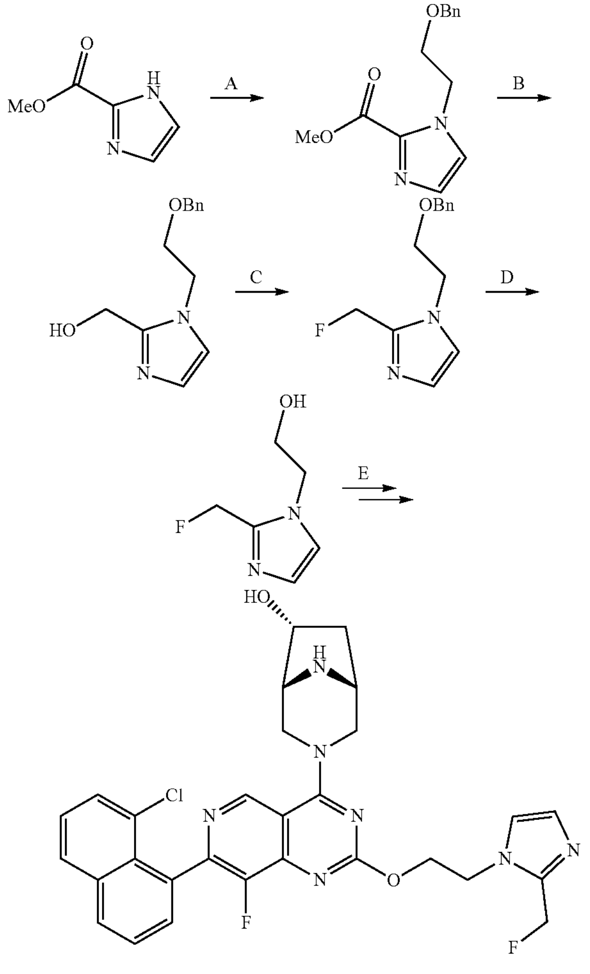

(1R,5R,6R)-3-(7-(8-chloronaphthalen-1-yl)-8-fluoro-2-(2-(2-(fluoromethyl)-1H-imidazol-1-yl)ethoxy)pyrido[4,3-d]pyrimidin-4-yl)-3,8-diazabicyclo[3.2.1]octan-6-ol. Synthesized according to Example 32 substituting 2-(2-(fluoromethyl)-1H-imidazol-1-yl)ethan-1-ol in place of 2-(5-fluoropyridin-2-yl)ethan-1-ol in Step B (10 mg, 0.016 mmol, 37% yield). LCMS (MM-ES+APCI, Pos): m/z 578.2 (M+H).

Example 169

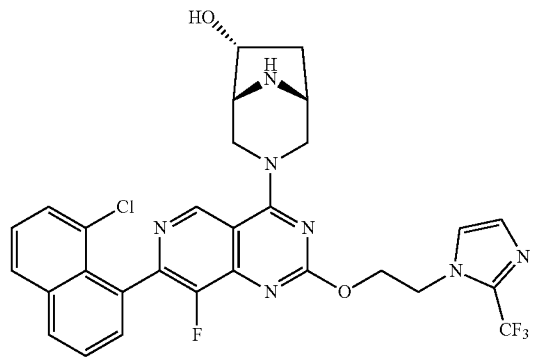 [SMILES: O[C@@H]1C[C@@H]2CN(c3nc(OCCn4ccnc4C(F)(F)F)nc4c(F)c(-c5cccc6cccc(Cl)c56)ncc34)C[C@H]1N2]

(1R,5R,6R)-3-(7-(8-chloronaphthalen-1-yl)-8-fluoro-2-(2-(2-(trifluoromethyl)-1H-imidazol-1-yl)ethoxy)pyrido[4,3-d]pyrimidin-4-yl)-3,8-diazabicyclo[3.2.1]octan-6-ol

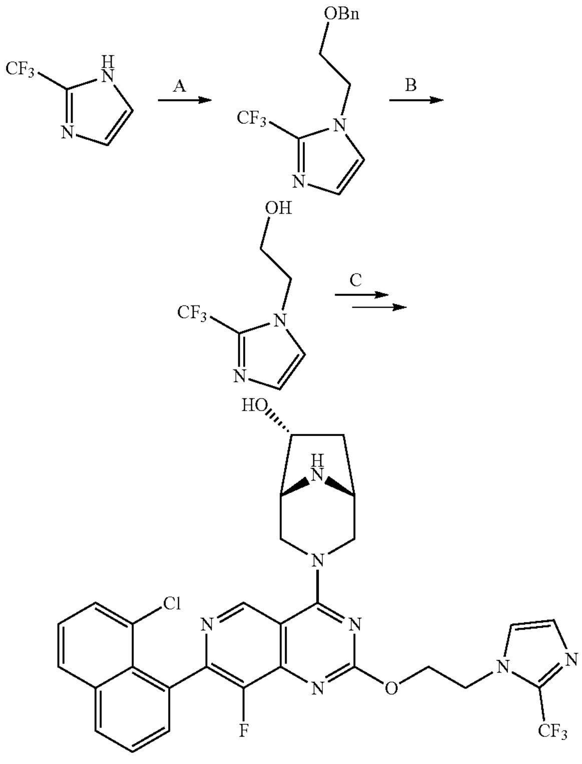

(1R,5R,6R)-3-(7-(8-chloronaphthalen-1-yl)-8-fluoro-2-(2-(2-(trifluoromethyl)-1H-imidazol-1-yl)ethoxy)pyrido[4,3-d]pyrimidin-4-yl)-3,8-diazabicyclo[3.2.1]octan-6-ol. Synthesized according to Example 32 substituting 2-(2-

(trifluoromethyl)-1H-imidazol-1-yl)ethan-1-ol in place of 2-(5-fluoropyridin-2-yl)ethan-1-ol in Step B (15 mg, 0.023 mmol, 77% yield). LCMS (MM-ES+APCI, Pos): m/z 614.2 (M+H).

Example 170

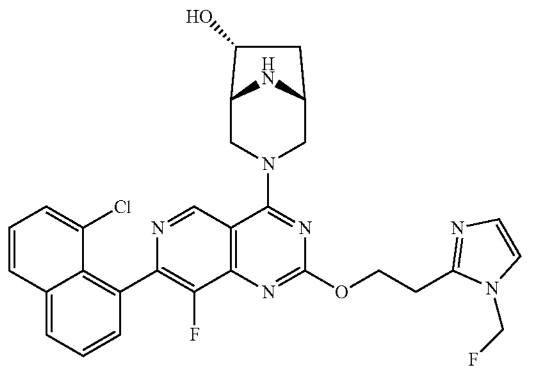 [SMILES: O[C@@H]1C[C@@H]2CN(c3nc(OCCc4nccn4CF)nc4c(F)c(-c5cccc6cccc(Cl)c56)ncc34)C[C@H]1N2]

(1R,5R,6R)-3-(7-(8-chloronaphthalen-1-yl)-8-fluoro-2-(2-(1-(fluoromethyl)-1H-imidazol-2-yl)ethoxy)pyrido[4,3-d]pyrimidin-4-yl)-3,8-diazabicyclo[3.2.1]octan-6-ol

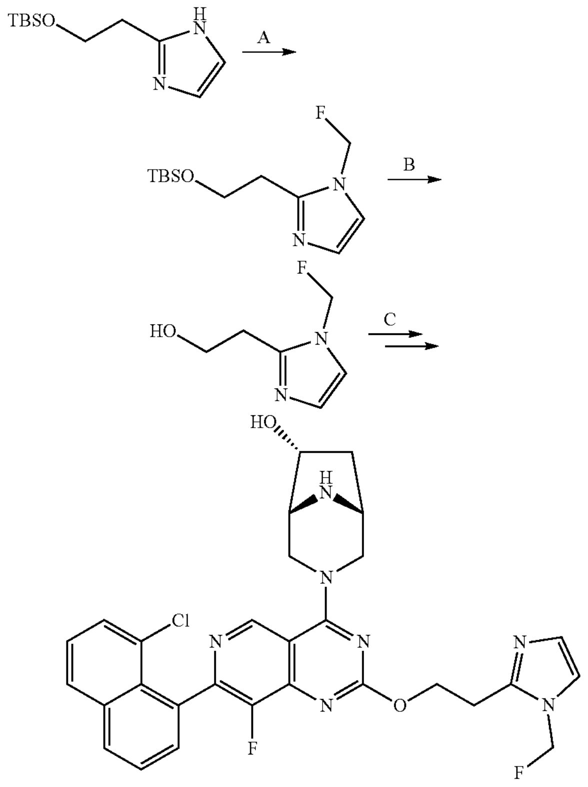

(1R,5R,6R)-3-(7-(8-chloronaphthalen-1-yl)-8-fluoro-2-(2-(1-(fluoromethyl)-1H-imidazol-2-yl)ethoxy)pyrido[4,3-d]pyrimidin-4-yl)-3,8-diazabicyclo[3.2.1]octan-6-ol. Synthesized according to Example 32 substituting 2-(1-

(fluoromethyl)-1H-imidazol-2-yl)ethan-1-ol in place of 2-(5-fluoropyridin-2-yl)ethan-1-ol in Step B (6 mg, 0.01 mmol, 33% yield). LCMS (MM-ES+APCI, Pos): m/z 578.2 (M+H).

Example 171

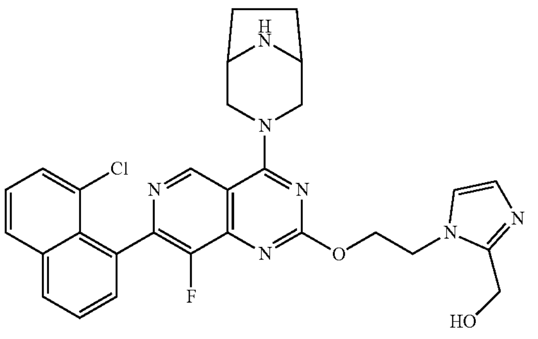 [SMILES: OCc1nccn1CCOc1nc(N2CC3CCC(C2)N3)c2cnc(-c3cccc4cccc(Cl)c34)c(F)c2n1]

(1-(2-((4-(3,8-diazabicyclo[3.2.1]octan-3-yl)-7-(8-chloronaphthalen-1-yl)-8-fluoropyrido[4,3-d]pyrimidin-2-yl)oxy)ethyl)-1H-imidazol-2-yl)methanol

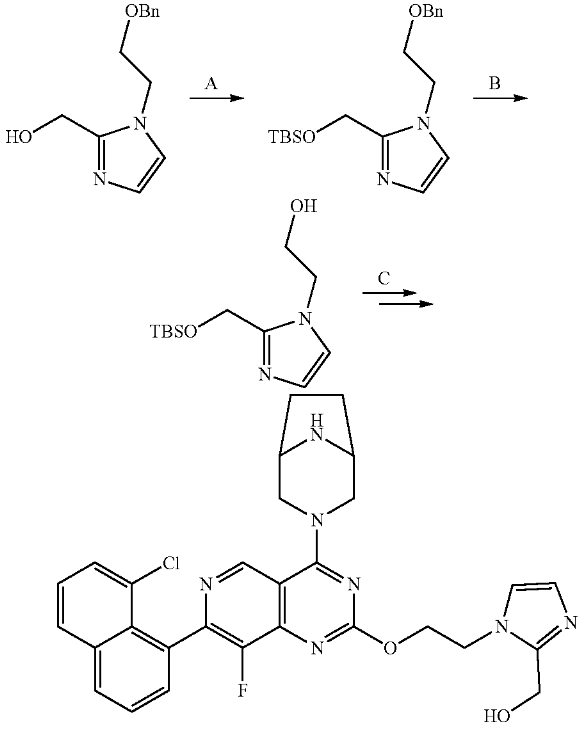

(1-(2-((4-(3,8-diazabicyclo[3.2.1]octan-3-yl)-7-(8-chloronaphthalen-1-yl)-8-fluoropyrido[4,3-d]pyrimidin-2-yl)oxy)ethyl)-1H-imidazol-2-yl)methanol. Synthesized according to Example 32 substituting tert-butyl(1R,5S)-3,8-diazabicyclo[3.2.1]octane-8-carboxylate in place of 6-((tert-butyldimethylsilyl)oxy)-3,8-diazabicyclo[3.2.1]octane-8-carboxylate in step A and 2-(2-(((tert-butyldimethylsilyl)oxy)methyl)-1H-imidazol-1-yl)ethan-1-ol in place of 2-(5-fluoropyridin-2-yl)ethan-1-ol in Step B (22 mg, 0.037 mmol, 58% yield). LCMS (MM-ES+APCI, Pos): m/z 560.2 (M+H).

Example 172

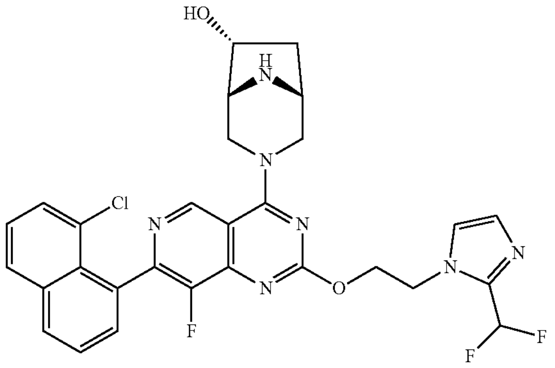 [SMILES: O[C@@H]1C[C@@H]2CN(c3nc(OCCn4ccnc4C(F)F)nc4c(F)c(-c5cccc6cccc(Cl)c56)ncc34)C[C@H]1N2]

(1R,5R,6R)-3-(7-(8-chloronaphthalen-1-yl)-2-(2-(2-(difluoromethyl)-1H-imidazol-1-yl)ethoxy)-8-fluoropyrido[4,3-d]pyrimidin-4-yl)-3,8-diazabicyclo[3.2.1]octan-6-ol

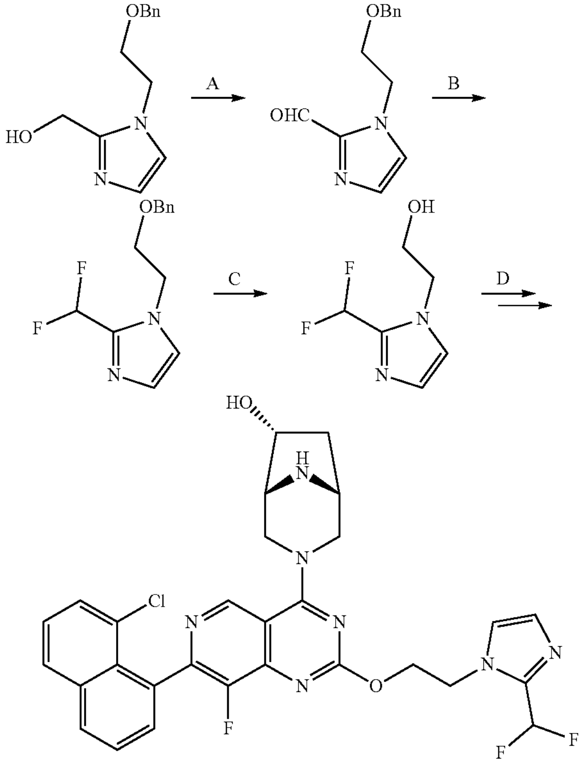

(1R,5R,6R)-3-(7-(8-chloronaphthalen-1-yl)-2-(2-(2-(difluoromethyl)-1H-imidazol-1-yl)ethoxy)-8-fluoropyrido[4,3-d]pyrimidin-4-yl)-3,8-diazabicyclo[3.2.1]octan-6-ol. Synthesized according to Example 32 substituting 2-(2-(difluoromethyl)-1H-imidazol-1-yl)ethan-1-ol in place of 2-(5-fluoropyridin-2-yl)ethan-1-ol in Step B (15 mg, 0.024 mmol, 64% yield). LCMS (MM-ES+APCI, Pos): m/z 596.2 (M+H).

Example 173

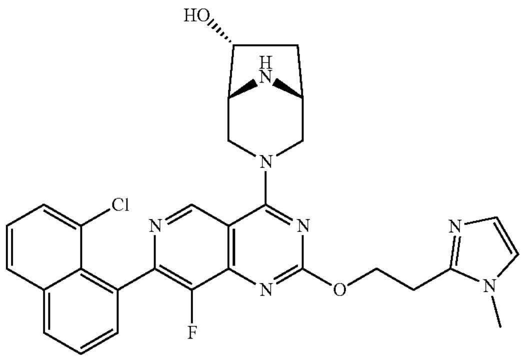 [SMILES: Cn1ccnc1CCOc1nc(N2C[C@H]3C[C@@H](O)[C@@H](C2)N3)c2cnc(-c3cccc4cccc(Cl)c34)c(F)c2n1]

(1R,5R,6R)-3-(7-(8-chloronaphthalen-1-yl)-8-fluoro-2-(2-(1-methyl-1H-imidazol-2-yl)ethoxy)pyrido[4,3-d]pyrimidin-4-yl)-3,8-diazabicyclo[3.2.1]octan-6-ol Synthesized according to Example 32 substituting 2-(1-methyl-1H-imidazol-2-yl)ethan-1-ol in place of 2-(5-fluoropyridin-2-yl)ethan-1-ol in Step B (15 mg, 0.024 mmol, 64% yield). LCMS (MM-ES+APCI, Pos): m/z 560.1 (M+H).

Example 174

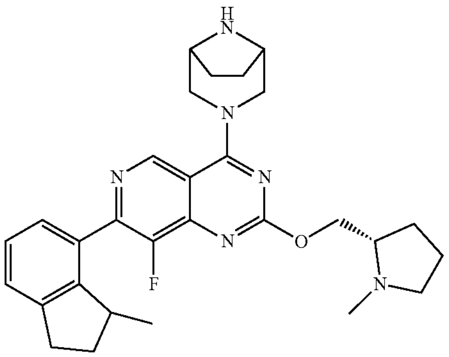 [SMILES: CC1CCc2cccc(-c3ncc4c(N5CC6CCC(C5)N6)nc(OC[C@@H]5CCCN5C)nc4c3F)c21]

4-((1R,5S)-3,8-diazabicyclo[3.2.1]octan-3-yl)-8-fluoro-7-(3-methyl-2,3-dihydro-1H-inden-4-yl)-2-(((S)-1-methylpyrrolidin-2-yl)methoxy)pyrido[4,3-d]pyrimidine

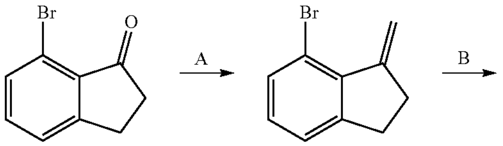

-continued

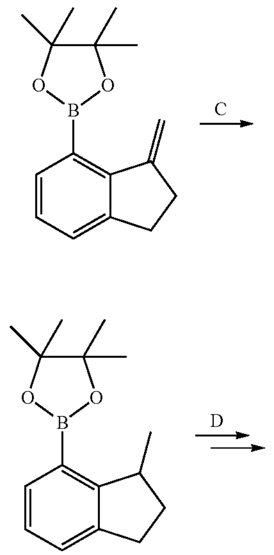

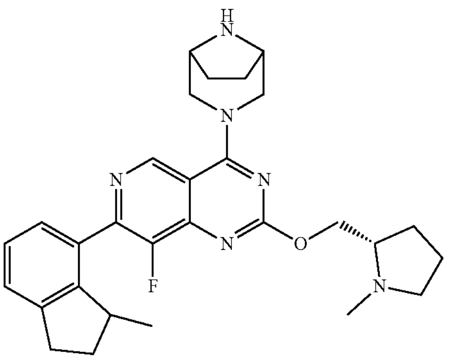

Synthesized according to Example 2, Steps C—I substituting 4,4,5,5-tetramethyl-2-(3-methyl-2,3-dihydro-1H-inden-4-yl)-1,3,2-dioxaborolane in place of 4-(4,4,5,5-tetramethyl-1,3,2-dioxaborolan-2-yl)naphthalen-2-yl pivalate. LCMS (MM-ES+APCI, Pos): m/z 503.3 (M+H).

Example 175

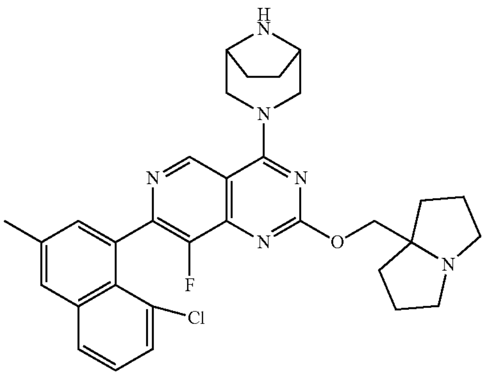 [SMILES: Cc1cc(-c2ncc3c(N4CC5CCC(C4)N5)nc(OCC45CCCN4CCC5)nc3c2F)c2c(Cl)cccc2c1]

4-((1R,5S)-3,8-diazabicyclo[3.2.1]octan-3-yl)-7-(8-chloro-3-methylnaphthalen-1-yl)-8-fluoro-2-((hexahydro-1H-pyrrolizin-7a-yl)methoxy)pyrido[4,3-d]pyrimidine
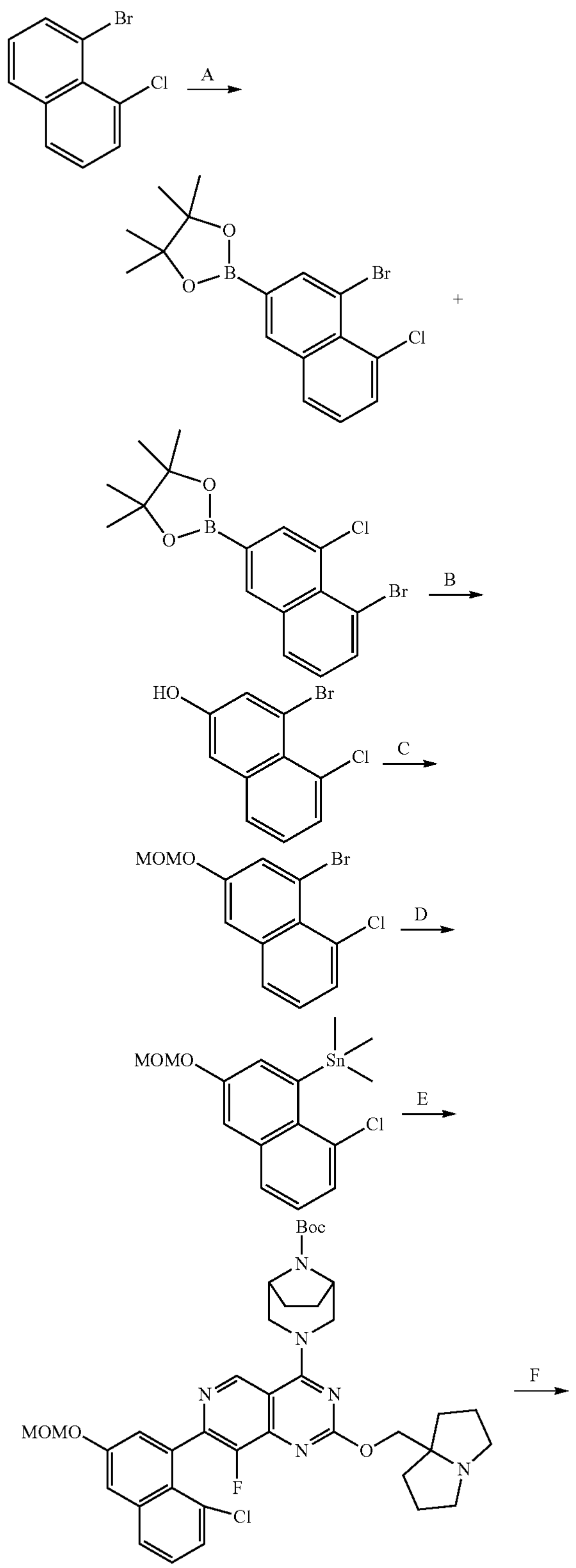
-continued
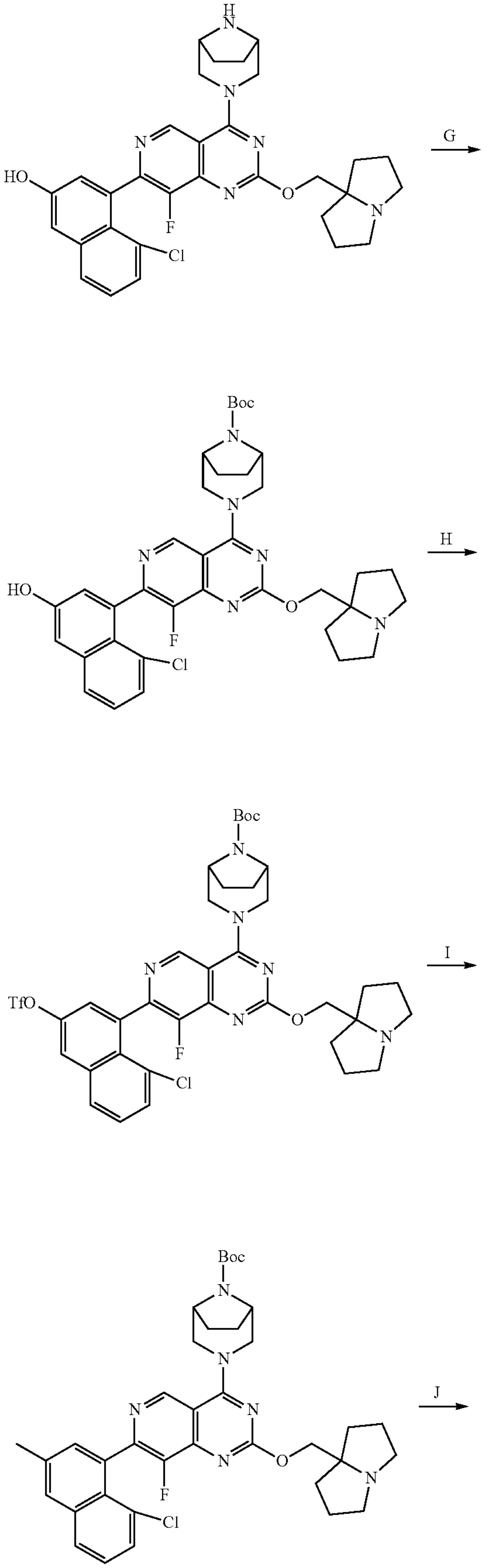

-continued

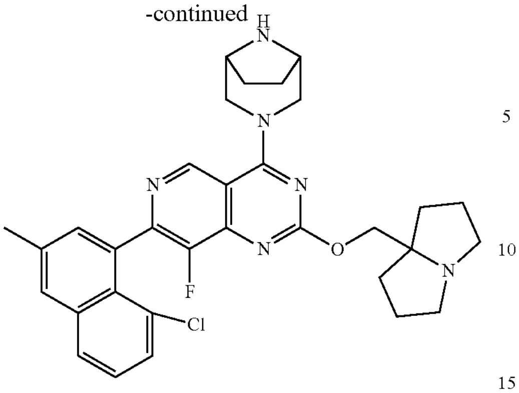

4-((1R,5S)-3,8-diazabicyclo[3.2.1]octan-3-yl)-7-(8-chloro-3-methylnaphthalen-1-yl)-8-fluoro-2-((hexahydro-1H-pyrrolizin-7a-yl)methoxy)pyrido[4,3-d]pyrimidine (4 mg, 23% yield). White solid. $^1H$ NMR (400 MHz, chloroform-d) δ=9.00 (s, 1H), 7.81-7.73 (m, 2H), 7.49-7.33 (m, 3H), 4.64 (d, J=12.4 Hz, 1H), 4.56 (d, J=11.2 Hz, 1H), 4.29 (br s, 2H), 3.72-3.57 (m, 4H), 3.25 (br s, 2H), 2.77-2.64 (m, 2H), 2.54 (s, 3H), 2.23-2.12 (m, 2H), 2.02-1.87 (m, 7H), 1.78-1.67 (m, 3H). LCMS [ESI, M+1]: 573.

Example 176

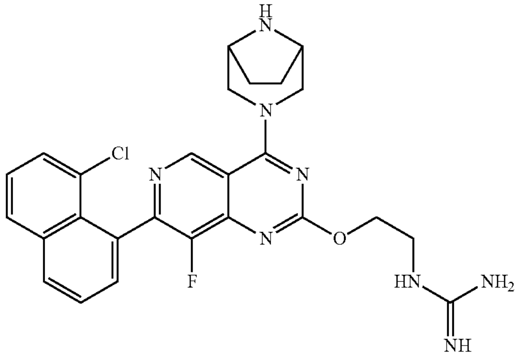 [SMILES: N=C(N)NCCOc1nc(N2CC3CCC(C2)N3)c2cnc(-c3cccc4cccc(Cl)c34)c(F)c2n1]

1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]guanidine

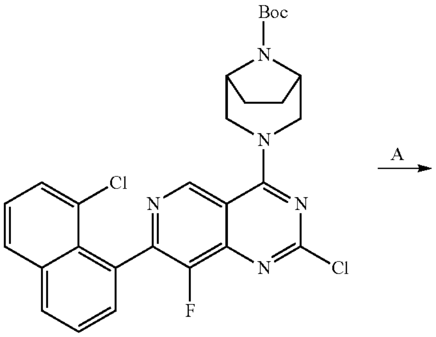

-continued

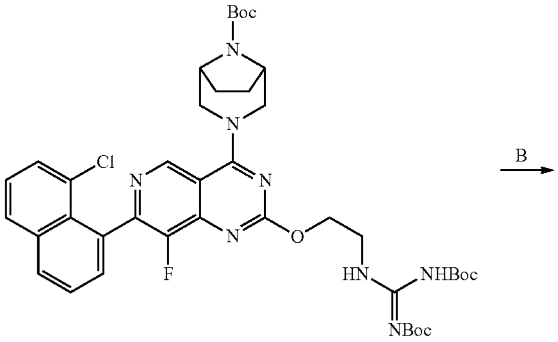

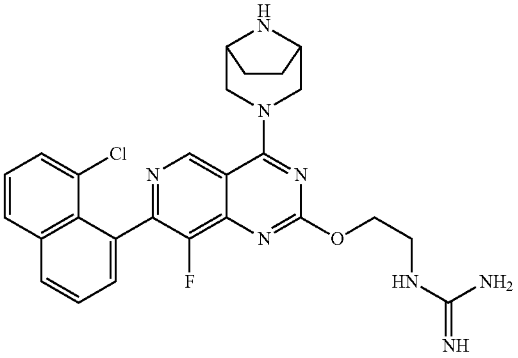

1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]guanidine (8.72 mg, 25% yield, formic acid) as a white solid; $^1H$ NMR (400 MHz, methanol-$d_4$) δ=9.10 (s, 1H), 8.49 (br s, 1H), 8.17-8.12 (m, 1H), 8.04-8.00 (m, 1H), 7.72-7.67 (m, 1H), 7.63-7.57 (m, 2H), 7.55-7.49 (m, 1H), 4.78 (br d, J=13.6 Hz, 2H), 4.62 (t, J=5.2 Hz, 2H), 4.15 (br s, 2H), 3.93 (br d, J=13.2 Hz, 2H), 3.66 (t, J=5.2 Hz, 2H), 2.13-2.00 (m, 4H); LCMS (ESI, M/2+1, M+1): 261, 521.

Example 177

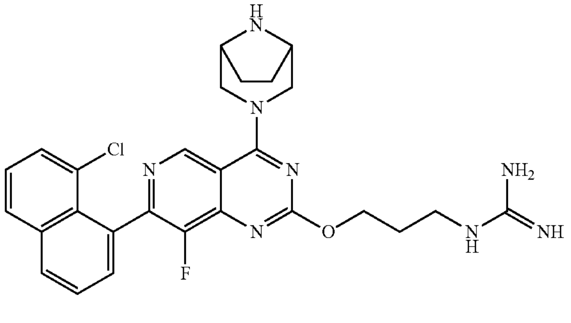 [SMILES: N=C(N)NCCCOc1nc(N2CC3CCC(C2)N3)c2cnc(-c3cccc4cccc(Cl)c34)c(F)c2n1]

1-[3-[7-(8-chloro-1-naphthyl)-4-(3,8-diazabicyclo[3.2.1]octan-3-yl)-8-fluoro-pyrido[4,3-d]pyrimidin-2-yl]oxypropyl]guanidine

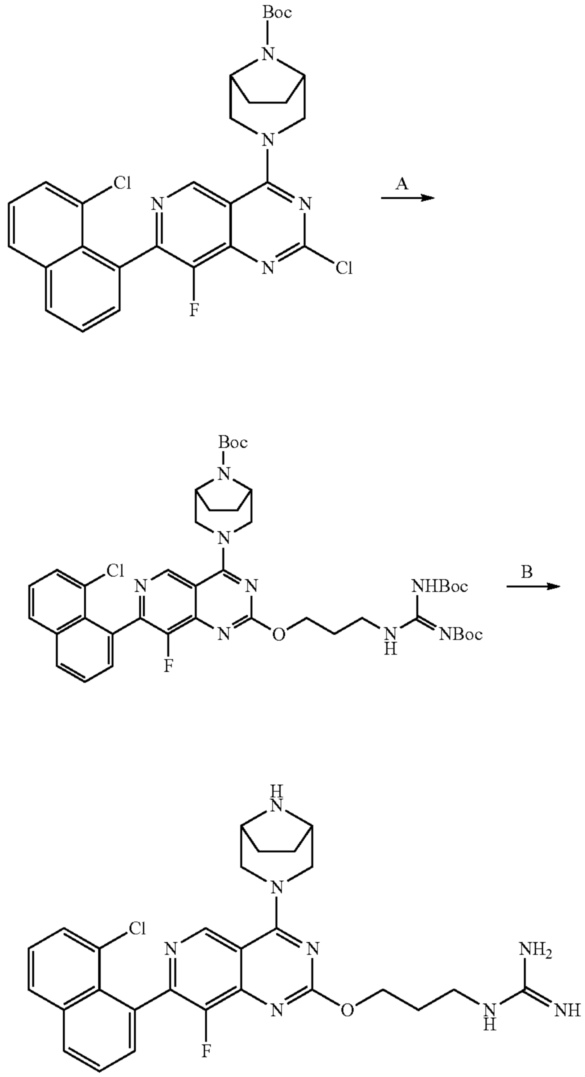

1-[3-[7-(8-chloro-1-naphthyl)-4-(3,8-diazabicyclo[3.2.1]octan-3-yl)-8-fluoro-pyrido[4,3-d]pyrimidin-2-yl]oxypropyl]guanidine. A mixture of tert-butyl 3-[2-[3-[[(Z)—N,N'-bis(tert-butoxycarbonyl)carbamimidoyl]amino]propoxy]-7-(8-chloro-1-naphthyl)-8-fluoro-pyrido[4,3-d]pyrimidin-4-yl]-3,8-diazabicyclo[3.2.1]octane-8-carboxylate (70 mg, 83.8 μmol, 1.0 eq) and TFA (191 mg, 1.68 mmol, 124 μL, 20 eq) was stirred at 15° C. for 1 hour. The solvent was removed under reduced pressure. The residue was diluted with MeOH (0.5 mL) and neutralized with saturated $Na_2CO_3$ solution (0.3 mL). The mixture was filtered, and the filtrate was purified with preparative HPLC (column: Phenomenex Synergi C18 150*25*10 μm; mobile phase: [water (0.225% formic acid)-ACN]; B %: 4%-34%, 10 min). The desired fractions were collected and lyophilized to give 1-[3-[7-(8-chloro-1-naphthyl)-4-(3,8-diazabicyclo[3.2.1]octan-3-yl)-8-fluoro-pyrido[4,3-d]pyrimidin-2-yl]oxypropyl]guanidine (23.2 mg, 47% yield, formic acid) as a yellow solid; $^1$H NMR (400 MHz, $CD_3OD$): δ 9.09 (s, 1H), 8.15 (dd, J=0.8, 8.0 Hz, 1H), 8.02 (dd, J=12, 8.4 Hz, 1H), 7.73-7.66 (m, 1H), 7.64-7.57 (m, 2H), 7.55-7.49 (m, 1H), 4.80 (br d, J=14.0 Hz, 2H), 4.58 (t, J=6.0 Hz, 2H), 4.18-4.10 (m, 2H), 3.97-3.86 (m, 2H), 3.43 (t, J=6.8 Hz, 2H), 2.15 (br s, 6H); LCMS [ESI, M+1]: 535.

Example 178

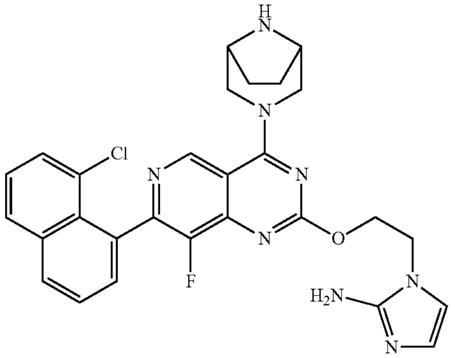 [SMILES: Nc1nccn1CCOc1nc(N2CC3CCC(C2)N3)c2cnc(-c3cccc4cccc(Cl)c34)c(F)c2n1]

1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]imidazol-2-amine

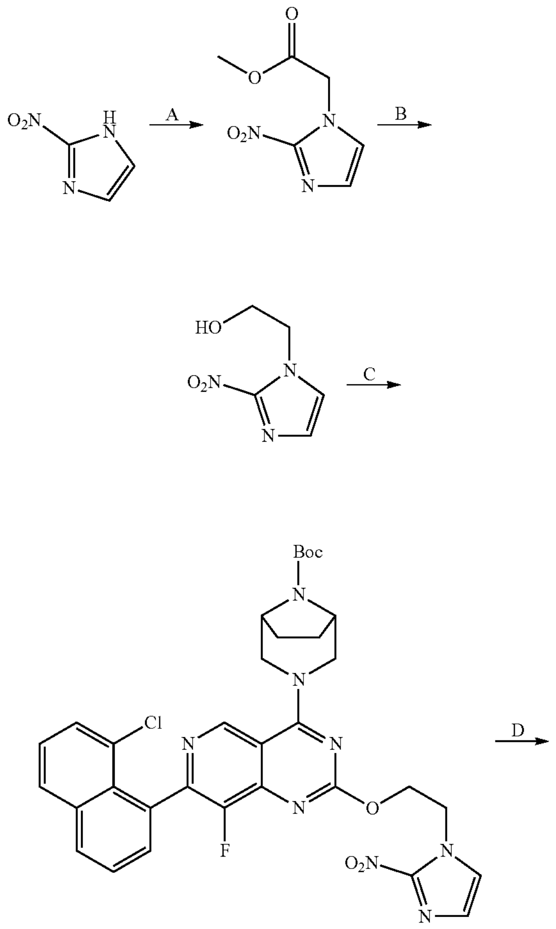

-continued

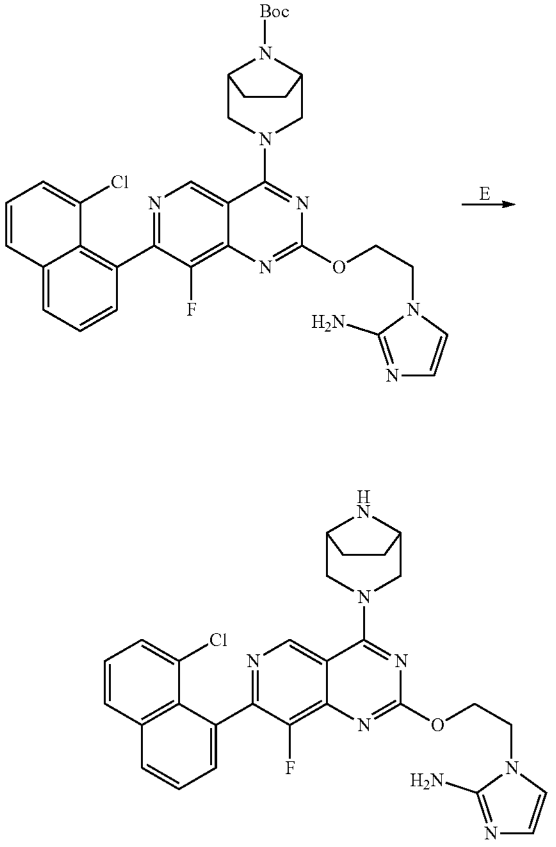

1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]imidazol-2-amine. To a solution of tert-butyl 3-[2-[2-(2-aminoimidazol-1-yl)ethoxy]-7-(8-chloro-1-naphthyl)-8-fluoro-pyrido[4,3-d]pyrimidin-4-yl]-3,8-diazabicyclo[3.2.1]octane-8-carboxylate (35 mg, crude) in dichloromethane (2.0 mL) was added 2,6-LUTIDINE (69.8 mg, 651 μmol, 75.8 ul) at −40° C., the mixture was stirred at −40° C. for 10 mins, and trimethylsilyl trifluoromethanesulfonate (72.4 mg, 326 μmol, 58.8 ul) was added. The mixture was stirred at 0° C. for 10 minutes. After completion, the mixture was concentrated under vacuum. The residue was purified using preparative HPLC (column: Waters Xbridge 150*25 mm*5 μm; mobile phase: [water (10 mM $NH_4HCO_3$)-ACN]; B %: 20%-50%, 10 min) to give 1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]imidazol-2-amine (6.63 mg, two steps 20% yield) as a white solid; $^{1}H$ NMR (400 MHz, chloroform-d) δ=9.06 (s, 1H), 8.02 (dd, J=1.2, 7.6 Hz, 1H), 7.90 (dd, J=1.2, 8.4 Hz, 1H), 7.65-7.55 (m, 3H), 7.41 (t, J=8.0 Hz, 1H), 6.59 (dd, J=1.6, 18.4 Hz, 2H), 4.73-4.64 (m, 2H), 4.62-4.47 (m, 4H), 4.17 (t, J=6.4 Hz, 2H), 3.70 (br s, 2H), 3.68-3.59 (m, 2H), 1.83 (br s, 4H). LCMS [ESI, M+1]: 545.

Example 179

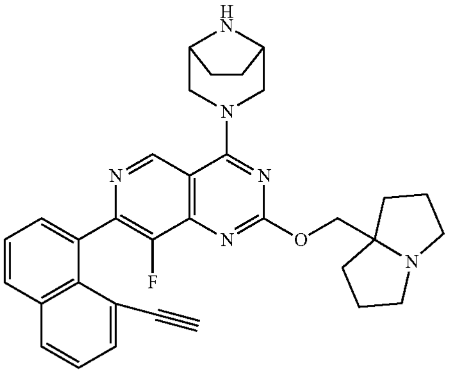 [SMILES: C#Cc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-ethynylnaphthalen-1-yl)-8-fluoro-2-((hexahydro-1H-pyrrolizin-7a-yl)methoxy)pyrido[4,3-d]pyrimidine

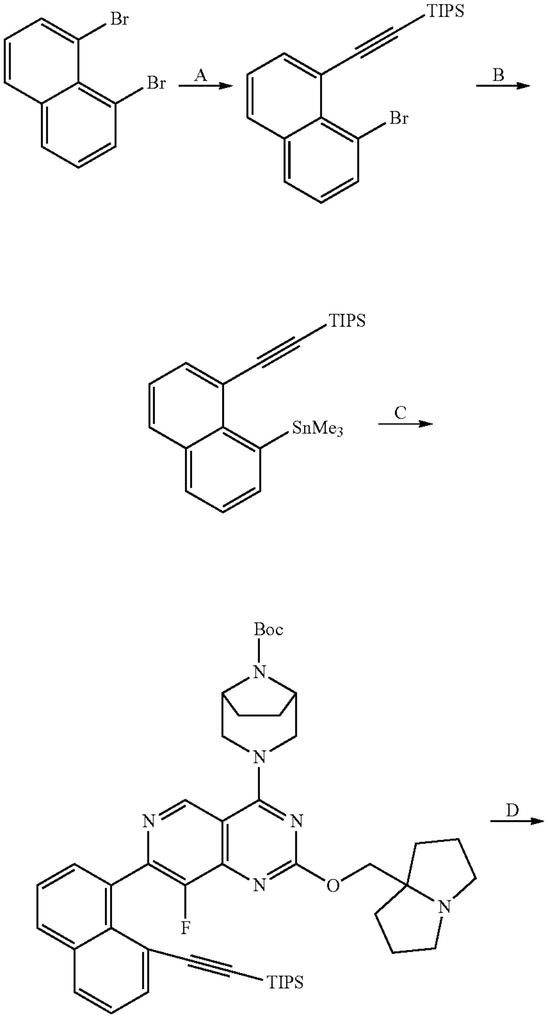

-continued
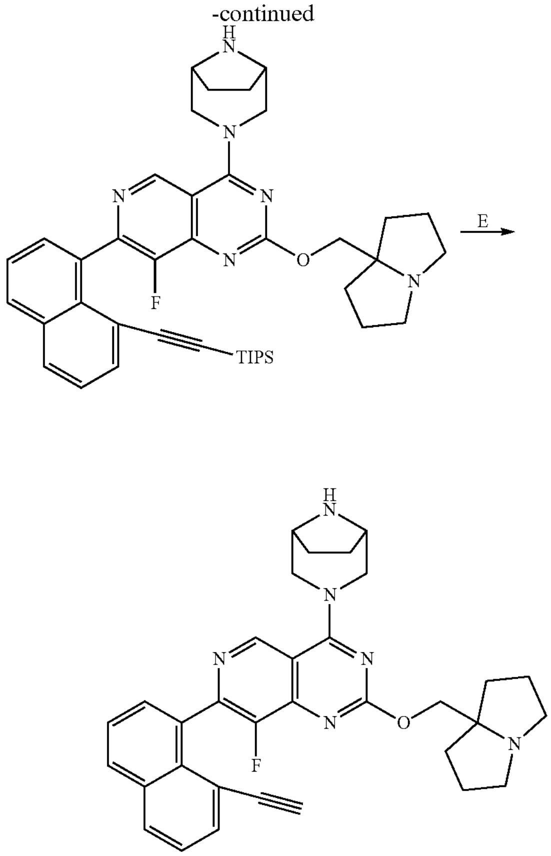
4-((1R,5S)-3,8-diazabicyclo[3.2.1]octan-3-yl)-7-(8-ethynylnaphthalen-1-yl)-8-fluoro-2-((hexahydro-1H-pyrrolizin-7a-yl)methoxy)pyrido[4,3-d]pyrimidine (6.17 mg, 17% yield) as a yellow solid. $^1$H NMR (400 MHz, chloroform-d) δ=8.99 (s, 1H), 8.03-7.92 (m, 2H), 7.75 (dd, J=1.2, 7.2 Hz, 1H), 7.64-7.56 (m, 2H), 7.46 (dd, J=7.2, 8.0 Hz, 1H), 4.73-4.50 (m, 2H), 4.32-4.15 (m, 2H), 3.72-3.53 (m, 4H), 3.24-3.07 (m, 2H), 2.72-2.60 (m, 2H), 2.56 (s, 1H), 2.21-2.07 (m, 2H), 1.94-1.75 (m, 10H); LCMS [ESI, M+1]: 549.
Example 180
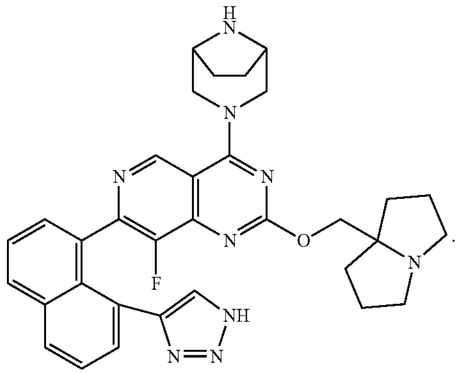 [SMILES: Fc1c(-c2cccc3cccc(-c4c[nH]nn4)c23)ncc2c(N3CC4CCC(C3)N4)nc(OCC34CCCN3CCC4)nc12]
7-(8-(1H-1,2,3-triazol-4-yl)naphthalen-1-yl)-4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidine
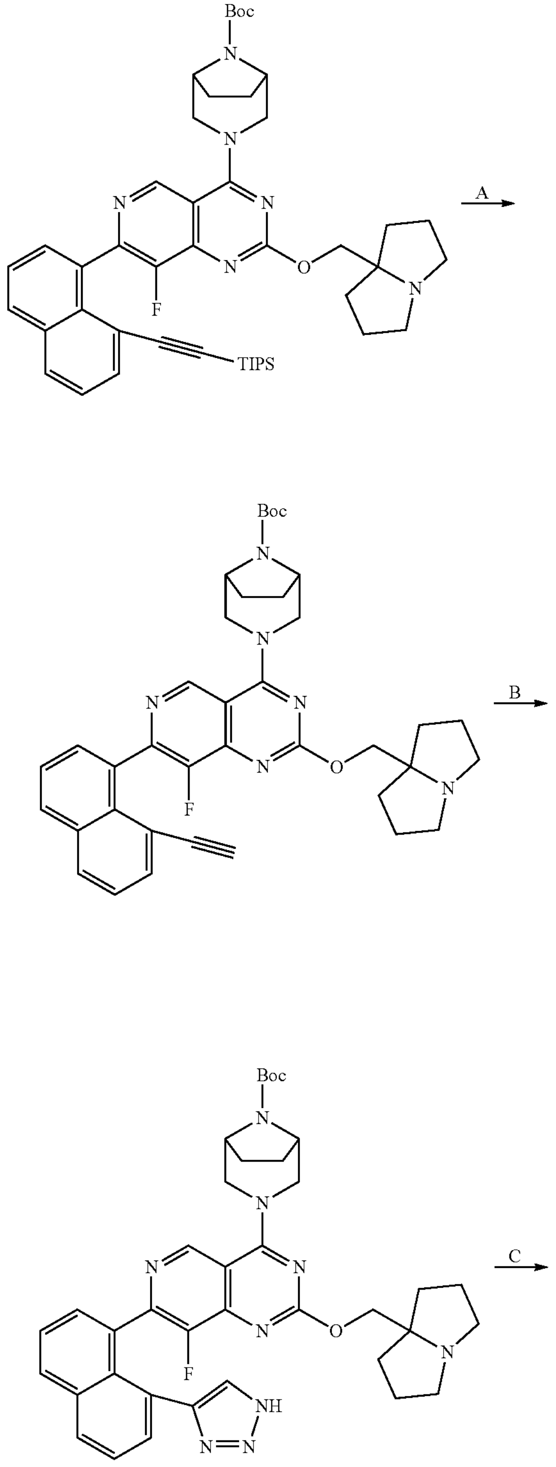

-continued

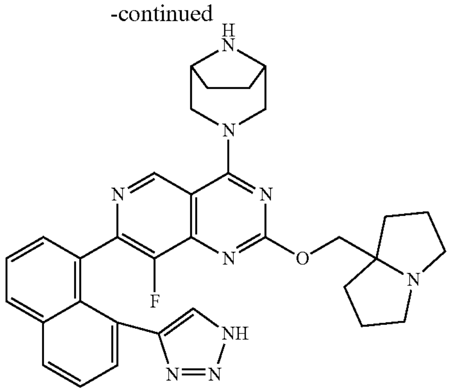

7-(8-(1H-1,2,3-triazol-4-yl)naphthalen-1-yl)-4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidine (2.73 mg, 36% yield,) as off-white solid. $^{1}H$ NMR (400 MHz, methanol-$d_4$) δ=8.87 (s, 1H), 8.2 (t, J=7.6 Hz, 2H), 7.80-7.63 (m, 3H), 7.53 (d, J=6.4 Hz, 1H), 7.36 (s, 1H), 4.95 (br s, 1H), 4.72-4.50 (m, 3H), 4.14-3.97 (m, 3H), 3.81-3.62 (m, 3H), 3.31-3.23 (m, 2H), 2.39-2.02 (m, 12H). LCMS [ESI, M+1]: 592. SFC analysis: Column: Chiralcel OD-3 50×4.6 mm I.D., 3 μm; Mobile phase: Phase A for $CO_2$, and Phase B for MeOH (0.05% DEA); Gradient elution: 40% MeOH (0.05% DEA) in $CO_2$; Flow rate: 3 mL/min; Wavelength: 220 nm; Column Temp: 35 C; Back Pressure: 100 Bar.

Example 181

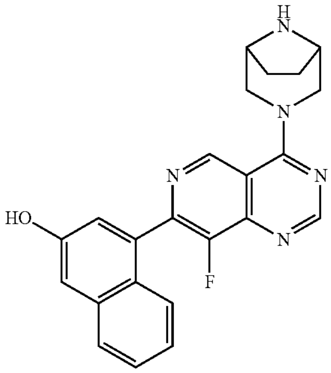 [SMILES: Oc1cc(-c2ncc3c(N4CC5CCC(C4)N5)ncnc3c2F)c2ccccc2c1]

4-(4-((1R,5S)-3,8-diazabicyclo[3.2.1]octan-3-yl)-8-fluoropyrido[4,3-d]pyrimidin-7-yl)naphthalen-2-ol

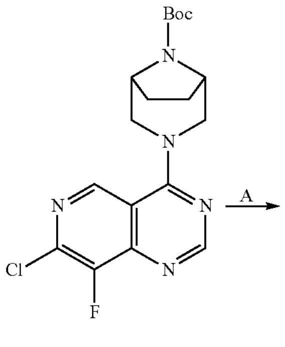

-continued

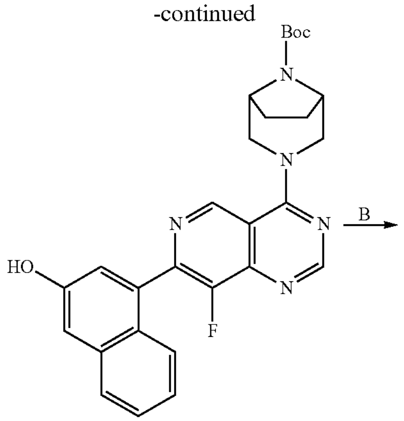

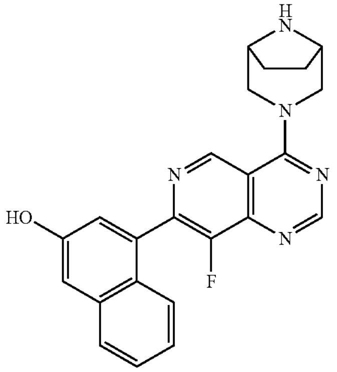

4-(4-((1R,5S)-3,8-diazabicyclo[3.2.1]octan-3-yl)-8-fluoropyrido[4,3-d]pyrimidin-7-yl)naphthalen-2-ol (51.7 mg, 39% yield) as an off-white solid. $^{1}H$ NMR (400 MHz, MeOD) δ=9.39-9.18 (m, 1H), 8.93-8.69 (m, 1H), 7.77 (d, J=8.0 Hz, 1H), 7.55 (br d, J=8.4 Hz, 1H), 7.49-7.40 (m, 1H), 7.31 (d, J=2.0 Hz, 1H), 7.29-7.21 (m, 2H), 4.89 (br s, 2H), 4.06 (br s, 2H), 3.90 (br dd, J=4.0, 13.6 Hz, 2H), 2.11-1.88 (m, 4H). LCMS [ESI, M+1]: 402.

Example 182

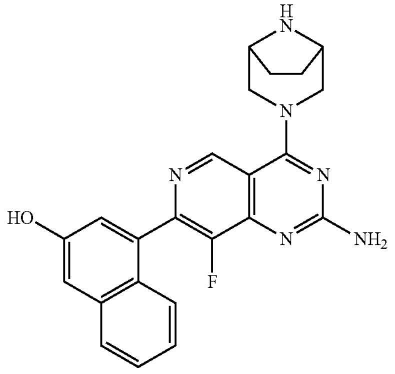 [SMILES: Nc1nc(N2CC3CCC(C2)N3)c2cnc(-c3cc(O)cc4ccccc34)c(F)c2n1]

4-[2-amino-4-(3,8-diazabicyclo[3.2.1]octan-3-yl)-8-fluoro-pyrido[4,3-d]pyrimidin-7-yl]naphthalen-2-ol
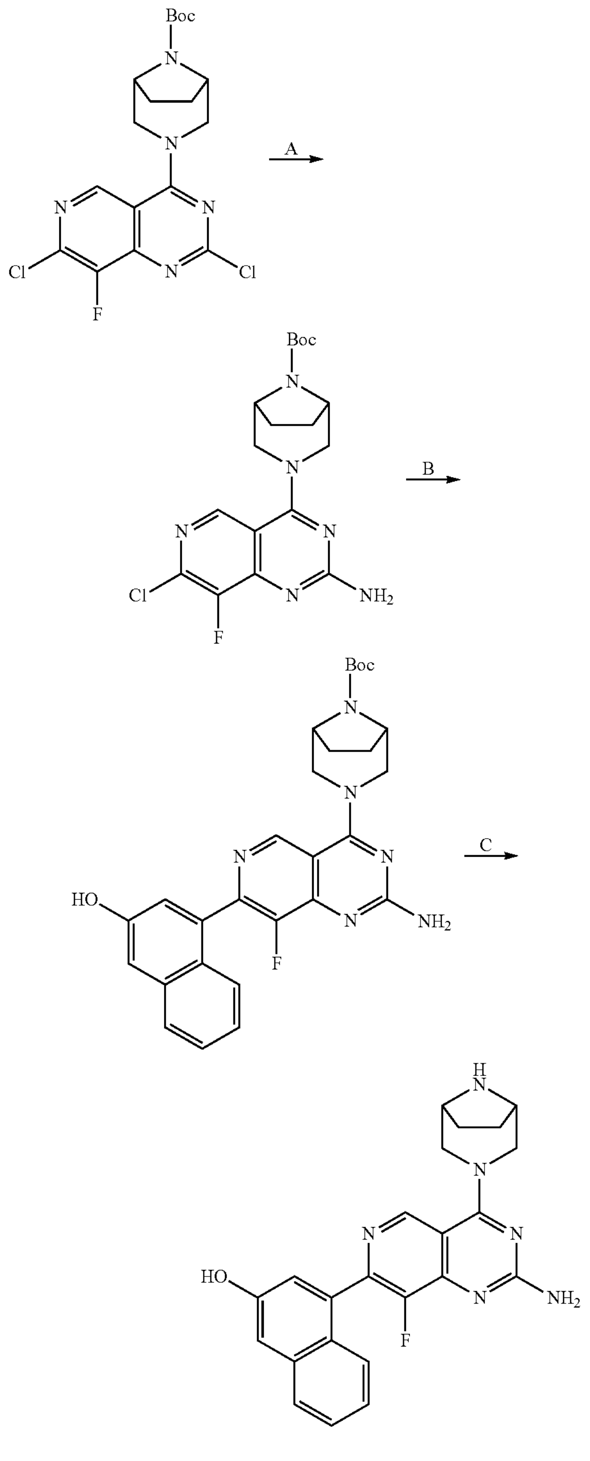
4-[2-amino-4-(3,8-diazabicyclo[3.2.1]octan-3-yl)-8-fluoro-pyrido[4,3-d]pyrimidin-7-yl]naphthalen-2-ol (43.7 mg, 58% yield, formic acid). Yellow solid; $^{1}$H NMR (400 MHz, $D_2O$): δ 8.47 (s, 1H), 7.77-7.72 (m, 1H), 7.45-7.39 (m, 1H), 7.36-7.31 (m, 1H), 7.29 (d, J=2.4 Hz, 1H), 7.22-7.16 (m, 1H), 7.07 (d, J=2.4 Hz, 1H), 4.45-4.37 (m, 2H), 4.12-4.05 (m, 2H), 3.67 (br d, J=14.0 Hz, 2H), 1.98-1.87 (m, 2H), 1.86-1.72 (m, 2H); LCMS [ESI, M+1]: 417.
Example 183
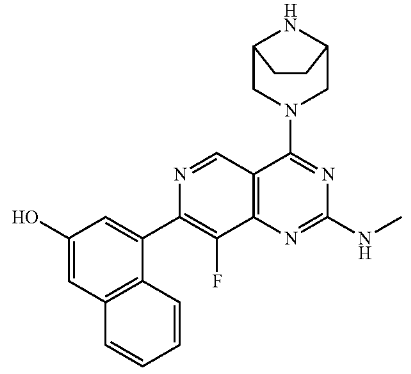 [SMILES: CNc1nc(N2CC3CCC(C2)N3)c2cnc(-c3cc(O)cc4ccccc34)c(F)c2n1]
4-[4-(3,8-diazabicyclo[3.2.1]octan-3-yl)-8-fluoro-2-(methylamino)pyrido[4,3-d]pyrimidin-7-yl]naphthalen-2-ol
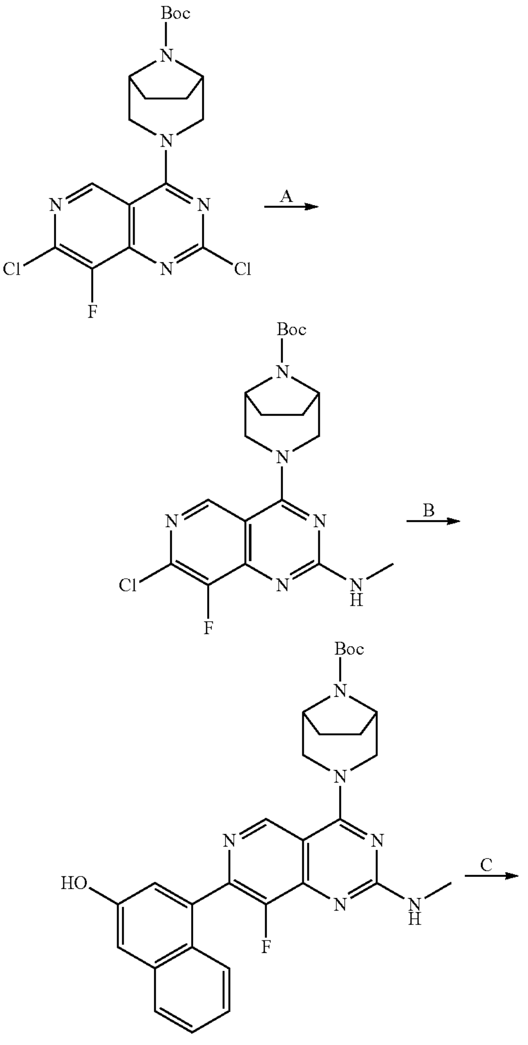

-continued

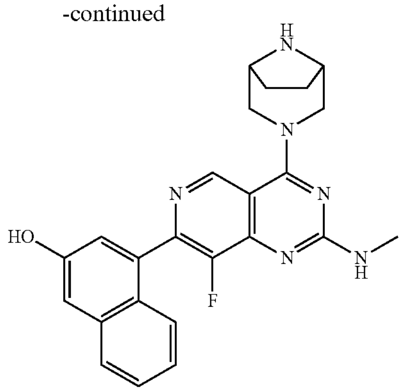

4-[4-(3,8-diazabicyclo[3.2.1]octan-3-yl)-8-fluoro-2-(methylamino)pyrido[4,3-d]pyrimidin-7-yl]naphthalen-2-ol (12.7 mg, 38% yield) as a yellow solid; $^{1}$H NMR (400 MHz, $CDCl_3$): δ 8.90 (s, 1H), 7.79-7.72 (m, 1H), 7.70 (br d, J=8.4 Hz, 1H), 7.50-7.42 (m, 1H), 7.41-7.35 (m, 1H), 7.27-7.20 (m, 2H), 5.96-5.75 (m, 1H), 4.62-4.26 (m, 2H), 3.69-3.46 (m, 4H), 3.02 (br s, 3H), 1.84-1.76 (m, 4H); LCMS [ESI, M+1]: 431.

Example 184

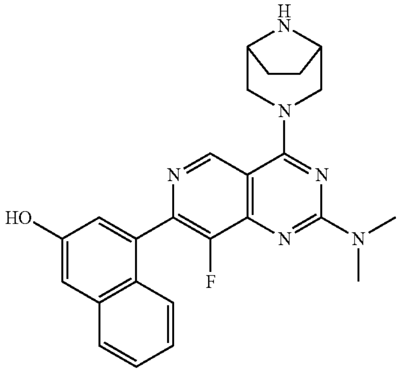 [SMILES: CN(C)c1nc(N2CC3CCC(C2)N3)c2cnc(-c3cc(O)cc4ccccc34)c(F)c2n1]

4-[4-(3,8-diazabicyclo[3.2.1]octan-3-yl)-2-(dimethylamino)-8-fluoro-pyrido[4,3-d]pyrimidin-7-yl]naphthalen-2-ol Synthesized according to Example 183 substituting dimethylamine in place of methylamine (15.0 mg, 24% yield) as a white solid; $^{1}$H NMR (400 MHz, $CDCl_3$): δ 8.87 (s, 1H), 7.67 (br d, J=8.4 Hz, 1H), 7.63 (d, J=8.0 Hz, 1H), 7.40-7.35 (m, 1H), 7.33-7.31 (m, 1H), 7.26-7.21 (m, 1H), 7.14-7.11 (m, 1H), 4.45-4.36 (m, 2H), 3.67-3.58 (m, 2H), 3.57-3.48 (m, 2H), 3.29 (s, 6H), 1.87-1.78 (m, 4H); LCMS [ESI, M+1]: 445.

Example 185

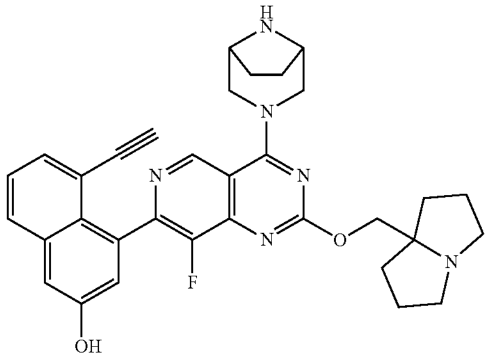 [SMILES: C#Cc1cccc2cc(O)cc(-c3ncc4c(N5CC6CCC(C5)N6)nc(OCC56CCCN5CCC6)nc4c3F)c12]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethynylnaphthalen-2-ol

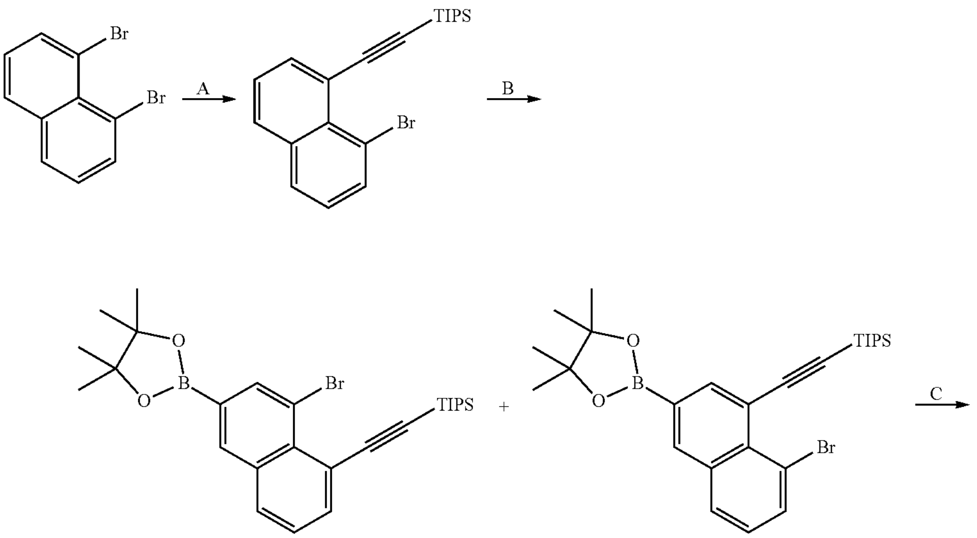

-continued
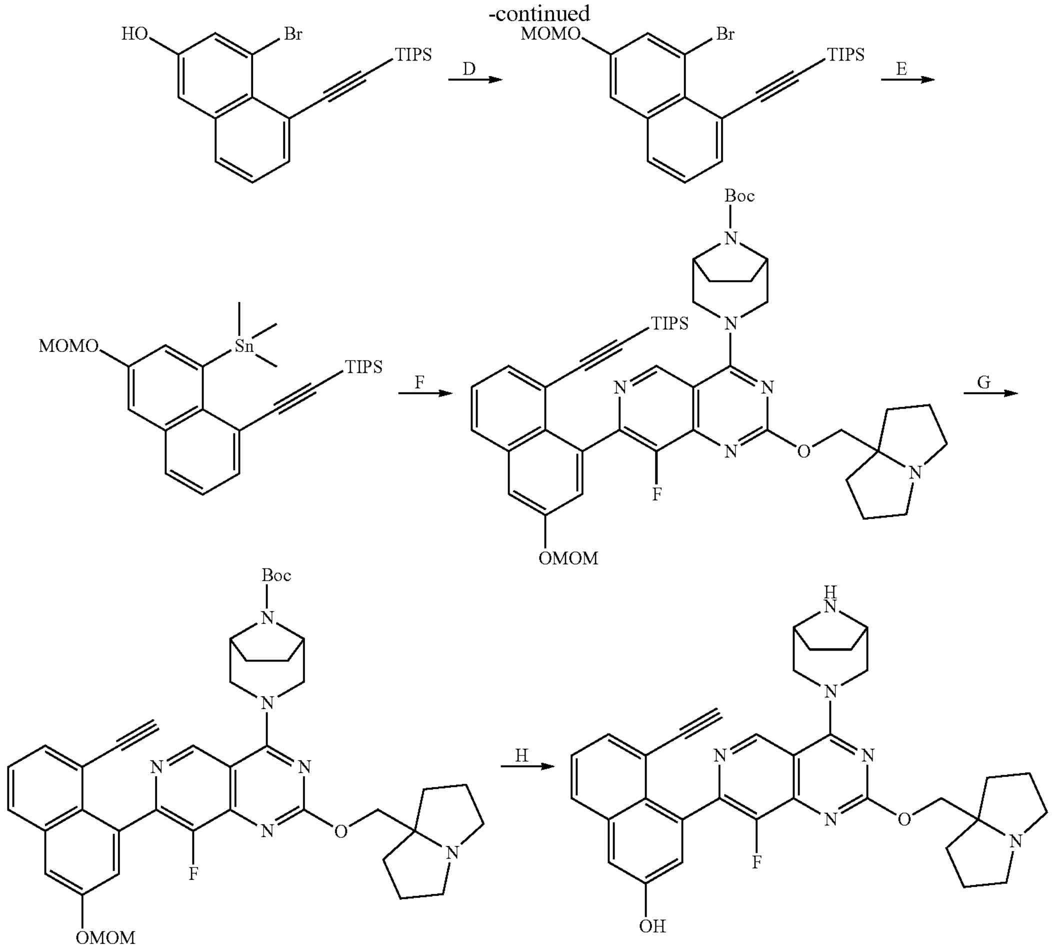
4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethynylnaphthalen-2-ol (2.12 mg, 8.8% yield, 2FA) as a brown solid. $^{1}H$ NMR (400 MHz, $CD_3OD$) δ=9.09 (s, 1H), 8.49 (br s, 2H), 7.83 (d, J=7.4 Hz, 1H), 7.51 (d, J=6.0 Hz, 1H), 7.42-7.34 (m, 2H), 7.16 (d, J=2.8 Hz, 1H), 4.72-4.61 (m, 4H), 4.04 (s, 2H), 3.90 (m, 2H), 3.72-3.68 (m, 2H), 3.26 (m, 2H), 3.04 (s, 1H), 2.33-1.98 (m, 12H). LCMS [ESI, M+1]: 565.
Example 186
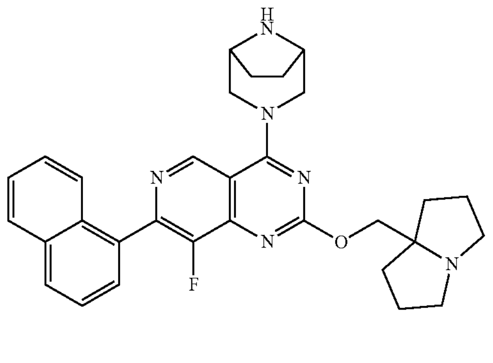 [SMILES: Fc1c(-c2cccc3ccccc23)ncc2c(N3CC4CCC(C3)N4)nc(OCC34CCCN3CCC4)nc12]
4-((1R,5S)-3,8-diazabicyclo[3.2.1]octan-3-yl)-8-fluoro-7-(naphthalen-1-yl)-2-((tetrahydro-1H-pyrrolizin-7a(5H)-yl)methoxy)pyrido[4,3-d]pyrimidine
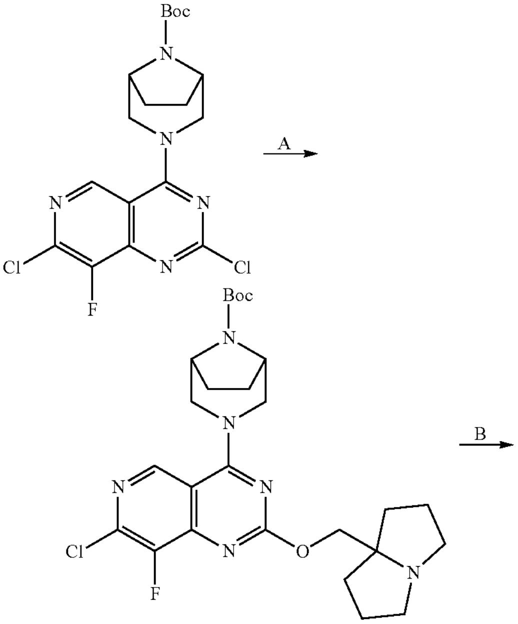

-continued

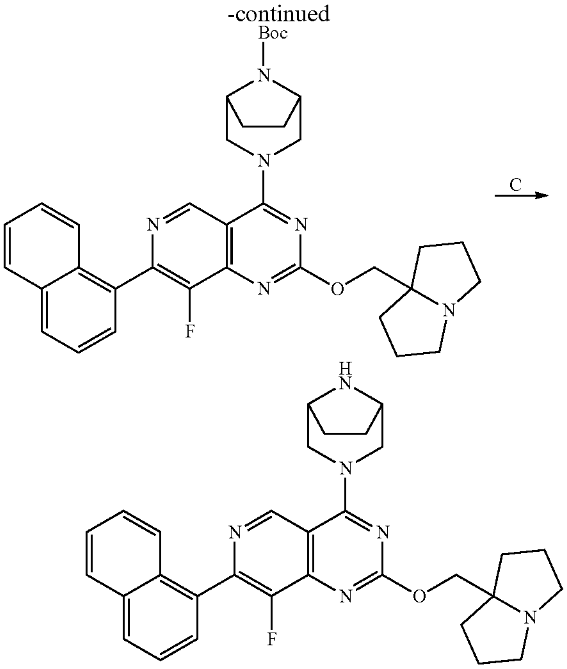

4-((1R,5S)-3,8-diazabicyclo[3.2.1]octan-3-yl)-8-fluoro-7-(naphthalen-1-yl)-2-((tetrahydro-1H-pyrrolizin-7a(5H)-yl)methoxy)pyrido[4,3-d]pyrimidine. To a mixture of tert-butyl(1R,5S)-3-(8-fluoro-7-(naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (150 mg, 175 μmol, 1.0 eq) in acetonitrile (1.5 mL) was added HCl·dioxane (4 M, 3 mL, 68 eq) at 0° C. The mixture was stirred at 0° C. for 0.5 hour. After completion, the mixture was concentrated under vacuum. Then the pH value was adjusted to 9 with saturated $Na_2CO_3$ solution and the mixture was washed with methanol (2×6 mL), filtered and concentrated under vacuum. The residue was purified with preparative HPLC (column: Waters Xbridge 150*25 mm*5 μm; mobile phase: [water (10 mM $NH_4HCO_3$)-ACN]; B %: 30%-60%, 10 min) twice the title compound (22.5 mg, 24% yield) as a white solid; $^1H$ NMR (400 MHz, $CDCl_3$-d) δ=9.10 (s, 1H), 7.95 (dd, J=7.6, 18.0 Hz, 2H), 7.85-7.80 (m, 1H), 7.68 (d, J=7.2 Hz, 1H), 7.63-7.57 (m, 1H), 7.55-7.42 (m, 2H), 4.61 (br d, J=11.2 Hz, 2H), 4.21 (s, 2H), 3.72-3.60 (m, 4H), 3.18-3.07 (m, 2H), 2.71-2.60 (m, 2H), 2.17-2.07 (m, 2H), 1.92-1.81 (m, 8H), 1.73-1.64 (m, 2H); LCMS [ESI, M/2+1, M+1]: 263, 525.

Example 187

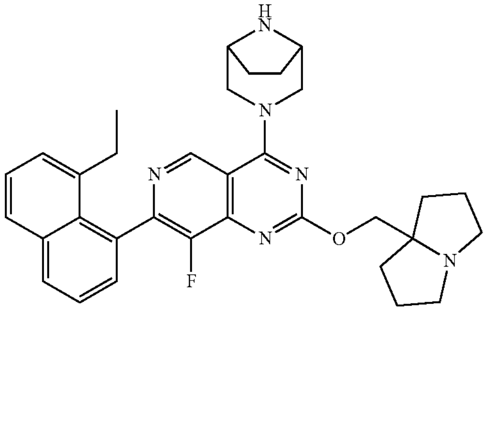 [SMILES: CCc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-ethylnaphthalen-1-yl)-8-fluoro-2-((tetrahydro-1H-pyrrolizin-7a(5H)-yl)methoxy)pyrido[4,3-d]pyrimidine

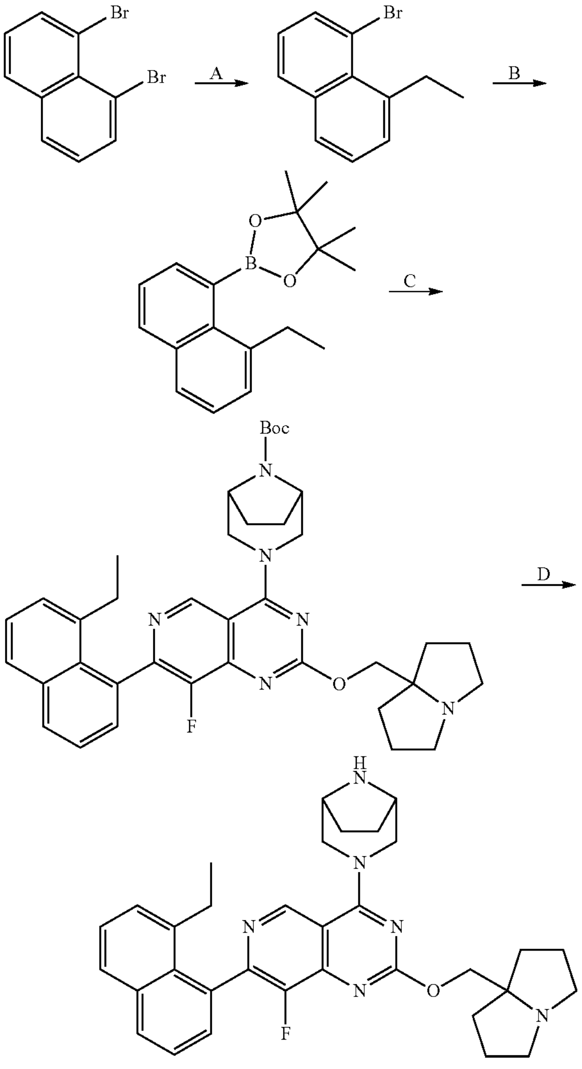

4-((1R,5S)-3,8-diazabicyclo[3.2.1]octan-3-yl)-7-(8-ethylnaphthalen-1-yl)-8-fluoro-2-((tetrahydro-1H-pyrrolizin-7a(5H)-yl)methoxy)pyrido[4,3-d]pyrimidine. To a solution of tert-butyl(1R,5S)-3-(7-(8-ethylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (45 mg, 68.9 μmol, 1 eq) in acetonitrile (0.5 mL) was added HCl·dioxane (4 M, 1.0 mL) at 0° C., the mixture was stirred at 0° C. for 30 minutes. The mixture was concentrated and was diluted with water (1.0 mL). The pH of the mixture was adjusted to ~8 with saturated $NaHCO_3$ aqueous solution and extracted with dichloromethane (3×5 mL). The combined organic layers were dried over $Na_2SO_4$, filtered and concentrated. The residue was purified with preparative HPLC (column: Waters X bridge 150*25 mm*5 μm; mobile phase: [water (10 mM $NH_4HCO_3$)-ACN]; B %: 28%-58%, 10 min). The desired fraction was collected and concentrated under vacuum to remove acetonitrile. The mixture was lyophilized to the title compound (15.2 mg, 39% yield) as a white solid; $^1$H NMR (400 MHz, $CDCl_3$-d) δ=8.99 (s, 1H), 7.96 (d, J=8.0 Hz, 1H), 7.80 (d, J=8.0 Hz, 1H), 7.54-7.41 (m, 3H), 7.36 (d, J=6.8 Hz, 1H), 4.65 (br d, J=12.0 Hz, 1H), 4.52 (br d, J=11.6 Hz, 1H), 4.23-4.16 (m, 2H), 3.72-3.56 (m, 4H), 3.15-3.06 (m, 2H), 2.69-2.60 (m, 2H), 2.49-2.33 (m, 2H), 2.14-2.08 (m, 2H), 1.94-1.81 (m, 8H), 1.72-1.63 (m, 2H), 0.96 (t, J=7.6 Hz, 3H); LCMS [ESI, M+1]: 553.

Example 188

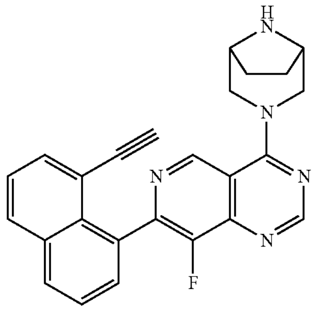 [SMILES: C#Cc1cccc2cccc(-c3ncc4c(N5CC6CCC(C5)N6)ncnc4c3F)c12]

4-(3,8-diazabicyclo[3.2.1]octan-3-yl)-7-(8-ethynyl-1-naphthyl)-8-fluoro-pyrido[4,3-d]pyrimidine

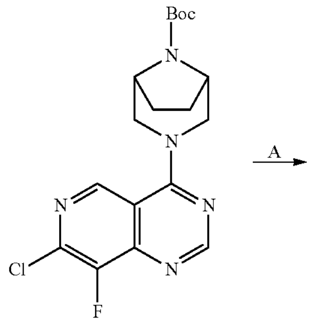

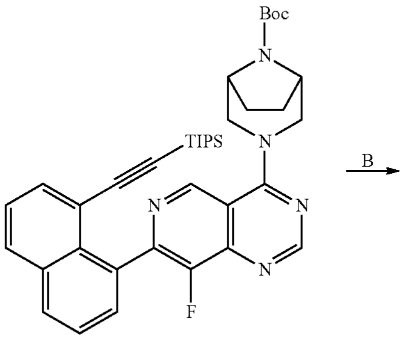

-continued

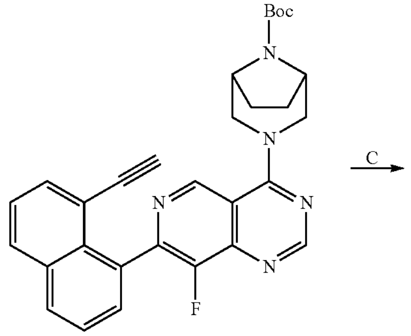

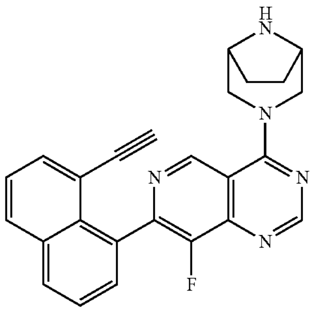

4-(3,8-diazabicyclo[3.2.1]octan-3-yl)-7-(8-ethynyl-1-naphthyl)-8-fluoro-pyrido[4,3-d]pyrimidine (35.7 mg, 63% yield) as a yellow solid; $^1$H NMR (400 MHz, $CDCl_3$-d) δ=9.12 (s, 1H), 8.81-8.77 (m, 1H), 8.04-7.95 (m, 2H), 7.77 (dd, J=1.2, 7.2 Hz, 1H), 7.64-7.60 (m, 2H), 7.48 (dd, J=7.2, 8.0 Hz, 1H), 4.69-4.56 (m, 2H), 3.73-3.63 (m, 4H), 2.49 (s, 1H), 1.86-1.72 (m, 4H); LCMS [ESI, M+1]: 410.

Example 189

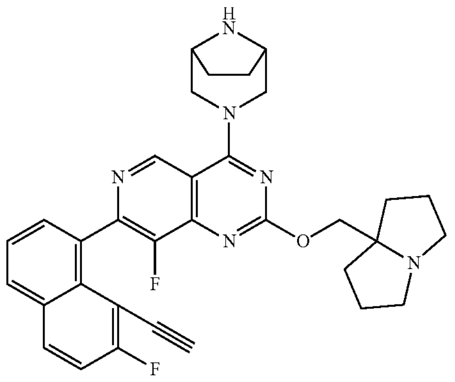 [SMILES: C#Cc1c(F)ccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-ethynyl-7-fluoronaphthalen-1-yl)-8-fluoro-2-((tetrahydro-1H-pyrrolizin-7a(5H)-yl)methoxy)pyrido[4,3-d]pyrimidine

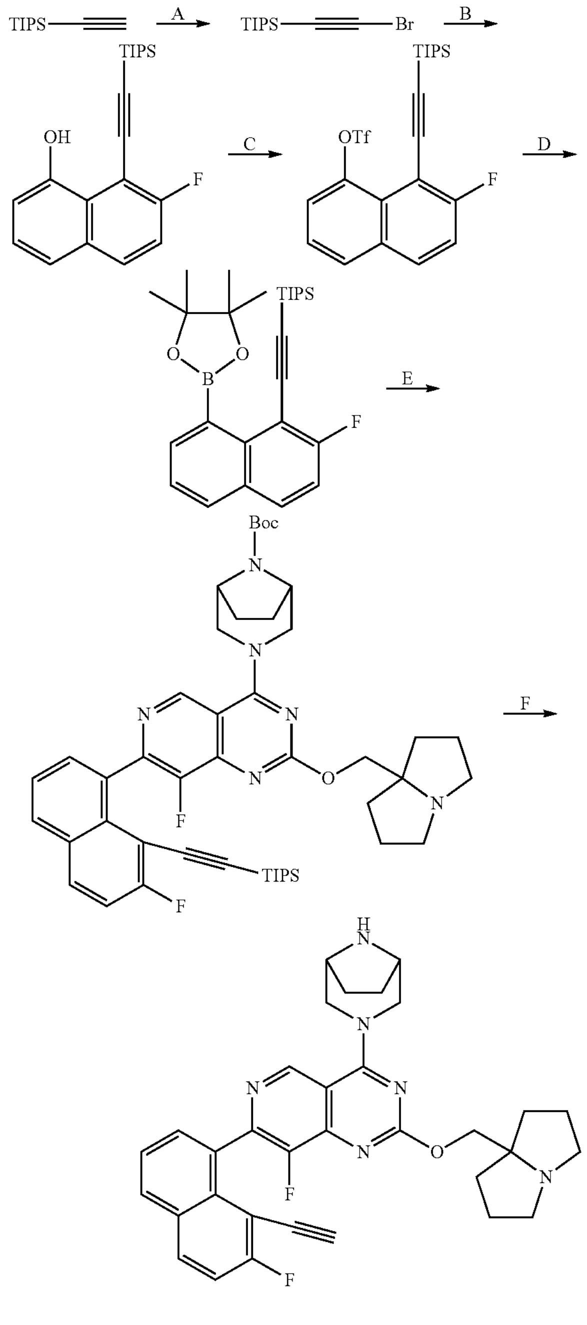

4-((1R,5S)-3,8-diazabicyclo[3.2.1]octan-3-yl)-7-(8-ethynyl-7-fluoronaphthalen-1-yl)-8-fluoro-2-((tetrahydro-1H-pyrrolizin-7a(5H)-yl)methoxy)pyrido[4,3-d]pyrimidine. To a solution of tert-butyl(1R,5S)-3-(8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (25.0 mg, 30.3 μmol, 1.00 eq) in DMF (0.50 mL) was added cesium fluoride (36.9 mg, 243 μmol, 8.96 μL, 8.00 eq). The mixture was stirred at 25° C. for 2 hours. The residue was poured into water (1.00 mL) and stirred for 5 minutes. The aqueous phase was extracted with ethyl acetate (2×3 mL). The combined organic phase was washed with brine (2×3 mL), dried with anhydrous sodium sulfate, filtered and concentrated in vacuum to give a residue. Then the residue was dissolved in acetonitrile (0.50 mL) and HCl·dioxane (0.50 mL) was added. The mixture was stirred at 25° C. for 0.5 hour. The mixture was concentrated in vacuum to give a residue. The resulting mixture was adjusted to pH~8 with ammonium hydroxide (1.00 mL) and dissolved in DMF (1.00 mL). The mixture was purified with preparative HPLC (neutral condition column: Waters Xbridge 150*25 mm*5 μm; mobile phase: [water (10 mM $NH_4HCO_3$)-ACN]; B %: 28%-58%, 10 min) affording the title compound (6.00 mg, 34% yield) as a yellow solid; $^1$H NMR (400 MHz, $CDCl_3$) δ 8.98 (s, 1H), 7.99-7.92 (m, 2H), 7.64-7.56 (m, 2H), 7.34 (t, J=8.8 Hz, 1H), 4.70-4.51 (m, 2H), 4.28-4.16 (m, 2H), 3.68 (br d, J=4.4 Hz, 3H), 3.61 (br d, J=12.8 Hz, 1H), 3.20-3.07 (m, 2H), 2.84 (s, 1H), 2.72-2.58 (m, 2H), 2.20-2.07 (m, 2H), 1.93-1.80 (m, 8H), 1.68-1.64 (m, 2H); LCMS [ESI, M+1]: 567.2.

Example 190

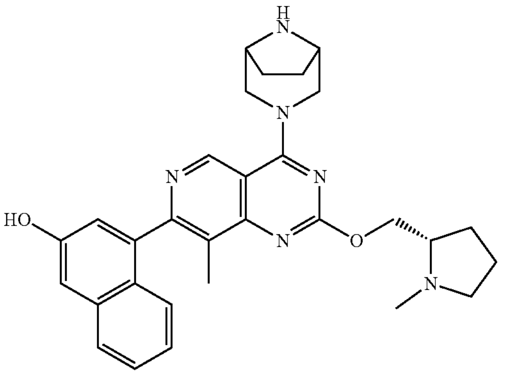 [SMILES: Cc1c(-c2cc(O)cc3ccccc23)ncc2c(N3CC4CCC(C3)N4)nc(OC[C@@H]3CCCN3C)nc12]

4-(4-((1R,5S)-3,8-diazabicyclo[3.2.1]octan-3-yl)-8-methyl-2-(((S)-1-methylpyrrolidin-2-yl)methoxy)pyrido[4,3-d]pyrimidin-7-yl)naphthalen-2-ol

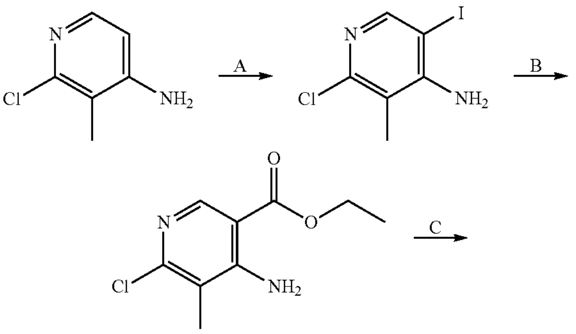

-continued

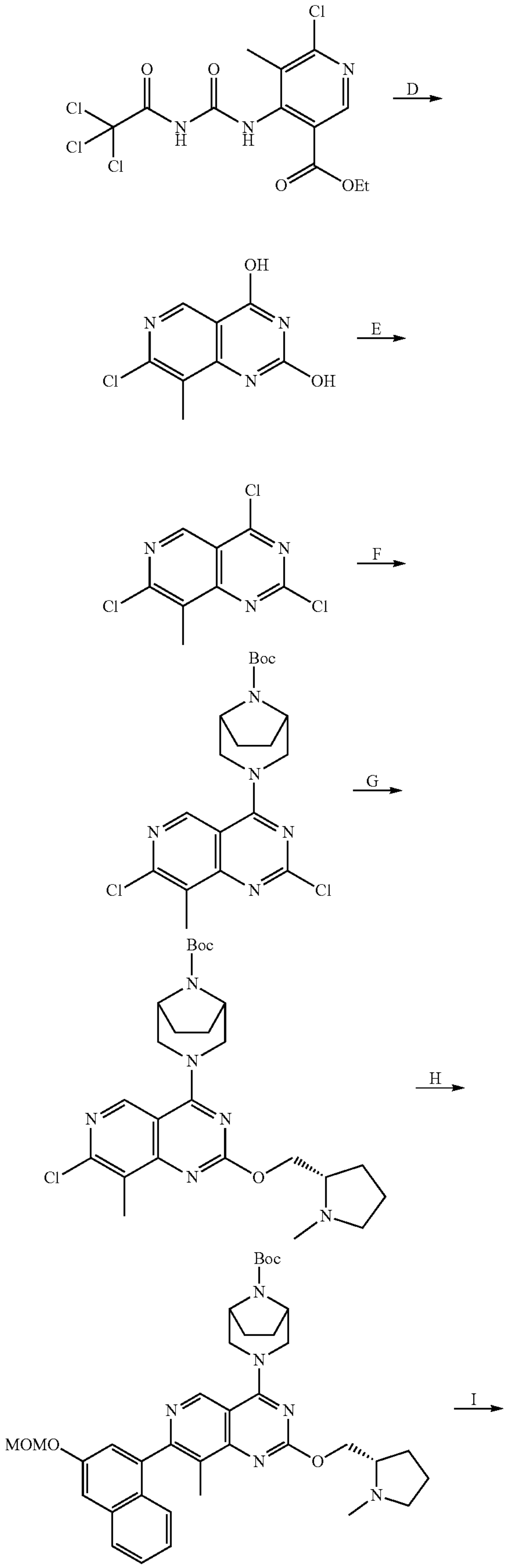

-continued

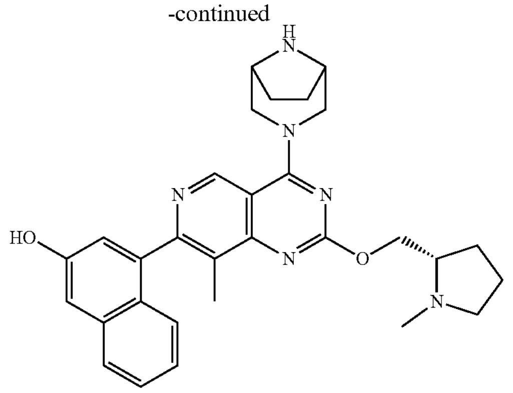

4-(4-((1R,5S)-3,8-diazabicyclo[3.2.1]octan-3-yl)-8-methyl-2-(((S)-1-methylpyrrolidin-2-yl)methoxy)pyrido[4,3-d]pyrimidin-7-yl)naphthalen-2-ol (5.29 mg, 8.17 μmol, 39% yield, 96% purity, TFA) as a yellow gum; $^1$H NMR (400 MHz, DMSO-$d_6$) δ 10.11 (br s, 1H), 9.51-9.46 (m, 1H), 9.27 (s, 2H), 7.81 (d, J=8.4 Hz, 1H), 7.47-7.40 (m, 1H), 7.27 (d, J=2.4 Hz, 1H), 7.24-7.17 (m, 2H), 7.06 (d, J=2.0 Hz, 1H), 4.81-4.75 (m, 1H), 4.74-4.63 (m, 3H), 4.21 (br s, 2H), 3.92-3.84 (m, 3H), 3.17-3.12 (m, 1H), 2.97 (br s, 3H), 2.91-2.75 (m, 1H), 2.37-2.25 (m, 1H), 2.21 (s, 3H), 2.15-1.88 (m, 8H); LCMS [ESI, M+1]: 511.1.

Example 191

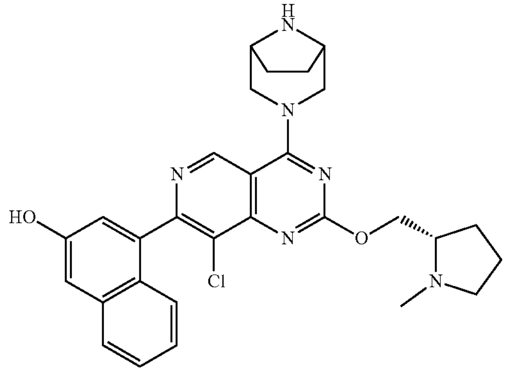 [SMILES: CN1CCC[C@H]1COc1nc(N2CC3CCC(C2)N3)c2cnc(-c3cc(O)cc4ccccc34)c(Cl)c2n1]

4-(4-((1R,5S)-3,8-diazabicyclo[3.2.1]octan-3-yl)-8-chloro-2-(((S)-1-methylpyrrolidin-2-yl)methoxy)pyrido[4,3-d]pyrimidin-7-yl)naphthalen-2-ol

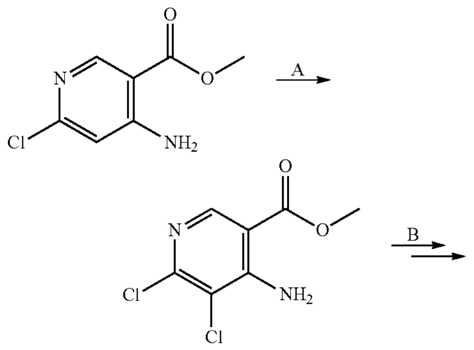

-continued

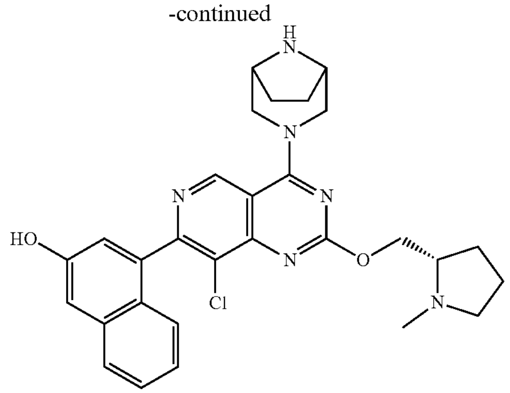

4-(4-((1R,5S)-3,8-diazabicyclo[3.2.1]octan-3-yl)-8-chloro-2-(((S)-1-methylpyrrolidin-2-yl)methoxy)pyrido[4,3-d]pyrimidin-7-yl)naphthalen-2-ol. Synthesized according to Example 190 step B—I, substituting methyl 4-amino-5,6-dichloronicotinate in place of ethyl-4-amino-6-chloro-5-methylnicotinate to afford the title compound (16.1 mg, 24.5 μmol, 33% yield, 98.4% purity, TFA) as a yellow solid. $^1$H NMR (400 MHz, DMSO-$d_6$) δ 9.30 (s, 1H), 7.79 (d, J=8.0 Hz, 1H), 7.46-7.37 (m, 1H), 7.29-7.23 (m, 2H), 7.22-7.15 (m, 1H), 7.09 (d, J=2.8 Hz, 1H), 4.84-4.76 (m, 1H), 4.73-4.65 (m, 3H), 4.22-4.18 (m, 2H), 3.91 (br d, J=13.6 Hz, 2H), 3.89-3.84 (m, 1H), 3.70-3.62 (m, 1H), 3.18-3.12 (m, 1H), 2.96 (br s, 3H), 2.30-2.23 (m, 1H), 2.10-2.02 (m, 1H), 1.99-1.82 (m, 6H); LCMS [ESI, M+1]: 531.3.

Example 192

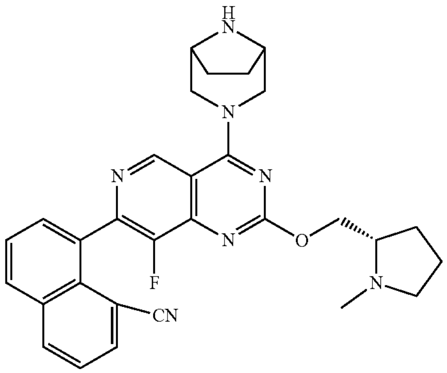 [SMILES: CN1CCC[C@H]1COc1nc(N2CC3CCC(C2)N3)c2cnc(-c3cccc4cccc(C#N)c34)c(F)c2n1]

4-(4-((1R,5S)-3,8-diazabicyclo[3.2.1]octan-3-yl)-8-fluoro-2-(2-(2-methyl-1H-imidazol-1-yl)ethoxy)pyrido[4,3-d]pyrimidin-7-yl)naphthalen-2-ol Synthesized according to Example 3, Steps G-I substituting S-prolinol for 2-(1-methyl-1H-imidazol-2-yl)ethan-1-ol in Step G and substituting 8-(4,4,5,5-tetramethyl-1,3,2-dioxaborolan-2-yl)-1-naphthonitrile for 4-(4,4,5,5-tetramethyl-1,3,2-dioxaborolan-2-yl)naphthalen-2-ol in Step H to afford 4-(4-((1R,5S)-3,8-diazabicyclo[3.2.1]octan-3-yl)-8-fluoro-2-(2-(2-methyl-1H-imidazol-1-yl)ethoxy)pyrido[4,3-d]pyrimidin-7-yl)naphthalen-2-ol (15 mg, 36%). LCMS (MM-ES+APCI, Pos): m/z 524.3 (M+H).

Example 193

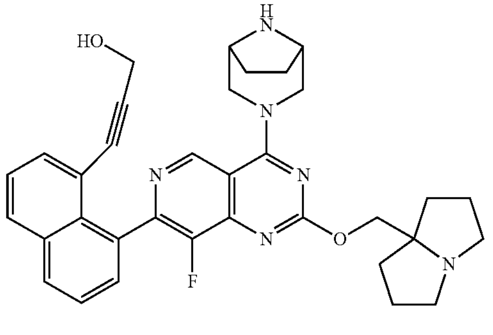 [SMILES: OCC#Cc1cccc2cccc(-c3ncc4c(N5CC6CCC(C5)N6)nc(OCC56CCCN5CCC6)nc4c3F)c12]

3-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl) prop-2-yn-1-ol

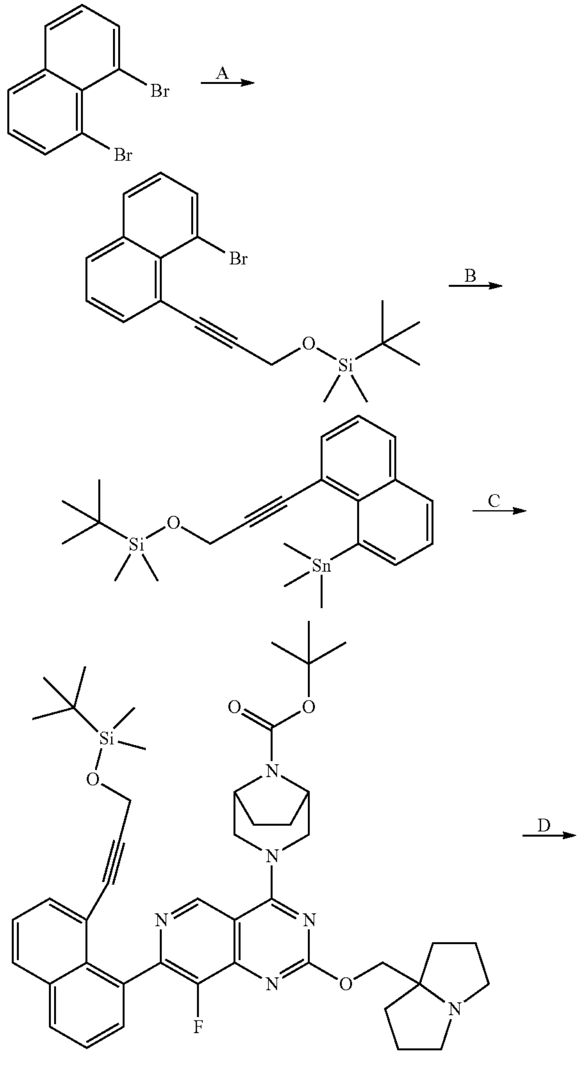

-continued

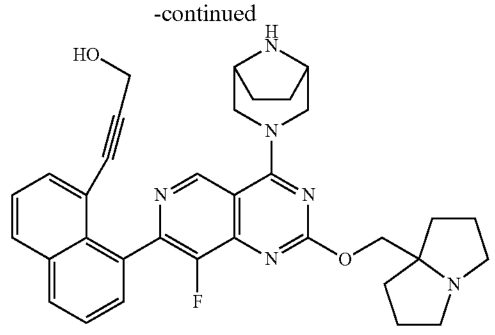

3-(8-(4-(3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl) prop-2-yn-1-ol (0.004 g, 0.0069 mmol, 11% yield). LCMS (MM-ES+APCI, Pos): m/z 579.3 (M+H).

Example 194

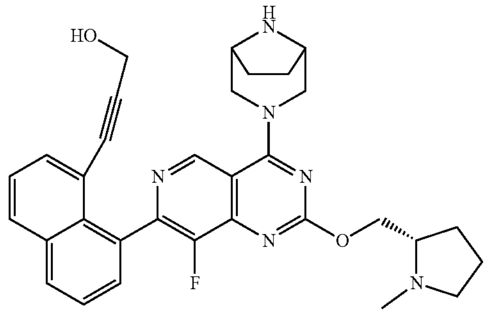 [SMILES: CN1CCC[C@H]1COc1nc(N2CC3CCC(C2)N3)c2cnc(-c3cccc4cccc(C#CCO)c34)c(F)c2n1]

3-(8-(4-((1R,5S)-3,8-diazabicyclo[3.2.1]octan-3-yl)-8-fluoro-2-(((S)-1-methylpyrrolidin-2-yl)methoxy) pyrido[4,3-d]pyrimidin-7-yl)naphthalen-1-yl) prop-2-yn-1-ol Synthesized according to Example 193, substituting tert-butyl 3-(7-chloro-8-fluoro-2-(((S)-1-methylpyrrolidin-2-yl) methoxy)pyrido[4,3-d]pyrimidin-4-yl)-3,8-diazabicyclo [3.2.1]octane-8-carboxylate in place of tert-butyl 3-(7-chloro-8-fluoro-2-((tetrahydro-1H-pyrrolizin-7a(5H)-yl) methoxy)pyrido[4,3-d]pyrimidin-4-yl)-3,8-diazabicyclo [3.2.1]octane-8-carboxylate to afford the title compound (11.4 mg, 31%). LCMS (MM-ES+APCI, Pos): m/z 553.3 (M+H).

Example 195

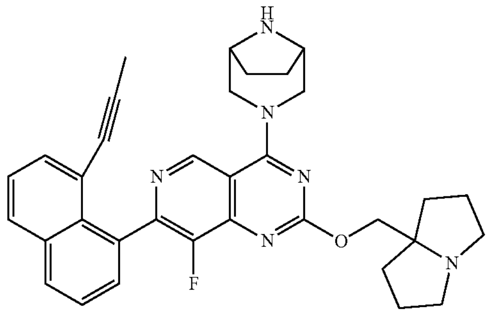 [SMILES: CC#Cc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-7-(8-(prop-1-yn-1-yl)naphthalen-1-yl)-2-((tetrahydro-1H-pyrrolizin-7a(5H)-yl)methoxy)pyrido[4,3-d]pyrimidine

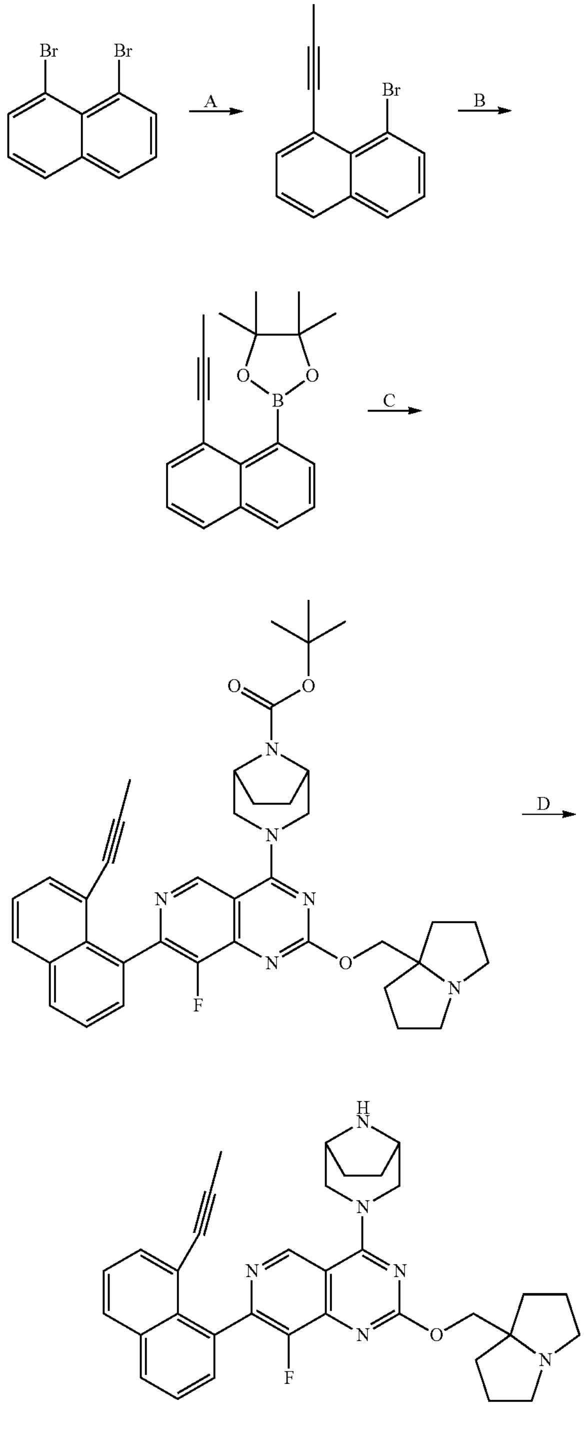

4-((1R,5S)-3,8-diazabicyclo[3.2.1]octan-3-yl)-8-fluoro-7-(8-(prop-1-yn-1-yl)naphthalen-1-yl)-2-((tetrahydro-1H-pyrrolizin-7a(5H)-yl)methoxy)pyrido[4,3-d]pyrimidine (0.0113 g, 0.0201 mmol, 26.6% yield). LCMS (MM-ES+APCI, Pos): m/z 563.3 (M+H).

Example 196

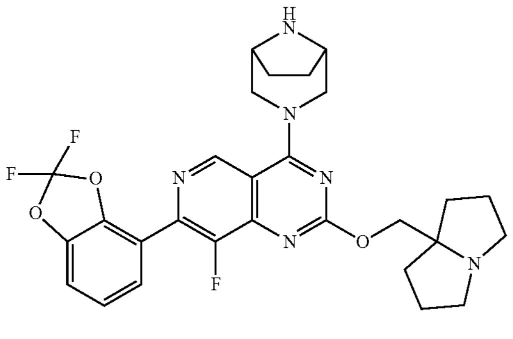 [SMILES: Fc1c(-c2cccc3c2OC(F)(F)O3)ncc2c(N3CC4CCC(C3)N4)nc(OCC34CCCN3CCC4)nc12]

4-((1R,5S)-3,8-diazabicyclo[3.2.1]octan-3-yl)-7-(2,2-difluorobenzo[d][1,3]dioxol-4-yl)-8-fluoro-2-((tetrahydro-1H-pyrrolizin-7a(5H)-yl)methoxy)pyrido[4,3-d]pyrimidine

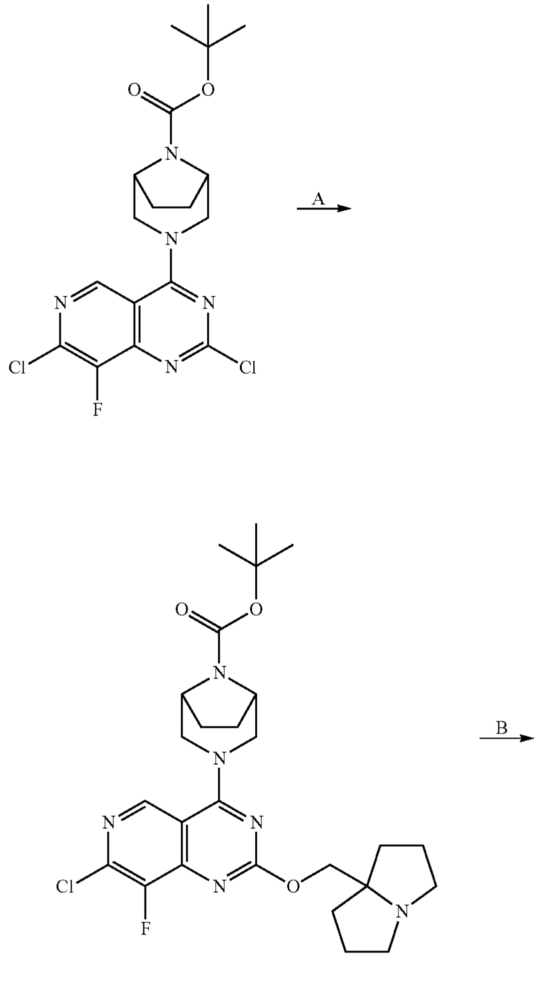

-continued

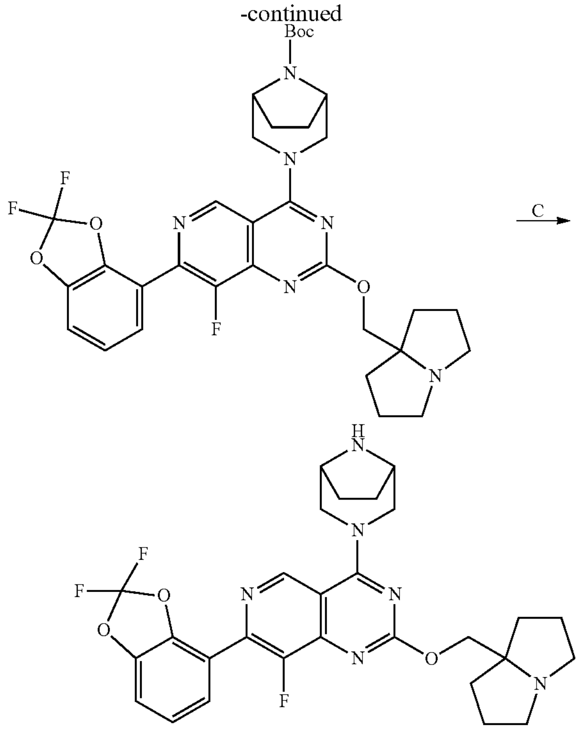

4-((1R,5S)-3,8-diazabicyclo[3.2.1]octan-3-yl)-7-(2,2-difluorobenzo[d][1,3]dioxol-4-yl)-8-fluoro-2-((tetrahydro-1H-pyrrolizin-7a(5H)-yl)methoxy)pyrido[4,3-d]pyrimidine (55.2 mg, 0.1 mmol, 76.7% yield). LCMS (MM-ES+APCI, Pos): m/z 555.3 (M+H).

Example 197

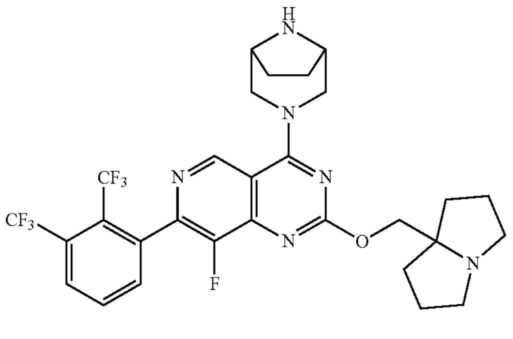 [SMILES: Fc1c(-c2cccc(C(F)(F)F)c2C(F)(F)F)ncc2c(N3CC4CCC(C3)N4)nc(OCC34CCCN3CCC4)nc12]

4-((1R,5S)-3,8-diazabicyclo[3.2.1]octan-3-yl)-7-(2,3-bis(trifluoromethyl)phenyl)-8-fluoro-2-((tetrahydro-1H-pyrrolizin-7a(5H)-yl)methoxy)pyrido[4,3-d]pyrimidine Synthesized substituting (2,3-according to Example 196 bis(trifluoromethyl)phenyl) boronic acid in place of 2,2-difluorobenzo[1,3]dioxole-4-boronic acid in step B to afford tert-butyl(1R,5S)-3-(7-(2,3-bis(trifluoromethyl)phenyl)-8-fluoro-2-((tetrahydro-1H-pyrrolizin-7a(5H)-yl)methoxy) pyrido[4,3-d]pyrimidin-4-yl)-3,8-diazabicyclo[3.2.1]octane-8-carboxylate (39.3 mg, 0.06 mmol, 29.5% yield). LCMS (MM-ES+APCI, Pos): m/z 611.2 (M+H).

Example 198

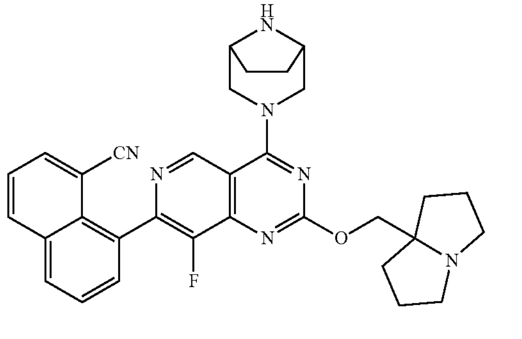 [SMILES: N#Cc1cccc2cccc(-c3ncc4c(N5CC6CCC(C5)N6)nc(OCC56CCCN5CCC6)nc4c3F)c12]

8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-1-naphthonitrile Synthesized according to Example 196 substituting 8-(4,4,5,5-tetramethyl-1,3,2-dioxaborolan-2-yl)-1-naphthonitrile in place of 2,2-difluorobenzo[1,3]dioxole-4-boronic acid and methanesulfonato (2-dicyclohexylphosphino-2',4',6'-tri-i-propyl-1,1'-biphenyl)(2'-amino-1,1'-biphenyl-2-yl)palladium(II) in place of RuPhos Palladacycle Gen. 3 in step B to afford 8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-1-naphthonitrile (10.8 mg, 0.02 mmol, 42.6% yield). LCMS (MM-ES+APCI, Pos): m/z 550.3 (M+H).

Example 199

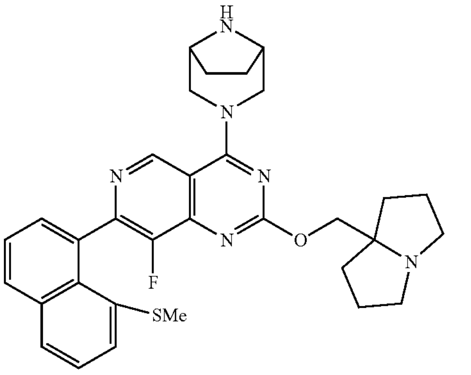 [SMILES: CSc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-7-(8-(methylthio)naphthalen-1-yl)-2-((tetrahydro-1H-pyrrolizin-7a(5H)-yl)methoxy)pyrido[4,3-d]pyrimidine

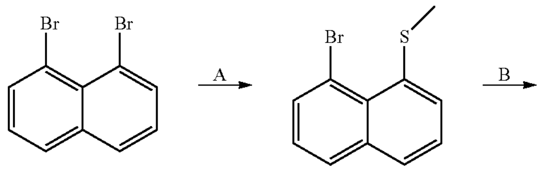

-continued

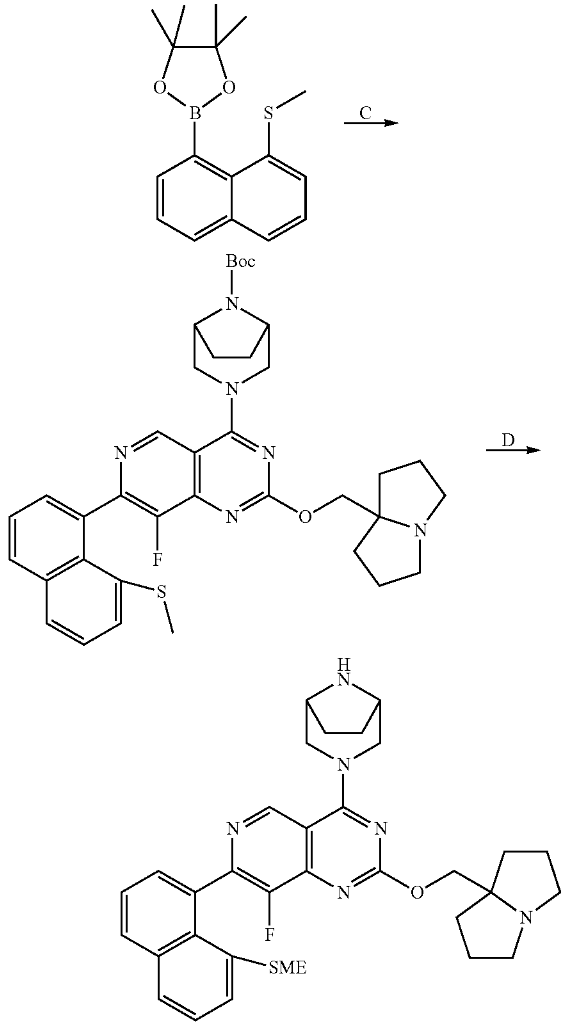

4-((1R,5S)-3,8-diazabicyclo[3.2.1]octan-3-yl)-8-fluoro-7-(8-(methylthio)naphthalen-1-yl)-2-((tetrahydro-1H-pyrrolizin-7a(5H)-yl)methoxy)pyrido[4,3-d]pyrimidine (3.28 mg, 96%). LCMS (MM-ES+APCI, Pos): m/z 571.3 [M+H].

Example 200

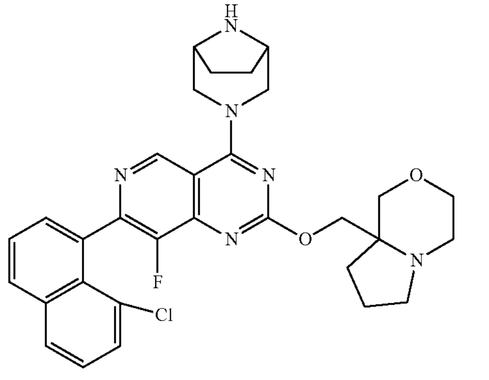 [SMILES: Fc1c(-c2cccc3cccc(Cl)c23)ncc2c(N3CC4CCC(C3)N4)nc(OCC34CCCN3CCOC4)nc12]

8a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolo[2,1-c][1,4]oxazine

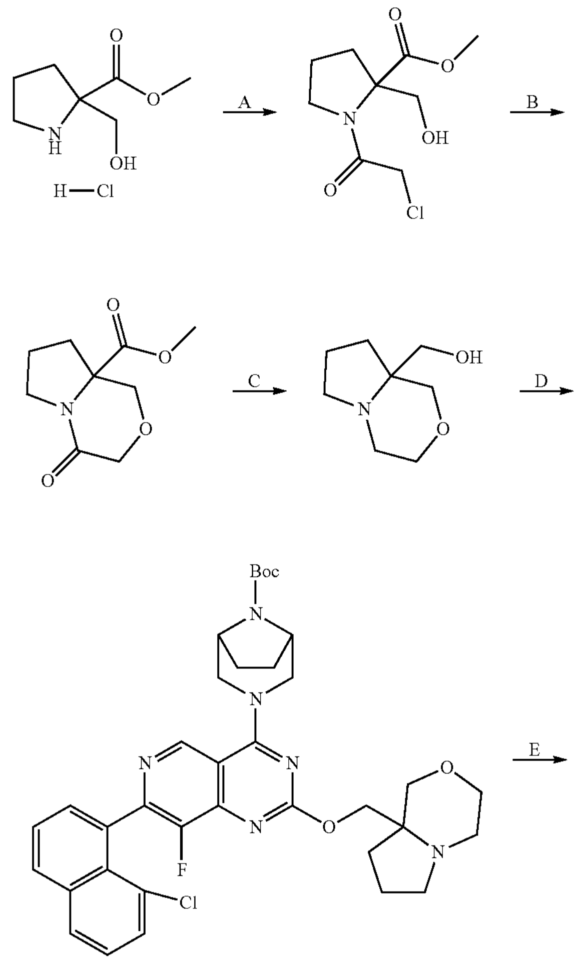

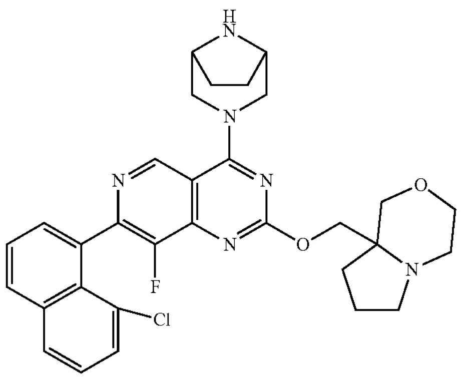

8a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolo[2,1-c][1,4]oxazine (22 mg, 71%). LCMS (MM-ES+APCI, Pos): m/z 575.2 [M+H].

Example 201

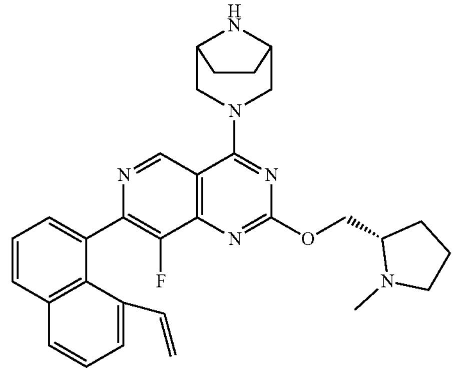 [SMILES: C=Cc1cccc2cccc(-c3ncc4c(N5CC6CCC(C5)N6)nc(OC[C@@H]5CCCN5C)nc4c3F)c12]

4-((1R,5S)-3,8-diazabicyclo[3.2.1]octan-3-yl)-8-fluoro-2-(((S)-1-methylpyrrolidin-2-yl)methoxy)-7-(8-vinylnaphthalen-1-yl)pyrido[4,3-d]pyrimidine

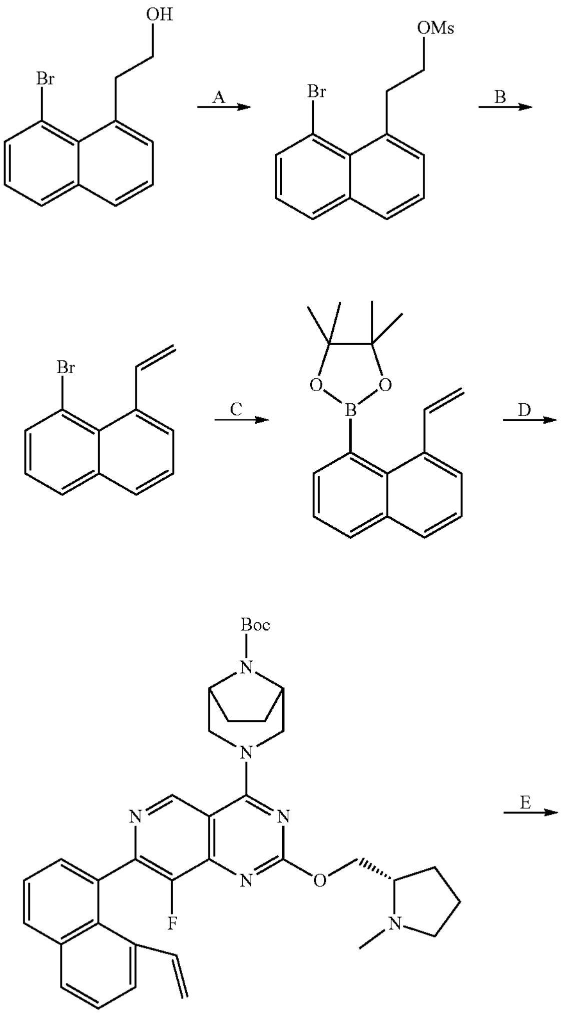

-continued

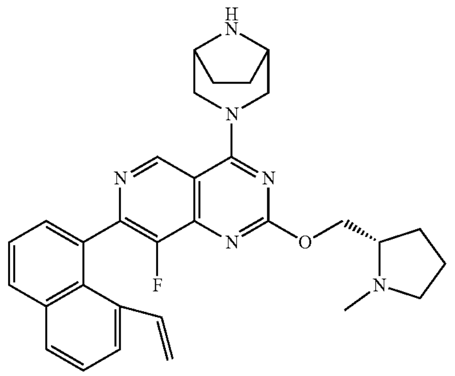

4-((1R,5S)-3,8-diazabicyclo[3.2.1]octan-3-yl)-8-fluoro-2-(((S)-1-methylpyrrolidin-2-yl)methoxy)-7-(8-vinylnaphthalen-1-yl)pyrido[4,3-d]pyrimidine. Synthesized according to Example 1, Step G using tert-butyl(1R,5S)-3-(8-fluoro-2-(((S)-1-methylpyrrolidin-2-yl)methoxy)-7-(8-vinylnaphthalen-1-yl)pyrido[4,3-d]pyrimidin-4-yl)-3,8-diazabicyclo[3.2.1]octane-8-carboxylate in place of tert-butyl 3-(7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate to yield the title compound (1.8 mg, 30%). LCMS (MM-ES+APCI, Pos): m/z 525.3 [M+H].

Example 202

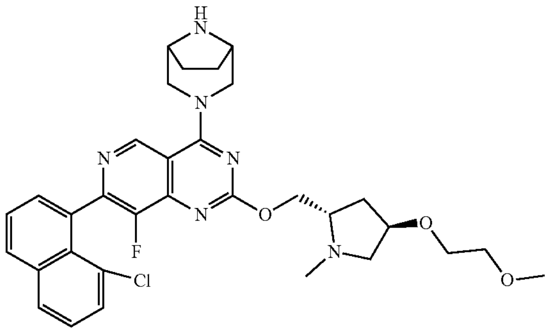 [SMILES: COCCO[C@@H]1C[C@@H](COc2nc(N3CC4CCC(C3)N4)c3cnc(-c4cccc5cccc(Cl)c45)c(F)c3n2)N(C)C1]

4-((1R,5S)-3,8-diazabicyclo[3.2.1]octan-3-yl)-7-(8-chloronaphthalen-1-yl)-8-fluoro-2-(((2S,4R)-4-(2-methoxyethoxy)-1-methylpyrrolidin-2-yl)methoxy)pyrido[4,3-d]pyrimidine

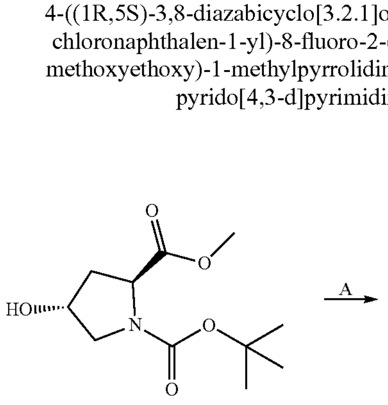

-continued

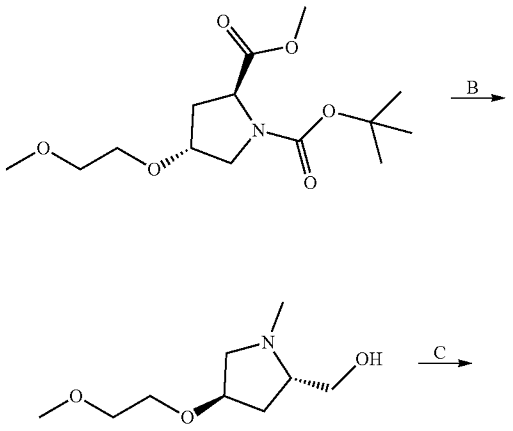

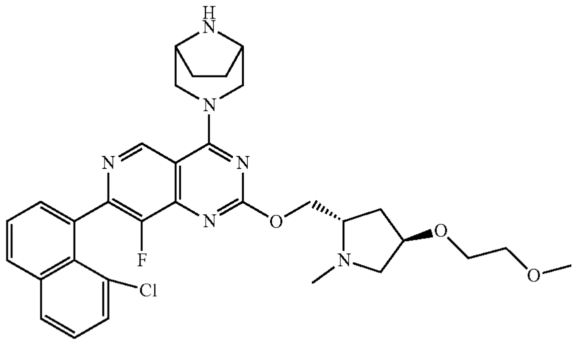

4-((1R,5S)-3,8-diazabicyclo[3.2.1]octan-3-yl)-7-(8-chloronaphthalen-1-yl)-8-fluoro-2-(((2S,4R)-4-(2-methoxyethoxy)-1-methylpyrrolidin-2-yl)methoxy)pyrido[4,3-d]pyrimidine (12.7 mg, 0.02 mmol, 74% yield). LCMS (MM-ES+APCI, Pos): m/z 607.3 (M+H).

Example 203

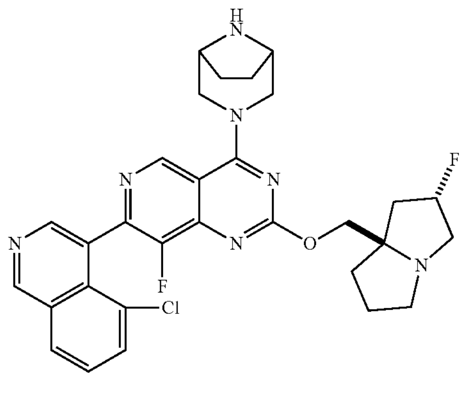

4-((1R,5S)-3,8-diazabicyclo[3.2.1]octan-3-yl)-7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidine

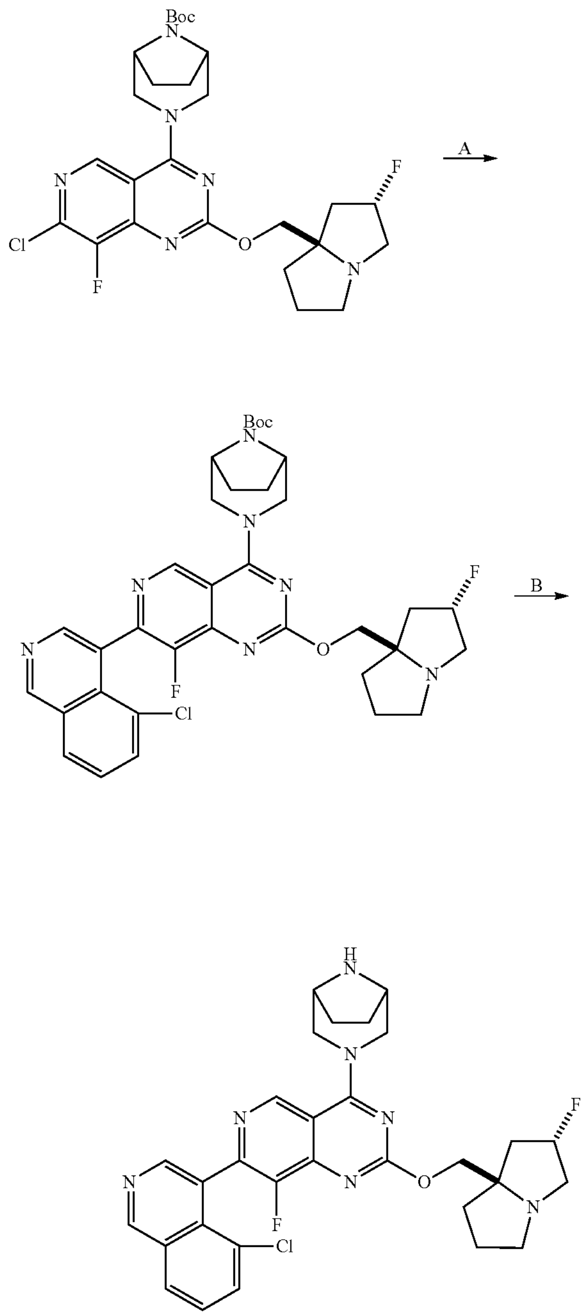

4-((1R,5S)-3,8-diazabicyclo[3.2.1]octan-3-yl)-7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidine as the dihydrochloride salt (16 mg, 0.025 mmol, 51%). LCMS (MM-ES+APCI, Pos): m/z 578.2 (M+H).

Example 204

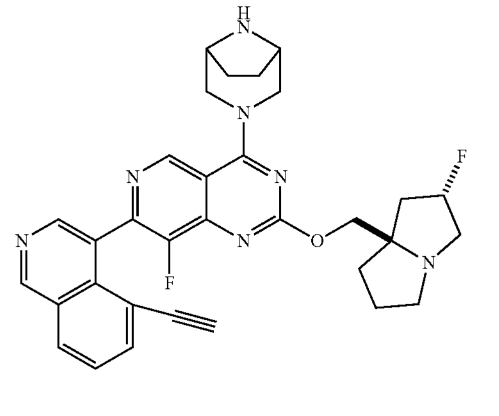

4-((1R,5S)-3,8-diazabicyclo[3.2.1]octan-3-yl)-7-(5-ethynylisoquinolin-4-yl)-8-fluoro-2-(((2S,7aR)-2-fluorotetrahydro-1H-pyrrolizin-7a(5H)-yl)methoxy)pyrido[4,3-d]pyrimidine

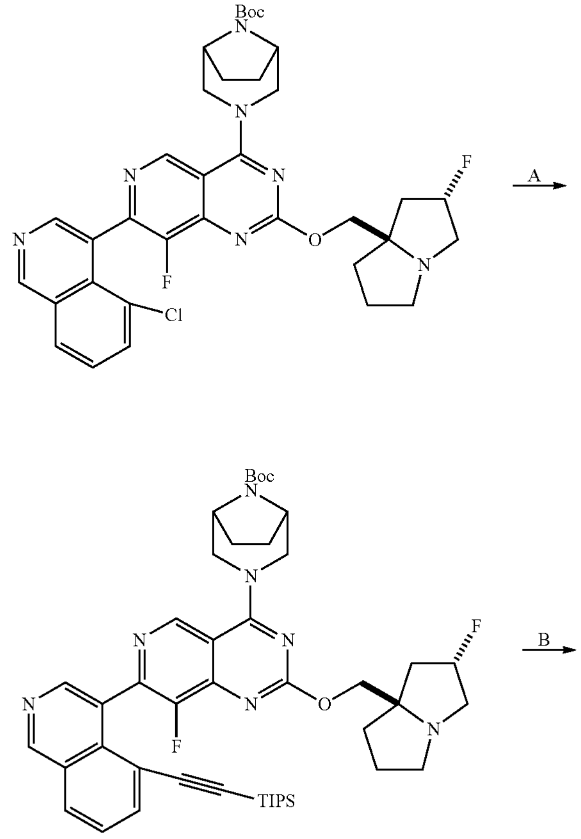

-continued

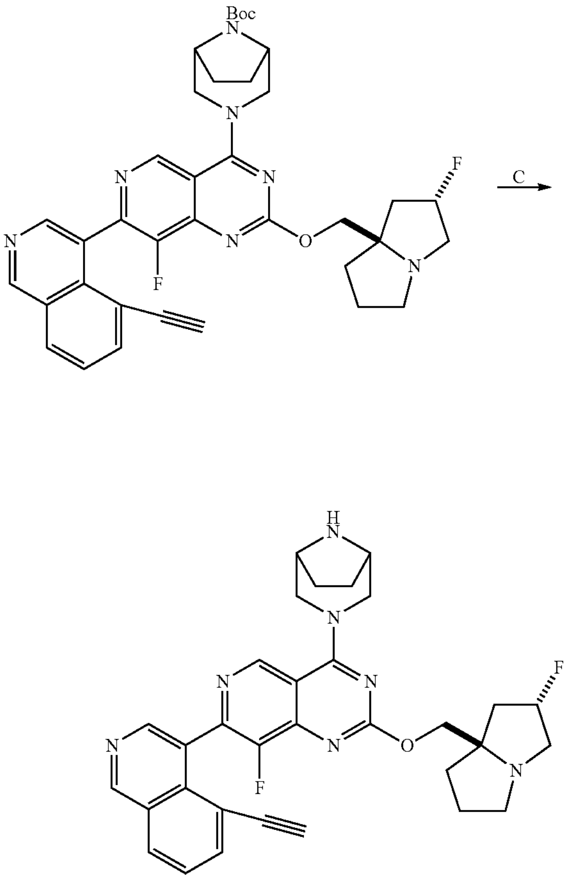

4-((1R,5S)-3,8-diazabicyclo[3.2.1]octan-3-yl)-7-(5-ethynylisoquinolin-4-yl)-8-fluoro-2-(((2S,7aR)-2-fluorotetrahydro-1H-pyrrolizin-7a(5H)-yl)methoxy)pyrido[4,3-d]pyrimidine as the dihydrochloride salt (1.8 mg, 0.003 mmol, 8%). LCMS (MM-ES+APCI, Pos): m/z 568.2 (M+H).

Example 205

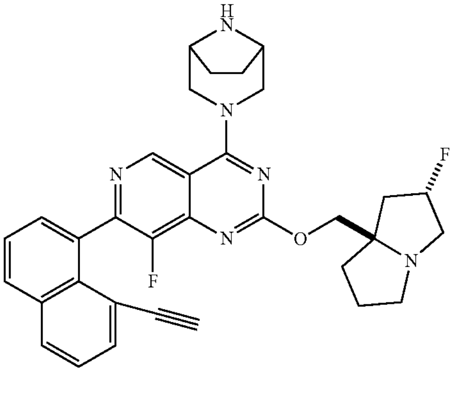

4-((1R,5S)-3,8-diazabicyclo[3.2.1]octan-3-yl)-7-(8-ethynylnaphthalen-1-yl)-8-fluoro-2-(((2S,7aR)-2-fluorotetrahydro-1H-pyrrolizin-7a(5H)-yl)methoxy)pyrido[4,3-d]pyrimidine

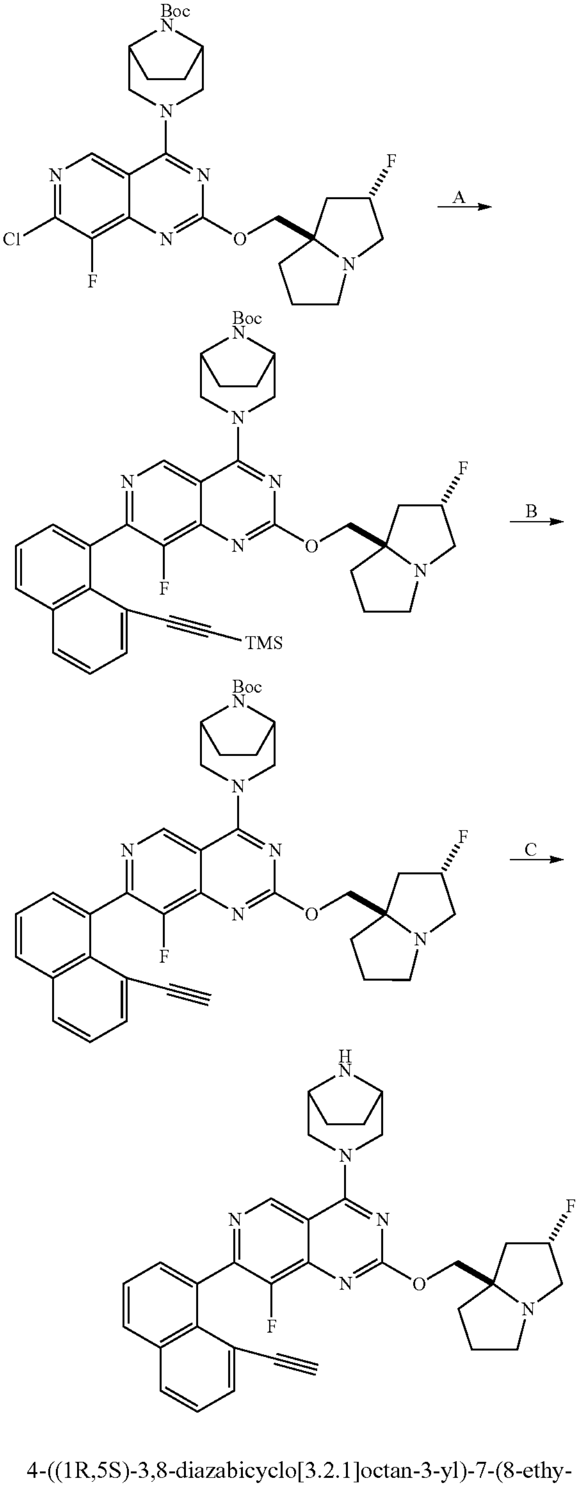

4-((1R,5S)-3,8-diazabicyclo[3.2.1]octan-3-yl)-7-(8-ethynylnaphthalen-1-yl)-8-fluoro-2-(((2S,7aR)-2-fluorotetrahydro-1H-pyrrolizin-7a(5H)-yl)methoxy)pyrido[4,3-d]pyrimidine as the dihydrochloride salt (3.9 mg, 0.006 mmol, 45%). LCMS (MM-ES+APCI, Pos): m/z 567.3 (M+H).

Example 206

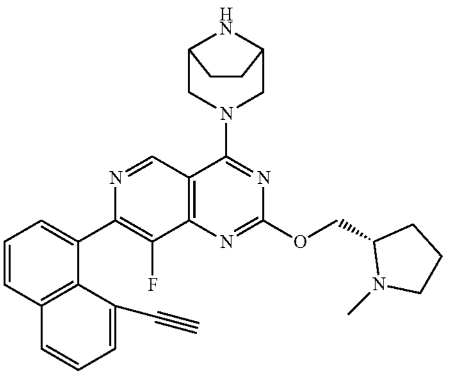 [SMILES: C#Cc1cccc2cccc(-c3ncc4c(N5CC6CCC(C5)N6)nc(OC[C@@H]5CCCN5C)nc4c3F)c12]

4-((1R,5S)-3,8-diazabicyclo[3.2.1]octan-3-yl)-7-(8-ethynylnaphthalen-1-yl)-8-fluoro-2-(((S)-1-methylpyrrolidin-2-yl)methoxy)pyrido[4,3-d]pyrimidine

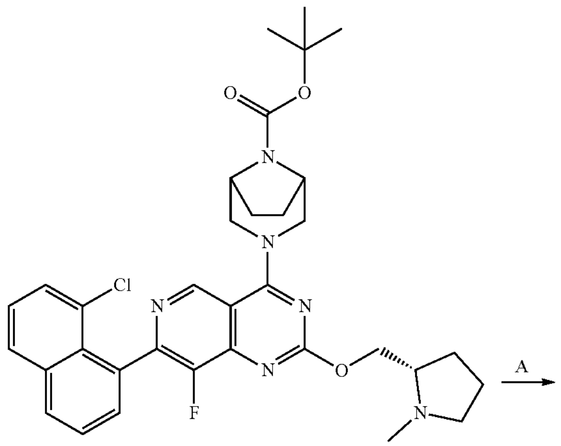

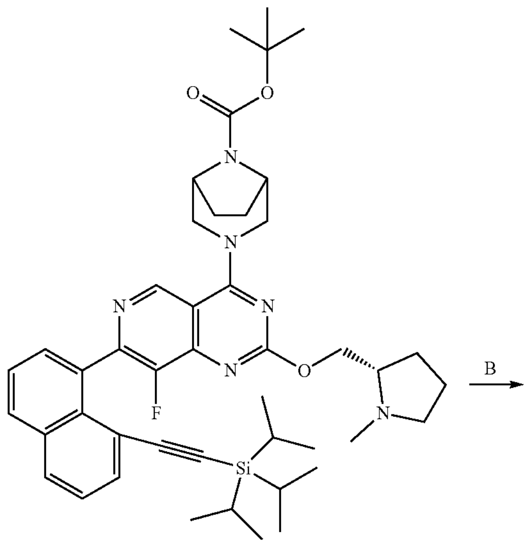

-continued

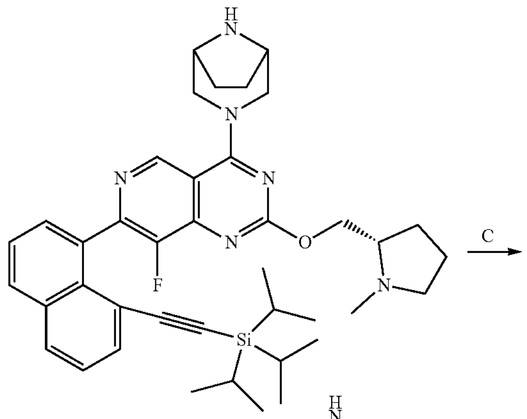

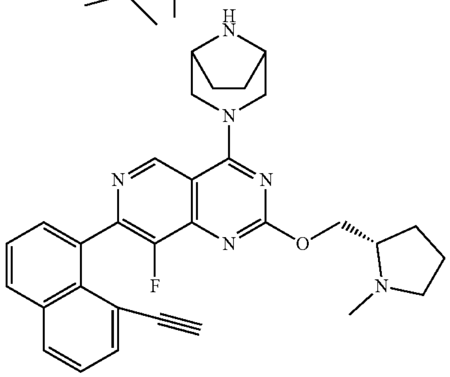

4-((1R,5S)-3,8-diazabicyclo[3.2.1]octan-3-yl)-7-(8-ethynylnaphthalen-1-yl)-8-fluoro-2-(((S)-1-methylpyrrolidin-2-yl)methoxy)pyrido[4,3-d]pyrimidine. To a solution of the 4-((1R,5S)-3,8-diazabicyclo[3.2.1]octan-3-yl)-8-fluoro-2-(((S)-1-methylpyrrolidin-2-yl)methoxy)-7-(8-((triisopropylsilyl)ethynyl)naphthalen-1-yl)pyrido[4,3-d]pyrimidine in THF (0.6 mL) was added TBAF (1.0 M, 0.050 mL, 0.050 mmol). The mixture was stirred at 0° C. for 0.5 h and was purified by preparative C18 HPLC (Gilson, 0-95% $CH_3CN$/$H_2O$ with 0.1% NH4OAc). The desired fractions were combined and neutralized with $NaHCO_3$ (sat.). The mixture was extracted with DCM/IPA (5:1). The extract was dried over $Na_2SO_4$ and concentrated to give the title compound (12 mg, 0.023 mmol, 82% yield over 2 steps) as a brown solid. LCMS (MM-ES+APCI, Pos): m/z 523.3 (M+H).

Example 207

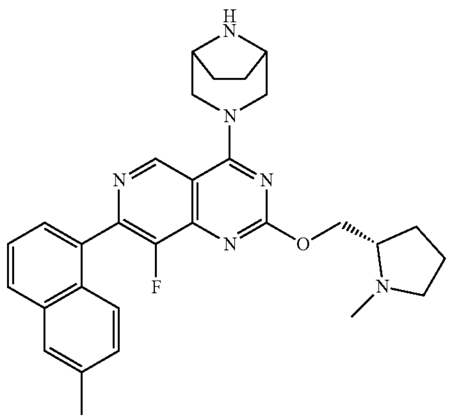 [SMILES: Cc1ccc2c(-c3ncc4c(N5CC6CCC(C5)N6)nc(OC[C@@H]5CCCN5C)nc4c3F)cccc2c1]

4-((1R,5S)-3,8-diazabicyclo[3.2.1]octan-3-yl)-8-fluoro-7-(6-methylnaphthalen-1-yl)-2-(((S)-1-methylpyrrolidin-2-yl)methoxy)pyrido[4,3-d]pyrimidine

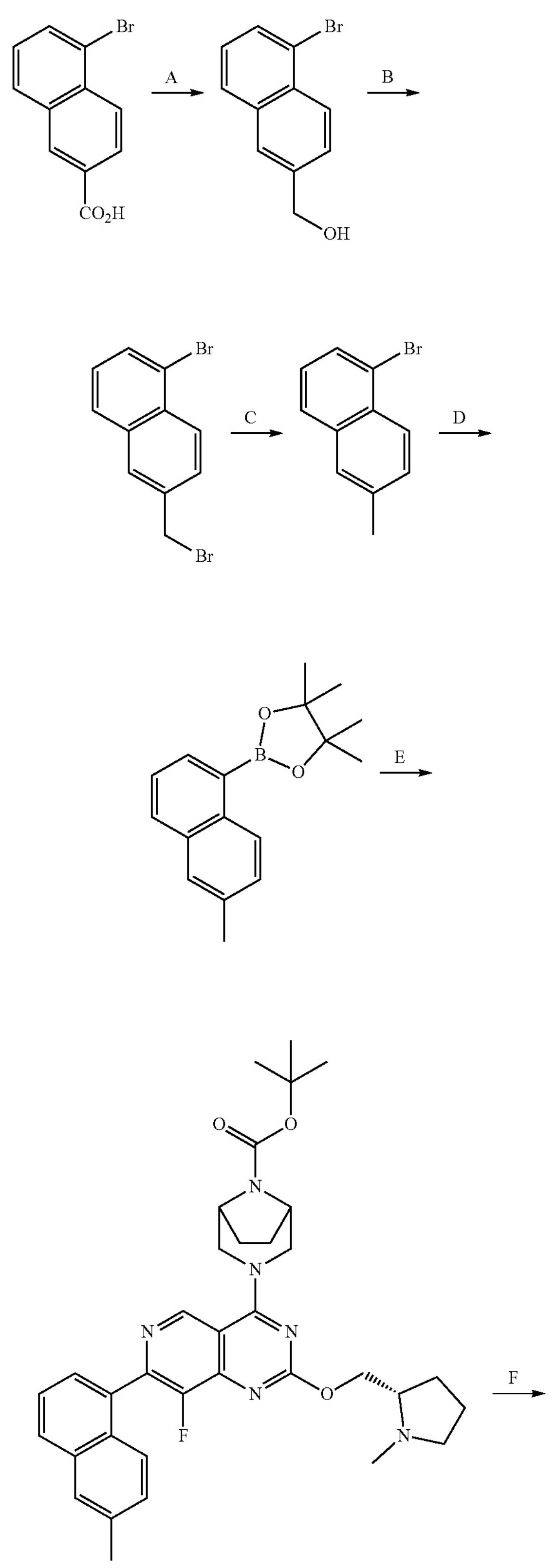

-continued

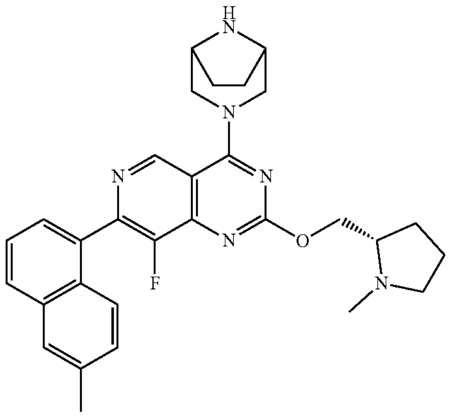

4-((1R,5S)-3,8-diazabicyclo[3.2.1]octan-3-yl)-8-fluoro-7-(6-methylnaphthalen-1-yl)-2-(((S)-1-methylpyrrolidin-2-yl)methoxy)pyrido[4,3-d]pyrimidine. To a solution of tert-butyl(1R,5S)-3-(8-fluoro-7-(6-methylnaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (40 mg, 0.065 mmol) in DCM (1.0 mL, 0.065 mmol) was added TFA (0.50 mL, 0,065 mmol). The solution was stirred at rt for 1 h and concentrated to dryness. The residue was purified by preparative C18 HPLC (Gilson, 0-95% $CH_3CN/H_2O$ with 0.1% TFA). The desired fractions were combined and neutralized with $NaHCO_3$ (sat.). The mixture was extracted with DCM. The combined extract was dried over $Na_2SO_4$ and concentrated to give the desired product (20 mg, 0.039 mmol, 60% yield) as a white solid. LCMS (MM-ES+APCI, Pos): m/z 513.3 (M+H).

Example 208

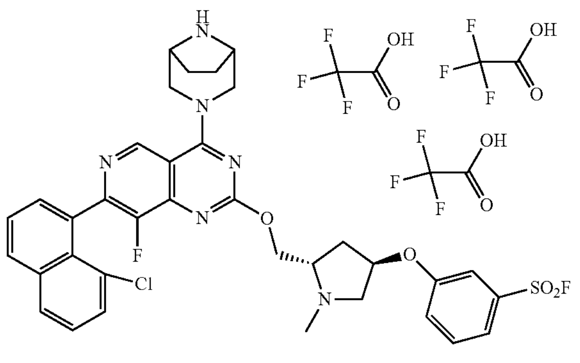

3-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate)

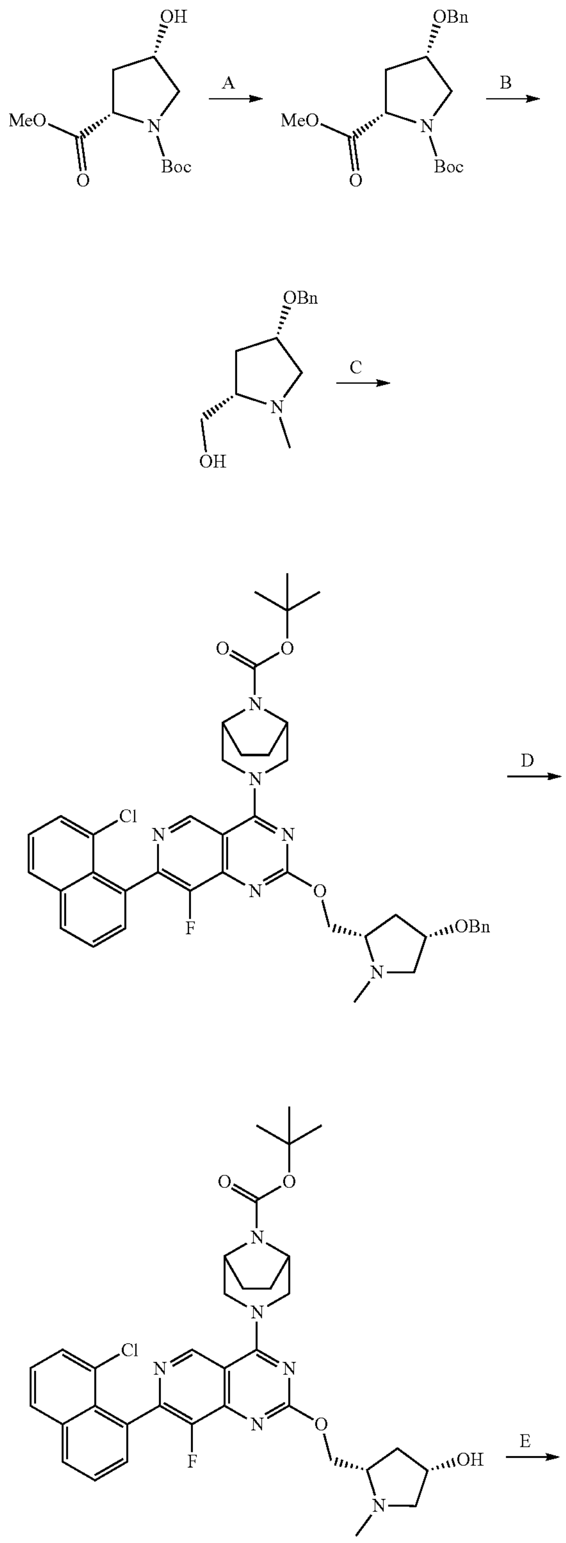

-continued

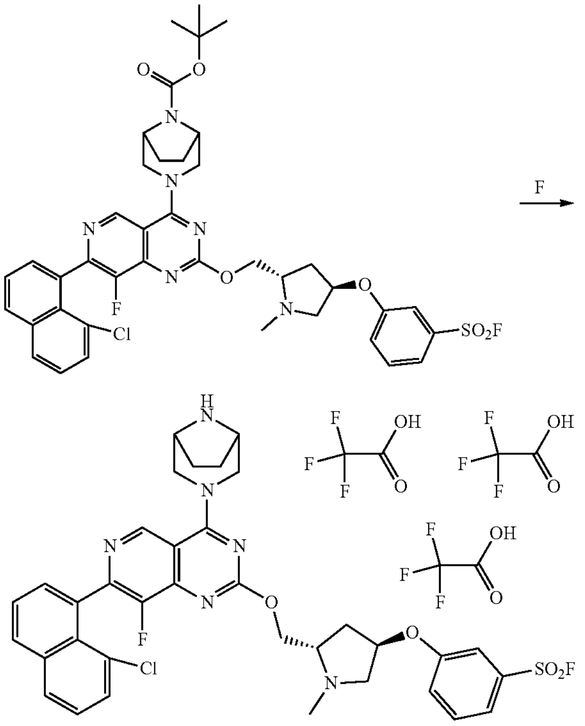

3-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate). To a solution of tert-butyl(1R,5S)-3-(7-(8-chloronaphthalen-1-yl)-8-fluoro-2-(((2S,4R)-4-(3-(fluorosulfonyl) phenoxy)-1-methylpyrrolidin-2-yl)methoxy)pyrido[4,3-d]pyrimidin-4-yl)-3,8-diazabicyclo[3.2.1]octane-8-carboxylate (20 mg, 0.025 mmol) in DCM (1.0 mL) at rt was added TFA (0.5 mL). The solution was stirred at rt for 1 h and concentrated to dryness. The residue was purified by preparative C18 HPLC (Gilson, 0-95% $CH_3CN/H_2O$ with 0.1% TFA). The desired fractions were combined and concentrated to give the title compound (22 mg, 0.021 mmol, 85% yield) as a white solid. LCMS (MM-ES+APCI, Pos): m/z 707.2 (100%), 709.2 (50%)(M+H, M+3).

Example 209

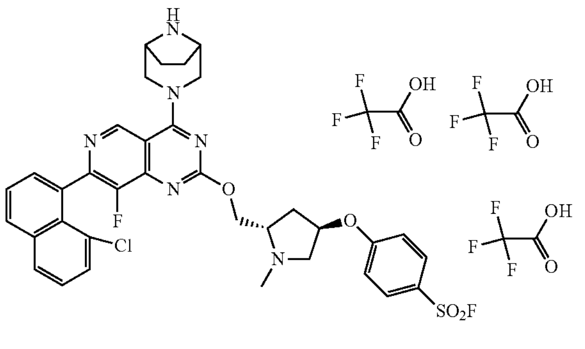

4-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate)

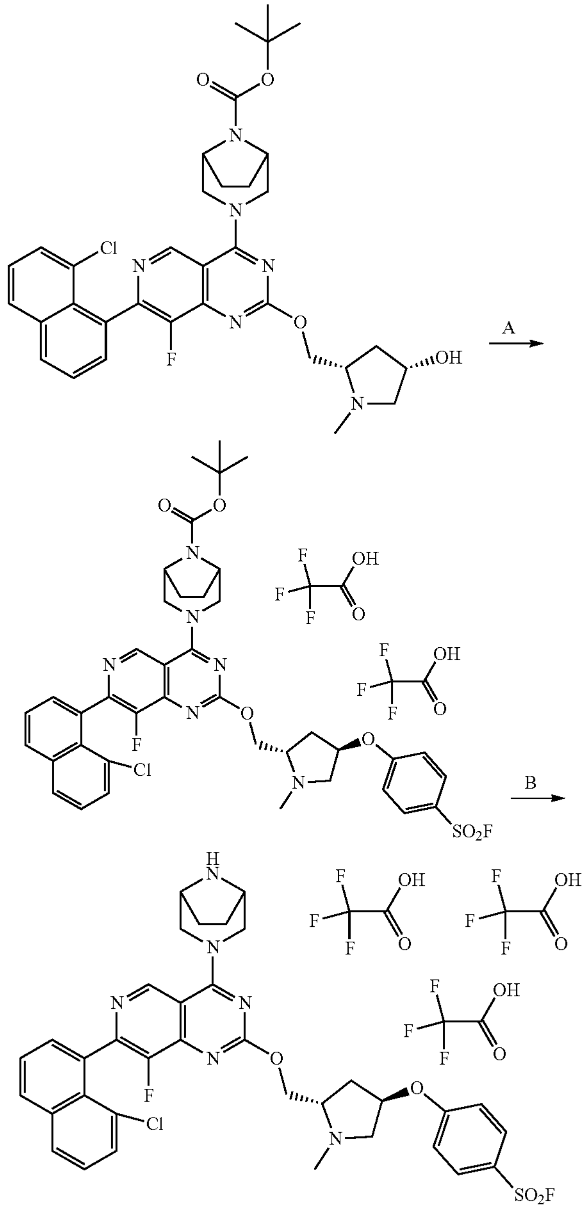

4-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate). To a solution of tert-butyl(1R,5S)-3-(7-(8-chloronaphthalen-1-yl)-8-fluoro-2-(((2S,4R)-4-(4-(fluorosulfonyl) phenoxy)-1-methylpyrrolidin-2-yl)methoxy)pyrido[4,3-d]pyrimidin-4-yl)-3,8-diazabicyclo[3.2.1]octane-8-carboxylate bis(2,2,2-trifluoroacetate) (9 mg, 0.009 mmol) in DCM (1.0 mL) at rt was added TFA (0.5 mL). The solution was stirred at rt for 1 h. The solution was concentrated to dryness to give the title compound (9 mg, 0.009 mmol, 99% yield) as a white solid. LCMS (MM-ES+APCI, Pos): m/z 707.2 (100%), 709.2 (50%)(M+H, M+3).

Example 210

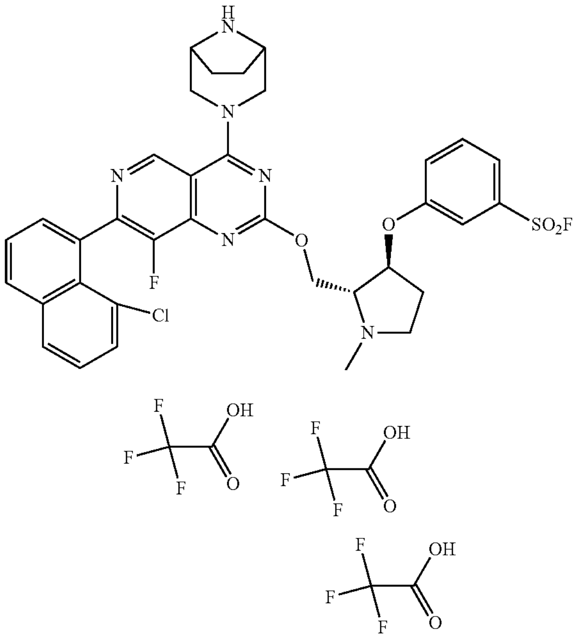

3-(((2R,3S)-2-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate)

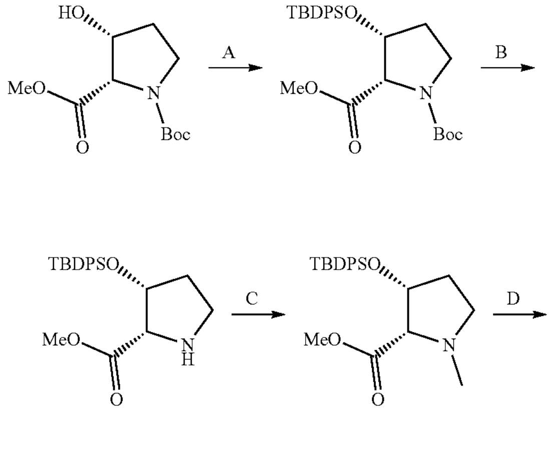

-continued

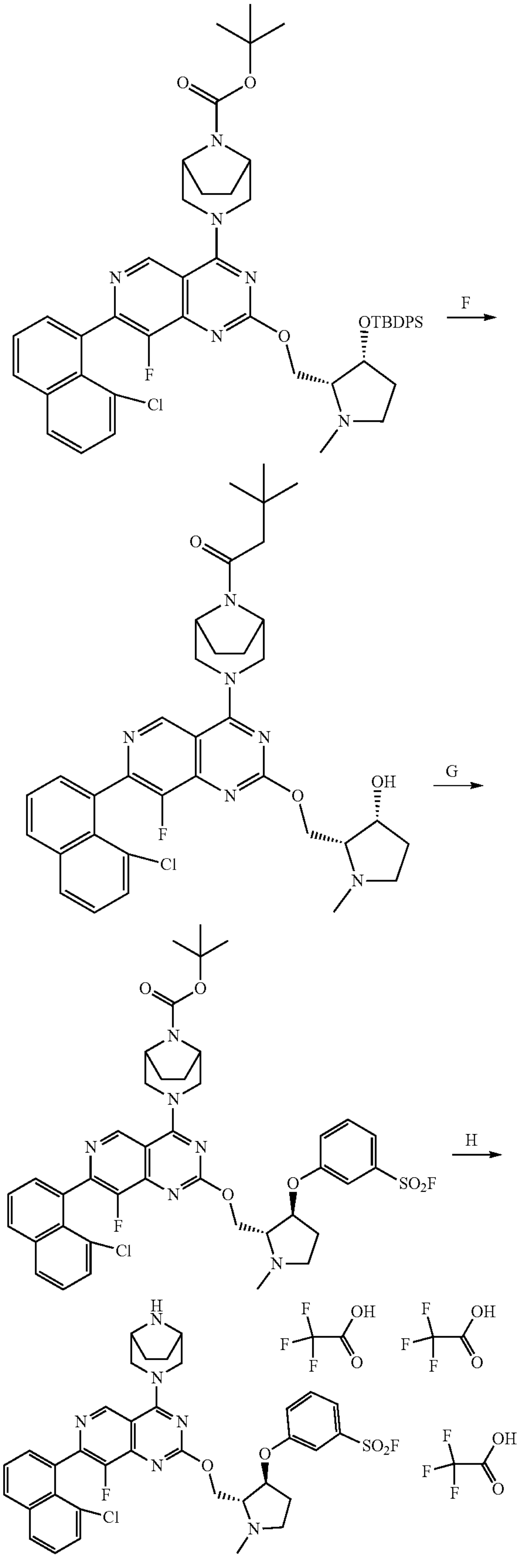

3-(((2R,3S)-2-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate). To a solution of tert-butyl(1R,5S)-3-(7-(8-chloronaphthalen-1-yl)-8-fluoro-2-(((2R,3S)-3-(3-(fluorosulfonyl) phenoxy)-1-methylpyrrolidin-2-yl)methoxy)pyrido[4,3-d]pyrimidin-4-yl)-3,8-diazabicyclo[3.2.1]octane-8-carboxylate (11 mg, 0.014 mmol) in DCM (1.0 mL) at rt was added TFA (0.5 mL). The solution was stirred at rt for 1 h and concentrated to dryness. The residue was purified by preparative C18 HPLC (Gilson, 0-95% $CH_3CN/H_2O$ with 0.1% TFA). The desired fractions were combined and lyophilized to give the title compound (11 mg, 0.011 mmol, 77% yield) as a white solid. LCMS (MM-ES+APCI, Pos): m/z 707.2 (100%), 709.2 (50%)(M+H, M+3).

Example 211

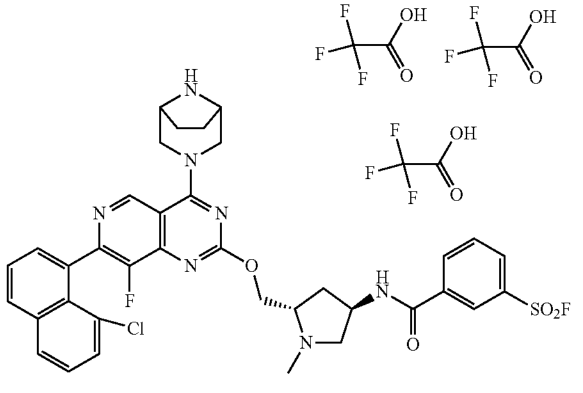

3-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)carbamoyl)benzenesulfonyl fluoride tris(2,2,2-trifluoroacetate)

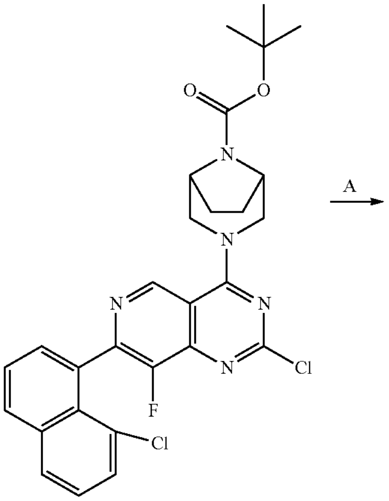

-continued

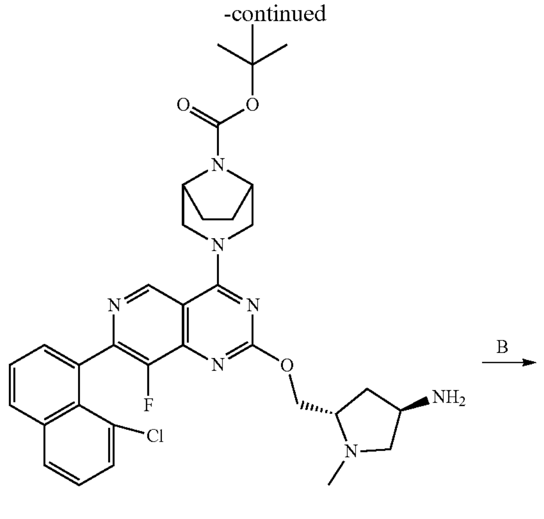

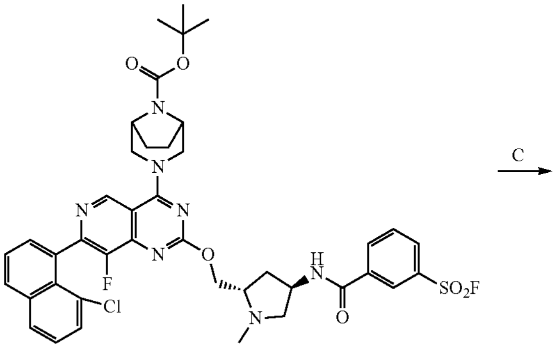

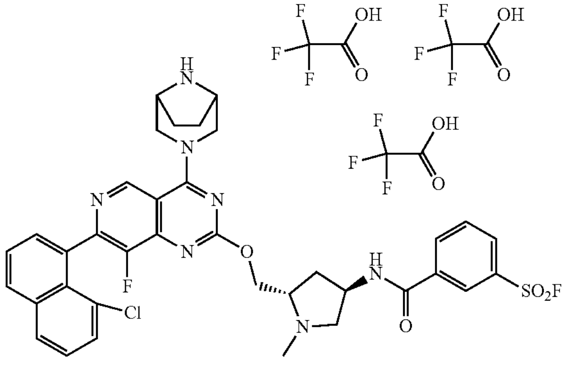

3-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)carbamoyl)benzenesulfonyl fluoride tris(2,2,2-trifluoroacetate). To a solution of tert-butyl(1R,5S)-3-(7-(8-chloronaphthalen-1-yl)-8-fluoro-2-(((2S,4R)-4-(3-(fluorosulfonyl)benzamido)-1-methylpyrrolidin-2-yl)methoxy)pyrido[4,3-d]pyrimidin-4-yl)-3,8-diazabicyclo[3.2.1]octane-8-carboxylate bis(2,2,2-trifluoroacetate) (20 mg, 0.019 mmol) in DCM (1.0 mL) was added 2,2,2-trifluoroacetic acid (0.50 mL). The solution was stirred at rt for 1 h and concentrated to dryness to give the title compound (21 mg, 0.020 mmol, 104% yield) as an off-white solid. LCMS (MM-ES+APCI, Pos): m/z 734.2 (100%), 736.2 (50%)(M+H, M+3).

Example 212

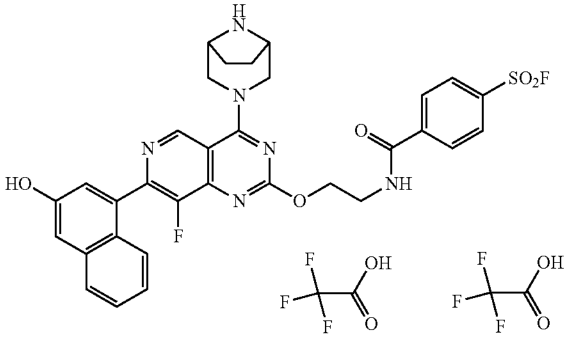 [SMILES: O=C(NCCOc1nc(N2CC3CCC(C2)N3)c2cnc(-c3cc(O)cc4ccccc34)c(F)c2n1)c1ccc(S(=O)(=O)F)cc1 ; O=C(O)C(F)(F)F ; O=C(O)C(F)(F)F]

4-((2-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)ethyl)carbamoyl)benzenesulfonyl fluoride bis(2,2,2-trifluoroacetate)

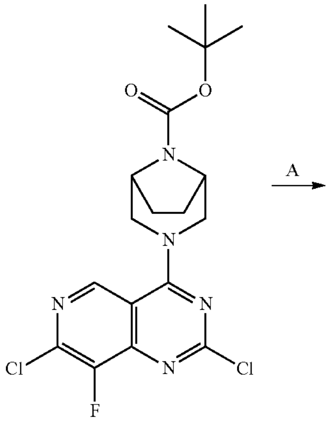

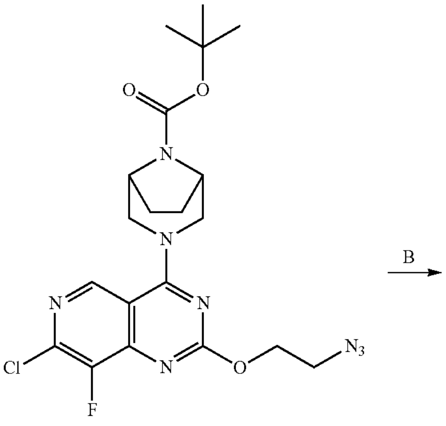

-continued

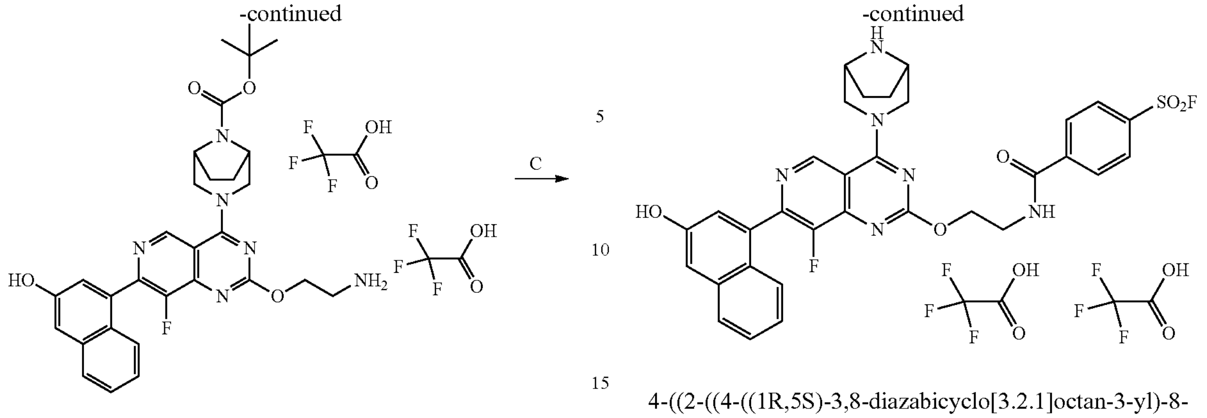

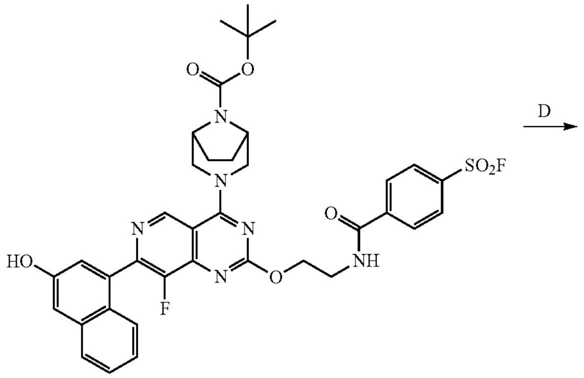

4-((2-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)ethyl)carbamoyl)benzenesulfonyl fluoride bis (2,2,2-trifluoroacetate). To a solution of tert-butyl(1R,5S)-3-(8-fluoro-2-(2-(4-(fluorosulfonyl)benzamido)ethoxy)-7-(3-hydroxynaphthalen-1-yl)pyrido[4,3-d]pyrimidin-4-yl)-3,8-diazabicyclo[3.2.1]octane-8-carboxylate 2,2,2-trifluoroacetate (11 mg, 0.013 mmol) in DCM (1.0 mL) was added 2,2,2-trifluoroacetic acid (0.50 mL). The solution was stirred at rt for 1 h and concentrated to dryness to give the title compound (5 mg, 0.0058 mmol, 45% yield) as an off-white solid. LCMS (MM-ES+APCI, Pos): m/z 647.1 (M+H).

Example 213

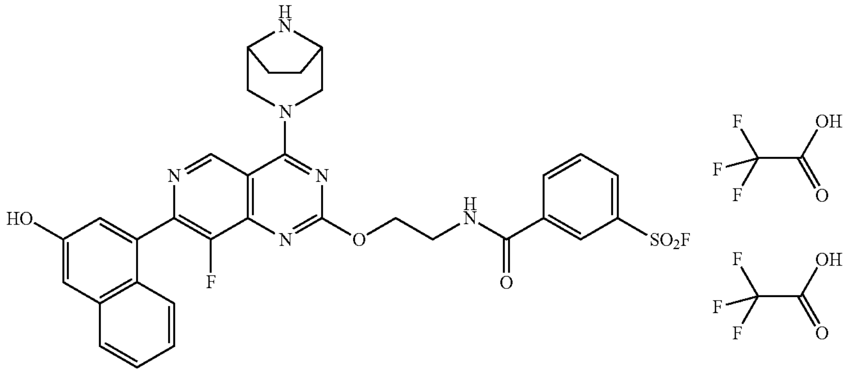 [SMILES: O=C(NCCOc1nc(N2CC3CCC(C2)N3)c2cnc(-c3cc(O)cc4ccccc34)c(F)c2n1)c1cccc(S(=O)(=O)F)c1 ; O=C(O)C(F)(F)F ; O=C(O)C(F)(F)F]

3-((2-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)ethyl)carbamoyl)benzenesulfonyl fluoride bis(2,2,2-trifluoroacetate)

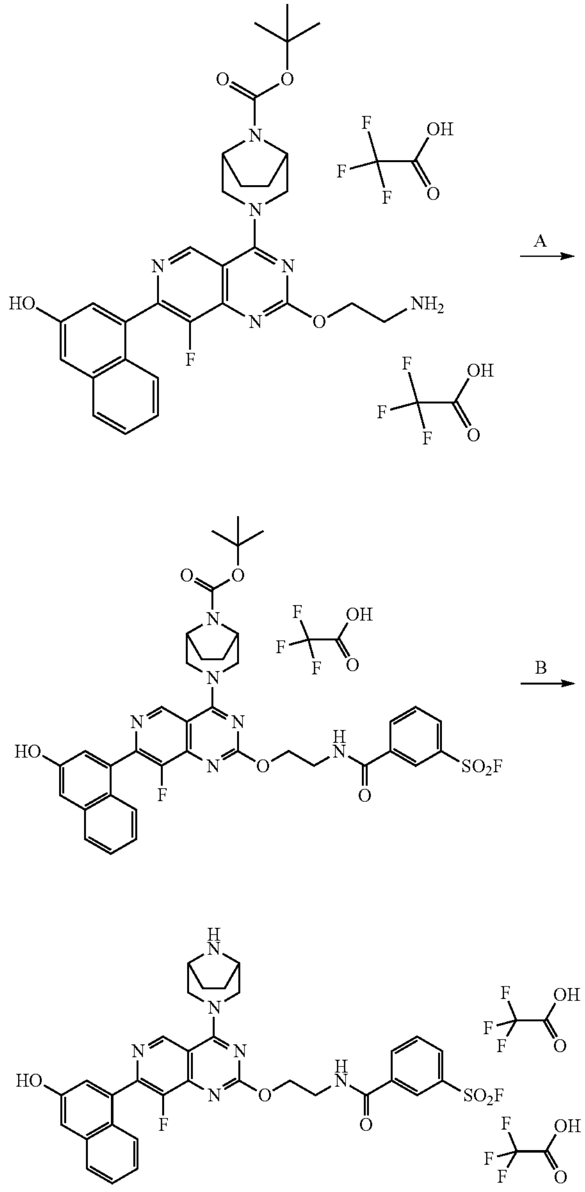

3-((2-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)ethyl)carbamoyl)benzenesulfonyl fluoride bis(2,2,2-trifluoroacetate). To a solution of tert-butyl(1R,5S)-3-(8-fluoro-2-(2-(3-(fluorosulfonyl)benzamido)ethoxy)-7-(3-hydroxynaphthalen-1-yl)pyrido[4,3-d]pyrimidin-4-yl)-3,8-diazabicyclo[3.2.1]octane-8-carboxylate 2,2,2-trifluoroacetate (11 mg, 0.013 mmol) in DCM (1.0 mL, 0.013 mmol) was added 2,2,2-trifluoroacetic acid (0.50 mL). The solution was stirred at rt for 1 h and concentrated to dryness to give the title compound (12 mg, 0.014 mmol, 107% yield) as an off-white solid. LCMS (MM-ES+APCI, Pos): m/z 647.1 (M+H).

Example 214

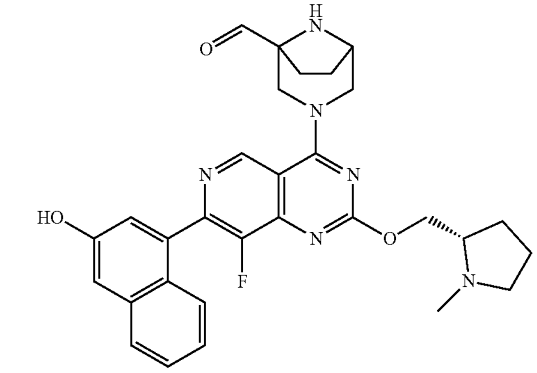 [SMILES: CN1CCC[C@H]1COc1nc(N2CC3CCC(C=O)(C2)N3)c2cnc(-c3cc(O)cc4ccccc34)c(F)c2n1]

3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carbaldehyde

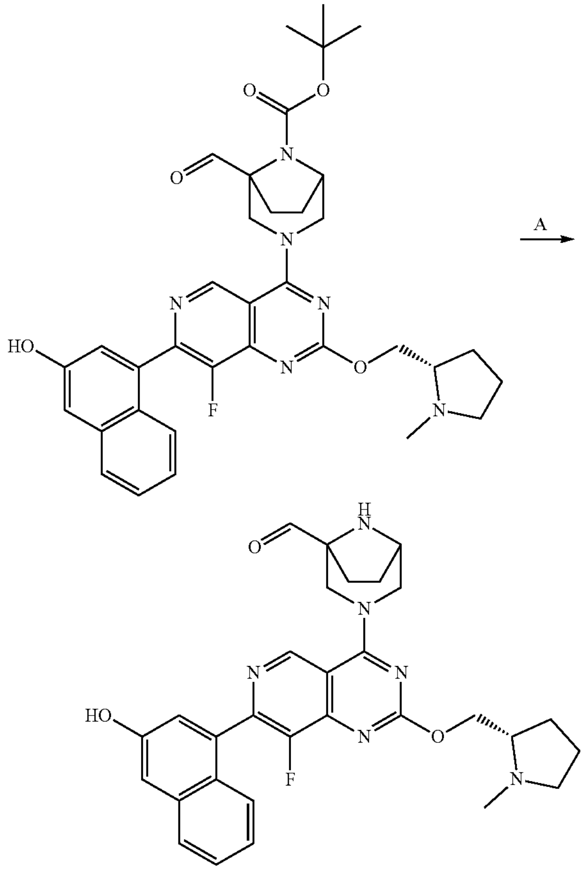

Step A. 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carbaldehyde. To a solution of tert-butyl 3-(8-fluoro-7-(3-hydroxynaphthalen-1-yl)-2-(((S)-1-methylpyrrolidin-2-yl)methoxy)pyrido[4,3-d]pyrimidin-4-yl)-1-formyl-3,8-diazabicyclo[3.2.1]octane-8-carboxylate (synthesized in Example 157) (50.0 mg, 0.078 mmol) in DCM (0.78 mL) was added TFA (0.26 mL, 0.078 mmol). The solution was stirred at rt for 0.5 h and concentrated to dryness to give a yellow solid. The solid was partitioned between $NaHCO_3$ (Sat.) and DCM/IPA (5:1). The two layers were separated, and the organic layer was dried over $Na_2SO_4$ and concentrated to give the title compound (36 mg, 85%) as a light brown solid. LCMS (MM-ES+APCI, Pos): m/z 543.2 (M+H).

Example 215

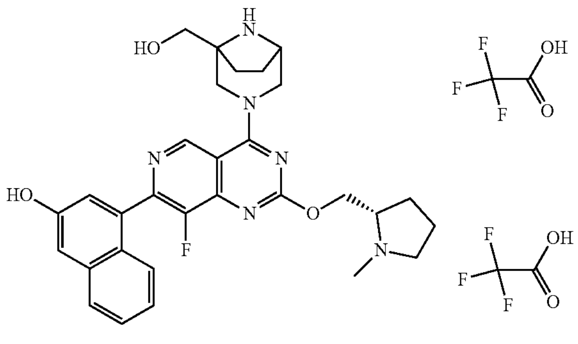

4-(8-fluoro-4-(1-(hydroxymethyl)-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol bis(2,2,2-trifluoroacetate)

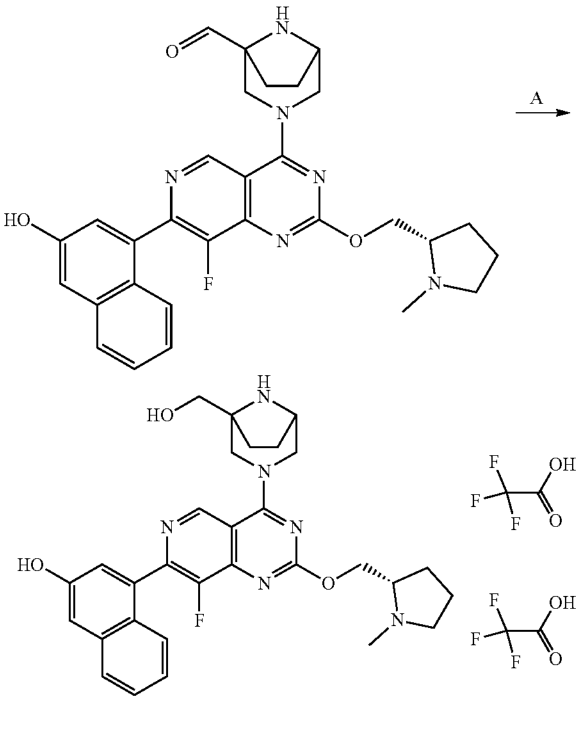

Step A. 4-(8-fluoro-4-(1-(hydroxymethyl)-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol bis (2,2,2-trifluoroacetate). To a solution of 3-(8-fluoro-7-(3-hydroxynaphthalen- 1-yl)-2-(((S)-1-methylpyrrolidin-2-yl)methoxy)pyrido[4,3-d]pyrimidin-4-yl)-3,8-diazabicyclo[3.2.1]octane-1-carbaldehyde (Example 158) (18 mg, 0.033 mmol) in methanol (1.0 mL) was added sodium borohydride (2.5 mg, 0.066 mmol). The solution was stirred at rt for 15 min and concentrated to dryness. The residue was purified by preparative C18 HPLC (Gilson, 0-95% $CH_3CN/H_2O$ with 0.1% TFA). The desired fractions were combined and concentrated to give the title compound (15 mg, 59%) as a yellow solid. LCMS (MM-ES+APCI, Pos): m/z 545.2 (M+H).

Example 216

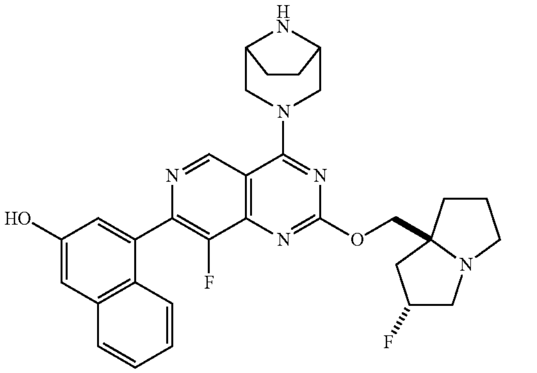

4-(4-((1R,5S)-3,8-diazabicyclo[3.2.1]octan-3-yl)-8-fluoro-2-(((2R)-2-fluorotetrahydro-1H-pyrrolizin-7a(5H)-yl)methoxy)pyrido[4,3-d]pyrimidin-7-yl)naphthalen-2-ol (racemic, trans)

Synthesized according to Example 3, Steps G-I substituting ((2R,7aS)-2-fluorotetrahydro-1H-pyrrolizin-7a(5H)-yl)methanol in place of 2-(1-methyl-1H-imidazol-2-yl)ethan-1-ol in Step G to afford 4-(4-((1R,5S)-3,8-diazabicyclo[3.2.1]octan-3-yl)-8-fluoro-2-(((2R)-2-fluorotetrahydro-1H-pyrrolizin-7a(5H)-yl)methoxy)pyrido[4,3-d]pyrimidin-7-yl)naphthalen-2-ol (1.5 mg, 0.002 mmol, 2%). LCMS (MM-ES+APCI, Pos): m/z 559.2 (M+H).

Example 217

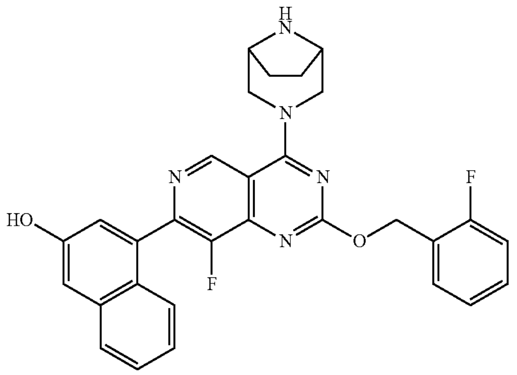 [SMILES: Oc1cc(-c2ncc3c(N4CC5CCC(C4)N5)nc(OCc4ccccc4F)nc3c2F)c2ccccc2c1]

4-(4-((1R,5S)-3,8-diazabicyclo[3.2.1]octan-3-yl)-8-fluoro-2-((2-fluorobenzyl)oxy)pyrido[4,3-d]pyrimidin-7-yl)naphthalen-2-ol Synthesized according to Example 3, Steps G and H substituting 2-fluorobenzyl alcohol in place of 2-(1-methyl-1H-imidazol-2-yl)ethan-1-ol followed by deprotection according to the method of Example 2, Step I (4.17 mg, 0.00794 mmol, 16%). LCMS (MM-ES+APCI, Pos): m/z 526.2 [M+H].

Example 218

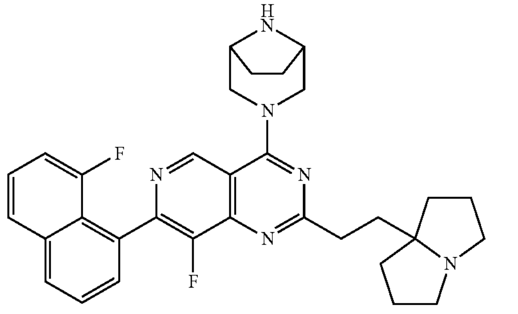

4-((1R,5S)-3,8-diazabicyclo[3.2.1]octan-3-yl)-8-fluoro-7-(8-fluoronaphthalen-1-yl)-2-(2-(tetrahydro-1H-pyrrolizin-7a(5H)-yl)ethyl)pyrido[4,3-d]pyrimidine

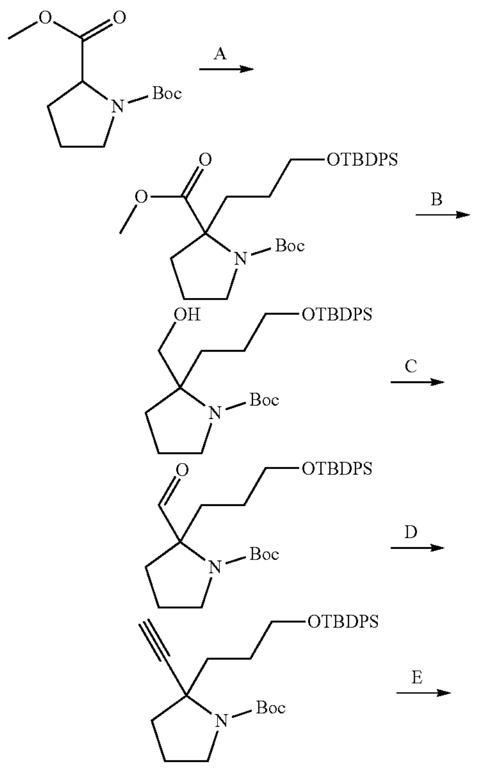

-continued

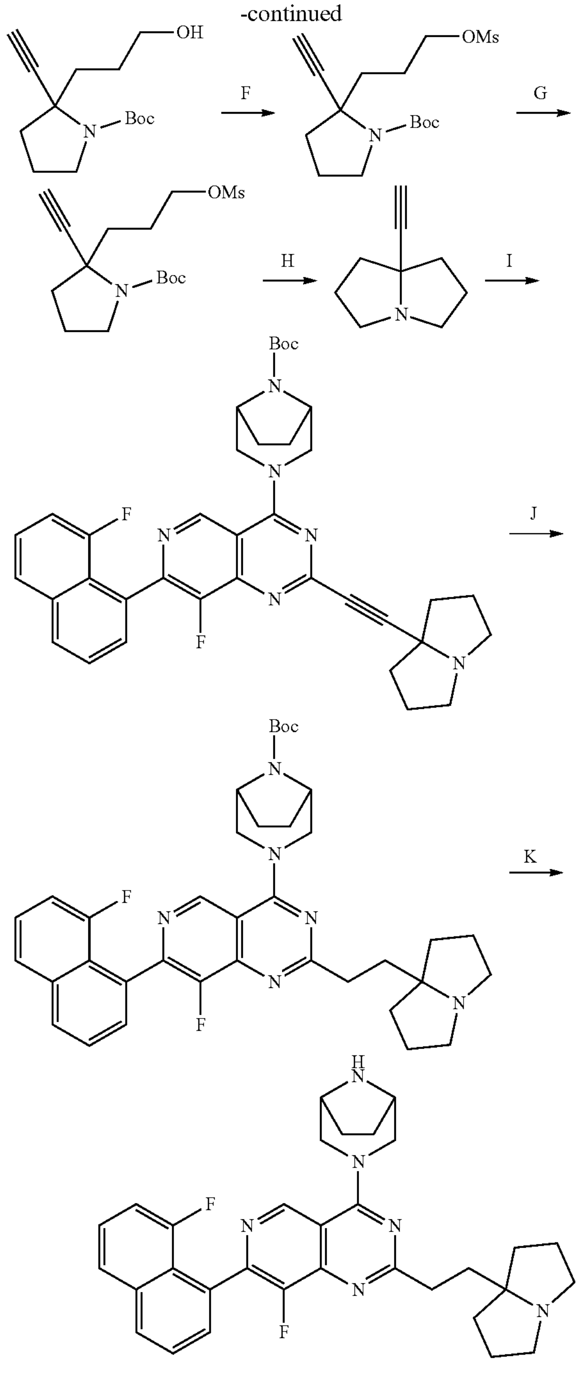

4-((1R,5S)-3,8-diazabicyclo[3.2.1]octan-3-yl)-8-fluoro-7-(8-fluoronaphthalen-1-yl)-2-(2-(hexahydro-1H-pyrrolizin-7a-yl)ethyl)pyrido[4,3-d]pyrimidine. To a solution of (1R,5S)-tert-butyl 3-(8-fluoro-7-(8-fluoronaphthalen-1-yl)-2-(2-(hexahydro-1H-pyrrolizin-7a-yl)ethyl)pyrido[4,3-d]pyrimidin-4-yl)-3,8-diazabicyclo[3.2.1]octane-8-carboxylate (80 mg, 125 μmol, 1.0 eq) in ACN (1.0 mL) was added HCl·dioxane (4.0 M, 1.14 mL, 36.6 eq). The mixture was stirred at 0° C. for 0.5 hour. After completion, the reaction mixture was concentrated under reduced pressure to give residue. The residue was purified by prep-HPLC (column: Phenomenex luna C18 150*25 mm*10 um; mobile phase: [water (0.225% FA)-ACN]; B %: 7%-37%, 11 min) and lyophilized to give the title compound (15.7 mg, 1.6 FA, two steps yield: 20%); Yellow solid. $^{1}$H NMR (400 MHz, methanol-d4) δ 9.24 (s, 1H), 8.15 (br d, J=8.0 Hz, 1H), 7.88 (d, J=7.6 Hz, 1H), 7.77-7.69 (m, 1H), 7.68-7.62 (m, 1H), 7.60-7.52 (m, 1H), 7.26-7.14 (m, 1H), 4.95-4.90 (m, 2H), 4.13-3.98 (m, 2H), 3.97-3.83 (m, 2H), 3.67-3.55 (m, 2H), 3.28-3.13 (m, 4H), 2.44-2.34 (m, 2H), 2.27-1.88 (m, 12H). LCMS [ESI, M+1]: 541.3.

Example 219

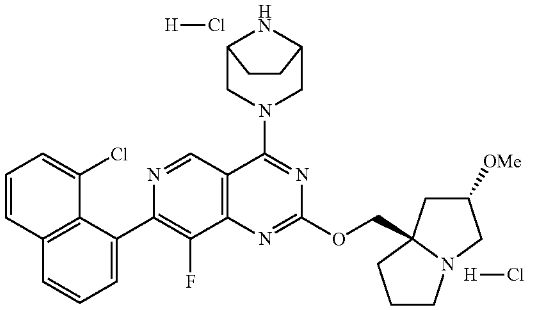

4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-hydrochloride

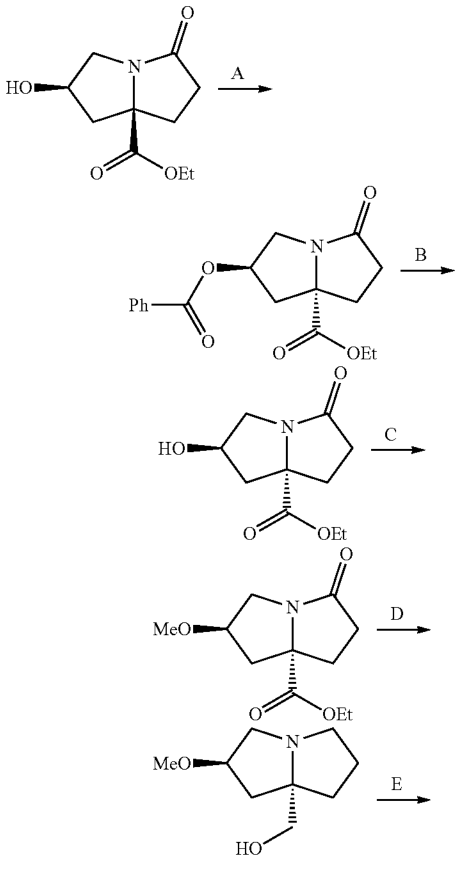

-continued

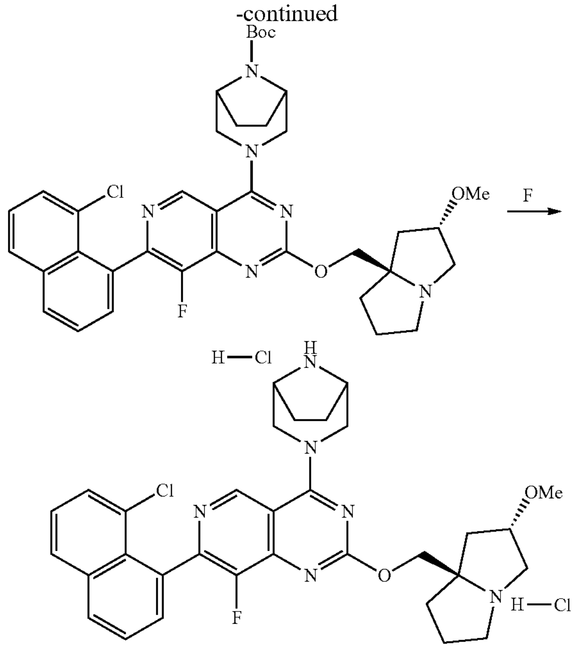

4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-hydrochloride as a yellow solid (13.1 mg, 0.0198 mmol, 78%). LCMS (MM-ES+APCI, Pos): m/z 589.3 (M+H).

Example 220

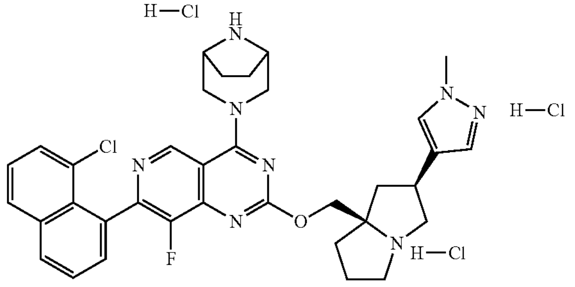

4-((1R,5S)-3,8-diazabicyclo[3.2.1]octan-3-yl)-7-(8-chloronaphthalen-1-yl)-8-fluoro-2-((2-(1-methyl-1H-pyrazol-4-yl)tetrahydro-1H-pyrrolizin-7a(5H)-yl)methoxy)pyrido[4,3-d]pyrimidine tris-hydrochloride salt Synthesized according to Example 219, steps E-F substituting (2-(1-methyl-1H-pyrazol-4-yl)tetrahydro-1H-pyrrolizin-7a(5H)-yl)methanol hydrochloride (cis racemate) for (2-methoxytetrahydro-1H-pyrrolizin-7a(5H)-yl)methanol to yield 4-((1R,5S)-3,8-diazabicyclo[3.2.1]octan-3-yl)-7-(8-chloronaphthalen-1-yl)-8-fluoro-2-((2-(1-methyl-1H-pyrazol-4-yl)tetrahydro-1H-pyrrolizin-7a(5H)-yl)methoxy)pyrido[4,3-d]pyrimidine bis-hydrochloride as a cis racemate (0.033 g, 0.044 mmol, 98% yield). LCMS (MM-ES+APCI, Pos): m/z 639.3 (M+H).

Example 221

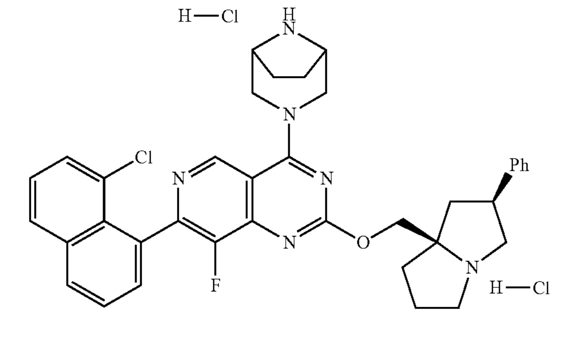

4-((1R,5S)-3,8-diazabicyclo[3.2.1]octan-3-yl)-7-(8-chloronaphthalen-1-yl)-8-fluoro-2-((2-phenyltetrahydro-1H-pyrrolizin-7a(5H)-yl)methoxy)pyrido[4,3-d]pyrimidine bis-hydrochloride salt Synthesized according to Example 219, steps E-F substituting (2-phenyltetrahydro-1H-pyrrolizin-7a(5H)-yl)methanol (cis racemate) for (2-methoxytetrahydro-1H-pyrrolizin-7a(5H)-yl)methanol. (14.2 mg, 0.0200 mmol, 95%). LCMS (MM-ES+APCI, Pos): m/z 635.3 (M+H).

Example 222

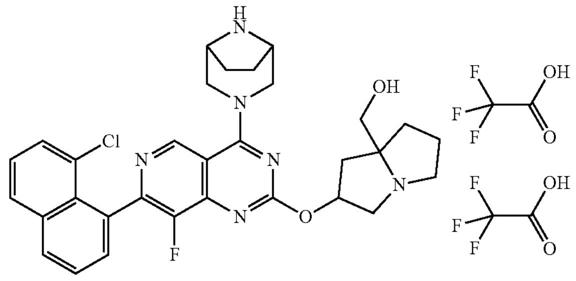

(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)tetrahydro-1H-pyrrolizin-7a(5H)-yl)methanol bis-TFA salt

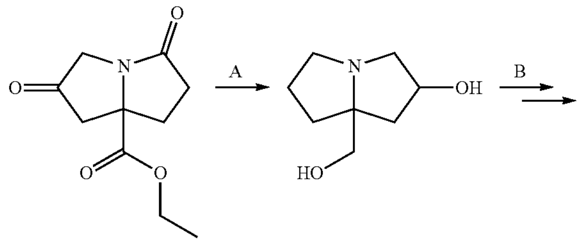

-continued

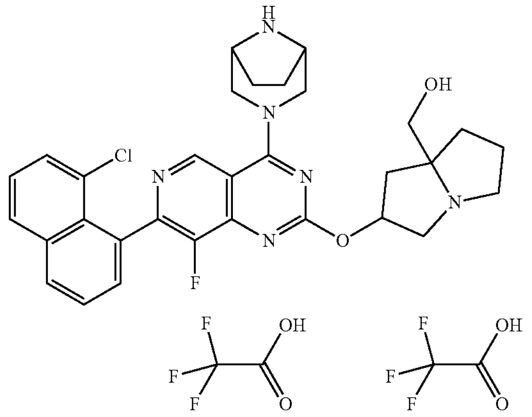

(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)tetrahydro-1H-pyrrolizin-7a(5H)-yl)methanol as the bis TFA salt (5.00 mg, 0.00623 mmol, 16.2%). LCMS (MM-ES+APCI, Pos): m/z 575.3 (M+H).

Example 223

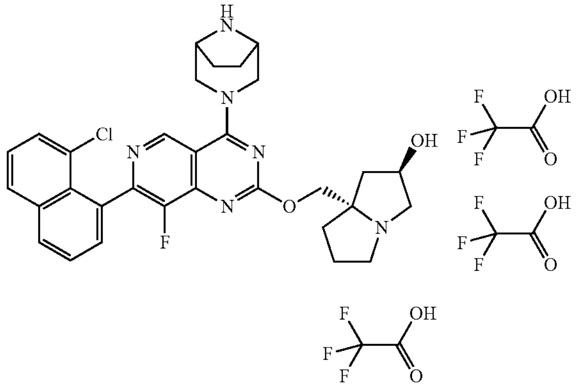

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-ol bis-2,2,2-trifluoroacetate Synthesized according to Example 219, steps E-F substituting 7a-(hydroxymethyl)hexahydro-1H-pyrrolizin-2-ol for ((2-methoxytetrahydro-1H-pyrrolizin-7a(5H)-yl)methanol. The crude residue was purified by preparative C18 HPLC (Gilson, 5-50% $CH_3CN/H_2O$ with 0.1% TFA). Fractions containing the desired product were pooled and lyophilized overnight to yield 7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-ol bis-2,2,2-trifluoroacetate (5.00 mg, 0.00623 mmol, 16.2%). LCMS (MM-ES+APCI, Pos): m/z 575.3 (M+H).

Example 224

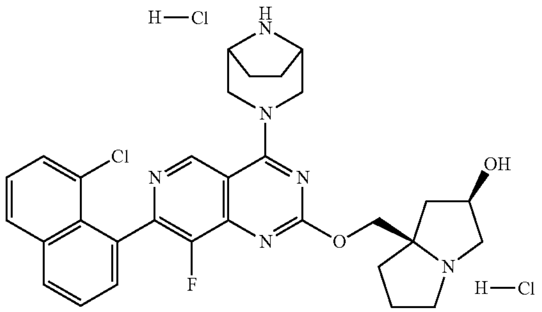

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-ol bis-hydrochloride Synthesized Example 219, steps E-F substituting 7a-(hydroxymethyl)hexahydro-1H-pyrrolizin-2-ol for (2-methoxytetrahydro-1H-pyrrolizin-7a(5H)-yl)methanol to yield (2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)tetrahydro-1H-pyrrolizin-7a(5H)-yl)methanol bis-hydrochloride as a colorless solid, cis racemate (6.07 mg, 0.0099 mmol, 100%). LCMS (MM-ES+APCI, Pos): m/z 575.3 (M+H).

Example 225

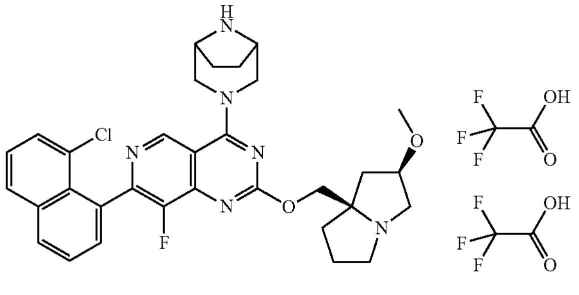

4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-2,2,2-trifluoroacetate

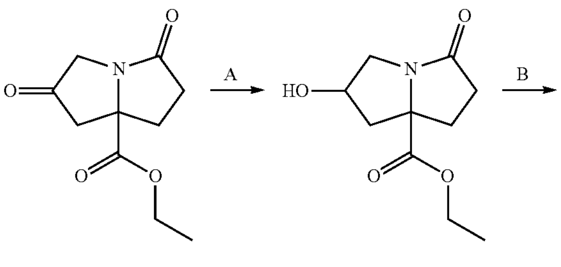

-continued

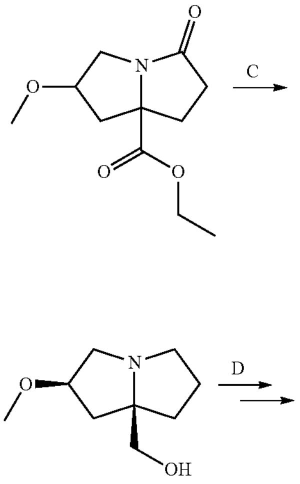

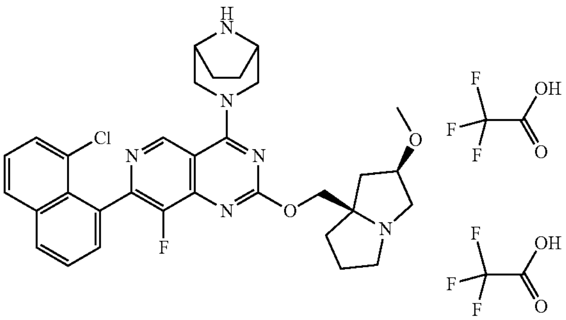

4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-2,2,2-trifluoroacetate as the cis racemate (3.63 mg, 0.00616 mmol, 76%), LCMS (MM-ES+APCI, Pos): m/z 589.2 (M+H).

Example 226

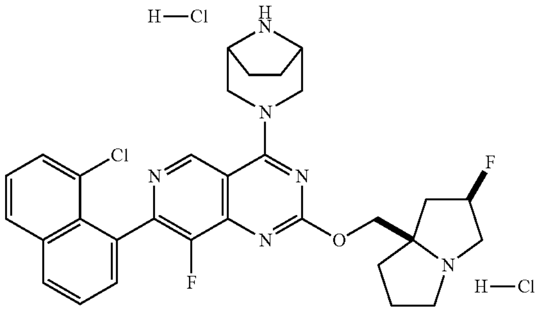

4-((1R,5S)-3,8-diazabicyclo[3.2.1]octan-3-yl)-7-(8-chloronaphthalen-1-yl)-8-fluoro-2-((2-fluorotetrahydro-1H-pyrrolizin-7a(5H)-yl)methoxy)pyrido[4,3-d]pyrimidine bis-hydrochloride

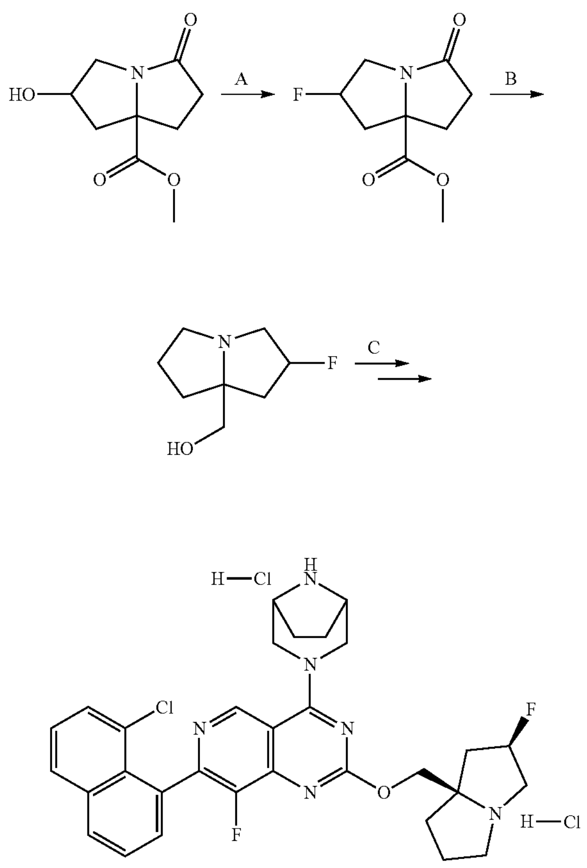

4-((1R,5S)-3,8-diazabicyclo[3.2.1]octan-3-yl)-7-(8-chloronaphthalen-1-yl)-8-fluoro-2-((2-fluorotetrahydro-1H-pyrrolizin-7a(5H)-yl)methoxy)pyrido[4,3-d]pyrimidine bis-hydrochloride as the cis racemate (3.84 mg, 0.00591 mmol, 80%). LCMS (MM-ES+APCI, Pos): m/z 577.2 (M+H).

Example 227

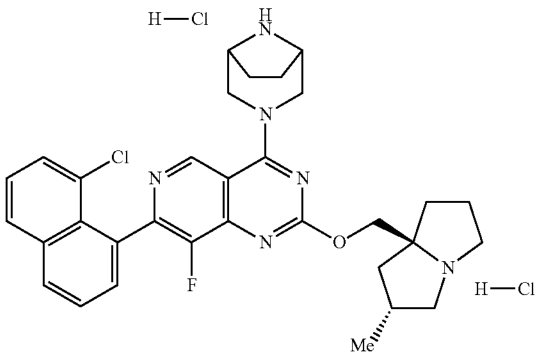

4-((1R,5S)-3,8-diazabicyclo[3.2.1]octan-3-yl)-7-(8-chloronaphthalen-1-yl)-8-fluoro-2-((2-methyltetrahydro-1H-pyrrolizin-7a(5H)-yl)methoxy)pyrido[4,3-d]pyrimidine bis-hydrochloride

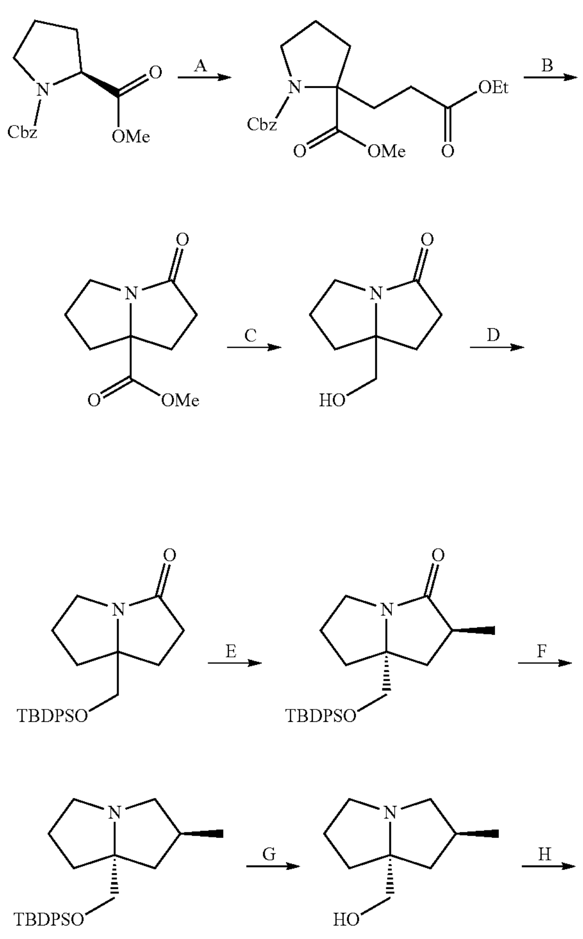

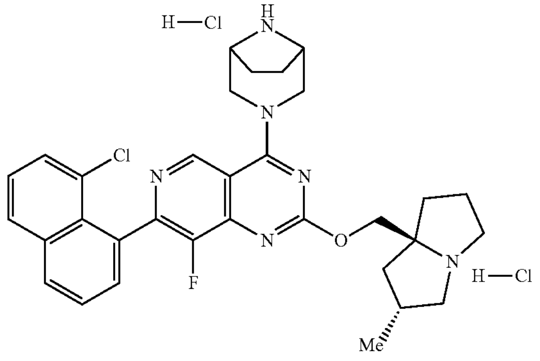

4-((1R,5S)-3,8-diazabicyclo[3.2.1]octan-3-yl)-7-(8-chloronaphthalen-1-yl)-8-fluoro-2-((2-methyltetrahydro-1H-pyrrolizin-7a(5H)-yl)methoxy)pyrido[4,3-d]pyrimidine bis-hydrochloride, trans racemate (10.0 mg, 0.0155 mmol, 99%). LCMS (MM-ES+APCI, Pos): m/z 573.3 (M+H).

Example 228

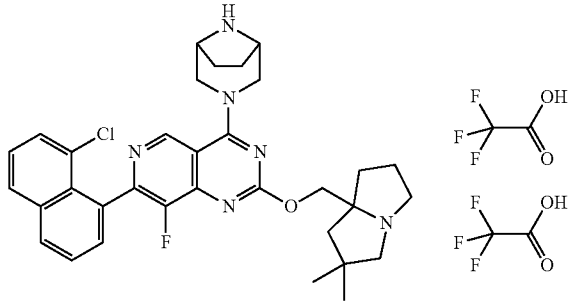

4-((1R,5S)-3,8-diazabicyclo[3.2.1]octan-3-yl)-7-(8-chloronaphthalen-1-yl)-2-((2,2-dimethyltetrahydro-1H-pyrrolizin-7a(5H)-yl)methoxy)-8-fluoropyrido[4,3-d]pyrimidine bis-2,2,2-trifluoroacetate

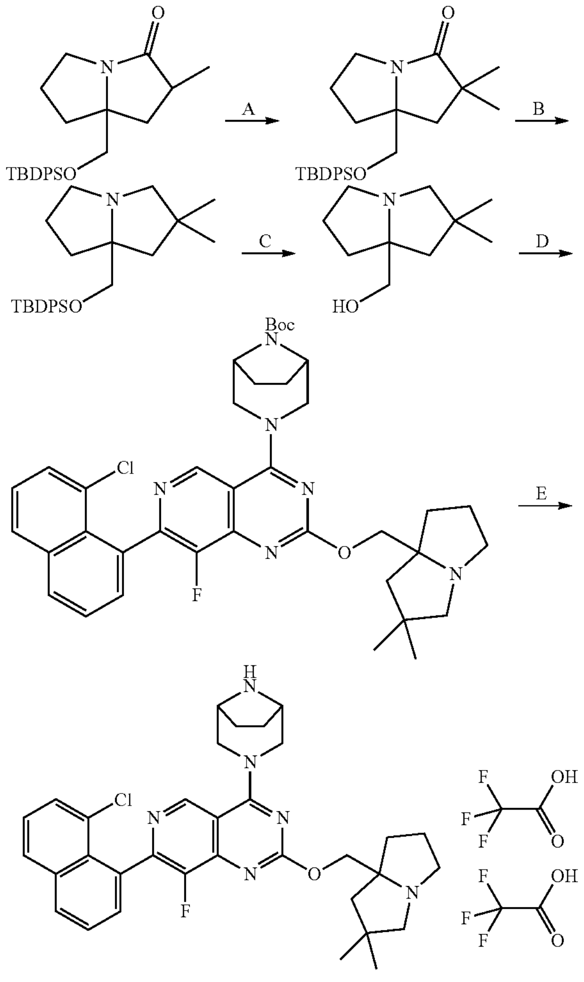

4-((1R,5S)-3,8-diazabicyclo[3.2.1]octan-3-yl)-7-(8-chloronaphthalen-1-yl)-2-((2,2-dimethyltetrahydro-1H-pyrrolizin-7a(5H)-yl)methoxy)-8-fluoropyrido[4,3-d]pyrimidine bis-2,2,2-trifluoroacetate as the racemate (3.60 mg, 0.0044 mmol, 20%), LCMS (MM-ES+APCI, Pos): m/z 587.2 (M+H).

Example 229

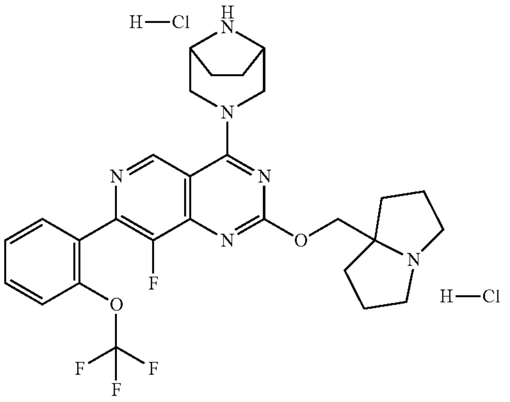

4-((1R,5S)-3,8-diazabicyclo[3.2.1]octan-3-yl)-8-fluoro-2-((tetrahydro-1H-pyrrolizin-7a(5H)-yl) methoxy)-7-(2-(trifluoromethoxy)phenyl)pyrido[4,3-d]pyrimidine bis-hydrochloride

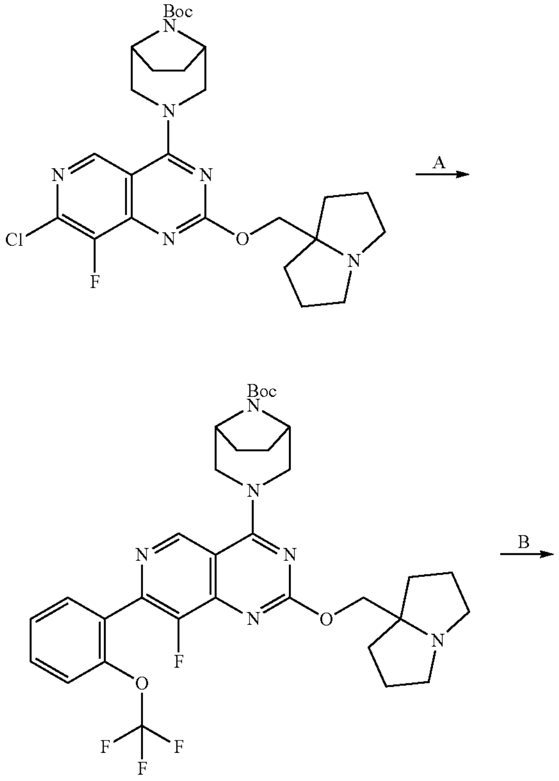

-continued

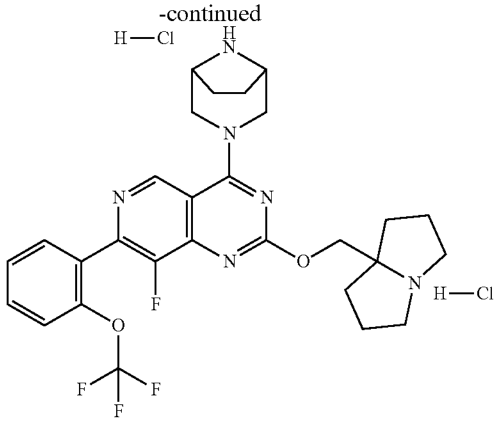

4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethoxy)phenyl)pyrido[4,3-d]pyrimidine bis-hydrochloride (25.0 mg, 0.0396 mmol, 87%). LCMS (MM-ES+APCI, Pos): m/z 559.2 (M+H).

Example 230

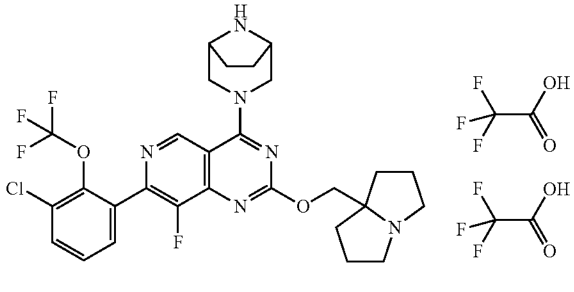

4-((1R,5S)-3,8-diazabicyclo[3.2.1]octan-3-yl)-7-(3-chloro-2-(trifluoromethoxy)phenyl)-8-fluoro-2-((tetrahydro-1H-pyrrolizin-7a(5H)-yl)methoxy)pyrido[4,3-d]pyrimidine bis(2,2,2-trifluoroacetate

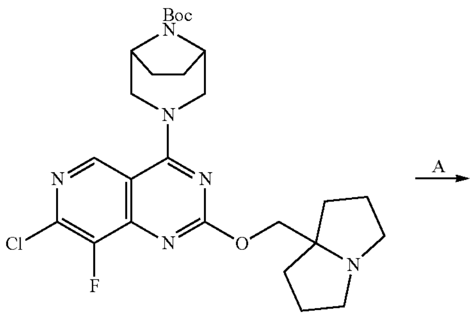

-continued

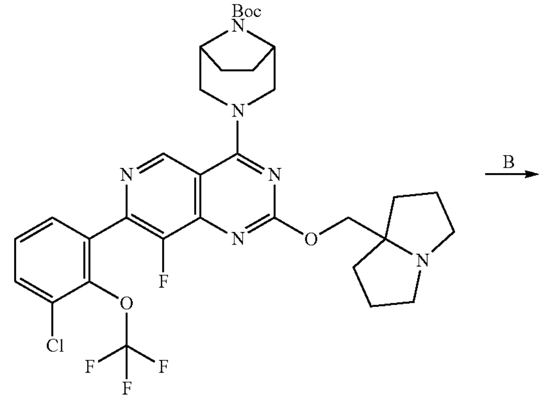

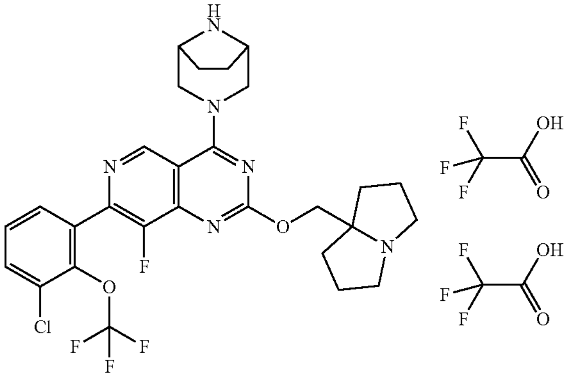

4-((1R,5S)-3,8-diazabicyclo[3.2.1]octan-3-yl)-7-(3-chloro-2-(trifluoromethoxy)phenyl)-8-fluoro-2-((tetrahydro-1H-pyrrolizin-7a(5H)-yl)methoxy)pyrido[4,3-d]pyrimidine bis(2,2,2-trifluoroacetate) (0.001 g, 0.0012 mmol, 17% yield). LCMS (MM-ES+APCI, Pos): m/z 593.2 (M+H).

Example 231

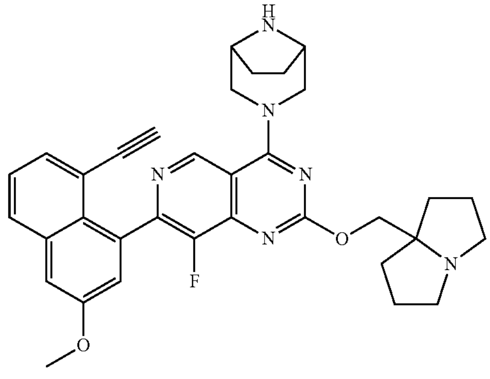 [SMILES: C#Cc1cccc2cc(OC)cc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-ethynyl-3-methoxynaphthalen-1-yl)-8-fluoro-2-((hexahydro-1H-pyrrolizin-7a-yl)methoxy)pyrido[4,3-d]pyrimidine

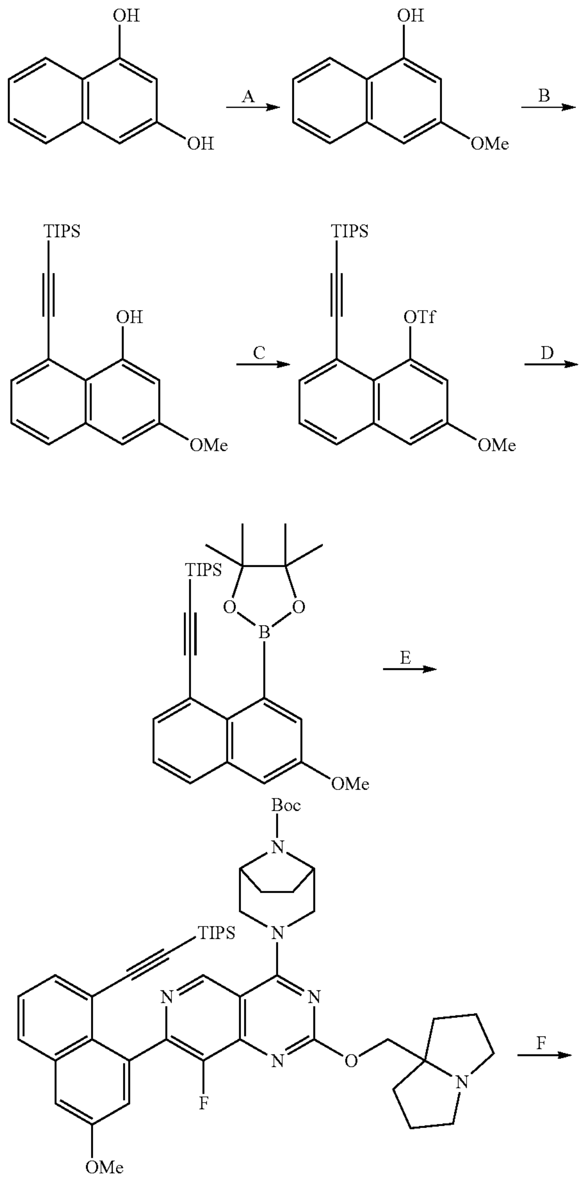

-continued

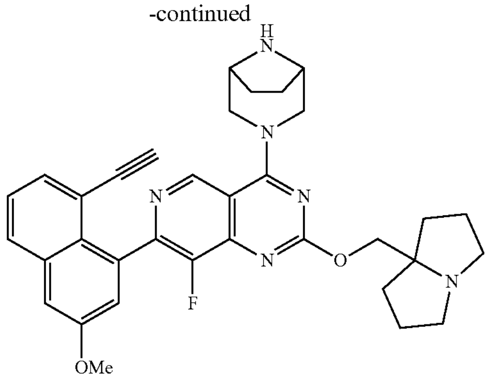

4-((1R,5S)-3,8-diazabicyclo[3.2.1]octan-3-yl)-7-(8-ethynyl-3-methoxynaphthalen-1-yl)-8-fluoro-2-((tetrahydro-1H-pyrrolizin-7a(5H)-yl)methoxy)pyrido[4,3-d]pyrimidine. To a mixture of tert-butyl(1R,5S)-3-(7-(8-ethynyl-3-methoxynaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (33.0 mg, 33.5 μmol, 1.0 eq) in acetonitrile (0.5 mL) was added HCl·dioxane (4 M, 1 mL, 119 eq) at 0° C. The mixture was stirred at 0° C. for 0.5 hour. After completion, the mixture was concentrated under vacuum and the pH value was adjusted to 9 with concentrate $NaHCO_3$ (3 mL). Then the mixture was diluted with ethyl acetate (4 mL) and water (2 mL) then separated. The aqueous phase was extracted with ethyl acetate (2×4 mL), the combined organic layer was washed with saturated brine (6 mL), dried over $Na_2SO_4$, filtered and concentrated under vacuum. The residue was purified by prep-HPLC (column: Shim-pack C18 150*25*10 um; mobile phase: [water (0.225% FA)-ACN]; B %: 7%-37%, 10 min) to give the title compound (8.92 mg, two steps 44% yield). Yellow solid. $^1H$ NMR (400 MHz, METHANOL-d4) δ=9.09 (s, 1H), 8.49 (s, 2H), 7.97 (dd, J=1.0, 8.3 Hz, 1H), 7.57 (dd, J=1.2, 7.2 Hz, 1H), 7.51 (d, J=2.6 Hz, 1H), 7.49-7.44 (m, 1H), 7.23 (d, J=2.7 Hz, 1H), 4.77 (m, 2H), 4.66 (d, J=2.2 Hz, 2H), 4.02 (br s, 2H), 3.99 (s, 3H), 3.90 (br t, J=12.8 Hz, 2H), 3.73-3.64 (m, 2H), 3.29-3.23 (m, 2H), 3.07 (s, 1H), 2.38-2.29 (m, 2H), 2.25-2.02 (m, 8H), 2.00-1.92 (m, 2H). LCMS (ESI, M/2+1, M+1): 290, 579.

Example 232

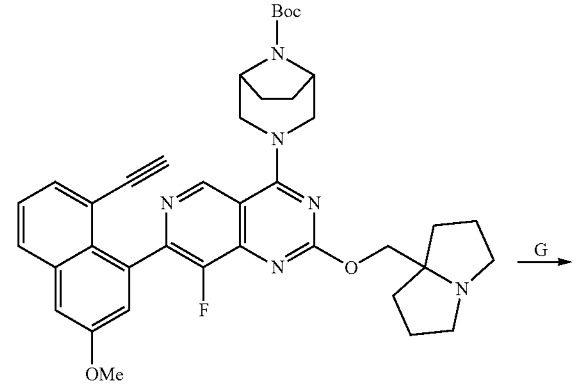

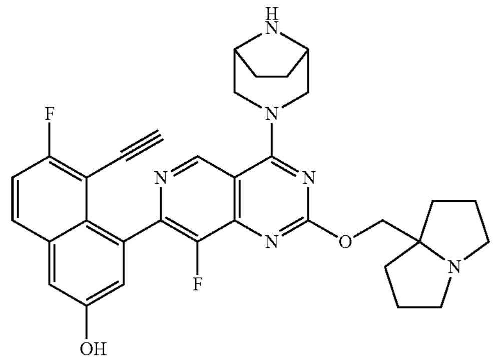 [SMILES: C#Cc1c(F)ccc2cc(O)cc(-c3ncc4c(N5CC6CCC(C5)N6)nc(OCC56CCCN5CCC6)nc4c3F)c12]

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-ethynyl-6-fluoronaphthalen-2-ol

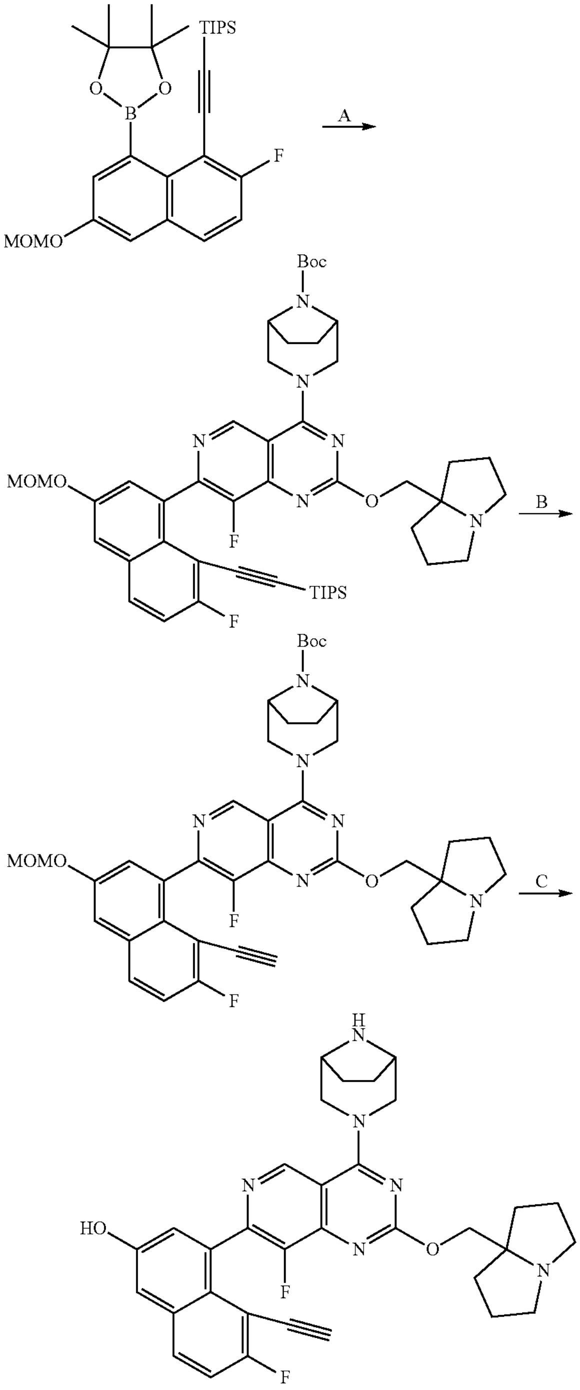

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-ethynyl-6-fluoronaphthalen-2-ol. A solution of tert-butyl(1R,5S)-3-(7-(8-ethynyl-7-fluoro-3-(methoxymethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (20.0 mg, 27.5 μmol, 1.00 eq) in acetonitrile (0.50 mL) and HCl·dioxane (0.50 mL) was stirred at 25° C. for 0.5 hour. The reaction was concentrated in vacuum at 25° C. to give a residue. Then the residue was adjusted to pH~7 with saturated sodium bicarbonate aqueous solution (0.50 mL), and the aqueous phase was extracted with DCM (2×10.0 mL). The combined organic phase was washed with brine (2×10.0 mL), dried with anhydrous sodium sulfate, filtered and concentrated in vacuum to give a residue. The residue was purified by prep-HPLC (column: Waters Xbridge C18 150*50 mm*10 um; mobile phase: [water (10 mM $NH_4HCO_3$)-ACN]; B %: 22%-52%, 10 min) affording the title compound (6.42 mg, 39% yield). Yellow solid; $^1$H NMR (400 MHz, $CDCl_3$) δ=8.90 (s, 1H), 7.64 (dd, J=6.0, 9.2 Hz, 1H), 7.22-7.14 (m, 3H), 4.61 (br d, J=11.6 Hz, 1H), 4.45 (br d, J=12.0 Hz, 1H), 4.22 (s, 2H), 3.71-3.45 (m, 4H), 3.20-3.10 (m, 2H), 2.77 (s, 1H), 2.70-2.62 (m, 2H), 2.15-2.05 (m, 2H), 1.92-1.84 (m, 4H), 1.76-1.63 (m, 6H); LCMS [ESI, M+1]: 583.2.

Example 233

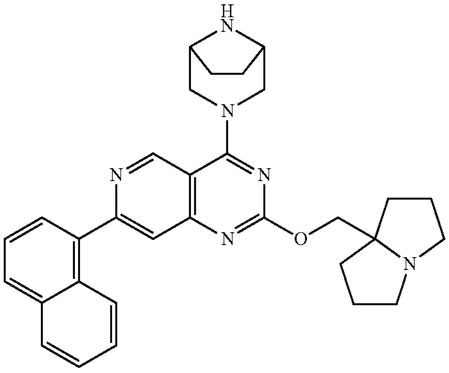 [SMILES: c1ccc2c(-c3cc4nc(OCC56CCCN5CCC6)nc(N5CC6CCC(C5)N6)c4cn3)cccc2c1]

4-((1R,5S)-3,8-diazabicyclo[3.2.1]octan-3-yl)-7-(naphthalen-1-yl)-2-((tetrahydro-1H-pyrrolizin-7a(5H)-yl)methoxy)pyrido[4,3-d]pyrimidine

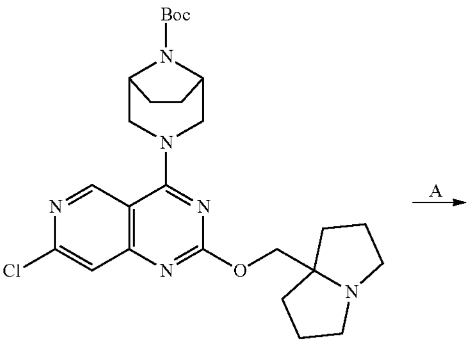

-continued

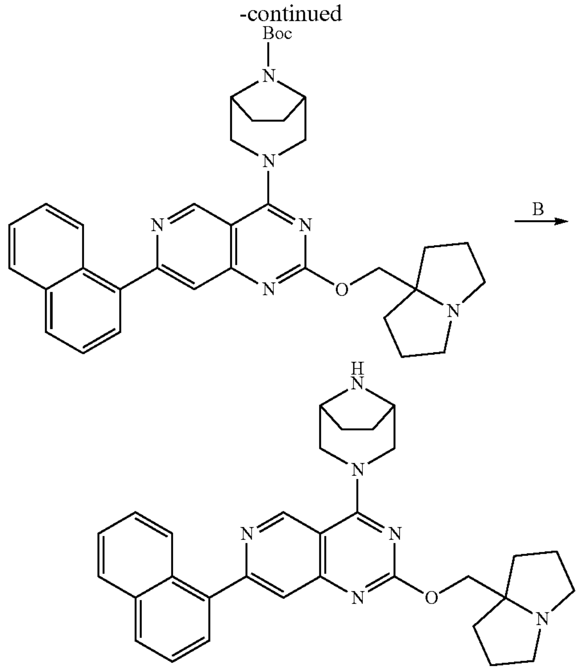

4-((1R,5S)-3,8-diazabicyclo[3.2.1]octan-3-yl)-7-(naphthalen-1-yl)-2-((tetrahydro-1H-pyrrolizin-7a(5H)-yl)methoxy)pyrido[4,3-d]pyrimidine. To a mixture of tert-butyl (1R,5S)-3-(7-(naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (300 mg, 494 μmol, 1 eq) and MeCN (2 mL) was added HCl/dioxane (4 M, 1 mL, 8.09 eq) in one portion. The mixture was stirred at 25° C. for 1 hour. The residue was concentrated under reduced pressure to give a residue. The residue was purified by prep-HPLC (column: Phenomenex Synergi C18 150*25*10 um; mobile phase: [water (0.225% FA)-ACN]; B %: 15%-45%, 9 min) to give 4-((1R,5S)-3,8-diazabicyclo[3.2.1]octan-3-yl)-2-((hexahydro-1H-pyrrolizin-7a-yl)methoxy)-7-(naphthalen-1-yl)pyrido[4,3-d]pyrimidine (8.97 mg, 3.5% yield). Off-white solid; $^1H$ NMR (400 MHz, DMSO-$d_6$) δ=9.35 (s, 1H), 8.31 (s, 1H), 8.10 (s, 1H), 8.05-8.01 (m, 1H), 7.69-7.68 (m, 1H), 7.66-7.64 (m, 1H), 7.61-7.64 (m, 3H), 4.54 (d, J=12.4 Hz, 2H), 4.41 (s, 2H), 3.71-3.68 (m, 4H), 3.38-3.34 (m, 2H), 3.06-3.01 (m, 2H), 2.09-2.01 (m, 4H), 1.96-1.87 (m, 4H), 1.80-1.78 (m, 2H), 1.76-1.69 (m, 2H). LCMS (ESI, M+1): 507.

Example 234

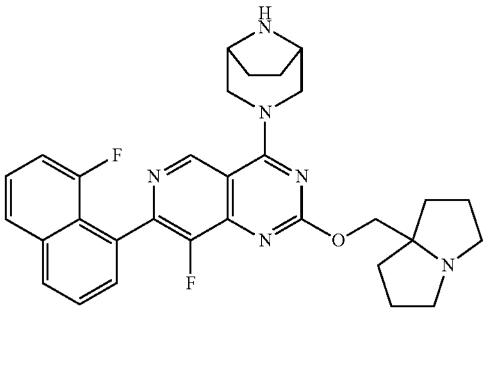

4-((1R,5S)-3,8-diazabicyclo[3.2.1]octan-3-yl)-8-fluoro-7-(8-fluoronaphthalen-1-yl)-2-((tetrahydro-1H-pyrrolizin-7a(5H)-yl)methoxy)pyrido[4,3-d]pyrimidine

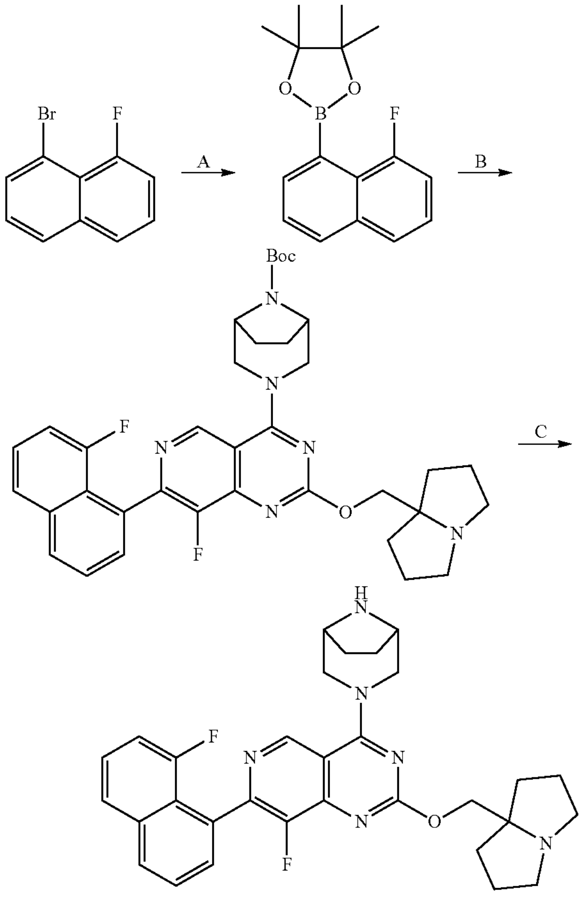

4-((1R,5S)-3,8-diazabicyclo[3.2.1]octan-3-yl)-8-fluoro-7-(8-fluoronaphthalen-1-yl)-2-((tetrahydro-1H-pyrrolizin-7a(5H)-yl)methoxy)pyrido[4,3-d]pyrimidine. To a mixture of tert-butyl(1R,5S)-3-(8-fluoro-7-(8-fluoronaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (45 mg, 70.0 μmol, 1.0 eq) in acetonitrile (0.5 mL) was added HCl·dioxane (4 M, 1 mL, 57 eq) at 0° C. The mixture was stirred at 0° C. for 0.5 hour. After completion, the mixture was concentrated under vacuum. Then the pH value was adjusted to 9 with saturated $Na_2CO_3$ solution and the mixture was extracted with EtOAc (2×8 mL). The organic layers were dried and concentrated under vacuum. The residue was purified by prep-HPLC (column: Waters Xbridge 150*25 mm*5 um; mobile phase: [water (10 mM $NH_4HCO_3$)-ACN]; B %: 18%-48%, 10 min) to give 4-((1R,5S)-3,8-diazabicyclo[3.2.1]octan-3-yl)-8-fluoro-7-(8-fluoronaphthalen-1-yl)-2-((tetrahydro-1H-pyrrolizin-7a(5H)-yl)methoxy)pyrido[4,3-d]pyrimidine (18.69 mg, 49% yield). White solid. $^1H$ NMR (400 MHz, $CDCl_3$-d) δ=9.02 (s, 1H), 7.98 (td, J=1.6, 7.6 Hz, 1H), 7.76-7.71 (m, 1H), 7.64-7.56 (m, 2H), 7.48-7.41 (m, 1H), 7.11 (ddd, J=0.8, 7.6, 12.4 Hz, 1H), 4.65 (br d, J=12.4 Hz, 1H), 4.54 (br d, J=11.6 Hz, 1H), 4.19 (s, 2H), 3.67 (br s, 3H), 3.59 (br d, J=12.4 Hz, 1H), 3.15-3.07 (m, 2H), 2.64 (td, J=6.8, 10.0 Hz, 2H), 2.14-2.06 (m, 2H), 1.92-1.82 (m, 8H), 1.70-1.64 (m, 2H). LCMS [ESI, M+1, M/2+1]: 543, 272.

Example 235

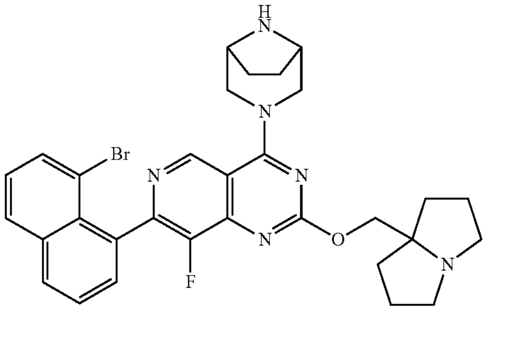 [SMILES: Fc1c(-c2cccc3cccc(Br)c23)ncc2c(N3CC4CCC(C3)N4)nc(OCC34CCCN3CCC4)nc12]

4-((1R,5S)-3,8-diazabicyclo[3.2.1]octan-3-yl)-7-(8-bromonaphthalen-1-yl)-8-fluoro-2-((tetrahydro-1H-pyrrolizin-7a(5H)-yl)methoxy)pyrido[4,3-d]pyrimidine

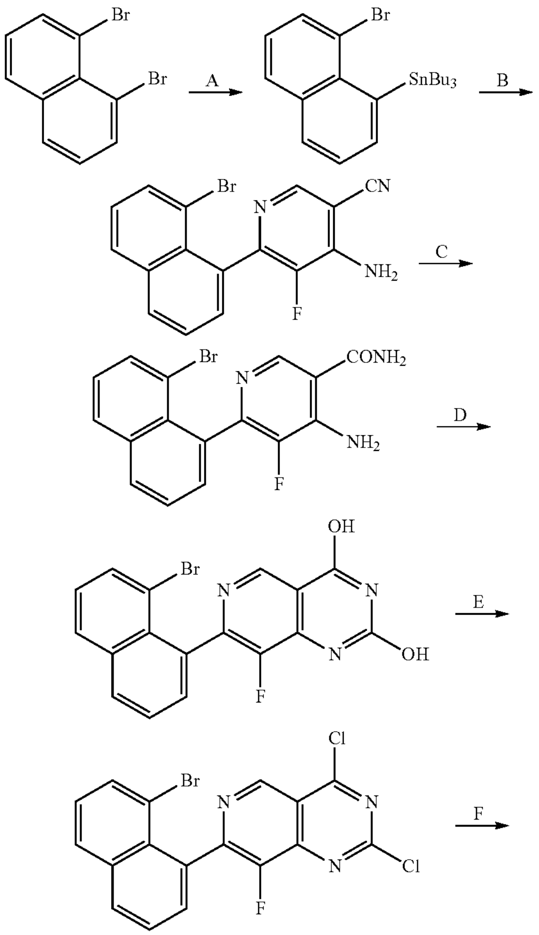

-continued

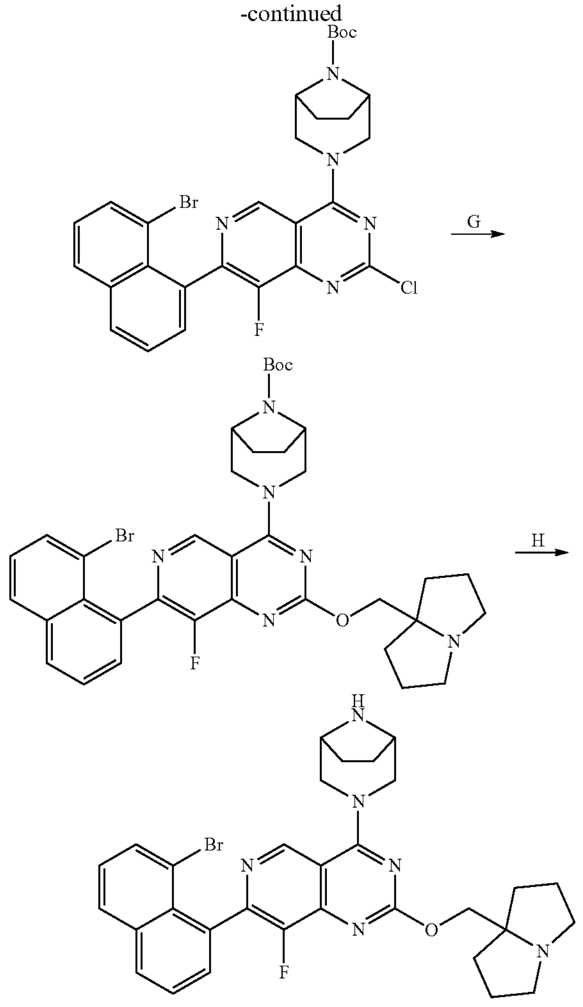

4-((1R,5S)-3,8-diazabicyclo[3.2.1]octan-3-yl)-7-(8-bromonaphthalen-1-yl)-8-fluoro-2-((tetrahydro-1H-pyrrolizin-7a(5H)-yl)methoxy)pyrido[4,3-d]pyrimidine. To a solution of (tert-butyl(1R,5S)-3-(7-(8-bromonaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (40 mg, 56.8 μmol, 1.0 eq) in ACN (0.5 mL) was added HCl·dioxane (4 M, 284 μL, 1.0 eq). The mixture was stirred at 30° C. for 1 hour. The reaction mixture was concentrated under vacuum and diluted with water (2 mL). The mixture was adjusted to PH~8 with saturated $NaHCO_3$ aqueous solution and extracted with ethyl acetate (3×10 mL). The combined organic layers were washed with brine (10 mL), dried over $Na_2SO_4$, filtered and concentrated under reduced pressure to give the residue. The residue was purified by prep-HPLC (column: Waters Xbridge 150*25 mm*5 um; mobile phase: [water (10 mM $NH_4HCO_3$)-ACN]; B %: 20%-50%, 10 min). The desired fraction was collected and lyophilized to give the title compound (10 mg, 29% yield) as a white solid. $^1H$ NMR (400 MHz, methanol-$d_4$) δ=9.07 (s, 1H), 8.14 (dd, J=1.2, 8.0 Hz, 1H), 8.06 (dd, J=1.0, 8.0 Hz, 1H), 7.85 (dd, J=1.2, 7.6 Hz, 1H), 7.72-7.60 (m, 2H), 7.43 (t, J=7.6 Hz, 1H), 4.64 (dd, J=5.2, 12.0 Hz, 2H), 4.38 (s, 2H), 3.80-3.61 (m, 4H), 3.29-3.21 (m, 2H), 2.98-2.79 (m, 2H), 2.21-2.10 (m, 2H), 2.07-1.72 (m, 10H). LCMS [ESI, M+1]: 605.

Example 236

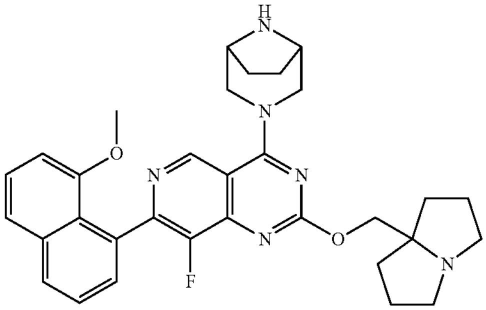 [SMILES: COc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-2-((hexahydro-1H-pyrrolizin-7a-yl)methoxy)-7-(8-methoxynaphthalen-1-yl)pyrido[4,3-d]pyrimidine

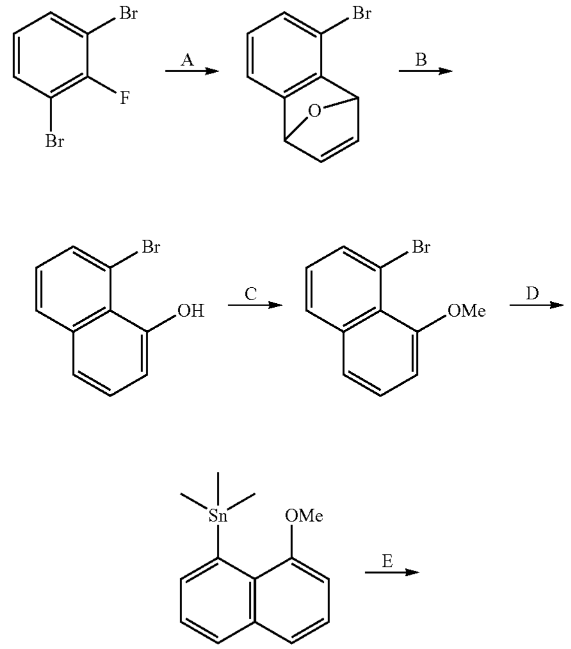

-continued

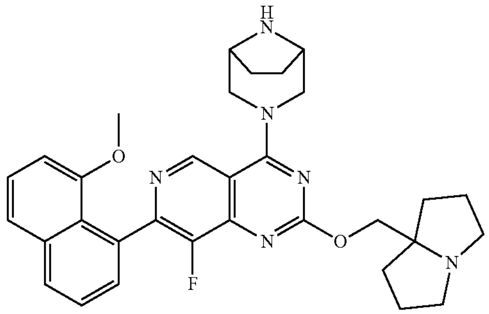

4-((1R,5S)-3,8-diazabicyclo[3.2.1]octan-3-yl)-8-fluoro-7-(8-methoxynaphthalen-1-yl)-2-((tetrahydro-1H-pyrrolizin-7a(5H)-yl)methoxy)pyrido[4,3-d]pyrimidine (13.9 mg, 35% yield). White solid; $^1$H NMR (400 MHz, $CDCl_3$-d) δ=9.00 (s, 1H), 7.92 (d, J=8.0 Hz, 1H), 7.60-7.50 (m, 2H), 7.45-7.38 (m, 2H), 6.81 (d, J=7.6 Hz, 1H), 4.75 (s, 1H), 4.65-4.55 (m, 2H), 4.20 (s, 2H), 3.70-3.60 (m, 4H), 3.52 (s, 3H), 3.13-3.06 (m, 2H), 2.70-2.60 (m, 2H), 2.15-2.05 (m, 2H), 1.90-1.76 (m, 10H). LCMS [ESI, M+1]: 555.

Example 237

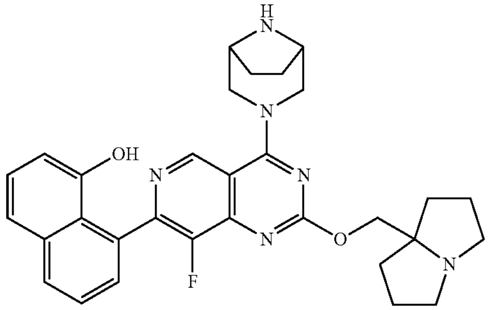 [SMILES: Oc1cccc2cccc(-c3ncc4c(N5CC6CCC(C5)N6)nc(OCC56CCCN5CCC6)nc4c3F)c12]

8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-ol

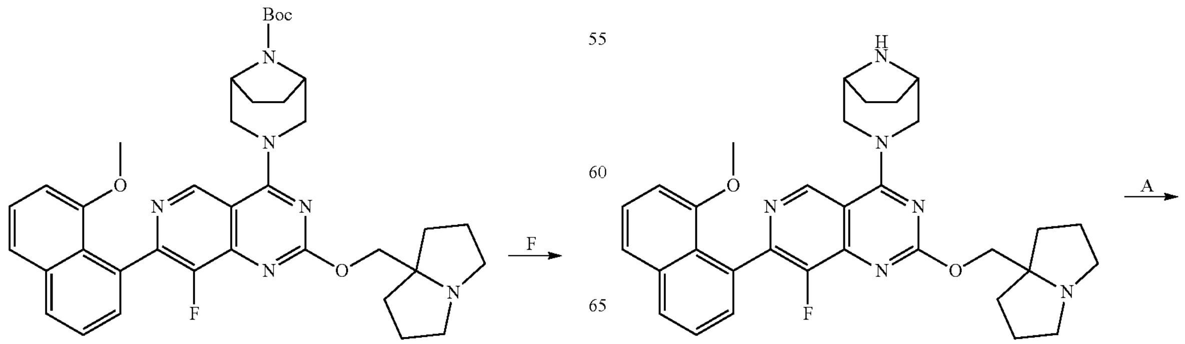

-continued

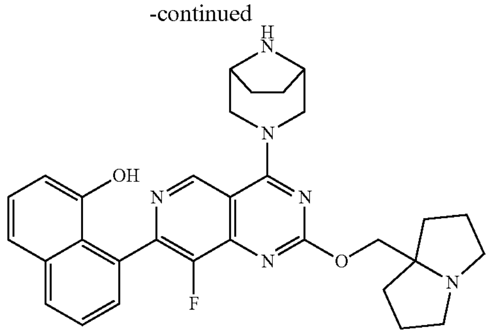

Step A. 8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-ol. To a solution of 4-((1R,5S)-3,8-diazabicyclo[3.2.1]octan-3-yl)-8-fluoro-7-(8-methoxynaphthalen-1-yl)-2-((tetrahydro-1H-pyrrolizin-7a(5H)-yl)methoxy)pyrido[4,3-d]pyrimidine (40.0 mg, 61.1 μmol, 1.0 eq) in DCM (0.5 mL) was added $BBr_3$ (115 mg, 458 μmol, 7.5 eq) in one portion at 0° C. under $N_2$. The mixture was stirred at 0° C. for 0.5 hour. The reaction mixture was diluted with $H_2O$ (5 mL) and ACN (1 mL). The solution was purified by prep-HPLC (column: Phenomenex Synergi C18 150*25*10 um; mobile phase: [water (0.225% FA)-ACN]; B %: 10%-40%, 10 min. The desired fraction was collected and lyophilized to affording 8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-ol (4.89 mg, 14% yield). Yellow solid; $^1H$ NMR (400 MHz, $CDCl_3$-d) δ=9.06 (s, 1H), 8.44 (br s, 2H), 8.02-7.93 (m, 1H), 7.56 (dd, J=7.2, 8.0 Hz, 1H), 7.52-7.45 (m, 1H), 7.38-7.28 (m, 2H), 6.81 (dd, J=1.2, 7.6 Hz, 1H), 4.75-4.71 (m, 2H), 4.61-4.52 (m, 2H), 3.94 (br s, 2H), 3.84 (br d, J=13.2 Hz, 2H), 3.70-3.60 (m, 2H), 3.27-3.22 (m, 2H), 2.35-2.06 (m, 8H), 2.05-1.86 (m, 4H). LCMS [ESI, M+1]: 541.

Example 238

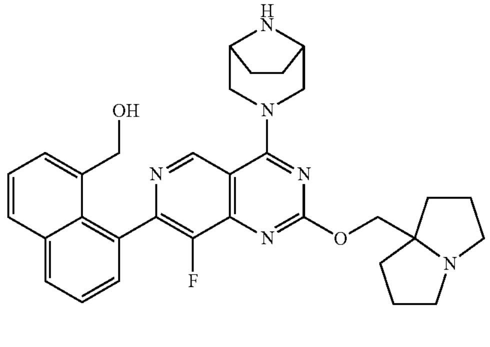 [SMILES: OCc1cccc2cccc(-c3ncc4c(N5CC6CCC(C5)N6)nc(OCC56CCCN5CCC6)nc4c3F)c12]

(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)methanol

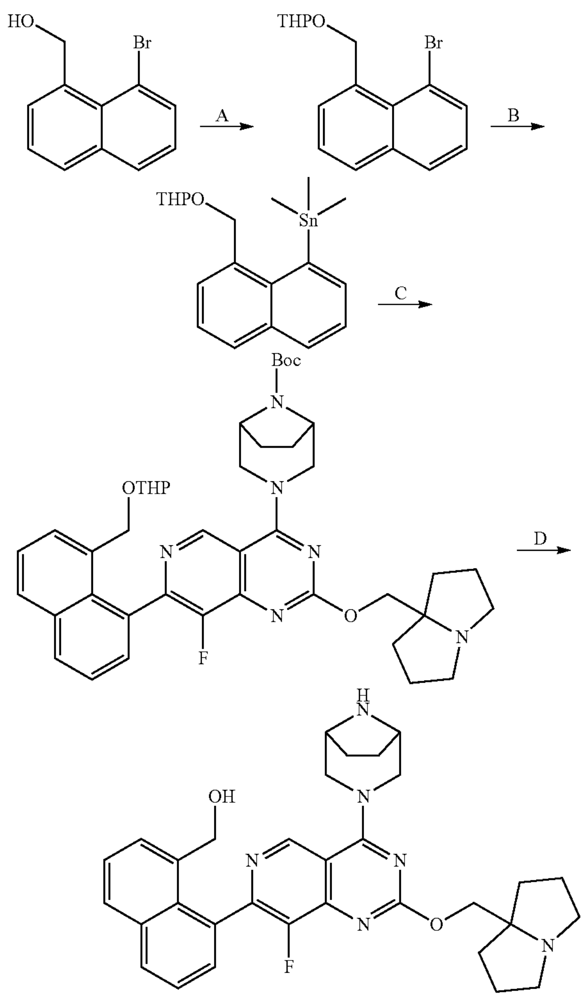

(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)methanol. To a solution of tert-butyl(1R,5S)-3-(8-fluoro-2-((tetrahydro-1H-pyrrolizin-7a(5H)-yl)methoxy)-7-(8-(((tetrahydro-2H-pyran-2-yl)oxy)methyl)naphthalen-1-yl)pyrido[4,3-d]pyrimidin-4-yl)-3,8-diazabicyclo[3.2.1]octane-8-carboxylate (50 mg, 67.7 μmol, 1.0 eq) in acetonitrile (0.5 mL) was added HCl·dioxane (4 M, 1.0 mL). The mixture was stirred at 0° C. for 30 minutes. The mixture was concentrated, and the reaction mixture was diluted with water (1.0 mL). Then the mixture was adjusted pH~8 with saturated $NaHCO_3$ aqueous solution and extracted with dichloromethane (3×5.0 mL), washed with brine (5.0 mL), dried over $Na_2SO_4$, filtered and concentrated. The residue was purified by prep-HPLC (column: Waters X bridge 150*25 mm*5 um; mobile phase: [water (10 mM $NH_4HCO_3$)-ACN]; B %: 15%-45%, 10 min). The desired fraction was collected and concentrated under vacuum to remove acetonitrile. The mixture was lyophilized to give the title compound (11.9 mg, 31% yield). Yellow solid; $^1H$ NMR (400 MHz, chloroform-d) δ=8.96 (s, 1H), 8.01 (d, J=8.0 Hz, 1H), 7.91 (d, J=8.0 Hz, 1H), 7.64 (dd, J=0.9, 7.2 Hz, 1H), 7.58-7.49 (m, 2H), 7.44 (d, J=6.8 Hz, 1H), 4.70 (br d, J=12.0 Hz, 1H), 4.49-4.28 (m, 3H), 4.18 (s, 2H), 3.75-3.61 (m, 3H), 3.59-3.50 (m, 1H), 3.15-3.05 (m, 2H), 2.69-2.60 (m, 2H), 2.15-2.06 (m, 2H), 1.94-1.84 (m, 6H), 1.75-1.62 (m, 4H); LCMS [ESI, M+1]: 555.

Example 239

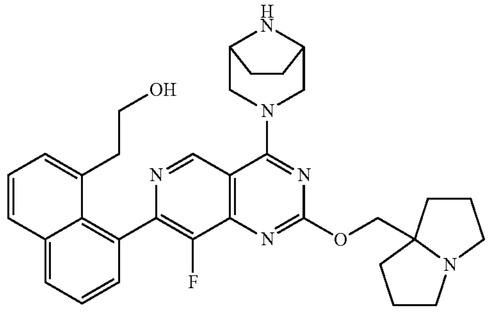 [SMILES: OCCc1cccc2cccc(-c3ncc4c(N5CC6CCC(C5)N6)nc(OCC56CCCN5CCC6)nc4c3F)c12]

2-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)ethan-1-ol

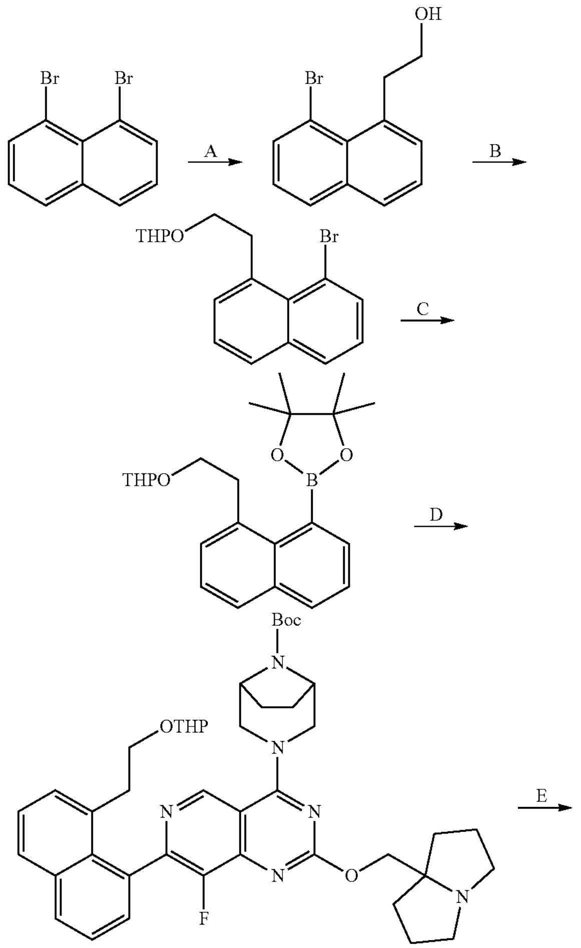

-continued

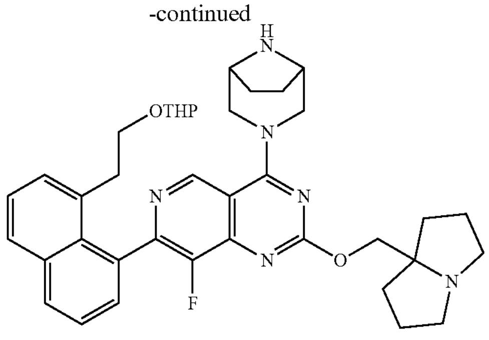

2-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)ethan-1-ol. To a mixture of tert-butyl(1R,5S)-3-(8-fluoro-2-((tetrahydro-1H-pyrrolizin-7a(5H)-yl)methoxy)-7-(8-(2-((tetrahydro-2H-pyran-2-yl)oxy)ethyl)naphthalen-1-yl)pyrido[4,3-d]pyrimidin-4-yl)-3,8-diazabicyclo[3.2.1]octane-8-carboxylate e (100 mg, 133 μmol, 1.0 eq) in acetonitrile (0.5 mL) was added HCl·dioxane (4 M, 1 mL, 30 eq) at 0° C. The mixture was stirred at 0° C. for 0.5 hour. After completion, the mixture was concentrated under vacuum. Then the residue was purified by prep-HPLC (column: Phenomenex luna C18 150*40 mm*15 um; mobile phase: [water (0.225% FA)-ACN]; B %: 1%-30%, 9 min) to give the title compound (15.1 mg, 20% yield, 2FA). Yellow solid. $^1$H NMR (400 MHz, METHANOL-d4) δ=9.13 (s, 1H), 8.07 (dd, J=1, 2, 8.0 Hz, 1H), 7.91 (dd, J=1.2, 8.0 Hz, 1H), 7.59 (dd, J=6.8, 8.0 Hz, 1H), 7.52-7.45 (m, 2H), 7.40 (dd, J=1.2, 6.8 Hz, 1H), 4.78 (br d, J=13.6 Hz, 2H), 4.68 (s, 2H), 4.05 (br s, 2H), 3.97 (br d, J=13.6 Hz, 1H), 3.85 (br d, J=13.6 Hz, 1H), 3.75-3.66 (m, 2H), 3.55-3.43 (m, 2H), 3.30-3.25 (m, 2H), 2.60-2.52 (m, 2H), 2.33 (ddd, J=2.0, 6.8, 12.4 Hz, 2H), 2.24-1.96 (m, 10H). LCMS [ESI, M+1]: 569.

Example 240

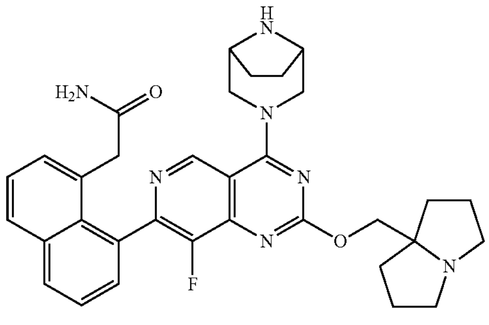 [SMILES: NC(=O)Cc1cccc2cccc(-c3ncc4c(N5CC6CCC(C5)N6)nc(OCC56CCCN5CCC6)nc4c3F)c12]

2-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl) acetamide

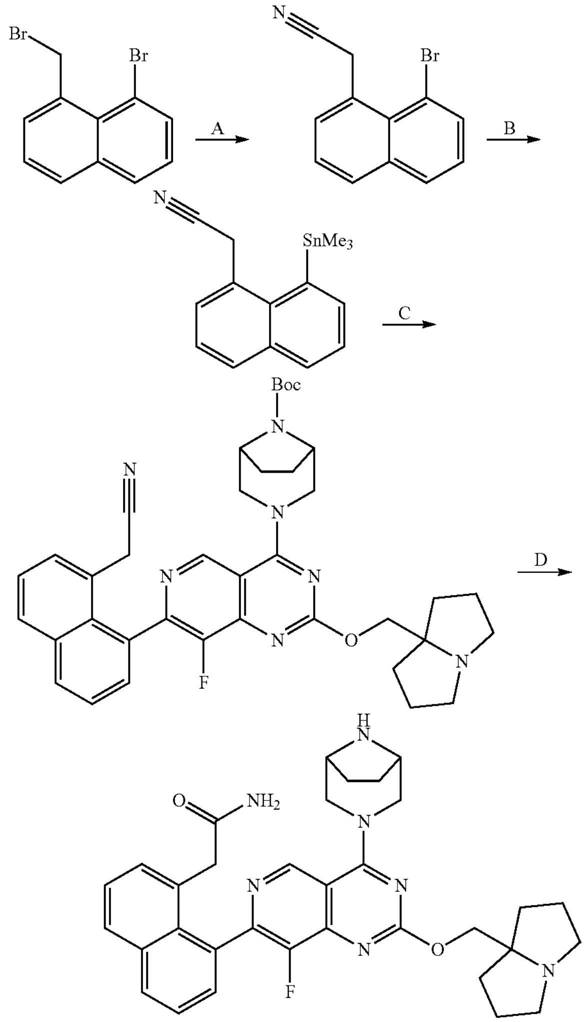

2-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl) acetamide. A solution of tert-butyl(1R,5S)-3-(7-(8-(cyanomethyl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (40 mg, 60.2 μmol, 1 eq) in $H_2SO_4$ (368 mg, 3.68 mmol, 200 μL, 98% purity, 61.0 eq) and TFA (1.54 g, 13.5 mmol, 1 mL, 224 eq) was stirred at 30° C. for 2 hours. After completion, the reaction mixture was poured into ice-cold water (1 mL). The mixture was adjusted to PH~9 with saturated $Na_2CO_3$ aqueous solution and extracted with dichloromethane (3×5 mL). The combined organic layers were washed with brine (3 mL), dried over $Na_2SO_4$, filtered and concentrated under reduced pressure. The residue was purified by prep-HPLC (column: Waters Xbridge 150*25 mm*5 um; mobile phase: [water (10 mM $NH_4HCO_3$)-ACN]; B %: 10%-40%, 10 min). The desired fraction was collected and lyophilized to give the title compound (5.84 mg, 16% yield). White solid. $^1$H NMR (400 MHz, chloroform-d) δ=8.95 (s, 1H), 8.02 (d, J=1.2, 8.0 Hz, 1H), 7.95 (d, J=8.0 Hz, 1H), 7.63-7.56 (m, 1H), 7.55-7.47 (m, 2H), 7.44-7.38 (m, 1H), 5.35 (s, 1H), 5.22 (s, 1H), 4.76-4.53 (m, 2H), 4.18 (s, 2H), 3.74-3.37 (m, 6H), 3.21-3.02 (m, 2H), 2.73-2.58 (m, 2H), 2.19-2.03 (m, 2H), 1.96-1.77 (m, 10H). LCMS [ESI, M+1]: 582.

Example 241

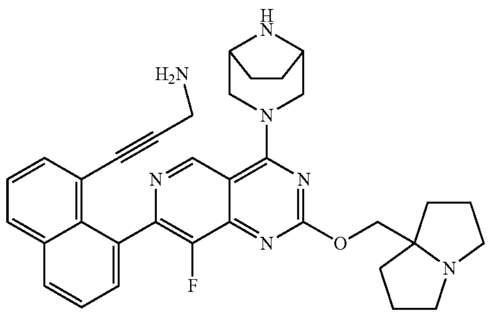 [SMILES: NCC#Cc1cccc2cccc(-c3ncc4c(N5CC6CCC(C5)N6)nc(OCC56CCCN5CCC6)nc4c3F)c12]

3-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl) prop-2-yn-1-amine

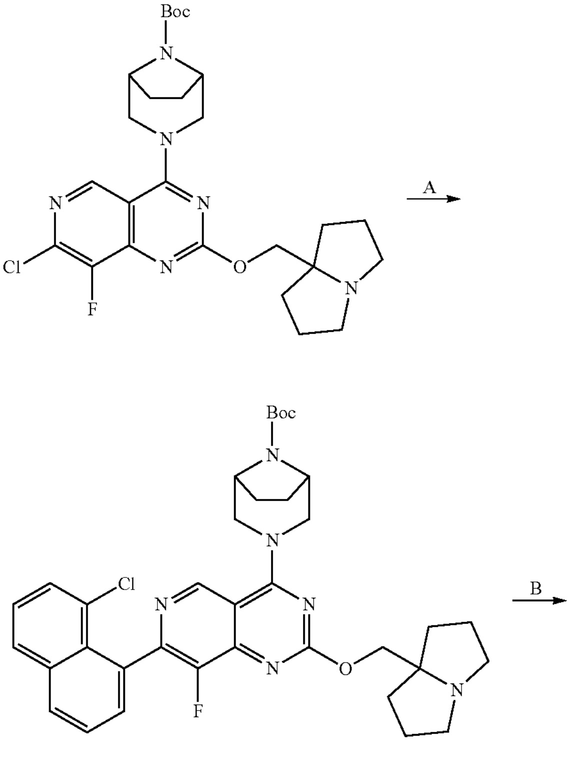

-continued

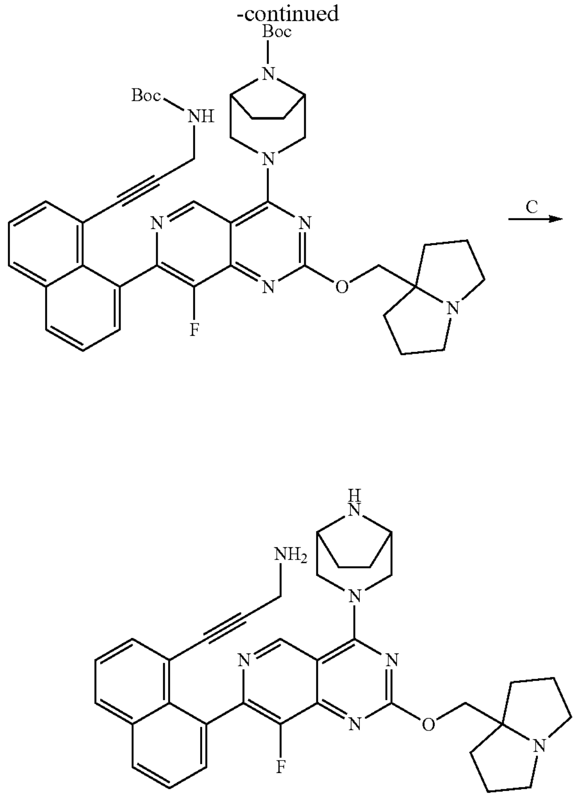

3-(8-(4-((1R,5S)-3,8-diazabicyclo[3.2.1]octan-3-yl)-8-fluoro-2-((tetrahydro-1H-pyrrolizin-7a(5H)-yl)methoxy) pyrido[4,3-d]pyrimidin-7-yl)naphthalen-1-yl) prop-2-yn-1-amine (18.9 mg, 46% yield). Yellow solid. $^1$H NMR (400 MHz, chloroform-d) δ=9.06 (s, 1H), 7.97 (dd, J=1.2, 8.0 Hz, 1H), 7.91 (dd, J=0.8, 8.0 Hz, 1H), 7.66 (dd, J=1.2, 7.2 Hz, 1H), 7.61-7.56 (t, J=7.6, 1H), 7.55-7.52 (m, 1H), 7.45 (dd, J=7.2, 8.0 Hz, 1H), 4.67-4.53 (m, 2H), 4.42-4.31 (m, 2H), 3.72-3.61 (m, 4H), 3.44-3.31 (m, 2H), 2.95-2.85 (m, 1H), 2.81-2.72 (m, 3H), 2.26-2.20 (m, 2H), 1.98 (m, 4H), 1.83-1.73 (m, 6H). LCMS [ESI, M+1]: 578.

Example 242

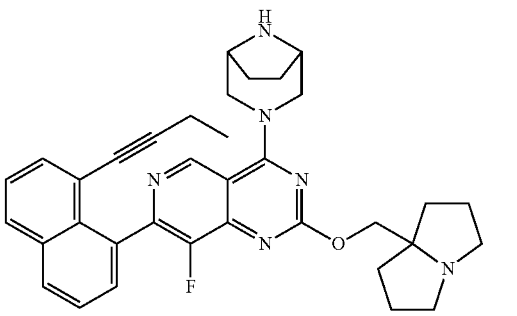 [SMILES: CCC#Cc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-(but-1-yn-1-yl)naphthalen-1-yl)-8-fluoro-2-((tetrahydro-1H-pyrrolizin-7a(5H)-yl)methoxy)pyrido[4,3-d]pyrimidine

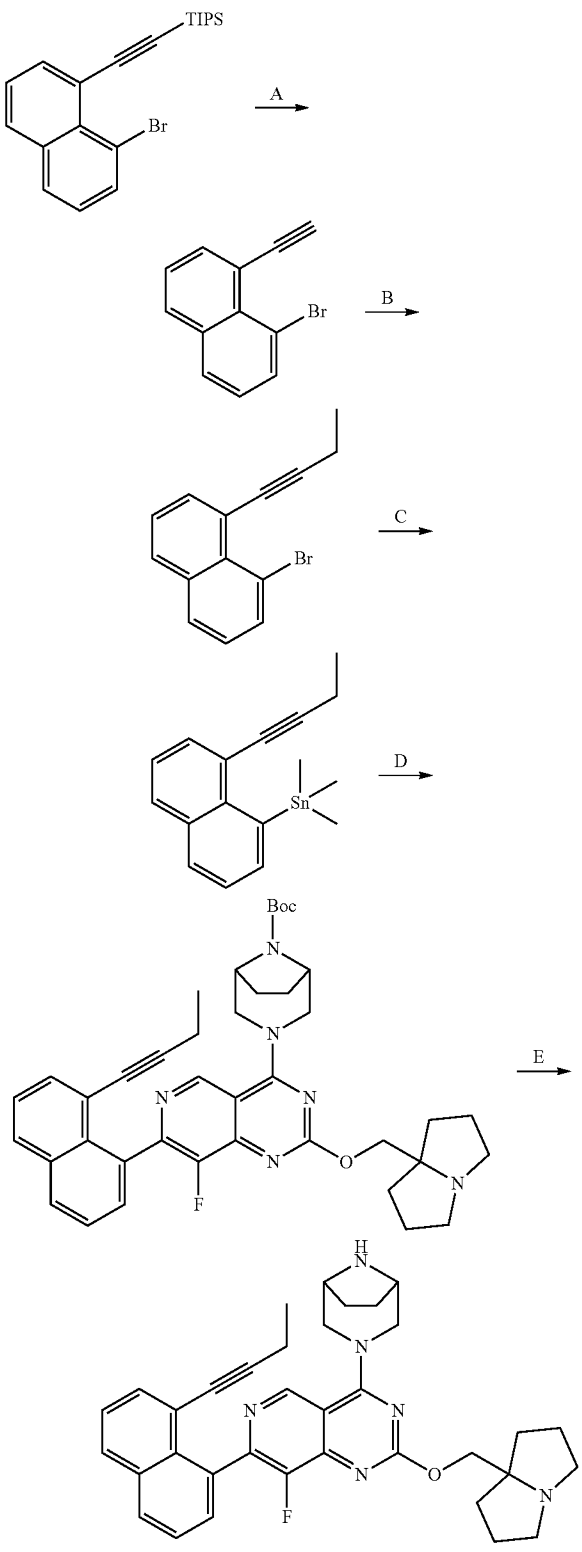

4-((1R,5S)-3,8-diazabicyclo[3.2.1]octan-3-yl)-7-(8-(but-1-yn-1-yl)naphthalen-1-yl)-8-fluoro-2-((tetrahydro-1H-pyrrolizin-7a(5H)-yl)methoxy)pyrido[4,3-d]pyrimidine. To a solution of tert-butyl(1R,5S)-3-(7-(8-(but-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (80 mg, 118 μmol, 1.0 eq) in acetonitrile (1.5 mL) was added HCl·dioxane (4.0 M, 0.75 mL). The mixture was stirred at 0° C. for 30 minutes. The mixture was concentrated, and the residue was diluted with water (1.0 mL). Then the mixture was adjusted pH~8 with saturated $NaHCO_3$ aqueous solution and extracted with (dichloromethane/methanol=10/1) (3×5.0 mL). The combined organic layers were dried over $Na_2SO_4$, filtered and concentrated. The residue was purified by prep-HPLC (column: Waters X bridge C18 150*50 mm*10 um; mobile phase: [water (10 mM $NH_4HCO_3$)-ACN]; B %: 35%-65%, 10 min). The desired fraction was collected and concentrated under vacuum to remove acetonitrile. The mixture was lyophilized to give the title compound (29.2 mg, 42% yield). White solid, $^1$H NMR (400 MHz, chloroform-d) δ=9.05 (s, 1H), 7.95 (dd, J=1.6, 8.0 Hz, 1H), 7.87 (d, J=8.0 Hz, 1H), 7.64 (d, J=7.2 Hz, 1H), 7.59-7.50 (m, 2H), 7.42 (t, J=8.0 Hz, 1H), 4.63 (br d, J=12.4 Hz, 1H), 4.54 (br d, J=11.6 Hz, 1H), 4.21 (d, J=1.2 Hz, 2H), 3.71-3.55 (m, 4H), 3.07-3.14 (m, 2H), 2.56-2.69 (m, 2H), 2.04-2.14 (m, 2H), 1.87-1.74 (m, 8H), 1.71-1.62 (m, 4H), 0.75 (t, J=7.6 Hz, 3H); LCMS [ESI, M+1]: 577.

Example 243

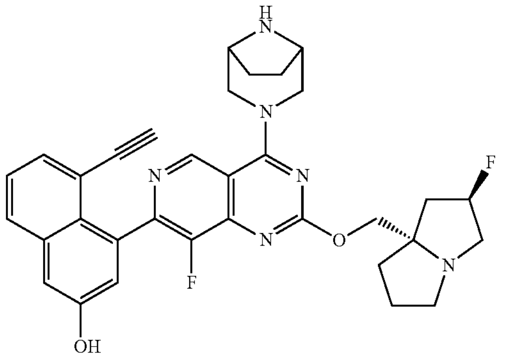 [SMILES: C#Cc1cccc2cc(O)cc(-c3ncc4c(N5CC6CCC(C5)N6)nc(OC[C@@]56CCCN5C[C@H](F)C6)nc4c3F)c12]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynylnaphthalen-2-ol

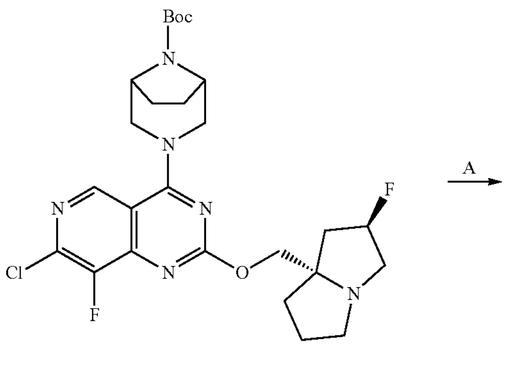

-continued

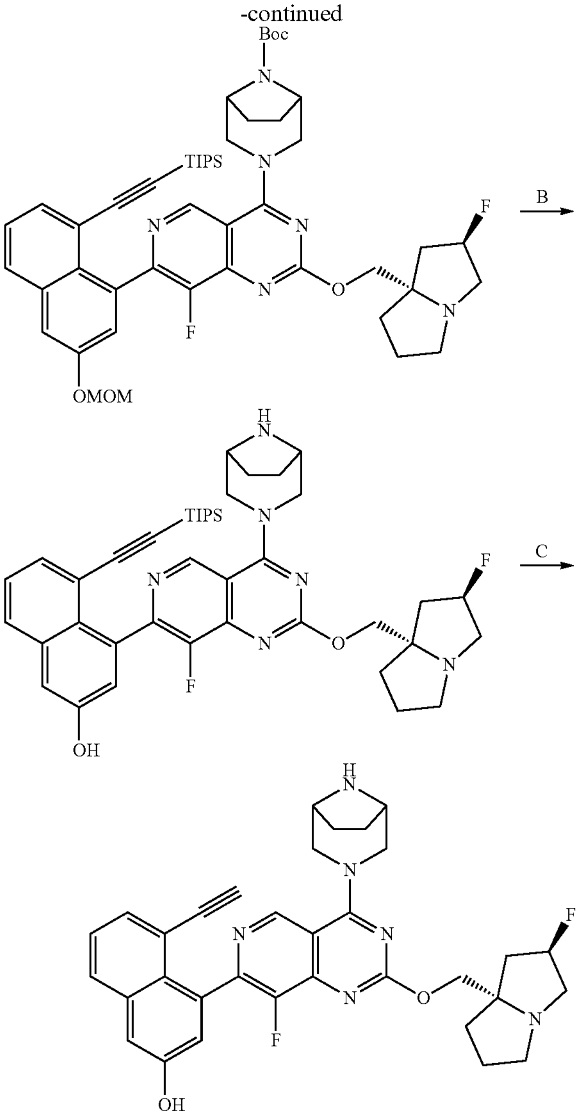

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynylnaphthalen-2-ol. To a mixture of 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-((triisopropylsilyl)ethynyl)naphthalen-2-ol (50 mg, 67.66 μmol, 1 eq) in DMF (2 mL) was added CsF (51.39 mg, 338.30 μmol, 12.47 μL, 5 eq) in one portion under $N_2$. The mixture was stirred at 20° C. for 1 hour. After completion, the mixture was purified by prep-HPLC (column: Waters Xbridge C18 150*50 mm*10 um; mobile phase: [water (10 mM $NH_4HCO_3$)-ACN]; B %: 25%-55%, 10 min) to give the title compound (7.28 mg, 18% yield). Yellow solid; $^1$H NMR (400 MHz, METHANOL-d4) δ=9.01 (s, 1H), 7.83 (d, J=7.3 Hz, 1H), 7.52 (d, J=6.2 Hz, 1H), 7.44-7.38 (m, 1H), 7.34 (d, J=2.6 Hz, 1H), 7.18 (d, J=2.4 Hz, 1H), 5.42-5.22 (m, 1H), 4.70-4.54 (m, 4H), 4.36-4.20 (m, 2H), 3.78-3.70 (m, 2H), 3.29-3.14 (m, 3H), 3.09-2.99 (m, 2H), 2.40-2.21 (m, 2H), 2.19-2.11 (m, 1H), 2.07-1.96 (m, 2H), 1.96-1.77 (m, 5H); LCMS [ESI, M+1]: 583.

Example 244

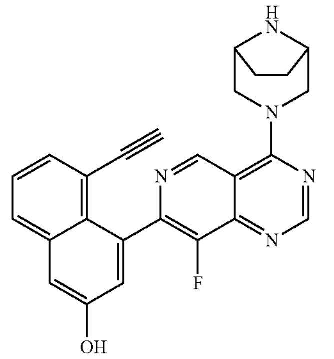 [SMILES: C#Cc1cccc2cc(O)cc(-c3ncc4c(N5CC6CCC(C5)N6)ncnc4c3F)c12]

4-(4-((1R,5S)-3,8-diazabicyclo[3.2.1]octan-3-yl)-8-fluoropyrido[4,3-d]pyrimidin-7-yl)-5-ethynylnaphthalen-2-ol

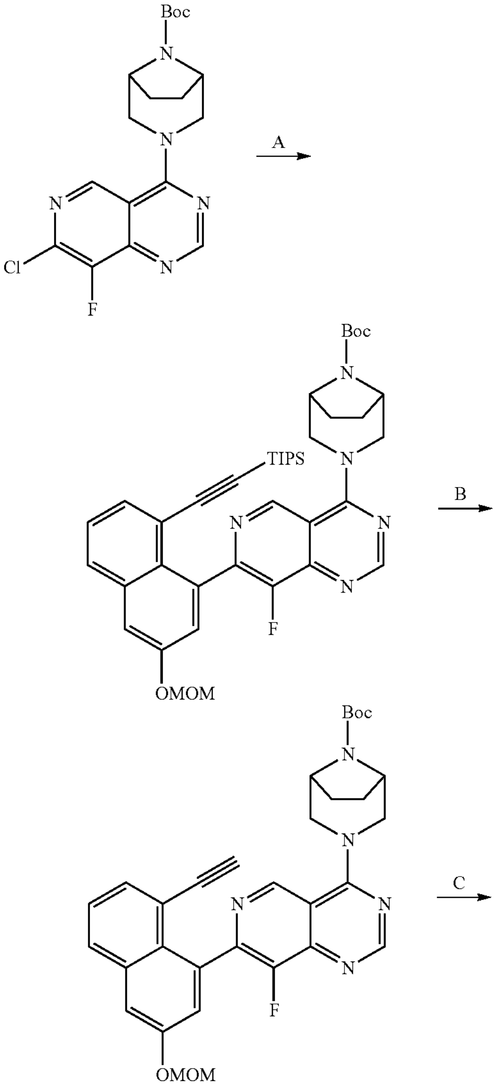

-continued

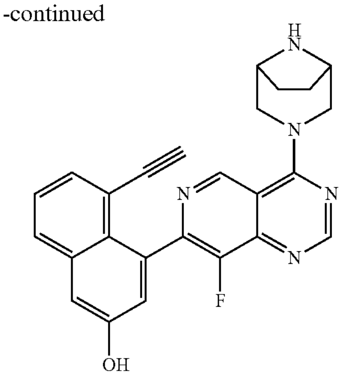

4-[4-(3,8-diazabicyclo[3.2.1]octan-3-yl)-8-fluoro-pyrido[4,3-d]pyrimidin-7-yl]-5-ethynyl-naphthalen-2-ol. To a mixture of tert-butyl 3-[7-[8-ethynyl-3-(methoxymethoxy)-1-naphthyl]-8-fluoro-pyrido[4,3-d]pyrimidin-4-yl]-3,8-diazabicyclo[3.2.1]octane-8-carboxylate (100 mg, 175 μmol, 1.0 eq) in acetonitrile (1 mL) was added HCl/dioxane (4 M, 2 mL, 45 eq) at 0° C. The mixture was stirred at 0° C. for 0.5 hours. After completion, the mixture was concentrated under vacuum and the pH was adjusted to 9 with concentrate $NaHCO_3$ (4 mL). Then the mixture was diluted with ethyl acetate (6 mL) and water (4 mL), and then separated. The aqueous phase was extracted with ethyl acetate (2×5 mL), and the combine organic layer was washed with brine (8 mL), dried over $Na_2SO_4$, filtered and concentrated under vacuum. The residue was purified by prep-HPLC (column: Waters Xbridge 150*25 mm*5 um; mobile phase: [water (10 mM $NH_4HCO_3$)-ACN]; B %: 20%-50%, 10 min) to give the title compound (30.2 mg, 40% yield). orange solid. $^1$H NMR (400 MHz, $CDCl_3$-d) δ=9.06 (s, 1H), 8.75 (s, 1H), 7.72 (d, J=8.0 Hz, 1H), 7.53 (d, J=6.8 Hz, 1H), 7.33 (t, J=7.6 Hz, 1H), 7.27 (s, 2H), 4.72 (br d, J=12.0 Hz, 1H), 4.51 (br d, J=12.0 Hz, 1H), 3.79-3.71 (br d, J=12.0 Hz, 1H), 3.67 (br s, 2H), 3.60 (br d, J=12.0 Hz, 1H), 2.44 (s, 1H), 1.82-1.76 (m, 3H), 1.64-1.57 (m, 1H). LCMS [ESI, M/2+1, M+1]: 214, 426.

Example 245

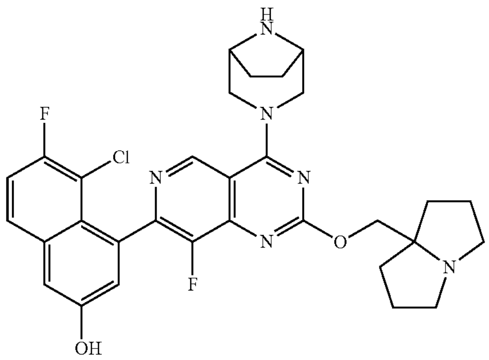 [SMILES: Oc1cc(-c2ncc3c(N4CC5CCC(C4)N5)nc(OCC45CCCN4CCC5)nc3c2F)c2c(Cl)c(F)ccc2c1]

4-(4-((1R,5S)-3,8-diazabicyclo[3.2.1]octan-3-yl)-8-fluoro-2-((hexahydro-1H-pyrrolizin-7a-yl)methoxy) pyrido[4,3-d]pyrimidin-7-yl)-5-chloro-6-fluoronaphthalen-2-ol

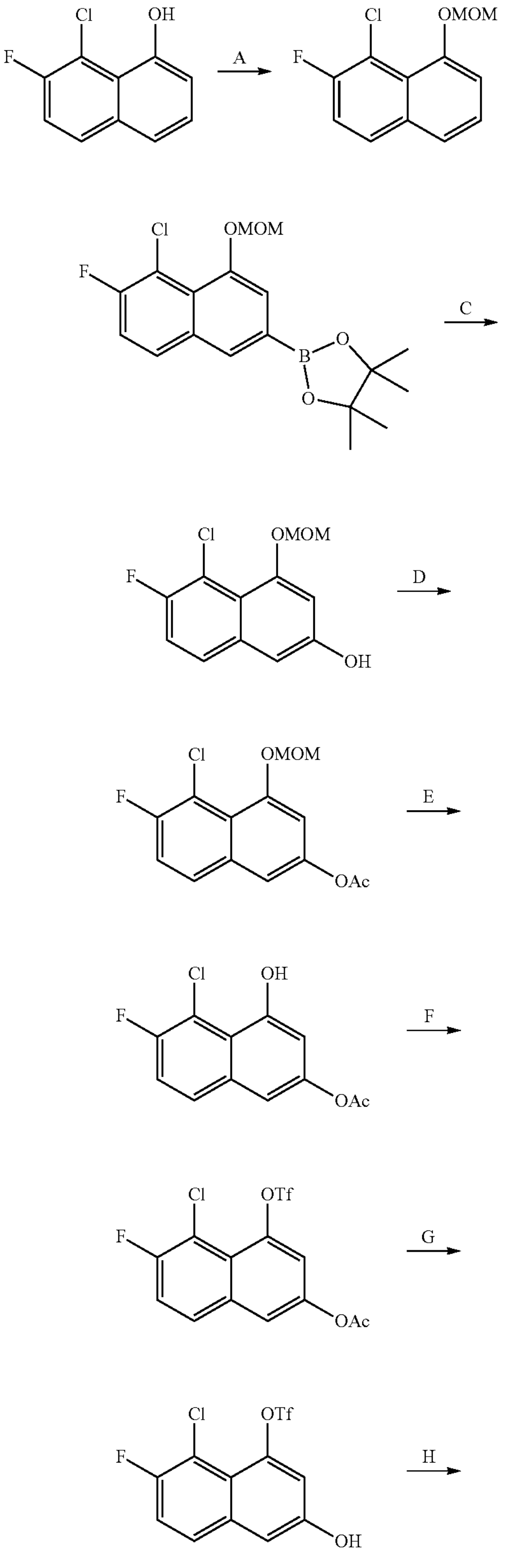

-continued

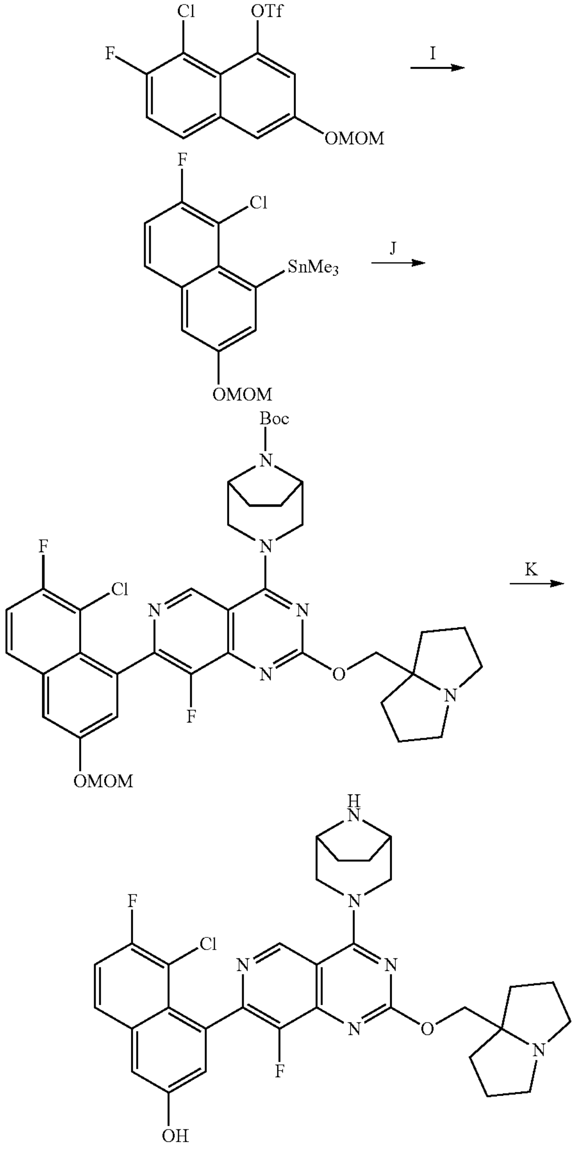

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-chloro-6-fluoronaphthalen-2-ol. To the solution of (1R,5S)-tert-butyl 3-(7-(8-chloro-7-fluoro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (60.0 mg, 81.4 μmol, 1.0 eq) in ACN (1 mL) was added HCl/dioxane (4 M, 2 mL, 98.3 eq) at 0° C., and the mixture was stirred at 0° C. for 0.5 hour. After completion, the reaction mixture was concentrated at 25° C. The residue was purified by prep-HPLC (column: 3_Phenomenex Luna C18 75*30 mm*3 um; mobile phase: [water (0.225% FA)-ACN]; B %: 7%-27%, 8 min) to give title compound (25.7 mg, 45% yield). Yellow solid. $^{1}H$ NMR (400 MHz, METHANOL-d4) δ=9.13 (s, 1H), 7.83 (dd, J=5.2, 8.8 Hz, 1H), 7.45-7.37 (m, 2H), 7.22 (d, J=2.4 Hz, 1H), 4.78 (br s, 2H), 4.67 (s, 2H), 4.00 (br s, 2H), 3.87 (br t, J=12.0 Hz, 2H), 3.74-3.64 (m, 2H), 3.28 (br s, 2H), 2.39-2.28 (m, 2H), 2.27-1.94 (m, 10H). LCMS [ESI, M+1]: 593.

Example 246

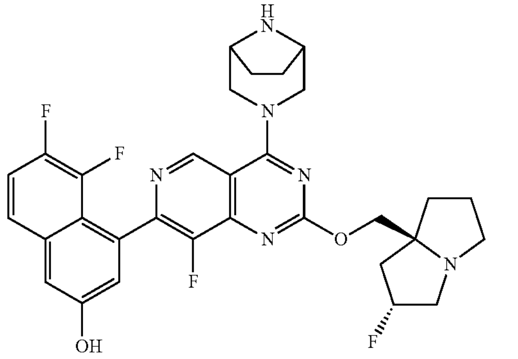 [SMILES: Oc1cc(-c2ncc3c(N4CC5CCC(C4)N5)nc(OC[C@@]45CCCN4C[C@H](F)C5)nc3c2F)c2c(F)c(F)ccc2c1]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5,6-difluoronaphthalen-2-ol

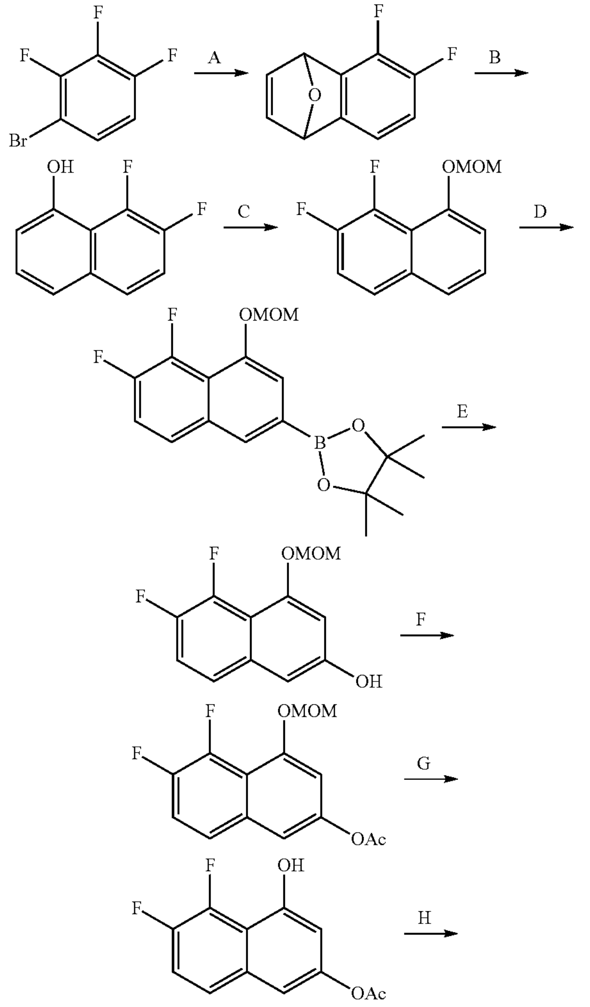

-continued

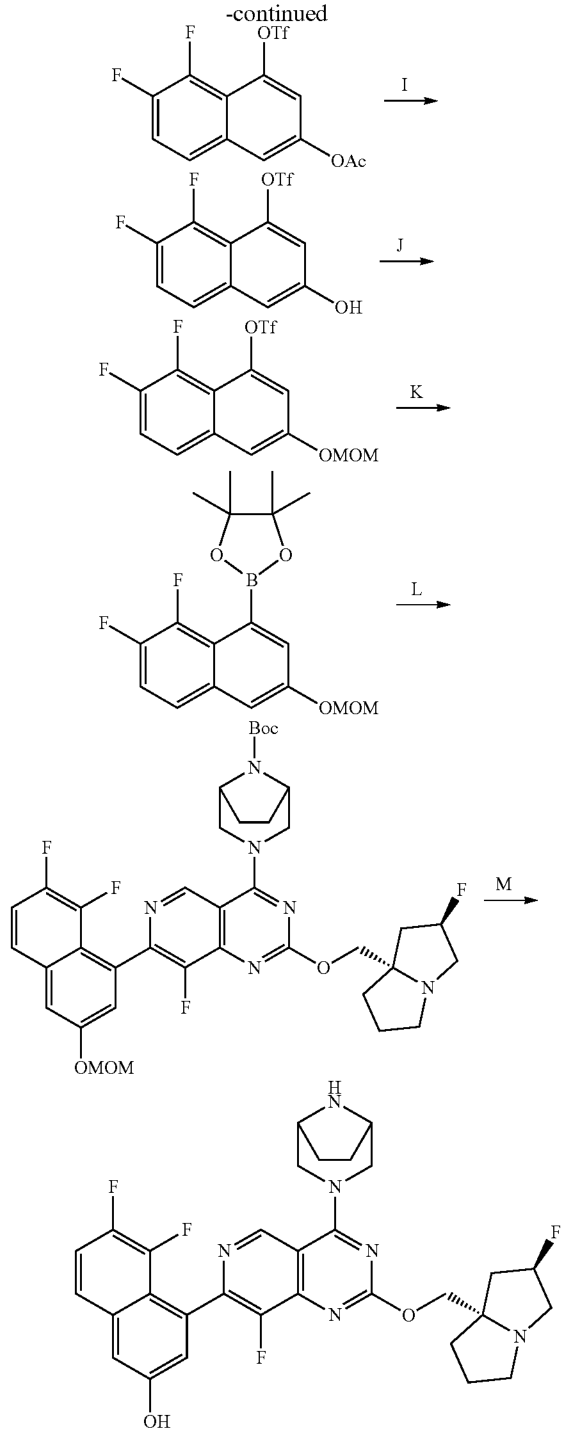

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5,6-difluoronaphthalen-2-ol. A solution of (1R,5S)-tert-butyl 3-(7-(7,8-difluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (90.0 mg, 122 μmol, 1 eq) in HCl·EtOAc (2.00 mL) was stirred at 0° C. for 1 hour. Upon completion, the reaction mixture was diluted with saturated $NaHCO_3$ (20.0 mL) and extracted with ethyl acetate (3×10.0 mL). The combined organic layers were washed with brine (15.0 mL), dried over $Na_2SO_4$, filtered and concentrated under vacuum. The residue was purified by prep-HPLC (column: Waters Xbridge BEH C18 100*25 mm*5 um; mobile phase: [water (10 mM $NH_4HCO_3$)-ACN]; B %: 30%-70%, 10 min) affording the title compound (18.8 mg, 31.0 μmol, 25% yield, 98.4% purity). White solid; $^1$H NMR (400 MHz, MeOD-d4) δ=9.06 (s, 1H), 7.66-7.56 (m, 1H), 7.46-7.35 (m, 1H), 7.34-7.31 (m, 1H), 7.23 (d, J=2.0 Hz, 1H), 5.44-5.20 (m, 1H), 4.69-4.54 (m, 2H), 4.38-4.18 (m, 2H), 3.82-3.58 (m, 4H), 3.27-3.12 (m, 3H), 3.08-2.94 (m, 1H), 2.41-2.09 (m, 3H), 2.07-1.69 (m, 7H); LCMS [ESI, M+1]: 595.1.

Example 247

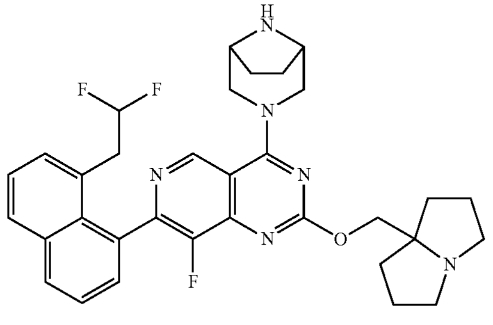 [SMILES: Fc1c(-c2cccc3cccc(CC(F)F)c23)ncc2c(N3CC4CCC(C3)N4)nc(OCC34CCCN3CCC4)nc12]

4-((1R,5S)-3,8-diazabicyclo[3.2.1]octan-3-yl)-7-(8-(2,2-difluoroethyl)naphthalen-1-yl)-8-fluoro-2-((hexahydro-1H-pyrrolizin-7a-yl)methoxy)pyrido[4,3-d]pyrimidine

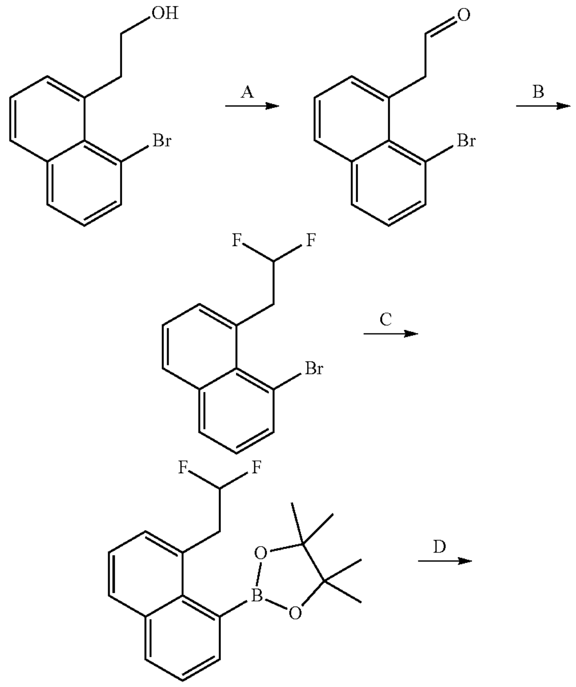

-continued

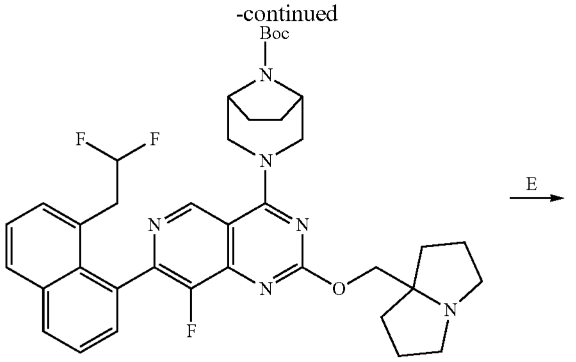

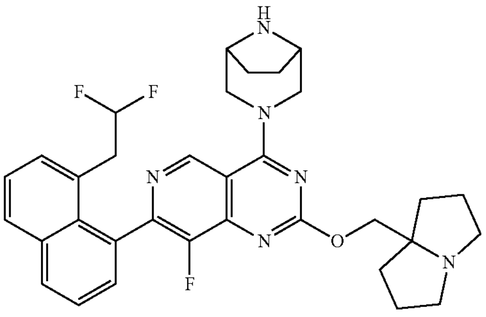

4-((1R,5S)-3,8-diazabicyclo[3.2.1]octan-3-yl)-7-(8-(2,2-difluoroethyl)naphthalen-1-yl)-8-fluoro-2-((hexahydro-1H-pyrrolizin-7a-yl)methoxy)pyrido[4,3-d]pyrimidine. To a mixture of tert-butyl(1R,5S)-3-(7-(8-(2,2-difluoroethyl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (37 mg, 46.2 μmol, 1.0 eq) in MeCN (0.4 mL) was added HCl/dioxane (4 M, 0.37 mL, 32.0 eq). The mixture was stirred at 25° C. for 0.5 hour, the solvent was removed under reduced pressure. The residue was neutralized with saturated aqueous $Na_2CO_3$ (0.5 mL) and extracted with ethyl acetate (5×1 mL). The organic layers were dried over $Na_2SO_4$ and concentrated under vacuum. The residue was purified by prep-HPLC (column: Waters Xbridge 150*25 mm*5 um; mobile phase: [water (10 mM $NH_4HCO_3$)-ACN]; B %: 24%-54%, 10 min). The desired fractions were collected and lyophilized to give the title compound (8.91 mg, 32%). White solid; $^1$H NMR (400 MHz, $CDCl_3$): δ 8.99 (s, 1H), 8.04-7.98 (m, 1H), 7.95-7.89 (m, 1H), 7.60-7.53 (m, 1H), 7.53-7.45 (m, 2H), 7.45-7.38 (m, 1H), 6.06-5.68 (m, 1H), 4.79-4.62 (m, 1H), 4.59-4.44 (m, 1H), 4.20 (s, 2H), 3.76-3.63 (m, 3H), 3.62-3.54 (m, 1H), 3.20-3.06 (m, 2H), 3.01-2.86 (m, 2H), 2.65 (td, J=7.2, 9.6 Hz, 2H), 2.19-2.05 (m, 2H), 1.96-1.72 (m, 10H); LCMS [ESI, M+1]: 589.

Example 248

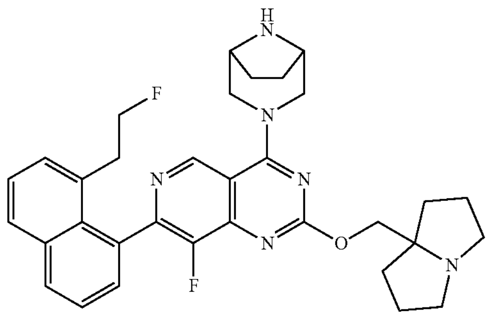 [SMILES: FCCc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-7-(8-(2-fluoroethyl)naphthalen-1-yl)-2-((tetrahydro-1H-pyrrolizin-7a(5H)-yl)methoxy)pyrido[4,3-d]pyrimidine

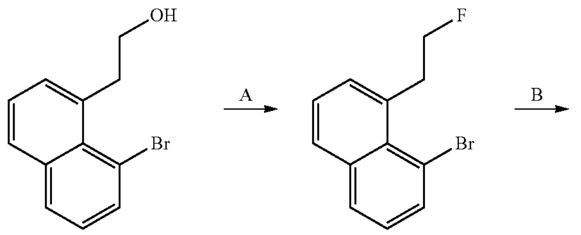

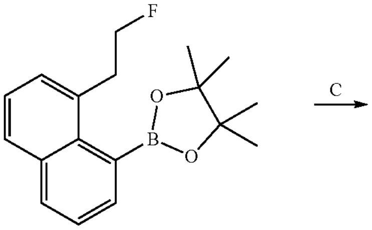

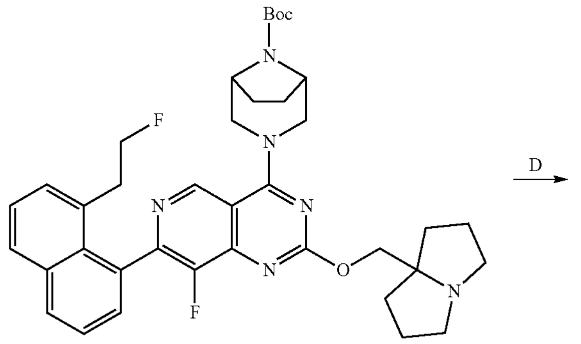

-continued

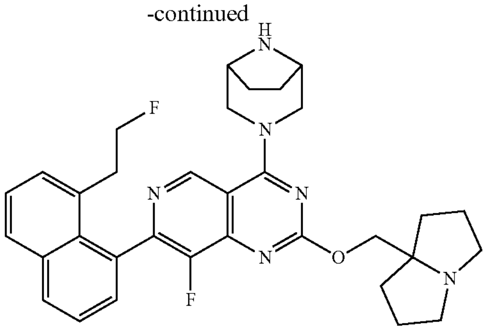

4-((1R,5S)-3,8-diazabicyclo[3.2.1]octan-3-yl)-8-fluoro-7-(8-(2-fluoroethyl)naphthalen-1-yl)-2-((tetrahydro-1H-pyrrolizin-7a(5H)-yl)methoxy)pyrido[4,3-d]pyrimidine. To a solution of tert-butyl(1R,5S)-3-(8-fluoro-7-(8-(2-fluoroethyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (45 mg, 61.57 μmol, 1.0 eq) in MeCN (0.6 mL) was added HCl·dioxane (4 M, 0.6 mL) below 10° C. The mixture was stirred at 25° C. for 1 hour. The reaction mixture was diluted with $H_2O$ (10 mL) and EA (5 mL). The pH of the mixture was adjusted to 8~9 with solid $NaHCO_3$ below 10° C. The mixture was extracted with ethyl acetate (3×20 mL). The combined organic layers were dried over anhydrous $Na_2SO_4$, filtered and concentrated under reduced pressure to give a residue. The residue was purified by prep-HPLC (column: Phenomenex Synergi C18 150*25*10 um; mobile phase: [water (0.225% FA)-ACN]; B %: 6%-36%, 10 min). The desired fractions were collected and lyophilized to give the title compound (10.30 mg, 26% yield, 2FA). Yellow solid; $^1H$ NMR (400 MHz, METHANOL-d4) δ=9.21-9.09 (m, 1H), 8.63-8.38 (m, 2H), 8.13-8.03 (m, 1H), 8.00-7.90 (m, 1H), 7.68-7.56 (m, 1H), 7.55-7.47 (m, 2H), 7.46-7.41 (m, 1H), 4.79-4.71 (m, 2H), 4.70-4.63 (m, 2H), 4.50-4.19 (m, 2H), 4.04-3.94 (m, 2H), 3.93-3.82 (m, 2H), 3.77-3.60 (m, 2H), 3.27 (q, J=6.0 Hz, 1H), 2.82-2.66 (m, 2H), 2.40-2.29 (m, 2H), 2.28-1.90 (m, 10H); $^{19}F$ NMR (377 MHz, METHANOL-d4) δ=−139.76, −214.10; LCMS [ESI, M+1]: 571.

Example 249

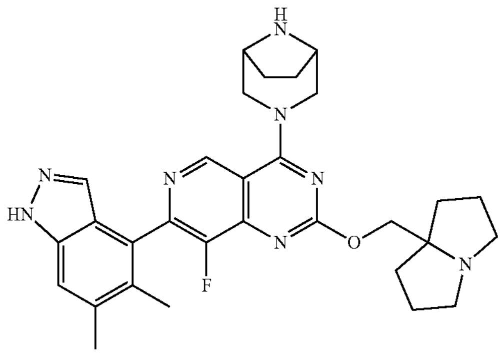 [SMILES: Cc1cc2[nH]ncc2c(-c2ncc3c(N4CC5CCC(C4)N5)nc(OCC45CCCN4CCC5)nc3c2F)c1C]

4-((1R,5S)-3,8-diazabicyclo[3.2.1]octan-3-yl)-7-(5,6-dimethyl-1H-indazol-4-yl)-8-fluoro-2-((hexahydro-1H-pyrrolizin-7a-yl)methoxy)pyrido[4,3-d]pyrimidine

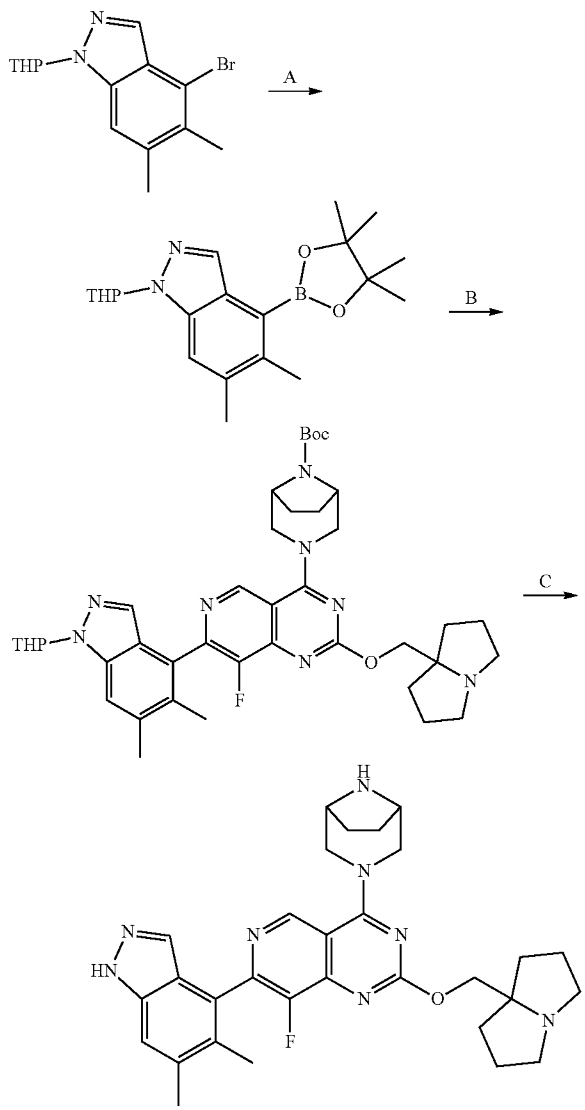

4-((1R,5S)-3,8-diazabicyclo[3.2.1]octan-3-yl)-7-(5,6-dimethyl-1H-indazol-4-yl)-8-fluoro-2-((hexahydro-1H-pyrrolizin-7a-yl)methoxy)pyrido[4,3-d]pyrimidine. To a solution of (1R,5S)-tert-butyl 3-(7-(5,6-dimethyl-1-(tetrahydro-2H-pyran-2-yl)-1H-indazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (50.0 mg, 68.8 μmol, 1.0 eq) in ACN (0.5 mL) was added HCl/dioxane (4 M, 0.5 mL, 29 eq) at 0° C. The mixture was stirred at 25° C. for 30 minutes. The solvent was concentrated under vacuum. The residue was diluted with methanol (1.0 mL) and neutralized with solid $Na_2CO_3$. The mixture was filtered and the filtrate was purified by prep-HPLC (column: Waters X bridge 150*25 mm*5 um; mobile phase: [water (10 mM $NH_4HCO_3$)-ACN]; B %: 28%-58%, 10 min). The desired fractions were collected and lyophilized to give the title compound (11.3 mg, 30%). White solid; $^1$H NMR (400 MHz, chloroform-d) δ 10.85-9.91 (m, 1H), 9.10 (s, 1H), 7.72 (s, 1H), 7.38 (s, 1H), 4.69-4.50 (m, 2H), 4.25-4.14 (m, 2H), 3.73-3.57 (m, 4H), 3.19-3.08 (m, 2H), 2.65 (td, J=6.9, 10.1 Hz, 2H), 2.47 (s, 3H), 2.23 (d, J=1.2 Hz, 3H), 2.11 (td, J=6.0, 12.4 Hz, 2H), 1.96-1.84 (m, 8H), 1.72-1.65 (m, 2H); LCMS [ESI, M+1]: 543.

Example 250

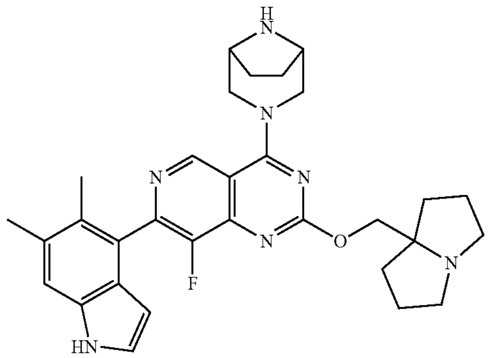 [SMILES: Cc1cc2[nH]ccc2c(-c2ncc3c(N4CC5CCC(C4)N5)nc(OCC45CCCN4CCC5)nc3c2F)c1C]

4-((1R,5S)-3,8-diazabicyclo[3.2.1]octan-3-yl)-7-(5,6-dimethyl-1H-indol-4-yl)-8-fluoro-2-((hexahydro-1H-pyrrolizin-7a-yl)methoxy)pyrido[4,3-d]pyrimidine

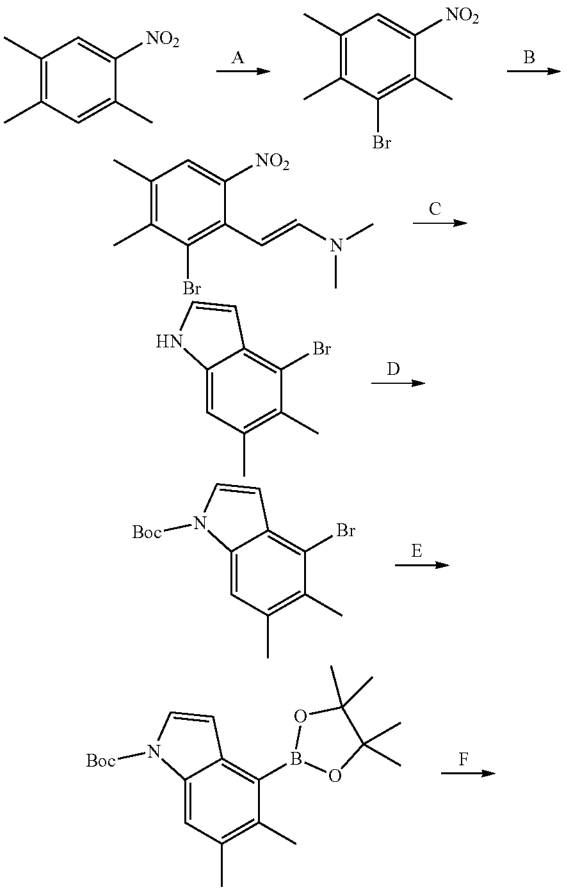

-continued

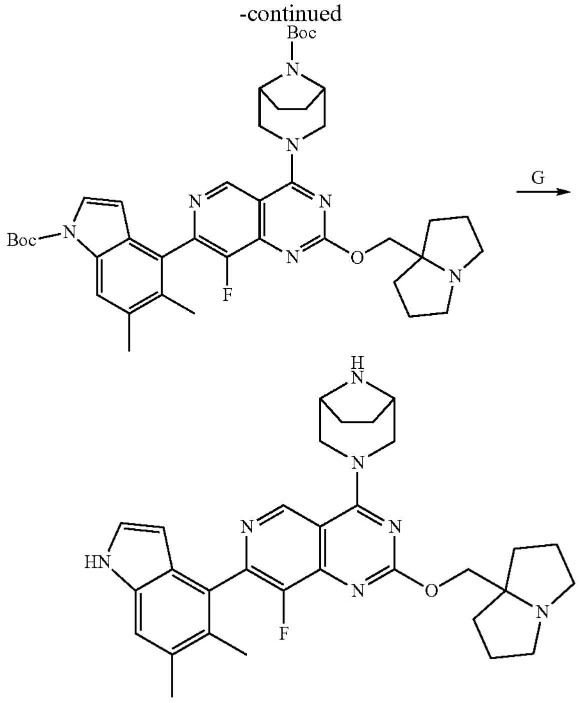

4-((1R,5S)-3,8-diazabicyclo[3.2.1]octan-3-yl)-7-(5,6-dimethyl-1H-indol-4-yl)-8-fluoro-2-((hexahydro-1H-pyrrolizin-7a-yl)methoxy)pyrido[4,3-d]pyrimidine. To a solution of tert-butyl 4-(4-((1R,5S)-8-(tert-butoxycarbonyl)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5,6-dimethyl-1H-indole-1-carboxylate (60 mg, 80.8 μmol, 1 eq) was added HCl·MeOH (4 M, 20.2 μL, 1 eq) in one portion at 0° C. under $N_2$. The mixture was stirred at 0° C. for 30 minutes. The mixture was concentrated in vacuum. The residue was purified by prep-HPLC column: Phenomenex Gemini-NX C18 75*30 mm*3 um; mobile phase: [water (0.225% FA)-ACN]; (B %: 6%-36%, 7 min) to afford the title compound (7.69 mg, 15% yield, 2FA). Yellow solid; $^{1}$H NMR (400 MHz, DMSO+D2O) δ=9.14 (s, 1H), 7.33 (s, 1H), 7.17 (d, J=2.8 Hz, 1H), 5.88 (br s, 1H), 4.62-4.50 (m, 2H), 4:46 (s, 2H), 3.78-3.72 (m, 4H), 3.47-3.36 (m, 2H), 3.13-3.03 (m, 2H), 2.35 (s, 3H), 2.16-1.91 (m, 11H), 1.86-1.69 (m, 4H); LCMS [ESI, M+1]: 542.

Example 251

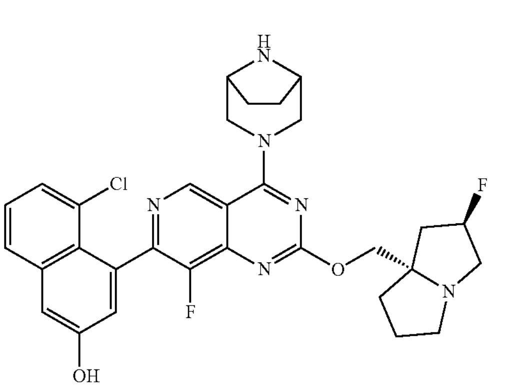 [SMILES: Oc1cc(-c2ncc3c(N4CC5CCC(C4)N5)nc(OC[C@@]45CCCN4C[C@H](F)C5)nc3c2F)c2c(Cl)cccc2c1]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloronaphthalen-2-ol

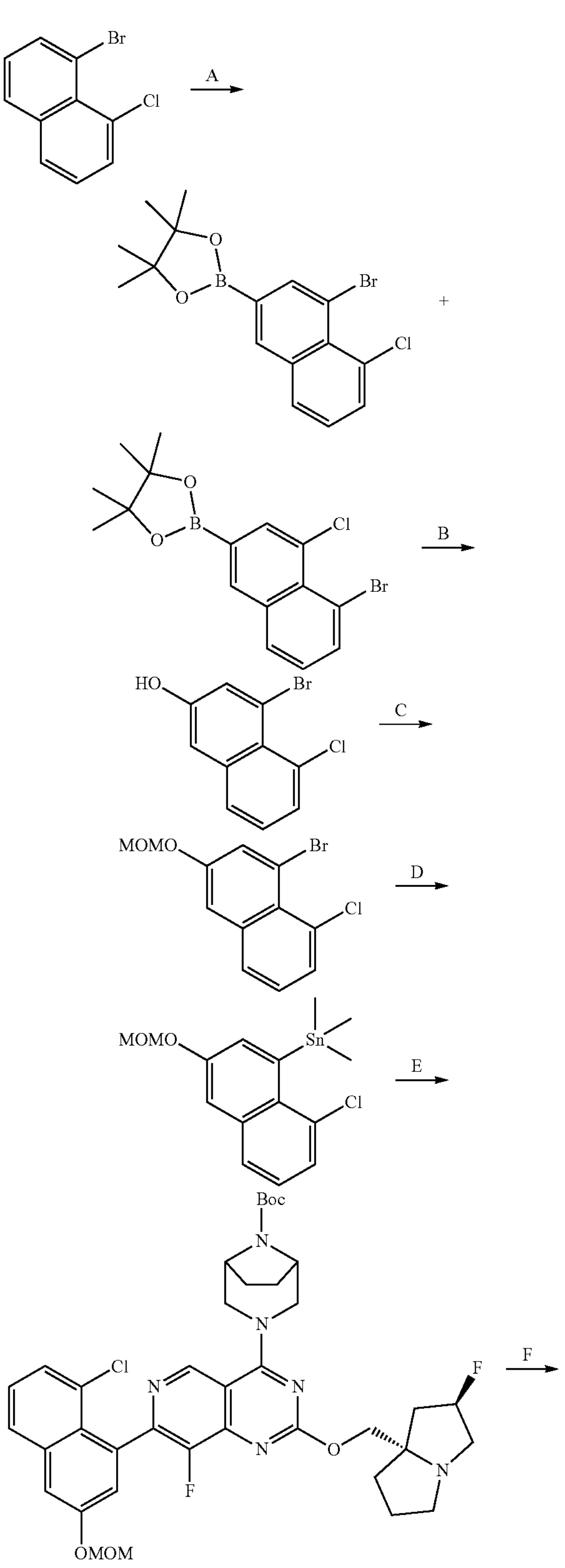

-continued

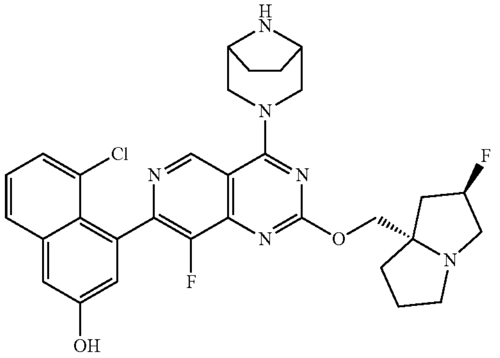 [SMILES: Oc1cc(-c2ncc3c(N4CC5CCC(C4)N5)nc(OC[C@@]45CCCN4C[C@H](F)C5)nc3c2F)c2c(Cl)cccc2c1]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloronaphthalen-2-ol. To tert-butyl(1R,5S)-3-(7-(8-chloro-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (330 mg, 448 μmol, 1.0 eq) was added HCl/MeOH (4 M, 5.21 mL, 47.0 eq) in one portion at 0° C. under $N_2$. The mixture was stirred at 0° C. for 10 minutes. Upon completion, the mixture was concentrated under reduced pressure. The residue was purified by prep-HPLC (column: Phenomenex luna C18 150*40 mm*15 um; mobile phase: [water (0.225% FA)-ACN]; B %: 1%-30%, 10 min), The desired fraction was collected and lyophilized to afford the title compound (140 mg, 43% yield, 2 FA). Yellow solid; $^1$H NMR (400 MHz, $CDCl_3$) δ=9.11 (s, 1H), 7.82-7.76 (m, 1H), 7.43-7.34 (m, 3H), 7.17 (d, J=2.4 Hz, 1H), 5.59-5.40 (m, 1H), 4.84-4.74 (m, 2H), 4.63-4.51 (m, 2H), 4.06 (br s, 2H), 3.95-3.59 (m, 5H), 3.32-3.26 (m, 1H), 2.66-2.44 (m, 2H), 2.39-2.17 (m, 3H), 2.16-1.95 (m, 5H). LCMS [ESI, M+1]: 593.2.

Example 252

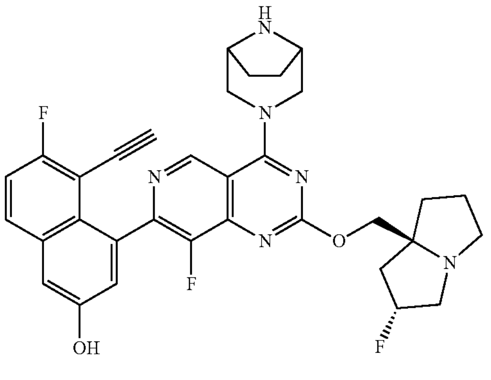 [SMILES: C#Cc1c(F)ccc2cc(O)cc(-c3ncc4c(N5CC6CCC(C5)N6)nc(OC[C@@]56CCCN5C[C@H](F)C6)nc4c3F)c12]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol

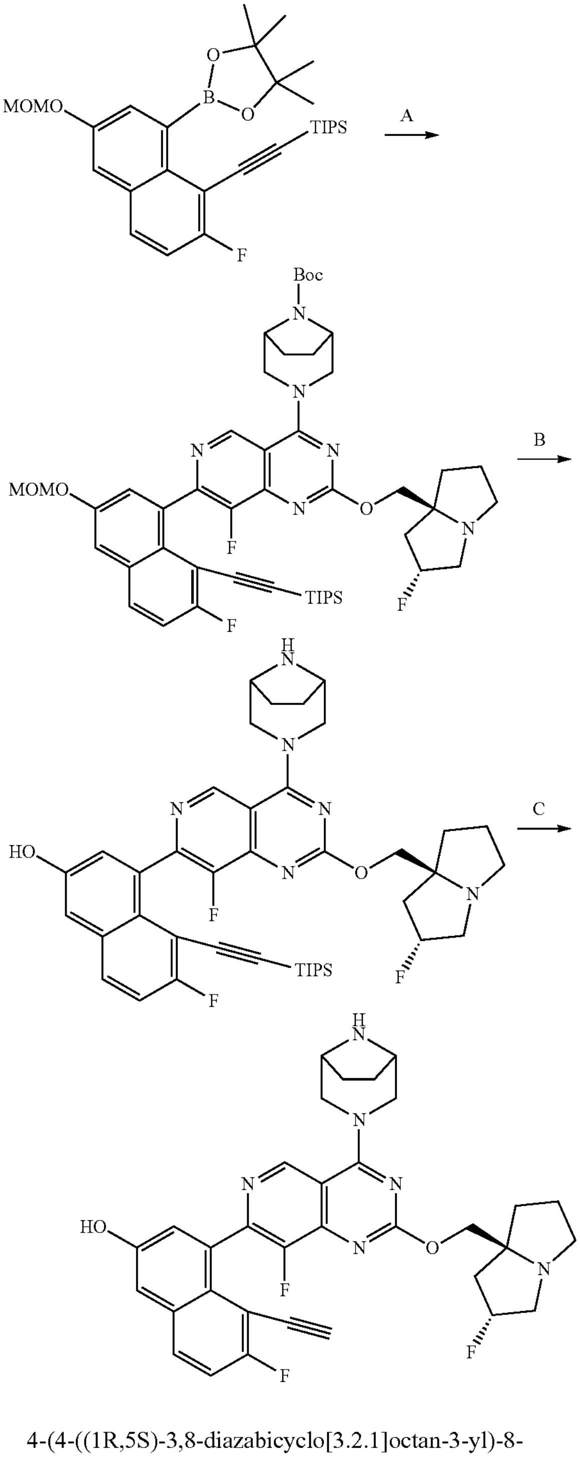

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol. To a mixture of (4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido

[4,3-d]pyrimidin-7-yl)-6-fluoro-5-((triisopropylsilyl)ethynyl)naphthalen-2-ol (40 mg, crude) in DMF (1 mL) was added CsF (40.13 mg, 264 μmol, 5.0 eq) in one portion under $N_2$. The mixture was stirred at 20° C. for 1 hour. After completion, the mixture was purified by prep-HPLC (column: Waters Xbridge C18 150*50 mm*10 um; mobile phase: [water (10 mM $NH_4HCO_3$)-ACN]; B %: 25%-55%, 10 min) to give the title compound (4.88 mg, 15% yield). Yellow solid; $^1$H NMR (400 MHz, methanol-$d_4$) δ=9.03 (s, 1H), 7.88 (dd, J=5.7, 9.1 Hz, 1H), 7.38-7.31 (m, 2H), 7.23 (d, J=2.5 Hz, 1H), 5.42-5.23 (m, 1H), 4.70-4.55 (m, 5H), 4.36-4.21 (m, 2H), 3.73 (br dd, J=7.1, 12.4 Hz, 2H), 3.37 (s, 1H), 3.25 (br s, 1H), 3.23-3.19 (m, 1H), 3.03 (dt, J=5.8, 9.5 Hz, 1H), 2.41-2.21 (m, 2H), 2.20-2.11 (m, 1H), 2.06-1.97 (m, 2H), 1.92-1.78 (m, 5H); LCMS [ESI, M+1]: 601.3.

Example 253

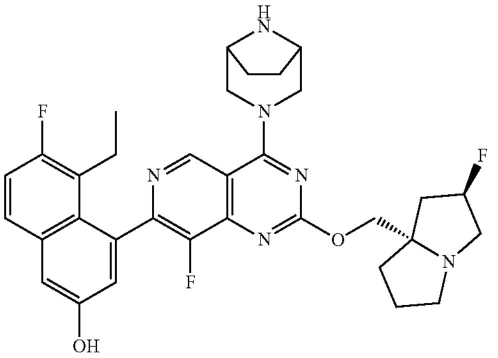 [SMILES: CCc1c(F)ccc2cc(O)cc(-c3ncc4c(N5CC6CCC(C5)N6)nc(OC[C@@]56CCCN5C[C@H](F)C6)nc4c3F)c12]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

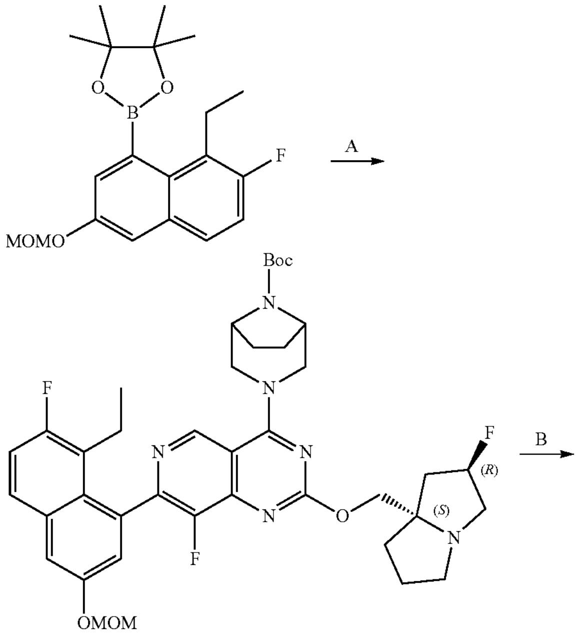

-continued

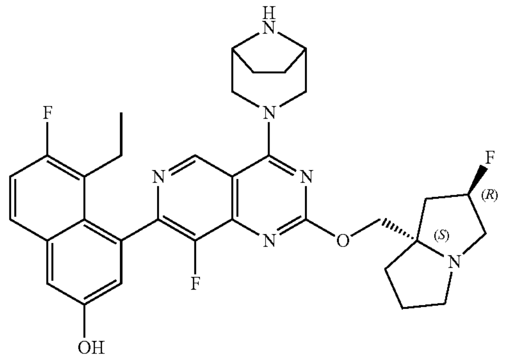

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol. To the solution of (1R,5S)-tert-butyl 3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (60.0 mg, 80.1 μmol, 1.0 eq) in ACN (1 mL) was added HCl·dioxane (4 M, 2 mL) at 0° C., and the mixture was stirred at 0° C. for 0.5 hr. After completion, the mixture was concentrated at 20° C. The residue was purified by prep-HPLC (column: Unisil 3-100 C18 ultra 150*50 mm*3 um; mobile phase: [water (0.225% FA)-ACN]; B %: 8%-28%, 10 min) to give the title compound (15.24 mg, 26% yield, 2FA). Off-white solid. $^1$H NMR (400 MHz, METHANOL-d4) δ=9.13 (s, 1H), 8.40 (br s, 2H), 7.73-7.65 (m, 1H), 7.35-7.20 (m, 2H), 7.04 (d, J=2.4 Hz, 1H), 5.63-5.35 (m, 1H), 4.85-4.73 (m, 2H), 4.65-4.52 (m, 2H), 4.11 (br d, J=9.2 Hz, 2H), 4.00-3.86 (m, 2H), 3.85-3.62 (m, 3H), 3.39-3.32 (m, 1H), 2.71-2.41 (m, 3H), 2.40-2.31 (m, 1H), 2.30-2.15 (m, 3H), 2.14-1.96 (m, 5H), 0.85-0.73 (m, 3H). LCMS [ESI, M+1]: 605.2.

Example 254

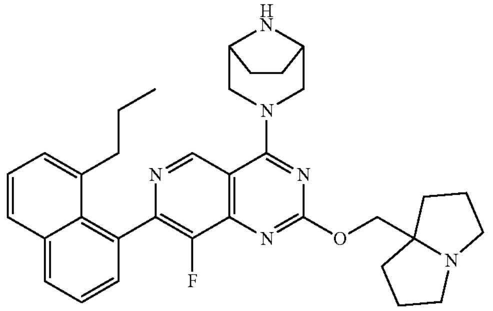 [SMILES: CCCc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-2-((hexahydro-1H-pyrrolizin-7a-yl)methoxy)-7-(8-propylnaphthalen-1-yl)pyrido[4,3-d]pyrimidine

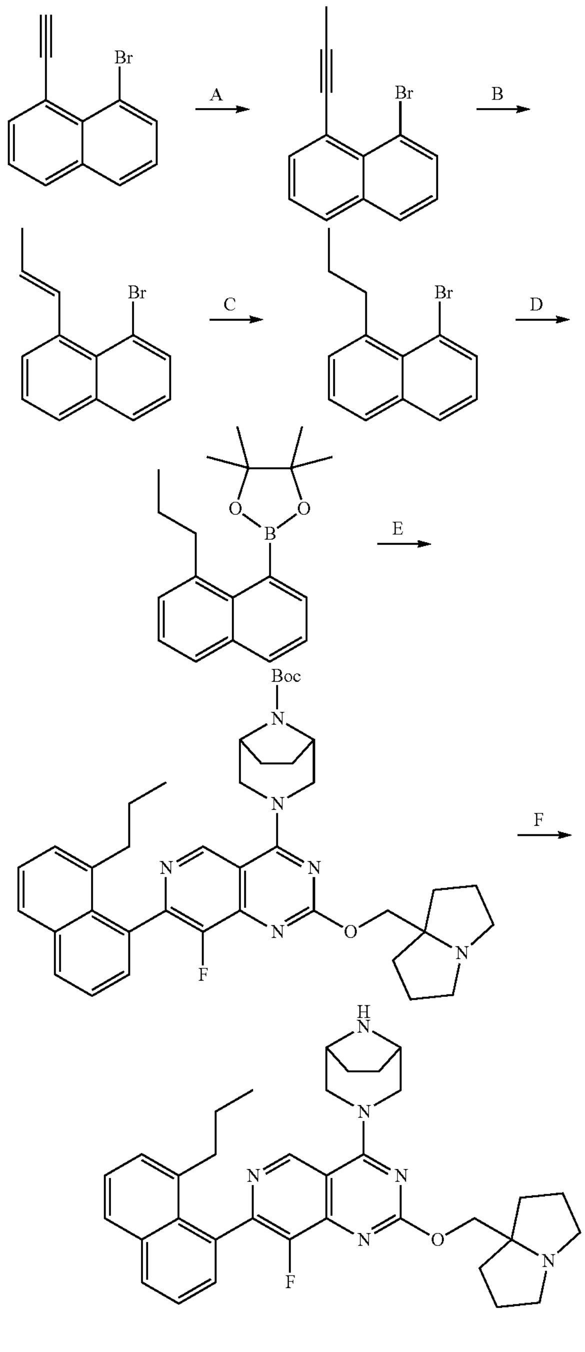

4-((1R,5S)-3,8-diazabicyclo[3.2.1]octan-3-yl)-8-fluoro-2-((hexahydro-1H-pyrrolizin-7a-yl)methoxy)-7-(8-propylnaphthalen-1-yl)pyrido[4,3-d]pyrimidine. To the solution of (1R,5S)-tert-butyl 3-(8-fluoro-2-((hexahydro-1H-pyrrolizin-7a-yl)methoxy)-7-(8-propylnaphthalen-1-yl)pyrido[4,3-d]pyrimidin-4-yl)-3,8-diazabicyclo[3.2.1]octane-8-carboxylate (70.0 mg, 105 μmol, 1.0 eq) in acetonitrile (1.0 mL) was added HCl·dioxane (4 M, 2.0 mL) at 0° C., and the mixture was stirred at 0° C. for 30 minutes. After completion, the mixture was concentrated at 25° C. The residue was purified by prep-HPLC (column: Unisil 3-100 C18 ultra 150*50 mm*3 um; mobile phase: [water (0.225% FA)-ACN]; B %: 8%-38%, 10 min) to give the title compound (28.8 mg, 41% yield). Yellow solid; $^1$H NMR (400 MHz, methanol-$d_4$) δ=9.14 (s, 1H), 8.12-8.01 (m, 1H), 7.88 (d, J=8.0 Hz, 1H), 7.60-7.54 (m, 1H), 7.51-7.45 (m, 1H), 7.45-7.42 (m, 1H), 7.38 (d, J=6.4 Hz, 1H), 4.81-4.74 (m, 2H), 4.68 (s, 2H), 4.02-3.98 (m, 2H), 3.89 (br d, J=13.6 Hz, 2H), 3.75-3.64 (m, 2H), 3.34-3.32 (m, 1H), 3.29-3.26 (m, 1H), 2.27 (br d, J=3.2 Hz, 4H), 2.26-2.15 (m, 4H), 2.14-2.07 (m, 2H), 2.06-1.97 (m, 2H), 1.96-1.83 (m, 2H), 1.40-1.25 (m, 2H), 0.42 (t, J=7.2 Hz, 3H); LCMS [ESI, M+1]: 567.3.

Example 255

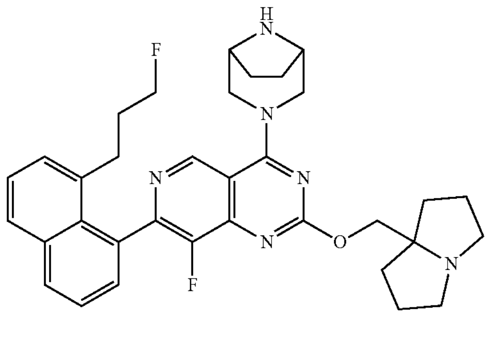 [SMILES: FCCCc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-7-(8-(3-fluoropropyl)naphthalen-1-yl)-2-((hexahydro-1H-pyrrolizin-7a-yl)methoxy)pyrido[4,3-d]pyrimidine

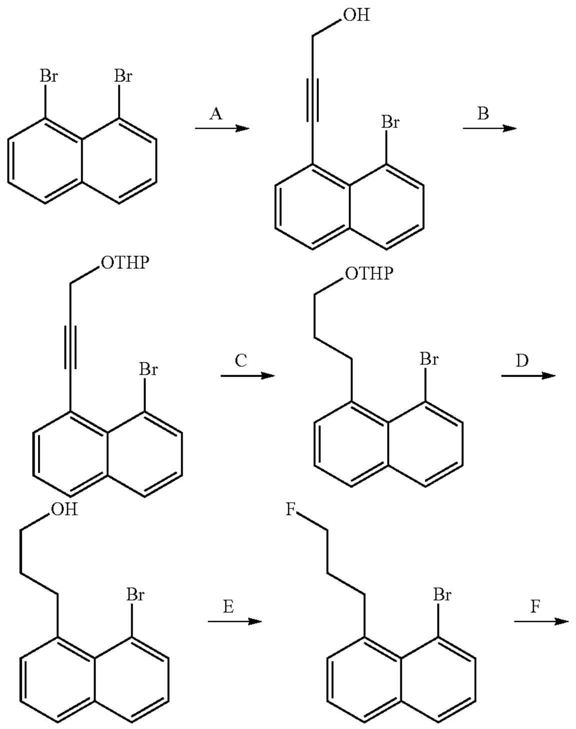

-continued

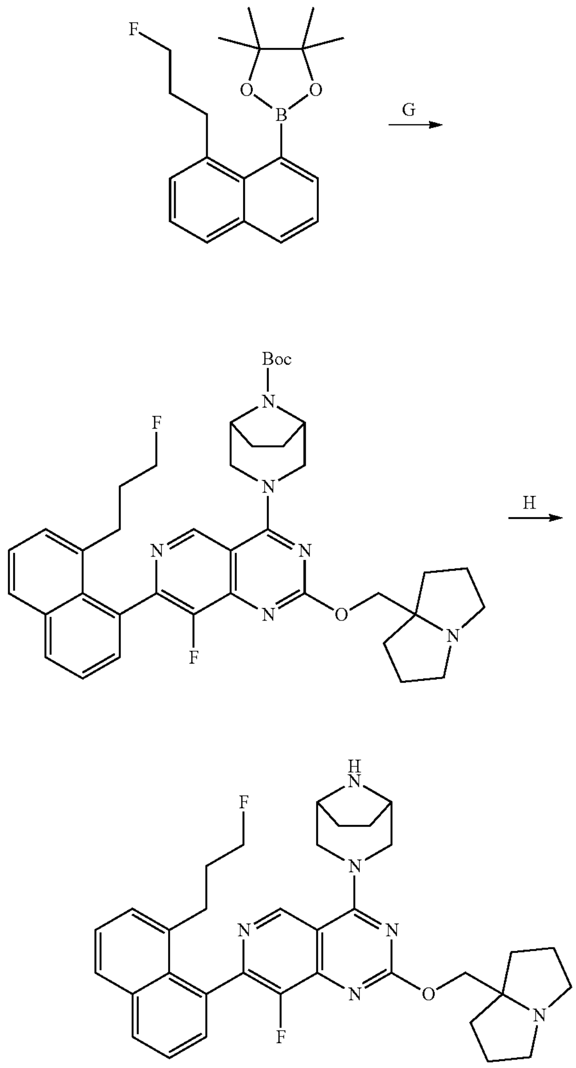

4-((1R,5S)-3,8-diazabicyclo[3.2.1]octan-3-yl)-8-fluoro-7-(8-(3-fluoropropyl)naphthalen-1-yl)-2-((tetrahydro-1H-pyrrolizin-7a(5H)-yl)methoxy)pyrido[4,3-d]pyrimidine. A mixture of tert-butyl(1R,5S)-3-(8-fluoro-7-(8-(3-fluoropropyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate in HCl/dioxane (4 M, 2 mL) and acetonitrile (0.1 mL) was stirred at 15° C. for 10 mins. After completion, the mixture was concentrated under vacuum, The residue was purified by prep-HPLC (column: Shim-pack C18 150*25*10 um; mobile phase: [water (0.225% FA)-ACN]; B %: 15%-35%, 9 min) to give the title compound (4.62 mg, 24% yield, 2FA) as a yellow oil. $^1H$ NMR (400 MHz, METHANOL-d4) δ=9.11 (s, 1H), 8.48 (br s, 2H), 8.08 (dd, J=1.2, 8.4 Hz, 1H), 7.91 (d, J=7.6 Hz, 1H), 7.59 (t, J=7.6 Hz, 1H), 7.53-7.40 (m, 3H), 4.72-4.56 (m, 4H), 4.19-4.07 (m, 1H), 4.04-3.91 (m, 4H), 3.79 (br d, J=12.8 Hz, 1H), 3.73-3.65 (m, 2H), 3.30-3.23 (m, 2H), 2.63-2.42 (m, 2H), 2.39-2.29 (m, 2H), 2.28-2.08 (m, 6H), 2.03-1.81 (m, 4H), 1.78-1.62 (m, 2H). FNMR: −139.603, −221.664. LCMS [ESI, M+1]: 585.3.

Example 256

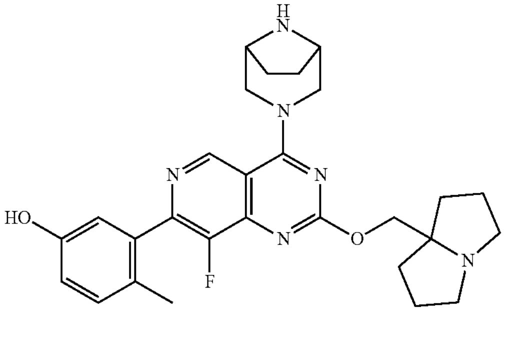 [SMILES: Cc1ccc(O)cc1-c1ncc2c(N3CC4CCC(C3)N4)nc(OCC34CCCN3CCC4)nc2c1F]

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-methylphenol

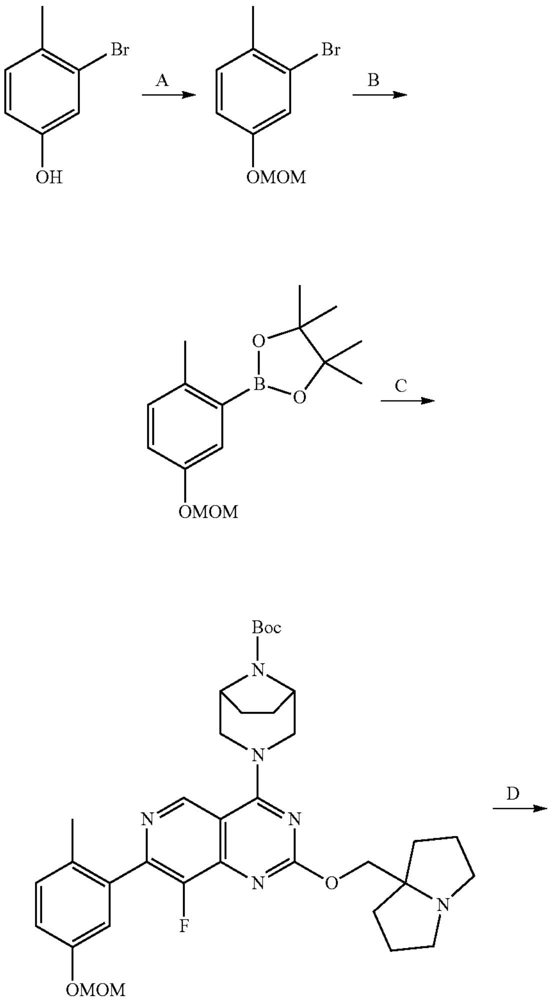

-continued

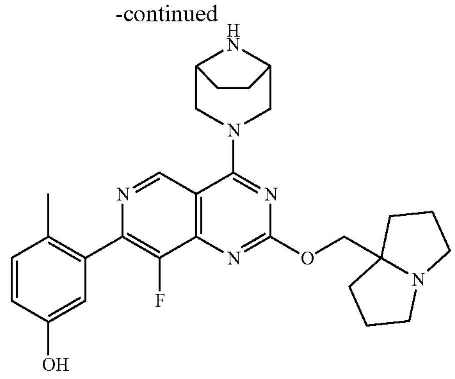

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-methylphenol. To a mixture of tert-butyl(1R,5S)-3-(8-fluoro-7-(5-(methoxymethoxy)-2-methylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 154 μmol, 1.0 eq) in ACN (2 mL) was added HCl·dioxane (4 M, 2.00 mL, 52.0 eq) in one portion at 0° C. under $N_2$. The mixture was stirred at 0° C. for 0.5 hours. The reaction mixture was filtered and concentrated under reduced pressure. The residue was purified by prep-HPLC (column: 3_Phenomenex Luna C18 75*30 mm*3 um; mobile phase: [water (0.225% FA)-ACN]; B %: 0%-18%, 8 min). The desired fraction was collected and concentrated under vacuum to remove acetonitrile. The desired fraction was collected and lyophilized to affording the title compound (26.7 mg, 28% yield, 2FA). Yellow solid; $^1$H NMR (400 MHz, $CDCl_3$-d) δ=9.14 (s, 1H), 7.20 (d, J=8.4 Hz, 1H), 6.91-6.81 (m, 2H), 4.85-4.80 (m, 2H), 4.69 (s, 2H), 4.05 (br s, 2H), 3.90 (br d, J=13.2 Hz, 2H), 3.78-3.66 (m, 2H), 3.32-3.26 (m, 2H), 2.40-2.29 (m, 2H), 2.23-2.17 (m, 4H), 2.16 (s, 3H), 2.15-2.09 (m, 2H), 2.08-2.02 (m, 2H), 2.01-1.92 (m, 2H); LCMS [ESI, M+1]: 505.5.

Example 257

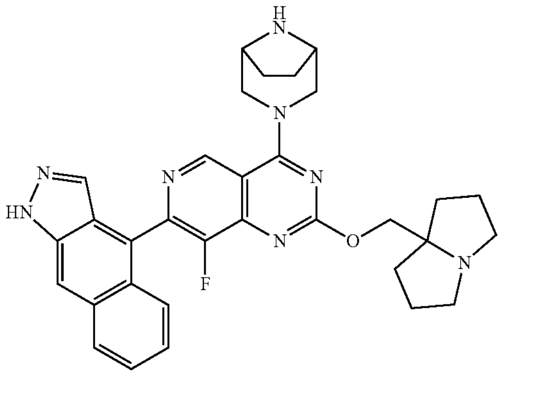 [SMILES: Fc1c(-c2c3ccccc3cc3[nH]ncc23)ncc2c(N3CC4CCC(C3)N4)nc(OCC34CCCN3CCC4)nc12]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-1H-benzo[f]indazole

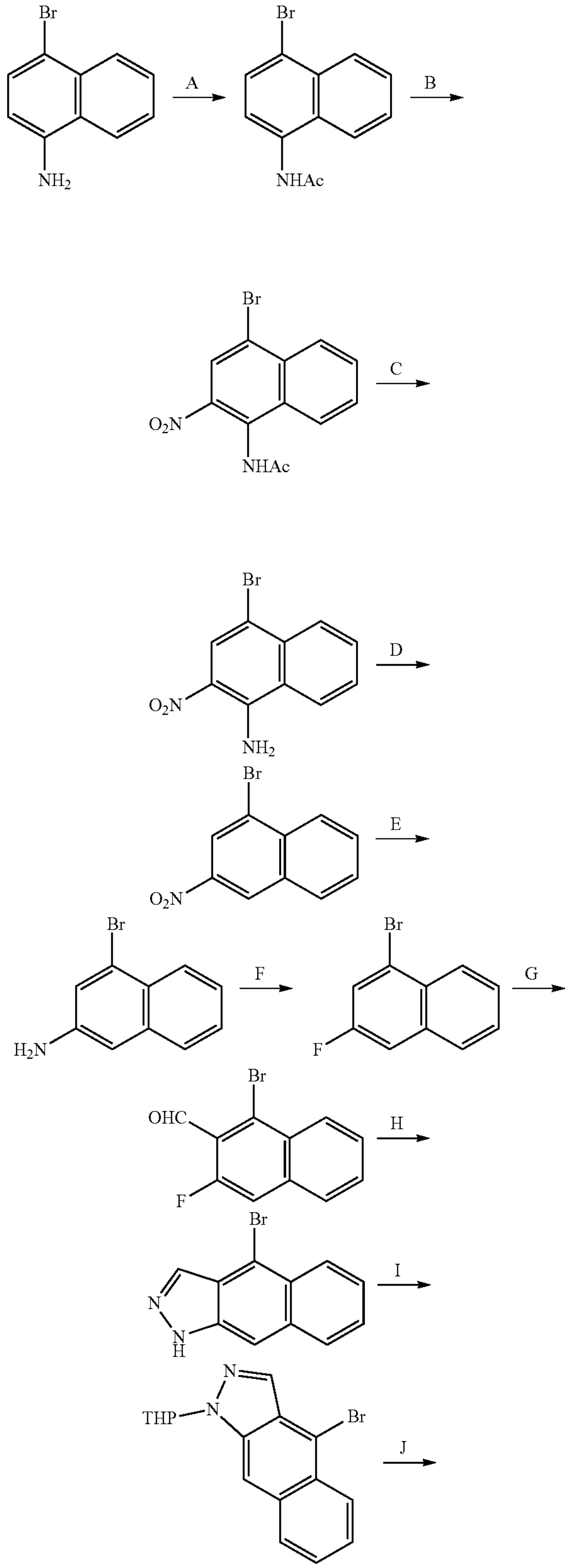

-continued

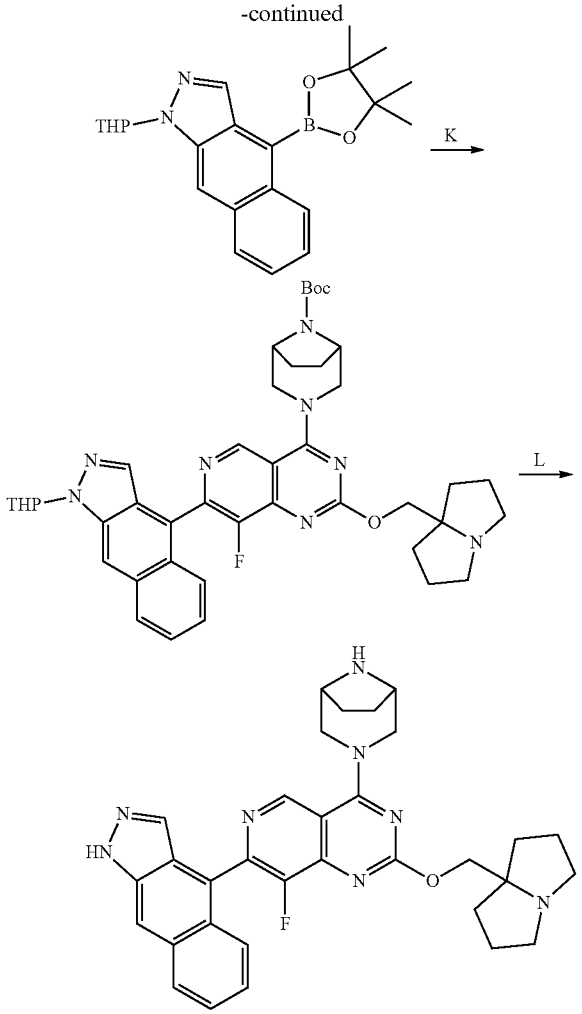

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-1H-benzo[f]indazole. To a mixture of (1R,5S)-tert-butyl 3-(8-fluoro-2-((hexahydro-1H-pyrrolizin-7a-yl)methoxy)-7-(1-(tetrahydro-2H-pyran-2-yl)-1H-benzo[f]indazol-4-yl)pyrido[4,3-d]pyrimidin-4-yl)-3,8-diazabicyclo[3.2.1]octane-8-carboxylate (40 mg, 53.4 μmol, 1.0 eq) in DCM (2.0 mL) was added TFA (3.08 g, 27.0 mmol, 2.0 mL, 506 eq) in one portion at 0° C. under $N_2$. The mixture was stirred at 20° C. for 10 min. After completion, the reaction mixture was concentrated under reduced pressure. The residue was purified by prep-HPLC (column: Phenomenex Synergi C18 150*25*10 um; mobile phase: [water (0.225% FA)-ACN]; B %: 5%-35%, 8.5 min) to give the title compound (5.39 mg, 16% yield, 1.1 FA). Yellow solid; $^1$H NMR (400 MHz, METHANOL-d4) δ=9.31 (s, 1H), 8.25 (s, 1H), 8.11 (d, J=8.7 Hz, 1H), 8.07 (s, 1H), 7.85-7.79 (m, 1H), 7.55-7.48 (m, 1H), 7.38 (ddd, J=1.2, 6.6, 8.7 Hz, 1H), 4.94-4.91 (m, 1H), 4.84 (br s, 1H), 4.72 (s, 2H), 4.08 (br s, 2H), 3.95 (br t, J=13.5 Hz, 2H), 3.78-3.66 (m, 2H), 3.32-3.26 (m, 2H), 2.45-2.32 (m, 1H), 2.30-2.01 (m, 10H). [ESI, M+1]: 565.3.

Example 258

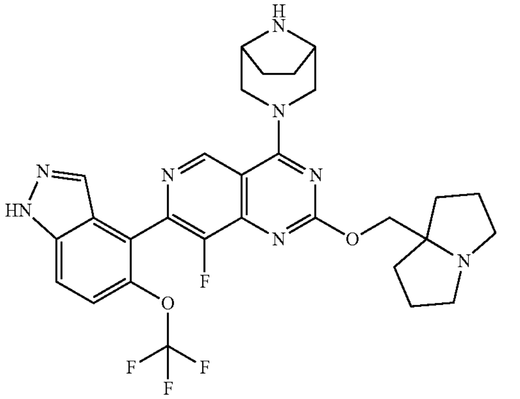 [SMILES: Fc1c(-c2c(OC(F)(F)F)ccc3[nH]ncc23)ncc2c(N3CC4CCC(C3)N4)nc(OCC34CCCN3CCC4)nc12]

4-((1R,5S)-3,8-diazabicyclo[3.2.1]octan-3-yl)-8-fluoro-2-((hexahydro-1H-pyrrolizin-7a-yl)methoxy)-7-(5-(trifluoromethoxy)-1H-indazol-4-yl)pyrido[4,3-d]pyrimidine

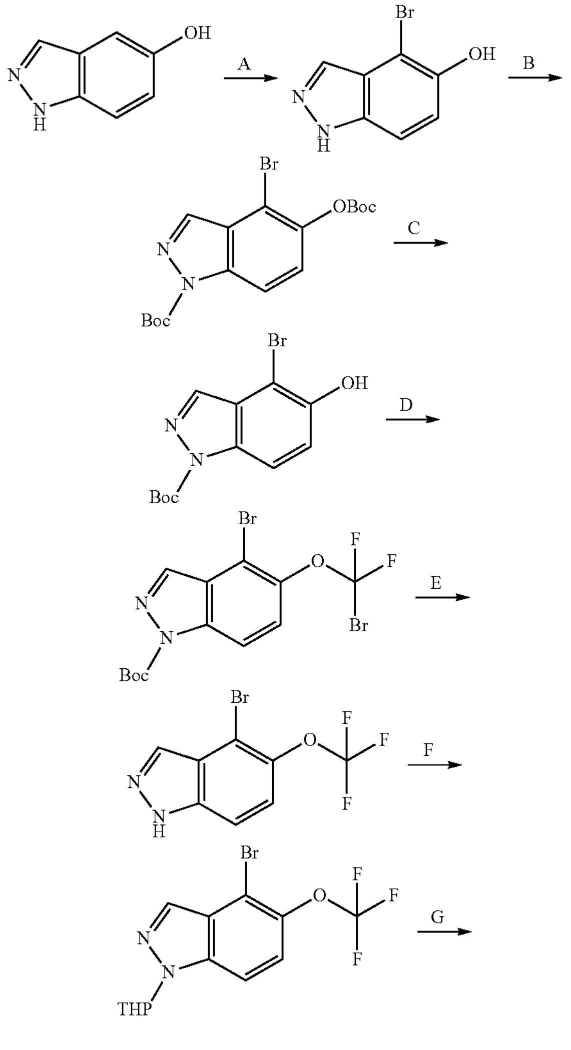

-continued

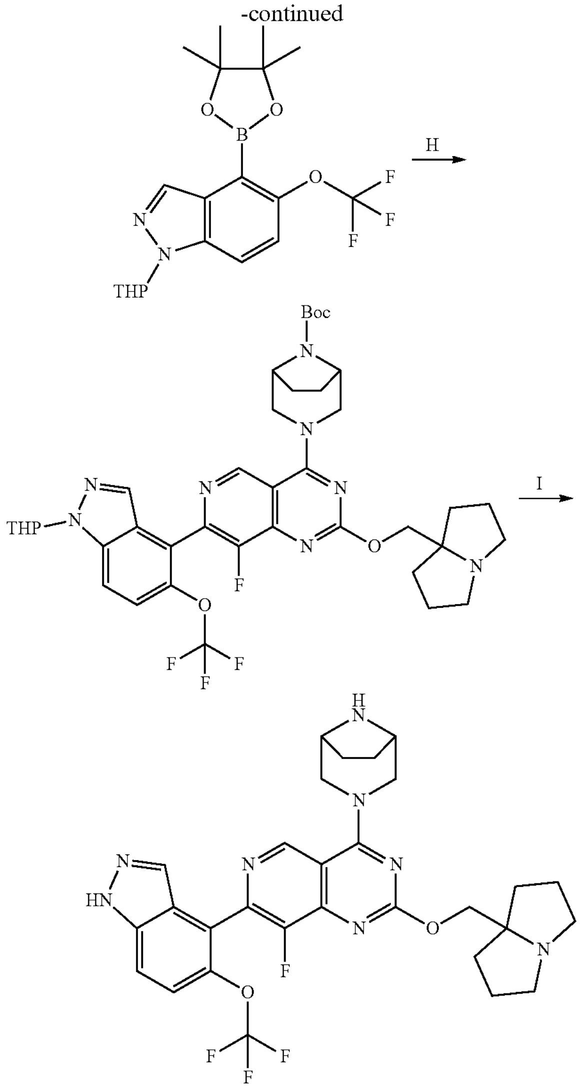

4-((1R,5S)-3,8-diazabicyclo[3.2.1]octan-3-yl)-8-fluoro-2-((hexahydro-1H-pyrrolizin-7a-yl)methoxy)-7-(5-(trifluoromethoxy)-1H-indazol-4-yl)pyrido[4,3-d]pyrimidine. To a solution of tert-butyl(1R,5S)-3-(8-fluoro-2-((tetrahydro-1H-pyrrolizin-7a(5H)-yl)methoxy)-7-(1-(tetrahydro-2H-pyran-2-yl)-5-(trifluoromethoxy)-1H-indazol-4-yl)pyrido[4,3-d]pyrimidin-4-yl)-3,8-diazabicyclo[3.2.1]octane-8-carboxylate (70 mg, 79.6 μmol, 1 eq) in ACN (2 mL) was added HCl·dioxane (4 M, 6 mL) dropwise below 15° C. The mixture was stirred at 15° C. for 0.5 hour. After completion, the reaction mixture was concentrated under reduced pressure to give a residue at 15° C. (without heating). The residue was dissolved in DCM (5 mL) and $H_2O$ (5 mL). The pH of the mixture was adjusted to 8~9 with $NaHCO_3$ solid below 5° C. The mixture was extracted with DCM (5 mL×5). The combined organic layers were dried over anhydrous $Na_2SO_4$, filtered and concentrated under reduced pressure to give a residue. The residue was purified by prep-HPLC (column: Shim-pack C18 150*25*10 um; mobile phase: [water (0.225% FA)-ACN]; B %: 9%-29%, 9 min) to give the title compound (5.37 mg, 10% yield, 1.8FA). Off-white solid; $^{1}H$ NMR (400 MHz, methanol-$d_4$) δ=9.26 (s, 1H), 7.99 (s, 1H), 7.82 (d, J=9.2 Hz, 1H), 7.54 (dd, J=1.2, 9.2 Hz, 1H), 4.77 (d, J=12.4 Hz, 2H), 4.67 (s, 2H), 3.93 (s, 2H), 3.84 (br d, J=12.8 Hz, 2H), 3.73-3.67 (m, 2H), 3.29-3.26 (m, 2H), 2.38-2.32 (m, 2H), 2.26-2.08 (m, 6H), 2.00-1.91 (m, 4H). $^{19}F$ NMR (377 MHz, methanol-$d_4$) δ=−59.1, −138. [ESI, M+1]: 599.2.

Example 259

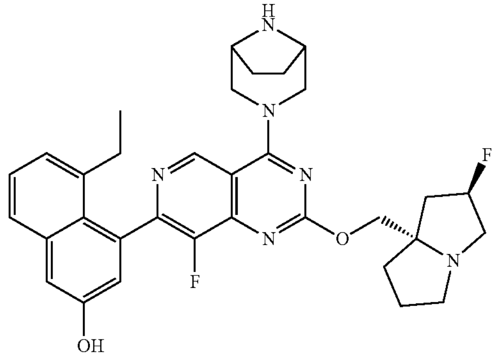 [SMILES: CCc1cccc2cc(O)cc(-c3ncc4c(N5CC6CCC(C5)N6)nc(OC[C@@]56CCCN5C[C@H](F)C6)nc4c3F)c12]

4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol

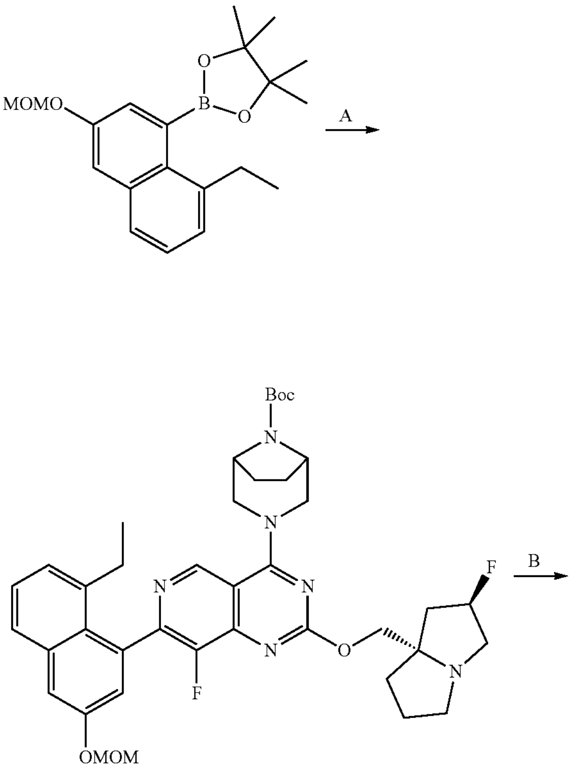

-continued

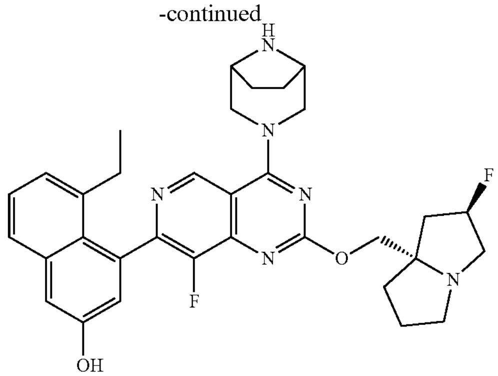

4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethyl-naphthalen-2-ol. A mixture of tert-butyl(1R,5S)-3-(7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (900 mg, 1.23 mmol, 1 eq) in HCl/dioxane (4 M, 3.79 mL, 12.3 eq) and acetonitrile (10 mL) was stirred at 20° C. for 0.5 hour. After completion, the mixture was concentrated under vacuum. The residue was purified by prep-HPLC (column: Phenomenex luna C18 150*40 mm*15 um; mobile phase: [water (0.225% FA)-ACN]; B %: 3%-33%, 10 min) to give the title compound (450 mg formic acid salt, 57% yield). Off-white solid. SFC: "Column: Chiralpak IC-3 50×4.6 mm I.D., 3 um Mobile phase: Phase A for $CO_2$, and Phase B for MeOH+ACN (0.05% DEA); Gradient elution: 60% MeOH+ACN (0.05% DEA) in $CO_2$. Flow rate: 3 mL/min; Detector: PDA; Column Temp: 35C; Back Pressure: 100 Bar". $^1$H NMR (400 MHz, METHANOL-d4) δ=9.11 (s, 1H), 7.64 (d, J=8.0 Hz, 1H), 7.37 (t, J=7.6 Hz, 1H), 7.30 (d, J=2.4 Hz, 1H), 7.17 (d, J=7.2 Hz, 1H), 7.00 (d, J=2.4 Hz, 1H), 5.54 (d, J=8.4 Hz, 1H), 4.80-4.68 (m, 2H), 4.61-4.49 (m, 2H), 4.13-4.01 (m, 2H), 3.98-3.61 (m, 5H), 3.37-3.33 (m, 1H), 2.68-2.17 (m, 7H), 2.04 (br d, J=13.2 Hz, 5H), 0.89 (dt, J=1.6, 7.6 Hz, 3H). [ESI, M+1]: 587.2.

Example 260

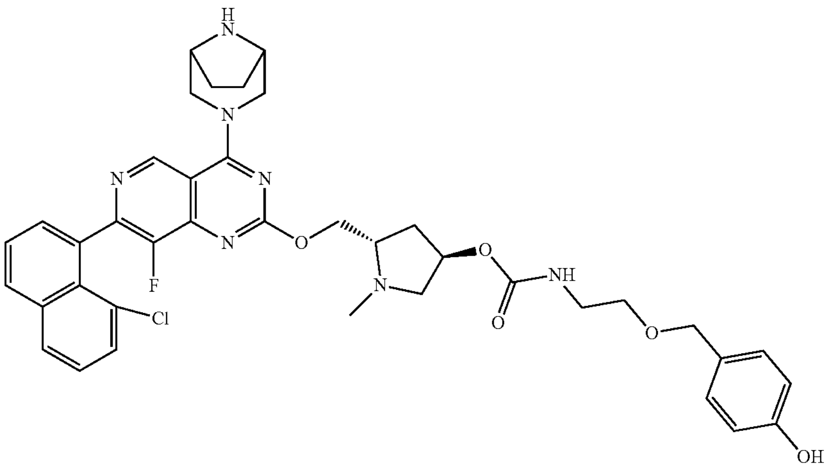 [SMILES: CN1C[C@H](OC(=O)NCCOCc2ccc(O)cc2)C[C@H]1COc1nc(N2CC3CCC(C2)N3)c2cnc(-c3cccc4cccc(Cl)c34)c(F)c2n1]

(3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl(2-((4-hydroxybenzyl)oxy)ethyl)carbamate

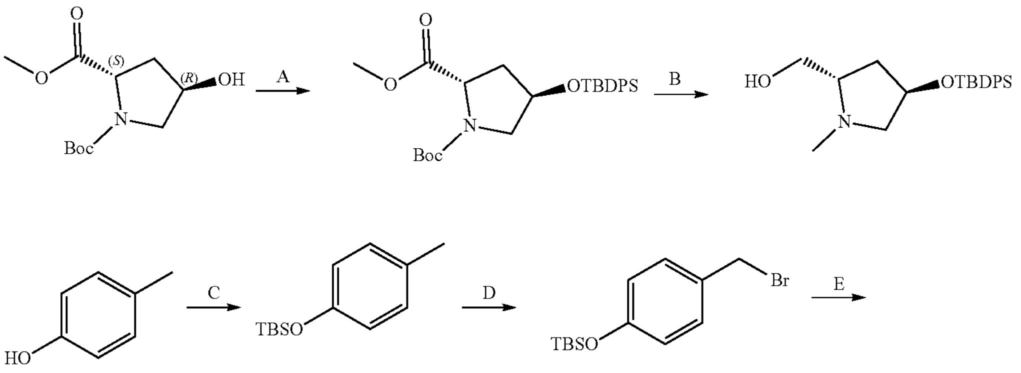

-continued
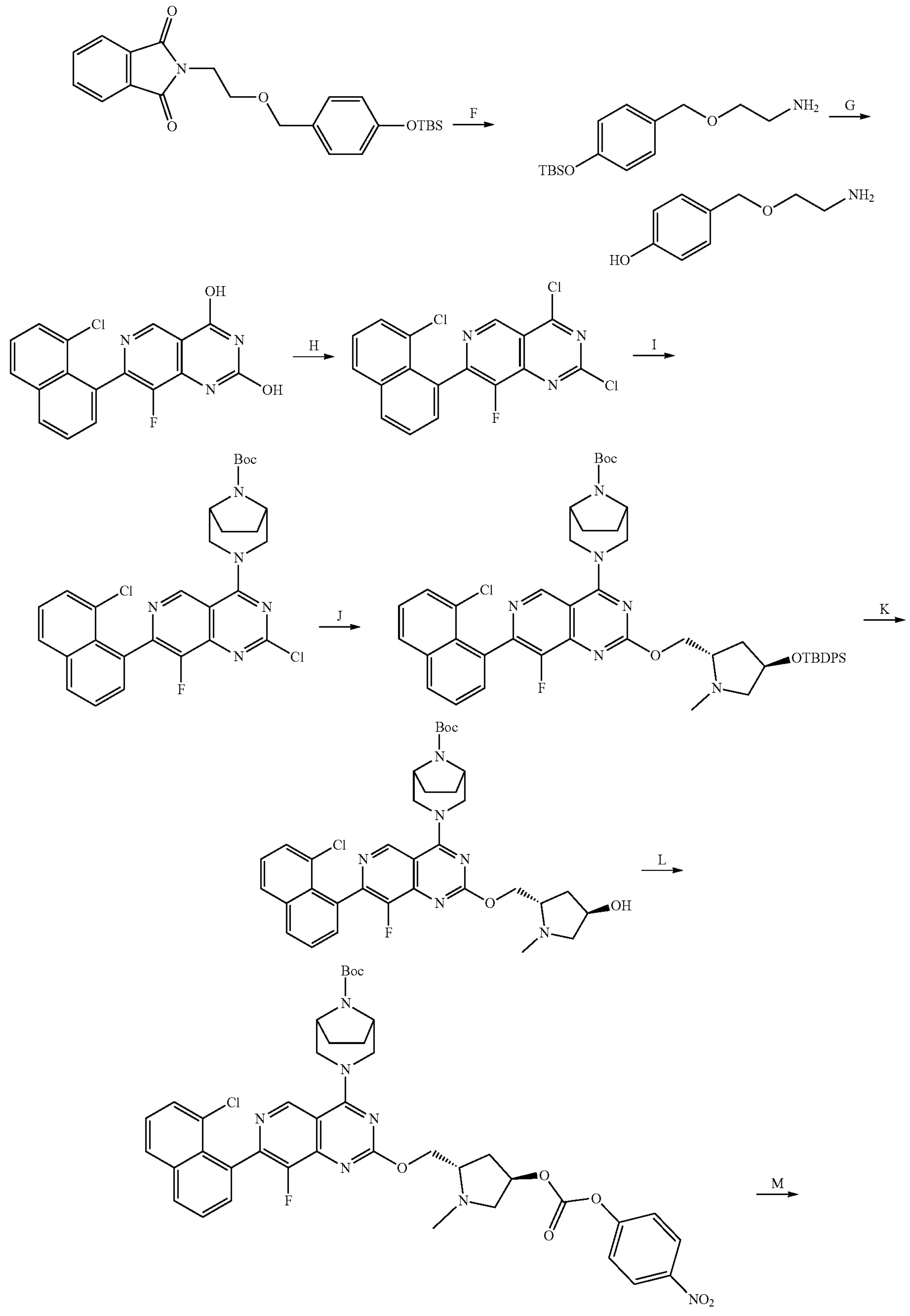

-continued

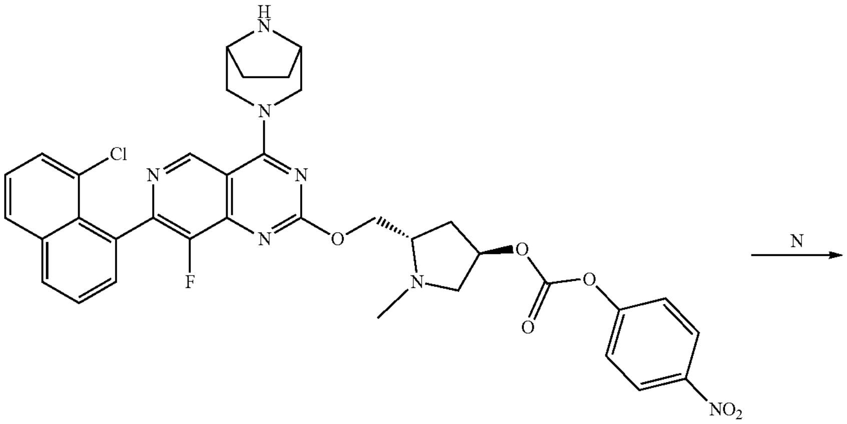

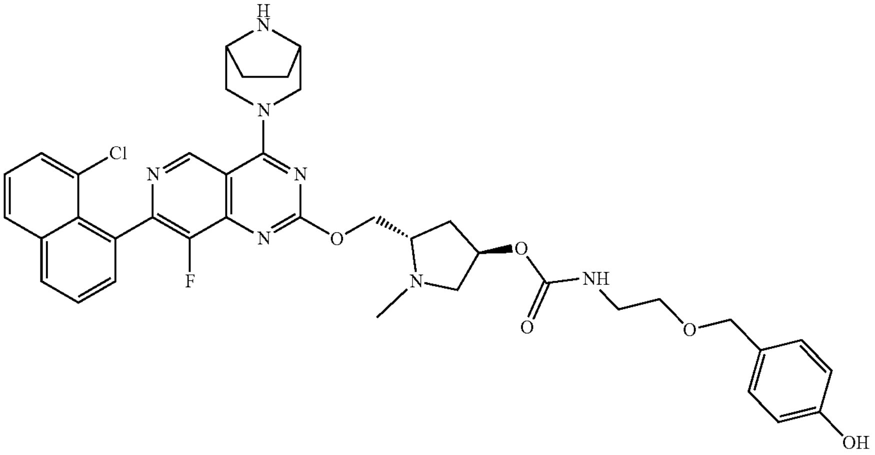

(3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl(2-((4-hydroxybenzyl)oxy)ethyl)carbamate. To a mixture of (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl(4-nitrophenyl) carbonate (30 mg, 42.0 μmol, 1.0 eq) and 4-((2-aminoethoxy)methyl)phenol (17.6 mg, 105 μmol, 2.5 eq) in DMF (1 mL) was added DIEA (27.1 mg, 210 μmol, 36.6 μL, 5.0 eq) in one portion under $N_2$. The mixture was stirred at 20° C. for 12 hours. After completion, the reaction mixture was concentrated under reduced pressure to give a residue. The residue was purified by prep-HPLC (column: Phenomenex Synergi C18 150*25*10 um; mobile phase: [water (0.225% FA)-ACN]; B %: 13%-43%, 8.5 min) to give the title compound (2.27 mg, two steps 6.5% yield). White solid; $^1$H NMR (400 MHz, DMSO+D2O) δ=9.07 (s, 1H), 8.27 (s, 1H), 8.20-8.15 (m, 1H), 8.09-8.04 (m, 1H), 7.71 (t, J=7.7 Hz, 1H), 7.66-7.62 (m, 1H), 7.60-7.52 (m, 2H), 7.10 (br d, J=8.5 Hz, 2H), 6.73-6.67 (m, 2H), 4.94-4.85 (m, 1H), 4.57 (br d, J=13.1 Hz, 2H), 4.47-4.39 (m, 1H), 4.38-4.26 (m, 3H), 3.99 (br s, 2H), 3.78 (br t, J=11.8 Hz, 2H), 3.41-3.31 (m, 3H), 3.16-3.06 (m, 2H), 2.88 (br d, J=2.0 Hz, 1H), 2.36 (s, 3H), 2.28 (br dd, J=5.0, 10.4 Hz, 1H), 2.04-1.76 (m, 6H). [ESI, M+1]: 742.3.

Example 261

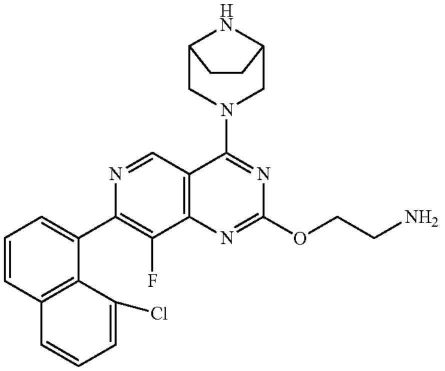 [SMILES: NCCOc1nc(N2CC3CCC(C2)N3)c2cnc(-c3cccc4cccc(Cl)c34)c(F)c2n1]

2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethanamine

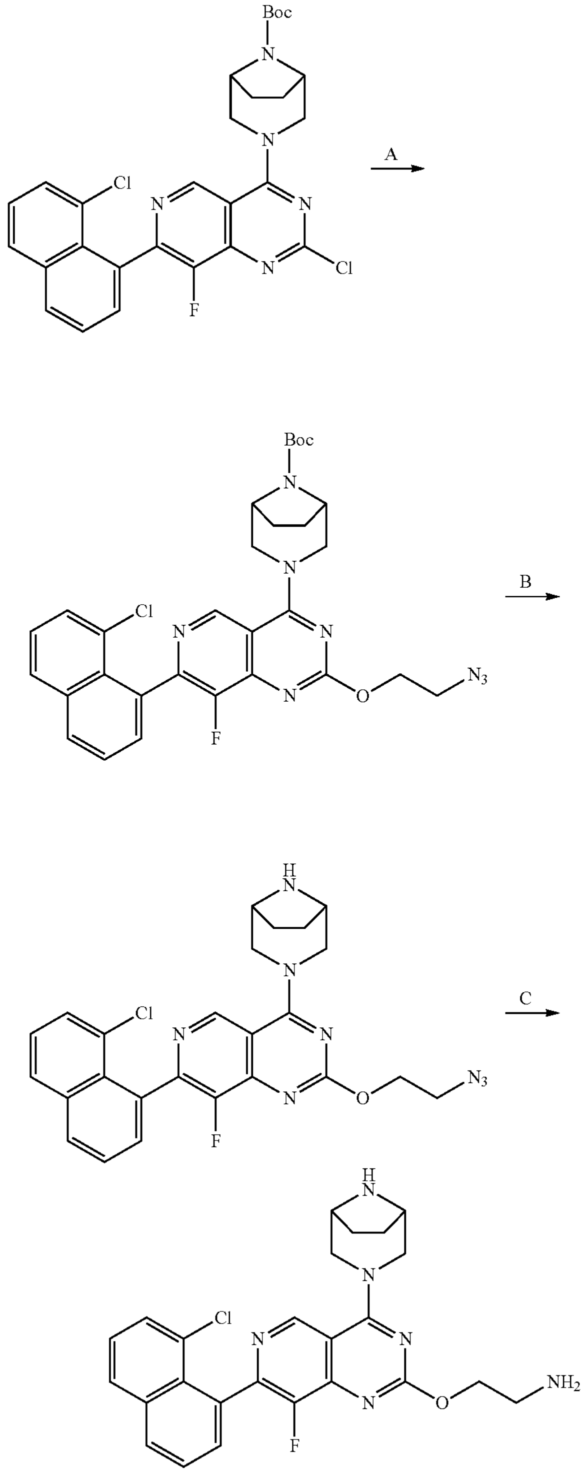

2-[7-(8-chloro-1-naphthyl)-4-(3,8-diazabicyclo[3.2.1]octan-3-yl)-8-fluoro-pyrido[4,3-d]pyrimidin-2-yl]oxy-ethanamine. To a solution of 2-(2-azidoethoxy)-7-(8-chloro-1-naphthyl)-4-(3,8-diazabicyclo[3.2.1]octan-3-yl)-8-fluoro-pyrido[4,3-d]pyrimidine (60 mg, 119 μmol, 1.0 eq) in $H_2O$ (1.0 mL) and THF (3.0 mL) was added $PPh_3$ (156 mg, 594 μmol, 5.0 eq). The mixture was stirred at 25° C. for 12 hours. The mixture was concentrated under vacuum. The residue was purified by prep-HPLC (column: Waters X bridge C18 150*50 mm*10 um; mobile phase: [water (10 mM $NH_4HCO_3$)-ACN]; B %: 18%-48%, 10 min) to give the title compound (6.83 mg, 11% yield). White solid; $^1H$ NMR (400 MHz, DMSO+D2O) δ=8.93-8.78 (m, 1H), 8.22-8.13 (m, 1H), 8.06 (br d, J=8.4 Hz, 1H), 7.72-7.66 (m, 1H), 7.64-7.60 (m, 1H), 7.59-7.51 (m, 2H), 4.69-4.55 (m, 1H), 4.42 (br d, J=14.0 Hz, 1H), 4.15-4.09 (m, 2H), 3.81-3.62 (m, 2H), 3.59-3.52 (m, 2H), 3.51-3.40 (m, 2H), 2.09-1.82 (m, 4H). [ESI, M+1]: 479.2.

Example 262

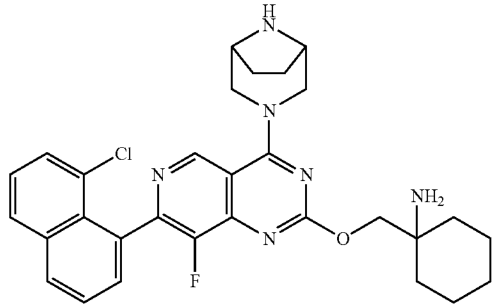 [SMILES: NC1(COc2nc(N3CC4CCC(C3)N4)c3cnc(-c4cccc5cccc(Cl)c45)c(F)c3n2)CCCCC1]

1-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)cyclohexanamine

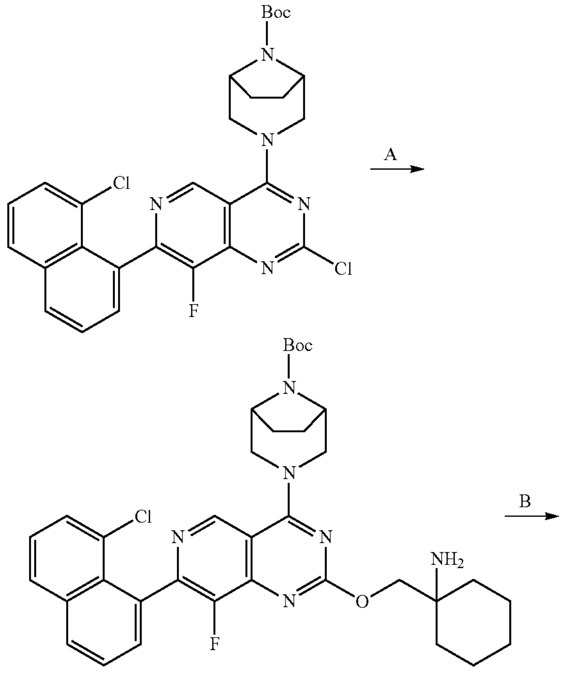

-continued

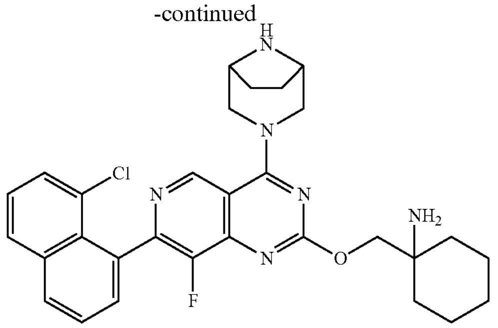

1-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)cyclohexanamine. To a mixture of (1R,5S)-tert-butyl 3-(2-((1-aminocyclohexyl)methoxy)-7-(8-chloronaphthalen-1-yl)-8-fluoropyrido[4,3-d]pyrimidin-4-yl)-3,8-diazabicyclo[3.2.1]octane-8-carboxylate (52.0 mg, 80.3 μmol, 1.0 eq) in DCM (1 mL) was added 2,6-dimethylpyridine (103 mg, 963 μmol, 112.2 μL, 12 eq), trimethylsilyl trifluoromethanesulfonate (107 mg, 482 μmol, 87.1 μL, 6.0 eq) in one portion at −40° C. under $N_2$. The mixture was stirred at 20° C. for 1 hour. After completion, the residue was concentrated under reduced pressure and the residue was purified by reversed phase flash chromatography [C18, 0.1% FA in water, 0-100% MeCN] give the title compound (6.08 mg, 13% yield). Yellow solid; $^1H$ NMR (400 MHz, DMSO-$d_6$) δ=8.84 (br s, 1H), 8.20-8.15 (m, 1H), 8.11-8.05 (m, 1H), 7.74-7.68 (m, 1H), 7.65 (dd, J=0.9, 7.3 Hz, 1H), 7.61-7.52 (m, 2H), 6.77-6.57 (m, 1H), 5.54-5.39 (m, 1H), 4.70-4.40 (m, 1H), 4.29 (br d, J=13.0 Hz, 1H), 3.77 (br s, 2H), 3.65 (br s, 2H), 3.58 (br d, J=12.4 Hz, 2H), 2.25 (br s, 2H), 1.78 (br s, 4H), 1.46 (br s, 7H), 1.35-1.19 (m, 1H); LCMS [ESI, M+1]: 547.2.

Example 263

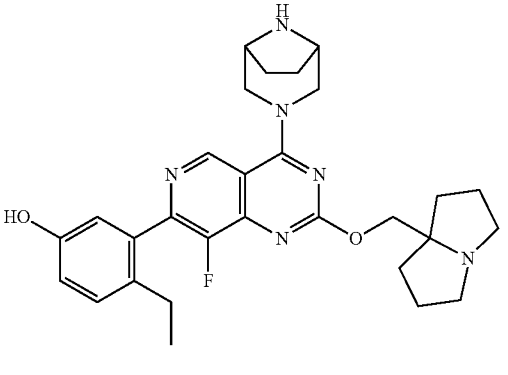 [SMILES: CCc1ccc(O)cc1-c1ncc2c(N3CC4CCC(C3)N4)nc(OCC34CCCN3CCC4)nc2c1F]

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-ethylphenol

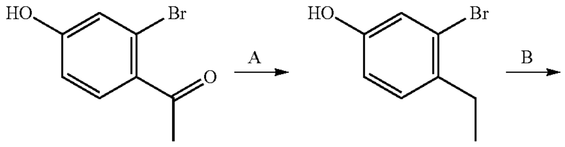

-continued

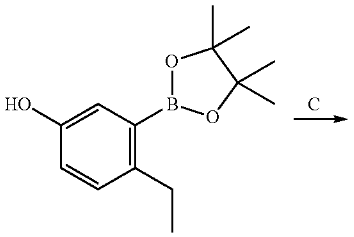

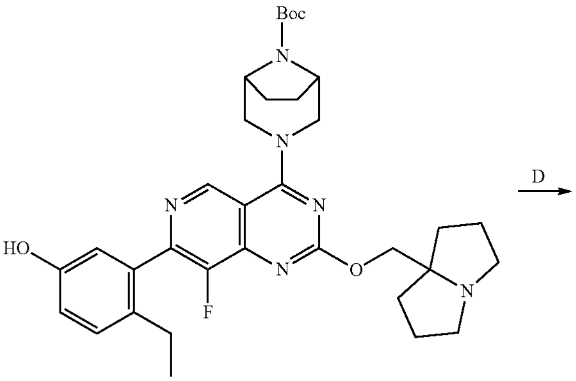

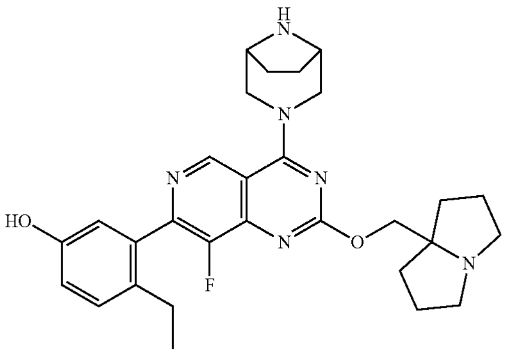

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-ethylphenol. To a solution of (1R,5S)-tert-butyl 3-(7-(2-ethyl-5-(methoxymethoxy)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (70 mg, 113 μmol, 1.0 eq) in ACN (1 mL) was added HCl·dioxane (4 M, 1 mL). The mixture was stirred at 20° C. for 0.5 hour. The mixture was concentrated under vacuum. The residue was purified by prep-HPLC (column: Waters Xbridge C18 150*50 mm*10 um; mobile phase: [water (10 mM $NH_4HCO_3$)-ACN]; B %: 22%-52%, 10 min) to give the title compound (11.5 mg, 19% yield). White solid; $^1H$ NMR (400 MHz, methanol-$d_4$) δ=9.03 (s, 1H), 7.21 (d, J=8.4 Hz, 1H), 6.87 (dd, J=2.4, 8.4 Hz, 1H), 6.75 (d, J=2.4 Hz, 1H), 4.61 (br d, J=12.4 Hz, 2H), 4.28 (s, 2H), 3.74-3.60 (m, 4H), 3.17-3.06 (m, 2H), 2.79-2.68 (m, 2H), 2.47 (q, J=7.6 Hz, 2H), 2.14-2.02 (m, 2H), 2.01-1.72 (m, 10H), 1.02 (t, J=7.6 Hz, 3H). LCMS [ESI, M+1]: 519.3.

Example 264

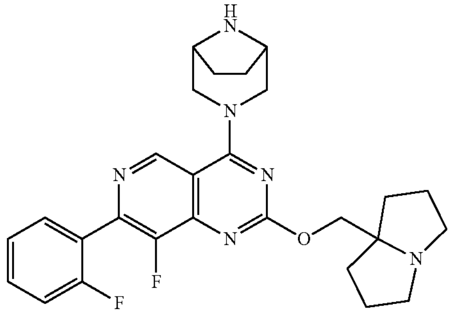 [SMILES: Fc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(2-fluorophenyl)-2-((hexahydro-1H-pyrrolizin-7a-yl)methoxy)pyrido[4,3-d]pyrimidine

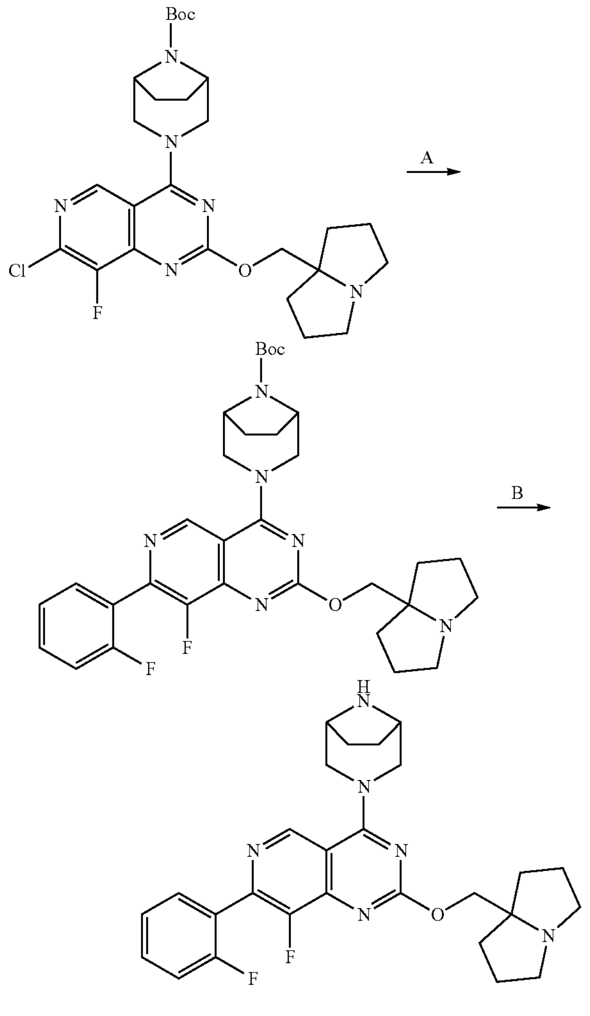

4-((1R,5S)-3,8-diazabicyclo[3.2.1]octan-3-yl)-8-fluoro-7-(2-fluorophenyl)-2-((hexahydro-1H-pyrrolizin-7a-yl)methoxy)pyrido[4,3-d]pyrimidine. To a solution of (1R,5S)-tert-butyl 3-(8-fluoro-7-(2-fluorophenyl)-2-((hexahydro-1H-pyrrolizin-7a-yl)methoxy)pyrido[4,3-d]pyrimidin-4-yl)-3,8-diazabicyclo[3.2.1]octane-8-carboxylate (45 mg, 75.9 μmol, 1.0 eq) in MeCN (0.5 mL) was added HCl·dioxane (4 M, 1 mL) at 0° C. The mixture was stirred at 0° C. for 0.5 hour. Upon completion, the reaction mixture was diluted with saturated $Na_2CO_3$ aqueous (5 mL) and extracted with ethyl acetate (3×10 mL). The combined organic layers were washed with saturated brine (20 mL), dried over $Na_2SO_4$, filtered and concentrated under reduced pressure to give a residue. The residue was purified by prep-HPLC (column: Waters Xbridge 150*25 mm*5 um; mobile phase: [water (10 mM $NH_4HCO_3$)-ACN]; B %: 12%-42%, 10 min) and lyophilized to afford the title compound (7.36 mg, 19% yield). Off-white solid; $^1$H NMR (400 MHz, $CDCl_3$-d) δ 9.02 (s, 1H), 7.67 (td, J=1.6, 7.6 Hz, 1H), 7.49-7.43 (m, 1H), 7.32-7.27 (m, 1H), 7.21 (t, J=9.2 Hz, 1H), 4.56 (br d, J=11.6 Hz, 2H), 4.19 (s, 2H), 3.68-3.58 (m, 4H), 3.15-3.08 (m, 2H), 2.68-2.61 (m, 2H), 2.14-2.05 (m, 2H), 1.91-1.84 (m, 4H), 1.81-1.75 (m, 4H), 1.71-1.63 (m, 2H); LCMS [ESI, M+1]: 493.3.

Example 265

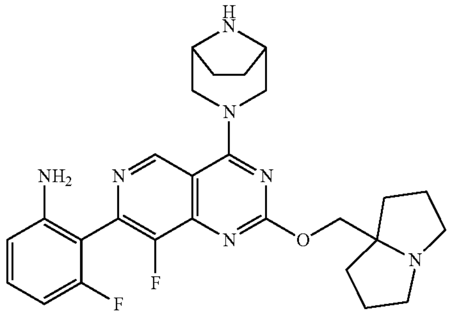 [SMILES: Nc1cccc(F)c1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-3-fluoroaniline

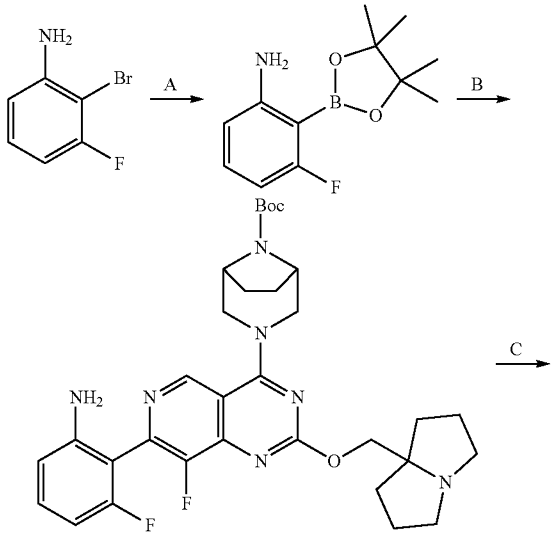

-continued

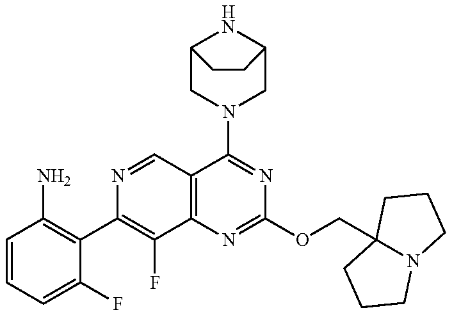

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-3-fluoroaniline. To a solution of (1R,5S)-tert-butyl 3-(7-(2-amino-6-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 165 μmol, 1.00 eq) in MeCN (1 mL) was added HCl·dioxane (4 M, 2 mL) at 0° C. The mixture was stirred at 0° C. for 0.5 hour. Upon completion, the reaction mixture was diluted with saturated $Na_2CO_3$ aqueous (5 mL) and extracted with ethyl acetate (3×10 mL). The combined organic layers were washed with saturated brine (20 mL), dried over $Na_2SO_4$, filtered and concentrated under reduced pressure to give a residue. The residue was purified by prep-HPLC (column: Phenomenex luna C18 150*40 mm*15 um; mobile phase: [water (0.225% FA)-ACN]; B %: 1%-30%, 10 min) and lyophilized affording the title compound (29.2 mg, 33% yield, 2FA). Yellow solid; $^1H$ NMR (400 MHz, methanol-$d_4$) δ=9.17 (s, 1H), 7.24-7.16 (m, 1H), 6.69 (d, J=8.4 Hz, 1H), 6.53-6.46 (m, 1H), 4.83-4.76 (m, 2H), 4.68 (s, 2H), 4.09 (br s, 2H), 3.92 (br d, J=13.6 Hz, 2H), 3.76-3.67 (m, 2H), 3.31-3.26 (m, 2H), 2.41-2.29 (m, 2H), 2.28-2.16 (m, 4H), 2.15-2.04 (m, 4H), 2.01-1.93 (m, 2H); LCMS [ESI, M+1]: 508.3.

Example 266

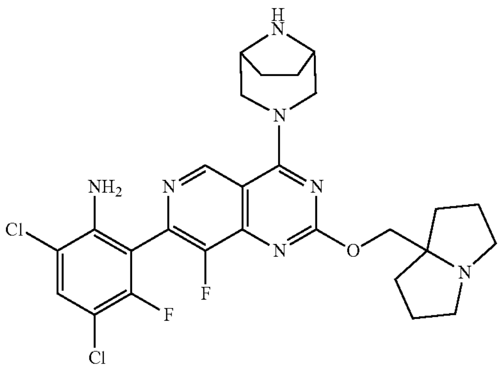 [SMILES: Nc1c(Cl)cc(Cl)c(F)c1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4,6-dichloro-3-fluoroaniline

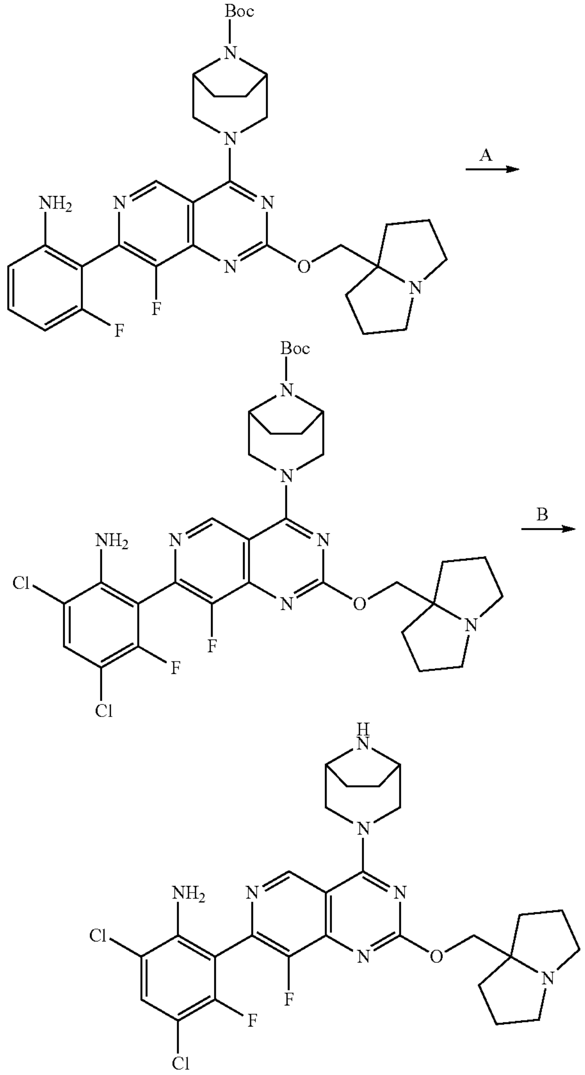

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4,6-dichloro-3-fluoroaniline. To a solution of 1R,5S)-tert-butyl 3-(7-(2-amino-3,5-dichloro-6-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (20 mg, 29.6 μmol, 1.00 eq) in MeCN (1 mL) was added HCl·dioxane (4 M, 0.5 mL) at 0° C. The mixture was stirred at 0° C. for 0.5 hour. Upon completion, the reaction mixture was concentrated under reduced pressure to give a residue. The residue was purified by prep-HPLC (column: Phenomenex Synergi C18 150*25*10 um; mobile phase: [water (0.225% FA)-ACN]; B %: 10%-50%, 8 min) and lyophilized affording the title compound (11.2 mg, 56% yield, 2FA). Yellow solid; $^1H$ NMR (400 MHz, methanol-$d_4$) δ 9.18 (s, 1H), 7.51 (d, J=7.2 Hz, 1H), 4.76 (br d, J=13.2 Hz, 2H), 4.66 (s, 2H), 4.04-3.93 (m, 2H), 3.88 (br d, J=13.2 Hz, 2H), 3.75-3.64 (m, 2H), 3.30-3.23 (m, 2H), 2.39-2.29 (m, 2H), 2.26-2.07 (m, 6H), 2.04-1.86 (m, 4H); LCMS [ESI, M+1]: 576.2.

Example 267

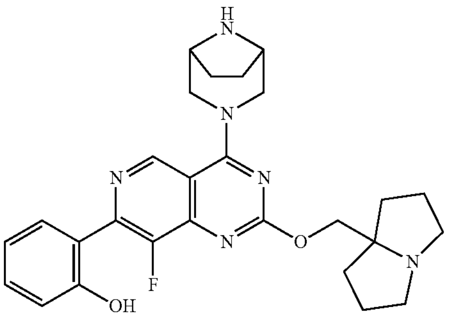 [SMILES: Oc1ccccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenol

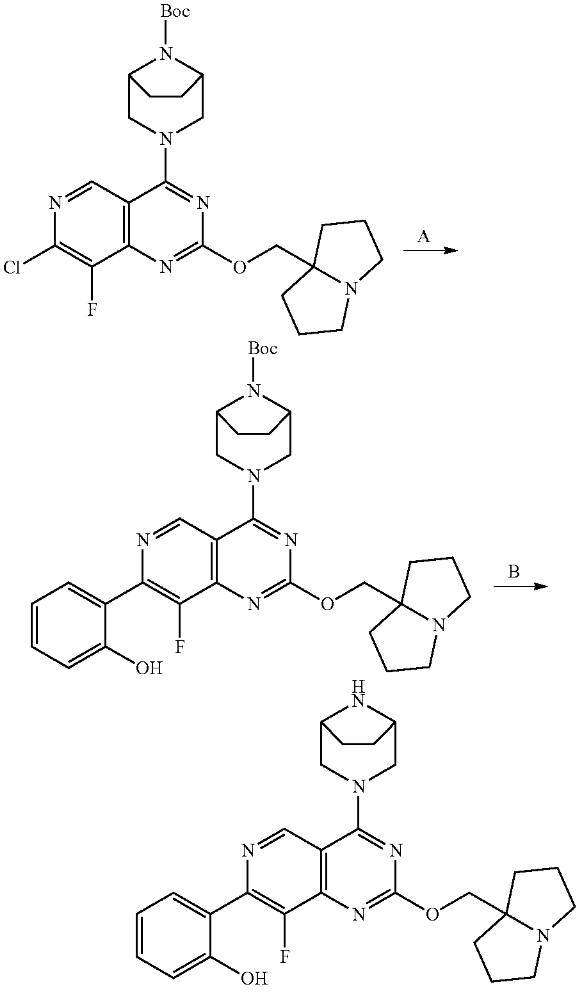

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenol. To a mixture of (1R,5S)-tert-butyl 3-(8-fluoro-2-((hexahydro-1H-pyrrolizin-7a-yl)methoxy)-7-(2-hydroxyphenyl)pyrido[4,3-d]pyrimidin-4-yl)-3,8-diazabicyclo[3.2.1]octane-8-carboxylate (50 mg, 64.3 μmol, 1.0 eq) in acetonitrile (0.5 mL) was added HCl·dioxane (4 M, 1.5 mL) at 0° C. The mixture was stirred at 0° C. for 0.5 hour. After completion, the reaction mixture was concentrated under reduced pressure to give a residue. The residue was diluted with MeOH (10 mL) and adjusted pH to 7 with $NaHCO_3$ solid, filtered and concentrated under reduced pressure to give a residue. The residue was purified by prep-HPLC (column: Waters Xbridge C18 150*50 mm*10 um; mobile phase: [water (10 mM $NH_4HCO_3$)-ACN]; B %: 25%-55%, 10 min) to give the title compound (17.6 mg, 55% yield). Off-white solid; $^1H$ NMR (400 MHz, $CDCl_3$) § 13.34 (br s, 1H), 8.89 (s, 1H), 8.18 (dd, J=1.2, 8.0 Hz, 1H), 7.43-7.32 (m, 1H), 7.06 (dd, J=1.2, 8.4 Hz, 1H), 7.03-6.93 (m, 1H), 4.56 (br d, J=11.6 Hz, 2H), 4.21 (s, 2H), 3.74-3.58 (m, 4H), 3.22-3.08 (m, 2H), 2.73-2.61 (m, 2H), 2.16-2.08 (m, 2H), 1.98-1.82 (m, 6H), 1.76-1.64 (m, 4H); LCMS [ESI, M+1]: 491.2.

Example 268

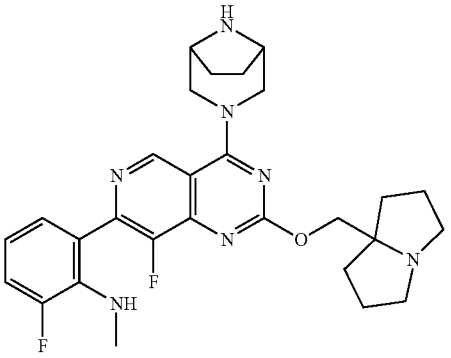 [SMILES: CNc1c(F)cccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-6-fluoro-N-methylaniline

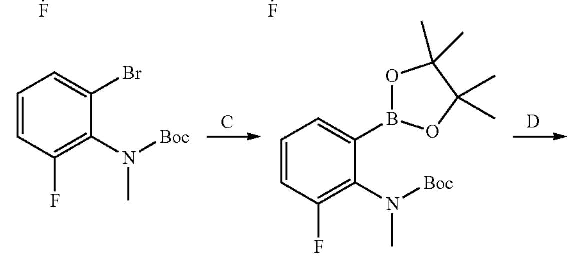

-continued

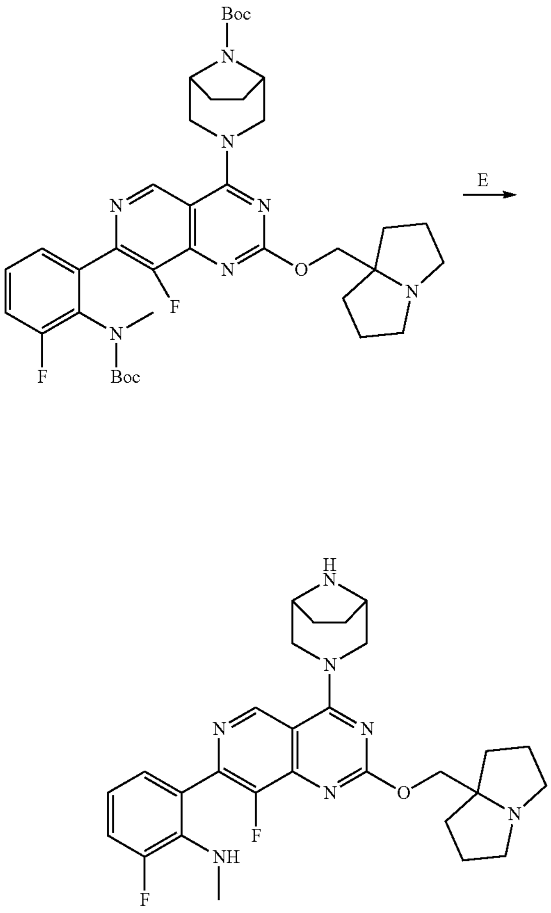

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-6-fluoro-N-methylaniline. To a solution of (1R,5S)-tert-butyl 3-(7-(2-((tert-butoxycarbonyl)(methyl)amino)-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (240 mg, 332 μmol, 1.0 eq) in acetonitrile (2 mL) was added HCl·dioxane (4 M, 2 mL). The mixture was stirred at 0° C. for 20 minutes. Upon completion, the reaction mixture was diluted with $H_2O$ (10 mL) and extracted with ethyl acetate (3×10 mL). The combined organic layers were washed with saturated brine (20 mL), dried over $Na_2SO_4$, filtered and concentrated under reduced pressure to give a residue. The residue was purified by prep-HPLC (column: Unisil 3-100 C18 ultra 150*50 mm*3 um; mobile phase: [water (0.225% FA)-ACN]; B %: 1%-30%, 10 min) and lyophilized to give the title compound (99.9 mg, 48% yield, 2FA). Yellow solid; $^1H$ NMR (400 MHz, methanol-$d_4$) δ=9.13 (s, 1H), 7.17-7.10 (m, 2H), 6.87-6.80 (m, 1H), 4.79 (d, J=13.2 Hz, 2H), 4.67 (s, 2H), 4.13-4.06 (m, 2H), 3.92 (d, J=13.2 Hz, 2H), 3.76-3.65 (m, 2H), 3.31-3.25 (m, 2H), 2.74 (d, J=3.2 Hz, 3H), 2.39-2.29 (m, 2H), 2.27-2.17 (m, 4H), 2.15-2.04 (m, 4H), 2.01-1.94 (m, 2H). [ESI, M+1]: 522.4.

Example 269

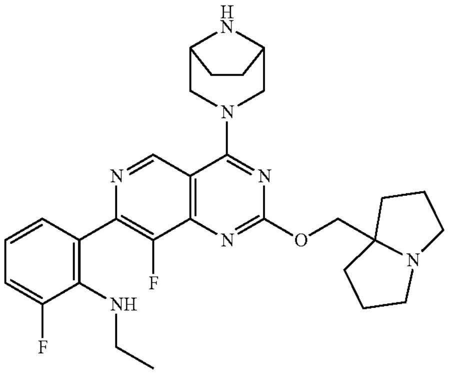 [SMILES: CCNc1c(F)cccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-N-ethyl-6-fluoroaniline Synthesized according to Example 268, substituting iodoethane in place of iodomethane and increasing reaction temperature to 20° C. in step B. Yellow solid (12.5 mg 1.7 eq HCOOH); $^1H$ NMR (400 MHz, $CDCl_3$) δ 9.03 (s, 1H), 7.19 (br d, J=7.6 Hz, 1H), 7.12-7.03 (m, 1H), 6.84-6.76 (m, 1H), 4.72-4.54 (m, 4H), 4.10-3.69 (m, 6H), 3.24-3.09 (m, 2H), 3.04-2.84 (m, 2H), 2.44-2.30 (m, 2H), 2.27-2.15 (m, 2H), 2.12-1.85 (m, 8H), 1.09 (t, J=7.2 Hz, 3H). [ESI, M+1]: 536.3.

Example 270

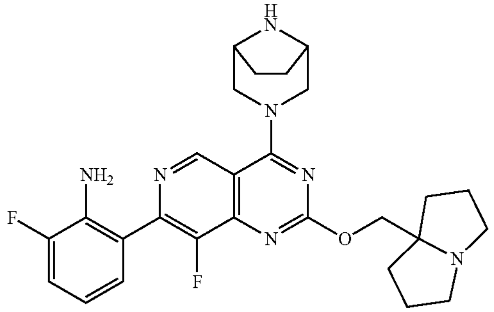 [SMILES: Nc1c(F)cccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-6-fluoroaniline

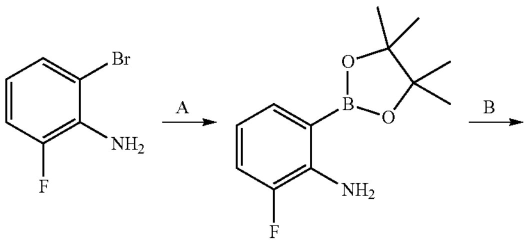

-continued

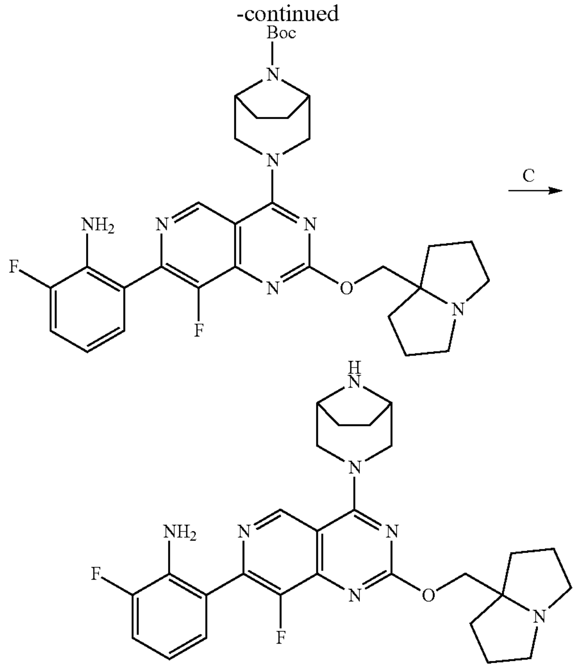

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-6-fluoroaniline. To a solution of (1R,5S)-tert-butyl 3-(7-(2-amino-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (90 mg, 148 μmol, 1.0 eq) in MeCN (0.5 mL) was added HCl·dioxane (4 M, 13.5 mL, 365 eq). The mixture was stirred at 0° C. for 0.5 hour. After completion, the mixture was concentrated. The residue was purified by prep-HPLC (column: Unisil 3-100 C18 ultra 150*50 mm*3 um; mobile phase: [water (0.225% FA)-ACN]; B %: 1%-30%, 10 min) to give the title compound (14.8 mg, 19% yield). Yellow solid; $^1H$ NMR (400 MHz, methanol-$d_4$) δ=9.18 (br s, 1H), 7.27 (br d, J=7.2 Hz, 1H), 7.20-7.06 (m, 1H), 6.71 (br s, 1H), 4.76 (br d, J=12.4 Hz, 2H), 4.66 (s, 2H), 4.00 (br s, 2H), 3.87 (br d, J=13.2 Hz, 2H), 3.75-3.66 (m, 2H), 3.30-3.24 (m, 2H), 2.40-2.28 (m, 2H), 2.27-2.14 (m, 4H), 2.13-2.06 (m, 2H), 2.05-1.96 (m, 2H), 1.95-1.87 (m, 2H). [ESI, M+1]: 508.3.

Example 271

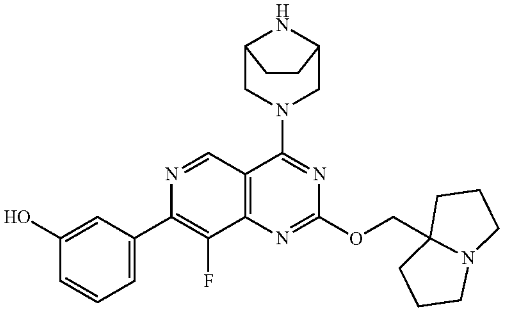 [SMILES: Oc1cccc(-c2ncc3c(N4CC5CCC(C4)N5)nc(OCC45CCCN4CCC5)nc3c2F)c1]

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenol

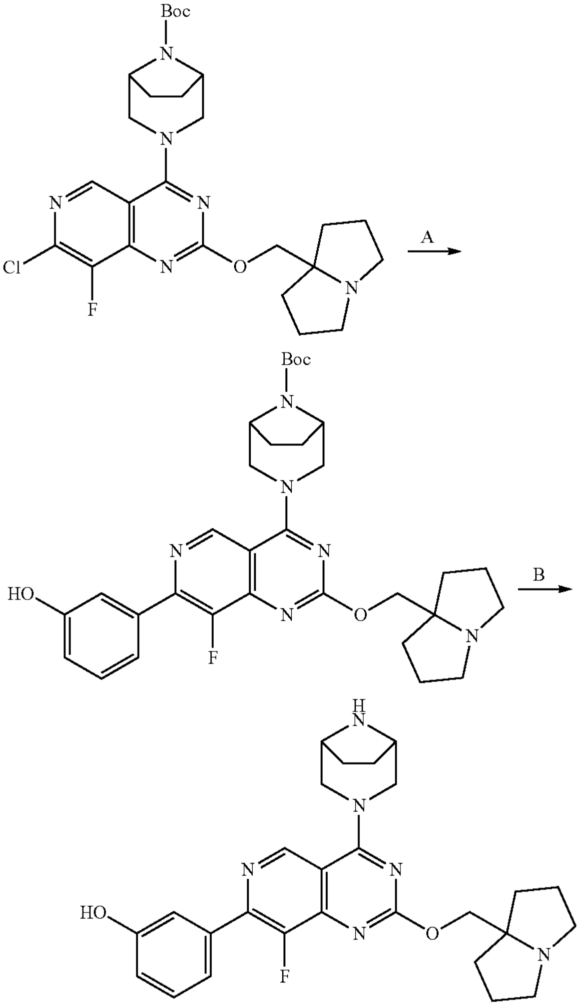

3-(4-((1R,5S)-3,8-diazabicyclo[3.2.1]octan-3-yl)-8-fluoro-2-((hexahydro-1H-Pyrrolizin-7a-yl)methoxy)pyrido[4,3-d]pyrimidin-7-yl)phenol. To a mixture of (1R,5S)-tert-butyl 3-(8-fluoro-2-((hexahydro-1H-pyrrolizin-7a-yl)methoxy)-7-(3-hydroxyphenyl)pyrido[4,3-d]pyrimidin-4-yl)-3,8-diazabicyclo[3.2.1]octane-8-carboxylate (40 mg, 67.7 μmol, 1.0 eq) in MeCN (2 mL) was added HCl·dioxane (4 M, 320 μL, 18.9 eq) in one portion under $N_2$. The mixture was stirred at 0° C. for 30 minutes. After completion, the residue was concentrated under reduced pressure. The residue was purified by prep-HPLC (column: Waters Xbridge C18 150*50 mm*10 um; mobile phase: [water (10 mM $NH_4HCO_3$)-ACN]; B %: 30%-60%, 10 min) to give the title compound (13.35 mg, 39% yield). White solid; $^1H$ NMR (400 MHz, DMSO-$d_6$) δ=9.66 (br s, 1H), 9.09 (s, 1H), 7.49-7.42 (m, 2H), 7.34 (t, J=8.1 Hz, 1H), 6.93-6.86 (m, 1H), 4.40 (br d, J=12.0 Hz, 2H), 4.05 (s, 2H), 3.62-3.48 (m, 4H), 2.99-2.90 (m, 2H), 2.59-2.53 (m, 3H), 1.93-1.85 (m, 2H), 1.85-1.71 (m, 4H), 1.66-1.53 (m, 6H). [ESI, M+1]: 491.2.

Example 272

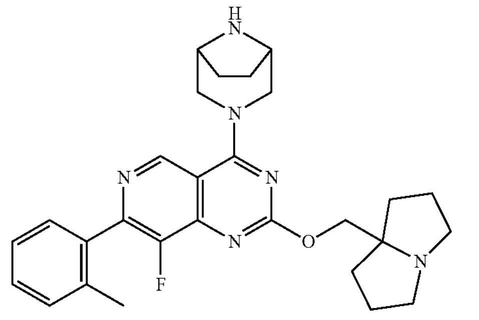 [SMILES: Cc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1 (H-pyrrolizin-7a-yl) methoxy)-7-(o-tolyl)pyrido[4,3-d]pyrimidine

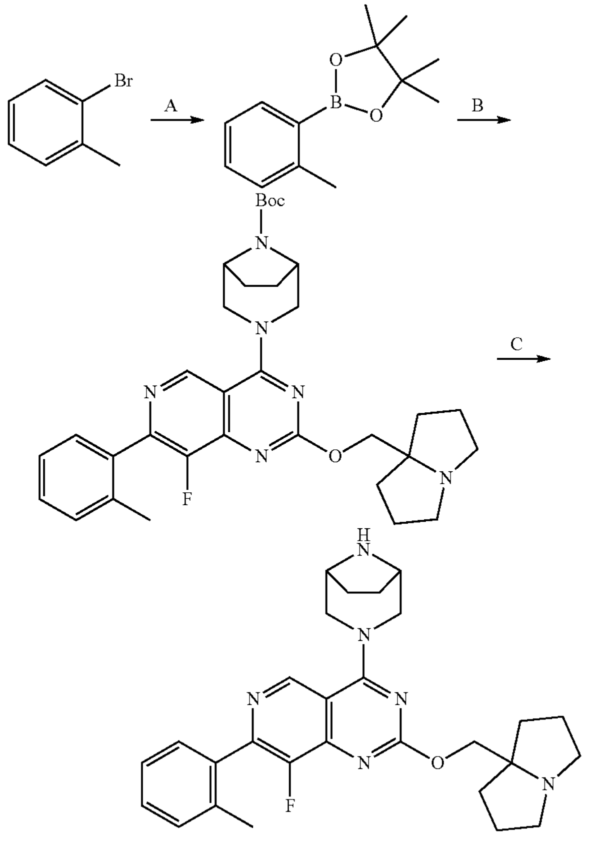

4-((1R,5S)-3,8-diazabicyclo[3.2.1]octan-3-yl)-8-fluoro-2-((hexahydro-1H-pyrrolizin-7a-yl)methoxy)-7-(o-tolyl)pyrido[4,3-d]pyrimidine. To a mixture of (1R,5S)-tert-butyl 3-(8-fluoro-2-((hexahydro-1H-pyrrolizin-7a-yl)methoxy)-7-(o-tolyl)pyrido[4,3-d]pyrimidin-4-yl)-3,8-diazabicyclo[3.2.1]octane-8-carboxylate (109 mg, 185 μmol, 1.0 eq) in acetonitrile (1 mL) was added HCl·dioxane (4 M, 2 mL, 43 eq) at 0° C. The mixture was stirred at 0° C. for 1 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 3%-23%, 7 min) to give the title compound (6.95 mg, 7.6% yield, 2FA). Off-white solid; $^1$H NMR (400 MHz, methanol-$d_4$) δ=9.14 (s, 1H), 7.44-7.31 (m, 4H), 4.78 (br d, J=13.2 Hz, 2H), 4.67 (s, 2H), 4.03 (br s, 2H), 3.89 (br d, J=13.2 Hz, 2H), 3.75-3.66 (m, 2H), 3.30-3.26 (m, 2H), 2.38-2.30 (m, 2H), 2.26 (s, 3H), 2.20 (m, 4H), 2.14-2.08 (m, 2H), 2.07-2.00 (m, 2H), 1.99-1.92 (m, 2H); LCMS [ESI, M+1]: 489.3.

Example 273

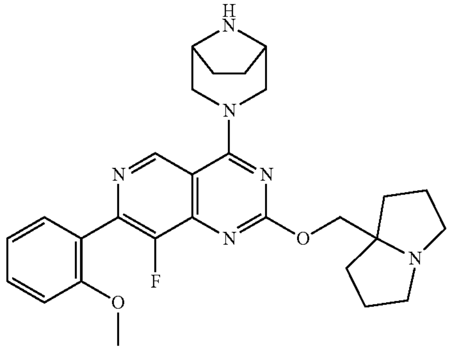 [SMILES: COc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-methoxyphenyl)pyrido[4,3-d]pyrimidine

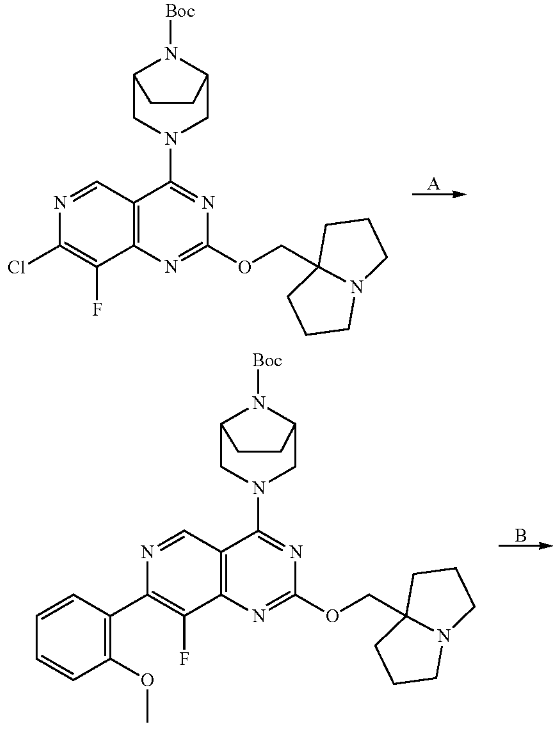

-continued

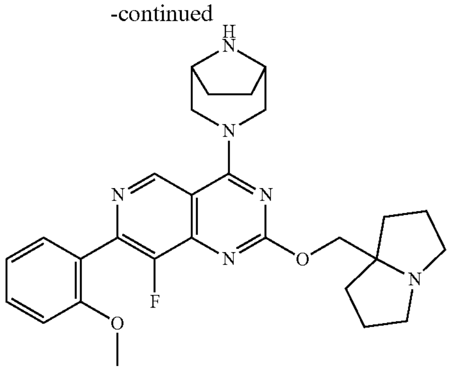

-((1R,5S)-3,8-diazabicyclo[3.2.1]octan-3-yl)-8-fluoro-2-((hexahydro-1H-pyrrolizin-7a-yl)methoxy)-7-(2-methoxyphenyl)pyrido[4,3-d]pyrimidine. To the solution of (1R,5S)-tert-butyl 3-(8-fluoro-2-((hexahydro-1H-pyrrolizin-7a-yl)methoxy)-7-(2-methoxyphenyl)pyrido[4,3-d]pyrimidin-4-yl)-3,8-diazabicyclo[3.2.1]octane-8-carboxylate (50 mg, 82.7 μmol, 1 eq) in ACN (0.5 mL) was added HCl·dioxane (4 M, 1 mL, 48.4 eq) at 0° C., the mixture was stirred at 0° C. for 0.5 hour. After completion, the mixture was concentrated. Then the residue was adjusted with saturated $NaHCO_3$ to pH~8, and extracted with the solvent (DCM: MeOH=10:1)(2×20 mL). The combined organic phase was dried over anhydrous sodium sulfate, filtered and concentrated to give a residue. The residue was purified by prep-HPLC (column: Waters Xbridge C18 150*50 mm*10 um; mobile phase: [water (10 mM $NH_4HCO_3$)-ACN]; B %: 18%-48%, 10 min) to give the title compound (16.3 mg, 38% yield). Off-white solid; $^1$H NMR (400 MHz, chloroform-d) δ=9.02 (s, 1H), 7.51 (dd, J=1.6, 7.6 Hz, 1H), 7.48-7.42 (m, 1H), 7.10 (td, J=0.8, 7.6 Hz, 1H), 7.04 (d, J=8.0 Hz, 1H), 4.57 (br d, J=11.6 Hz, 2H), 4.18 (s, 2H), 3.85 (s, 3H), 3.69-3.55 (m, 4H), 3.17-3.02 (m, 2H), 2.68-2.61 (m, 2H), 2.16-2.04 (m, 2H), 1.91-1.83 (m, 4H), 1.70-1.64 (m, 6H); LCMS [ESI, M+1]: 505.4.

Example 274

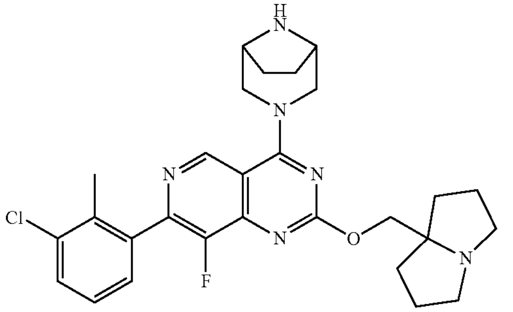 [SMILES: Cc1c(Cl)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(3-chloro-2-methylphenyl)-8-fluoro-2-((hexahydro-1H-pyrrolizin-7a-yl)methoxy)pyrido[4,3-d]pyrimidine

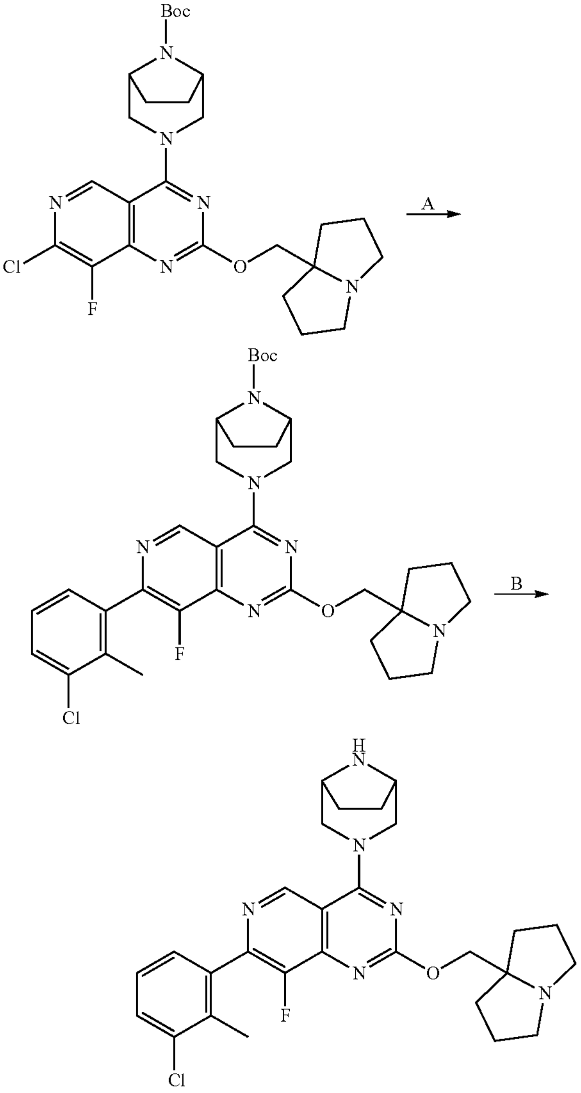

4-((1R,5S)-3,8-diazabicyclo[3.2.1]octan-3-yl)-7-(3-chloro-2-methylphenyl)-8-fluoro-2-((hexahydro-1H-pyrrolizin-7a-yl)methoxy)pyrido[4,3-d]pyrimidine. To the solution of (1R,5S)-tert-butyl 3-(7-(3-chloro-2-methylphenyl)-8-fluoro-2-((hexahydro-1H-pyrrolizin-7a-yl)methoxy) pyrido[4,3-d]pyrimidin-4-yl)-3,8-diazabicyclo[3.2.1]octane-8-carboxylate (70.0 mg, 112 μmol, 1.0 eq) in ACN (0.5 mL) was added HCl·dioxane (4 M, 1 ml, 36 eq) at 0° C., and then the mixture was stirred at 0° C. for 0.5 hour. After completion, the mixture was concentrated at 25° C. The residue was purified by prep-HPLC (column: 3_Phenomenex Luna C18 75*30 mm*3 um; mobile phase: [water (0.225% FA)-ACN]; B %: 6%-26%, 8 min) to give the title compound (10.0 mg, 14% yield). Yellow Solid. $^1$H NMR (400 MHz, METHANOL-d4) δ=9.15 (s, 1H), 7.56 (t, J=4.8 Hz, 1H), 7.35 (d, J=4.4 Hz, 2H), 4.78 (br d, J=13.2 Hz, 2H), 4.67 (s, 2H), 4.02 (br s, 2H), 3.88 (br d, J=13.2 Hz, 2H), 3.75-3.65 (m, 2H), 3.30-3.26 (m, 2H), 2.33 (dd, J=6.8, 12.4 Hz, 2H), 2.29-2.25 (m, 3H), 2.25-1.87 (m, 10H). LCMS [ESI, M+1]: 523.3.

Example 275

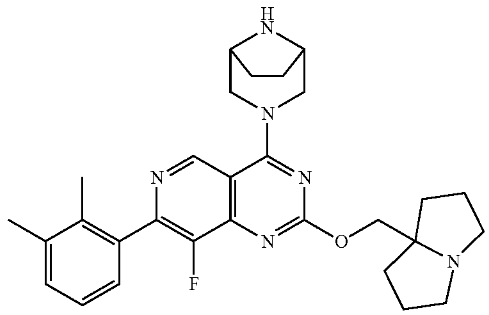

4-((1R,5S)-3,8-diazabicyclo[3.2.1]octan-3-yl)-7-(2,3-dimethylphenyl)-8-fluoro-2-((hexahydro-1H-pyrrolizin-7a-yl)methoxy)pyrido[4,3-d]pyrimidine

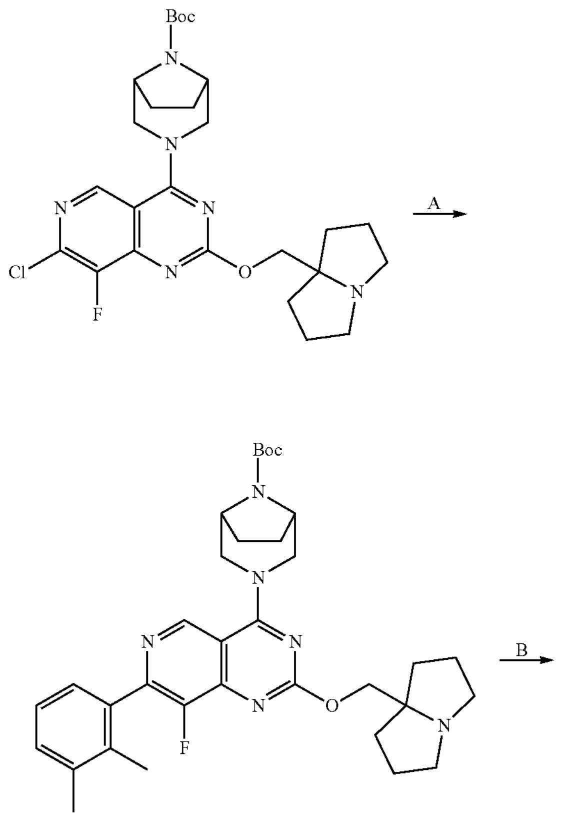

-continued

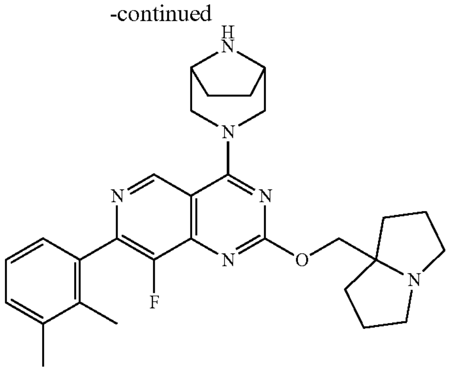

4-((1R,5S)-3,8-diazabicyclo[3.2.1]octan-3-yl)-7-(2,3-dimethylphenyl)-8-fluoro-2-((hexahydro-1H-pyrrolizin-7a-yl)methoxy)pyrido[4,3-d]pyrimidine. To a mixture of (1R,5S)-tert-butyl 3-(7-(2,3-dimethylphenyl)-8-fluoro-2-((hexahydro-1H-pyrrolizin-7a-yl) methoxy)pyrido[4,3-d]pyrimidin-4-yl)-3,8-diazabicyclo[3.2.1]octane-8-carboxylate (140 mg, 158 μmol, 1.0 eq) in acetonitrile (1 mL) was added HCl·dioxane (4 M, 2 mL, 51 eq) at 0° C. The mixture was stirred at 0° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 6%-26%, 8 min) to give the title compound (21.3 mg, 22% yield, 2FA). White solid. $^{1}H$ NMR (400 MHz, METHANOL-d4) δ=9.13 (s, 1H), 7.32 (d, J=7.2 Hz, 1H), 7.27-7.18 (m, 2H), 4.80 (br d, J=13.2 Hz, 2H), 4.67 (s, 2H), 4.08 (br s, 2H), 3.91 (br d, J=13.2 Hz, 2H), 3.74-3.67 (m, 2H), 3.30-3.26 (m, 2H), 2.38 (s, 3H), 2.37-2.30 (m, 2H), 2.27-2.18 (m, 4H), 2.14 (s, 3H), 2.12-1.97 (m, 6H). LCMS [ESI, M+1, M/2+1]: 252.4, 503.3.

Example 276

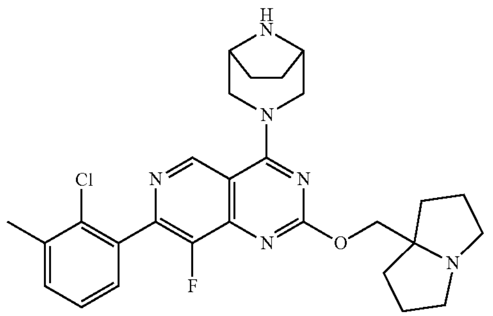 [SMILES: Cc1cccc(-c2ncc3c(N4CC5CCC(C4)N5)nc(OCC45CCCN4CCC5)nc3c2F)c1C]

4-((1R,5S)-3,8-diazabicyclo[3.2.1]octan-3-yl)-7-(2-chloro-3-methylphenyl)-8-fluoro-2-((hexahydro-1H-pyrrolizin-7a-yl)methoxy)pyrido[4,3-d]pyrimidine

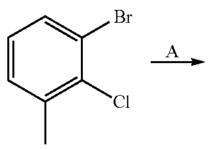

-continued

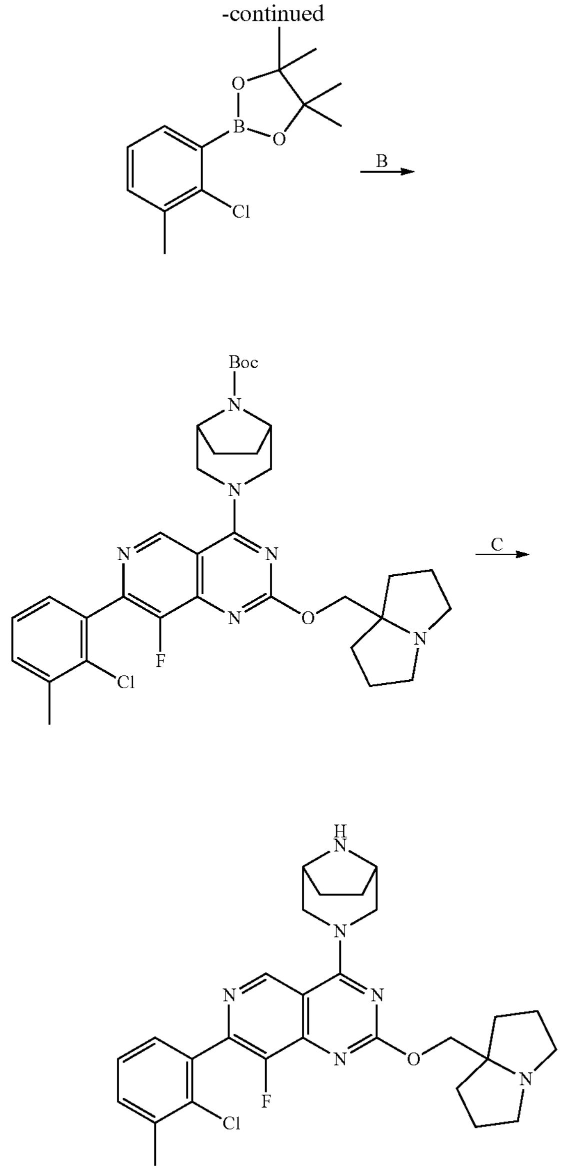

4-((1R,5S)-3,8-diazabicyclo[3.2.1]octan-3-yl)-7-(2-chloro-3-methylphenyl)-8-fluoro-2-((hexahydro-1H-pyrrolizin-7a-yl)methoxy)pyrido[4,3-d]pyrimidine. To a solution of (1R,5S)-tert-butyl 3-(7-(2-chloro-3-methylphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (75 mg, 118 μmol, 1.0 eq) in MeCN (3 mL) was added HCl·dioxane (4 M, 0.7 mL, 24 eq) dropwise below 5° C. The mixture was stirred at 5 to 15° C. for 0.5 hour. The reaction mixture was concentrated without heating under reduced pressure. The residue was purified by prep-HPLC (column: 3_Phenomenex Luna C18 75*30 mm*3 um; mobile phase: [water (0.225% FA)-ACN]; B %: 9%-29%, 8 min). The desired fractions were collected and lyophilized to give the title compound (29.4 mg, 39% yield, 2FA). Off-white Solid; $^{1}$H NMR (400 MHz, METHANOL-d4) δ=9.04 (s, 1H), 8.36 (s, 2H), 7.39 (dd, J=7.6, 1.22 Hz, 1H), 7.31-7.24 (m, 2H), 4.68 (d, J=13.2 Hz, 2H), 4.57 (s, 2H), 3.92 (s, 2H), 3.78 (d, J=13.2 Hz, 2H), 3.64-3.57 (m, 2H), 3.20-3.17 (m, 2H), 2.39 (s, 3H), 2.26-1.98 (m, 8H), 1.94-1.84 (m, 4H); LCMS [ESI, M+1]: 523.

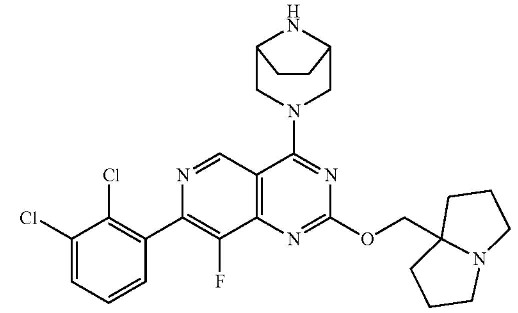 [SMILES: Fc1c(-c2cccc(Cl)c2Cl)ncc2c(N3CC4CCC(C3)N4)nc(OCC34CCCN3CCC4)nc12]

4-((1R,5S)-3,8-diazabicyclo[3.2.1]octan-3-yl)-7-(2,3-dichlorophenyl)-8-fluoro-2-((hexahydro-1H-pyrrolizin-7a-yl)methoxy)pyrido[4,3-d]pyrimidine

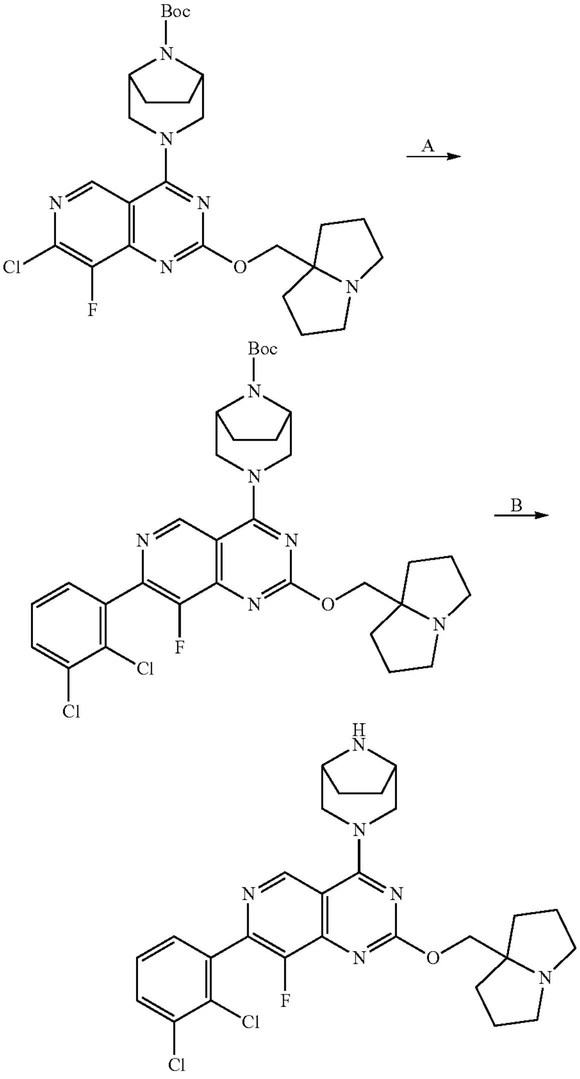

4-((1R,5S)-3,8-diazabicyclo[3.2.1]octan-3-yl)-7-(2,3-dichlorophenyl)-8-fluoro-2-((hexahydro-1H-pyrrolizin-7a-yl)methoxy)pyrido[4,3-d]pyrimidine. To a solution of (1R,5S)-tert-butyl 3-(7-(2,3-dichlorophenyl)-8-fluoro-2-

((hexahydro-1H-pyrrolizin-7a-yl) methoxy)pyrido[4,3-d]pyrimidin-4-yl)-3,8-diazabicyclo[3.2.1]octane-8-carboxylate (72 mg, 110 μmol, 1.0 eq) in MeCN (3.6 mL) was added HCl·dioxane (4 M, 0.9 mL) below 10° C. The mixture was stirred at 5 to 15° C. for 0.5 hour. The reaction mixture was concentrated without heating under reduced pressure. The residue was purified by prep-HPLC (column: 3_Phenomenex Luna C18 75*30 mm*3 um; mobile phase: [water (0.225% FA)-ACN]; B %: 8%-28%, 8 min). The desired fractions were collected and lyophilized to give the title compound (12.91 mg, 18% yield, 2FA). Off-white solid; $^{1}$H NMR (400 MHz, METHANOL-d4) δ=9.15 (s, 1H), 8.46 (s, 2H), 7.79-7.67 (m, 1H), 7.49 (d, J=4.8 Hz, 2H), 4.73 (br d, J=12.96 Hz, 2H), 4.66 (s, 2H), 3.91 (br s, 2H), 3.83 (br d, J=13.20 Hz, 2H), 3.75-3.64 (m, 2H), 3.30-3.24 (m, 2H), 2.35-2.07 (m, 8H), 1.98-1.89 (m, 4H); LCMS [ESI, M+1]: 543.

Example 278

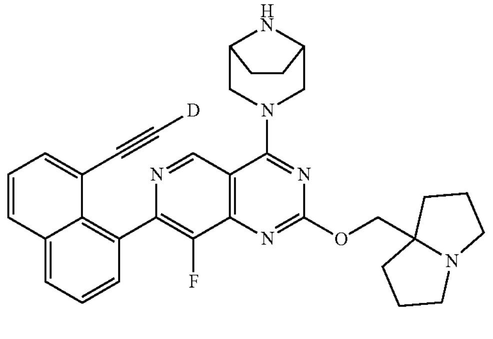 [SMILES: [2H]C#Cc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-(ethynyl-d)naphthalen-1-yl)-8-fluoro-2-((tetrahydro-1H-pyrrolizin-7a(5H)-yl)methoxy)pyrido[4,3-d]pyrimidine

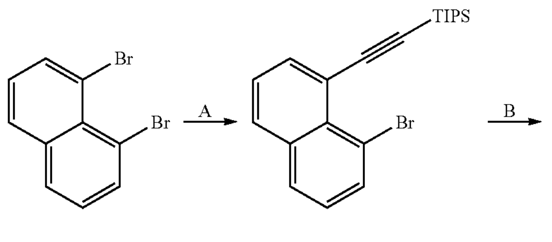

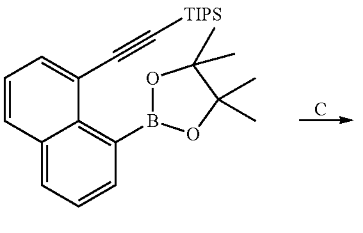

-continued

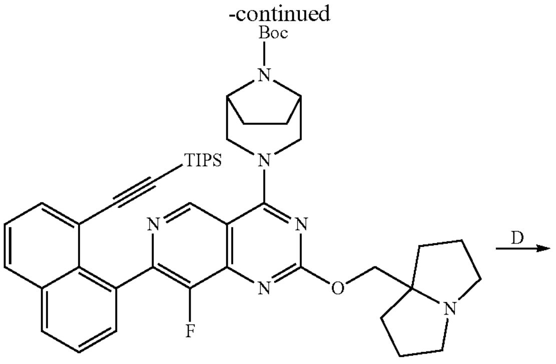

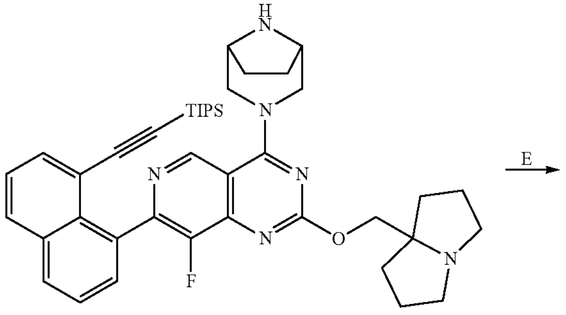

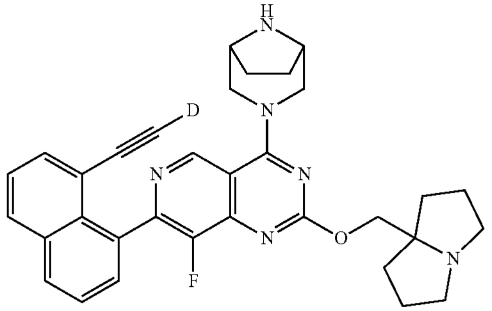

4-((1R,5S)-3,8-diazabicyclo[3.2.1]octan-3-yl)-7-(8-(ethynyl-d)naphthalen-1-yl)-8-fluoro-2-((tetrahydro-1H-pyrrolizin-7a(5H)-yl)methoxy)pyrido[4,3-d]pyrimidine. To a solution of 4-((1R,5S)-3,8-diazabicyclo[3.2.1]octan-3-yl)-8-fluoro-2-((tetrahydro-1H-pyrrolizin-7a(5H)-yl)methoxy)-7-(8-((triisopropylsilyl)ethynyl)naphthalen-1-yl)pyrido[4,3-d]pyrimidine (40.0 mg, 56.2 μmol, 1.00 eq) in DMAc (1 mL) were added $CH_3OD$ (1 mL) and CsF (76.8 mg, 505 μmol, 18.6 μL, 9 eq), and the mixture was stirred at 40° C. for 12 hours. Upon completion, the mixture was concentrated under reduced pressure. The residue was purified by prep-HPLC (column: Waters Xbridge BEH C18 100*25 mm*5 um; mobile phase: [water (10 mM $NH_4HCO_3$)-ACN]; B %: 25%-70%, 10 min) to give the title compound (5.14 mg, 8.90 μmol, 16% yield, 95.2% purity). Light yellow solid; $^{1}$H NMR (400 MHz, MeOD) δ 9.02 (s, 1H), 8.11-8.05 (m, 2H), 7.76-7.74 (m, 1H), 7.66 (t, J=8.0 Hz, 1H), 7.59 (dd, J=0.8, 6.8 Hz, 1H), 7.52 (t, J=8.0 Hz, 1H), 4.65-4.58 (m, 2H), 4.29 (s, 2H), 3.72 (br dd, J=4.4, 12.4 Hz, 2H), 3.68-3.63 (m, 2H), 3.17-3.11 (m, 2H), 2.79-2.73 (m, 2H), 2.12-2.06 (m, 2H), 1.99-1.75 (m, 10H); LCMS [ESI, M+1]: 550.3.

Example 279

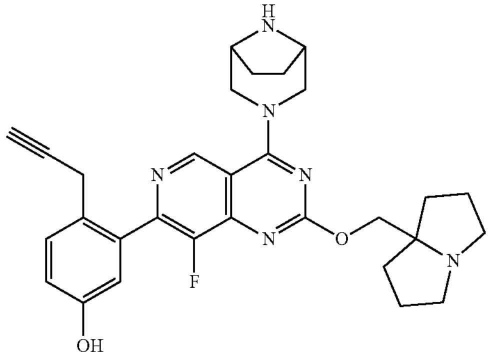 [SMILES: C#CCc1ccc(O)cc1-c1ncc2c(N3CC4CCC(C3)N4)nc(OCC34CCCN3CCC4)nc2c1F]

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-(prop-2-yn-1-yl)phenol

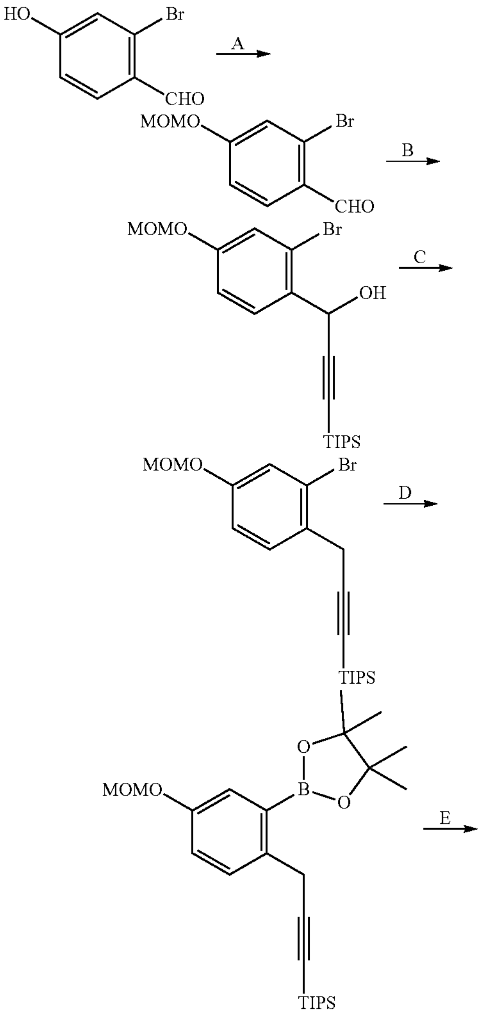

-continued

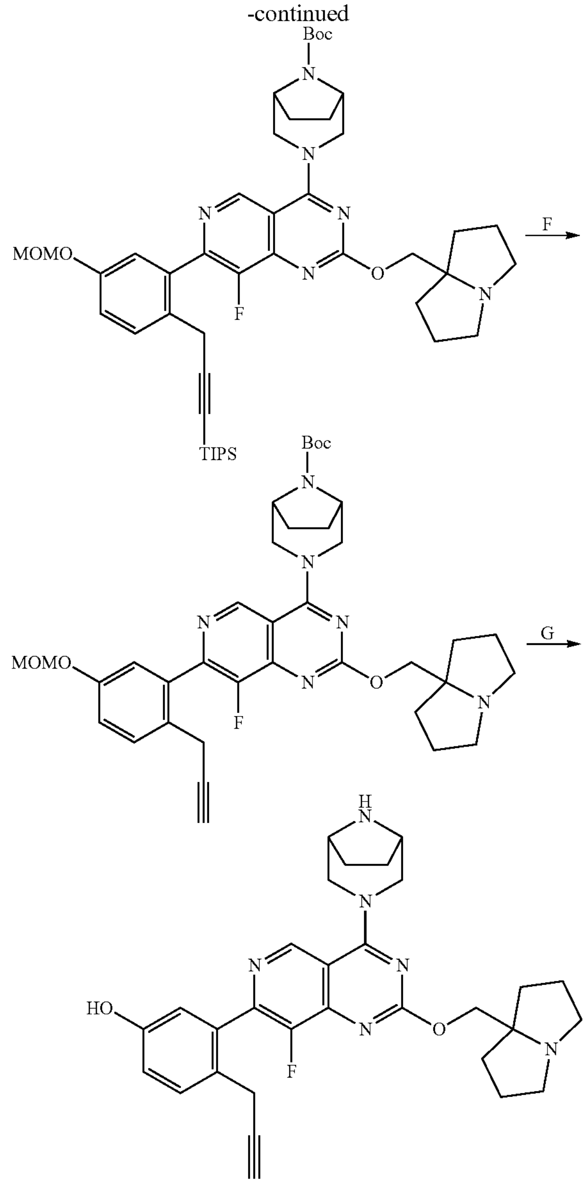

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-(prop-2-yn-1-yl)phenol. To a solution of (1R,5S)-tert-butyl 3-(8-fluoro-2-((hexahydro-1H-pyrrolizin-7a-yl)methoxy)-7-(5-(methoxymethoxy)-2-(prop-2-yn-1-yl)phenyl)pyrido[4,3-d]pyrimidin-4-yl)-3,8-diazabicyclo[3.2.1]octane-8-carboxylate (20 mg, 29.7 μmol, 1 eq) in EtOAc (1 mL) was added drop-wise HCl·EtOAc (4 M, 1 mL, 134 eq). The mixture was stirred at 25° C. for 10 minutes. Upon completion, the reaction mixture was concentrated under reduced pressure to give a residue. Then the residue was dissolved in MeCN (1 mL) and $NH_3 \cdot H_2O$ (7 M) was added dropwise to PH~9. The residue was purified by prep-HPLC (column: Waters Xbridge BEH C18 100*25 mm*5 um; mobile phase: [water (10 mM $NH_4HCO_3$)-ACN]; B %: 15%-55%, 10 min) to give the title compound (6.34 mg, 37% yield). White solid; $^1$H NMR (400 MHz, MeOD-d4) δ 9.04 (s, 1H), 7.46 (d, J=8.8 Hz, 1H), 6.90 (dd, J=2.8, 8.4 Hz, 1H), 6.84 (d, J=2.4 Hz, 1H), 4.63-4.59 (m, 2H), 4.28 (s, 2H), 3.73-3.66 (m, 2H), 3.65-3.59 (m, 2H), 3.46 (d, J=2.4 Hz, 2H), 3.17-3.09 (m, 2H), 2.80-2.70 (m, 2H), 2.26 (t, J=2.4 Hz, 1H), 2.13-2.04 (m, 2H), 1.99-1.75 (m, 10H); LCMS [ESI, M+1]: 529.3.

Example 280
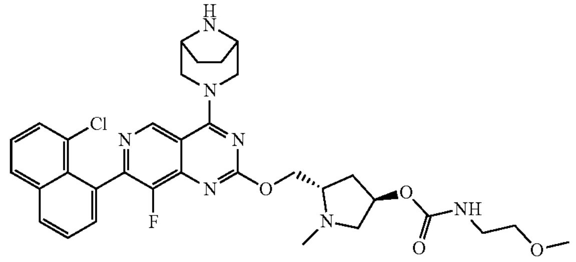 [SMILES: COCCNC(=O)O[C@@H]1C[C@@H](COc2nc(N3CC4CCC(C3)N4)c3cnc(-c4cccc5cccc(Cl)c45)c(F)c3n2)N(C)C1]
(3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl methoxyethyl)carbamate
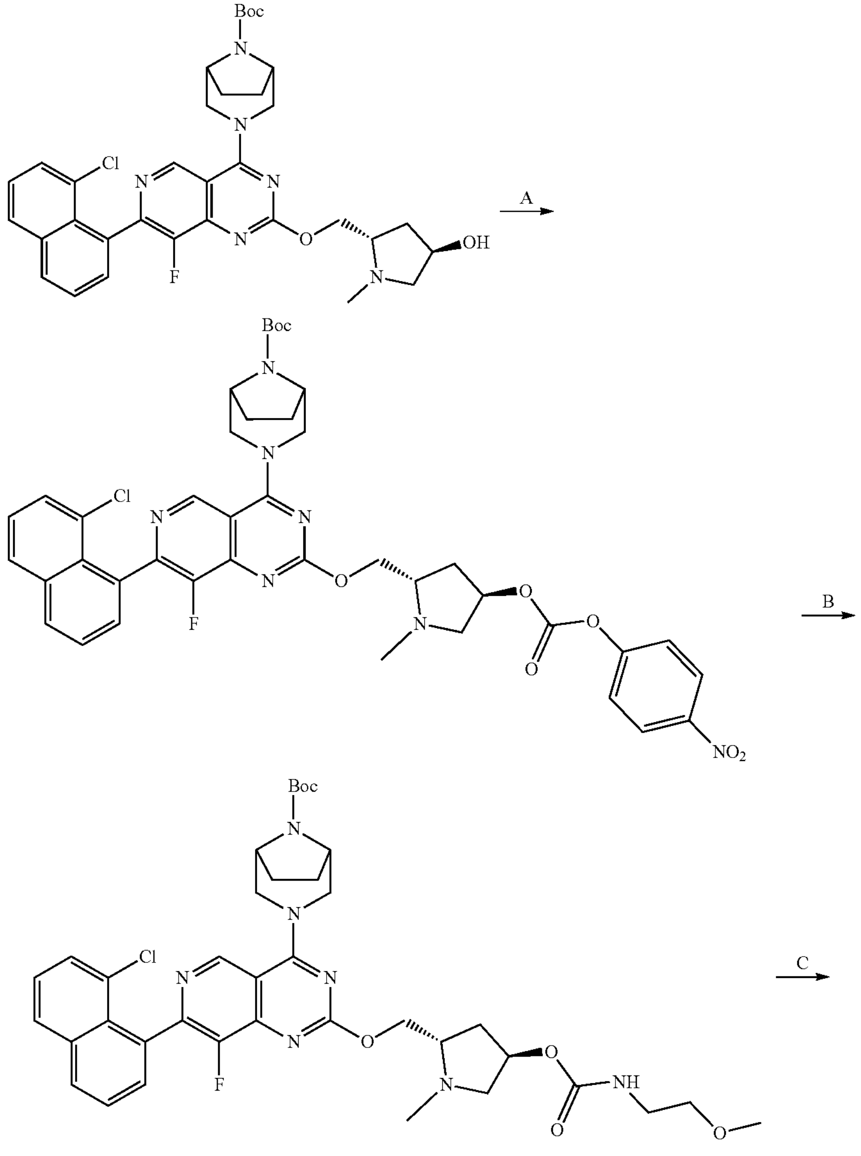

-continued

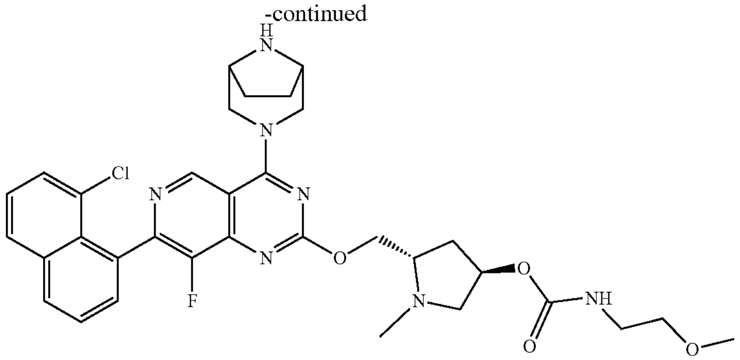

(3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl(2-methoxyethyl)carbamate. To a mixture of tert-butyl(1R,5S)-3-(7-(8-chloronaphthalen-1-yl)-8-fluoro-2-(((2S,4R)-4-(((2-methoxyethyl)carbamoyl)oxy)-1-methylpyrrolidin-2-yl)methoxy)pyrido[4,3-d]pyrimidin-4-yl)-3,8-diazabicyclo[3.2.1]octane-8-carboxylate (40.0 mg, 53.3 μmol, 1.0 eq) in MeCN (1.0 mL) was added HCl·dioxane (4.0 M, 0.2 mL, 15.0 eq) in one portion under $N_2$. The mixture was stirred at 0° C. for 0.5 hour. After completion, the mixture was concentrated under reduced pressure to give the residue and the residue was purified by prep-HPLC (column: Waters Xbridge C18 150*50 mm*10 um; mobile phase: [water (10 mM $NH_4HCO_3$)-ACN]; B %: 30%-60%, 10 min) to give the title compound (2.21 mg, 6.2% yield). White solid; $^1H$ NMR (400 MHz, methanol-$d_4$) δ=9.06 (s, 1H), 8.15 (dd, J=1.2, 8.4 Hz, 1H), 8.03 (dd, J=1.0, 8.2 Hz, 1H), 7.73-7.68 (m, 1H), 7.65-7.60 (m, 2H), 7.56-7.49 (m, 1H), 5.14-5.04 (m, 1H), 4.66-4.57 (m, 2H), 4.53-4.47 (m, 2H), 3.79-3.65 (m, 4H), 3.56-3.49 (m, 1H), 3.47-3.42 (m, 2H), 3.35 (s, 3H), 3.30-3.26 (m, 2H), 3.12-3.02 (m, 1H), 2.55 (s, 3H), 2.48 (dd, J=4.8, 10.8 Hz, 1H), 2.20-2.09 (m, 2H), 1.93-1.77 (m, 4H); LCMS [ESI, M+1]: 650.4.

Example 281

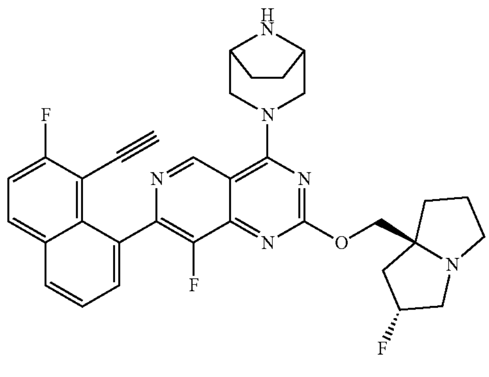 [SMILES: C#Cc1c(F)ccc2cccc(-c3ncc4c(N5CC6CCC(C5)N6)nc(OC[C@@]56CCCN5C[C@H](F)C6)nc4c3F)c12]

4-((1R,5S)-3,8-diazabicyclo[3.2.1]octan-3-yl)-7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidine

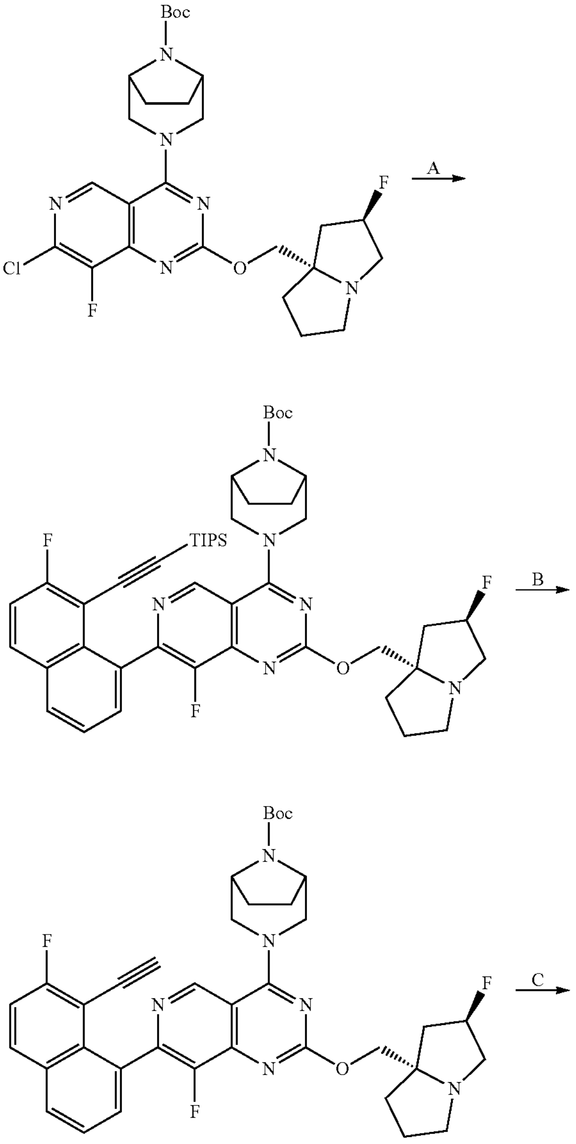

-continued

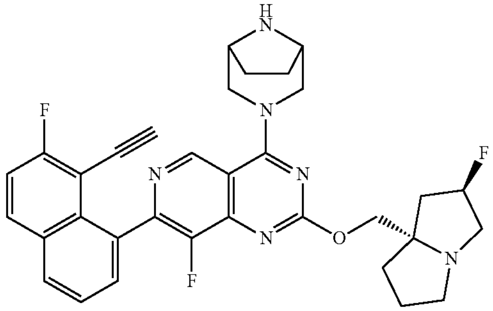

4-((1R,5$)-3,8-diazabicyclo[3.2.1]octan-3-yl)-7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidine. To a solution tert-butyl(1R,5S)-3-(7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (1.20 g, 1.73 mmol, 1.0 eq) in MeCN (15 mL) was added HCl·dioxane (4.0 M, 15 mL, 34.6 eq) dropwise below 5° C. The mixture was stirred at 15° C. for 0.5 hour. The reaction mixture was concentrated under reduced pressure at room temperature (without heating) to give a residue. The residue was dissolved in DCM (30 mL) and $H_2O$ (10 mL). The pH of the mixture was adjusted to 8~9 with $NaHCO_3$ solid in portions below 5° C. The mixture was extracted with DCM (20 mL×4). The combined organic layers were dried over anhydrous $Na_2SO_4$, filtered and concentrated under reduced pressure to give a residue. The residue was purified by prep-HPLC (Phenomenex luna C18 150*40 mm*15 um; mobile phase: [water (0.225% FA)-ACN]; B %: 3%-33%, 10 min). The desired fractions were collected and lyophilized to give the title compound (986 mg, 68% yield, 2FA). Yellow solid; $^{1}H$ NMR (400 MHz, methanol-$d_4$) δ=9.10 (s, 1H), 8.15-8.11 (m, 2H), 7.69-7.63 (m, 2H), 7.48-7.43 (m, 1H), 5.57-5.43 (m, 1H), 4.83-4.76 (m, 2H), 4.62-4.54 (m, 2H), 4.10 (s, 2H), 3.96-3.88 (m, 2H), 3.84-3.61 (m, 3H), 3.44 (s, 1H), 3.36-3.32 (m, 1H), 2.65-2.00 (m, 10H); $^{19}F$ NMR (376 MHz, methanol-d4) δ=−106.77, −139.32, −173.93; LCMS [ESI, M+1]: 585.3.

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-fluoronaphthalen-2-ol

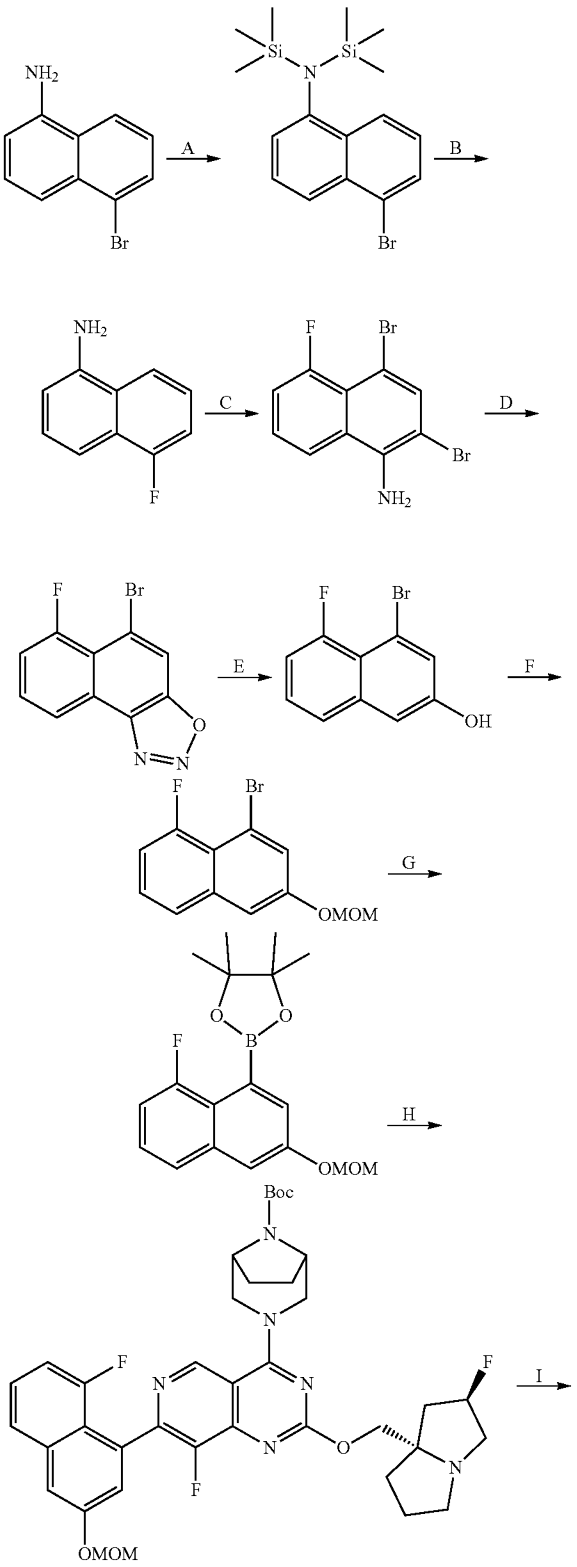

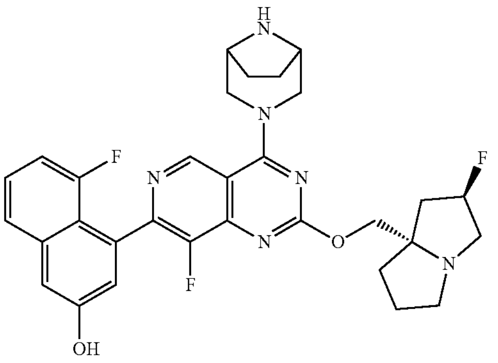 [SMILES: Oc1cc(-c2ncc3c(N4CC5CCC(C4)N5)nc(OC[C@@]45CCCN4C[C@H](F)C5)nc3c2F)c2c(F)cccc2c1]

-continued

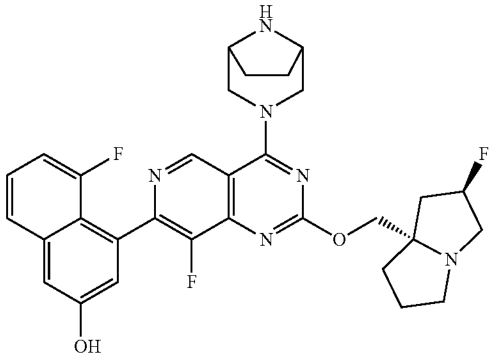

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-fluoronaphthalen-2-ol. To a solution of (1R,5S)-tert-butyl 3-(8-fluoro-7-(8-fluoro-3-(methoxymethoxy)naphthalen-1-yl)-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (630 mg, 874 μmol, 1.0 eq) in ACN (7 mL) was added HCl·dioxane (4 M, 7 mL). The mixture was stirred at 0° C. for 0.5 hour. The mixture was concentrated under vacuum. The residue was purified by prep-HPLC (column: Phenomenex luna C18 150*40 mm*15 um; mobile phase: [water (0.225% FA)-ACN]; B %: 1%-30%, 11 min). The desired fraction was collected and lyophilized to give the title compound (400.1 mg, 68% yield, 1.7FA) as a off-white solid. $^1$H NMR (400 MHz, methanol-$d_4$) δ=9.11 (s, 1H), 8.43 (s, 2H), 7.60 (d, J=8.4 Hz, 1H), 7.40 (td, J=5.2, 8.0 Hz, 1H), 7.34 (t, J=2.0 Hz, 1H), 7.19-7.14 (m, 1H), 6.92 (dd, J=7.6, 13.2 Hz, 1H), 5.53 (dt, J=3.2, 52.4 Hz, 1H), 4.84-4.76 (m, 2H), 4.67-4.52 (m, 2H), 4.13 (br s, 2H), 4.01-3.89 (m, 2H), 3.86-3.64 (m, 3H), 3.41-3.32 (m, 1H), 2.71-2.43 (m, 2H), 2.42-2.19 (m, 3H), 2.17-1.95 (m, 5H). LCMS [ESI, M+1]: 577.3.

Example 283

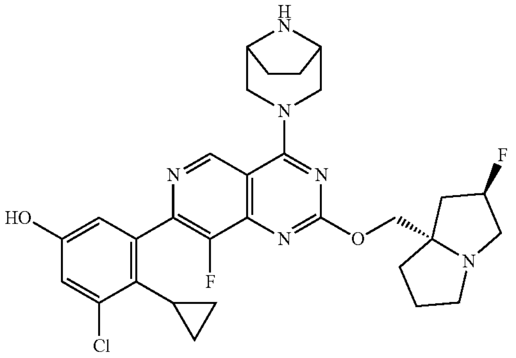 [SMILES: Oc1cc(Cl)c(C2CC2)c(-c2ncc3c(N4CC5CCC(C4)N5)nc(OC[C@@]45CCCN4C[C@H](F)C5)nc3c2F)c1]

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-cyclopropylphenol

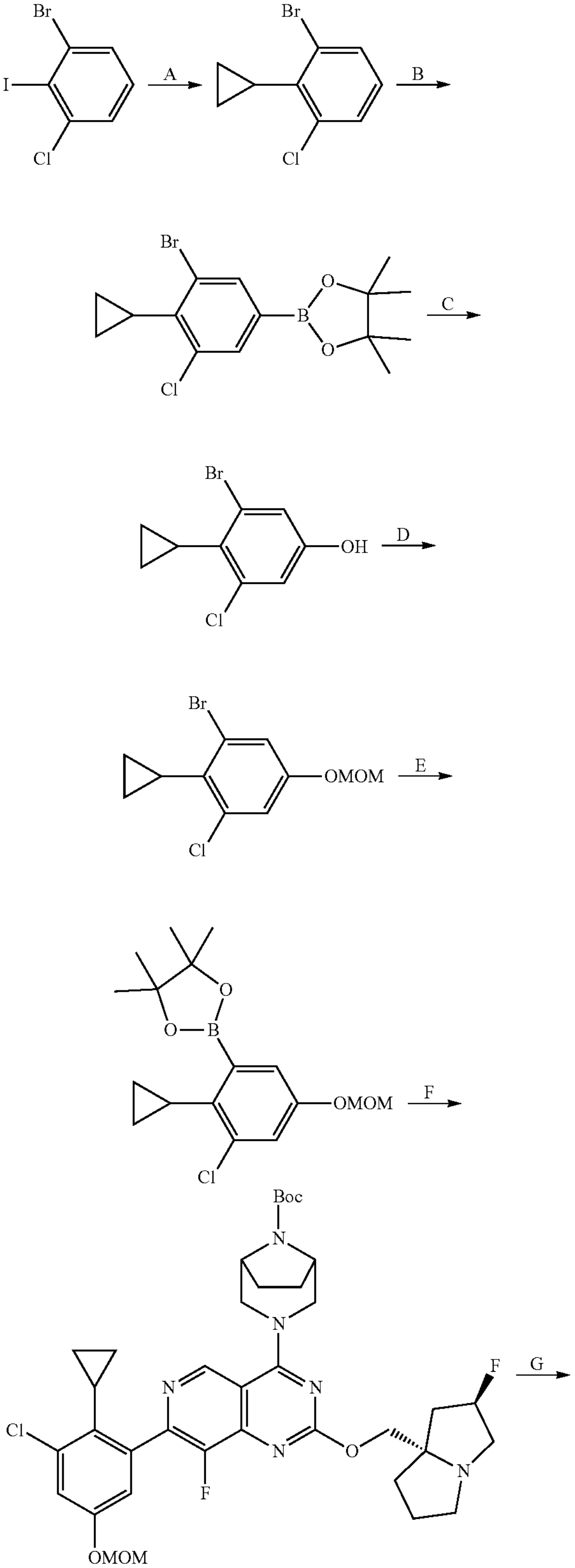

-continued

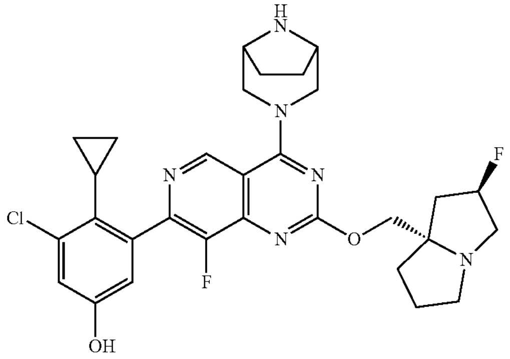

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-cyclopropylphenol. To a solution of (1R,5S)-tert-butyl-3-(7-(3-chloro-2-cyclopropyl-5-(methoxymethoxy)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (55 mg, 75.6 μmol, 1.0 eq) in MeCN (1 mL) was added HCl·dioxane (4 M, 2 mL, 106 eq). The mixture was stirred at 20° C. for 0.5 hour. After completion, the mixture was concentrated. The residue was purified by prep-HPLC (column: Shim-pack C18 150*25*10 um; mobile phase: [water (0.225% FA)-ACN]; B %: 12%-32%, 9 min) affording the title compound (9.71 mg, 22% yield, 1.7 HCOOH). Yellow solid; SFC analysis: Column: Chiralpak IC-3 50×4.6 mm I.D., 3 um Mobile phase: Phase A for CO2, and Phase B for MeOH+CAN (0.05% DEA); Gradient elution: 50% MeOH+CAN (0.05% DEA) in $CO_2$ Flow rate: 3 mL/min; Detector: PDAColumn Temp: 35° C.; Back Pressure: 100 Bar; $^1$H NMR (400 MHz, methanol-$d_4$) δ 9.12 (s, 1H), 6.98 (d, J=2.4 Hz, 1H), 6.80 (d, J=2.8 Hz, 1H), 5.62-5.40 (m, 1H), 4.85-4.75 (m, 2H), 4.63-4.52 (m, 2H), 4.09 (br s, 2H), 3.89 (br dd, J=5.2, 13.6 Hz, 2H), 3.85-3.74 (m, 1H), 3.73-3.62 (m, 2H), 3.39-3.32 (m, 1H), 2.68-2.42 (m, 2H), 2.40-2.31 (m, 1H), 2.30-2.19 (m, 2H), 2.16-1.96 (m, 5H), 1.89-1.79 (m, 1H), 0.62 (br d, J=7.6 Hz, 2H), 0.07 (br d, J=3.6 Hz, 2H); LCMS [ESI, M+1]: 583.3.

Example 284

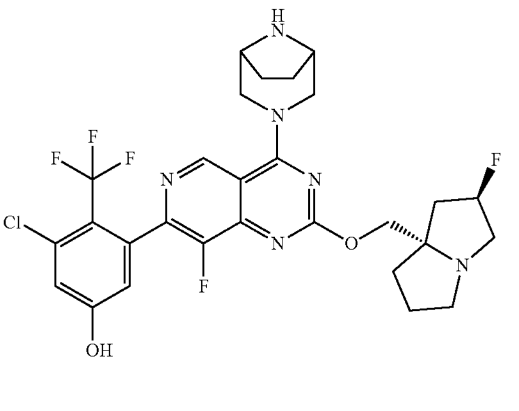 [SMILES: Oc1cc(Cl)c(C(F)(F)F)c(-c2ncc3c(N4CC5CCC(C4)N5)nc(OC[C@@]45CCCN4C[C@H](F)C5)nc3c2F)c1]

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-(trifluoromethyl)phenol

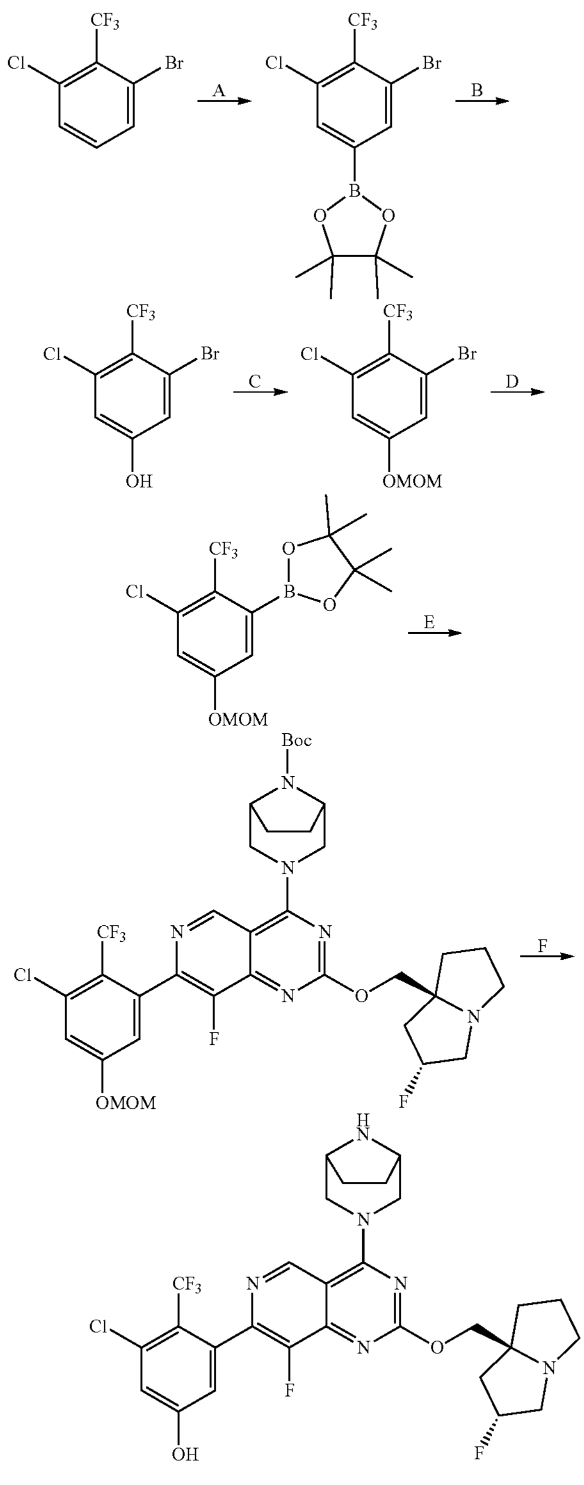

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-(trifluoromethyl)phenol. To the solution of (1R,5S)-tert-butyl 3-(7-(3-chloro-5-(methoxymethoxy)-2-(trifluoromethyl)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (40.0 mg, 53.0 μmol, 1.0 eq) in ACN (0.8 mL) was added HCl·dioxane (4 M, 1.6 mL, 121 eq) at 0° C., the mixture was stirred at 0° C. for 0.5 hour. The mixture was concentrated at 20° C. to give a residue, and then saturated $NaHCO_3$ was added to adjust the pH to 8. The mixture was diluted with MeOH (2 mL), filtered and concentrated to give a residue. The residue was purified by prep-HPLC (column: Waters Xbridge C18 150*50 mm*10 um; mobile phase: [water (10 mM $NH_4HCO_3$)-ACN]; B %: 25%-55%, 10 min) to give the title compound (9.72 mg, 29% yield). White Solid. $^1H$ NMR (400 MHz, methanol-$d_4$) δ=9.01 (s, 1H), 7.09 (d, J=2.0 Hz, 1H), 6.70 (d, J=2.4 Hz, 1H), 5.43-5.18 (m, 1H), 4.67-4.51 (m, 2H), 4.37-4.14 (m, 2H), 3.75-3.60 (m, 4H), 3.30-3.16 (m, 3H), 3.10-2.96 (m, 1H), 2.42-2.19 (m, 2H), 2.18-2.07 (m, 1H), 2.06-1.94 (m, 2H), 1.93-1.73 (m, 5H). LCMS [ESI, M+1]: 611.1.

Example 285

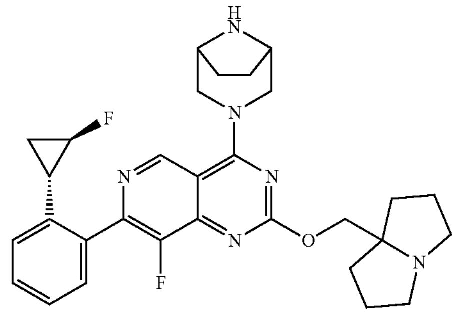 [SMILES: Fc1c(-c2ccccc2[C@@H]2C[C@H]2F)ncc2c(N3CC4CCC(C3)N4)nc(OCC34CCCN3CCC4)nc12]

4-((1R,5S)-3,8-diazabicyclo[3.2.1]octan-3-yl)-8-fluoro-7-(2-(trans-2-fluorocyclopropyl)phenyl)-2-((hexahydro-1H-pyrrolizin-7a-yl)methoxy)pyrido[4,3-d]pyrimidine

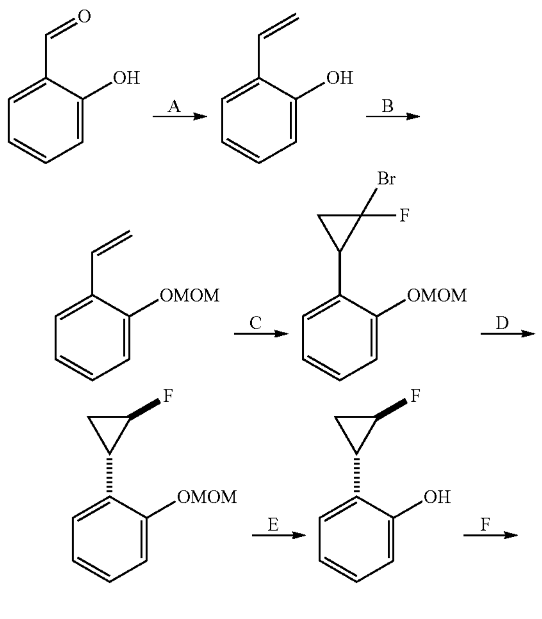

-continued

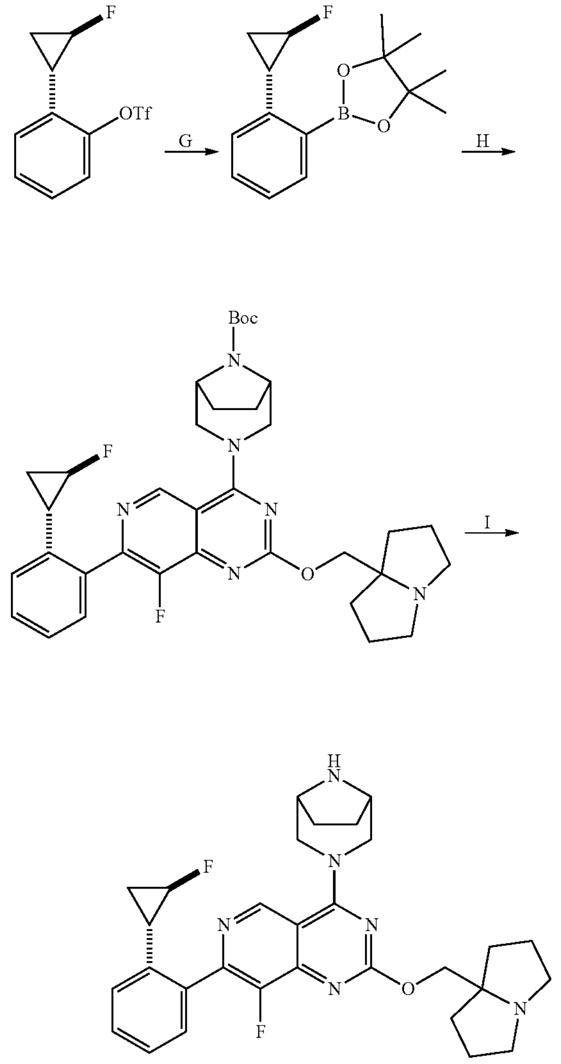

4-((1R,5S)-3,8-diazabicyclo[3.2.1]octan-3-yl)-8-fluoro-7-(2-(trans-2-fluorocyclopropyl)phenyl)-2-((hexahydro-1H-pyrrolizin-7a-yl)methoxy)pyrido[4,3-d]pyrimidine. To a solution of tert-butyl3-(8-fluoro-7-(2-(trans-2-fluorocyclopropyl)phenyl)-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 237 μmol, 1.0 eq) in MeCN (1 mL) was added HCl·dioxane (4 M, 3 mL, 50.6 eq). The mixture was stirred at 10° C. for 0.5 hour. Upon completion, the reaction mixture was concentrated. The residue was purified by prep-HPLC (column: Unisil 3-100 C18 ultra 150*50 mm*3 um; mobile phase: [water (0.225% FA)-ACN]; B %: 1%-30%, 10 min) affording the title compound (5.44 mg, 4.2% yield). Yellow solid; $^1H$ NMR (400 MHz, methanol-$d_4$) δ=9.18 (s, 1H), 7.48-7.34 (m, 3H), 7.09 (d, J=7.6 Hz, 1H), 4.83-4.76 (m, 2H), 4.68 (s, 2H), 4.66-4.45 (m, 1H), 4.07 (br s, 2H), 3.96-3.87 (m, 2H), 3.76-3.65 (m, 2H), 3.31-3.25 (m, 2H), 2.40-2.28 (m, 3H), 2.28-2.16 (m, 4H), 2.15-2.03 (m, 4H), 2.01-1.94 (m, 2H), 1.38-1.25 (m, 1H), 1.15-1.06 (m, 1H); LCMS [ESI, M+1]: 533.3.

Example 286

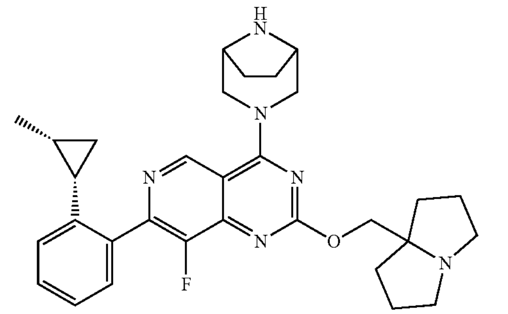 [SMILES: C[C@@H]1C[C@@H]1c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-((1S,2R)-2-methylcyclopropyl)phenyl)pyrido[4,3-d]pyrimidine

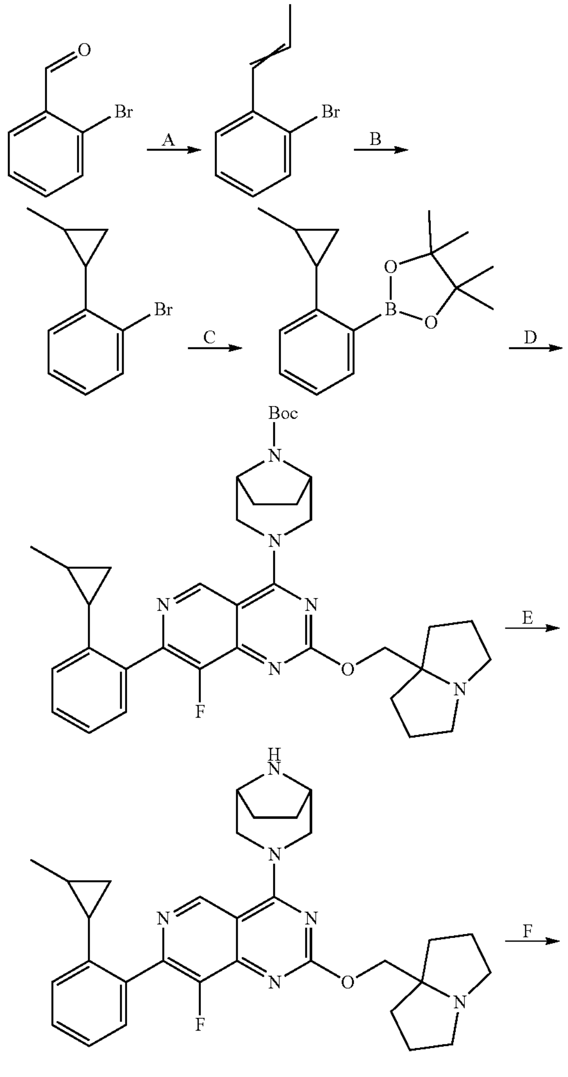

-continued

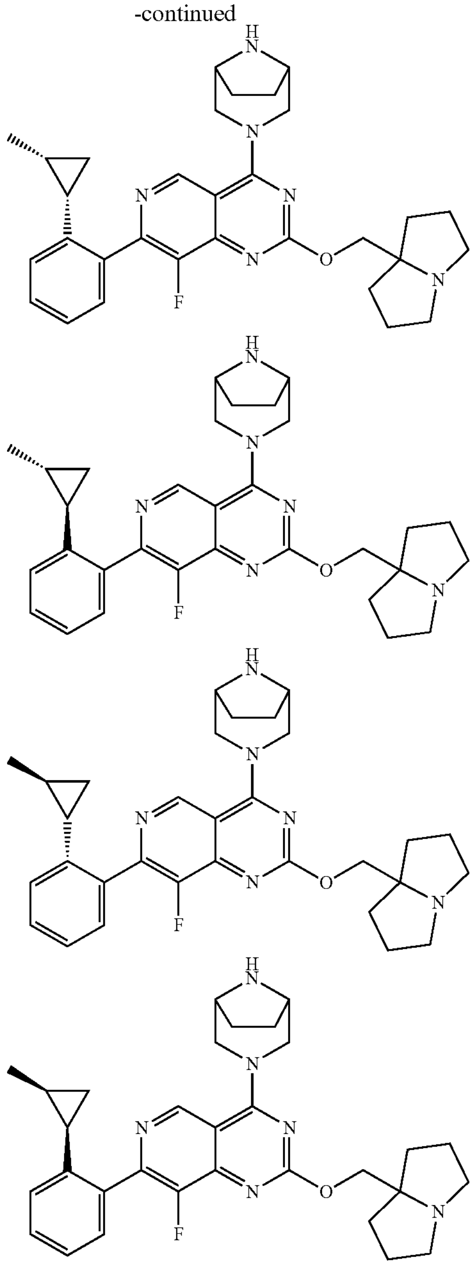

4-((1R,5S)-3,8-diazabicyclo[3.2.1]octan-3-yl)-8-fluoro-2-((hexahydro-1H-pyrrolizin-7a-yl)methoxy)-7-(2-((1S,2R)-2-methylcyclopropyl)phenyl)pyrido[4,3-d]pyrimidine (Example 286). 4-((1R,5S)-3,8-diazabicyclo[3.2.1]octan-3-yl)-8-fluoro-2-((hexahydro-1H-pyrrolizin-7a-yl)methoxy)-7-(2-((1R,2R)-2-methylcyclopropyl)phenyl)pyrido[4,3-d]pyrimidine (Example 288). 4-((1R,5S)-3,8-diazabicyclo[3.2.1]octan-3-yl)-8-fluoro-2-((hexahydro-1H-pyrrolizin-7a-yl)methoxy)-7-(2-((1S,2S)-2-methylcyclopropyl)phenyl)pyrido[4,3-d]pyrimidine (Example 289). 4-((1R,5S)-3,8-diazabicyclo[3.2.1]octan-3-yl)-8-fluoro-2-((hexahydro-1H-pyrrolizin-7a-yl)methoxy)-7-(2-((1R,2S)-2-methylcyclopropyl)phenyl)pyrido[4,3-d]pyrimidine (Example 287). The mixture of stereoisomers was purified by SFC (column: DAICEL CHIRALCEL OD (250 mm*30 mm, 10 um); mobile phase: [0.1% $NH_3H_2O$ IPA]; B %: 55%-55%, 50 min; 180 min) to afford Peak 3 (Rt=6.440) and Peak 4 (Rt-7.435), peak 3 was purified by prep-HPLC (column: Phenomenex Synergi C18 150*25*10 um; mobile phase: [water (0.225% FA) ACN]; B %: 8%-38%, 8.5 min) to afford Example 289 (14.8 mg, 23.2 μmol, 5% yield). Off-white Gum; LCMS [ESI, M+1]: 529.2. $^1$H NMR (400 MHz, $CDCl_3$-d) δ=9.08 (s, 1H), 8.43 (s, 2H), 7.40-7.33 (m, 2H), 7.30-7.25 (m, 1H), 7.07 (d, J=7.2 Hz, 1H), 4.71-4.57 (m, 5H), 3.96-3.74 (m, 7H), 2.98-2.87 (m, 2H), 2.43-2.32 (m, 2H), 2.26-2.15 (m, 2H), 2.14-2.04 (m, 2H), 2.04-1.93 (m, 4H), 1.92-1.85 (m, 2H), 1.64-1.57 (m, 1H), 0.93 (m, 4H), 0.88-0.80 (m, 1H), 0.61-0.53 (m, 1H). Peak 4 was purified by prep-HPLC (column: Phenomenex Synergi C18 150*25*10 um; mobile phase: [water (0.225% FA)-ACN]; B %: 8%-38%, 8.5 min) to Example 287 (5.39 mg, 8.61 μmol, 2% yield). Off-white Gum; $^1$H NMR (400 MHz, $CDCl_3$-d) δ=9.05 (s, 1H), 8.47 (s, 1H), 7.45-7.40 (m, 1H), 7.38 (dd, J=1.6, 7.6 Hz, 1H), 7.36-7.30 (m, 1H), 7.28-7.25 (m, 1H), 4.64-4.56 (m, 4H), 3.91-3.66 (m, 6H), 2.89 (td, J=6.4, 11.2 Hz, 2H), 2.41-2.29 (m, 2H), 2.24-2.12 (m, 3H), 2.12-2.00 (m, 2H), 1.99-1.83 (m, 6H), 0.94-0.79 (m, 2H), 0.65 (d, J=6.0 Hz, 3H), 0.39 (q, J=5.2 Hz, 1H). LCMS [ESI, M+1]: 529.2. The other two peaks was purified by SFC (column: DAICEL CHIRALPAK IC (250 mm*30 mm, 10 um); mobile phase: [0.1% $NH_3$·$H_2O$ IPA]; B %: 25%-25%, 14.2 min; 241 minmin) to afford Peak 1 (Rt=3.964) and Peak 2 (Rt=5.402). Then Peak 1 was purified by prep-HPLC (column: Phenomenex Synergi C18 150*25*10 um; mobile phase: [water (0.225% FA)-ACN]; B %: 10%-40%, 8.5 min) to afford Example 286 (4.22 mg, 6.65 μmol, 2% yield). Yellow Gum; LCMS [ESI, M+1]: 529.2. $^1$H NMR (400 MHz, $CDCl_3$-d) δ=9.07 (s, 1H), 8.38 (br s, 2H), 7.46-7.31 (m, 3H), 7.29 (br s, 1H), 4.69-4.57 (m, 4H), 3.88-3.78 (m, 6H), 2.98-2.87 (m, 2H), 2.39 (m, 2H), 2.25-2.16 (m, 3H), 2.10 (m, 2H), 2.02-1.87 (m, 6H), 0.93-0.82 (m, 2H), 0.65 (d, J=6.0 Hz, 3H), 0.44-0.36 (m, 1H). Peak 2 was purified by prep-HPLC (column: Phenomenex Synergi C18 150*25*10 um; mobile phase: [water (0.225% FA)-ACN]; B %: 10%-40%, 8.5 min) to afford Example 288 (11.4 mg, 19.8 μmol, 5% yield), White Solid; LCMS [ESI, M+1]: 529.2; $^1$H NMR (400 MHz, $CDCl_3$-d) δ=9.05 (s, 1H), 7.40-7.33 (m, 2H), 7.29-7.25 (m, 1H), 7.06 (d, J=8.0 Hz, 1H), 4.65-4.36 (m, 4H), 3.74-3.36 (m, 6H), 2.85-2.70 (m, 2H), 2.32-2.19 (m, 2H), 2.05-1.94 (m, 4H), 1.81 (br s, 6H), 0.92 (d, J=1.6 Hz, 3H), 0.92-0.81 (m, 2H), 0.60-0.54 (m, 1H).

Example 287

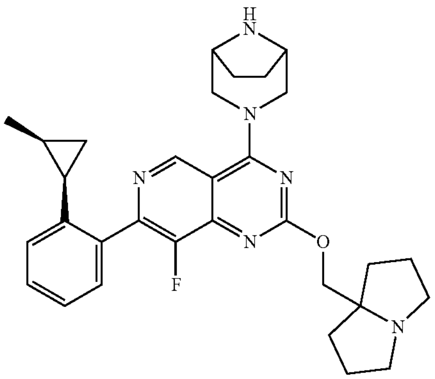 [SMILES: C[C@H]1C[C@H]1c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-((1R,2S)-2-methylcyclopropyl)phenyl)pyrido[4,3-d]pyrimidine See the synthesis of Example 286.

Example 288

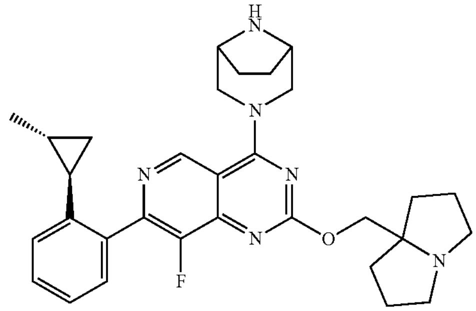 [SMILES: C[C@@H]1C[C@H]1c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-((1R,2R)-2-methylcyclopropyl)phenyl)pyrido[4,3-d]pyrimidine See the synthesis of Example 286.

Example 289

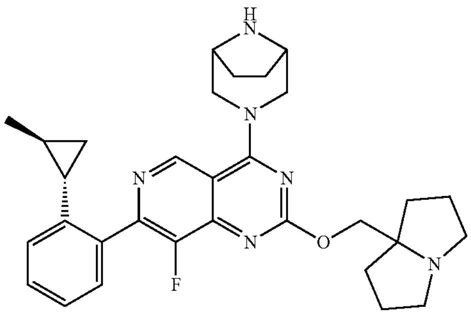 [SMILES: C[C@H]1C[C@@H]1c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-((1S,2S)-2-methylcyclopropyl)phenyl)pyrido[4,3-d]pyrimidine See the synthesis of Example 286.

Example 290

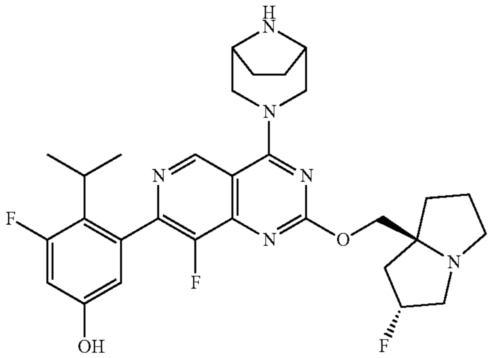 [SMILES: CC(C)c1c(F)cc(O)cc1-c1ncc2c(N3CC4CCC(C3)N4)nc(OC[C@@]34CCCN3C[C@H](F)C4)nc2c1F]

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoro-4-isopropylphenol

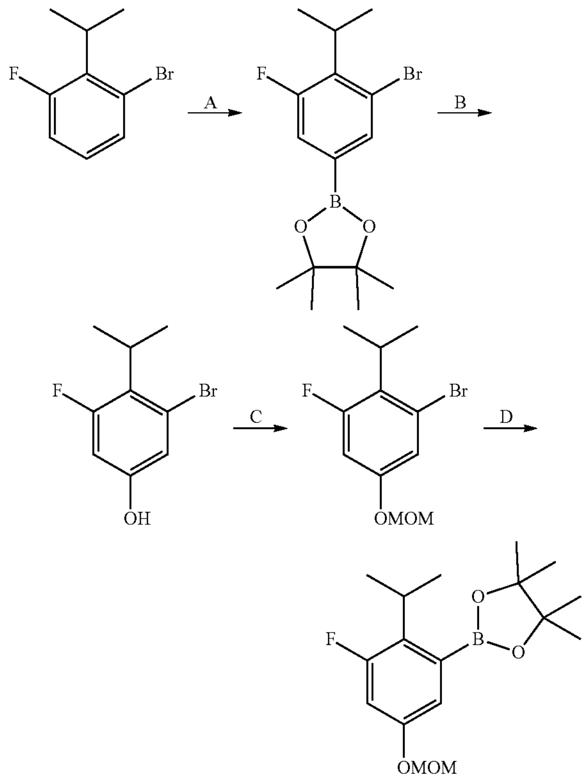

-continued

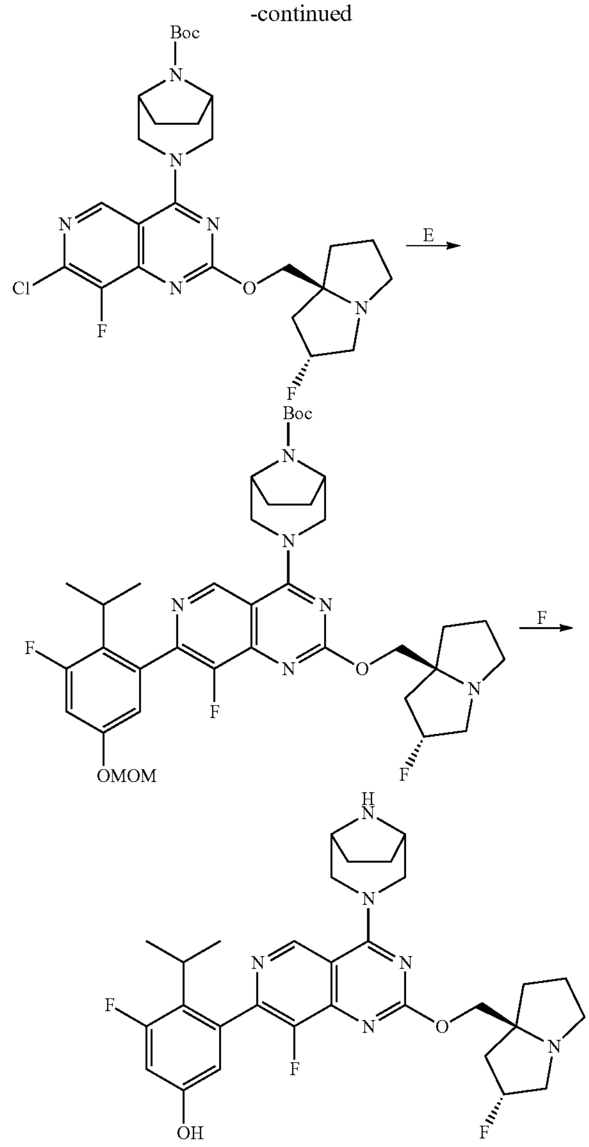

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoro-4-isopropylphenol. To a mixture of tert-butyl(1R,5S)-3-(8-fluoro-7-(3-fluoro-2-isopropyl-5-(methoxymethoxy)phenyl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (45.0 mg, 63.1 μmol, 1.0 eq) in MeCN (0.5 mL) was added HCl·dioxane (4 M, 1 mL, 63 eq) at 10° C. The mixture was stirred at 10° C. for 0.5 hour. After completion, the mixture was concentrated under vacuum. Then the pH value was adjusted to 9 with saturated $Na_2CO_3$ solution and the mixture was filtered (solid was washed with methanol) and concentrated under vacuum. The residue was purified by prep-HPLC (column: Waters Xbridge C18 150*50 mm*10 um; mobile phase: [water (10 mM $NH_4HCO_3$)-ACN]; B %: 40%-70%, 10 min) to give the title compound (19.5 mg, 54% yield). White solid; $^1H$ NMR (400 MHz, methanol-d4) δ=9.03 (d, J=3.2 Hz, 1H), 6.61 (dt, J=2.8, 13.6 Hz, 1H), 6.55-6.50 (m, 1H), 5.30 (d, J=54.8 Hz, 1H), 4.64-4.57 (m, 2H), 4.31-4.20 (m, 2H), 3.72-3.61 (m, 4H), 3.29-3.18 (m, 3H), 3.06-2.97 (m, 1H), 2.68-2.60 (m, 1H), 2.33-2.13 (m, 3H), 1.99 (br s, 2H), 1.91-1.74 (m, 5H), 1.31-1.20 (m, 6H). $^{19}F$ NMR (400 MHz, methanol-$d_4$) δ=−113.963, −140.053, −173.647. SFC condition: "Column: Chiralcel OD-3 50×4.6 mm I.D., 3 um; Mobile phase: Phase A for CO2, and Phase B for MeOH+ACN (0.05% DEA); Gradient elution: 50% MeOH+ACN (0.05% DEA) in CO2; Flow rate: 3 mL/min; Detector: PDA; Column Temp: 35C; Back Pressure: 100 Bar". LCMS [ESI, M/2+1, M+1]: 285.4, 569.2.

Example 291

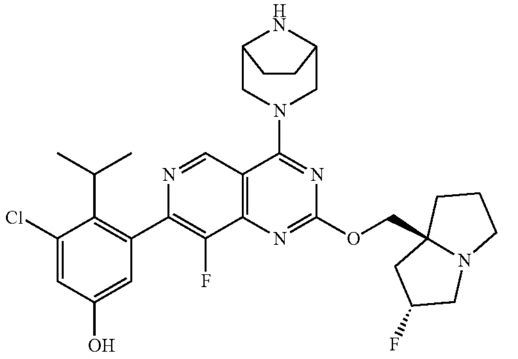 [SMILES: CC(C)c1c(Cl)cc(O)cc1-c1ncc2c(N3CC4CCC(C3)N4)nc(OC[C@@]34CCCN3C[C@H](F)C4)nc2c1F]

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-isopropylphenol

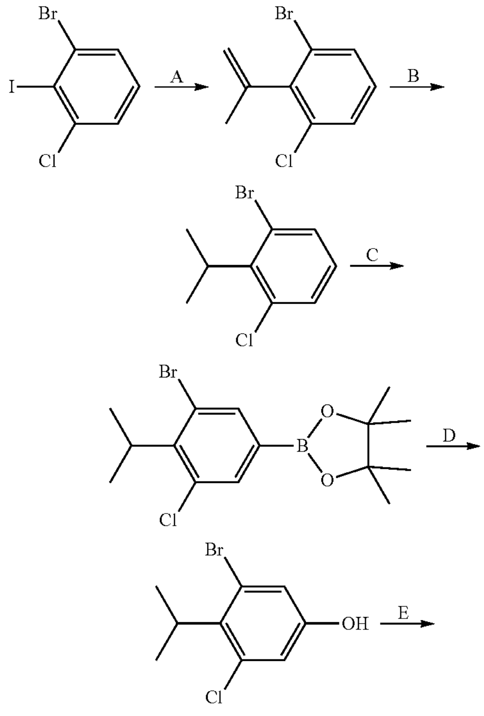

-continued

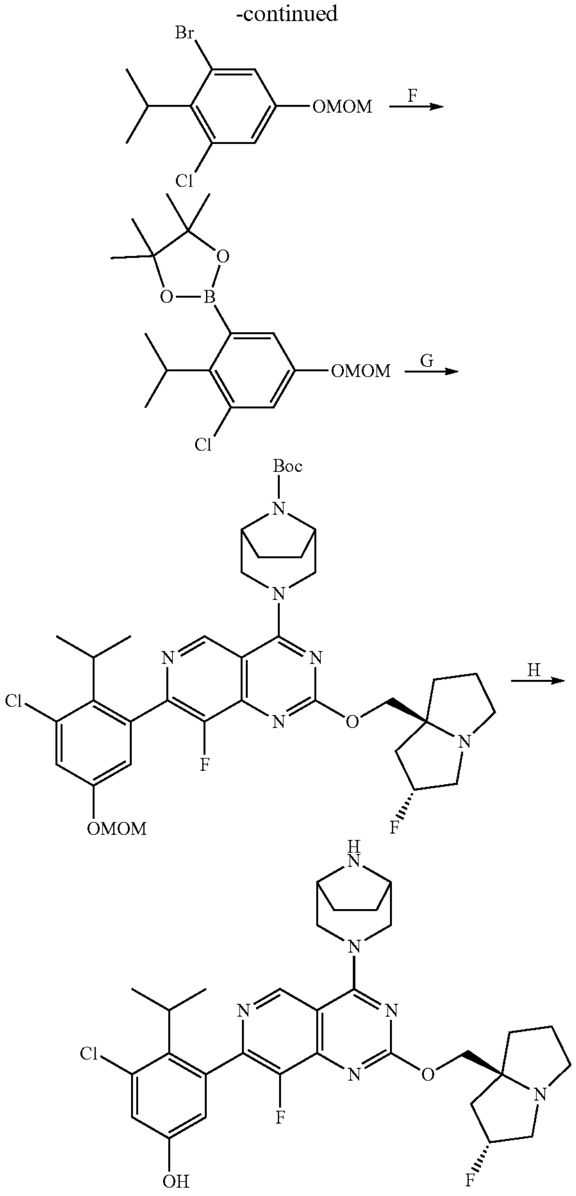

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-isopropylphenol. To a solution of (1R,5S)-tert-butyl 3-(7-(3-chloro-2-isopropyl-5-(methoxymethoxy)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (35 mg, 47.9 μmol, 1.0 eq) in ACN (0.5 mL) was added HCl·dioxane (4 M, 700 ul). The mixture was stirred at 20° C. for 0.5 hour. The mixture was concentrated under vacuum. The residue was diluted with saturated $NaHCO_3$ aqueous solution (0.5 mL) and purified by prep-HPLC (column: Waters Xbridge C18 150*50 mm*10 um; mobile phase: [water (10 mM $NH_4HCO_3$)-ACN]; B %: 30%-60%, 10 min). The desired fraction was collected and lyophilized to give the title compound (11.8 mg, 40% yield). White solid; $^1H$ NMR (400 MHz, chloroform-d) δ=8.93 (s, 1H), 6.87 (d, J=2.4 Hz, 1H), 6.54 (d, J=2.4 Hz, 1H), 5.40-5.13 (m, 1H), 4.52 (br d, J=12.0 Hz, 2H), 4.20 (d, J=10.4 Hz, 1H), 4.14 (d, J=10.0 Hz, 1H), 3.72-3.52 (m, 4H), 3.31-3.10 (m, 3H), 3.04-2.86 (m, 2H), 2.27-2.09 (m, 3H), 2.00-1.74 (m, 7H), 1.24 (br d, J=6.8 Hz, 6H). LCMS [ESI, M+1]: 585.2.

Example 292

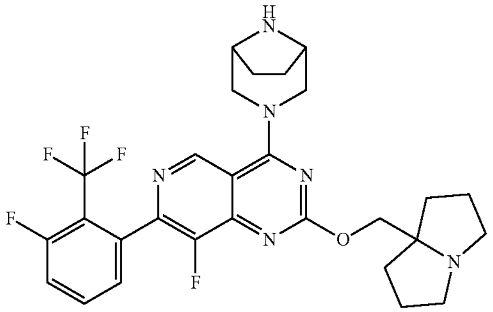 [SMILES: Fc1cccc(-c2ncc3c(N4CC5CCC(C4)N5)nc(OCC45CCCN4CCC5)nc3c2F)c1C(F)(F)F]

4-((1R,5S)-3,8-diazabicyclo[3.2.1]octan-3-yl)-8-fluoro-7-(3-fluoro-2-(trifluoromethyl)phenyl)-2-((tetrahydro-1H-pyrrolizin-7a(5H)-yl)methoxy) pyrido[4,3-d]pyrimidine

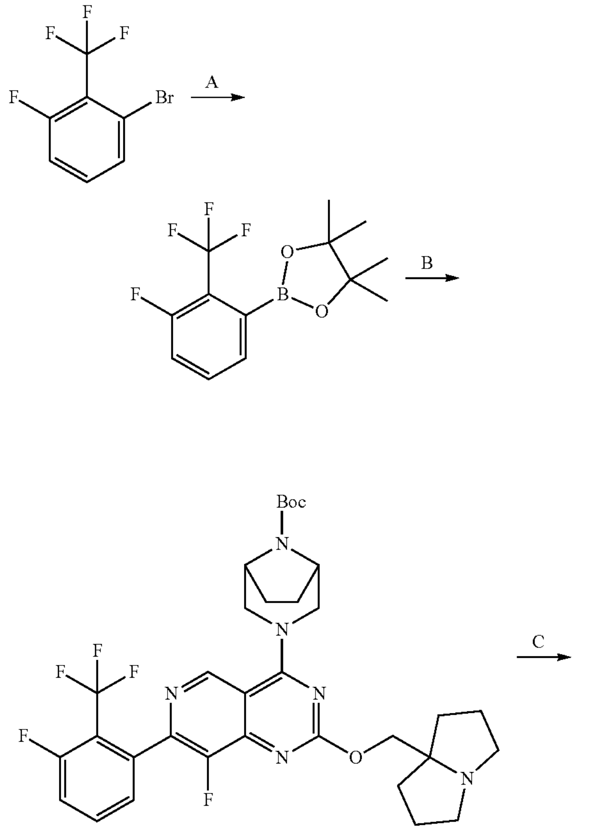

-continued

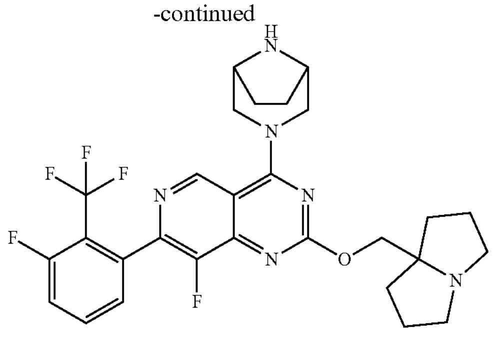

4-((1R,5S)-3,8-diazabicyclo[3.2.1]octan-3-yl)-8-fluoro-7-(3-fluoro-2-(trifluoromethyl)phenyl)-2-((tetrahydro-1H-pyrrolizin-7a(5H)-yl)methoxy)pyrido[4,3-d]pyrimidine. A mixture of tert-butyl(1R,5S)-3-(8-fluoro-7-(3-fluoro-2-(trifluoromethyl)phenyl)-2-((tetrahydro-1H-pyrrolizin-7a(5H)-yl)methoxy)pyrido[4,3-d]pyrimidin-4-yl)-3,8-diazabicyclo [3.2.1]octane-8-carboxylate (95 mg, 144 μmol, 1 eq) in HCl·dioxane (4 M, 2 mL, 55.6 eq) and acetonitrile (1 mL) was stirred at 25° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 9%-29%, 8 min) to give the title compound (25.6 mg, 27% yield, 2FA). White solid; $^1$H NMR (400 MHz, methanol-$d_4$) δ=9.14 (s, 1H), 7.82 (dt, J=5.2, 8.0 Hz, 1H), 7.59-7.48 (m, 1H), 7.36 (d, J=7.6 Hz, 1H), 4.77 (br d, J=13.2 Hz, 2H), 4.66 (s, 2H), 4.05 (br d, J=13.6 Hz, 2H), 3.95-3.84 (m, 2H), 3.75-3.66 (m, 2H), 3.30-3.24 (m, 2H), 2.39-2.30 (m, 2H), 2.27-1.94 (m, 10H); LCMS [ESI, M+1]: 561.3.

Example 293

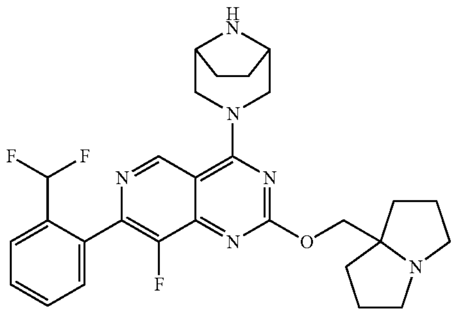 [SMILES: Fc1c(-c2ccccc2C(F)F)ncc2c(N3CC4CCC(C3)N4)nc(OCC34CCCN3CCC4)nc12]

4-((1R,5S)-3,8-diazabicyclo[3.2.1]octan-3-yl)-7-(2-(difluoromethyl)phenyl)-8-fluoro-2-((hexahydro-1H-pyrrolizin-7a-yl)methoxy)pyrido[4,3-d]pyrimidine

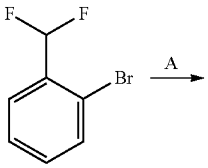

-continued

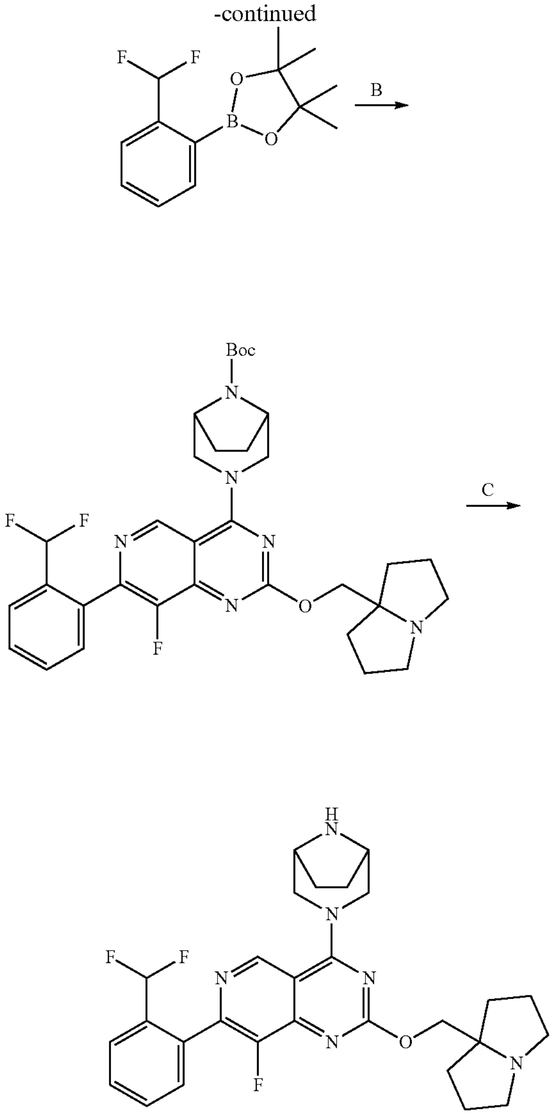

4-((1R,5S)-3,8-diazabicyclo[3.2.1]octan-3-yl)-7-(2-(difluoromethyl)phenyl)-8-fluoro-2-((hexahydro-1H-pyrrolizin-7a-yl)methoxy)pyrido[4,3-d]pyrimidine. To the solution of (1R,5S)-tert-butyl 3-(7-(2-(difluoromethyl)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (65.0 mg, 104 μmol, 1.0 eq) in ACN (1 mL) was added HCl/dioxane (4 M, 2 mL, 76.9 eq) at 0° C., the mixture was stirred at 0° C. for 1 hour. After completion, the mixture was concentrated at 25° C. The residue was purified by prep-HPLC (column: Unisil 3-100 C18 ultra 150*50 mm*3 um; mobile phase: [water (0.225% FA)-ACN]; B %: 1%-30%, 10 min) to give the title compound (31.45 mg, 49% yield, 2FA). Yellow Solid; $^{1}H$ NMR (400 MHz, chloroform-d) δ=9.05 (s, 1H), 7.87-7.82 (m, 1H), 7.60 (d, J=3.2 Hz, 3H), 7.15-6.86 (m, 1H), 4.67 (s, 2H), 4.61 (br d, J=12.4 Hz, 2H), 3.98-3.87 (m, 4H), 3.84-3.76 (m, 2H), 3.00-2.88 (m, 2H), 2.42-2.31 (m, 2H), 2.26-2.16 (m, 2H), 2.14-1.84 (m, 8H). LCMS [ESI, M+1]: 525.

Example 294

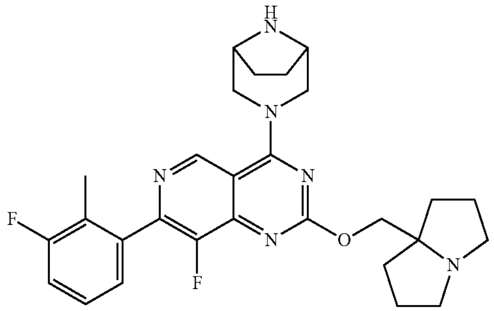 [SMILES: Cc1c(F)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(3-fluoro-2-methylphenyl)-2-((hexahydro-1H-pyrrolizin-7a-yl)methoxy)pyrido[4,3-d]pyrimidine

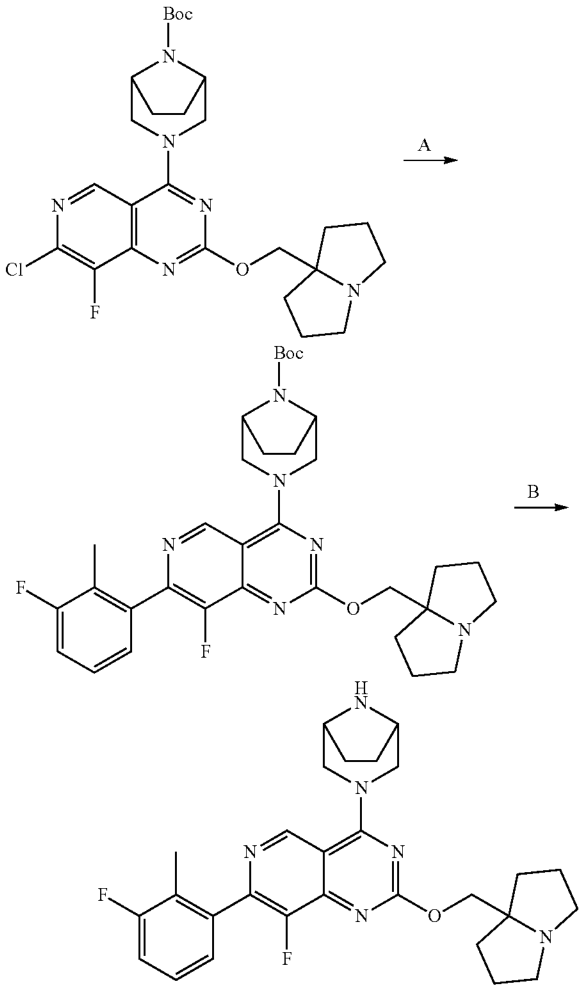

4-((1R,5S)-3,8-diazabicyclo[3.2.1]octan-3-yl)-8-fluoro-7-(3-fluoro-2-methylphenyl)-2-((hexahydro-1H-pyrrolizin-7a-yl)methoxy)pyrido[4,3-d]pyrimidine. A mixture of (1R,5S)-tert-butyl 3-(8-fluoro-7-(3-fluoro-2-methylphenyl)-2-

((hexahydro-1H-pyrrolizin-7a-yl)methoxy)pyrido[4,3-d]pyrimidin-4-yl)-3,8-diazabicyclo[3.2.1]octane-8-carboxylate (95 mg, 157 μmol, 1.0 eq), HCl·dioxane (4 M, 2 mL, 51.1 eq) and acetonitrile (1 mL) was stirred at 25° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 6%-26%, 8 min) to give the title compound (15.1 mg, 16% yield, 2FA). White solid; $^1$H NMR (400 MHz, methanol-$d_4$) δ=9.15 (s, 1H), 7.41-7.33 (m, 1H), 7.26-7.20 (m, 2H), 4.80 (br d, J=13.2 Hz, 2H), 4.67 (s, 2H), 4.09 (br s, 2H), 3.92 (br d, J=13.6 Hz, 2H), 3.75-3.66 (m, 2H), 3.30-3.26 (m, 2H), 2.39-2.30 (m, 2H), 2.26-2.05 (m, 11H), 2.02-1.95 (m, 2H); LCMS [ESI, M+1]: 507.3.

Example 295

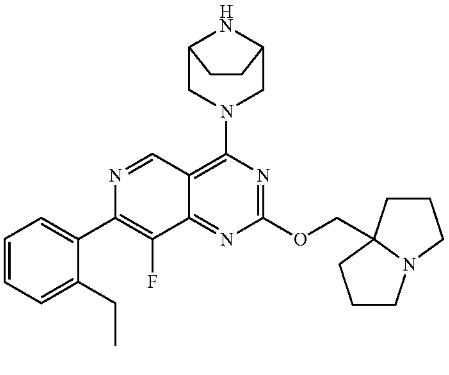 [SMILES: CCc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(2-ethylphenyl)-8-fluoro-2-((hexahydro-1H-pyrrolizin-7a-yl)methoxy)pyrido[4,3-d]pyrimidine

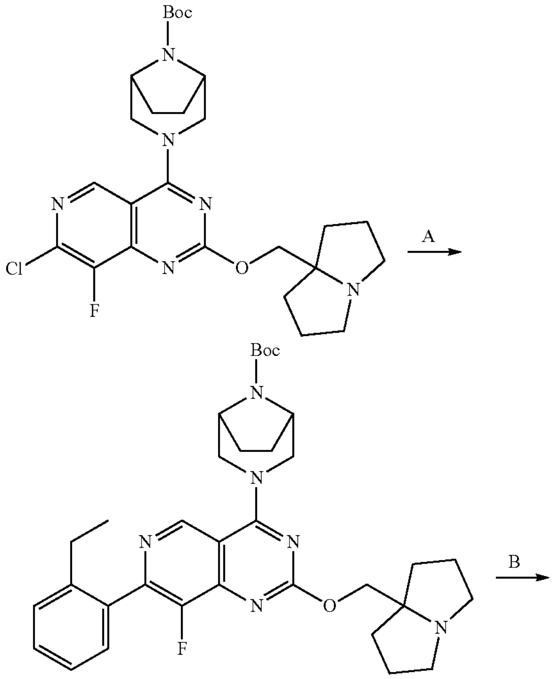

-continued

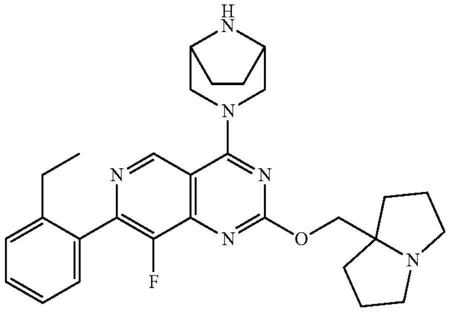

4-((1R,5S)-3,8-diazabicyclo[3.2.1]octan-3-yl)-7-(2-ethylphenyl)-8-fluoro-2-((hexahydro-1H-pyrrolizin-7a-yl)methoxy)pyrido[4,3-d]pyrimidine. To a mixture of tert-butyl (1R,5S)-3-(7-(2-ethylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (65 mg, 108 μmol, 1.0 eq) in MeCN (1 mL) was added HCl·dioxane (4 M, 2 mL, 74 eq) at 0° C. The mixture was stirred at 0° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 7%-27%, 8 min) to give the title compound (23.0 mg, 37% yield, 1.5 FA). Off-white solid. $^1$H NMR (400 MHz, methanol-$d_4$) δ=9.14 (s, 1H), 7.49-7.41 (m, 2H), 7.37-7.31 (m, 2H), 4.84-4.78 (m, 2H), 4.68 (s, 2H), 4.13 (br s, 2H), 3.95 (br d, J=13.6 Hz, 2H), 3.76-3.68 (m, 2H), 3.31-3.25 (m, 2H), 2.60 (q, J=7.6 Hz, 2H), 2.39-2.31 (m, 2H), 2.28-2.16 (m, 4H), 2.15-2.07 (m, 4H), 2.05-1.98 (m, 2H), 1.08 (t, J=7.6 Hz, 3H). LCMS [ESI, M/2+1, M+1]: 252.3, 503.3.

Example 296

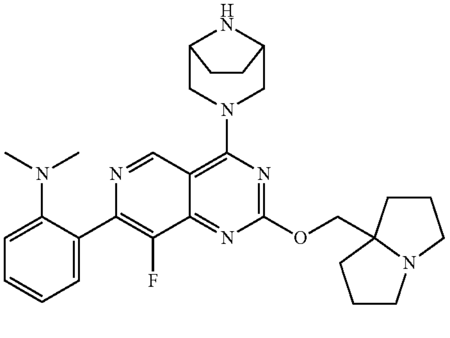 [SMILES: CN(C)c1ccccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-N,N-dimethylaniline

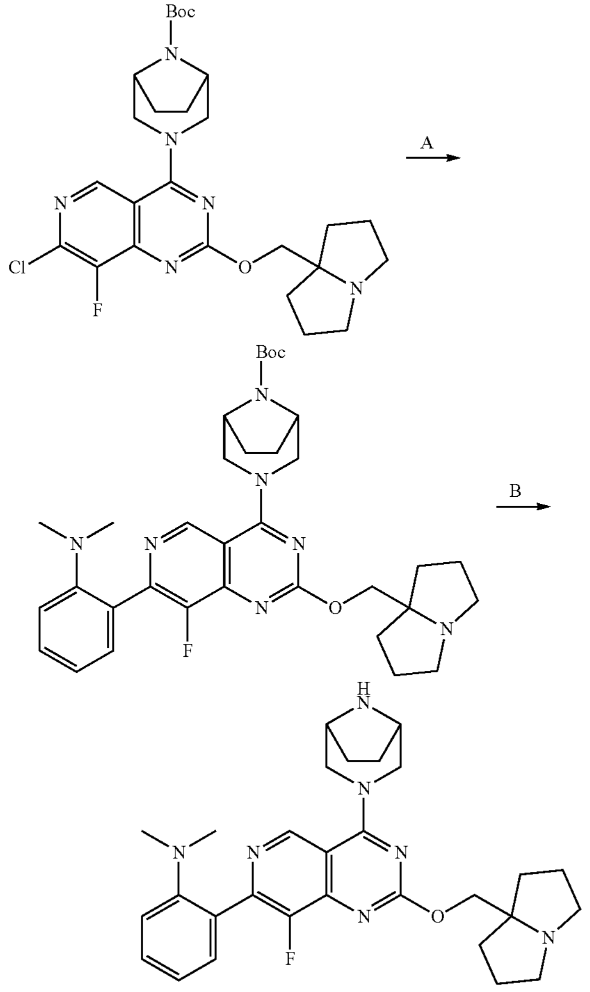

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-N,N-dimethylaniline. To a mixture of (1R,5S)-tert-butyl 3-(7-(2-(dimethylamino)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (91.0 mg, 147 μmol, 1.0 eq) in MeCN (1 mL) was added HCl·dioxane (4 M, 2 mL, 54.0 eq) at 0° C. The mixture was stirred at 0° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 0%-20%, 8 min) to give the title compound (19.4 mg, 21% yield, 2FA). Yellow solid. $^1$H NMR (400 MHz, methanol-$d_4$) δ=9.14 (s, 1H), 7.48-7.41 (m, 1H), 7.33 (dd, J=1.2, 7.6 Hz, 1H), 7.23 (d, J=7.6 Hz, 1H), 7.10 (td, J=0.8, 7.6 Hz, 1H), 4.80 (br d, J=13.2 Hz, 2H), 4.67 (s, 2H), 4.13 (br s, 2H), 3.94 (br d, J=13.6 Hz, 2H), 3.76-3.66 (m, 2H), 3.30-3.25 (m, 2H), 2.56 (s, 6H), 2.38-2.31 (m, 2H), 2.28-2.16 (m, 4H), 2.15-2.06 (m, 4H), 2.04-1.97 (m, 2H). LCMS [ESI, M/2+1, M+1]: 259.9, 518.3.

Example 297

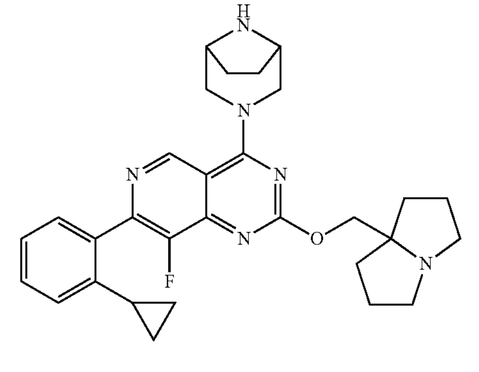 [SMILES: Fc1c(-c2ccccc2C2CC2)ncc2c(N3CC4CCC(C3)N4)nc(OCC34CCCN3CCC4)nc12]

4-((1R,5S)-3,8-diazabicyclo[3.2.1]octan-3-yl)-7-(2-cyclopropylphenyl)-8-fluoro-2-((hexahydro-1H-pyrrolizin-7a-yl)methoxy)pyrido[4,3-d]pyrimidine

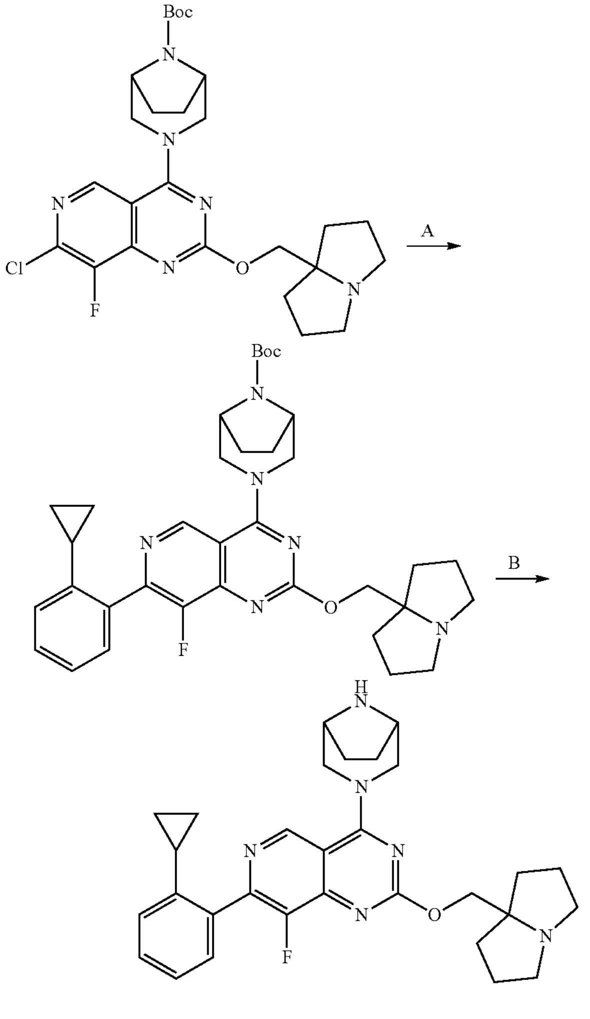

4-((1R,5S)-3,8-diazabicyclo[3.2.1]octan-3-yl)-7-(2-cyclopropylphenyl)-8-fluoro-2-((hexahydro-1H-pyrrolizin-7a-yl)methoxy)pyrido[4,3-d]pyrimidine. To the solution of (1R, 5S)-tert-butyl 3-(7-(2-cyclopropylphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (60.0 mg, 97.6 μmol, 1.0 eq) in ACN (1 mL) was added HCl·dioxane (4 M, 2.0 mL, 82.0 eq) at 0° C., and the mixture was stirred at 0° C. for 0.5 hour. After completion, the mixture was concentrated at 20° C. to give a residue. The residue was purified by prep-HPLC (column: Unisil 3-100 C18 ultra 150*50 mm*3 um; mobile phase: [water (0.225% FA)-ACN]; B %: 3%-33%, 10 min) to give the title compound (29.45 mg, 51% yield). White Solid. $^1$H NMR (400 MHz, CHLOROFORM-d) δ=9.08 (s, 1H), 8.43 (br s, 2H), 7.42-7.34 (m, 2H), 7.29 (d, J=7.6 Hz, 1H), 7.06 (d, J=8.0 Hz, 1H), 4.65 (s, 2H), 4.61 (br d, J=12.4 Hz, 2H), 3.94-3.70 (m, 6H), 2.98-2.83 (m, 2H), 2.43-2.28 (m, 2H), 2.26-2.14 (m, 2H), 2.14-2.04 (m, 2H), 1.92-1.84 (m, 2H), 2.02-1.84 (m, 5H), 0.87-0.73 (m, 2H), 0.69-0.57 (m, 2H). LCMS [ESI, M+1]: 515.3.

Example 298

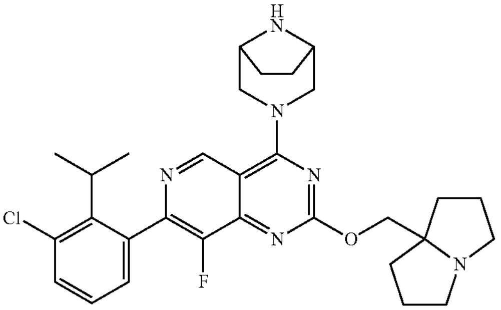 [SMILES: CC(C)c1c(Cl)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(3-chloro-2-isopropylphenyl)-8-fluoro-2-((hexahydro-1H-pyrrolizin-7a-yl)methoxy)pyrido[4,3-d]pyrimidine

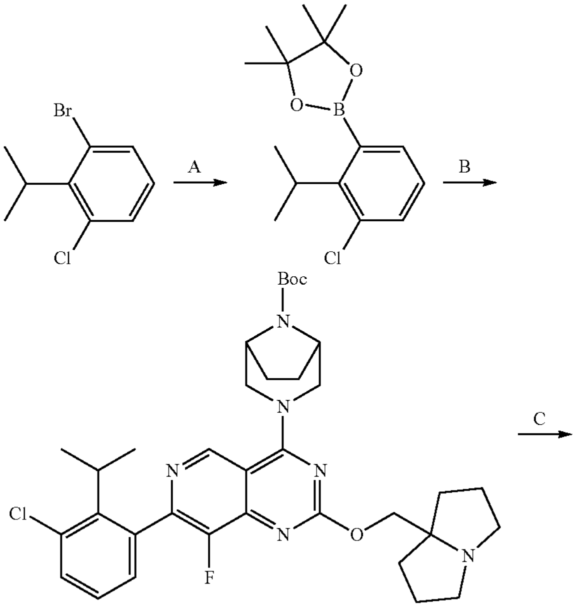

-continued

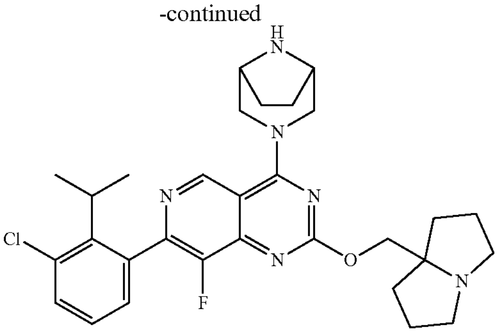

4-((1R,5S)-3,8-diazabicyclo[3.2.1]octan-3-yl)-7-(3-chloro-2-isopropylphenyl)-8-fluoro-2-((hexahydro-1H-pyrrolizin-7a-yl)methoxy)pyrido[4,3-d]pyrimidine. To a mixture of tert-butyl(1R,5S)-3-(7-(3-chloro-2-isopropylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (80 mg, 123 μmol, 1.0 eq) in ACN (0.5 mL) was added HCl·dioxane (4 M, 0.5 mL, 16 eq) in one portion at 0° C. under $N_2$. The mixture was stirred at 20° C. for 0.5 hour. Upon completion, the mixture was concentrated. Then the residue was basified to pH~8 with saturated $NaHCO_3$ aqueous solution and extracted with DCM (3×15 mL). The combined organic layers were washed with brine (15 mL), dried over $Na_2SO_4$, filtered and concentrated. The residue was purified by prep-HPLC (column: Phenomenex Gemini NX—C18 (75*30 mm*3 um); mobile phase: [water (10 mM $NH_4HCO_3$)-ACN]; B %: 24%-54%, 8 min). The desired fraction was collected and concentrated under vacuum to remove acetonitrile. The mixture was lyophilized to give the title compound (17.3 mg, 25% yield); White solid; $^1$H NMR (400 MHz, $CDCl_3$-d) δ=8.99 (s, 1H), 7.47-7.41 (m, 1H), 7.25-7.18 (m, 1H), 7.18-7.13 (m, 1H), 4.58 (br d, J=12.0 Hz, 2H), 4.19 (s, 2H), 3.72-3.58 (m, 4H), 3.19-3.07 (m, 3H), 2.71-2.60 (m, 2H), 2.16-2.06 (m, 2H), 1.99-1.81 (m, 7H), 1.75-1.60 (m, 3H), 1.33 (br d, J=6.8 Hz, 6H). LCMS [ESI, M+1]: 551.3.

Example 299

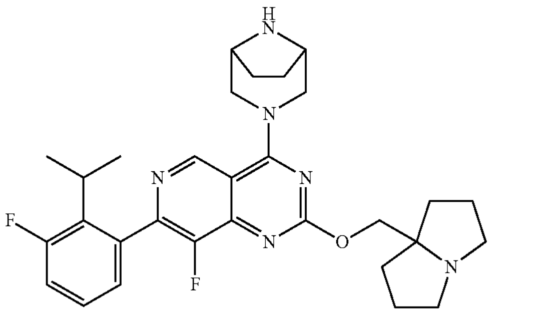 [SMILES: CC(C)c1c(F)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(3-fluoro-2-isopropylphenyl)-2-((hexahydro-1H-pyrrolizin-7a-yl)methoxy)pyrido[4,3-d]pyrimidine

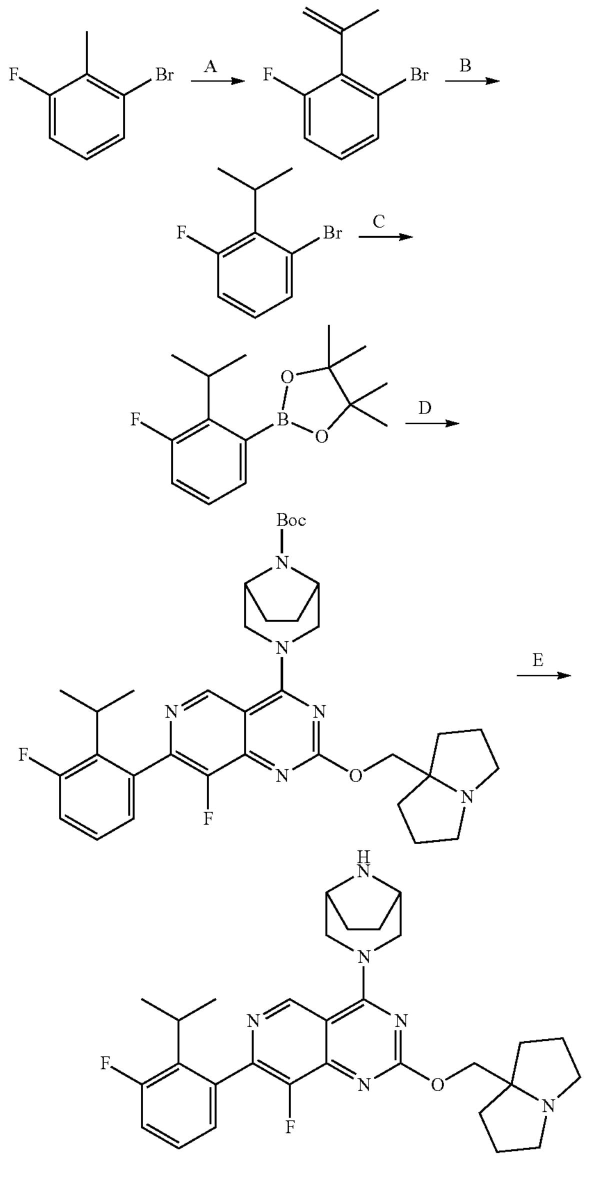

4-((1R,5S)-3,8-diazabicyclo[3.2.1]octan-3-yl)-8-fluoro-7-(3-fluoro-2-isopropylphenyl)-2-((tetrahydro-1H-pyrrolizin-7a(5H)-yl)methoxy)pyrido[4,3-d]pyrimidine. To a mixture of tert-butyl(1R,5S)-3-(8-fluoro-7-(3-fluoro-2-isopropylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 157 μmol, 1.0 eq) in MeCN (1 mL) was added HCl·dioxane (4 M, 2 mL, 51 eq) at 0° C. The mixture was stirred at 0° C. for 0.5 hour. After completion, the mixture was concentrated under vacuum. The residue was purified by prep-HPLC (column: Shim-pack C18 150*25*10 um; mobile phase: [water (0.225% FA)-ACN]; B %: 12%-32%, 9 min) to give the title compound (53.0 mg, 55% yield, FA). Yellow solid. $^1$H NMR (400 MHz, METHANOL-d4) δ=9.14 (s, 1H), 7.36 (td, J=5.2, 8.0 Hz, 1H), 7.24-7.18 (m, 1H), 7.13 (d, J=7.6 Hz, 1H), 4.82 (br d, J=13.2 Hz, 2H), 4.68 (s, 2H), 4.12 (br s, 2H), 3.95 (br d, J=13.6 Hz, 2H), 3.72 (m, 2H), 3.34-3.26 (m, 2H), 2.79 (m, 1H), 2.39-2.30 (m, 2H), 2.28-2.17 (m, 4H), 2.16-2.05 (m, 4H), 2.04-1.97 (m, 2H), 1.31 (s, 3H), 1.29 (s, 3H). LCMS [ESI, M/2+1, M+1]: 268.4, 535.3.

Example 300

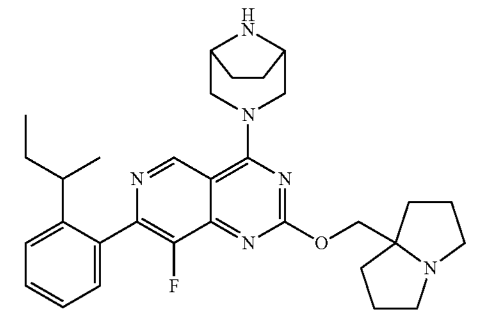 [SMILES: CCC(C)c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(2-(sec-butyl)phenyl)-8-fluoro-2-((hexahydro-1H-pyrrolizin-7a-yl)methoxy)pyrido[4,3-d]pyrimidine

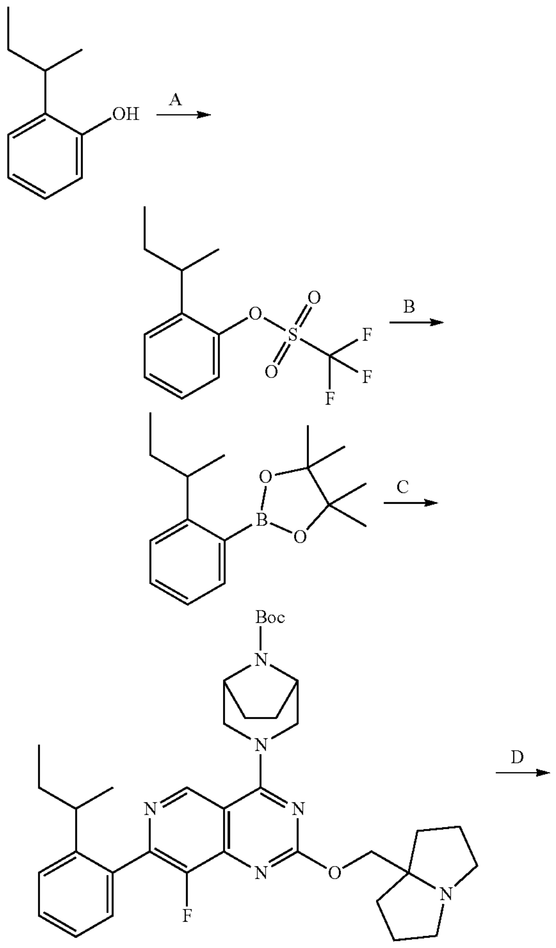

-continued

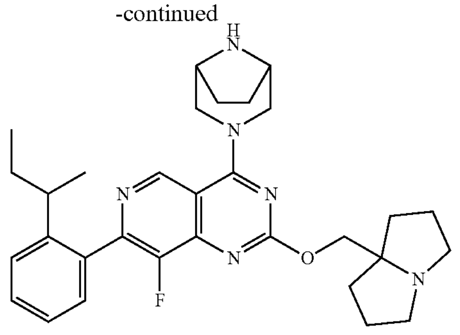

4-((1R,5S)-3,8-diazabicyclo[3.2.1]octan-3-yl)-7-(2-(sec-butyl)phenyl)-8-fluoro-2-((hexahydro-1H-pyrrolizin-7a-yl)methoxy)pyrido[4,3-d]pyrimidine. To a mixture of (1R,5S)-tert-butyl 3-(7-(2-(sec-butyl)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (105 mg, 166 μmol, 1.0 eq) in MeCN (1 mL) was added HCl·dioxane (4 M, 2 mL, 48 eq) at 0° C. The mixture was stirred at 0° C. for 0.5 hour. After completion, the mixture was concentrated under vacuum. The residue was purified by prep-HPLC (column: Shim-pack C18 150*25*10 um; mobile phase: [water (0.225% FA)-ACN]; B %: 15%-35%, 8 min) to give to give the title compound (51.4 mg, 58% yield). Yellow solid. $^1$H NMR (400 MHz, METHANOL-d4) δ=9.14 (s, 1H), 7.53-7.45 (m, 2H), 7.36-7.28 (m, 2H), 4.84-4.79 (m, 2H), 4.68 (s, 2H), 4.13 (br s, 2H), 3.94 (br d, J=14.4 Hz, 2H), 3.76-3.67 (m, 2H), 3.34-3.32 (m, 1H), 3.30-3.26 (m, 1H), 2.61-2.51 (m, 1H), 2.39-2.31 (m, 2H), 2.28-2.16 (m, 4H), 2.14-1.99 (m, 6H), 1.68-1.47 (m, 2H), 1.21 (d, J=6.8 Hz, 3H), 0.68 (t, J=7.2 Hz, 3H). LCMS [ESI, M/2+1, M+1]: 266.4, 531.4.

Example 301

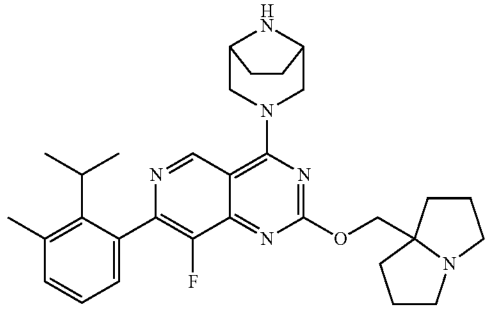 [SMILES: Cc1cccc(-c2ncc3c(N4CC5CCC(C4)N5)nc(OCC45CCCN4CCC5)nc3c2F)c1C(C)C]

4-((1R,5S)-3,8-diazabicyclo[3.2.1]octan-3-yl)-8-fluoro-2-((hexahydro-1H-pyrrolizin-7a-yl)methoxy)-7-(2-isopropyl-3-methylphenyl)pyrido[4,3-d]pyrimidine

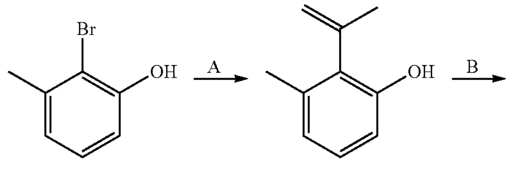

-continued

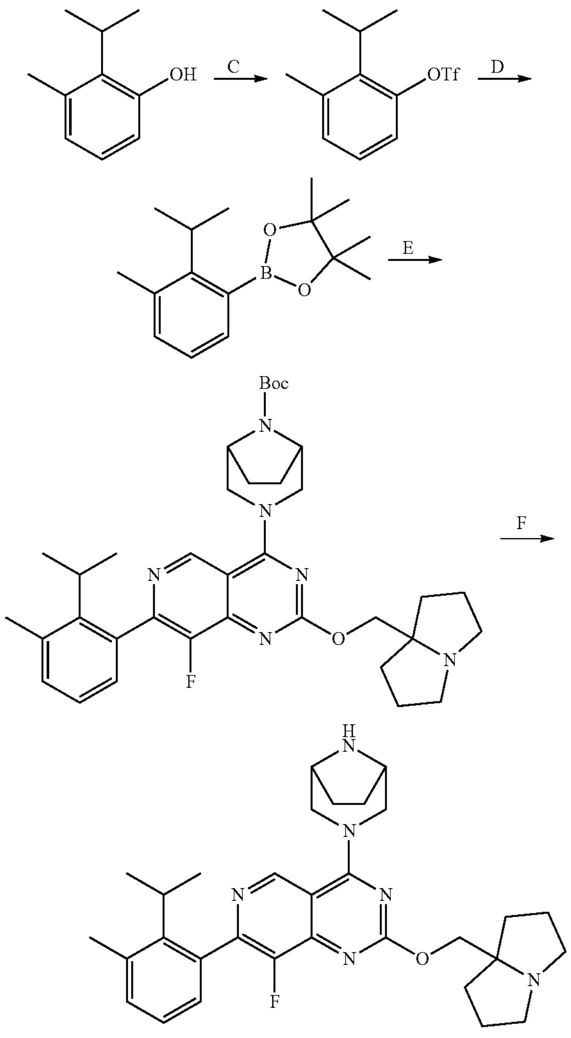

4-((1R,5S)-3,8-diazabicyclo[3.2.1]octan-3-yl)-8-fluoro-2-((hexahydro-1H-pyrrolizin-7a-yl)methoxy)-7-(2-isopropyl-3-methylphenyl)pyrido[4,3-d]pyrimidine. To a solution of (1R,5S)-tert-butyl 3-(8-fluoro-2-((hexahydro-1H-pyrrolizin-7a-yl)methoxy)-7-(2-isopropyl-3-methylphenyl)pyrido[4,3-d]pyrimidin-4-yl)-3,8-diazabicyclo[3.2.1]octane-8-carboxylate (60 mg, 95.1 μmol, 1.0 eq) in MeCN (0.5 mL) was added HCl·dioxane (4 M, 1.0 mL). The mixture was stirred at 0° C. for 30 minutes. The mixture was concentrated, and then the reaction mixture was diluted with water (0.5 mL). The mixture was basified to pH~8 with saturated $NaHCO_3$ aqueous solution. The residue was purified by prep-HPLC (column: Waters X bridge C18 150*50 mm*10 um; mobile phase: [water (10 mM $NH_4HCO_3$)-ACN]; B %: 30%-60%, 10 min). The desired fraction was collected and concentrated under vacuum to remove acetonitrile. The mixture was lyophilized to give the title compound (25.66 mg 51% yield). White solid. $^1$H NMR (400 MHz, chloroform-d) δ=8.99 (s, 1H), 7.24-7.20 (m, 1H), 7.20-7.14 (m, 1H), 7.08-7.03 (m, 1H), 4.58 (br d, J=11.6 Hz, 2H), 4.16 (s, 2H), 3.69-3.56 (m, 4H), 3.15-3.04 (m, 3H), 2.68-2.58 (m, 2H), 2.51 (s, 3H), 2.15-2.04 (m, 2H), 1.93-1.79 (m, 7H), 1.76-1.56 (m, 3H), 1.23 (br d, J=6.0 Hz, 6H); LCMS [ESI, M+1]: 531.4.

Example 302

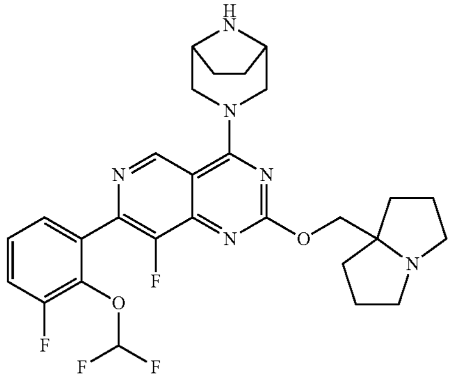 [SMILES: Fc1cccc(-c2ncc3c(N4CC5CCC(C4)N5)nc(OCC45CCCN4CCC5)nc3c2F)c1OC(F)F]

4-((1R,5S)-3,8-diazabicyclo[3.2.1]octan-3-yl)-7-(2-(difluoromethoxy)-3-fluorophenyl)-8-fluoro-2-((hexahydro-1H-pyrrolizin-7a-yl)methoxy)pyrido[4,3-d]pyrimidine

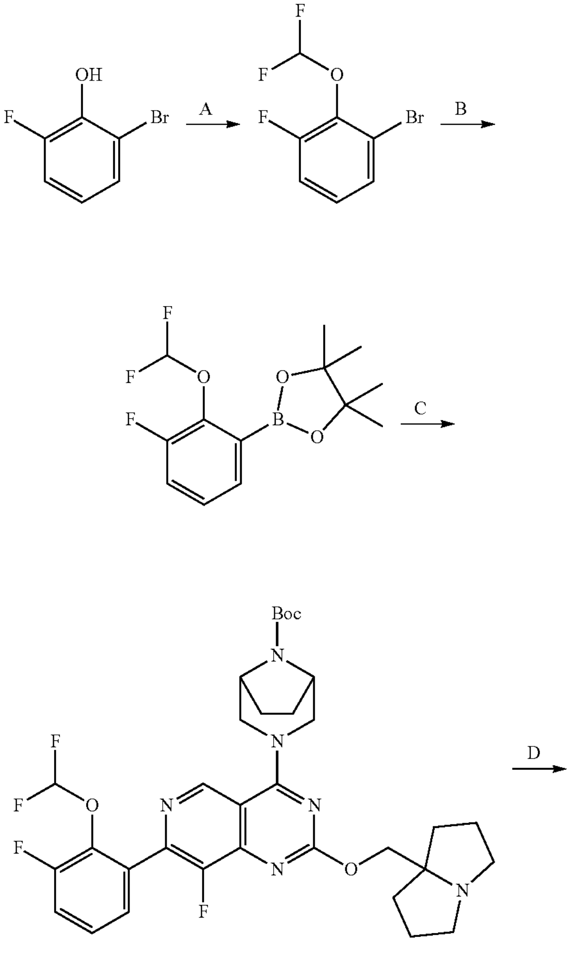

-continued

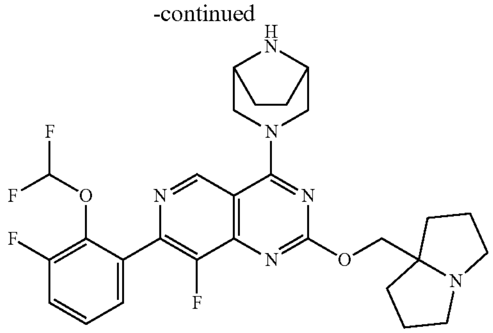

4-((1R,5S)-3,8-diazabicyclo[3.2.1]octan-3-yl)-7-(2-(difluoromethoxy)-3-fluorophenyl)-8-fluoro-2-((hexahydro-1H-pyrrolizin-7a-yl)methoxy)pyrido[4,3-d]pyrimidine. A mixture of (1R,5S)-tert-butyl 3-(7-(2-(difluoromethoxy)-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 152 μmol, 1 eq) and HCl/dioxane (4 M, 1 mL, 26.4 eq) and acetonitrile (0.5 mL) was stirred at 15° C. for 0.5 hour. After completion, the mixture was concentrated under vacuum. The residue was purified by prep-HPLC (column: Shim-pack C18 150*25*10 um; mobile phase: [water (0.225% FA)-ACN]; B %: 9%-29%, 8 min) to give the title compound (57.39 mg, 60% yield, 1.4 FA). Off-white solid. $^1H$ NMR (400 MHz, METHANOL-d4) δ=9.17 (s, 1H), 8.45 (br s, 1H), 7.54-7.39 (m, 3H), 6.95-6.55 (m, 1H), 4.82 (br d, J=13.2 Hz, 2H), 4.69 (s, 2H), 4.16 (br s, 2H), 3.97 (br d, J=13.6 Hz, 2H), 3.72 (td, J=6.8, 11.6 Hz, 2H), 3.33-3.26 (m, 2H), 2.40-2.30 (m, 2H), 2.30-1.99 (m, 10H). FNMR: −83.170, −130.150, −139.040. LCMS [ESI, M+1]: 559.3.

Example 303

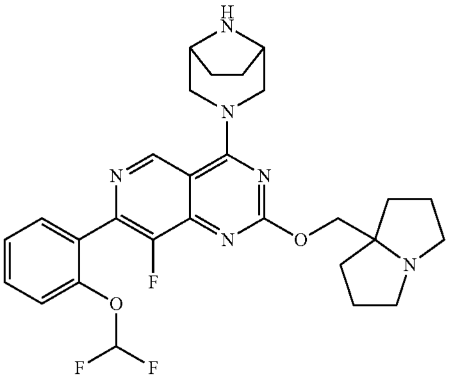 [SMILES: Fc1c(-c2ccccc2OC(F)F)ncc2c(N3CC4CCC(C3)N4)nc(OCC34CCCN3CCC4)nc12]

4-((1R,5S)-3,8-diazabicyclo[3.2.1]octan-3-yl)-7-(2-(difluoromethoxy)phenyl)-8-fluoro-2-((hexahydro-1H-pyrrolizin-7a-yl)methoxy)pyrido[4,3-d]pyrimidine

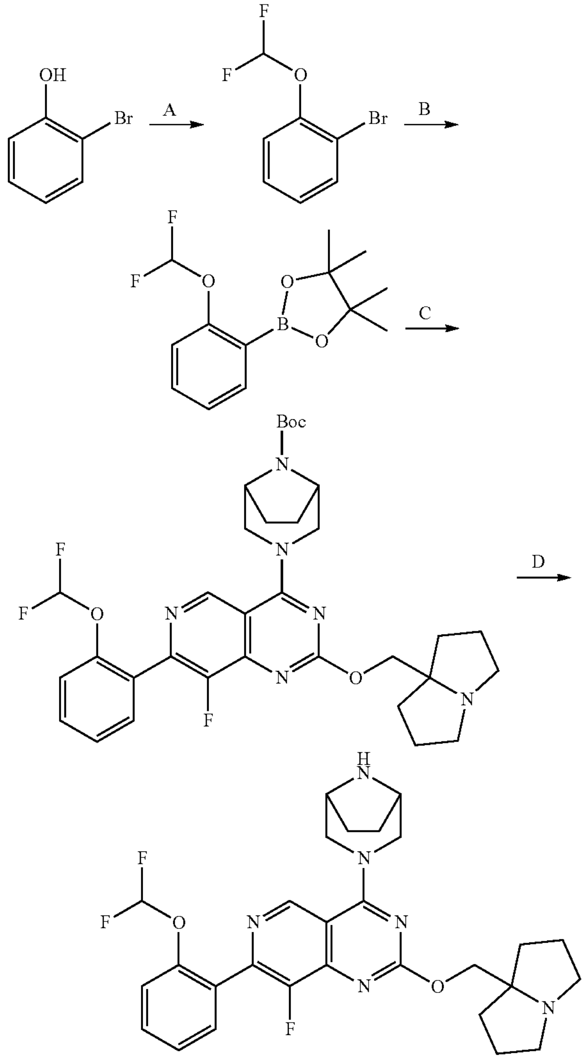

4-((1R,5S)-3,8-diazabicyclo[3.2.1]octan-3-yl)-7-(2-(difluoromethoxy)phenyl)-8-fluoro-2-((hexahydro-1H-pyrrolizin-7a-yl)methoxy)pyrido[4,3-d]pyrimidine. To a solution of (1R,5S)-tert-butyl 3-(7-(2-(difluoromethoxy)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (90 mg, 139 μmol, 1 eq) in MeCN (2 mL) was added HCl·dioxane (4 M, 0.5 mL) below 15° C. The mixture was stirred at 15° C. for 0.5 hour. The reaction mixture was concentrated under reduced pressure to give a residue at room temperature (without heating). The residue was dissolved in DCM (20 mL) and $H_2O$ (5 mL). The pH of the mixture was adjusted to 8 with $NaHCO_3$ solid below 10° C. The mixture was extracted with DCM (10 mL×4). The combined organic layers were dried over anhydrous $Na_2SO_4$, filtered and concentrated under reduced pressure to give a residue. The residue was purified by prep-HPLC (column: 3_Phenomenex Luna C18 75*30 mm*3 um; mobile phase: [water (0.225% FA)-ACN]; B %: 5%-25%, 8 min). The desired fractions were collected and lyophilized to give the title compound (30.5 mg, 34% yield, 1.8FA). Off-white solid; $^1$H NMR (400 MHz, methanol-$d_4$) δ=9.16 (s, 1H), 8.47 (s, 1.8H), 7.63-7.58 (m, 2H), 7.44-7.34 (m, 2H), 6.86 (t, 1H), 4.79 (d, J=13.2 Hz, 2H), 4.67 (s, 2H), 4.07 (s, 2H), 3.91 (d, J=13.2 Hz, 2H), 3.74-3.68 (m, 2H), 3.30-3.26 (m, 2H), 2.38-2.32 (m, 2H), 2.26-2.16 (m, 4H), 2.14-1.94 (m, 6H); $^{19}$F NMR (376 MHz, methanol-$d_4$) δ=−82.7, −139; LCMS [ESI, M+1]: 541.2.

Example 304

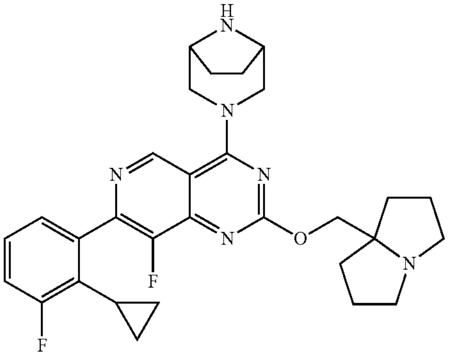 [SMILES: Fc1cccc(-c2ncc3c(N4CC5CCC(C4)N5)nc(OCC45CCCN4CCC5)nc3c2F)c1C1CC1]

4-((1R,5S)-3,8-diazabicyclo[3.2.1]octan-3-yl)-7-(2-cyclopropyl-3-fluorophenyl)-8-fluoro-2-((hexahydro-1H-pyrrolizin-7a-yl)methoxy)pyrido[4,3-d]pyrimidine

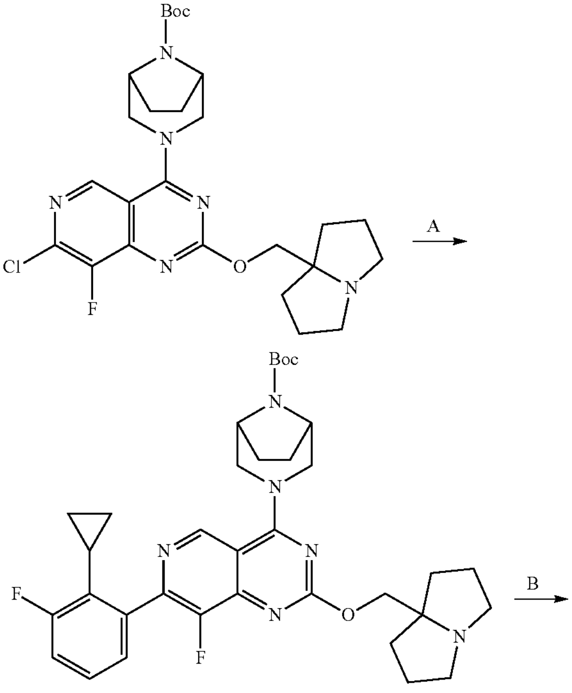

-continued

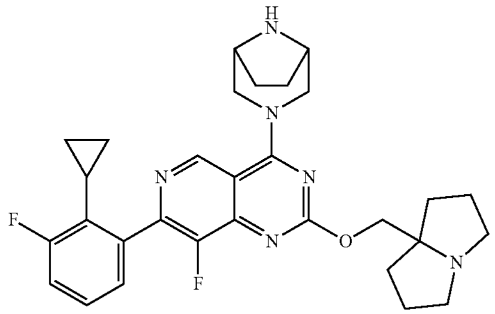

4-(3,8-diazabicyclo[3.2.1]octan-3-yl)-7-(2-cyclopropyl-3-fluorophenyl)-8-fluoro-2-((hexahydro-1H-pyrrolizin-7a-yl)methoxy)pyrido[4,3-d]pyrimidine. To a solution of tert-butyl 3-(7-(2-cyclopropyl-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (35 mg, 55.3 μmol, 1.0 eq) in ACN (0.1 mL) was added HCl·dioxane (4 M, 1.75 mL). The mixture was stirred at 20° C. for 0.5 hour. The mixture was concentrated under vacuum. The residue was purified by prep-HPLC (column: Phenomenex luna C18 150*25 mm*10 um; mobile phase: [water (0.225% FA)-ACN]; B %: 3%-33%, 10 min). The desired fraction was collected and lyophilized to give the title compound (13.7 mg, 39% yield, 1.9 FA) as off-white solid. $^1$H NMR (400 MHz, methanol-d4) δ=9.15 (s, 1H), 7.42-7.32 (m, 1H), 7.27-7.16 (m, 2H), 4.79 (br d, J=13.2 Hz, 2H), 4.67 (s, 2H), 4.06 (br s, 2H), 3.90 (br d, J=13.2 Hz, 2H), 3.75-3.65 (m, 2H), 3.30-3.23 (m, 2H), 2.39-2.30 (m, 2H), 2.27-1.94 (m, 10H), 1.89-1.80 (m, 1H), 0.73-0.60 (m, 2H), 0.43-0.31 (m, 2H); LCMS [ESI, M+1]: 533.3.

Example 305

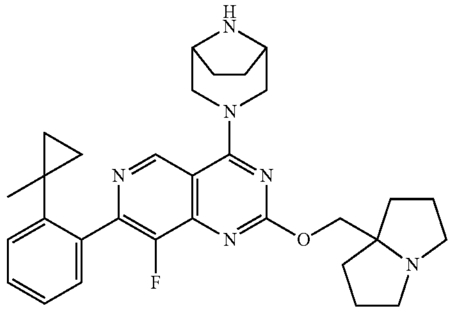 [SMILES: CC1(c2ccccc2-c2ncc3c(N4CC5CCC(C4)N5)nc(OCC45CCCN4CCC5)nc3c2F)CC1]

4-((1R,5S)-3,8-diazabicyclo[3.2.1]octan-3-yl)-8-fluoro-2-((hexahydro-1H-pyrrolizin-7a-yl)methoxy)-7-(2-(1-methylcyclopropyl)phenyl)pyrido[4,3-d]pyrimidine

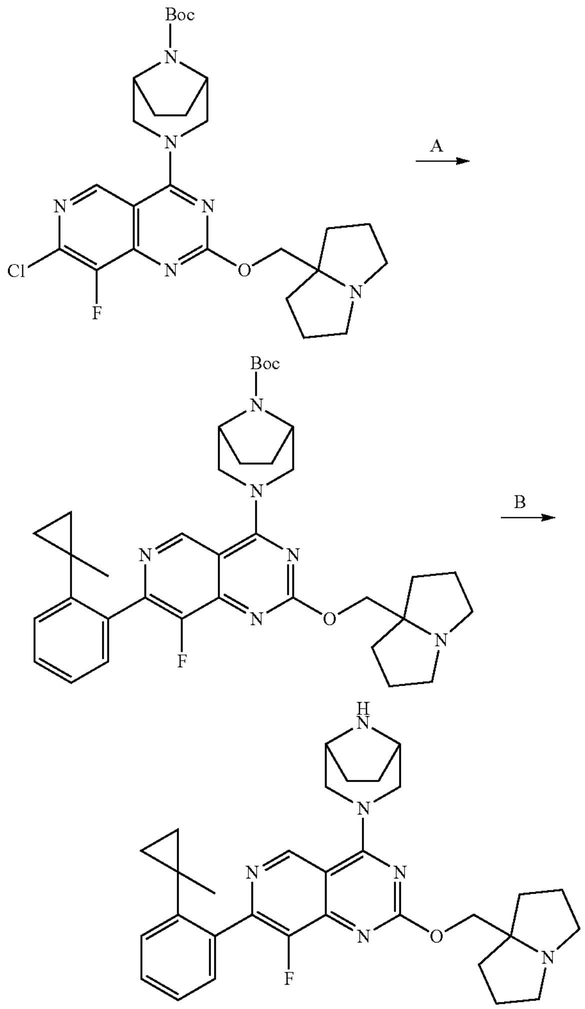

4-(3,8-diazabicyclo[3.2.1]octan-3-yl)-8-fluoro-2-((hexahydro-1H-pyrrolizin-7a-yl)methoxy)-7-(2-(1-methylcyclopropyl)phenyl)pyrido[4,3-d]pyrimidine. To a mixture of tert-butyl 3-(8-fluoro-2-((hexahydro-1H-pyrrolizin-7a-yl)methoxy)-7-(2-(1-methylcyclopropyl)phenyl)pyrido[4,3-d]pyrimidin-4-yl)-3,8-diazabicyclo[3.2.1]octane-8-carboxylate (100 mg, 159 μmol, 1.0 eq) and acetonitrile (1 mL) was added HCl·dioxane (4 M, 2 mL, 50 eq) at 0° C. The mixture was stirred at 0° C. for 0.5 hour. After completion, the mixture was concentrated under vacuum. The residue was purified by prep-HPLC (column: Shim-pack C18 150*25*10 um; mobile phase: [water (0.225% FA)-ACN]; B %: 10%-30%, 9 min) to give the title compound (67.1 mg, 73% yield, FA). Off-white. $^1$H NMR (400 MHz, METHANOL-d4) δ=9.15 (s, 1H), 7.59 (dd, J=0.8, 8.0 Hz, 1H), 7.46 (td, J=1.2, 7.6 Hz, 1H), 7.34 (dt, J=1.2, 7.6 Hz, 1H), 7.25 (dd, J=1.2, 7.6 Hz, 1H), 4.80 (br d, J=13.6 Hz, 2H), 4.68 (s, 2H), 4.11 (br s, 2H), 3.92 (br d, J=13.2 Hz, 2H), 3.75-3.67 (m, 2H), 3.34-3.26 (m, 2H), 2.39-2.32 (m, 2H), 2.21 (m, 4H), 2.15-2.06 (m, 4H), 2.04-1.98 (m, 2H), 1.32 (s, 3H), 0.61-0.56 (m, 2H), 0.40-0.34 (m, 2H). LCMS [ESI, M/2+1, M+1]: 265.4, 529.3.

Example 306

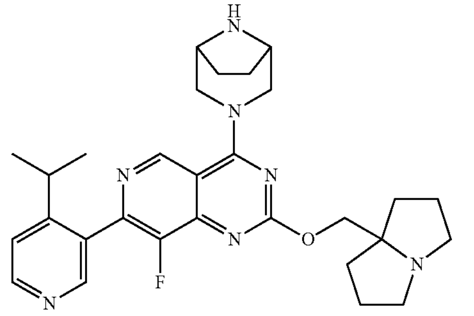 [SMILES: CC(C)c1ccncc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(4-isopropylpyridin-3-yl)pyrido[4,3-d]pyrimidine

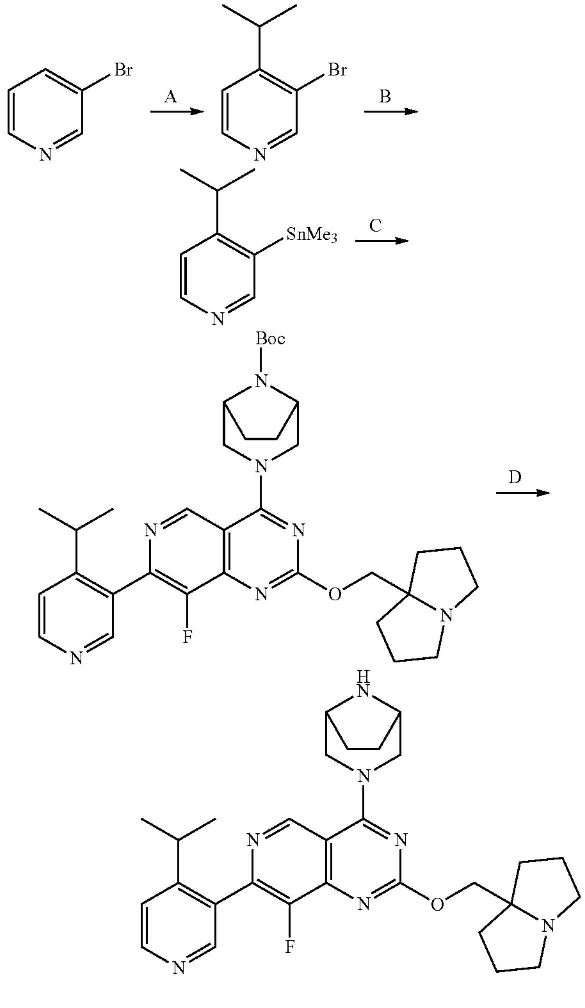

4-(3,8-diazabicyclo[3.2.1]octan-3-yl)-8-fluoro-2-((hexahydro-1H-pyrrolizin-7a-yl)methoxy)-7-(4-isopropylpyridin-3-yl)pyrido[4,3-d]pyrimidine. To a mixture of tert-butyl3-(8-fluoro-2-((hexahydro-1H-pyrrolizin-7a-yl)methoxy)-7-(4-isopropylpyridin-3-yl)pyrido[4,3-d]pyrimidin-4-yl)-3,8-diazabicyclo[3.2.1]octane-8-carboxylate (90 mg, 146 μmol, 1.0 eq) and ACN (2 mL) was added HCl·dioxane (4 M, 2 mL, 54.9 eq) at 0° C. Then it was degassed and purged with $N_2$ for 3 times. The reaction was stirred at 15° C. for 20 minutes. Upon completion, the mixture was concentrated. The residue was adjusted to pH=8 with saturated $NaHCO_3$ aqueous solution. The mixture was diluted by MeOH and purified by prep-HPLC (column: Waters Xbridge C18 150*50 mm*10 um; mobile phase: [water (10 mM $NH_4HCO_3$)-ACN]; B %: 16%-46%, 10 min). The desired fraction was collected and concentrated under vacuum to remove ACN. The desired fraction was collected and lyophilized to affording the title compound (25.3 mg, 33% yield), Off-white solid; $^1$H NMR (400 MHz, CHLOROFORM-d) δ=9.03 (s, 1H), 8.62 (d, J=5.6 Hz, 1H), 8.55 (s, 1H), 7.36 (d, J=5.6 Hz, 1H), 4.64-4.55 (m, 2H), 4.17 (s, 2H), 3.72-3.59 (m, 4H), 3.15-3.06 (m, 2H), 3.05-2.96 (m, 1H), 2.69-2.59 (m, 2H), 2.16-2.05 (m, 2H), 1.95-1.79 (m, 8H), 1.71-1.62 (m, 2H), 1.20 (d, J=6.8 Hz, 6H). LCMS [ESI, M+1]: 518.3.

Example 307

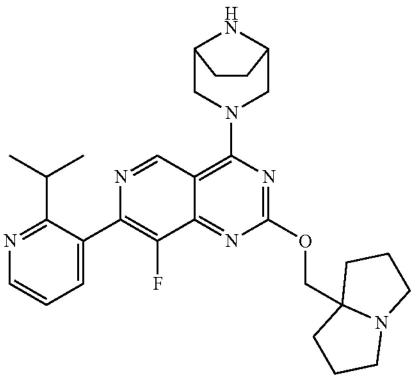 [SMILES: CC(C)c1ncccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-isopropylpyridin-3-yl)pyrido[4,3-d]pyrimidine

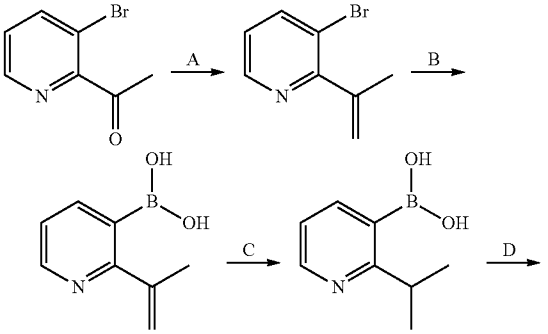

-continued

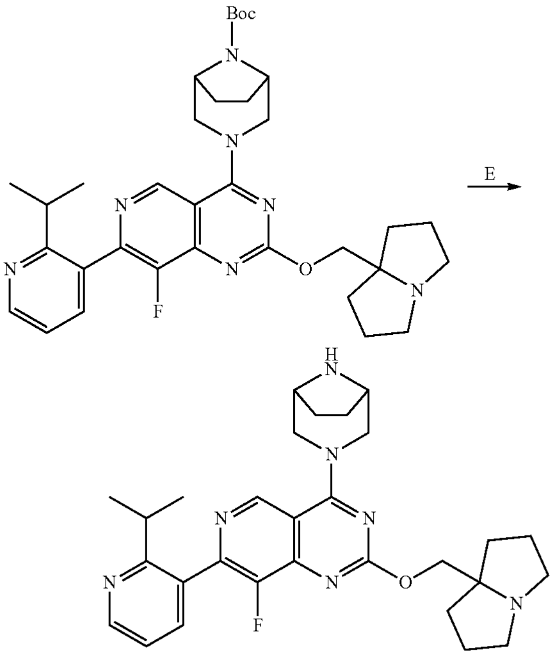

4-((1R,5S)-3,8-diazabicyclo[3.2.1]octan-3-yl)-8-fluoro-2-((hexahydro-1H-pyrrolizin-7a-yl)methoxy)-7-(2-isopropylpyridin-3-yl)pyrido[4,3-d]pyrimidine. To a solution tert-butyl(1R,5S)-3-(8-fluoro-7-(2-isopropylpyridin-3-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (23 mg, 37.2 μmol, 1.0 eq) in ACN (1 mL) was added HCl·dioxane (4 M, 1 mL) dropwise below 10° C. The mixture was stirred at 10° C. for 1 hour. The reaction mixture was concentrated under reduced pressure to give a residue at 10° C. (without heating). The residue was dissolved in MeOH (0.5 mL) and MeCN (1 mL). The pH of the mixture was adjusted to 7~8 with 25% $NH_3 \cdot H_2O$ (0.1 mL) dissolved in MeCN (3 mL)]. The residue was purified by prep-HPLC (column: Shim-pack C18 150*25*10 um; mobile phase: [water (0.225% FA)-ACN]; B %: 0%-20%, 10 min) to give the title compound (7.36 mg, 31% yield, 1.8 FA). Yellow solid; $^1H$ NMR (400 MHz, methanol-$d_4$) δ=9.19 (s, 1H), 8.68 (dd, J=1.6, 4.8 Hz, 1H), 7.82 (dd, J=1.6, 8.0 Hz, 1H), 7.43 (dd, J=4.8, 8.0 Hz, 1H), 4.79 (d, J=13.2 Hz, 2H), 4.69 (s, 2H), 4.02 (s, 2H), 3.90 (d, J=12.8 Hz, 2H), 3.75-3.69 (m, 2H), 3.32-3.28 (m, 2H), 3.10-3.00 (m, 1H), 2.40-2.33 (m, 2H), 2.28-2.20 (m, 4H), 2.16-2.09 (m, 2H), 2.06-1.95 (m, 4H), 1.25 (d, J=6.8 Hz, 6H); LCMS [ESI, M+1]: 518.3.

Example 308

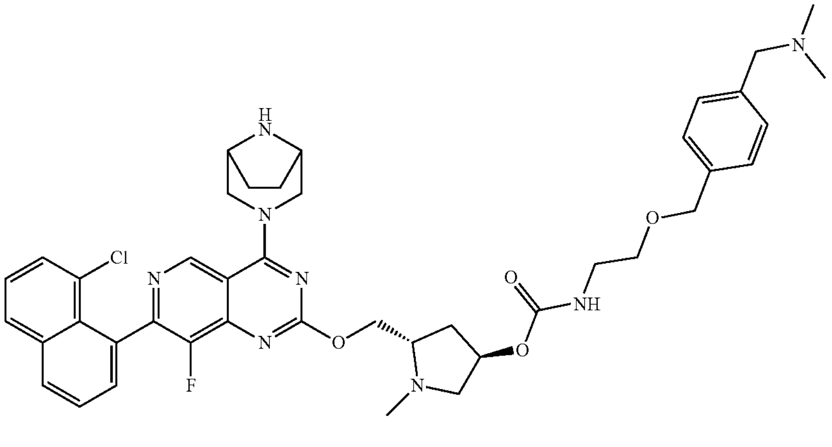 [SMILES: CN(C)Cc1ccc(COCCNC(=O)O[C@@H]2C[C@@H](COc3nc(N4CC5CCC(C4)N5)c4cnc(-c5cccc6cccc(Cl)c56)c(F)c4n3)N(C)C2)cc1]

(3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl(2-((4-((dimethylamino)methyl)benzyl)oxy)ethyl)carbamate

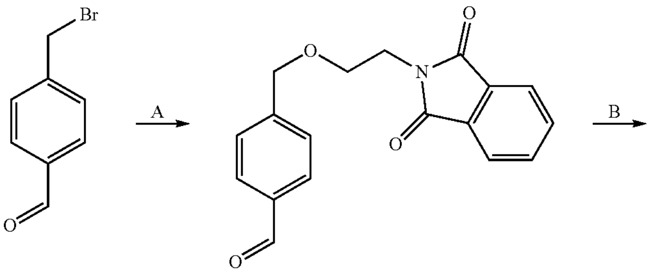

-continued
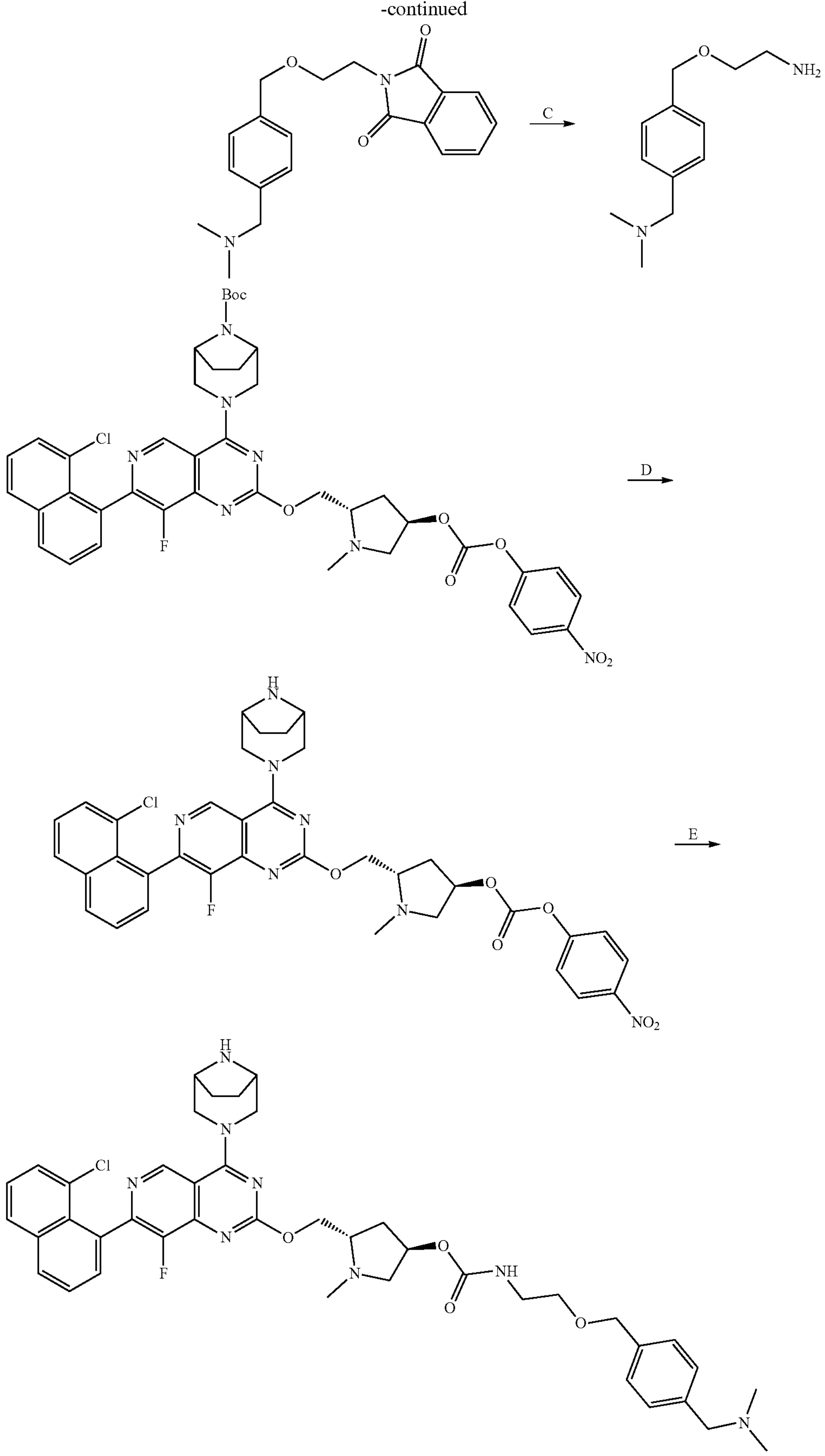

(3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl(2-((4-((dimethylamino)methyl)benzyl)oxy)ethyl)carbamate. To a solution of (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl(4-nitrophenyl) carbonate (57 mg, 79.8 μmol, 1.0 eq) and 2-((4-((dimethylamino)methyl)benzyl)oxy)ethanamine (49.9 mg, 239 μmol, 3.0 eq) in DMF (1 mL) was added DIEA (51.6 mg, 399 μmol, 69.5 μL, 5.0 eq). The mixture was stirred at 20° C. for 12 hours. After completion, The mixture was filtrated and the filtrate was purified by prep-HPLC (column: Phenomenex Gemini-NX C18 75*30 mm*3 um; mobile phase: [water (0.1% TFA)-ACN]; B %: 20%-30%, 7 min). The desired fraction was collected and lyophilized to give the title compound (10.5 mg, 10% yield, 3TFA). Yellow solid; $^{1}$H NMR (400 MHz, methanol-d4) δ=9.14 (s, 1H), 8.16 (dd, J=1.2, 8.4 Hz, 1H), 8.03 (dd, J=1.2, 8.4 Hz, 1H), 7.74-7.66 (m, 1H), 7.64-7.57 (m, 2H), 7.56-7.44 (m, 5H), 5.35 (br s, 1H), 5.03-4.89 (m, 3H), 4.80-4.72 (m, 1H), 4.59 (s, 2H), 4.33-4.24 (m, 4H), 4.23-4.02 (m, 2H), 4.02-3.93 (m, 2H), 3.58 (t, J=5.2 Hz, 2H), 3.51-3.34 (m, 3H), 3.18 (br s, 3H), 2.84 (s, 6H), 2.56-2.35 (m, 2H), 2.24-2.06 (m, 4H); LCMS [ESI, M+1]: 783.0.

Example 309

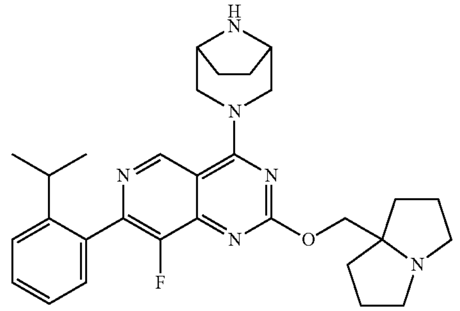 [SMILES: CC(C)c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(2-isopropylphenyl)-2-((tetrahydro-1H-pyrrolizin-7a(5H)-yl)methoxy)pyrido[4,3-d]pyrimidine

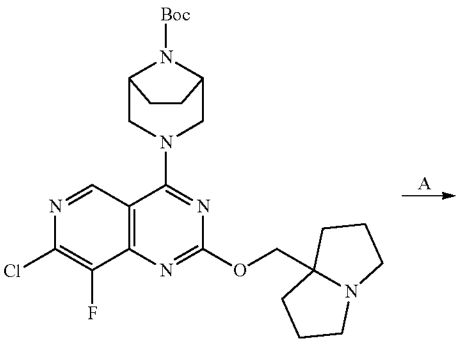

-continued

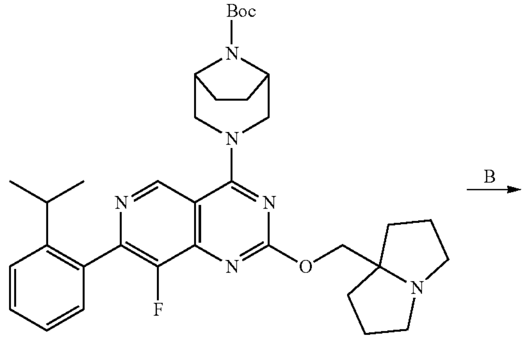

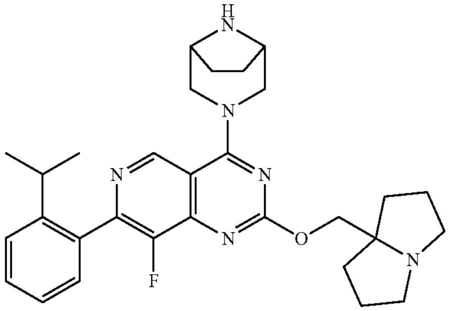

4-((1R,5S)-3,8-diazabicyclo[3.2.1]octan-3-yl)-8-fluoro-7-(2-isopropylphenyl)-2-((tetrahydro-1H-pyrrolizin-7a(5H)-yl)methoxy)pyrido[4,3-d]pyrimidine. To a solution of tert-butyl(1R,5S)-3-(8-fluoro-7-(2-isopropylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (120 mg, 194 μmol, 1 eq) in MeCN (4 mL) was added HCl·dioxane (4 M, 1 mL) at 0° C. The mixture was stirred at 0-15° C. for 0.5 hour. After completion, the reaction mixture was concentrated under reduced pressure at room temperature (without heating) to give a residue. The residue was dissolved in EtOAc (5 mL) and $H_2O$ (2 mL). The pH of the mixture was adjusted to 7~8 with $NaHCO_3$ solid below 10° C. The mixture was extracted with EtOAc (5 mL×4). The combined organic layers were dried over anhydrous $Na_2SO_4$, filtered and concentrated under reduced pressure to give a residue. The residue was purified by prep-HPLC (column: Shim-pack C18 150*25*10 um; mobile phase: [water (0.225% FA)-ACN]; B %: 11%-31%, 9 min). The desired fractions were collected and lyophilized to give the title compound (74.2 mg, 62% yield, 2FA). Off-white solid; $^{1}$H NMR (400 MHz, methanol-d4) δ=9.14 (s, 1H), 7.54-7.48 (m, 2H), 7.35-7.28 (m, 2H), 4.80 (d, J=13.2 Hz, 2H), 4.67 (s, 2H), 4.06 (br s, 2H), 3.91 (d, J=13.2 Hz, 2H), 3.74-3.68 (m, 2H), 3.30-3.26 (m, 2H), 2.87-2.82 (m, 1H), 2.38-2.31 (m, 2H), 2.26-1.95 (m, 10H), 1.18 (d, J=6.8 Hz, 6H); LCMS [ESI, M+1]: 517.3.

Example 310

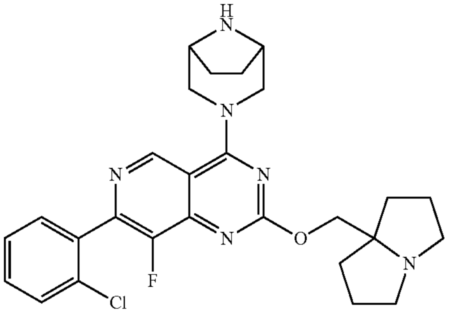 [SMILES: Fc1c(-c2ccccc2Cl)ncc2c(N3CC4CCC(C3)N4)nc(OCC34CCCN3CCC4)nc12]

4-((1R,5S)-3,8-diazabicyclo[3.2.1]octan-3-yl)-7-(2-chlorophenyl)-8-fluoro-2-((hexahydro-1H-pyrrolizin-7a-yl)methoxy)pyrido[4,3-d]pyrimidine

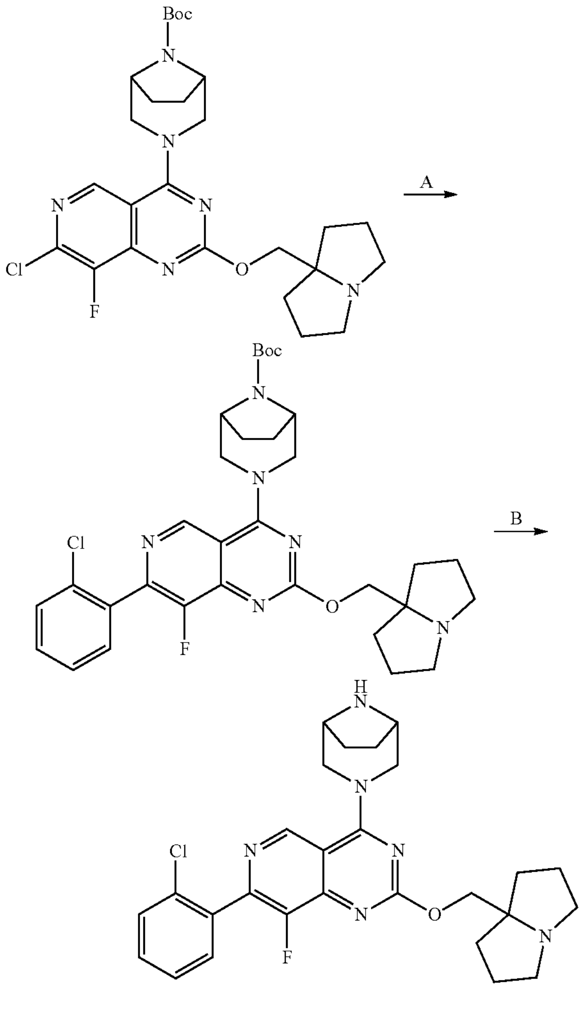

4-((1R,5S)-3,8-diazabicyclo[3.2.1]octan-3-yl)-7-(2-chlorophenyl)-8-fluoro-2-((hexahydro-1H-pyrrolizin-7a-yl)methoxy)pyrido[4,3-d]pyrimidine. To a mixture of (1R,5S)-tert-butyl 3-(7-(2-chlorophenyl)-8-fluoro-2-((hexahydro-1H-pyrrolizin-7a-yl)methoxy)pyrido[4,3-d]pyrimidin-4-yl)-

3,8-diazabicyclo[3.2.1]octane-8-carboxylate (180 mg, 295 μmol, 1 eq) and ACN (0.5 mL) was added HCl·dioxane (0.5 mL), and the reaction mixture was stirred at 25° C. for 10 minutes. Upon completion, the mixture was concentrated in vacuum to give a residue. The residue was purified by prep-HPLC (column: Phenomenex Luna C18 150*25 mm*10 um; mobile phase: [water (0.225% FA)-ACN]; B %: 1%-30%, 10 min) affording the title compound (70.1 mg, 43% yield, 1.9FA). Off-white solid; $^1$H NMR (400 MHz, methanol-d4) δ=9.15 (s, 1H), 7.62-7.47 (m, 4H), 4.80 (br d, J=13.2 Hz, 2H), 4.67 (s, 2H), 4.11-4.06 (m, 2H), 3.92 (br d, J=13.2 Hz, 2H), 3.76-3.65 (m, 2H), 3.30-3.26 (m, 2H), 2.40-2.30 (m, 2H), 2.25-1.96 (m, 10H); LCMS [ESI, M+1]: 509.

Example 311

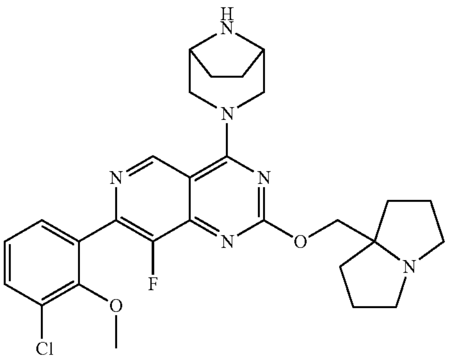

4-((1R,5S)-3,8-diazabicyclo[3.2.1]octan-3-yl)-7-(3-chloro-2-methoxyphenyl)-8-fluoro-2-((hexahydro-1H-pyrrolizin-7a-yl)methoxy)pyrido[4,3-d]pyrimidine

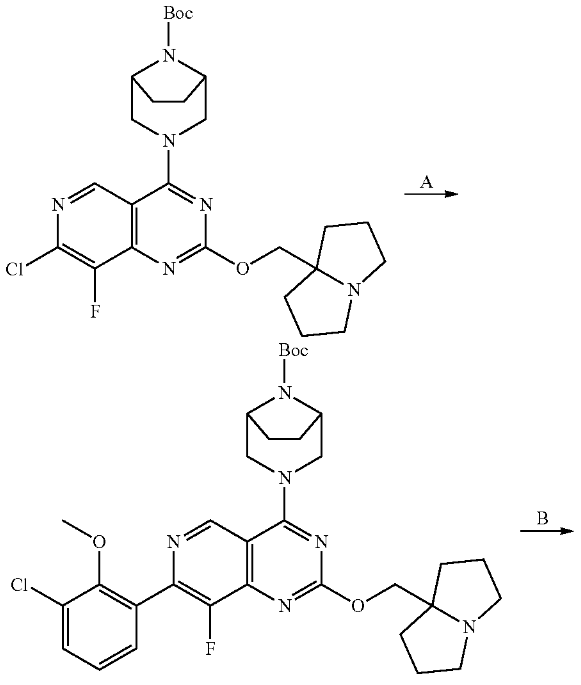

-continued

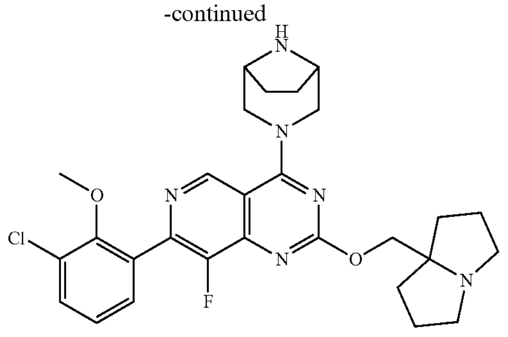

4-(3,8-Diazabicyclo[3.2.1]octan-3-yl)-7-(3-chloro-2-methoxyphenyl)-8-fluoro-2-((hexahydro-1H-pyrrolizin-7a-yl)methoxy)pyrido[4,3-d]pyrimidine. To a solution of Tert-butyl-3-(7-(3-chloro-2-methoxyphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (50 mg, 78.2 μmol, 1.0 eq) in MeCN (1 mL) was added HCl·dioxane (4 M, 1 mL) at 20° C. The mixture was stirred at 20° C. for 1 hour. After completion, the reaction mixture was concentrated under reduced pressure at room temperature to give a residue. The residue was dissolved in MeOH (1 mL). The pH of the mixture was adjusted to 7~8 with saturated $Na_2CO_3$ solution. The mixture was purified by prep-HPLC (column: Shim-pack C18 150*25*10 um; mobile phase: [water (0.225% FA)-ACN]; B %: 7%-27%, 9 min). The desired fractions were collected and lyophilized to give the title compound (23.8 mg, 49% yield, 1.7FA). Off-white solid; $^1$H NMR (400 MHz, methanol-d4) δ=9.16 (s, 1H), 7.61 (dd, J=1.6, 8.0 Hz, 1H), 7.42 (dd, J=1.6, 8.0 Hz, 1H), 7.33-7.23 (m, 1H), 4.79 (br d, J=13.2 Hz, 2H), 4.67 (s, 2H), 4.05 (br s, 2H), 3.90 (br d, J=13.6 Hz, 2H), 3.76-3.64 (m, 5H), 3.31-3.26 (m, 2H), 2.38-1.94 (m, 12H); LCMS [ESI, M+1]: 539.2.

Example 312

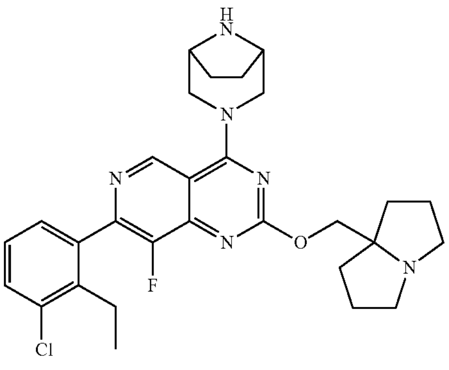 [SMILES: CCc1c(Cl)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(3-chloro-2-ethylphenyl)-8-fluoro-2-((hexahydro-1H-pyrrolizin-7a-yl)methoxy)pyrido[4,3-d]pyrimidine

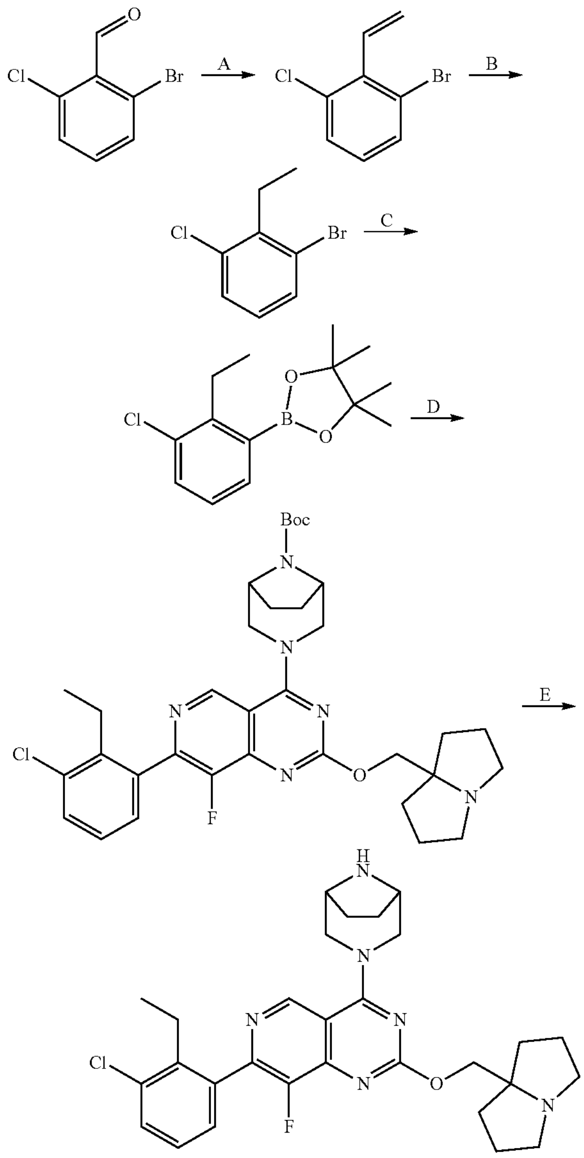

4-((1R,5S)-3,8-diazabicyclo[3.2.1]octan-3-yl)-7-(3-chloro-2-ethylphenyl)-8-fluoro-2-((hexahydro-1H-pyrrolizin-7a-yl)methoxy)pyrido[4,3-d]pyrimidine. To a mixture of tert-butyl(1R,5S)-3-(7-(3-chloro-2-ethylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (60.0 mg, 94.2 μmol, 1.0 eq) and MeCN (0.5 mL) was added HCl·dioxane (4 M, 1 mL, 42 eq) at 10° C. The mixture was stirred at 10° C. for 0.5 hour. After completion, the mixture was concentrated under vacuum. The residue was purified by prep-HPLC (column: Shim-pack C18 150*25*10 um; mobile phase: [water (0.225% FA)-ACN]; B %: 13%-33%, 9 min) to give the title compound (12.5 mg, 22% yield, 1.5 FA). $^1$H NMR (400 MHz, METHANOL-d4) δ=9.15 (s, 1H), 7.55 (dd, J=0.8, 7.6 Hz, 1H), 7.36-7.31 (m, 1H), 7.29-7.24 (m, 1H), 4.81 (br d, J=13.6 Hz, 2H), 4.68 (s, 2H), 4.12 (br s, 2H), 3.94 (br d, J=13.6 Hz, 2H), 3.76-3.67 (m, 2H), 3.34-3.25 (m, 2H), 2.74-2.66 (m, 2H), 2.39-2.31 (m, 2H), 2.28-2.16 (m, 4H), 2.14-1.97 (m, 6H), 1.05 (t, J=7.2 Hz, 3H). LCMS [ESI, M/2+1, M+1]: 269.4, 537.1.

Example 313

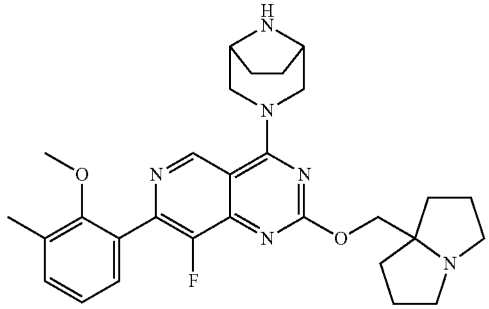 [SMILES: COc1c(C)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-methoxy-3-methylphenyl)pyrido[4,3-d]pyrimidine

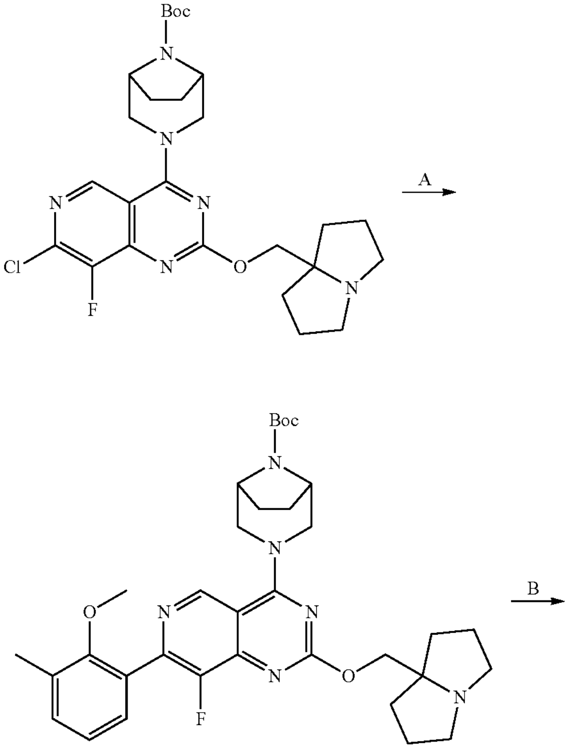

-continued

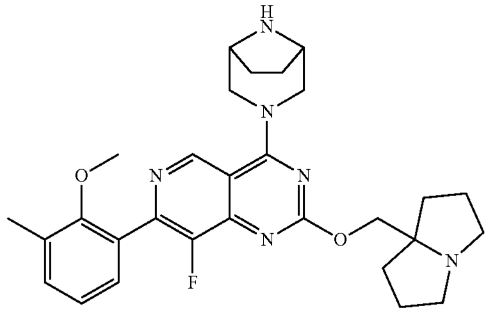

4-((1R,5S)-3,8-diazabicyclo[3.2.1]octan-3-yl)-8-fluoro-2-((hexahydro-1H-pyrrolizin-7a-yl)methoxy)-7-(2-methoxy-3-methylphenyl)pyrido[4,3-d]pyrimidine. To a solution of (1R,5S)-tert-butyl 3-(8-fluoro-2-((hexahydro-1H-pyrrolizin-7a-yl)methoxy)-7-(2-methoxy-3-methylphenyl)pyrido[4,3-d]pyrimidin-4-yl)-3,8-diazabicyclo[3.2.1]octane-8-carboxylate (100 mg, 162 μmol, 1.00 eq) in MeCN (2.0 mL) was added HCl·dioxane (4 M, 1.0 mL). The mixture was stirred at 0° C. for 15 minutes. After completion, the reaction mixture was diluted with $H_2O$ (5 mL) and extracted with ethyl acetate (3×5 mL). The combined organic layers were washed with saturated brine (10 mL), dried over $Na_2SO_4$, filtered and concentrated under reduced pressure to give a residue. The residue was purified by prep-HPLC (column: Shim-pack C18 150*25*10 um; mobile phase: [water (0.225% FA)-ACN]; B %: 7%-27%, 9 min) and lyophilized affording the title compound (53.4 mg, 54% yield, 1.9FA). Off-white solid; $^1$H NMR (400 MHz, $CDCl_3$-d) δ=9.14 (s, 1H), 7.38 (d, J=7.2 Hz, 1H), 7.32-7.25 (m, 1H), 7.19 (t, J=7.6 Hz, 1H), 4.83-4.75 (m, 2H), 4.67 (s, 2H), 4.11-4.05 (m, 2H), 3.91 (d, J=13.2 Hz, 2H), 3.76-3.66 (m, 2H), 3.50 (s, 3H), 3.30-3.25 (m, 2H), 2.41-2.37 (m, 3H), 2.36-2.31 (m, 2H), 2.30-2.15 (m, 4H), 2.14-1.96 (m, 6H); LCMS [ESI, M+1]: 519.2.

Example 314

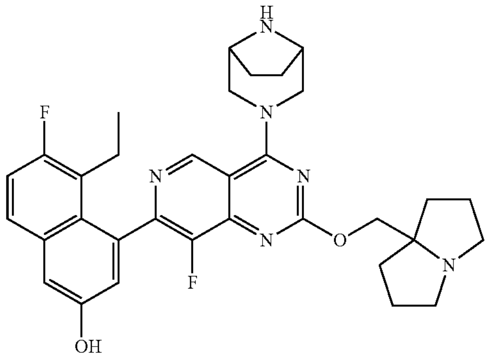 [SMILES: CCc1c(F)ccc2cc(O)cc(-c3ncc4c(N5CC6CCC(C5)N6)nc(OCC56CCCN5CCC6)nc4c3F)c12]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethyl-6-fluoronaphthalen-2-ol

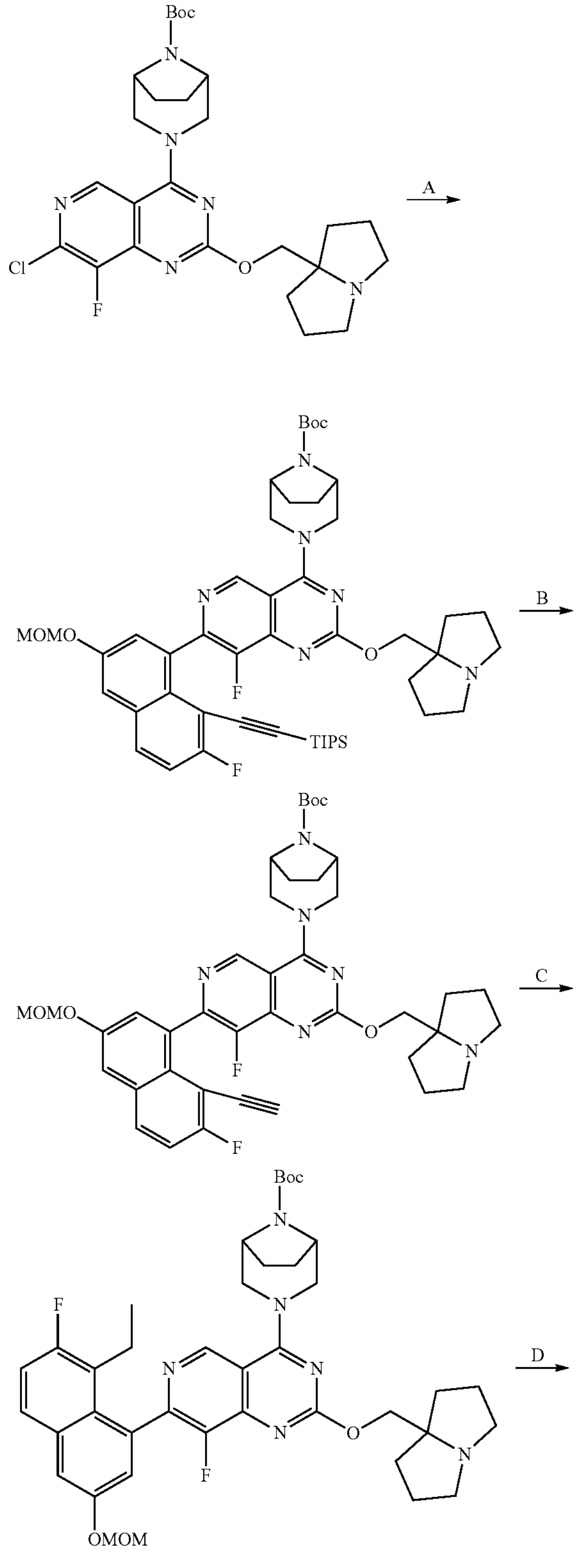

-continued

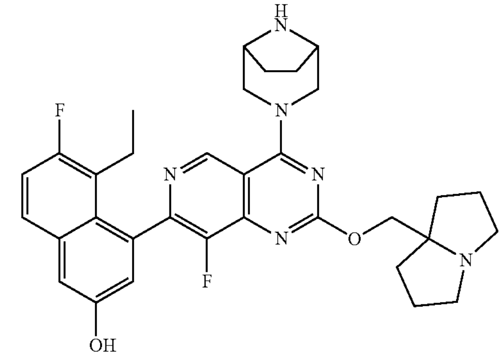

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethyl-6-fluoronaphthalen-2-ol. To a solution of (1R,5S)-tert-butyl 3-(7-(8-ethyl-7-fluoro-3-(methoxymethoxy)naphthalene-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (105 mg, 144 μmol, 1.0 eq) in ACN (1 mL) was added HCl·dioxane (4 M, 2 mL) at 0° C., and the mixture was stirred at 0° C. for 0.5 hour. After completion, the mixture was concentrated at 20° C. to give a residue. The pH of the residue was adjusted to ~8 with saturated $NaHCO_3$ solution. The mixture was purified by prep-HPLC (column: Shim-pack C18 150*25*10 um; mobile phase: [water (0.225% FA)-ACN]; B %: 13%-33%, 10 min) to give the title compound (47.65 mg, 51% yield). Off-white Solid. $^1$H NMR (400 MHz, methanol-d4) δ=9.14 (s, 1H), 7.74-7.63 (m, 1H), 7.32 (d, J=2.4 Hz, 1H), 7.26 (t, J=9.6 Hz, 1H), 7.05 (d, J=2.8 Hz, 1H), 4.86-4.74 (m, 2H), 4.67 (s, 2H), 4.06 (br d, J=7.6 Hz, 2H), 4.00-3.84 (m, 2H), 3.78-3.64 (m, 2H), 3.30-3.25 (m, 2H), 2.56-2.42 (m, 1H), 2.41-2.29 (m, 2H), 2.29-1.95 (m, 11H), 0.79 (t, J=7.6 Hz, 3H). LCMS [ESI, M+1]: 587.4.

Example 315

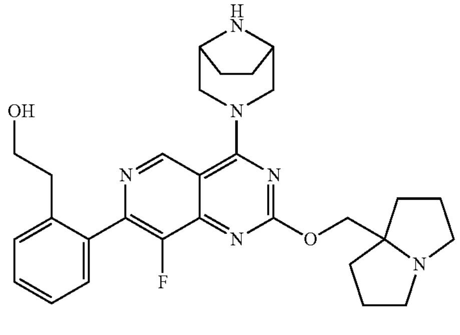 [SMILES: OCCc1ccccc1-c1ncc2c(N3CC4CCC(C3)N4)nc(OCC34CCCN3CCC4)nc2c1F]

2-(2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenyl)ethanol

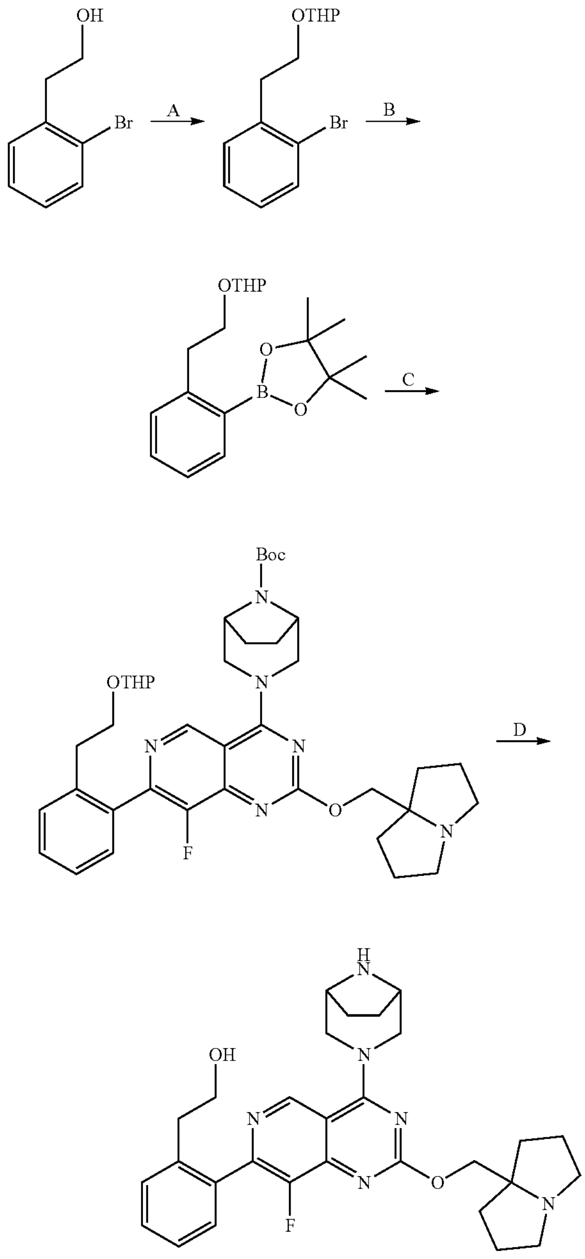

2-(2-(4-((1R,5R)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenyl)ethanol. To a solution of (1R,5S)-tert-butyl 3-(8-fluoro-2-((hexahydro-1H-pyrrolizin-7a-yl)methoxy)-7-(2-(2-((tetrahydro-2H-pyran-2-yl)oxy)ethyl)phenyl)pyrido[4,3-d]pyrimidin-4-yl)-3,8-diazabicyclo[3.2.1]octane-8-carboxylate (80 mg, 114 μmol, 1.0 eq) in MeCN (2 mL) was added HCl·dioxane (4 M, 4 mL, 140 eq) dropwise at 10° C. The mixture was stirred at 10° C. for 0.5 hour. After completion, the reaction mixture was concentrated under reduced pressure to give a residue at 10° C. (without heating). The residue was dissolved in MeOH (0.5 mL) and MeCN (1 mL). The pH of the mixture was adjusted to 7~8 with 25% $NH_3 \cdot H_2O$ (0.1 mL dissolved in MeCN (3 mL)). The mixture was purified by prep-HPLC (column: Shim-pack C18 150*25*10 um; mobile phase: [water (0.225% FA)-ACN]; B %: 2%-22%, 10 min) to give the title compound (13.3 mg, 19% yield, 1.8FA). Yellow solid; $^1H$ NMR (400 MHz, methanol-d4) δ=9.14 (s, 1H), 7.49-7.39 (m, 4H), 4.79 (d, J=13.2 Hz, 2H), 4.67 (s, 2H), 4.05 (s, 2H), 3.90 (d, J=13.6 Hz, 2H), 3.73-3.60 (m, 4H), 2.82 (t, J=6.4 Hz, 2H), 2.36-1.89 (m, 14H); LCMS [ESI, M+1]: 519.3.

Example 316

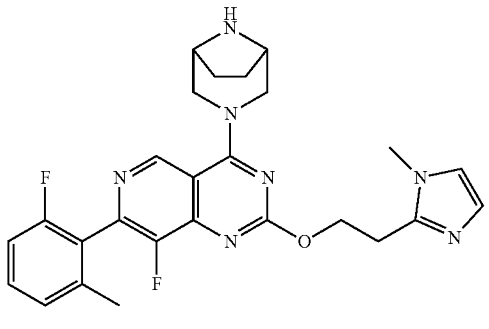 [SMILES: Cc1cccc(F)c1-c1ncc2c(N3CC4CCC(C3)N4)nc(OCCc3nccn3C)nc2c1F]

4-((1R,5S)-3,8-diazabicyclo[3.2.1]octan-3-yl)-8-fluoro-7-(2-fluoro-6-methylphenyl)-2-(2-(1-methyl-1H-imidazol-2-yl)ethoxy)pyrido[4,3-d]pyrimidine Synthesized according to Example 3, Steps H—I substituting (2-fluoro-6-methylphenyl) boronic acid in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-7-(2-fluoro-6-methylphenyl)-2-(2-(1-methyl-1H-imidazol-2-yl)ethoxy)pyrido[4,3-d]pyrimidine (12 mg, 71%). LCMS (MM-ES+APCI, Pos): m/z 492.2 (M+H).

Example 317

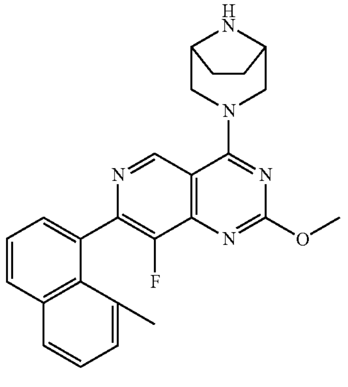 [SMILES: COc1nc(N2CC3CCC(C2)N3)c2cnc(-c3cccc4cccc(C)c34)c(F)c2n1]

4-((1R,5S)-3,8-diazabicyclo[3.2.1]octan-3-yl)-8-fluoro-2-methoxy-7-(8-methylnaphthalen-1-yl) pyrido[4,3-d]pyrimidine

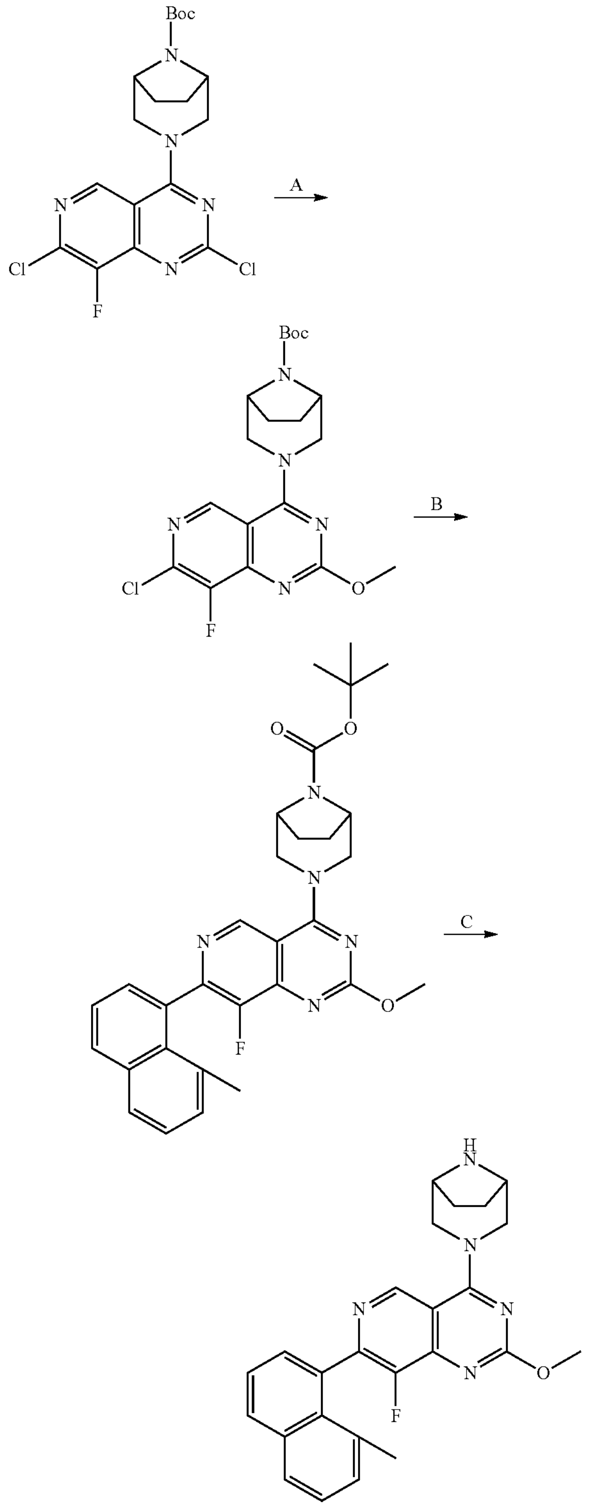

4-((1R,5S)-3,8-diazabicyclo[3.2.1]octan-3-yl)-8-fluoro-2-methoxy-7-(8-methylnaphthalen-1-yl)pyrido[4,3-d]pyrimidine. To a 0° C. solution of tert-butyl(1R,5S)-3-(8-fluoro-2-methoxy-7-(8-methylnaphthalen-1-yl)pyrido[4,3-d]pyrimidin-4-yl)-3,8-diazabicyclo[3.2.1]octane-8-carboxylate (44 mg, 0.084 mmol) in DCM (2 mL) was added TFA (0.15 mL, 1.7 mmol). The mixture was stirred at room temperature for 4.5 hours. The solution was poured into a mixture of saturated bicarbonate (20 mL) and EtOAc (15 mL). The aqueous layer was extracted with EtOAc (2×15 mL). The combined organic layers were washed with saturated bicarbonate (15 mL), brine (15 mL), dried over sodium sulfate, and concentrated in vacuo. The residue was purified by column chromatography eluting with 0-20% MeOH/DCM to afford 4-((1R,5S)-3,8-diazabicyclo[3.2.1]octan-3-yl)-8-fluoro-2-methoxy-7-(8-methylnaphthalen-1-yl)pyrido[4,3-d]pyrimidine (33 mg, 90%) as a yellow foam. LCMS (MM-ES+APCI, Pos): m/z 430.2 (M+H).

Example 318

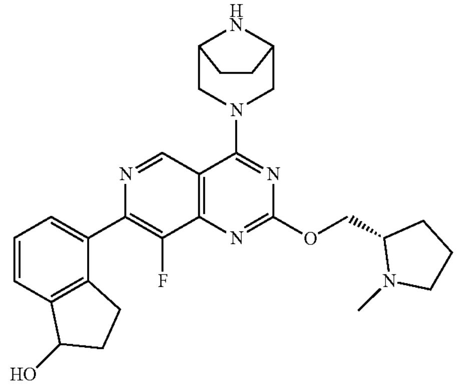 [SMILES: CN1CCC[C@H]1COc1nc(N2CC3CCC(C2)N3)c2cnc(-c3cccc4c3CCC4O)c(F)c2n1]

4-(4-((1R,5S)-3,8-diazabicyclo[3.2.1]octan-3-yl)-8-fluoro-2-(((S)-1-methylpyrrolidin-2-yl)methoxy) pyrido[4,3-d]pyrimidin-7-yl)-2,3-dihydro-1H-inden-1-ol

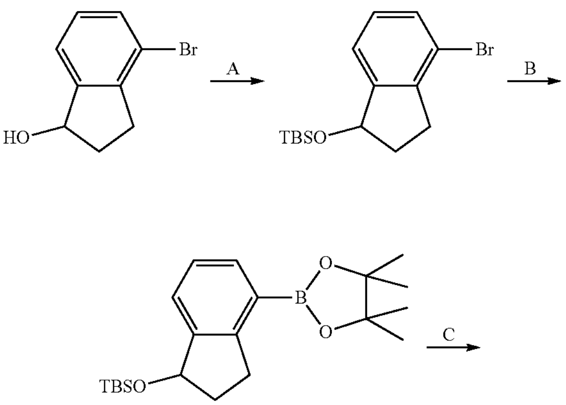

-continued

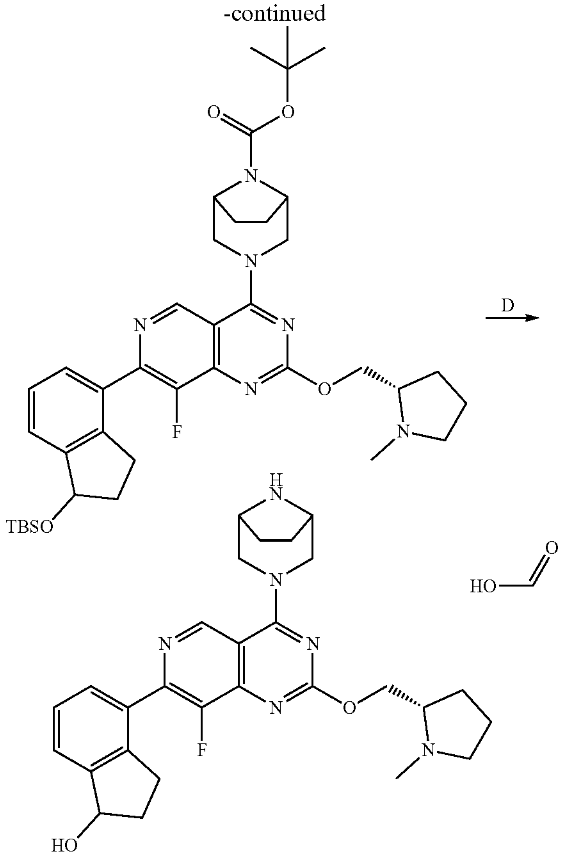

4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)-2,3-dihydro-1H-inden-1-ol formate. To a solution of tert-butyl(1R,5S)-3-(7-(1-((tert-butyldimethylsilyl)oxy)-2,3-dihydro-1H-inden-4-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (17 mg, 0.024 mmol) in DCM (1.2 mL) was added TFA (0.3 mL). The mixture was stirred at rt for 1 h and concentrated to dryness. The residue was dissolved in dioxane (1 mL) and treated with ammonium hydroxide (0.5 mL) at rt for 15 min. The mixture was concentrated to dryness and purified by preparative C18 HPLC (Gilson, 0-95% $CH_3CN/H_2O$ with 0.1% formic acid). The desired fractions were combined and concentrated to dryness to give the title product (10 mg, 84%) as the bis formic acid salt. LCMS (MM-ES+APCI, Pos): m/z 505.3 (M+H).

Example 319

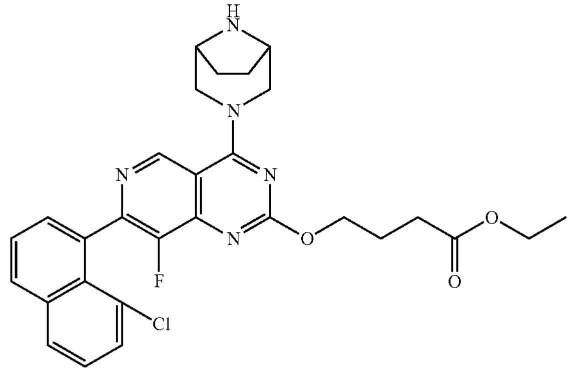 [SMILES: CCOC(=O)CCCOc1nc(N2CC3CCC(C2)N3)c2cnc(-c3cccc4cccc(Cl)c34)c(F)c2n1]

Ethyl 4-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)butanoate Synthesized according to Example 29, Step H and I, substituting ethyl 4-hydroxybutanoate in place of (S)-(1-isopropylpyrrolidin-2-yl)methanol in step H to give the title product (2.2 mg, 14%). LCMS (MM-ES+APCI, Pos): m/z 550.2 (M+H).

Example 320

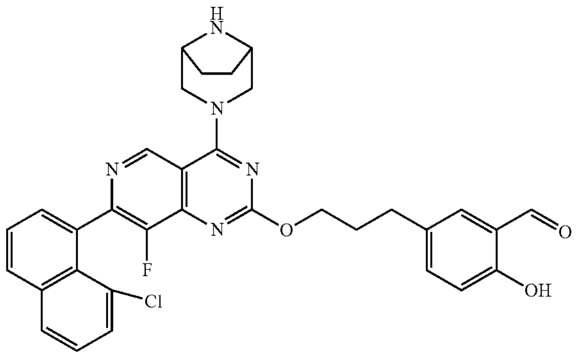 [SMILES: O=Cc1cc(CCCOc2nc(N3CC4CCC(C3)N4)c3cnc(-c4cccc5cccc(Cl)c45)c(F)c3n2)ccc1O]

5-(3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) propyl)-2-hydroxybenzaldehyde Synthesized according to Example 62, substituting 2-hydroxy-5-(3-hydroxypropyl)benzaldehyde in place of 2-hydroxy-5-(2-hydroxyethyl)-benzaldehyde to give the title product (4.6 mg, 15%). LCMS (MM-ES+APCI, Pos): m/z 598.2 (M+H).

Example 321

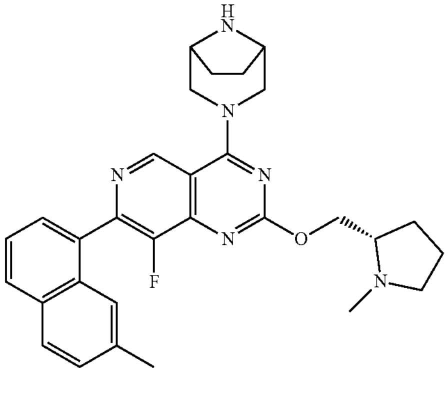 [SMILES: Cc1ccc2cccc(-c3ncc4c(N5CC6CCC(C5)N6)nc(OC[C@@H]5CCCN5C)nc4c3F)c2c1]

4-((1R,5S)-3,8-diazabicyclo[3.2.1]octan-3-yl)-8-fluoro-7-(7-methylnaphthalen-1-yl)-2-(((S)-1-methylpyrrolidin-2-yl)methoxy)pyrido[4,3-d]pyrimidine

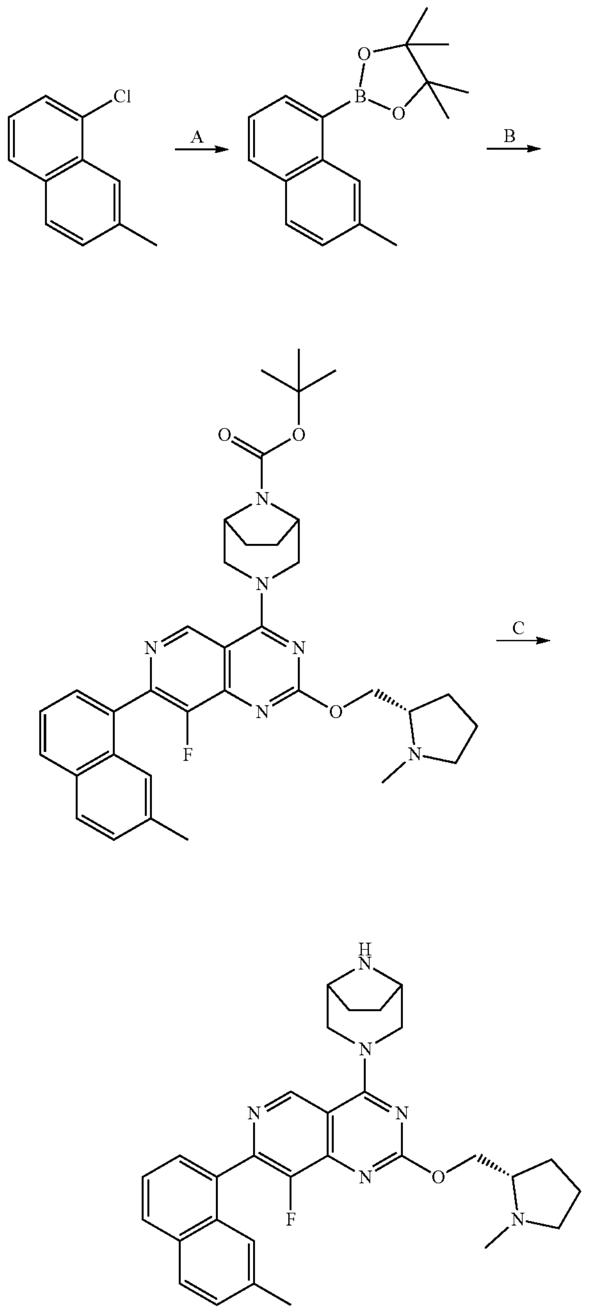

4-((1R,5S)-3,8-diazabicyclo[3.2.1]octan-3-yl)-8-fluoro-7-(7-methylnaphthalen-1-yl)-2-(((S)-1-methylpyrrolidin-2-yl)methoxy)pyrido[4,3-d]pyrimidine. To a solution of tert-butyl(1R,5S)-3-(8-fluoro-7-(7-methylnaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (19 mg, 0.031 mmol) in DCM (1 mL) was added TFA (0.5 mL). The mixture was stirred at rt for 1 h and concentrated to dryness. The residue was neutralized with $NH_3 \cdot H_2O$ and purified by preparative C18 HPLC (Gilson, 0-90% $CH_3CN/H_2O$ with 0.2% $NH_4 \cdot HCO_3$). The desired fractions were combined and concentrated to give the title compound (15 mg, 94%) as a white solid. LCMS (MM-ES+APCI, Pos): m/z 513.3 (M+H).

Example 322

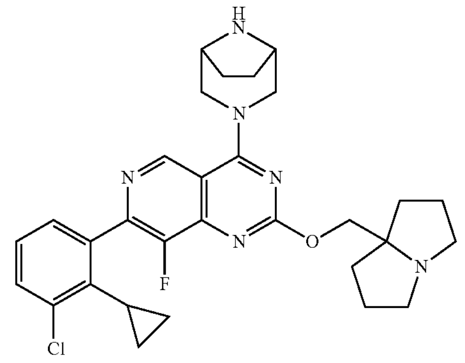 [SMILES: Fc1c(-c2cccc(Cl)c2C2CC2)ncc2c(N3CC4CCC(C3)N4)nc(OCC34CCCN3CCC4)nc12]

4-((1R,5S)-3,8-diazabicyclo[3.2.1]octan-3-yl)-7-(3-chloro-2-cyclopropylphenyl)-8-fluoro-2-((tetrahydro-1H-pyrrolizin-7a(5H)-yl)methoxy)pyrido[4,3-d]pyrimidine Synthesized according to Example 196 substituting 2-(3-chloro-2-place of 2,2-cyclopropylphenyl)-4,4,5,5-tetramethyl-1,3,2-dioxaborolane in difluorobenzo[1,3]dioxole-4-boronic acid in step B to afford 4-((1R,5S)-3,8-diazabicyclo[3.2.1]octan-3-yl)-7-(3-chloro-2-cyclopropylphenyl)-8-fluoro-2-((tetrahydro-1H-pyrrolizin-7a(5H)-yl)methoxy)pyrido[4,3-d]pyrimidine (3.8 mg, 21%). LCMS (MM-ES+APCI, Pos): m/z 549.3 (M+H).

Example 323

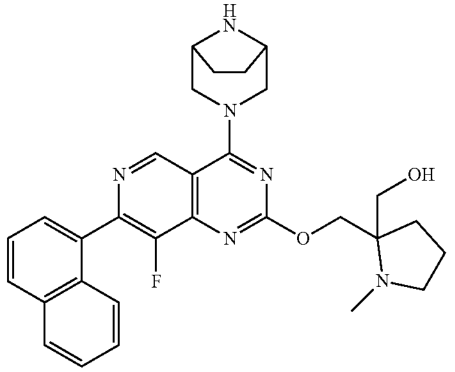 [SMILES: CN1CCCC1(CO)COc1nc(N2CC3CCC(C2)N3)c2cnc(-c3cccc4ccccc34)c(F)c2n1]

(2-(((4-((1R,5S)-3,8-diazabicyclo[3.2.1]octan-3-yl)-8-fluoro-7-(naphthalen-1-yl)pyrido[4,3-d]pyrimidin-2-yl)oxy)methyl)-1-methylpyrrolidin-2-yl)methanol

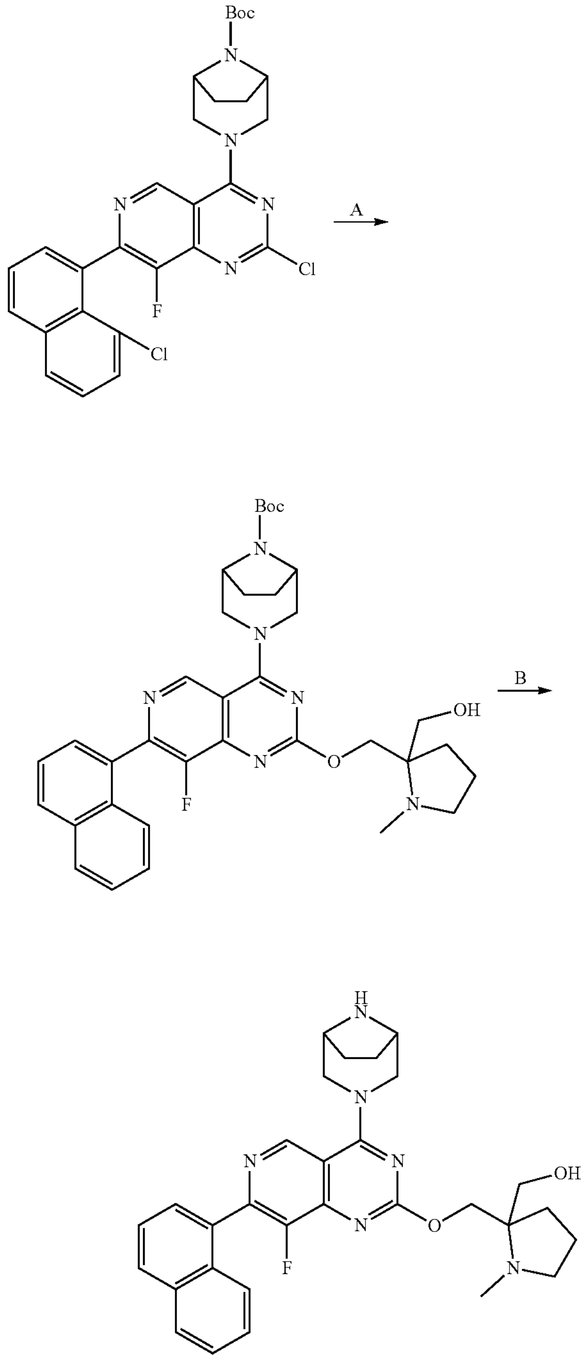

(2-(((4-((1R,5S)-3,8-diazabicyclo[3.2.1]octan-3-yl)-8-fluoro-7-(naphthalen-1-yl)pyrido[4,3-d]pyrimidin-2-yl)oxy)methyl)-1-methylpyrrolidin-2-yl)methanol bis(2,2,2-trifluoroacetate): Synthesized according to Example 2, Step I, substituting tert-butyl(1R,5S)-3-(8-fluoro-2-((2-(hydroxymethyl)-1-methylpyrrolidin-2-yl)methoxy)-7-(naphthalen-1-yl)pyrido[4,3-d]pyrimidin-4-yl)-3,8-diazabicyclo[3.2.1]octane-8-carboxylate in place of tert-butyl(1R,5S)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate to give the title product (1.1 mg, 3%) as the bis TFA salt. LCMS (MM-ES+APCI, Pos): m/z 529.3 (M+H).

Example 324

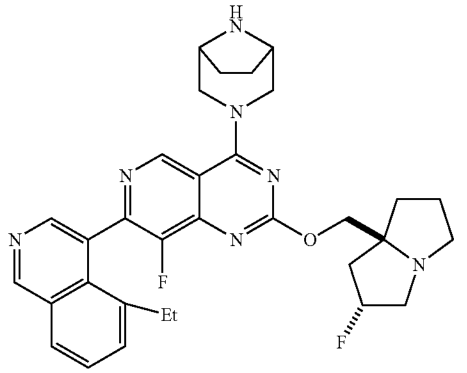

4-((1R,5S)-3,8-diazabicyclo[3.2.1]octan-3-yl)-7-(5-ethylisoquinolin-4-yl)-8-fluoro-2-((2-fluorotetrahydro-1H-pyrrolizin-7a(5H)-yl)methoxy)pyrido[4,3-d]pyrimidine (racemic, trans)

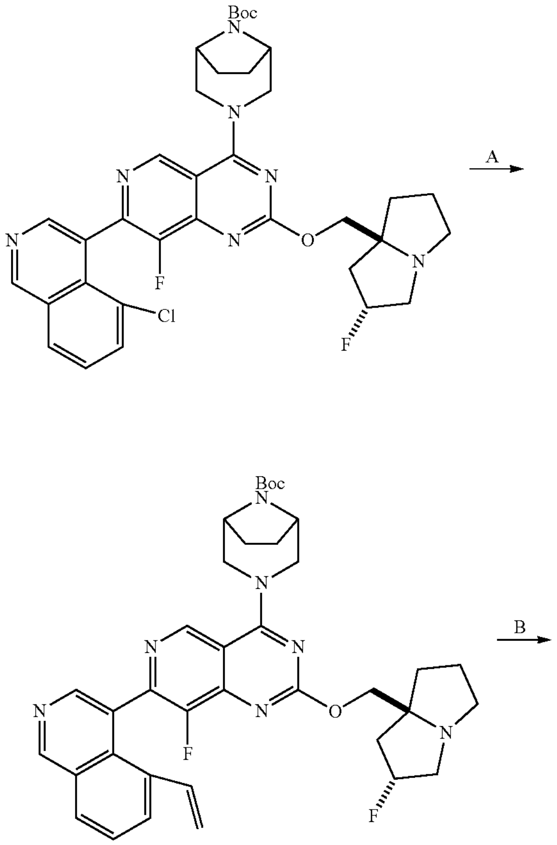

-continued

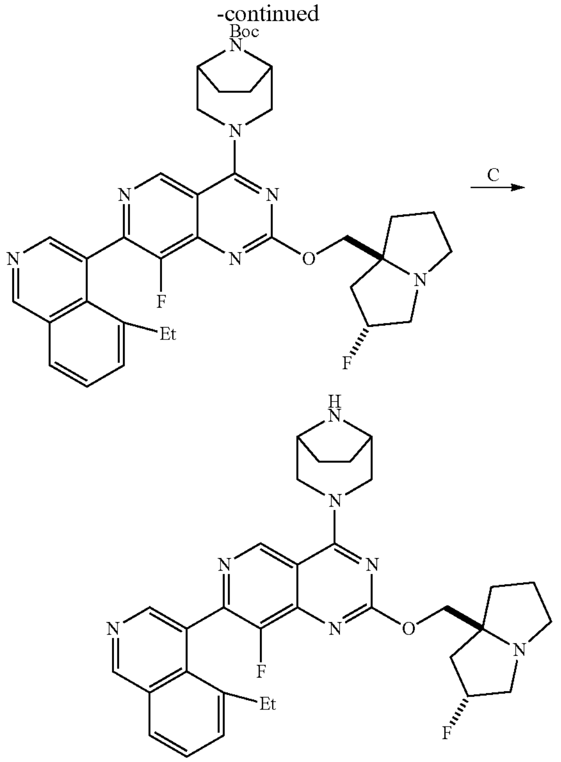

4-(3,8-diazabicyclo[3.2.1]octan-3-yl)-7-(5-ethylisoquinolin-4-yl)-8-fluoro-2-((2-fluorotetrahydro-1H-pyrrolizin-7a(5H)-yl)methoxy)pyrido[4,3-d]pyrimidine dihydrochloride (racemic, trans): Synthesized according to Example 229, Step B substituting tert-butyl(1R,5S)-3-(7-(5-ethylisoquinolin-4-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl(1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-(3,8-diazabicyclo[3.2.1]octan-3-yl)-7-(5-ethylisoquinolin-4-yl)-8-fluoro-2-((2-fluorotetrahydro-1H-pyrrolizin-7a(5H)-yl)methoxy)pyrido[4,3-d]pyrimidine dihydrochloride (racemic, trans) (5 mg, 24%). LCMS (MM-ES+APCI, Pos): m/z 572.3 (M+H).

Example 325

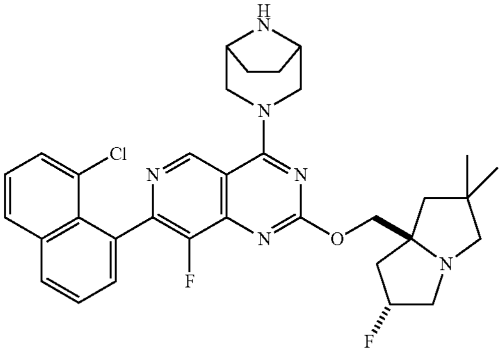

4-((1R,5S)-3,8-diazabicyclo[3.2.1]octan-3-yl)-7-(8-chloronaphthalen-1-yl)-8-fluoro-2-((6-fluoro-2,2-dimethyltetrahydro-1H-pyrrolizin-7a(5H)-yl)methoxy)pyrido[4,3-d]pyrimidine (racemic, trans)

Synthesized according to Example 219, steps E and F substituting ((6S,7aR)-6-fluoro-2,2 dimethyltetrahydro-1H-pyrrolizin-7a(5H)-yl)methanol hydrochloride (trans racemate) for (2-methoxytetrahydro-1H-pyrrolizin-7a(5H)-yl) methanol (trans racemate) to yield 4-((1R,5S)-3,8-diazabicyclo[3.2.1]octan-3-yl)-7-(8-chloronaphthalen-1-yl)-8-fluoro-2-((6-fluoro-2,2-dimethyltetrahydro-1H-pyrrolizin-7a(5H)-yl)methoxy)pyrido[4,3-d]pyrimidine bis-hydrochloride salt (racemic, trans) (25 mg, 0.037 mmol, 100%). LCMS (MM-ES+APCI, Pos): m/z 605.2 (M+H).

Example 326

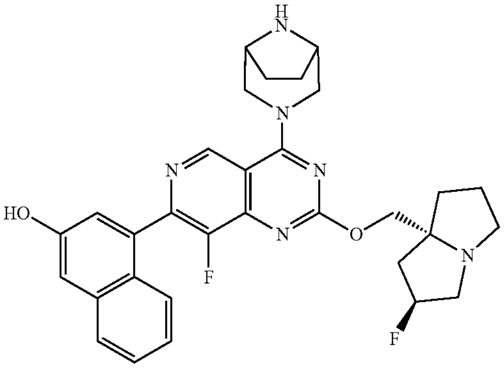 [SMILES: Oc1cc(-c2ncc3c(N4CC5CCC(C4)N5)nc(OC[C@]45CCCN4C[C@@H](F)C5)nc3c2F)c2ccccc2c1]

4-(4-((1R,5S)-3,8-diazabicyclo[3.2.1]octan-3-yl)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol

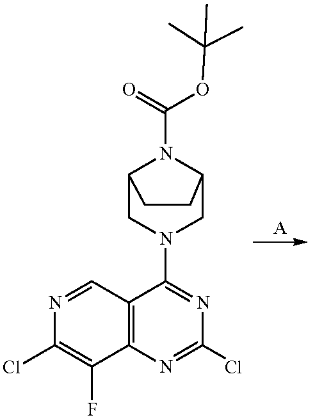

-continued

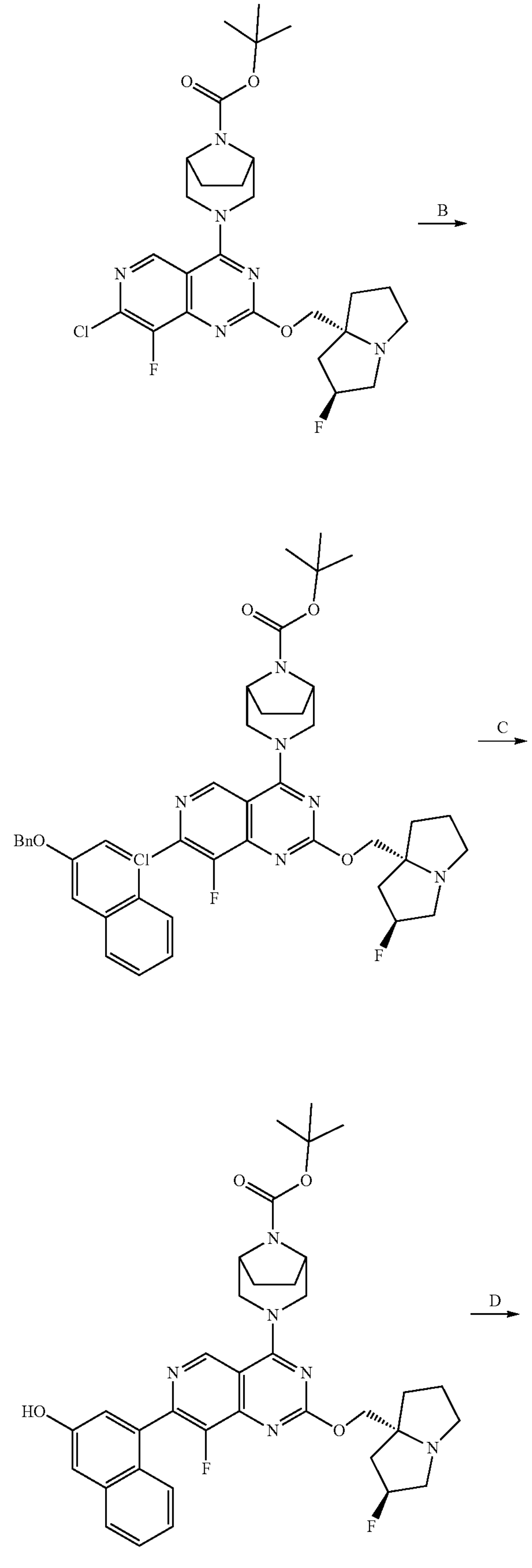

-continued

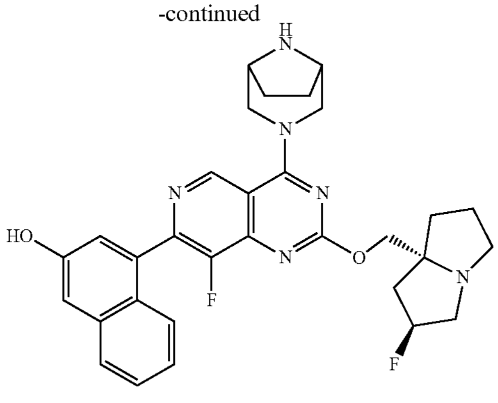

4-(4-((1R,5S)-3,8-diazabicyclo[3.2.1]octan-3-yl)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol dihydrochloride. To a solution of tert-butyl(1R,5S)-3-(8-fluoro-2-(((2S,7aR)-2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octane-8-carboxylate (0.19 g, 0.029 mmol) in DCM (0.5 mL) was added 4 M HCl in dioxanes (0.5 mL, 2.00 mmol). More HCl (100 ul) was added to the reaction after 1 hour. After stirred for 90 minutes at room temperature, the reaction was concentrated in vacuo. The solid was triturated with ether and filtered to afford 4-(4-((1R,5S)-3,8-diazabicyclo[3.2.1]octan-3-yl)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol dihydrochloride (10 mg, 58%) as a yellow powder. LCMS (MM-ES+APCI, Pos): m/z 559.2 (M+H).

Example 327

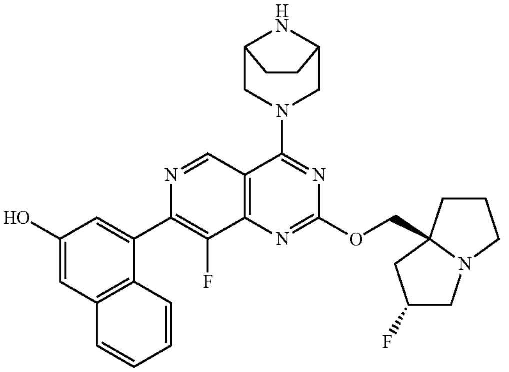 [SMILES: Oc1cc(-c2ncc3c(N4CC5CCC(C4)N5)nc(OC[C@@]45CCCN4C[C@H](F)C5)nc3c2F)c2ccccc2c1]

4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol Synthesized according to Example 326, Steps A-D substituting ((2R,7aS)-2-fluorotetrahydro-1H-pyrrolizin-7a(5H)-yl)methanol in place of ((2S,7aR)-2-fluorotetrahydro-1H-pyrrolizin-7a(5H)-yl)methanol (racemic, trans) in Step A to afford 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)

naphthalen-2-ol dihydrochloride (18 mg, 69%). LCMS (MM-ES+APCI, Pos): m/z 559.3 (M+H).

Example 328

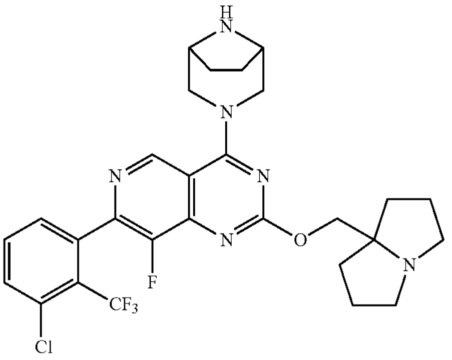 [SMILES: Fc1c(-c2cccc(Cl)c2C(F)(F)F)ncc2c(N3CC4CCC(C3)N4)nc(OCC34CCCN3CCC4)nc12]

4-((1R,5S)-3,8-diazabicyclo[3.2.1]octan-3-yl)-7-(3-chloro-2-(trifluoromethyl)phenyl)-8-fluoro-2-((tetrahydro-1H-pyrrolizin-7a(5H)-yl)methoxy)pyrido[4,3-d]pyrimidine Synthesized according to Example 196 substituting 2-(3-chloro-2-(trifluoromethyl)phenyl)-4,4,5,5-tetramethyl-1,3,2-dioxaborolane in place of 2,2-difluorobenzo[1,3]dioxole-4-boronic acid in step B to afford 4-((1R,5S)-3,8-diazabicyclo[3.2.1]octan-3-yl)-7-(3-chloro-2-(trifluoromethyl)phenyl)-8-fluoro-2-((tetrahydro-1H-pyrrolizin-7a(5H)-yl)methoxy)pyrido[4,3-d]pyrimidine (12 mg, 68%). LCMS (MM-ES+APCI, Pos): m/z 577.2 (M+H).

Example 329

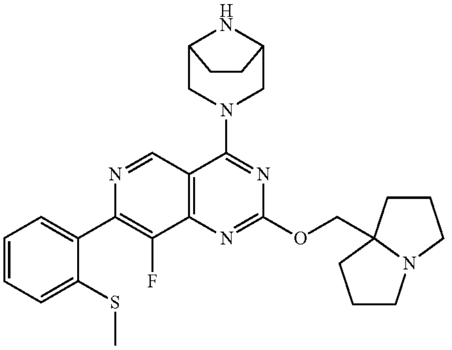 [SMILES: CSc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(2-(methylthio)phenyl)-2-((tetrahydro-1H-pyrrolizin-7a(5H)-yl)methoxy)pyrido[4,3-d]pyrimidine Synthesized according to Example 196 substituting 2-(methylthio)phenylboronic acid in place of 2,2-difluorobenzo[1,3]dioxole-4-boronic acid in step B to afford 4-((1R,5S)-3,8-diazabicyclo[3.2.1]octan-3-yl)-8-fluoro-7-(2-(methylthio)phenyl)-2-((tetrahydro-1H-pyrrolizin-7a(5H)-yl)methoxy)pyrido[4,3-d]pyrimidine (22 mg, 24%). LCMS (MM-ES+APCI, Pos): m/z 521.3 (M+H).

Example 330

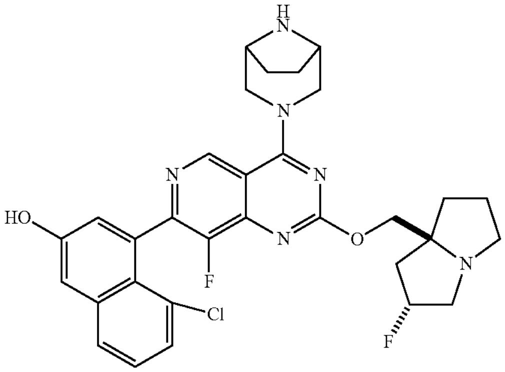

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-chloronaphthalen-2-ol (racemic, trans)

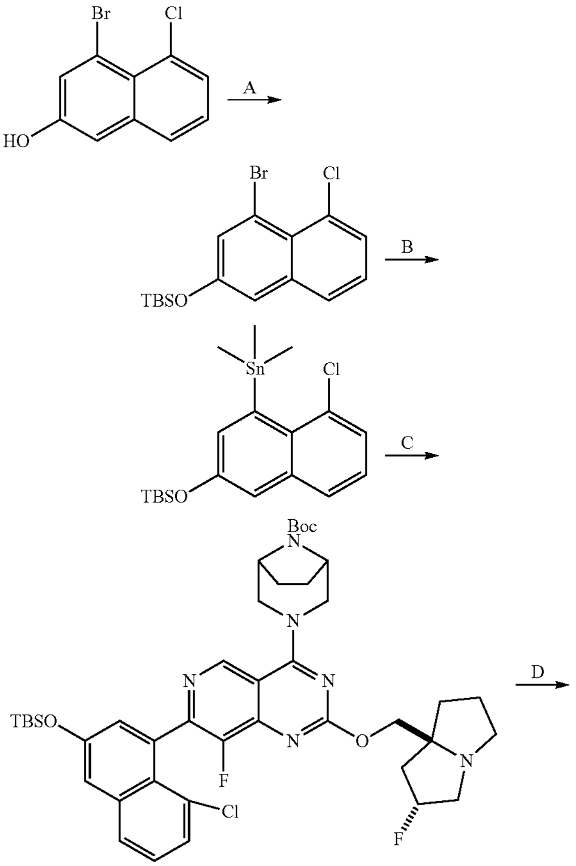

-continued

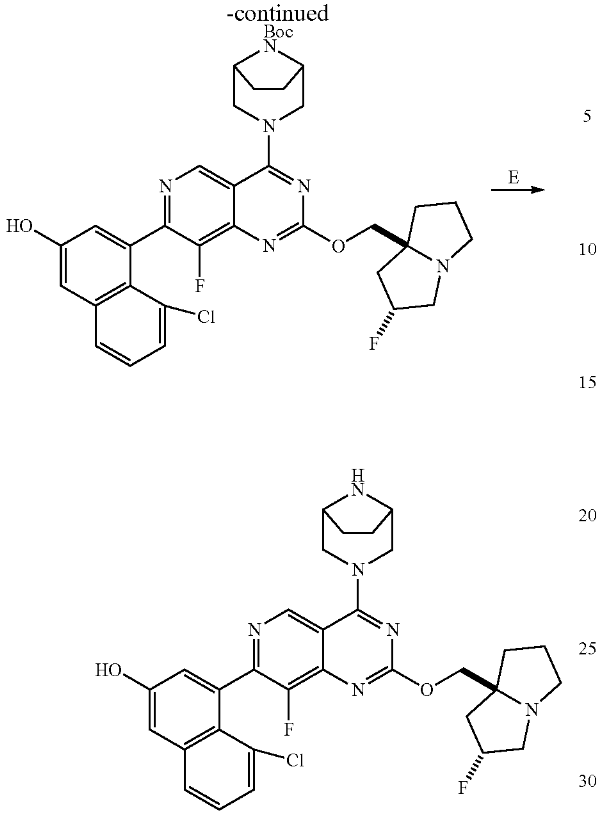

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-chloronaphthalen-2-ol (racemic, trans). Synthesized according to Example 229, Step B substituting tert-butyl 3-(7-(8-chloro-3-hydroxynaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl(1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford the title compound (4.0 mg, 46%). LCMS (MM-ES+APCI, Pos): m/z 593.2 (M+H).

Example 331

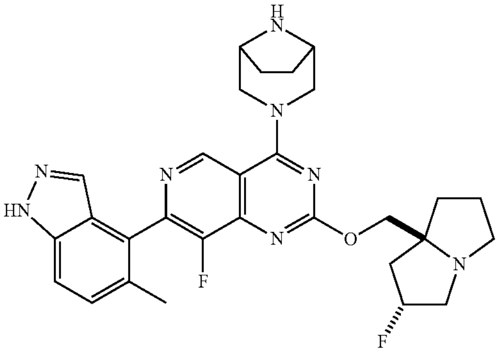

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methyl-1H-indazol-4-yl)pyrido[4,3-d]pyrimidine (racemic, trans)

Synthesized according to Example 3, Steps G-I substituting (2-fluorotetrahydro-1H-pyrrolizin-7a(5H)-yl)methanol (racemic, trans) in place of 2-(1-methyl-1H-imidazol-2-yl)ethan-1-ol in Step G and (5-methyl-1H-indazol-4-yl)boronic acid in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methyl-1H-indazol-4-yl)pyrido[4,3-d]pyrimidine bis(2,2,2-trifluoroacetate) (racemic, trans) (27 mg, 68%). LCMS (MM-ES+APCI, Pos): m/z 547.3 (M+H).

Example 332

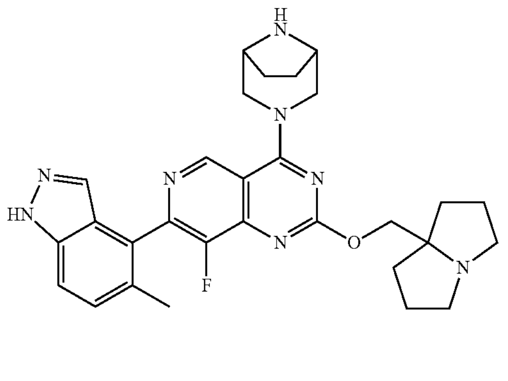 [SMILES: Cc1ccc2[nH]ncc2c1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(5-methyl-1H-indazol-4-yl)-2-((tetrahydro-1H-pyrrolizin-7a(5H)-yl)methoxy)pyrido[4,3-d]pyrimidine Synthesized according to Example 3, Steps G-I substituting (tetrahydro-1H-pyrrolizin-7a(5H)-yl)methanol in place of 2-(1-methyl-1H-imidazol-2-yl)ethan-1-ol in Step G and (5-methyl-1H-indazol-4-yl) boronic acid in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-7-(5-methyl-1H-indazol-4-yl)-2-((tetrahydro-1H-pyrrolizin-7a(5H)-yl)methoxy)pyrido[4,3-d]pyrimidine bis(2,2,2-trifluoroacetate) (14 mg, 45%). LCMS (MM-ES+APCI, Pos): m/z 529.3 (M+H).

Example 333

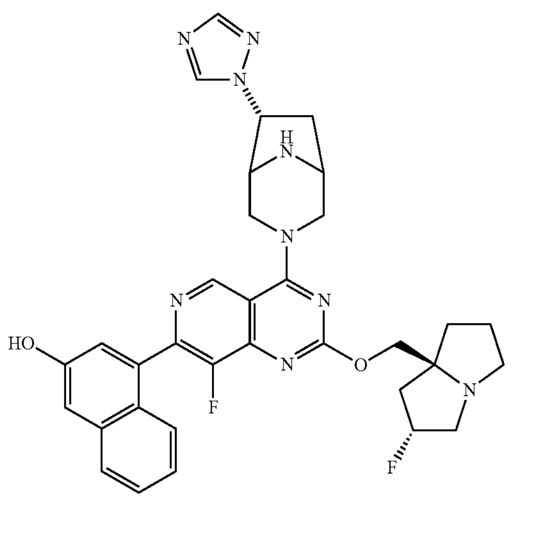 [SMILES: Oc1cc(-c2ncc3c(N4CC5C[C@@H](n6cncn6)C(C4)N5)nc(OC[C@@]45CCCN4C[C@H](F)C5)nc3c2F)c2ccccc2c1]

4-(4-((6R)-6-(1H-1,2,4-triazol-1-yl)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)naphthalen-2-ol (racemic, trans)

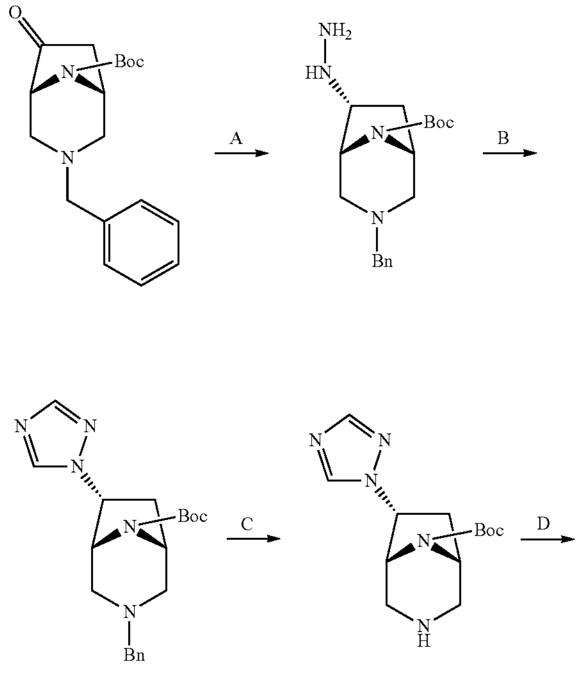

-continued

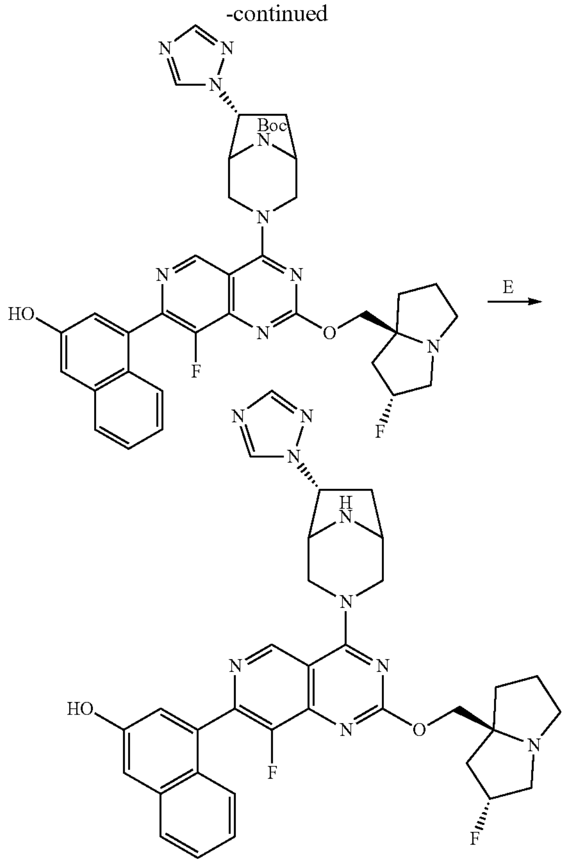

4-(4-((6R)-6-(1H-1,2,4-triazol-1-yl)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)naphthalen-2-ol (racemic, trans). Synthesized according to Example 3, Step I, substituting tert-butyl(6R)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-6-(1H-1,2,4-triazol-1-yl)-3,8-diazabicyclo[3.2.1]octane-8-carboxylate (racemic, trans) in place of tert-butyl(1R,5S)-3-(8-fluoro-7-(3-hydroxynaphthalen-1-yl)-2-(2-(1-methyl-1H-imidazol-2-yl)ethoxy)pyrido[4,3-d]pyrimidin-4-yl)-3,8-diazabicyclo[3.2.1]octane-8-carboxylate (4.5 mg, 41%). LCMS (MM-ES+APCI, Pos): m/z 626.4 (M+H).

Example 334

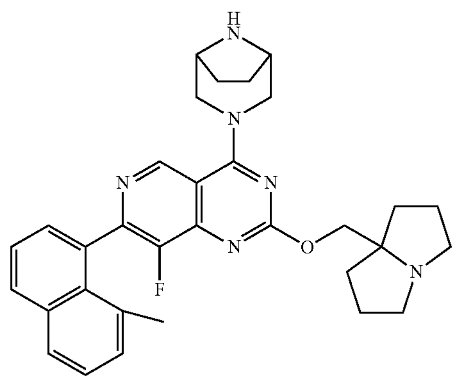 [SMILES: Cc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-7-(8-methylnaphthalen-1-yl)-2-((tetrahydro-1H-pyrrolizin-7a(5H)-yl)methoxy)pyrido[4,3-d]pyrimidine Synthesized according to Example 196 substituting 4,4,5,5-tetramethyl-2-(8-methylnaphthalen-1-yl)-1,3,2-dioxaborolane in place of 2,2-difluorobenzo[1,3]dioxole-4-boronic acid in step B to afford 4-((1R,5S)-3,8-diazabicyclo[3.2.1]octan-3-yl)-8-fluoro-7-(8-methylnaphthalen-1-yl)-2-((tetrahydro-1H-pyrrolizin-7a(5H)-yl)methoxy)pyrido[4,3-d]pyrimidine (13 mg, 29%). LCMS (MM-ES+APCI, Pos): m/z 539.3 (M+H).

Example 335

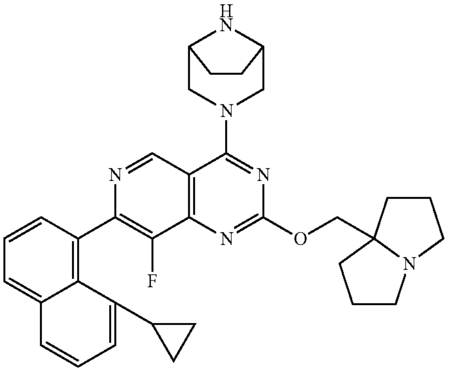 [SMILES: Fc1c(-c2cccc3cccc(C4CC4)c23)ncc2c(N3CC4CCC(C3)N4)nc(OCC34CCCN3CCC4)nc12]

4-((1R,5S)-3,8-diazabicyclo[3.2.1]octan-3-yl)-7-(8-cyclopropylnaphthalen-1-yl)-8-fluoro-2-((tetrahydro-1H-pyrrolizin-7a(5H)-yl)methoxy)pyrido[4,3-d]pyrimidine

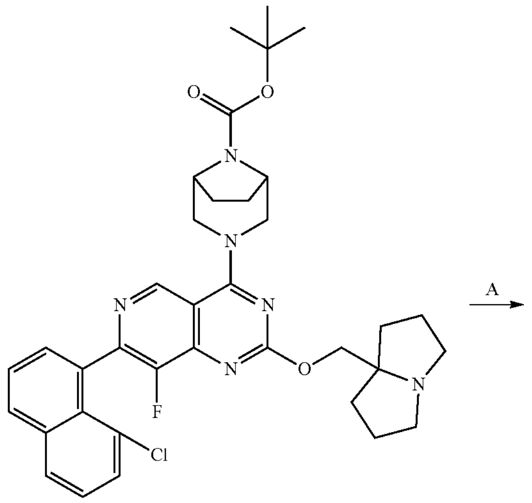

-continued

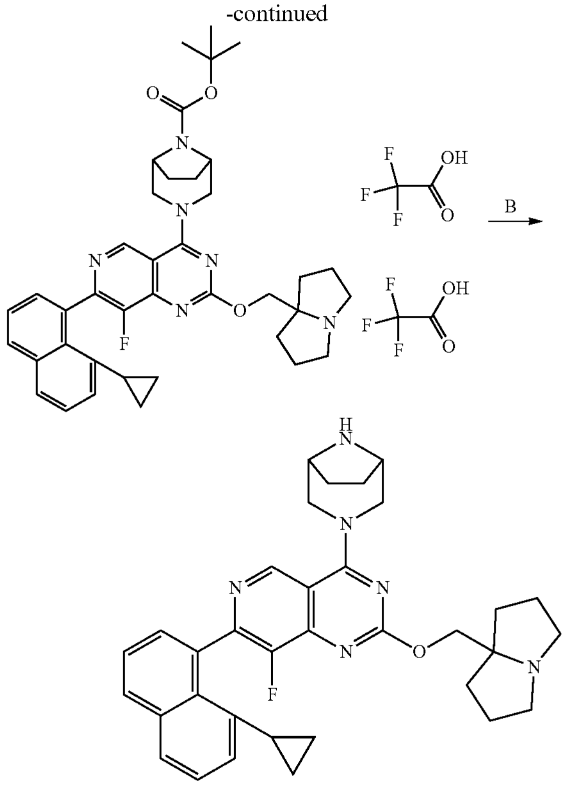

4-((1R,5S)-3,8-diazabicyclo[3.2.1]octan-3-yl)-7-(8-cyclopropylnaphthalen-1-yl)-8-fluoro-2-((tetrahydro-1H-pyrrolizin-7a(5H)-yl)methoxy)pyrido[4,3-d]pyrimidine tris(2,2,2-trifluoroacetate). To a solution of tert-butyl(1R,5S)-3-(7-(8-cyclopropylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate bis(2,2,2-trifluoroacetate) (4 mg, 0.002 mmol) in DCM (0.4 mL) was added TFA (0.2 mL). The mixture was stirred at rt for 0.5 h and concentrated. The residue was purified by preparative C18 HPLC (Gilson, 0-95% $CH_3CN/H_2O$ with 0.1% TFA). The desired fractions were combined and concentrated to give the title compound (0.5 mg, 28%) as the bis TFA salt. LCMS (MM-ES+APCI, Pos): m/z 565.2 (M+H).

Example 336

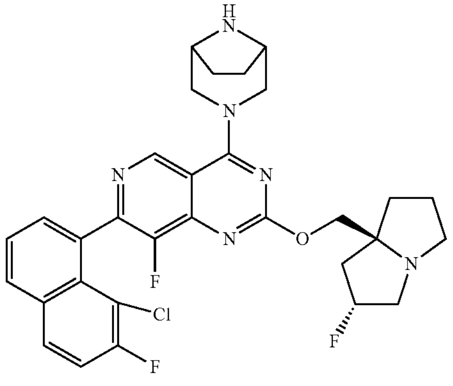 [SMILES: Fc1ccc2cccc(-c3ncc4c(N5CC6CCC(C5)N6)nc(OC[C@@]56CCCN5C[C@H](F)C6)nc4c3F)c2c1Cl]

4-((1R,5S)-3,8-diazabicyclo[3.2.1]octan-3-yl)-7-(8-chloro-7-fluoronaphthalen-1-yl)-8-fluoro-2-((2-fluorotetrahydro-1H-pyrrolizin-7a(5H)-yl)methoxy)pyrido[4,3-d]pyrimidine (racemic, trans)

Synthesized according to Example 29, Steps C—H substituting 2-(8-chloro-7-fluoronaphthalen-1-yl)-4,4,5,5-tetramethyl-1,3,2-dioxaborolane (synthesized according to Example 44, step A-C) in place of 2-(8-chloronaphthalen-1-yl)-4,4,5,5-tetramethyl-1,3,2-dioxaborolane in Step C and (2-fluorotetrahydro-1H-pyrrolizin-7a(5H)-yl)methanol (racemic, trans) in place of (S)-(1-isopropylpyrrolidin-2-yl)methanol in Step H followed by deprotection using Example 391, Step A to afford 4-((1R,5S)-3,8-diazabicyclo[3.2.1]octan-3-yl)-7-(8-chloro-7-fluoronaphthalen-1-yl)-8-fluoro-2-((2-fluorotetrahydro-1H-pyrrolizin-7a(5H)-yl)methoxy)pyrido[4,3-d]pyrimidine dihydrochloride (racemic, trans) (11 mg, 56%). LCMS (MM-ES+APCI, Pos): m/z 595.2 (M+H).

Example 337

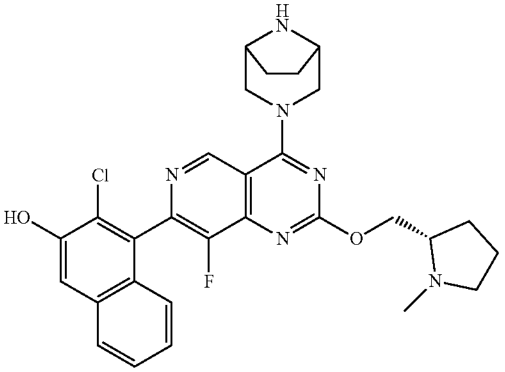 [SMILES: CN1CCC[C@H]1COc1nc(N2CC3CCC(C2)N3)c2cnc(-c3c(Cl)c(O)cc4ccccc34)c(F)c2n1]

4-(4-(3,8-diazabicyclo[3.2.1]octan-3-yl)-8-fluoro-2-(((S)-1-methylpyrrolidin-2-yl)methoxy)pyrido[4,3-d]pyrimidin-7-yl)-3-chloronaphthalen-2-ol

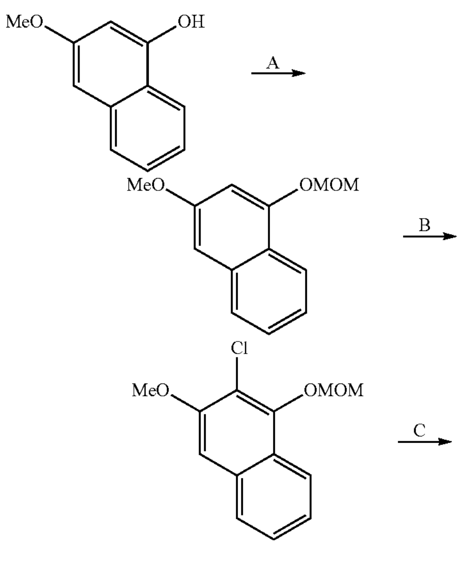

-continued

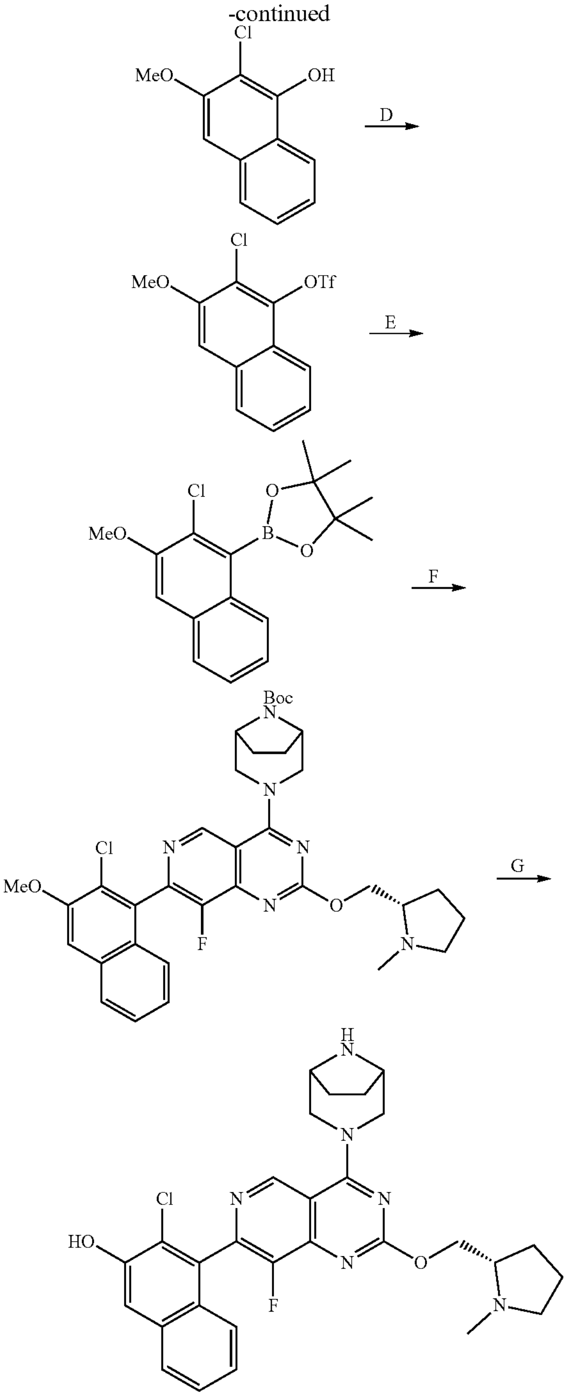

4-(4-(3,8-diazabicyclo[3.2.1]octan-3-yl)-8-fluoro-2-(((S)-1-methylpyrrolidin-2-yl)methoxy)pyrido[4,3-d]pyrimidin-7-yl)-3-chloronaphthalen-2-ol tris(2,2,2-trifluoroacetate). To a solution of tert-butyl(1R,5S)-3-(7-(2-chloro-3-methoxynaphthalen-1-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (10 mg, 0.0151 mmol) in DCM (0.50 mL) at 0° C. was added dropwise a solution of BCl3 (1.0 M in DCM, 75 μL, 0.075 mmol). The mixture was stirred at 0° C. for 15 min and at rt for 1 h. The mixture was cooled to 0° C. and $BBr_3$ (1.0 M in DCM, 0.1 mL, 0.10 mmol) was added. The mixture was stirred at r.t. for 0.5 h. Additional $BBr_3$ (1.0 M in DCM, 0.1 mL, 0.10 mmol) was added and the mixture was stirred at r.t. for 2 h. The reaction was quenched with $Na_2CO_3$ (2.0 M, 0.5 mL, 1.0 mmol). The mixture was concentrated to dryness and the residue was purified by preparative C18 HPLC (Gilson, 0-95% $CH_3CN/H_2O$ with 0.1% TFA). The desired fractions were combined and lyophilized to give the title compound (6 mg, 39%) as a TFA salt. LCMS (MM-ES+APCI, Pos): m/z 549.2 (M+H).

Example 338

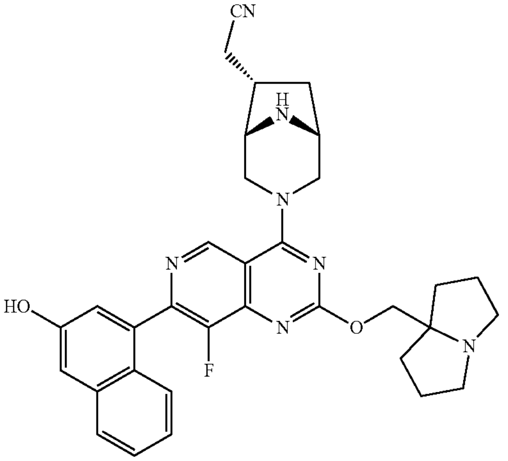 [SMILES: N#CC[C@@H]1C[C@@H]2CN(c3nc(OCC45CCCN4CCC5)nc4c(F)c(-c5cc(O)cc6ccccc56)ncc34)C[C@H]1N2]

2-((1R,5S,6S)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octan-6-yl)acetonitrile

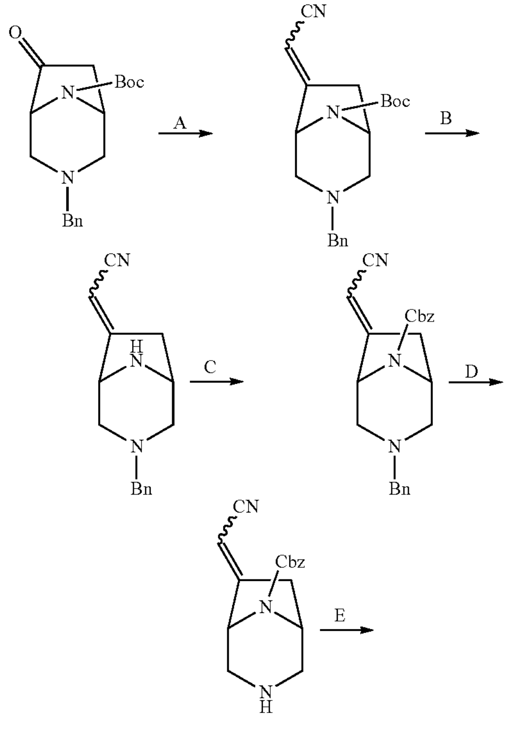

-continued

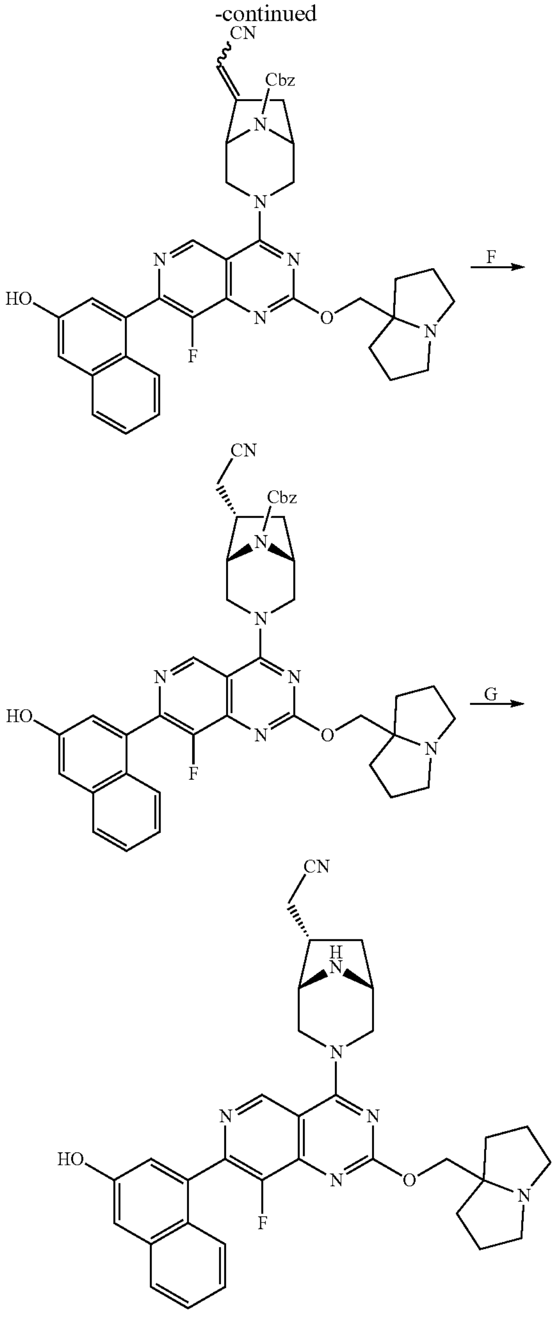

2-((1R,5S,6S)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octan-6-yl)acetonitrile trihydrochloride. To a solution of benzyl(1R,5S,6S)-6-(cyanomethyl)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (12 mg, 0.017 mmol) in DCM (0.80 mL) at rt was added $BCl_3$ (1.0 M in hexanes, 84 μL, 0.084 mmol). The mixture was stirred at rt for 10 min. To the mixture was added additional $BCl_3$ (1.0 M in hexanes, 0.10 mL, 0.10 mmol) and the reaction stirred at rt for 0.5 h. The mixture was concentrated to dryness and the residue was purified by preparative C18 HPLC (Gilson, 0-95% $CH_3CN/H_2O$ with 0.1% TFA). The desired fractions were combined and lyophilized to give the title compound (8 mg, 67%) as the bis TFA salt. LCMS (MM-ES+APCI, Pos): m/z 580.3 (M+H).

Example 339

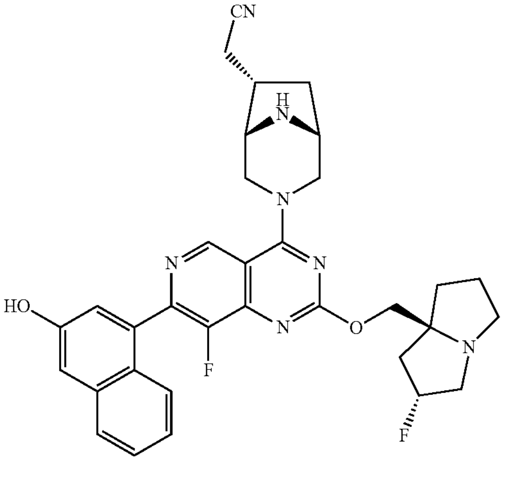 [SMILES: N#CC[C@@H]1C[C@@H]2CN(c3nc(OC[C@@]45CCCN4C[C@H](F)C5)nc4c(F)c(-c5cc(O)cc6ccccc56)ncc34)C[C@H]1N2]

2-((1R,5S,6S)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octan-6-yl)acetonitrile (racemic, trans)

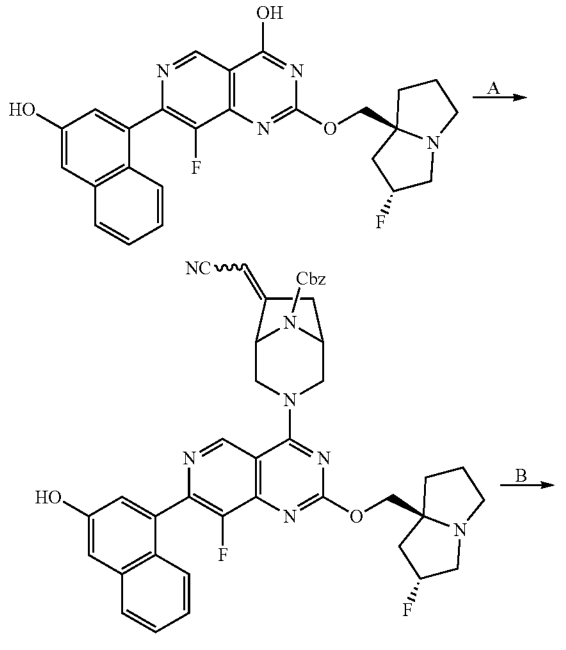

-continued

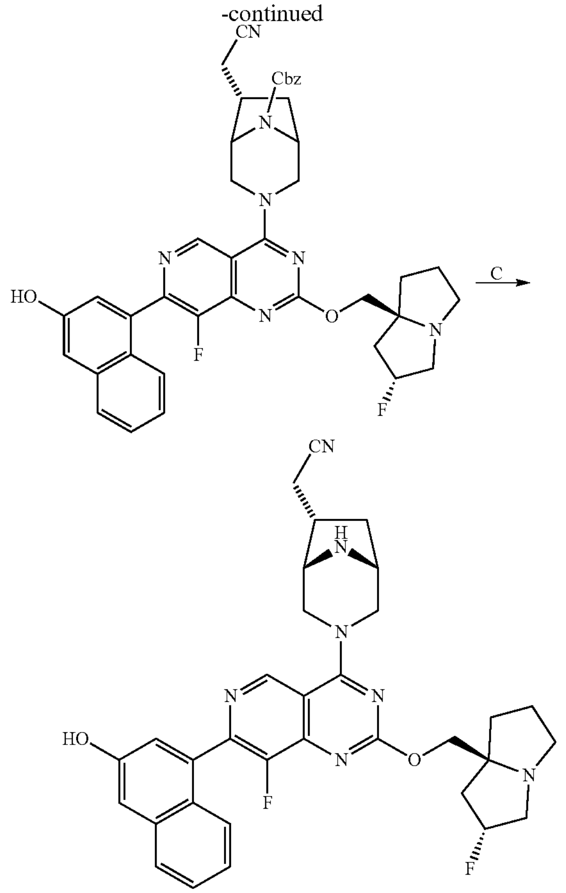

2-((1R,5S,6S)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl) 3,8-diazabicyclo[3.2.1]octan-6-yl)acetonitrile trihydrochloride (racemic, trans). To a solution of benzyl(1R,5S,6S)-6-(cyanomethyl)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octane-8-carboxylate (racemic, trans) (4 mg, 0.00547 mmol) in DCM (1.1 mL) at r.t. was added $BCl_3$ (1.0 M in hexanes, 0.11 mL, 0.11 mmol). The mixture was stirred at r.t. for 30 min., concentrated to dryness, and the residue was purified by preparative C18 HPLC (Gilson, 0-95% $CH_3CN/H_2O$ with 0.1% TFA). The desired fractions were combined and lyophilized to give the title compound (2.5 mg, 65%) as the bis TFA salt. LCMS (MM-ES+APCI, Pos): m/z 598.2 (M+H).

Example 340

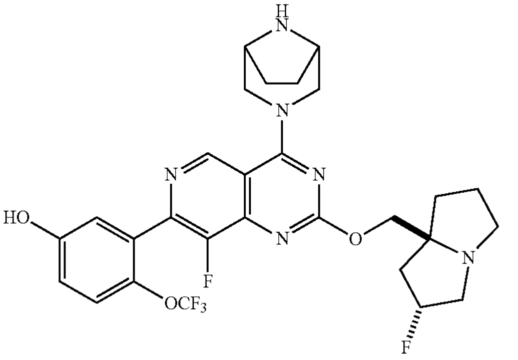

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(trifluoromethoxy)phenol (racemic, trans)

Synthesized according to Example 3, Steps G-I substituting (2-fluorotetrahydro-1H-pyrrolizin-7a(5H)-yl)methanol (racemic, trans) in place of 2-(1-methyl-1H-imidazol-2-yl)ethan-1-ol in Step G and (5-hydroxy-2-(trifluoromethoxy)phenyl) boronic acid in place of 4-(4,4,5,5-tetramethyl-1,3,2-dioxaborolan-2-yl)naphthalen-2-ol in Step H to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(trifluoromethoxy)phenol bis(2,2,2-trifluoroacetate) (racemic, trans) (20 mg, 32%). LCMS (MM-ES+APCI, Pos): m/z 593.2 (M+H).

Example 341

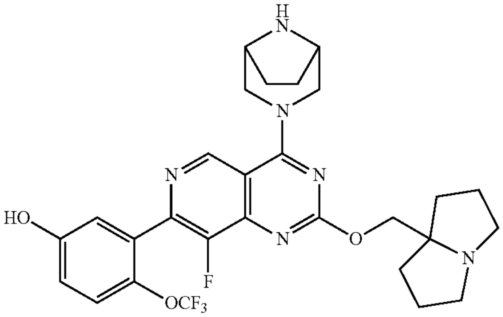 [SMILES: Oc1ccc(OC(F)(F)F)c(-c2ncc3c(N4CC5CCC(C4)N5)nc(OCC45CCCN4CCC5)nc3c2F)c1]

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-(trifluoromethoxy)phenol Synthesized according to Example 3, Steps G-I substituting (tetrahydro-1H-pyrrolizin-7a(5H)-yl)methanol in place of 2-(1-methyl-1H-imidazol-2-yl)ethan-1-ol in Step G and (5-hydroxy-2-(trifluoromethoxy)phenyl) boronic acid in place of 4-(4,4,5,5-tetramethyl-1,3,2-dioxaborolan-2-yl)naphthalen-2-ol in Step H to afford 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-(trifluoromethoxy)phenol bis(2,2,2-trifluoroacetate) (17 mg, 32%). LCMS (MM-ES+APCI, Pos): m/z 575.2 (M+H).

Example 342

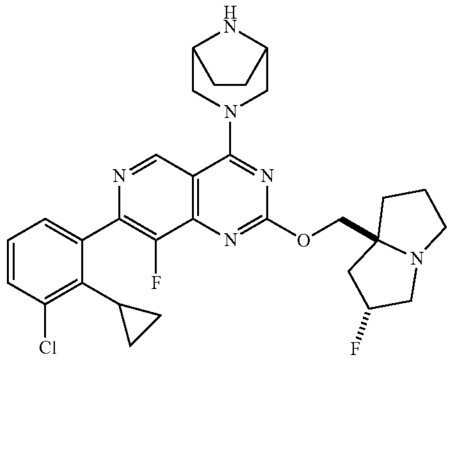

4-((1R,5S)-3,8-diazabicyclo[3.2.1]octan-3-yl)-7-(3-chloro-2-cyclopropylphenyl)-8-fluoro-2-((2-fluorotetrahydro-1H-pyrrolizin-7a(5H)-yl)methoxy)pyrido[4,3-d]pyrimidine (racemic, trans)

Synthesized according to Example 196 substituting (2-fluorotetrahydro-1H-pyrrolizin-7a(5H)-yl)methanol (racemic, trans) in place of (tetrahydro-1H-pyrrolizin-7a(5H)-yl)methanol in step A and also substituting (3-chloro-2-cyclopropylphenyl) boronic acid in place of 2,2-difluorobenzo[1,3]dioxole-4-boronic acid in step B to afford 4-((1R,5S)-3,8-diazabicyclo[3.2.1]octan-3-yl)-7-(3-chloro-2-cyclopropylphenyl)-8-fluoro-2-((2-fluorotetrahydro-1H-pyrrolizin-7a(5H)-yl)methoxy)pyrido[4,3-d]pyrimidine (racemic, trans) (19 mg, 48%). LCMS (MM-ES+APCI, Pos): m/z 567.2 (M+H).

Example 343

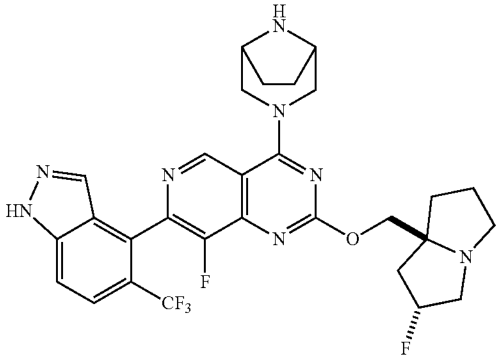

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-(trifluoromethyl)-1H-indazol-4-yl)pyrido[4,3-d]pyrimidine (racemic, trans)

Synthesized according to Example 3, Steps G-H substituting (2-fluorotetrahydro-1H-pyrrolizin-7a(5H)-yl)methanol (racemic, trans) in place of 2-(1-methyl-1H-imidazol-2-yl)ethan-1-ol in Step G and 1-(tetrahydro-2H-pyran-2-yl)-4-(4,4,5,5-tetramethyl-1,3,2-dioxaborolan-2-yl)-5-(trifluoromethyl)-1H-indazole in place of 4-(4,4,5,5-tetramethyl-1,3,2-dioxaborolan-2-yl)naphthalen-2-ol in Step H followed by deprotection using Example 391, Step A to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-(trifluoromethyl)-1H-indazol-4-yl)pyrido[4,3-d]pyrimidine (racemic, trans) (28 mg, 84%). LCMS (MM-ES+APCI, Pos): m/z 601.2 (M+H).

Example 344

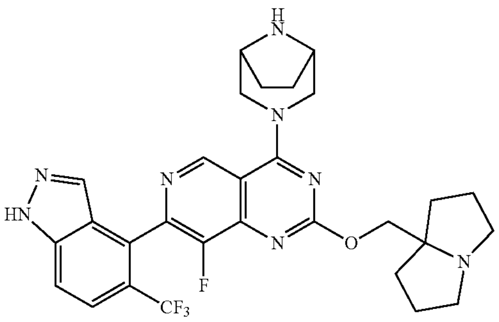 [SMILES: Fc1c(-c2c(C(F)(F)F)ccc3[nH]ncc23)ncc2c(N3CC4CCC(C3)N4)nc(OCC34CCCN3CCC4)nc12]

4-((1R,5S)-3,8-diazabicyclo[3.2.1]octan-3-yl)-8-fluoro-2-((tetrahydro-1H-pyrrolizin-7a(5H)-yl)methoxy)-7-(5-(trifluoromethyl)-1H-indazol-4-yl)pyrido[4,3-d]pyrimidine Synthesized according to Example 3, Steps G-H substituting (tetrahydro-1H-pyrrolizin-7a(5H)-yl)methanol in place of 2-(1-methyl-1H-imidazol-2-yl)ethan-1-ol in Step G and 1-(tetrahydro-2H-pyran-2-yl)-4-(4,4,5,5-tetramethyl-1,3,2-dioxaborolan-2-yl)-5-(trifluoromethyl)-1H-indazole in place of 4-(4,4,5,5-tetramethyl-1,3,2-dioxaborolan-2-yl)naphthalen-2-ol in Step H followed by deprotection using Example 391, Step A to afford 4-((1R,5S)-3,8-diazabicyclo[3.2.1]octan-3-yl)-8-fluoro-2-((tetrahydro-1H-pyrrolizin-7a(5H)-yl)methoxy)-7-(5-(trifluoromethyl)-1H-indazol-4-yl)pyrido[4,3-d]pyrimidine (9.8 mg, 63%). LCMS (MM-ES+APCI, Pos): m/z 583.3 (M+H).

Example 345

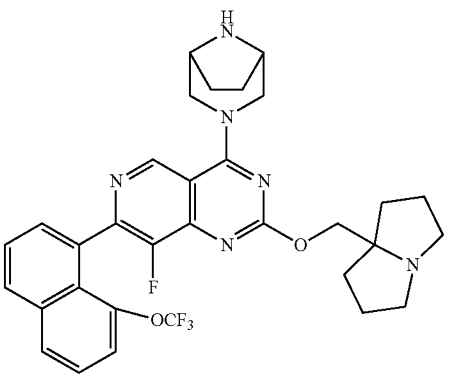 [SMILES: Fc1c(-c2cccc3cccc(OC(F)(F)F)c23)ncc2c(N3CC4CCC(C3)N4)nc(OCC34CCCN3CCC4)nc12]

4-((1R,5S)-3,8-diazabicyclo[3.2.1]octan-3-yl)-8-fluoro-2-((tetrahydro-1H-pyrrolizin-7a(5H)-yl)methoxy)-7-(8-(trifluoromethoxy)naphthalen-1-yl)pyrido[4,3-d]pyrimidine

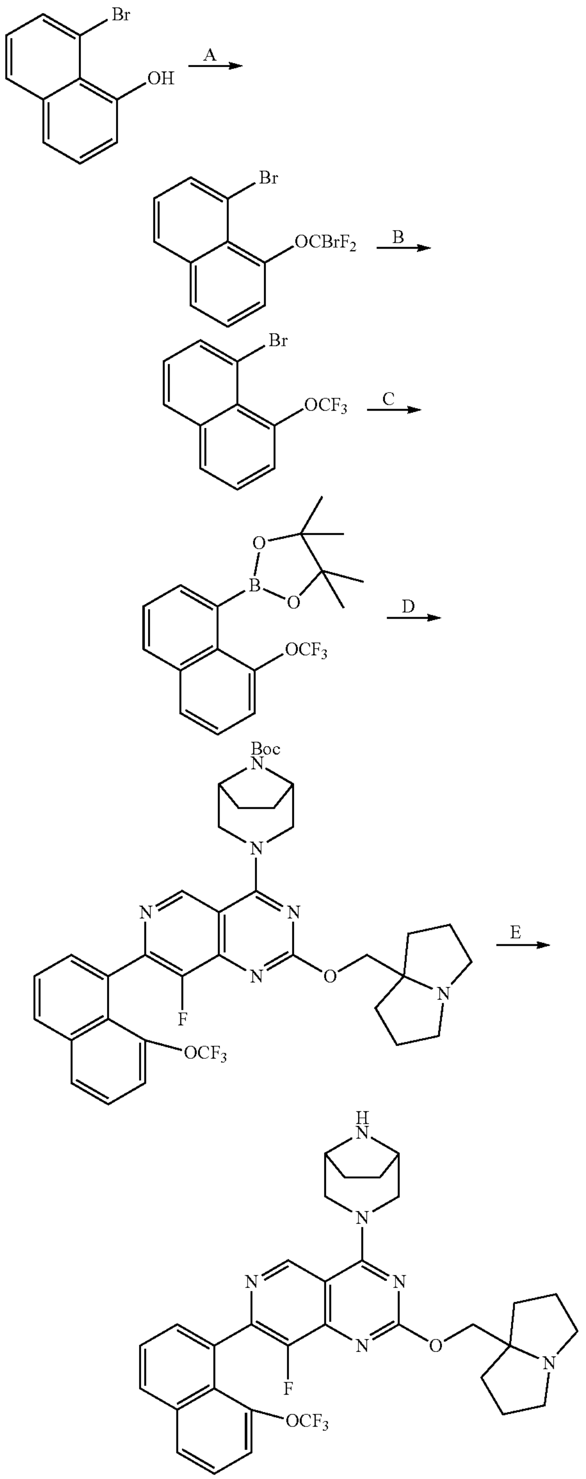

4-((1R,5S)-3,8-diazabicyclo[3.2.1]octan-3-yl)-8-fluoro-2-((tetrahydro-1H-pyrrolizin-7a(5H)-yl)methoxy)-7-(8-(trifluoromethoxy)naphthalen-1-yl)pyrido[4,3-d]pyrimidine tris(2,2,2-trifluoroacetate). To a solution of tert-butyl(1R,5S)-3-(8-fluoro-2-((tetrahydro-1H-pyrrolizin-7a(5H)-yl)methoxy)-7-(8-(trifluoromethoxy)naphthalen-1-yl)pyrido[4,3-d]pyrimidin-4-yl)-3,8-diazabicyclo[3.2.1]octane-8-carboxylate (14 mg, 0.020 mmol) in DCM (1 mL) at rt was added TFA (0.50 mL). The solution was stirred at rt for 2 h and concentrated to dryness. The residue was purified by preparative C18 HPLC (Gilson, 0-95% $CH_3CN/H_2O$ with 0.1% TFA). The desired fractions were combined and lyophilized to give the title compound (13 mg, 69%) as a bis TFA salt. LCMS (MM-ES+APCI, Pos): m/z 609.3 (M+H).

Example 346

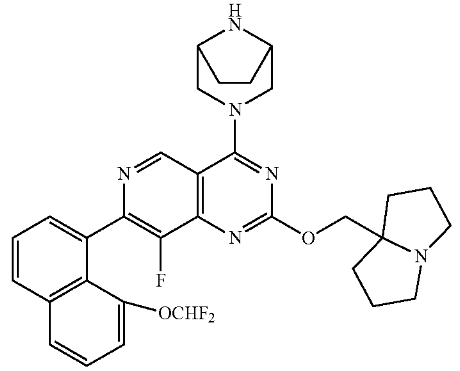 [SMILES: Fc1c(-c2cccc3cccc(OC(F)F)c23)ncc2c(N3CC4CCC(C3)N4)nc(OCC34CCCN3CCC4)nc12]

4-((1R,5S)-3,8-diazabicyclo[3.2.1]octan-3-yl)-7-(8-(difluoromethoxy)naphthalen-1-yl)-8-fluoro-2-((tetrahydro-1H-pyrrolizin-7a(5H)-yl)methoxy)pyrido[4,3-d]pyrimidine

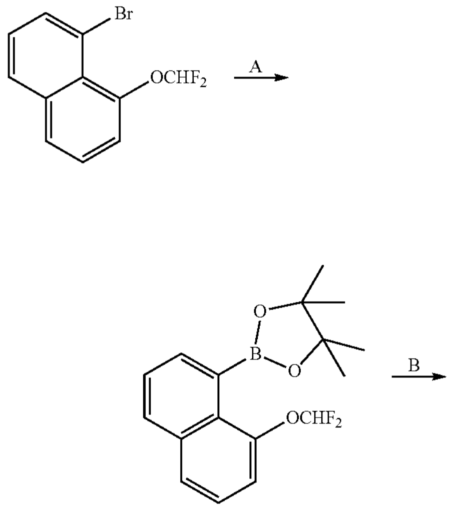

-continued

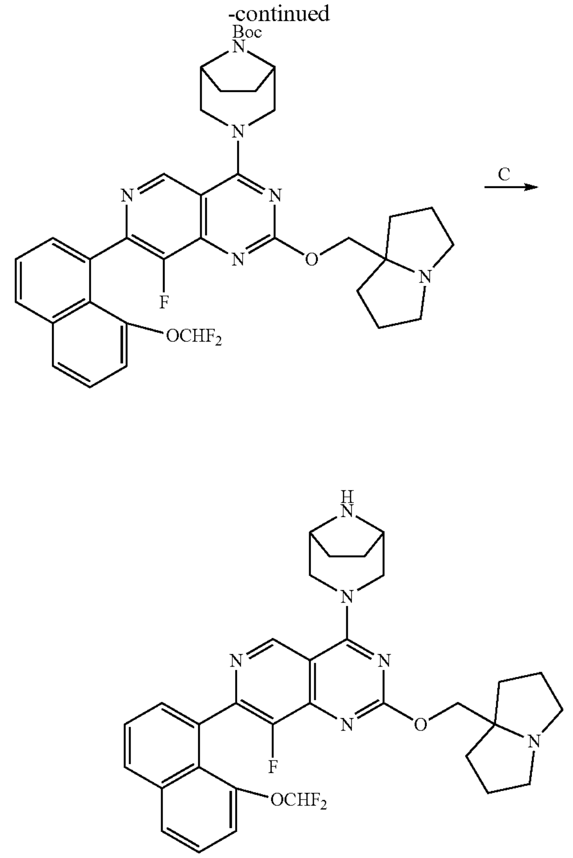

4-((1R,5S)-3,8-diazabicyclo[3.2.1]octan-3-yl)-7-(8-(difluoromethoxy)naphthalen-1-yl)-8-fluoro-2-((tetrahydro-1H-pyrrolizin-7a(5H)-yl)methoxy)pyrido[4,3-d]pyrimidine tris(2,2,2-trifluoroacetate). To a solution of tert-butyl(1R,5S)-3-(7-(8-(difluoromethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (5 mg, 0.007 mmol) in DCM (1 mL) at rt was added TFA (0.50 mL). The solution was stirred at rt for 0.5 h and concentrated to dryness. The residue was purified by preparative C18 HPLC (Gilson, 0-95% $CH_3CN/H_2O$ with 0.1% TFA). The desired fractions were combined and lyophilized to give the title compound (3 mg, 44%) as the bis TFA salt. LCMS (MM-ES+APCI, Pos): m/z 591.3 (M+H).

Example 347

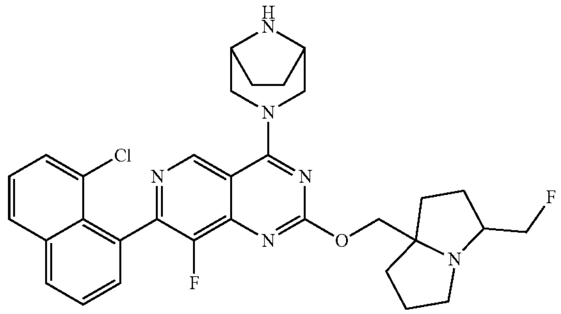 [SMILES: FCC1CCC2(COc3nc(N4CC5CCC(C4)N5)c4cnc(-c5cccc6cccc(Cl)c56)c(F)c4n3)CCCN12]

4-((1R,5S)-3,8-diazabicyclo[3.2.1]octan-3-yl)-7-(8-chloronaphthalen-1-yl)-8-fluoro-2-((3-(fluoromethyl)tetrahydro-1H-pyrrolizin-7a(5H)-yl)methoxy)pyrido[4,3-d]pyrimidine (mixture of isomers)

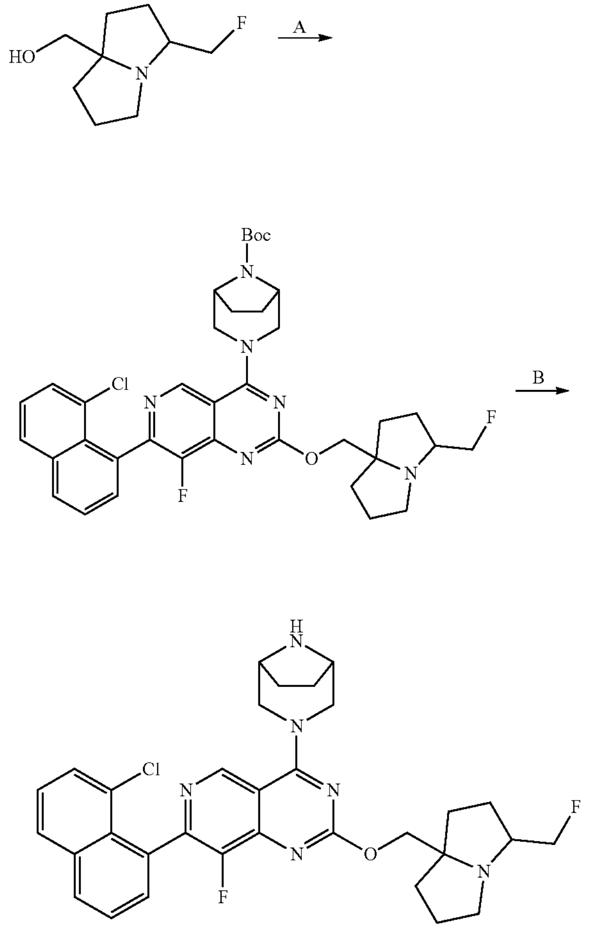

4-((1R,5S)-3,8-diazabicyclo[3.2.1]octan-3-yl)-7-(8-chloronaphthalen-1-yl)-8-fluoro-2-(((3R,7aR)-3-(fluoromethyl)tetrahydro-1H-pyrrolizin-7a(5H)-yl)methoxy)pyrido[4,3-d]pyrimidine. A solution of tert-butyl(1R,5S)-3-(7-(8-chloronaphthalen-1-yl)-8-fluoro-2-(((3S,7aR)-3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (16 mg, 0.023 mmol) in 4M HCl/dioxane (0.1 mL) and DCM (0.1 mL) was stirred for 45 minutes. Diethyl ether (0.3 mL) was added and the slurry was filtered. The solid was dried in vacuo to give the crude product which was purified by reverse-phase chromatography (5-95% MeCN/water with 0.1% TFA as modifier). The pooled product fractions were lyophilized to give 4-((1R,5S)-3,8-diazabicyclo[3.2.1]octan-3-yl)-7-(8-chloronaphthalen-1-yl)-8-fluoro-2-(((3R,7aR)-3-(fluoromethyl)tetrahydro-1H-pyrrolizin-7a(5H)-yl)methoxy)pyrido[4,3-d]pyrimidine (1.5 mg, 11%). LCMS (MM-ES+APCI, Pos): m/z 591.2 (M+H).

Example 348

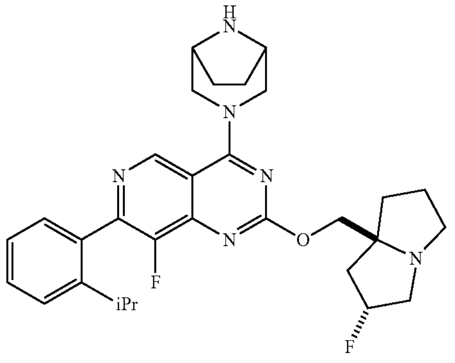

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropylphenyl)pyrido[4,3-d]pyrimidine (racemic, trans)

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropylphenyl)pyrido[4,3-d]pyrimidine dihydrochloride (racemic, trans). Synthesized according to Example 229, Step B substituting tert-butyl(1R,5S)-3-(8-fluoro-2-((2-fluorotetrahydro-1H-pyrrolizin-7a(5H)-yl)methoxy)-7-(2-isopropylphenyl)pyrido[4,3-d]pyrimidin-4-yl)-3,8-diazabicyclo[3.2.1]octane-8-carboxylate (racemic, trans) in place of tert-butyl(1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropylphenyl)pyrido[4,3-d]pyrimidine dihydrochloride (racemic, trans) (1 mg, 2%). LCMS (MM-ES+APCI, Pos): m/z 535.3 (M+H).

Example 349

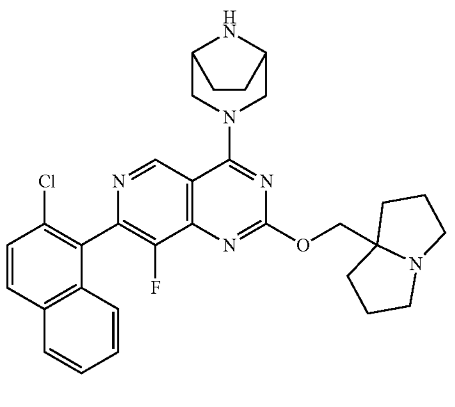 [SMILES: Fc1c(-c2c(Cl)ccc3ccccc23)ncc2c(N3CC4CCC(C3)N4)nc(OCC34CCCN3CCC4)nc12]

4-((1R,5S)-3,8-diazabicyclo[3.2.1]octan-3-yl)-7-(2-chloronaphthalen-1-yl)-8-fluoro-2-((tetrahydro-1H-pyrrolizin-7a(5H)-yl)methoxy)pyrido[4,3-d]pyrimidine

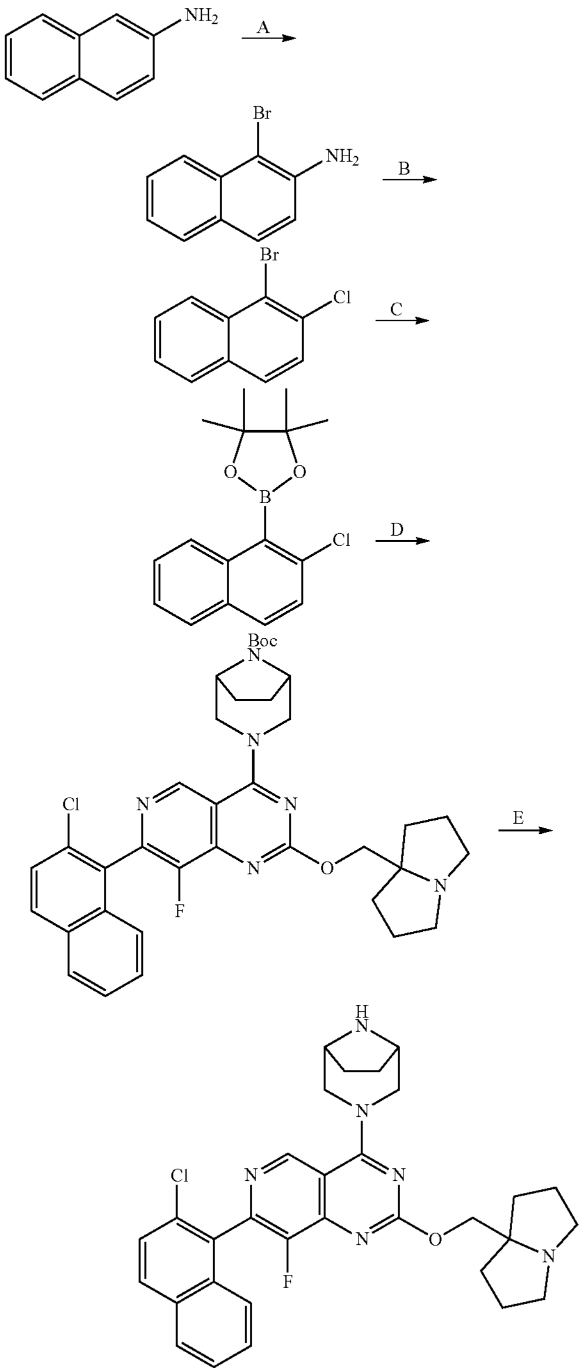

4-((1R,5S)-3,8-diazabicyclo[3.2.1]octan-3-yl)-7-(2-chloronaphthalen-1-yl)-8-fluoro-2-((tetrahydro-1H-pyrrolizin-7a(5H)-yl)methoxy)pyrido[4,3-d]pyrimidine. Tert-butyl (1R,5S)-3-(7-(2-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (10 mg, 0.015 mmol) was added to a vial with a stir bar. DCM (0.5 mL) and TFA (0.15 mL) were added. The reaction was stirred at room temperature for 30 minutes before being diluted with saturated $NaHCO_3$ and extracted with DCM 3 times. The DCM layers were combined, dried with $Na_2SO_4$, filtered, and concentrated to yield 4-((1R,5S)-3,8-diazabicyclo[3.2.1]octan-3-yl)-7-(2-chloronaphthalen-1-yl)-8-fluoro-2-((tetrahydro-1H-pyrrolizin-7a(5H)-yl)methoxy)pyrido[4,3-d]pyrimidine (9.3 mg, 100%). LCMS (MM-ES+APCI, Pos): m/z 559.2 (M+H).

Example 350

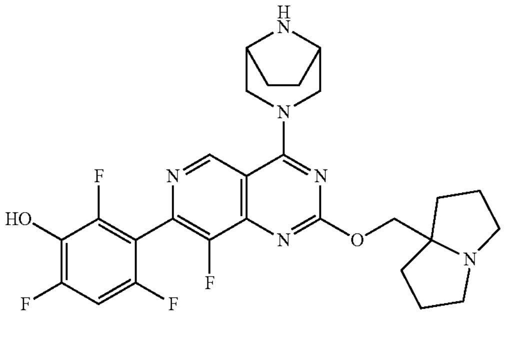 [SMILES: Oc1c(F)cc(F)c(-c2ncc3c(N4CC5CCC(C4)N5)nc(OCC45CCCN4CCC5)nc3c2F)c1F]

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-2,4,6-trifluorophenol

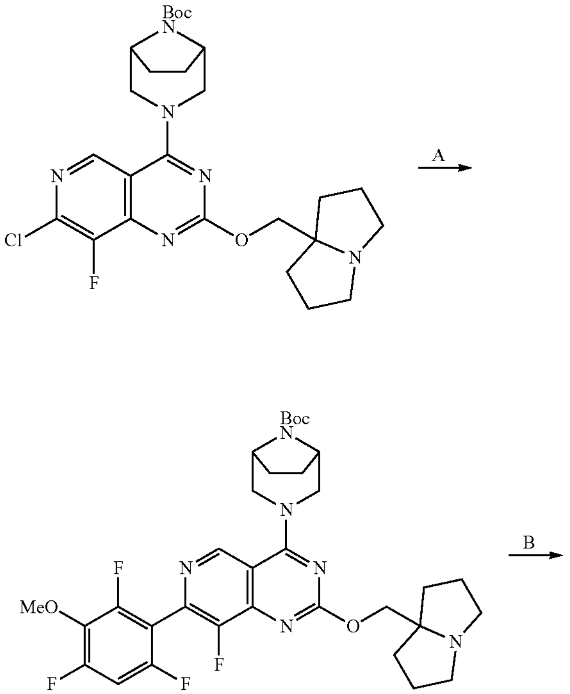

-continued

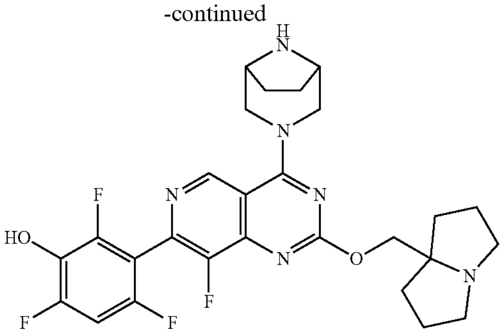

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-2,4,6-trifluorophenol tris(2,2,2-trifluoroacetate). The 2:1 mixture of tert-butyl(1R,5S)-3-(8-fluoro-2-((tetrahydro-1H-pyrrolizin-7a(5H)-yl)methoxy)-7-(2,4,6-trifluoro-3-methoxyphenyl)pyrido[4,3-d]pyrimidin-4-yl)-3,8-diazabicyclo[3.2.1]octane-8-carboxylate and tert-butyl(1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (29 mg) was added to a round bottom flask with a stir bar and septa. The round bottom flask was degassed and purged with $N_2$ 3 times before dry DCM was added. The round bottom flask was cooled to 0° C. and 1M trichloroborane (0.10 mL, 0.10 mmol) was added dropwise. The reaction was stirred at 0° C. for 30 minutes. 1M $BBr_3$ (0.10 mL, 0.10 mmol) was added at room temperature and the reaction was stirred for 1 hour. Additional $BBr_3$ (0.10 mL, 0.10 mmol) was added and the reaction was stirred for 30 minutes. 1M NaOH (1.5 mL) was added to quench the reaction. The aqueous layer was washed with DCM 6 times before being purified via a Biotage (0-100% MeCN in water with 0.1% TFA). The fractions containing the product were combined, frozen, and lyophilized to yield 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-2,4,6-trifluorophenol tris(2,2,2-trifluoroacetate) (7.7 mg, 39%). LCMS (MM-ES+APCI, Pos): m/z 545.3 (M+H).

Example 351

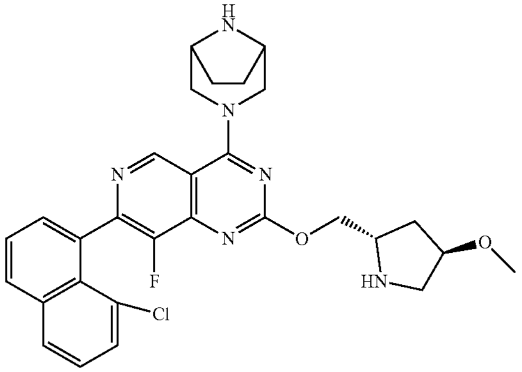 [SMILES: CO[C@H]1CN[C@H](COc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-8-fluoro-2-(((2S,4R)-4-methoxypyrrolidin-2-yl)methoxy)pyrido[4,3-d]pyrimidine Synthesized according to Example 29, Step H substituting tert-butyl(2S,4R)-2-(hydroxymethyl)-4-methoxypyrrolidine-1-carboxylate in place of (S)-(1-isopropylpyrrolidin-2-yl) methanol followed by deprotection using Example 2, Step I, (21 mg, 10%). LCMS (MM-ES+APCI, Pos): m/z 549.3 (M+H).

Example 352

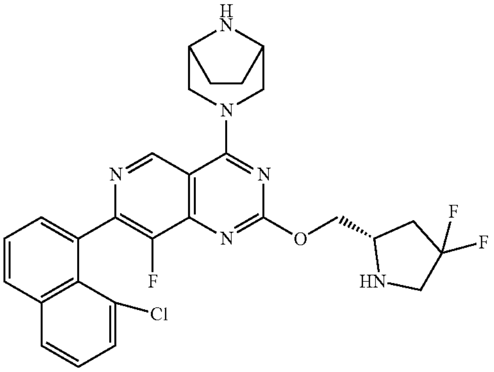 [SMILES: Fc1c(-c2cccc3cccc(Cl)c23)ncc2c(N3CC4CCC(C3)N4)nc(OC[C@@H]3CC(F)(F)CN3)nc12]

4-((1R,5S)-3,8-diazabicyclo[3.2.1]octan-3-yl)-7-(8-chloronaphthalen-1-yl)-2-(((S)-4,4-difluoropyrrolidin-2-yl)methoxy)-8-fluoropyrido[4,3-d]pyrimidine bis(2,2,2-trifluoroacetate)

Synthesized according to Example 29, Step H substituting (S)-tert-butyl 4,4-difluoro-2-(hydroxymethyl)pyrrolidine-1-carboxylate in place of (S)-(1-isopropylpyrrolidin-2-yl) methanol followed by deprotection using Example 2, Step I, (29 mg, 15%). LCMS (MM-ES+APCI, Pos): m/z 555.2 (M+H).

Example 353

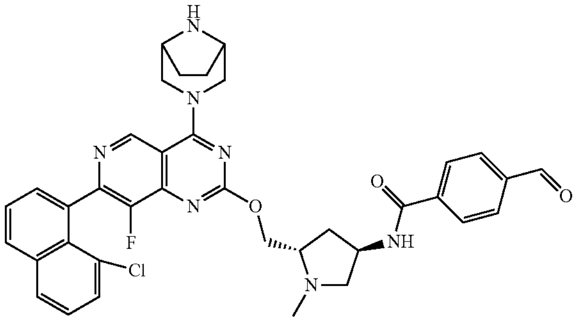 [SMILES: CN1C[C@H](NC(=O)c2ccc(C=O)cc2)C[C@H]1COc1nc(N2CC3CCC(C2)N3)c2cnc(-c3cccc4cccc(Cl)c34)c(F)c2n1]

N-((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)-4-formylbenzamide

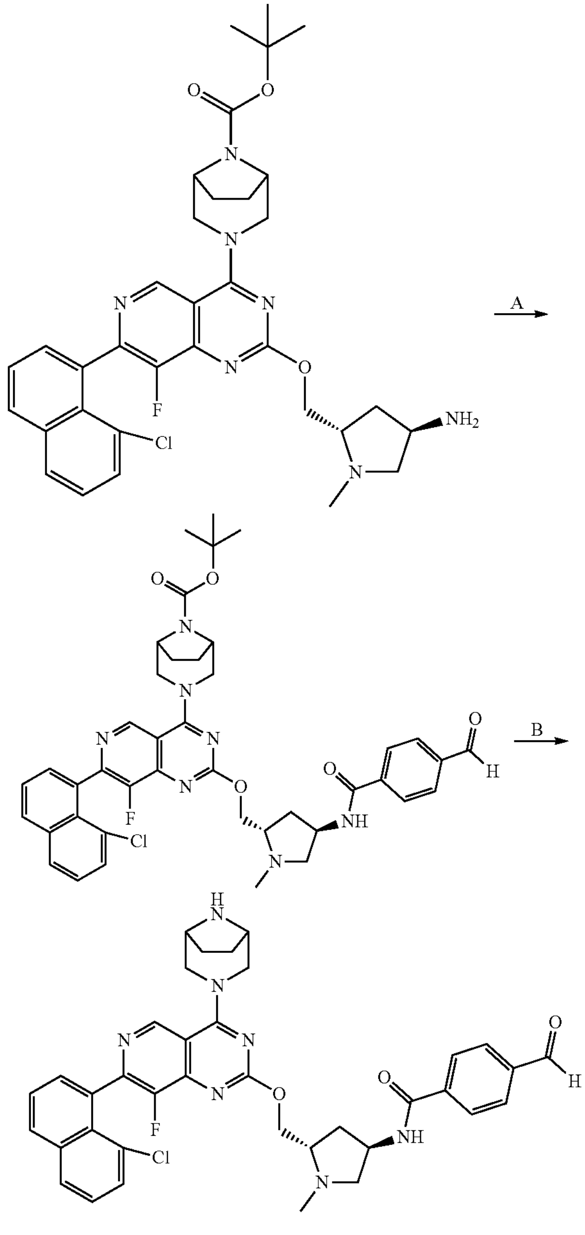

N-((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)-4-formylbenzamide tris(2,2,2-trifluoroacetate). To a solution of tert-butyl(1R,5S)-3-(7-(8-chloronaphthalen-1-yl)-8-fluoro-2-(((2S,4R)-4-(4-formylbenzamido)-1-methylpyrrolidin-2-yl)methoxy)pyrido[4,3-d]pyrimidin-4-yl)-3,8-diazabicyclo[3.2.1]octane-8-carboxylate (14 mg, 0.018 mmol) in DCM (0.60 mL) was added TFA (0.30 mL). The solution was stirred at rt for 45 min and concentrated to dryness. The residue was purified by preparative C18 HPLC (Gilson, 0-95% $CH_3CN/H_2O$ with 0.1% TFA). The desired fractions were combined and lyophilized to give the title product (7.0 mg, 38%) as a bis TFA salt. LCMS (MM-ES+APCI, Pos): m/z 680.3 (M+H).

Example 354

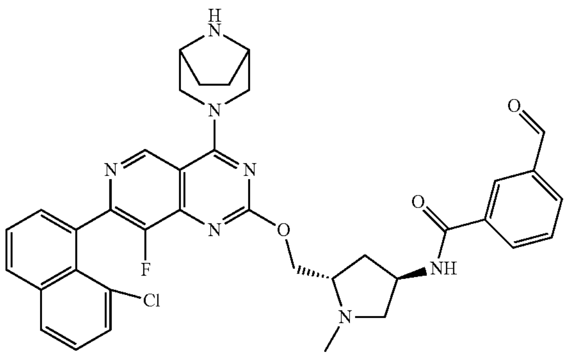 [SMILES: CN1C[C@H](NC(=O)c2cccc(C=O)c2)C[C@H]1COc1nc(N2CC3CCC(C2)N3)c2cnc(-c3cccc4cccc(Cl)c34)c(F)c2n1]

N-((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)-3-formylbenzamide Synthesized according to Example 353 substituting 3-formyl benzoic acid for 4-formyl benzoic acid in Step A to give product as the bis TFA salt (11 mg, 66%). LCMS (MM-ES+APCI, Pos): m/z 680.3 (M+H).

Example 355

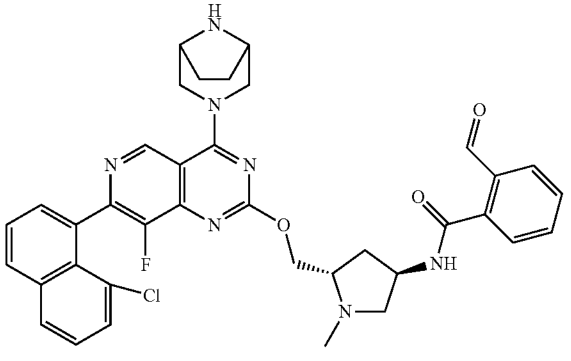 [SMILES: CN1C[C@H](NC(=O)c2ccccc2C=O)C[C@H]1COc1nc(N2CC3CCC(C2)N3)c2cnc(-c3cccc4cccc(Cl)c34)c(F)c2n1]

N-((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)-2-formylbenzamide Synthesized according to Example 353 substituting 2-formyl benzoic acid for 4-formyl benzoic acid in Step A to give product as the bis TFA salt (4.5 mg, 37%). LCMS (MM-ES+APCI, Pos): m/z 680.3 (M+H).

Example 356

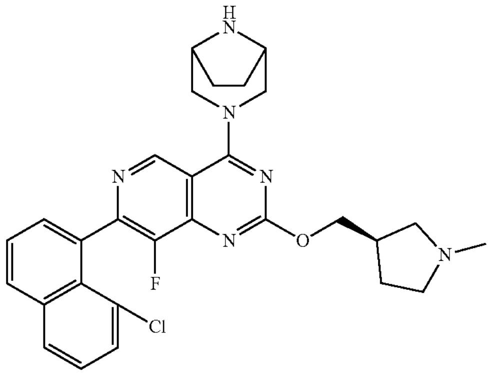 [SMILES: CN1CC[C@@H](COc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-8-fluoro-2-(((R)-1-methylpyrrolidin-3-yl)methoxy)pyrido[4,3-d]pyrimidine

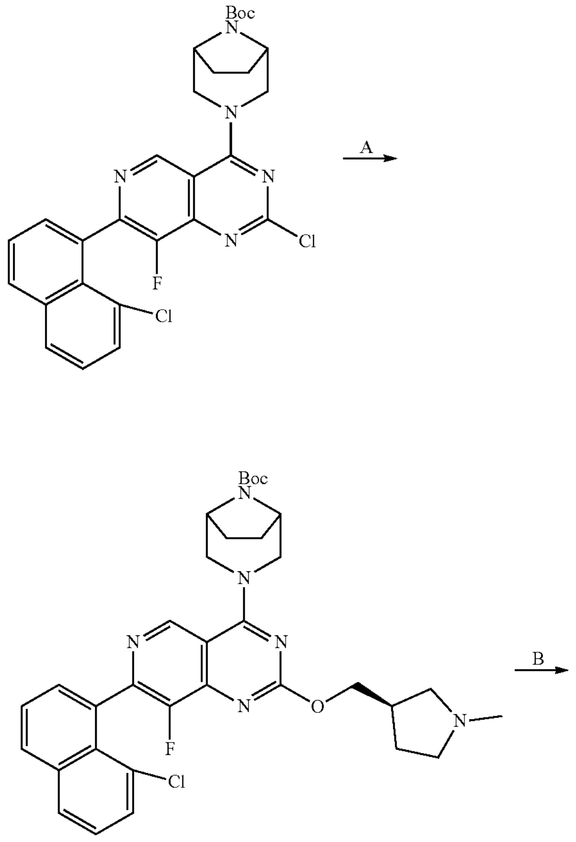

-continued

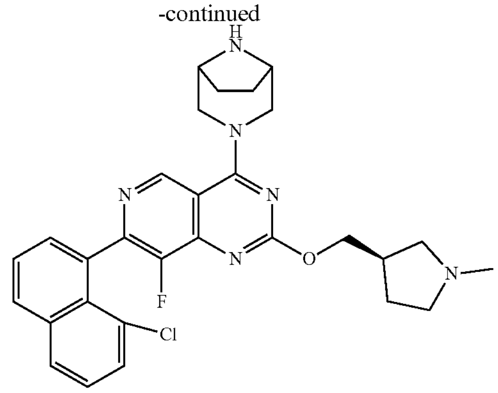

4-((1R,5S)-3,8-diazabicyclo[3.2.1]octan-3-yl)-7-(8-chloronaphthalen-1-yl)-8-fluoro-2-(((R)-1-methylpyrrolidin-3-yl)methoxy)pyrido[4,3-d]pyrimidine bis(2,2,2-trifluoroacetate). Tert-butyl(1R,5S)-3-(7-(8-chloronaphthalen-1-yl)-8-fluoro-2-(((S)-1-methylpyrrolidin-3-yl)methoxy)pyrido[4,3-d]pyrimidin-4-yl)-3,8-diazabicyclo[3.2.1]octane-8-carboxylate (36 mg, 0.056 mmol) was added to a round bottom flask with a stir bar. DCM (1 mL) and TFA (0.5 mL) were added at room temperature and the reaction was stirred for 2 hours. The reaction was concentrated to dryness, and the residue was purified via reverse phase chromatography (C18, 0-60% MeCN in water with 0.1% TFA). The fractions containing the product were combined, frozen, and lyophilized to yield 4-((1R,5S)-3,8-diazabicyclo[3.2.1]octan-3-yl)-7-(8-chloronaphthalen-1-yl)-8-fluoro-2-(((R)-1-methylpyrrolidin-3-yl)methoxy)pyrido[4,3-d]pyrimidine bis(2,2,2-trifluoroacetate) as a white solid (42 mg, 98%). LCMS (MM-ES+APCI, Pos): m/z 533.3 (M+H).

Example 357

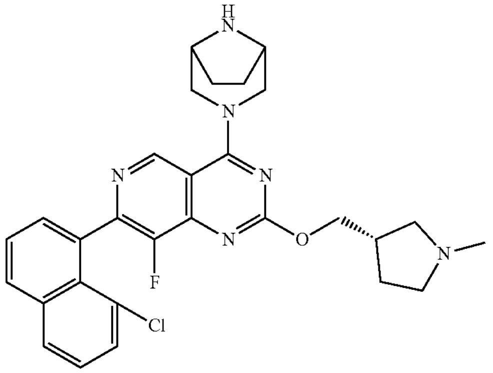 [SMILES: CN1CC[C@H](COc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-8-fluoro-2-(((S)-1-methylpyrrolidin-3-yl)methoxy)pyrido[4,3-d]pyrimidine Synthesized according to Example 356 substituting (S)-(1-methylpyrrolidin-3-yl)methanol for (R)-(1-methylpyrrolidin-3-yl)methanol in step A to give 4-((1R,5S)-3,8-diazabicyclo[3.2.1]octan-3-yl)-7-(8-chloronaphthalen-1-yl)-8-fluoro-2-(((S)-1-methylpyrrolidin-3-yl)methoxy)pyrido[4,3-d]pyrimidine as the bis TFA salt (54 mg, 85% as). LCMS (MM-ES+APCI, Pos): m/z 533.2 (M+H).

Example 358

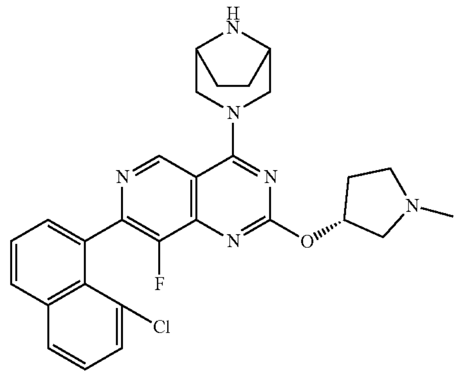 [SMILES: CN1CC[C@@H](Oc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-8-fluoro-2-(((R)-1-methylpyrrolidin-3-yl)oxy)pyrido[4,3-d]pyrimidine Synthesized according to Example 356 substituting (R)-1-methylpyrrolidin-3-ol for (R)-(1-methylpyrrolidin-3-yl)methanol in step A to give 4-((1R,5S)-3,8-diazabicyclo[3.2.1]octan-3-yl)-7-(8-chloronaphthalen-1-yl)-8-fluoro-2-(((R)-1-methylpyrrolidin-3-yl)oxy)pyrido[4,3-d]pyrimidine as the bis TFA salt (30 mg, 56%). LCMS (MM-ES+APCI, Pos): m/z 519.2 (M+H).

Example 359

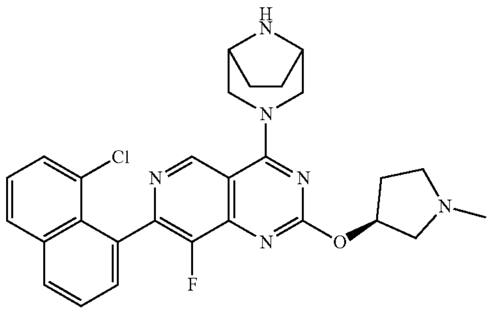 [SMILES: CN1CC[C@H](Oc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-8-fluoro-2-(((S)-1-methylpyrrolidin-3-yl)oxy)pyrido[4,3-d]pyrimidine Synthesized according to Example 356 substituting (S)-1-methylpyrrolidin-3-ol in for (R)-(1-methylpyrrolidin-3-yl)methanol in step A to give 4-((1R,5S)-3,8-diazabicyclo[3.2.1]octan-3-yl)-7-(8-chloronaphthalen-1-yl)-8-fluoro-2-(((S)-1-methylpyrrolidin-3-yl)oxy)pyrido[4,3-d]pyrimidine bis(2,2,2-trifluoroacetate) as the bis TFA salt (27 mg, 62%). LCMS (MM-ES+APCI, Pos): m/z 519.2 (M+H).

Example 360

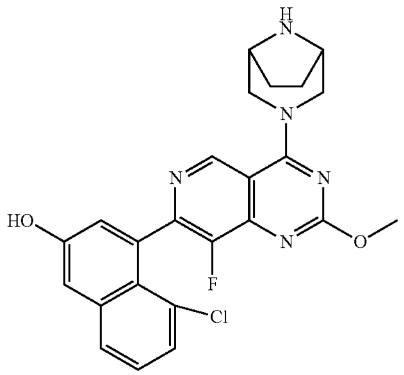 [SMILES: COc1nc(N2CC3CCC(C2)N3)c2cnc(-c3cc(O)cc4cccc(Cl)c34)c(F)c2n1]

4-(4-((1R,5S)-3,8-diazabicyclo[3.2.1]octan-3-yl)-8-fluoro-2-methoxypyrido[4,3-d]pyrimidin-7-yl)-5-chloronaphthalen-2-ol

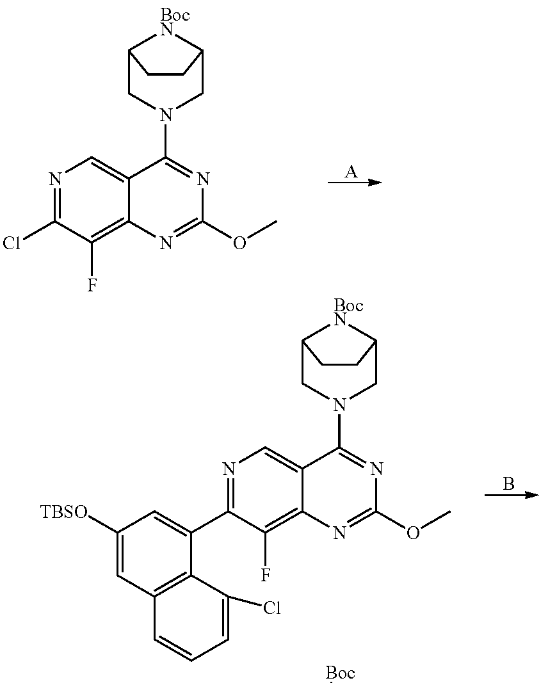

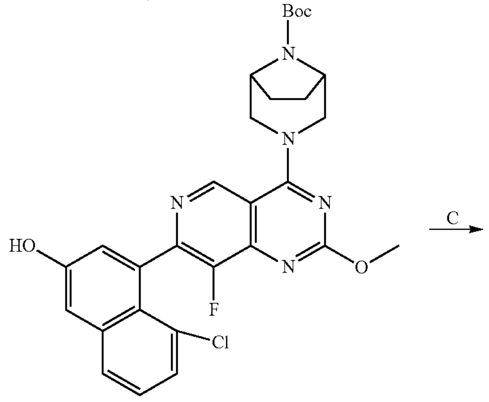

-continued

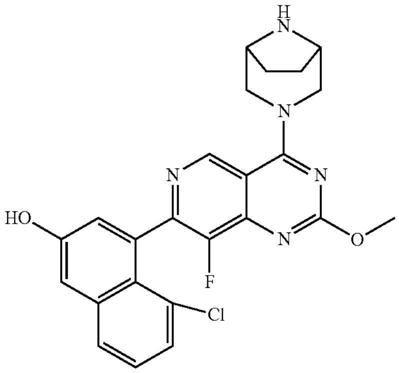

4-(4-((1R,5S)-3,8-diazabicyclo[3.2.1]octan-3-yl)-8-fluoro-2-methoxypyrido[4,3-d]pyrimidin-7-yl)-5-chloronaphthalen-2-ol: To a solution of tert-butyl(1R,5S)-3-(7-(8-chloro-3-hydroxynaphthalen-1-yl)-8-fluoro-2-methoxypyrido[4,3-d]pyrimidin-4-yl)-3,8-diazabicyclo[3.2.1]octane-8-carboxylate (6.1 mg, 0.011 mmol) in DCM (0.5 mL) was added 4N HCl/dioxane (0.5 mL). The mixture was stirred at ambient temperature for 1 hour, concentrated, and dried in vacuo. The residue was triturated with $Et_2O$, filtered, and dried in vacuo to afford 4-(4-((1R,5S)-3,8-diazabicyclo[3.2.1]octan-3-yl)-8-fluoro-2-methoxypyrido[4,3-d]pyrimidin-7-yl)-5-chloronaphthalen-2-ol HCl salt. LCMS (MM-ES+APCI, Pos): m/z 466.1 [M+H].

Example 361

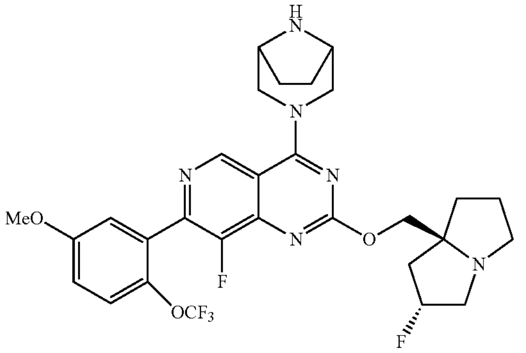 [SMILES: COc1ccc(OC(F)(F)F)c(-c2ncc3c(N4CC5CCC(C4)N5)nc(OC[C@@]45CCCN4C[C@H](F)C5)nc3c2F)c1]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methoxy-2-(trifluoromethoxy)phenyl)pyrido[4,3-d]pyrimidine (racemic, trans)

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methoxy-2-(trifluoromethoxy)phenyl)pyrido[4,3-d]pyrimidine dihydrochloride (racemic, trans) (15 mg, 40%). LCMS (MM-ES+APCI, Pos): m/z 607.2 (M+H).

Example 362

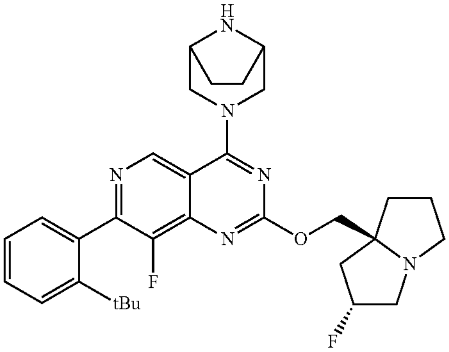 [SMILES: CC(C)(C)c1ccccc1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-7-(2-(tert-butyl)phenyl)-8-fluoro-2-((2-fluorotetrahydro-1H-pyrrolizin-7a(5H)-yl)methoxy)pyrido[4,3-d]pyrimidine (racemic, trans)

4-((1R,5S)-3,8-diazabicyclo[3.2.1]octan-3-yl)-7-(2-(tert-butyl)phenyl)-8-fluoro-2-((2-fluorotetrahydro-1H-pyrrolizin-7a(5H)-yl)methoxy)pyrido[4,3-d]pyrimidine dihydrochloride (racemic, trans) (15 mg, 65%). LCMS (MM-ES+APCI, Pos): m/z 549.3 (M+H).

Example 363

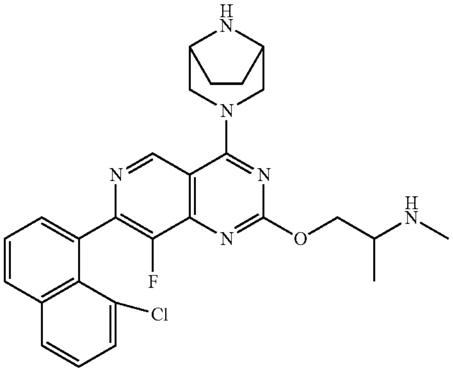 [SMILES: CNC(C)COc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-2-(((S)-4,4-difluoropyrrolidin-2-yl)methoxy)-8-fluoropyrido[4,3-d]pyrimidine bis(2,2,2-trifluoroacetate)

Synthesized according to Example 29, Step H substituting 2-(methylamino)-1-propanol in place of (S)-(1-isopropylpyrrolidin-2-yl)methanol followed by deprotection using Example 2, Step I (19 mg, 21%). LCMS (MM-ES+APCI, Pos): m/z 507.2 (M+H).

Example 364
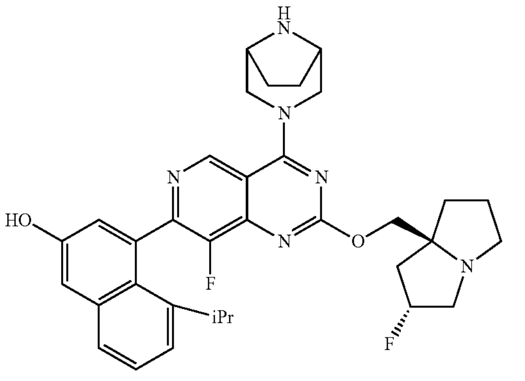 [SMILES: CC(C)c1cccc2cc(O)cc(-c3ncc4c(N5CC6CCC(C5)N6)nc(OC[C@@]56CCCN5C[C@H](F)C6)nc4c3F)c12]
4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-isopropylnaphthalen-2-ol (racemic, trans)
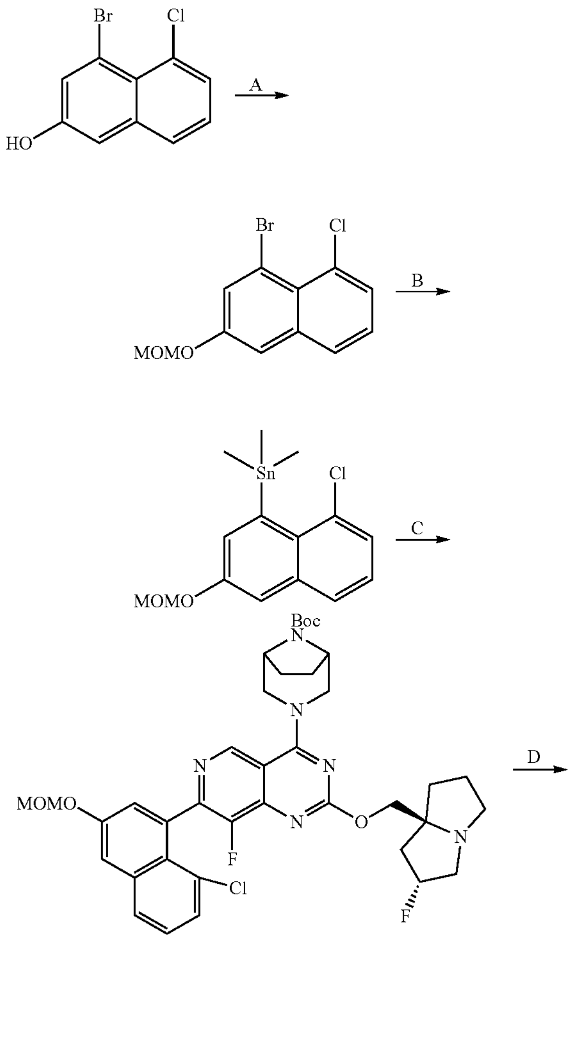
-continued
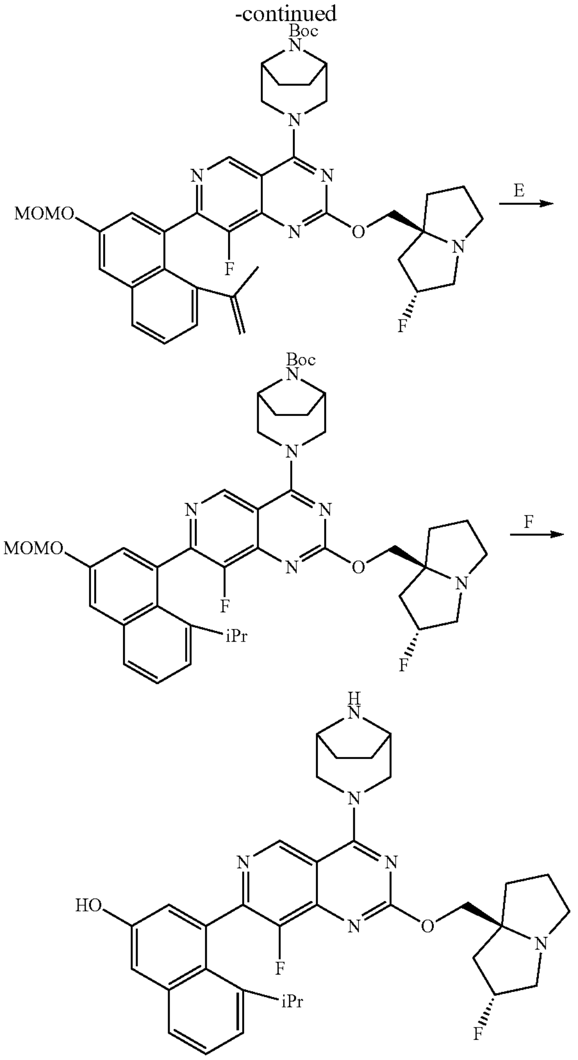
4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-isopropylnaphthalen-2-ol dihydrochloride (racemic, trans) (4.0 mg, 55%). LCMS (MM-ES+APCI, Pos): m/z 601.3 (M+H).
Example 365
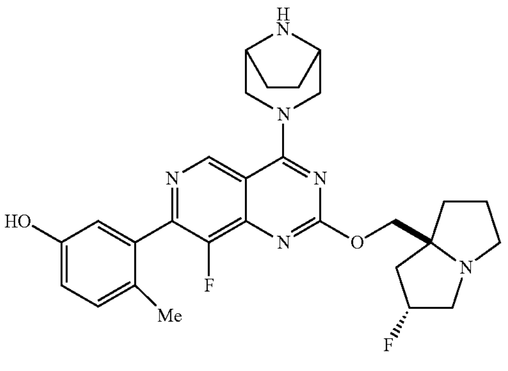

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-methylphenol (racemic, trans)

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-methylphenol dihydrochloride (racemic, trans). Synthesized according to Example 229, Step B substituting tert-butyl(1R,5S)-3-(8-fluoro-2-((2-fluorotetrahydro-1H-pyrrolizin-7a(5H)-yl)methoxy)-7-(5-hydroxy-2-methylphenyl)pyrido[4,3-d]pyrimidin-4-yl)-3,8-diazabicyclo[3.2.1]octane-8-carboxylate (racemic, trans) in place of tert-butyl(1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-methylphenol dihydrochloride (racemic, trans) (34 mg, 100%). LCMS (MM-ES+APCI, Pos): m/z 523.2 (M+H).

Example 366

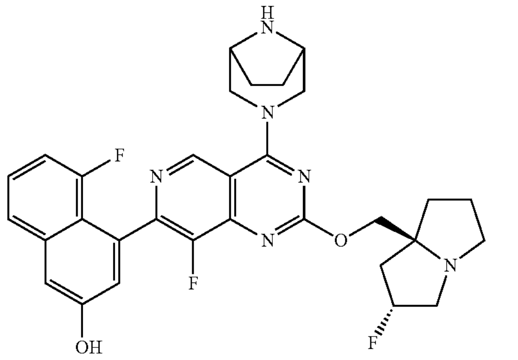 [SMILES: Oc1cc(-c2ncc3c(N4CC5CCC(C4)N5)nc(OC[C@@]45CCCN4C[C@H](F)C5)nc3c2F)c2c(F)cccc2c1]

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-fluoronaphthalen-2-ol (racemic, trans)

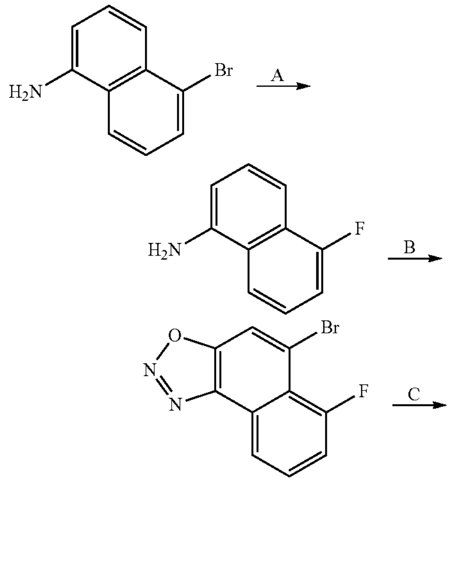

-continued

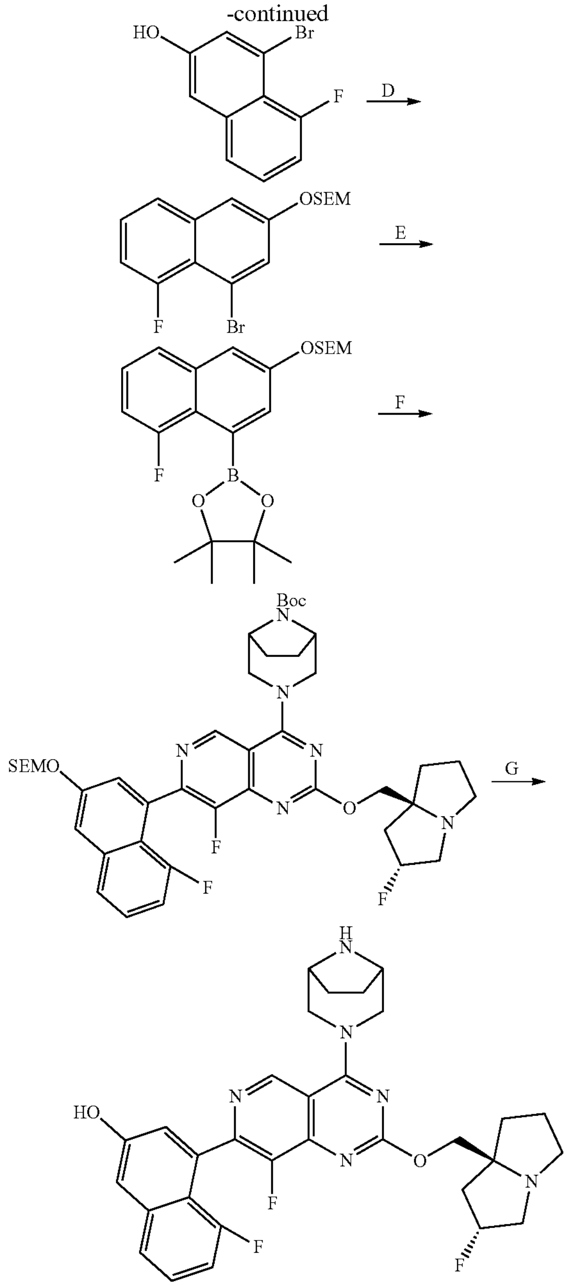

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-fluoronaphthalen-2-ol tris(2,2,2-trifluoroacetate) (racemic, trans). To a vial containing tert-butyl(1R,5S)-3-(8-fluoro-7-(8-fluoro-3-((2-(trimethylsilyl)ethoxy)methoxy)naphthalen-1-yl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (20 mg, 0.025 mmol) was added DCM (0.5 mL) and TFA (1 mL). The mixture was stirred at rt for 0.5 h and concentrated to dryness. The residue was purified by preparative C18 HPLC (Gilson, 0-95% $CH_3CN/H_2O$ with 0.1% TFA). The desired fractions were combined and lyophilized to give the title compound (23 mg, 101%) as the bis TFA salt. LCMS (MM-ES+APCI, Pos): m/z 577.3 (M+H).

Example 367

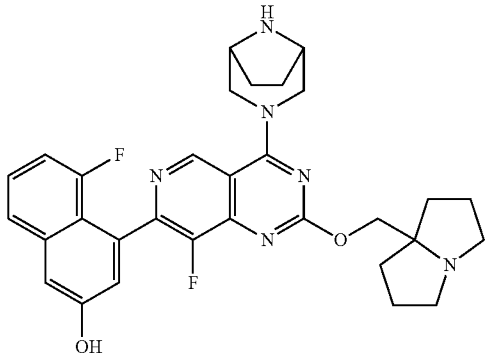 [SMILES: Oc1cc(-c2ncc3c(N4CC5CCC(C4)N5)nc(OCC45CCCN4CCC5)nc3c2F)c2c(F)cccc2c1]

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-fluoronaphthalen-2-ol tris(2,2,2-trifluoroacetate)

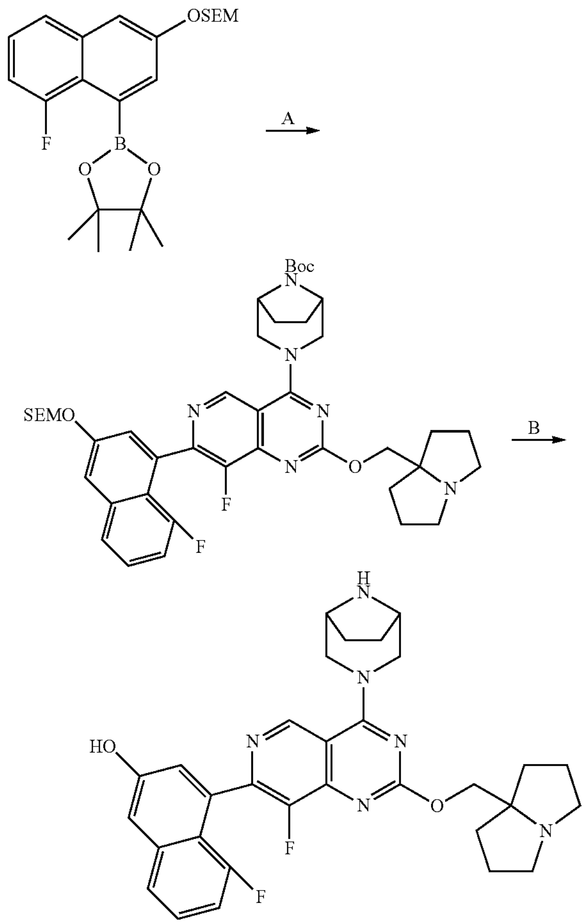

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-fluoronaphthalen-2-ol tris(2,2,2-trifluoroacetate). To a vial containing tert-butyl(1R,5S)-3-(8-fluoro-7- (8-fluoro-3-((2-(trimethylsilyl)ethoxy)methoxy)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (20 mg, 0.025 mmol) was added TFA (1 mL). The mixture was stirred at rt for 0.5 h and concentrated to dryness. The residue was purified by preparative C18 HPLC (Gilson, 0-95% $CH_3CN$/$H_2O$ with 0.1% TFA). The desired fractions were combined and lyophilized to give the title compound (23 mg, 101%) as the bis TFA salt. LCMS (MM-ES+APCI, Pos): m/z 559.3 (M+H).

Example 368

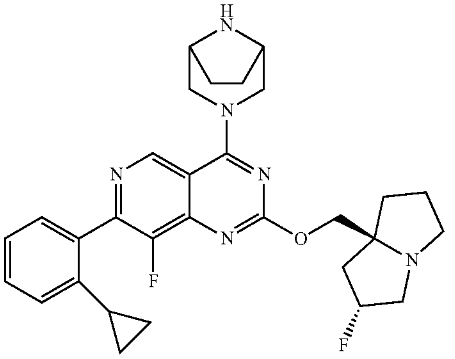 [SMILES: Fc1c(-c2ccccc2C2CC2)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-7-(2-cyclopropylphenyl)-8-fluoro-2-((2-fluorotetrahydro-1H-pyrrolizin-7a(5H)-yl)methoxy)pyrido[4,3-d]pyrimidine (racemic, trans)

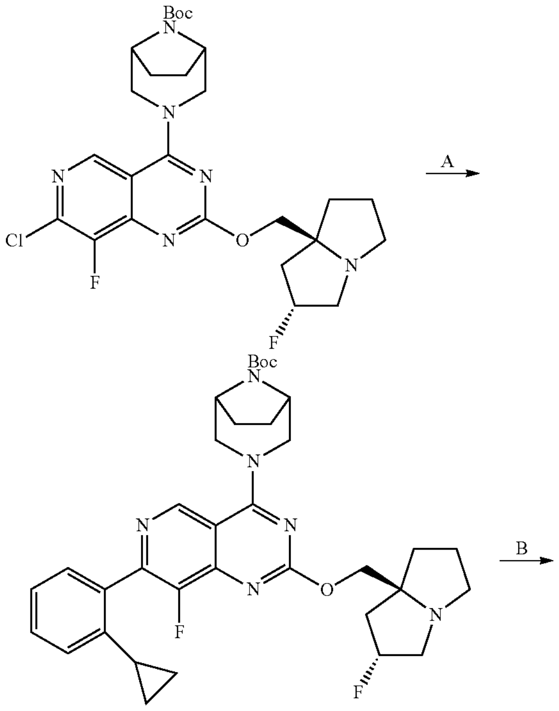

-continued

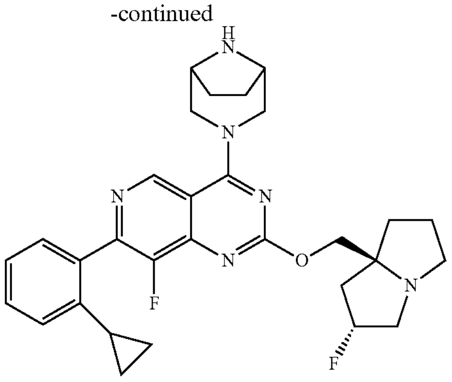

4-((1R,5S)-3,8-diazabicyclo[3.2.1]octan-3-yl)-7-(2-cyclopropylphenyl)-8-fluoro-2-((2-fluorotetrahydro-1H-pyrrolizin-7a(5H)-yl)methoxy)pyrido[4,3-d]pyrimidine dihydrochloride (racemic, trans). Synthesized according to Example 229, Step B substituting tert-butyl(1R,5S)-3-(7-(2-cyclopropylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl(1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-7-(2-cyclopropylphenyl)-8-fluoro-2-((2-fluorotetrahydro-1H-pyrrolizin-7a(5H)-yl)methoxy)pyrido[4,3-d]pyrimidine dihydrochloride (racemic, trans) (25 mg, 55%). LCMS (MM-ES+APCI, Pos): m/z 533.3 (M+H).

Example 369

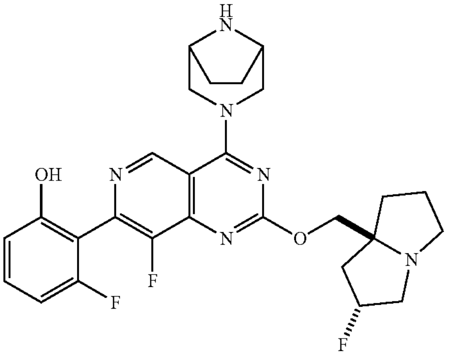

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-fluorophenol (racemic, trans)

Synthesized according to Example 3, Steps G-I substituting (2-fluorotetrahydro-1H-pyrrolizin-7a(5H)-yl)methanol (racemic, trans) in place of 2-(1-methyl-1H-imidazol-2-yl)ethan-1-ol in Step G and (2-fluoro-6-hydroxyphenyl)boronic acid in place of 4-(4,4,5,5-tetramethyl-1,3,2-dioxaborolan-2-yl)naphthalen-2-ol in Step H to afford 2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-fluorophenol bis(2,2,2-trifluoroacetate) (racemic, trans) (31 mg, 83%). LCMS (MM-ES+APCI, Pos): m/z 527.2 (M+H).

Example 370

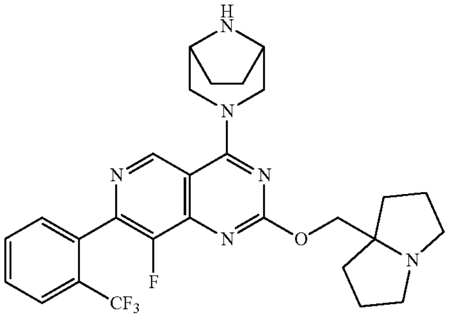 [SMILES: Fc1c(-c2ccccc2C(F)(F)F)ncc2c(N3CC4CCC(C3)N4)nc(OCC34CCCN3CCC4)nc12]

4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethyl)phenyl)pyrido[4,3-d]pyrimidine

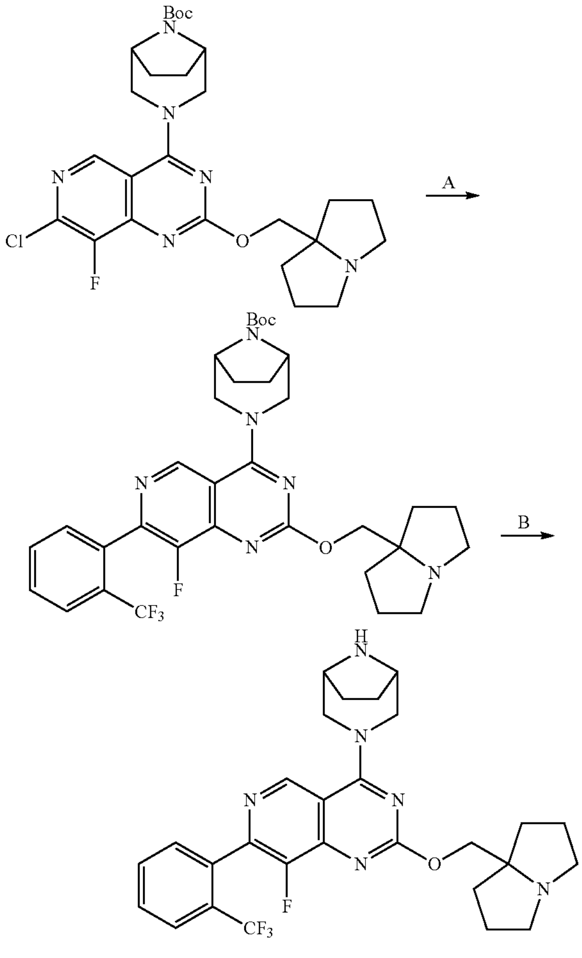

4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethyl)phenyl)pyrido[4,3-d]pyrimidine bis(2,2,2-trifluoroacetate) (35 mg, 82%). LCMS (MM-ES+APCI, Pos): m/z 543.3 (M+H).

Example 371

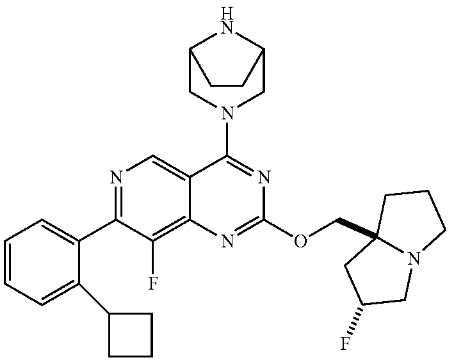

4-((1R,5S)-3,8-diazabicyclo[3.2.1]octan-3-yl)-7-(2-cyclobutylphenyl)-8-fluoro-2-((2-fluorotetrahydro-1H-pyrrolizin-7a(5H)-yl)methoxy)pyrido[4,3-d]pyrimidine (racemic, trans)

4-((1R,5S)-3,8-diazabicyclo[3.2.1]octan-3-yl)-7-(2-cyclobutylphenyl)-8-fluoro-2-((2-fluorotetrahydro-1H-pyrrolizin-7a(5H)-yl)methoxy)pyrido[4,3-d]pyrimidine dihydrochloride (racemic, trans). Synthesized according to Example 229, Step B substituting tert-butyl(1R,5S)-3-(7-(2-cyclobutylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place tert-butyl(1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-7-(2-cyclobutylphenyl)-8-fluoro-2-((2-fluorotetrahydro-1H-pyrrolizin-7a(5H)-yl)methoxy)pyrido[4,3-d]pyrimidine dihydrochloride (racemic, trans) (9.0 mg, 31%). LCMS (MM-ES+APCI, Pos): m/z 547.3 (M+H).

Example 372

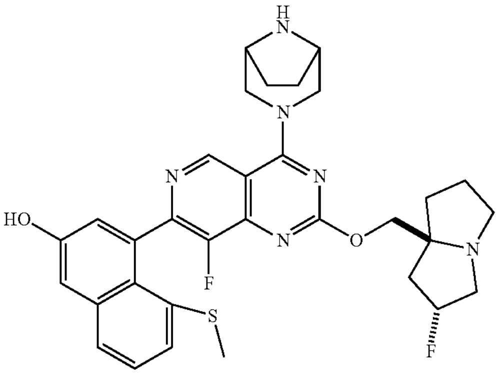

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-(methylthio)naphthalen-2-ol (racemic, trans)

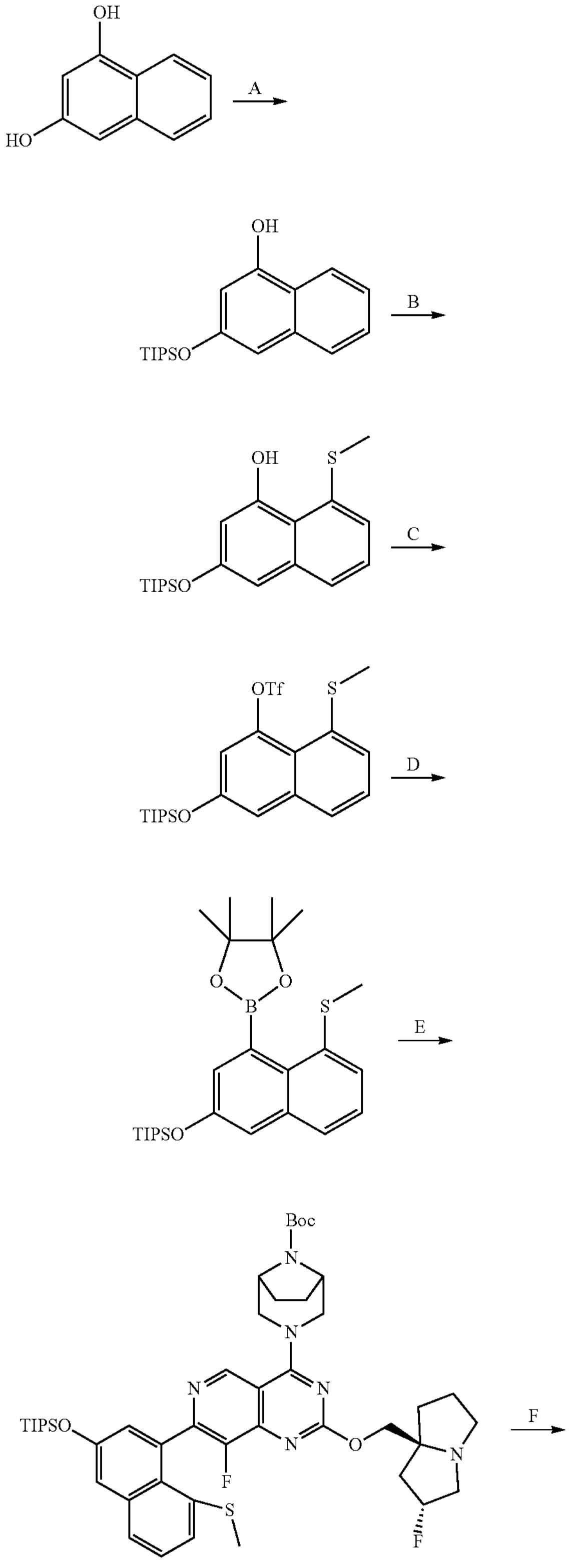

-continued

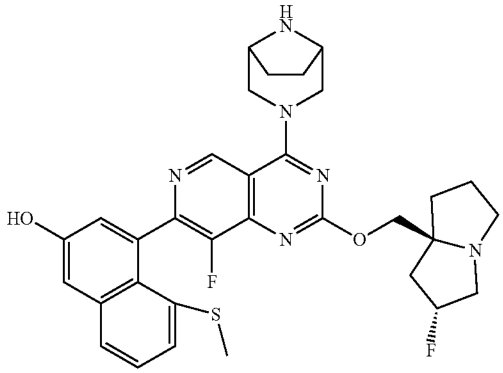

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-(methylthio)naphthalen-2-ol (racemic, trans). A stirred solution of tert-butyl (1R,5S)-3-(8-fluoro-2-((2-fluorotetrahydro-1H-pyrrolizin-7a(5H)-yl)methoxy)-7-(8-(methylthio)-3-((triisopropylsilyl)oxy)naphthalen-1-yl)pyrido[4,3-d]pyrimidin-4-yl)-3,8-diazabicyclo[3.2.1]octane-8-carboxylate (racemic, trans) (12 mg, 0.014 mmol) in DCM was cooled to −20° C. and 4M hydrogen chloride in dioxane (0.35 mL, 1.4 mmol) was added. The reaction mixture was stirred at r.t. for 1.5 h, diluted with chloroform, cooled to −70° C., and evaporated under high vacuum. The residue was dissolved in 1M tetrabutylammonium fluoride in THF (0.14 mL, 0.14 mmol) and stirred at r.t. for 15 min. The solution was diluted with aq. buffer pH~8 (3 mL) and saturated with NaCl. The solution was extracted with DCM (5×7 mL) and 10% MeOH/DCM (3×5 mL). The combined organic phases were chromatographed on a reverse phase column, C18, using 5-95% MeCN/$H_2O$+0.1% TFA and freebased (Agilent PL-HCO3 MP SPE tube) to yield the target product as yellow solid (6.0 mg, 65%). LCMS (MM-ES+APCI, Pos): m/z 605.3 (M+H).

Example 373

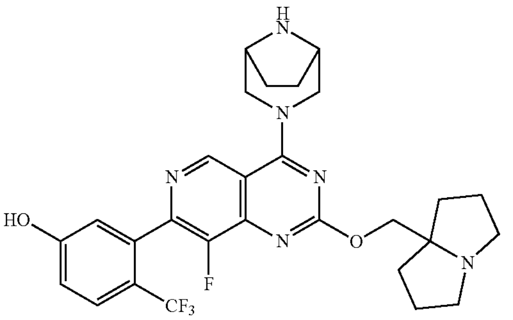 [SMILES: Oc1ccc(C(F)(F)F)c(-c2ncc3c(N4CC5CCC(C4)N5)nc(OCC45CCCN4CCC5)nc3c2F)c1]

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-(trifluoromethyl)phenol

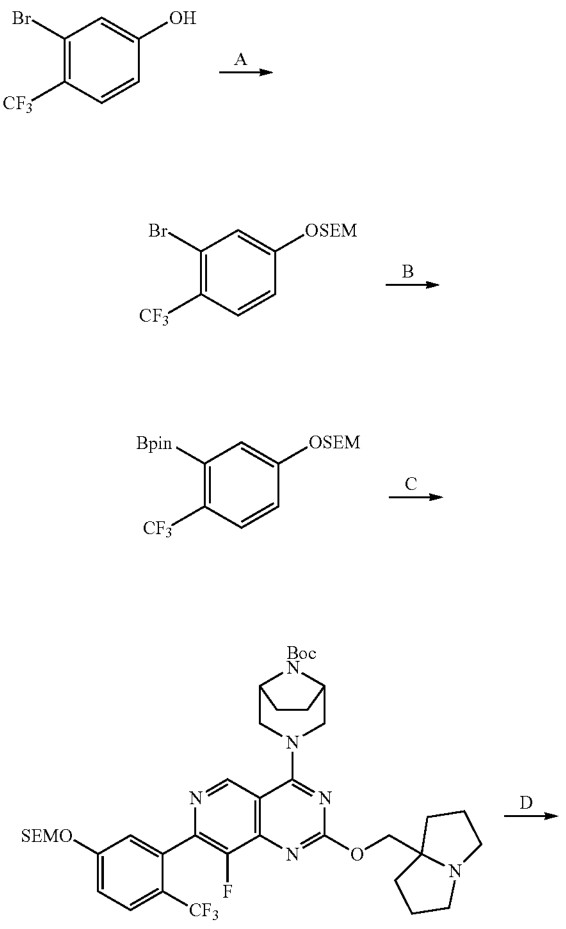

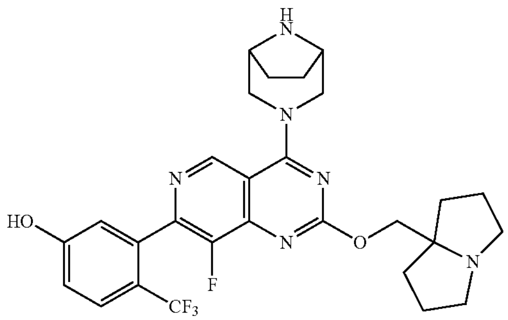

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-(trifluoromethyl)phenol bis(2,2,2-trifluoroacetate) (30 mg, 72%). LCMS (MM-ES+APCI, Pos): m/z 559.3 (M+H).

Example 374

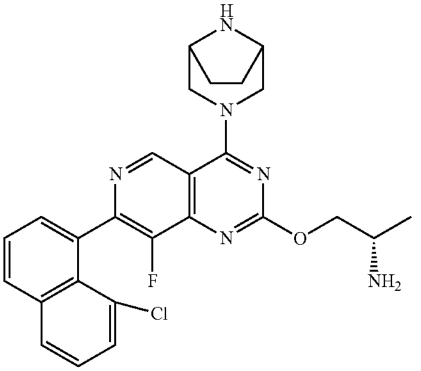 [SMILES: C[C@H](N)COc1nc(N2CC3CCC(C2)N3)c2cnc(-c3cccc4cccc(Cl)c34)c(F)c2n1]

(S)-1-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) propan-2-amine bis(2,2,2-trifluoroacetate)

Synthesized according to Example 29, Step H substituting BOC-L-alaninol in place of (S)-(1-isopropylpyrrolidin-2-yl) methanol followed by deprotection using Example 2, Step I, (9 mg, 23%). LCMS (MM-ES+APCI, Pos): m/z 493.2 (M+H).

Example 375

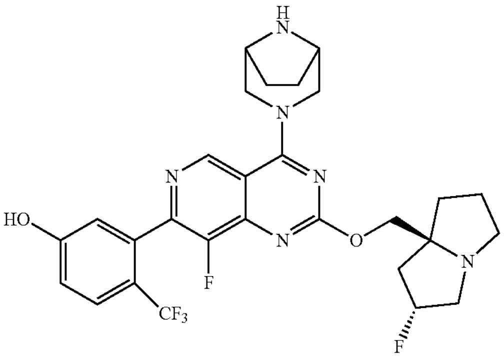 [SMILES: Oc1ccc(C(F)(F)F)c(-c2ncc3c(N4CC5CCC(C4)N5)nc(OC[C@@]45CCCN4C[C@H](F)C5)nc3c2F)c1]

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(trifluoromethyl)phenol (racemic, trans)

3-(4-((1R,5S)-3,8-diazabicyclo[3.2.1]octan-3-yl)-8-fluoro-2-((2-fluorotetrahydro-1H-pyrrolizin-7a(5H)-yl) methoxy)pyrido[4,3-d]pyrimidin-7-yl)-4-(trifluoromethyl) phenol bis(2,2,2-trifluoroacetate) (racemic, trans) (30 mg, 59%). LCMS (MM-ES+APCI, Pos): m/z 577.3 (M+H).

Example 376

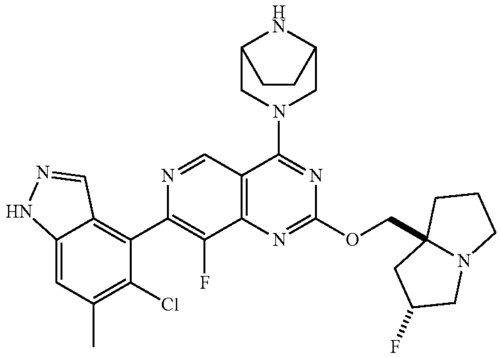

4-((1R,5S)-3,8-diazabicyclo[3.2.1]octan-3-yl)-7-(5-chloro-6-methyl-1H-indazol-4-yl)-8-fluoro-2-((2-fluorotetrahydro-1H-pyrrolizin-7a(5H)-yl)methoxy) pyrido[4,3-d]pyrimidine (racemic, trans)

Synthesized according to Example 3, Steps G-I substituting (2-fluorotetrahydro-1H-pyrrolizin-7a(5H)-yl)methanol (racemic, trans) in place of 2-(1-methyl-1H-imidazol-2-yl) ethan-1-ol in Step G and 5-chloro-6-methyl-1-(tetrahydro-2H-pyran-2-yl)-4-(4,4,5,5-tetramethyl-1,3,2-dioxaborolan-2-yl)-1H-indazole in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-7-(5-chloro-6-methyl-1H-indazol-4-yl)-8-fluoro-2-((2-fluorotetrahydro-1H-pyrrolizin-7a(5H)-yl)methoxy)pyrido[4,3-d]pyrimidine (racemic, trans) (18 mg, 59%). LCMS (MM-ES+APCI, Pos): m/z 581.3 (M+H).

Example 377

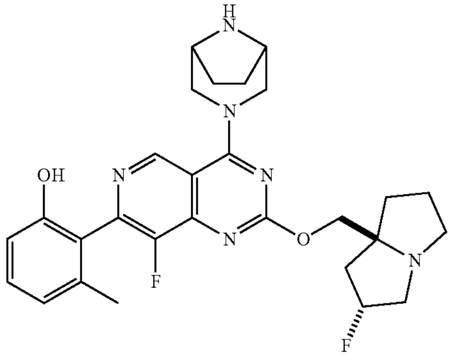

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-methylphenol (racemic, trans)

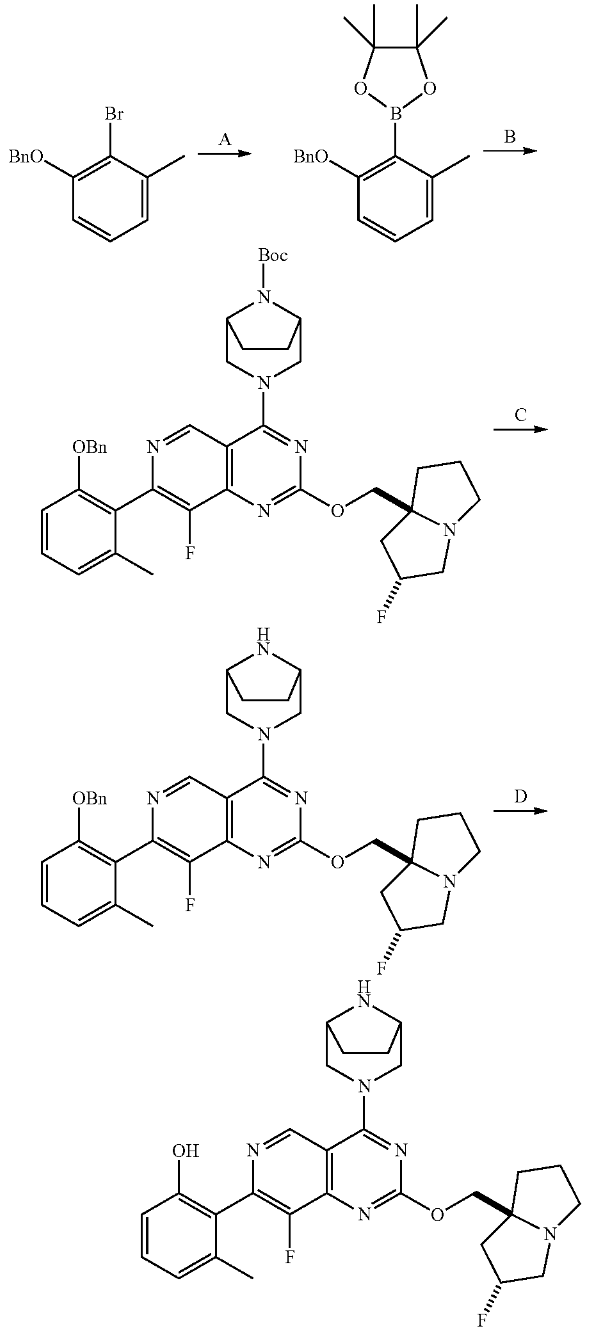

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-methylphenol (racemic, trans). A mixture of 7-(2-(benzyloxy)-6-methylphenyl)-4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidine (racemic, trans) (26 mg, 0.042 mmol), methanol (4 mL) and 10% palladium on carbon (20 mg) was degassed and stirred under hydrogen atmosphere for 5 h. The reaction mixture was filtered through Celite, the filtrate was evaporated in vacuo and chromatographed on a reverse phase column, C18, Gilson, eluting with 5-95% MeCN/$H_2O$+0.1% TFA. Fractions containing product were concentrated in vacuo, basified with phosphate buffer to pH 10 and extracted with DCM twice to give the product (4.0 mg, 18%) as a colorless solid. LCMS (MM-ES+APCI, Pos): m/z 523.3 (M+H).

Example 378

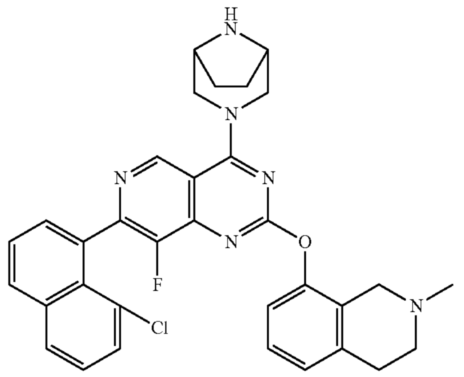 [SMILES: CN1CCc2cccc(Oc3nc(N4CC5CCC(C4)N5)c4cnc(-c5cccc6cccc(Cl)c56)c(F)c4n3)c2C1]

4-((1R,5S)-3,8-diazabicyclo[3.2.1]octan-3-yl)-7-(8-chloronaphthalen-1-yl)-8-fluoro-2-((2-methyl-1,2,3,4-tetrahydroisoquinolin-8-yl)oxy)pyrido[4,3-d]pyrimidine Synthesized according to Example 356 substituting 2-methyl-1,2,3,4-tetrahydroisoquinolin-8-ol for (R)-(1-methylpyrrolidin-3-yl)methanol in step A to give 4-((1R,5S)-3,8-diazabicyclo[3.2.1]octan-3-yl)-7-(8-chloronaphthalen-1-yl)-8-fluoro-2-((2-methyl-1,2,3,4-tetrahydroisoquinolin-8-yl)oxy)pyrido[4,3-d]pyrimidine as the bis TFA salt (45 mg, 60%). LCMS (MM-ES+APCI, Pos): m/z 581.2 (M+H).

Example 379

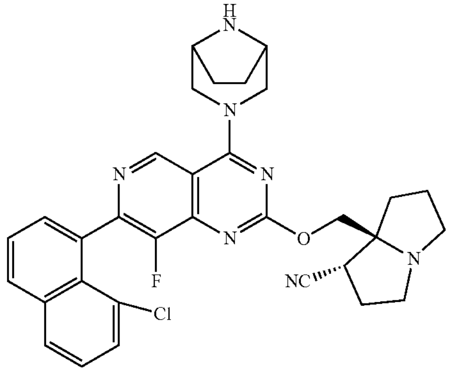 [SMILES: N#C[C@H]1CCN2CCC[C@@]12COc1nc(N2CC3CCC(C2)N3)c2cnc(-c3cccc4cccc(Cl)c34)c(F)c2n1]

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizine-1-carbonitrile (Mixture of trans Diastereomers)

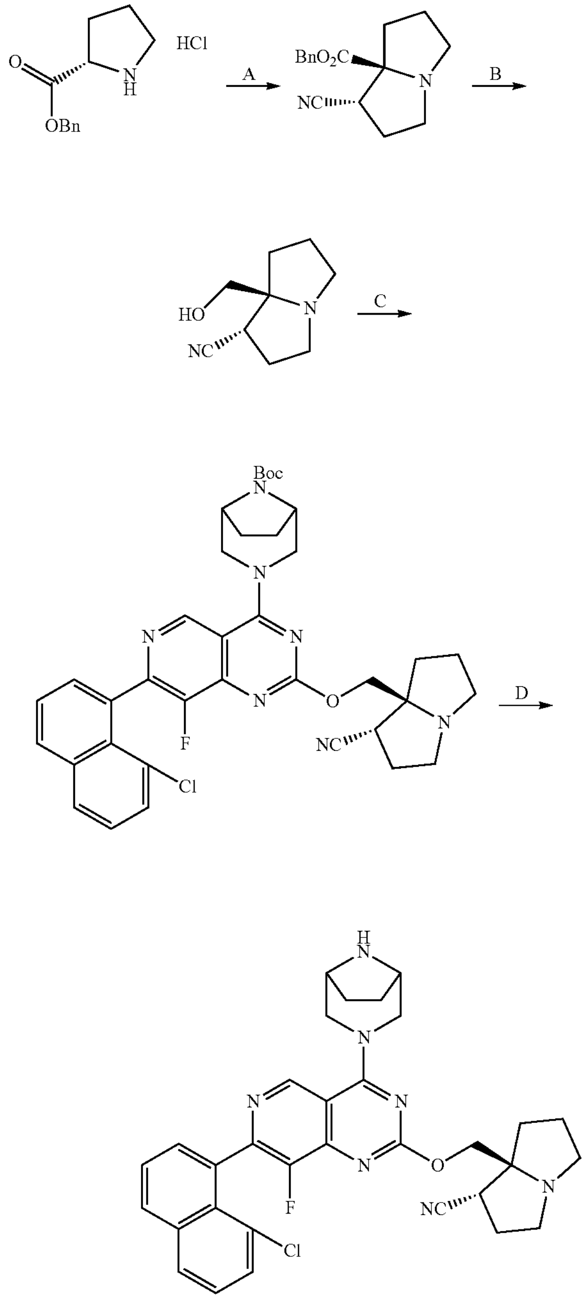

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizine-1-carbonitrile (Mixture of trans Diastereomers). To a solution of tert-butyl (1R,5S)-3-(7-(8-chloronaphthalen-1-yl)-2-((1-cyanotetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (mixture of trans diastereomers) (4.0 mg, 0.0058 mmol) in DCM (0.5 mL) at rt was added TFA (0.25 mL). The solution was stirred at r.t. for 0.5 h and concentrated to dryness. The residue was purified by preparative C18 HPLC (Gilson, 0-95% $CH_3CN/H_2O$ with 0.1% TFA). The desired fractions were combined, basified with $NaHCO_3$ (sat.), and extracted with DCM. The combined extract was dried ($Na_2SO_4$) and concentrated to give the title compound (3.0 mg, 88%) as a white solid. LCMS (MM-ES+APCI, Pos): m/z 584.2 (M+H).

Example 380

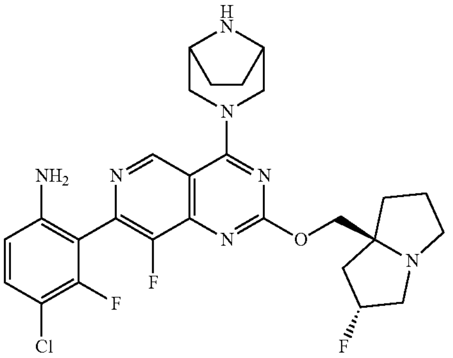 [SMILES: Nc1ccc(Cl)c(F)c1-c1ncc2c(N3CC4CCC(C3)N4)nc(OC[C@@]34CCCN3C[C@H](F)C4)nc2c1F]

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-chloro-3-fluoroaniline bis(2,2,2-trifluoroacetate) (racemic, trans)

Synthesized according to Example 196 substituting (2-fluorotetrahydro-1H-pyrrolizin-7a(5H)-yl)methanol (racemic, trans) in place of (tetrahydro-1H-pyrrolizin-7a(5H)-yl)methanol in step A and substituting (6-amino-3-chloro-2-fluorophenyl) boronic acid in place of 2,2-difluorobenzo[1,3]dioxole-4-boronic acid in step B to afford 2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-chloro-3-fluoroaniline bis(2,2,2-trifluoroacetate) (racemic, trans) (5.6 mg, 39%). LCMS (MM-ES+APCI, Pos): m/z 560.2 (M+H).

Example 381

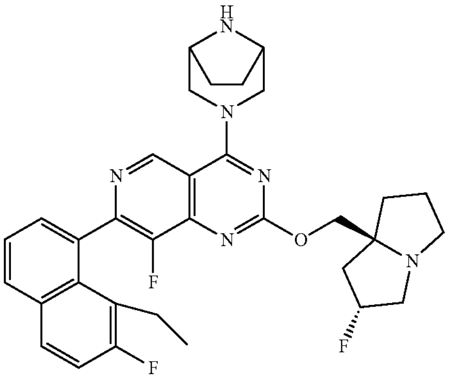 [SMILES: CCc1c(F)ccc2cccc(-c3ncc4c(N5CC6CCC(C5)N6)nc(OC[C@@]56CCCN5C[C@H](F)C6)nc4c3F)c12]

4-((1R,5S)-3,8-diazabicyclo[3.2.1]octan-3-yl)-7-(8-ethyl-7-fluoronaphthalen-1-yl)-8-fluoro-2-((2-fluoro-tetrahydro-1H-pyrrolizin-7a(5H)-yl)methoxy)pyrido[4,3-d]pyrimidine

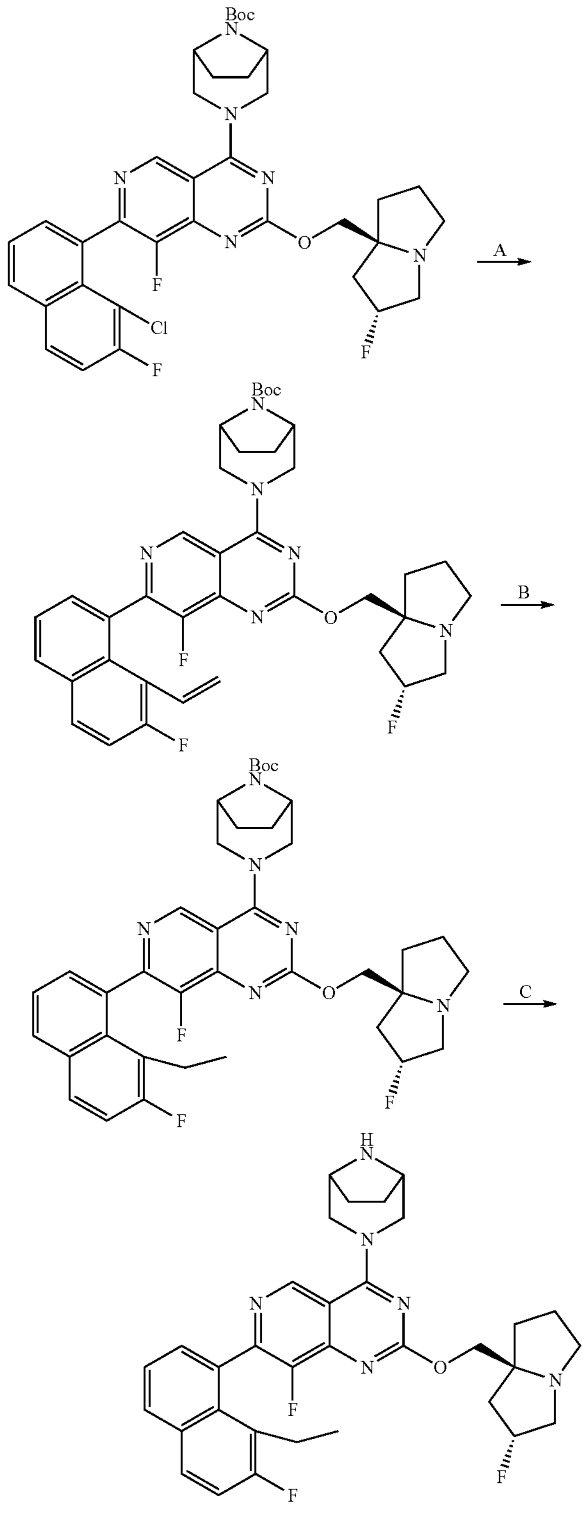

4-((1R,5S)-3,8-diazabicyclo[3.2.1]octan-3-yl)-7-(8-ethyl-7-fluoronaphthalen-1-yl)-8-fluoro-2-((2-fluorotetrahydro-1H-pyrrolizin-7a(5H)-yl)methoxy)pyrido[4,3-d]pyrimidine di-TFA salt (racemic, trans) (11 mg, 51%). LCMS (MM-ES+APCI, Pos): m/z 589.3 [M+H].

Example 382

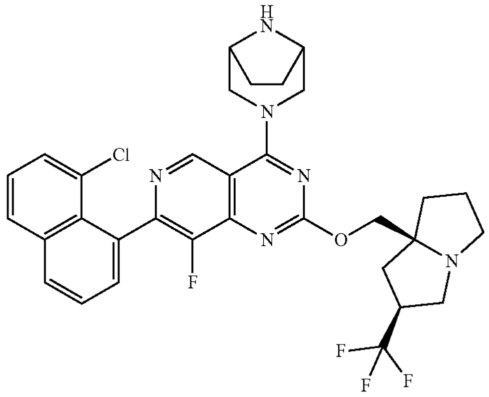 [SMILES: Fc1c(-c2cccc3cccc(Cl)c23)ncc2c(N3CC4CCC(C3)N4)nc(OC[C@@]34CCCN3C[C@@H](C(F)(F)F)C4)nc12]

4-((1R,5S)-3,8-diazabicyclo[3.2.1]octan-3-yl)-7-(8-chloronaphthalen-1-yl)-8-fluoro-2-(((2S,7aS)-2-(trifluoromethyl)tetrahydro-1H-pyrrolizin-7a(5H)-yl)methoxy)pyrido[4,3-d]pyrimidine)(Mixture of Cis Diastereomers)

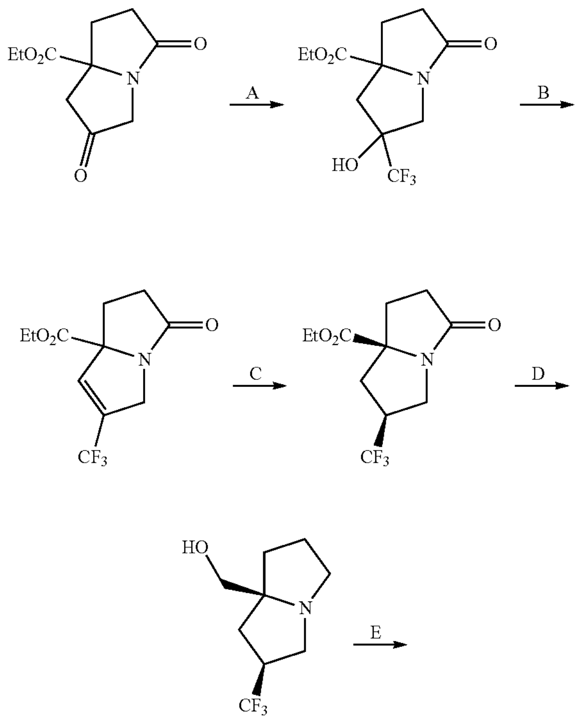

-continued

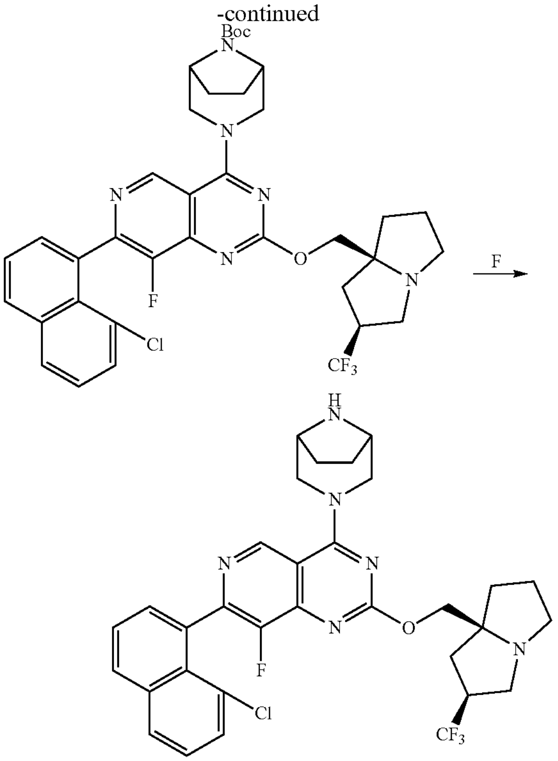

4-((1R,5S)-3,8-diazabicyclo[3.2.1]octan-3-yl)-7-(8-chloronaphthalen-1-yl)-8-fluoro-2-((2-(trifluoromethyl)tetrahydro-1H-pyrrolizin-7a(5H)-yl)methoxy)pyrido[4,3-d]pyrimidine bis(2,2,2-trifluoroacetate) (mixture of cis diastereomers). To a solution of tert-butyl(1R,5S)-3-(7-(8-chloronaphthalen-1-yl)-8-fluoro-2-((2-(trifluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers) (22 mg, 0.030 mmol) in DCM (1 mL) was added TFA (0.50 mL). The solution was stirred at r.t. for 0.5 h and was concentrated. The residue was purified by preparative C18 HPLC (Gilson, 0-95% $CH_3CN/H_2O$ with 0.1% TFA). The desired fractions were combined and lyophilized to give the title compound (22 mg, 73%) as the bis TFA salt. LCMS (MM-ES+APCI, Pos): m/z 627.2 (M+H).

Example 383

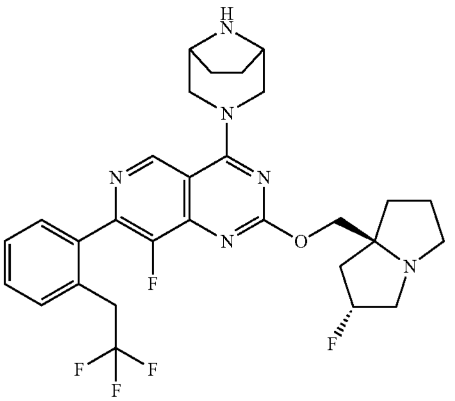 [SMILES: Fc1c(-c2ccccc2CC(F)(F)F)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-(2,2,2-trifluoroethyl)phenyl)pyrido[4,3-d]pyrimidine (racemic, trans)

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-(2,2,2-trifluoroethyl)phenyl)pyrido[4,3-d]pyrimidine dihydrochloride (racemic, trans) (26 mg, 67%). LCMS (MM-ES+APCI, Pos): m/z 575.3 (M+H).

Example 384

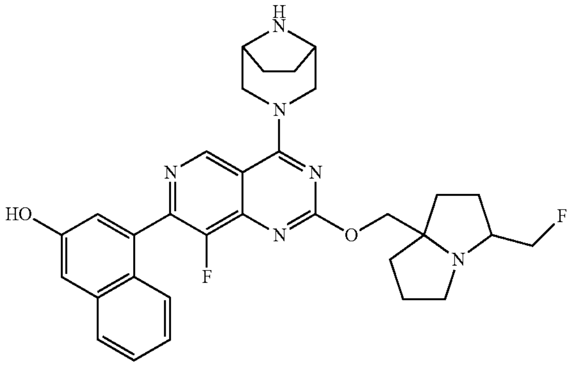 [SMILES: Oc1cc(-c2ncc3c(N4CC5CCC(C4)N5)nc(OCC45CCCN4C(CF)CC5)nc3c2F)c2ccccc2c1]

4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)naphthalen-2-ol (Mixture of Isomers)

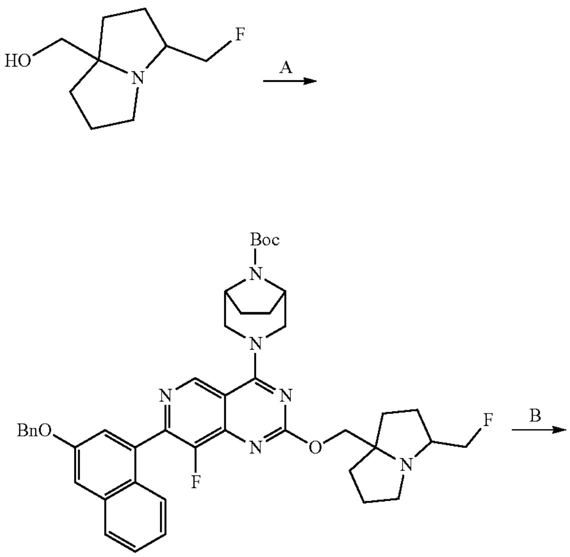

-continued

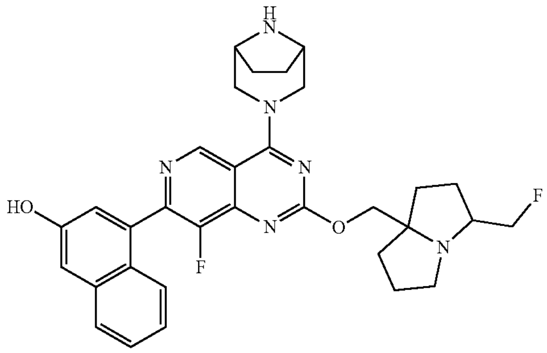

4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)naphthalen-2-ol (mixture of isomers) (3.5 mg, 25%). LCMS (MM-ES+APCI, Pos): m/z 573.3 (M+H).

Example 385

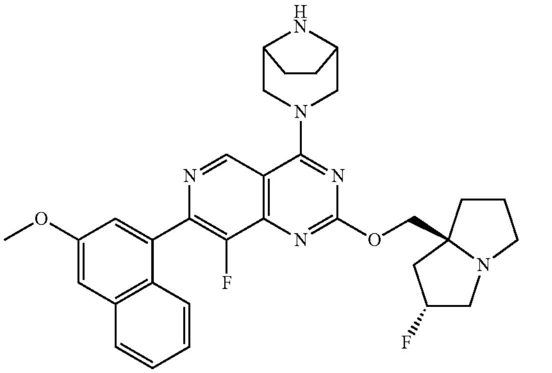 [SMILES: COc1cc(-c2ncc3c(N4CC5CCC(C4)N5)nc(OC[C@@]45CCCN4C[C@H](F)C5)nc3c2F)c2ccccc2c1]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(3-methoxynaphthalen-1-yl)pyrido[4,3-d]pyrimidine (racemic, trans)

Synthesized according to Example 3, Steps G-H substituting (2-fluorotetrahydro-1H-pyrrolizin-7a(5H)-yl)methanol (racemic, trans) in place of 2-(1-methyl-1H-imidazol-2-yl)ethan-1-ol in Step G and (3-methoxynaphthalen-1-yl) boronic acid in place of 4-(4,4,5,5-tetramethyl-1,3,2-dioxaborolan-2-yl)naphthalen-2-ol in Step H followed by deprotection using Example 391, Step A to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(3-methoxynaphthalen-1-yl)pyrido[4,3-d]pyrimidine (racemic, trans) (38 mg, 85%). LCMS (MM-ES+APCI, Pos): m/z 573.3 (M+H).

Example 386

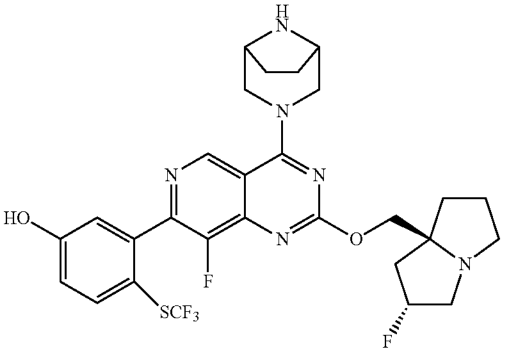

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-((trifluoromethyl)thio)phenol (racemic, trans)

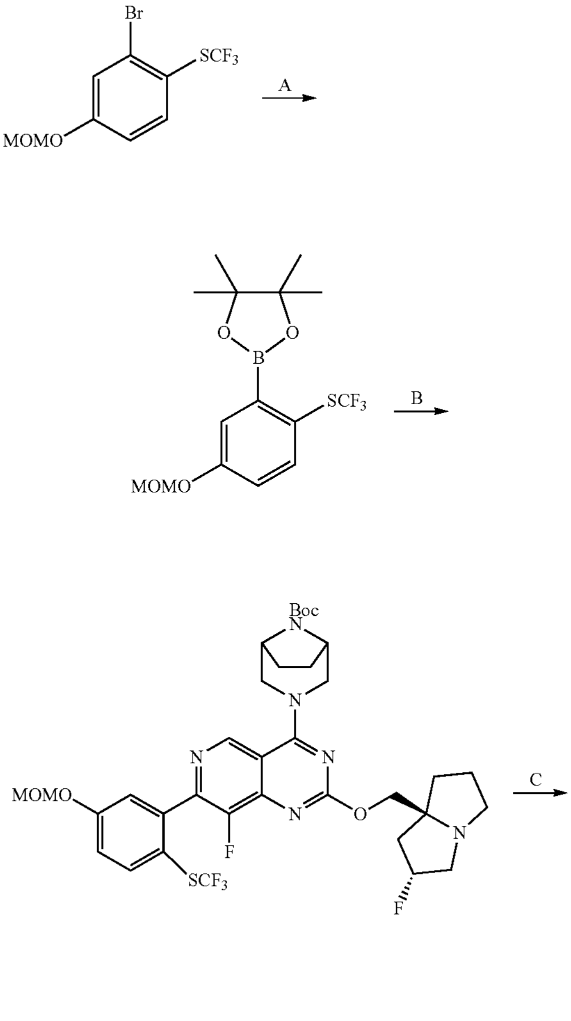

-continued

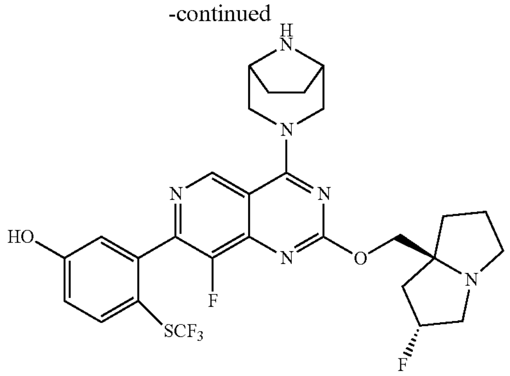

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-((trifluoromethyl)thio)phenol (racemic, trans) (29 mg, 73%). LCMS (MM-ES+APCI, Pos): m/z 609.2 (M+H).

Example 387

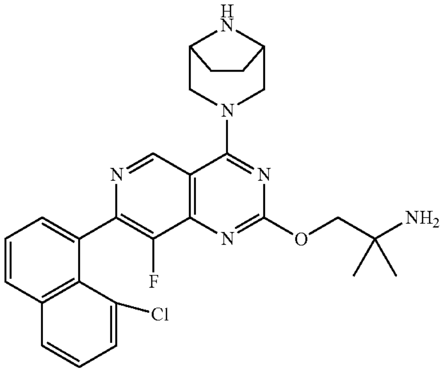 [SMILES: CC(C)(N)COc1nc(N2CC3CCC(C2)N3)c2cnc(-c3cccc4cccc(Cl)c34)c(F)c2n1]

(S)-1-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy) propan-2-amine bis(2,2,2-trifluoroacetate)

Synthesized according to Example 29, Step H substituting N-Boc-2-amino-2-methyl-1-propanol in place of (S)-(1-isopropylpyrrolidin-2-yl)methanol followed by deprotection using Example 2, Step I, (28 mg, 30%). LCMS (MM-ES+APCI, Pos): m/z 507.2 (M+H).

Example 388

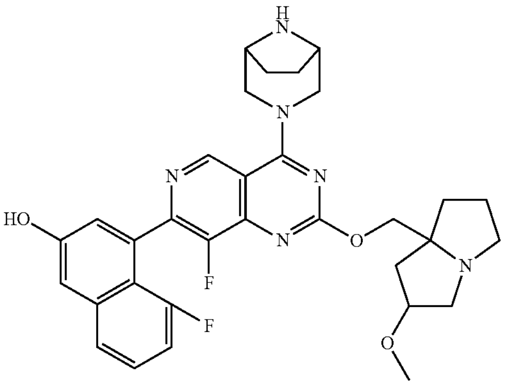 [SMILES: COC1CN2CCCC2(COc2nc(N3CC4CCC(C3)N4)c3cnc(-c4cc(O)cc5cccc(F)c45)c(F)c3n2)C1]

4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-fluoronaphthalen-2-ol (Mixture of trans Diastereomers)

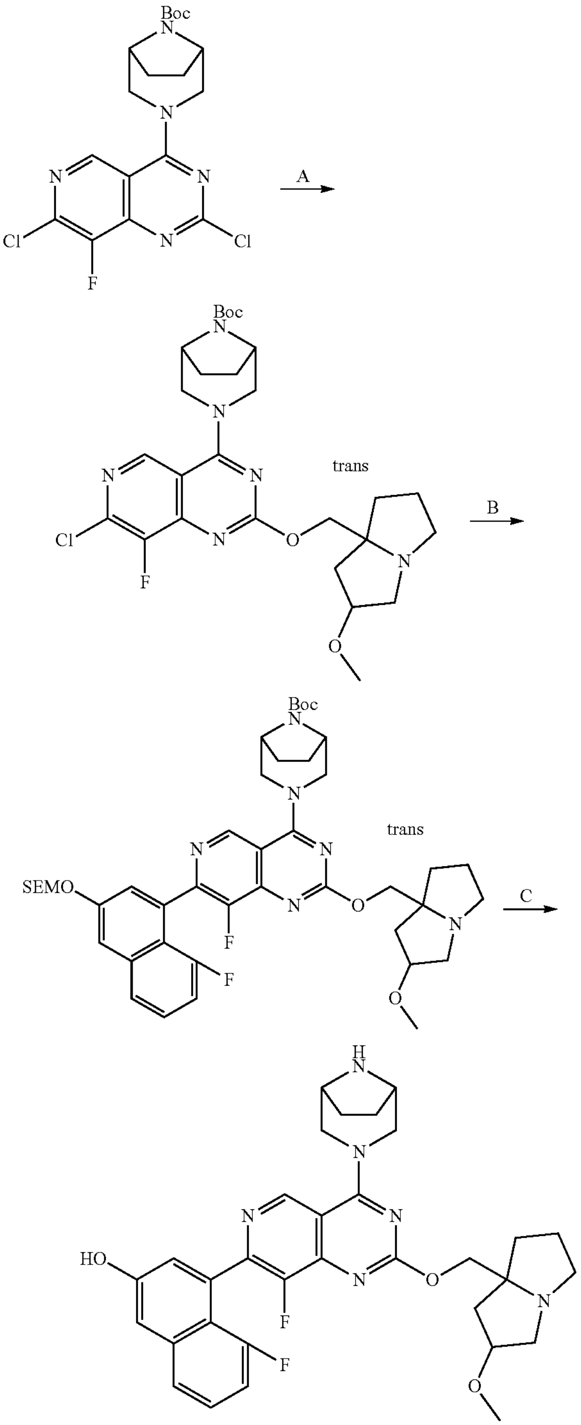

4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-fluoronaphthalen- 2-ol bis(2,2,2-trifluoroacetate) (mixture of trans diastereomers) (21 mg, 71%). LCMS (MM-ES+APCI, Pos): m/z 589.3 (M+H).

Example 389

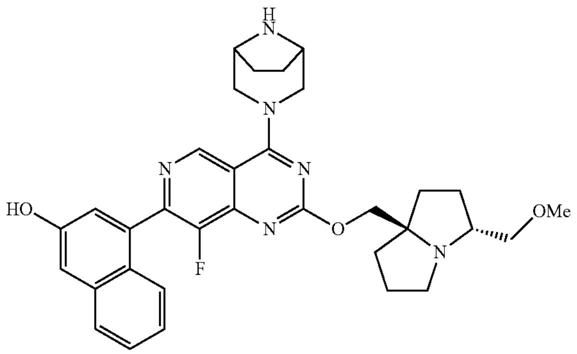 [SMILES: COC[C@H]1CC[C@@]2(COc3nc(N4CC5CCC(C4)N5)c4cnc(-c5cc(O)cc6ccccc56)c(F)c4n3)CCCN12]

4-(4-((1R,5S)-3,8-diazabicyclo[3.2.1]octan-3-yl)-8-fluoro-2-((3-(methoxymethyl)tetrahydro-1H-pyrrolizin-7a(5H)-yl)methoxy)pyrido[4,3-d]pyrimidin-7-yl)naphthalen-2-ol (Mixture of Trans Diastereomers)

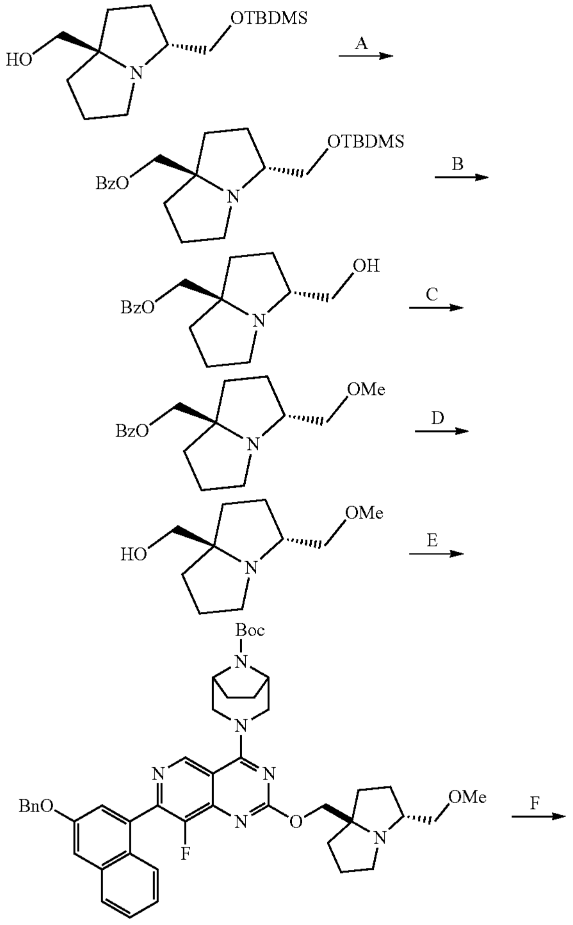

-continued

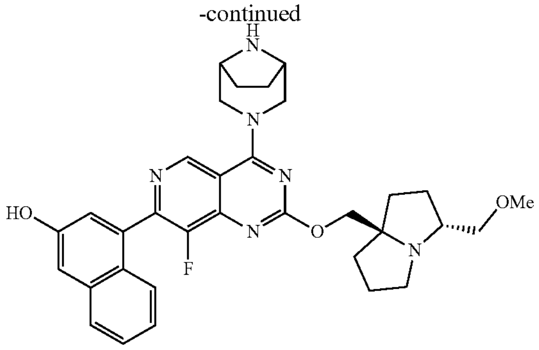

4-(4-((1R,5S)-3,8-diazabicyclo[3.2.1]octan-3-yl)-8-fluoro-2-((3-(methoxymethyl)tetrahydro-1H-pyrrolizin-7a(5H)-yl)methoxy)pyrido[4,3-d]pyrimidin-7-yl)naphthalen-2-ol (mixture of trans diastereomers) (7.7 mg, 79%). LCMS (MM-ES+APCI, Pos): m/z 585.3 (M+H).

Example 390

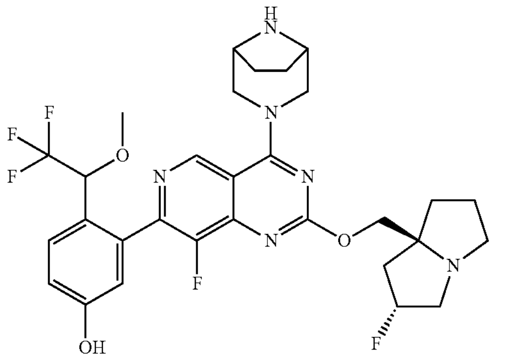 [SMILES: COC(c1ccc(O)cc1-c1ncc2c(N3CC4CCC(C3)N4)nc(OC[C@@]34CCCN3C[C@H](F)C4)nc2c1F)C(F)(F)F]

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoro-1-methoxyethyl)phenol (racemic, trans)

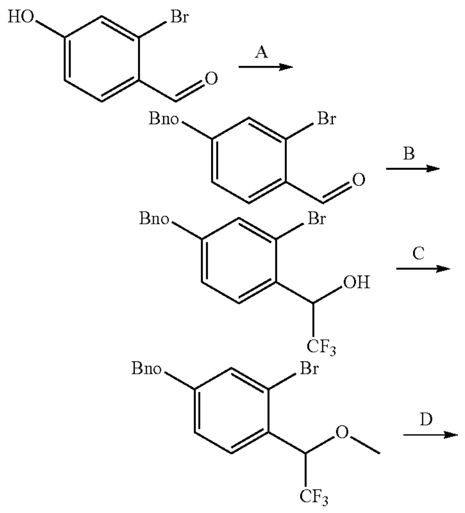

-continued

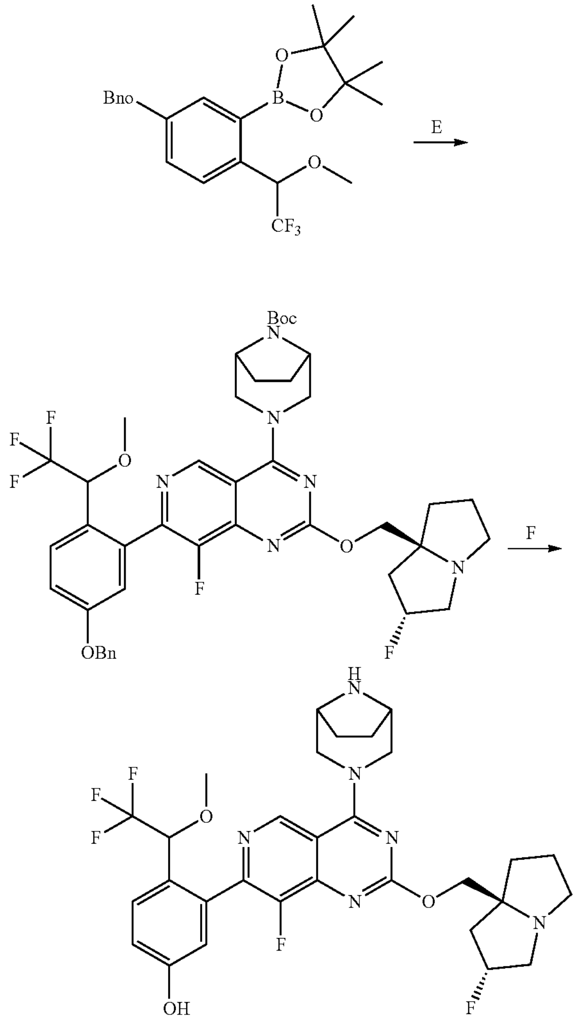

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoro-1-methoxyethyl)phenol (racemic, trans) (10 mg, 26%). LCMS (MM-ES+APCI, Pos): m/z 621.3 (M+H).

Example 391

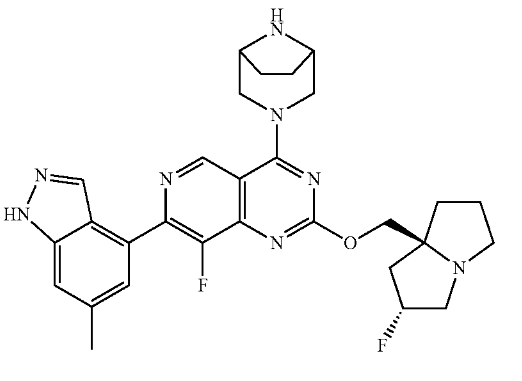 [SMILES: Cc1cc(-c2ncc3c(N4CC5CCC(C4)N5)nc(OC[C@@]45CCCN4C[C@H](F)C5)nc3c2F)c2cn[nH]c2c1]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(6-methyl-1H-indazol-4-yl)pyrido[4,3-d]pyrimidine (racemic, trans)

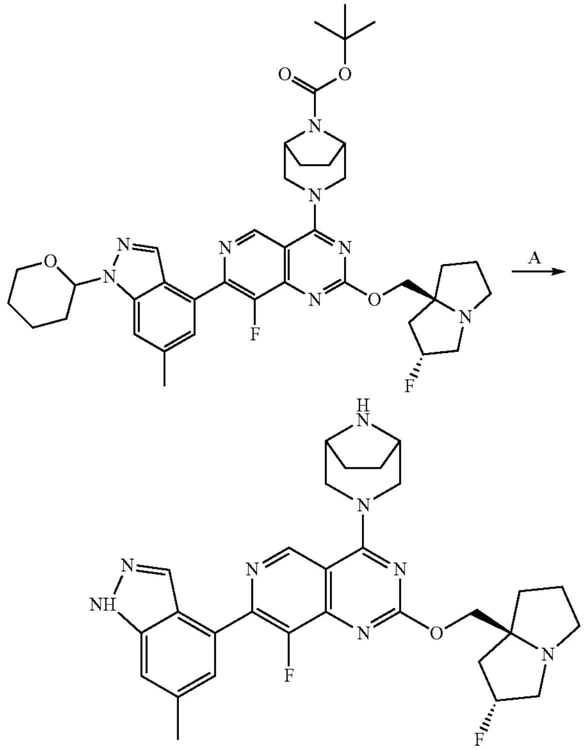

Synthesized according to Example 3, Steps G-H substituting (2-fluorotetrahydro-1H-pyrrolizin-7a(5H)-yl)methanol (racemic, trans) in place of 2-(1-methyl-1H-imidazol-2-yl)ethan-1-ol in Step G and 6-methyl-1-(tetrahydro-2H-pyran-2-yl)-4-(4,4,5,5-tetramethyl-1,3,2-dioxaborolan-2-yl)-1H-indazole in place of 4-(4,4,5,5-tetramethyl-1,3,2-dioxaborolan-2-yl)naphthalen-2-ol in Step H to afford tert-butyl(1R,5S)-3-(8-fluoro-2-((2-fluorotetrahydro-1H-pyrrolizin-7a(5H)-yl)methoxy)-7-(6-methyl-1-(tetrahydro-2H-pyran-2-yl)-1H-indazol-4-yl)pyrido[4,3-d]pyrimidin-4-yl)-3,8-diazabicyclo[3.2.1]octane-8-carboxylate (racemic, trans) (34 mg, 52%). LCMS (MM-ES+APCI, Pos): m/z 731.4 (M+H).

Step A. 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(6-methyl-1H-indazol-4-yl)pyrido[4,3-d]pyrimidine (racemic, trans). To a solution of tert-butyl(1R,5S)-3-(8-fluoro-2-((2-fluorotetrahydro-1H-pyrrolizin-7a(5H)-yl)methoxy)-7-(6-methyl-1-(tetrahydro-2H-pyran-2-yl)-1H-indazol-4-yl)pyrido[4,3-d]pyrimidin-4-yl)-3,8-diazabicyclo[3.2.1]octane-8-carboxylate (racemic, trans) (34 mg, 0.048 mmol) in DCM (1 mL) was added 4 M HCl in dioxane (1 ml, 4 mmol). After stirring for 2.5 hours at room temperature, more 4 M HCl in dioxane (1 ml, 4 mmol) was added. After 7 hours the reaction was concentrated in vacuo. The residue was purified by reverse phase chromatography eluting with 5-95% MeCN/water to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(6-methyl-1H-indazol-4-yl)pyrido[4,3-d]pyrimidine (racemic, trans) (13 mg, 51%) as a yellow foam. LCMS (MM-ES+APCI, Pos): m/z 547.3 (M+H).

Example 392

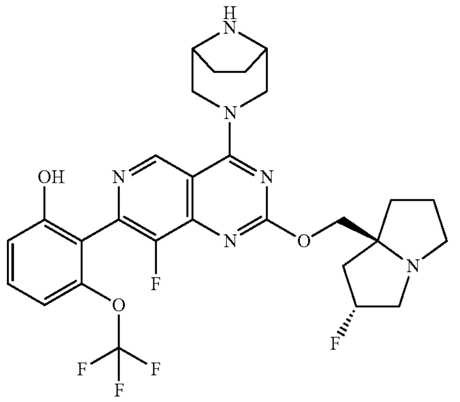 [SMILES: Oc1cccc(OC(F)(F)F)c1-c1ncc2c(N3CC4CCC(C3)N4)nc(OC[C@@]34CCCN3C[C@H](F)C4)nc2c1F]

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-(trifluoromethoxy)phenol (racemic, trans)

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-(trifluoromethoxy)phenol (racemic, trans) (14 mg, 86%). LCMS (MM-ES+APCI, Pos): m/z 593.3 (M+H).

Example 393

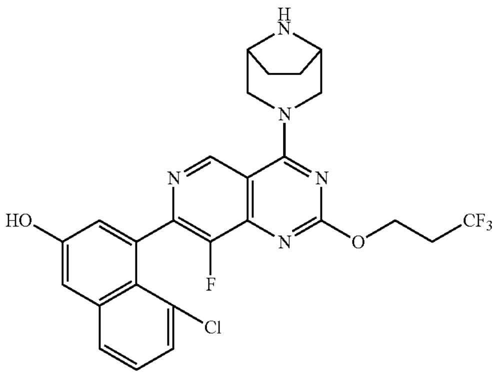 [SMILES: Oc1cc(-c2ncc3c(N4CC5CCC(C4)N5)nc(OCCC(F)(F)F)nc3c2F)c2c(Cl)cccc2c1]

4-(4-((1R,5S)-3,8-diazabicyclo[3.2.1]octan-3-yl)-8-fluoro-2-(3,3,3-trifluoropropoxy)pyrido[4,3-d]pyrimidin-7-yl)-5-chloronaphthalen-2-ol Synthesized according to Example 36, substituting 4-((1R,5S)-3,8-diazabicyclo[3.2.1]octan-3-yl)-7-chloro-8-fluoro-2-(3,3,3-trifluoropropoxy)pyrido[4,3-d]pyrimidine in place of tert-butyl(1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate in Step F to afford 4-(4-((1R,5S)-3,8-diazabicyclo[3.2.1]octan-3-yl)-8-fluoro-2-(3,3,3-trifluoropropoxy)pyrido[4,3-d]pyrimidin-7-yl)-5-chloronaphthalen-2-ol (10 mg, 74%). LCMS (MM-ES+APCI, Pos): m/z 548.2 [M+H].

Example 394

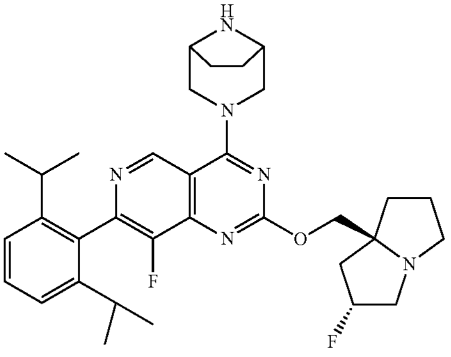 [SMILES: CC(C)c1cccc(C(C)C)c1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-7-(2,6-diisopropylphenyl)-8-fluoro-2-((2-fluorotetrahydro-1H-pyrrolizin-7a(5H)-yl)methoxy)pyrido[4,3-d]pyrimidine (racemic, trans)

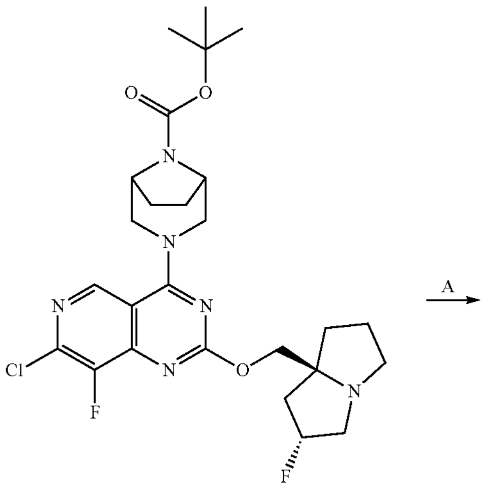

-continued
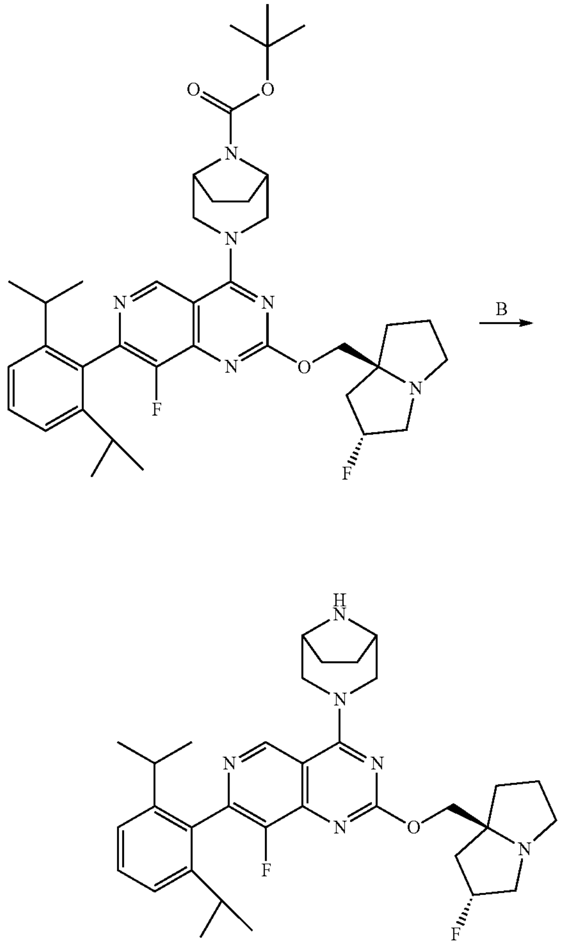
4-((1R,5S)-3,8-diazabicyclo[3.2.1]octan-3-yl)-7-(2,6-diisopropylphenyl)-8-fluoro-2-((2-fluorotetrahydro-1H-pyrrolizin-7a(5H)-yl)methoxy)pyrido[4,3-d]pyrimidine (racemic, trans) (31 mg, 96%). LCMS (MM-ES+APCI, Pos): m/z 577.3 [M+H].
Example 395
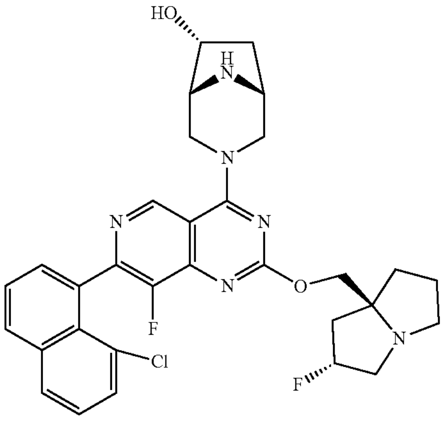 [SMILES: O[C@@H]1C[C@@H]2CN(c3nc(OC[C@@]45CCCN4C[C@H](F)C5)nc4c(F)c(-c5cccc6cccc(Cl)c56)ncc34)C[C@H]1N2]
(1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octan-6-ol (racemic, trans)
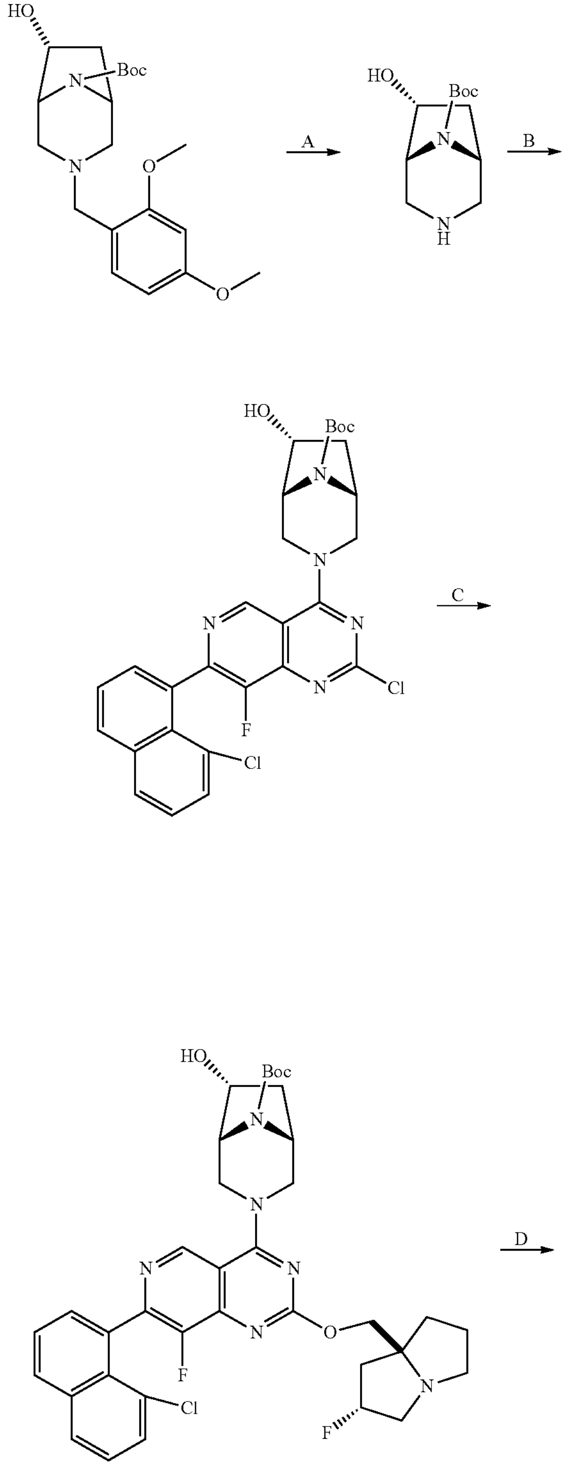

-continued

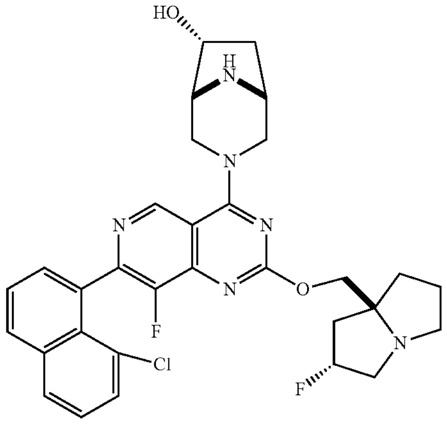

(1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octan-6-ol bis(2,2,2-trifluoroacetate) (racemic, trans). To a solution of tert-butyl(1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-hydroxy-3,8-diazabicyclo[3.2.1]octane-8-carboxylate (racemic, trans) (7.0 mg, 0.010 mmol) in DCM (0.50 mL) was added TFA (0.25 mL). The mixture was stirred at r.t. for 20 min, concentrated, and was purified by preparative C18 HPLC (Gilson, 0-95% $CH_3CN/H_2O$ with 0.1% TFA). The desired fractions were combined and lyophilized to give the title compound (7.0 mg, 84%) as the bis TFA salt. LCMS (MM-ES+APCI, Pos): m/z 593.2 (M+H).

Example 396

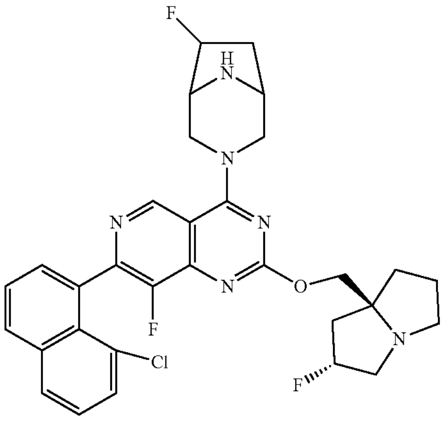 [SMILES: Fc1c(-c2cccc3cccc(Cl)c23)ncc2c(N3CC4CC(F)C(C3)N4)nc(OC[C@@]34CCCN3C[C@H](F)C4)nc12]

7-(8-chloronaphthalen-1-yl)-8-fluoro-4-(6-fluoro-3,8-diazabicyclo[3.2.1]octan-3-yl)-2-((2-fluorotetrahydro-1H-pyrrolizin-7a(5H)-yl)methoxy)pyrido[4,3-d]pyrimidine (racemic, trans)

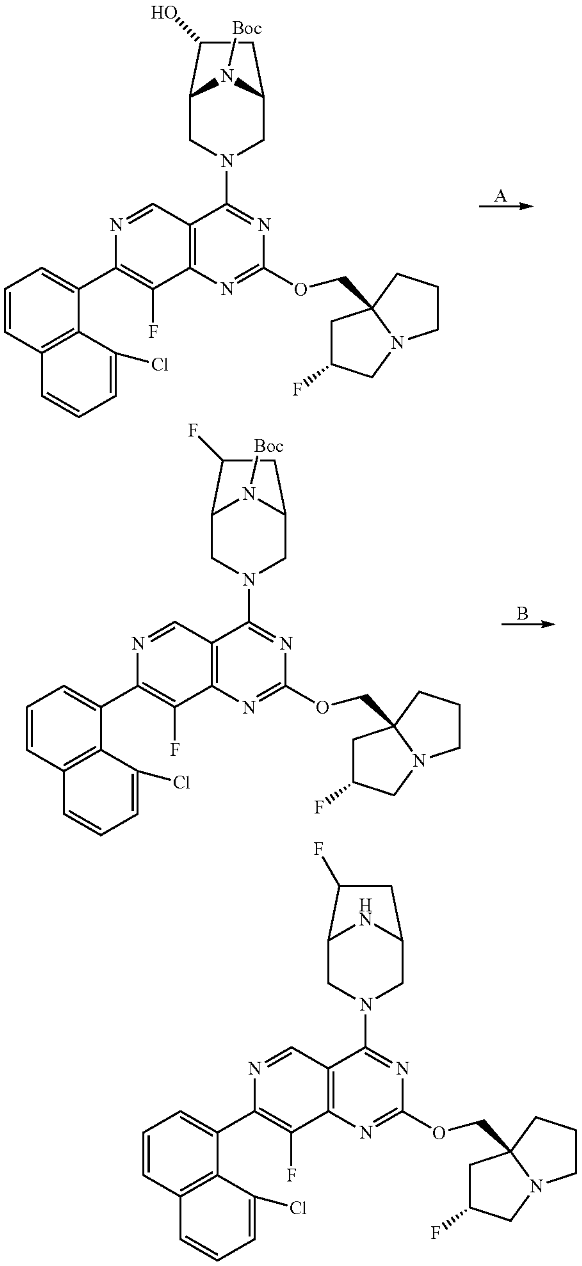

7-(8-chloronaphthalen-1-yl)-8-fluoro-4-(6-fluoro-3,8-diazabicyclo[3.2.1]octan-3-yl)-2-((2-fluorotetrahydro-1H-pyrrolizin-7a(5H)-yl)methoxy)pyrido[4,3-d]pyrimidine bis(2,2,2-trifluoroacetate) (racemic, trans). To a solution of tert-butyl 3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-fluoro-3,8-diazabicyclo[3.2.1]octane-8-carboxylate (racemic, trans) (5 mg, 0.007 mmol) in DCM (1 mL) was added TFA (0.5 mL). The solution was stirred at rt for 15 min, and concentrated to dryness. The residue was purified by preparative C18 HPLC (Gilson, 0-95% $CH_3CN/H_2O$ with 0.1% TFA). The desired fractions were combined and lyophilized to give the title compound (2.0 mg, 34%) as the bis TFA salt. LCMS (MM-ES+APCI, Pos): m/z 595.2 (M+H).

Example 397

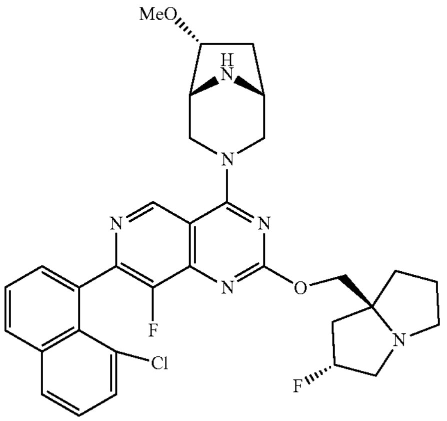 [SMILES: CO[C@@H]1C[C@@H]2CN(c3nc(OC[C@@]45CCCN4C[C@H](F)C5)nc4c(F)c(-c5cccc6cccc(Cl)c56)ncc34)C[C@H]1N2]

7-(8-chloronaphthalen-1-yl)-8-fluoro-2-((2-fluorotetrahydro-1H-pyrrolizin-7a(5H)-yl)methoxy)-4-((1R,5R,6R)-6-methoxy-3,8-diazabicyclo[3.2.1]octan-3-yl)pyrido[4,3-d]pyrimidine (racemic, trans)

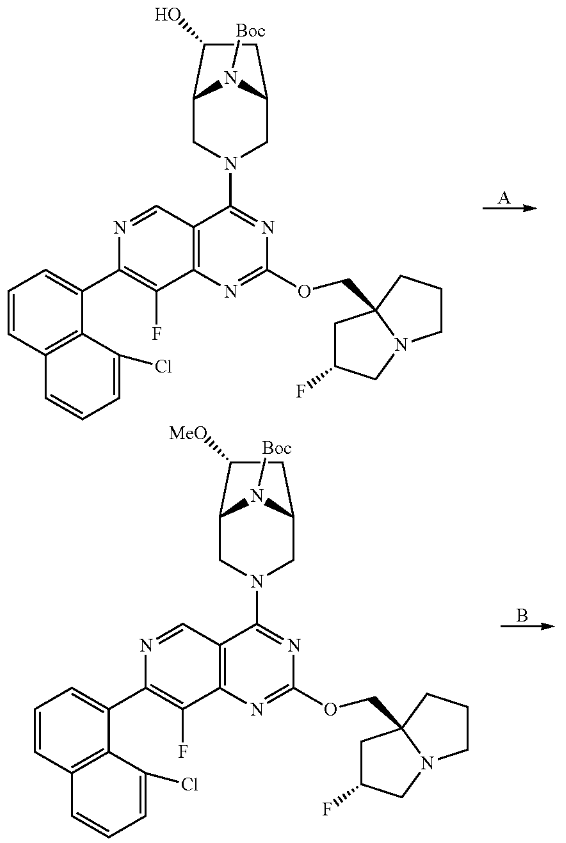

-continued

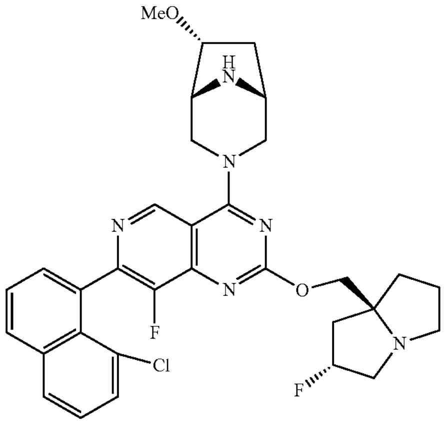

7-(8-chloronaphthalen-1-yl)-8-fluoro-2-((2-fluorotetrahydro-1H-pyrrolizin-7a(5H)-yl)methoxy)-4-((1R,5R,6R)-6-methoxy-3,8-diazabicyclo[3.2.1]octan-3-yl)pyrido[4,3-d]pyrimidine bis(2,2,2-trifluoroacetate) (racemic, trans). To a solution of tert-butyl(1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-methoxy-3,8-diazabicyclo[3.2.1]octane-8-carboxylate (racemic, trans) (5.0 mg, 0.0071 mmol) in DCM (1 mL) was added TFA (0.50 mL). The solution was stirred at rt for 30 min, concentrated to dryness, and the residue was purified by preparative C18 HPLC (Gilson, 0-95% $CH_3CN/H_2O$ with 0.1% TFA). The desired fractions were combined and lyophilized to give the title compound (3 mg, 51%) as the bis TFA salt. LCMS (MM-ES+APCI, Pos): m/z 607.2 (M+H).

Example 398

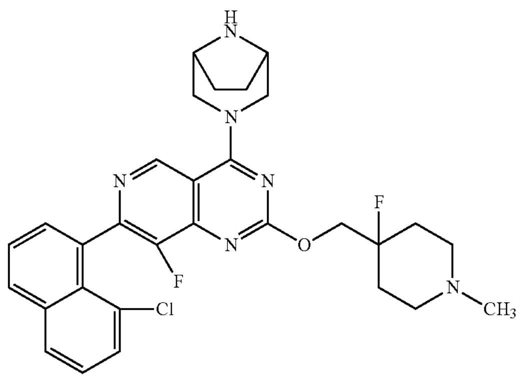 [SMILES: CN1CCC(F)(COc2nc(N3CC4CCC(C3)N4)c3cnc(-c4cccc5cccc(Cl)c45)c(F)c3n2)CC1]

4-((1R,5S)-3,8-diazabicyclo[3.2.1]octan-3-yl)-7-(8-chloronaphthalen-1-yl)-8-fluoro-2-((4-fluoro-1-methylpiperidin-4-yl)methoxy)pyrido[4,3-d]pyrimidine

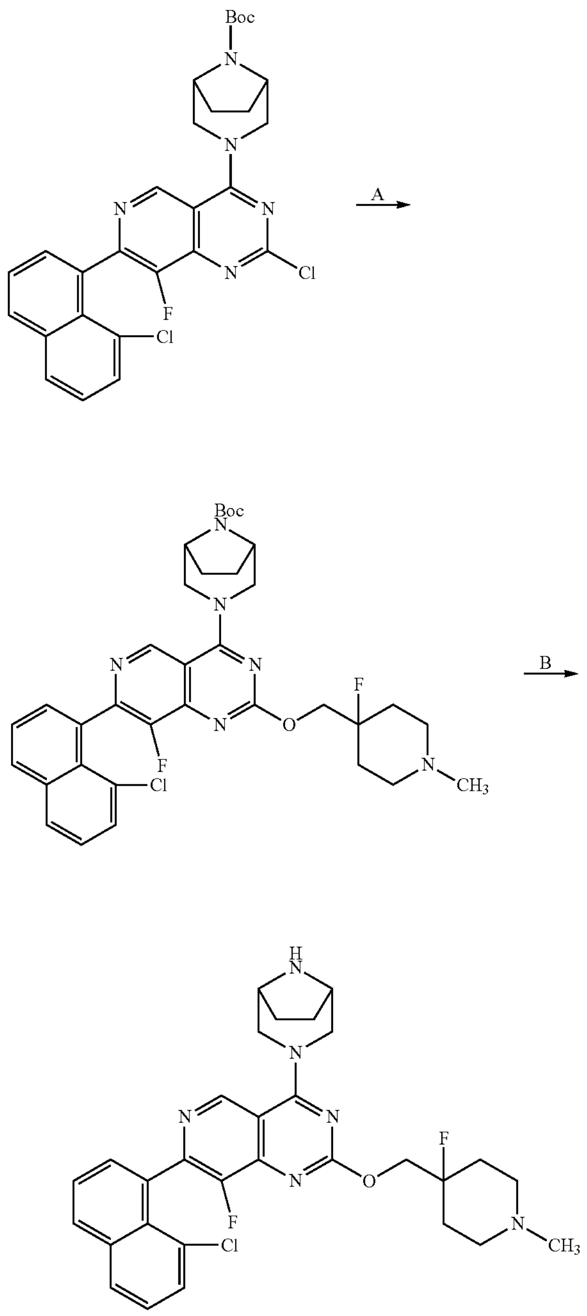

4-((1R,5S)-3,8-diazabicyclo[3.2.1]octan-3-yl)-7-(8-chloronaphthalen-1-yl)-8-fluoro-2-((4-fluoro-1-methylpiperidin-4-yl)methoxy)pyrido[4,3-d]pyrimidine. A stirred solution of tert-butyl(1R,5S)-3-(7-(8-chloronaphthalen-1-yl)-8-fluoro-2-((4-fluoro-1-methylpiperidin-4-yl)methoxy)pyrido[4,3-d]pyrimidin-4-yl)-3,8-diazabicyclo[3.2.1]octane-8-carboxylate (37 mg, 0.056 mmol) in dichloromethane (0.5 mL) was cooled to −20° C. and 4M hydrogen chloride in dioxane (1 mL, 4.0 mmol) was added. The reaction mixture was stirred for 1 h at r.t. and concentrated in vacuo. The residue was freebased by partitioning between sat. $NaHCO_3$ and DCM to yield the target compound (28 mg, 89%) as yellow solid. LCMS (MM-ES+APCI, Pos): m/z 565.2 (M+H).

Example 399

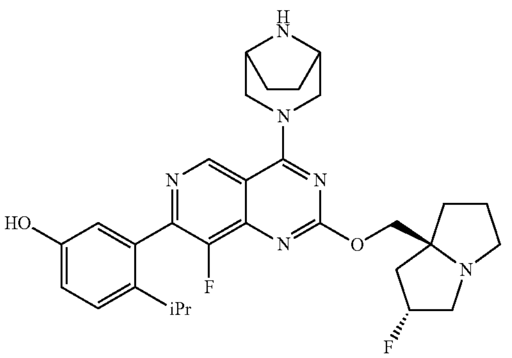 [SMILES: CC(C)c1ccc(O)cc1-c1ncc2c(N3CC4CCC(C3)N4)nc(OC[C@@]34CCCN3C[C@H](F)C4)nc2c1F]

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-isopropylphenol (racemic, trans)

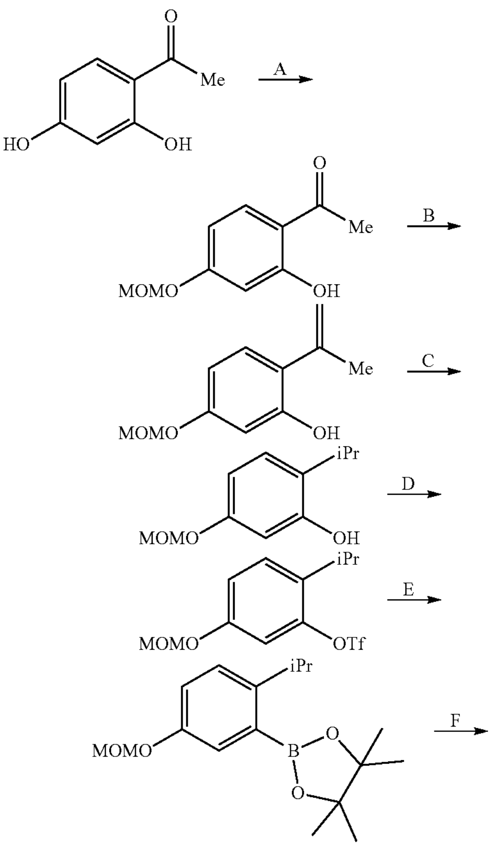

-continued

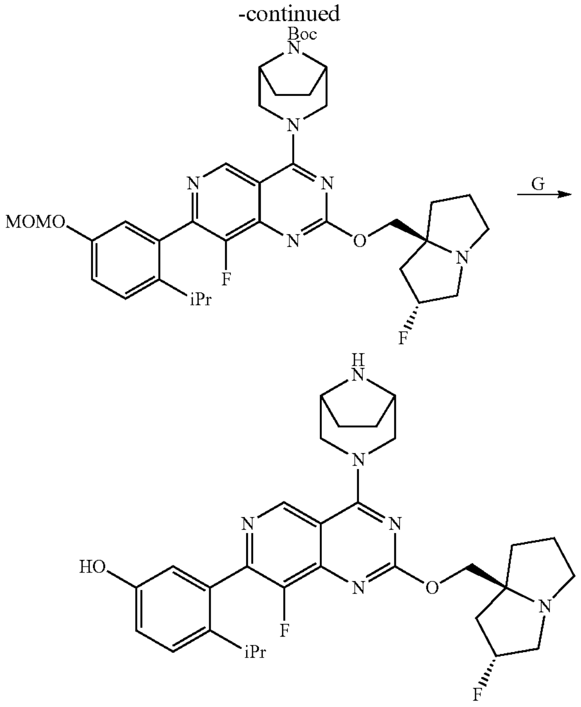

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-isopropylphenol dihydrochloride (racemic, trans). Synthesized according to Example 229, Step B substituting tert-butyl(1R,5S)-3-(8-fluoro-2-((2-fluorotetrahydro-1H-pyrrolizin-7a(5H)-yl)methoxy)-7-(2-isopropyl-5-(methoxymethoxy)phenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-isopropylphenol dihydrochloride (racemic, trans) (10 mg, 37%). LCMS (MM-ES+APCI, Pos): m/z 551.3 (M+H).

Example 400

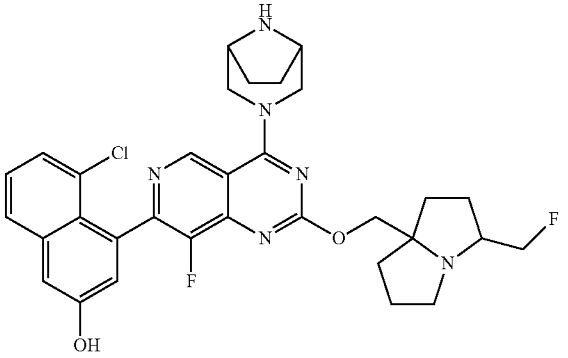 [SMILES: Oc1cc(-c2ncc3c(N4CC5CCC(C4)N5)nc(OCC45CCCN4C(CF)CC5)nc3c2F)c2c(Cl)cccc2c1]

4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)-5-chloronaphthalen-2-ol (Mixture of Isomers)

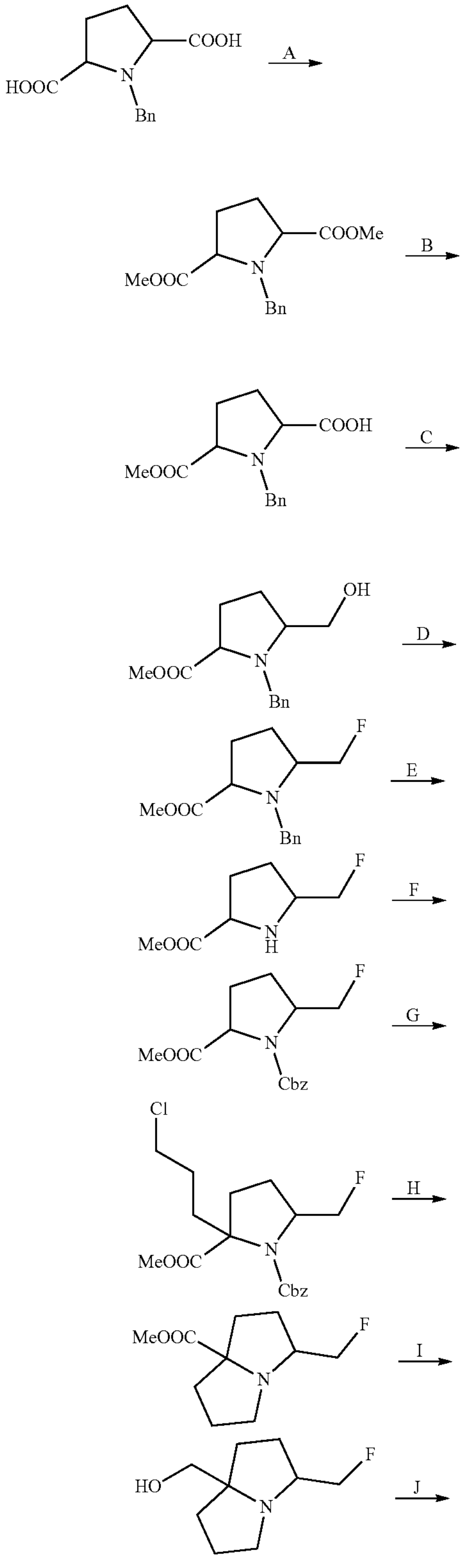

-continued

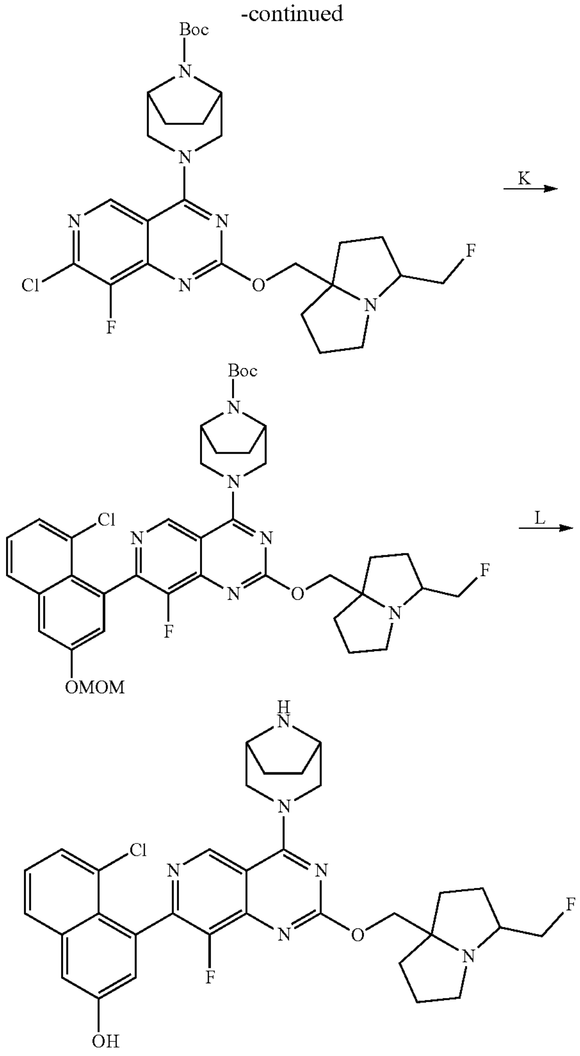

4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)-5-chloronaphthalen-2-ol bis(2,2,2-trifluoroacetate) (mixture of isomers) (0.7 mg, 52%). LCMS (MM-ES+APCI, Pos): m/z 607.2 (M+H).

Example 401

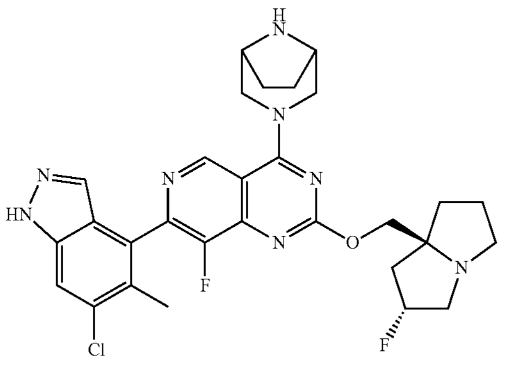 [SMILES: Cc1c(Cl)cc2[nH]ncc2c1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-7-(6-chloro-5-methyl-1H-indazol-4-yl)-8-fluoro-2-((2-fluorotetrahydro-1H-pyrrolizin-7a(5H)-yl)methoxy)pyrido[4,3-d]pyrimidine (racemic, trans)

Synthesized according to Example 3, Steps G-H substituting (2-fluorotetrahydro-1H-pyrrolizin-7a(5H)-yl)methanol (racemic, trans) in place of 2-(1-methyl-1H-imidazol-2-yl)ethan-1-ol in Step G and 6-chloro-5-methyl-1-(tetrahydro-2H-pyran-2-yl)-4-(4,4,5,5-tetramethyl-1,3,2-dioxaborolan-2-yl)-1H-indazole in place of 4-(4,4,5,5-tetramethyl-1,3,2-dioxaborolan-2-yl)naphthalen-2-ol in Step H followed by deprotection using Example 391, Step A to afford 4-((1R,5S)-3,8-diazabicyclo[3.2.1]octan-3-yl)-7-(6-chloro-5-methyl-1H-indazol-4-yl)-8-fluoro-2-((2-fluorotetrahydro-1H-pyrrolizin-7a(5H)-yl)methoxy)pyrido[4,3-d]pyrimidine (racemic, trans) (6.9 mg, 28%). LCMS (MM-ES+APCI, Pos): m/z 581.3 (M+H).

Example 402

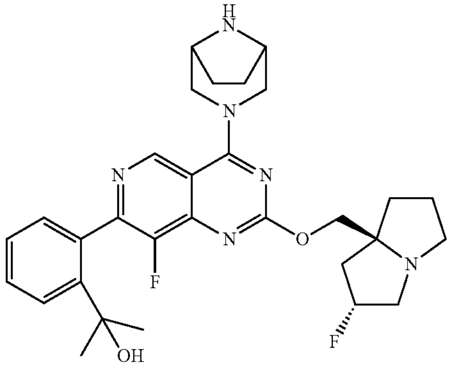 [SMILES: CC(C)(O)c1ccccc1-c1ncc2c(N3CC4CCC(C3)N4)nc(OC[C@@]34CCCN3C[C@H](F)C4)nc2c1F]

2-(2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)phenyl) propan-2-ol (racemic, trans)

2-(2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)phenyl) propan-2-ol (racemic, trans) (5.0 mg, 10%). LCMS (MM-ES+APCI, Pos): m/z 551.3 (M+H).

Example 403

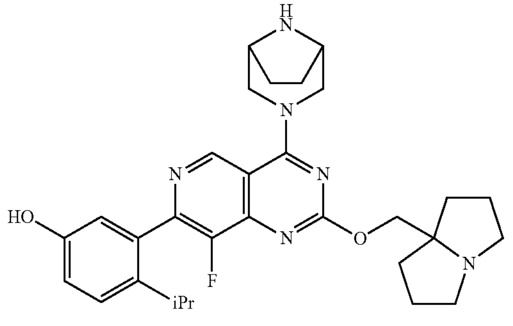 [SMILES: CC(C)c1ccc(O)cc1-c1ncc2c(N3CC4CCC(C3)N4)nc(OCC34CCCN3CCC4)nc2c1F]

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-isopropylphenol

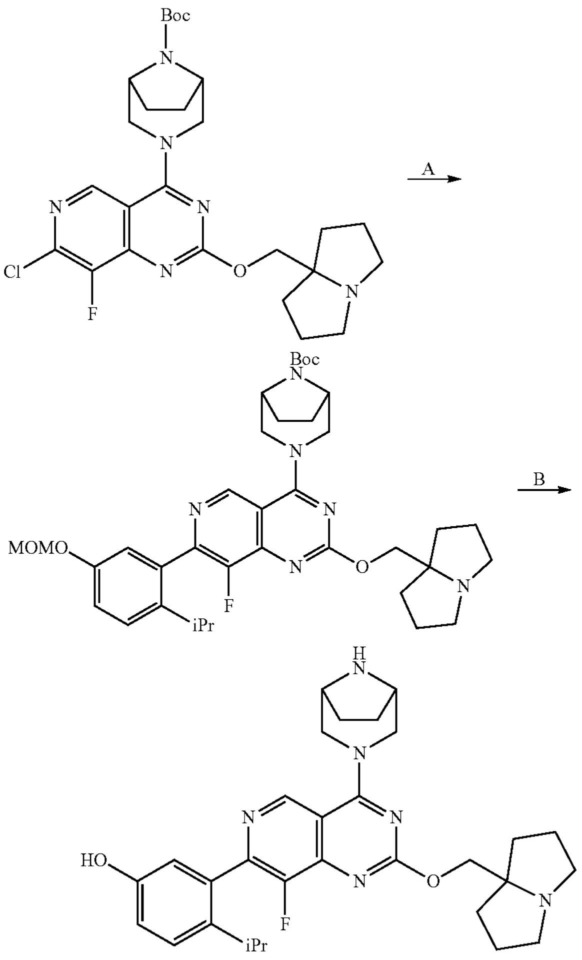

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-isopropylphenol. Tert-butyl (1R,5S)-3-(8-fluoro-7-(2-isopropyl-5-(methoxymethoxy)phenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (33 mg, 0.049 mmol) was added to a round bottom flask with a stir bar, DCM (1.5 mL) and 4M HCl in dioxanes (1.5 mL) were added at room temperature and the reaction was stirred for 40 minutes. The reaction was concentrated to dryness, and the residue was purified via reverse phase chromatography (C18, 0-80% MeCN in water with 0.1% TFA). The fractions containing the product were combined, frozen, and lyophilized. The acid salt was passed through two PL-$HCO_3$ ME Resin plugs with methanol and concentrated to yield a solid. The solid was triturated with ether and dried to give 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-isopropylphenol (9.2 mg, 34%). LCMS (MM-ES+APCI, Pos): m/z 533.3 (M+H).

Example 404

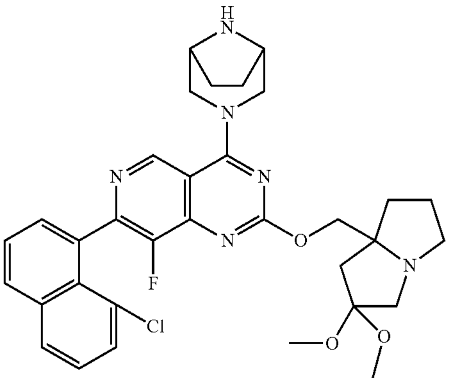 [SMILES: COC1(OC)CN2CCCC2(COc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-2-((2,2-dimethoxytetrahydro-1H-pyrrolizin-7a(5H)-yl)methoxy)-8-fluoropyrido[4,3-d]pyrimidine (Mixture of Isomers)

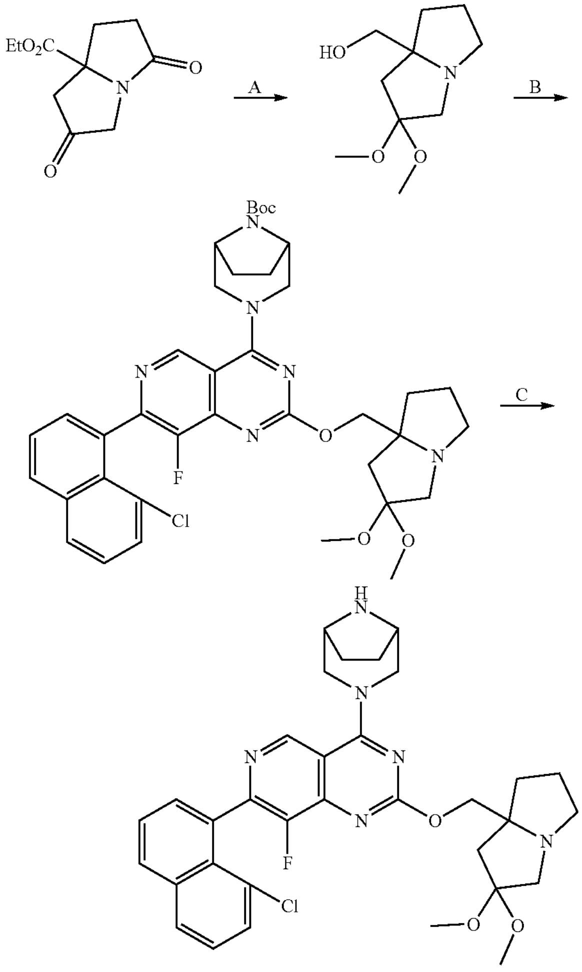

4-((1R,5S)-3,8-diazabicyclo[3.2.1]octan-3-yl)-7-(8-chloronaphthalen-1-yl)-2-((2,2-dimethoxytetrahydro-1H-pyrrolizin-7a(5H)-yl)methoxy)-8-fluoropyrido[4,3-d]pyrimidine (Mixture of isomers) as a waxy white solid (1.8 mg, 21%). LCMS (MM-ES+APCI, Pos): m/z 619.3 (M+H).

Example 405

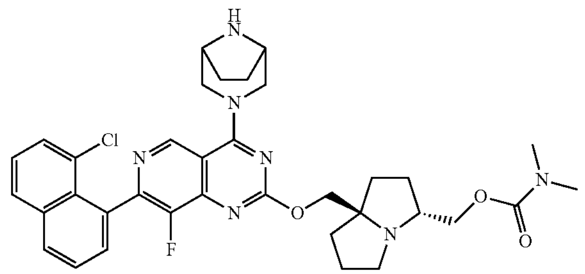 [SMILES: CN(C)C(=O)OC[C@H]1CC[C@@]2(COc3nc(N4CC5CCC(C4)N5)c4cnc(-c5cccc6cccc(Cl)c56)c(F)c4n3)CCCN12]

(7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl dimethylcarbamate (Mixture of trans Diastereomers)

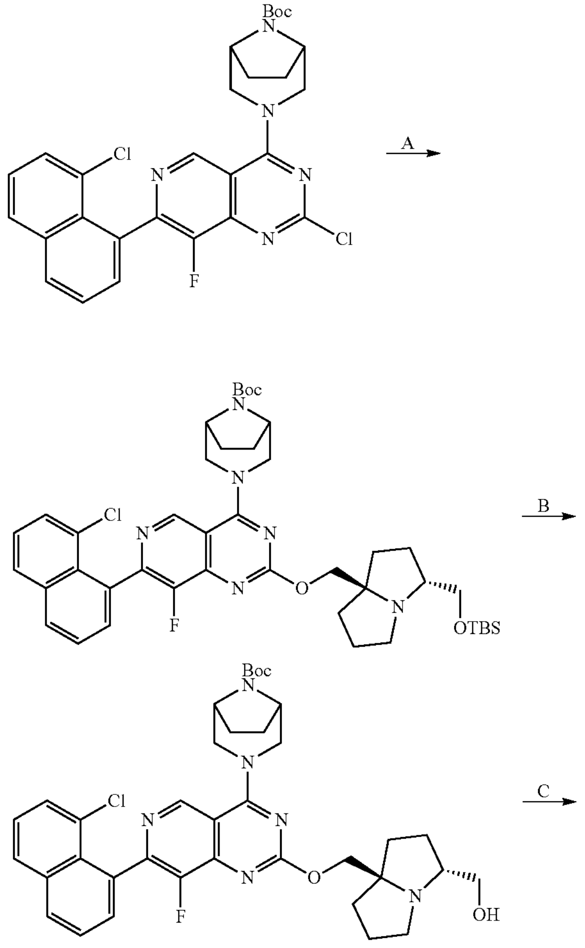

-continued

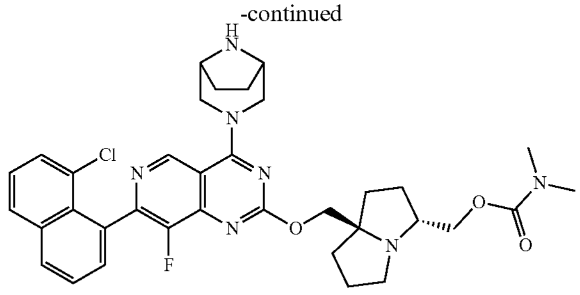

(7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl dimethylcarbamate (mixture of trans diastereomers). To a solution of crude tert-butyl 3-(7-(8-chloronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers) (25 mg, 0.036 mmol) and $Et_3N$ (0.010 mL, 0.073 mmol) in THF (0.7 mL) was added 4-nitrophenyl chloroformate (8.8 mg, 0.044 mmol). The mixture was stirred at r.t. for 0.5 h and dimethylamine (2.0 M, 0.073 mL, 0.15 mmol) was added. The mixture was stirred at r.t. for 0.5 h and concentrated to dryness. The residue was dissolved in DCM (1 mL), TFA (0.50 mL) was added at r.t., and the reaction was stirred for 30 min. The solution was concentrated to dryness and the residue purified by preparative C18 HPLC (Gilson, 0-95% $CH_3CN/H_2O$ with 0.1% TFA). The desired fractions were combined, basified with $NaHCO_3$ (sat.), and extracted with DCM/IPA (5:1). The combined extract was dried ($Na_2SO_4$) and concentrated to give the title compound (11 mg, 46%) as a yellow solid. LCMS (MM-ES+APCI, Pos): m/z 660.3 (M+H).

Example 406

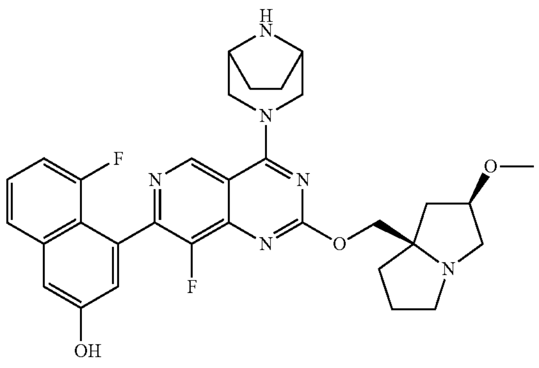 [SMILES: CO[C@H]1CN2CCC[C@]2(COc2nc(N3CC4CCC(C3)N4)c3cnc(-c4cc(O)cc5cccc(F)c45)c(F)c3n2)C1]

4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-fluoronaphthalen-2-ol (Mixture of cis Diastereomers)

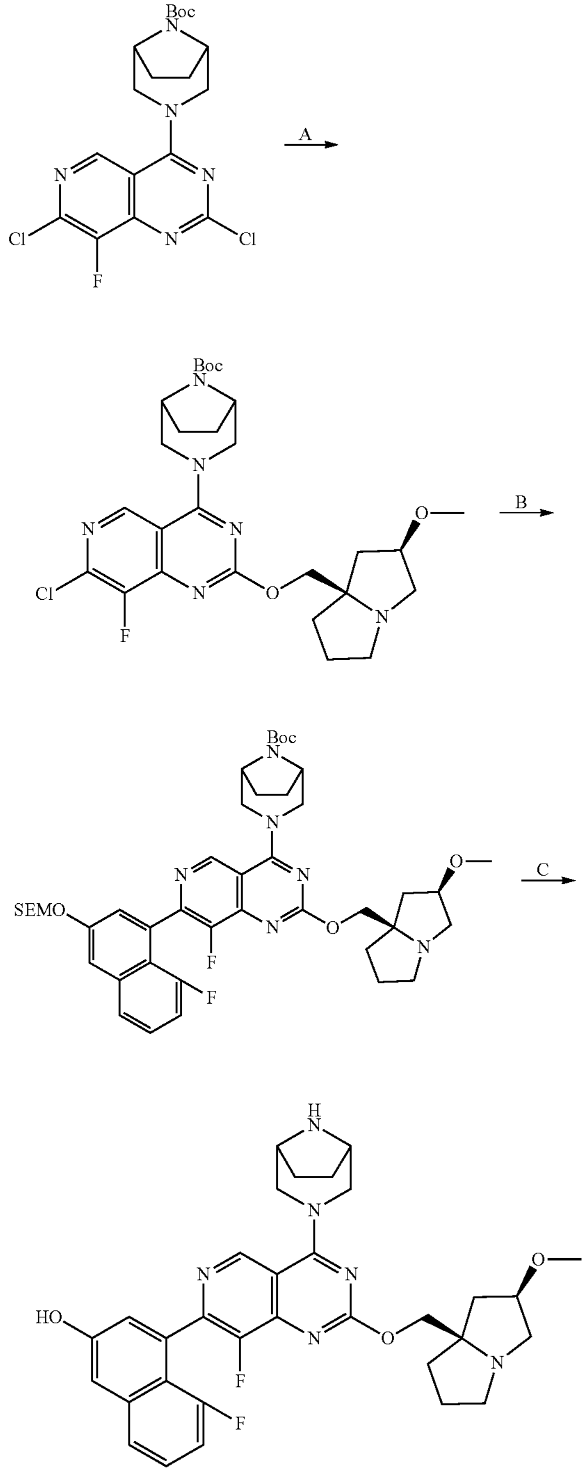

4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-fluoronaphthalen-2-ol (mixture of cis diastereomers) as a pale yellow solid (2.8 mg, 51%). LCMS (MM-ES+APCI, Pos): m/z 589.2 (M+H).

Example 407

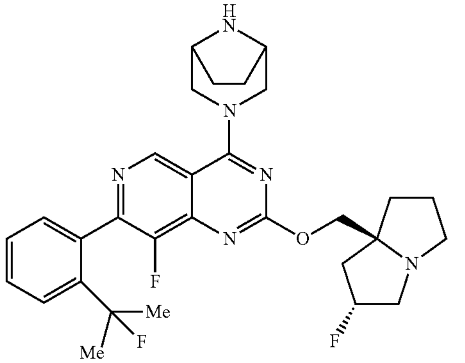 [SMILES: CC(C)(F)c1ccccc1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-8-fluoro-7-(2-(2-fluoropropan-2-yl)phenyl)-2-((2-fluorotetrahydro-1H-pyrrolizin-7a(5H)-yl)methoxy)pyrido[4,3-d]pyrimidine (racemic, trans)

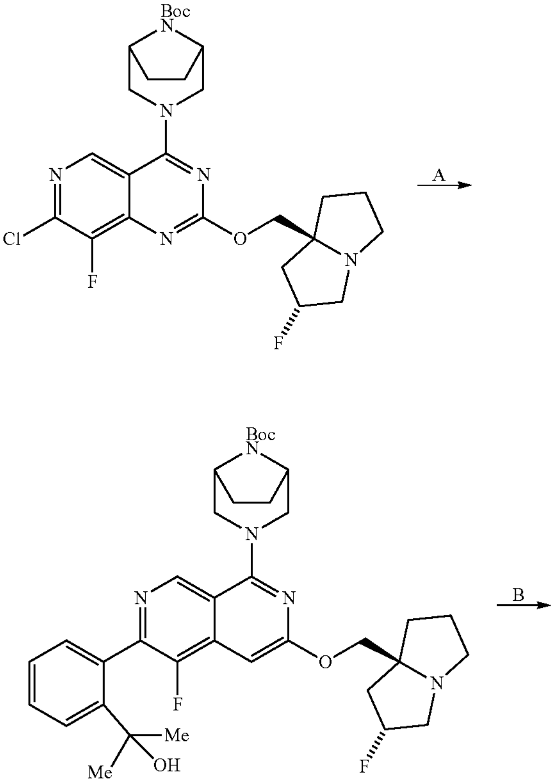

-continued

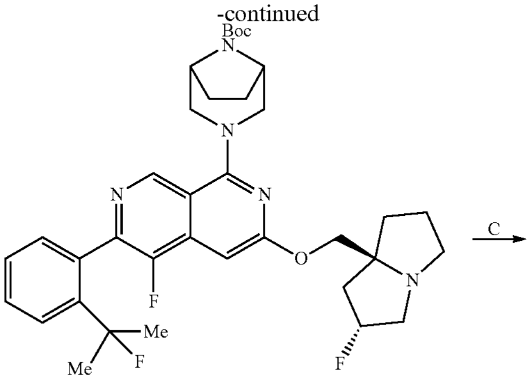

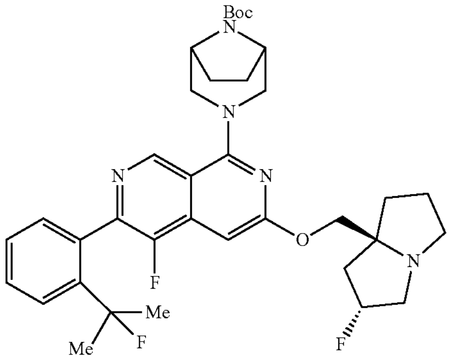

4-((1R,5S)-3,8-diazabicyclo[3.2.1]octan-3-yl)-8-fluoro-7-(2-(2-fluoropropan-2-yl)phenyl)-2-((2-fluorotetrahydro-1H-pyrrolizin-7a(5H)-yl)methoxy)pyrido[4,3-d]pyrimidine bis(2,2,2-trifluoroacetate) (racemic, trans) (1.2 mg, 5%). LCMS (MM-ES+APCI, Pos): m/z 553.3 (M+H).

Example 408

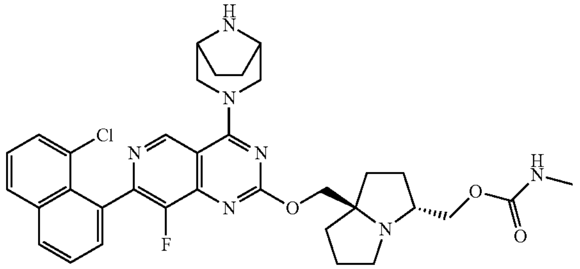 [SMILES: CNC(=O)OC[C@H]1CC[C@@]2(COc3nc(N4CC5CCC(C4)N5)c4cnc(-c5cccc6cccc(Cl)c56)c(F)c4n3)CCCN12]

(7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl methylcarbamate (Mixture of trans Diastereomers)

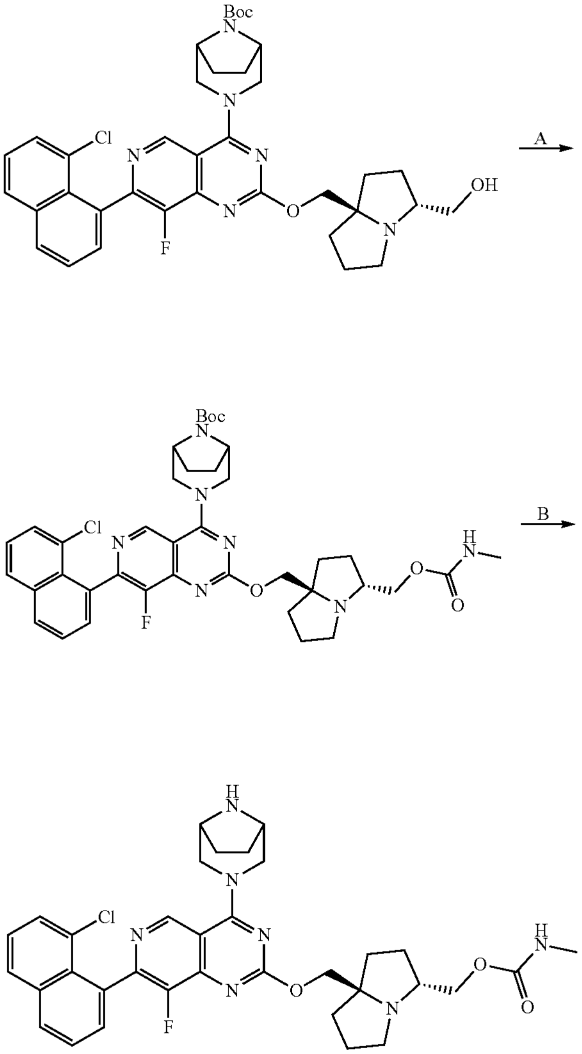

(7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl methylcarbamate (mixture of trans diastereomers). To a solution of tert-butyl 3-(7-(8-chloronaphthalen-1-yl)-8-fluoro-2-((3-(((methylcarbamoyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers) (15 mg, 0.020 mmol) in DCM (1 mL) was added TFA (0.5 mL). The solution was stirred at r.t. for 0.5 h. The solution was concentrated to dryness, basified with $NaHCO_3$ (sat.), and extracted with DCM/IPA (5:1). The extract was dried ($Na_2SO_4$) and concentrated to give the title compound (12 mg, 92%) as a white solid. LCMS (MM-ES+APCI, Pos): m/z 646.3 (M+H).

Example 409
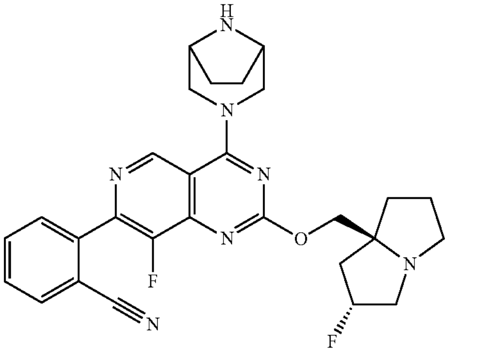 [SMILES: N#Cc1ccccc1-c1ncc2c(N3CC4CCC(C3)N4)nc(OC[C@@]34CCCN3C[C@H](F)C4)nc2c1F]
2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)benzonitrile (racemic, trans)
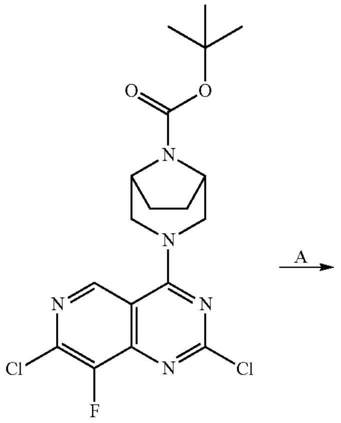
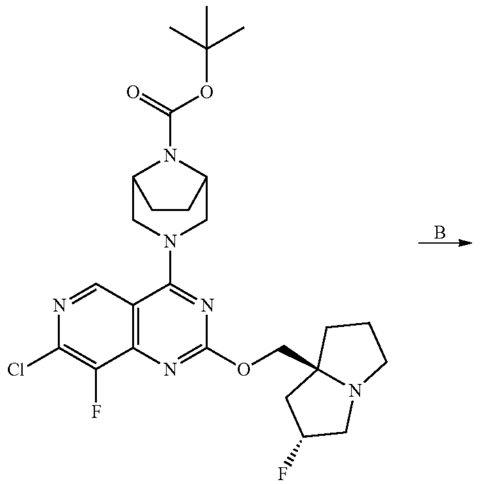
-continued
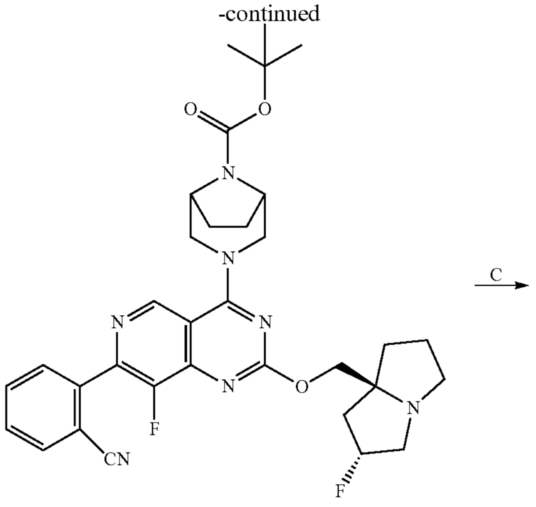
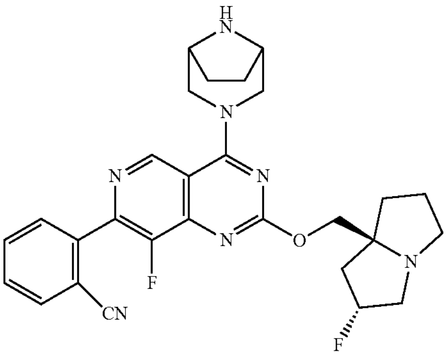
2-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)benzonitrile (9.4 mg, 37% yield). LCMS (MM-ES+APCI, Pos): m/z 518.2 (M+H).
Example 410
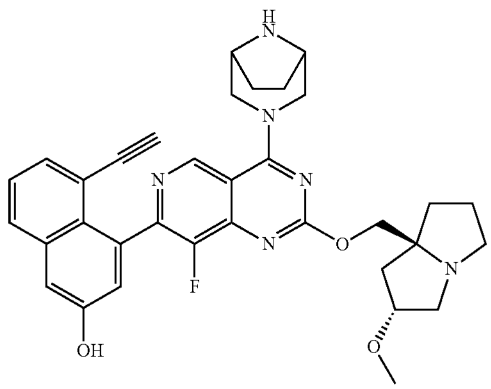 [SMILES: C#Cc1cccc2cc(O)cc(-c3ncc4c(N5CC6CCC(C5)N6)nc(OC[C@@]56CCCN5C[C@H](OC)C6)nc4c3F)c12]

4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-ethynylnaphthalen-2-ol (Mixture of trans Diastereomers)

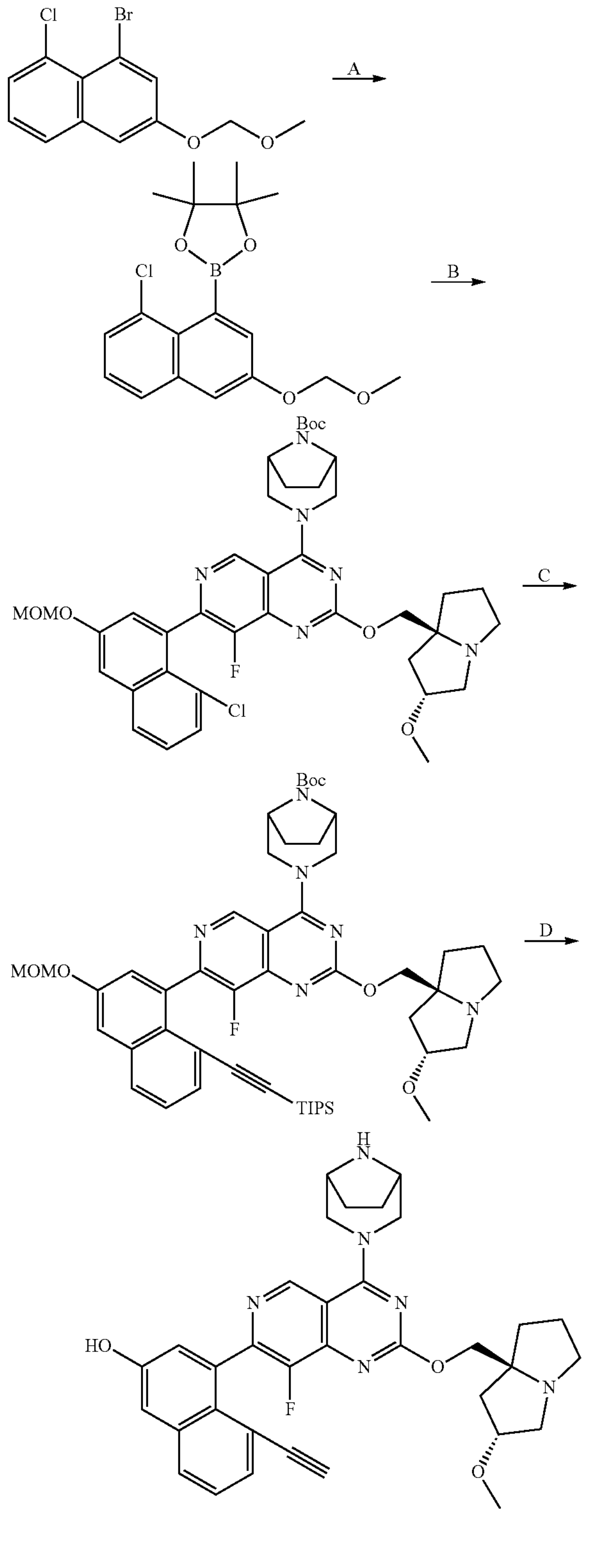

4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-ethynylnaphthalen-2-ol (mixture of trans diastereomers) as a brown solid (1.1 mg, 18%). LCMS (MM-ES+APCI, Pos): m/z 595.2 (M+H).

Example 411

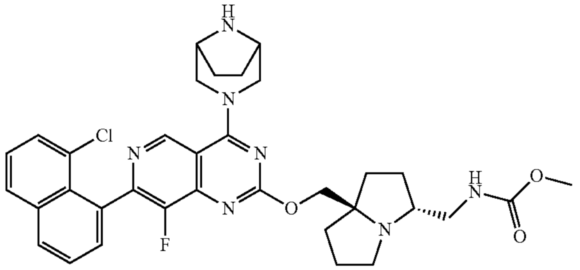 [SMILES: COC(=O)NC[C@H]1CC[C@@]2(COc3nc(N4CC5CCC(C4)N5)c4cnc(-c5cccc6cccc(Cl)c56)c(F)c4n3)CCCN12]

methyl ((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)carbamate (Mixture of trans Diastereomers)

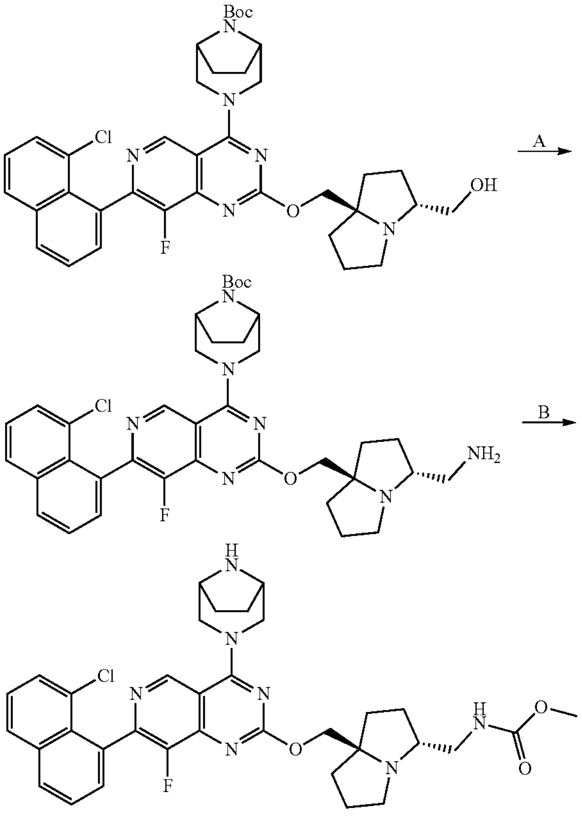

methyl ((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)carbamate bis(2,2,2-trifluoroacetate) (mixture of trans diastereomers). To a solution of tert-butyl(1R,5S)-3-(2-((3-(aminomethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate bis(2,2,2-trifluoroacetate) (mixture of trans diastereomers) (8 mg, 0.009 mmol) in DCM (0.5 mL) at rt was added $Et_3N$ (5 μL, 0.035 mmol) followed by addition of methyl chloroformate (3 μL, 0.03 mmol). The solution was stirred at rt for 0.5 h followed by addition of TFA (0.44 mL). The mixture was stirred at r.t. for 0.5 h, concentrated, and was purified by preparative C18 HPLC (Gilson, 0-95% $CH_3CN/H_2O$ with 0.1% TFA). The desired fractions were combined and lyophilized to give the title compound (5.0 mg, 66%) as the bis TFA salt. LCMS (MM-ES+APCI, Pos): m/z 646.3 (M+H).

Example 412

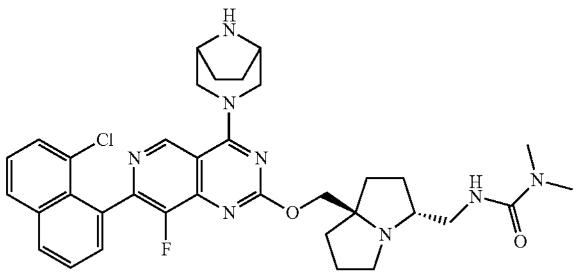 [SMILES: CN(C)C(=O)NC[C@H]1CC[C@@]2(COc3nc(N4CC5CCC(C4)N5)c4cnc(-c5cccc6cccc(Cl)c56)c(F)c4n3)CCCN12]

3-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)-1,1-dimethylurea (Mixture of trans Diastereomers)

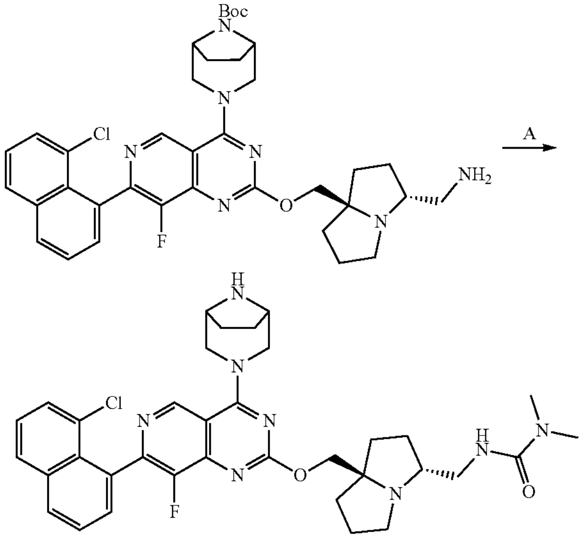

Step A. 3-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)-1,1-dimethylurea bis(2,2,2-trifluoroacetate) (mixture of trans diastereomers). To a solution of tert-butyl (1R,5S)-3-(2-((3-(aminomethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate bis(2,2,2-trifluoroacetate) (mixture of trans diastereomers) (8.0 mg, 0.0087 mmol) in DCM (0.5 mL) at rt was added $Et_3N$ (5 μL, 0.04 mmol) followed by addition of dimethylcarbamyl chloride (3 μL, 0.04 mmol). The solution was stirred at r.t. for 15 h followed by addition of TFA (0.44 mL). The mixture was stirred at r.t. for 0.5 h, concentrated, and was purified by preparative C18 HPLC (Gilson, 0-95% $CH_3CN/H_2O$ with 0.1% TFA). The desired fractions were combined and lyophilized to give the title compound (6 mg, 77%) as the bis TFA salt. LCMS (MM-ES+APCI, Pos): m/z 659.3 (M+H).

Example 413

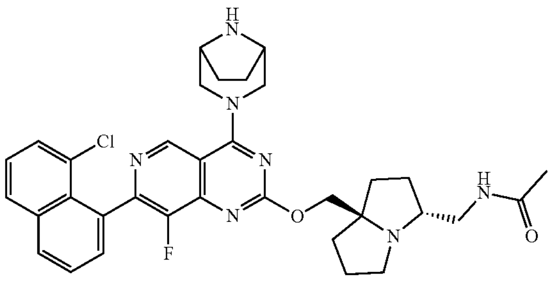 [SMILES: CC(=O)NC[C@H]1CC[C@@]2(COc3nc(N4CC5CCC(C4)N5)c4cnc(-c5cccc6cccc(Cl)c56)c(F)c4n3)CCCN12]

N-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl) acetamide (mixture of trans diastereomers)

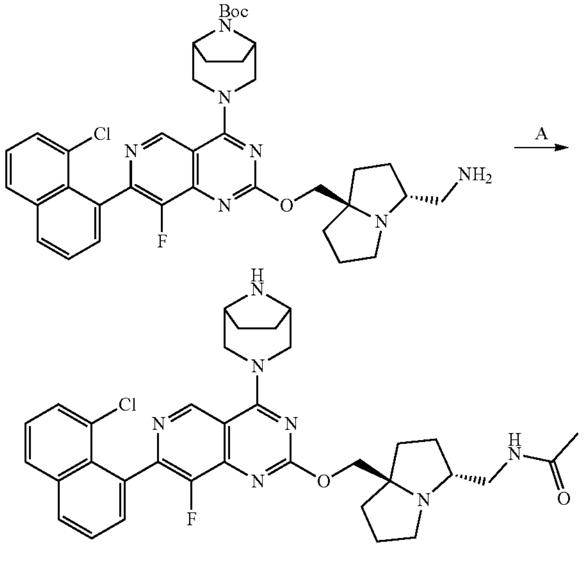

Step A. N-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl) acetamide bis(2,2,2-trifluoroacetate) (mixture of trans diastereomers). To a solution of tert-butyl(1R,5S)-3-(2-((3-

(aminomethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate bis(2,2,2-trifluoroacetate) (mixture of trans diastereomers) (8 mg, 0.009 mmol) in DCM (0.5 mL) was added $Et_3N$ (5 μL, 0.04 mmol) at r.t. followed by addition of acetic anhydride (3 μL, 0.03 mmol). The solution was stirred at r.t. for 0.5 h and TFA (0.5 mL) was added. The mixture was stirred at r.t. for 1 h, concentrated, and was purified by preparative C18 HPLC (Gilson, 0-95% $CH_3CN/H_2O$ with 0.1% TFA). The desired fractions were combined and lyophilized to give the title compound (4 mg, 53%) as the bis TFA salt. LCMS (MM-ES+APCI, Pos): m/z 630.4 (M+H).

Example 414

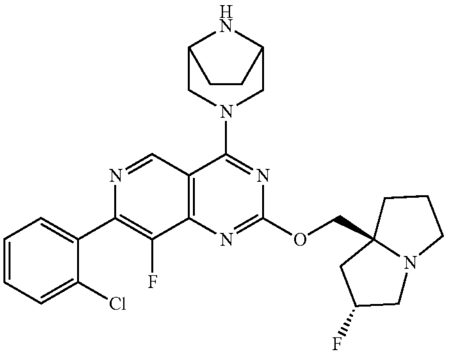 [SMILES: Fc1c(-c2ccccc2Cl)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-7-(2-chlorophenyl)-8-fluoro-2-((2-fluorotetrahydro-1H-pyrrolizin-7a(5H)-yl)methoxy)pyrido[4,3-d]pyrimidine (racemic, trans)

Synthesized according to Example 409 substituting (2-chlorophenyl) boronic acid in place of 2-cyanophenylboronic acid in step B to afford 4-((1R,5S)-3,8-diazabicyclo[3.2.1]octan-3-yl)-7-(2-chlorophenyl)-8-fluoro-2-((2-fluorotetrahydro-1H-pyrrolizin-7a(5H)-yl)methoxy)pyrido[4,3-d]pyrimidine (racemic, trans) (29 mg, 39%). LCMS (MM-ES+APCI, Pos): m/z 527.2 (M+H).

Example 415

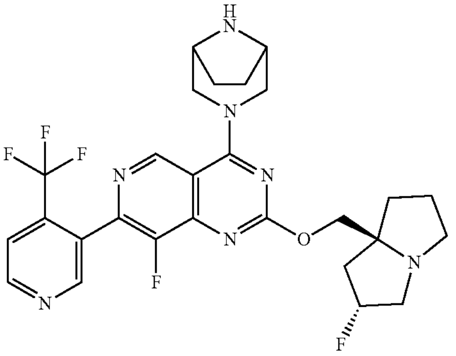 [SMILES: Fc1c(-c2cnccc2C(F)(F)F)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(4-(trifluoromethyl)pyridin-3-yl)pyrido[4,3-d]pyrimidine (racemic, trans)

Synthesized according to Example 409 substituting (2-(trifluoromethyl)pyridin-3-yl) boronic acid in place of 2-cyanophenylboronic acid in step B to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(4-(trifluoromethyl)pyridin-3-yl)pyrido[4,3-d]pyrimidine (racemic, trans) (20 mg, 67%). LCMS (MM-ES+APCI, Pos): m/z 562.2 (M+H).

Example 416

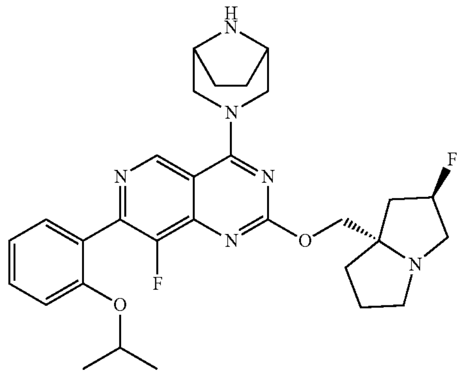 [SMILES: CC(C)Oc1ccccc1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropoxyphenyl)pyrido[4,3-d]pyrimidine (racemic, trans)

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropoxyphenyl)pyrido[4,3-d]pyrimidine (racemic, trans) (22 mg, 58%). LCMS (MM-ES+APCI, Pos): m/z 551.3 (M+H).

Example 417

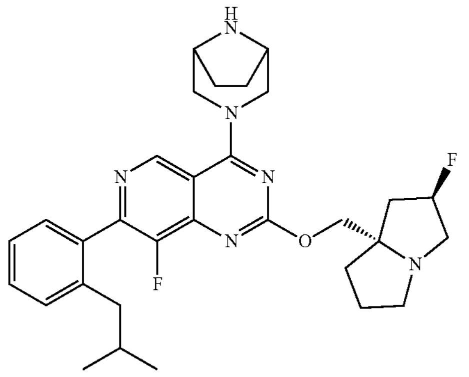

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isobutylphenyl)pyrido[4,3-d]pyrimidine (racemic, trans)

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isobutylphenyl)pyrido[4,3-d]pyrimidine bis(2,2,2-trifluoroacetate) (racemic, trans) (29 mg, 68%). LCMS (MM-ES+APCI, Pos): m/z 549.3 (M+H).

Example 418

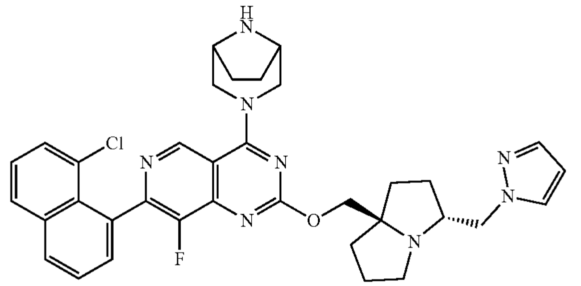 [SMILES: Fc1c(-c2cccc3cccc(Cl)c23)ncc2c(N3CC4CCC(C3)N4)nc(OC[C@]34CCCN3[C@@H](Cn3cccn3)CC4)nc12]

2-(((3R,7aR)-3-((1H-pyrazol-1-yl)methyl)hexahydro-1H-pyrrolizin-7a-yl)methoxy)-4-((1R,5S)-3,8-diazabicyclo[3.2.1]octan-3-yl)-7-(8-chloronaphthalen-1-yl)-8-fluoropyrido[4,3-d]pyrimidine (Mixture of trans Diastereomers)

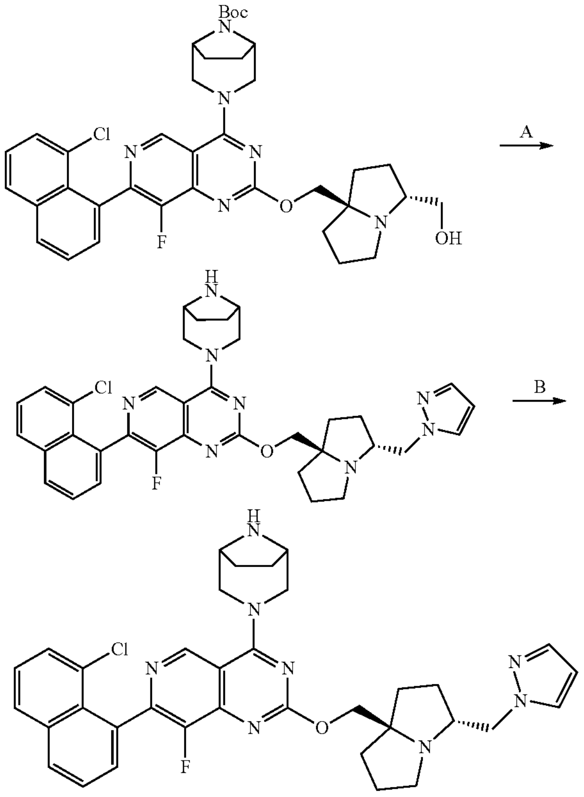

2-((3-((1H-pyrazol-1-yl)methyl)tetrahydro-1H-pyrrolizin-7a(5H)-yl)methoxy)-4-(3,8-diazabicyclo[3.2.1]octan-3-yl)-7-(8-chloronaphthalen-1-yl)-8-fluoropyrido[4,3-d]pyrimidine bis(2,2,2-trifluoroacetate) (mixture of trans diastereomers). To a solution of tert-butyl 3-(2-((3-((1H-pyrazol-1-yl)methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (mixture of trans diastereomers) (7 mg, 0.009 mmol) in DCM (0.50 mL) was added TFA (0.25 mL). The solution was stirred at r.t. for 0.5 h, concentrated, and was purified by preparative C18 HPLC (Gilson, 0-95% $CH_3CN$/$H_2O$ with 0.1% TFA). The desired fractions were combined and lyophilized to give the title compound (4.0 mg, 49%) as the bis TFA salt. LCMS (MM-ES+APCI, Pos): m/z 639.3 (M+H).

Example 419

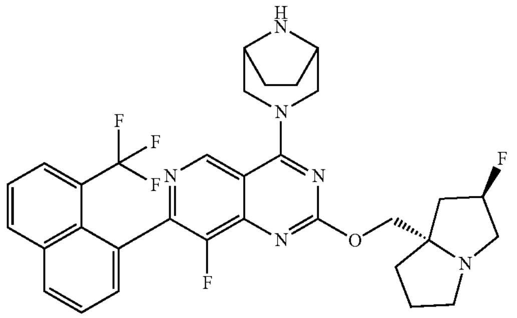 [SMILES: Fc1c(-c2cccc3cccc(C(F)(F)F)c23)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)-7-(8-(trifluoromethyl)naphthalen-1-yl)pyrido[4,3-d]pyrimidine (racemic, trans)

4-((1R,5S)-3,8-diazabicyclo[3.2.1]octan-3-yl)-7-chloro-8-fluoro-2-((2-fluorotetrahydro-1H-pyrrolizin-7a(5H)-yl)methoxy)pyrido[4,3-d]pyrimidine (racemic, trans) (20 mg, 55%). LCMS (MM-ES+APCI, Pos): m/z 611.2 (M+H).

Example 420

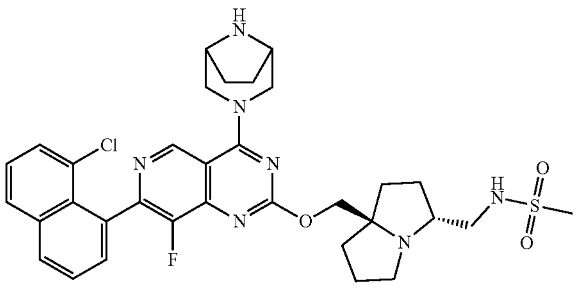 [SMILES: CS(=O)(=O)NC[C@H]1CC[C@@]2(COc3nc(N4CC5CCC(C4)N5)c4cnc(-c5cccc6cccc(Cl)c56)c(F)c4n3)CCCN12]

N-(((3R,7aR)-7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl) methanesulfonamide (Mixture of trans Diastereomers)

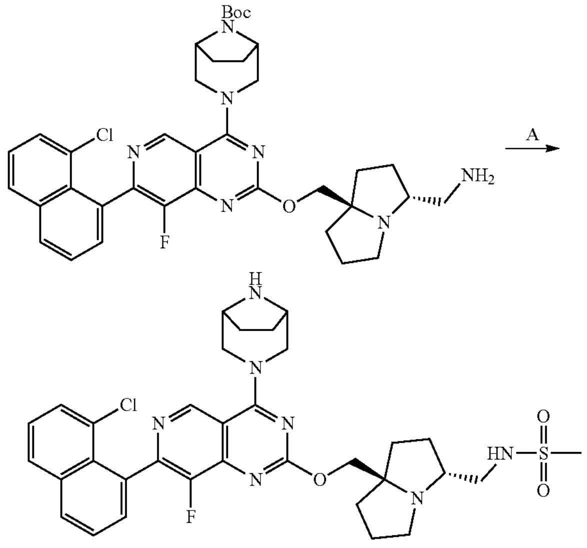

Step A. N-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl) methanesulfonamide bis(2,2,2-trifluoroacetate) (mixture of trans diastereomers). To a solution of tert-butyl(1R,5S)-3-(2-((3-(aminomethyl)tetrahydro-1H-pyrrolizin-7a(5H)-yl) methoxy)-7-(8-chloronaphthalen-1-yl)-8-fluoropyrido[4,3-d]pyrimidin-4-yl)-3,8-diazabicyclo[3.2.1]octane-8-carboxylate (mixture of trans diastereomers) (9 mg, 0.01 mmol) in DCM (1 mL) was added $Et_3N$ (0.013 mL, 0.092 mmol), followed by Ms-Cl (0.0051 mL 0.065 mmol). The mixture was stirred at r.t. for 15 min. MeOH (1 drop) was added and the mixture was concentrated to dryness. The residue was dissolved in DCM (1 mL) and TFA (0.50 mL) and the reaction was stirred for 30 min. The solution was concentrated and the residue was purified by preparative C18 HPLC (Gilson, 0-95% $CH_3CN/H_2O$ with 0.1% TFA). The desired fractions were combined and lyophilized to give the title compound (6 mg, 51%) the bis TFA salt. LCMS (MM-ES+APCI, Pos): m/z 666.2 (M+H).

Example 421

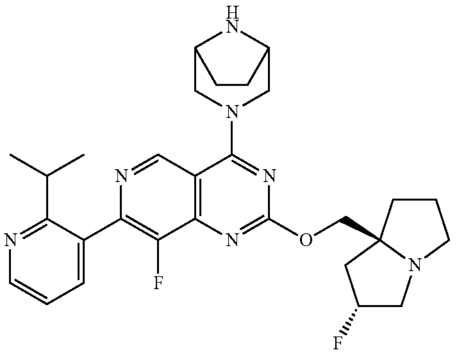 [SMILES: CC(C)c1ncccc1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-8-fluoro-2-(((2R,7aS)-2-fluorohexahydro-1H-pyrrolizin-7a-yl)methoxy)-7-(2-isopropylpyridin-3-yl) pyrido[4,3-d]pyrimidine Synthesized according to Example 394, substituting (2-isopropylpyridin-3-yl) boronic acid in place of (2,6-diisopropylphenyl) boronic acid in Step A (7.3 mg, 16%). LCMS (MM-ES+APCI, Pos): m/z 536.3 [M+H].

Example 422

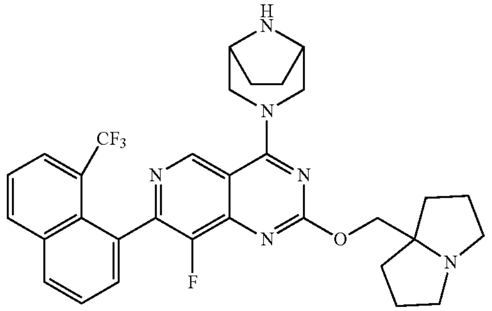 [SMILES: Fc1c(-c2cccc3cccc(C(F)(F)F)c23)ncc2c(N3CC4CCC(C3)N4)nc(OCC34CCCN3CCC4)nc12]

4-((1R,5S)-3,8-diazabicyclo[3.2.1]octan-3-yl)-8-fluoro-2-((hexahydro-1H-pyrrolizin-7a-yl)methoxy)-7-(8-(trifluoromethyl)naphthalen-1-yl)pyrido[4,3-d] pyrimidine

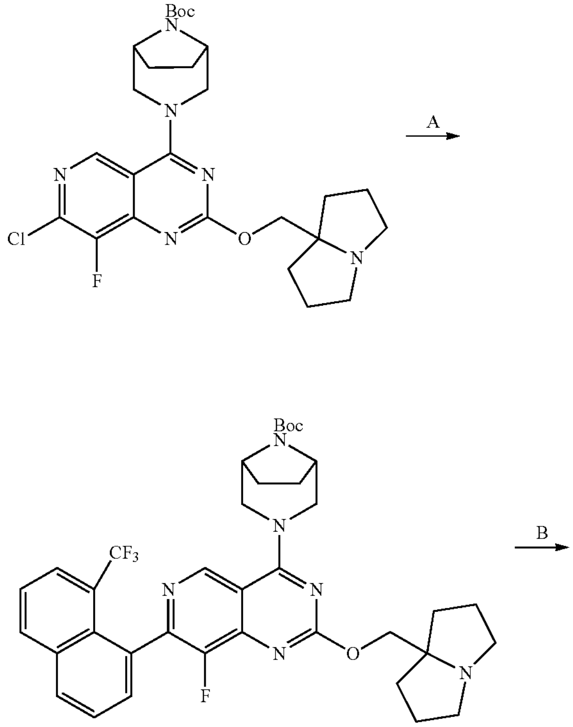

-continued

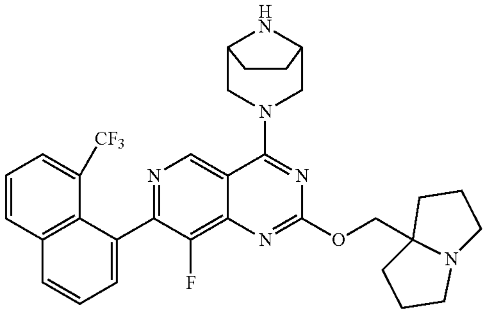

4-((1R,5S)-3,8-diazabicyclo[3.2.1]octan-3-yl)-8-fluoro-2-((tetrahydro-1H-pyrrolizin-7a(5H)-yl)methoxy)-7-(8-(trifluoromethyl)naphthalen-1-yl)pyrido[4,3-d]pyrimidine (20 mg, 50%). LCMS (MM-ES+APCI, Pos): m/z 593.3 (M+H).

Example 423

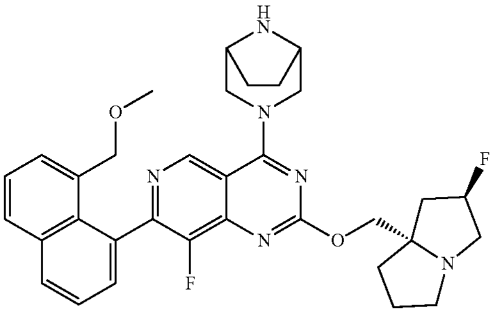 [SMILES: COCc1cccc2cccc(-c3ncc4c(N5CC6CCC(C5)N6)nc(OC[C@@]56CCCN5C[C@H](F)C6)nc4c3F)c12]

4-((1R,5S)-3,8-diazabicyclo[3.2.1]octan-3-yl)-8-fluoro-2-(((2R,7aS)-2-fluorohexahydro-1H-pyrrolizin-7a-yl)methoxy)-7-(8-(methoxymethyl)naphthalen-1-yl)pyrido[4,3-d]pyrimidine (racemic, trans)

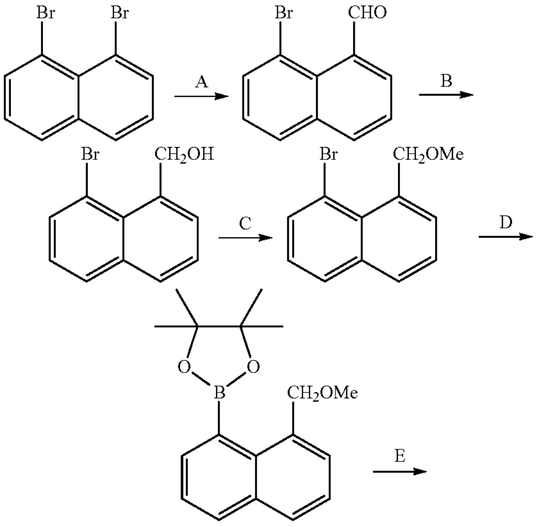

-continued

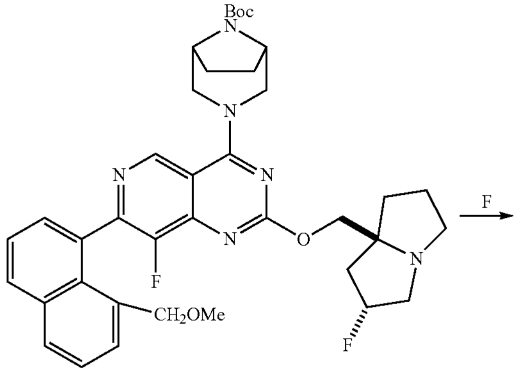

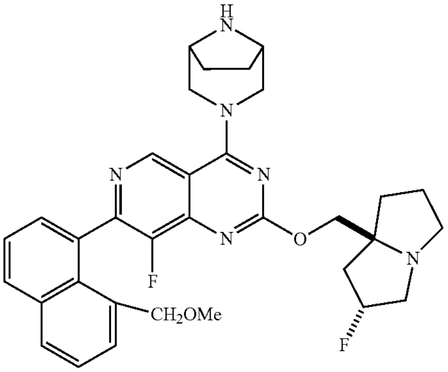

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(8-(methoxymethyl)naphthalen-1-yl)pyrido[4,3-d]pyrimidine dihydrochloride (racemic, trans) (5 mg, 58%). LCMS (MM-ES+APCI, Pos): m/z 587.3 (M+H).

Example 424

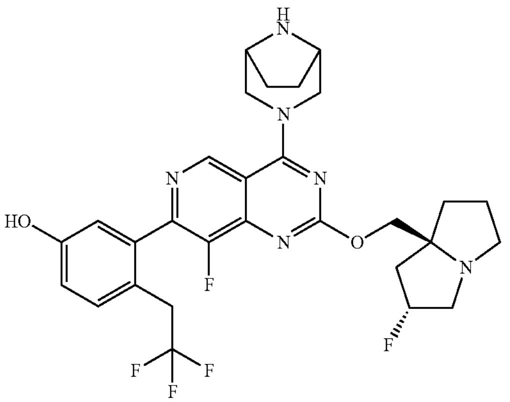 [SMILES: Oc1ccc(CC(F)(F)F)c(-c2ncc3c(N4CC5CCC(C4)N5)nc(OC[C@@]45CCCN4C[C@H](F)C5)nc3c2F)c1]

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-4-(2,2,2-trifluoroethyl)phenol (racemic, trans)

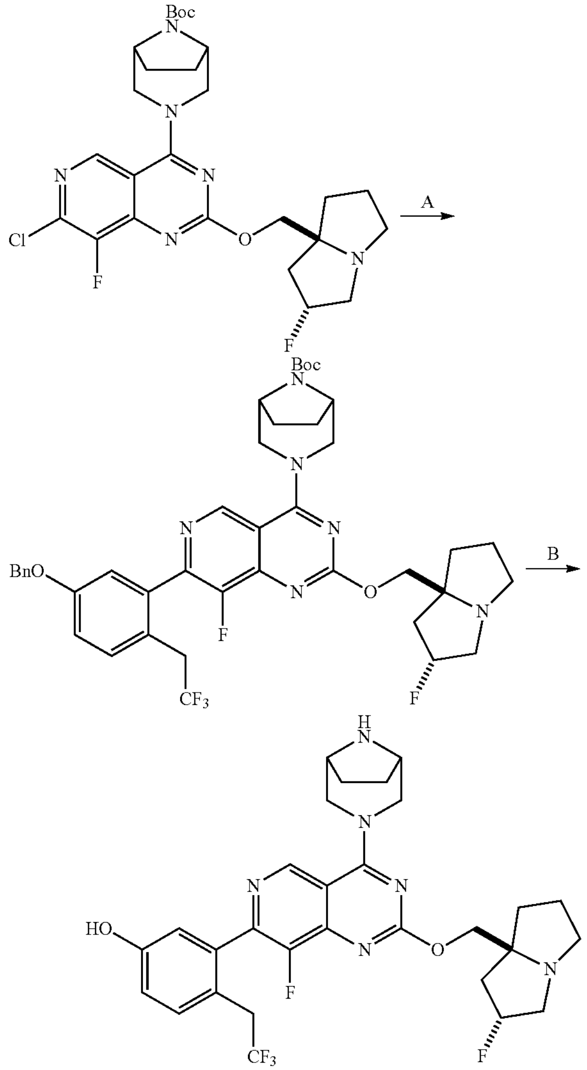

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoroethyl)phenol bis(2,2,2-trifluoroacetate) (racemic, trans). Tert-butyl(1R,5S)-3-(7-(5-(benzyloxy)-2-(2,2,2-trifluoroethyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (42 mg, 0.054 mmol) and pentamethylbenzene (24 mg, 0.16 mmol) were dissolved in DCM (2 mL). The solution was cooled to −78° C. and 1 M boron trichloride in DCM (0.3 mL) was added dropwise. The mixture was warmed to 0° C. over 30 minutes. The reaction was quenched with 1:1 MeCN:MeOH (5 mL) and condensed. The residue was purified (prep HPLC, 5-95% MeCN/$H_2O$/0.1% TFA) and lyophilization gave 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoroethyl)phenol bis(2,2,2-trifluoroacetate) (racemic, trans) (10 mg, 27%). LCMS (MM-ES+APCI, Pos): m/z 591 (M+H).

Example 425

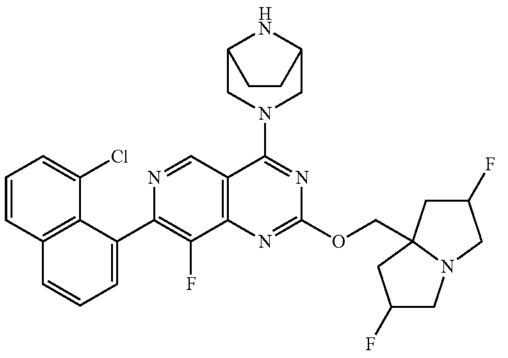 [SMILES: Fc1c(-c2cccc3cccc(Cl)c23)ncc2c(N3CC4CCC(C3)N4)nc(OCC34CC(F)CN3CC(F)C4)nc12]

4-((1R,5S)-3,8-diazabicyclo[3.2.1]octan-3-yl)-7-(8-chloronaphthalen-1-yl)-2-((2,6-difluorohexahydro-1H-pyrrolizin-7a-yl)methoxy)-8-fluoropyrido[4,3-d]pyrimidine (Mixture of Isomers)

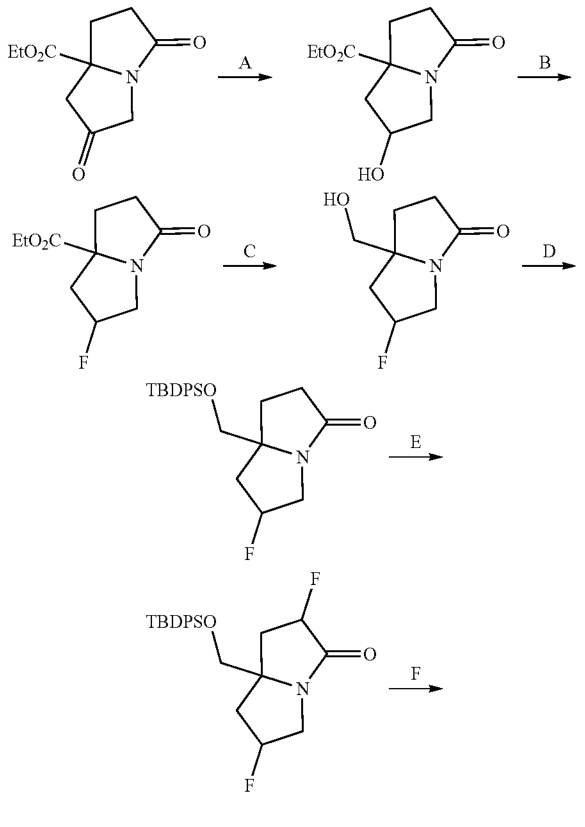

-continued
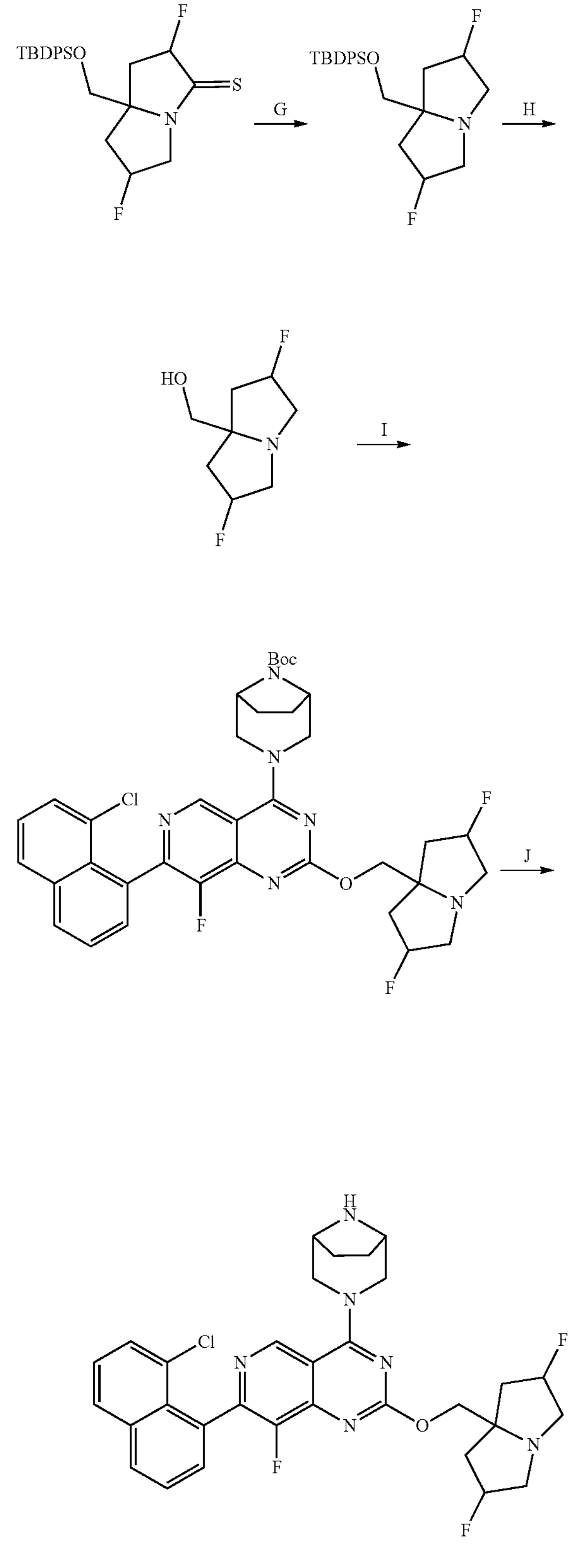
4-((1R,5S)-3,8-diazabicyclo[3.2.1]octan-3-yl)-7-(8-chloronaphthalen-1-yl)-2-((2,6-difluorotetrahydro-1H-pyrrolizin-7a(5H)-yl)methoxy)-8-fluoropyrido[4,3-d]pyrimidine bis(2,2,2-trifluoroacetate) (mixture of isomers) (1.3 mg, 43%). LCMS (MM-ES+APCI, Pos): m/z 595.2 (M+H).
Example 426
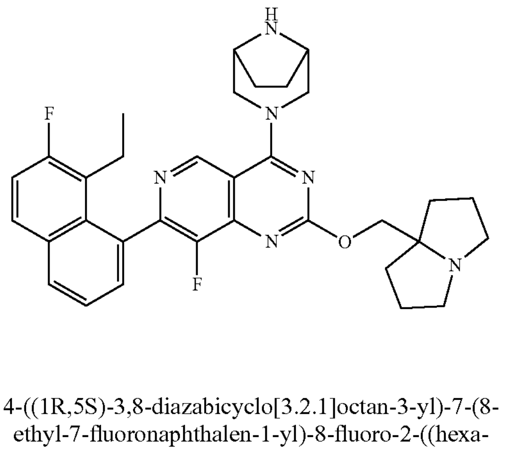
4-((1R,5S)-3,8-diazabicyclo[3.2.1]octan-3-yl)-7-(8-ethyl-7-fluoronaphthalen-1-yl)-8-fluoro-2-((hexahydro-1H-pyrrolizin-7a-yl)methoxy)pyrido[4,3-d]pyrimidine
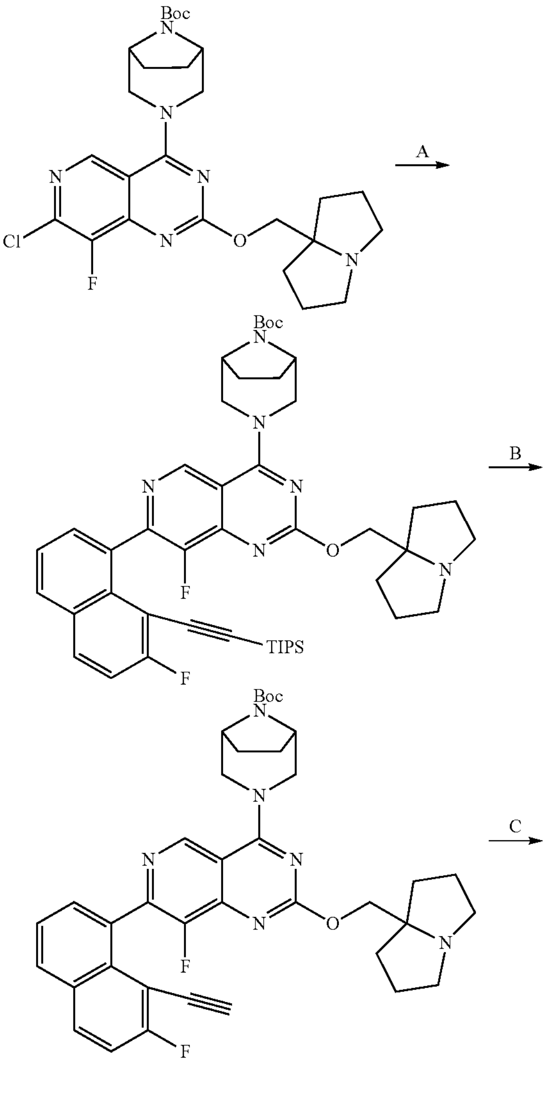

-continued

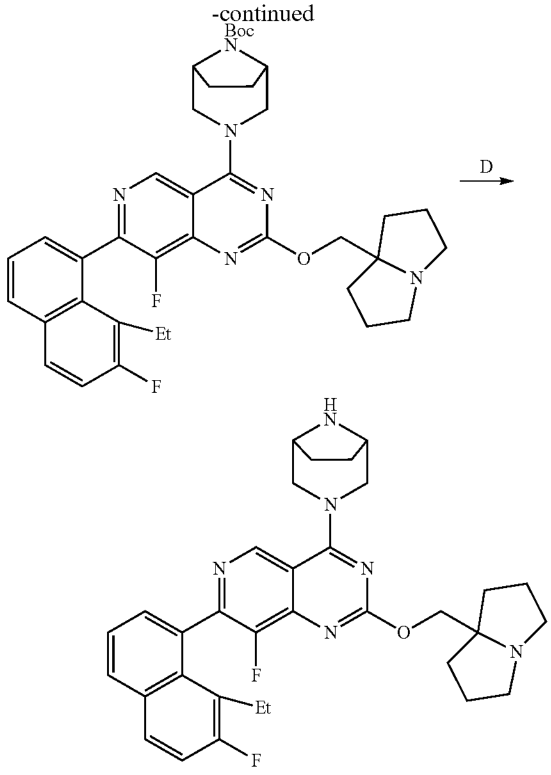

4-((1R,5S)-3,8-diazabicyclo[3.2.1]octan-3-yl)-7-(8-ethyl-7-fluoronaphthalen-1-yl)-8-fluoro-2-((tetrahydro-1H-pyrrolizin-7a(5H)-yl)methoxy)pyrido[4,3-d]pyrimidine dihydrochloride (15 mg, 56%). LCMS (MM-ES+APCI, Pos): m/z 571.0 (M+H).

Example 427

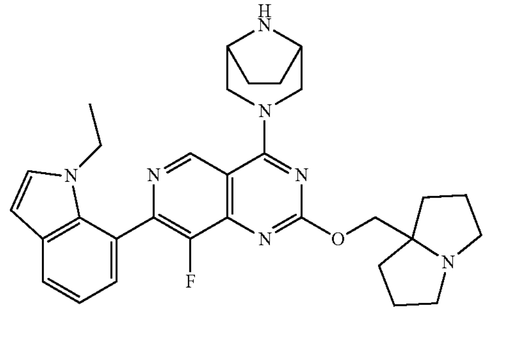 [SMILES: CCn1ccc2cccc(-c3ncc4c(N5CC6CCC(C5)N6)nc(OCC56CCCN5CCC6)nc4c3F)c21]

4-((1R,5S)-3,8-diazabicyclo[3.2.1]octan-3-yl)-7-(1-ethyl-1H-indol-7-yl)-8-fluoro-2-((hexahydro-1H-pyrrolizin-7a-yl)methoxy)pyrido[4,3-d]pyrimidine

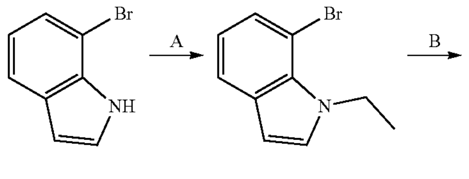

-continued

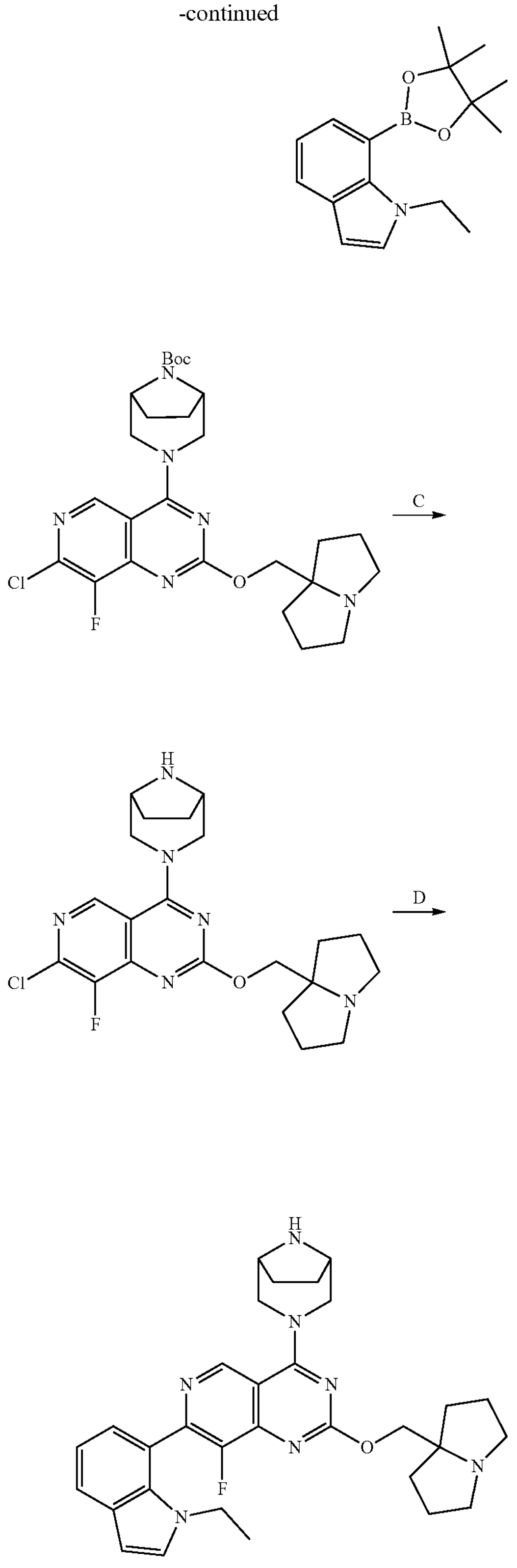

4-((1R,5S)-3,8-diazabicyclo[3.2.1]octan-3-yl)-7-(1-ethyl-1H-indol-7-yl)-8-fluoro-2-((tetrahydro-1H-pyrrolizin-7a(5H)-yl)methoxy)pyrido[4,3-d]pyrimidine as a white solid (10 mg, 35%). LCMS (MM-ES+APCI, Pos): m/z 542.4 (M+H).

Example 428

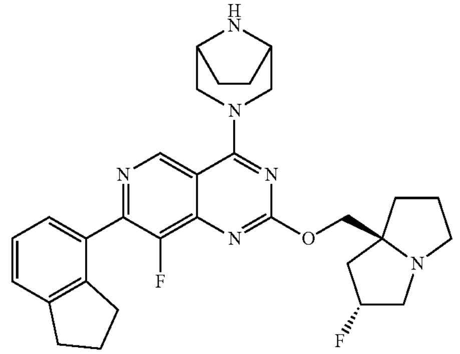 [SMILES: Fc1c(-c2cccc3c2CCC3)ncc2c(N3CC4CCC(C3)N4)nc(OC[C@@]34CCCN3C[C@H](F)C4)nc12]

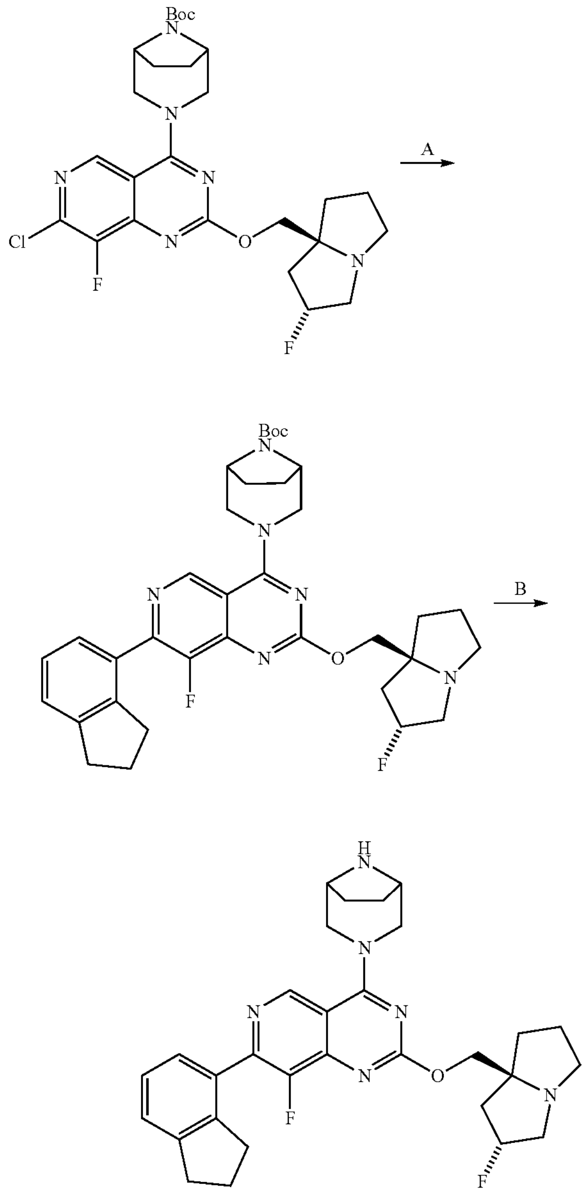

4-(3,8-diazabicyclo[3.2.1]octan-3-yl)-7-(2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidine (racemic, trans)

4-(3,8-diazabicyclo[3.2.1]octan-3-yl)-7-(2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidine. To the above crude tert-butyl 3-(7-(2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate in DCM (1.0 ml) was added TFA (0.50 ml). The solution was stirred at rt for 0.5 h, concentrated and the residue was purified by preparative C18 HPLC eluting with 0-95% $CH_3CN/H_2O$ with 0.1% TFA as modifier. The desired fractions were combined, basified with $NaHCO_3$(Sat.) and extracted with DCM. The combined extract was dried over $Na_2SO_4$ and concentrated to give the title compound as a white solid (6.0 mg, 15% over 2 steps). LCMS (MM-ES+APCI, Pos): m/z 533.4 (M+H).

Example 429

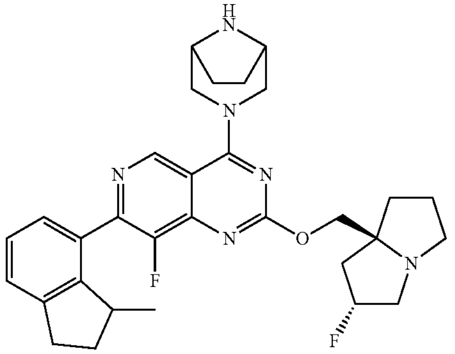 [SMILES: CC1CCc2cccc(-c3ncc4c(N5CC6CCC(C5)N6)nc(OC[C@@]56CCCN5C[C@H](F)C6)nc4c3F)c21]

4-(3,8-diazabicyclo[3.2.1]octan-3-yl)-8-fluoro-2-(((2R,7aS)-2-fluorotetrahydro-1H-pyrrolizin-7a(5H)-yl)methoxy)-7-(3-methyl-2,3-dihydro-1H-inden-4-yl)pyrido[4,3-d]pyrimidine (racemic, trans)

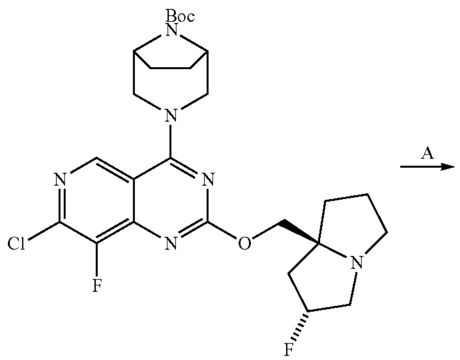

-continued

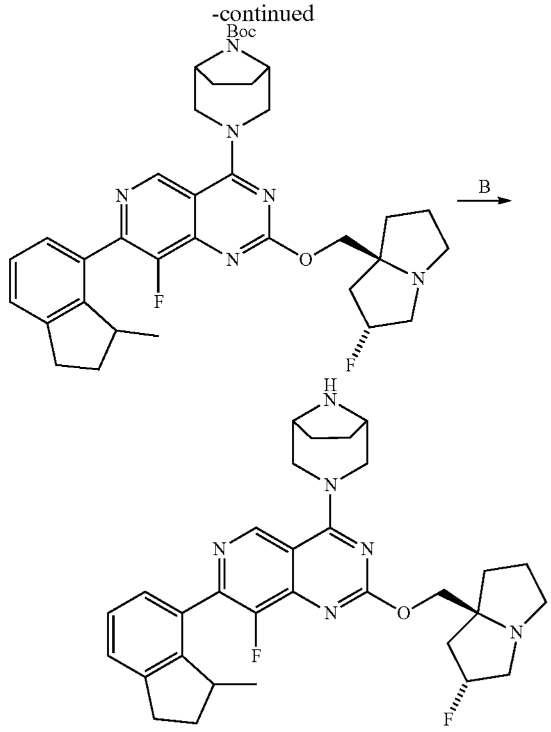

4-(3,8-diazabicyclo[3.2.1]octan-3-yl)-8-fluoro-2-(((2R,7aS)-2-fluorotetrahydro-1H-pyrrolizin-7a(5H)-yl)methoxy)-7-(3-methyl-2,3-dihydro-1H-inden-4-yl)pyrido[4,3-d]pyrimidine. To a solution of tert-butyl 3-(8-fluoro-2-(((2R,7aS)-2-fluorotetrahydro-1H-pyrrolizin-7a(5H)-yl)methoxy)-7-(3-methyl-2,3-dihydro-1H-inden-4-yl)pyrido[4,3-d]pyrimidin-4-yl)-3,8-diazabicyclo[3.2.1]octane-8-carboxylate in DCM (1.0 ml) was added TFA (0.50 ml). The solution was stirred at rt for 0.5 h, and concentrated. The residue was purified by preparative C18 HPLC eluting with 0-95% $CH_3CN/H_2O$ with 0.1% TFA as modifier. The desired fractions were combined, basified with $NaHCO_3$(Sat.) and extracted with DCM. The combined extract was dried over $Na_2SO_4$ and concentrated to give the title compound as a white solid (40 mg, 73% over 2 steps). LCMS (MM-ES+APCI, Pos): m/z 547.3 (M+H).

Example 430

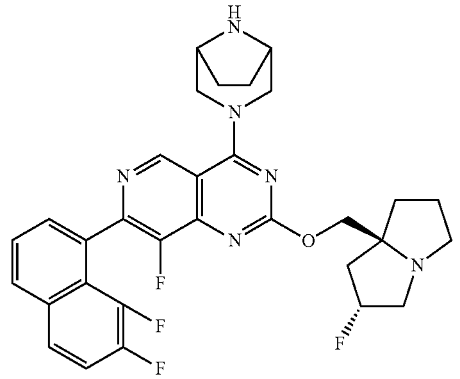 [SMILES: Fc1ccc2cccc(-c3ncc4c(N5CC6CCC(C5)N6)nc(OC[C@@]56CCCN5C[C@H](F)C6)nc4c3F)c2c1F]

4-((1R,5S)-3,8-diazabicyclo[3.2.1]octan-3-yl)-7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidine (racemic, trans)

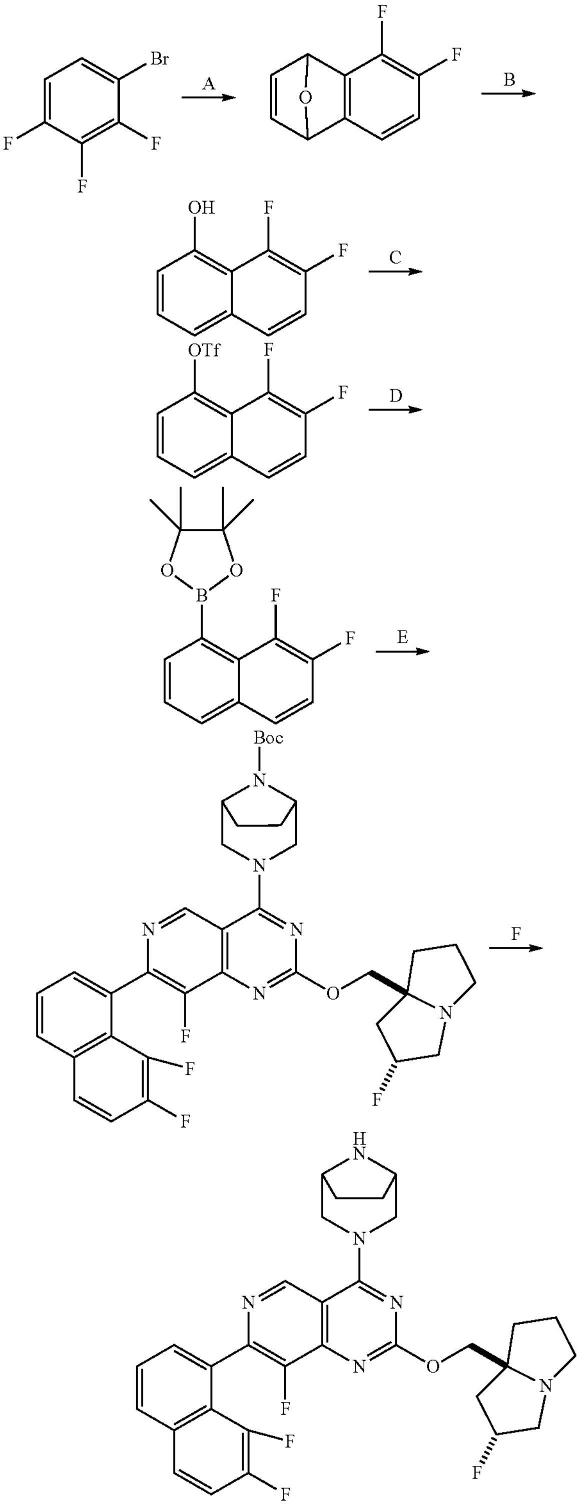

4-((1R,5S)-3,8-diazabicyclo[3.2.1]octan-3-yl)-7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidine. A mixture of tert-butyl(1R,5S)-3-(7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (23 mg, 0.034 mmol) and DCM (0.8 mL) was cooled to 0° C. with stirring and 4 M hydrogen chloride in dioxane (0.84 mL, 3.4 mmol) was added at once. The reaction mixture was kept at r.t. for 2 h. The dioxane-HCl phase was decanted and discarded. The precipitate was dried under a stream of nitrogen, wetted with 2 drops of water, mixed with DCM (10 mL) and 2M $Na_2CO_3$ (0.5 mL), and sonicated. The organic phase was dried over $Na_2CO_3$, filtered and evaporated in vacuo to yield the target compound (20 mg, 97%). LCMS (MM-ES+APCI, Pos): m/z 579.3 (M+H)+.

Example 431

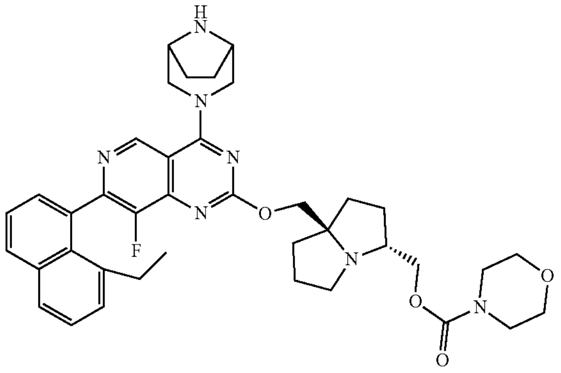 [SMILES: CCc1cccc2cccc(-c3ncc4c(N5CC6CCC(C5)N6)nc(OC[C@]56CCCN5[C@@H](COC(=O)N5CCOCC5)CC6)nc4c3F)c12]

((3R,7aR)-7a-(((4-(3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizin-3-yl)methyl morpholine-4-carboxylate (trans enantiomer)

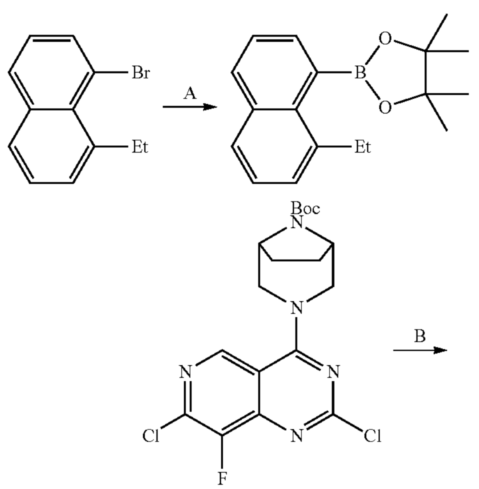

-continued

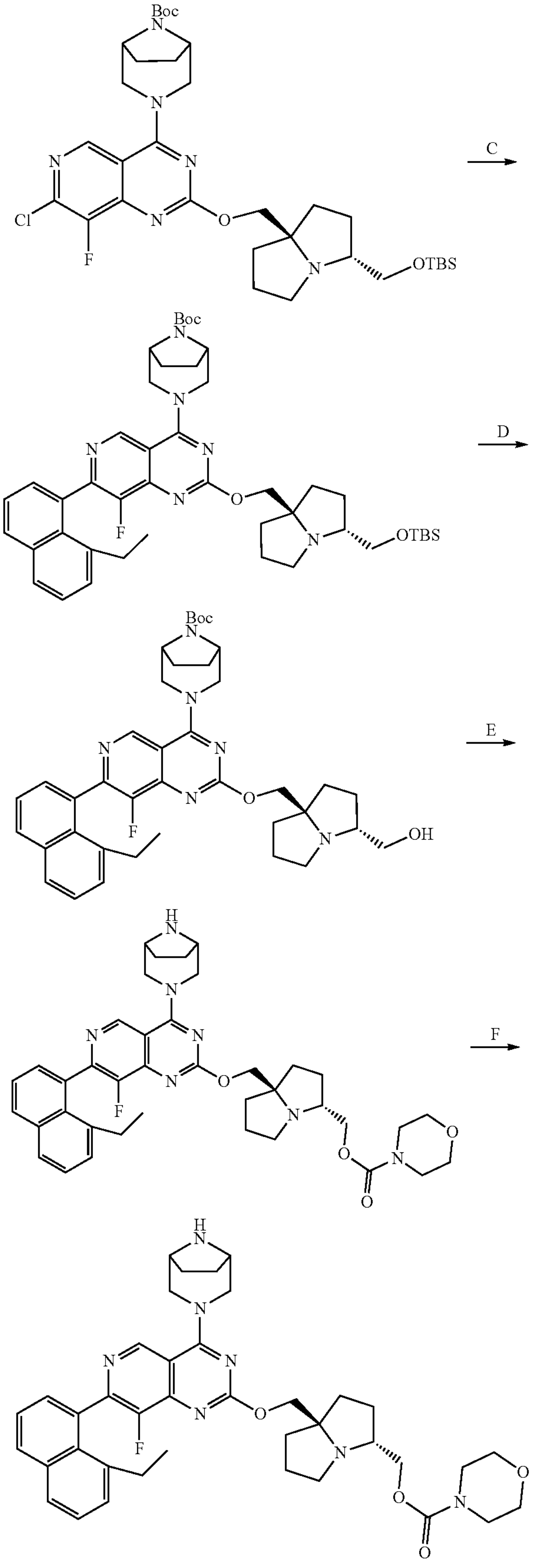

((3R,7aR)-7a-(((4-(3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizin-3-yl)methyl morpholine-4-carboxylate. To a solution of ((3R,7aR)-7a-(((4-(8-(tert-butoxycarbonyl)-3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizin-3-yl)methyl morpholine-4-carboxylate (10 mg, 0.013 mmol) in DCM (1.0 ml) was added TFA (0.50 ml). The solution was stirred at rt for 45 min and concentrated. The residue was purified by preparative C18 HPLC eluting with 0-95% $CH_3CN/H_2O$ with 0.1% TFA as modifier. The desired fractions were combined, basified with $NaHCO_3$ and extracted with DCM/IPA (10:1). The combined extract was dried over $Na_2SO_4$ and concentrated to give the title compound (5 mg, 57%) as a white solid. LCMS (MM-ES+APCI, Pos): m/z 696.4 (M+H).

Example 432

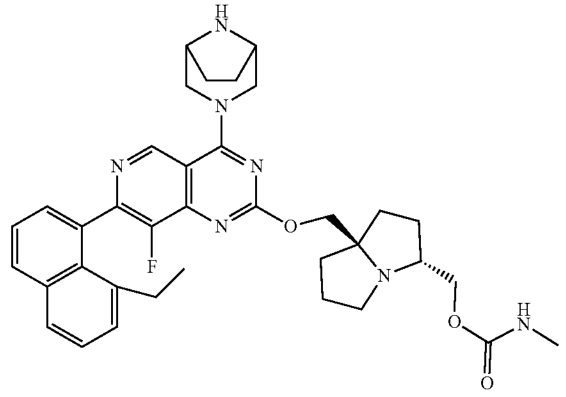 [SMILES: CCc1cccc2cccc(-c3ncc4c(N5CC6CCC(C5)N6)nc(OC[C@]56CCCN5[C@@H](COC(=O)NC)CC6)nc4c3F)c12]

((3R,7aR)-7a-(((4-(3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizin-3-yl)methyl methylcarbamate. (trans enantiomer)

Synthesized according to Example 431 substituting methyl amine for morpholine in step E. LCMS (MM-ES+APCI, Pos): m/z 640.4 (M+H).

Example 433

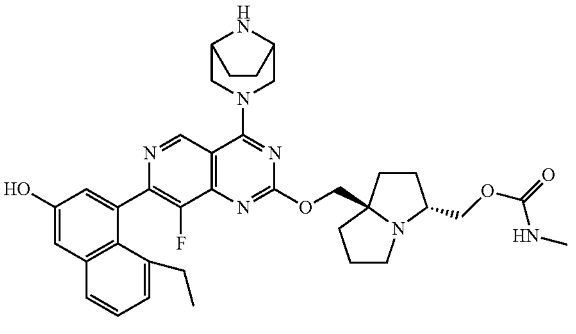 [SMILES: CCc1cccc2cc(O)cc(-c3ncc4c(N5CC6CCC(C5)N6)nc(OC[C@]56CCCN5[C@@H](COC(=O)NC)CC6)nc4c3F)c12]

((3R,7aR)-7a-(((4-((1R,5S)-3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl methylcarbamate (trans racemic)

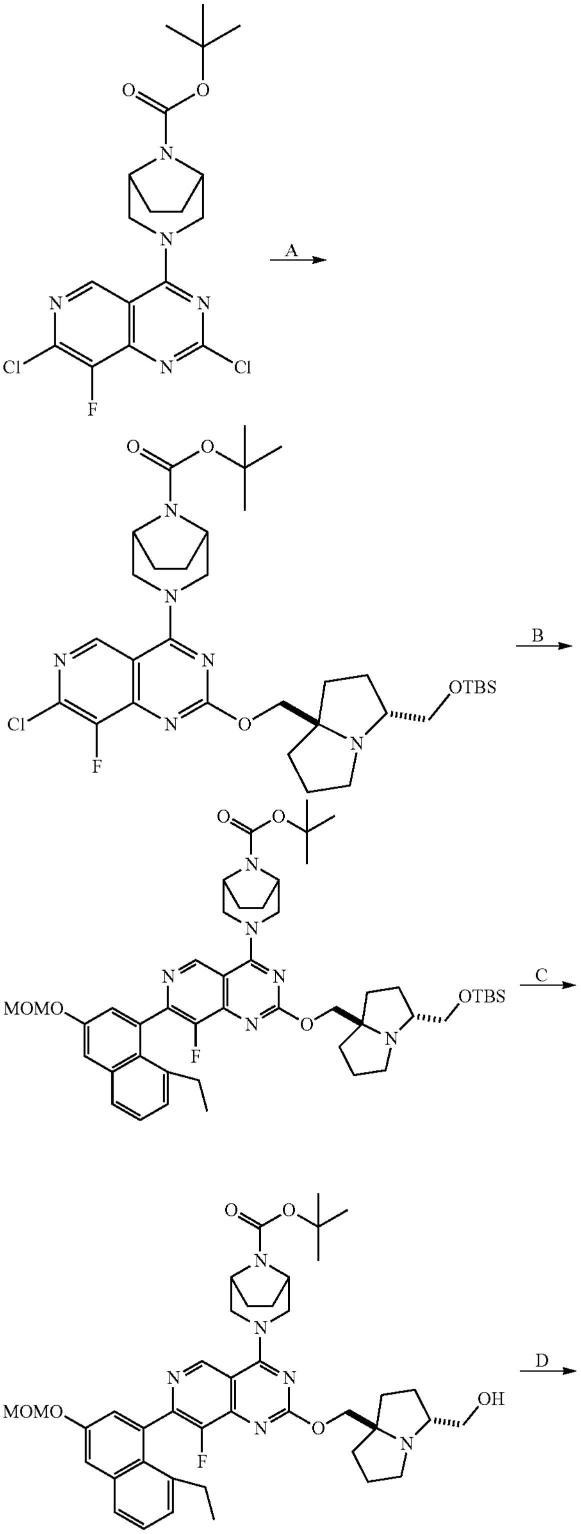

-continued

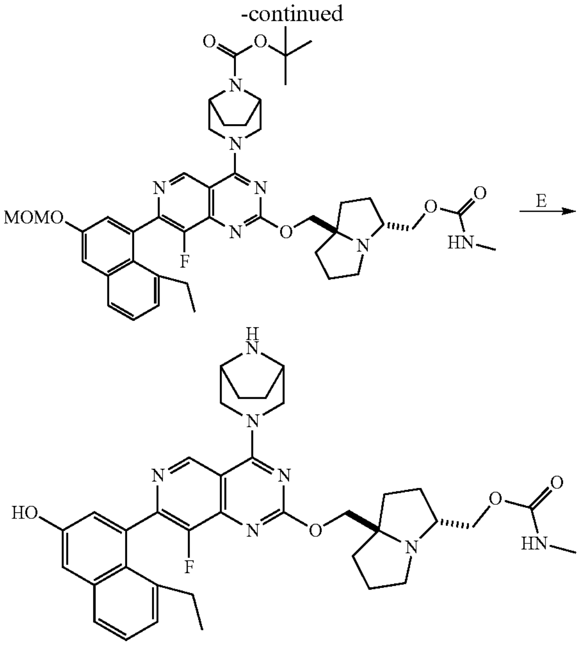

((3R,7aR)-7a-(((4-((1R,5S)-3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl methylcarbamate. To a solution of tert-butyl(1R,5S)-3-(7-(8-ethyl-3-(methoxymethoxy)naphthalen-1-yl)-8-fluoro-2-((-3-(((methylcarbamoyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (15 mg, 0.018 mmol) in DCM (0.5 mL) was added 4N HCl/dioxane (0.5 mL). The mixture was stirred for 1 hour and then concentrated in vacuo. The residue was triturated with $Et_2O$, filtered and dried in vacuo to give the title compound as the HCl salt (10 mg, 72%) as a yellow solid. LCMS (MM-ES+APCI, Pos): m/z 656.4 (M+H).

Example 434

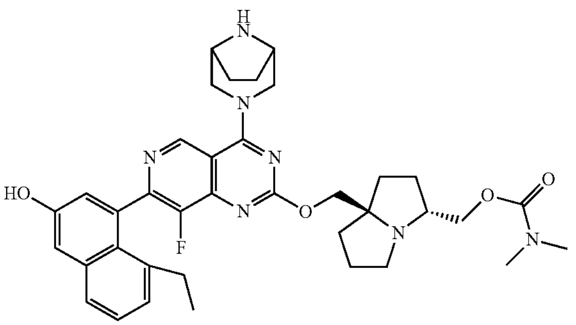 [SMILES: CCc1cccc2cc(O)cc(-c3ncc4c(N5CC6CCC(C5)N6)nc(OC[C@]56CCCN5[C@@H](COC(=O)N(C)C)CC6)nc4c3F)c12]

7a-(((4-((1R,5S)-3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl dimethyl carbamate (trans racemic)

Synthesized according to Example 433 substituting dimethylamine in place of methylamine in Step D to give title product as the HCl salt (18 mg, 77%). LCMS (MM-ES+APCI, Pos): m/z 670.4 (M+H).

Example 435

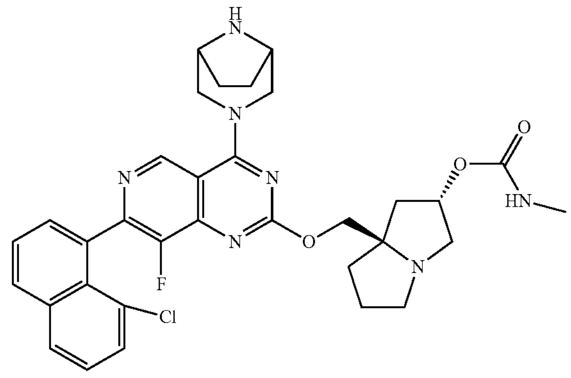 [SMILES: CNC(=O)O[C@@H]1CN2CCC[C@]2(COc2nc(N3CC4CCC(C3)N4)c3cnc(-c4cccc5cccc(Cl)c45)c(F)c3n2)C1]

(2S,7aR)-7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-yl methylcarbamate (racemic, trans)

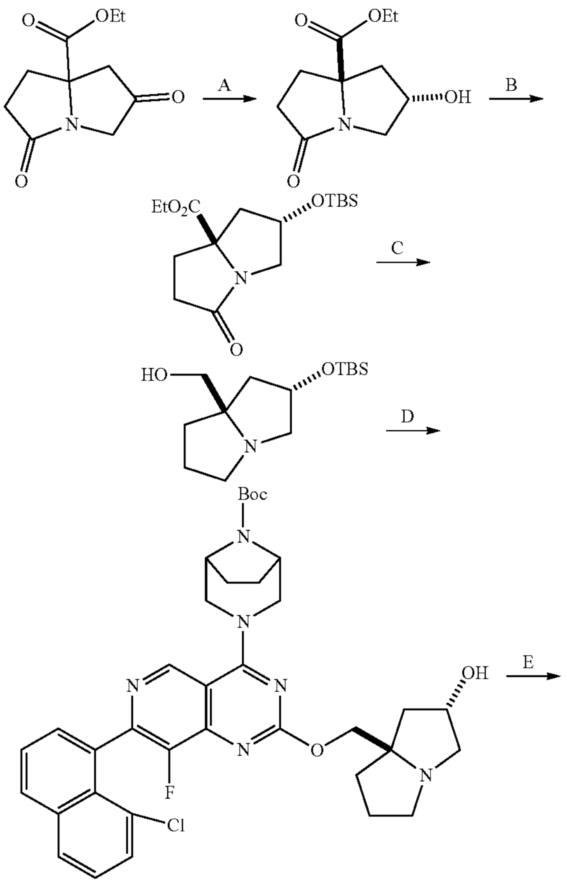

-continued

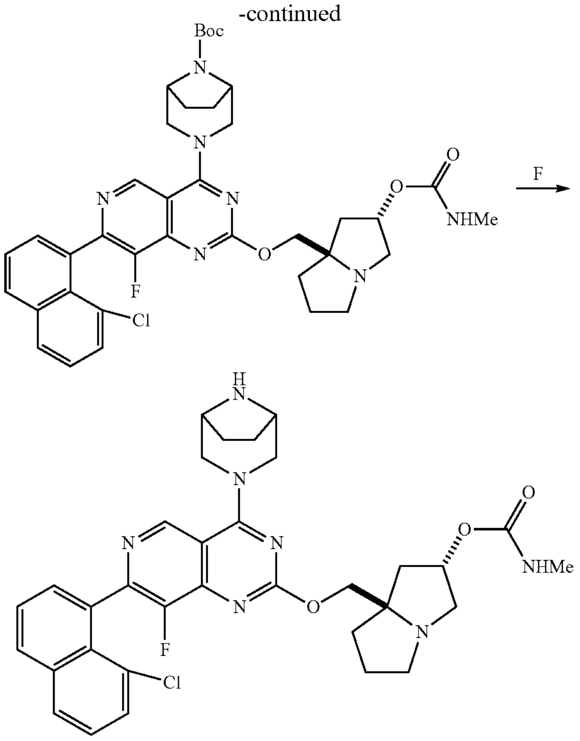

(2S,7aR)-7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-yl methylcarbamate. To a solution of tert-butyl(1R,5S)-3-(7-(8-chloronaphthalen-1-yl)-8-fluoro-2-(((2S,7aR)-2-((methylcarbamoyl)oxy)tetrahydro-1H-pyrrolizin-7a(5H)-yl)methoxy)pyrido[4,3-d]pyrimidin-4-yl)-3,8-diazabicyclo[3.2.1]octane-8-carboxylate (8.0 mg, 0.011 mmol) in DCM (0.60 ml) was added TFA (0.30 ml). The solution was stirred at rt for 0.5 h, and concentrated. The residue was purified by preparative C18 HPLC eluting with 0-95% $CH_3CN/H_2O$ with 0.1% TFA as modifier. The desired fractions were combined, basified with $NaHCO_3$ (sat.) and extracted with CHCl3/IPA (5:1). The combined extract was dried over $Na_2SO_4$ and concentrated to give the title compound (5.0 mg, 72%) as a light yellow solid. LCMS (MM-ES+APCI, Pos): m/z 632.4 (100%)(M+H).

Example 436

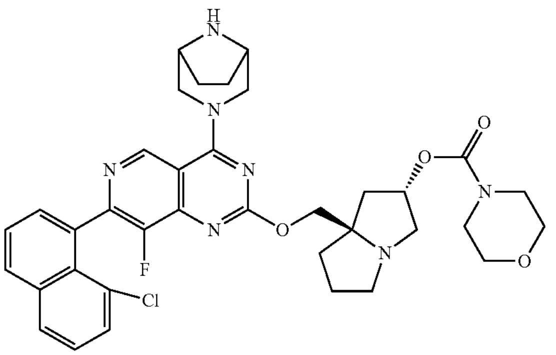 [SMILES: O=C(O[C@@H]1CN2CCC[C@]2(COc2nc(N3CC4CCC(C3)N4)c3cnc(-c4cccc5cccc(Cl)c45)c(F)c3n2)C1)N1CCOCC1]

(2S,7aR)-7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-yl morpholine-4-carboxylate (racemic, trans)

Synthesized according to Example 435 substituting morpholine for methyl amine in step E to give product (7.0 mg, 80%) as a light yellow solid. LCMS (MM-ES+APCI, Pos): m/z 688.5 (M+H).

Example 437

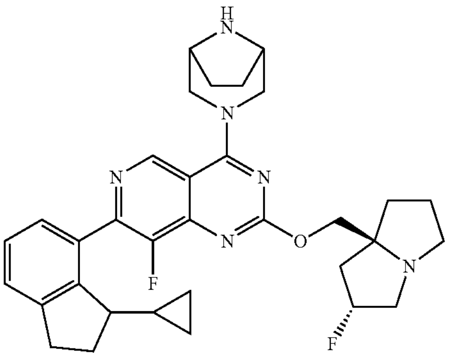 [SMILES: Fc1c(-c2cccc3c2C(C2CC2)CC3)ncc2c(N3CC4CCC(C3)N4)nc(OC[C@@]34CCCN3C[C@H](F)C4)nc12]

4-(3,8-diazabicyclo[3.2.1]octan-3-yl)-7-(3-cyclopropyl-2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidine

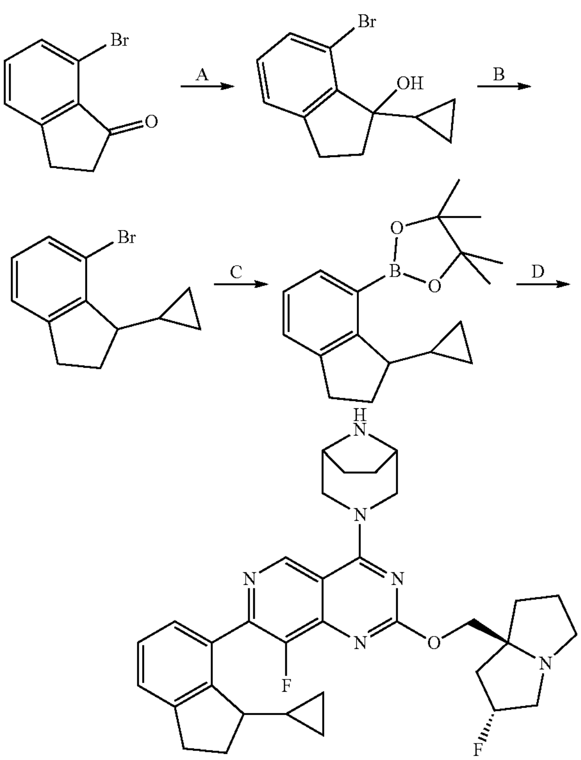

tert-butyl 3-(7-(3-cyclopropyl-2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. To a vial containing tert-butyl 3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (43 mg, 0.15 mmol), 2-(3-cyclopropyl-2,3-dihydro-1H-inden-4-yl)-4,4,5,5-tetramethyl-1,3,2-dioxaborolane (55 mg, 0.10 mmol), Pd(Ph3)4 (12 mg, 0.010 mmol) under N2 was added K2CO3 (2.0 M, 0.15 ml, 0.30 mmol) followed by 1,4-dioxane (1.0 ml). The vial was closed and the mixture was heated at 80° C. for 15 h. The mixture was cooled to rt, diluted with water and extracted with EtOAc. The extract was dried over $Na_2SO_4$ and concentrated to give the crude title compound as a yellow oil. The material was taken up in DCM (1.0 ml) and TFA (0.50 ml) was added. The solution was stirred at rt for 2 h, concentrated, and the residue was purified by preparative C18 HPLC eluting with 0-95% CH3CN/H2O with 0.1% TFA as modifier. The desired fractions were combined, basified with $NaHCO_3$ (sat.) and extracted with DCM. The combined extract was dried over $Na_2SO_4$ and concentrated to give the title compound (32 mg, 52%). LCMS (MM-ES+APCI, Pos): m/z 573.3 (M+H).

Example 438

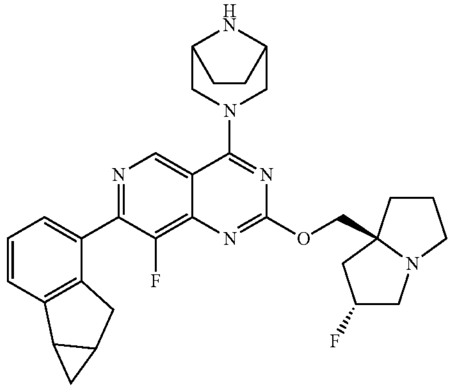 [SMILES: Fc1c(-c2cccc3c2CC2CC32)ncc2c(N3CC4CCC(C3)N4)nc(OC[C@@]34CCCN3C[C@H](F)C4)nc12]

4-(3,8-diazabicyclo[3.2.1]octan-3-yl)-8-fluoro-2-(((2R,7aS)-2-fluorotetrahydro-1H-pyrrolizin-7a(5H)-yl)methoxy)-7-(1,1a,6,6a-tetrahydrocyclopropa[a]inden-5-yl)pyrido[4,3-d]pyrimidine (racemic, trans)

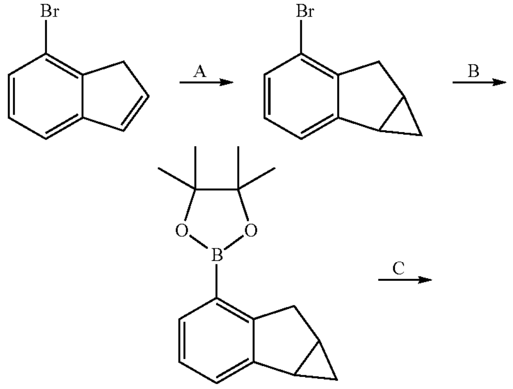

-continued

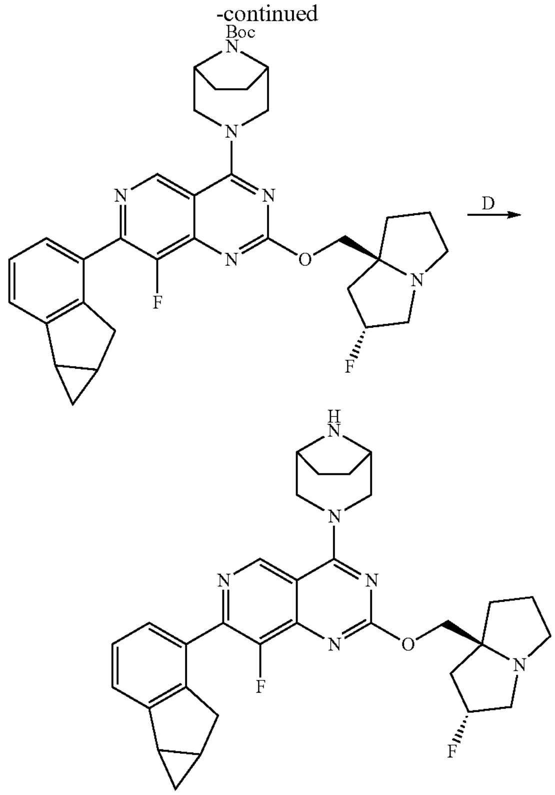

4-(3,8-diazabicyclo[3.2.1]octan-3-yl)-8-fluoro-2-(((2R,7aS)-2-fluorotetrahydro-1H-pyrrolizin-7a(5H)-yl)methoxy)-7-(1,1a,6,6a-tetrahydrocyclopropa[a]inden-5-yl)pyrido[4,3-d]pyrimidine. To a solution of tert-butyl 3-(8-fluoro-2-(((2R,7aS)-2-fluorotetrahydro-1H-pyrrolizin-7a(5H)-yl)methoxy)-7-(1,1a,6,6a-tetrahydrocyclopropa[a]inden-5-yl)pyrido[4,3-d]pyrimidin-4-yl)-3,8-diazabicyclo[3.2.1]octane-8-carboxylate (15 mg, 0.023 mmol) in DCM (1.0 ml) was added TFA (0.50 ml). The solution was stirred at rt for 30 min, and concentrated. The residue was purified by preparative C18 HPLC eluting with 0-95% CH3CN/H2O with 0.1% TFA as modifier. The desired fractions were combined, basified with $NaHCO_3$ (sat.) and extracted with DCM/IPA (5:1). The combined extract was dried over $Na_2SO_4$ and concentrated to give the title compound (7.0 mg, 55%) as a white solid. LCMS (MM-ES+APCI, Pos): m/z 545.2 (M+H).

Example 439

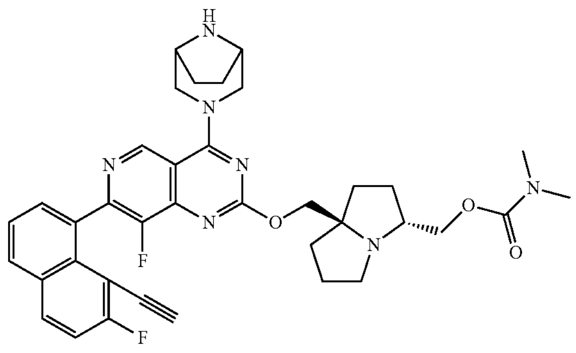 [SMILES: C#Cc1c(F)ccc2cccc(-c3ncc4c(N5CC6CCC(C5)N6)nc(OC[C@]56CCCN5[C@@H](COC(=O)N(C)C)CC6)nc4c3F)c12]

((3R,7aR)-7a-(((4-((1R,5S)-3,8-diazabicyclo[3.2.1]octan-3-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl)methyl dimethylcarbamate (trans racemic)

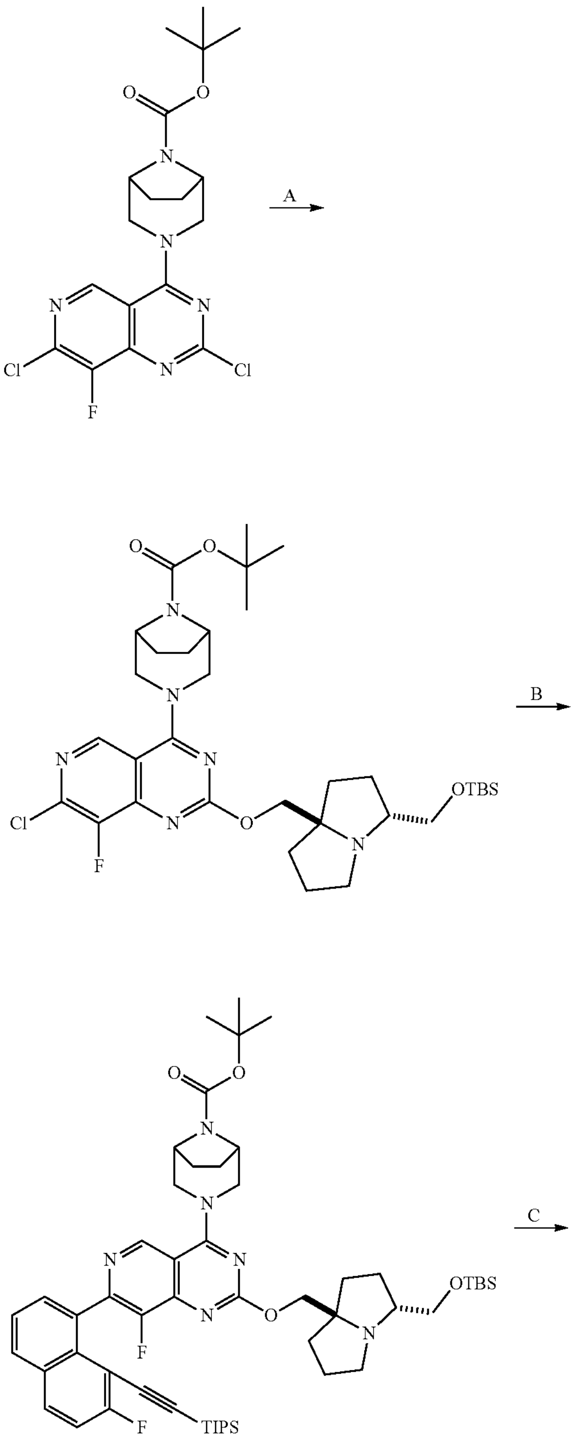

-continued

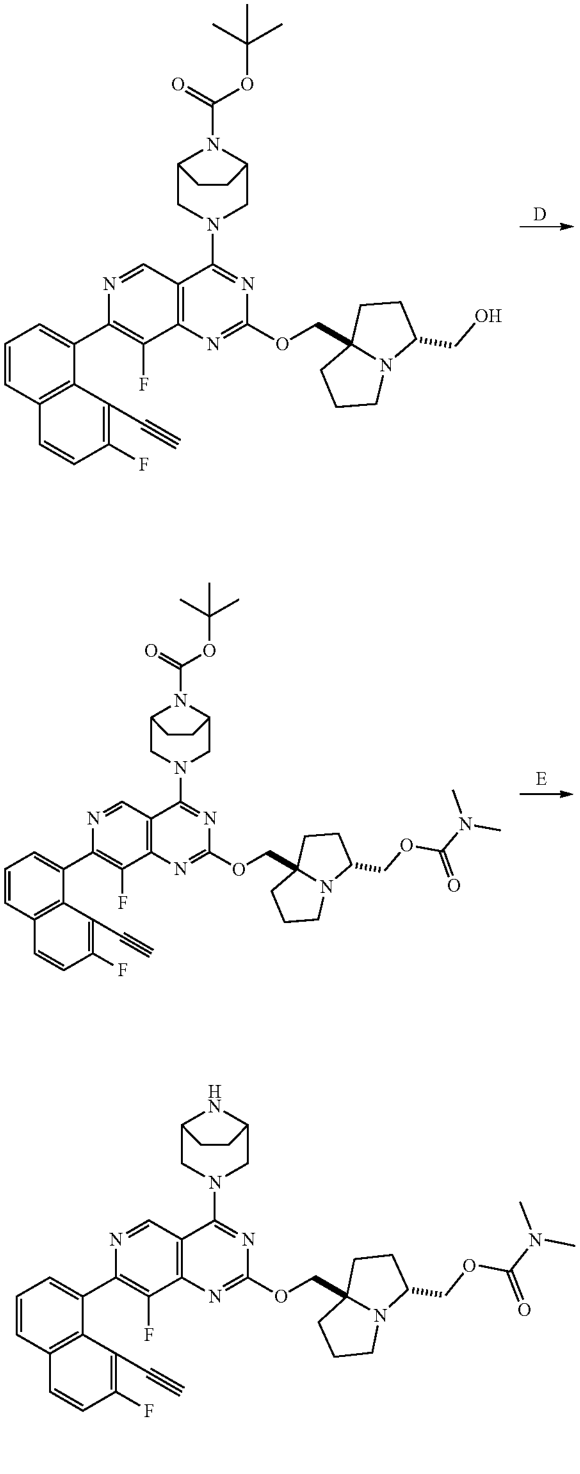

((3R,7aR)-7a-(((4-((1R,5S)-3,8-diazabicyclo[3.2.1]octan-3-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl)methyl dimethylcarbamate as the HCl salt (6.8 mg, 79% yield). LCMS (MM-ES+APCI, Pos): m/z 668.3 (M+H).

Example 440
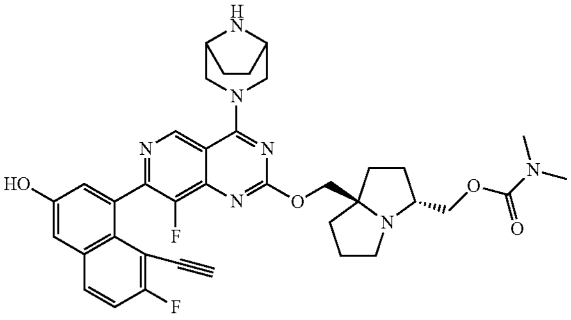 [SMILES: C#Cc1c(F)ccc2cc(O)cc(-c3ncc4c(N5CC6CCC(C5)N6)nc(OC[C@]56CCCN5[C@@H](COC(=O)N(C)C)CC6)nc4c3F)c12]
((3R,7aR)-7a-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethyl carbamate (trans racemic)
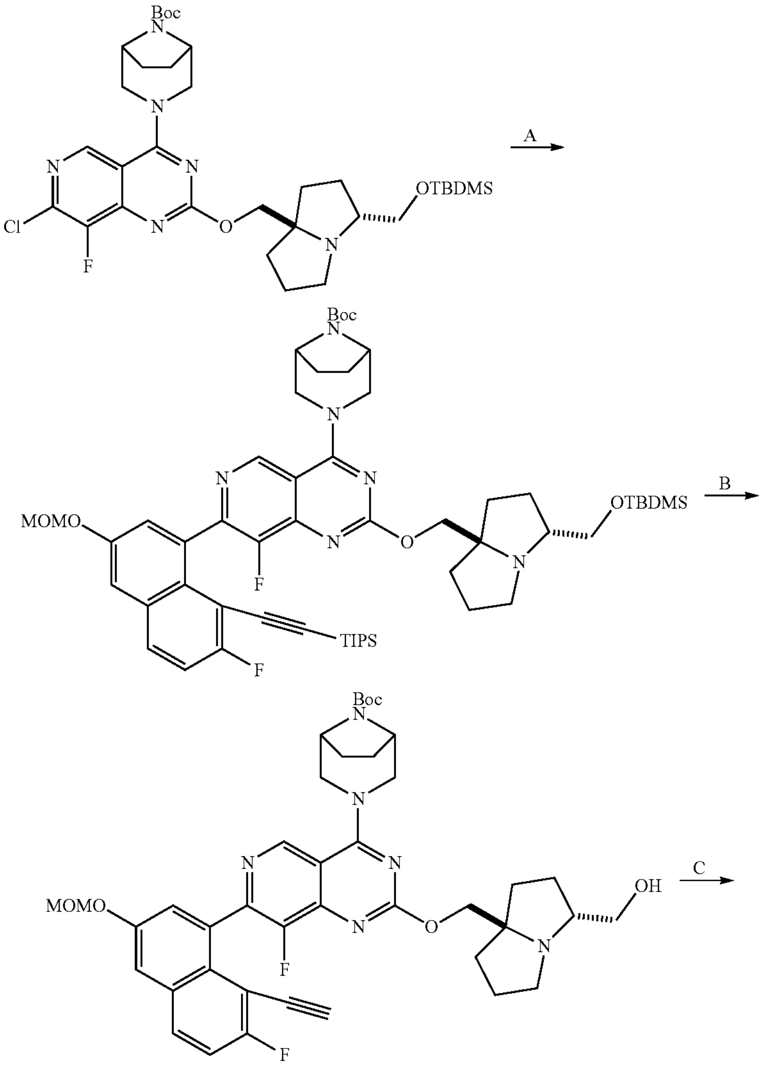

-continued
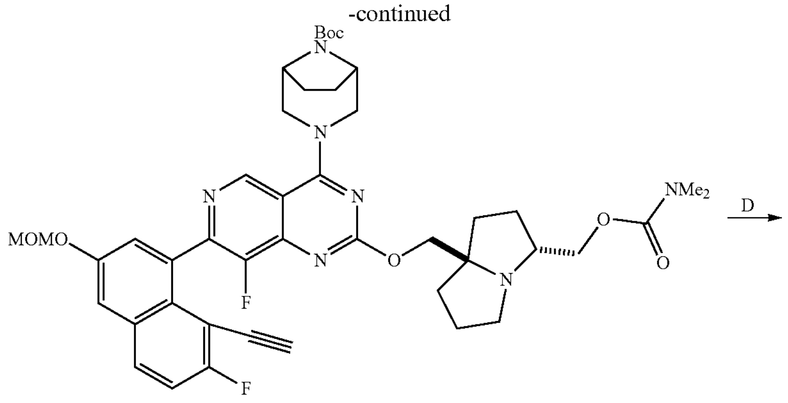
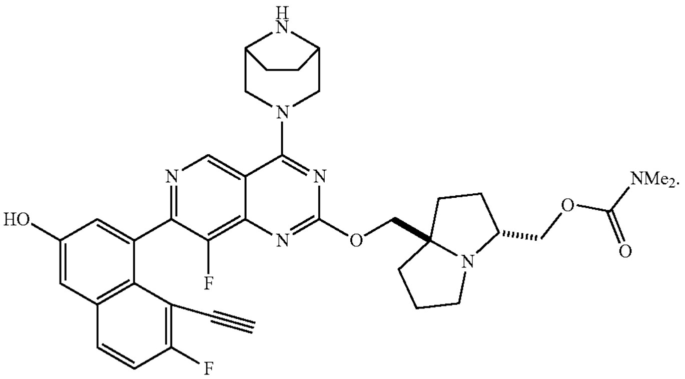
((3R,7aR)-7a-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate as the TFA salt (17 mg, 55%). LCMS (MM-ES+APCI, Pos): m/z 684.3 (M+H).
Example 441
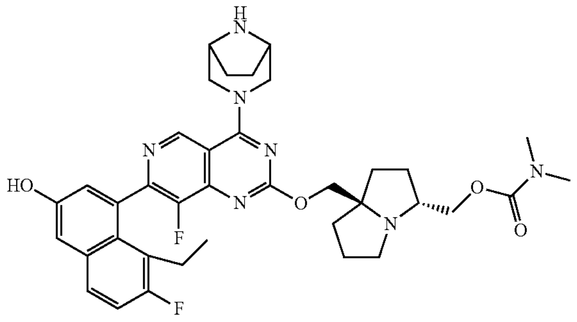 [SMILES: CCc1c(F)ccc2cc(O)cc(-c3ncc4c(N5CC6CCC(C5)N6)nc(OC[C@]56CCCN5[C@@H](COC(=O)N(C)C)CC6)nc4c3F)c12]

((3R,7aR)-7a-(((4-((1R,5S)-3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate (trans racemic)
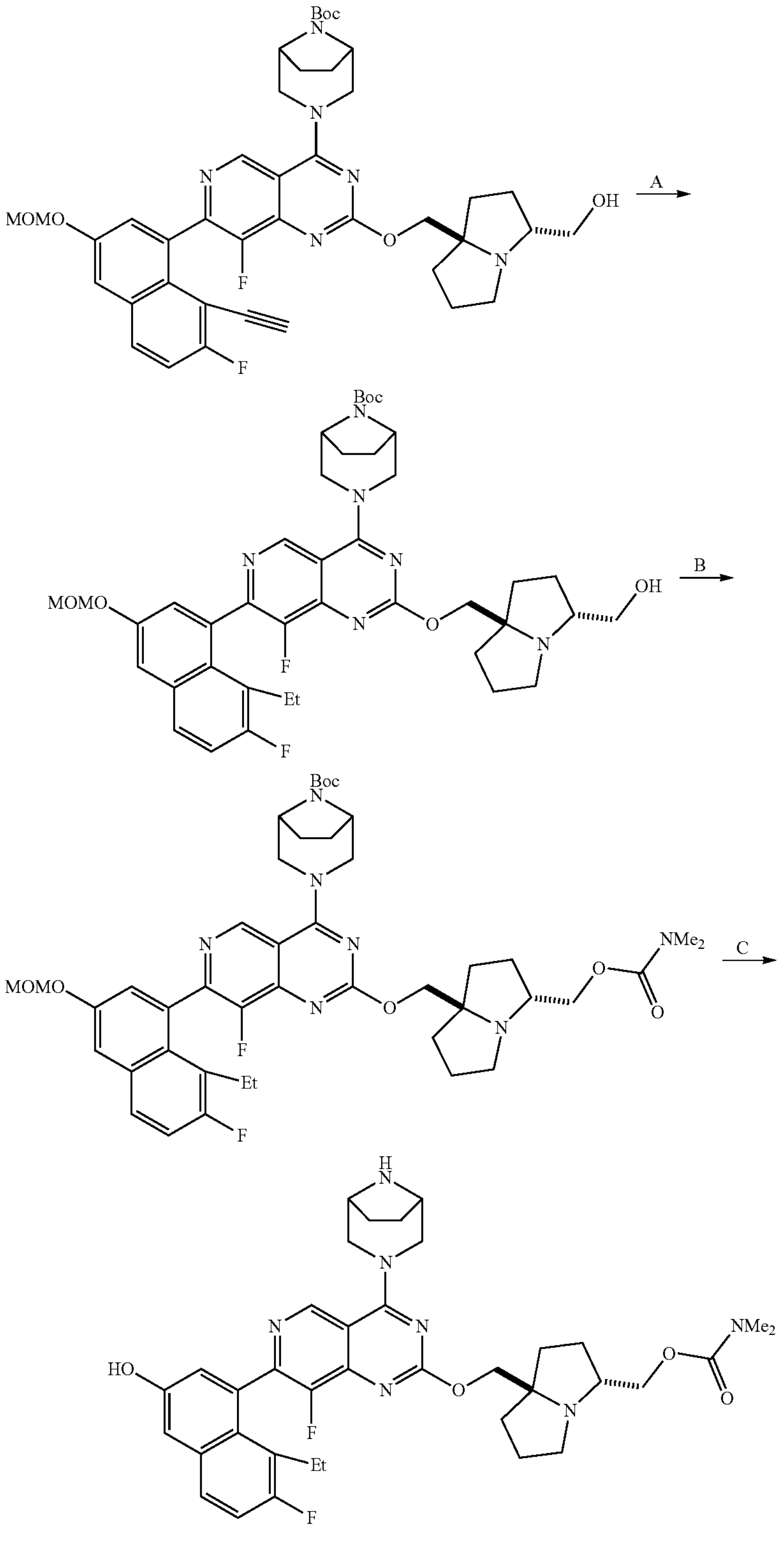

((3R,7aR)-7a-(((4-((1R,5S)-3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate as the TFA salt (18 mg, 48%). LCMS (MM-ES+APCI, Pos): m/z 688.3 (M+H).

Example 442

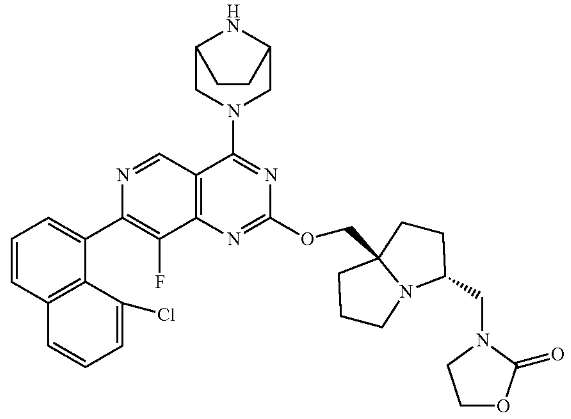 [SMILES: O=C1OCCN1C[C@H]1CC[C@@]2(COc3nc(N4CC5CCC(C4)N5)c4cnc(-c5cccc6cccc(Cl)c56)c(F)c4n3)CCCN12]

3-(((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)oxazolidin-2-one (trans racemic)

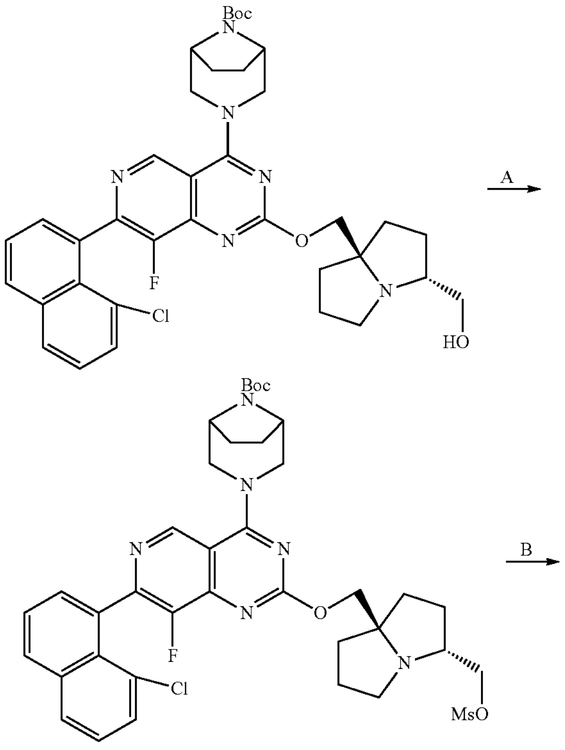

-continued

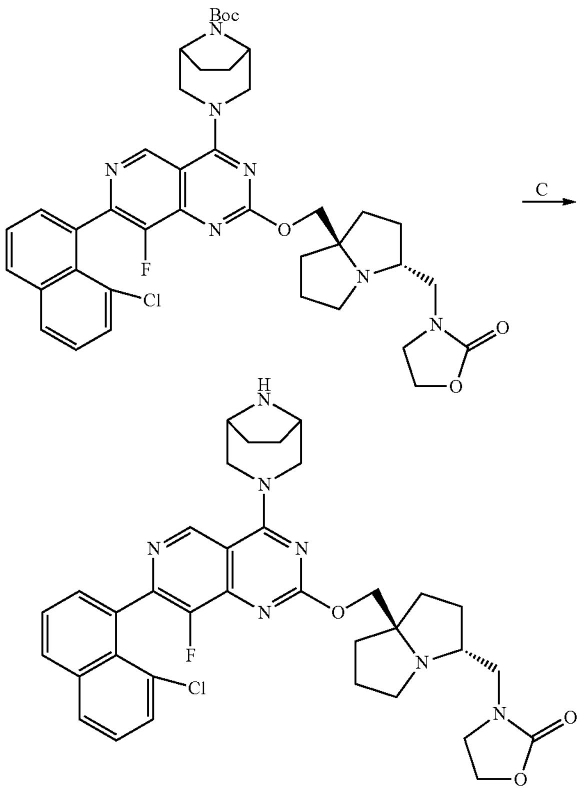

3-(((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)oxazolidin-2-one bis(2,2,2-trifluoroacetate). To a solution of tert-butyl 3-(7-(8-chloronaphthalen-1-yl)-8-fluoro-2-(((3R,7aR)-3-((2-oxooxazolidin-3-yl)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (6 mg, 0.0079 mmol) in DCM (1.0 ml) was added TFA (0.50 ml). The solution was stirred at rt for 35 min, concentrated and the residue was purified by preparative C18 HPLC eluting with 0-95% CH3CN/H2O with 0.1% TFA as modifier. The desired fractions were combined and lyophilized to give about the title compound (2.0 mg, 29%) as the TFA salt. LCMS (MM-ES+APCI, Pos): m/z 658.3 (M+H).

Example 443

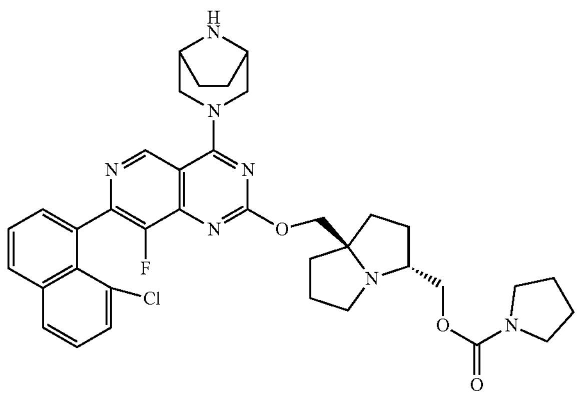 [SMILES: O=C(OC[C@H]1CC[C@@]2(COc3nc(N4CC5CCC(C4)N5)c4cnc(-c5cccc6cccc(Cl)c56)c(F)c4n3)CCCN12)N1CCCC1]

((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl pyrrolidine-1-carboxylate (trans racemic)

Synthesized according to Example 445 substituting pyrrolidine for morpholine in step A to give the title compound (6.0 mg, 53%) as a white solid. LCMS (MM-ES+APCI, Pos): m/z 686.3 (M+H).

Example 444

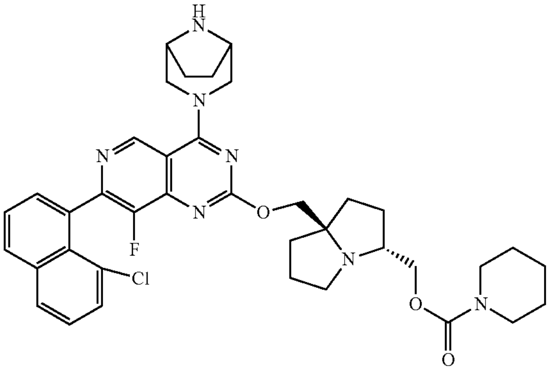 [SMILES: O=C(OC[C@H]1CC[C@@]2(COc3nc(N4CC5CCC(C4)N5)c4cnc(-c5cccc6cccc(Cl)c56)c(F)c4n3)CCCN12)N1CCCCC1]

((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl piperidine-1-carboxylate (trans racemic)

Synthesized according to Example 445 substituting piperidine for morpholine in step A to give the title compound (8.0 mg, 44%) as a white solid. LCMS (MM-ES+APCI, Pos): m/z 700.3 (M+H).

Example 445

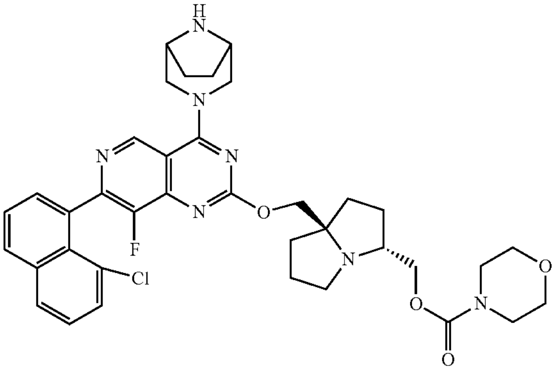 [SMILES: O=C(OC[C@H]1CC[C@@]2(COc3nc(N4CC5CCC(C4)N5)c4cnc(-c5cccc6cccc(Cl)c56)c(F)c4n3)CCCN12)N1CCOCC1]

((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl morpholine-4-carboxylate

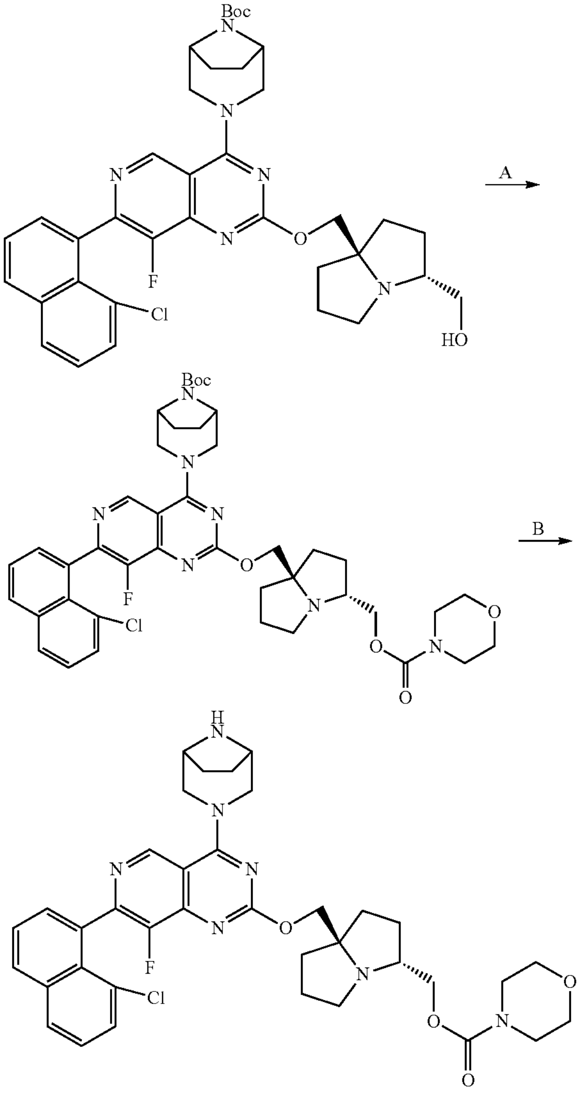

((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl morpholine-4-carboxylate. To a solution of ((3R,7aR)-7a-(((4-(8-(tert-butoxycarbonyl)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl morpholine-4-carboxylate (10 mg, 0.012 mmol) in DCM (1.0 ml) was added TFA (0.50 ml). The solution was stirred at rt for 30 min and concentrated. The residue was purified by preparative C18 HPLC eluting with 0-95% CH3CN/H2O with 0.1% TFA as modifier. The desired fractions were combined, basified with $NaHCO_3$(Sat.) and extracted with DCM. The combined extract was dried over $Na_2SO_4$ and concentrated to give the title compound (8.0 mg, 91%) as a white solid. LCMS (MM-ES+APCI, Pos): m/z 702.3 (M+H).

Example 446

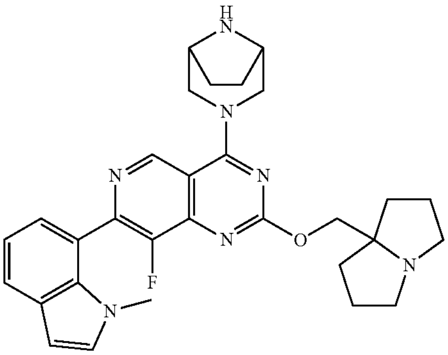 [SMILES: Cn1ccc2cccc(-c3ncc4c(N5CC6CCC(C5)N6)nc(OCC56CCCN5CCC6)nc4c3F)c21]

4-((1R,5S)-3,8-diazabicyclo[3.2.1]octan-3-yl)-8-fluoro-7-(1-methyl-1H-indol-7-yl)-2-((tetrahydro-1H-pyrrolizin-7a(5H)-yl)methoxy)pyrido[4,3-d]pyrimidine

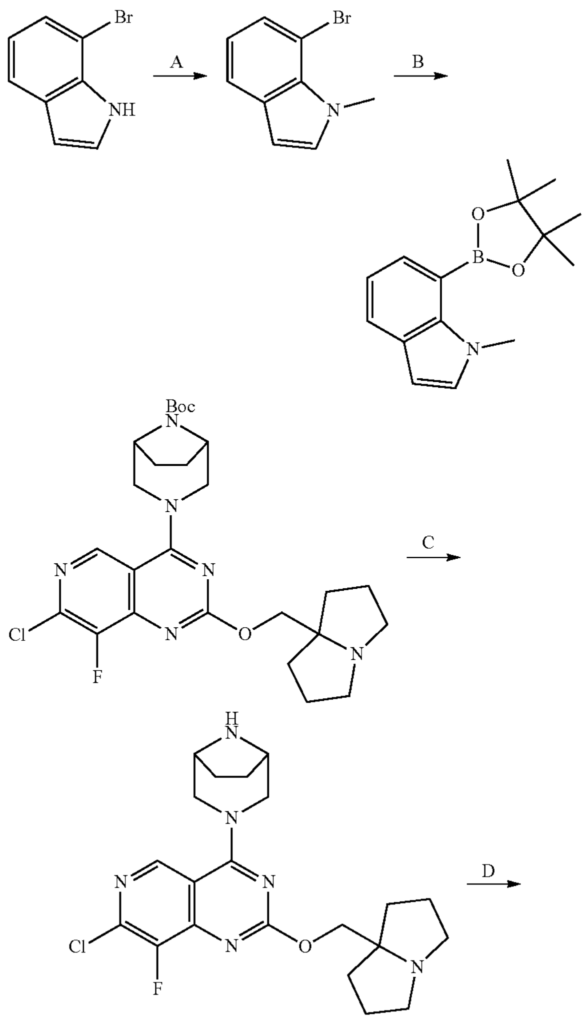

-continued

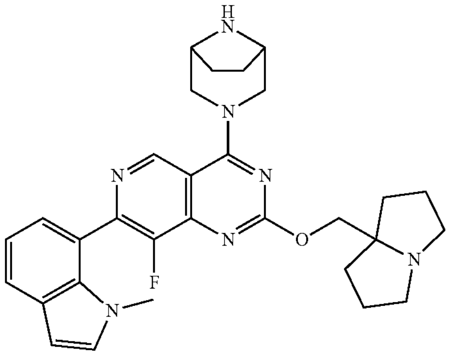

1-methyl-7-(4,4,5,5-tetramethyl-1,3,2-dioxaborolan-2-yl)-1H-indole. 7-Bromo-1-methyl-1H-indole (0.11 g, 0.50 mmol), 4,4,4',4',5,5,5',5'-octamethyl-2,2'-bi (1,3,2-dioxaborolane) (0.38 g, 1.5 mmol), PdCl2 (dppf) (37 mg, 0.05 mmol), and KOAc (0.15 g, 1.5 mmol) were added to a vial with stir bar and septa cap. The vial was degassed and purged with $N_2$ 3 times before dioxane (3 mL) was added. The vial was sparged with $N_2$ for 15 minutes and the reaction was heated to 95° C. for 2 hours. The reaction was diluted with DCM, filtered through a Celite plug, and the filtrate was concentrated. The residue was purified via reverse phase chromatography eluting with 0-100% MeCN/water with 0.1% TFA as modifier. The fractions containing the product were combined, diluted with Et2O, and washed with saturated NaHCO3 followed by water. The Et2O layer was dried with $Na_2SO_4$, filtered, and concentrated to yield 1-methyl-7-(4,4,5,5-tetramethyl-1,3,2-dioxaborolan-2-yl)-1H-indole as a light brown solid (75 mg, 59%). LCMS (MM-ES+APCI, Pos): m/z 258.3 (M+H).

Step C and D. Synthesized according to Example 427, Step C-D, substituting 1-methyl-7-(4,4,5,5-tetramethyl-1,3,2-dioxaborolan-2-yl)-1H-indole for 1-ethyl-7-(4,4,5,5-tetramethyl-1,3,2-dioxaborolan-2-yl)-1H-indole. (9.5 mg, 32%). LCMS (MM-ES+APCI, Pos): m/z 528.3 (M+H).

Example 447

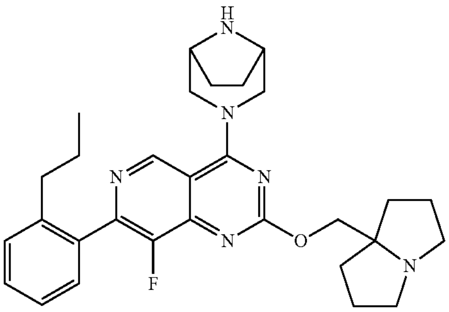 [SMILES: CCCc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(2-propylphenyl)-2-((tetrahydro-1H-pyrrolizin-7a(5H)-yl)methoxy)pyrido[4,3-d]pyrimidine

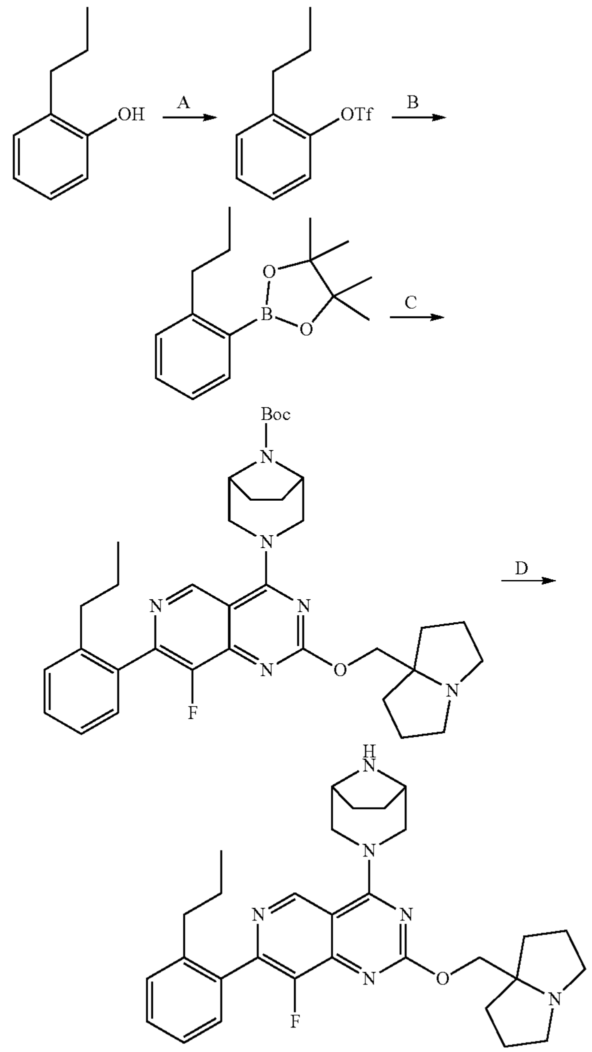

4-((1R,5S)-3,8-diazabicyclo[3.2.1]octan-3-yl)-8-fluoro-7-(2-propylphenyl)-2-((tetrahydro-1H-pyrrolizin-7a(5H)-yl)methoxy)pyrido[4,3-d]pyrimidine. To a solution of 3-(8-fluoro-2-((hexahydro-1H-pyrrolizin-7a-yl)methoxy)-7-(2-propylphenyl)pyrido[4,3-d]pyrimidin-4-yl)-3,8-diazabicyclo[3.2.1]octane-8-carboxylate (54 mg, 87.5 μmol, 1.0 eq) in $CH_3CN$ (1 mL) was added HCl·dioxane (4 M, 1 mL, 45.7 eq). The mixture was stirred at 20° C. for 0.5 hour. After completion, the mixture was directly concentrated under reduced pressure. Then the residue was diluted with MeOH (1 mL) and the pH was adjusted to ~8 with saturated $Na_2CO_3$ solution. The mixture was purified by prep-HPLC (column: Shim-pack C18 150*25*10 um; mobile phase: [water (0.225% FA)-ACN]; B %: 12%-32%, 10 min). The desired fraction was collected and lyophilized to give the title compound (23.4 mg, 44% yield, 1.8FA). Yellow solid; $^1$H NMR (400 MHz, methanol-d4) δ=9.14 (s, 1H), 7.53-7.25 (m, 4H), 4.78 (br d, J=13.2 Hz, 2H), 4.67 (s, 2H), 4.03 (br s, 2H), 3.88 (br d, J=13.2 Hz, 2H), 3.78-3.62 (m, 2H), 3.30-3.24 (m, 2H), 2.57 (br t, J=7.6 Hz, 2H), 2.41-1.89 (m, 12H), 1.56-1.40 (m, 2H), 0.77 (t, J=7.2 Hz, 3H); LCMS [ESI, M+1]: 517.3.

Example 448

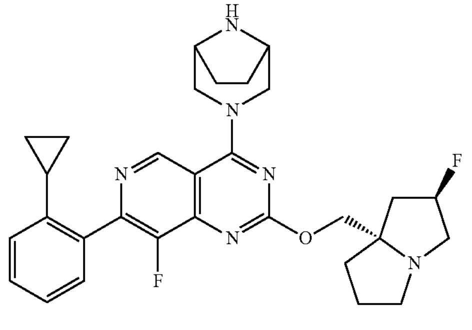 [SMILES: Fc1c(-c2ccccc2C2CC2)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-7-(2-cyclopropylphenyl)-8-fluoro-2-(((2R,7aS)-2-fluoro-hexahydro-1H-pyrrolizin-7a-yl)methoxy)pyrido[4,3-d]pyrimidine

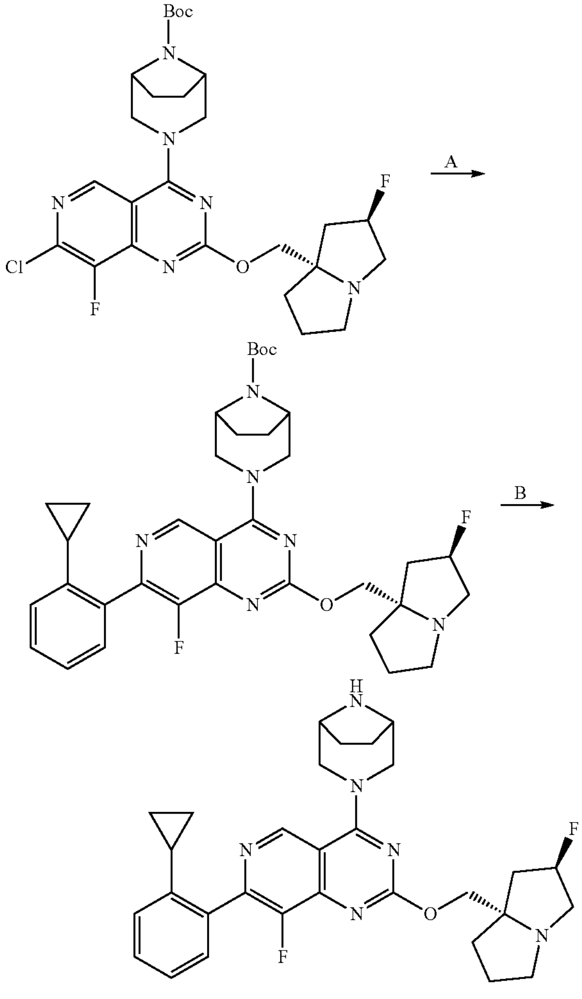

4-((1R,5S)-3,8-diazabicyclo[3.2.1]octan-3-yl)-7-(2-cyclopropylphenyl)-8-fluoro-2-(((2R,7aS)-2-fluorohexahydro-1H-pyrrolizin-7a-yl)methoxy)pyrido[4,3-d]pyrimidine. To a solution of (1R,5S)-tert-butyl 3-(7-(2-cyclopropylphenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (130 mg, 205 μmol, 1.0 eq) in MeCN (1 mL) was added HCl·dioxane (4 M, 3.0 mL, 58.4 eq). The mixture was stirred at 15° C. for 0.5 hour. After completion, the mixture was added water (5 mL) and extracted with ethyl acetate (3×5 mL). The organic layer was dried over $Na_2SO_4$, filtered and concentrated. The residue was purified by prep-HPLC (column: Waters Xbridge 150*25 mm*5 um; mobile phase: [water (10 mM $NH_4HCO_3$)-ACN]; B %: 28%-58%, 8 min) affording the title compound (48.9 mg, 45% yield). White solid; SFC analysis: Column: Chiralcel OD-3 50×4.6 mm I.D., 3 um Mobile phase: Phase A for CO2, and Phase B for MeOH+CAN (0.05% DEA); Gradient elution: 60% MeOH+ACN (0.05% DEA) in CO2 Flow rate: 3 mL/min; Detector: PDA Column Temp: 35° C.; Back Pressure: 100 Bar; $^1$H NMR (400 MHz, $CDCl_3$) δ=9.04 (s, 1H), 7.42-7.34 (m, 2H), 7.31-7.25 (m, 1H), 7.05 (d, J=8.0 Hz, 1H), 5.44-5.16 (m, 1H), 4.56 (br t, J=10.4 Hz, 2H), 4.27 (d, J=10.4 Hz, 1H), 4.14 (d, J=10.0 Hz, 1H), 3.73-3.58 (m, 4H), 3.35-3.23 (m, 2H), 3.22-3.12 (m, 1H), 3.04-2.94 (m, 1H), 2.37-2.13 (m, 3H), 2.03-1.81 (m, 8H), 0.84-0.76 (m, 2H), 0.68-0.60 (m, 2H); LCMS [ESI, M+1]: 533.2.

Example 449

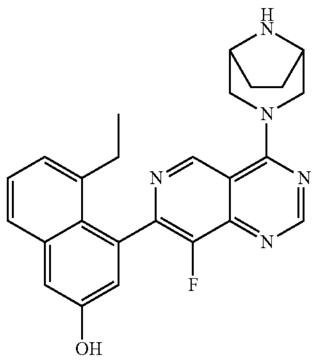 [SMILES: CCc1cccc2cc(O)cc(-c3ncc4c(N5CC6CCC(C5)N6)ncnc4c3F)c12]

4-(4-((1R,5S)-3,8-diazabicyclo[3.2.1]octan-3-yl)-8-fluoropyrido[4,3-d]pyrimidin-7-yl)-5-ethylnaphthalen-2-ol

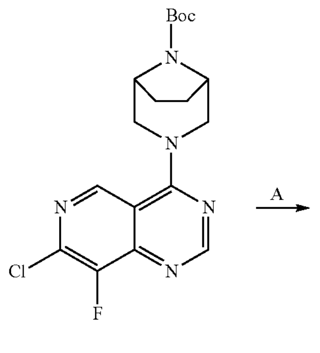

-continued

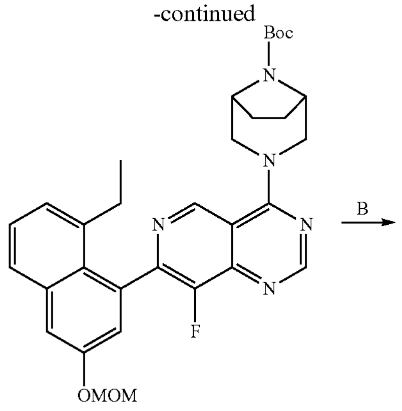

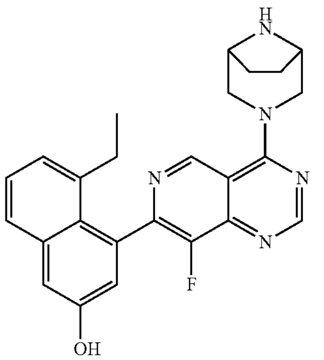

4-((1R,5S)-3,8-diazabicyclo[3.2.1]octan-3-yl)-7-(8-ethylnaphthalen-1-yl)-8-fluoropyrido[4,3-d]pyrimidine. A solution of (1R,5S)-tert-butyl 3-(7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (100 mg, 174 μmol, 1 eq) in HCl/EtOAc (4 M, 1.00 mL) was stirring at 20° C. for 1 hour. Upon completion, the reaction mixture was adjust pH~8 with sat. $NaHCO_3$ (20.0 mL) and extracted with ethyl acetate (3×10.0 mL). The combined organic layer was washed with brine (20 mL), dried over $Na_2SO_4$, filtered and concentrated under reduced pressure to give a residue, the mixture was concentrated under vacuum and was purified by prep-HPLC (column: Waters Xbridge BEH C18 100*25 mm*5 um; mobile phase: [water (10 mM $NH_4HCO_3$)-ACN]; B %: 25%-55%, 10 min) to give the title compound (20.7 mg, 27% yield); White solid; $^1$H NMR (400 MHz, DMSO-$d_6$) δ=9.90 (s, 1H), 9.21 (s, 1H), 8.67 (s, 1H), 7.67 (d, J=8.0 Hz, 1H), 7.37 (t, J=7.6 Hz, 1H), 7.29 (d, J=2.4 Hz, 1H), 7.12 (d, J=7.2 Hz, 1H), 7.00 (d, J=2.4 Hz, 1H), 4.56-4.40 (m, 2H), 3.73-3.57 (m, 2H), 3.53 (d, J=10.4 Hz, 2H), 2.71 (s, 1H), 2.28-2.10 (m, 2H), 1.67-1.53 (m, 4H), 0.79 (t, J=7.2 Hz, 3H); $^1$H NMR (400 MHz, DMSO-d6+D2O) δ 9.16 (s, 1H), 8.63 (s, 1H), 7.65 (d, J=801 Hz, 1H), 7.37 (t, J=7.6 Hz, 1H), 7.29 (d, J=2.4 Hz, 1H), 7.12 (d, J=7.2 Hz, 1H), 6.98 (d, J=2.4 Hz, 1H), 4.54-4.37 (m, 2H), 3.71-3.57 (m, 2H), 3.52 (s, 2H), 2.26-2.04 (m, 2H), 1.73-1.58 (m, 2H), 1.58-1.44 (m, 2H), 0.76 (t, J=7.2 Hz, 3H). LCMS [ESI, M+1]: 430.3.

Example 450

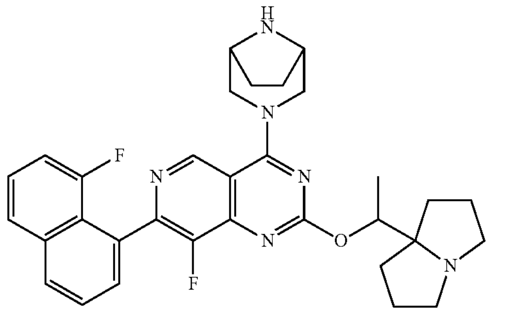 [SMILES: CC(Oc1nc(N2CC3CCC(C2)N3)c2cnc(-c3cccc4cccc(F)c34)c(F)c2n1)C12CCCN1CCC2]

4-((1R,5S)-3,8-diazabicyclo[3.2.1]octan-3-yl)-8-fluoro-7-(8-fluoronaphthalen-1-yl)-2-(1-(hexahydro-1H-pyrrolizin-7a-yl)ethoxy)pyrido[4,3-d]pyrimidine

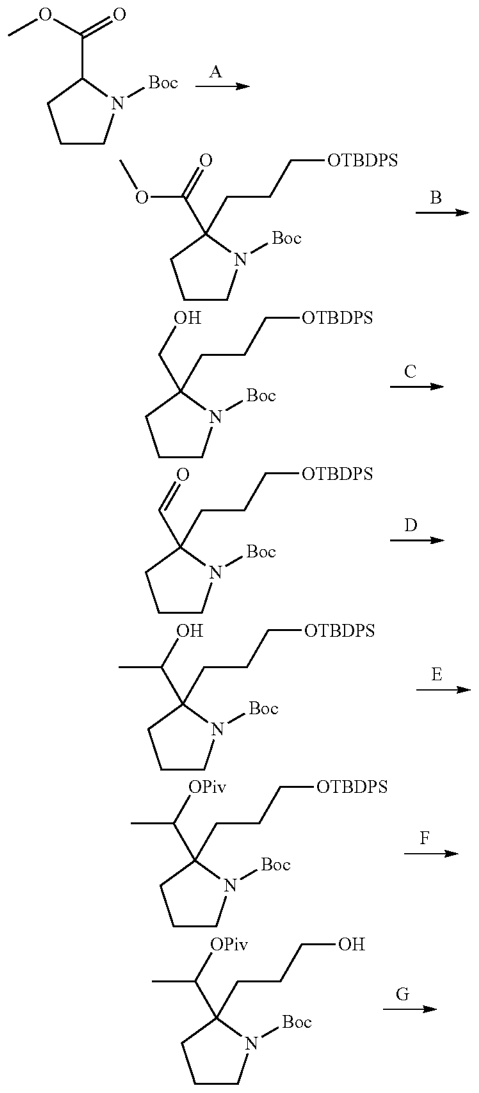

-continued

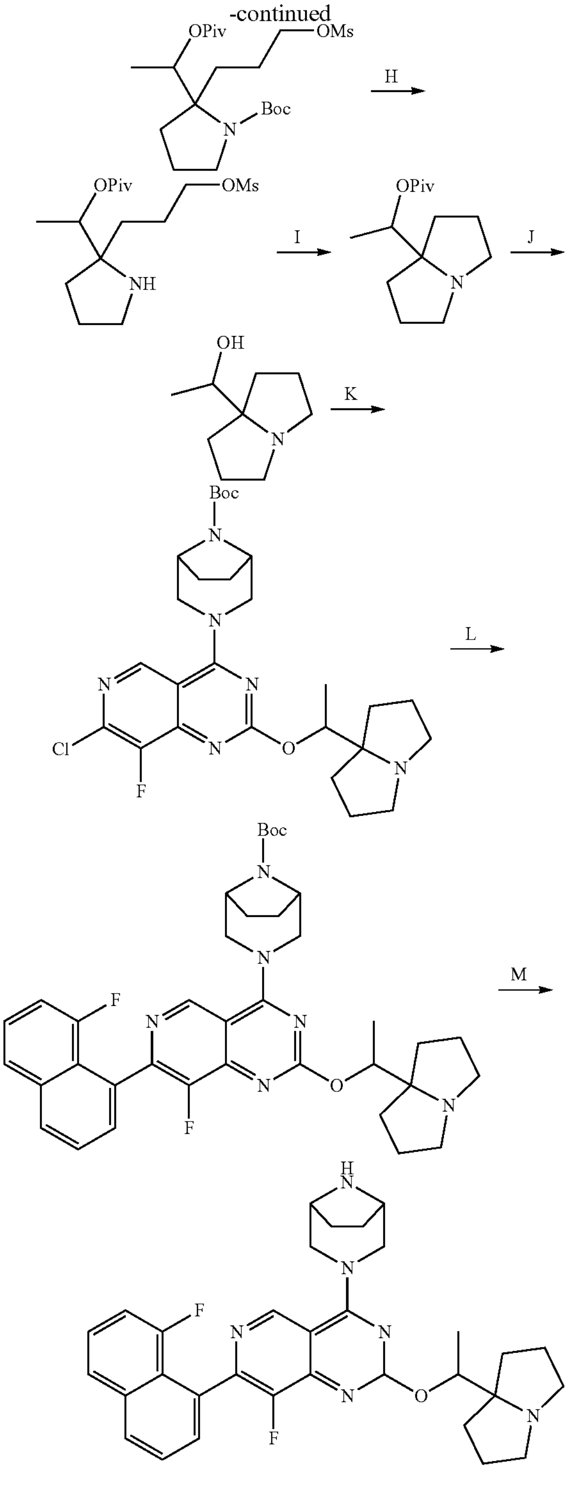

4-((1R,5S)-3,8-diazabicyclo[3.2.1]octan-3-yl)-8-fluoro-7-(8-fluoronaphthalen-1-yl)-2-(1-(hexahydro-1H-pyrrolizin-7a-yl)ethoxy)pyrido[4,3-d]pyrimidine. To a solution of (1R,5S)-tert-butyl 3-(8-fluoro-7-(8-fluoronaphthalen-1-yl)-2-(1-(hexahydro-1H-pyrrolizin-7a-yl)ethoxy)pyrido[4,3-d]pyrimidin-4-yl)-3,8-diazabicyclo[3.2.1]octane-8-carboxylate (63 mg, 95.9 μmol, 1.0 eq) in $CH_3CN$ (2 mL) was added HCl·dioxane (4 M, 1 mL, 41.70 eq) at 0° C., and the mixture was stirred under $N_2$ at 0° C. for 30 minutes. After completion, the reaction mixture was concentrated under reduced pressure below 30° C., and then basified with saturated $NaHCO_3$ solution to pH~8. The mixture was extracted with ethyl acetate (3×10 mL), and the combined organic phases were dried over $Na_2SO_4$, filtered and concentrated. The residue was purified by prep-HPLC (column: Phenomenex Gemini-NX C18 75*30 mm*3 um; mobile phase: [water (0.225% FA)-ACN]; B %: 15%-25%, 9 min). The fractions were collected, basified with saturated $NaHCO_3$ solution to pH~8, and then extracted with DCM (3×5 mL). The organic phase was dried over $Na_2SO_4$, filtered, concentrated and lyophilized to give the title compound (12.0 mg, 22% yield). White solid. $^1H$ NMR (400 MHz, methanol-d4) δ=9.05 (s, 1H), 8.12 (d, J=8.8 Hz, 1H), 7.85 (d, J=8.4 Hz, 1H), 7.70 (dd, J=7.2, 8.4 Hz, 1H), 7.60 (d, J=7.2 Hz, 1H), 7.57-7.48 (m, 1H), 7.20 (dd, J=7.2, 13.2 Hz, 1H), 5.21 (dd, J=4.8, 6.0 Hz, 1H), 4.70-4.53 (m, 2H), 3.75-3.64 (m, 4H), 3.19-2.98 (m, 2H), 2.79-2.68 (m, 2H), 2.30-2.19 (m, 1H), 2.12-2.00 (m, 1H), 1.97-1.62 (m, 10H), 1.43 (d, J=6.4 Hz, 3H). $^{19}F$ NMR (400 MHz, methanol-d4) δ=115.18, −141.14. LCMS [ESI, M+1]: 557.2.

Example 451

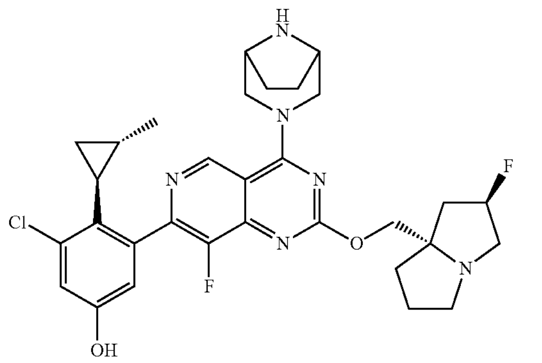 [SMILES: C[C@H]1C[C@@H]1c1c(Cl)cc(O)cc1-c1ncc2c(N3CC4CCC(C3)N4)nc(OC[C@@]34CCCN3C[C@H](F)C4)nc2c1F]

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-chloro-4-((1S,2S)-2-methylcyclopropyl) phenol

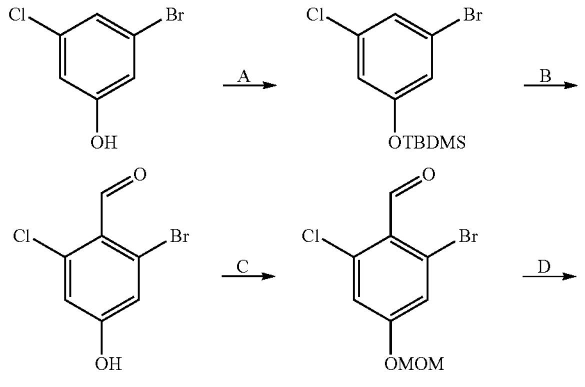

-continued

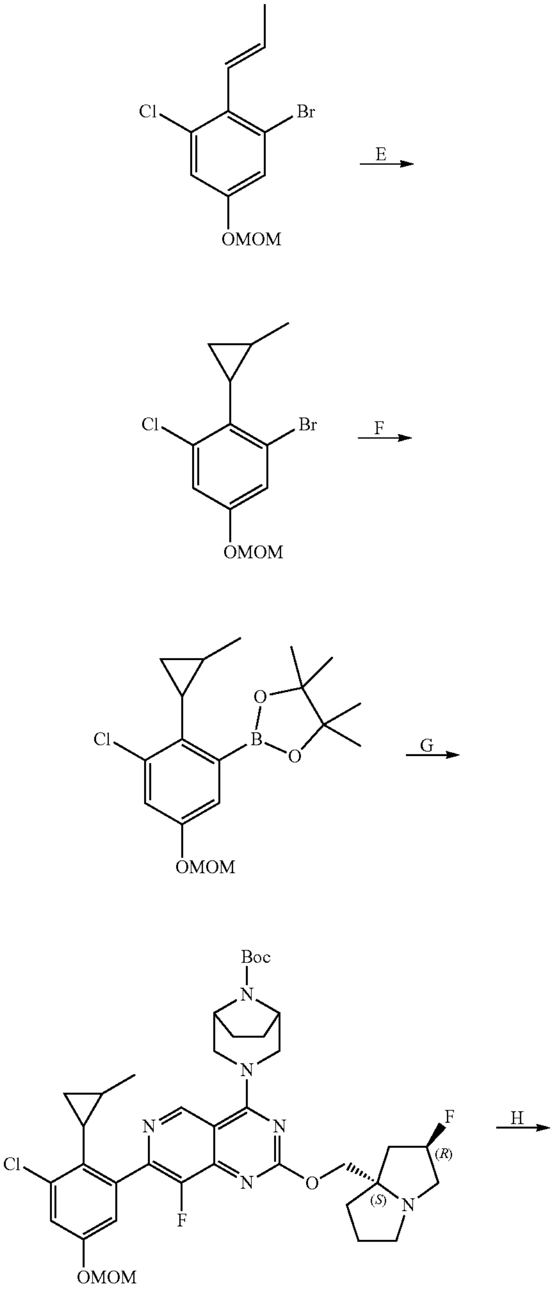

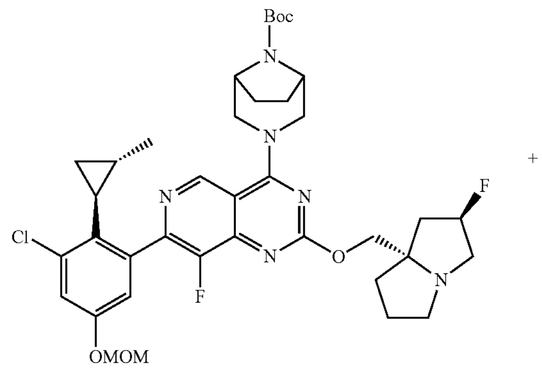

-continued

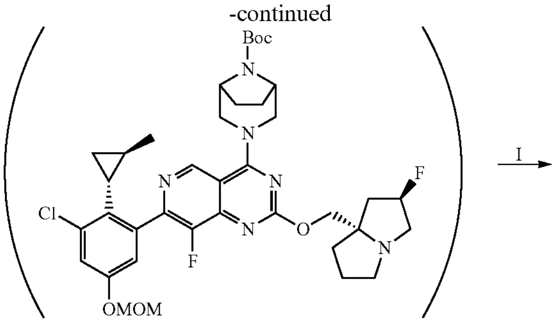

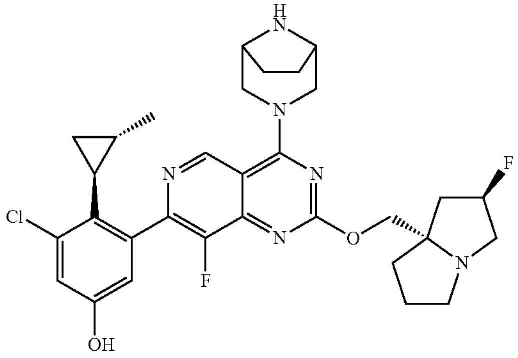

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-chloro-4-((1S,2S)-2-methylcyclopropyl)phenol. To a mixture of tert-butyl(1R,5S)-3-(7-(3-chloro-5-(methoxymethoxy)-2-((1S,2S)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (200 mg, 2701 μmol, 1.0 eq) in MeCN (1.5 mL) was added HCl·dioxane (4 M, 3 mL, 44 eq) at 0° C. and the mixture was stirred at 0° C. for 0.5 hour. After completion, the mixture was concentrated under vacuum. Then the pH value was adjusted to 8 with saturated Na2CO3 solution and the mixture was washed with methanol (2×20 mL), filtered and concentrated under vacuum. The residue was purified by prep-HPLC (column: Shim-pack C18 150*25*10 um; mobile phase: [water (0.225% FA)-ACN]; B %: 12%-32%, 10 min) to give the title compound (100 mg, 57% yield, FA). White solid. $^1$H NMR (400 MHz, METHANOL-d4) δ=9.13 (s, 1H), 6.97 (d, J=2.4 Hz, 1H), 6.77 (d, J=2.4 Hz, 1H), 5.58-5.42 (m, 1H), 4.79 (br dd, J=5.6, 13.2 Hz, 2H), 4.61-4.55 (m, 2H), 4.10 (br s, 2H), 3.92 (br dd, J=5.6, 13.2 Hz, 2H), 3.86-3.62 (m, 3H), 3.37-3.32 (m, 1H), 2.67-2.33 (m, 3H), 2.28-2.20 (m, 2H), 2.16-1.97 (m, 5H), 1.55-1.48 (m, 1H), 0.83 (br s, 3H), 0.49-0.19 (m, 3H). LCMS [ESI, M/2+1, M+1]: 299.5, 597.2.

Example 452

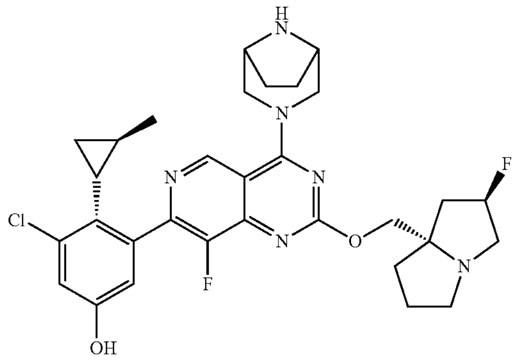

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-chloro-4-((1R,2R)-2-methylcyclopropyl)phenol Synthesized according to Example 451, Step I substituting tert-butyl(1R,5S)-3-(7-(3-chloro-5-(methoxymethoxy)-2-((1R,2R)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate in place of (1R,5S)-3-(7-(3-chloro-5-(methoxymethoxy)-2-((1S,2S)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate to afford the title compound (100 mg, 57% yield, FA). White solid. $^1$H NMR (400 MHz, METHANOL-d4) δ=9.13 (s, 1H), 6.97 (d, J=2.8 Hz, 1H), 6.78 (d, J=2.4 Hz, 1H), 5.59-5.43 (m, 1H), 4.83-4.77 (m, 2H), 4.63-4.55 (m, 2H), 4.11 (br s, 2H), 3.92 (br dd, J=6.4, 13.6 Hz, 2H), 3.88-3.64 (m, 3H), 3.38-3.32 (m, 1H), 2.68-2.34 (m, 3H), 2.29-2.21 (m, 2H), 2.16-1.97 (m, 5H), 1.55-1.49 (m, 1H), 0.83 (br s, 3H), 0.48-0.20 (m, 3H). LCMS [ESI, M/2+1, M+1]: 299.4, 597.1.

Example 453

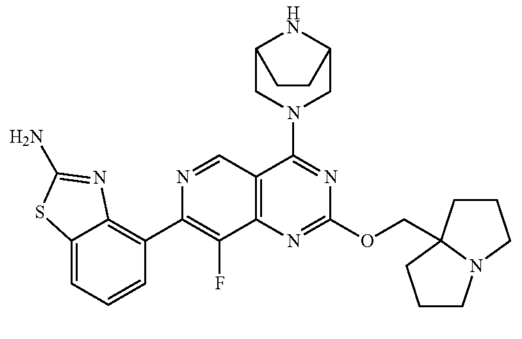 [SMILES: Nc1nc2c(-c3ncc4c(N5CC6CCC(C5)N6)nc(OCC56CCCN5CCC6)nc4c3F)cccc2s1]

4-(4-((1R,5S)-3,8-diazabicyclo[3.2.1]octan-3-yl)-8-fluoro-2-((hexahydro-1H-pyrrolizin-7a-yl)methoxy) pyrido[4,3-d]pyrimidin-7-yl)benzo[d]thiazol-2-amine

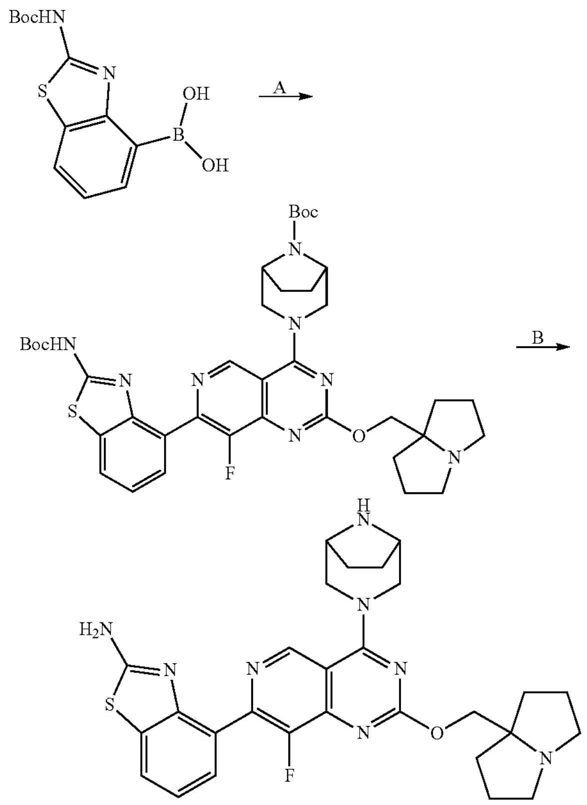

4-(4-((1R,5S)-3,8-diazabicyclo[3.2.1]octan-3-yl)-8-fluoro-2-((hexahydro-1H-pyrrolizin-7a-yl)methoxy)pyrido [4,3-d]pyrimidin-7-yl)benzo[d]thiazol-2-amine. To a solution of (1R,5S)-tert-butyl 3-(7-(2-((tert-butoxycarbonyl) amino)benzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (400 mg, 536 μmol, 1.0 eq) in DCM (4.0 mL) was added TFA (6.16 g, 54.0 mmol, 4.0 mL, 101 eq). The reaction mixture was stirred at 20° C. for 1 hour. The reaction mixture was concentrated at 20° C. to give a residue. The pH of the residue was adjusted with saturated $Na_2CO_3$ aqueous solution to ~7 and the mixture was extracted with EtOAc (2×5 mL). The combined organic layers were dried over $Na_2SO_4$, filtered and concentrated to give a residue. The residue was purified by prep-HPLC (column: Phenomenex luna C18 150*25 mm*10 um; mobile phase: [water (0.225% FA)-ACN]; B %: 6%-36%, 10 min), followed by prep-HPLC (column: Phenomenex luna C18 150*25 mm*10 um; mobile phase: [water (0.225% FA)-ACN]; B %: 6%-36%, 10 min) to afford product as yellow solid (107 mg, 36% yield). $^1H$ NMR (400 MHz, METHANOL-$d_4$) δ=9.12 (s, 1H), 7.78 (dd, J=1.2, 8.0 Hz, 1H), 7.46 (dd, J=1.2, 7.6 Hz, 1H), 7.25 (t, J=8.0 Hz, 1H), 4.80 (br d, J=13.2 Hz, 4H), 4.07 (br s, 2H), 3.90 (br d, J=13.2 Hz, 2H), 3.75-3.64 (m, 2H), 3.35-3.32 (m, 1H), 3.30-3.26 (m, 1H), 2.40-2.29 (m, 2H), 2.28-2.02 (m, 8H), 2.01-1.93 (m, 2H); LCMS [ESI, M+1]: 547.1.

Example 454

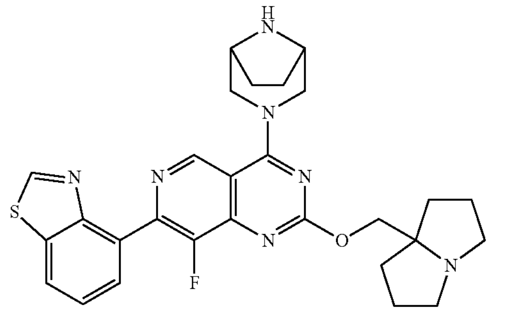 [SMILES: Fc1c(-c2cccc3scnc23)ncc2c(N3CC4CCC(C3)N4)nc(OCC34CCCN3CCC4)nc12]

4-(4-((1R,5S)-3,8-diazabicyclo[3.2.1]octan-3-yl)-8-fluoro-2-((hexahydro-1H-pyrrolizin-7a-yl)methoxy) pyrido[4,3-d]pyrimidin-7-yl)benzo[d]thiazole

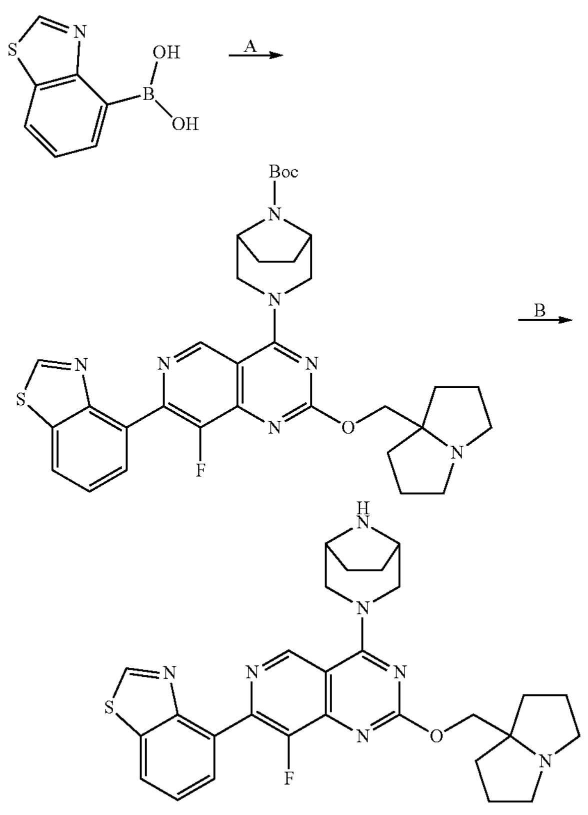

4-(4-((1R,5S)-3,8-diazabicyclo[3.2.1]octan-3-yl)-8-fluoro-2-((hexahydro-1H-pyrrolizin-7a-yl)methoxy)pyrido [4,3-d]pyrimidin-7-yl)benzo[d]thiazole. To a solution of (1R,5S)-tert-butyl 3-(7-(benzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (70 mg, 111 μmol, 1.0 eq) in ACN (0.2 mL) was added HCl·dioxane (4 M, 27.7 uL, 1.0 eq). The reaction mixture was stirred at 25° C. for 30 minutes. The reaction mixture was concentrated in vacuum to give a residue. The residue was purified by prep-HPLC (column: Phenomenex Luna C18 150*25 mm*10 um; mobile phase: [water (0.225% FA)-ACN]; B %: 1%-30%, 10 min) to afford product as yellow solid (4.34 mg, 7% yield). $^1$H NMR (400 MHz, methanol-$d_4$) δ 9.30 (s, 1H) 9.18 (s, 1H), 8.44 (s, 2H), 8.29 (dd, J=1.2 Hz, 8.0 Hz, 1H), 7.79 (dd, J=1.2 Hz, 7.6 Hz, 1H), 7.70 (t, J=7.6 Hz, 1H), 4.80 (d, J=12.8 Hz, 2H), 4.68 (s, 2H), 4.00 (s, 2H), 3.88 (d, J=12.8 Hz, 2H), 3.74-3.66 (m, 2H), 3.30-3.26 (m, 2H), 2.40-2.30 (m, 2H), 2.29-2.09 (m, 6H), 2.06-1.91 (m, 4H); LCMS [ESI, M+1]: 532.3

Example 455

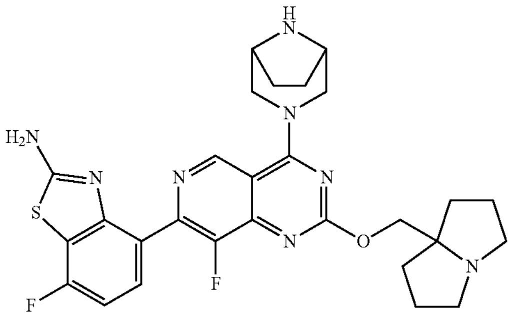 [SMILES: Nc1nc2c(-c3ncc4c(N5CC6CCC(C5)N6)nc(OCC56CCCN5CCC6)nc4c3F)ccc(F)c2s1]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-7-fluorobenzo[d]thiazol-2-amine

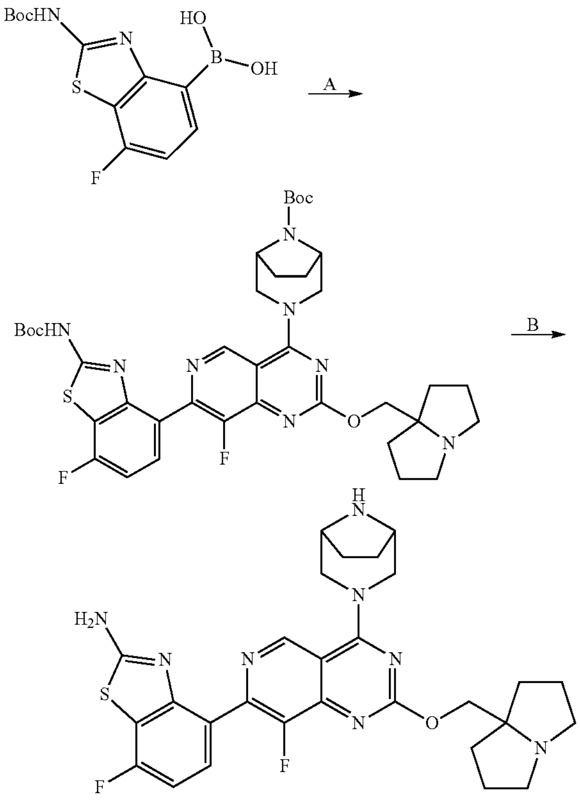

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-7-fluorobenzo[d]thiazol-2-amine. To a mixture of (1R,5S)-tert-butyl 3-(7-(2-((tert-butoxycarbonyl)amino)-7-fluorobenzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (50 mg, 65.4 μmol, 1.0 eq) in DCM (0.1 mL) was added TFA (1.54 g, 13.5 mmol, 1000.0 μL, 207 eq) at 0° C. under $N_2$. The reaction mixture was stirred at 25° C. for 1 hour. Then sat. $Na_2CO_3$ aqueous (5 mL) was added and the reaction mixture was extracted with ethyl acetate (5.0 mL×3). The combined organic phase was washed with brine (5.0 mL) and dried with anhydrous $Na_2SO_4$. The mixture was filtered and concentrated to give a residue. The residue was purified by prep-HPLC (column: Phenomenex luna C18 150*25 mm*10 um; mobile phase: [water (0.225% FA)-ACN]; B %: 8%-38%, 10 min) to afford product as yellow gum (9.59 mg, 26% yield). $^1$H NMR (400 MHz, MeOH-$d_4$) δ 9.12 (s, 1H) 7.49 (dd, J=5.6 Hz, 8.8 Hz, 1H), 7.04 (t, J=8.8 Hz, 1H), 4.83-4.80 (m, 2H), 4.70-4.68 (m, 2H), 4.13 (s, 2H), 3.95 (d, J=14.0 Hz, 2H), 3.76-3.65 (m, 2H), 3.35-3.32 (m, 2H), 2.40-2.30 (m, 2H), 2.30-1.95 (m, 10H); LCMS [ESI, M+1]: 565.3

Example 456

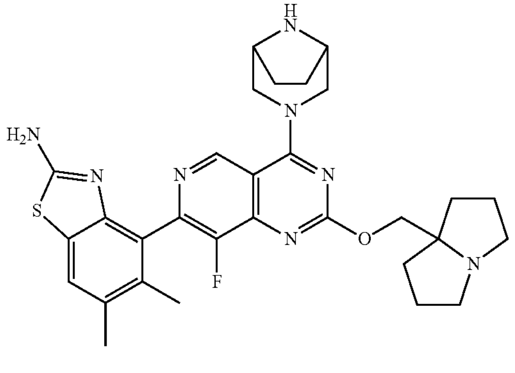 [SMILES: Cc1cc2sc(N)nc2c(-c2ncc3c(N4CC5CCC(C4)N5)nc(OCC45CCCN4CCC5)nc3c2F)c1C]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5,6-dimethylbenzo[d]thiazol-2-amine

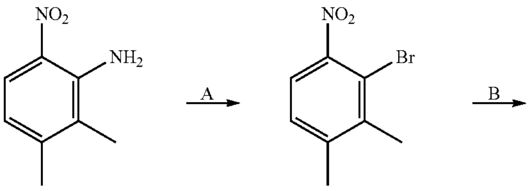

-continued

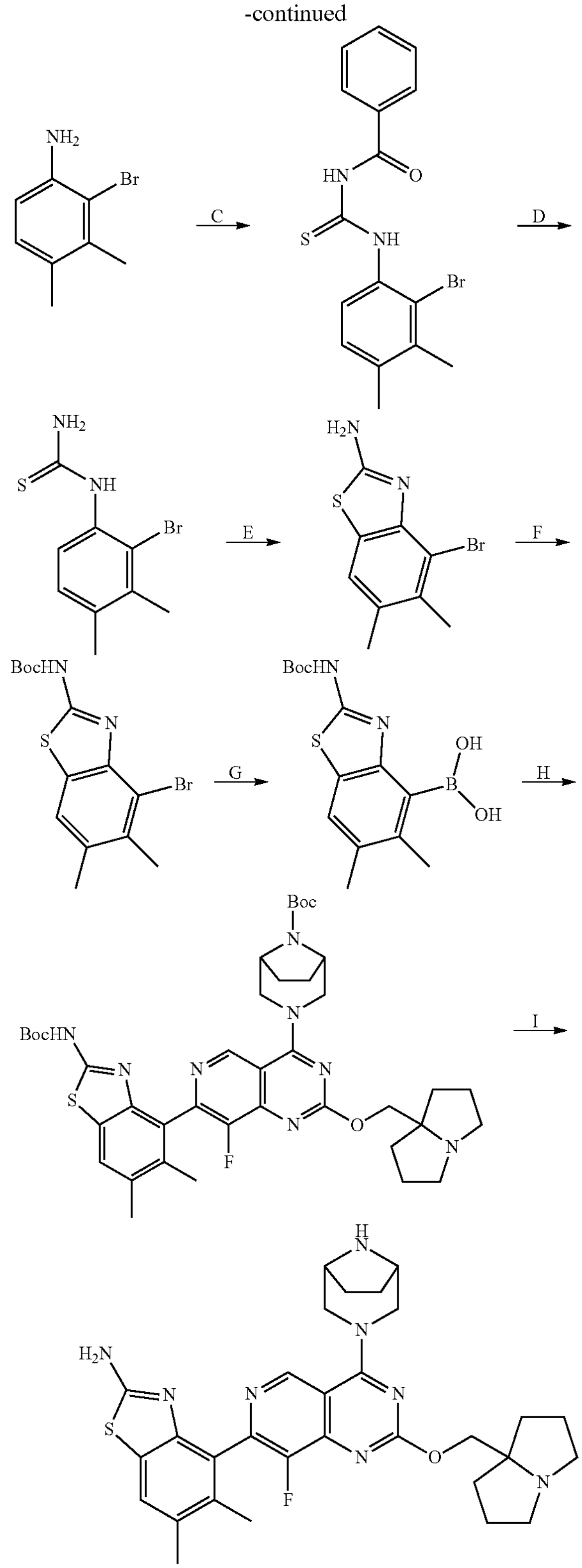

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5,6-dimethylbenzo[d]thiazol-2-amine. To a solution of (1R,5S)-tert-butyl 3-(7-(2-((tert-butoxycarbonyl)amino)-5,6-dimethylbenzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (80 mg, 103 μmol, 1.0 eq) in DCM (1.2 mL) was added TFA (1.85 g, 16.2 mmol) at 0° C. The mixture was stirred at 0~15° C. for 1 hour. The reaction mixture was concentrated under reduced pressure to give a residue. The residue was dissolved in ethyl acetate (20.0 mL) and $H_2O$ (5.0 mL). The pH of the mixture was adjusted to 8~9 with $NaHCO_3$ solid. The mixture was extracted with ethyl acetate (15.0 mL×4) and the combined organic layers were dried over anhydrous $Na_2SO_4$. The mixture was filtered and concentrated under reduced pressure to give a residue. The residue was purified by prep-HPLC (column: Phenomenex luna C18 150*25 mm*10 um; mobile phase: [water (0.225% FA)-ACN]; B %: 7%-37%, 10 min) and lyophilized to give product as an off-white solid (41.50 mg, 65% yield, 0.7FA). $^1$H NMR (400 MHz, methanol-d4) δ=9.14 (s, 1H), 7.56 (s, 1H), 4.80-4.75 (m, 2H), 4.68 (s, 2H), 4.13 (br s, 2H), 3.99 (d, J=13.6 Hz, 1H), 3.89 (d, J=14.0 Hz, 1H), 3.74-3.69 (m, 2H), 3.31-3.24 (m, 2H), 2.39 (s, 3H), 2.24-2.19 (m, 2H), 2.14-2.08 (m, 13H). LCMS [ESI, M+1]: 575.3.

Example 457

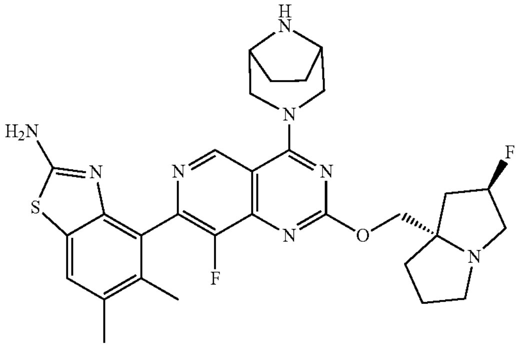 [SMILES: Cc1cc2sc(N)nc2c(-c2ncc3c(N4CC5CCC(C4)N5)nc(OC[C@@]45CCCN4C[C@H](F)C5)nc3c2F)c1C]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5,6-dimethylbenzo[d]thiazol-2-amine

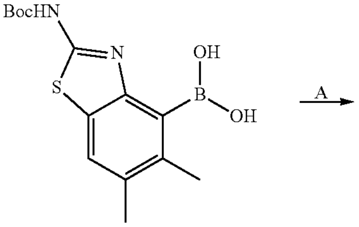

-continued

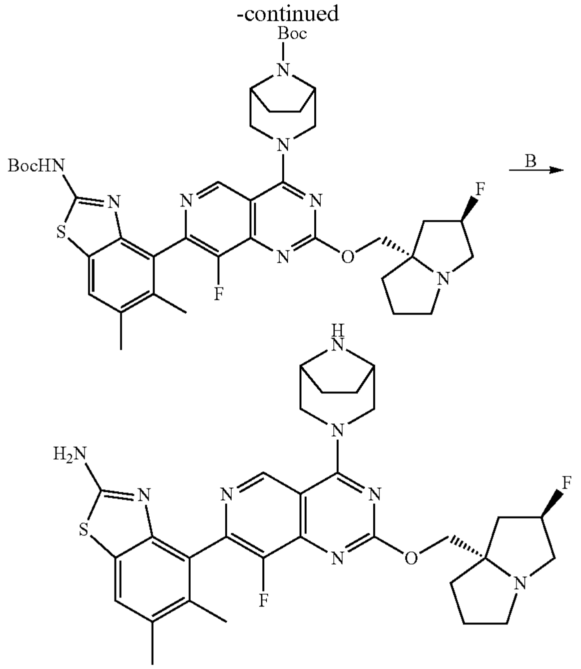

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5,6-dimethylbenzo[d]thiazol-2-amine. To a mixture of (1R,5S)-tert-butyl 3-(7-(2-((tert-butoxycarbonyl)amino)-5,6-dimethylbenzo[d]thiazol-4-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (110 mg, 139 μmol, 1.0 eq) in DCM (0.1 mL) was added TFA (1.69 g, 14.9 mmol, 1.10 mL, 107 eq) at 0° C. under $N_2$. The mixture was stirred at 20° C. for 1 hour. Then the pH of the mixture was adjusted to 8 with the saturated $Na_2CO_3$ aqueous and the mixture was extracted with ethyl acetate (3.0 mL×5). The combined organic phase was washed with brine (5.0 mL) and dried over anhydrous $Na_2SO_4$. The mixture was filtered and concentrated to give a residue. The residue was purified by prep-HPLC (column: Phenomenex luna C18 150*25 mm*10 um; mobile phase: [water (0.225% FA)-ACN]; B %: 8%-38%, 10 min) to afford the product as a white solid (28.5 mg, 34% yield). $^1$H NMR (400 MHz, methanol-d4) δ 9.12 (s, 1H), 7.56 (s, 1H), 5.50 (d, J=52.4 Hz, 1H), 4.78-4.72 (m, 1H), 4.65-4.55 (m, 1H), 4.10 (s, 2H), 4.01-3.92 (m, 1H), 3.90-3.68 (m, 4H), 3.40-3.32 (m, 2H), 2.68-2.47 (m, 2H), 2.41-2.32 (m, 4H), 2.30-2.20 (m, 2H), 2.17-1.92 (m, 8H); LCMS [ESI, M+1]: 593.3.

Example 458

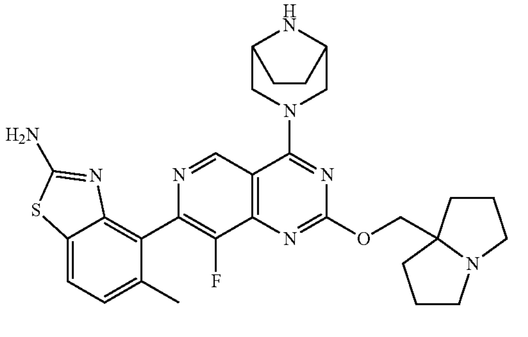 [SMILES: Cc1ccc2sc(N)nc2c1-c1ncc2c(N3CC4CCC(C3)N4)nc(OCC34CCCN3CCC4)nc2c1F]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-methylbenzo[d]thiazol-2-amine

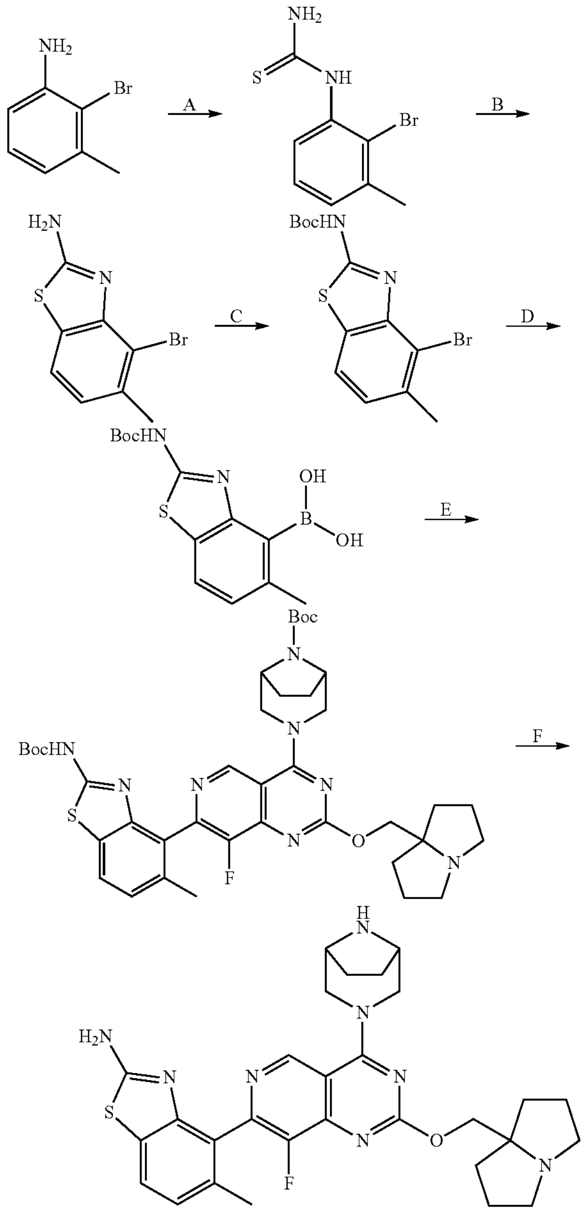

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-methylbenzo[d]thiazol-2-amine: To a solution of (1R,5S)-tert-butyl 3-(7-(2-((tert-butoxycarbonyl)amino)-5-methylbenzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (81.5 mg, 107 μmol, 1.0 eq) in DCM (1.50 mL) was added TFA (2.31 g, 20.3 mmol, 1.50 mL, 189 eq). The reaction mixture was stirred at 20° C. for 0.5 hour. Then the mixture was diluted with water (10.0 mL) and extracted with EtOAc (2×10.0 mL). The combined organic layer was dried over $Na_2SO_4$, then filtered and concentrated to give a residue. The residue was purified by prep-HPLC (column: Phenomenex luna C18 150*25 mm*10 um; mobile phase: [water (0.225% FA)-ACN]; B %: 7%-37%, 10 min) to afford title compound as yellow solid (26.3 mg, 42% yield). $^1$H NMR (400 MHz, METHANOL-$d_4$) δ=9.14 (s, 1H), 7.64 (d, J=8.0 Hz, 1H), 7.12 (d, J=8.0 Hz, 1H), 4.77 (br d, J=13.6 Hz, 2H), 4.68 (s, 2H), 4.13 (br s, 2H), 3.99 (br d, J=13.6 Hz, 1H), 3.89 (br d, J=13.6 Hz, 1H), 3.76-3.66 (m, 2H), 3.34-3.32 (m, 1H), 3.30-3.25 (m, 1H), 2.39-2.29 (m, 2H), 2.28-2.16 (m, 7H), 2.15-2.04 (m, 5H), 2.04-1.95 (m, 1H); LCMS [ESI, M+1]: 561.2.

Example 459

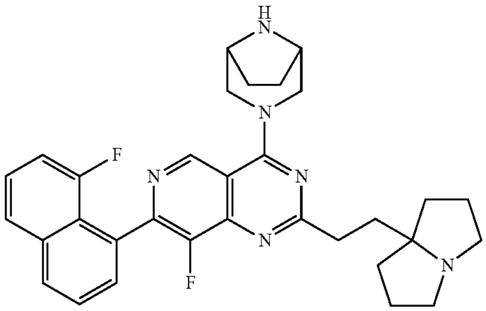 [SMILES: Fc1c(-c2cccc3cccc(F)c23)ncc2c(N3CC4CCC(C3)N4)nc(CCC34CCCN3CCC4)nc12]

4-((1R,5S)-3,8-diazabicyclo[3.2.1]octan-3-yl)-8-fluoro-7-(8-fluoronaphthalen-1-yl)-2-(2-(hexahydro-1H-pyrrolizin-7a-yl)ethyl)pyrido[4,3-d]pyrimidine

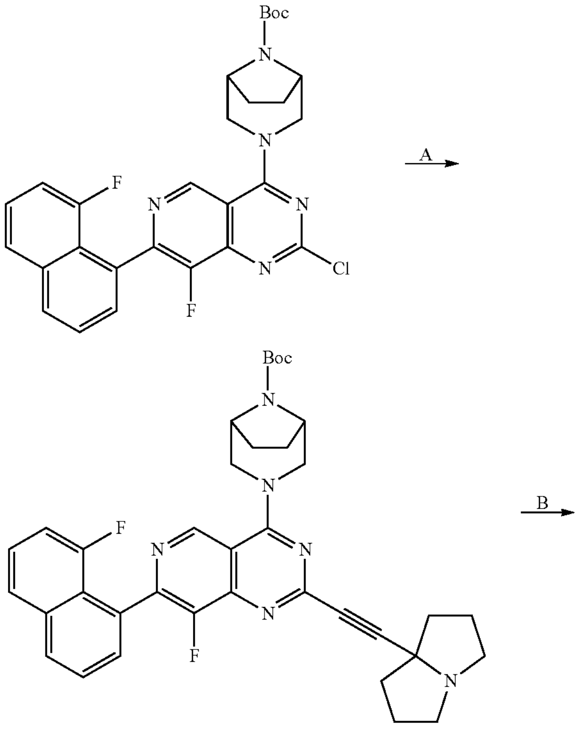

-continued

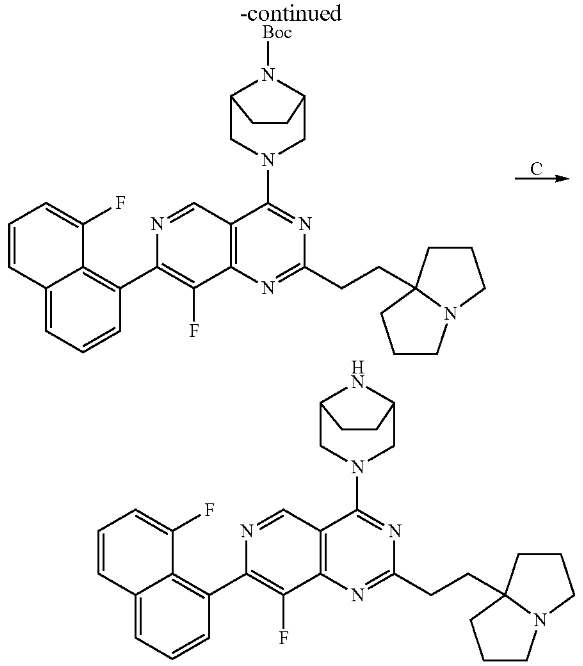

Step A. (1R,5S)-tert-butyl 3-(8-fluoro-7-(8-fluoronaphthalen-1-yl)-2-((hexahydro-1H-pyrrolizin-7a-yl)ethynyl)pyrido[4,3-d]pyrimidin-4-yl)-3,8-diazabicyclo[3.2.1]octane-8-carboxylate: To a solution of (1R,5S)-tert-butyl 3-(2-chloro-8-fluoro-7-(8-fluoronaphthalen-1-yl)pyrido[4,3-d]pyrimidin-4-yl)-3,8-diazabicyclo[3.2.1]octane-8-carboxylate (100 mg, 186 μmol) and 7a-ethynylhexahydro-1H-pyrrolizine (126 mg, 929 μmol) in TEA (1.0 mL) and ACN (1.0 mL) were added $Pd(PPh_3)_2Cl_2$ (26.1 mg, 37.2 μmol), and CuI (35.4 mg, 186 μmol). The mixture was stirred at 80° C. for 2 hours. The reaction mixture was concentrated under reduced pressure to remove solvent. The residue was diluted with $H_2O$ (10 mL) and extracted with ethyl acetate (3×10 mL). The combined organic layers were dried over $Na_2SO_4$ and filtered. The filtrate was concentrated under reduced pressure to give a residue. The residue was purified by prep-TLC ($SiO_2$, DCM:MeOH=10:1) affording (1R,5S)-tert-butyl 3-(8-fluoro-7-(8-fluoronaphthalen-1-yl)-2-((hexahydro-1H-pyrrolizin-7a-yl)ethynyl)pyrido[4,3-d]pyrimidin-4-yl)-3,8-diazabicyclo[3.2.1]octane-8-carboxylate (80 mg, 67% yield); Yellow solid. LCMS (ESI, M+1): m/z 637.2.

Step B. (1R,5S)-tert-butyl 3-(8-fluoro-7-(8-fluoronaphthalen-1-yl)-2-(2-(hexahydro-1H-pyrrolizin-7a-yl)ethyl)pyrido[4,3-d]pyrimidin-4-yl)-3,8-diazabicyclo[3.2.1]octane-8-carboxylate: To a solution of (1R,5S)-tert-butyl 3-(8-fluoro-7-(8-fluoronaphthalen-1-yl)-2-((hexahydro-1H-pyrrolizin-7a-yl)ethynyl)pyrido[4,3-d]pyrimidin-4-yl)-3,8-diazabicyclo[3.2.1]octane-8-carboxylate (80 mg, 126 μmol) in MeOH (3 mL) was added Pd/C (20 mg, 10% purity). The suspension was degassed under vacuum and purged with $H_2$ several times. The mixture was stirred under $H_2$ (15 psi) at 20° C. for 1 hour. The reaction mixture was filtered and concentrated under reduced pressure to give (1R,5S)-tert-butyl 3-(8-fluoro-7-(8-fluoronaphthalen-1-yl)-2-(2-(hexahydro-1H-pyrrolizin-7a-yl)ethyl)pyrido[4,3-d]pyrimidin-4-yl)-3,8-diazabicyclo[3.2.1]octane-8-carboxylate (80 mg, crude). Yellow solid. LCMS (ESI, M+1): m/z 641.3.

Step C. 4-((1R,5S)-3,8-diazabicyclo[3.2.1]octan-3-yl)-8-fluoro-7-(8-fluoronaphthalen-1-yl)-2-(2-(hexahydro-1H-pyrrolizin-7a-yl)ethyl)pyrido[4,3-d]pyrimidine: To a solution of (1R,5S)-tert-butyl 3-(8-fluoro-7-(8-fluoronaphthalen-1-yl)-2-(2-(hexahydro-1H-pyrrolizin-7a-yl)ethyl)pyrido[4,3-d]pyrimidin-4-yl)-3,8-diazabicyclo[3.2.1]octane-8-carboxylate (80 mg, 125 μmol) in ACN (1.0 mL) was added HCl·dioxane (4.0 M, 1.14 mL). The mixture was stirred at 0° C. for 0.5 hour. After completion, the reaction mixture was concentrated under reduced pressure to give a residue. The residue was purified with prep-HPLC (column: Phenomenex luna C18 150×25 mm×10 μm; mobile phase: [water (0.225% FA)-ACN]; B %: 7%-37%, 11 min) to give 4-((1R,5S)-3,8-diazabicyclo[3.2.1]octan-3-yl)-8-fluoro-7-(8-fluoronaphthalen-1-yl)-2-(2-(hexahydro-1H-pyrrolizin-7a-yl)ethyl)pyrido[4,3-d]pyrimidine (15.7 mg, 1.6 FA, two steps yield: 20%); Yellow solid. $^1$H NMR (400 MHz, methanol-$d_4$) δ 9.24 (s, 1H), 8.15 (br d, J=8.0 Hz, 1H), 7.88 (d, J=7.6 Hz, 1H), 7.77-7.69 (m, 1H), 7.68-7.62 (m, 1H), 7.60-7.52 (m, 1H), 7.26-7.14 (m, 1H), 4.95-4.90 (m, 2H), 4.13-3.98 (m, 2H), 3.97-3.83 (m, 2H), 3.67-3.55 (m, 2H), 3.28-3.13 (m, 4H), 2.44-2.34 (m, 2H), 2.27-1.88 (m, 12H). LCMS (ESI, M+1): m/z 541.3.

Example 460

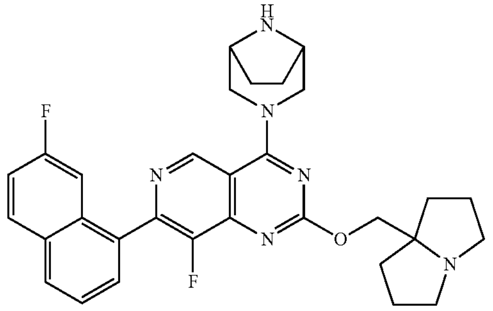 [SMILES: Fc1ccc2cccc(-c3ncc4c(N5CC6CCC(C5)N6)nc(OCC56CCCN5CCC6)nc4c3F)c2c1]

4-((1R,5S)-3,8-diazabicyclo[3.2.1]octan-3-yl)-8-fluoro-7-(7-fluoronaphthalen-1-yl)-2-((hexahydro-1H-pyrrolizin-7a-yl)methoxy)pyrido[4,3-d]pyrimidine

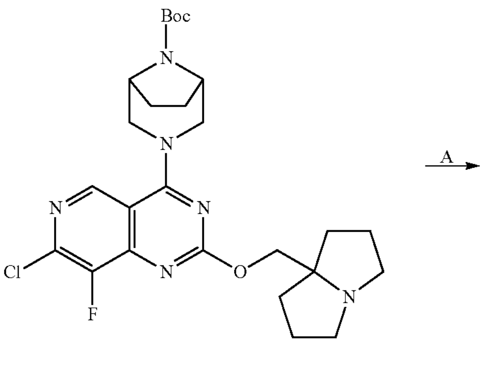

-continued

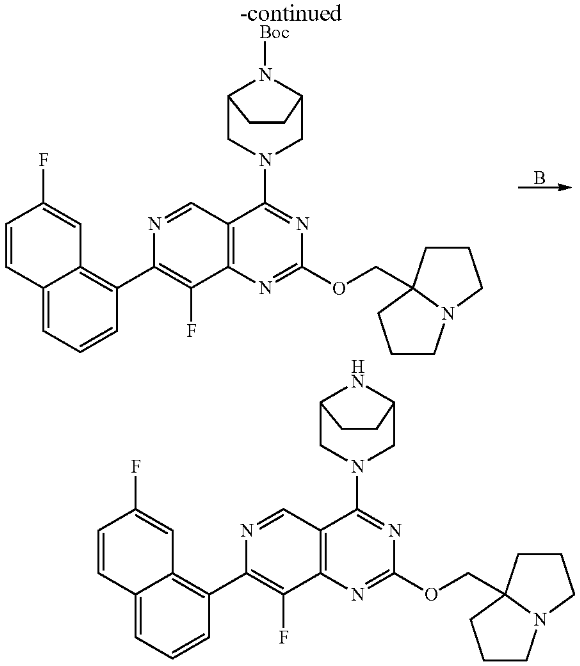

Step A. (1R,5S)-tert-butyl 3-(8-fluoro-7-(7-fluoronaphthalen-1-yl)-2-((hexahydro-1H-pyrrolizin-7a-yl)methoxy)pyrido[4,3-d]pyrimidin-4-yl)-3,8-diazabicyclo[3.2.1]octane-8-carboxylate: To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (300 mg, 563 μmol) and 2-(7-fluoronaphthalen-1-yl)-4,4,5,5-tetramethyl-1,3,2-dioxaborolane (184 mg, 675 μmol) in THF (3.0 mL) were added $K_3PO_4$ (1.5 M in water, 1.13 mL) and [2-(2-aminophenyl)phenyl]palladium (1+); bis(1-adamantyl)-butyl-phosphane; methanesulfonate (40.9 mg, 56.3 μmol) under $N_2$. The mixture was stirred at 60° C. for 2 hours. The reaction mixture was diluted with water (5.0 mL) and extracted with DCM (3×10 mL). The combined organic phase was washed with brine (15 mL), dried over $Na_2SO_4$ and filtered. The filtrate was concentrated in vacuum. The crude product was purified with reversed-phase flash chromatography (0.1% FA condition) to afford (1R,5S)-tert-butyl 3-(8-fluoro-7-(7-fluoronaphthalen-1-yl)-2-((hexahydro-1H-pyrrolizin-7a-yl)methoxy)pyrido[4,3-d]pyrimidin-4-yl)-3,8-diazabicyclo[3.2.1]octane-8-carboxylate (300 mg, 81% yield). Yellow solid. LCMS (ESI, M+1): m/z 643.3; $^1$H NMR (400 MHz, $CDCl_3$) δ (ppm)=9.09 (s, 1H), 7.97 (d, J=8.4 Hz, 1H), 7.92 (dd, J=6.0, 9.2 Hz, 1H), 7.72 (d, J=6.8 Hz, 1H), 7.59-7.54 (m, 1H), 7.48 (br d, J=11.2 Hz, 1H), 7.33-7.28 (m, 1H), 4.61 (br d, J=12.0 Hz, 2H), 4.40 (br s, 2H), 4.22 (s, 2H), 3.71 (br s, 2H), 3.18-3.05 (m, 2H), 2.65 (td, J=6.8, 10.0 Hz, 2H), 2.15-2.06 (m, 2H), 2.02-1.95 (m, 2H), 1.89-1.79 (m, 6H), 1.68 (td, J=7.6, 12.6 Hz, 2H), 1.53 (s, 9H).

Step B. 4-((1R,5S)-3,8-diazabicyclo[3.2.1]octan-3-yl)-8-fluoro-7-(7-fluoronaphthalen-1-yl)-2-((hexahydro-1H-pyrrolizin-7a-yl)methoxy)pyrido[4,3-d]pyrimidine: To a mixture of (1R,5S)-tert-butyl 3-(8-fluoro-7-(7-fluoronaphthalen-1-yl)-2-((hexahydro-1H-pyrrolizin-7a-yl)methoxy)pyrido[4,3-d]pyrimidin-4-yl)-3,8-diazabicyclo[3.2.1]octane-8-carboxylate (350 mg, 544 μmol) in ACN (1.0 mL) was added HCl·dioxane (4 M, 2.0 mL) in one portion at 0° C. under $N_2$. The mixture was stirred at 0° C.

for 30 minutes. The mixture was concentrated in vacuum and water (1.0 mL) and ACN (1.0 mL) were added. The pH of the mixture was adjusted to 8 with $NaHCO_3$. The residue was purified by prep-HPLC [Phenomenex Synergi C18 150×25 mm×10 μm; A: water (0.225% FA), B: ACN, B %: 7%-37% over 10 min]. The pH of the desired fractions was adjusted to pH=11 with $Na_2CO_3$. The mixture was concentrated in vacuum. The aqueous phase was extracted with DCM (3×10 mL). The organic phase was dried over $Na_2SO_4$ and filtered. The filtrate was concentrated in vacuum and lyophilized to afford 4-((1R,5S)-3,8-diazabicyclo[3.2.1]octan-3-yl)-8-fluoro-7-(7-fluoronaphthalen-1-yl)-2-((hexahydro-1H-pyrrolizin-7a-yl)methoxy)pyrido[4,3-d]pyrimidine (107 mg, 196 μmol, 36% yield, 99.9% purity). White solid. LCMS (ESI, M+1): m/z 543.3; $^1H$ NMR (400 MHz, $CDCl_3$) δ (ppm)=9.08 (s, 1H), 7.98-7.88 (m, 2H), 7.71 (d, J=7.2 Hz, 1H), 7.59-7.53 (m, 1H), 7.48 (br d, J=11.2 Hz, 1H), 7.33-7.27 (m, 1H), 4.60 (br d, J=11.6 Hz, 2H), 4.20 (s, 2H), 3.71-3.59 (m, 4H), 3.16-3.04 (m, 2H), 2.64 (td, J=6.8, 10.4 Hz, 2H), 2.10 (td, J=6.0, 12.4 Hz, 2H), 2.00 (br d, J=1.6 Hz, 3H), 1.92-1.80 (m, 5H), 1.67 (td, J=7.6, 12.4 Hz, 2H).

Example 461

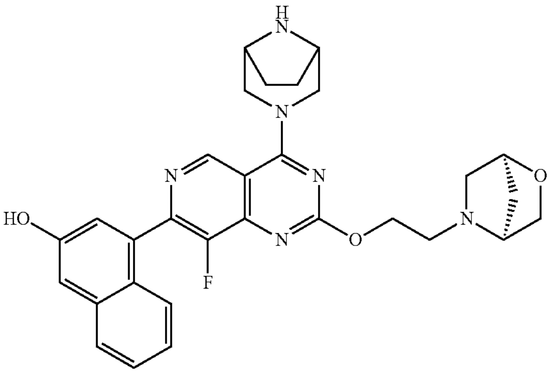 [SMILES: Oc1cc(-c2ncc3c(N4CC5CCC(C4)N5)nc(OCCN4C[C@@H]5C[C@H]4CO5)nc3c2F)c2ccccc2c1]

4-(2-(2-((1S,4S)-2-oxa-5-azabicyclo[2.2.1]heptan-5-yl)ethoxy)-4-((1R,5S)-3,8-diazabicyclo[3.2.1]octan-3-yl)-8-fluoropyrido[4,3-d]pyrimidin-7-yl)naphthalen-2-ol

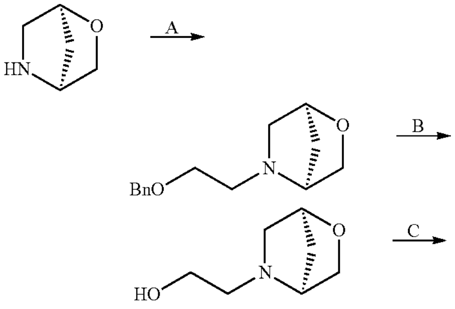

-continued

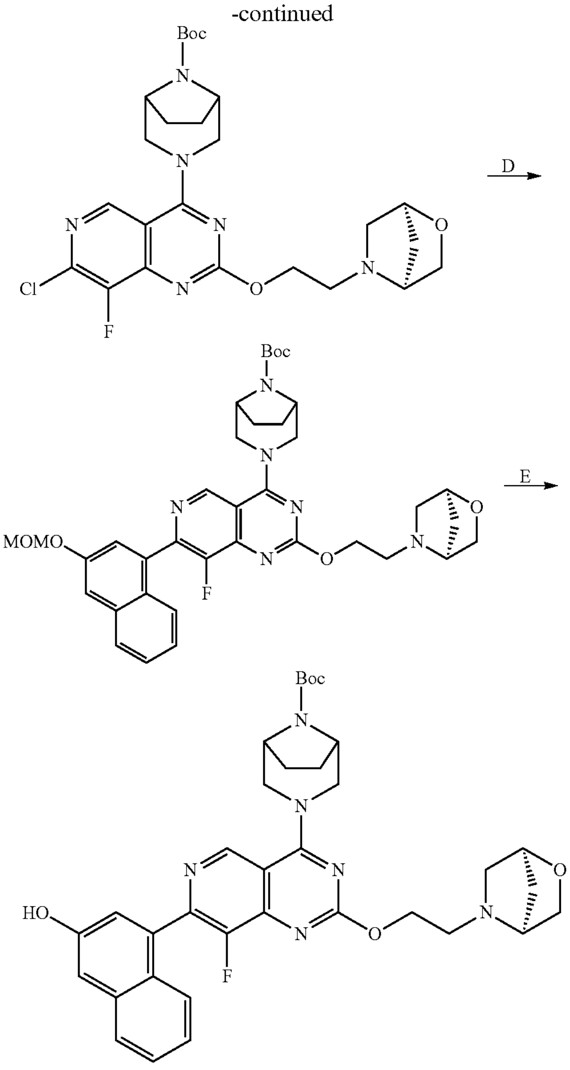

Step A. (1S,4S)-5-(2-(benzyloxy)ethyl)-2-oxa-5-azabicyclo[2.2.1]heptane: To a mixture of (1S,4S)-2-oxa-5-azabicyclo[2.2.1]heptane (2 g, 14.75 mmol, HCl) and 2-bromoethoxymethylbenzene (3.49 g, 16.2 mmol, 2.57 mL) in ACN (25 mL) was added $K_2CO_3$ (6.12 g, 44.25 mmol). The mixture was stirred at 80° C. for 2 hours. The mixture was concentrated under vacuum. The residue was purified by column chromatography ($SiO_2$, Petroleum ether/Ethyl acetate=10/1 to 1/1) to afford the title compound (1.9 g, 53% yield). Yellow oil. $^1H$ NMR (400 MHz, CHLOROFORM-d) δ=7.39-7.27 (m, 5H), 4.56 (s, 2H), 4.38 (s, 1H), 4.06 (d, J=7.6 Hz, 1H), 3.62 (dd, J=1.6, 8.0 Hz, 1H), 3.59-3.53 (m, 3H), 2.98 (dd, J=1.6, 10.0 Hz, 1H), 2.91-2.75 (m, 2H), 2.57 (d, J=10.0 Hz, 1H), 1.95-1.82 (mz, 1H), 1.78-1.64 (m, 1H).

Step B. 2-((1S,4S)-2-oxa-5-azabicyclo[2.2.1]heptan-5-yl)ethanol: To a mixture of (1S,4S)-5-(2-benzyloxyethyl)-2-oxa-5-azabicyclo[2.2.1]heptane (1 g, 4.29 mmol) and MeOH (15 mL) was added Pd/C (200 mg, 10% purity). The mixture was stirred at 40° C. for 48 h under $H_2$, and more Pd/C (1 g, 10% purity) was added. Then the reaction was stirred at 50° C. for 24 h under $H_2$. The mixture was concentrated under vacuum to afford the title compound (0.8 g, crude). Yellow oil.

Step C. (1R,5S)-tert-butyl 3-(2-(2-((1S,4S)-2-oxa-5-azabicyclo[2.2.1]heptan-5-yl)ethoxy)-7-chloro-8-fluoro-pyrido[4,3-d]pyrimidin-4-yl)-3,8-diazabicyclo[3.2.1]octane-8-carboxylate: To a mixture of (1R,5S)-tert-butyl 3-(2,7-dichloro-8-fluoropyrido[4,3-d]pyrimidin-4-yl)-3,8-diazabicyclo[3.2.1]octane-8-carboxylate (1.5 g, 3.50 mmol) and 2-((1S,4S)-2-oxa-5-azabicyclo[2.2.1]heptan-5-yl)ethanol (752 mg, 5.25 mmol) in DMAC (10 mL) was added CsF (1.60 g, 10.5 mmol). The mixture was stirred at 60° C. for 4 h. The reaction mixture was diluted with water (30 mL), and the aqueous phase was extracted with ethyl acetate (3x30 mL). The combined organic phase was washed with brine (15 mL) and dried over anhydrous $Na_2SO_4$. The mixture was filtered, and the filtrate was concentrated under vacuum. The residue was purified by column chromatography ($SiO_2$, Petroleum ether/Ethyl acetate=20/1 to 0/1) to afford the title compound (1.1 g, 49% yield). Yellow solid. LCMS (ESI, M+1): m/z: 535.2; $^1$H NMR (400 MHz, DMSO-$d_6$) δ=8.90 (s, 1H), 4.52-4.19 (m, 7H), 3.82 (br d, J=7.6 Hz, 1H), 3.68-3.47 (m, 5H), 2.92-2.82 (m, 3H), 1.85-1.75 (m, 2H), 1.71 (br d, J=8.8 Hz, 1H), 1.66-1.54 (m, 3H), 1.46 (s, 9H)

Step D. (1R,5S)-tert-butyl 3-(2-(2-((1S,4S)-2-oxa-5-azabicyclo[2.2.1]heptan-5-yl)ethoxy)-8-fluoro-7-(3-hydroxynaphthalen-1-yl)pyrido[4,3-d]pyrimidin-4-yl)-3,8-diazabicyclo[3.2.1]octane-8-carboxylate: To a mixture of (1R,5S)-tert-butyl 3-(2-(2-((1S,4S)-2-oxa-5-azabicyclo[2.2.1]heptan-5-yl)ethoxy)-7-chloro-8-fluoropyrido[4,3-d]pyrimidin-4-yl)-3,8-diazabicyclo[3.2.1]octane-8-carboxylate (500 mg, 934 μmol) and 2-[3-(methoxymethoxy)-1-naphthyl]-4,4,5,5-tetramethyl-1,3,2-dioxaborolane (440 mg, 1.40 mmol) in toluene (5.0 mL) were added [2-(2-aminophenyl)phenyl]palladium (1+); bis(1-adamantyl)-butyl-phosphane; methanesulfonate (68.06 mg, 93.46 μmol) and $K_3PO_4$ (1.5 M in water, 1.87 mL) under $N_2$. The mixture was stirred at 90° C. for 2 h. The reaction mixture was diluted with water (5.0 mL), and the aqueous phase was extracted with ethyl acetate (3x10 mL). The combined organic phase was washed with brine (15 mL), dried over anhydrous $Na_2SO_4$, filtered and concentrated under vacuum. The crude product was purified by reversed-phase flash chromatography (0.1% FA condition) to afford the title compound (400 mg, 62% yield). Yellow solid. LCMS (ESI, M+1): m/z 687.4; $^1$H NMR (400 MHz, CHLOROFORM-d) δ=9.10 (s, 1H), 7.83 (d, J=8.0 Hz, 1H), 7.70 (br d, J=8.0 Hz, 1H), 7.54 (d, J=2.3 Hz, 1H), 7.50-7.42 (m, 2H), 7.37-7.30 (m, 1H), 5.34 (s, 2H), 4.59-4.56 (m, 2H), 4.40 (br s, 2H), 4.05 (d, J=7.6 Hz, 1H), 3.74-3.58 (m, 4H), 3.54 (s, 3H), 3.10-3.00 (m, 3H), 2.65 (d, J=10.4 Hz, 1H), 2.00 (s, 3H), 1.86 (br s, 3H), 1.83-1.71 (m, 3H), 1.53 (s, 9H).

Step E. 4-(2-(2-((1S,4S)-2-oxa-5-azabicyclo[2.2.1]heptan-5-yl)ethoxy)-4-((1R,5S)-3,8-diazabicyclo[3.2.1]octan-3-yl)-8-fluoropyrido[4,3-d]pyrimidin-7-yl)naphthalen-2-ol: To a mixture of (1R,5S)-tert-butyl 3-(2-(2-((1S,4S)-2-oxa-5-azabicyclo[2.2.1]heptan-5-yl)ethoxy)-8-fluoro-7-(3-hydroxynaphthalen-1-yl)pyrido[4,3-d]pyrimidin-4-yl)-3,8-diazabicyclo[3.2.1]octane-8-carboxylate (400 mg, 582 μmol) and ACN (1.0 mL) was added HCl·dioxane (4 M, 2.0 mL) in one portion at 0° C. under $N_2$. The mixture was stirred at 0° C. for 30 minutes, and then concentrated under vacuum. The reaction mixture was diluted water (0.5 mL) and ACN (2.0 mL). The pH was adjusted to pH=8 with $NaHCO_3$. The residue was purified by prep-HPLC [Waters Xbridge 150x25 mmx5 μm; A: water (10 mM $NH_4HCO_3$), B: ACN, B %: 19%-49% over 10 min] to afford the title compound (121 mg, 38% yield). Yellow solid. $^1$HNMR (400 MHz, CHLOROFORM-d) δ=9.02 (s, 1H), 7.68 (d, J=8.0 Hz, 1H), 7.61 (br d, J=7.2 Hz, 1H), 7.38 (t, J=7.6 Hz, 1H), 7.29-7.28 (m, 1H), 7.25-7.20 (m, 2H), 4.57 (t, J=6.0 (m, 2H), 4.50-4.39 (m, 3H), 4.09 (d, J=8.0 Hz, 1H), 3.70-3.63 (m, 2H), 3.60-3.49 (m, 4H), 3.16-3.02 (m, 3H), 2.70 (br d, J=10.0 Hz, 1H), 1.93-1.90 (m, 1H), 1.77-1.75 (m, 1H), 1.66-1.58 (m, 4H); HRMS (ESI+) calcd, for $C_{30}H_{32}FN_6O_3^+$ (M+H$^+$) 543.6113, found 543.2510.

Example 462

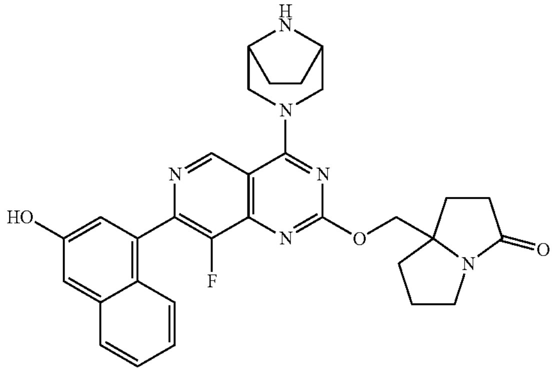 [SMILES: O=C1CCC2(COc3nc(N4CC5CCC(C4)N5)c4cnc(-c5cc(O)cc6ccccc56)c(F)c4n3)CCCN12]

7a-(((4-(3,8-diazabicyclo[3.2.1]octan-3-yl)-8-fluoro-7-(3-hydroxynaphthalen-1-yl)pyrido[4,3-d]pyrimidin-2-yl)oxy)methyl)tetrahydro-1H-pyrrolizin-3(2H)-one

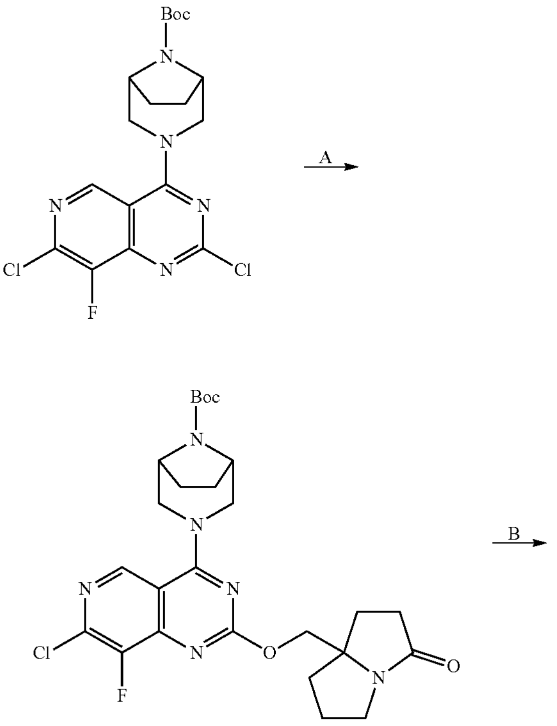

-continued

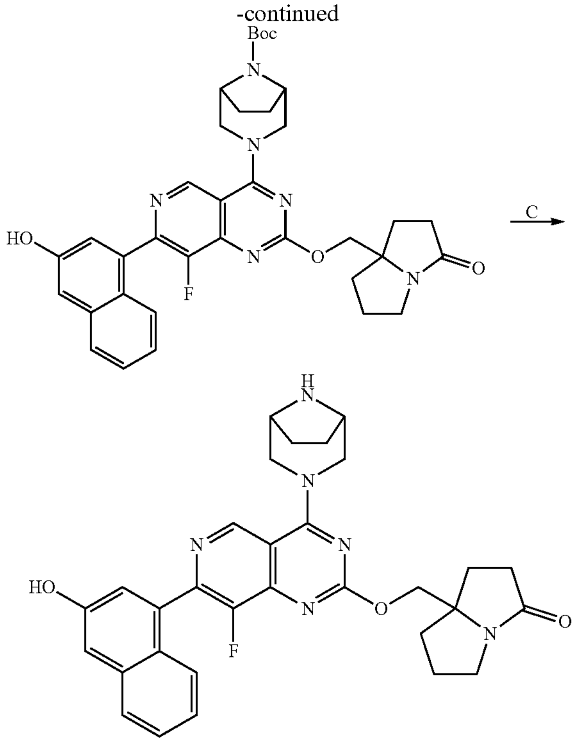

Step A. tert-butyl 3-(7-chloro-8-fluoro-2-((3-oxohexahydro-1H-pyrrolizin-7a-yl) methoxy)pyrido[4,3-d]pyrimidin-4-yl)-3,8-diazabicyclo[3.2.1]octane-8-carboxylate. To a solution of tert-butyl 3-(2,7-dichloro-8-fluoropyrido[4,3-d]pyrimidin-4-yl)-3,8-diazabicyclo[3.2.1]octane-8-carboxylate (370 mg, 864 μmol) in DMAC (4.0 mL) were added 7a-(hydroxymethyl)tetrahydro-1H-pyrrolizin-3 (2H)-one (268 mg, 1.73 mmol) and CsF (328 mg, 2.16 mmol). The mixture was stirred at 60° C. for 2 hrs. Upon completion, the mixture was filtered and purified by reversed-phase flash chromatography [water (0.1% FA)/acetonitrile]. The desired fractions were neutralized with solid $NaHCO_3$, concentrated under vacuum to remove MeCN, and extracted with ethyl acetate (2×20 mL). The organic layer was dried over anhydrous $Na_2SO_4$ and filtered. The filtrate was concentrated under vacuum to afford tert-butyl 3-(7-chloro-8-fluoro-2-((3-oxohexahydro-1H-pyrrolizin-7a-yl)methoxy)pyrido[4,3-d]pyrimidin-4-yl)-3,8-diazabicyclo[3.2.1]octane-8-carboxylate (420 mg, 691 μmol, 80% yield, 90% purity) as off-white solid. $^1$H NMR (400 MHz, $CDCl_3$) δ 8.75 (s, 1H), 4.60 (d, J=10.8 Hz, 1H), 4.53-4.34 (m, 4H), 4.31 (d, J=11.2 Hz, 1H), 3.77-3.53 (m, 3H), 3.18-3.08 (m, 1H), 3.00-2.88 (m, 1H), 2.50-2.40 (m, 2H), 2.29-2.10 (m, 3H), 2.04-1.92 (m, 3H), 1.77-1.65 (m, 3H), 1.53 (s, 9H). LCMS [ESI, M+1]: m/z 547.1.

Step B. tert-butyl 3-(8-fluoro-7-(3-hydroxynaphthalen-1-yl)-2-((3-oxohexahydro-1H-pyrrolizin-7a-yl)methoxy) pyrido[4,3-d]pyrimidin-4-yl)-3,8-diazabicyclo[3.2.1]octane-8-carboxylate. To a solution of tert-butyl 3-(7-chloro-8-fluoro-2-((3-oxohexahydro-1H-pyrrolizin-7a-yl) methoxy)pyrido[4,3-d]pyrimidin-4-yl)-3,8-diazabicyclo [3.2.1]octane-8-carboxylate (370 mg, 676 μmol) and 4-(4,4,5,5-tetramethyl-1,3,2-dioxaborolan-2-yl)naphthalen-2-ol (219 mg, 812 μmol) in toluene (8.0 mL) were added $K_3PO_4$ (1.5 M in water, 1.35 mL) and [2-(2-aminophenyl)phenyl] palladium (1+); bis(1-adamantyl)-butyl-phosphane; methanesulfonate (49.3 mg, 67.6 μmol). The mixture was stirred at 90° C. for 1.5 h under $N_2$. Upon completion, the mixture was diluted with water (10 mL) and extracted with ethyl acetate (2×20 mL). The organic layers were dried over anhydrous $Na_2SO_4$, concentrated under vacuum, and purified by reversed-phase flash chromatography [water (0.1% FA)/acetonitrile]. The desired fractions were neutralized with solid $NaHCO_3$, concentrated under vacuum to remove MeCN and extracted with ethyl acetate (2×20 mL). The organic layer was dried over anhydrous $Na_2SO_4$, filtered and concentrated under vacuum to afford tert-butyl 3-(8-fluoro-7-(3-hydroxynaphthalen-1-yl)-2-((3-oxohexahydro-1H-pyrrolizin-7a-yl)methoxy)pyrido[4,3-d]pyrimidin-4-yl)-3,8-diazabicyclo[3.2.1]octane-8-carboxylate (420 mg, 577 μmol, 85% yield, 90% purity) as yellow solid. $^1$H NMR (400 MHz, $CDCl_3$) δ 9.08-8.84 (m, 1H), 7.73-7.59 (m, 2H), 7.43-7.37 (m, 1H), 7.30-7.27 (m, 1H), 7.25-7.17 (m, 2H), 4.87-4.69 (m, 1H), 4.61-4.33 (m, 4H), 4.28 (d, J=11.2 Hz, 1H), 3.77-3.51 (m, 3H), 3.24-3.11 (m, 1H), 3.08-2.93 (m, 1H), 2.53-2.44 (m, 2H), 2.29-2.22 (m, 1H), 2.15-2.08 (m, 2H), 2.02-1.91 (m, 3H), 1.79-1.65 (m, 3H), 1.58-1.50 (m, 9H). LCMS [ESI, M+1]: m/z=655.3.

Step C. 7a-(((4-(3,8-diazabicyclo[3.2.1]octan-3-yl)-8-fluoro-7-(3-hydroxynaphthalen-1-yl)pyrido[4,3-d]pyrimidin-2-yl)oxy)methyl)tetrahydro-1H-pyrrolizin-3 (2H)-one. To a mixture of tert-butyl 3-(8-fluoro-7-(3-hydroxynaphthalen-1-yl)-2-((3-oxohexahydro-1H-pyrrolizin-7a-yl) methoxy)pyrido[4,3-d]pyrimidin-4-yl)-3,8-diazabicyclo [3.2.1]octane-8-carboxylate (260 mg, 397 μmol) and MeCN (0.7 mL) was added HCl·dioxane (4 M, 1.49 mL) at 10° C. under $N_2$. The mixture was stirred at 10° C. for 0.5 h. Upon completion, the solvent was removed under reduced pressure. The residue was diluted with MeOH (3.0 mL), neutralized with solid $NaHCO_3$, filtered and purified with prep-HPLC [Waters Xbridge 150×25 mm×5 μm; A: water (10 mM $NH_4HCO_3$), B: ACN, B %: 21%-51% over 10 min] to afford 7a-(((4-(3,8-diazabicyclo[3.2.1]octan-3-yl)-8-fluoro-7-(3-hydroxynaphthalen-1-yl)pyrido[4,3-d]pyrimidin-2-yl) oxy)methyl)tetrahydro-1H-pyrrolizin-3 (2H)-one (108 mg, 188 μmol, 47% yield, 96% purity) as yellow solid. $^1$H NMR (400 MHz, MeOD) δ 9.09 (s, 1H), 7.78-7.72 (m, 1H), 7.56-7.50 (m, 1H), 7.46-7.38 (m, 1H), 7.30-7.27 (m, 1H), 7.26-7.20 (m, 2H), 4.69, -4.57 (m, 3H), 4.43 (d, J=11.2 Hz, 1H), 3.75-3.57 (m, 5H), 3.17-2.99 (m, 2H), 2.50-2.36 (m, 2H), 2.33-2.20 (m, 1H), 2.19-2.00 (m, 3H), 1.90-1.69 (m, 5H). HRMS (ESI+) calcd for $C31H_{32}FN_6O_3^+$ (M+H$^+$) 555.2514, found 555.2519.

Example 463

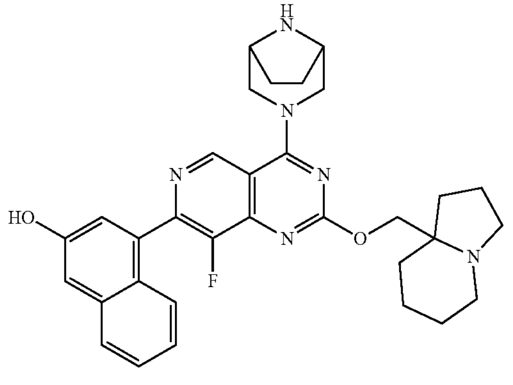 [SMILES: Oc1cc(-c2ncc3c(N4CC5CCC(C4)N5)nc(OCC45CCCCN4CCC5)nc3c2F)c2ccccc2c1]

4-(4-(3,8-diazabicyclo[3.2.1]octan-3-yl)-8-fluoro-2-((octahydroindolizin-8a-yl)methoxy)pyrido[4,3-d]pyrimidin-7-yl)naphthalen-2-ol

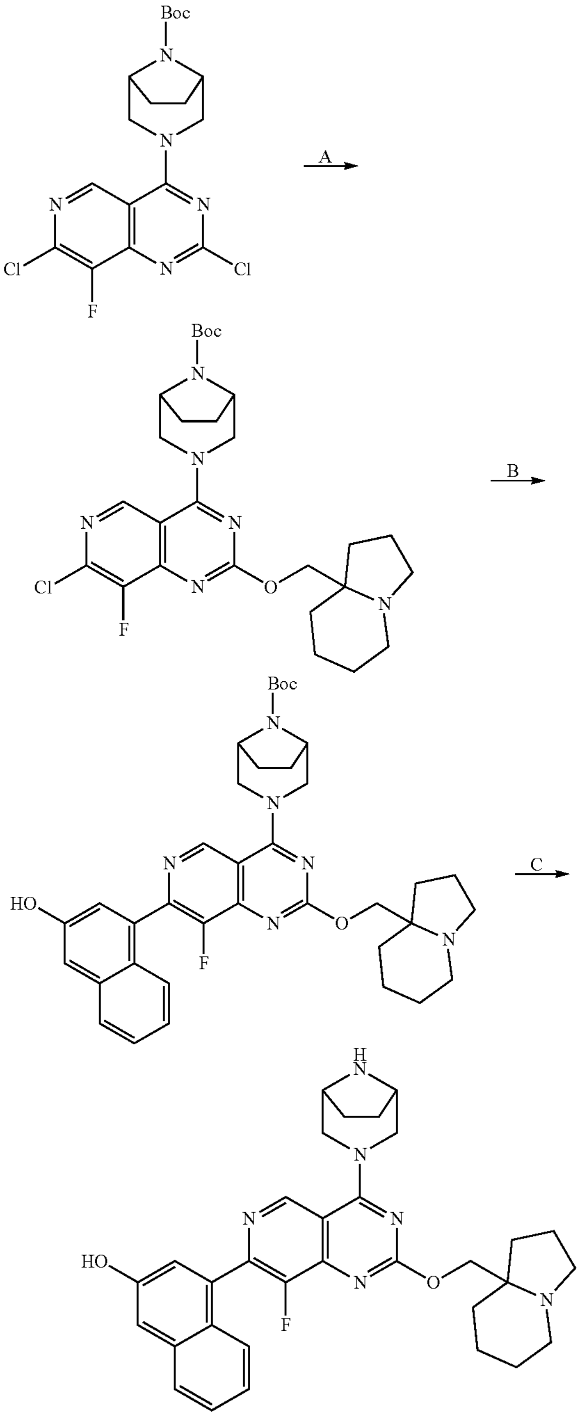

Step A. tert-butyl(1R,5S)-3-(7-chloro-8-fluoro-2-((hexahydroindolizin-8a(1H)-yl)methoxy)pyrido[4,3-d]pyrimidin-4-yl)-3,8-diazabicyclo[3.2.1]octane-8-carboxylate. To a solution of (octahydroindolizin-8a-yl)methanol (246 mg, 1.59 mmol) in THF (8.0 mL) was added NaH (93.4 mg, 2.33 mmol, 60% purity) at 0° C. After stirring at 0° C. for 0.5 h, tert-butyl 3-(2,7-dichloro-8-fluoropyrido[4,3-d]pyrimidin-4-yl)-3,8-diazabicyclo[3.2.1]octane-8-carboxylate (400 mg, 934 μmol) was added. The mixture was stirred at 0° C. for 0.5 h. The mixture was quenched with water (10 mL) and extracted with ethyl acetate (2×15 mL). Combined organic layer was dried over $Na_2SO_4$. The mixture was filtered and the filtrate was concentrated under vacuum. The residue was purified by reversed-phase flash chromatography [water (0.1% FA)/acetonitrile]. The desired fractions were collected and neutralized with solid $NaHCO_3$. The mixture was concentrated under vacuum to remove MeCN and extracted with ethyl acetate (2×20 mL). The organic layer was dried over anh $Na_2SO_4$ and filtered. The filtrate was concentrated under vacuum to afford tert-butyl 3-[7-chloro-8-fluoro-2-(2,3,5,6,7,8-hexahydro-1H-indolizin-8a-ylmethoxy)pyrido[4,3-d]pyrimidin-4-yl]-3,8-diazabicyclo[3.2.1]octane-8-carboxylate (180 mg, 296 μmol, 32% yield, 90% purity) as yellow solid. $^1$H NMR: 400 MHz $CDCl_3$ δ:8.74 (s, 1H), 4.77-4.66 (m, 1H), 4.56-4.33 (m, 5H), 3.78-3.59 (m, 2H), 3.22-2.86 (m, 4H), 2.03-1.86 (m, 6H), 1.78-1.65 (m, 8H), 1.52 (s, 9H).

Step B. tert-butyl 3-[8-fluoro-2-(2,3,5,6,7,8-hexahydro-1H-indolizin-8a-ylmethoxy)-7-(3-hydroxy-1-naphthyl)pyrido[4,3-d]pyrimidin-4-yl]-3,8-diazabicyclo[3.2.1]octane-8-carboxylate: To a solution of tert-butyl(1R,5S)-3-(7-chloro-8-fluoro-2-((hexahydroindolizin-8a(1H)-yl)methoxy)pyrido[4,3-d]pyrimidin-4-yl)-3,8-diazabicyclo[3.2.1]octane-8-carboxylate (150 mg, 274 μmol) and 4-(4,4,5,5-tetramethyl-1,3,2-dioxaborolan-2-yl)naphthalen-2-ol (88.9 mg, 329 μmol) in toluene (3.0 mL) were added $K_3PO_4$ (1.5 M in water, 548 μL) and [2-(2-aminophenyl)phenyl]palladium (1+); bis(1-adamantyl)-butyl-phosphane; methanesulfonate (20.0 mg, 27.4 μmol). After stirring at 90° C. for 1.5 h under $N_2$, and layers were separated. The aqueous phase was extracted with ethyl acetate (3.0 mL). Combined organic layer was dried over anhydrous $Na_2SO_4$, filtered, concentrated under vacuum, and purified by reversed-phase flash chromatography [water (0.1% FA)/acetonitrile]. The desired fractions were collected and neutralized with solid $NaHCO_3$, concentrated under vacuum to remove MeCN and extracted with ethyl acetate (2×10 mL). The organic layer was dried over anhydrous $Na_2SO_4$ and filtered. The filtrate was concentrated under vacuum to afford tert-butyl 3-[8-fluoro-2-(2,3,5,6,7,8-hexahydro-1H-indolizin-8a-ylmethoxy)-7-(3-hydroxy-1-naphthyl)pyrido[4,3-d]pyrimidin-4-yl]-3,8-diazabicyclo[3.2.1]octane-8-carboxylate (120 mg, 174 μmol, 63% yield, 95% purity) as a yellow solid. LCMS [ESI, M+1]: m/z 655.5.

Step C. 4-(4-(3,8-diazabicyclo[3.2.1]octan-3-yl)-8-fluoro-2-((octahydroindolizin-8a-yl)methoxy)pyrido[4,3-d]pyrimidin-7-yl)naphthalen-2-ol: To a solution of tert-butyl 3-[8-fluoro-2-(2,3,5,6,7,8-hexahydro-1H-indolizin-8a-yl-methoxy)-7-(3-hydroxy-1-naphthyl)pyrido[4,3-d]pyrimidin-4-yl]-3,8-diazabicyclo[3.2.1]octane-8-carboxylate (120 mg, 183 μmol) in ACN (0.34 mL) was added HCl·dioxane (4 M, 687 μL). The mixture was stirred at 25° C. for 0.5 hour. Upon completion, the solvent was removed under reduced pressure. The residue was diluted with MeOH (1.0 mL) and neutralized with solid $NaHCO_3$. The mixture was filtered and the filtrate was purified by prep-HPLC [Waters Xbridge 150×25 mm×5 μm; A: water (10 mM $NH_4HCO_3$), B: ACN, B %: 14%-44% over 10 min] to afford 4-(4-(3,8-diazabicyclo[3.2.1]octan-3-yl)-8-fluoro-2-((octahydroindolizin-8a-yl)methoxy)pyrido[4,3-d]pyrimidin-7-yl)naphthalen-2-ol (40.9 mg, 71.0 μmol, 39% yield, 96% purity) as yellow solid. $^1$H NMR (400 MHz, MeOD) δ 9.09 (s, 1H), 7.79-7.70 (m, 1H), 7.57-7.50 (m, 1H), 7.46-7.37 (m, 1H), 7.30-7.26

(m, 1H), 7.26-7.18 (m, 2H), 4.69 (d, J=10.8 Hz, 1H), 4.63 (br dd, J=7.2, 12.0 Hz, 2H), 4.40-4.33 (m, 1H), 3.75-3.67 (m, 2H), 3.66-3.58 (m, 2H), 3.17-3.07 (m, 1H), 3.05-2.91 (m, 2H), 2.89-2.79 (m, 1H), 2.04-1.53 (m, 13H), 1.47-1.36 (m, 1H). HRMS (ESI+) calcd for $C_{32}H_{36}FN_6O_2^+$ (M+H$^+$) 555.2878, found 555.2892.

Example 464

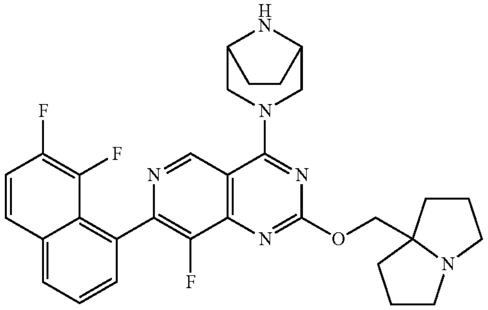 [SMILES: Fc1ccc2cccc(-c3ncc4c(N5CC6CCC(C5)N6)nc(OCC56CCCN5CCC6)nc4c3F)c2c1F]

4-((1R,5S)-3,8-diazabicyclo[3.2.1]octan-3-yl)-7-(7,8-difluoronaphthalen-1-yl)-8-fluoro-2-((hexahydro-1H-pyrrolizin-7a-yl)methoxy)pyrido[4,3-d]pyrimidine

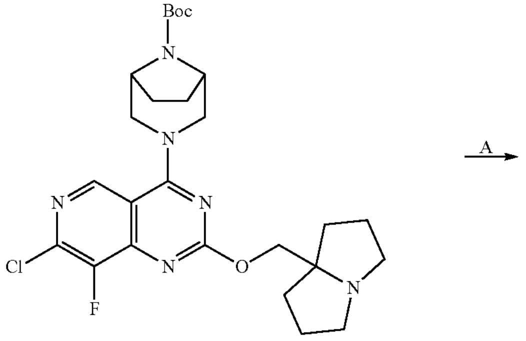

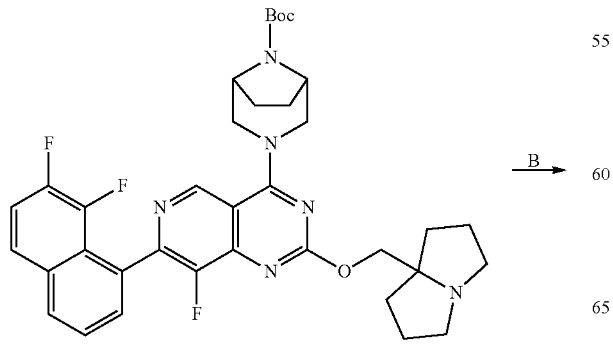

-continued

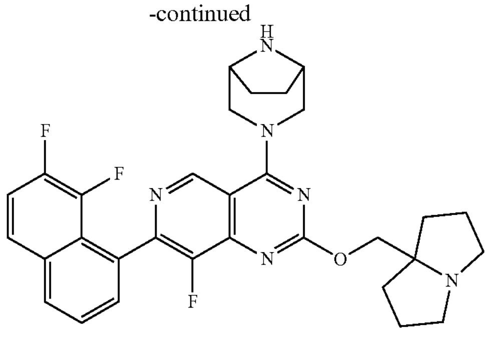

Step A. (1R,5S)-tert-butyl 3-(7-(7,8-difluoronaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate: To a solution of 2-(7,8-difluoronaphthalen-1-yl)-4,4,5,5-tetramethyl-1,3,2-dioxaborolane (250 mg, 862 μmol) and (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (306 mg, 574 μmol) in THF (2.0 mL) were added $K_3PO_4$ (1.5 M in water, 1.15 mL) and [2-(2-aminophenyl)phenyl]palladium (1+); bis(1-adamantyl)-butyl-phosphane; methanesulfonate (41.8 mg, 57.4 μmol) under nitrogen atmosphere. Then the mixture was stirred at 65° C. for 2 hours under nitrogen atmosphere. After completion, the reaction mixture was quenched with water (30 mL) and extracted with ethyl acetate (2×30 mL). The combined organic layer was dried over anhydrous $Na_2SO_4$, filtered, and concentrated under vacuum. The residue was purified by column chromatography ($SiO_2$, dichloromethane:methanol=20/1 to 4/1) to afford (1R,5S)-tert-butyl 3-(7-(7,8-difluoronaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (280 mg, 74% yield) as yellow solid; Rf=0.36 (dichloromethane:methanol=10:1).

Step B. 4-((1R,5S)-3,8-diazabicyclo[3.2.1]octan-3-yl)-7-(7,8-difluoronaphthalen-1-yl)-8-fluoro-2-((hexahydro-1H-pyrrolizin-7a-yl)methoxy)pyrido[4,3-d]pyrimidine: To a solution of (1R,5S)-tert-butyl 3-(7-(7,8-difluoronaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (250 mg, 378 μmol) in MeCN (5.0 mL) was added HCl·dioxane (4 M, 5 mL) at 0° C. The mixture was stirred at 25° C. for 1 hour. After completion, the reaction mixture was concentrated under vacuum. The pH of the residue was adjusted to 8 with aqueous solution of sodium bicarbonate. The crude was purified by prep-HPLC [Phenomenex luna C18 150×25 mm×10 μm; A: water (0.225% FA), B: ACN, B %: 10%-40% over 10 min). The pH of the desired fractions was adjusted to 8 with sodium bicarbonate. The obtained aqueous solution was extracted with ethyl acetate (5×10 mL). The combined organic layer was dried over anhydrous $Na_2SO_4$ and filtered. The filtrate was concentrated under vacuum to afford the title compound (141 mg, 68% yield) as white solid; $^1$H NMR (400 MHz, $CDCl_3$): δ 9.02 (s, 1H), 7.95 (br d, J=8.0 Hz, 1H), 7.71 (ddd, J=1.6, 4.8, 9.2 Hz, 1H), 7.66-7.56 (m, 2H), 7.39 (dt, J=7.2, 9.2 Hz, 1H), 4.68 (br d, J=12.4 Hz, 1H), 4.53 (br d, J=11.6 Hz, 1H), 4.25 (s, 2H), 3.76-3.65 (m, 3H), 3.59 (br d, J=12.0 Hz, 1H), 3.19 (td, J=5.2, 10.0 Hz, 2H), 2.68 (td, J=6.8, 10.4 Hz, 2H), 2.14 (br dd, J=5.2, 11.2 Hz, 2H), 1.94-1.86 (m, 8H), 1.75-1.66 (m, 2H); HRMS (ESI+) calcd for C31H32F3N6O+ (M+H+): 561.2584, found 561.2593.

Example 465

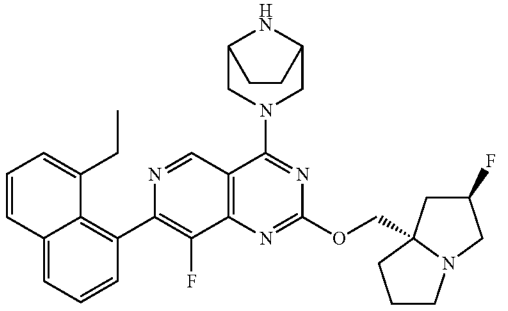 [SMILES: CCc1cccc2cccc(-c3ncc4c(N5CC6CCC(C5)N6)nc(OC[C@@]56CCCN5C[C@H](F)C6)nc4c3F)c12]

4-((1R,5S)-3,8-diazabicyclo[3.2.1]octan-3-yl)-7-(8-ethylnaphthalen-1-yl)-8-fluoro-2-(((2R,7aS)-2-fluorohexahydro-1H-pyrrolizin-7a-yl)methoxy)pyrido[4,3-d]pyrimidine

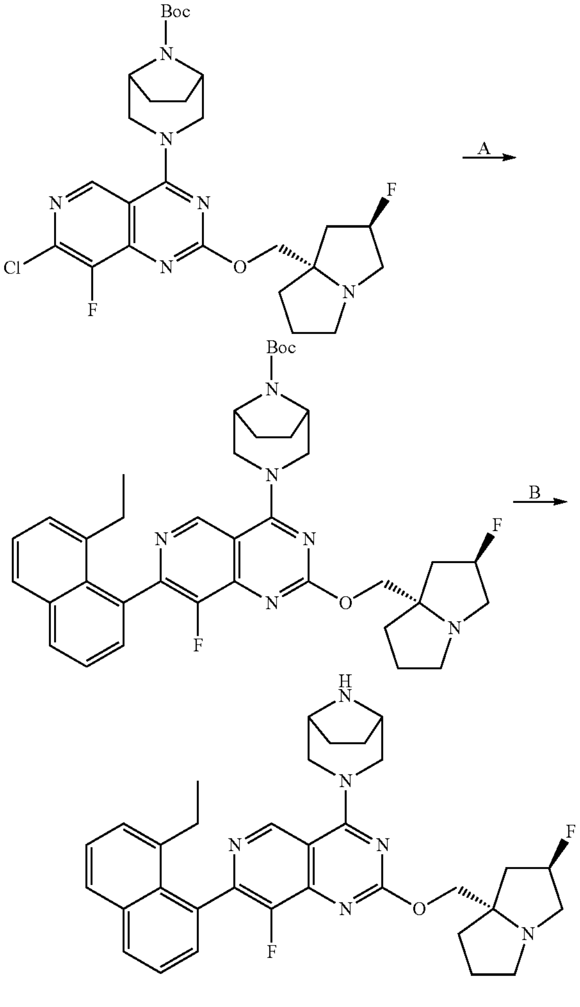

Step A. (1R,5S)-tert-butyl 3-(7-(8-ethylnaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate: To a mixture of (1R,5S)-tert-butyl 3-(7-chloro-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (100 mg, 181 μmol) in THF (2.0 mL) were added 2-(8-ethylnaphthalen-1-yl)-4,4,5,5-tetramethyl-1,3,2-dioxaborolane (76.8 mg, 272 μmol), $K_3PO_4$ (1.5 M, 363 μL) and [2-(2-aminophenyl)phenyl]palladium (1+); bis(1-adamantyl)-butyl-phosphane; methanesulfonate (26.4 mg, 36.3 μmol). The reaction mixture was degassed and stirred at 60° C. for 2 hours under $N_2$ atmosphere. The mixture was diluted with water (10 mL) and extracted with ethyl acetate (2×10 mL). The combined organic layer was washed with brine (15 mL), dried over $Na_2SO_4$, filtered and concentrated. The residue was purified by reversed-phase flash chromatography (FA condition, 30-60% MeCN in water) to give (1R,5S)-tert-butyl 3-(7-(8-ethylnaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (40 mg, 31% yield). Yellow oil; LCMS [ESI, M+1]: 671.2.

Step B. 4-((1R,5S)-3,8-diazabicyclo[3.2.1]octan-3-yl)-7-(8-ethylnaphthalen-1-yl)-8-fluoro-2-(((2R,7aS)-2-fluorohexahydro-1H-pyrrolizin-7a-yl)methoxy)pyrido[4,3-d]pyrimidine:

To a solution of (1R,5S)-tert-butyl 3-(7-(8-ethylnaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (40.0 mg, 59.6 μmol) in ACN (1 mL) was added HCl·dioxane (4 M, 1 mL) at 0° C. The mixture was stirred at 15° C. for 1 hour. Upon completion, the reaction mixture was concentrated under reduced pressure to remove solvent. The pH of the residue was adjusted to ~7 with saturated $NaHCO_3$ aqueous and the mixture was extracted with ethyl acetate (3×10 mL). The combined organic layers were dried over $Na_2SO_4$ and filtered. The filtrate was concentrated under reduced pressure to give a residue. The residue was purified by prep-HPLC (column: Phenomenex Gemini-NX C18 75×30 mm×3 μm; mobile phase: [water (10 mM $NH_4HCO_3$)-ACN]; B %: 35%-65%, 8 min) to give 4-((1R,5S)-3,8-diazabicyclo[3.2.1]octan-3-yl)-7-(8-ethylnaphthalen-1-yl)-8-fluoro-2-(((2R,7aS)-2-fluorohexahydro-1H-pyrrolizin-7a-yl)methoxy)pyrido[4,3-d]pyrimidine (9.16 mg, 26% yield). White solid; $^1$H NMR (400 MHz, $CDCl_3$-d) § 9.01 (s, 1H), 7.97 (dd, J=1.2, 8.0 Hz, 1H), 7.80 (d, J=7.6 Hz, 1H), 7.54-7.41 (m, 3H), 7.37 (d, J=6.8 Hz, 1H), 5.41-5.18 (m, 1H), 4.71-4.45 (m, 2H), 4.28 (dd, J=4.4, 10.4 Hz, 1H), 4.16 (dd, J=2.4, 10.4 Hz, 1H), 3.76-3.54 (m, 4H), 3.33-3.11 (m, 3H), 3.05-2.94 (m, 1H), 2.49-2.14 (m, 5H), 2.05-1.81 (m, 7H), 0.97 (t, J=7.6 Hz, 3H). LCMS [ESI, M+1]: 571.1.

Example 466
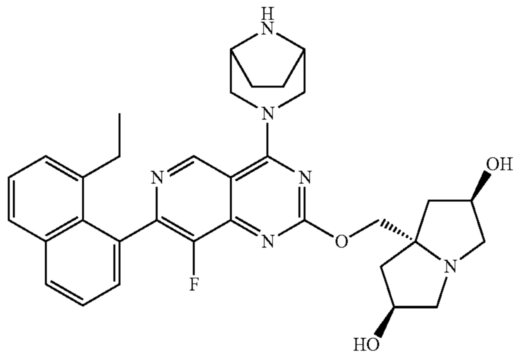 [SMILES: CCc1cccc2cccc(-c3ncc4c(N5CC6CCC(C5)N6)nc(OC[C@@]56C[C@H](O)CN5C[C@H](O)C6)nc4c3F)c12]
(2R,6S,7as)-7a-(((4-((1R,5S)-3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizine-2,6-diol
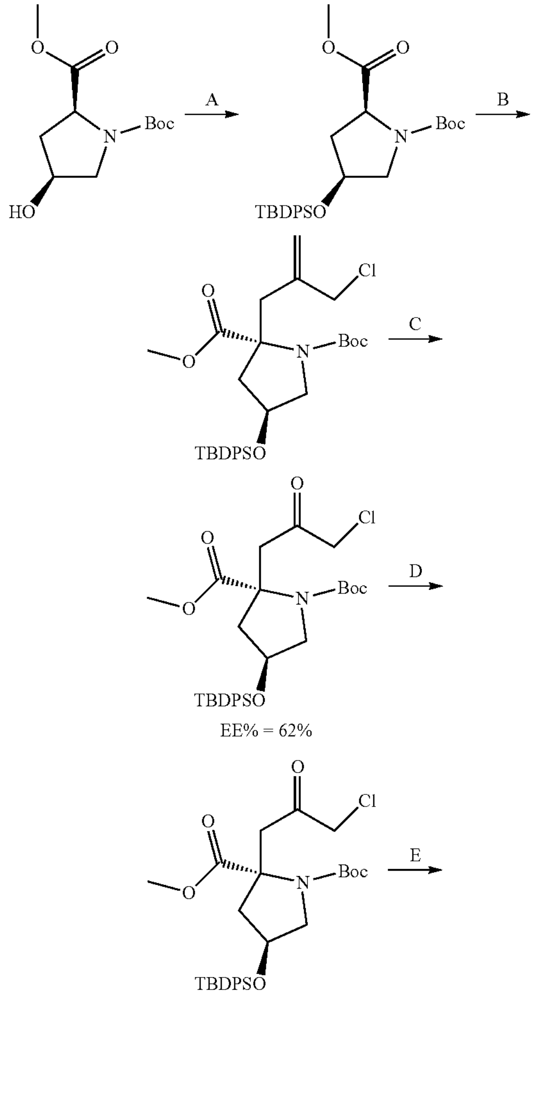
-continued
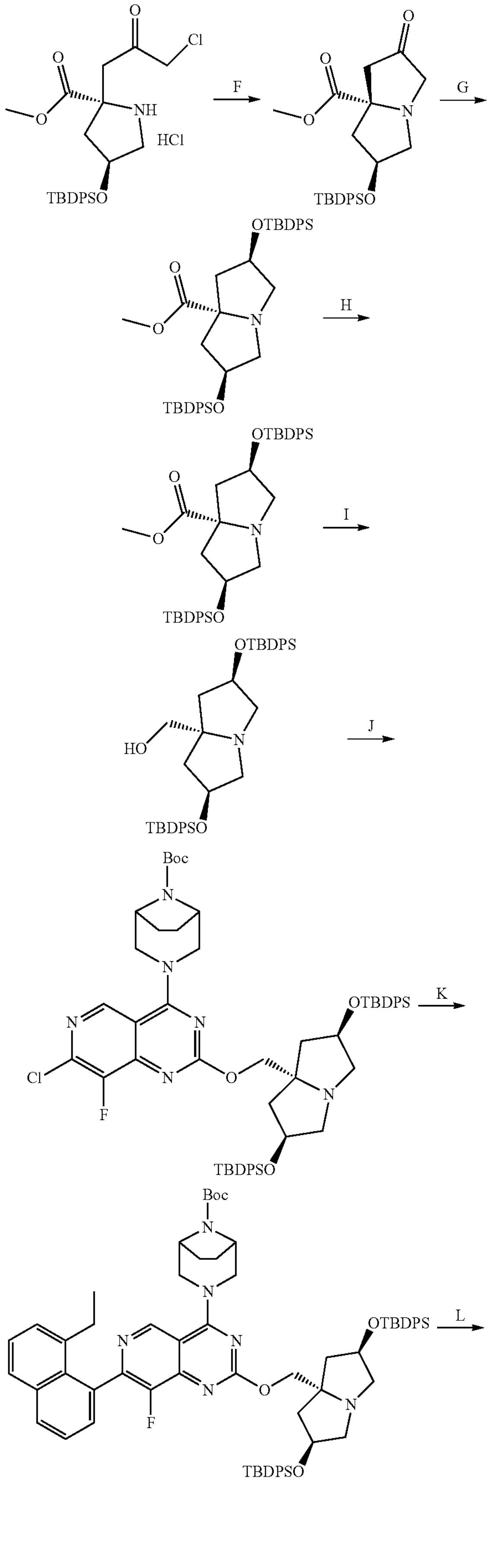

-continued

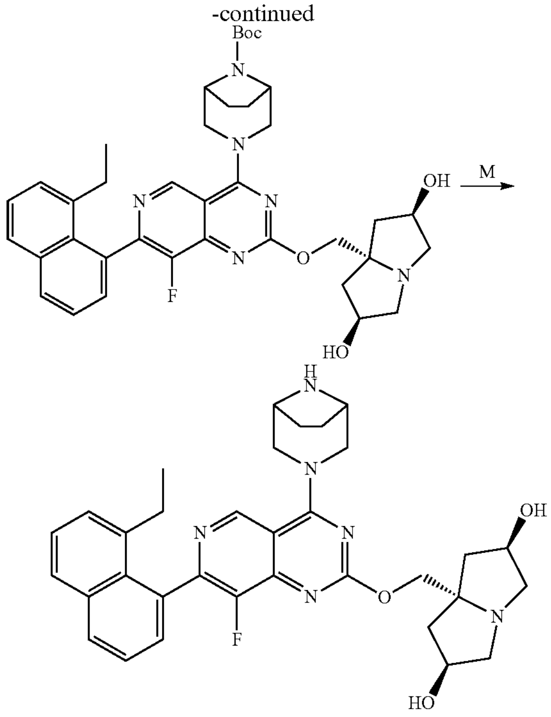

Step A. O1-tert-butyl O2-methyl(2S,4S)-4-[tert-butyl(diphenyl)silyl]oxypyrrolidine-1,2-dicarboxylate: To a solution of O1-tert-butyl O2-methyl(2S,4S)-4-hydroxypyrrolidine-1,2-dicarboxylate (5 g, 20.39 mmol) and tert-butyl-chloro-diphenyl-silane (8.40 g, 30.58 mmol, 7.85 mL) in DCM (100 mL) was added imidazole (2.78 g, 40.77 mmol) and the mixture was stirred at 20° C. for 14 hours. After completion, the reaction mixture was quenched with $H_2O$ (50 mL) at 20° C. The organic layer was washed with brine (30 mL×2) and dried over anhydrous sodium sulfate. The mixture was filtered, and concentrated under reduced pressure to give a residue. The residue was purified by column chromatography ($SiO_2$, Petroleum ether/Ethyl acetate=10:1) affording O1-tert-butyl O2-methyl(2S,4S)-4-[tert-butyl(diphenyl)silyl]oxypyrrolidine-1,2-dicarboxylate (8.02 g, 78% yield). White solid. $^1$H NMR (400 MHz, $CDCl_3$) δ=7.66-7.64 (m, 4H), 7.45-7.40 (m, 6H), 7.37-7.24 (m, 2H), 3.77 (s, 3H), 3.55-3.40 (m, 2H), 2.24-2.18 (m, 2H), 1.47-1.43 (m, 9H), 1.05 (s, 9H). LCMS [ESI, M−99]: m/z 384.3.

Step B. O1-tert-butyl O2-methyl(4S)-4-[tert-butyl(diphenyl)silyl]oxy-2-[2-(chloromethyl)allyl]pyrrolidine-1,2-dicarboxylate: To a solution of 01-tert-butyl 02-methyl(2S,4S)-4-[tert-butyl(diphenyl)silyl]oxypyrrolidine-1,2-dicarboxylate (1 g, 2.07 mmol) in THF (20 mL) was added dropwise LDA (2 M solution in THF, 1.24 mL) at −40° C. After addition, the mixture was stirred at −40° C. for 1 hour, and then 3-chloro-2-(chloromethyl) prop-1-ene (1.29 g, 10.3 mmol, 1.20 mL) was added. The resulting mixture was warmed to 20° C. and stirred for 1 hour. After completion, the mixture was quenched with saturated $NH_4Cl$ solution (50 mL), and then extracted with ethyl acetate (30 mL×3). The combined organic layers were washed with brine (20 mL×2), dried over anhydrous $Na_2SO_4$, filtered, and concentrated under reduced pressure to give a residue. The residue was purified by reversed-phase flash chromatography (0.1% FA condition) to afford O1-tert-butyl O2-methyl(4S)-4-[tert-butyl(diphenyl)silyl]oxy-2-[2-(chloromethyl)allyl]pyrrolidine-1,2-dicarboxylate (1.07 g, 87% yield). Colorless oil. $^1$H NMR (400 MHz, $CDCl_3$) δ=7.61-7.59 (m, 4H), 7.45-7.36 (m, 6H), 5.12-4.95 (m, 1H), 4.71-4.40 (m, 1H), 4.18-4.12 (m, 1H), 3.77 (s, 3H), 3.67-3.03 (m, 4H), 2.50-2.46 (m, 1H), 2.19-2.02 (m, 2H), 1.44-1.40 (m, 9H), 1.05 (s, 9H). LCMS [ESI, M−55]: m/z 516.2.

Step C. O1-tert-butyl O2-methyl(4S)-4-[tert-butyl(diphenyl)silyl]oxy-2-(3-chloro-2-oxo-propyl)pyrrolidine-1,2-dicarboxylate: Ozone (15 psi) was bubbled into a solution of O1-tert-butyl O2-methyl(4S)-4-[tert-butyl(diphenyl)silyl]oxy-2-[2-(chloromethyl)allyl]pyrrolidine-1,2-dicarboxylate (9.8 g, 17.13 mmol) in DCM (200 mL) at −70° C. for 5 minutes. After excess $O_3$ was purged by $N_2$, $Me_2S$ (5.32 g, 85.63 mmol, 6.29 mL) was added at −70° C. The mixture was warmed to 20° C. and stirred for 1 hour. After completion, the mixture was directly concentrated under reduced pressure to give a residue. The residue was purified by column chromatography ($SiO_2$, Petroleum ether/Ethyl acetate=10:1). Affording 01-tert-butyl 02-methyl(4S)-4-[tert-butyl(diphenyl)silyl]oxy-2-(3-chloro-2-oxo-propyl) pyrrolidine-1,2-dicarboxylate (8.7 g, 87% yield). Colorless oil. LCMS [ESI, M−55]: m/z 474.2.

Step D. (2S,4S)-1-tert-butyl 2-methyl 4-((tert-butyldiphenylsilyl)oxy)-2-(3-chloro-2-oxopropyl)pyrrolidine-1,2-dicarboxylate: (4S)-1-tert-butyl 2-methyl 4-((tert-butyldiphenylsilyl)oxy)-2-(3-chloro-2-oxopropyl)pyrrolidine-1,2-dicarboxylate was separated by SFC (DAICEL Chiralpak AD-3 250×50 mm I.D., 10 μm column A: $CO_2$, B: IPA (w/0.1% $NH_3H_2O$), 2 min) affording (2S,4S)-1-tert-butyl 2-methyl 4-((tert-butyldiphenylsilyl)oxy)-2-(3-chloro-2-oxopropyl)pyrrolidine-1,2-dicarboxylate (6.5 g, 17% yield). Yellow oil; HPLC: >99% ee, Chiralpak AD-3 100×4.6 mm I.D., 3 μm column A: $CO_2$, B: IPA (w/0.05% DEA), 3.4 mL/min, 220 nm, $t_R$: 0.885 min; $^1$H NMR (400 MHz, MeOD) δ=7.66-7.63 (m, 4H), 7.46-7.40 (m, 6H), 4.46-4.42 (m, 1H), 4.41-4.39 (m, 2H), 4.41-4.08 (m, 1H), 3.60-3.59 (m, 3H), 3.40-3.39 (m, 2H), 3.38-3.14 (m, 1H), 3.13-3.09 (m, 1H), 2.25-2.12 (m, 1H), 1.43-1.40 (m, 9H), 1.05 (s, 9H).

Step E. (2S,4S)-methyl 4-((tert-butyldiphenylsilyl)oxy)-2-(3-chloro-2-oxopropyl)pyrrolidine-2-carboxylate: (2S,4S)-1-tert-butyl 2-methyl 4-((tert-butyldiphenylsilyl)oxy)-2-(3-chloro-2-oxopropyl)pyrrolidine-1,2-dicarboxylate (500 mg, 870.8 μmol) was added to HCl/EtOAc (4 M, 5 mL). The mixture was stirred at 20° C. for 1 hour. Upon completion, the mixture was concentrated under the reduced pressure affording (2S,4S)-methyl 4-((tert-butyldiphenylsilyl)oxy)-2-(3-chloro-2-oxopropyl)pyrrolidine-2-carboxylate (400 mg, crude, HCl salt). Yellow oil.

Step F. (2S,7aS)-methyl 2-((tert-butyldiphenylsilyl)oxy)-6-oxohexahydro-1H-pyrrolizine-7a-carboxylate: To a solution of (2S,4S)-methyl 4-((tert-butyldiphenylsilyl)oxy)-2-(3-chloro-2-oxopropyl)pyrrolidine-2-carboxylate (400 mg, 783.5 μmol, HCl salt) in ACN (5 mL) was added $K_2CO_3$ (433.15 mg, 3.13 mmol). The mixture was stirred at 60° C. for 12 hours. Upon completion, the mixture was filtered and concentrated under the reduced pressure affording (2S,7aS)-methyl 2-((tert-butyldiphenylsilyl)oxy)-6-oxohexahydro-1H-pyrrolizine-7a-carboxylate (450 mg, crude). Yellow solid; $^1$H NMR (400 MHz, MeOD) δ=7.67-7.64 (m, 4H), 7.45-7.41 (m, 6H), 4.47-4.40 (m, 2H), 3.57 (s, 2H), 3.34-3.31 (m, 1H), 3.05-3.04 (m, 1H), 3.03-3.02 (m, 2H), 2.51-2.49 (m, 1H), 2.47-2.33 (m, 1H), 2.14-2.01 (m, 1H), 1.28-1.18 (m, 1H), 1.08-1.02 (m, 9H).

Step G. (2S,6R,7aR)-methyl 2-((tert-butyldiphenylsilyl)oxy)-6-hydroxyhexahydro-1H-pyrrolizine-7a-carboxylate: To a solution of (2S,7aS)-methyl 2-((tert-butyldiphenylsilyl)oxy)-6-oxohexahydro-1H-pyrrolizine-7a-carboxylate (2 g, 4.57 mmol) in MeOH (40 mL) was added $NaBH_4$ (86.45 mg, 2.29 mmol) at 0° C. The mixture was stirred at 0° C. for 15 minutes. Upon completion, the mixture was quenched with $H_2O$ (30 mL) and then extracted with EA (90 mL). The combined organic layers were washed with brine (30 mL) and dried over $Na_2SO_4$. The mixture was filtered and concentrated under the reduced pressure to give a residue. The residue was purified by column chromatography ($SiO_2$, Petroleum ether:Ethyl acetate=5:1 to 0:1) affording (2S,6R,7aR)-methyl 2-((tert-butyldiphenylsilyl)oxy)-6-hydroxy-hexahydro-1H-pyrrolizine-7a-carboxylate (2.35 g, 58% yield). Yellow oil; LCMS [ESI, M+1]: m/z 440.2.

Step H. (2R,6S,7as)-methyl 2,6-bis((tert-butyldiphenylsilyl)oxy)hexahydro-1H-pyrrolizine-7a-carboxylate: To a solution of (2S,6R,7aR)-methyl 2-((tert-butyldiphenylsilyl) oxy)-6-hydroxyhexahydro-1H-pyrrolizine-7a-carboxylate (200 mg, 454.9 μmol) and imidazole (92.9 mg, 1.4 mmol) in DCM (3 mL) was added tert-butyl-chlorodiphenyl-silane (187.6 mg, 682.4 μmol, 175.3 μL) dropwise at 0° C. under $N_2$. The mixture was stirred at 25° C. for 2 hours. Upon completion, the mixture was filtered and $H_2O$ (10 mL) was added at 0° C. The aqueous layer was extracted with DCM (30 mL). The combined organic layers were washed with brine (10 mL), dried over $Na_2SO_4$, filtered, and concentrated under the reduced pressure to give a residue. The residue was purified with prep-TLC (PE:EA=10:1) affording (2R,6S,7as)-methyl 2,6-bis((tert-butyldiphenylsilyl)oxy)hexahydro-1H-pyrrolizine-7a-carboxylate (140 mg, 45% yield). Yellow oil; LCMS [ESI, M+1]: m/z 678.5.

Step I. ((2R,6S,7as)-2,6-bis((tert-butyldiphenylsilyl)oxy) hexahydro-1H-pyrrolizin-7a-yl)methanol: To a solution of (2R,6S,7as)-methyl 2,6-bis((tert-butyldiphenylsilyl)oxy) hexahydro-1H-pyrrolizine-7a-carboxylate (1 g, 1.47 mmol) in THF (10 mL) was added $LiAlH_4$ (111.96 mg, 2.95 mmol) at 0° C. The mixture was stirred at 20° C. for 1 hour. Upon completion, the mixture was quenched with $H_2O$ (30 mL) and then extracted with EA (50 mL). The combined organic layers were washed with brine (30 mL), dried over $Na_2SO_4$, filtered, and concentrated under the reduced pressure to give a residue. The residue was purified by column chromatography ($SiO_2$, Petroleum ether/Ethyl acetate=10/1 to 0/1) affording ((2R,6S,7as)-2,6-bis((tert-butyldiphenylsilyl)oxy) hexahydro-1H-pyrrolizin-7a-yl)methanol (460 mg, 48% yield). Yellow oil; LCMS [ESI, M+1]: m/z 650.3.

Step J. (1R,5S)-tert-butyl 3-(2-(((2R,6S,7as)-2,6-bis ((tert-butyldiphenylsilyl)oxy)hexahydro-1H-pyrrolizin-7a-yl)methoxy)-7-chloro-8-fluoropyrido[4,3-d]pyrimidin-4-yl)-3,8-diazabicyclo[3.2.1]octane-8-carboxylate: To a solution of (1R,5S)-tert-butyl 3-(2,7-dichloro-8-fluoro-pyrido[4,3-d]pyrimidin-4-yl)-3,8-diazabicyclo[3.2.1]octane-8-carboxylate (250 mg, 583.7 μmol) and ((2R,6S,7as)-2,6-bis((tert-butyldiphenylsilyl)oxy)hexahydro-1H-pyrrolizin-7a-yl)methanol (260 mg, 400 μmol) in dioxane (5 mL) was added DIEA (516.9 mg, 4.00 mmol, 696.72 μL). The mixture was stirred at 80° C. for 48 hours. Upon completion, the mixture was filtered, quenched with $H_2O$ (30 mL) and then extracted with EA (60 mL). The combined organic layers were washed with brine (20 mL), dried over $Na_2SO_4$, filtered and concentrated under the reduced pressure to give a residue. The residue was purified by column chromatography ($SiO_2$, Petroleum ether/Ethyl acetate=10/1 to 0/1) affording (1R,5S)-tert-butyl 3-(2-(((2R,6S,7as)-2,6-bis((tert-butyldiphenylsilyl)oxy)hexahydro-1H-pyrrolizin-7a-yl)methoxy)-7-chloro-8-fluoropyrido[4,3-d]pyrimidin-4-yl)-3,8-diazabicyclo[3.2.1]octane-8-carboxylate (200 mg, 48% yield). Yellow solid; LCMS [ESI, M+1]: m/z 1041.4

Step K. (1R,5S)-tert-butyl 3-(2-(((2R,6S,7as)-2,6-bis ((tert-butyldiphenylsilyl)oxy)hexahydro-1H-pyrrolizin-7a-yl)methoxy)-7-(8-ethylnaphthalen-1-yl)-8-fluoropyrido[4,3-d]pyrimidin-4-yl)-3,8-diazabicyclo[3.2.1]octane-8-carboxylate: To a solution of (1R,5S)-tert-butyl 3-(2-(((2R,6S,7as)-2,6-bis((tert-butyldiphenylsilyl)oxy)hexahydro-1H-pyrrolizin-7a-yl)methoxy)-7-chloro-8-fluoropyrido[4,3-d]pyrimidin-4-yl)-3,8-diazabicyclo[3.2.1]octane-8-carboxylate (200 mg, 191.97 μmol) and 2-(8-ethylnaphthalen-1-yl)-4,4,5,5-tetramethyl-1,3,2-dioxaborolane (108.34 mg, 383.94 μmol) in dioxane (3 mL) were added $K_3PO_4$ (1.5 M, 383.94 μL), and [2-(2-aminophenyl)phenyl]palladium (1+); bis(1-adamantyl)-butyl-phosphane; methanesulfonate (27.96 mg, 38.39 μmol) under $N_2$. The mixture was stirred at 100° C. for 16 hours. Upon completion, the mixture was filtered, quenched with $H_2O$ (10 mL), and then extracted with ethyl acetate (30 mL). The combined organic layers were washed with brine (10 mL), dried over $Na_2SO_4$, filtered and concentrated under the reduced pressure to give the residue. The residue was purified by column chromatography ($SiO_2$, PE/EA=10/1 to 1/1) to afford (1R,5S)-tert-butyl 3-(2-(((2R,6S,7as)-2,6-bis ((tert-butyldiphenylsilyl)oxy)hexahydro-1H-pyrrolizin-7a-yl)methoxy)-7-(8-ethylnaphthalen-1-yl)-8-fluoropyrido[4,3-d]pyrimidin-4-yl)-3,8-diazabicyclo[3.2.1]octane-8-carboxylate (170 mg, 76% yield). Yellow oil; LCMS [ESI, M+1]: m/z 1161.6.

Step L. (tert-butyl(1R,5S)-3-(2-(((2R,6S,7as)-2,6-dihydroxytetrahydro-1H-pyrrolizin-7a(5H)-yl)methoxy)-7-(8-ethylnaphthalen-1-yl)-8-fluoropyrido[4,3-d]pyrimidin-4-yl)-3,8-diazabicyclo[3.2.1]octane-8-carboxylate: To a solution of (1R,5S)-tert-butyl(3-(2-(((2R,6S,7as)-2,6-bis ((tert-butyldiphenylsilyl)oxy)hexahydro-1H-pyrrolizin-7a-yl)methoxy)-7-(8-ethylnaphthalen-1-yl)-8-fluoropyrido[4,3-d]pyrimidin-4-yl)-3,8-diazabicyclo[3.2.1]octane-8-carboxylate (80 mg, 68.87 μmol) in THF (2 mL) was added TBAF (1 M, 206.61 μL). The mixture was stirred at 20° C. for 16 hours. The mixture was filtered, quenched with $H_2O$ (10 mL), and then extracted with EA (30 mL). The combined organic layers were washed with brine (10 mL), dried over $Na_2SO_4$, filtered, and concentrated under reduced pressure to give the residue. The residue was purified by prep-HPLC (column: Waters Xbridge BEH C18 100×25 mm×5 μm; mobile phase: [water (10 mM $NH_4HCO_3$)-ACN]; B %: 35%-65%, 10 min) to afford the title compound (20 mg, 42% yield, 99.7% purity). White solid; HPLC: >99%, $^1H$ NMR (400 MHz, DMSO) δ=9.11 (s, 1H), 8.14-8.03 (m, 1H), 7.97-7.86 (m, 1H), 7.63-7.55 (m, 1H), 7.52-7.46 (m, 1H), 7.42-7.34 (m, 2H), 4.60-4.41 (m, 2H), 4.33-4.21 (m, 4H), 4.03-3.92 (m, 2H), 3.77-3.53 (m, 3H), 3.19-3.10 (m, 3H), 3.08-3.00 (m, 2H), 2.81-2.70 (m, 2H), 2.38-2.23 (m, 2H), 2.13-2.03 (m, 2H), 1.90-1.78 (m, 4H), 1.76-1.62 (m, 2H), 1.59 (s, 3H), 1.35-1.26 (m, 3H), 0.97-0.88 (m, 4H), 0.86-0.79 (m, 3H); LCMS [ESI, M+1]: m/z 685.3.

Step M. (2R,6S,7as)-7a-(((4-((1R,5S)-3,8-diazabicyclo [3.2.1]octan-3-yl)-7-(8-ethylnaphthalen-1-yl)-8-fluoro-pyrido[4,3-d]pyrimidin-2-yl)oxy)methyl)hexahydro-1H-pyrrolizine-2,6-diol: To a solution of tert-butyl(1R,5S)-3-(2-(((2R,6S,7as)-2,6-dihydroxytetrahydro-1H-pyrrolizin-7a (5H)-yl)methoxy)-7-(8-ethylnaphthalen-1-yl)-8-fluoropyrido[4,3-d]pyrimidin-4-yl)-3,8-diazabicyclo[3.2.1] octane-8-carboxylate (16 mg, 23.36 μmol) in $CH_3CN$ (1 mL) was added $AlCl_3$ (31.15 mg, 233.65 μmol, 12.77 μL) at 0° C. and the mixture was stirred at 20° C. for 0.5 hour. The mixture was filtered and the filtrate was purified by prep-HPLC (column: Phenomenex Luna C18 200×40 mm×10 um; mobile phase: [water (0.2% FA)-ACN]; B %: 1%-40%, 8 min) to afford (2R,6S,7as)-7a-(((4-((1R,5S)-3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizine-2,6-diol (4.85 mg, 33% yield, 98.8% purity, FA salt). White solid; $^1$H NMR (400 MHz, DMSO) δ=9.09 (s, 1H), 8.23 (s, 2H), 8.07 (dd, J=1.0, 8.4 Hz, 1H), 7.90 (d, J=7.8 Hz, 1H), 7.58 (t, J=7.6 Hz, 1H), 7.51 (t, J=7.6 Hz, 1H), 7.44-7.35 (m, 2H), 4.58-4.40 (m, 2H), 4.33 (q, J=5.8 Hz, 2H), 4.07 (s, 2H), 3.78-3.72 (m, 2H), 3.69-3.61 (m, 2H), 3.17 (dd, J=5.0, 10.2 Hz, 2H), 2.88 (dd, J=5.6, 10.2 Hz, 2H), 2.38-2.20 (m, 2H), 2.13 (dd, J=5.8, 12.8 Hz, 2H), 1.92 (dd, J=6.2, 12.8 Hz, 2H), 1.82-1.64 (m, 4H), 0.82 (t, J=7.4 Hz, 3H); LCMS [ESI, M+1]: m/z 585.3.

Example 467

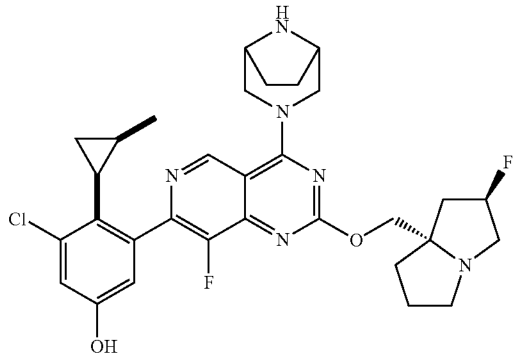

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-chloro-4-((1S,2R)-2-methylcyclopropyl)phenol

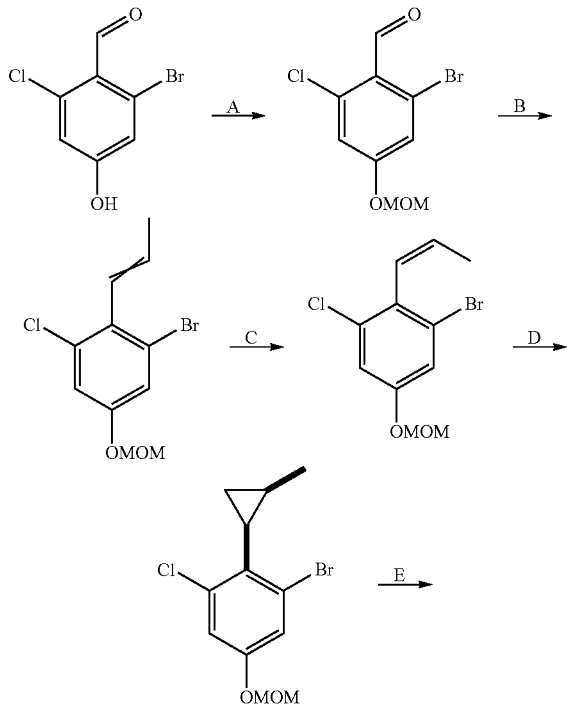

-continued

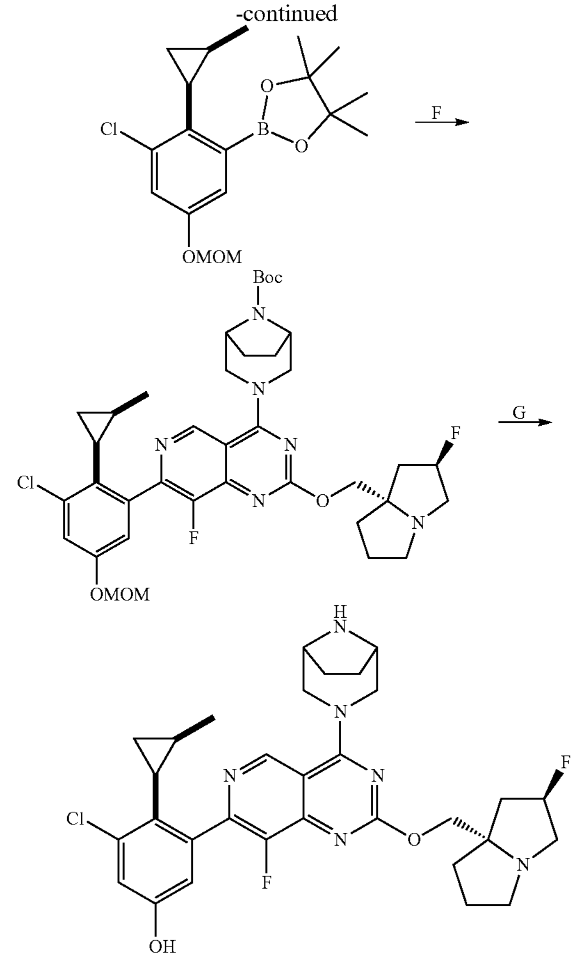

Step A. 2-bromo-6-chloro-4-(methoxymethoxy)benzaldehyde: To a mixture of 2-bromo-6-chloro-4-hydroxy-benzaldehyde (2.40 g, 10.2 mmol) in dichloromethane (30 mL) were added DIEA (3.95 g, 30.6 mmol, 5.33 mL) and MOMCl (1.23 g, 15.3 mmol, 1.16 mL) at 0° C. The mixture was stirred at 0° C. for 0.5 h. After completion, the mixture was quenched with water (15 mL) and then separated. The aqueous phase was extracted with dichloromethane (10 mL). The combined organic layer was washed with brine (15 mL), dried over $Na_2SO_4$, filtered and concentrated under vacuum. The residue was purified by column chromatography ($SiO_2$, petroleum ether/ethyl=10/1-5/1) to acetate give 2-bromo-6-chloro-4-(methoxymethoxy)benzaldehyde (2.09 g, 72% yield). White solid. Rf=0.5 (5:1, petroleum ether/ethyl acetate). $^1$H NMR (400 MHz, $CDCl_3$-d) δ=10.33 (s, 1H), 7.29 (d, J=2.4 Hz, 1H), 7.12 (d, J=2.4 Hz, 1H), 5.23 (s, 2H), 3.50 (s, 3H). LCMS [ESI, M+1]: m/z 280.9.

Step B. 1-bromo-3-chloro-5-(methoxymethoxy)-2-[prop-1-enyl]benzene: To a mixture of ethyl(triphenyl)phosphonium; bromide (35.9 g, 96.6 mmol) in THF (180 mL) was added t-BuOK (1 M in THF, 83.72 mL) dropwise at 0° C. The mixture was stirred at 10° C. for 1 h. 2-bromo-6-chloro-4-(methoxymethoxy)benzaldehyde (18 g, 64.4 mmol) in THF (90 mL) was added to the reaction and the mixture was stirred at 10° C. for 40 mins. After completion, the mixture was quenched with $H_2O$ (220 mL) and concentrated under vacuum. Then the mixture was extracted with ethyl acetate twice (200 and 100 mL). The combined organic layer was washed with brine (150 mL), dried over $Na_2SO_4$, filtered and concentrated under vacuum. The residue was purified by column chromatography ($SiO_2$, petroleum ether/ethyl acetate=50/1) to give 1-bromo-3-chloro-5-(methoxymethoxy)-2-[(E)-prop-1-enyl]benzene (18.0 g, 95% yield). Yellow oil. Rf=0.6 (10:1, petroleum ether/ethyl acetate). Yellow oil. $^1$H NMR (400 MHz, $CDCl_3$-d) δ=7.25-7.22 (m, 1H), 7.11-7.07 (m, 1H), 6.30-6.17 (m, 1H), 6.13-5.90 (m, 1H), 5.16-5.13 (m, 2H), 3.50-3.47 (m, 3H), 1.95-1.56 (m, 3H).

Step C. 1-bromo-3-chloro-5-(methoxymethoxy)-2-[(Z)-prop-1-enyl]benzene: 1-bromo-3-chloro-5-(methoxymethoxy)-2-[prop-1-enyl]benzene was purified by prep-HPLC (Phenomenex luna C18 (250×70 mm, 10 μm); mobile phase: [water (0.225% FA)-ACN]; B %: 55%-90%, 32 min) to give 1-bromo-3-chloro-5-(methoxymethoxy)-2-[(Z)-prop-1-enyl]benzene (2.48 g, 35% yield). $^1$H NMR (400 MHz, $CDCl_3$-d) δ=7.24 (d, J=2.4 Hz, 1H), 7.10 (d, J=2.4 Hz, 1H), 6.19 (dd, J=1.6, 11.2 Hz, 1H), 5.94 (qd, J=6.8, 11.2 Hz, 1H), 5.15 (s, 2H), 3.49 (s, 3H), 1.57 (dd, J=1.6, 7.2 Hz, 3H).

Step D. 1-bromo-3-chloro-5-(methoxymethoxy)-2-(2-methylcyclopropyl)benzene: To a mixture of $ZnEt_2$ (1.0 M, 10.3 mL) in dichloromethane (10 mL) was added TFA (1.17 g, 10.3 mmol, 762 μL) in dichloromethane (2.0 mL) drop-wise slowly at −40° C. under $N_2$. After stirring for 0.5 h, diiodomethane (2.76 g, 10.3 mmol, 830 μL) was added into the above mixture at −40° C. The mixture was stirred at −40° C. for 0.5 hour, and then 1- bromo-3-chloro-5-(methoxymethoxy)-2-[(Z)-prop-1-enyl]benzene (0.5 g, 1.71 mmol) in dichloromethane (2.0 mL) was added to the above mixture at −40° C. The mixture was stirred at 28° C. for 14 h. After completion, the mixture was quenched with $H_2O$ (10 mL) and then filtered. The aqueous phase was extracted with dichloromethane (8.0 mL). The combined organic layer was washed with brine (10 mL), dried over $Na_2SO_4$, filtered and, concentrated under vacuum. The residue was purified by reversed-phase flash chromatography [water (FA, 0.1%)/acetonitrile] to give 1-bromo-3-chloro-5-(methoxymethoxy)-2-(2-methylcyclopropyl)benzene (47 mg, 8.4% yield) Yellow oil. $^1$H NMR (400 MHz, $CDCl_3$-d) δ 7.22 (d, J=2.4 Hz, 1H), 7.06 (d, J=2.4 Hz, 1H), 5.13 (s, 2H), 3.48 (s, 3H), 1.39-1.24 (m, 4H), 0.85 (d, J=6.0 Hz, 3H).

Step E. 2-[3-chloro-5-(methoxymethoxy)-2-[(2R)-2-methylcyclopropyl]phenyl]-4,4,5,5-tetramethyl-1,3,2-dioxaborolane: A mixture of 1-bromo-3-chloro-5-(methoxymethoxy)-2-(2-methylcyclopropyl)benzene (100 mg, 327 μmol), 4,4,5,5-tetramethyl-2-(4,4,5,5-tetramethyl-1,3,2-dioxaborolan-2-yl)-1,3,2-dioxaborolane (208 mg, 818 μmol), KOAc (96.3 mg, 982 μmol) and Pd(dppf)$Cl_2$ (23.9 mg, 32.7 μmol) in dioxane (2.0 mL) was stirred at 100° C. for 1 h. After completion, the mixture was concentrated under vacuum. The residue was purified by reversed-phase flash chromatography [water (FA, 0.1%)/acetonitrile] to give 2-[3-chloro-5-(methoxymethoxy)-2-[(2R)-2-methylcyclopropyl]phenyl]-4,4,5,5-tetramethyl-1,3,2-dioxaborolane (70 mg, 45% yield). Yellow oil. LCMS [ESI, M+1]: m/z 353.1.

Step F. tert-butyl(1R,5S)-3-(7-(3-chloro-5-(methoxymethoxy)-2-((1S,2R)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate: A mixture of (1R,5S)-tert-butyl 3-(7-chloro-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (70 mg, 127.04 μmol), 2-[3-chloro-5-(methoxymethoxy)-2-[(2R)-2-methylcyclopropyl]phenyl]-4,4,5,5-tetramethyl-1,3,2-dioxaborolane (44.80 mg, 127 μmol), $K_3PO_4$ (1.5 M, 254 μL) and [2-(2-aminophenyl)phenyl]palladium (1+); bis(1-adamantyl)-butyl-phosphane; methanesulfonate (9.25 mg, 12.7 μmol) in THF (1.0 mL) was stirred at 60° C. for 2 h. After completion, the mixture was diluted with ethyl acetate (10 mL), washed with brine (10 mL), dried over $Na_2SO_4$, filtered and, concentrated under vacuum. The residue was purified by reversed-phase flash chromatography [water (FA, 0.1%)/acetonitrile] to give the title compound (30 mg, 31% yield). Yellow solid. LCMS [ESI, M+1]: m/z 741.2.

Step G. 3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-chloro-4-((1S,2R)-2-methylcyclopropyl)phenol: A mixture of give tert-butyl(1R,5S)-3-(7-(3-chloro-5-(methoxymethoxy)-2-((1S,2R)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (27 mg, 36.4 μmol) and HCl/dioxane (4 M, 0.5 mL) in MeCN (0.5 mL) was stirred at 0° C. for 0.5 h. After completion, the mixture was concentrated under vacuum. The residue was purified by prep-HPLC (Phenomenex luna C18 150×25 mm×10 um; mobile phase: [water (0.225% FA)-ACN]; B %: 3%-33%, 10 min) to afford the title compound (10.9 mg, 43% yield, 1.5FA). Yellow solid. $^1$H NMR (400 MHz, METHANOL-d4) δ=9.13-9.07 (m, 1H), 7.01-7.01 (m, 1H), 7.04-6.95 (m, 1H), 6.85-6.76 (m, 1H), 5.54-5.34 (m, 1H), 4.77-4.66 (m, 2H), 4.55-4.41 (m, 2H), 3.98 (br s, 2H), 3.91-3.78 (m, 2H), 3.74-3.51 (m, 3H), 3.29-3.21 (m, 1H), 2.23-2.12 (m, 6H), 2.10-1.90 (m, 6H), 1.54-1.03 (m, 1H), 0.92-0.19 (m, 4H). LCMS [ESI, M+1]: m/z 597.2.

Example 468

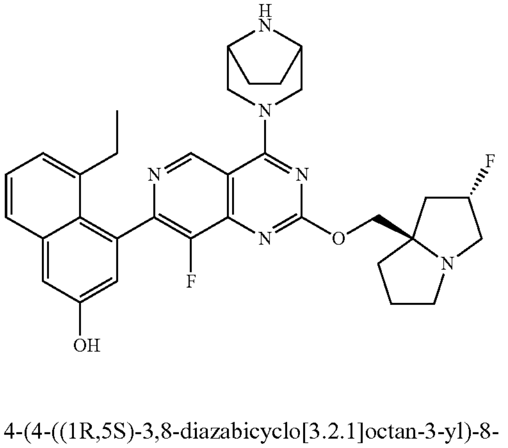

4-(4-((1R,5S)-3,8-diazabicyclo[3.2.1]octan-3-yl)-8-fluoro-2-(((2S,7aR)-2-fluorohexahydro-1H-pyrrolizin-7a-yl)methoxy)pyrido[4,3-d]pyrimidin-7-yl)-5-ethylnaphthalen-2-ol

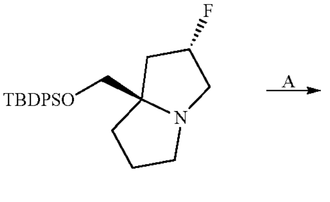

-continued

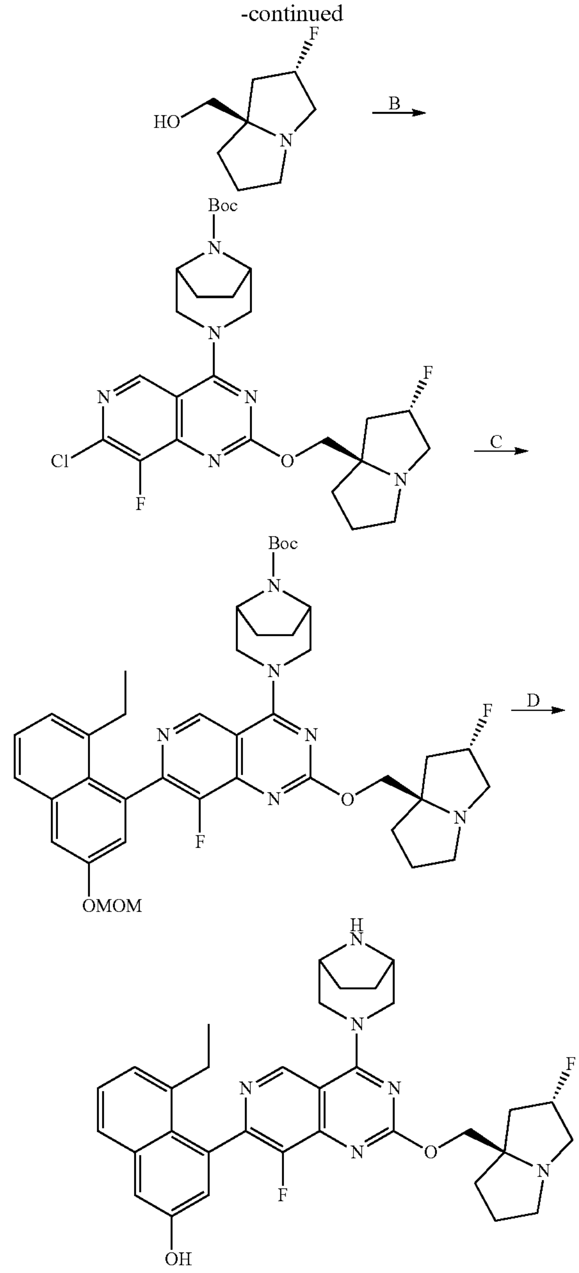

Step A. ((2S,7aR)-2-fluorohexahydro-1H-pyrrolizin-7a-yl)methanol: To a solution of (2S,7aR)-7a-(((tert-butyldiphenylsilyl)oxy)methyl)-2-fluorohexahydro-1H-pyrrolizine (6.5 g, 16.3 mmol) in MeOH (120 mL) was added KF (2.85 g, 49.04 mmol). Then it was degassed and purged with $N_2$ for 3 times. The reaction was stirred at 60° C. for 12 hours. After completion, the reaction mixture was filtered and concentrated under reduced pressure. The residue was purified by column chromatography ($Al_2O_3$, Petroleum ether: Ethyl acetate=1/0 to 1:1) to give ((2S,7aR)-2-fluorohexahydro-1H-pyrrolizin-7a-yl)methanol (1.4 g, 54% yield). Yellow oil. $^1H$ NMR (400 MHz, CHLOROFORM-d) δ=5.38-5.00 (m, 1H), 3.25-2.73 (m, 5H), 2.18-1.69 (m, 7H).

Step B. (1R,5S)-tert-butyl 3-(7-chloro-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate: To a mixture of (1R,5S)-tert-butyl 3-(2,7-dichloro-8-fluoropyrido[4,3-d]pyrimidin-4-yl)-3,8-diazabicyclo[3.2.1]octane-8-carboxylate (2 g, 4.67 mmol) and ((2S,7aR)-2-fluorohexahydro-1H-pyrrolizin-7a-yl)methanol (1.12 g, 7.00 mmol) in dioxane (8 mL) were added DIEA (1.5 g, 11.7 mmol) and 4 Å MS (0.5 g). Then it was degassed and purged with $N_2$ for 3 times. The mixture was heated to 95° C. and stirred for 12 hours. After completion, the reaction mixture was filtered and concentrated under reduced pressure. The residue was purified by reversed-phase flash chromatography [water (0.1% formic acid)/acetonitrile)] to give 3-(7-chloro-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (1.6 g, 62% yield). White solid. $^1H$ NMR (400 MHz, CHLOROFORM-d) δ=8.73 (s, 1H), 5.36-5.18 (m, 1H), 4.54-4.44 (m, 2H), 4.37 (s, 2H), 4.28-4.21 (m, 1H), 3.77-3.54 (m, 2H), 3.32-2.93 (m, 4H), 2.35-2.08 (m, 3H), 2.01-1.65 (m, 8H), 1.52 (s, 9H). LCMS [ESI, M+1]: m/z 551.2.

Step C. (1R,5S)-tert-butyl 3-(7-(8-ethyl-3-(methoxymethoxy)naphthalen-1-yl)-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate: To a mixture of 3-(7-chloro-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (0.7 g, 1.27 g, mmol) and 2-(8-ethyl-3-(methoxymethoxy)naphthalen-1-yl)-4,4,5,5-tetramethyl-1,3,2-dioxaborolane (652 mg, 1.91 mmol) in THF (14 mL) were added [2-(2-aminophenyl)phenyl]palladium (1+); bis(1-adamantyl)-butyl-phosphane; methanesulfonate (185 mg, 254 μmol) and $K_3PO_4$ (1.5 M, 2.54 mL). Then it was degassed and purged with $N_2$ for 3 times. The reaction was stirred at 60° C. for 2 hours. After completion, the reaction mixture was diluted with water (20 mL), and extracted with Ethyl acetate (30 mL×3). The combined organic layers were washed with brine (30 mL), dried over $Na_2SO_4$, filtered, and concentrated under reduced pressure. The residue was purified by reversed-phase flash chromatography [water (0.1% formic acid)/acetonitrile)] to give (1R,5S)-tert-butyl 3-(7-(8-ethyl-3-(methoxymethoxy)naphthalen-1-yl)-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (900 mg, 97% yield). White solid. $^1H$ NMR (400 MHz, METHANOL-$d_4$) δ=9.07 (s, 1H), 7.74 (d, J=7.6 Hz, 1H), 7.59 (d, J=2.8 Hz, 1H), 7.42 (t, J=7.7 Hz, 1H), 7.25 (d, J=6.9 Hz, 1H), 7.16 (d, J=2.6 Hz, 1H), 5.40-5.22 (m, 3H), 4.78-4.56 (m, 2H), 4.45-4.35 (m, 2H), 4.35-4.21 (m, 2H), 3.85-3.67 (m, 2H), 3.50 (s, 3H), 3.29-2.95 (m, 4H), 2.44-2.10 (m, 5H), 2.01-1.74 (m, 7H), 1.53 (s, 9H), 0.93-0.87 (m, 3H). LCMS [ESI, M+1]: m/z: 731.6.

Step D. 4-(4-((1R,5S)-3,8-diazabicyclo[3.2.1]octan-3-yl)-8-fluoro-2-(((2S,7aR)-2-fluorohexahydro-1H-pyrrolizin-7a-yl)methoxy)pyrido[4,3-d]pyrimidin-7-yl)-5-ethylnaphthalen-2-ol: To a mixture of (1R,5S)-tert-butyl 3-(7-(8-ethyl-3-(methoxymethoxy)naphthalen-1-yl)-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (0.5 g, 684 μmol) and ACN (10 mL) was added HCl·dioxane (4 M, 10.0 mL). Then it was degassed and purged with $N_2$ for 3 times. The reaction was stirred at 0° C. for 0.5 hour. After completion, the reaction mixture was concentrated, and its pH was adjusted to 8 with saturated $NaHCO_3$ aqueous solution. The mixture was extracted with DCM (20 mL×3) The combined organic layers were washed with brine (15 mL), dried over $Na_2SO_4$, filtered and, concentrated. The residue was purified by prep-HPLC (column: Waters Xbridge 150×25 mm×5 μm; mobile phase: [water (10 mM $NH_4HCO_3$)-ACN]; B %: 35%-62%, 10 min). The desired fractions were collected and concentrated under vacuum to remove acetonitrile. The mixture was lyophilized. to give 4-(4-((1R,5S)-3,8-diazabicyclo[3.2.1]octan-3-yl)-8-fluoro-2-(((2S,7aR)-2-fluorohexahydro-1H-pyrrolizin-7a-yl)methoxy)pyrido[4,3-d]pyrimidin-7-yl)-5-ethylnaphthalen-2-ol (100.91 mg, 25% yield). White solid. $^1$H NMR (400 MHz, METHANOL-$d_4$) δ=9.04 (s, 1H), 7.68-7.57 (m, 1H), 7.39-7.33 (m, 1H), 7.28 (d, J=2.8 Hz, 1H), 7.15 (d, J=6.8 Hz, 1H), 7.01 (d, J=2.8 Hz, 1H), 5.41-5.21 (m, 1H), 4.69-4.55 (m, 2H), 4.33-4.20 (m, 2H), 3.78-3.61 (m, 4H), 3.29-3.16 (m, 3H), 3.07-2.97 (m, 1H), 2.40-2.09 (m, 5H), 2.05-1.93 (m, 2H), 1.93-1.74 (m, 5H), 0.89 (dt, J=2.0, 7.2 Hz, 3H). LCMS [ESI, M+1]: m/z: 587.2.

Example 469

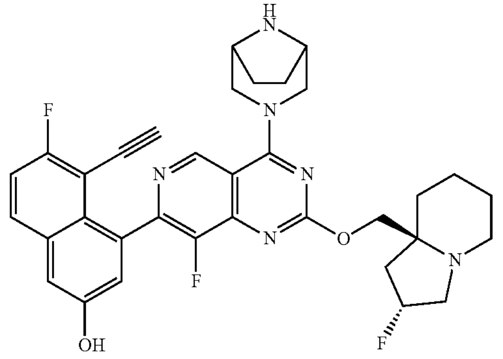 [SMILES: C#Cc1c(F)ccc2cc(O)cc(-c3ncc4c(N5CC6CCC(C5)N6)nc(OC[C@@]56CCCCN5C[C@H](F)C6)nc4c3F)c12]

4-(4-((1R,5S)-3,8-diazabicyclo[3.2.1]octan-3-yl)-8-fluoro-2-(((2R,8aS)-2-fluorooctahydroindolizin-8a-yl)methoxy)pyrido[4,3-d]pyrimidin-7-yl)-5-ethynyl-6-fluoronaphthalen-2-ol

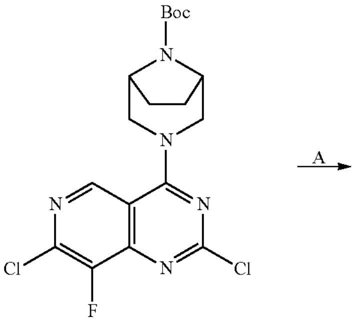

-continued

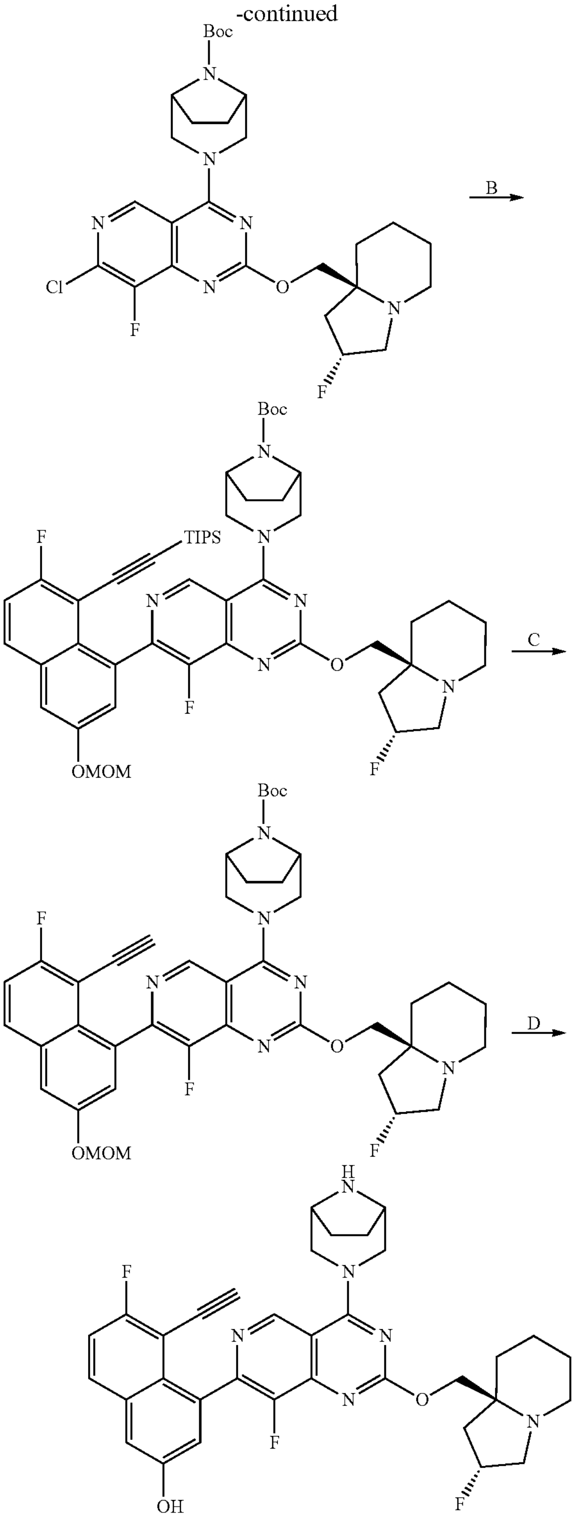

Step A. (1R,5S)-tert-butyl 3-(7-chloro-8-fluoro-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate: To the mixture of (1R,5S)-tert-butyl 3-(2,7-dichloro-8-fluoropyrido[4,3-d]pyrimidin-4-yl)-3,8-diazabicyclo[3.2.1]octane-8-carboxylate (296 mg, 691 μmol), ((2R,8aS)-2-fluorooctahydroindolizin-8a-yl)methanol (100 mg, 577 μmol), Xantphos (66.8 mg, 115 μmol), $Cs_2CO_3$ (564 mg, 1.73 mmol) in toluene (3 mL) was added $Pd_2(dba)_3$ (52.9 mg, 57.7 μmol). The mixture was degassed and stirred at 90° C. for 14 h. Upon completion, the reaction mixture was diluted with ethyl acetate (15 mL) and water (10 mL). The aqueous layer was extracted with ethyl acetate (15 mL). The combined organic phase was washed with brine (10 mL), dried over $Na_2SO_4$, filtered, and concentrated to give a residue. The residue was purified by reversed-phase flash chromatography [water (FA 0.1%)/acetonitrile] to give (1R,5S)-tert-butyl 3-(7-chloro-8-fluoro-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate (90.0 mg, 26% yield). Yellow Solid; LCMS (ESI, M+1): m/z 565.4.

Step B. (1R,5S)-tert-butyl 3-(8-fluoro-7-(7-fluoro-3-(methoxymethoxy)-8-((triisopropylsilyl)ethynyl)naphthalen-1-yl)-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate: To the solution of (1R,5S)-tert-butyl 3-(7-chloro-8-fluoro-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate (80.0 mg, 142 μmol), ((2-fluoro-6-(methoxymethoxy)-8-(4,4,5,5-tetramethyl-1,3,2-dioxaborolan-2-yl)naphthalen-1-yl)ethynyl)triisopropylsilane (102 mg, 199 μmol), $K_3PO_4$ (1.5 M, 283 μL) in THF (2 mL) was added [2-(2-aminophenyl)phenyl]palladium (1+); bis(1-adamantyl)-butyl-phosphane; methanesulfonate (10.3 mg, 14.2 μmol) under $N_2$. The mixture was stirred at 60° C. for 2 h. Upon completion, the reaction mixture was diluted with ethyl acetate (10 mL) and water (5 mL). The aqueous layer was extracted with ethyl acetate (10 mL). The combined organic phase was washed with brine (10 mL), dried over $Na_2SO_4$, filtered, and concentrated to give a residue. The residue was purified by reversed-phase flash chromatography [water (FA 0.1%)/acetonitrile] to give (1R,5S)-tert-butyl 3-(8-fluoro-7-(7-fluoro-3-(methoxymethoxy)-8-((triisopropylsilyl)ethynyl)naphthalen-1-yl)-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate (97.8 mg, 70% yield). Yellow Solid; $^1H$ NMR (400 MHz, CHLOROFORM-d) δ=9.07 (s, 1H), 7.83-7.75 (m, 1H), 7.52 (d, J=2.4 Hz, 1H), 7.34-7.29 (m, 2H), 5.37-5.23 (m, 1H), 5.41-5.18 (m, 2H), 4.84-4.68 (m, 1H), 4.57-4.30 (m, 3H), 4.26-4.15 (m, 2H), 3.89-3.61 (m, 1H), 3.51 (s, 3H), 3.48-3.25 (m, 2H), 3.08-2.79 (m, 2H), 2.49-2.26 (m, 1H), 2.16-2.07 (m, 1H), 2.03-1.91 (m, 3H), 1.89-1.64 (m, 8H), 1.53 (s, 9H), 0.87 (t, J=7.2 Hz, 18H), 0.62-0.46 (m, 3H); LCMS (ESI, M+1): m/z 915.6.

Step C. (1R,5S)-tert-butyl 3-(7-(8-ethynyl-7-fluoro-3-(methoxymethoxy)naphthalen-1-yl)-8-fluoro-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate: To the solution of (1R,5S)-tert-butyl 3-(8-fluoro-7-(7-fluoro-3-(methoxymethoxy)-8-((triisopropylsilyl)ethynyl)naphthalen-1-yl)-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate (110 mg, 120 μmol) in DMF (1 mL) was added CsF (183 mg, 1.20 mmol). The mixture was stirred at 20° C. for 0.5 h. Upon completion, the mixture was filtered and purified by reversed-phase flash chromatography [water (FA 0.1%)/acetonitrile] to give (1R,5S)-tert-butyl 3-(7-(8-ethynyl-7-fluoro-3-(methoxymethoxy)naphthalen-1-yl)-8-fluoro-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate (75.0 mg, 79% yield). Yellow Solid; LCMS (ESI, M+1): m/z 759.4.

Step D. 4-(4-((1R,5S)-3,8-diazabicyclo[3.2.1]octan-3-yl)-8-fluoro-2-(((2R,8aS)-2-fluorooctahydroindolizin-8a-yl)methoxy)pyrido[4,3-d]pyrimidin-7-yl)-5-ethynyl-6-fluoronaphthalen-2-ol: To the solution of (1R,5S)-tert-butyl 3-(7-(8-ethynyl-7-fluoro-3-(methoxymethoxy)naphthalen-1-yl)-8-fluoro-2-(((2R,8aS)-2-fluorooctahydroindolizin-8a-yl)methoxy)pyrido[4,3-d]pyrimidin-4-yl)-3,8-diazabicyclo[3.2.1]octane-8-carboxylate (45.0 mg, 59.3 μmol) in ACN (0.6 mL) was added HCl·dioxane (4 M, 1 mL) at 0° C. The mixture was stirred at 0° C. for 20 minutes. Upon completion, the mixture was concentrated to give a residue. To the residue was added sat. $NaHCO_3$ to adjust the pH to 8. DMF (0.8 mL) was added and the mixture was filtered to give a solution. The residue was purified by prep-HPLC (column: Phenomenex luna C18 150×25 mm×10 μm; mobile phase: [water (0.225% FA)-ACN]; B %: 6%-36%, 10 min) to afford 4-(4-((1R,5S)-3,8-diazabicyclo[3.2.1]octan-3-yl)-8-fluoro-2-(((2R,8aS)-2-fluorooctahydroindolizin-8a-yl)methoxy)pyrido[4,3-d]pyrimidin-7-yl)-5-ethynyl-6-fluoronaphthalen-2-ol (9.82 mg, 24% yield). Orange Solid; $^1H$ NMR (400 MHz, METHANOL-$d_4$) δ=9.06 (s, 1H), 7.93-7.81 (m, 1H), 7.42-7.27 (m, 2H), 7.21 (d, J=2.4 Hz, 1H), 5.49-5.25 (m, 1H), 4.79-4.71 (m, 2H), 4.68-4.53 (m, 2H), 4.10 (br s, 2H), 3.88 (br d, J=13.6 Hz, 2H), 3.76-3.59 (m, 1H), 3.51-3.41 (m, 1H), 3.38-3.35 (m, 1H), 3.23-3.14 (m, 1H), 3.05-2.97 (m, 1H), 2.55-2.40 (m, 1H), 2.25-1.98 (m, 5H), 1.96-1.67 (m, 5H), 1.60-1.49 (m, 1H); LCMS (ESI, M+1): m/z 615.4.

Example 470

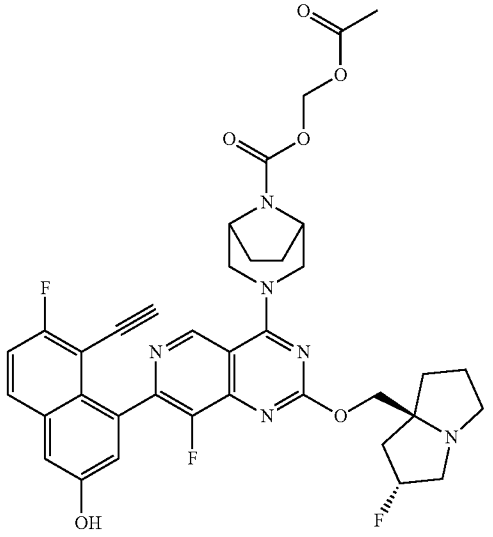 [SMILES: C#Cc1c(F)ccc2cc(O)cc(-c3ncc4c(N5CC6CCC(C5)N6C(=O)OCOC(C)=O)nc(OC[C@@]56CCCN5C[C@H](F)C6)nc4c3F)c12]

(1R,5S)-acetoxymethyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy) pyrido[4,3-d]pyrimidin-4-yl)-3,8-diazabicyclo[3.2.1] octane-8-carboxylate

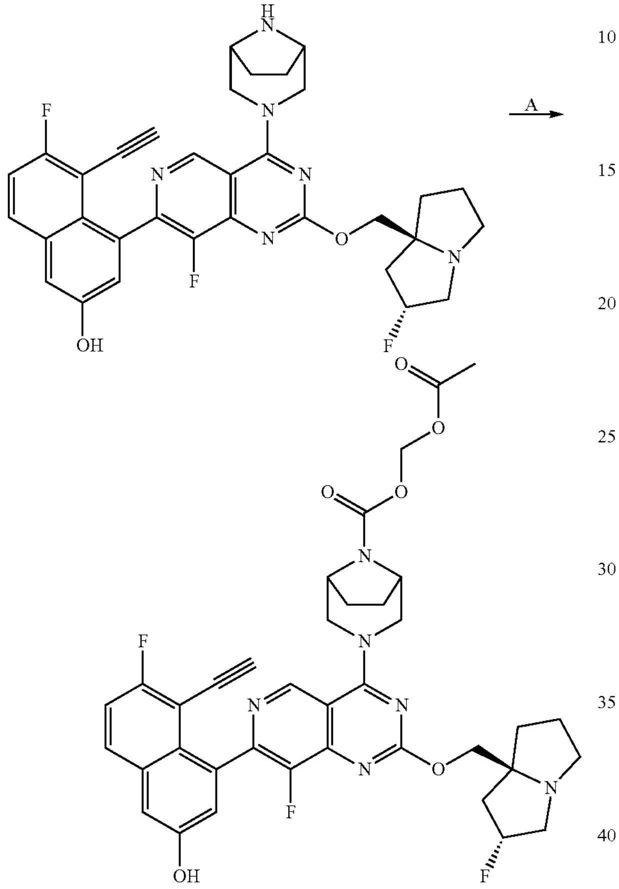

Step A. (1R,5S)-acetoxymethyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate: To a mixture of 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol (262 mg, 437 μmol) and DIEA (565 mg, 4.37 mmol) in dichloromethane (5.0 mL) was added ((chlorocarbonyl)oxy)methyl acetate (100 mg, crude) at −40° C. The mixture was stirred at −40° C. for 0.5 h. After completion, the mixture was concentrated under reduced pressure to give a residue. The crude product was purified by reversed-phase flash chromatography (0.1% FA condition) and prep-HPLC (column: Phenomenex luna C18 150×25 mm×10 μm; mobile phase: [water (0.225% FA)-ACN]; B %: 13%-46%, 11 min) and lyophilized to afford (1R,5S)-acetoxymethyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (17.7 mg, 5% yield). Yellow solid; $^{1}H$ NMR (400 MHz, METHANOL-d4): δ=9.06 (s, 1H), 8.54 (s, 1H), 7.88 (dd, J=6.0, 9.2 Hz, 1H), 7.41-7.28 (m, 2H), 7.22 (d, J=2.4 Hz, 1H), 5.84 (s, 2H), 5.47-5.29 (m, 1H), 4.78-4.64 (m, 2H), 4.53 (br s, 2H), 4.45-4.31 (m, 2H), 3.81 (br dd, J=3.6, 8.0 Hz, 2H), 3.52-3.36 (m, 4H), 3.18-3.08 (m, 1H), 2.49-2.29 (m, 2H), 2.27-2.19 (m, 1H), 2.13 (s, 3H), 2.11-1.93 (m, 5H), 1.88 (br d, J=8.0 Hz, 2H); LCMS (ESI, M+1): m/z 717.3.

Example 471

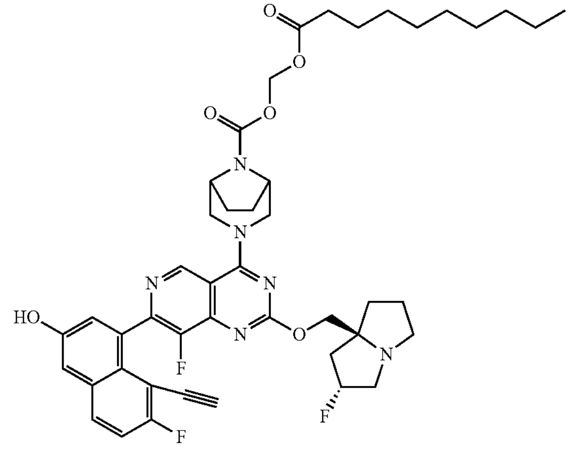 [SMILES: C#Cc1c(F)ccc2cc(O)cc(-c3ncc4c(N5CC6CCC(C5)N6C(=O)OCOC(=O)CCCCCCCCC)nc(OC[C@@]56CCCN5C[C@H](F)C6)nc4c3F)c12]

(Decanoyloxy)methyl(1R,5S)-3-(7-(8-ethynyl-7-fluoro-3-hydroxynaphthalen-1-yl)-8-fluoro-2-(((2R,7aS)-2-fluorotetrahydro-1H-pyrrolizin-7a(5H)-yl) methoxy)pyrido[4,3-d]pyrimidin-4-yl)-3,8-diazabicyclo[3.2.1]octane-8-carboxylate

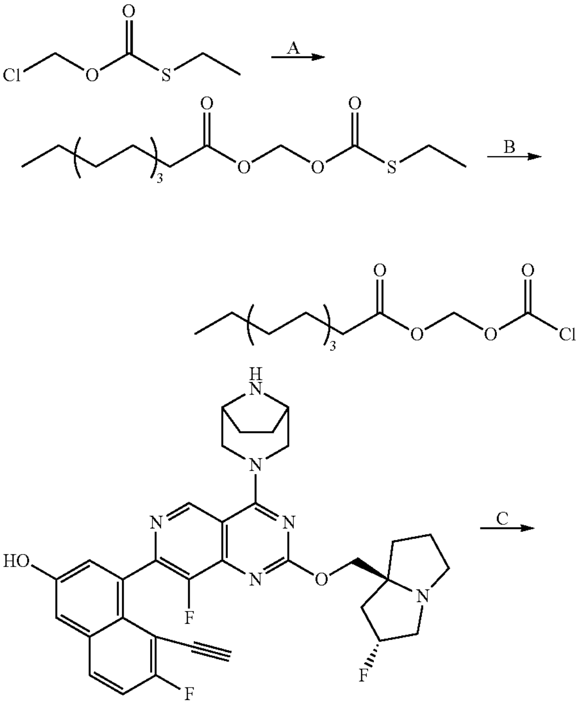

-continued

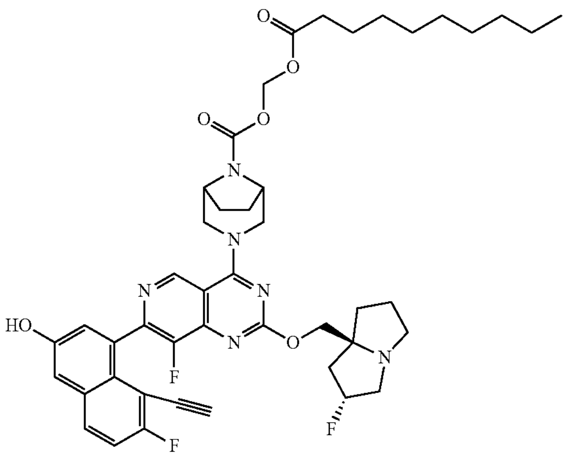

Step A. ethylsulfanylcarbonyloxymethyl decanoate: A mixture of O-(chloromethyl) S-ethyl carbonothioate (600 mg, 3.88 mmol), decanoyloxypotassium (816 mg, crude) and 18-CROWN-6 (102 mg, 388 μmol) in DMAC (6 mL) was stirred at 25° C. for 12 h. After completion, the mixture was diluted with ethyl acetate (20 mL), washed with brine (2×20 mL), dried over $Na_2SO_4$, filtered, and concentrated under vacuum. The residue was purified by column chromatography ($SiO_2$, petroleum ether/ethyl acetate=10/1) to give ethylsulfanylcarbonyloxymethyl decanoate (300 mg, 27%). Yellow oil. $^1H$ NMR (400 MHz, CHLOROFORM-d) δ 5.77 (s, 2H), 3.39-3.17 (m, 4H), 2.35 (t, J=7.6 Hz, 2H), 1.68-1.60 (m, 2H), 1.35-1.27 (m, 7H), 1.20-1.06 (m, 6H), 0.87 (t, J=6.8 Hz, 3H).

Step B. chlorocarbonyloxymethyl decanoate: A mixture of ethylsulfanylcarbonyloxymethyl decanoate (250 mg, 861 μmol) and sulfuryl chloride (174 mg, 1.29 mmol, 129 μL) in dichloromethane (3.0 mL) was stirred at 25° C. for 0.5 hour. After completion, the mixture was concentrated under vacuum to give chlorocarbonyloxymethyl decanoate (250 mg, crude). The crude product was used in the next step without further purification. Yellow oil.

Step C. (Decanoyloxy)methyl(1R,5S)-3-(7-(8-ethynyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate: To a mixture of 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol (500 mg, 832 μmol) and DIEA (430 mg, 3.33 mmol, 580 μL) in dichloromethane (2.0 mL) was added chlorocarbonyloxymethyl decanoate (220 mg, crude) at −40° C. The mixture was stirred at −40° C. for 0.5 hour and 25° C. for 1 h. After completion, the mixture was concentrated under vacuum. The residue was purified by prep-HPLC (Phenomenex luna C18 250×50 mm×15 μm; mobile phase: [water (0.225% FA)-ACN]; B %: 28%-58%, 10 min) to the title compound (80 mg, 11%). Yellow Solid. $^1H$ NMR (400 MHz, DMSO-$d_6$) δ 9.05 (s, 1H), 7.97 (dd, J=6.0, 9.2 Hz, 1H), 7.46 (t, J=8.8 Hz, 1H), 7.39 (d, J=2.4 Hz, 1H), 7.17 (d, J=2.4 Hz, 1H), 5.76 (s, 2H), 5.39-5.18 (m, 1H), 4.60 (br d, J=12.0 Hz, 1H), 4.47-4.37 (m, 3H), 4.15-4.02 (m, 2H), 3.92 (s, 1H), 3.11-3.01 (m, 3H), 2.86-2.79 (m, 1H), 2.37 (t, J=7.2 Hz, 2H), 2.17-1.99 (m, 3H), 1.92-1.74 (m, 7H), 1.58-1.48 (m, 2H), 1.4-1.15 (m, 14H), 0.86-0.78 (m, 3H) LCMS [ESI, M+1]: m/z 829.4.

Example 472

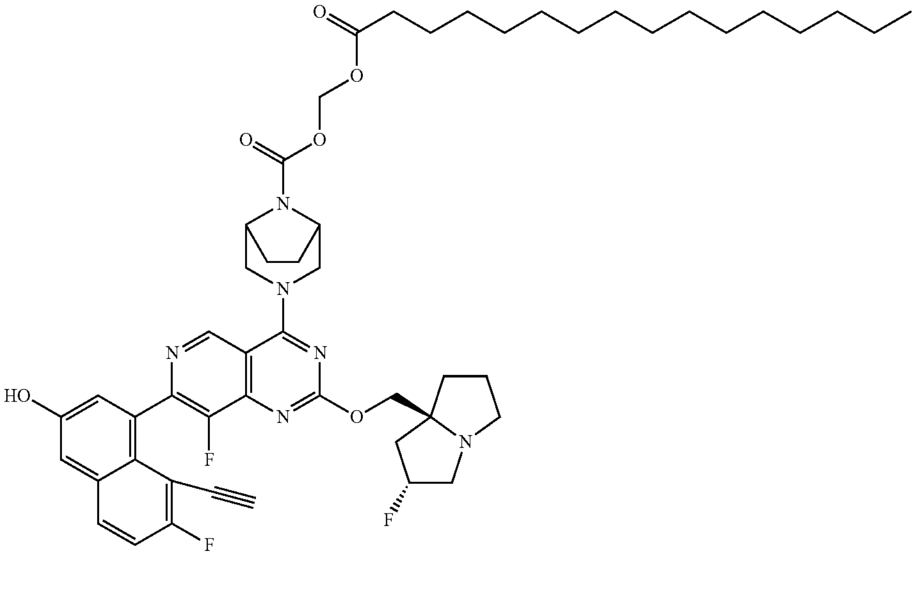 [SMILES: C#Cc1c(F)ccc2cc(O)cc(-c3ncc4c(N5CC6CCC(C5)N6C(=O)OCOC(=O)CCCCCCCCCCCCCCC)nc(OC[C@@]56CCCN5C[C@H](F)C6)nc4c3F)c12]

(Palmitoyloxy)methyl(1R,5S)-3-(7-(8-ethynyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate

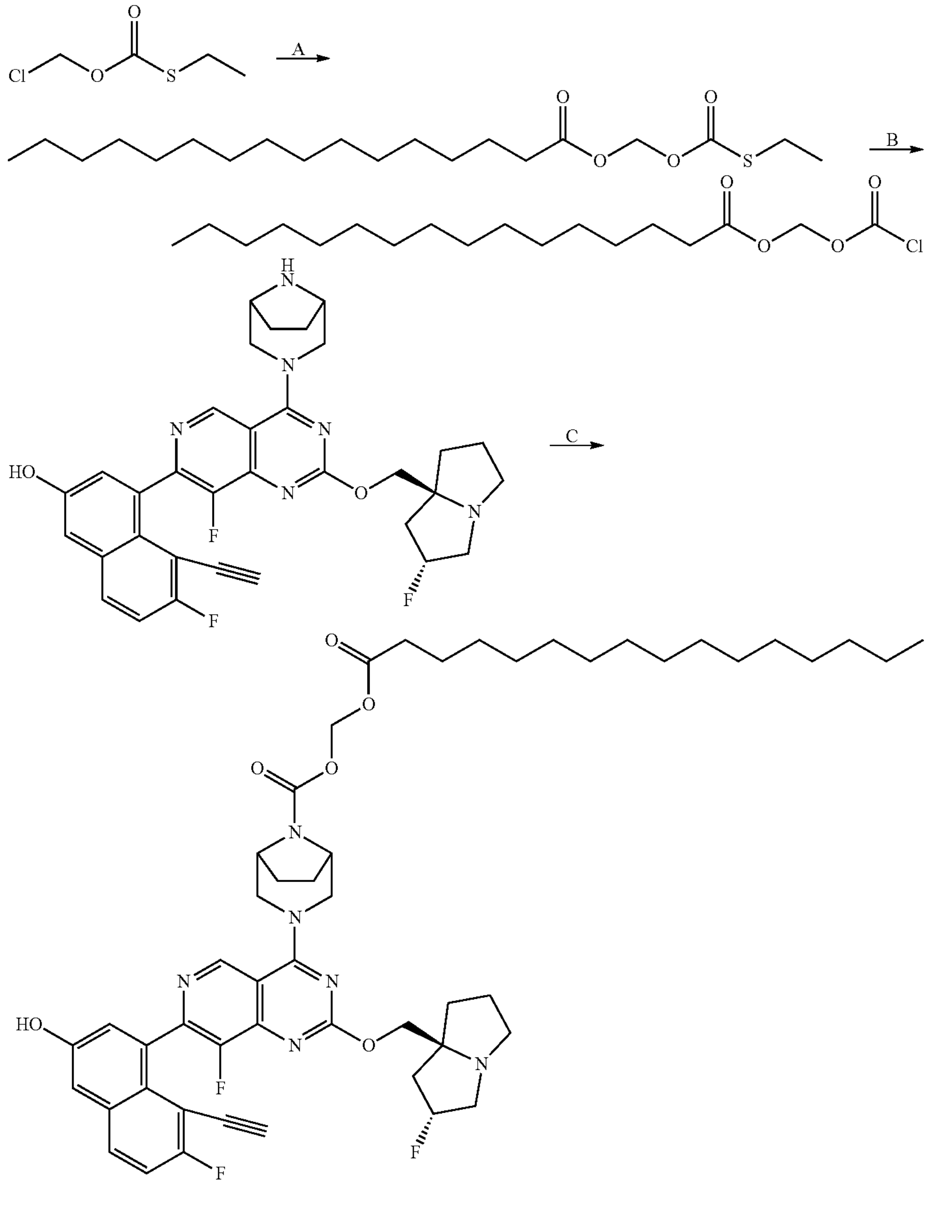

Step A. (((ethylthio)carbonyl)oxy)methyl palmitate: To a mixture of chloromethyl ethylsulfanylformate (300 mg, 1.94 mmol) and DMAC (5 mL) was added potassium palmitate (571 mg, 1.94 mmol) in DMAC (5.0 mL) followed with 18-CROWN-6 (51.3 mg, 194 μmol). The mixture was stirred at 25° C. for 12 h. After completion, the mixture was diluted with ethyl acetate (10 mL). The mixture was washed with brine (10 mL), dried over $Na_2SO_4$, filtered and, concentrated under vacuum. The residue was purified by column chromatography ($SiO_2$, petroleum ether/ethyl acetate=10/1) to give (((ethylthio)carbonyl)oxy)methyl palmitate. (150 mg, 400 μmol). Yellow oil. $^1$HNMR (400 MHz, chloroform-d) δ 5.77 (s, 2H), 2.95-2.90 (m, 2H), 1.67-1.59 (m, 2H), 1.37-1.25 (m, 29H), 0.91-0.85 (m, 3H).

Step B. ((chlorocarbonyl)oxy)methyl palmitate: To a mixture of (((ethylthio)carbonyl)oxy)methyl palmitate (0.40 g, 1.07 mmol) in dichloromethane (3.0 mL) was added sulfuryl chloride (216 mg, 1.60 mmol, 160 μL) at 0° C. The mixture was stirred at 0° C. for 15 mins. After completion, the mixture was concentrated under vacuum to give ((chlorocarbonyl)oxy)methyl palmitate (373 mg, crude). The crude product was used in the next step without further purification. Yellow oil.

Step C. (Palmitoyloxy)methyl(1R,5S)-3-(7-(8-ethynyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate: To a mixture of 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol (500 mg, 832 μmol), TEA (421 mg, 4.16 mmol, 579 μL) in dichloromethane (3.0 mL) was added a solution of ((chlorocarbonyl)oxy)methyl palmitate (349 mg, crude) in dichloromethane (3.0 mL) at −40° C. The mixture was stirred at −40° C. for 0.5 h. After completion, the mixture was concentrated under vacuum. The residue was purified by prep-HPLC (Phenomenex Synergi C18 150×25 mm×10 μm; mobile phase: [water (0.225% FA)-ACN]; B %: 43%-76%, min). The desired fractions were collected and lyophilized to give the title compound (100 mg, 13% yield). Yellow Solid. $^1$H NMR (400 MHz, DMSO-d6) δ 11.02-9.34 (m, 1H), 9.05 (s, 1H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 1H), 5.76 (s, 2H), 5.37-5.17 (m, 1H), 4.61 (br d, J=11.6 Hz, 1H), 4.47-4.35 (m, 3H), 4.16-3.99 (m, 2H), 3.92 (s, 1H), 3.11-3.00 (m, 3H), 2.87-2.79 (m, 1H), 2.40-2.32 (m, 2H), 2.14-1.94 (m, 3H), 1.92-1.71 (m, 7H), 1.56-1.49 (m, 2H), 1.37-1.02 (m, 26H), 0.86-0.80 (m, 3H). LCMS [ESI, M+1]: m/z 913.4.

Example 473

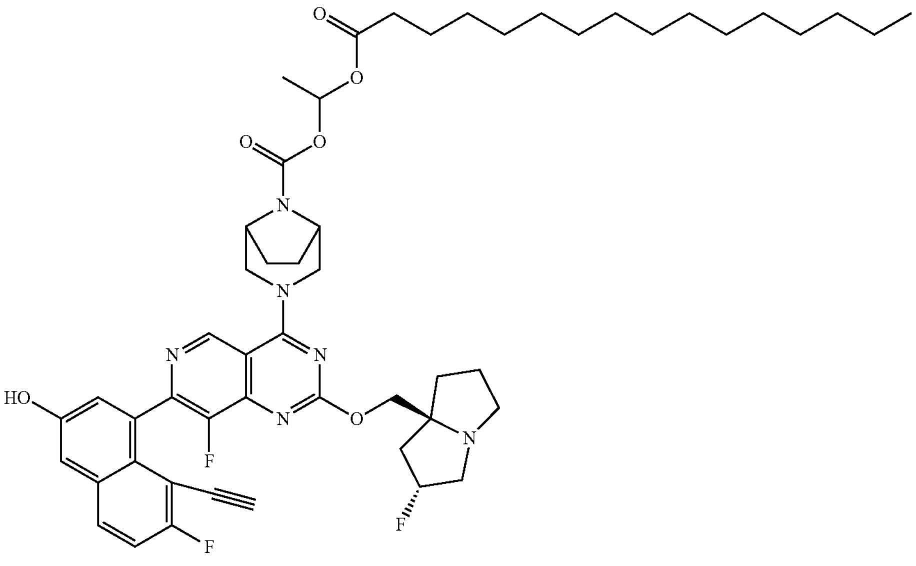 [SMILES: C#Cc1c(F)ccc2cc(O)cc(-c3ncc4c(N5CC6CCC(C5)N6C(=O)OC(C)OC(=O)CCCCCCCCCCCCCCC)nc(OC[C@@]56CCCN5C[C@H](F)C6)nc4c3F)c12]

(1R,5S)-1-(palmitoyloxy)ethyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate

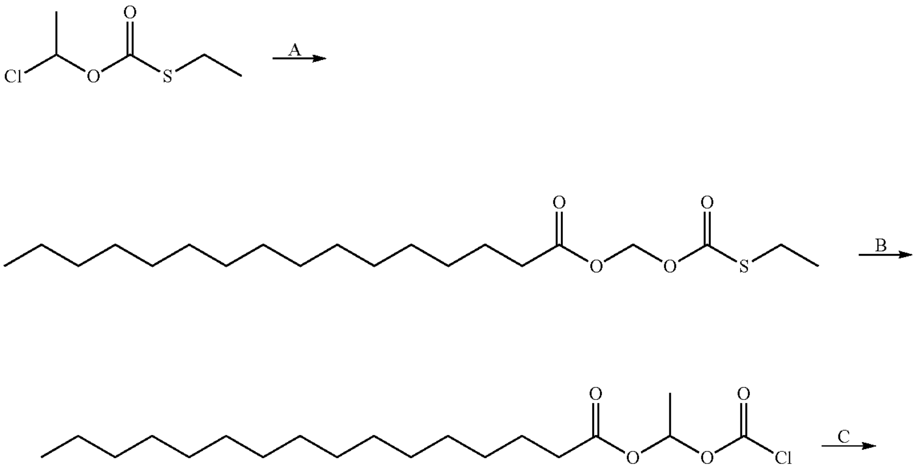

-continued

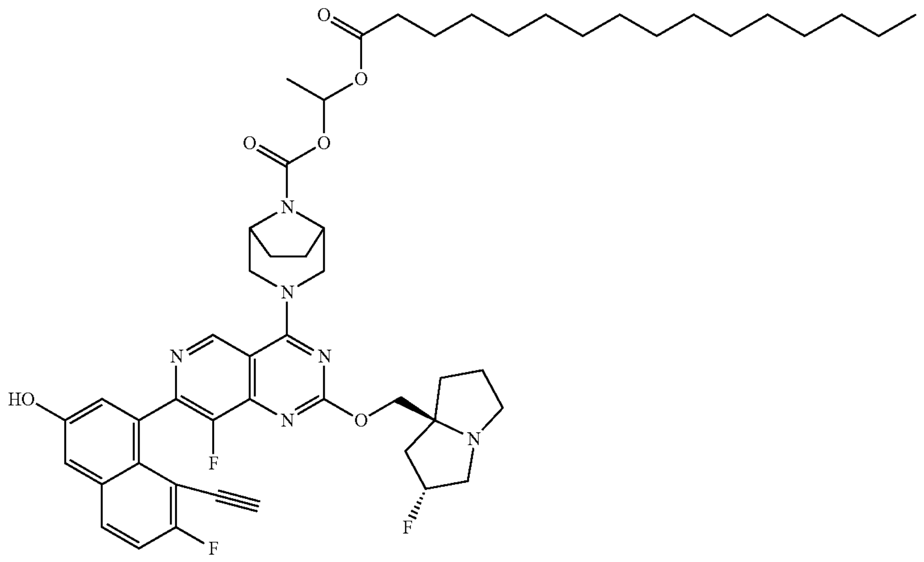

Step A. 1-(((ethylthio)carbonyl)oxy)ethyl palmitate: A mixture of O-(1-chloroethyl) S-ethyl carbonothioate (500 mg), potassium palmitate (2.62 g, 8.89 mmol), and 18-CROWN-6 (784 mg, 2.96 mmol) in DMAC (10 mL) was stirred at 50° C. for 12 h. The mixture was diluted with ethyl acetate (50 mL), washed with water (50 mL×3), dried over $Na_2SO_4$, filtered, and concentrated under vacuum. The residue was purified by column chromatography ($SiO_2$, Petroleum ether/Ethyl acetate=10/1) to give 1-(((ethylthio)carbonyl)oxy)ethyl palmitate (600 mg, 49% yield over two steps). Yellow Oil; $^1$H NMR (400 MHz, CHLOROFORM-d) δ=6.95 (q, J=5.6 Hz, 1H), 2.92-2.83 (m, 2H), 2.32 (dt, J=2.4, 7.6 Hz, 2H), 1.66-1.58 (m, 2H), 1.50 (d, J=5.4 Hz, 3H), 1.34-1.24 (m, 26H), 0.93-0.83 (m, 3H).

Step B. 1-((chlorocarbonyl)oxy)ethyl palmitate: To the solution of 1-(((ethylthio)carbonyl)oxy)ethyl palmitate (500 mg, 1.29 mmol) in dichloromethane (3 mL) was added sulfuryl chloride (260 mg, 1.93 mmol). The mixture was stirred at 25° C. for 2 h. The mixture was concentrated to give 1-((chlorocarbonyl)oxy)ethyl palmitate (500 mg, crude). Colorless oil.

Step C. (1R,5S)-1-(palmitoyloxy)ethyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate: To the solution of 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol (689 mg, 1.15 mmol) and DIEA (742 mg, 5.74 mmol) in dichloromethane (5 mL) was added 1-((chlorocarbonyl)oxy)ethyl palmitate (500 mg, crude) at −40° C. The mixture was stirred at 25° C. for 0.5 h. The mixture was concentrated to give a residue. The residue was purified by prep-HPLC (column: Phenomenex luna C18 150×40 mm×15 μm; mobile phase: [water (0.225% FA)-ACN]; B %: 47%-77%, 10 min) and 2$^{nd}$ prep-HPLC (column: Phenomenex Gemini-NX C18 75×30 mm×3 μm; mobile phase: [water (0.225% FA)-ACN]; B %: 48%-78%, 7 min) to afford (1R,5S)-1-(palmitoyloxy)ethyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (23.5 mg, 2% yield). Yellow Solid; $^1$H NMR (400 MHz, METHANOL-$d_4$) δ=9.04 (s, 1H), 7.95-7.80 (m, 1H), 7.42-7.29 (m, 2H), 7.21 (d, J=2.4 Hz, 1H), 6.93-6.75 (m, 1H), 5.51-5.28 (m, 1H), 4.71-4.55 (m, 2H), 4.53-4.34 (m, 4H), 3.85-3.67 (m, 2H), 3.62-3.40 (m, 3H), 3.34 (br d, J=5.4 Hz, 1H), 3.23-3.13 (m, 1H), 2.52-2.20 (m, 5H), 2.16-1.94 (m, 5H), 1.85 (br d, J=8.0 Hz, 2H), 1.61 (br d, J=6.8 Hz, 2H), 1.53 (br d, J=4.9 Hz, 3H), 1.38-1.17 (m, 24H), 0.88 (br t, J=6.8 Hz, 3H); LCMS (ESI, M+1): m/z 927.6.

Example 474
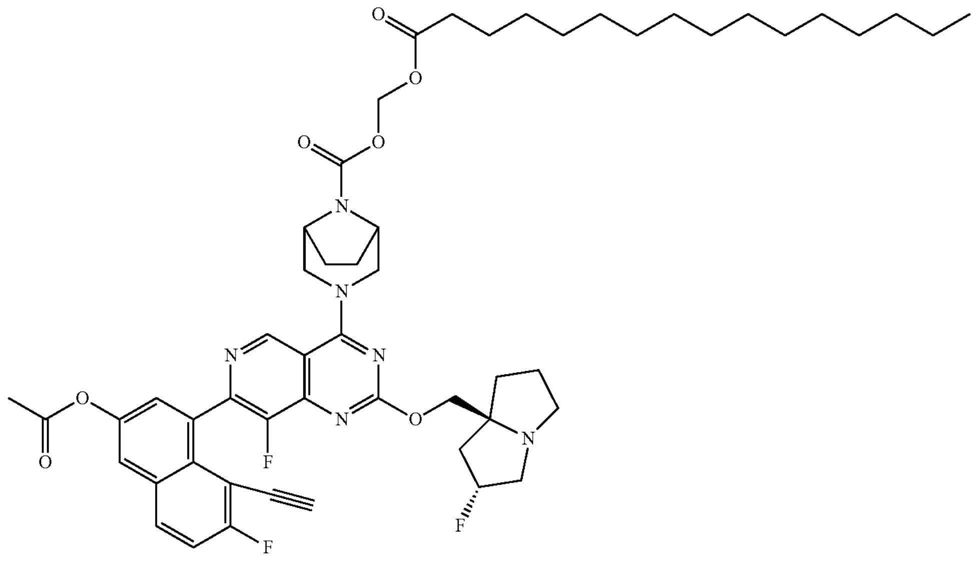 [SMILES: C#Cc1c(F)ccc2cc(OC(C)=O)cc(-c3ncc4c(N5CC6CCC(C5)N6C(=O)OCOC(=O)CCCCCCCCCCCCCCC)nc(OC[C@@]56CCCN5C[C@H](F)C6)nc4c3F)c12]
(Palmitoyloxy)methyl(1R,5S)-3-(7-(3-acetoxy-8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate
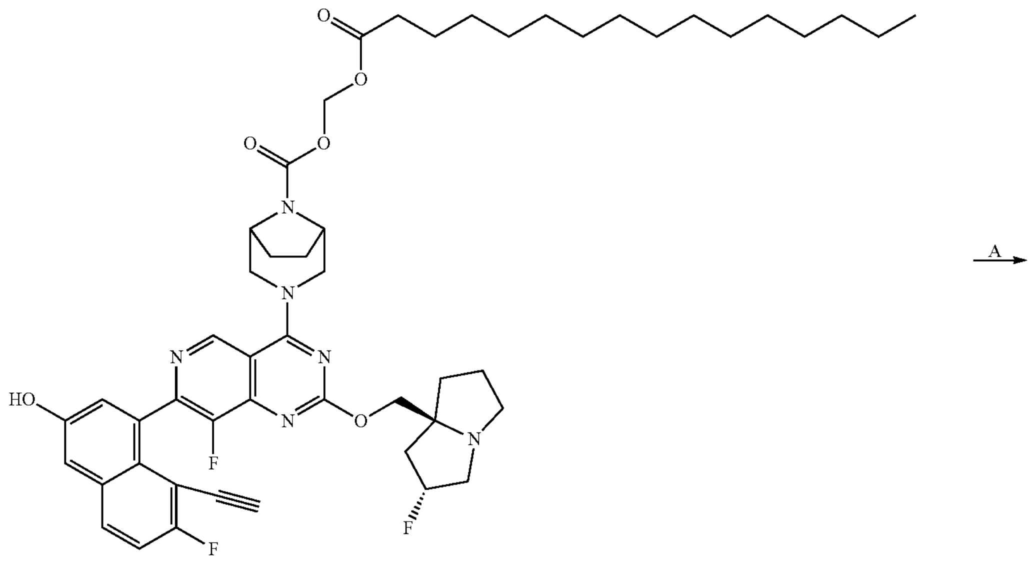

-continued

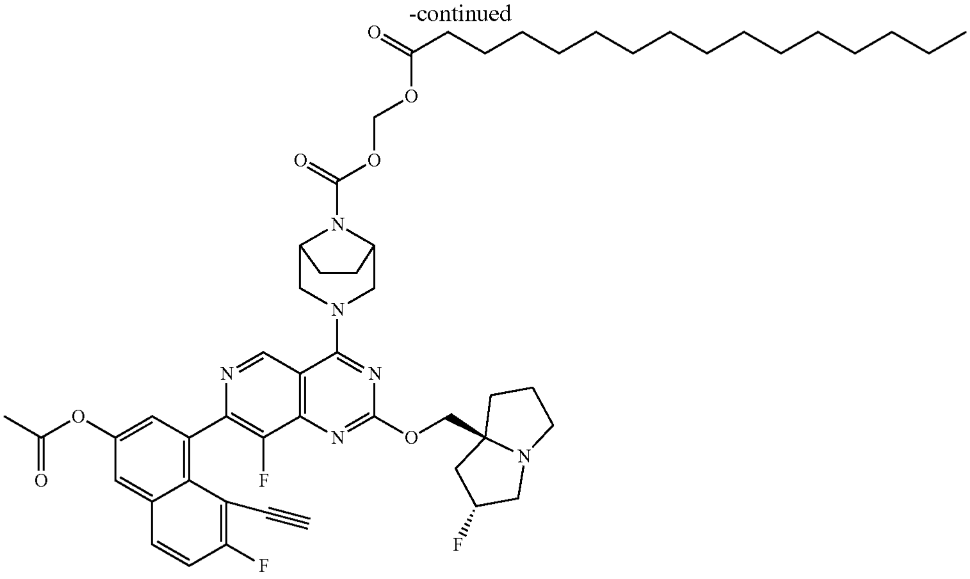

Step A. (Palmitoyloxy)methyl(1R,5S)-3-(7-(3-acetoxy-8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate: To a mixture of (1R,5S)-(palmitoyloxy)methyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (60.0 mg, 62.6 μmol, FA) and DIEA (56.6 mg, 438 μmol, 76.3 μL) in dichloromethane (1.0 mL) was added acetic anhydride (19.2 mg, 188 μmol, 17.6 μL) at 0° C. The mixture was stirred at 0° C. for 15 minutes. After completion, the mixture was concentrated under vacuum. The residue was purified by prep-HPLC (Shim-pack C18 150×25×10 μm; mobile phase: [water (0.225% FA)-ACN]; B %: 55%-75%, 10 min to give the title compound (24.8 mg, 41% yield). Yellow Solid. $^{1}H$ NMR (400 MHz, DMSO-$d_6$) δ 9.06 (s, 1H), 8.21 (dd, J=6.0, 9.2 Hz, 1H), 7.99 (d, J=2.0 Hz, 1H), 7.72-7.60 (m, 1H), 7.50 (s, 1H), 5.75 (s, 2H), 5.39-5.14 (m, 1H), 4.60 (br d, J=12.8 Hz, 1H), 4.47-4.33 (m, 3H), 4.16-4.08 (m, 1H), 4.08-3.97 (m, 2H), 3.12-3.00 (m, 3H), 2.88-2.77 (m, 1H), 2.36 (br t, J=7.2 Hz, 2H), 2.33 (s, 3H), 2.13-1.95 (m, 3H), 1.92-1.70 (m, 7H), 1.57-1.46 (m, 2H), 1.38-1.02 (m, 26H), 0.83 (br t, J=6.4 Hz, 3H). LCMS [ESI, M+1]: m/z 955.5.

Example 475

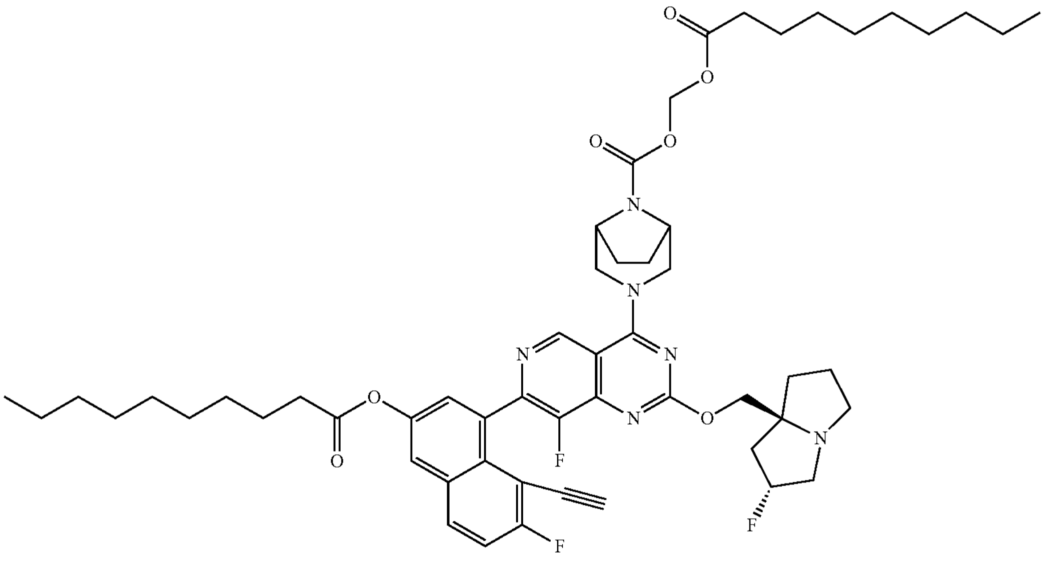 [SMILES: C#Cc1c(F)ccc2cc(OC(=O)CCCCCCCCC)cc(-c3ncc4c(N5CC6CCC(C5)N6C(=O)OCOC(=O)CCCCCCCCC)nc(OC[C@@]56CCCN5C[C@H](F)C6)nc4c3F)c12]

(1R,5S)-(decanoyloxy)methyl 3-(7-(3-(decanoyloxy)-8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (26.7 mg, crude) at −40° C. The mixture was stirred at −40° C. for 0.5 h. The mixture was concentrated to give a residue. The residue was purified by prep-HPLC (column: Phenomenex Gemini-NX C18 75×30 mm×3 μm; mobile phase: [water (0.225% FA)-ACN]; B %: 50%-80%, 7 min) to afford (1R,5S)-(decanoyloxy)methyl 3-(7-(3-(decanoyloxy)-8-

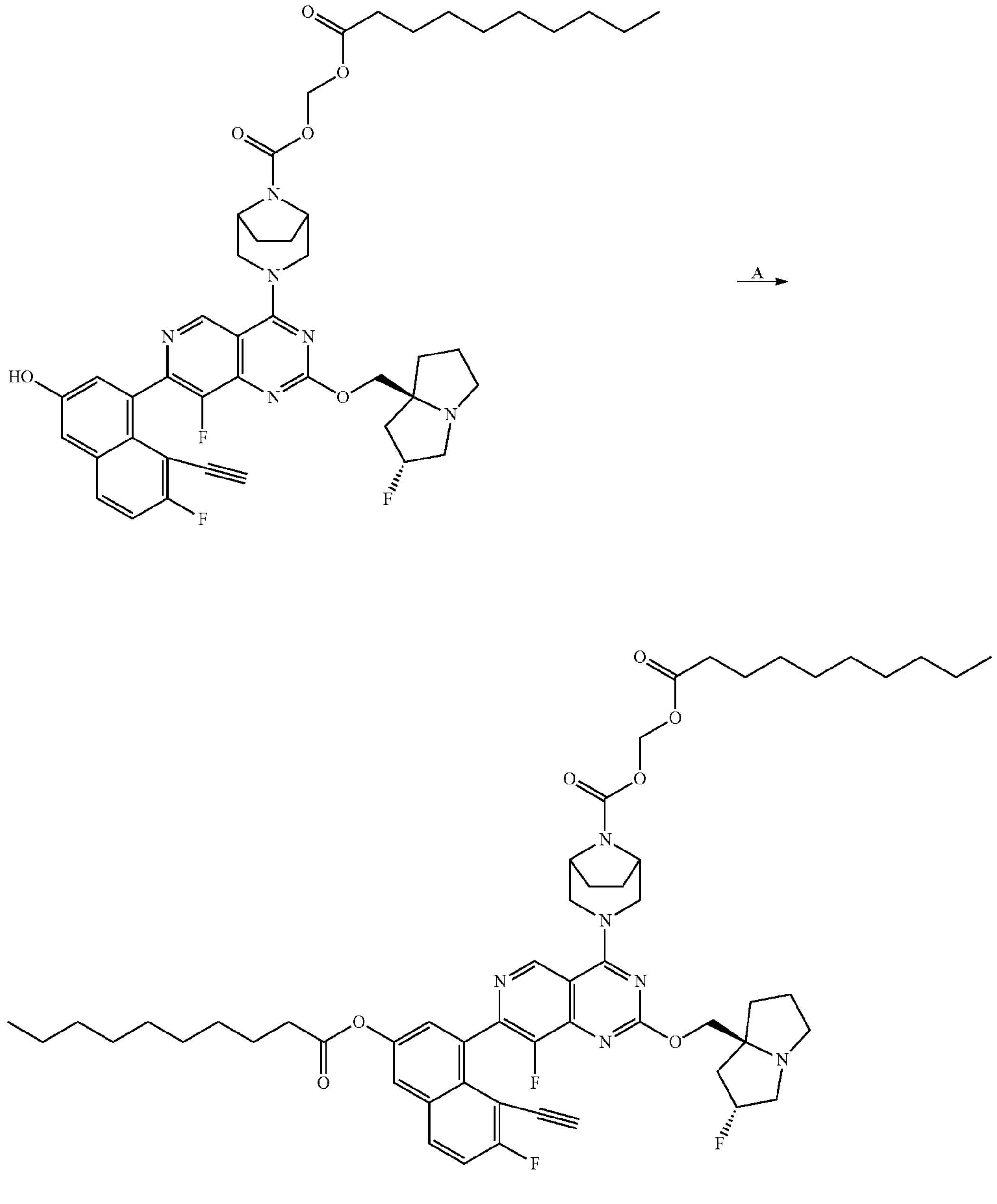

Step A. (1R,5S)-(decanoyloxy)methyl 3-(7-(3-(decanoyloxy)-8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate: To the solution of (1R,5S)-(decanoyloxy)methyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (58.0 mg, 70.0 μmol), TEA (35.4 mg, 350 μmol) in dichloromethane (2 mL) was added decanoyl chloride ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (45.4 mg, 65% yield). Yellow Solid; $^{1}$H NMR (400 MHz, METHANOL-$d_4$) δ=9.08 (s, 1H), 8.15-8.04 (m, 1H), 7.88 (d, J=2.4 Hz, 1H), 7.55-7.38 (m, 2H), 5.83 (s, 2H), 5.58-5.35 (m, 1H), 4.76-4.62 (m, 2H), 4.61-4.45 (m, 4H), 3.93-3.51 (m, 5H), 3.45 (d, J=6.4 Hz, 1H), 3.29-3.24 (m, 1H), 2.73-2.12 (m, 9H), 1.97 (br s, 3H), 1.85 (br d, J=7.6 Hz, 2H), 1.80-1.70 (m, 2H), 1.68-1.57 (m, 2H), 1.48-1.23 (m, 24H), 0.94-0.80 (m, 6H); LCMS (ESI, M+1): m/z 983.6.

Example 476
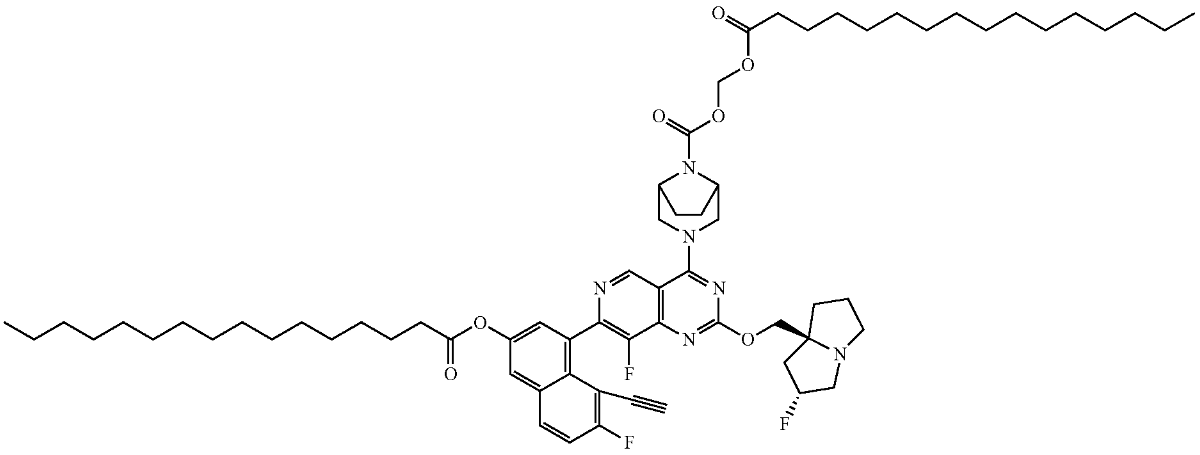 [SMILES: C#Cc1c(F)ccc2cc(OC(=O)CCCCCCCCCCCCCCC)cc(-c3ncc4c(N5CC6CCC(C5)N6C(=O)OCOC(=O)CCCCCCCCCCCCCCC)nc(OC[C@@]56CCCN5C[C@H](F)C6)nc4c3F)c12]
(Palmitoyloxy)methyl(1R,5S)-3-(7-(8-ethynyl-7-fluoro-3-(palmitoyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate
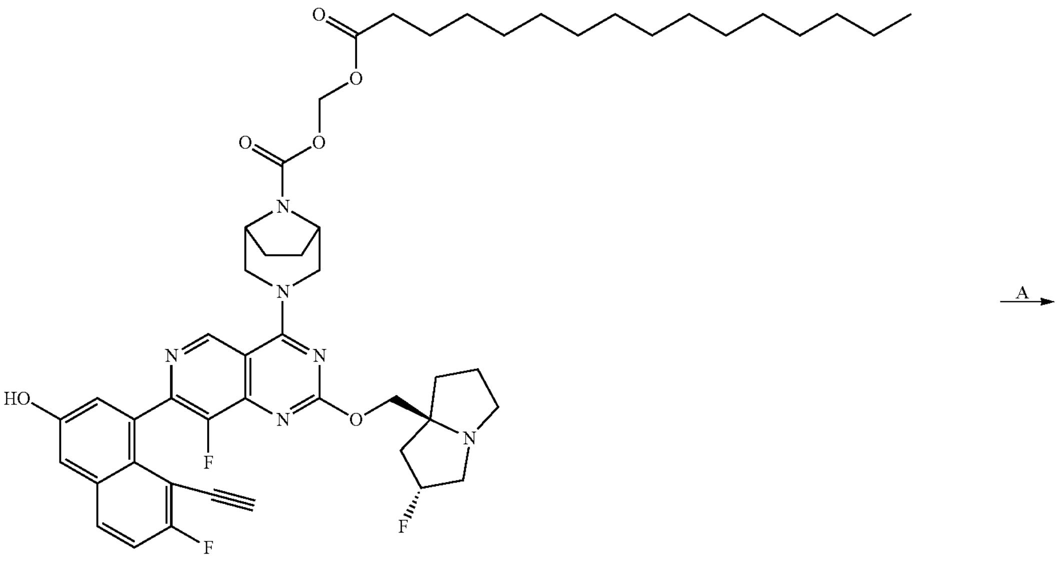

-continued

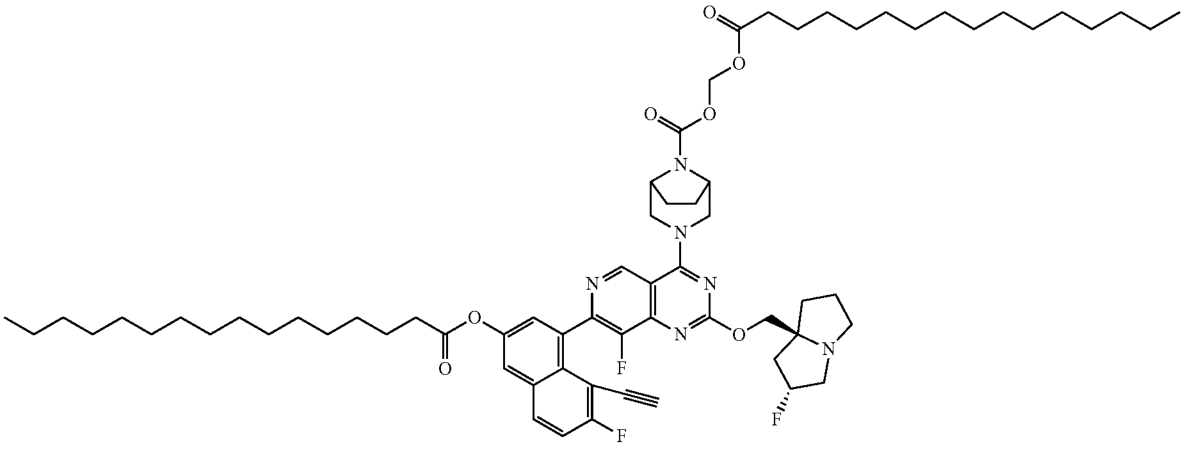

Step A. (Palmitoyloxy)methyl(1R,5S)-3-(7-(8-ethynyl-7-fluoro-3-(palmitoyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate: To a solution of (1R,5S)-(palmitoyloxy)methyl 3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (30 mg, 31.3 μmol, FA) and DIEA (40.4 mg, 313 μmol, 54.5 μL) in dichloromethane (1.0 mL) was added a solution of palmitoyl chloride (17.2 mg, crude) in dichloromethane (1.0 mL) at −40° C. The mixture was stirred at −40° C. for 10 mins. After completion, the mixture was concentrated under vacuum. The residue was purified by prep-TLC (dichloromethane/methanol=1/1) twice and then prep-HPLC (Phenomenex Synergi C18 150×25 mm×10 μm; mobile phase: [water (0.1% TFA)-ACN]; B %: 80%-100%, 10 min) to give the title compound (9.2 mg, 46% yield). Yellow Solid. $^{1}$H NMR (400 MHz, METHANOL-d4) δ 9.11 (s, 1H), 8.10 (dd, J=5.6, 9.2 Hz, 1H), 7.89 (d, J=2.4 Hz, 1H), 7.52-7.43 (m, 2H), 5.83 (br s, 2H), 5.69-5.47 (m, 1H), 4.75-4.62 (m, 4H), 4.52 (br s, 2H), 4.07-3.76 (m, 5H), 3.51-3.41 (m, 2H), 2.75-2.50 (m, 4H), 2.47-2.29 (m, 5H), 2.23-2.11 (m, 1H), 2.08-1.99 (m, 2H), 1.88-1.80 (m, 2H), 1.79-1.72 (m, 2H), 1.68-1.56 (m, 2H), 1.49-1.41 (m, 2H), 1.33-1.23 (m, 46H), 0.91-0.87 (m, 6H). LCMS [ESI, M+1]: m/z 1151.7.

Example 477

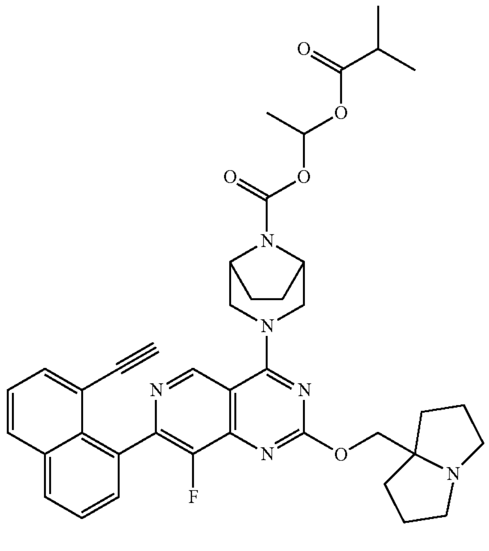 [SMILES: C#Cc1cccc2cccc(-c3ncc4c(N5CC6CCC(C5)N6C(=O)OC(C)OC(=O)C(C)C)nc(OCC56CCCN5CCC6)nc4c3F)c12]

1-(isobutyryloxy)ethyl(1R,5S)-3-(7-(8-ethynylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate

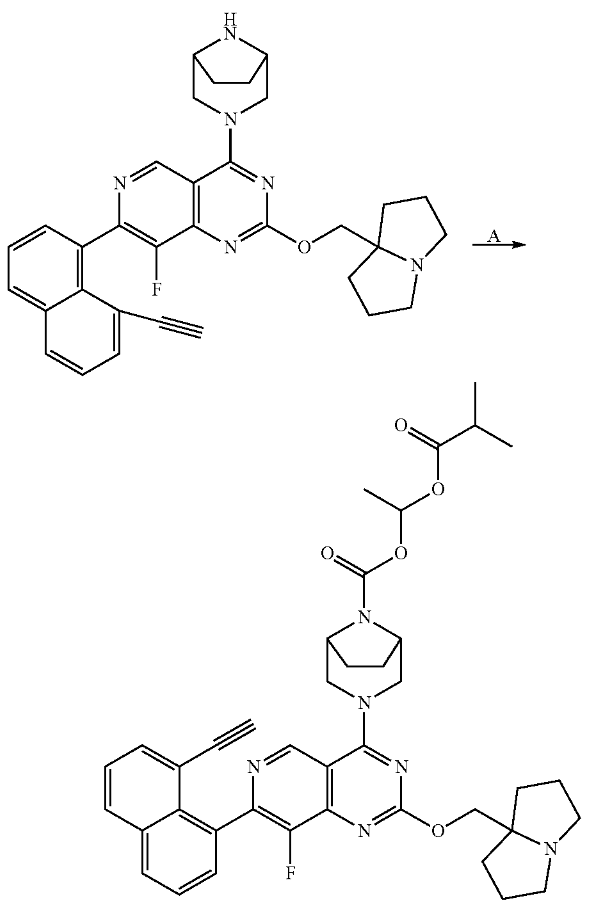

Step A: 1-(isobutyryloxy)ethyl(1R,5S)-3-(7-(8-ethynylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate: To a solution of 4-((1R,5S)-3,8-diazabicyclo[3.2.1]octan-3-yl)-7-(8-ethynylnaphthalen-1-yl)-8-fluoro-2-((tetrahydro-1H-pyrrolizin-7a(5H)-yl)methoxy)pyrido[4,3-d]pyrimidine (20 mg, 36.4 μmol, 1.0 eq) in dichloromethane (1.0 mL) was added DIEA (47.11 mg, 364 μmol, 63.5 μL, 10 eq) and 1-((chlorocarbonyl)oxy)ethyl isobutyrate (21.3 mg, 109 μmol, 3.0 eq). The mixture was stirred at 0° C. for 1 hour. The reaction mixture was diluted with water (5.0 mL) and extracted with dichloromethane (3×5.0 mL). The combined organic layers were washed with brine (5.0 mL), dried over $Na_2SO_4$, filtered, and concentrated under reduced pressure. The residue was purified by prep-HPLC (column: Waters X bridge 150*25 mm*5 um; mobile phase: [water (10 mM $NH_4HCO_3$)-ACN]; B %: 40%-70%, 10 min). The desired fractions were collected and concentrated under vacuum to remove acetonitrile. The mixture was lyophilized to give the title compound (12 mg, 46% yield). Yellow solid. $^1$H NMR (400 MHz, chloroform-d) δ=8.98 (s, 1H), 7.98 (br dd, J=7.2, 12.0 Hz, 2H), 7.76 (br d, J=6.8 Hz, 1H), 7.67-7.55 (m, 2H), 7.52-7.42 (m, 1H), 6.87 (d, J=4.8 Hz, 1H), 4.84-4.13 (m, 7H), 3.88-3.56 (m, 2H), 3.47-3.07 (m, 2H), 2.85-2.40 (m, 5H), 2.29-2.13 (m, 2H), 2.08-1.90 (m, 8H), 1.55 (br d, J=4.4 Hz, 3H), 1.20 (br d, J=5.2 Hz, 6H); LCMS [ESI, M+1]: 707.4.

Example 478

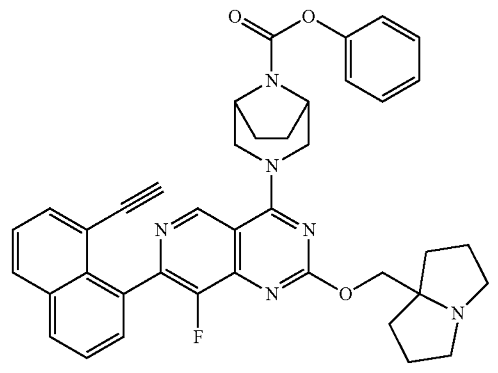 [SMILES: C#Cc1cccc2cccc(-c3ncc4c(N5CC6CCC(C5)N6C(=O)Oc5ccccc5)nc(OCC56CCCN5CCC6)nc4c3F)c12]

Phenyl(1R,5S)-3-(7-(8-ethynylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate

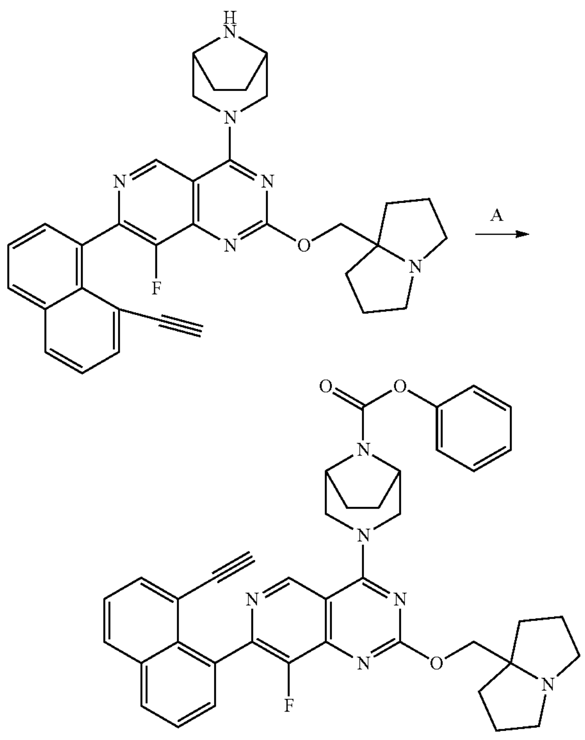

Step A: phenyl(1R,5S)-3-(7-(8-ethynylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate: To a solution of 4-((1R,5S)-3,8-diazabicyclo[3.2.1]octan-3-yl)-7-(8-ethynylnaphthalen-1-yl)-8-fluoro-2-((tetrahydro-1H-pyrrolizin-7a(5H)-yl)methoxy)pyrido[4,3-d]pyrimidine (20 mg, 36.4 μmol, 1.0 eq) and $Et_3N$ (11.1 mg, 109 μmol, 15 μL, 3.0 eq) in dichloromethane (1.0 mL) was added phenyl carbonochloridate (8.56 mg, 54.7 μmol, 6.85 μL, 1.5 eq) in dichloromethane (1.0 mL) at −40° C., and then the mixture was stirred at −40° C. for 30 minutes. The reaction mixture was diluted with water (5.0 mL) and extracted with dichloromethane (3×5.0 mL). The combined organic layers were washed with brine (10 mL), dried over $Na_2SO_4$, filtered, and concentrated under reduced pressure. The residue was purified by prep-HPLC (column: Waters X bridge 150*25 mm*5 um; mobile phase: [water (10 mM $NH_4HCO_3$)-ACN]; B %: 45%-75%, 10 min). to give the title compound (14.03 mg, 57% yield). Orange solid. $^1H$ NMR (400 MHz, chloroform-d) δ=9.02 (s, 1H), 8.01-7.95 (m, 2H), 7.76 (dd, J=1.2, 7.2 Hz, 1H), 7.65-7.57 (m, 2H), 7.48-7.38 (m, 3H), 7.26-7.22 (m, 1H), 7.21-7.16 (m, 2H), 4.76-4.55 (m, 4H), 4.29-4.19 (m, 2H), 3.83 (br d, J=2.4 Hz, 2H), 3.19-3.06 (m, 2H), 2.72-2.60 (m, 2H), 2.55 (s, 1H), 2.18-2.05 (m, 4H), 1.94-1.82 (m, 6H), 1.73-1.66 (m, 2H); LCMS [ESI, M+1]: 669.

Example 479

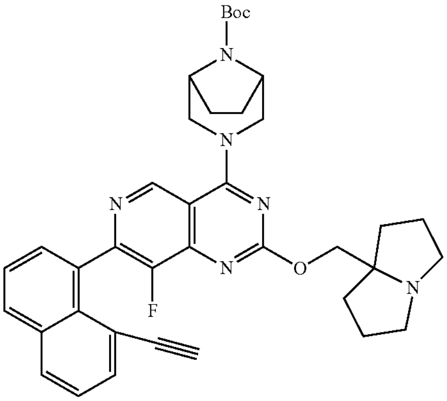 [SMILES: C#Cc1cccc2cccc(-c3ncc4c(N5CC6CCC(C5)N6C(=O)OC(C)(C)C)nc(OCC56CCCN5CCC6)nc4c3F)c12]

tert-butyl(1R,5S)-3-(7-(8-ethynylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate

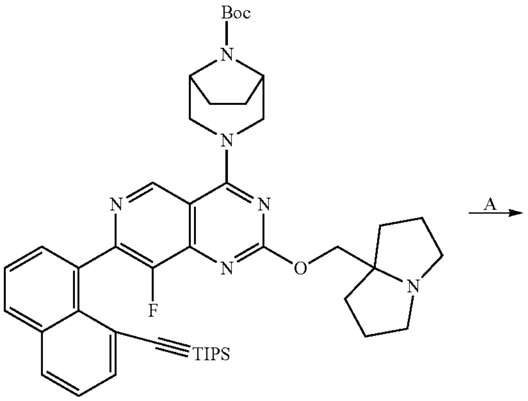

-continued

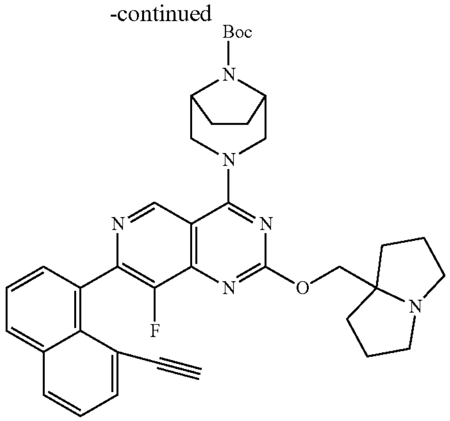

Step A: tert-butyl(1R,5S)-3-(7-(8-ethynylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate: A mixture of tert-butyl(1R,5S)-3-(8-fluoro-2-((tetrahydro-1H-pyrrolizin-7a(5H)-yl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate (30 mg, 37.3 μmol, 1.0 eq) and CsF (28.3 mg, 186 μmol, 6.87 μL, 5.0 eq) in DMF (1 mL) was stirred at 15° C. for 3 hours. The reaction mixture was diluted with ethyl acetate (10 mL) and washed with water (3×5 mL). The organic layer was washed with brine (5 mL), dried over $Na_2SO_4$, filtered, and concentrated under reduced pressure to give the title compound (12 mg, 58% yield). Yellow oil. $^1H$ NMR (400 MHz, chloroform-d) δ=8.99 (s, 1H), 8.02-7.92 (m, 2H), 7.75 (dd, J=1.2, 7.2 Hz, 1H), 7.64-7.57 (m, 2H), 7.49-7.43 (m, 1H), 4.58 (dd, J=12.8, 20.0 Hz, 2H), 4.40 (br s, 2H), 4.21 (s, 2H), 3.70 (s, 2H), 3.19-3.05 (m, 2H), 2.72-2.59 (m, 2H), 2.54 (s, 1H), 2.16-1.70 (m, 12H), 1.53 (s, 9H). LCMS [ESI, M+1]: 649. SFC analysis: Column: Chiralcel OJ-3 50×4.6 mm I.D., 3 um; Mobile phase: Phase A for $CO_2$, and Phase B for MeOH (0.05% DEA); Gradient elution: 40% MeOH (0.05% DEA) in $CO_2$; Flow rate: 3 mL/min; Detector: PDA; Column Temp: 35° C.; Back Pressure: 100 Bar.

Example 480

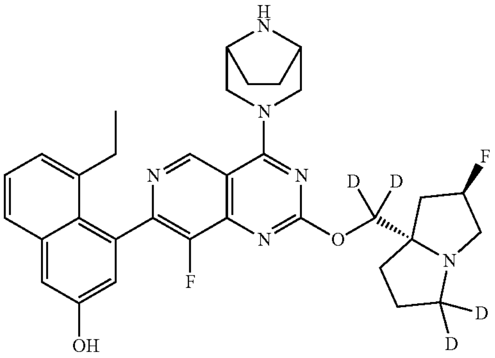 [SMILES: [2H]C1([2H])CC[C@@]2(C([2H])([2H])Oc3nc(N4CC5CCC(C4)N5)c4cnc(-c5cc(O)cc6cccc(CC)c56)c(F)c4n3)C[C@@H](F)CN12]

4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl-5,5-d2)methoxy-d2)pyrido[4,3-d]pyrimidin-7-yl)-5-ethylnaphthalen-2-ol

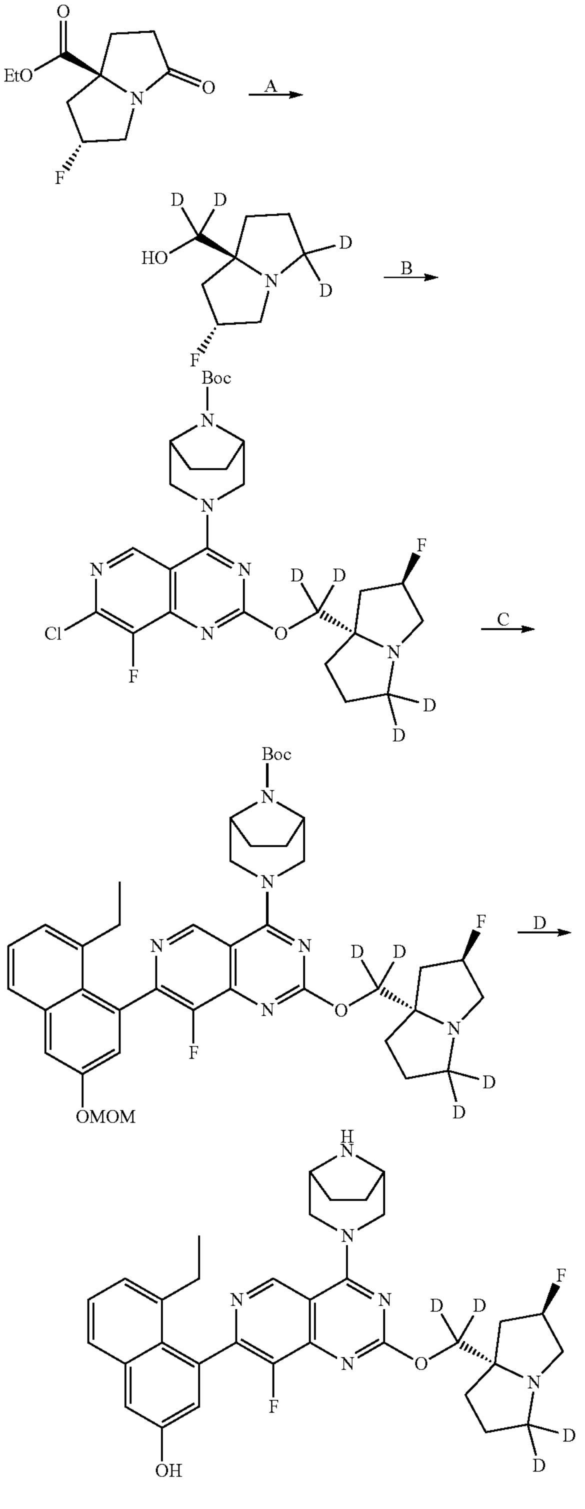

Step A. ((2R,7aS)-2-fluorotetrahydro-1H-pyrrolizin-7a(5H)-yl-5,5-$d_2$) methan-$d_2$-ol: To a solution of $LiAlD_4$ (2.65 g, 69.70 mmol, 3.59 mL, 1.50 eq) in THF (50.0 mL) was added a solution of ethyl(2R,7aS)-2-fluoro-5-oxotetrahydro-1H-pyrrolizine-7a(5H)-carboxylate (10.0 g, 46.46 mmol, 1.0 eq) in THF (30.0 mL) drop-wise at 0° C. under $N_2$. The reaction mixture was warmed to 70° C. and stirred at 70° C. for 3 hr. The mixture was cooled to 0° C. Then to the mixture was added drop-wise water (2.6 mL), NaOH aqueous (15%, 7.8 mL) and water (7.80 mL) at 0° C. in sequence. To the resulting mixture was added $MgSO_4$ (15 g) and stirred at stirred at room temperature for 30 min. The suspension was filtered and concentrated under reduced pressure to give a residue. The residue was purified by column chromatography ($SiO_2$, Petroleum ether/Ethyl acetate=10/1 to 0/1, $R_f$=0.40) to afford the title compound (5.50 g, 33.70 mmol, 72.52% yield, 100% purity) as a yellow oil. LCMS: Rt=2.096 min, m/z=164.1 (M+H).

Step B. tert-butyl(1R,5S)-3-(7-chloro-8-fluoro-2-(((2R,7aS)-2-fluorotetrahydro-1H-pyrrolizin-7a(5H)-yl-5,5-d2)methoxy-d2)pyrido[4,3-d]pyrimidin-4-yl)-3,8-diazabicyclo[3.2.1]octane-8-carboxylate. A mixture of 2-(8-ethyl-3-(methoxymethoxy)naphthalen-1-yl)-4,4,5,5-tetramethyl-1,3,2-dioxaborolane (1.0 g, 2.33 mmol), ((2R,7aS)-2-fluorotetrahydro-1H-pyrrolizin-7a(5H)-yl-5,5-d2) methan-d2-ol (572 mg, 3.50 mmol) and DIEA (905 mg, 7.00 mmol, 1.22 mL) in dioxane (5 mL) was stirred at 90° C. for 7.5 hours. After completion, the mixture was diluted with ethyl acetate (20 mL) and water (20 mL), and then separated. The organic layer was concentrated under vacuum. The crude product was triturated with MeCN (20 mL) at 25° C. for 3 minutes to give the title compound (1.05 g, 70% yield). White solid. Rf=0.3 (10:1, dichloromethane/methanol). LCMS (ESI, M+1): m/z 555.3.

Step C. tert-butyl(1R,5S)-3-(7-(8-ethyl-3-(methoxymethoxy)naphthalen-1-yl)-8-fluoro-2-(((2R,7aS)-2-fluorotetrahydro-1H-pyrrolizin-7a(5H)-yl-5,5-d2)methoxy-d2)pyrido[4,3-d]pyrimidin-4-yl)-3,8-diazabicyclo[3.2.1]octane-8-carboxylate. To a solution of tert-butyl(1R,5S)-3-(7-chloro-8-fluoro-2-(((2R,7aS)-2-fluorotetrahydro-1H-pyrrolizin-7a(5H)-yl-5,5-d2)methoxy-d2)pyrido[4,3-d]pyrimidin-4-yl)-3,8-diazabicyclo[3.2.1]octane-8-carboxylate (1.0 g, 1.80 mmol), 2-(8-ethyl-3-(methoxymethoxy)naphthalen-1-yl)-4,4,5,5-tetramethyl-1,3,2-dioxaborolane (1.23 g, 3.60 mmol) and $K_3PO_4$ (1.5 M, 3.60 mL) in THF (10.8 mL) was added [2-(2-aminophenyl)phenyl]palladium (1+); bis(1-adamantyl)-butyl-phosphane; methanesulfonate (131.21 mg, 180.16 μmol) under $N_2$. The mixture was de-gassed and then heated to 65° C. for 6 hours under $N_2$. After completion, the mixture was diluted with ethyl acetate (10 mL) and water (10 mL), and then separated. The aqueous phase was extracted with ethyl acetate (2×10 mL) and dichloromethane/methanol=10/1 (5 mL). The combined organic layers were dried over $Na_2SO_4$, filtered, concentrated, and purified by reversed-phase flash chromatography [water (FA, 0.1%)/acetonitrile] to give the title compound (684 mg, 52% yield). Green solid. LCMS (ESI, M+1): m/z 735.4.

Step D. 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl-5,5-d2)methoxy-d2)pyrido[4,3-d]pyrimidin-7-yl)-5-ethylnaphthalen-2-ol. To a mixture of tert-butyl (1R,5S)-3-(7-(8-ethyl-3-(methoxymethoxy)naphthalen-1-yl)-8-fluoro-2-(((2R,7aS)-2-fluorotetrahydro-1H-pyrrolizin-7a(5H)-yl-5,5-d2)methoxy-d2)pyrido[4,3-d]pyrimidin-4-yl)-3,8-diazabicyclo[3.2.1]octane-8-carboxylate (742 mg, 1.01 mmol) and MeCN (3 mL) was added HCl·dioxane (4 M, 6 mL) at 0° C. and the mixture was stirred at 0° C. for 0.5 hour. After completion, the mixture was concentrated under vacuum and the pH value was adjusted to 8 with saturated ice $NaHCO_3$ solution (10 mL). Then the mixture was diluted with ethyl acetate (15 mL) then separated. The aqueous phase was extracted with ethyl acetate (8 mL). The combined organic layer was washed with brine (15 mL), dried over $Na_2SO_4$, filtered and, concentrated under vacuum. The residue was purified by prep-HPLC (column: Phenomenex luna C18 150×40 mm×15 μm; mobile phase: [water (0.225% FA)-ACN]; B %: 2%-32%, 10 min) to give the title compound (438 mg, 68% yield, FA). Off-white solid. $^{1}H$ NMR (400 MHz, METHANOL-d4) δ=9.10 (s, 1H), 7.65-7.62 (m, 1H), 7.40-7.33 (m, 1H), 7.30 (d, J=2.4 Hz, 1H), 7.16 (d, J=6.8 Hz, 1H), 7.00 (d, J=2.8 Hz, 1H), 5.58-5.40 (m, 1H), 4.84-4.78 (m, 1H), 4.73 (br dd, J=6.8, 13.2 Hz, 1H), 4.11-4.02 (m, 2H), 3.97-3.83 (m, 2H), 3.82-3.59 (m, 2H), 2.65-2.43 (m, 2H), 2.40-2.18 (m, 5H), 2.14-1.95 (m, 5H), 0.97-0.84 (m, 3H). $^{19}F$ NMR (400 MHz, METHANOL-d4) δ=−138.987, −173.932. LCMS (ESI, M+1): m/z 591.4.

Example 481

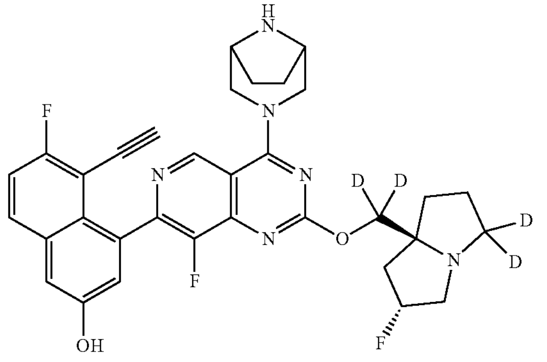 [SMILES: [2H]C1([2H])CC[C@@]2(C([2H])([2H])Oc3nc(N4CC5CCC(C4)N5)c4cnc(-c5cc(O)cc6ccc(F)c(C#C)c56)c(F)c4n3)C[C@@H](F)CN12]

4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl-5,5-d2)methoxy-d2)pyrido[4,3-d]pyrimidin-7-yl)-5-ethynyl-6-fluoronaphthalen-2-ol

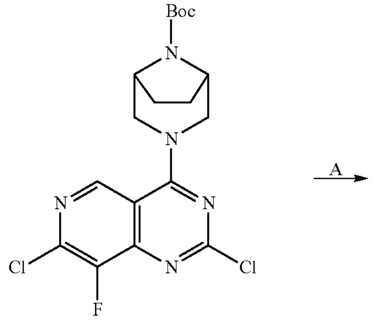

-continued

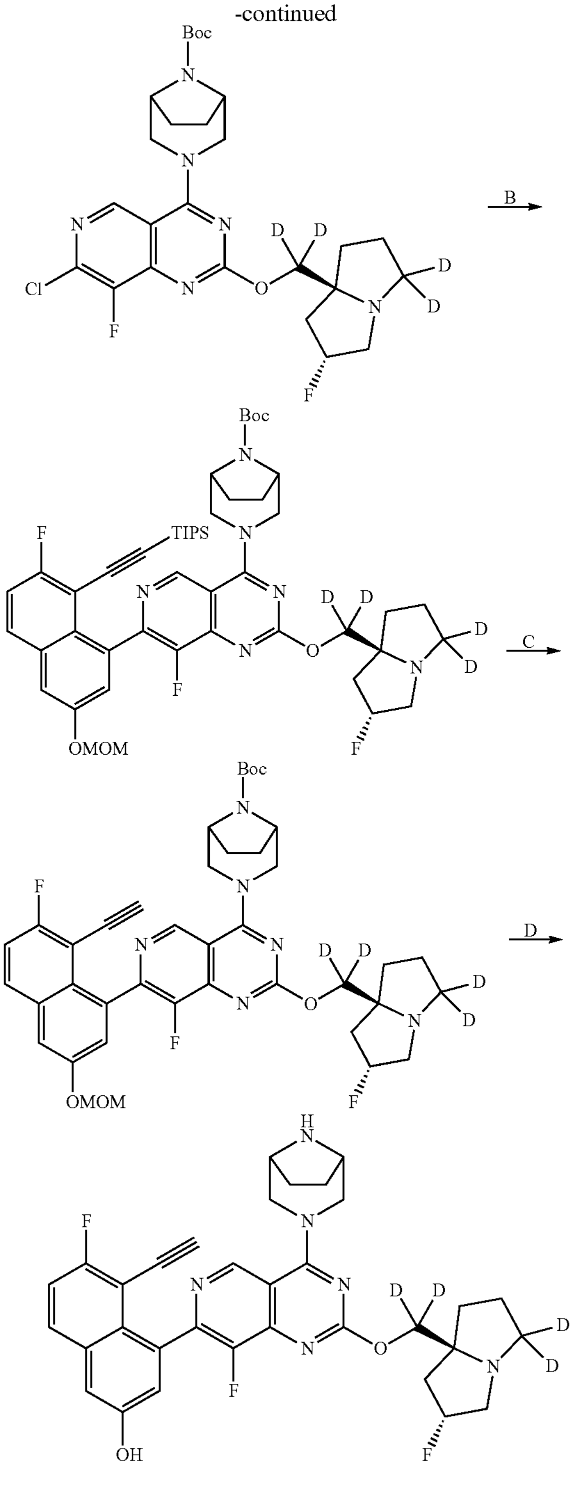

Step A. tert-butyl(1R,5S)-3-(7-chloro-8-fluoro-2-(((2R,7aS)-2-fluorotetrahydro-1H-pyrrolizin-7a(5H)-yl-5,5-d2)methoxy-d2)pyrido[4,3-d]pyrimidin-4-yl)-3,8-diazabicyclo[3.2.1]octane-8-carboxylate: To a solution of (1R,5S)-tert-butyl 3-(2,7-dichloro-8-fluoropyrido[4,3-d]pyrimidin-4-yl)-3,8-diazabicyclo[3.2.1]octane-8-carboxylate (1.30 g, 3.04 mmol) and 4 A MS (500 mg) in dioxane (6 mL) were added DIEA (1.18 g, 9.11 mmol, 1.59 mL) and ((2R,7aS)-2-fluorotetrahydro-1H-pyrrolizin-7a(5H)-yl-5,5-d2) methan-d2-ol (743 mg, 4.55 mmol). The mixture was stirred at 95°

C. for 12 hours. After completion, the reaction mixture was filtered and concentrated under reduced pressure to give a residue. The crude product was triturated with ACN (20 mL) at 20° C. for 10 minute to give the title compound (1.30 g, 72% yield); White solid. LCMS (ESI, M+1): m/z 555.4.

Step B. tert-butyl(1R,5S)-3-(8-fluoro-7-(7-fluoro-3-(methoxymethoxy)-8-((triisopropylsilyl)ethynyl)naphthalen-1-yl)-2-(((2R,7aS)-2-fluorotetrahydro-1H-pyrrolizin-7a(5H)-yl-5,5-d2)methoxy-d2)pyrido[4,3-d]pyrimidin-4-yl)-3,8-diazabicyclo[3.2.1]octane-8-carboxylate: To a solution of tert-butyl(1R,5S)-3-(7-chloro-8-fluoro-2-(((2R,7aS)-2-fluorotetrahydro-1H-pyrrolizin-7a(5H)-yl-5,5-d2)methoxy-d2)pyrido[4,3-d]pyrimidin-4-yl)-3,8-diazabicyclo[3.2.1]octane-8-carboxylate (1.0 g, 1.80 mmol) and ((2-fluoro-6-(methoxymethoxy)-8-(4,4,5,5-tetramethyl-1,3,2-dioxaborolan-2-yl)naphthalen-1-yl)ethynyl) triisopropylsilane (1.85 g, 3.60 mmol) in THF (10 mL) were added $K_3PO_4$ (1.5 M, 3.60 mL) and [2-(2-aminophenyl) phenyl]palladium (1+); bis(1-adamantyl)-butyl-phosphane; methanesulfonate (131.21 mg, 180.16 μmol). The mixture was stirred at 60° C. for 2 hours. After completion, the reaction mixture was concentrated under reduced pressure to remove THE. The residue was diluted with $H_2O$ (50 mL) and extracted with ethyl acetate (3×50 mL). The combined organic layers were dried over $Na_2SO_4$. The mixture was filtered and the filtrate was concentrated under reduced pressure to give a residue. The residue was purified by reversed-phase flash chromatography [water (FA, 0.1%)/acetonitrile] to give the title compound (1.30 g, 74% yield); Yellow solid. $^1$H NMR (400 MHz, $CDCl_3$) δ 9.05 (s, 1H), 7.79 (dd, J=5.6, 8.8 Hz, 1H), 7.51 (d, J=2.4 Hz, 1H), 7.34-7.27 (m, 2H), 5.40-5.18 (m, 3H), 4.91-4.73 (m, 1H), 4.57-4.28 (m, 2H), 4.24-4.15 (m, 1H), 3.94-3.68 (m, 1H), 3.51 (s, 3H), 3.49-3.34 (m, 1H), 3.28-3.10 (m, 2H), 2.36-2.08 (m, 3H), 2.05 (s, 1H), 2.02-1.78 (m, 6H), 1.53 (s, 9H), 0.94-0.80 (m, 18H), 0.59-0.48 (m, 3H). LCMS (ESI, M+1): m/z 905.6.

Step C. tert-butyl(1R,5S)-3-(7-(8-ethynyl-7-fluoro-3-(methoxymethoxy)naphthalen-1-yl)-8-fluoro-2-(((2R,7aS)-2-fluorotetrahydro-1H-pyrrolizin-7a(5H)-yl-5,5-d2) methoxy-d2)pyrido[4,3-d]pyrimidin-4-yl)-3,8-diazabicyclo [3.2.1]octane-8-carboxylate: To a solution of tert-butyl(1R, 5S)-3-(8-fluoro-7-(7-fluoro-3-(methoxymethoxy)-8-((triisopropylsilyl)ethynyl)naphthalen-1-yl)-2-(((2R,7aS)-2-fluorotetrahydro-1H-pyrrolizin-7a(5H)-yl-5,5-d2)methoxy-d2)pyrido[4,3-d]pyrimidin-4-yl)-3,8-diazabicyclo[3.2.1] octane-8-carboxylate (600 mg, 663 μmol) in DMF (6 mL) was added CsF (1.01 g, 6.63 mmol). The mixture was stirred at 20° C. for 1 hour. After completion, the reaction mixture was filtered and concentrated under reduced pressure to give a residue. The residue was purified by reversed-phase flash chromatography [water (FA, 0.1%)/acetonitrile] to give the title compound (0.45 g, 91% yield); Yellow solid. LCMS (ESI, M+1): m/z 749.4.

Step D. 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl-5,5-d2)methoxy-d2)pyrido[4,3-d]pyrimidin-7-yl)-5-ethynyl-6-fluoronaphthalen-2-ol: To a solution of tert-butyl(1R,5S)-3-(7-(8-ethynyl-7-fluoro-3-(methoxymethoxy)naphthalen-1-yl)-8-fluoro-2-(((2R,7aS)-2-fluorotetrahydro-1H-pyrrolizin-7a(5H)-yl-5,5-d2) methoxy-d2)pyrido[4,3-d]pyrimidin-4-yl)-3,8-diazabicyclo [3.2.1]octane-8-carboxylate (400 mg, 534 μmol) in ACN (2 mL) was added HCl·dioxane (4 M, 2 mL). The mixture was stirred at 0° C. for 0.5 hour. After completion, the reaction mixture was concentrated under reduced pressure to give a residue. The residue was purified by prep-HPLC (column: Phenomenex luna C18 150×40 mm×15 μm; mobile phase: [water (0.225% FA)-ACN]; B %: 1%-30%, 10 min) to give the title compound (268 mg, 74% yield, 1.5FA); Yellow solid. $^1$H NMR (400 MHz, METHANOL-d4) δ 9.08 (s, 1H), 8.47 (s, 2H), 7.87 (dd, J=5.6, 9.2 Hz, 1H), 7.44-7.29 (m, 2H), 7.21 (d, J=2.4 Hz, 1H), 5.60-5.41 (m, 1H), 4.85-4.73 (m, 2H), 4.12 (br s, 2H), 3.99-3.85 (m, 2H), 3.84-3.61 (m, 2H), 3.39 (s, 1H), 2.67-2.41 (m, 2H), 2.39-2.30 (m, 1H), 2.29-2.18 (m, 2H), 2.16-1.97 (m, 5H). LCMS (ESI, M+1): m/z 605.4

Example 482

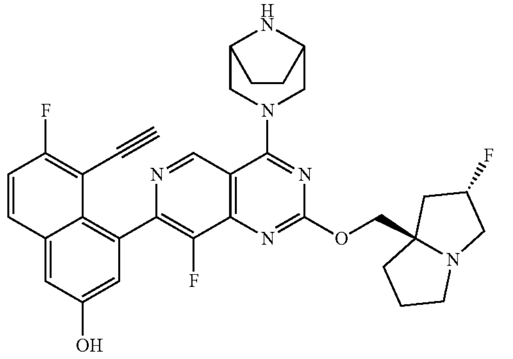 [SMILES: C#Cc1c(F)ccc2cc(O)cc(-c3ncc4c(N5CC6CCC(C5)N6)nc(OC[C@]56CCCN5C[C@@H](F)C6)nc4c3F)c12]

4-(4-((1R,5S)-3,8-diazabicyclo[3.2.1]octan-3-yl)-8-fluoro-2-(((2S,7aR)-2-fluorohexahydro-1H-pyrrolizin-7a-yl)methoxy)pyrido[4,3-d]pyrimidin-7-yl)-5-ethynyl-6-fluoronaphthalen-2-ol

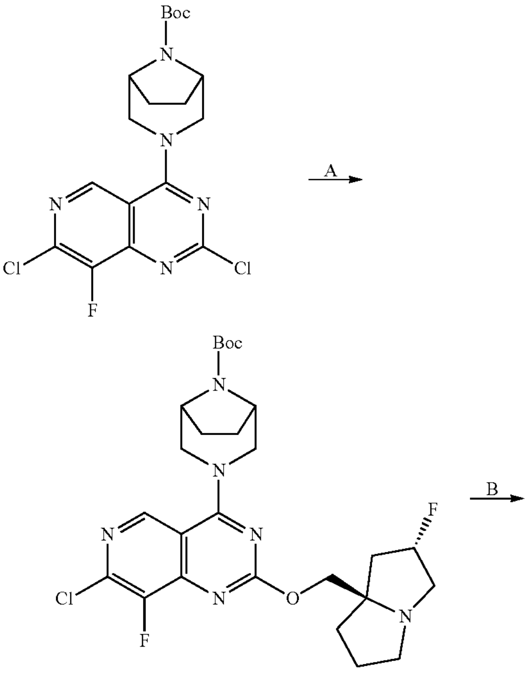

-continued

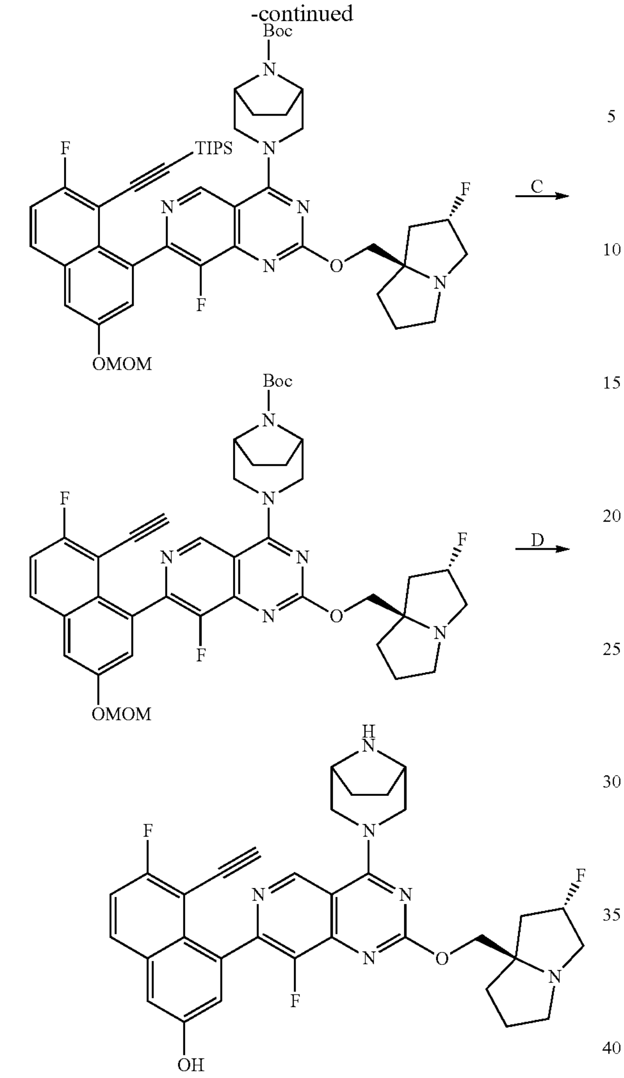

Step A. (1R,5S)-tert-butyl 3-(7-chloro-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate: To a mixture of (1R,5S)-tert-butyl 3-(2,7-dichloro-8-fluoropyrido[4,3-d]pyrimidin-4-yl)-3,8-diazabicyclo[3.2.1]octane-8-carboxylate (2.0 g, 4.67 mmol) and ((2S,7aR)-2-fluorohexahydro-1H-pyrrolizin-7a-yl)methanol (1.12 g, 7.00 mmol) in dioxane (8 mL) were added DIEA (1.51 g, 11.7 mmol) and 4 Å MS (0.5 g, 4.67 mmol). Then it was degassed and purged with $N_2$ for 3 times. The reaction was heated to 95° C. and stirred for 12 hours. After completion, the reaction mixture was filtered and concentrated under reduced pressure and purified by reversed-phase flash chromatography [water (0.1% formic acid)/acetonitrile)] to give (1R,5S)-tert-butyl 3-(7-chloro-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (1.60 g, 62% yield). White solid; LCMS [ESI, M+1]: 551.2.

Step B. (1R,5S)-tert-butyl 3-(8-fluoro-7-(7-fluoro-3-(methoxymethoxy)-8-((triisopropylsilyl)ethynyl)naphthalen-1-yl)-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate: To a solution of (1R,5S)-tert-butyl 3-(7-chloro-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (900 mg, 1.63 mmol) and ((2-fluoro-6-(methoxymethoxy)-8-(4,4,5,5-tetramethyl-1,3,2-dioxaborolan-2-yl)naphthalen-1-yl)ethynyl)triisopropylsilane (1.26 g, 2.45 mmol) in THF (15 mL) were added $K_3PO_4$ (1.5 M, 3.27 mL) and [2-(2-aminophenyl)phenyl]palladium (1+); bis(1-adamantyl)-butyl-phosphane; methanesulfonate (178 mg, 245 μmol) under $N_2$. The mixture was stirred at 60° C. for 2 hours. After completion, the mixture was diluted with water (20 mL), and extracted with ethyl acetate (3×20 mL), the combined organic layer was washed with brine (20 mL), dried over $Na_2SO_4$, filtered and, concentrated under vacuum to give residue. The residue was purified by reversed-phase flash chromatography (column: Phenomenex luna C18 150×40 mm×15 μm; mobile phase: [water (0.225% FA)-ACN]; B %: 42%-72%, 10 min) affording (1R,5S)-tert-butyl 3-(8-fluoro-7-(7-fluoro-3-(methoxymethoxy)-8-((triisopropylsilyl)ethynyl)naphthalen-1-yl)-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (1.1 g, 74% yield). Yellow solid; $^1H$ NMR (400 MHz, $CDCl_3$-d) δ 9.09 (s, 1H), 8.26 (s, 1H), 7.78 (dd, J=5.6, 8.8 Hz, 1H), 7.51 (d, J=2.4 Hz, 1H), 7.36-7.25 (m, 2H), 5.58-5.35 (m, 1H), 5.33-5.23 (m, 2H), 4.94-4.62 (m, 2H), 4.60-4.20 (m, 4H), 4.04-3.69 (m, 3H), 3.62-3.36 (m, 5H), 3.27-3.11 (m, 1H), 2.68-2.31 (m, 3H), 2.29-2.10 (m, 3H), 2.03-1.89 (m, 3H), 1.52 (s, 9H), 0.95-0.79 (m, 18H), 0.61-0.46 (m, 3H). LCMS [ESI, M/2+1, M+1]: 451.4, 901.5.

Step C. (1R,5S)-tert-butyl 3-(7-(8-ethynyl-7-fluoro-3-(methoxymethoxy)naphthalen-1-yl)-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate: To a solution of (1R,5S)-tert-butyl 3-(8-fluoro-7-(7-fluoro-3-(methoxymethoxy)-8-((triisopropylsilyl)ethynyl)naphthalen-1-yl)-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (800 mg, 888 μmol) in DMF (10 mL) was added CsF (1.35 g, 8.88 mmol, 327 μL). The mixture was stirred at 40° C. for 1 hour. After completion, the reaction mixture was diluted with $H_2O$ (30 mL) and extracted with ethyl acetate (3×20 mL). The combined organic layers were washed with brine (30 mL), dried over $Na_2SO_4$, filtered and, concentrated under reduced pressure to give a residue. The residue was purified by reversed-phase flash chromatography (C18, 0.1% FA in water, 0-40% ACN) affording (1R,5S)-tert-butyl 3-(7-(8-ethynyl-7-fluoro-3-(methoxymethoxy)naphthalen-1-yl)-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (600 mg, 89% yield). Yellow solid; LCMS [ESI, M/2+1, M+1]: 373.3, 745.3.

Step D. 4-(4-((1R,5S)-3,8-diazabicyclo[3.2.1]octan-3-yl)-8-fluoro-2-(((2S,7aR)-2-fluorohexahydro-1H-pyrrolizin-7a-yl)methoxy)pyrido[4,3-d]pyrimidin-7-yl)-5-ethynyl-6-fluoronaphthalen-2-ol: To a solution of (1R,5S)-tert-butyl 3-(7-(8-ethynyl-7-fluoro-3-(methoxymethoxy)naphthalen-1-yl)-8-fluoro-2-(((2S,7aR)-2-fluorohexahydro-1H-pyrrolizin-7a-yl)methoxy)pyrido[4,3-d]pyrimidin-4-yl)-3,8-diazabicyclo[3.2.1]octane-8-carboxylate (600 mg, 805 μmol) in ACN (2 mL) was added HCl·dioxane (4.0 M, 2.0 mL). The mixture was stirred at 0° C. for 0.5 hour. After completion, the reaction mixture was concentrated under reduced pressure to give a residue. The residue added saturated $NaHCO_3$ aqueous solution (10 mL) and extracted with ethyl acetate (3×20 mL). The combined organic layers were dried over $Na_2SO_4$, filtered, and concentrated under reduced pressure to give a residue. The residue was purified by prep-HPLC (column: Waters Xbridge 150×25 mm×5 μm; mobile phase: [water (10 mM $NH_4HCO_3$)-ACN]; B %: 29%-59%, 10 min) to afford 4-(4-((1R,5S)-3,8-diazabicyclo[3.2.1]octan-3-yl)-8-fluoro-2-(((2S,7aR)-2-fluorohexahydro-1H-pyrrolizin-7a-yl)methoxy)pyrido[4,3-d]pyrimidin-7-yl)-5-ethynyl-6-fluoronaphthalen-2-ol (353 mg, 72% yield). Yellow solid; $^1H$ NMR (400 MHz, $CDCl_3$-d) δ 8.89 (d, J=11.6 Hz, 1H), 7.60 (dd, J=5.6, 8.8 Hz, 1H), 7.24-7.07 (m, 3H), 5.42-5.10 (m, 1H), 4.64-4.51 (m, 1H), 4.50-4.36 (m, 1H), 4.26-4.12 (m, 2H), 3.68-3.49 (m, 4H), 3.33-3.13 (m, 3H), 3.03-2.94 (m, 1H), 2.74 (d, J=2.8 Hz, 1H), 2.32-2.18 (m, 2H), 2.15-2.07 (m, 1H), 2.04-1.76 (m, 4H), 1.71-1.50 (m, 3H); LCMS [ESI, M+1]: 601.3.

Example A

KRas G12D Surface Plasmon Resonance (SPR) Binding Assay

This Example illustrates that exemplary compounds of the present invention bind to KRas G12D as measured by surface plasmon resonance (SPR).

Briefly, 1 L of 1.05×HBS-Mg buffer (262.5 mM Bioultra Hepes, pH 7.5, 157.5 mM NaCl, 105 mM $MgCl_2$, 0.525 mM TCEP, 0.0305% Brij-35) was prepared and filter sterilized using a 0.22 μm bottle top filter. Approximately 50 mL of 1.05×HBS-Mg buffer was removed and saved for future dilutions. A 50 mL aliquot of DMSO (Sigma Aldrich DMSO Lot. #SHBK2079) was added and continued to stir for 10 minutes, creating the final 1.0×HBS-Mg buffer (250 mM Bioultra Hepes pH 7.5, 150 mM NaCl, 100 mM $MgCl_2$, 0.5 mM TCEP, 0.03% Brij-35).

Biacore T200 instrument was primed using 1.0×HBS-Mg buffer before docking a GE Streptavidin (SA) chip and then primed two additional times prior to beginning the immobilization step. All immobilized protein mixtures were created using 3-5 mg/mL Biotinylated Avidin-tagged KRAS protein using the following immobilization settings: SA chip type, 1 flow cells per cycle, 720 second contact time, and 5 ul/min flow rate. Normalization of the detector was also performed during the immobilization step using the GE BiaNormalize solution.

All compounds were diluted to 10 mM in 100% DMSO prior to being diluted 20× in 1.05× buffer. Another 10× dilution was created using 1.0× buffer prior to performing a series of 3× dilutions to create a compound concentration curve using the following assay settings: 20C analysis temperature, General Settings=10 Hz data collection rate and multi-detection; Assay Steps=all set to LMW kinetics; Cycle Types=LMW kinetics (60 s contact time, 120 s dissociation time, 100 ul/min flow rate, extra wash after injection with 50% DMSO, flow path 1,2,3,4); Flow path detection=2-1, 4-3). Data evaluation was performed using the Biacore T200 Evaluation software and data fit to 1:1 binding model. The results for exemplary compounds of Formula (I) are shown in Table 1. ND=not determined.

TABLE 1

Determination of KRas G12D $K_D$ for Exemplary Compounds of Formula (I)

| Example No. | $K_D$ (nM) |
|---|---|
| 1 | 97.7 |
| 2 | 2.4 |
| 3 | 8.3 |
| 4 | 155.7 |
| 5 | 294.8 |
| 6 | 442.2 |
| 7 | 463.5 |
| 8 | 2143.7 |
| 9 | 258.9 |
| 10 | 33.8 |
| 11 | 4.9 |
| 12 | 11.0 |
| 13 | 510.7 |
| 14 | 5.1 |
| 15 | 208.5 |
| 16 | 31.3 |
| 17 | 2209.6 |
| 18 | 3.1 |
| 19 | 664.8 |
| 20 | 967.0 |
| 21 | 447.5 |
| 22 | 19.6 |
| 23 | 807.2 |
| 24 | 5.0 |
| 25 | 269.7 |
| 26 | 27.9 |
| 27 | 25.9 |
| 28 | 58.7 |
| 29 | 169.6 |
| 30 | 179.5 |
| 33 | 71.7 |
| 34 | 119.3 |
| 35 | 1381.8 |
| 37 | 494.5 |
| 38 | 750.3 |
| 39 | 67770.0 |
| 40 | 1.7 |
| 41 | 180.8 |
| 42 | 5.6 |
| 43 | 188.0 |
| 44 | 31.7 |
| 45 | 5.1 |
| 46 | 797.8 |
| 47 | 509.9 |
| 48 | 930.8 |
| 49 | 0.4 |
| 50 | 2.1 |
| 51 | 611.1 |
| 52 | 507.4 |
| 53 | 4369.4 |
| 54 | 117.5 |
| 55 | 22441.7 |
| 56 | 5168.9 |
| 57 | >1000000 |
| 58 | 4733.6 |
| 59 | 1118.3 |
| 60 | >1000000 |
| 61 | 115.5 |
| 67 | 1151.1 |
| 68 | 292.8 |
| 69 | 521.6 |
| 70 | 416.7 |
| 71 | 137.6 |
| 72 | 507.2 |
| 73 | 666744.3 |
| 74 | 140.6 |
| 75 | 303.7 |
| 76 | 196.9 |
| 77 | 3065.8 |
| 78 | 367.5 |
| 79 | >1000000 |
| 80 | >500000 |
| 81 | 320.6 |
| 82 | 214.8 |
| 84 | 14.4 |
| 85 | 147.8 |

TABLE 1-continued

| Determination of KRas G12D $K_D$ for Exemplary Compounds of Formula (I) | |
|---|---|
| Example No. | $K_D$ (nM) |
| 86 | 527559.5 |
| 87 | 195.8 |
| 88 | 15593.2 |
| 89 | 4308.7 |
| 90 | 7805.4 |
| 91 | 25.9 |
| 92 | 2303.5 |
| 94 | 7462.4 |
| 95 | 1129.0 |
| 96 | 709.6 |
| 97 | 5916.9 |
| 99 | 896.6 |
| 100 | 1089.4 |
| 101 | 11958.2 |
| 102 | 259.1 |
| 103 | 271.2 |
| 104 | 362.0 |
| 105 | 2264.8 |
| 106 | 53.5 |
| 107 | 1437.0 |
| 108 | 63516.8 |
| 109 | >500000 |
| 110 | 42.3 |
| 111 | 275.8 |
| 112 | 983.3 |
| 113 | 2503.9 |
| 114 | 383.7 |
| 115 | 333377.0 |
| 116 | 3628.8 |
| 117 | 1004.8 |
| 118 | 1061.5 |
| 119 | 511.4 |
| 120 | 42.1 |
| 121 | 197.0 |
| 122 | 3417.4 |
| 123 | 785.7 |
| 124 | 22.7 |
| 126 | 16.1 |
| 127 | 864.1 |
| 131 | 1553.0 |
| 132 | 64.7 |
| 133 | 112.6 |
| 134 | 6.9 |
| 139 | 25.4 |
| 140 | 5591.7 |
| 142 | 13834.0 |
| 143 | 14933.6 |
| 147 | 18778.9 |
| 151 | 448.0 |
| 153 | 70.5 |
| 156 | 500006.0 |
| 157 | 22.9 |
| 158 | 329.9 |
| 160 | 0.3 |
| 161 | 403.2 |
| 162 | 554.6 |
| 173 | 116.7 |
| 174 | 186.1 |
| 179 | 0.1 |
| 185 | 0.0 |
| 190 | 76.1 |
| 214 | 283.6 |
| 215 | 70.4 |
| 216 | 1.7 |
| 217 | 2977.0 |
| 219 | 8.1 |
| 316 | 157480.3 |
| 317 | 91269.8 |
| 318 | 367549.7 |
| 319 | 255881.2 |
| 320 | 71584.2 |
| 339 | 21.6 |
| 395 | 2.6 |
| 396 | 34.8 |
| 397 | 183.2 |

Example B

KRas G12D Binding Assay

This Example illustrates that exemplary compounds of the present invention bind to KRas G12D and are capable of displacing a labeled tracer ligand occupying the KRas G12D binding site.

The ability of a compound to bind to KRAS G12D was measured using a TR-FRET displacement assay. Biotinylated GDP-loaded recombinant human KRAS G12D (corresponding to amino acids 1:169, produced at Array BioPharma) was incubated with a custom-made Cy5 labelled tracer, europium labelled streptavidin and compound (2% DMSO final) in buffer (50 mM HEPES [pH 7.5], 5 mM $MgCl_2$, 0.005% Tween-20 & 1 mM DTT). After a 60 minute incubation at 22° C., the reaction was measured using a PerkinElmer En Vision multimode plate reader via TR-FRET dual wavelength detection, and the percent of control (POC) calculated using a ratiometric emission factor. 100 POC is determined using no test compound and 0 POC is determined using a concentration of control compound that completely inhibits binding of the tracer to KRAS. The POC values were fit to a 4-parameter logistic curve and the $IC_{50}$ value was determined as the concentration where the curve crosses 50 POC.

The results for exemplary compounds of Formula (I) are shown in Table 2. ND stands for "not determined."

TABLE 2

| Binding to KRas G12D by Exemplary Compounds of Formula (I) | |
|---|---|
| Example No. | $IC_{50}$ (nM) |
| 1 | 124.7 |
| 2 | 2.7 |
| 3 | 9.5 |
| 4 | 496.2 |
| 5 | 722.9 |
| 6 | 434.1 |
| 7 | 1867.3 |
| 8 | 1522.0 |
| 9 | 820.7 |
| 14 | 73.9 |
| 15 | 260.3 |
| 16 | 54.1 |
| 17 | 666.2 |
| 18 | 76.8 |
| 19 | 122.0 |
| 20 | 691.8 |
| 21 | 262.9 |
| 22 | 50.3 |
| 24 | 7.9 |
| 25 | 338.4 |
| 26 | 42.1 |
| 29 | 160.4 |
| 30 | 417.6 |
| 31 | 1.6 |
| 32 | 2145.0 |
| 33 | 21.1 |
| 34 | 135.4 |

TABLE 2-continued

Binding to KRas G12D by Exemplary Compounds of Formula (I)

| Example No. | $IC_{50}$ (nM) |
|---|---|
| 35 | 475.0 |
| 36 | 0.4 |
| 37 | 404.8 |
| 38 | 174.2 |
| 39 | >10000 |
| 40 | 4.0 |
| 41 | 76.7 |
| 42 | 3.1 |
| 43 | 72.2 |
| 44 | 33.7 |
| 45 | 5.5 |
| 46 | 720.8 |
| 47 | 264.6 |
| 48 | 433.9 |
| 49 | 5.9 |
| 50 | 2.5 |
| 51 | 291.7 |
| 52 | 318.3 |
| 53 | 1881.4 |
| 54 | 68.7 |
| 55 | 6131.3 |
| 56 | 5916.7 |
| 57 | 7285.9 |
| 58 | 2326.7 |
| 59 | 946.3 |
| 60 | 1660.7 |
| 61 | 4081.0 |
| 62 | 8407.4 |
| 63 | 0.4 |
| 64 | 3.3 |
| 65 | 3.2 |
| 66 | 544.4 |
| 67 | 1245.6 |
| 68 | 256.6 |
| 69 | 529.9 |
| 70 | 356.2 |
| 71 | 125.7 |
| 72 | 512.9 |
| 73 | 572.7 |
| 74 | 188.2 |
| 75 | 240.4 |
| 76 | 131.2 |
| 77 | 3137.6 |
| 78 | 358.3 |
| 79 | 336.5 |
| 80 | 646.9 |
| 81 | 152.9 |
| 82 | 226.8 |
| 83 | 8694.9 |
| 84 | 31.7 |
| 85 | 453.7 |
| 86 | 7919.9 |
| 87 | 535.6 |
| 88 | 7021.4 |
| 89 | 679.3 |
| 90 | 4494.9 |
| 91 | 32.7 |
| 92 | 1348.4 |
| 93 | 104.6 |
| 94 | 3652.5 |
| 95 | 561.0 |
| 96 | 2221.0 |
| 97 | 934.1 |
| 98 | 1.0 |
| 99 | 623.8 |
| 100 | 1949.7 |
| 101 | 8081.6 |
| 102 | 95.8 |
| 103 | 371.0 |
| 104 | 1675.8 |
| 105 | 867.1 |
| 106 | 155.9 |
| 107 | 2118.1 |
| 108 | 4841.5 |
| 109 | 0.5 |

TABLE 2-continued

Binding to KRas G12D by Exemplary Compounds of Formula (I)

| Example No. | $IC_{50}$ (nM) |
|---|---|
| 110 | 57.5 |
| 111 | 281.0 |
| 112 | 718.4 |
| 113 | 2866.1 |
| 114 | 482.1 |
| 115 | 174.3 |
| 116 | 1437.7 |
| 117 | 731.5 |
| 118 | 476.6 |
| 119 | 684.3 |
| 120 | 28.8 |
| 121 | 204.2 |
| 122 | 3265.3 |
| 123 | 754.4 |
| 124 | 8.6 |
| 125 | 667.5 |
| 126 | 9.9 |
| 127 | 250.9 |
| 128 | 500.6 |
| 129 | 4092.5 |
| 130 | 1647.0 |
| 131 | 423.9 |
| 132 | 60.5 |
| 133 | 48.8 |
| 134 | 3.7 |
| 135 | 2.1 |
| 136 | 5150.6 |
| 137 | 2633.4 |
| 138 | 8067.8 |
| 139 | 113.3 |
| 140 | 5161.4 |
| 141 | 891.1 |
| 142 | 8846.4 |
| 143 | 4563.2 |
| 144 | 1702.3 |
| 145 | 5002.5 |
| 146 | 2285.7 |
| 147 | 5876.2 |
| 148 | 5180.0 |
| 149 | 869.5 |
| 150 | 1981.1 |
| 151 | 387.5 |
| 152 | 2647.1 |
| 153 | 50.8 |
| 154 | 6533.8 |
| 155 | 3417.0 |
| 156 | 9.1 |
| 157 | 26.6 |
| 158 | 73.7 |
| 159 | 331.0 |
| 160 | 120.3 |
| 161 | 273.2 |
| 162 | 677.3 |
| 163 | 5552.5 |
| 164 | 4046.0 |
| 165 | 97.8 |
| 166 | 1286.1 |
| 167 | 226.2 |
| 168 | 583.0 |
| 169 | 656.9 |
| 170 | 841.7 |
| 171 | 757.4 |
| 172 | 689.1 |
| 173 | 99.2 |
| 174 | 63.9 |
| 175 | 63.8 |
| 176 | 235.1 |
| 177 | 187.1 |
| 178 | 105.0 |
| 179 | 1.1 |
| 180 | 76.1 |
| 181 | 572.5 |
| 182 | 269.1 |
| 183 | 393.3 |
| 184 | 1990.6 |

TABLE 2-continued

Binding to KRas G12D by Exemplary Compounds of Formula (I)

| Example No. | $IC_{50}$ (nM) |
|---|---|
| 185 | 0.3 |
| 186 | 29.2 |
| 187 | 1.7 |
| 188 | 1919.7 |
| 189 | 0.5 |
| 190 | 64.1 |
| 191 | 69.1 |
| 192 | 224.9 |
| 193 | 12.5 |
| 194 | 150.8 |
| 195 | 20.7 |
| 196 | 467.0 |
| 197 | 99.9 |
| 198 | 20.3 |
| 199 | 2.0 |
| 200 | 229.7 |
| 201 | 70.2 |
| 202 | 94.0 |
| 203 | 28.1 |
| 204 | 4.4 |
| 205 | 1.2 |
| 206 | 5.1 |
| 207 | 4906.8 |
| 208 | 1836.7 |
| 209 | 2746.7 |
| 210 | 5464.7 |
| 211 | 211.5 |
| 212 | 1218.4 |
| 213 | 7529.0 |
| 216 | 0.9 |
| 218 | 1600 |
| 219 | 8.1 |
| 220 | 8.7 |
| 221 | 15.7 |
| 222 | 1126.7 |
| 223 | 7.1 |
| 224 | 27.0 |
| 225 | 9.2 |
| 226 | 25.9 |
| 227 | 6.4 |
| 228 | 87.7 |
| 229 | 121.0 |
| 230 | 1433.1 |
| 231 | 19.8 |
| 232 | 0.6 |
| 233 | 387.2 |
| 234 | 5.9 |
| 235 | 1.2 |
| 236 | 25.0 |
| 237 | 500.3 |
| 238 | 16.1 |
| 239 | 2.0 |
| 240 | 314.8 |
| 241 | 79.2 |
| 242 | 82.2 |
| 243 | 0.4 |
| 244 | 4.2 |
| 245 | 0.5 |
| 246 | 0.6 |
| 247 | 12.6 |
| 248 | 3.2 |
| 249 | 3.5 |
| 250 | 28.2 |
| 251 | 0.2 |
| 252 | 0.4 |
| 253 | 0.8 |
| 254 | 6.1 |
| 255 | 8.7 |
| 256 | 13.2 |
| 257 | 5.1 |
| 258 | 6.5 |
| 259 | 0.8 |
| 260 | 107.1 |
| 261 | 8304.2 |
| 262 | 2255.6 |

TABLE 2-continued

Binding to KRas G12D by Exemplary Compounds of Formula (I)

| Example No. | $IC_{50}$ (nM) |
|---|---|
| 263 | 1.5 |
| 264 | 4698.9 |
| 265 | 794.0 |
| 266 | 278.0 |
| 267 | 3261.6 |
| 268 | 1546.3 |
| 269 | 4037.9 |
| 270 | 4492.4 |
| 271 | 1621.9 |
| 272 | 1178.7 |
| 273 | 1340.8 |
| 274 | 35.9 |
| 275 | 53.8 |
| 276 | 16.2 |
| 277 | 35.2 |
| 278 | 0.7 |
| 279 | 1.6 |
| 280 | 99.8 |
| 281 | 0.9 |
| 282 | 0.7 |
| 283 | 0.7 |
| 284 | 0.1 |
| 285 | 279.0 |
| 286 | 17.2 |
| 287 | 90.7 |
| 288 | 589.5 |
| 289 | 218.4 |
| 290 | 2.1 |
| 291 | 1.6 |
| 292 | 13.1 |
| 293 | 692.3 |
| 294 | 620.4 |
| 295 | 191.5 |
| 296 | 111.5 |
| 297 | 88.9 |
| 298 | 8.3 |
| 299 | 131.7 |
| 300 | 767.8 |
| 301 | 35.1 |
| 302 | 43.6 |
| 303 | 357.3 |
| 304 | 29.2 |
| 305 | 366.8 |
| 306 | 260.4 |
| 307 | 3164.3 |
| 308 | 117.4 |
| 309 | 204.7 |
| 310 | 558.7 |
| 311 | 135.3 |
| 312 | 9.0 |
| 313 | 231.3 |
| 314 | 0.6 |
| 315 | 2537.4 |
| 316 | >10000 |
| 317 | >10000 |
| 318 | >10000 |
| 319 | >10000 |
| 320 | >10000 |
| 321 | 612.8 |
| 322 | 4.9 |
| 323 | 1689.3 |
| 324 | 10.2 |
| 325 | 140.9 |
| 326 | 1.9 |
| 327 | 1.9 |
| 328 | 9.4 |
| 329 | 202.5 |
| 330 | 2.5 |
| 331 | 114.4 |
| 332 | 163.9 |
| 333 | 450.5 |
| 334 | 10.0 |
| 335 | 25.8 |
| 336 | 3.1 |
| 337 | 2.2 |

TABLE 2-continued

| Binding to KRas G12D by Exemplary Compounds of Formula (I) | |
|---|---|
| Example No. | $IC_{50}$ (nM) |
| 338 | 33.1 |
| 339 | 21.0 |
| 340 | 0.4 |
| 341 | 0.7 |
| 342 | 3.4 |
| 343 | 10.4 |
| 344 | 10.9 |
| 345 | 10.6 |
| 346 | 10.5 |
| 347 | 2.1 |
| 348 | 15.5 |
| 349 | 560.7 |
| 350 | 3822.1 |
| 351 | 94.8 |
| 352 | 844.8 |
| 353 | 333.4 |
| 354 | 368.1 |
| 355 | 869.9 |
| 356 | 87.2 |
| 357 | 438.0 |
| 358 | 1980.6 |
| 359 | 1637.1 |
| 360 | 50.8 |
| 361 | 2700.3 |
| 362 | 105.8 |
| 363 | 3932.5 |
| 364 | 2.3 |
| 365 | 34.9 |
| 366 | 0.5 |
| 367 | 0.7 |
| 368 | 207.6 |
| 369 | 221.4 |
| 370 | 86.1 |
| 371 | 394.2 |
| 372 | 0.7 |
| 373 | 1.6 |
| 374 | 347.9 |
| 375 | 1.7 |
| 376 | 2.6 |
| 377 | 416.9 |
| 378 | 6250.0 |
| 379 | 248.7 |
| 380 | 65.7 |
| 381 | 0.7 |
| 382 | 21.1 |
| 383 | 585.9 |
| 384 | 2.4 |
| 385 | 3083.3 |
| 386 | 2.0 |
| 387 | 532.8 |
| 388 | 0.6 |
| 389 | 1.4 |
| 390 | 36.8 |
| 391 | 661.7 |
| 392 | 208.2 |
| 393 | 76.3 |
| 394 | 2500.0 |
| 395 | 6.9 |
| 396 | 206.8 |
| 397 | 886.9 |
| 398 | 593.2 |
| 399 | 2.7 |
| 400 | 4.2 |
| 401 | 2.8 |
| 402 | 8017.6 |
| 403 | 1.9 |
| 404 | 60.8 |
| 405 | 2.2 |
| 406 | 0.9 |
| 407 | 560.0 |
| 408 | 3.1 |
| 409 | 2231.4 |
| 410 | 1.0 |
| 411 | 17.0 |
| 412 | 17.7 |

TABLE 2-continued

| Binding to KRas G12D by Exemplary Compounds of Formula (I) | |
|---|---|
| Example No. | $IC_{50}$ (nM) |
| 413 | 9.2 |
| 414 | 873.2 |
| 415 | 2578.3 |
| 416 | 1946.5 |
| 417 | 594.7 |
| 418 | 7.5 |
| 419 | 50.9 |
| 420 | 20.0 |
| 421 | 7746.7 |
| 422 | 11.4 |
| 423 | 238.0 |
| 424 | 5.0 |
| 425 | 90.2 |
| 426 | 0.9 |
| 427 | 35.3 |
| 428 | 92.1 |
| 429 | 18.5 |
| 430 | 1.0 |
| 431 | 1.4 |
| 432 | 1.9 |
| 433 | 0.9 |
| 434 | 0.7 |
| 435 | 28.2 |
| 436 | 48.3 |
| 437 | 233.7 |
| 438 | 20.1 |
| 439 | 0.4 |
| 140 | 0.8 |
| 441 | 0.5 |
| 442 | 25.0 |
| 443 | 3.2 |
| 444 | 5.5 |
| 445 | 2.7 |
| 446 | 357.0 |
| 447 | 297.0 |
| 448 | 130.0 |
| 449 | 71.0 |
| 450 | 37.0 |
| 451 | 1.0 |
| 452 | 1.0 |
| 453 | 27 |
| 454 | 295 |
| 455 | 17 |
| 456 | 966 |
| 457 | 475 |
| 458 | 143 |
| 459 | 1.6 |
| 460 | 0.027 |
| 461 | 0.062 |
| 462 | 0.751 |
| 463 | 0.012 |
| 464 | 0.007 |
| 465 | 0.001 |
| 466 | 0.006 |
| 467 | <0.002 |
| 468 | <0.002 |
| 469 | <0.002 |
| 480 | <0.002 |
| 481 | <0.002 |
| 482 | <0.002 |

Example C

Inhibition of KRas G12D-mediated Phosphorylation of ERK by Exemplary Compounds of Formula (I)

This Example illustrates that exemplary compounds of the present invention inhibit the phosphorylation of ERK downstream of KRAS G12D.

AGS cells (ATCC CRL-1739) expressing G12D were grown in DMEM medium supplemented with 10% fetal bovine serum, 10 mM HEPES, and Penicillin/Streptomycin. Cells were plated in tissue culture treated 96 well plates at a density of 40,000 cells/well and allowed to attach for 12-14 hours. Diluted compounds were then added in a final concentration of 0.5% DMSO. After 3 hours, the medium was removed, 150 µL of 4.0% formaldehyde was added and the plates incubated at room temperature for 20 minutes. The plates were washed with PBS, and permeabilized with 150 µL of ice cold 100% methanol for 10 minutes. Non-specific antibody binding to the plates was blocked using 100 µL Licor blocking buffer (Li-Cor Biotechnology, Lincoln NE) for 1 hour at room temperature.

The amount of phospho-ERK was determined using an antibody specific for the phosphorylated form of ERK and compared to the amount of GAPDH. Primary antibodies used for the detection were added as follows: Phospho-ERK (Cell Signaling cs-9101) diluted 1:500 and GAPDH (Millipore MAB374) diluted 1:5000 in Licor block+0.05% Tween 20. The plates were incubated for 2 hours at room temperature. The plates were washed with PBS+0.05% Tween 20.

Secondary antibodies used to visualize primary antibodies were added as follows: Anti-rabbit-680 diluted 1:1000 and Anti-mouse-800 diluted 1:1000 both in Licor block +0.05% $TweeN_20$, and were incubated for 1 hour at room temperature. The plates were washed with PBS +0.05% Tween 20. A 100 µL aliquot of PBS was added to each well and the plates were read on a Li-Cor Odyssey CLX plate reader.

The phospho-ERK (Thr202/Tyr204 signal was normalized to the GAPDH signal for each well and percent of DMSO control values were calculated. IC50 values were generated using a 4-parameter fit of the dose response curve. The results for exemplary compounds of Formula (I) are shown in Table 3. ND is not determined.

TABLE 3

Inhibition of KRas G12D-mediated Phosphorylation of ERK by Exemplary Compounds of Formula (I)

| Example No. | $IC_{50}$ (nM) |
|---|---|
| 1 | 3159.1 |
| 2 | 721.4 |
| 3 | 10283.1 |
| 4 | 8530.0 |
| 5 | 8193.8 |
| 6 | 11518.2 |
| 10 | 8115.5 |
| 11 | 1078.2 |
| 12 | 4905.2 |
| 14 | 4843.5 |
| 15 | >16666.7 |
| 16 | 3834.5 |
| 18 | 3742.5 |
| 19 | >16666.7 |
| 22 | 1888.7 |
| 24 | 2890.0 |
| 26 | 4282.7 |
| 27 | 1275.8 |
| 28 | 11736.0 |
| 29 | 13630.9 |
| 30 | 9600.4 |
| 31 | 2425.6 |
| 32 | >50000 |
| 33 | 2052.1 |
| 34 | 4207.8 |
| 35 | 11332.1 |
| 36 | 107.8 |
| 40 | 4241.8 |
| 41 | 6647.2 |
| 42 | 637.6 |
| 43 | 6204.1 |
| 44 | 2290.1 |
| 45 | 840.0 |
| 47 | 4445.6 |

TABLE 3-continued

Inhibition of KRas G12D-mediated Phosphorylation of ERK by Exemplary Compounds of Formula (I)

| Example No. | $IC_{50}$ (nM) |
|---|---|
| 48 | 4875.6 |
| 49 | 2123.1 |
| 50 | 15404.5 |
| 51 | 12066.6 |
| 52 | 8380.0 |
| 54 | >16666.7 |
| 60 | >16666.7 |
| 63 | 186.7 |
| 64 | 3971.0 |
| 65 | 1332.6 |
| 68 | 7530.9 |
| 69 | >16666.7 |
| 71 | >16666.7 |
| 72 | 7260.8 |
| 73 | >5555.6 |
| 74 | 5465.1 |
| 75 | >16666.7 |
| 76 | 7412.9 |
| 78 | >16666.7 |
| 81 | 8288.3 |
| 82 | >16666.7 |
| 84 | 5722.3 |
| 85 | >16666.7 |
| 87 | 10553.8 |
| 91 | 5514.1 |
| 93 | >16666.7 |
| 98 | 388.6 |
| 102 | 7955.9 |
| 103 | >16666.7 |
| 104 | >16666.7 |
| 106 | 3096.3 |
| 109 | 330.5 |
| 110 | >16666.7 |
| 114 | 10259.6 |
| 115 | 9514.0 |
| 118 | >16666.7 |
| 119 | 3700.2 |
| 120 | 2092.9 |
| 121 | 4077.1 |
| 122 | >16666.7 |
| 124 | 11087.4 |
| 126 | 3470.6 |
| 127 | >16666.7 |
| 131 | >16666.7 |
| 132 | 2558.7 |
| 133 | 2048.8 |
| 134 | 895.4 |
| 135 | 4820.9 |
| 139 | 5245.1 |
| 141 | >16666.7 |
| 152 | >50000 |
| 153 | 2369.2 |
| 156 | 1786.9 |
| 157 | 7998.7 |
| 158 | 4222.3 |
| 159 | >16666.7 |
| 160 | 6930.7 |
| 161 | >16666.7 |
| 162 | >16666.7 |
| 163 | >16666.7 |
| 164 | >16666.7 |
| 165 | 11068.5 |
| 167 | 16142.4 |
| 168 | >16666.7 |
| 173 | 10504.3 |
| 174 | 12816.8 |
| 175 | >5555.6 |
| 178 | >16666.7 |
| 179 | 71.2 |
| 180 | >16666.7 |
| 181 | 12839.1 |
| 182 | 13549.2 |
| 183 | 5252.5 |
| 185 | 7.1 |
| 186 | 3383.1 |

TABLE 3-continued

Inhibition of KRas G12D-mediated Phosphorylation of ERK by Exemplary Compounds of Formula (I)

| Example No. | $IC_{50}$ (nM) |
|---|---|
| 187 | 450.1 |
| 189 | 24.1 |
| 190 | 16314.3 |
| 191 | 5047.0 |
| 193 | 8517.9 |
| 195 | 2461.5 |
| 197 | >16666.7 |
| 198 | 2425.5 |
| 199 | 464.8 |
| 201 | 13915.2 |
| 202 | 10186.8 |
| 203 | 2183.2 |
| 204 | 306.7 |
| 205 | 242.1 |
| 206 | 899.6 |
| 208 | >16666.7 |
| 209 | >16666.7 |
| 210 | >16666.7 |
| 211 | 13506.7 |
| 214 | >16666.7 |
| 215 | >16666.7 |
| 216 | 51.0 |
| 219 | 2032.0 |
| 220 | 1344.9 |
| 221 | 15840.8 |
| 223 | 4272.7 |
| 224 | 6375.8 |
| 225 | 3058.3 |
| 226 | 6745.4 |
| 227 | 2976.0 |
| 228 | 13718.5 |
| 229 | 11330.3 |
| 231 | 2806.1 |
| 232 | 15.2 |
| 233 | 15568.1 |
| 234 | 409.0 |
| 235 | 338.6 |
| 236 | 2626.3 |
| 238 | 4656.9 |
| 239 | 2951.1 |
| 240 | >16666.7 |
| 241 | >16666.7 |
| 242 | >16666.7 |
| 243 | 0.8 |
| 244 | 763.0 |
| 245 | 23.4 |
| 246 | 1.0 |
| 247 | 4310.5 |
| 248 | 1082.8 |
| 249 | 7705.6 |
| 250 | 7477.7 |
| 251 | 10.3 |
| 252 | 0.8 |
| 253 | 2.0 |
| 254 | 2428.8 |
| 255 | 673.4 |
| 256 | >16666.7 |
| 257 | 530.7 |
| 258 | 1460.4 |
| 259 | 3.9 |
| 260 | >16666.7 |
| 263 | 7641.0 |
| 274 | 4706.4 |
| 275 | 7058.7 |
| 276 | 3789.2 |
| 277 | 3675.0 |
| 278 | 104.4 |
| 279 | 7401.8 |
| 280 | 6115.7 |
| 281 | 97.8 |
| 282 | 4.9 |
| 283 | 7.0 |
| 284 | 17.4 |
| 286 | 1733.1 |
| 287 | 8067.4 |

TABLE 3-continued

Inhibition of KRas G12D-mediated Phosphorylation of ERK by Exemplary Compounds of Formula (I)

| Example No. | $IC_{50}$ (nM) |
|---|---|
| 290 | 110.5 |
| 291 | 46.5 |
| 292 | 1696.0 |
| 296 | 8472.0 |
| 297 | 6562.0 |
| 298 | 1228.7 |
| 299 | >5555.6 |
| 301 | 3173.2 |
| 302 | 1993.3 |
| 304 | 1415.1 |
| 308 | >5555.6 |
| 312 | 1877.6 |
| 314 | 3.7 |
| 321 | >16666.7 |
| 322 | 664.8 |
| 324 | 863.9 |
| 325 | >16666.7 |
| 326 | 121.6 |
| 327 | 31.4 |
| 328 | 896.9 |
| 330 | 11.8 |
| 331 | 10826.0 |
| 332 | >16666.7 |
| 334 | 2909.3 |
| 335 | 10440.5 |
| 336 | 1057.2 |
| 337 | 1620.7 |
| 338 | >16666.7 |
| 339 | 8659.5 |
| 340 | 51.5 |
| 341 | 837.3 |
| 342 | 1001.2 |
| 343 | 1616.5 |
| 344 | 8069.6 |
| 345 | 1468.2 |
| 346 | 1351.5 |
| 347 | 458.9 |
| 348 | 778.6 |
| 351 | >16666.7 |
| 356 | 11920.1 |
| 360 | 8353.4 |
| 362 | 10457.0 |
| 364 | 322.0 |
| 365 | 3949.0 |
| 366 | 7.0 |
| 367 | 111.8 |
| 370 | 10730.6 |
| 372 | 10.5 |
| 373 | >16666.7 |
| 375 | 1310.3 |
| 376 | 582.3 |
| 380 | >16666.7 |
| 381 | 708.4 |
| 382 | >16666.7 |
| 384 | 398.2 |
| 385 | >16666.7 |
| 386 | 320.3 |
| 388 | 40.2 |
| 389 | 780.7 |
| 390 | 6108.7 |
| 393 | 7579.3 |
| 395 | 1089.1 |
| 396 | 8173.3 |
| 397 | >16666.7 |
| 399 | 509.9 |
| 400 | 260.6 |
| 401 | 603.5 |
| 403 | 2881.0 |
| 404 | 8331.6 |
| 405 | 297.0 |
| 406 | 440.3 |
| 408 | 238.0 |
| 410 | 8.0 |
| 411 | 745.3 |
| 412 | 4779.3 |

TABLE 3-continued

| Inhibition of KRas G12D-mediated Phosphorylation of ERK by Exemplary Compounds of Formula (I) | |
|---|---|
| Example No. | $IC_{50}$ (nM) |
| 413 | 2156.3 |
| 418 | 2741.5 |
| 419 | 2776.1 |
| 420 | 7816.4 |
| 422 | 2357.8 |
| 424 | 680.9 |
| 425 | 5414.1 |
| 426 | 228.0 |
| 427 | 1981.7 |
| 428 | 6964.4 |
| 429 | 1696.0 |
| 430 | 141.0 |
| 431 | 74.3 |
| 432 | 106.3 |
| 433 | 43.2 |
| 434 | 6.7 |
| 435 | 1822.4 |
| 436 | 3989.5 |
| 438 | 1630.8 |
| 439 | 12.8 |
| 440 | 8.4 |
| 441 | 4.1 |
| 442 | 1162.0 |
| 443 | 160.0 |
| 444 | 365.0 |
| 445 | 130.0 |
| 451 | 78.3 |
| 452 | 13.7 |
| 468 | 28.8 |
| 469 | 31.6 |
| 482 | 3.4 |

Example D

Whole Blood Stability (WBS) of Exemplary Compounds of Formula (I)

This Example illustrates that exemplary compounds of the present invention can be cleaved in whole blood stability and converted to the parent compound.

Compounds (2 μM) were incubated at 37° C. for 0, 10, 30, 60, and 120 min in a 1:1 (v/v) blood and PBS, pH 7.4. Diluted blood was preincubated for 15 min at 37° C. before the reactions were initiated with the dosing of the compound. At the end of incubation, the same volume of water was mixed with the spiked blood samples, and then stop solution (200 ng/mL tolbutamide and 200 ng/ml labetalol in MeOH) was added to precipitate protein. Mixed thoroughly. Samples were centrifuged, and supernatants were analyzed by LC-MS/MS. Results are shown in Table 6.

TABLE 4

| Whole Blood Stability (WBS) of Exemplary Compounds of Formula (I) | | |
|---|---|---|
| Example No. | $T_{1/2}$ in human whole blood | $T_{1/2}$ in SD rat whole blood |
| 471 | 65 | 2.7 |
| 472 | >289 | 92 |
| 473 | 250 | >289 |
| 474 | >289 | 227 |
| 475 | >289 | >289 |
| 476 | 178 | 129 |

Increased amount of parent compound (example 252) was observed with the depletion of example 471 in human whole blood.

| Time point (min) | Example 471% remaining | Parent Compound % formation |
|---|---|---|
| 0 | 100 | 1.4 |
| 10 | 105 | 15 |
| 30 | 77 | 28 |
| 60 | 51 | 31 |
| 120 | 31 | 26 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound of Formula (II):

Formula (II)

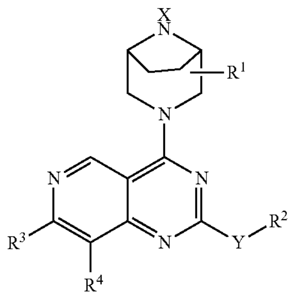

or a pharmaceutically acceptable salt thereof, wherein:

$R^1$ is hydrogen, hydroxy, halogen, C1-C3 alkyl, C1-C3 cyanoalkyl, C1-C3 hydroxyalkyl, HC(=O)—, —$CO_2R^5$, —$C(O)N(R^5)_2$ or a 5-6 membered heteroaryl;

X is —C(O)—O—$CH(R^9)$—O—C(O)—Z, —C(O)—O-aryl or —C(O)—C1-C6 alkyl;

Y is a bond, O or $NR^5$;

Z is —$(CH_2)_n$—$CH_3$ or C1-C3 alkyl;

n is 0-20;

$R^2$ is hydrogen, —$N(R^5)_2$, heterocyclyl, C1-C6 alkyl, -L-heterocyclyl, -L-aryl, -L-heteroaryl, -L-cycloalkyl, -L-$N(R^5)_2$, -L-NHC(=NH)$NH_2$, -L-C(O)$N(R^5)_2$, -L-C1-C6 haloalkyl, -L-$OR^5$, -L-$NR^5$C(O)-aryl, -L-COOH, or -LC(=O)OC1-C6 alkyl, wherein the heterocyclyl, the aryl portion of -L-$NR^5$C(O)-aryl, the heterocyclyl portion of -L-heterocyclyl, and the cycloalkyl portion of the -L-cycloalkyl may be optionally substituted with one or more $R^6$, and wherein the aryl or heteroaryl of the -L-aryl and the -L-heteroaryl may be optionally substituted with one or more $R^7$;

each L is independently a C1-C4 alkylene optionally substituted with hydroxy, C1-C4 hydroxyalkyl, heteroaryl or 1-2 deuterium;

$R^3$ is aryl or heteroaryl, wherein the aryl or the heteroaryl is optionally substituted with one or more $R^8$;

$R^4$ is hydrogen, halogen or C1-C3 alkyl;

each $R^5$ is independently hydrogen or C1-C3 alkyl;

each $R^6$ is independently halogen, hydroxy, C1-C3 hydroxyalkyl, C1-C3 alkyl, C1-C3 haloalkyl, C1-C3 alkoxy, cyano, -Q-phenyl, -Q-phenyl$SO_2$F, —NHC(O)phenyl, —NHC(O)phenyl$SO_2$F, C1-C3 alkyl substituted pyrazolyl, araC1-C3 alkyl-, tert-butyldimethylsilyloxy$CH_2$—, —N($R^5$)$_2$, (C1-C3 alkoxy)C1-C3 alkyl-, (C1-C3 alkyl)C(═O), oxo, (C1-C3 haloalkyl)C(═O)—, —$SO_2$F, (C1-C3 alkoxy)C1-C3 alkoxy, —$CH_2$OC(O)N($R^5$)$_2$, —$CH_2$NHC(O)OC1-C6 alkyl, —$CH_2$NHC(O)N($R^5$)$_2$, —$CH_2$NHC(O)C1-C6 alkyl, —$CH_2$ (pyrazolyl), —$CH_2$NH$SO_2$C1-C6 alkyl, —$CH_2$OC(O)heterocyclyl, —OC(O)N($R^5$)$_2$, —OC(O)NH(C1-C3 alkyl)O(C1-C3 alkyl), —OC(O)NH(C1-C3 alkyl)O(C1-C3 alkyl)phenyl(C1-C3 alkyl)N($CH_3$) 2, —OC(O)NH(C1-C3 alkyl)O(C1-C3 alkyl)phenyl, —OC(O)heterocyclyl, —$CH_2$heterocyclyl or deuterium, wherein the phenyl of —NHC(O)phenyl or —OC(O)NH(C1-C3 alkyl)O(C1-C3 alkyl)phenyl is optionally substituted with —C(O)H or OH and wherein the heterocyclyl of —$CH_2$heterocyclyl is optionally substituted with oxo;

Q is a bond or O;

each $R^7$ is independently, halogen, hydroxy, HC(═O)—, C1-C4 alkyl, C1-C4 alkoxy, C1-C4 haloalkyl, C1-C4 hydroxyalkyl, or —N($R^5$)$_2$;

each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxy C1-C3 alkyl, —$CH_2$C(═O)N($R^5$)$_2$, —C3-C4 alkynyl(N$R^5$)$_2$, —N($R^5$)$_2$, deuteroC2-C4 alkynyl, (C1-C3 alkoxy)haloC1-C3 alkyl-, —O—C(O)—Z, or C3-C6 cycloalkyl wherein said C3-C6 cycloalkyl is optionally substituted with halogen or C1-C3 alkyl; and $R^9$ is hydrogen or C1-C3 alkyl.

2. The compound or salt of claim 1, wherein $R^1$ is hydrogen.

3. The compound or salt of claim 1, wherein Y is a O.

4. The compound or salt of claim 1, wherein $R^2$ is L-heterocycle, wherein L is C1-C2 alkylene and heterocycle is:

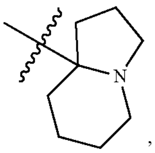
,
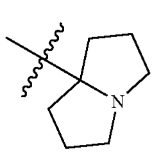
or
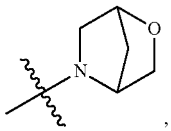
, optionally substituted with $R^6$.

5. The compound or salt of claim 4, wherein the heterocycle is:

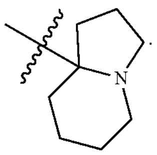 [SMILES: *C12CCCCN1CCC2]

6. The compound or salt of claim 4, wherein the heterocycle is:

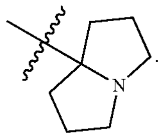 [SMILES: *C12CCCN1CCC2]

7. The compound or salt of claim 4, wherein the heterocycle is:

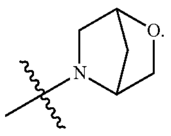 [SMILES: *N1CC2CC1CO2]

8. The compound or salt of claim 4, wherein said heterocycle is substituted with one or more $R^6$ selected from: oxo and halogen.

9. The compound or salt of claim 1, wherein X is —C(O)—O—CH($R^9$)—O—C(O)—Z, $R^9$ is hydrogen or $CH_3$, and Z is-$CH_3$, —$(CH_2)_8$—$CH_3$, —$(CH_2)_{14}$—$CH_3$ or —CH$(CH_3)_2$.

10. The compound or salt of claim 1, wherein X is —C(O)—O-phenyl.

11. The compound or salt of claim 1, wherein $R^3$ is naphthyl optionally substituted with one or more $R^8$.

12. The compound or salt of claim 11, wherein each $R^8$ is halogen, hydroxy, cyano, C1-C2 alkyl, C3-C6 cycloalkyl optionally substituted with C1-C3 alkyl, or —O—C(O)—Z.

13. The compound or salt of claim 12, wherein Z is-$CH_3$, —$(CH_2)_8$—$CH_3$, or —$(CH_2)_{14}$—$CH_3$.

14. The compound or salt of claim 1, wherein X is —C(O)—C$(CH_3)_3$.

15. The compound or salt of claim 5, wherein at least one $R^6$ is fluoro, X is —C(O)—O—CH($R^9$)—O—C(O)—Z, $R^9$ is hydrogen or $CH_3$, and Z is —$(CH_2)_8$—$CH_3$.

16. The compound or salt of claim 15, wherein $R^3$ is naphthyl.

17. The compound or salt of claim 16, wherein naphthyl is substituted with —O—C(O)—$(CH_2)_8$—$CH_3$.

18. The compound or salt of claim 16, wherein naphthyl is substituted with —O—C(O)—$(CH_2)_{14}$—$CH_3$.

19. The compound or salt of claim 5, wherein at least one $R^6$ is fluoro, X is —C(O)—O—CH($R^9$)—O—C(O)—Z, $R^9$ is hydrogen or $CH_3$, and Z is —$(CH_2)_{14}$—$CH_3$.

20. The compound or salt of claim 19, wherein $R^3$ is naphthyl.

21. The compound or salt of claim 20, wherein naphthyl is substituted with —O—C(O)—$(CH_2)_8$—$CH_3$.

22. The compound or salt of claim 20, wherein naphthyl is substituted with —O—C(O)—$(CH_2)_{14}$—$CH_3$.

23. The compound or salt of claim 1, wherein $R^2$ is L-heterocyclyl and L is $CH_2$ or $CD_2$.

24. The compound or salt of claim 23, wherein L is $CD_2$.

25. The compound or salt of claim 1, wherein $R^2$ is L-heterocycle and one or two $R^6$ are deuterium.

26. A compound selected from:
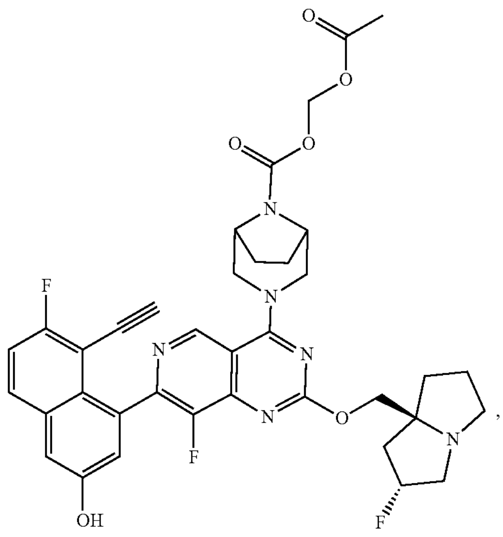
,
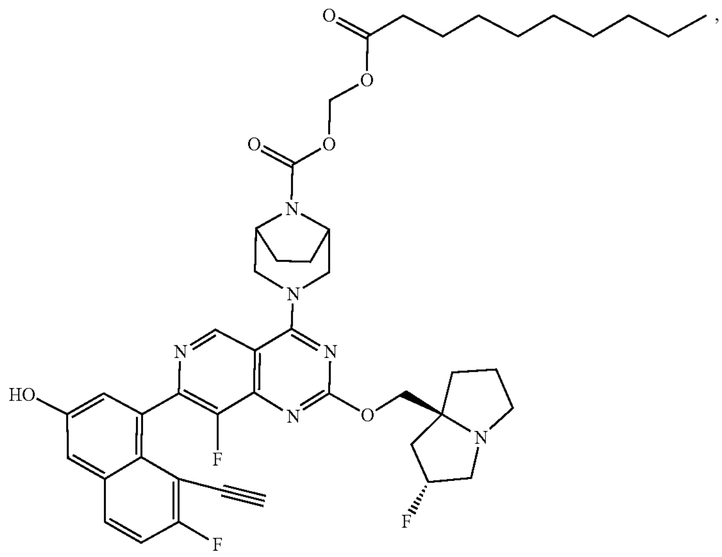
,
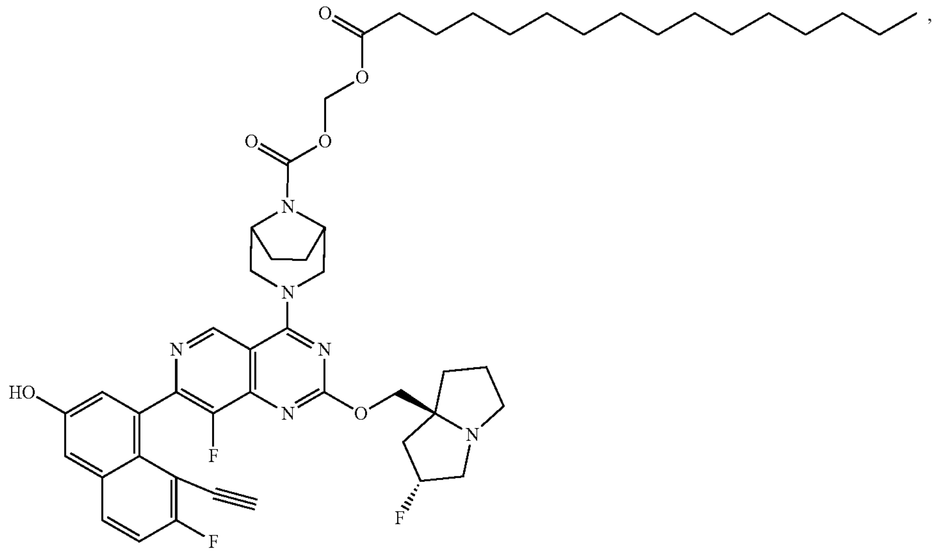
,

-continued
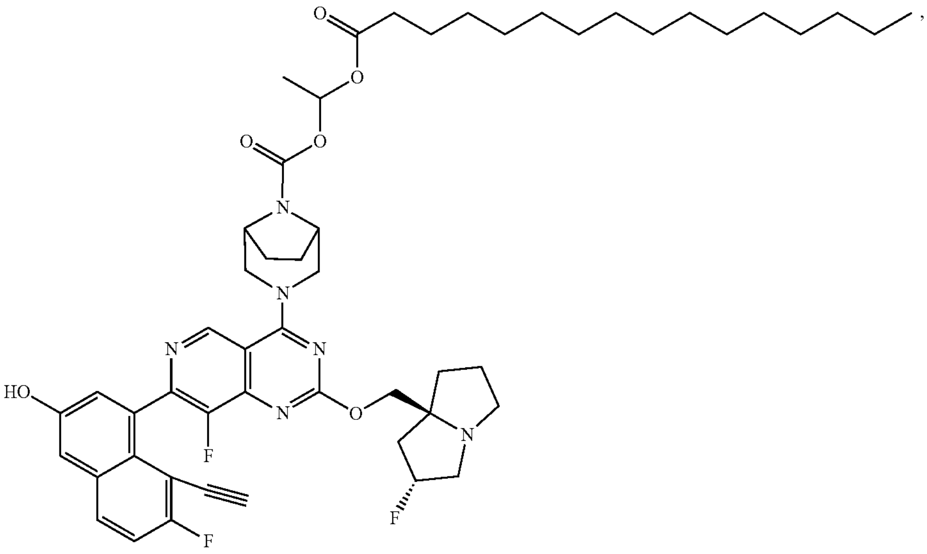
,
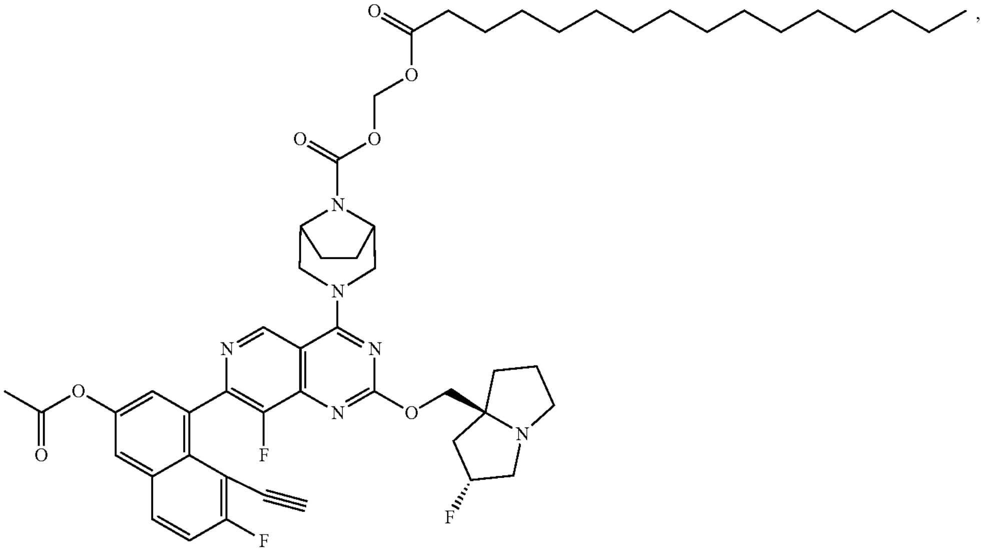
,
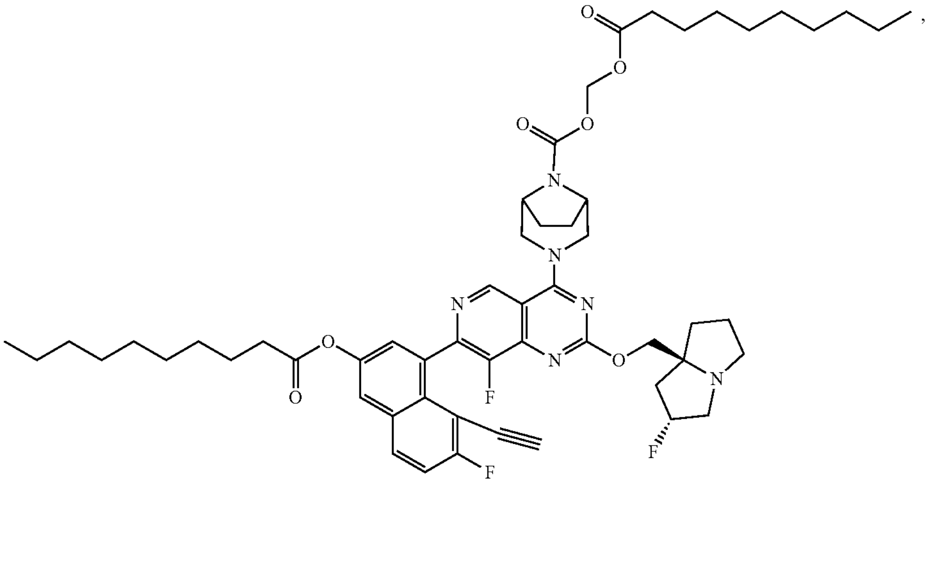
,

-continued
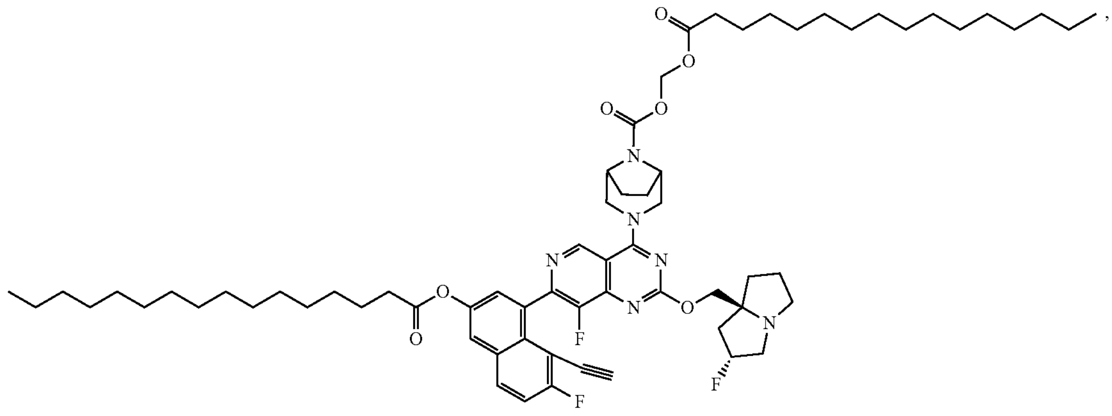
,
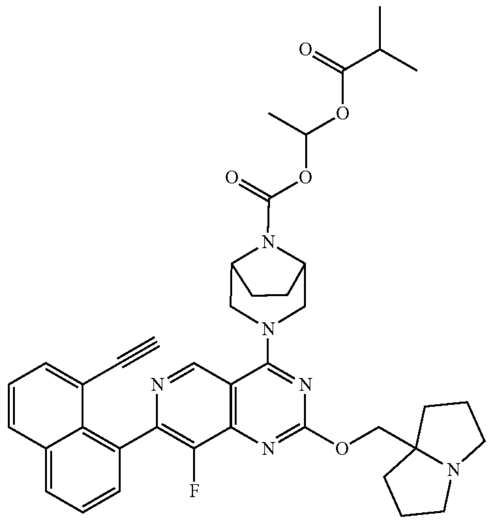
,
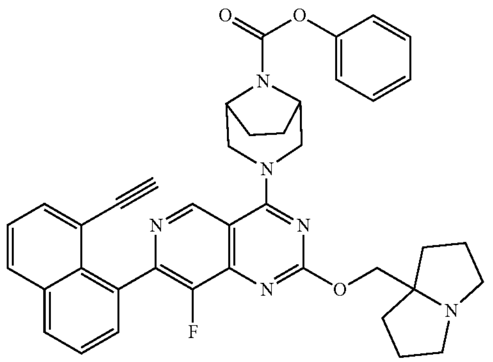
,
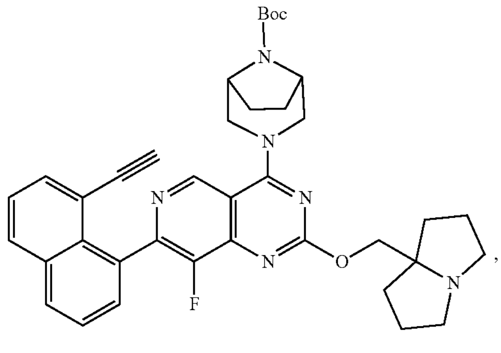
,

-continued

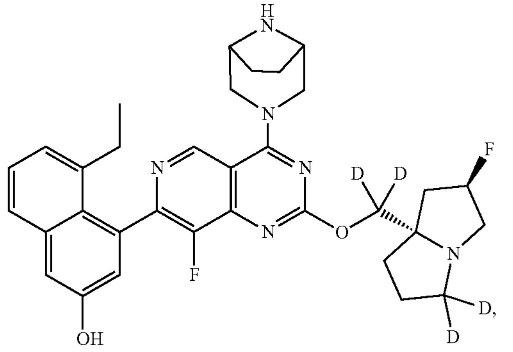

and

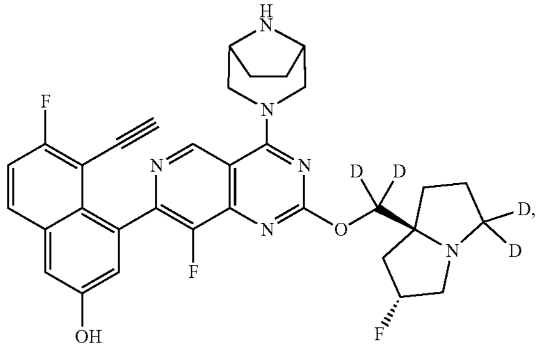

or pharmaceutically acceptable salts thereof.

27. A pharmaceutical composition, comprising a therapeutically effective amount of a compound of claim 1 or a pharmaceutically acceptable salt thereof, and a pharmaceutically acceptable excipient, wherein the therapeutically effective amount is sufficient to ameliorate, or reduce a symptom or stop or reverse progression of a KRas G12D-associated cancer, or negatively modulate or inhibit the activity of KRas G12D.

28. A method for inhibiting KRas G12D activity in a cell, comprising contacting the cell in which inhibition of KRas G12D activity is desired with an effective amount of a compound of according to claim 1.

29. A method for treating cancer comprising administering to a patient having cancer a therapeutically effective amount of a compound according to claim 1, wherein the cancer is a KRas G12D-associated cancer.

30. The method of claim 29, wherein the therapeutically effective amount of the compound is between about 0.01 to 100 mg/kg per day.

31. The method of claim 29, wherein the therapeutically effective amount of the compound is between about 0.1 to 50 mg/kg per day.

32. The method of claim 29, wherein the cancer is selected from the group consisting of Cardiac: sarcoma, myxoma, rhabdomyoma, fibroma, lipoma and teratoma; Lung: bronchogenic carcinoma, alveolar carcinoma, bronchiolar carcinoma, bronchial adenoma, sarcoma, lymphoma, chondromatous hamartoma, mesothelioma; Gastrointestinal: esophagus squamous cell carcinoma, esophagus adenocarcinoma, esophagus leiomyosarcoma, esophagus lymphoma, stomach carcinoma, stomach lymphoma, stomach leiomyosarcoma, pancreas ductal adenocarcinoma, pancreas insulinoma, pancreas glucagonoma, pancreas gastrinoma, pancreas carcinoid tumors, pancreas vipoma, small bowel adenocarcinoma, small bowel lymphoma, small bowel carcinoid tumors, small bowel Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma; Genitourinary tract: kidney adenocarcinoma, Wilm's tumor, nephroblastoma, kidney lymphoma, bladder and urethra squamous cell carcinoma, bladder and urethra transitional cell carcinoma, bladder and urethra adenocarcinoma, prostate adenocarcinoma, prostate sarcoma, testicular seminoma, testicular teratoma, testicular embryonal carcinoma, testicular teratocarcinoma, testicular choriocarcinoma, testicular sarcoma, testicular interstitial cell carcinoma, testicular fibroma, testicular fibroadenoma, testicular adenomatoid tumors, testicular lipoma; Liver: hepatoma, liver cholangiocarcinoma, hepatoblastoma, liver angiosarcoma, liver hepatocellular adenoma, liver hemangioma; Biliary tract: gall bladder carcinoma, ampullary carcinoma, biliary tract cholangiocarcinoma; Bone: osteogenic sarcoma, bone fibrosarcoma, bone malignant fibrous histiocytoma, bone chondrosarcoma, Ewing's sarcoma, bone malignant lymphoma, bone reticulum cell sarcoma, bone multiple myeloma, malignant giant cell tumor chordoma, osteochondroma, osteocartilaginous exostoses, benign chondroma, chondroblastoma, chondromyxofibroma, osteoid osteoma and giant cell tumors; Nervous system: skull osteoma, skull hemangioma, skull granuloma, skull xanthoma, skull osteitis deformans, meningioma, meningiosarcoma, gliomatosis, brain astrocytoma, brain medulloblastoma, brain glioma, brain ependymoma, brain germinoma, brain pinealoma, brain glioblastoma multiform, brain oligodendroglioma, brain schwannoma, brain retinoblastoma, brain congenital tumors, spinal cord neurofibroma, spinal cord meningioma, spinal cord glioma, spinal cord sarcoma; Gynecological: uterus endometrial carcinoma, uterus serous cystadenocarcinoma, uterus mucinous cystadenocarcinoma, uterus unclassified carcinoma, granulosa-thecal cell tumors, Sertoli-Leydig cell tumors, dysgerminoma, malignant teratoma, vulva squamous cell carcinoma, vulva intraepithelial carcinoma, vulva adenocarcinoma, vulva fibrosarcoma, vulva melanoma, vagina clear cell carcinoma, vagina squamous cell carcinoma, vagina botryoid sarcoma, vagina embryonal rhabdomyosarcoma, fallopian tube carcinoma; Hematologic: acute myeloid leukemia, chronic myeloid leukemia, acute lymphoblastic leukemia, chronic lymphocytic leukemia, myeloproliferative diseases, multiple myeloma, myelodysplastic syndrome, Hodgkin's disease, non-Hodgkin's lymphoma, malignant lymphoma; Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

33. The method of claim 29, wherein the cancer is non-small cell lung cancer, small cell lung cancer, colorectal cancer, rectal cancer or pancreatic cancer.

34. A method for treating cancer in a patient in need thereof, the method comprising (a) determining that the cancer is associated with a KRas G12D mutation; and (b) administering to the patient a therapeutically effective amount of a compound according to claim 1.

35. The method of claim 34 wherein the administering is done via a route selected from the group consisting of parenteral, intraperitoneal, intradermal, intracardiac, intraventricular, intracranial, intracerebrospinal, intrasynovial, intrathecal administration, intramuscular injection, intravitreous injection, intravenous injection, intra-arterial injection, oral, buccal, sublingual, transdermal, intratracheal, intrarectal, subcutaneous, and topical administration.

36. The method of claim 35, wherein the administering is done via an intravenous injection.

37. The method of claim 35, wherein the administering is done via an intramuscular injection.

38. The method of claim 35, wherein the administering is done via an intra-arterial injection.

39. The method of claim 35, wherein the administering comprises utilizing a delivery device.

40. The method of claim 29, wherein the cancer is selected from the group consisting of cardiac, lung, esophagus, stomach, pancreas, small bowel, large bowel, kidney, bladder, urethra, prostate, testis, liver, biliary tract, bone, skull, meninges, brain, spinal cord, uterus, vulva, vagina, fallopian tubes, blood, skin, and adrenal gland cancer.

41. The method of claim 29, wherein the cancer is selected from the group consisting of cardiac angiosarcoma, cardiac fibrosarcoma, cardiac rhabdomyosarcoma, cardiac liposarcoma, squamous cell bronchogenic carcinoma, undifferentiated small cell bronchogenic carcinoma, undifferentiated large cell bronchogenic carcinoma, and bronchogenic adenocarcinoma.

* * * * *